US012565665B2

(12) United States Patent
Marzilli et al.

(10) Patent No.: US 12,565,665 B2
(45) Date of Patent: Mar. 3, 2026

(54) COMPOSITIONS AND METHODS FOR CONTROLLED mRNA TRANSLATION AND STABILITY

(71) Applicant: TRUSTEES OF BOSTON UNIVERSITY, Boston, MA (US)

(72) Inventors: Alexander Michael Marzilli, Cambridge, MA (US); John Tuan Ngo, Cambridge, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 18/392,928

(22) Filed: Dec. 21, 2023

(65) Prior Publication Data

US 2024/0263193 A1 Aug. 8, 2024

Related U.S. Application Data

(60) Provisional application No. 63/434,275, filed on Dec. 21, 2022.

(51) Int. Cl.

| | |
|---|---|
| ***C12N 15/87*** | (2006.01) |
| ***C07K 14/005*** | (2006.01) |
| ***C12N 9/78*** | (2006.01) |
| ***C12N 15/11*** | (2006.01) |

(52) U.S. Cl.

CPC ............ *C12N 15/87* (2013.01); *C07K 14/005* (2013.01); *C12N 9/78* (2013.01); *C12N 15/11* (2013.01); *C12Y 305/04* (2013.01); *C12N 2310/20* (2017.05); *C12N 2310/531* (2013.01); *C12N 2795/18022* (2013.01)

(58) Field of Classification Search

CPC .......... C12N 15/87; C12N 9/78; C12N 15/11; C12N 2310/20; C12N 2310/531; C12N 2795/18022; C07K 14/005; C07K 2319/00; C12Y 305/04

See application file for complete search history.

(56) References Cited

U.S. PATENT DOCUMENTS

| | | | | |
|---|---|---|---|---|
| 2020/0248155 | A1 | 8/2020 | Halperin | |
| 2020/0263180 | A1 | 8/2020 | Mali | |
| 2020/0377564 | A1* | 12/2020 | Khalil | C12N 9/506 |
| 2021/0206818 | A1 | 7/2021 | Huang et al. | |
| 2021/0355494 | A1 | 11/2021 | Wei | |
| 2022/0048947 | A1 | 2/2022 | Frey | |

FOREIGN PATENT DOCUMENTS

| | | | | |
|---|---|---|---|---|
| WO | 2021150646 A1 | | 7/2021 | |
| WO | 2021178717 A2 | | 9/2021 | |
| WO | 2021226558 A1 | | 11/2021 | |
| WO | WO-2022056041 A2 | * | 3/2022 | C12N 15/102 |
| WO | 2023020574 A1 | | 2/2023 | |

OTHER PUBLICATIONS

Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
Buenrostro et al., Quantitative analysis of RNA-protein interactions on a massively parallel array reveals biophysical and evolutionary landscapes. Nat Biotechnol 32, 562-568 (2014).
Chung et al., A compact synthetic pathway rewires cancer signaling to therapeutic effector release. Science eaat6982 (2019).
Cunningham-Bryant et al., "A chemically disrupted proximity system for controlling dynamic cellular processes." Journal of the American Chemical Society 141.8: 3352-3355 (2019).
Drabkin et al., Initiation of Protein Synthesis in Mammalian Cells with Codons Other Than AUG and Amino Acids Other Than Methionine. Mol. Cell. Biol. 18, 5140-5147 (1998).
Feng et al., Improved split fluorescent proteins for endogenous protein labeling. Nat Commun 8, 370 (2017).
Goreshnik et al., "A small molecule-regulated guanine nucleotide exchange factor." Journal of the American Chemical Society 132.3: 938-940 (2010).
Götzke et al., The ALFA-tag is a highly versatile tool for nanobody-based bioscience applications. Nat Commun 10, 4403 (2019).
Jacobs et al., "StaPLs: versatile genetically encoded modules for engineering drug-inducible proteins." Nature methods 15.7: 523-526 (2018).
Jiang et al., "Programmable eukaryotic protein synthesis with RNA sensors by harnessing ADAR." Nat Biotechnol. 41 698-707 (2022).
Johansson et al., "A thermodynamic analysis of the sequence-specific binding of RNA by bacteriophage MS2 coat protein." Proceedings of the National Academy of Sciences 95.16: 9244-9249 (1998).
Katrekar et al., "Comprehensive interrogation of the ADAR2 deaminase domain for engineering enhanced RNA editing activity and specificity." Elife 11, e75555 (2022).

(Continued)

*Primary Examiner* — Paul J Holland

(74) *Attorney, Agent, or Firm* — Nixon Peabody LLP; Ronald I. Eisenstein; Alissa R. Young

(57) ABSTRACT

The technology described herein is directed to compositions, kits, systems and methods related to an engineered, inducible adenosine deaminase (iAD) enzymes, including but not limited to, an engineered inducible adenosine deaminase acting on RNA (ADAR) enzyme, which can be activated in the presence of an inducer. Also described are synthetic RNA molecules, to which the iAD can be specifically recruited to edit at least one target codon, leading to decreased or increased translation of the RNA molecules depending on the specific construct. The technology described herein is also directed to systems comprising the iAD and synthetic RNA molecule, nucleic acids and vectors encoding the iAD and synthetic RNA molecule, and methods of using such systems, nucleic acids, and vectors.

17 Claims, 229 Drawing Sheets

Specification includes a Sequence Listing.

(56) References Cited

OTHER PUBLICATIONS

Katrekar et al., "In vivo RNA editing of point mutations via RNA-guided adenosine deaminases". Nat Methods 16.3, 239-242 (2019).
Klauer et al., "Degradation of mRNAs that lack a stop codon: a decade of nonstop progress." Wiley Interdisciplinary Reviews: RNA 3.5: 649-660 (2012).
Kotschy et al., "The MCL1 inhibitor S63845 is tolerable and effective in diverse cancer models." Nature 538.7626: 477-482 (2016).
Kügler et al., "High Affinity Peptide Inhibitors of the Hepatitis C Virus NS3-4A Protease Refractory to Common Resistant Mutants." J Biol Chem 287.46, 39224-39232 (2012).
Li et al., "Structural analysis and optimization of the covalent association between SpyCatcher and a peptide Tag." Journal of molecular biology 426.2: 309-317 (2014).
Liu et al., "Systematic comparison of 2A peptides for cloning multi-genes in a polycistronic vector." Scientific Reports 7, 2193 (2017).
Matthews et al., "Structures of human ADAR2 bound to dsRNA reveal base-flipping mechanism and basis for site selectivity." Nat Struct Mol Biol 23.5, 426-433 (2016).
Park et al. "High-throughput mutagenesis reveals unique structural features of human ADAR1". Nat Commun 11, 5130 (2020).
Rose et al., "Rapidly inducible Cas9 and DSB-ddPCR to probe editing kinetics." Nat Methods 14.9, 891-896 (2017).
Sharma et al., "2A peptides provide distinct solutions to driving stop-carry on translational recoding." Nucleic acids research 40.7: 3143-3151 (2012).
Stripecke et al., "Proteins binding to 5' untranslated region sites: a general mechanism for translational regulation of mRNAs in human and yeast cells." Molecular and cellular biology 14.9: 5898-5909 (1994).
Tague et al., "Chemogenetic control of gene expression and cell signaling with antiviral drugs." Nature methods 15.7: 519-522 (2018).
Tague et al., "Controlled protein activities with viral proteases, antiviral peptides, and antiviral drugs." bioRxiv (available on the world wide web at https://doi.org/10.1101/2023.02.27.530290; Feb. 27, 2023).
Wang et al., "Discovery of A-1331852, a first-in-class, potent, and orally-bioavailable BCL-XL inhibitor." ACS medicinal chemistry letters 11.10: 1829-1836 (2020).
Wood et al., "Defining the Role of Arginine 96 in Green Fluorescent Protein Fluorophore Biosynthesis." Biochemistry 44, 16211-16220 (2005).
Zakeri et al., Peptide tag forming a rapid covalent bond to a protein, through engineering a bacterial adhesin. Proc National Acad Sci 109, E690-E697 (2012).
Zhang et al., "Optogenetic control with a photocleavable protein, PhoCl." Nature Methods 14.4.
Hajji et al. "ADAR2 enzymes: efficient site-specific RNA editors with gene therapy aspirations." RNA 28.10: 1281-1297 (Jul. 21, 2022).

* cited by examiner

| CMV | MCP | Linker | ADAR2-DD (316-468) | ALFA Var | ADAR2-DD (469-700) | ALFA Nanobody | TagBFP |
|-----|-----|--------|--------------------|----------|--------------------|---------------|--------|

| CMV | miRFP670 | ALFA |
|-----|----------|------|

ALFA :        SRLEEELRRRLTE

ALFA-PE :    GRLEEELRRRLSP

ALFA-78 :    GRLEQEIRARLSP

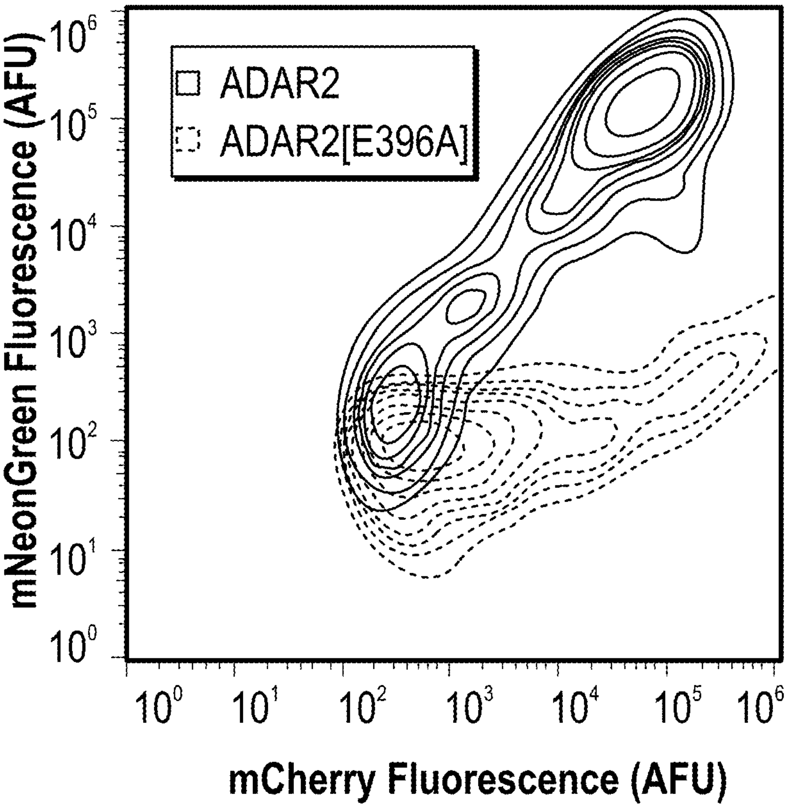
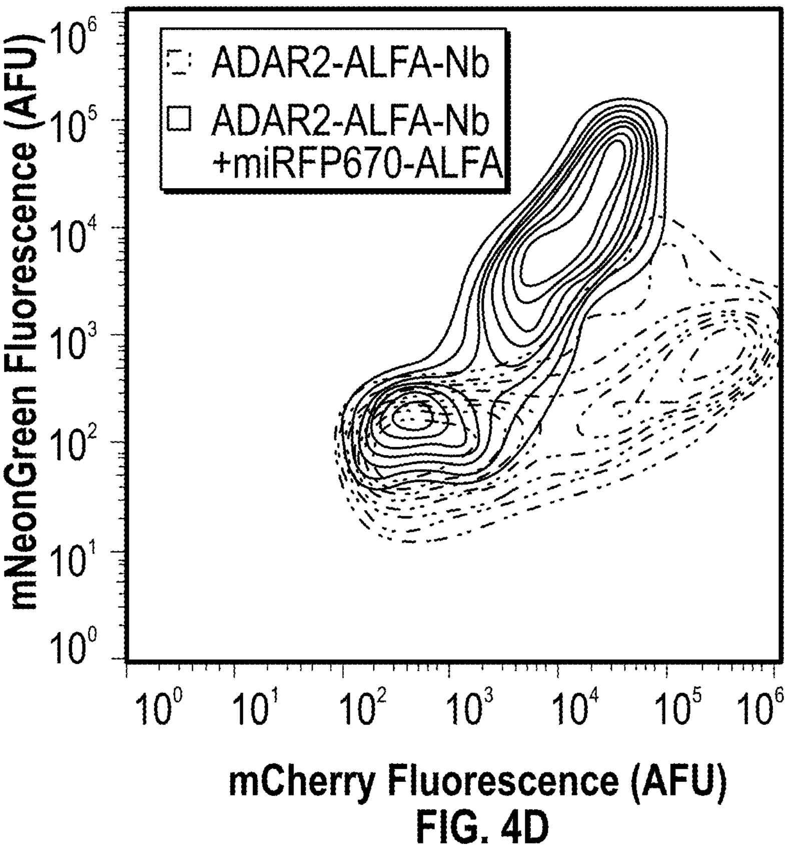
FIG. 4D

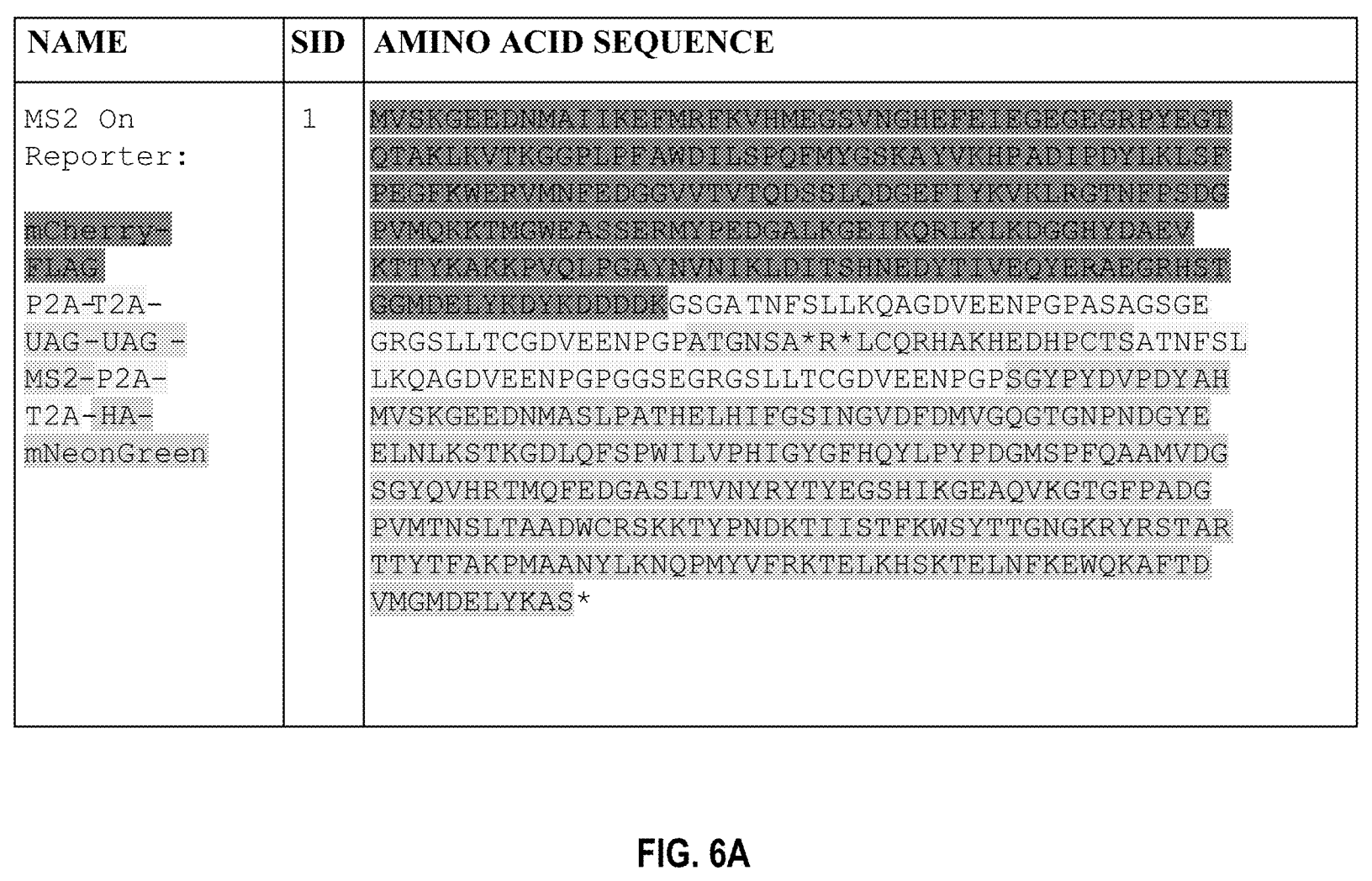

| NAME | SID | AMINO ACID SEQUENCE |
|---|---|---|
| MS2 On Reporter:<br><br>mCherry-FLAG P2A-T2A-UAG-UAG -MS2-P2A-T2A-HA-mNeonGreen | 1 | MVSKGEEDNMAIIKEFMRFKVHMEGSVNGHEFEIEGEGEGRPYEGT<br>QTAKLKVTKGGPLPFAWDILSPQFMYGSKAYVKHPADIPDYLKLSF<br>PEGFKWERVMNFEDGGVVTVTQDSSLQDGEFIYKVKLRGTNFPSDG<br>PVMQKKTMGWEASSERMYPEDGALKGEIKQRLKLKDGGHYDAEV<br>KTTYKAKKPVQLPGAYNVNIKLDITSHNEDYTIVEQYERAEGRHST<br>GGMDELYKDYKDDDDKGSGATNFSLLKQAGDVEENPGPASAGSGE<br>GRGSLLTCGDVEENPGPATGNSA*R*LCQRHAKHEDHPCTSATNFSL<br>LKQAGDVEENPGPGGSEGRGSLLTCGDVEENPGPSGYPYDVPDYAH<br>MVSKGEEDNMASLPATHELHIFGSINGVDFDMVGQGTGNPNDGYE<br>ELNLKSTKGDLQFSPWILVPHIGYGFHQYLPYPDGMSPFQAAMVDG<br>SGYQVHRTMQFEDGASLTVNYRYTYEGSHIKGEAQVKGTGFPADG<br>PVMTNSLTAADWCRSKKTYPNDKTIISTFKWSYTTGNGKRYRSTAR<br>TTYTFAKPMAANYLKNQPMYVFRKTELKHSKTELNFKEWQKAFTD<br>VMGMDELYKAS* |

FIG. 6A

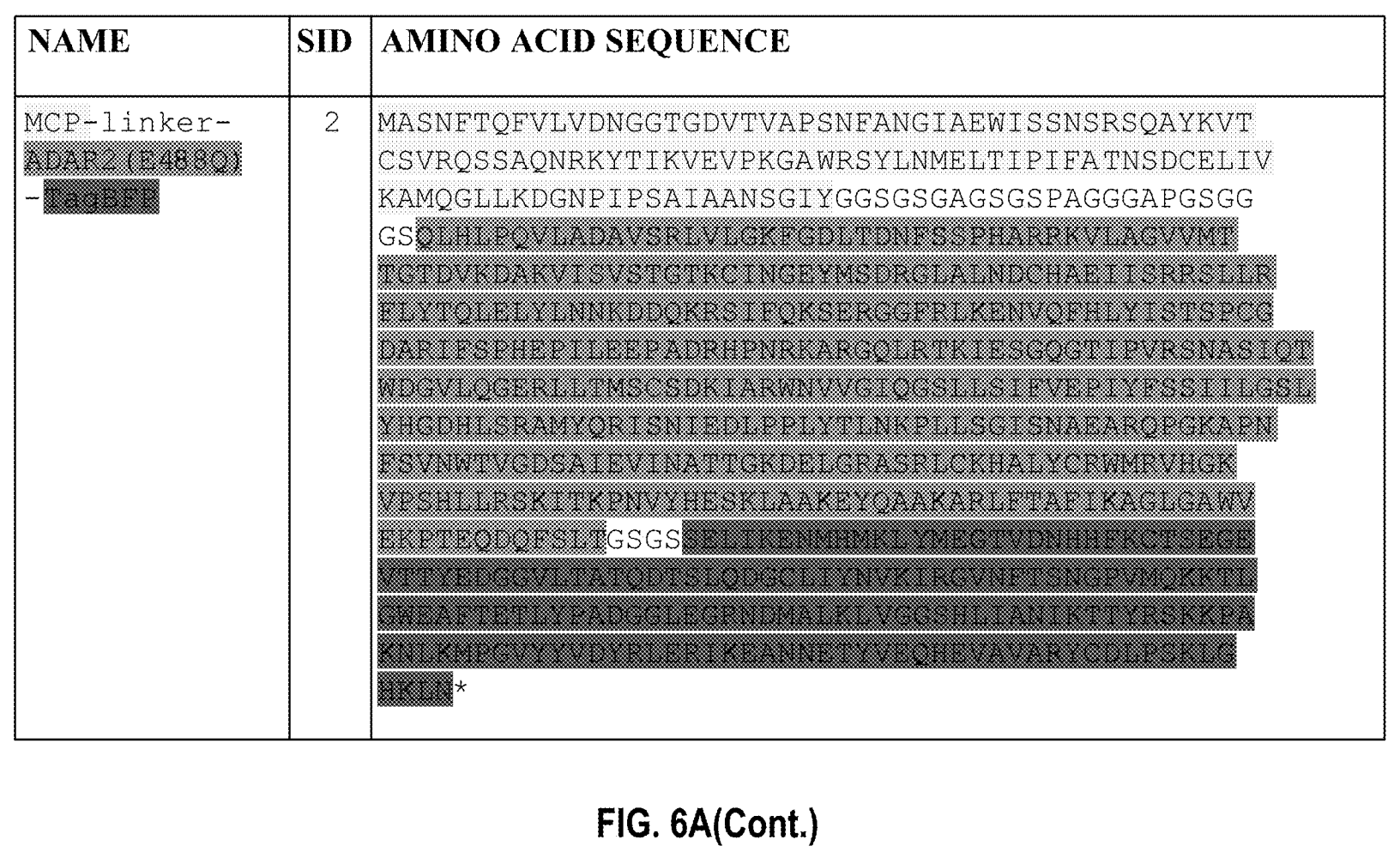

| NAME | SID | AMINO ACID SEQUENCE |
| --- | --- | --- |
| MCP-linker-ADAR2(E488Q)-TagBFP | 2 | MASNFTQFVLVDNGGTGDVTVAPSNFANGIAEWISSNSRSQAYKVT<br>CSVRQSSAQNRKYTIKVEVPKGAWRSYLNMELTIPIFATNSDCELIV<br>KAMQGLLKDGNPIPSAIAANSGIYGGSGSGAGSGSPAGGGAPGSGG<br>GSQLHLPQVLADAVSRLVLGKFGDLTDNFSSPHARRKVLAGVVMT<br>TGTDVKDAKVISVSTGTKCINGEYMSDRGLALNDCHAEIISRRSLLR<br>FLYTQLELYLNNKDDQKRSIFQKSERGGFRLKENVQFHLYISTSPCG<br>DARIFSPHEPILEEPADRHPNRKARGQLRTKIESGQGTIPVRSNASIQT<br>WDGVLQGERLLTMSCSDKIARWNVVGIQGSLLSIFVEPIYFSSIILGSL<br>YHGDHLSRAMYQRISNIEDLPPLYTLNKPLLSGISNAEARQPGKAPN<br>FSVNWTVGDSAIEVINATTGKDELGRASRLCKHALYCRWMRVHGK<br>VPSHLLRSKITKPNVYHESKLAAKEYQAAKARLFTAFIKAGLGAWV<br>EKPTEQDQFSLTGSGSSELIKENMHMKLYMEGTVDNHHFKCTSEGE<br>VTTYEDGGVLTATQDTSLQDGCLIYNVKIRGVNFTSNGPVMQKKTL<br>GWEAFTETLYPADGGLEGRNDMALKLVGGSHLIANIKTTYRSKKPA<br>KNLKMPGVYYVDYRLERIKEANNETYVEQHEVAVARYCDLPSKLG<br>HKLN* |

FIG. 6A(Cont.)

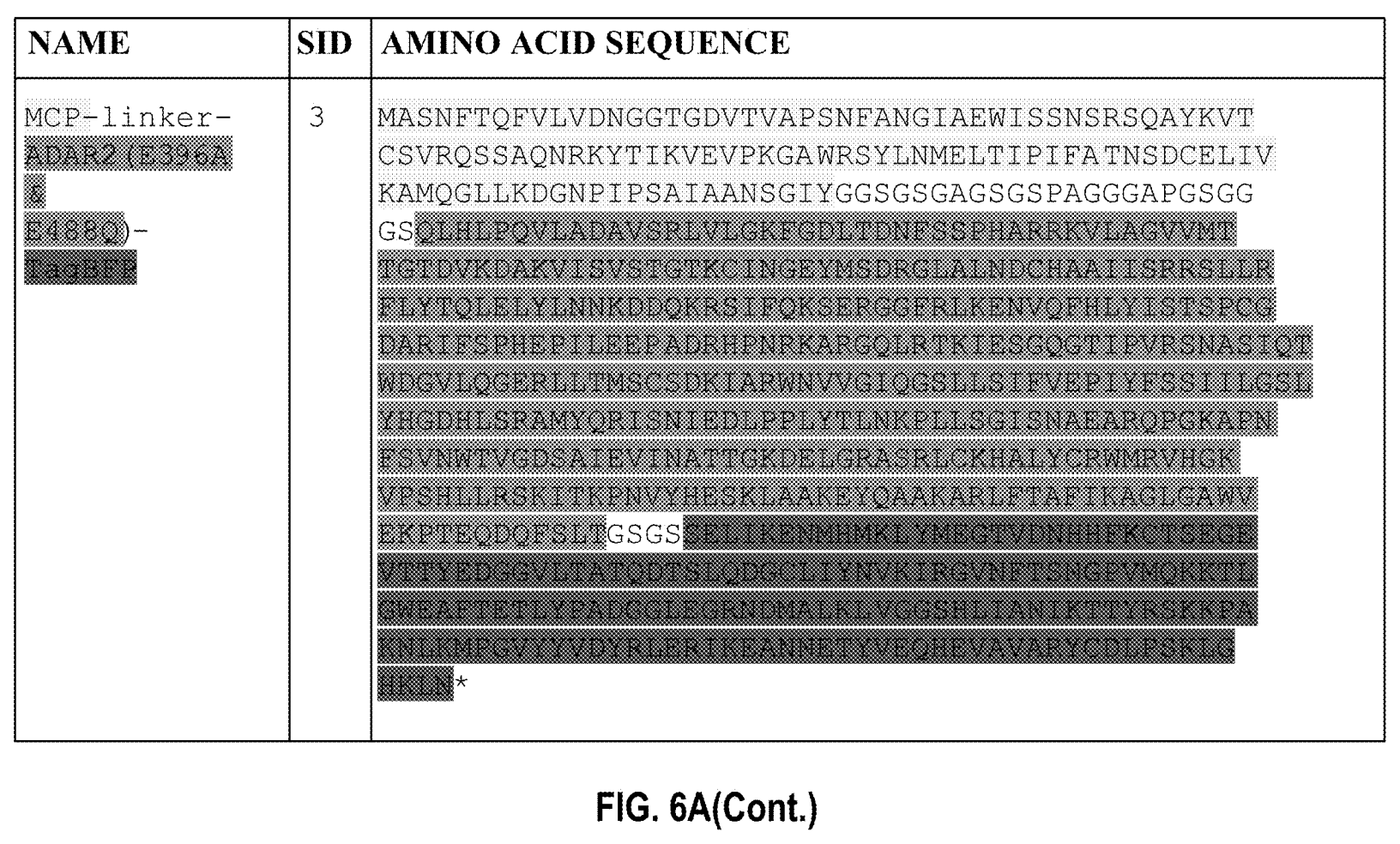

| NAME | SID | AMINO ACID SEQUENCE |
| --- | --- | --- |
| MCP-linker-ADAR2(E396A & E488Q)-TagBFP | 3 | MASNFTQFVLVDNGGTGDVTVAPSNFANGIAEWISSNSRSQAYKVT<br>CSVRQSSAQNRKYTIKVEVPKGAWRSYLNMELTIPIFATNSDCELIV<br>KAMQGLLKDGNPIPSAIAANSGIYGGSGSGAGSGSPAGGGAPGSGG<br>GSQLHLPQVLADAVSRLVLGKFGDLTDNFSSPHARRKVLAGVVMT<br>TGTDVKDAKVISVSTGTKCINGEYMSDRGLALNDCHAAIISRRSLLR<br>FLYTQLELYLNNKDDQKRSIFQKSERGGFRLKENVQFHLYISTSPCG<br>DARIFSPHEPILEEPADRHPNRKARGQLRTKIESGQGTIPVRSNASIQT<br>WDGVLQGERLLTMSCSDKIARWNVVGIQGSLLSIFVEPIYFSSIILGSL<br>YHGDHLSRAMYQRISNIEDLPPLYTLNKPLLSGISNAEARQPGKAPN<br>FSVNWTVGDSAIEVINATTGKDELGRASRLCKHALYCRWMRVHGK<br>VPSHLLRSKITKPNVYHESKLAAKEYQAAKARLFTAFIKAGLGAWV<br>EKPTEQDQFSLTGSGSSELIKENMHMKLYMEGTVDNHHFKCTSEGE<br>VTTYEDGGVLTATQDTSLQDGCLIYNVKIRGVNFTSNGPVMQKKTL<br>GWEAFTETLYPADGGLEGRNDMALKLVGGSHLIANIKTTYRSKKPA<br>KNLKMPGVYYVDYRLERIKEANNETYVEQHEVAVARYCDLPSKLG<br>HKLN* |

FIG. 6A(Cont.)

| NAME | SID | AMINO ACID SEQUENCE |
|---|---|---|
| mCherry-<br>FLAG -<br>UGG-UGG -<br>P2A-T2A-<br>HA -<br>mNeonGreen | 4 | MVSKGEEDNMAIIKEFMRFKVHMEGSVNGHEFEIEGEGEGRPYEGTQ<br>TAKLKVTKGGPLPFAWDILSPQFMYGSKAYVKHPADIPDYLKLSFPE<br>GFKWERVMNFEDGGVVTVTQDSSLQDGEFIYKVKLRGTNFPSDGPV<br>MQKKTMGWEASSERMYPEDGALKGEIKQRLKLKDGGHYDAEVKTT<br>YKAKKPVQLPGAYNVNIKLDITSHNEDYTIVEQYERAEGRHSTGGMD<br>ELYKDYKDDDDKNSAWRWLPCQRHATSATNFSLLKQAGDVEENPG<br>PGGSEGRGSLLTCGDVEENPGPSGYPYDVPDYAHMVSKGEEDNMAS<br>LPATHELHIFGSINGVDFDMVGQGTGNPNDGYEELNLKSTKGDLQFS<br>PWILVPHIGYGFHQYLPYPDGMSPFQAAMVDGSGYQVHRTMQFEDG<br>ASLTVNYRYTYEGSHIKGEAQVKGTGFPADGPVMTNSLTAADWCRS<br>KKTYPNDKTIISTFKWSYTTGNGKRYRSTARTTYTFAKPMAANYLKN<br>QPMYVFRKTELKHSKTELNFKEWQKAFTDVMGMDELYKAS* |

FIG. 6B

| NAME | SID | AMINO ACID SEQUENCE |
|---|---|---|
| mCherry-<br>FLAG -<br>UAG -UGG -<br>P2A-T2A-<br>HA -<br>mNeonGreen | 5 | MVSKGEEDNMAIIKEFMRFKVHMEGSVNGHEFEIEGEGEGRPYEGTQ<br>TAKLKVTKGGPLPFAWDILSPQFMYGSKAYVKHPADIPDYLKLSFPE<br>GFKWERVMNFEDGGVVTVTQDSSLQDGEFIYKVKLRGTNFPSDGPV<br>MQKKTMGWEASSERMYPEDGALKGEIKQRLKLKDGGHYDAEVKTT<br>YKAKKPVQLPGAYNVNIKLDITSHNEDYTIVEQYERAEGRHSTGGMD<br>ELYKDYKDDDDKNSA*RWLPCQRHATSATNFSLLKQAGDVEENPGP<br>GGSEGRGSLLTCGDVEENPGPSGYPYDVPDYAHMVSKGEEDNMASL<br>PATHELHIFGSINGVDFDMVGQGTGNPNDGYEELNLKSTKGDLQFSP<br>WILVPHIGYGFHQYLPYPDGMSPFQAAMVDGSGYQVHRTMQFEDGA<br>SLTVNYRYTYEGSHIKGEAQVKGTGFPADGPVMTNSLTAADWCRSK<br>KTYPNDKTIISTFKWSYTTGNGKRYRSTARTTYTFAKPMAANYLKNQ<br>PMYVFRKTELKHSKTELNFKEWQKAFTDVMGMDELYKAS* |

FIG. 6B(Cont.)

| NAME | SID | AMINO ACID SEQUENCE |
|---|---|---|
| mCherry-<br>FLAG -<br>UAG-UAG -<br>P2A-T2A-<br>HA -<br>mNeonGreen | 6 | MVSKGEEDNMAIIKEFMRFKVHMEGSVNGHEFEIEGEGEGRPYEGTQ<br>TAKLKVTKGGPLPFAWDILSPQFMYGSKAYVKHPADIPDYLKLSFPE<br>GFKWERVMNFEDGGVVTVTQDSSLQDGEFIYKVKLRGTNFPSDGPV<br>MQKKTMGWEASSERMYPEDGALKGEIKQRLKLKDGGHYDAEVKTT<br>YKAKKPVQLPGAYNVNIKLDITSHNEDYTIVEQYERAEGRHSTGGMD<br>ELYKDYKDDDDKNSA*R*LPCQRHATSATNFSLLKQAGDVEENPGP<br>GGSEGRGSLLTCGDVEENPGPSGYPYDVPDYAHMVSKGEEDNMASL<br>PATHELHIFGSINGVDFDMVGQGTGNPNDGYEELNLKSTKGDLQFSP<br>WILVPHIGYGFHQYLPYPDGMSPFQAAMVDGSGYQVHRTMQFEDGA<br>SLTVNYRYTYEGSHIKGEAQVKGTGFPADGPVMTNSLTAADWCRSK<br>KTYPNDKTIISTFKWSYTTGNGKRYRSTARTTYTFAKPMAANYLKNQ<br>PMYVFRKTELKHSKTELNFKEWQKAFTDVMGMDELYKAS* |

FIG. 6B(Cont.)

| NAME | SID | AMINO ACID SEQUENCE |
| --- | --- | --- |
| mCherry-FLAG-UAG-UGG-MS2-P2A-T2A-HA-mNeonGreen | 7 | MVSKGEEDNMAIIKEFMRFKVHMEGSVNGHEFEIEGEGEGRPYEGTQ<br>TAKLKVTKGGPLPFAWDILSPQFMYGSKAYVKHPADIPDYLKLSFPE<br>GFKWERVMNFEDGGVVTVTQDSSLQDGEFIYKVKLRGTNFPSDGPV<br>MQKKTMGWEASSERMYPEDGALKGEIKQRLKLKDGGHYDAEVKTT<br>YKAKKPVQLPGAYNVNIKLDITSHNEDYTIVEQYERAEGRHSTGGMD<br>ELYKDYKDDDDKNSAWR*LCQRHAKHEDHPCTSATNFSLLKQAGD<br>VEENPGPGGSEGRGSLLTCGDVEENPGPSGYPYDVPDYAHMVSKGE<br>EDNMASLPATHELHIFGSINGVDFDMVGQGTGNPNDGYEELNLKSTK<br>GDLQFSPWILVPHIGYGFHQYLPYPDGMSPFQAAMVDGSGYQVHRT<br>MQFEDGASLTVNYRYTYEGSHIKGEAQVKGTGFPADGPVMTNSLTA<br>ADWCRSKKTYPNDKTIISTFKWSYTTGNGKRYRSTARTTYTFAKPMA<br>ANYLKNQPMYVFRKTELKHSKTELNFKEWQKAFTDVMGMDELYKA<br>S* |

FIG. 6B(Cont.)

| NAME | SID | AMINO ACID SEQUENCE |
|---|---|---|
| mCherry-<br>FLAG-<br>UAG-<br>UAG-MS2-<br>P2A-T2A-<br>HA-<br>mNeonGreen | 8 | MVSKGEEDNMAIIKEFMRFKVHMEGSVNGHEFEIEGEGEGRPY<br>EGTQTAKLKVTKGGPLPFAWDILSPQFMYGSKAYVKHPADIPD<br>YLKLSFPEGFKWERVMNFEDGGVVTVTQDSSLQDGEFIYKVKL<br>RGTNFPSDGPVMQKKTMGWEASSERMYPEDGALKGEIKQRLK<br>LKDGGHYDAEVKTTYKAKKPVQLPGAYNVNIKLDITSHNEDYT<br>IVEQYERAEGRHSTGGMDELYKDYKDDDDKNSA*R*LCQRHA<br>KHEDHPCTSATNFSLLKQAGDVEENPGPGGSEGRGSLLTCGDV<br>EENPGPSGYPYDVPDYAHMVSKGEEDNMASLPATHELHIFGSIN<br>GVDFDMVGQGTGNPNDGYEELNLKSTKGDLQFSPWILVPHIGY<br>GFHQYLPYPDGMSPFQAAMVDGSGYQVHRTMQFEDGASLTVN<br>YRYTYEGSHIKGEAQVKGTGFPADGPVMTNSLTAADWCRSKK<br>TYPNDKTIISTFKWSYTTGNGKRYRSTARTTYTFAKPMAANYL<br>KNQPMYVFRKTELKHSKTELNFKEWQKAFTDVMGMDELYKAS<br>* |

FIG. 6C

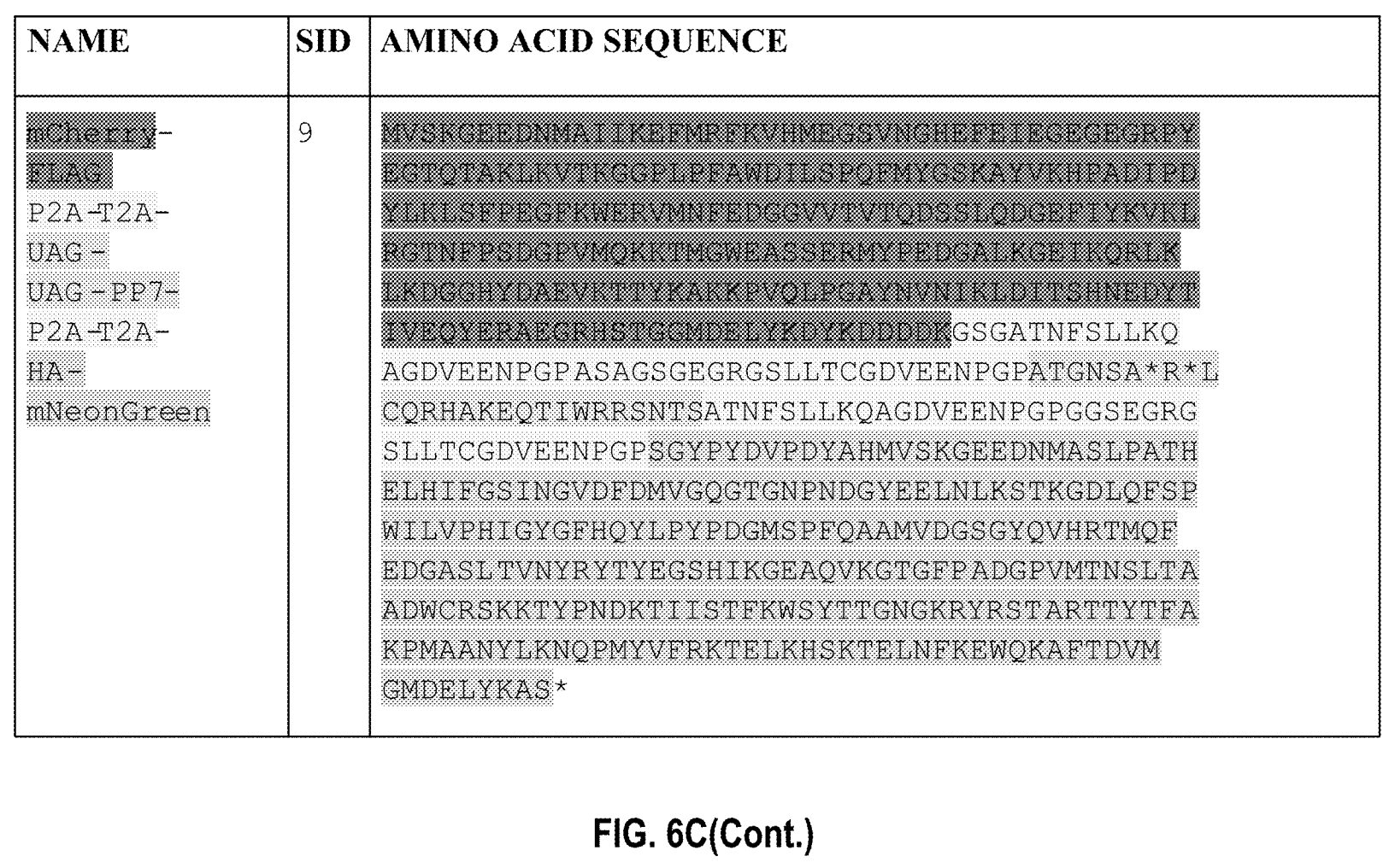

| NAME | SID | AMINO ACID SEQUENCE |
|---|---|---|
| mCherry-<br>FLAG<br>P2A-T2A-<br>UAG-<br>UAG-PP7-<br>P2A-T2A-<br>HA-<br>mNeonGreen | 9 | MVSKGEEDNMAIIKEFMRFKVHMEGSVNGHEFEIEGEGEGRPY<br>EGTQTAKLKVTKGGPLPFAWDILSPQFMYGSKAYVKHPADIPD<br>YLKLSFPEGFKWERVMNFEDGGVVTVTQDSSLQDGEFIYKVKL<br>RGTNFPSDGPVMQKKTMGWEASSERMYPEDGALKGEIKQRLK<br>LKDGGHYDAEVKTTYKAKKPVQLPGAYNVNIKLDITSHNEDYT<br>IVEQYERAEGRHSTGGMDELYKDYKDDDDKGSGATNFSLLKQ<br>AGDVEENPGPASAGSGEGRGSLLTCGDVEENPGPATGNSA*R*L<br>CQRHAKEQTIWRRSNTSATNFSLLKQAGDVEENPGPGGSEGRG<br>SLLTCGDVEENPGPSGYPYDVPDYAHMVSKGEEDNMASLPATH<br>ELHIFGSINGVDFDMVGQGTGNPNDGYEELNLKSTKGDLQFSP<br>WILVPHIGYGFHQYLPYPDGMSPFQAAMVDGSGYQVHRTMQF<br>EDGASLTVNYRYTYEGSHIKGEAQVKGTGFPADGPVMTNSLTA<br>ADWCRSKKTYPNDKTIISTFKWSYTTGNGKRYRSTARTTYTFA<br>KPMAANYLKNQPMYVFRKTELKHSKTELNFKEWQKAFTDVM<br>GMDELYKAS* |

FIG. 6C(Cont.)

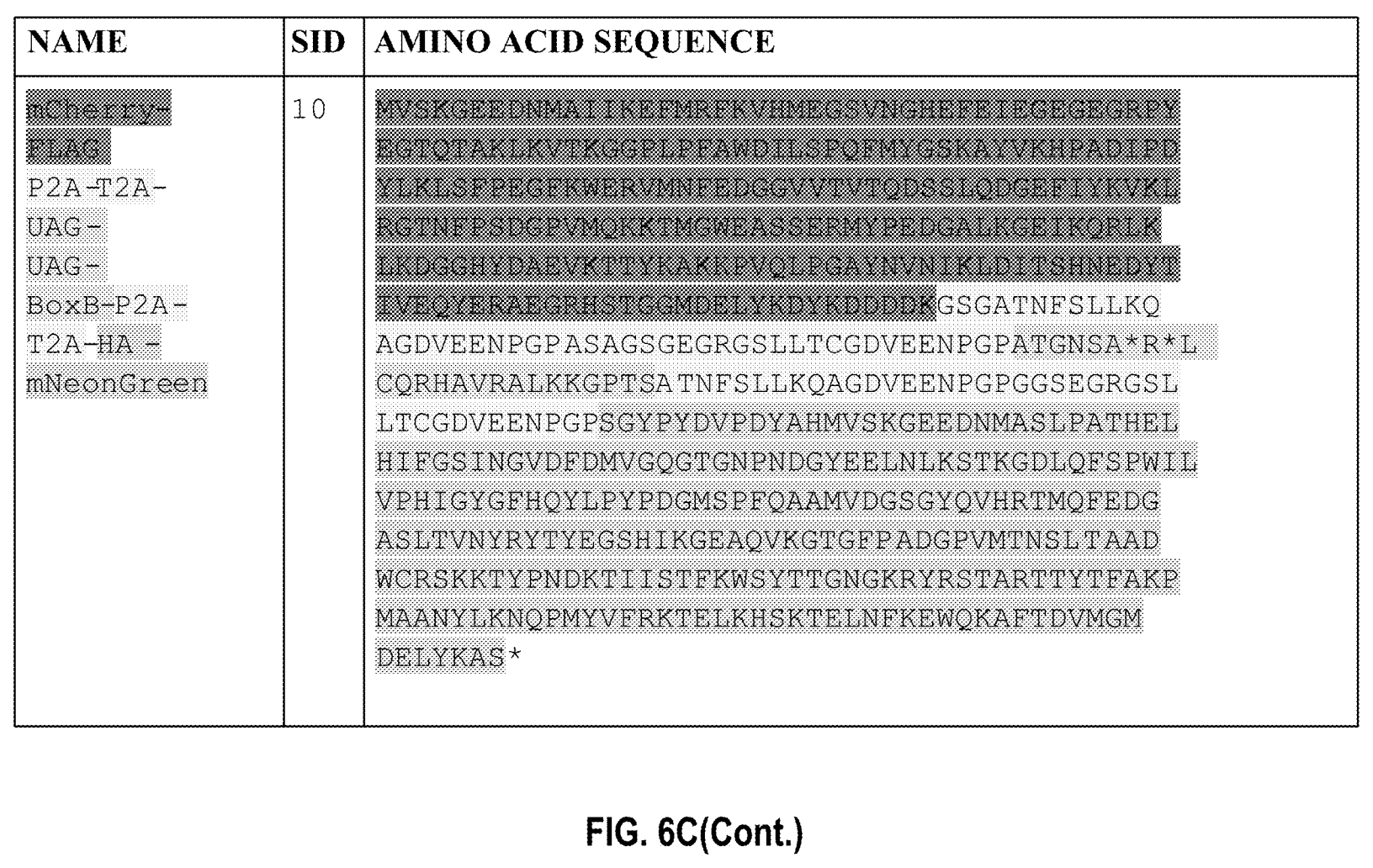

| NAME | SID | AMINO ACID SEQUENCE |
|---|---|---|
| mCherry-<br>FLAG<br>P2A-T2A-<br>UAG-<br>UAG-<br>BoxB-P2A-<br>T2A-HA -<br>mNeonGreen | 10 | MVSKGEEDNMAIIKEFMRFKVHMEGSVNGHEFEIEGEGEGRPY<br>EGTQTAKLKVTKGGPLPFAWDILSPQFMYGSKAYVKHPADIPD<br>YLKLSFPEGFKWERVMNFEDGGVVTVTQDSSLQDGEFIYKVKL<br>RGTNFPSDGPVMQKKTMGWEASSERMYPEDGALKGEIKQRLK<br>LKDGGHYDAEVKTTYKAKKPVQLPGAYNVNIKLDITSHNEDYT<br>IVEQYERAEGRHSTGGMDELYKDYKDDDDKGSGATNFSLLKQ<br>AGDVEENPGPASAGSGEGRGSLLTCGDVEENPGPATGNSA*R*L<br>CQRHAVRALKKGPTSATNFSLLKQAGDVEENPGPGGSEGRGSL<br>LTCGDVEENPGPSGYPYDVPDYAHMVSKGEEDNMASLPATHEL<br>HIFGSINGVDFDMVGQGTGNPNDGYEELNLKSTKGDLQFSPWIL<br>VPHIGYGFHQYLPYPDGMSPFQAAMVDGSGYQVHRTMQFEDG<br>ASLTVNYRYTYEGSHIKGEAQVKGTGFPADGPVMTNSLTAAD<br>WCRSKKTYPNDKTIISTFKWSYTTGNGKRYRSTARTTYTFAKP<br>MAANYLKNQPMYVFRKTELKHSKTELNFKEWQKAFTDVMGM<br>DELYKAS* |

FIG. 6C(Cont.)

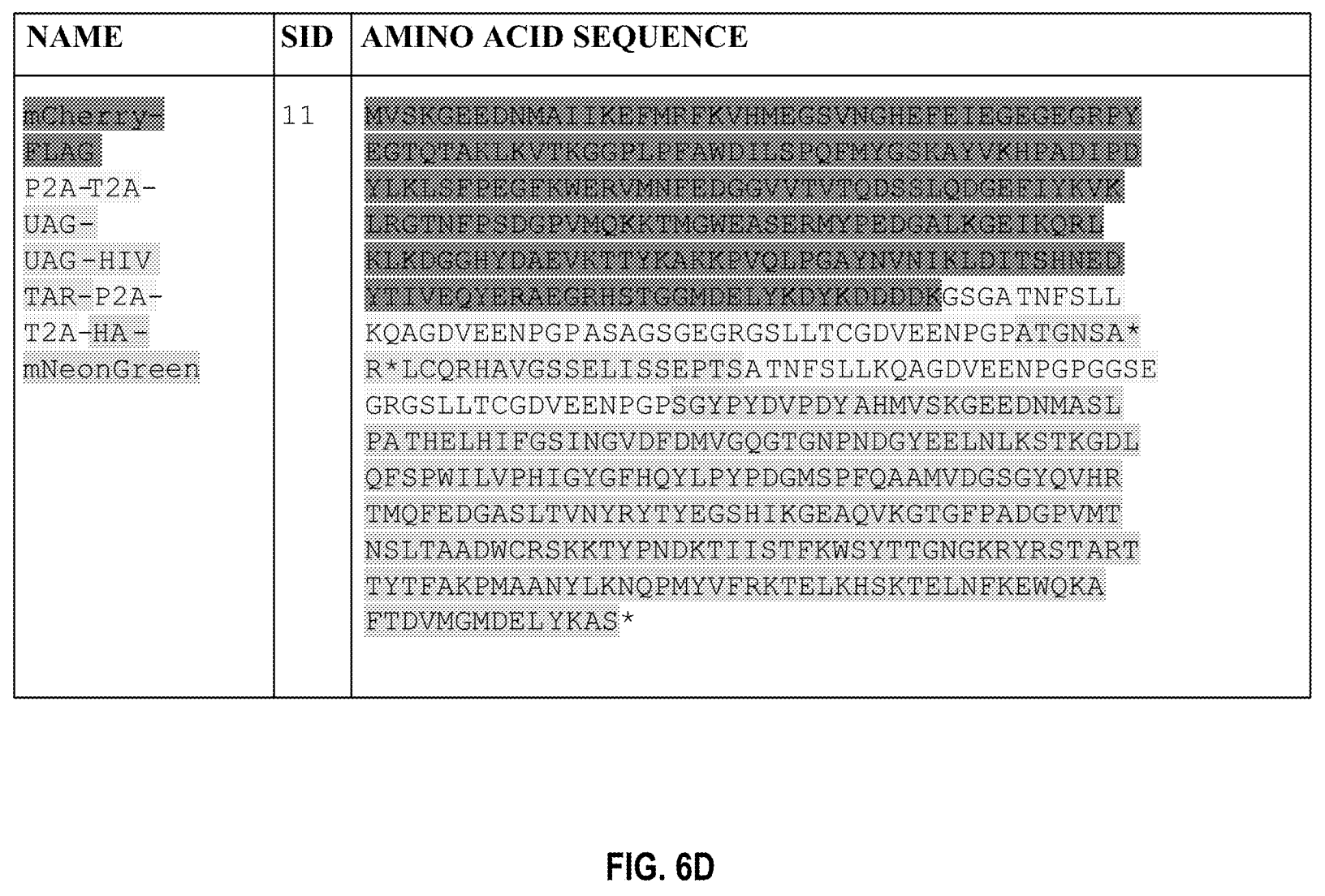

| NAME | SID | AMINO ACID SEQUENCE |
|---|---|---|
| mCherry-<br>FLAG<br>P2A-T2A-<br>UAG-<br>UAG-HIV<br>TAR-P2A-<br>T2A-HA-<br>mNeonGreen | 11 | MVSKGEEDNMAIIKEFMRFKVHMEGSVNGHEFEIEGEGEGRPY<br>EGTQTAKLKVTKGGPLPFAWDILSPQFMYGSKAYVKHPADIPD<br>YLKLSFPEGFKWERVMNFEDGGVVTVTQDSSLQDGEFIYKVK<br>LRGTNFPSDGPVMQKKTMGWEASERMYPEDGALKGEIKQRL<br>KLKDGGHYDAEVKTTYKAKKPVQLPGAYNVNIKLDITSHNED<br>YTIVEQYERAEGRHSTGGMDELYKDYKDDDDKGSGATNFSLL<br>KQAGDVEENPGPASAGSGEGRGSLLTCGDVEENPGPATGNSA*<br>R*LCQRHAVGSSELISSEPTSATNFSLLKQAGDVEENPGPGGSE<br>GRGSLLTCGDVEENPGPSGYPYDVPDYAHMVSKGEEDNMASL<br>PATHELHIFGSINGVDFDMVGQGTGNPNDGYEELNLKSTKGDL<br>QFSPWILVPHIGYGFHQYLPYPDGMSPFQAAMVDGSGYQVHR<br>TMQFEDGASLTVNYRYTYEGSHIKGEAQVKGTGFPADGPVMT<br>NSLTAADWCRSKKTYPNDKTIISTFKWSYTTGNGKRYRSTART<br>TYTFAKPMAANYLKNQPMYVFRKTELKHSKTELNFKEWQKA<br>FTDVMGMDELYKAS* |

FIG. 6D

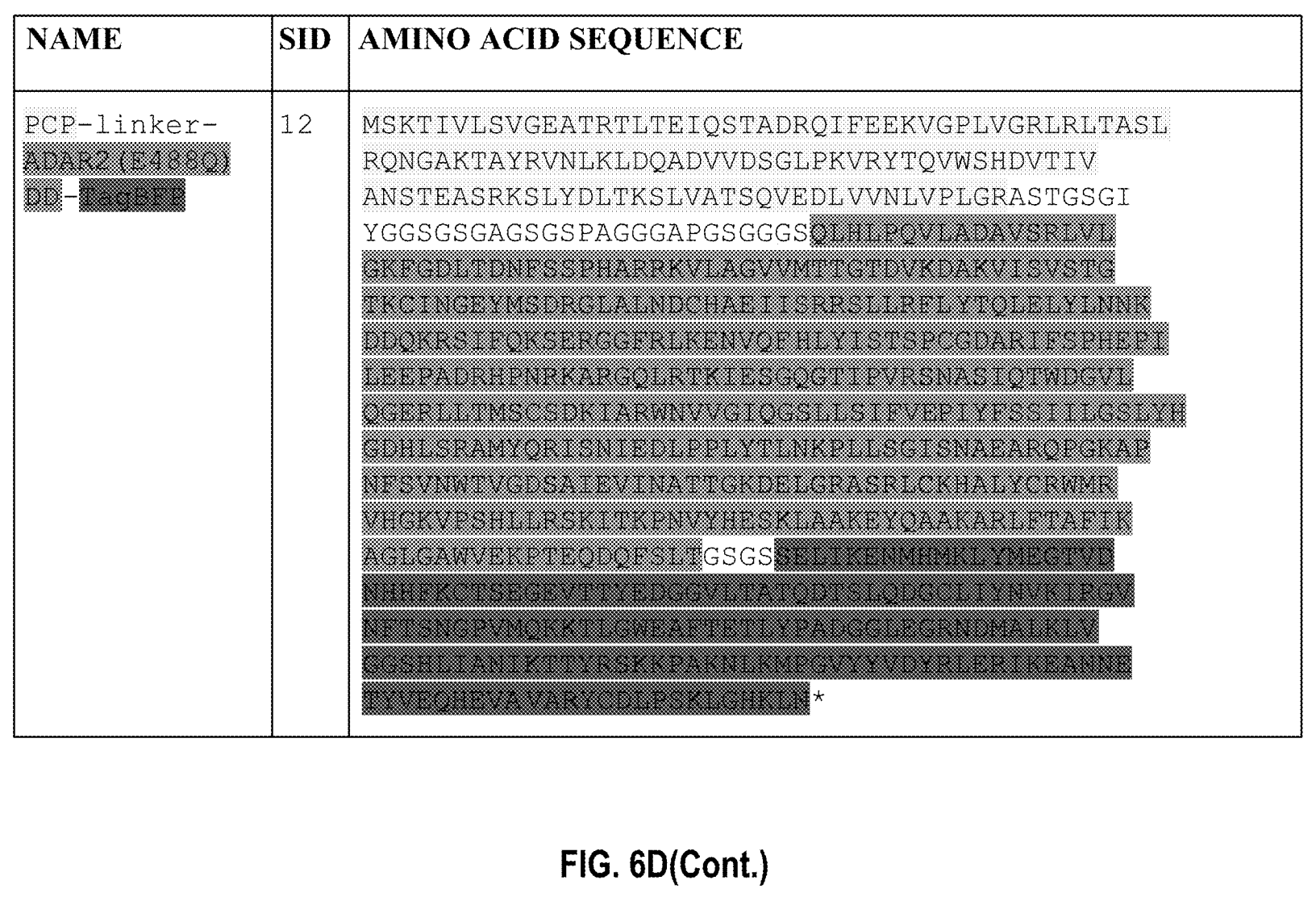

| NAME | SID | AMINO ACID SEQUENCE |
|---|---|---|
| PCP-linker-<br>ADAR2(E488Q)<br>DD-TagBFP | 12 | MSKTIVLSVGEATRTLTEIQSTADRQIFEEKVGPLVGRLRLTASL<br>RQNGAKTAYRVNLKLDQADVVDSGLPKVRYTQVWSHDVTIV<br>ANSTEASRKSLYDLTKSLVATSQVEDLVVNLVPLGRASTGSGI<br>YGGSGSGAGSGSPAGGGAPGSGGGSQLHLPQVLADAVSRLVL<br>GKFGDLTDNFSSPHARRKVLAGVVMTTGTDVKDAKVISVSTG<br>TKCINGEYMSDRGLALNDCHAEIISRRSLLRFLYTQLELYLNNK<br>DDQKRSIFQKSERGGFRLKENVQFHLYISTSPCGDARIFSPHEPI<br>LEEPADRHPNRKARGQLRTKIESGQGTIPVRSNASIQTWDGVL<br>QGERLLTMSCSDKIARWNVVGIQGSLLSIFVEPIYFSSIILGSLYH<br>GDHLSRAMYQRISNIEDLPPLYTLNKPLLSGISNAEARQPGKAP<br>NFSVNWTVGDSAIEVINATTGKDELGRASRLCKHALYCRWMR<br>VHGKVPSHLLRSKITKPNVYHESKLAAKEYQAAKARLFTAFIK<br>AGLGAWVEKPTEQDQFSLTGSGSSELIKENMHMKLYMEGTVD<br>NHHFKCTSEGEVTTYEDGGVLTATQDTSLQDGCLIYNVKIRGV<br>NFTSNGPVMQKKTLGWEAFTETLYPADGGLEGRNDMALKLV<br>GGSHLIANIKTTYRSKKPAKNLKMPGVYYVDYRLERIKEANNE<br>TYVEQHEVAVARYCDLPSKLGHKLN* |

FIG. 6D(Cont.)

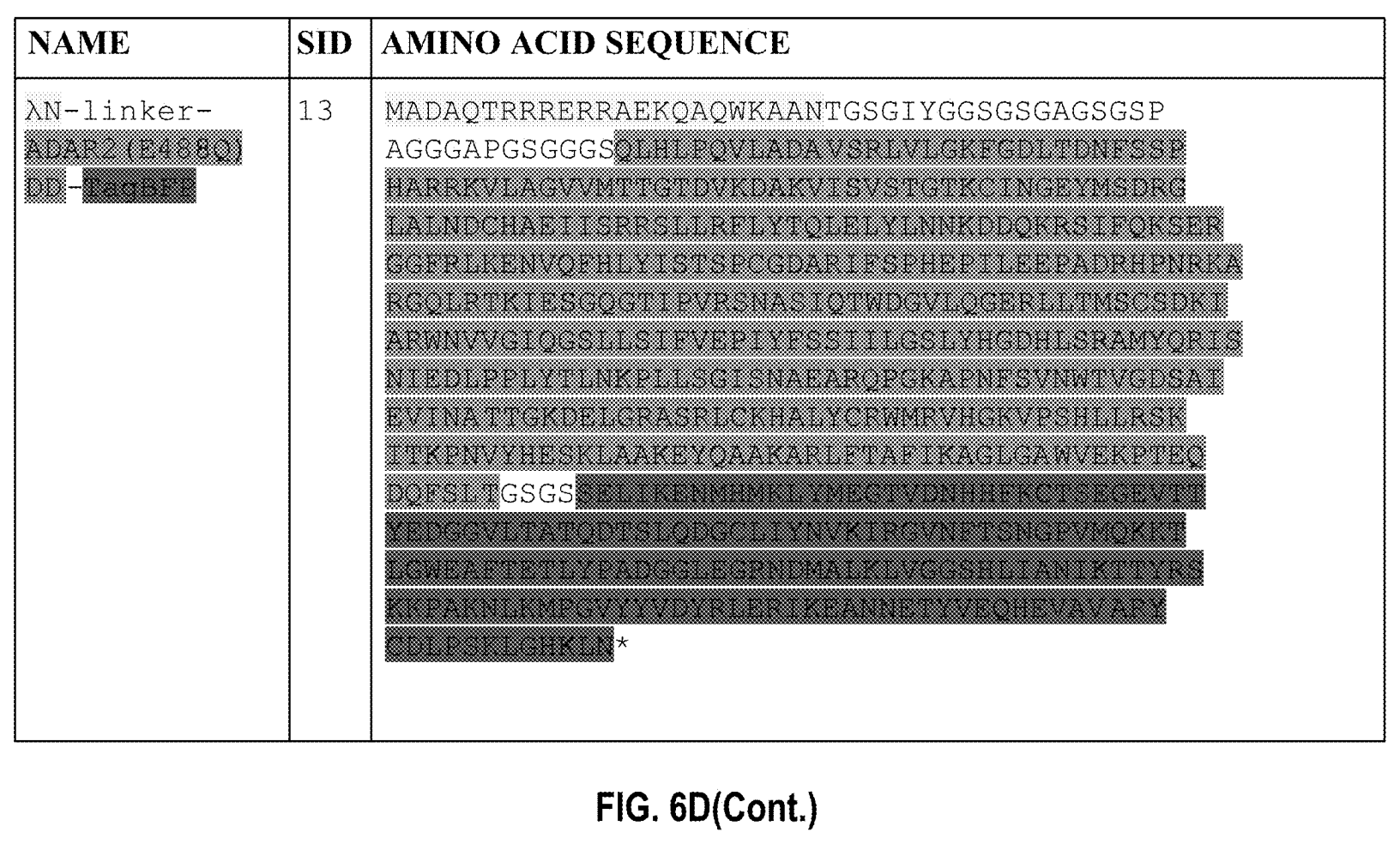

| NAME | SID | AMINO ACID SEQUENCE |
|---|---|---|
| λN-linker-ADAR2(E488Q) DD-TagBFP | 13 | MADAQTRRRERRAEKQAQWKAANTGSGIYGGSGSGAGSGSP<br>AGGGAPGSGGGSQLHLPQVLADAVSRLVLGKFGDLTDNFSSP<br>HARRKVLAGVVMTTGTDVKDAKVISVSTGTKCINGEYMSDRG<br>LALNDCHAEIISRRSLLRFLYTQLELYLNNKDDQKRSIFQKSER<br>GGFRLKENVQFHLYISTSPCGDARIFSPHEPILEEPADRHPNRKA<br>RGQLRTKIESGQGTIPVRSNASIQTWDGVLQGERLLTMSCSDKI<br>ARWNVVGIQGSLLSIFVEPIYFSSIILGSLYHGDHLSRAMYQRIS<br>NIEDLPPLYTLNKPLLSGISNAEARQPGKAPNFSVNWTVGDSAI<br>EVINATTGKDELGRASRLCKHALYCRWMRVHGKVPSHLLRSK<br>ITKPNVYHESKLAAKEYQAAKARLFTAFIKAGLGAWVEKPTEQ<br>DQFSLTGSGSSELIKENMHMKLYMEGTVDNHHFKCTSEGEVTI<br>YEDGGVLTATQDTSLQDGCLIYNVKIRGVNFTSNGPVMQKKT<br>LGWEAFTETLYPADGGLEGRNDMALKLVGGSHLIANIKTTYRS<br>KKPAKNLKMPGVYYVDYRLERIKEANNETYVEQHEVAVARY<br>CDLPSKLGHKLN* |

FIG. 6D(Cont.)

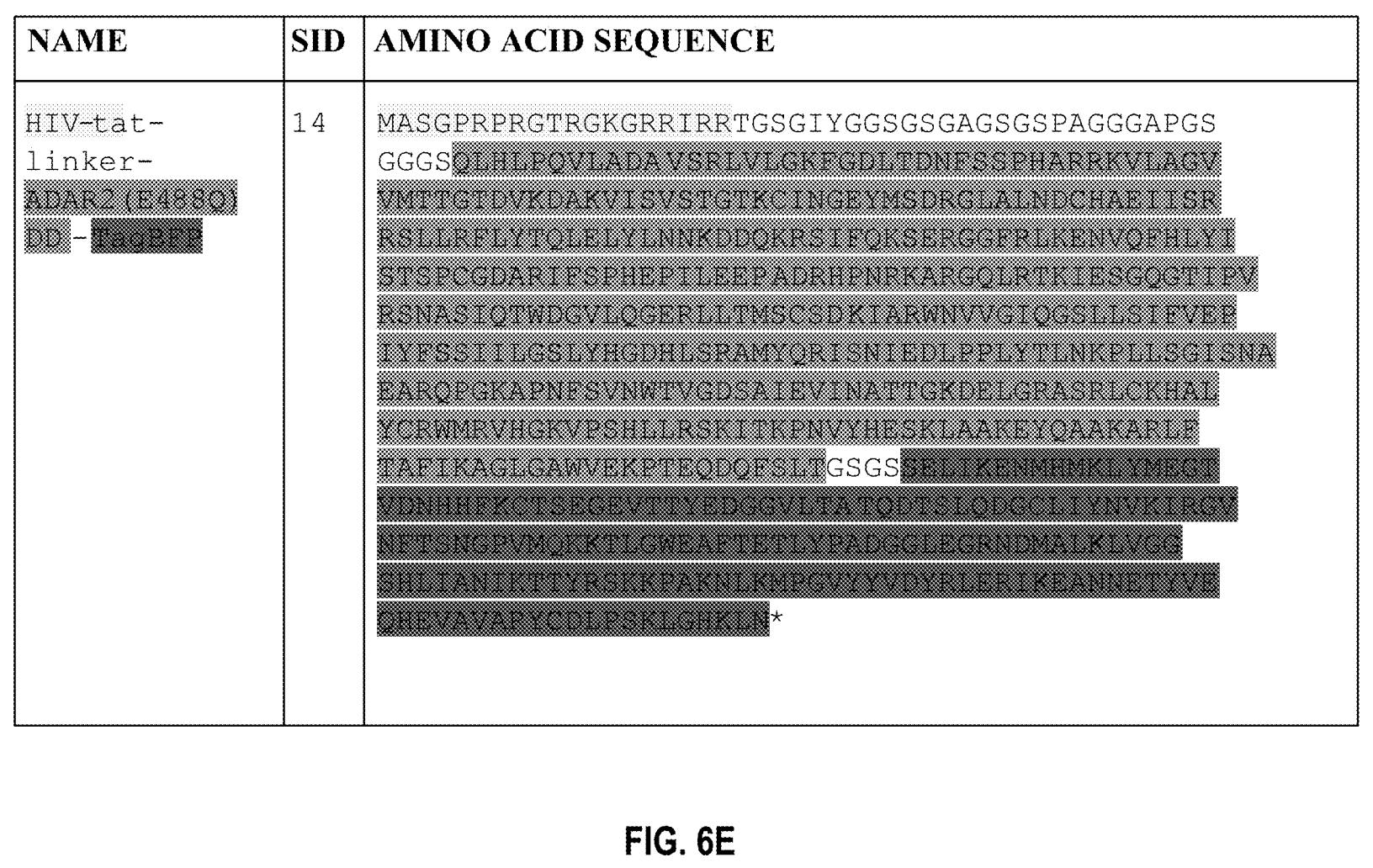

| NAME | SID | AMINO ACID SEQUENCE |
|---|---|---|
| HIV-tat-linker-ADAR2(E488Q) DD-TagBFP | 14 | MASGPRPRGTRGKGRRIRRTGSGIYGGSGSGAGSGSPAGGGAPGS GGGSQLHLPQVLADAVSRLVLGKFGDLTDNFSSPHARRKVLAGV VMTTGTDVKDAKVISVSTGTKCINGEYMSDRGLALNDCHAEIISR RSLLRFLYTQLELYLNNKDDQKRSIFQKSERGGFRLKENVQFHLYI STSPCGDARIFSPHEPILEEPADRHPNRKARGQLRTKIESGQGTIPV RSNASIQTWDGVLQGERLLTMSCSDKIARWNVVGIQGSLLSIFVEP IYFSSIILGSLYHGDHLSRAMYQRISNIEDLPPLYTLNKPLLSGISNA EARQPGKAPNFSVNWTVGDSAIEVINATTGKDELGRASRLCKHAL YCRWMRVHGKVPSHLLRSKITKPNVYHESKLAAKEYQAAKARLF TAFIKAGLGAWVEKPTEQDQFSLTGSGSSELIKENMHMKLYMEGT VDNHHFKCTSEGEVTTYEDGGVLTATQDTSLQDGCLIYNVKIRGV NFTSNGPVMQKKTLGWEAFTETLYPADGGLEGRNDMALKLVGG SHLIANIKTTYRSKKPAKNLKMPGVYYVDYRLERIKEANNETYVE QHEVAVARYCDLPSKLGHKLN* |

FIG. 6E

| NAME | SID | AMINO ACID SEQUENCE |
|---|---|---|
| dTomato | 15 | MVSKGEEVIKEFMRFKVRMEGSMNGHEFEIEGEGEGRPYEGTQT<br>AKLKVTKGGPLPFAWDILSPQFMYGSKAYVKHPADIPDYKKLSFP<br>EGFKWERVMNFEDGGLVTVTQDSSLQDGTLIYKVKMRGTNFPPD<br>GPVMQKKTMGWEASTERLYPRDGVLKGEIHQALKLKDGGHYLV<br>EFKTIYMAKKPVQLPGYYYVDTKLDITSHNEDYTIVEQYERSEGR<br>HHLFLYGMDELYK |
| EGFPd2-<br>UAG -UAG-<br>MS2-polyA | 16 | MVSKGEELFTGVVPILVELDGDVNGHKFSVSGEGEGDATYGKLTL<br>KFICTTGKLPVPWPTLVTTLTYGVQCFSRYPDHMKQHDFFKSAMP<br>EGYVQERTIFFKDDGNYKTRAEVKFEGDTLVNRIELKGIDFKEDG<br>NILGHKLEYNYNSHNVYIMADKQKNGIKVNFKIRHNIEDGSVQLA<br>DHYQQNTPIGDGPVLLPDNHYLSTQSALSKDPNEKRDHMVLLEFV<br>TAAGITLGMDELYKKLSHGFPPEVEEQDDGTLPMSCAQESGMDR<br>HPAACASARINV*R*LCQRHTKHEDHPCRPHSSGAGCLSEGGGWC<br>GQCPGSQIPLRSFSLCQKLWGHHEAPWASDFWLIKEIYF... |

FIG. 6E(Cont.)

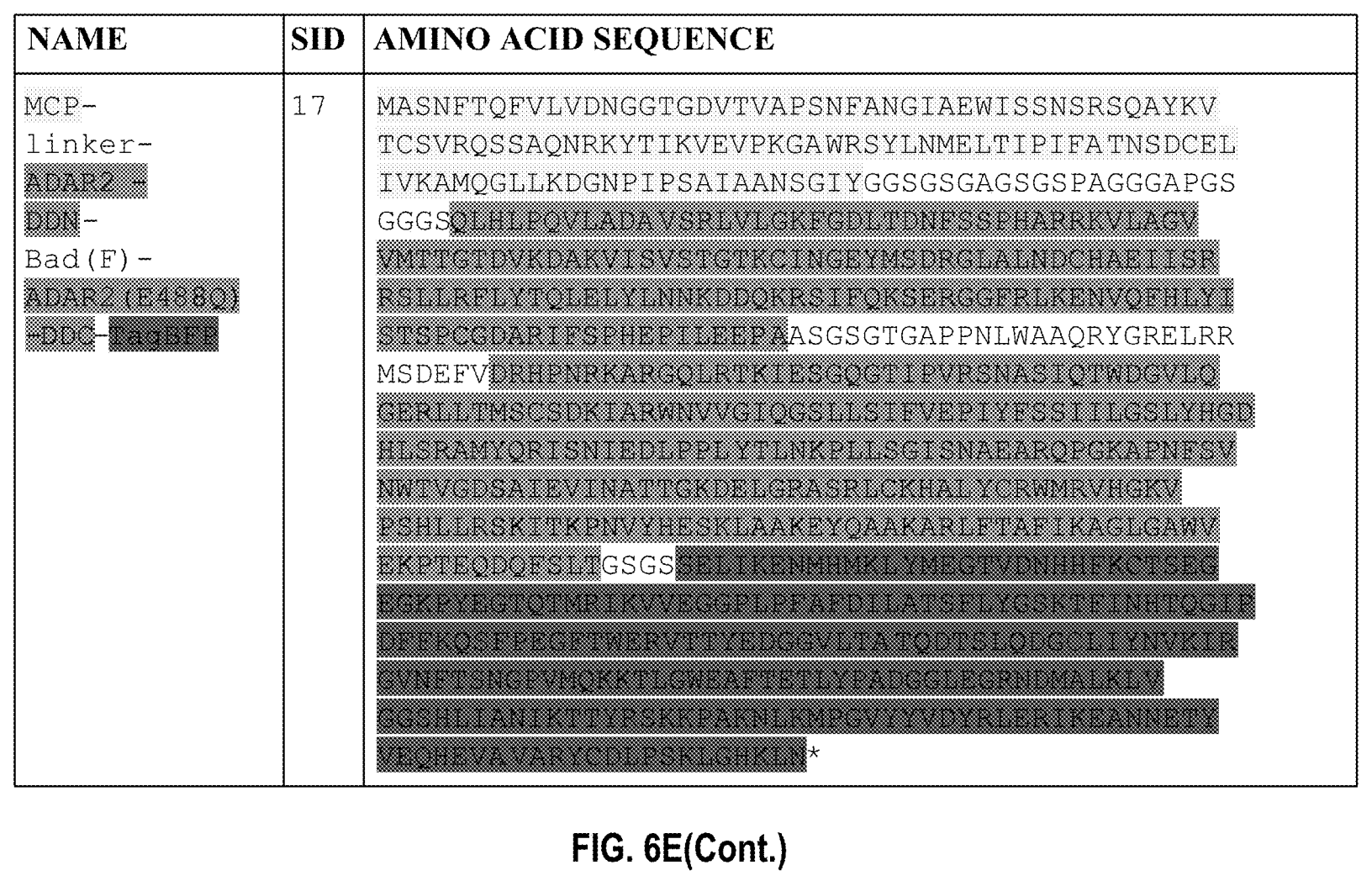

| NAME | SID | AMINO ACID SEQUENCE |
|---|---|---|
| MCP-<br>linker-<br>ADAR2 -<br>DDN-<br>Bad(F)-<br>ADAR2(E488Q)<br>-DDC-TagBFP | 17 | MASNFTQFVLVDNGGTGDVTVAPSNFANGIAEWISSNSRSQAYKV<br>TCSVRQSSAQNRKYTIKVEVPKGAWRSYLNMELTIPIFATNSDCEL<br>IVKAMQGLLKDGNPIPSAIAANSGIYGGSGSGAGSGSPAGGGAPGS<br>GGGSQLHLPQVLADAVSRLVLGKFGDLTDNFSSPHARRKVLAGV<br>VMTTGTDVKDAKVISVSTGTKCINGEYMSDRGLALNDCHAEIISR<br>RSLLRFLYTQLELYLNNKDDQKRSIFQKSERGGFRLKENVQFHLYI<br>STSPCGDARIFSPHEPILEEPAASGSGTGAPPNLWAAQRYGRELRR<br>MSDEFVDRHPNRKARGQLRTKIESGQGTIPVRSNASIQTWDGVLQ<br>GERLLTMSCSDKIARWNVVGIQGSLLSIFVEPIYFSSIILGSLYHGD<br>HLSRAMYQRISNIEDLPPLYTLNKPLLSGISNAEARQPGKAPNFSV<br>NWTVGDSAIEVINATTGKDELGRASRLCKHALYCRWMRVHGKV<br>PSHLLRSKITKPNVYHESKLAAKEYQAAKARLFTAFIKAGLGAWV<br>EKPTEQDQFSLTGSGSSELIKENMHMKLYMEGTVDNHHFKCTSEG<br>EGKPYEGTQTMRIKVVEGGPLPFAFDILATSFLYGSKTFINHTQGIP<br>DFFKQSFPEGFTWERVTTYEDGGVLTATQDTSLQDGCLIYNVKIR<br>GVNFTSNGPVMQKKTLGWEAFTETLYPADGGLEGRNDMALKLV<br>GGSHLIANIKTTYRSKKPAKNLKMPGVYYVDYRLERIKEANNETY<br>VEQHEVAVARYCDLPSKLGHKLN* |

FIG. 6E(Cont.)

| NAME | SID | AMINO ACID SEQUENCE |
|---|---|---|
| MCP-<br>linker-<br>ADAR2 -<br>DDN -<br>Bad(F)-<br>ADAR2(E488Q)-<br>DDC-Bcl-<br>xL-TagRFP | 18 | MASNFTQFVLVDNGGTGDVTVAPSNFANGIAEWISSNSRSQAY<br>KVTCSVRQSSAQNRKYTIKVEVPKGAWRSYLNMELTIPIFATNS<br>DCELIVKAMQGLLKDGNPIPSAIAANSGIYGGSGSGAGSGSPAG<br>GGAPGSGGGSQLHLPQVLADAVSRLVLGKFGDLTDNFSSPHAR<br>RKVLAGVVMTTGTDVKDAKVISVSTGTKCINGEYMSDRGLAL<br>NDCHAEIISRRSLLRFLYTQLELYLNNKDDQKRSIFQKSERGGFR<br>LKENVQFHLYISTSPCGDARIFSPHEPILEEPAASGSGTGAPPNLW<br>AAQRYGRELRRMSDEFVDRHPNRKARGQLRTKIESGQGTIPVR<br>SNASIQTWDGVLQGERLLTMSCSDKIARWNVVGIQGSLLSIFVE<br>PIYFSSIILGSLYHGDHLSRAMYQRISNIEDLPPLYTLNKPLLSGIS<br>NAEARQPGKAPNFSVNWTVGDSAIEVINATTGKDELGRASRLC<br>KHALYCRWMRVHGKVPSHLLRSKITKPNVYHESKLAAKEYQA<br>AKARLFTAFIKAGLGAWVEKPTEQDQFSLTGSAAGGSGGSAAA<br>SSNRELVVDFLSYKLSQKGYSWSQFSDVEENRTEAPEGTESEME<br>TPSAINGNPSWHLADSPAVNGATGHSSSLDAREVIPMAAVKQA<br>LREAGDEFELRYRRAFSDLTSQLHITPGTAYQSFEQVVNELFRD<br>GVNWGRIVAFFSFGGALCVESVDKEMQVLVSRIAAWMATYLN<br>DHLEPWIQENGGWDTFVELYGNNGSSELIKENMHMKLYMEGT<br>VDNHHFKCTSEGEGKPYEGTQTMRIKVVEGGPLPFAFDILATSF<br>LYGSKTFINHTQGIPDFFKQSFPEGFTWERVTTYEDGGVLTATQ<br>DTSLQDGCLIYNVKIRGVNFTSNGPVMQKKTLGWEAFTETLYP<br>ADGGLEGRNDMALKLVGGSHLIANIKTTYRSKKPAKNLKMPG<br>VYYVDYRLERIKEANNETYVEQHEVAVARYCDLPSKLGHKLN* |

FIG. 6F

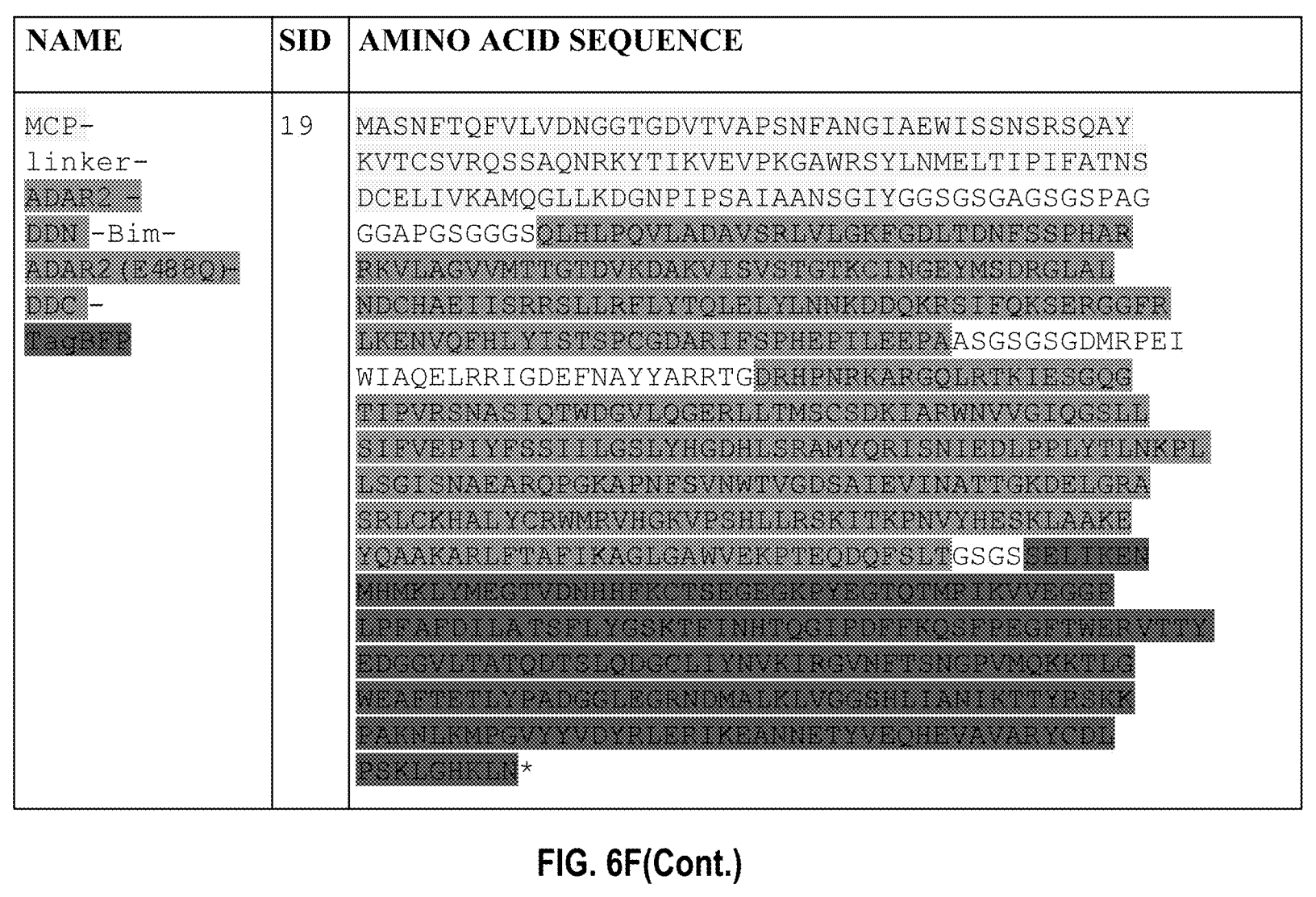

| NAME | SID | AMINO ACID SEQUENCE |
|---|---|---|
| MCP-<br>linker-<br>ADAR2 -<br>DDN -Bim-<br>ADAR2(E488Q)-<br>DDC -<br>TagBFP | 19 | MASNFTQFVLVDNGGTGDVTVAPSNFANGIAEWISSNSRSQAY<br>KVTCSVRQSSAQNRKYTIKVEVPKGAWRSYLNMELTIPIFATNS<br>DCELIVKAMQGLLKDGNPIPSAIAANSGIYGGSGSGAGSGSPAG<br>GGAPGSGGGSQLHLPQVLADAVSRLVLGKFGDLTDNFSSPHAR<br>RKVLAGVVMTTGTDVKDAKVISVSTGTKCINGEYMSDRGLAL<br>NDCHAEIISRRSLLRFLYTQLELYLNNKDDQKRSIFQKSERGGFR<br>LKENVQFHLYISTSPCGDARIFSPHEPILEEPAASGSGSGDMRPEI<br>WIAQELRRIGDEFNAYYARRTGDRHPNRKARGQLRTKIESGQG<br>TIPVRSNASIQTWDGVLQGERLLTMSCSDKIARWNVVGIQGSLL<br>SIFVEPIYFSSIILGSLYHGDHLSRAMYQRISNIEDLPPLYTLNKPL<br>LSGISNAEARQPGKAPNFSVNWTVGDSAIEVINATTGKDELGRA<br>SRLCKHALYCRWMRVHGKVPSHLLRSKITKPNVYHESKLAAKE<br>YQAAKARLFTAFIKAGLGAWVEKPTEQDQFSLTGSGSSELIKEN<br>MHMKLYMEGTVDNHHFKCTSEGEGKPYEGTQTMRIKVVEGGP<br>LPFAFDILATSFLYGSKTFINHTQGIPDFFKQSFPEGFTWERVTTY<br>EDGGVLTATQDTSLQDGCLIYNVKIRGVNFTSNGPVMQKKTLG<br>WEAFTETLYPADGGLEGRNDMALKLVGGSHLIANIKTTYRSKK<br>PAKNLKMPGVYYVDYRLERIKEANNETYVEQHEVAVARYCDL<br>PSKLGHKLN* |

FIG. 6F(Cont.)

| NAME | SID | AMINO ACID SEQUENCE |
| --- | --- | --- |
| MCP-<br>linker-<br>ADAR2-<br>DDN-Bim-<br>ADAR2(E488Q)-<br>DDC-Bcl-<br>xL-<br>TagRFP | 20 | MASNFTQFVLVDNGGTGDVTVAPSNFANGIAEWISSNSRSQ<br>AYKVTCSVRQSSAQNRKYTIKVEVPKGAWRSYLNMELTIPIF<br>ATNSDCELIVKAMQGLLKDGNPIPSAIAANSGIYGGSGSGAG<br>SGSPAGGGAPGSGGGSQLHLPQVLADAVSRLVLGKFGDLTD<br>NFSSPHARRKVLAGVVMTTGTDVKDAKVISVSTGTKCINGE<br>YMSDRGLALNDCHAEIISRRSLLRFLYTQLELYLNNKDDQKR<br>SIFQKSERGGFRLKENVQFHLYISTSPCGDARIFSPHEPILEEPA<br>ASGSGSGDMRPEIWIAQELRRIGDEFNAYYARRTGDRHPNRK<br>ARGQLRTKIESGQGTIPVRSNASIQTWDGVLQGERLLTMSCS<br>DKIARWNVVGIQGSLLSIFVEPIYFSSIILGSLYHGDHLSRAMY<br>QRISNIEDLPPLYTLNKPLLSGISNAEARQPGKAPNFSVNWTV<br>GDSAIEVINATTGKDELGRASRLCKHALYCRWMRVHGKVPS<br>HLLRSKITKPNVYHESKLAAKEYQAAKARLFTAFIKAGLGA<br>WVEKPTEQDQFSLTGSAAGGSGGSAAASSNRELVVDFLSYK<br>LSQKGYSWSQFSDVEENRTEAPEGTESEMETPSAINGNPSWH<br>LADSPAVNGATGHSSSLDAREVIPMAAVKQALREAGDEFEL<br>RYRRAFSDLTSQLHITPGTAYQSFEQVVNELFRDGVNWGRIV<br>AFFSFGGALCVESVDKEMQVLVSRIAAWMATYLNDHLEPWI<br>QENGGWDTFVELYGNNGSSELIKENMHMKLYMEGTVDNHH<br>FKCTSEGEGKPYEGTQTMRIKVVEGGPLPFAFDILATSFLYGS<br>KTFINHTQGIPDFFKQSFPEGFTWERVTTYEDGGVLTATQDTS<br>LQDGCLIYNVKIRGVNFTSNGPVMQKKTLGWEAFTETLYPA<br>DGGLEGRNDMALKLVGGSHLIANIKTTYRSKKPAKNLKMPG<br>VYYVDYRLERIKEANNETYVEQHEVAVARYCDLPSKLGHKL<br>N* |

FIG. 6G

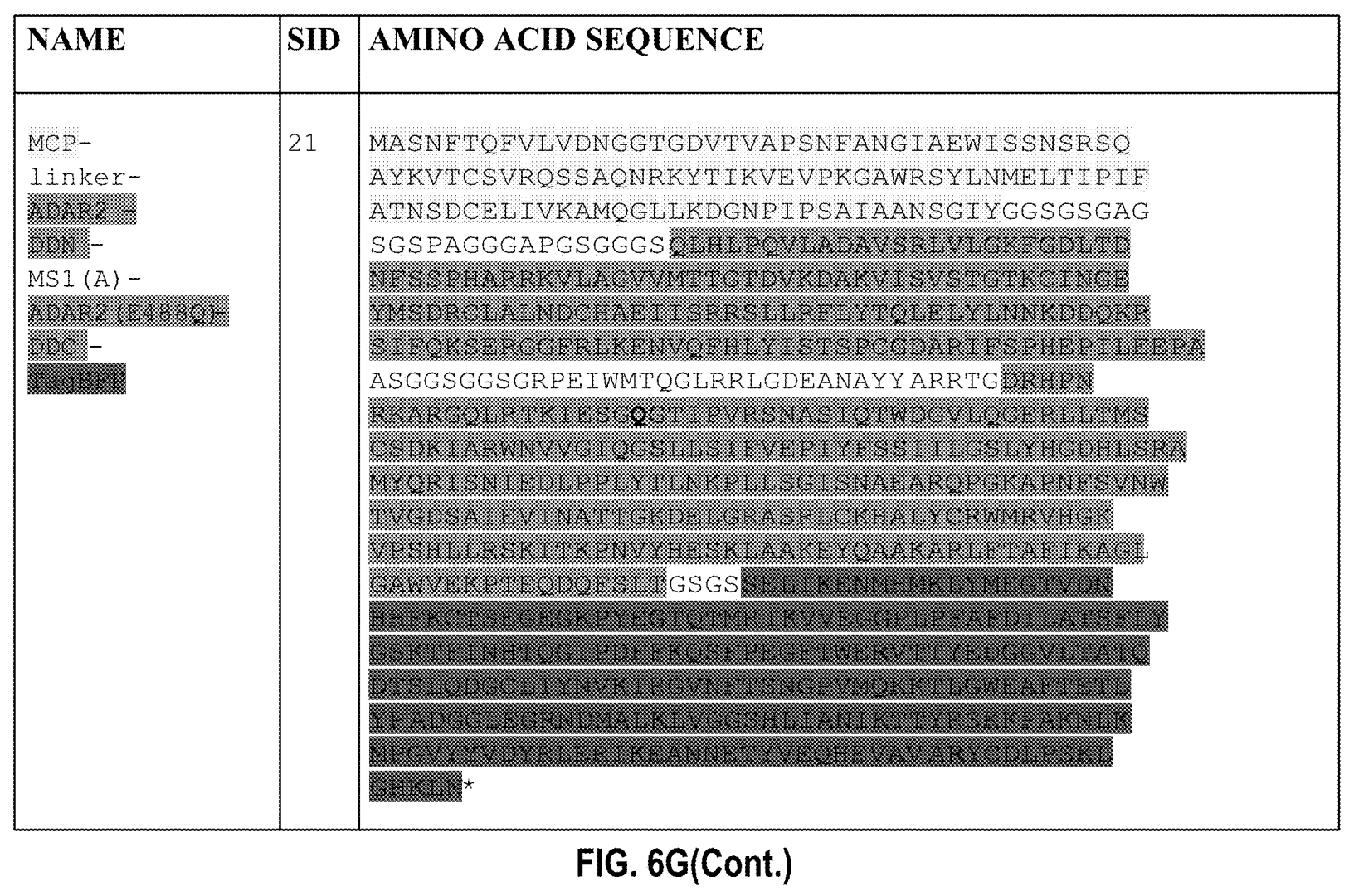

| NAME | SID | AMINO ACID SEQUENCE |
|---|---|---|
| MCP-<br>linker-<br>ADAR2 -<br>DDN -<br>MS1(A)-<br>ADAR2(E488Q)-<br>DDC -<br>TagBFP | 21 | MASNFTQFVLVDNGGTGDVTVAPSNFANGIAEWISSNSRSQ<br>AYKVTCSVRQSSAQNRKYTIKVEVPKGAWRSYLNMELTIPIF<br>ATNSDCELIVKAMQGLLKDGNPIPSAIAANSGIYGGSGSGAG<br>SGSPAGGGAPGSGGGSQLHLPQVLADAVSRLVLGKFGDLTD<br>NFSSPHARRKVLAGVVMTTGTDVKDAKVISVSTGTKCINGE<br>YMSDRGLALNDCHAEIISRRSLLRFLYTQLELYLNNKDDQKR<br>SIFQKSERGGFRLKENVQFHLYISTSPCGDARIFSPHEPILEEPA<br>ASGGSGGSGRPEIWMTQGLRRLGDEANAYYARRTGDRHPN<br>RKARGQLRTKIESGQGTIPVRSNASIQTWDGVLQGERLLTMS<br>CSDKIARWNVVGIQGSLLSIFVEPIYFSSIILGSLYHGDHLSRA<br>MYQRISNIEDLPPLYTLNKPLLSGISNAEARQPGKAPNFSVNW<br>TVGDSAIEVINATTGKDELGRASRLCKHALYCRWMRVHGK<br>VPSHLLRSKITKPNVYHESKLAAKEYQAAKARLFTAFIKAGL<br>GAWVEKPTEQDQFSLTGSGSSELIKENMHMKLYMEGTVDN<br>HHFKCTSEGEGKPYEGTQTMRIKVVEGGPLPFAFDILATSFLY<br>GSKTFINHTQGIPDFFKQSFPEGFTWERVTTYEDGGVLTATQ<br>DTSLQDGCLIYNVKIRGVNFTSNGPVMQKKTLGWEAFTETL<br>YPADGGLEGRNDMALKLVGGSHLIANIKTTYRSKKPAKNLK<br>MPGVYYVDYRLERIKEANNETYVEQHEVAVARYCDLPSKL<br>GHKLN* |

FIG. 6G(Cont.)

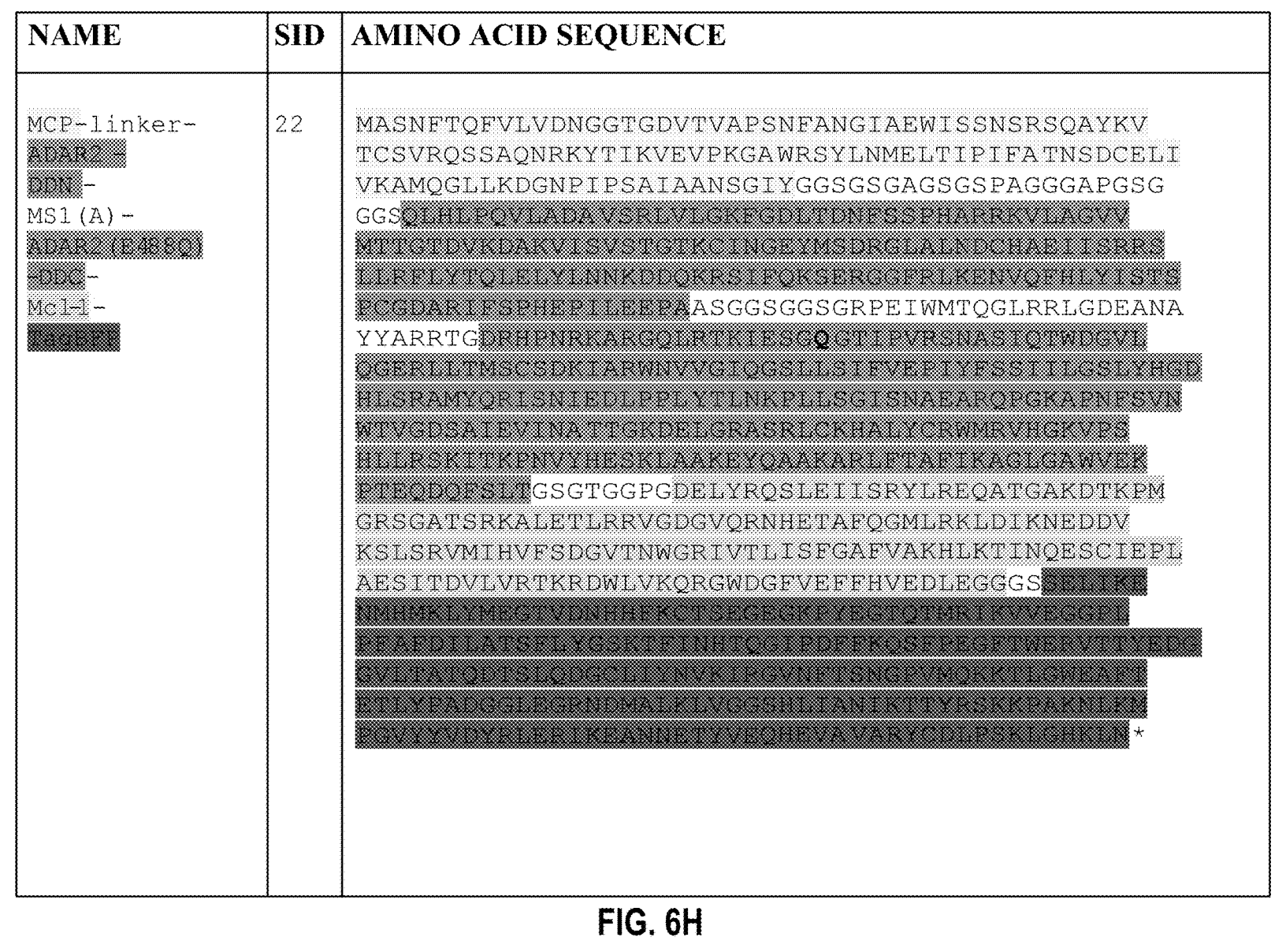

| NAME | SID | AMINO ACID SEQUENCE |
|---|---|---|
| MCP-linker-<br>ADAR2-<br>DDN-<br>MS1(A)-<br>ADAR2(E488Q)<br>-DDC-<br>Mcl-1-<br>tagBFP | 22 | MASNFTQFVLVDNGGTGDVTVAPSNFANGIAEWISSNSRSQAYKV<br>TCSVRQSSAQNRKYTIKVEVPKGAWRSYLNMELTIPIFATNSDCELI<br>VKAMQGLLKDGNPIPSAIAANSGIYGGSGSGAGSGSPAGGGAPGSG<br>GGSQLHLPQVLADAVSRLVLGKFGDLTDNFSSPHARRKVLAGVV<br>MTTGTDVKDAKVISVSTGTKCINGEYMSDRGLALNDCHAEIISRRS<br>LLRFLYTQLELYLNNKDDQKRSIFQKSERGGFRLKENVQFHLYISTS<br>PCGDARIFSPHEPILEEPAASGGSGGSGRPEIWMTQGLRRLGDEANA<br>YYARRTGDRHPNRKARGQLRTKIESGQGTIPVRSNASIQTWDGVL<br>QGERLLTMSCSDKIARWNVVGIQGSLLSIFVEPIYFSSIILGSLYHGD<br>HLSRAMYQRISNIEDLPPLYTLNKPLLSGISNAEARQPGKAPNFSVN<br>WTVGDSAIEVINATTGKDELGRASRLCKHALYCRWMRVHGKVPS<br>HLLRSKITKPNVYHESKLAAKEYQAAKARLFTAFIKAGLGAWVEK<br>PTEQDQFSLTGSGTGGPGDELYRQSLEIISRYLREQATGAKDTKPM<br>GRSGATSRKALETLRRVGDGVQRNHETAFQGMLRKLDIKNEDDV<br>KSLSRVMIHVFSDGVTNWGRIVTLISFGAFVAKHLKTINQESCIEPL<br>AESITDVLVRTKRDWLVKQRGWDGFVEFFHVEDLEGGGSSELIKE<br>NMHMKLYMEGTVDNHHFKCTSEGEGKPYEGTQTMRIKVVEGGPL<br>PFAFDILATSFLYGSKTFINHTQGIPDFFKQSFPEGFTWERVTTYEDG<br>GVLTATQDTSLQDGCLIYNVKIRGVNFTSNGPVMQKKTLGWEAFT<br>ETLYPADGGLEGRNDMALKLVGGSHLIANIKTTYRSKKPAKNLKM<br>PGVYYVDYRLERIKEANNETYVEQHEVAVARYCDLPSKLGHKLN* |

FIG. 6H

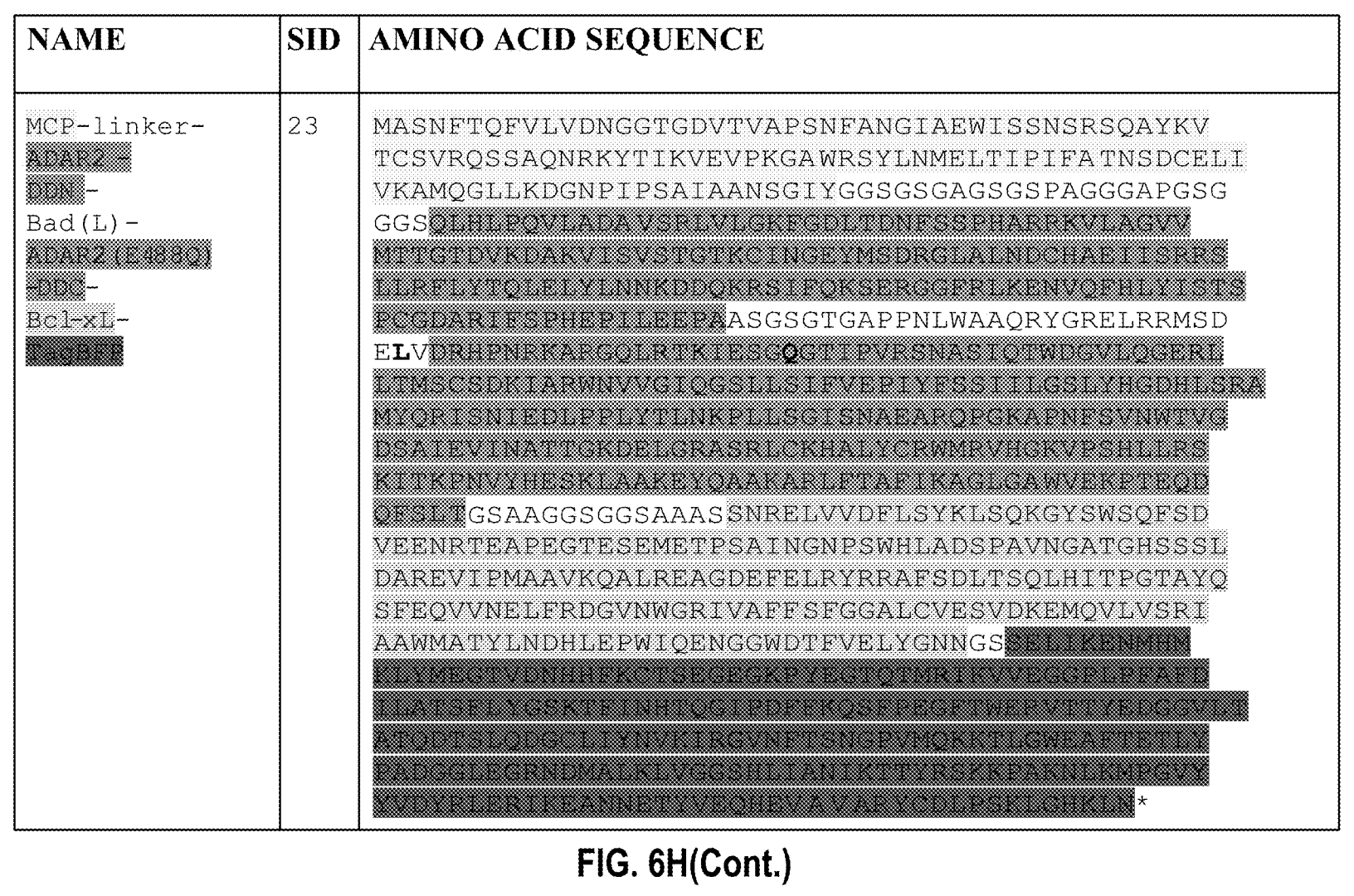

| NAME | SID | AMINO ACID SEQUENCE |
|---|---|---|
| MCP-linker-<br>ADAR2-<br>DDN-<br>Bad(L)-<br>ADAR2(E488Q)<br>-DDC-<br>Bcl-xL-<br>TagRFP | 23 | MASNFTQFVLVDNGGTGDVTVAPSNFANGIAEWISSNSRSQAYKV<br>TCSVRQSSAQNRKYTIKVEVPKGAWRSYLNMELTIPIFATNSDCELI<br>VKAMQGLLKDGNPIPSAIAANSGIYGGSGSGAGSGSPAGGGAPGSG<br>GGSQLHLPQVLADAVSRLVLGKFGDLTDNFSSPHARRKVLAGVV<br>MTTGTDVKDAKVISVSTGTKCINGEYMSDRGLALNDCHAEIISRRS<br>LLRFLYTQLELYLNNKDDQKRSIFQKSERGGFRLKENVQFHLYISTS<br>PCGDARIFSPHEPILEEPAASGSGTGAPPNLWAAQRYGRELRRMSD<br>E**L**VDRHPNRKARGQLRTKIESG**Q**GTIPVRSNASIQTWDGVLQGERL<br>LTMSCSDKIARWNVVGIQGSLLSIFVEPIYFSSIILGSLYHGDHLSRA<br>MYQRISNIEDLPPLYTLNKPLLSGISNAEARQPGKAPNFSVNWTVG<br>DSAIEVINATTGKDELGRASRLCKHALYCRWMRVHGKVPSHLLRS<br>KITKPNVYHESKLAAKEYQAAKARLFTAFIKAGLGAWVEKPTEQD<br>QFSLTGSAAGGSGGSAAASSNRELVVDFLSYKLSQKGYSWSQFSD<br>VEENRTEAPEGTESEMETPSAINGNPSWHLADSPAVNGATGHSSSL<br>DAREVIPMAAVKQALREAGDEFELRYRRAFSDLTSQLHITPGTAYQ<br>SFEQVVNELFRDGVNWGRIVAFFSFGGALCVESVDKEMQVLVSRI<br>AAWMATYLNDHLEPWIQENGGWDTFVELYGNNGSSELIKENMHM<br>KLYMEGTVDNHHFKCTSEGEGKPYEGTQTMRIKVVEGGPLPFAFD<br>ILATSFLYGSKTFINHTQGIPDFFKQSFPEGFTWERVTTYEDGGVLT<br>ATQDTSLQDGCLIYNVKIRGVNFTSNGPVMQKKTLGWEAFTETLY<br>PADGGLEGRNDMALKLVGGSHLIANIKTTYRSKKPAKNLKMPGVY<br>YVDYRLERIKEANNETYVEQHEVAVARYCDLPSKLGHKLN* |

FIG. 6H(Cont.)

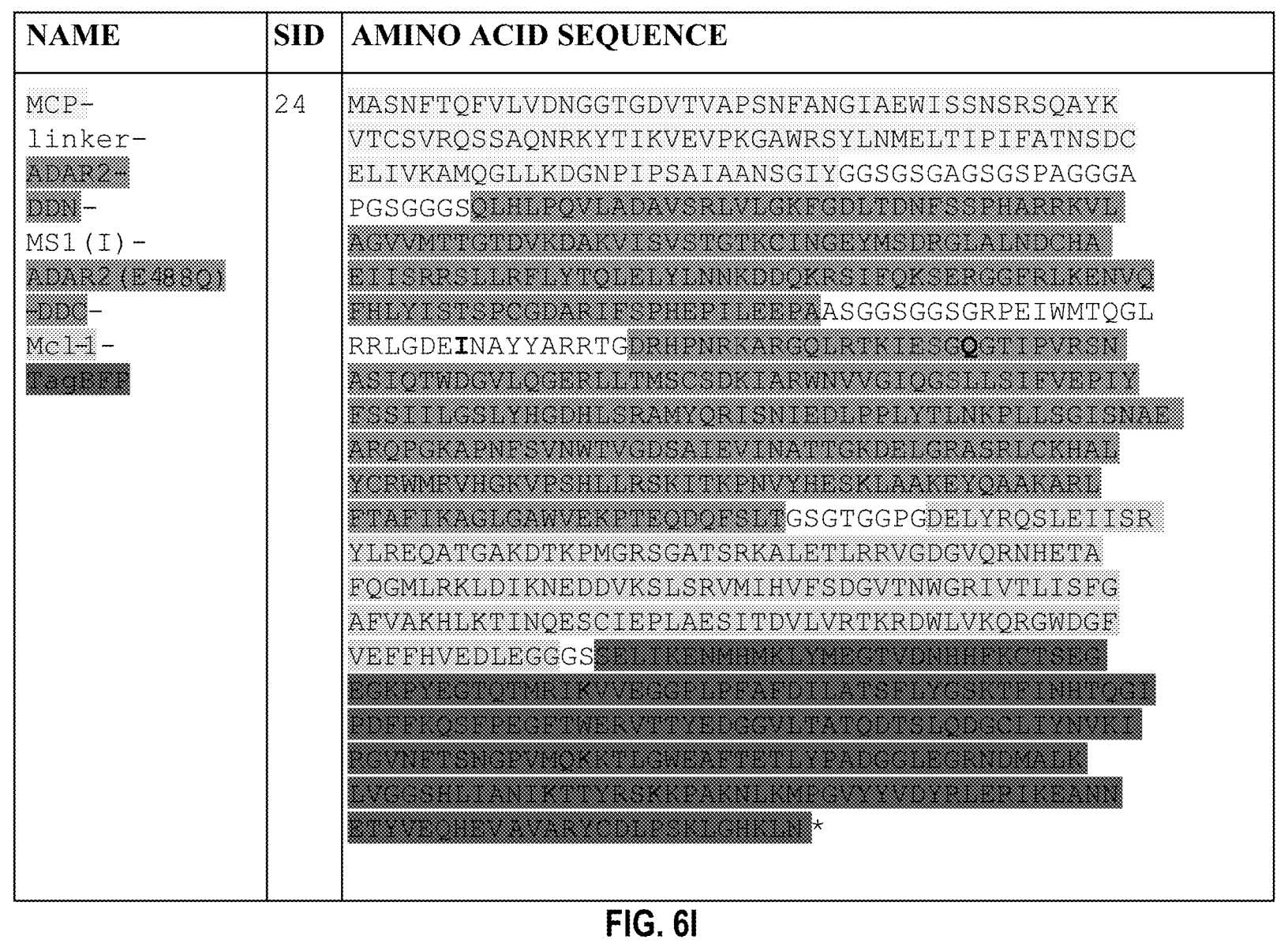

| NAME | SID | AMINO ACID SEQUENCE |
|---|---|---|
| MCP-<br>linker-<br>ADAR2-<br>DDN-<br>MS1(I)-<br>ADAR2(E488Q)<br>-DDC-<br>Mcl-1-<br>TagRFP | 24 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGA<br>PGSGGGSQLHLPQVLADAVSRLVLGKFGDLTDNFSSPHARRKVL<br>AGVVMTTGTDVKDAKVISVSTGTKCINGEYMSDRGLALNDCHA<br>EIISRRSLLRFLYTQLELYLNNKDDQKRSIFQKSERGGFRLKENVQ<br>FHLYISTSPCGDARIFSPHEPILEEPAASGGSGGSGRPEIWMTQGL<br>RRLGDE**I**NAYYARRTGDRHPNRKARGQLRTKIESG**Q**GTIPVRSN<br>ASIQTWDGVLQGERLLTMSCSDKIARWNVVGIQGSLLSIFVEPIY<br>FSSIILGSLYHGDHLSRAMYQRISNIEDLPPLYTLNKPLLSGISNAE<br>ARQPGKAPNFSVNWTVGDSAIEVINATTGKDELGRASRLCKHAL<br>YCRWMRVHGKVPSHLLRSKITKPNVYHESKLAAKEYQAAKARL<br>FTAFIKAGLGAWVEKPTEQDQFSLTGSGTGGPGDELYRQSLEIISR<br>YLREQATGAKDTKPMGRSGATSRKALETLRRVGDGVQRNHETA<br>FQGMLRKLDIKNEDDVKSLSRVMIHVFSDGVTNWGRIVTLISFG<br>AFVAKHLKTINQESCIEPLAESITDVLVRTKRDWLVKQRGWDGF<br>VEFFHVEDLEGGGSSELIKENMHMKLYMEGTVDNHHFKCTSEG<br>EGKPYEGTQTMRIKVVEGGPLPFAFDILATSFLYGSKTFINHTQGI<br>PDFFKQSFPEGFTWERVTTYEDGGVLTATQDTSLQDGCLIYNVKI<br>RGVNFTSNGPVMQKKTLGWEAFTETLYPADGGLEGRNDMALK<br>LVGGSHLIANIKTTYRSKKPAKNLKMPGVYYVDYRLERIKEANN<br>ETYVEQHEVAVARYCDLPSKLGHKLN* |

FIG. 6I

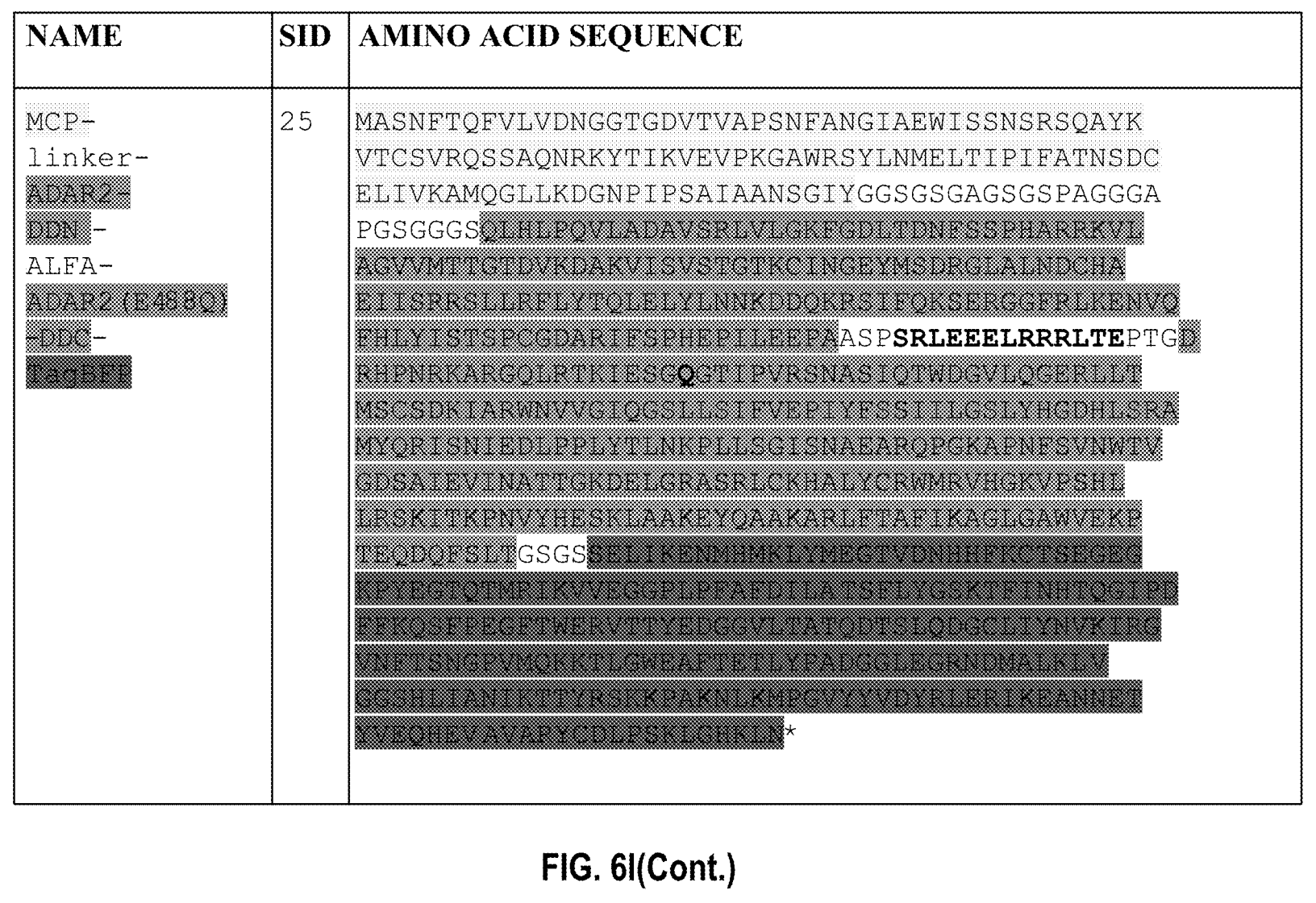

| NAME | SID | AMINO ACID SEQUENCE |
|---|---|---|
| MCP-<br>linker-<br>ADAR2-<br>DDN -<br>ALFA-<br>ADAR2(E488Q)<br>-DDC-<br>TagBFP | 25 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGA<br>PGSGGGSQLHLPQVLADAVSRLVLGKFGDLTDNFSSPHARRKVL<br>AGVVMTTGTDVKDAKVISVSTGTKCINGEYMSDRGLALNDCHA<br>EIISRRSLLRFLYTQLELYLNNKDDQKRSIFQKSERGGFRLKENVQ<br>FHLYISTSPCGDARIFSPHEPILEEPAASP**SRLEEELRRRLTE**PTGD<br>RHPNRKARGQLRTKIESG**Q**GTIPVRSNASIQTWDGVLQGERLLT<br>MSCSDKIARWNVVGIQGSLLSIFVEPIYFSSIILGSLYHGDHLSRA<br>MYQRISNIEDLPPLYTLNKPLLSGISNAEARQPGKAPNFSVNWTV<br>GDSAIEVINATTGKDELGRASRLCKHALYCRWMRVHGKVPSHL<br>LRSKITKPNVYHESKLAAKEYQAAKARLFTAFIKAGLGAWVEKP<br>TEQDQFSLTGSGSSELIKENMHMKLYMEGTVDNHHFKCTSEGEG<br>KPYEGTQTMRIKVVEGGPLPFAFDILATSFLYGSKTFINHTQGIPD<br>FFKQSFPEGFTWERVTTYEDGGVLTATQDTSLQDGCLIYNVKIRG<br>VNFTSNGPVMQKKTLGWEAFTETLYPADGGLEGRNDMALKLV<br>GGSHLIANIKTTYRSKKPAKNLKMPGVYYVDYRLERIKEANNET<br>YVEQHEVAVARYCDLPSKLGHKLN* |

FIG. 6I(Cont.)

<table>
<tr><th>NAME</th><th>SID</th><th>AMINO ACID SEQUENCE</th></tr>
<tr><td>MCP-<br>linker-<br>ADAR2-<br>DDN-<br>ALFA-<br>ADAR2(E488Q)<br>-<br>DDC-<br>NbALFA-<br>TagBFP</td><td>26</td><td>MASNFTQFVLVDNGGTGDVTVAPSNFANGIAEWISSNSRSQAY<br>KVTCSVRQSSAQNRKYTIKVEVPKGAWRSYLNMELTIPIFATNS<br>DCELIVKAMQGLLKDGNPIPSAIAANSGIYGGSGSGAGSGSPAG<br>GGAPGSGGGSQLHLPQVLADAVSRLVLGKFGDLTDNFSSPHAR<br>RKVLAGVVMTTGTDVKDAKVISVSTGTKCINGEYMSDRGLAL<br>NDCHAEIISRRSLLRFLYTQLELYLNNKDDQKRSIFQKSERGGFR<br>LKENVQFHLYISTSPCGDARIFSPHEPILEEPAASPSRLEEELRRR<br>LTEPTGDRHPNRKARGQLRTKIESGQGTIPVRSNASIQTWDGVL<br>QGERLLTMSCSDKIARWNVVGIQGSLLSIFVEPIYFSSIILGSLYH<br>GDHLSRAMYQRISNIEDLPPLYTLNKPLLSGISNAEARQPGKAPN<br>FSVNWTVGDSAIEVINATTGKDELGRASRLCKHALYCRWMRV<br>HGKVPSHLLRSKITKPNVYHESKLAAKEYQAAKARLFTAFIKAG<br>LGAWVEKPTEQDQFSLTGSGGTAEVQLQESGGGLVQPGGSLRL<br>SCTASGVTISALNAMAMGWYRQAPGERRVMVAAVSERGNAM<br>YRESVQGRFTVTRDFTNKMVSLQMDNLKPEDTAVYYCHVLED<br>RVDSFHDYWGQGTQVTVSSGAGSSELIKENMHMKLYMEGTVD<br>NHHFKCTSEGEGKPYEGTQTMRIKVVEGGPLPFAFDILATSFLY<br>GSKTFINHTQGIPDFFKQSFPEGFTWERVTTYEDGGVLTATQDTS<br>LQDGCLIYNVKIRGVNFTSNGPVMQKKTLGWEAFTETLYPADG<br>GLEGRNDMALKLVGGSHLIANIKTTYRSKKPAKNLKMPGVYY<br>VDYRLERIKEANNETYVEQHEVAVARYCDLPSKLGHKLN*</td></tr>
</table>

FIG. 6J

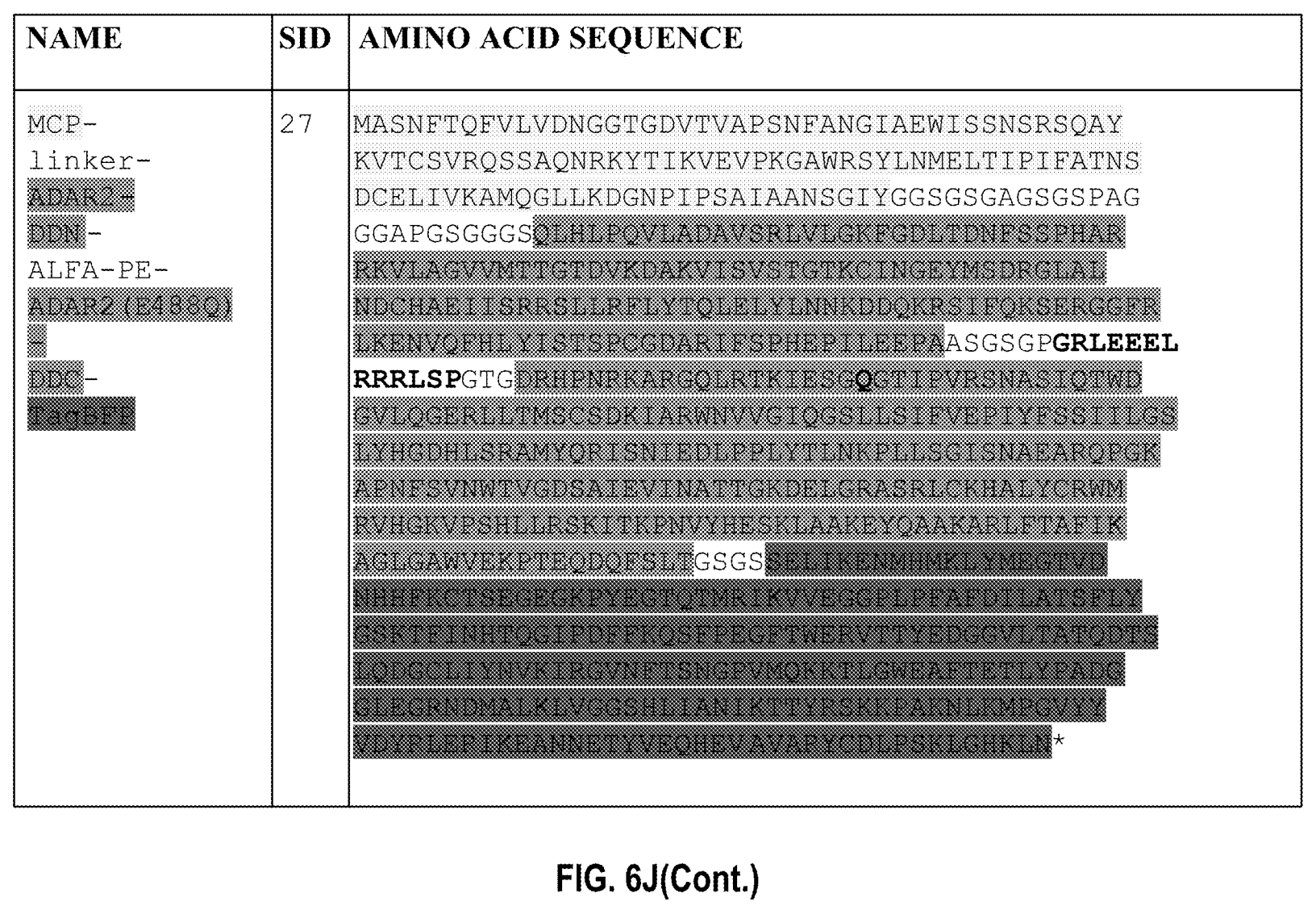

| NAME | SID | AMINO ACID SEQUENCE |
| --- | --- | --- |
| MCP-<br>linker-<br>ADAR2-<br>DDN-<br>ALFA-PE-<br>ADAR2(E488Q)<br>-<br>DDC-<br>TagBFP | 27 | MASNFTQFVLVDNGGTGDVTVAPSNFANGIAEWISSNSRSQAY<br>KVTCSVRQSSAQNRKYTIKVEVPKGAWRSYLNMELTIPIFATNS<br>DCELIVKAMQGLLKDGNPIPSAIAANSGIYGGSGSGAGSGSPAG<br>GGAPGSGGGSQLHLPQVLADAVSRLVLGKFGDLTDNFSSPHAR<br>RKVLAGVVMTTGTDVKDAKVISVSTGTKCINGEYMSDRGLAL<br>NDCHAEIISRRSLLRFLYTQLELYLNNKDDQKRSIFQKSERGGFR<br>LKENVQFHLYISTSPCGDARIFSPHEPILEEPAASGSGP**GRLEEEL**<br>**RRRLSP**GTGDRHPNRKARGQLRTKIESG**Q**GTIPVRSNASIQTWD<br>GVLQGERLLTMSCSDKIARWNVVGIQGSLLSIFVEPIYFSSIILGS<br>LYHGDHLSRAMYQRISNIEDLPPLYTLNKPLLSGISNAEARQPGK<br>APNFSVNWTVGDSAIEVINATTGKDELGRASRLCKHALYCRWM<br>RVHGKVPSHLLRSKITKPNVYHESKLAAKEYQAAKARLFTAFIK<br>AGLGAWVEKPTEQDQFSLTGSGSSELIKENMHMKLYMEGTVD<br>NHHFKCTSEGEGKPYEGTQTMRIKVVEGGPLPFAFDILATSFLY<br>GSKTFINHTQGIPDFFKQSFPEGFTWERVTTYEDGGVLTATQDTS<br>LQDGCLIYNVKIRGVNFTSNGPVMQKKTLGWEAFTETLYPADG<br>GLEGRNDMALKLVGGSHLIANIKTTYRSKKPAKNLKMPGVYY<br>VDYRLERIKEANNETYVEQHEVAVARYCDLPSKLGHKLN* |

FIG. 6J(Cont.)

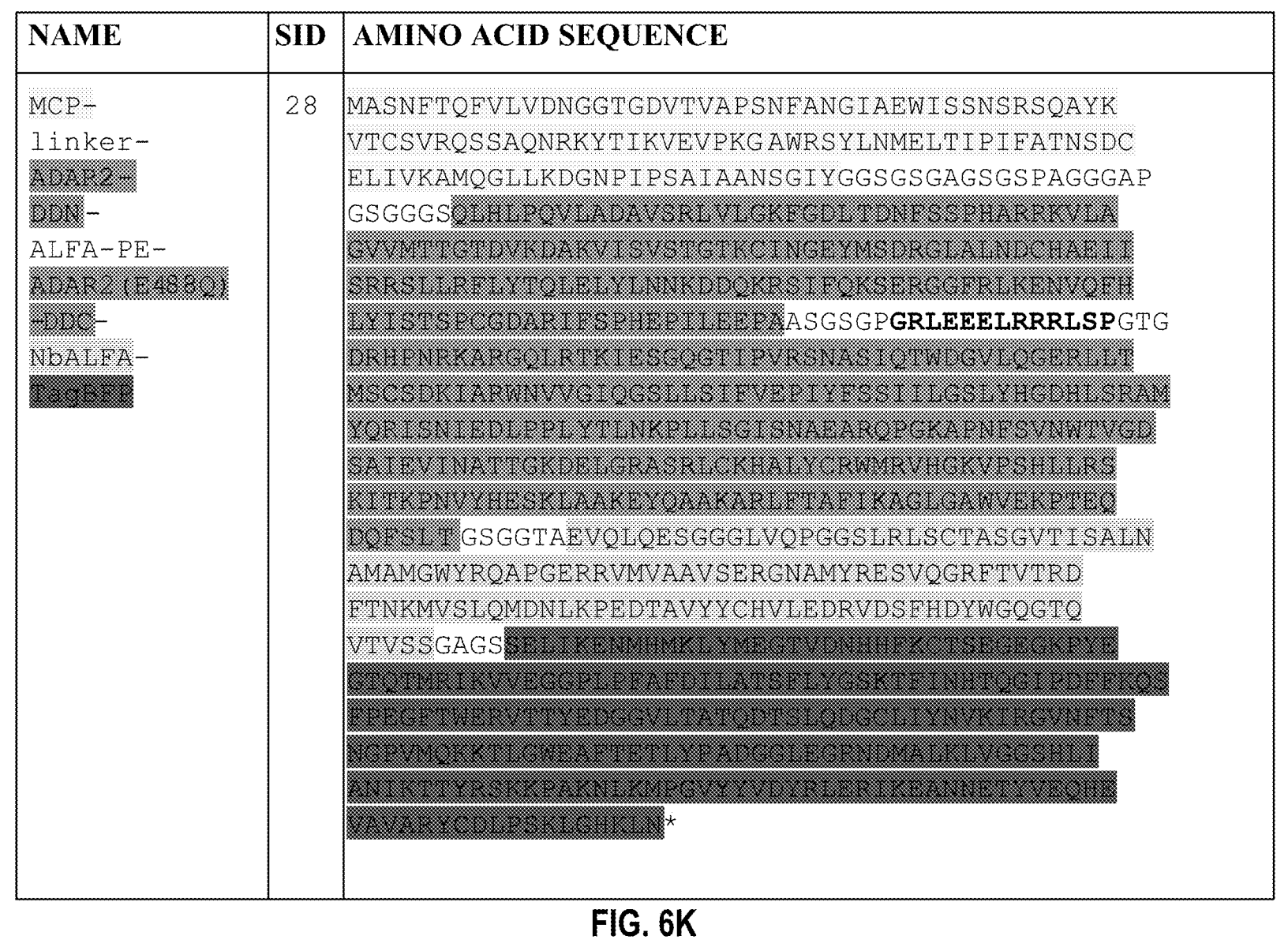

| NAME | SID | AMINO ACID SEQUENCE |
|---|---|---|
| MCP-<br>linker-<br>ADAR2-<br>DDN-<br>ALFA-PE-<br>ADAR2(E488Q)<br>-DDC-<br>NbALFA-<br>TagBFP | 28 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGAP<br>GSGGGSQLHLPQVLADAVSRLVLGKFGDLTDNFSSPHARRKVLA<br>GVVMTTGTDVKDAKVISVSTGTKCINGEYMSDRGLALNDCHAEII<br>SRRSLLRFLYTQLELYLNNKDDQKRSIFQKSERGGFRLKENVQFH<br>LYISTSPCGDARIFSPHEPILEEPAASGSGP**GRLEEELRRRLSP**GTG<br>DRHPNRKARGQLRTKIESGQGTIPVRSNASIQTWDGVLQGERLLT<br>MSCSDKIARWNVVGIQGSLLSIFVEPIYFSSIILGSLYHGDHLSRAM<br>YQRISNIEDLPPLYTLNKPLLSGISNAEARQPGKAPNFSVNWTVGD<br>SAIEVINATTGKDELGRASRLCKHALYCRWMRVHGKVPSHLLRS<br>KITKPNVYHESKLAAKEYQAAKARLFTAFIKAGLGAWVEKPTEQ<br>DQFSLTGSGGTAEVQLQESGGGLVQPGGSLRLSCTASGVTISALN<br>AMAMGWYRQAPGERRVMVAAVSERGNAMYRESVQGRFTVTRD<br>FTNKMVSLQMDNLKPEDTAVYYCHVLEDRVDSFHDYWGQGTQ<br>VTVSSGAGSSELIKENMHMKLYMEGTVDNHHFKCTSEGEGKPYE<br>GTQTMRIKVVEGGPLPFAFDILATSFLYGSKTFINHTQGIPDFFKQS<br>FPEGFTWERVTTYEDGGVLTATQDTSLQDGCLIYNVKIRGVNFTS<br>NGPVMQKKTLGWEAFTETLYPADGGLEGRNDMALKLVGGSHLI<br>ANIKTTYRSKKPAKNLKMPGVYYVDYRLERIKEANNETYVEQHE<br>VAVARYCDLPSKLGHKLN* |

FIG. 6K

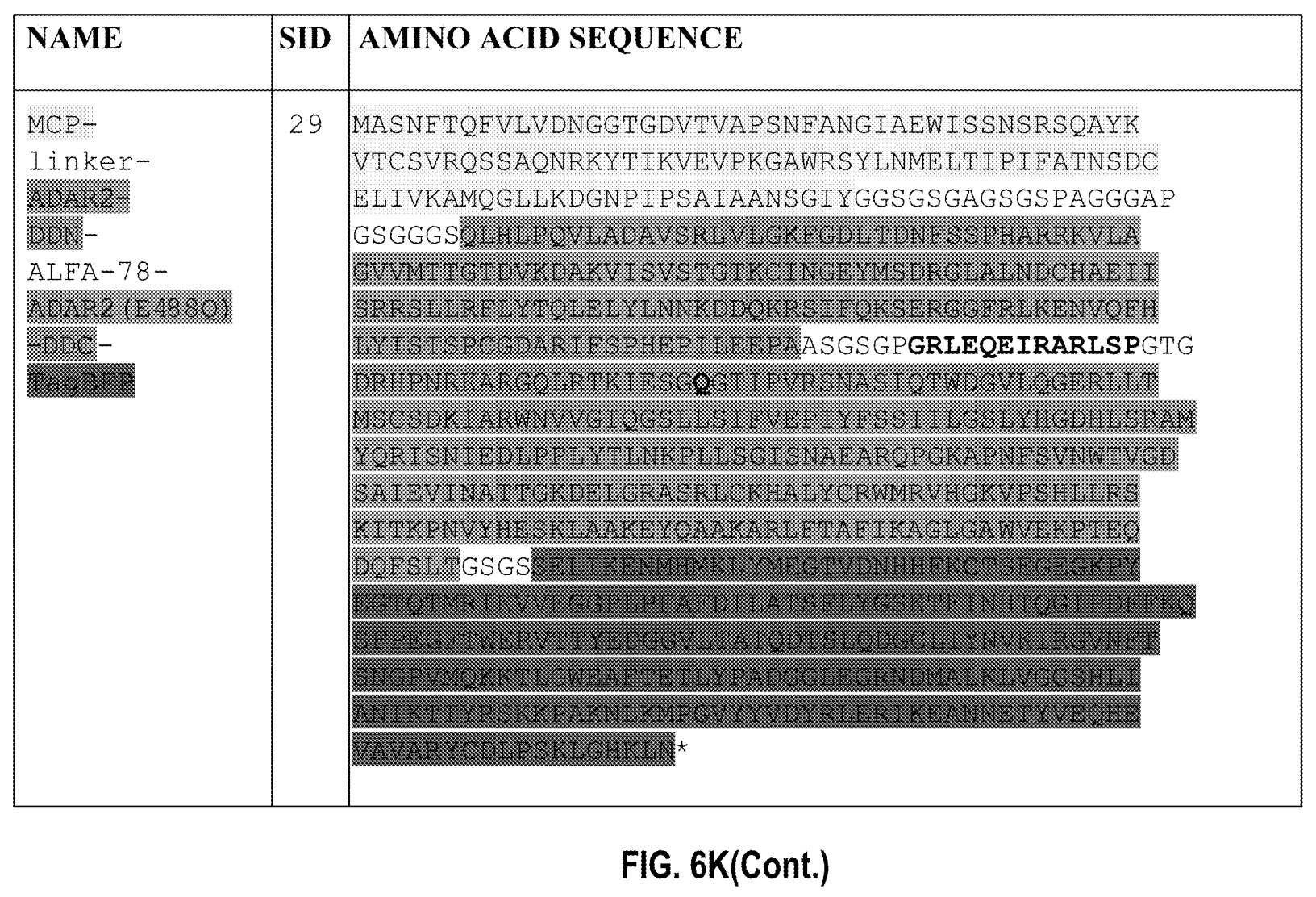

| NAME | SID | AMINO ACID SEQUENCE |
|---|---|---|
| MCP-<br>linker-<br>ADAR2-<br>DDN-<br>ALFA-78-<br>ADAR2(E488Q)<br>-DDC-<br>TagBFP | 29 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGAP<br>GSGGGSQLHLPQVLADAVSRLVLGKFGDLTDNFSSPHARRKVLA<br>GVVMTTGTDVKDAKVISVSTGTKCINGEYMSDRGLALNDCHAEII<br>SRRSLLRFLYTQLELYLNNKDDQKRSIFQKSERGGFRLKENVQFH<br>LYISTSPCGDARIFSPHEPILEEPAASGSGP**GRLEQEIRARLSP**GTG<br>DRHPNRKARGQLRTKIESG**Q**GTIPVRSNASIQTWDGVLQGERLLT<br>MSCSDKIARWNVVGIQGSLLSIFVEPIYFSSIILGSLYHGDHLSRAM<br>YQRISNIEDLPPLYTLNKPLLSGISNAEARQPGKAPNFSVNWTVGD<br>SAIEVINATTGKDELGRASRLCKHALYCRWMRVHGKVPSHLLRS<br>KITKPNVYHESKLAAKEYQAAKARLFTAFIKAGLGAWVEKPTEQ<br>DQFSLTGSGSSELIKENMHMKLYMEGTVDNHHFKCTSEGEGKPY<br>EGTQTMRIKVVEGGPLPFAFDILATSFLYGSKTFINHTQGIPDFFKQ<br>SFPEGFTWERVTTYEDGGVLTATQDTSLQDGCLIYNVKIRGVNFT<br>SNGPVMQKKTLGWEAFTETLYPADGGLEGRNDMALKLVGGSHLI<br>ANIKTTYRSKKPAKNLKMPGVYYVDYRLERIKEANNETYVEQHE<br>VAVARYCDLPSKLGHKLN* |

FIG. 6K(Cont.)

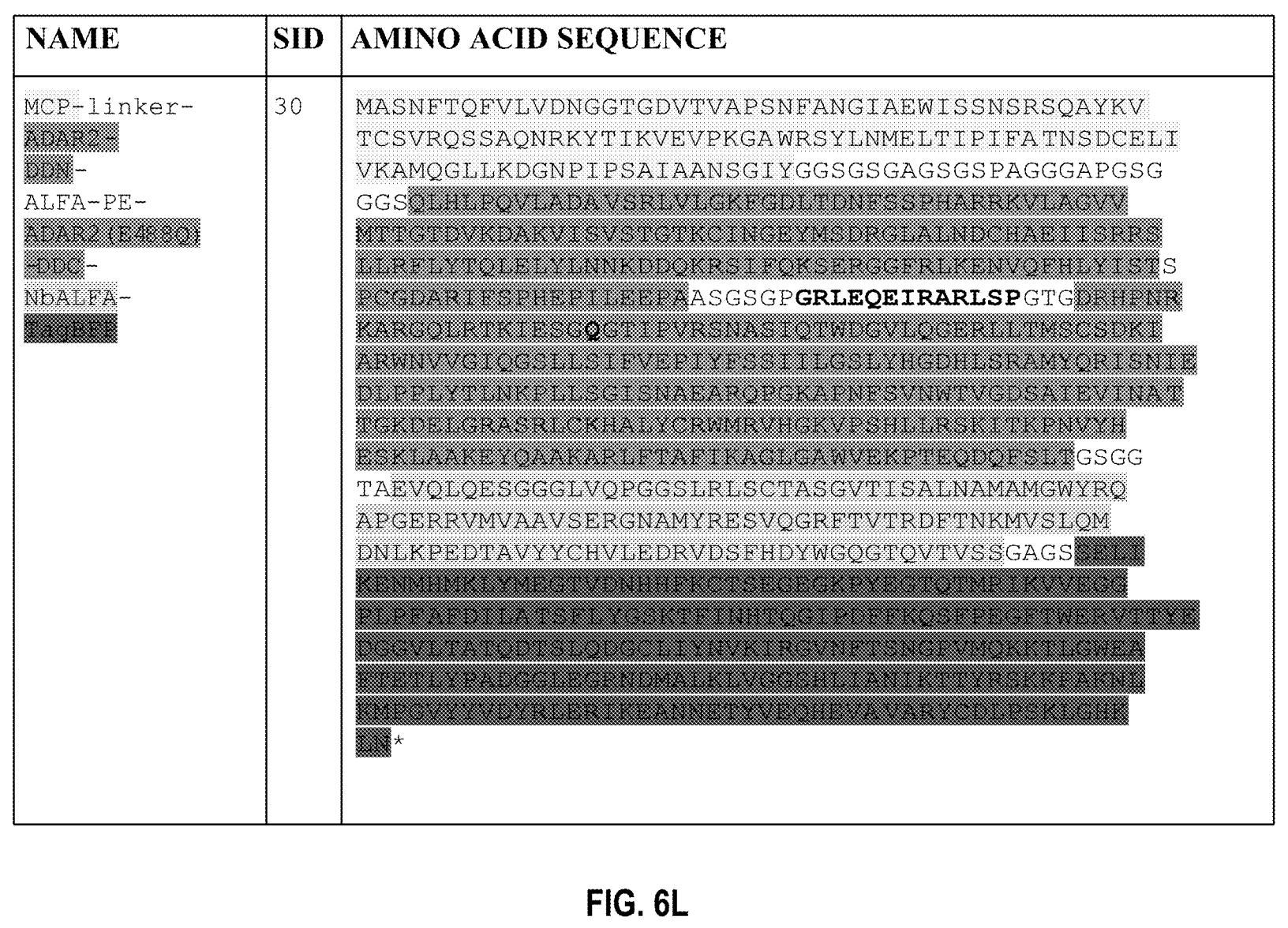

| NAME | SID | AMINO ACID SEQUENCE |
|---|---|---|
| MCP-linker-<br>ADAR2-<br>DDN-<br>ALFA-PE-<br>ADAR2(E488Q)<br>-DDC-<br>NbALFA-<br>TagBFP | 30 | MASNFTQFVLVDNGGTGDVTVAPSNFANGIAEWISSNSRSQAYKV<br>TCSVRQSSAQNRKYTIKVEVPKGAWRSYLNMELTIPIFATNSDCELI<br>VKAMQGLLKDGNPIPSAIAANSGIYGGSGSGAGSGSPAGGGAPGSG<br>GGSQLHLPQVLADAVSRLVLGKFGDLTDNFSSPHARRKVLAGVV<br>MTTGTDVKDAKVISVSTGTKCINGEYMSDRGLALNDCHAEIISRRS<br>LLRFLYTQLELYLNNKDDQKRSIFQKSERGGFRLKENVQFHLYISTS<br>PCGDARIFSPHEPILEEPAASGSGP**GRLEQEIRARLSP**GTGDRHPNR<br>KARGQLRTKIESG**Q**GTIPVRSNASIQTWDGVLQGERLLTMSCSDKI<br>ARWNVVGIQGSLLSIFVEPIYFSSIILGSLYHGDHLSRAMYQRISNIE<br>DLPPLYTLNKPLLSGISNAEARQPGKAPNFSVNWTVGDSAIEVINAT<br>TGKDELGRASRLCKHALYCRWMRVHGKVPSHLLRSKITKPNVYH<br>ESKLAAKEYQAAKARLFTAFIKAGLGAWVEKPTEQDQFSLTGSGG<br>TAEVQLQESGGGLVQPGGSLRLSCTASGVTISALNAMAMGWYRQ<br>APGERRVMVAAVSERGNAMYRESVQGRFTVTRDFTNKMVSLQM<br>DNLKPEDTAVYYCHVLEDRVDSFHDYWGQGTQVTVSSGAGSSELI<br>KENMHMKLYMEGTVDNHHFKCTSEGEGKPYEGTQTMRIKVVEGG<br>PLPFAFDILATSFLYGSKTFINHTQGIPDFFKQSFPEGFTWERVTTYE<br>DGGVLTATQDTSLQDGCLIYNVKIRGVNFTSNGPVMQKKTLGWEA<br>FTETLYPADGGLEGRNDMALKLVGGSHLIANIKTTYRSKKPAKNL<br>KMPGVYYVDYRLERIKEANNETYVEQHEVAVARYCDLPSKLGHK<br>LN* |

FIG. 6L

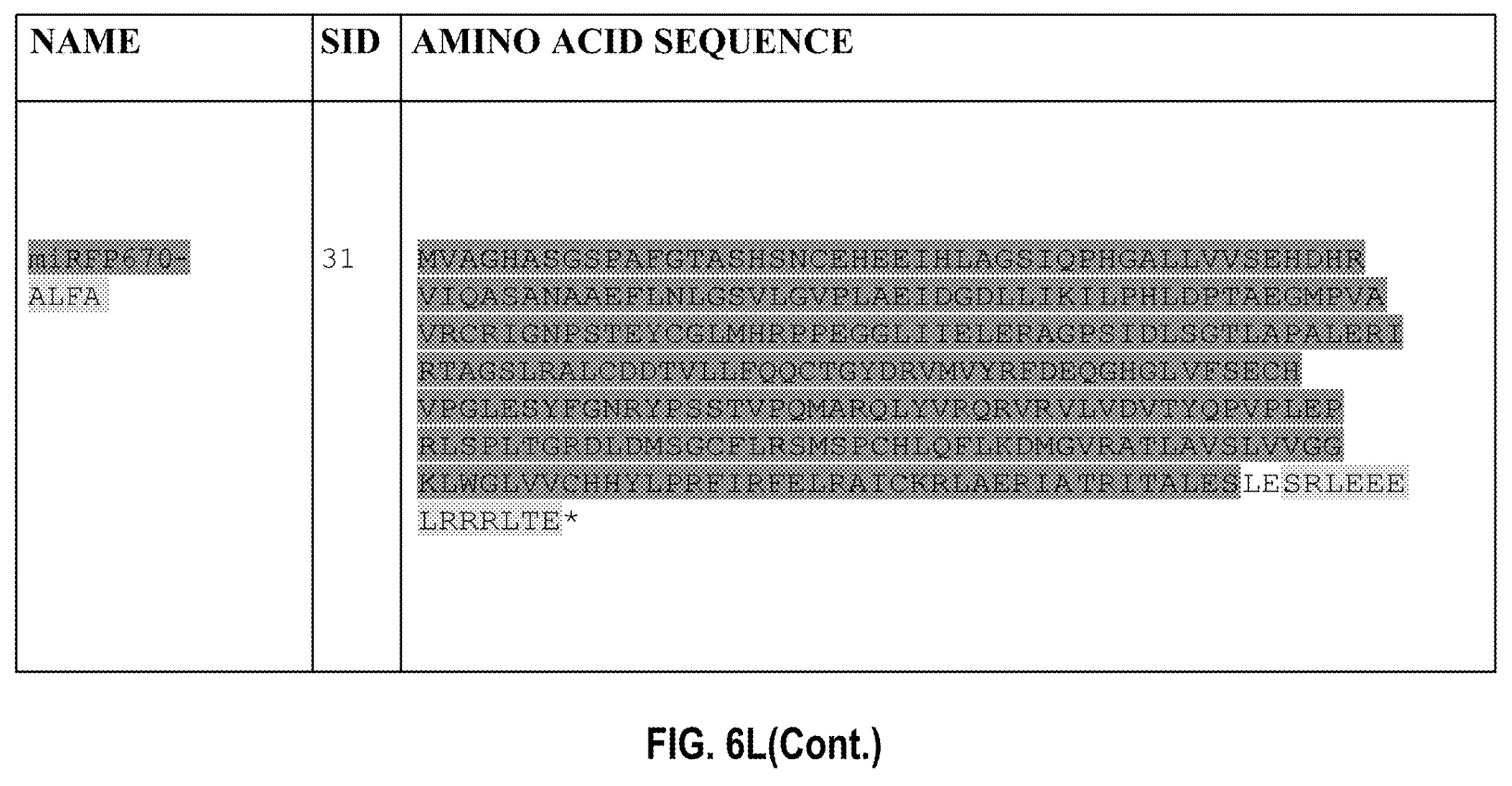

| NAME | SID | AMINO ACID SEQUENCE |
| --- | --- | --- |
| miRFP670-ALFA | 31 | MVAGHASGSPAFGTASHSNCEHEEIHLAGSIQPHGALLVVSEHDHR<br>VIQASANAAEFLNLGSVLGVPLAEIDGDLLIKILPHLDPTAEGMPVA<br>VRCRIGNPSTEYCGLMHRPPEGGLIIELERAGPSIDLSGTLAPALERI<br>RTAGSLRALCDDTVLLFQQCTGYDRVMVYRFDEQGHGLVFSECH<br>VPGLESYFGNRYPSSTVPQMARQLYVRQRVRVLVDVTYQPVPLEP<br>RLSPLTGRDLDMSGCFLRSMSPCHLQFLKDMGVRATLAVSLVVGG<br>KLWGLVVCHHYLPRFIRFELRAICKRLAERIATRITALESLESRLEEE<br>LRRRLTE* |

FIG. 6L(Cont.)

| NAME | SID | AMINO ACID SEQUENCE |
|---|---|---|
| MCP-linker-<br>ADAR2-<br>DDN-<br>SpyTag-<br>ADAR2(E488Q)<br>-DDC-<br>TagRFP | 32 | MASNFTQFVLVDNGGTGDVTVAPSNFANGIAEWISSNSRSQAYKV<br>TCSVRQSSAQNRKYTIKVEVPKGAWRSYLNMELTIPIFATNSDCELI<br>VKAMQGLLKDGNPIPSAIAANSGIYGGSGSGAGSGSPAGGGAPGSG<br>GGSQLHLPQVLADAVSRLVLGKFGDLTDNFSSPHARRKVLAGVV<br>MTTGTDVKDAKVISVSTGTKCINGEYMSDRGLALNDCHAEIISRRS<br>LLRFLYTQLELYLNNKDDQKRSIFQKSERGGFRLKENVQFHLYISTS<br>PCGDARIFSPHEPILEEPAASGGSG**AHIVMVDAYKPTK**GTGDRHPN<br>RKARGQLRTKIESG**Q**GTIPVRSNASIQTWDGVLQGERLLTMSCSDK<br>IARWNVVGIQGSLLSIFVEPIYFSSIILGSLYHGDHLSRAMYQRISNIE<br>DLPPLYTLNKPLLSGISNAEARQPGKAPNFSVNWTVGDSAIEVINAT<br>TGKDELGRASRLCKHALYCRWMRVHGKVPSHLLRSKITKPNVYH<br>ESKLAAKEYQAAKARLFTAFIKAGLGAWVEKPTEQDQFSLTGSGS<br>SELIKENMHMKLYMEGTVDNHHFKCTSEGEGKPYEGTQTMRIKVV<br>EGGPLPFAFDILATSFLYGSKTFINHTQGIPDFFKQSFPEGFTWERVT<br>TYEDGGVLTATQDTSLQDGCLIYNVKIRGVNFTSNGPVMQKKTLG<br>WEAFTETLYPADGGLEGRNDMALKLVGGSHLIANIKTTYRSKKPA<br>KNLKMPGVYYVDYRLERIKEANNETYVEQHEVAVARYCDLPSKL<br>GHKLN* |

FIG. 6L(Cont.)

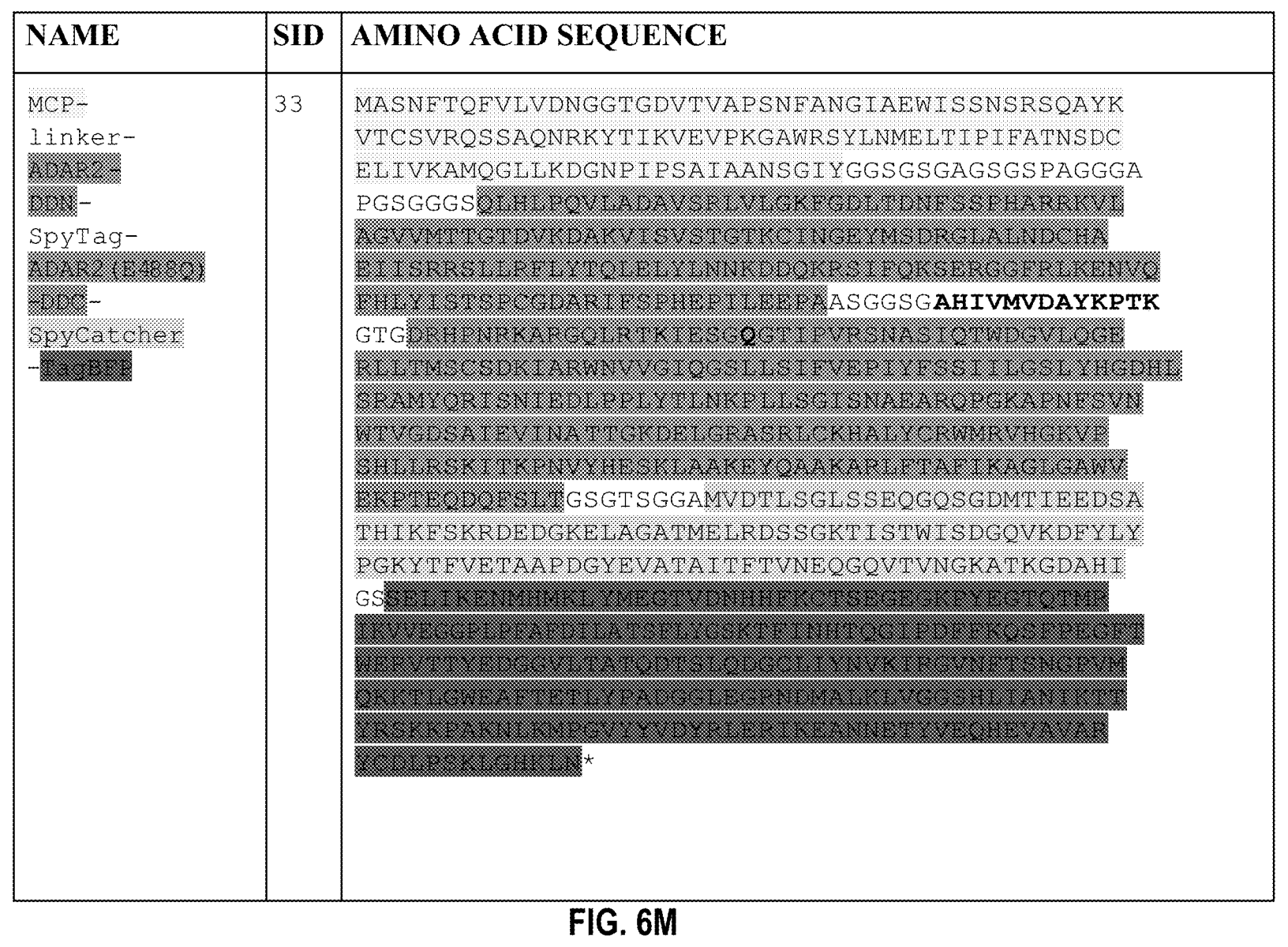

| NAME | SID | AMINO ACID SEQUENCE |
| --- | --- | --- |
| MCP-<br>linker-<br>ADAR2-<br>DDN-<br>SpyTag-<br>ADAR2(E488Q)<br>-DDC-<br>SpyCatcher<br>-TagBFP | 33 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGA<br>PGSGGGSQLHLPQVLADAVSRLVLGKFGDLTDNFSSPHARRKVL<br>AGVVMTTGTDVKDAKVISVSTGTKCINGEYMSDRGLALNDCHA<br>EIISRRSLLRFLYTQLELYLNNKDDQKRSIFQKSERGGFRLKENVQ<br>FHLYISTSPCGDARIFSPHEPILEEPAASGGSG**AHIVMVDAYKPTK**<br>GTGDRHPNRKARGQLRTKIESG**Q**GTIPVRSNASIQTWDGVLQGE<br>RLLTMSCSDKIARWNVVGIQGSLLSIFVEPIYFSSIILGSLYHGDHL<br>SRAMYQRISNIEDLPPLYTLNKPLLSGISNAEARQPGKAPNFSVN<br>WTVGDSAIEVINATTGKDELGRASRLCKHALYCRWMRVHGKVP<br>SHLLRSKITKPNVYHESKLAAKEYQAAKARLFTAFIKAGLGAWV<br>EKPTEQDQFSLTGSGTSGGAMVDTLSGLSSEQGQSGDMTIEEDSA<br>THIKFSKRDEDGKELAGATMELRDSSGKTISTWISDGQVKDFYLY<br>PGKYTFVETAAPDGYEVATAITFTVNEQGQVTVNGKATKGDAHI<br>GSSELIKENMHMKLYMEGTVDNHHFKCTSEGEGKPYEGTQTMR<br>IKVVEGGPLPFAFDILATSFLYGSKTFINHTQGIPDFFKQSFPEGFT<br>WERVTTYEDGGVLTATQDTSLQDGCLIYNVKIRGVNFTSNGPVM<br>QKTLGWEAFTETLYPADGGLEGRNDMALKLVGGSHLIANIKTT<br>YRSKKPAKNLKMPGVYYVDYRLERIKEANNETYVEQHEVAVAR<br>YCDLPSKLGHKLN* |

FIG. 6M

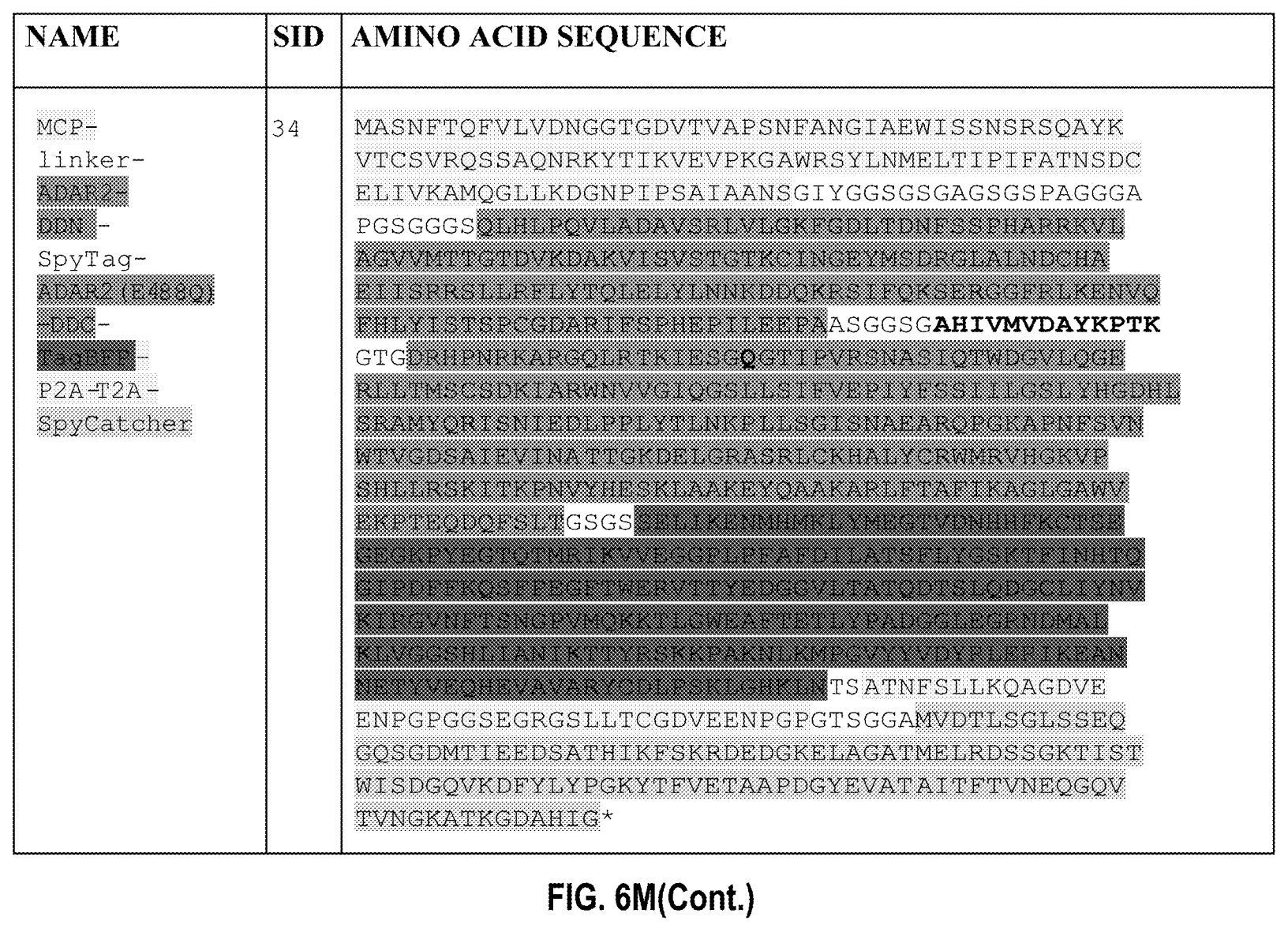

| NAME | SID | AMINO ACID SEQUENCE |
|---|---|---|
| MCP-<br>linker-<br>ADAR2-<br>DDN -<br>SpyTag-<br>ADAR2(E488Q)<br>-DDC-<br>TagBFP -<br>P2A-T2A -<br>SpyCatcher | 34 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGA<br>PGSGGGSQLHLPQVLADAVSRLVLGKFGDLTDNFSSPHARRKVL<br>AGVVMTTGTDVKDAKVISVSTGTKCINGEYMSDRGLALNDCHA<br>EIISRRSLLRFLYTQLELYLNNKDDQKRSIFQKSERGGFRLKENVQ<br>FHLYISTSPCGDARIFSPHEPILEEPAASGGSG**AHIVMVDAYKPTK**<br>GTGDRHPNRKARGQLRTKIESG**Q**GTIPVRSNASIQTWDGVLQGE<br>RLLTMSCSDKIARWNVVGIQGSLLSIFVEPIYFSSIILGSLYHGDHL<br>SRAMYQRISNIEDLPPLYTLNKPLLSGISNAEARQPGKAPNFSVN<br>WTVGDSAIEVINATTGKDELGRASRLCKHALYCRWMRVHGKVP<br>SHLLRSKITKPNVYHESKLAAKEYQAAKARLFTAFIKAGLGAWV<br>EKPTEQDQFSLTGSGSSELIKENMHMKLYMEGTVDNHHFKCTSE<br>GEGKPYEGTQTMRIKVVEGGPLPFAFDILATSFLYGSKTFINHTQ<br>GIPDFFKQSFPEGFTWERVTTYEDGGVLTATQDTSLQDGCLIYNV<br>KIRGVNFTSNGPVMQKKTLGWEAFTETLYPADGGLEGRNDMAL<br>KLVGGSHLIANIKTTYRSKKPAKNLKMPGVYYVDYRLERIKEAN<br>NETYVEQHEVAVARYCDLPSKLGHKLNTSATNFSLLKQAGDVE<br>ENPGPGGSEGRGSLLTCGDVEENPGPGTSGGAMVDTLSGLSSEQ<br>GQSGDMTIEEDSATHIKFSKRDEDGKELAGATMELRDSSGKTIST<br>WISDGQVKDFYLYPGKYTFVETAAPDGYEVATAITFTVNEQGQV<br>TVNGKATKGDAHIG* |

FIG. 6M(Cont.)

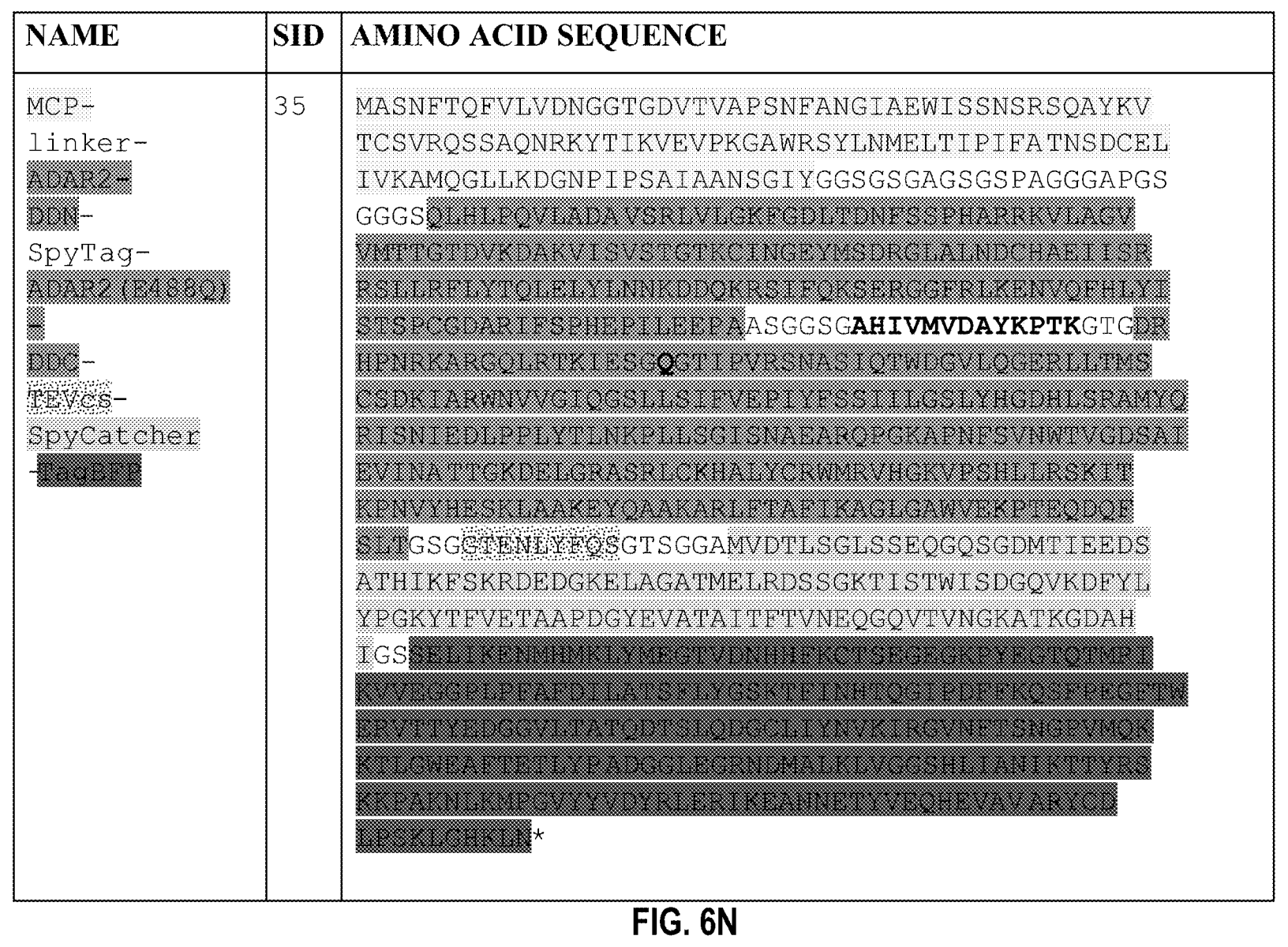

| NAME | SID | AMINO ACID SEQUENCE |
|---|---|---|
| MCP-<br>linker-<br>ADAR2-<br>DDN-<br>SpyTag-<br>ADAR2(E488Q)<br>-<br>DDC-<br>TEVcs-<br>SpyCatcher<br>-TagBFP | 35 | MASNFTQFVLVDNGGTGDVTVAPSNFANGIAEWISSNSRSQAYKV<br>TCSVRQSSAQNRKYTIKVEVPKGAWRSYLNMELTIPIFATNSDCEL<br>IVKAMQGLLKDGNPIPSAIAANSGIYGGSGSGAGSGSPAGGGAPGS<br>GGGSQLHLPQVLADAVSRLVLGKFGDLTDNFSSPHARRKVLAGV<br>VMTTGTDVKDAKVISVSTGTKCINGEYMSDRGLALNDCHAEIISR<br>RSLLRFLYTQLELYLNNKDDQKRSIFQKSERGGFRLKENVQFHLYI<br>STSPCGDARIFSPHEPILEEPAASGGSG**AHIVMVDAYKPTK**GTGDR<br>HPNRKARGQLRTKIESG**Q**GTIPVRSNASIQTWDGVLQGERLLTMS<br>CSDKIARWNVVGIQGSLLSIFVEPIYFSSIILGSLYHGDHLSRAMYQ<br>RISNIEDLPPLYTLNKPLLSGISNAEARQPGKAPNFSVNWTVGDSAI<br>EVINATTGKDELGRASRLCKHALYCRWMRVHGKVPSHLLRSKIT<br>KPNVYHESKLAAKEYQAAKARLFTAFIKAGLGAWVEKPTEQDQF<br>SLTGSGGTENLYFQSGTSGGAMVDTLSGLSSEQGQSGDMTIEEDS<br>ATHIKFSKRDEDGKELAGATMELRDSSGKTISTWISDGQVKDFYL<br>YPGKYTFVETAAPDGYEVATAITFTVNEQGQVTVNGKATKGDAH<br>IGSSELIKENMHMKLYMEGTVDNHHFKCTSEGEGKPYEGTQTMRI<br>KVVEGGPLPFAFDILATSFLYGSKTFINHTQGIPDFFKQSFPEGFTW<br>ERVTTYEDGGVLTATQDTSLQDGCLIYNVKIRGVNFTSNGPVMQK<br>KTLGWEAFTETLYPADGGLEGRNDMALKLVGGSHLIANIKTTYRS<br>KKPAKNLKMPGVYYVDYRLERIKEANNETYVEQHEVAVARYCD<br>LPSKLGHKLN* |

FIG. 6N

| NAME | SID | AMINO ACID SEQUENCE |
|---|---|---|
| TEV Protease | 36 | MGESLFKGPRDYNPISSTICHLTNESDGHTTSLYGIGFGPFIITNKHL<br>FRRNNGTLLVQSLHGVFKVKNTTTLQQHLIDGRDMIIIRMPKDFPP<br>FPQKLKFREPQREERICLVTTNFQTKSMSSMVSDTSCTFPSSDGIFW<br>KHWIQTKDGQCGSPLVSTRDGFIVGIHSASNFTNTNNYFTSVPKNF<br>MELLTNQEAQQWVSGWRLNADSVLWGGHKVFMVKPEEPFQPVK<br>EATQL* |

FIG. 6N(Cont.)

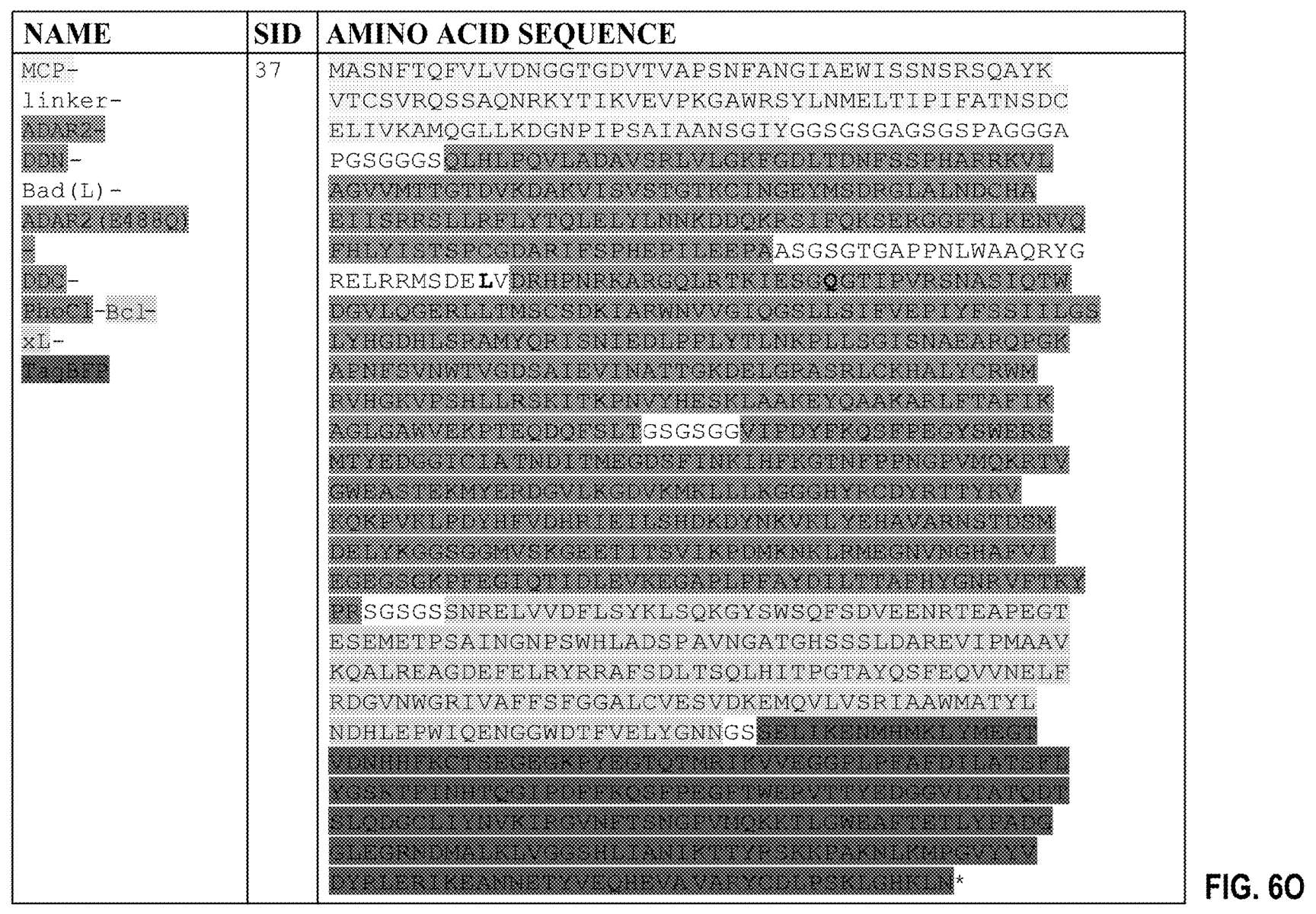

| NAME | SID | AMINO ACID SEQUENCE |
|---|---|---|
| MCP-<br>linker-<br>ADAR2-<br>DDN-<br>Bad(L)-<br>ADAR2(E488Q)<br>-<br>DDC-<br>PhoCl-Bcl-<br>xL-<br>TagRFP | 37 | MASNFTQFVLVDNGGTGDVTVAPSNFANGIAEWISSNSRSQAYK<br>VTCSVRQSSAQNRKYTIKVEVPKGAWRSYLNMELTIPIFATNSDC<br>ELIVKAMQGLLKDGNPIPSAIAANSGIYGGSGSGAGSGSPAGGGA<br>PGSGGGSQLHLPQVLADAVSRLVLGKFGDLTDNFSSPHARRKVL<br>AGVVMTTGTDVKDAKVISVSTGTKCINGEYMSDRGLALNDCHA<br>EIISRRSLLRFLYTQLELYLNNKDDQKRSIFQKSERGGFRLKENVQ<br>FHLYISTSPCGDARIFSPHEPILEEPAASGSGTGAPPNLWAAQRYG<br>RELRRMSDE**L**VDRHPNRKARGQLRTKIESG**Q**GTIPVRSNASIQTW<br>DGVLQGERLLTMSCSDKIARWNVVGIQGSLLSIFVEPIYFSSIILGS<br>LYHGDHLSRAMYQRISNIEDLPPLYTLNKPLLSGISNAEARQPGK<br>APNFSVNWTVGDSAIEVINATTGKDELGRASRLCKHALYCRWM<br>RVHGKVPSHLLRSKITKPNVYHESKLAAKEYQAAKARLFTAFIK<br>AGLGAWVEKPTEQDQFSLTGSGSGGVIPDYFKQSFPEGYSWERS<br>MTYEDGGICIATNDITMEGDSFINKIHFKGTNFPPNGPVMQKRTV<br>GWEASTEKMYERDGVLKGDVKMKLLLKGGGHYRCDYRTTYKV<br>KQKPVKLPDYHFVDHRIEILSHDKDYNKVKLYEHAVARNSTDSM<br>DELYKGGSGGMVSKGEETITSVIKPDMKNKLRMEGNVNGHAFVI<br>EGEGSGKPFEGIQTIDLEVKEGAPLPFAYDILTTAFHYGNRVFTKY<br>PRSGSGSSNRELVVDFLSYKLSQKGYSWSQFSDVEENRTEAPEGT<br>ESEMETPSAINGNPSWHLADSPAVNGATGHSSSLDAREVIPMAAV<br>KQALREAGDEFELRYRRAFSDLTSQLHITPGTAYQSFEQVVNELF<br>RDGVNWGRIVAFFSFGGALCVESVDKEMQVLVSRIAAWMATYL<br>NDHLEPWIQENGGWDTFVELYGNNGSSELIKENMHMKLYMEGT<br>VDNHHFKCTSEGEGKPYEGTQTMRIKVVEGGPLPFAFDILATSFL<br>YGSKTFINHTQGIPDFFKQSFPEGFTWERVTTYEDGGVLTATQDT<br>SLQDGCLIYNVKIRGVNFTSNGPVMQKKTLGWEAFTETLYPADG<br>GLEGRNDMALKLVGGSHLIANIKTTYRSKKPAKNLKMPGVYYV<br>DYRLERIKEANNETYVEQHEVAVARYCDLPSKLGHKLN* |

FIG. 6O

```
CLUSTAL O(1.2.4) multiple sequence alignment of ADAR1 (DSRAD), ADAR2 (RED1), and ADAR3(RED2)

*deaminase domain used in application is highlighted in yellow

sp|P55265|DSRAD_HUMAN      MNPRQGYSLSGYYTHPFQGYEHRQLRYQQPGPGSSPSSFLLKQIEFLKGQLPEAPVIGKQ  60
sp|P78563-2|RED1_HUMAN     ------------------------------------------------------------  0
sp|Q9NS39|RED2_HUMAN       ------------------------------------------------------------  0

sp|P55265|DSRAD_HUMAN      TPSLPPSLPGLRPRFPVLLASSTRGRQVDIRGVPRGVHLRSQGLQRGFQHPSPRGRSLPQ  120
sp|P78563-2|RED1_HUMAN     ------------------------------------------------------------  0
sp|Q9NS39|RED2_HUMAN       ------------------------------------------------------------  0

sp|P55265|DSRAD_HUMAN      RGVDCLSSHFQELSIYQDQEQRILKFLEELGEGKATTAHDLSGKLGTPKKEINRVLYSLA  180
Sp|P78563-2|RED1_HUMAN     ------------------------------------------------------------  0
sp|Q9NS39|RED2_HUMAN       ------------------------------------------------------------  0

sp|P55265|DSRAD_HUMAN      KKGKLQKEAGTPPLWKIAVSTQAWNQHSGVVRPDGHSQGAPNSDPSLEPEDRNSTSVSED  240
sp|P78563-2|RED1_HUMAN     ------------------------------------------------------------  0
Sp|Q9NS39|RED2_HUMAN       ------------------------------------------------------------  0

sp|P55265|DSRAD_HUMAN      LLEPFIAVSAQAWNQHSGVVRPDSHSQGSPNSDPGLEPEDSNSTSALEDPLEFLDMAEIK  300
sp|P78563-2|RED1_HUMAN     ------------------------------------------------------------  0
sp|Q9NS39|RED2_HUMAN       ------------------------------------------------------------  0
```

FIG. 7A

```
sp|P55265|DSRAD_HUMAN      EKICDYLFNVSDSSALNLAKNIGLTKARDINAVLIDMERQGDVYRQGTTPPIWHLTDKKR 360
sp|P78563-2|RED1_HUMAN     ------------------------------------------------------------ 0
sp|Q9NS39|RED2_HUMAN       -----------------------------MASVLGSGRGSG------GLSSQLKCKSKRR 25

sp|P55265|DSRAD_HUMAN      ERMQIKRN-TNSVPETAPAAIPETKRNAEFLTCNIPTSNASNNMVTTEKVENGQEPVIKL 419
sp|P78563-2|RED1_HUMAN     -----------------------------------MDIEDEENMSSSS------TDVKEN 19
sp|Q9NS39|RED2_HUMAN       RRRRSKRKDKVSILSTFLA--P-----FKHLSPGITNTEDDDTLSTSS------AEVKEN 72
                                                                 : .:.: ::.        * :

sp|P55265|DSRAD_HUMAN      ENRQEARPEPARLKPPVHYNGPSKAGYVDFENGQWATDDIPDDLNSIRAAPGEFRAIMEM 479
sp|P78563-2|RED1_HUMAN     RNLDNVSPKDG------STPGPGEGSQL--SNGG-------------GGGPGRKRPLEEG 58
sp|Q9NS39|RED2_HUMAN       RNVGNLAARPP------------PSGDR--ARGG-------------APGAKRKRPLEEG 105
                           .*  :   .               ..     .*                .  . * : *

sp|P55265|DSRAD_HUMAN      PSFYSHGLPRCSPYKKLTECQLKNPISGLLEYAQFASQTCEFNMIEQSGPPHEPRFKFQV 539
sp|P78563-2|RED1_HUMAN     S--NGHSKYRLKKRRKTPGP--VLPKNALMQLN-EIKPGLQYTLLSQTGPVHAPLFVMSV 113
sp|Q9NS39|RED2_HUMAN       N--GGHLCKLQLVWKKLSWS--VAPKNALVQLH-ELRPGLQYRTVSQTGPVHAPVFAVAV 160
                               .*        :*        * ..*::         ::  :.*:** * * * . *

sp|P55265|DSRAD_HUMAN      VINGREFPPAEAGSKKVAKQDAAMKAMTILLEEAKAKDS-----GKSEESSHYSTEKE-- 592
sp|P78563-2|RED1_HUMAN     EVNGQVFEGSGPTKKK-AKLHAAEKALRSFVQFPNASEAHLAMGRTLSVNTDFTSDQADF 172
sp|Q9NS39|RED2_HUMAN       EVNGLTFEGTGPTKKK-AKMRAAELALRSFVQFPNACQAHLAMGGGPGPGTDFTSDQADF 219
                            :**  *  :   .** **  **  *:  :::  :* ::          .:.:::::

sp|P55265|DSRAD_HUMAN      -SEKTAESQTPTPSATSFFSGKSPVTTLLECMHKLGNSCEFRLLSKEGPAHEPKFQYCVA 651
sp|P78563-2|RED1_HUMAN     PDTLFNGFETPDKAEPPFYVGSNGD----------------------------------- 197
sp|Q9NS39|RED2_HUMAN       PDTLFQEFEPPAPR-PGLAGGRPGD----------------------------------- 243
                            .      : *      :  *
```

FIG. 7A(Cont.)

```
sp|P55265|DSRAD_HUMAN      VGAQTFPSVSAPSKKVAKQMAAEEAMKALHGEATNSMASDNQPEGMISESLDNLESMMPN 711
sp|P78563-2|RED1_HUMAN     ---DSFSSSG-----------------------DLSLSASPVPASLAQPPLPVLPPF--- 228
sp|Q9NS39|RED2_HUMAN       ----AALLSAAYG--------------------RRRLLCRAL--D-LVGPTPAT--P--- 271
                               :: * .                          : .     .

sp|P55265|DSRAD_HUMAN      KVRKIGELVRYLNTNPVGGLLEYARSHGFAAEFKLVDQSGPPHEPKFVYQAKVGGRWFPA 771
sp|P78563-2|RED1_HUMAN     --------PPPSGKNPVMILNE----LRPGLKYDFLSESGESHAKSFVMSVVVDGQFFEG 276
sp|Q9NS39|RED2_HUMAN       --------AAPGERNPVVLLNR----LRAGLRYVCLAEPAERRARSFVMAVSVDGRTFEG 319
                                         ***  * .       . .:  : : .  :  .**  . *.*: * .
```

FIG. 7A(Cont.)

```
sp|P55265|DSRAD_HUMAN      VCAHSKKQGKQEAADAALRVLIGENEKAERMGFTEVTPVTGASLRRTMLLLSRSPEAQPK  831
sp|P78563-2|RED1_HUMAN     SGRN-KKLAKARAAQSALAAIFNLHLD----QTPSRQPIPSEGLQ---------------  316
sp|Q9NS39|RED2_HUMAN       SGRS-KKLARGQAAQAALQELFDIQMP----GH-----APGRARR---------------  354
                                ** .: .**::**  ::. :                . . :

sp|P55265|DSRAD_HUMAN      TLPLTGSTFHDQIAMLSHRCFNTLTNSFQPSLLGRKILAAIIMKKDSED-MGVVVSLGTG  890
sp|P78563-2|RED1_HUMAN     -L-HLPQVLADAVSRLVLGKFGDLTDNFSSPHARRKVLAGVVMTTGTDVKDAKVISVSTG  374
sp|Q9NS39|RED2_HUMAN       -T-PMPQEFADSISQLVTQKFREVTTDLTPMHARHKALAGIVMTKGLDARQAQVVALSSG  412
                                . : * :: *     *   :* .:       :* **.::*... :    . *:::.:*

sp|P55265|DSRAD_HUMAN      NRCVKGDSLSLKGETVNDCHAEIISRRGFIRFLYSELMKYNSQT---AKDSIFEPAKGGE  947
sp|P78563-2|RED1_HUMAN     TKCINGEYMSDRGLALNDCHAEIISRRSLLRFLYTQLELYLNN-KDDQKRSIFQKSERG-  432
sp|Q9NS39|RED2_HUMAN       TKCISGEHLSDQGLVVNDCHAEVVARRAFLHFLYTQLELHLSKRREDSERSIFVRLKEG-  471
                           .:*:.*: :* :* .:******:::**.:::***::*  : .:      : ***   : *

sp|P55265|DSRAD_HUMAN      KLQIKKTVSFHLYISTAPCGDGALFDKSCSDRAMESTESRHYPVFENPKQGKLRTKVENG  1007
sp|P78563-2|RED1_HUMAN     GFRLKENVQFHLYISTSPCGDARIFSPHEPILE--EPADRH---PNRKARGQLRTKIESG  487
sp|Q9NS39|RED2_HUMAN       GYRLRENILFHLYVSTSPCGDARLHSPYEITTD--LHSSKH----LVRKFRGHLRTKIESG  526
                             ::::.: ****:**:****. :..              .:*      .   :*:****:*.*

sp|P55265|DSRAD_HUMAN      EGTIPVESSDIVPTWDGIRLGERLRTMSCSDKILRWNVLGLQGALLTHFLQPIYLKSVTL  1067
sp|P78563-2|RED1_HUMAN     EGTIPVRSNASIQTWDGVLQGERLLTMSCSDKIARWNVVGIQGSLLSIFVEPIYFSSIIL  547
sp|Q9NS39|RED2_HUMAN       EGTVPVRGPSAVQTWDGVLLGEQLITMSCTDKIARWNVLGLQGALLSHFVEPVYLQSIVV  586
                           ***:**..    : ****:   **:* ****:*** ****:*:**:**: *::*:*:.*: :
```

FIG. 7B

```
sp|P55265|DSRAD_HUMAN      GYLFSQGHLTRAICCRVTRDGSAFEDGLRHPFIVNHPKVGRVSIYDSKRQSGKTKETSVN 1127
sp|P78563-2|RED1_HUMAN     GSLYHGDHLSRAMYQRISNIED-----LPPLYTLNKPLLSGISN-AEARQPGKAPNFSVN 601
sp|Q9NS39|RED2_HUMAN       GSLHHTGHLARVMSHRMEGVGQ-----LPASYRHNRPLLSGVSD-AEARQPGKSPPFSMN 640
                           * *.  .**:*.:  *:    .     *   :  *:* :. :*   . ** **:   *:*

sp|P55265|DSRAD_HUMAN      WCLADGYDLEILDGTRGTVDGPRNELSRVSKKNIFLLFKKL----CSFRYR-RDLLRLSY 1182
sp|P78563-2|RED1_HUMAN     WTVGDS-AIEVINATTGKDELG--RASRLCKHALYCRWMRVHGKVPSHLLRSKITKPNVY 658
sp|Q9NS39|RED2_HUMAN       WVVGSA-DLEIINATTGRRSCG--GPSRLCKHVLSARWARLYGRLSTRT-PSPGDTPSMY 696
                           * :...  :*:::.* *  .      **:.*: :   : ::      :            *

sp|P55265|DSRAD_HUMAN      GEAKKAARDYETAKNYFKKGLKDMGYGNWISKPQEEKNFYLCPV 1226
sp|P78563-2|RED1_HUMAN     HESKLAAKEYQAAKARLFTAFIKAGLGAWVEKPTEQDQFSLTP- 701
sp|Q9NS39|RED2_HUMAN       CEAKLGAHTYQSVKQQLFKAFQKAGLGTWVRKPPEQQQFLLTL- 739
                            *:* .*: *::.*  : ..: . * * *: ** *:.:* *
```

FIG. 7B(Cont.)

CLUSTAL O(1.2.4) multiple sequence alignment of ADAR1 (DSRAD), ADAR2 (RED1), ADAR3(RED2), ADAD1 and ADAD2

*deaminase domain used in application is highlighted in yellow

```
sp|P55265|DSRAD_HUMAN      MNPRQGYSLSGYYTHPFQGYEHRQLRYQQPGPGSSPSSFLLKQIEFLKGQLPEAPVIGKQ  60
sp|P78563-2|RED1_HUMAN     ------------------------------------------------------------  0
sp|Q9NS39|RED2_HUMAN       ------------------------------------------------------------  0
sp|Q96M93|ADAD1_HUMAN      ------------------------------------------------------------  0
sp|Q8NCV1|ADAD2_HUMAN      ------------------------------------------------------------  0

sp|P55265|DSRAD_HUMAN      TPSLPPSLPGLRPRFPVLLASSTRGRQVDIRGVPRGVHLRSQGLQRGFQHPSPRGRSLPQ  120
sp|P78563-2|RED1_HUMAN     ------------------------------------------------------------  0
sp|Q9NS39|RED2_HUMAN       ------------------------------------------------------------  0
sp|Q96M93|ADAD1_HUMAN      ------------------------------------------------------------  0
sp|Q8NCV1|ADAD2_HUMAN      ------------------------------------------------------------  0

sp|P55265|DSRAD_HUMAN      RGVDCLSSHFQELSIYQDQEQRILKFLEELGEGKATTAHDLSGKLGTPKKEINRVLYSLA  180
sp|P78563-2|RED1_HUMAN     ------------------------------------------------------------  0
sp|Q9NS39|RED2_HUMAN       ------------------------------------------------------------  0
sp|Q96M93|ADAD1_HUMAN      ------------------------------------------------------------  0
sp|Q8NCV1|ADAD2_HUMAN      ------------------------------------------------------------  0

sp|P55265|DSRAD_HUMAN      KKGKLQKEAGTPPLWKIAVSTQAWNQHSGVVRPDGHSQGAPNSDPSLEPEDRNSTSVSED  240
sp|P78563-2|RED1_HUMAN     ------------------------------------------------------------  0
sp|Q9NS39|RED2_HUMAN       ------------------------------------------------------------  0
sp|Q96M93|ADAD1_HUMAN      ------------------------------------------------------------  0
sp|Q8NCV1|ADAD2_HUMAN      ------------------------------------------------------------  0
```

FIG. 8A

```
sp|P55265|DSRAD_HUMAN      LLEPFIAVSAQAWNQHSGVVRPDSHSQGSPNSDPGLEPEDSNSTSALEDPLEFLDMAEIK 300
sp|P78563-2|RED1_HUMAN     ------------------------------------------------------------ 0
sp|Q9NS39|RED2_HUMAN       ------------------------------------------------------------ 0
sp|Q96M93|ADAD1_HUMAN      ------------------------------------------------------------ 0
sp|Q8NCV1|ADAD2_HUMAN      ------------------------------------------------------------ 0

sp|P55265|DSRAD_HUMAN      EKICDYLFNVSDSSALNLAKNIGLTKARDINAVLIDMERQGDVYRQGTTPPIWHLTDKKR 360
sp|P78563-2|RED1_HUMAN     ------------------------------------------------------------ 0
sp|Q9NS39|RED2_HUMAN       -----------------------------MASVLGSGRGSG------GLSSQLKCKSKRR 25
sp|Q96M93|ADAD1_HUMAN      ------------------------------------------------------------ 0
sp|Q8NCV1|ADAD2_HUMAN      ------------------------------------------------------------ 0

sp|P55265|DSRAD_HUMAN      ERMQIKRN-TNSVPETAPAAIPETKRNAEFLTCNIPTSNASNNMVTTEKVENGQEPVIKL 419
sp|P78563-2|RED1_HUMAN     -----------------------------------MDIEDEENMSSSS------TDVKEN 19
sp|Q9NS39|RED2_HUMAN       RRRRSKRKDKVSILSTFLA--P-----FKHLSPGITNTEDDDTLSTSS------AEVKEN 72
sp|Q96M93|ADAD1_HUMAN      ------------------------------------------------------------ 0
sp|Q8NCV1|ADAD2_HUMAN      ------------------------------------------------------------ 0

sp|P55265|DSRAD_HUMAN      ENRQEARPEPARLKPPVHYNGPSKAGYVDFENGQWATDDIPDDLNSIRAAPGEFRAIMEM 479
sp|P78563-2|RED1_HUMAN     RNLDNVSPKDG------STPGPGEGSQL--SNGG-------------GGGPGRKRPLEEG 58
sp|Q9NS39|RED2_HUMAN       RNVGNLAARPP------------PSGDR--ARGG-------------APGAKRKRPLEEG 105
sp|Q96M93|ADAD1_HUMAN      ------------------------------------------------------------ 0
sp|Q8NCV1|ADAD2_HUMAN      ------------------------------------------------------------ 0

sp|P55265|DSRAD_HUMAN      PSFYSHGLPRCSPYKKLTECQLKNPISGLLEYAQFASQTCEFNMIEQSGPPHEPRFKFQV 539
sp|P78563-2|RED1_HUMAN     S--NGHSKYRLKKRRKTPGP--VLPKNALMQLN-EIKPGLQYTLLSQTGPVHAPLFVMSV 113
sp|Q9NS39|RED2_HUMAN       N--GGHLCKLQLVWKKLSWS--VAPKNALVQLH-ELRPGLQYRTVSQTGPVHAPVFAVAV 160
sp|Q96M93|ADAD1_HUMAN      ------------------------------------------------------------ 0
sp|Q8NCV1|ADAD2_HUMAN      ------------------------------------------------------------ 0
```

FIG. 8A(Cont.)

```
sp|P55265|DSRAD_HUMAN       VINGREFPPAEAGSKKVAKQDAAMKAMTILLEEAKAKDS-----GKSEESSHYST-EKE-  592
sp|P78563-2|RED1_HUMAN      EVNGQVFEGSGPTKKK-AKLHAAEKALRSFVQFPNASEAHLAMGRTLSVNTDFTS-DQAD  171
sp|Q9NS39|RED2_HUMAN        EVNGLTFEGTGPTKKK-AKMRAAELALRSFVQFPNACQAHLAMGGGPGPGTDFTS-DQAD  218
sp|Q96M93|ADAD1_HUMAN       ------------------------------------------MA----------------  2
sp|Q8NCV1|ADAD2_HUMAN       ------------------------------------------MASASQGADDDGSRRKPR  18

sp|P55265|DSRAD_HUMAN       -----------SEKTAESQTPTPSATSFFSGKSPVTTLLECMHKLGNSCEFRLLSKEGPA  641
sp|P78563-2|RED1_HUMAN      ---------FPDTLFNGFETPDKAEPPFYVGSNGD-------------------------  197
sp|Q9NS39|RED2_HUMAN        ---------FPDTLFQEFEPPAPR-PGLAGGRPGD-------------------------  243
sp|Q96M93|ADAD1_HUMAN       ---------SNNHWFQSSQVPSFA--QMLK------------------------KNLPVQ  27
sp|Q8NCV1|ADAD2_HUMAN       LAASLQISPQPRPWRPL---PAQ-----AQ------------------------SAWGPA  46
                                                *

sp|P55265|DSRAD_HUMAN       HEPKFQYCVAVGAQTFPSVSAPSKKVAKQMAAEEAMKALHGEATNSMASDNQPEGMISES  701
sp|P78563-2|RED1_HUMAN      -------------DSFSSSG-----------------------DLSLSASPVPASLAQPP  221
sp|Q9NS39|RED2_HUMAN        -------------AALLSAAYG---------------------RRRLLCRAL--D-LVGP  266
sp|Q96M93|ADAD1_HUMAN       PATK-TI---TTPTGWSSESYGLSKMASK------VTQVTGNFPEPL----LSKNLSSIS  73
sp|Q8NCV1|ADAD2_HUMAN       PAPA-TY---RAEGGWPQVSVLRDSGP-G------AGAGVGELGAARAWENLGEQMGKAP  95
                                             . .

sp|P55265|DSRAD_HUMAN       LDNLESMMPNKVRKIGELVRYLNTNPVGGLLEYARSHGFAAEFKLVDQSGPPHEPKFVYQ  761
sp|P78563-2|RED1_HUMAN      LPVLPPF-----------PPPSGKNPVMILNE----LRPGLKYDFLSESGESHAKSFVMS  266
sp|Q9NS39|RED2_HUMAN        TPAT--P-----------AAPGERNPVVLLNR----LRAGLRYVCLAEPAERRARSFVMA  309
sp|Q96M93|ADAD1_HUMAN       NPVLPPKKI-PKEFIMKYKR-GEINPVSALHQFAQMQRVQLDLKETVTTGNVMGPYFAFC  131
sp|Q8NCV1|ADAD2_HUMAN       RVPVPPAGL-S----LPLKDPPASQAVSLLTEYAASLGIFLLFR----EDQPPGPCFPFS  146
                                                    : *  * .                        *
```

FIG. 8B

```
sp|P55265|DSRAD_HUMAN    --AKVGGRWFPAVCAHSKKQGKQEAADAALRVLIGENEKAE-R-MGFTEVTPVTGASLRR    817
sp|P78563-2|RED1_HUMAN   --VVVDGQFEEGSGRN-KKLAKARAAQSALAAIFNLHLD------QTPSRQPIPSEGLQ-    316
sp|Q9NS39|RED2_HUMAN     --VSVDGRTFEGSGRS-KKLARGQAAQAALQELFDIQMP------GH-----APGRARR-    354
sp|Q96M93|ADAD1_HUMAN    ---AVVDGIQYKTGLGQNKKESRSNAAKLALDEL--LQLDEPEPRILETSGPPFPAEPVVL   188
sp|Q8NCV1|ADAD2_HUMAN    VSAELDGVVCPAGTANSKTEAKQQAALSALCYIRSQLENPE---SPQTSSRPPLAP---LSV  202
                                *    .  .:  .  .* **  .

sp|P55265|DSRAD_HUMAN    TMLLLSRSPEAQPKTLPLTGSTFHDQIAMLSHRCFNTLTNSFQPSLLGRKILAAITMKKD   877
sp|P78563-2|RED1_HUMAN   -------L-HLPQVLADAVSRLVLGKFGDLTDNFSSPHARRKVLAGVVMTTG          360
sp|Q9NS39|RED2_HUMAN     -------T-PMPQEFADSISQLVTQKFREVTTDLTPMHARHKALAGIVMTKG          398
sp|Q96M93|ADAD1_HUMAN    SELAYVSKV--------HYEGRHIQYAKISQIVKERFNQLISNRSEYLKYSSLAAFIIERA  242
sp|Q8NCV1|ADAD2_HUMAN    -------ENILTHEQRCAALVSAGFDLLLDERSPYWACKGTVAGVILERE            245
                                .:   .   :    .      *      :* .:.  ::

sp|P55265|DSRAD_HUMAN    SE-------D-MGVVVSLGTGNRCVKGDSLSLKGETVNDCHAEIISRRGFIRFLYSELMKY   930
sp|P78563-2|RED1_HUMAN   TD-------VKDAKVISVSTGTKCINGEYMSDRGLAINDCHAEIISRRSLLRFLYTQIELY  414
sp|Q9NS39|RED2_HUMAN     LD-------ARQAQVVALSSGTKCISGEHLSDQGLVVNDCHAEVVARRAFLHFLYTQLELH  452
sp|Q96M93|ADAD1_HUMAN    G--------QHEVVAIGTGEYNYSQD-IKPDGRVLHDTHAVVTARRSLLRVFYRQLLLF    292
sp|Q8NCV1|ADAD2_HUMAN    IPRARGHVKEIYKLVALGTGSSCCAGW-LEFSGQQLHDCHGLVIARRALLRFLFRQLLLA   304
                            :::..:*        *        *   .: ** .* : :.  :* .:.:::. :*

sp|P55265|DSRAD_HUMAN    NSQT---AKDSIFEPAKG-GEKLQIKKTVSFHLYISTAPCGDGALFDKSCSD----RAME   982
sp|P78563-2|RED1_HUMAN   LNN-KDDQKRSIFQKSER-G-GFRLKENVQFHLYISTSPCGDARIFSPHE------E--    465
sp|Q9NS39|RED2_HUMAN     LSKRREDSERSIFVRLKE-G-GYRLRENILFHLYVSTSPCGDARLHSPYEIT----TD---  504
sp|Q96M93|ADAD1_HUMAN    YSKNPAMMEKSIFCTEPTS-NLLTLKQNINICLYMNQLPKGSAQIKSQLRLNPHSISAFE  351
sp|Q8NCV1|ADAD2_HUMAN    TQGGPKGKEQSVLAPQPGPGPPFTLKPRVFLHLYISNTPKGAARD---IYLPPTSEGGLP  361
                             .: ::           ::  :  : ** **:.:*     *
```

FIG. 8B(Cont.)

```
sp|P55265|DSRAD_HUMAN      STESRHYPVFENPKQGKLRTKVENGEGTIPVESSDIVPTW-DGIRLGERLRTMSCSDKIL 1041
sp|P78563-2|RED1_HUMAN     EPADRH---PNRKARGQLRTKIESGEGTIPVRSNASIQTW-DGVLQGERLLTMSCSDKIA 521
sp|Q9NS39|RED2_HUMAN       LHSSKH---LVRKFRGHLRTKIESGEGTVPVRGPSAVQTW-DGVLLGEQLITMSCTDKIA 560
sp|Q96M93|ADAD1_HUMAN      ANEELC---LHVAVEGKIYL-----------------TVY-CPKDGVNRISSMSSSDKLT 390
sp|Q8NCV1|ADAD2_HUMAN      HSPPMR---LQAHVLGQLKP-----------------VCYVAPSLCDTHVGCLSASDKLA 401
                                          *::                     :        ::  :*.:**:

sp|P55265|DSRAD_HUMAN      RWNVLGLQGALLTHFLQPIYLKSVTLGY--LFSQGHLTRAICCRVTRDGSAFEDGLRHPF 1099
sp|P78563-2|RED1_HUMAN     RWNVVGIQGSLLSIFVEPIYFSSIILGS--LYHGDHLSRAMYQRISNIED-----LPPLY 574
sp|Q9NS39|RED2_HUMAN       RWNVLGLQGALLSHFVEPVYLQSIVVGS--LHHTGHLARVMSHRMEGVGQ-----LPASY 613
sp|Q96M93|ADAD1_HUMAN      RWEVLGVQGALLSHFIQPVYISSILIGDGNCSDTRGLEIAIKQ---RVDDALTSKLPMFY 447
sp|Q8NCV1|ADAD2_HUMAN      RWAVLGLGGALLAHLVSPLYSTSLILAD-SCHDPPTLSRAIHTRP-CLDSVLGPCLPPPY 459
                           ** *:*: *:**: ::.*:*  *: :.         *  .:        .     *   :
```

FIG. 8B(Cont.)

```
sp|P55265|DSRAD_HUMAN      IVNHPKVGRVS-IYDSKRQSGKTKETSVNWCLADGYDLEILDGTRGTVDG------PRNE  1152
sp|P78563-2|RED1_HUMAN     TLNKPLLSGIS-N-AEARQPGKAPNFSVNWTVGDS-AIEVINATTGKDEL------G--R  623
sp|Q9NS39|RED2_HUMAN       RHNRPLLSGVS-D-AEARQPGKSPPFSMNWVVGSA-DLEIINATTGRRSC------G--G  662
sp|Q96M93|ADAD1_HUMAN      LVNRPHISLVPSAYPL-QMNLEYKFLSLNWAQGDV-SLEIVDGLSGKITESSPFKSGMSM  505
sp|Q8NCV1|ADAD2_HUMAN      VRTALHLFAGPPVAPSEPTPDTCRGLSLNWSLGDP-GIEVVDVATGRVKANA----ALGP  514
                             .   :                    *:**  ..   :*:::   *

sp|P55265|DSRAD_HUMAN      LSRVSKKNIFLLFKKL----CSFRYR-RDLLRLSYGEAKKAARDYETAKNYFKKGLKDMG  1207
sp|P78563-2|RED1_HUMAN     ASRLCKHALYCRWMRVHGKVPSHLLRSKITKPNVYHESKLAAKEYQAAKARLFTAFIKAG  683
sp|Q9NS39|RED2_HUMAN       PSRLCKHVLSARWARLYGRLSTRT-PSPGDTPSMYCEAKLGAHTYQSVKQQLFKAFQKAG  721
sp|Q96M93|ADAD1_HUMAN      ASRLCKAAMLSRFNLLAKEAKK----E-LLEAGTYHAAKCMSASYQEAKCKLKSYLQQHG  560
sp|Q8NCV1|ADAD2_HUMAN      PSRLCKASFLRAFHQAARAVGK----PYLLALKTYEAAK--AGPYQEARRQLSLLLDQQG  568
                            **:.*  :   :         .            *  :*  :  *: .:  :   : . *

sp|P55265|DSRAD_HUMAN      YGNWISKPQEEKNFYLCPV     1226
sp|P78563-2|RED1_HUMAN     LGAWVEKPTEQDQFSLTP-     701
sp|Q9NS39|RED2_HUMAN       LGTWVRKPPEQQQFLLTL-     739
sp|Q96M93|ADAD1_HUMAN      YGSWIVKSPCIEQFNM---     576
sp|Q8NCV1|ADAD2_HUMAN      LGAWPSKPLV-GKFRN---     583
                            * *  *     :*
```

FIG. 8C

```
CLUSTAL O(1.2.4) multiple sequence alignment of ADAT1, ADAR1 (DSRAD), ADAR2 (RED1), ADAR3(RED2),
ADAD1, and ADAD2

*deaminase domain used in application is highlighted in yellow

sp|Q9BUB4|ADAT1_HUMAN      ------------------------------------------------------------   0
sp|P55265|DSRAD_HUMAN      MNPRQGYSLSGYYTHPFQGYEHRQLRYQQPGPGSSPSSFLLKQIEFLKGQLPEAPVIGKQ   60
sp|P78563|RED1_HUMAN       ------------------------------------------------------------   0
sp|Q9NS39|RED2_HUMAN       ------------------------------------------------------------   0
sp|Q96M93|ADAD1_HUMAN      ------------------------------------------------------------   0
sp|Q8NCV1|ADAD2_HUMAN      ------------------------------------------------------------   0

sp|Q9BUB4|ADAT1_HUMAN      ------------------------------------------------------------   0
sp|P55265|DSRAD_HUMAN      TPSLPPSLPGLRPRFPVLLASSTRGRQVDIRGVPRGVHLRSQGLQRGFQHPSPRGRSLPQ   120
sp|P78563|RED1_HUMAN       ------------------------------------------------------------   0
sp|Q9NS39|RED2_HUMAN       ------------------------------------------------------------   0
sp|Q96M93|ADAD1_HUMAN      ------------------------------------------------------------   0
sp|Q8NCV1|ADAD2_HUMAN      ------------------------------------------------------------   0

sp|Q9BUB4|ADAT1_HUMAN      ------------------------------------------------------------   0
sp|P55265|DSRAD_HUMAN      RGVDCLSSHFQELSIYQDQEQRILKFLEELGEGKATTAHDLSGKLGTPKKEINRVLYSLA   180
sp|P78563|RED1_HUMAN       ------------------------------------------------------------   0
sp|Q9NS39|RED2_HUMAN       ------------------------------------------------------------   0
sp|Q96M93|ADAD1_HUMAN      ------------------------------------------------------------   0
sp|Q8NCV1|ADAD2_HUMAN      ------------------------------------------------------------   0

sp|Q9BUB4|ADAT1_HUMAN      ------------------------------------------------------------   0
sp|P55265|DSRAD_HUMAN      KKGKLQKEAGTPPLWKIAVSTQAWNQHSGVVRPDGHSQGAPNSDPSLEPEDRNSTSVSED   240
sp|P78563|RED1_HUMAN       ------------------------------------------------------------   0
sp|Q9NS39|RED2_HUMAN       ------------------------------------------------------------   0
sp|Q96M93|ADAD1_HUMAN      ------------------------------------------------------------   0
sp|Q8NCV1|ADAD2_HUMAN      ------------------------------------------------------------   0
```

FIG. 9A

```
sp|Q9BUB4|ADAT1_HUMAN    ------------------------------------------------------------    0
sp|P55265|DSRAD_HUMAN    LLEPFIAVSAQAWNQHSGVVRPDSHSQGSPNSDPGLEPEDSNSTSALEDPLEFLDMAEIK    300
sp|P78563|RED1_HUMAN     ------------------------------------------------------------    0
sp|Q9NS39|RED2_HUMAN     ------------------------------------------------------------    0
sp|Q96M93|ADAD1_HUMAN    ------------------------------------------------------------    0
sp|Q8NCV1|ADAD2_HUMAN    ------------------------------------------------------------    0

sp|Q9BUB4|ADAT1_HUMAN    ------------------------------------------------------------    0
sp|P55265|DSRAD_HUMAN    EKICDYLFNVSDSSALNLAKNIGLTKARDINAVLIDMERQGDVYRQGTTPPIWHLTDKKR    360
sp|P78563|RED1_HUMAN     ------------------------------------------------------------    0
sp|Q9NS39|RED2_HUMAN     -----------------------------MASVLGSGRGSG------GLSSQLKCKSKRR    25
sp|Q96M93|ADAD1_HUMAN    ------------------------------------------------------------    0
sp|Q8NCV1|ADAD2_HUMAN    ------------------------------------------------------------    0

sp|Q9BUB4|ADAT1_HUMAN    ------------------------------------------------------------    0
sp|P55265|DSRAD_HUMAN    ERMQIKRN-TNSVPETAPAAIPETKRNAEFLTCNIPTSNASNNMVTTEKVENGQEPVIKL    419
sp|P78563|RED1_HUMAN     -----------------------------------MDIEDEENMSSSS------TDVKEN    19
sp|Q9NS39|RED2_HUMAN     RRRRSKRKDKVSILSTFLA--P-----FKHLSPGITNTEDDDTLSTSS------AEVKEN    72
sp|Q96M93|ADAD1_HUMAN    ------------------------------------------------------------    0
sp|Q8NCV1|ADAD2_HUMAN    ------------------------------------------------------------    0

sp|Q9BUB4|ADAT1_HUMAN    ------------------------------------------------------------    0
sp|P55265|DSRAD_HUMAN    ENRQEARPEPARLKPPVHYNGPSKAGYVDFENGQWATDDIPDDLNSIRAAPGEFRAIMEM    479
sp|P78563|RED1_HUMAN     RNLDNVSPKDG------STPGPGEGSQL--SNGG-------------GGGPGRKRPLEEG    58
sp|Q9NS39|RED2_HUMAN     RNVGNLAARPP------------PSGDR--ARGG-------------APGAKRKRPLEEG    105
sp|Q96M93|ADAD1_HUMAN    ------------------------------------------------------------    0
sp|Q8NCV1|ADAD2_HUMAN    ------------------------------------------------------------    0
```

FIG. 9A(Cont.)

```
sp|Q9BUB4|ADAT1_HUMAN    ------------------------------------------------------------   0
sp|P55265|DSRAD_HUMAN    PSFYSHGLPRCSPYKKLTECQLKNPISGLLEYAQFASQTCEFNMIEQSGPPHEPRFKFQV   539
sp|P78563|RED1_HUMAN     S--NGHSKYRLKKRRKTPGP--VLPKNALMQLN-EIKPGLQYTLLSQTGPVHAPLFVMSV   113
sp|Q9NS39|RED2_HUMAN     N--GGHLCKLQLVWKKLSWS--VAPKNALVQLH-ELRPGLQYRTVSQTGPVHAPVFAVAV   160
sp|Q96M93|ADAD1_HUMAN    ------------------------------------------------------------   0
sp|Q8NCV1|ADAD2_HUMAN    ------------------------------------------------------------   0

sp|Q9BUB4|ADAT1_HUMAN    ------------------------------------------------------------   0
sp|P55265|DSRAD_HUMAN    VINGREFPPAEAGSKKVAKQDAAMKAMTILLEEAKAKDSG-----KSEESSHYSTEKE--   592
sp|P78563|RED1_HUMAN     EVNGQVFEGSGPTKKK-AKLHAAEKALRSFVQFPNASEAHLAMGRTLSVNTDFTSDQADF   172
sp|Q9NS39|RED2_HUMAN     EVNGLTFEGTGPTKKK-AKMRAAELALRSFVQFPNACQAHLAMGGGPGPGTDFTSDQADF   219
sp|Q96M93|ADAD1_HUMAN    --------------------------------MA-------------------------S   3
sp|Q8NCV1|ADAD2_HUMAN    --------------------------------MASASQGADDDGSRRKPRLAASLQISPQ   28

sp|Q9BUB4|ADAT1_HUMAN    ------------------------------------------------------------   0
sp|P55265|DSRAD_HUMAN    -SEKTAESQTPTPSATSFFSGKSPVTTLLECMHKLGNSCEFRLLSKEGPAHEPKFQYCVA   651
sp|P78563|RED1_HUMAN     PDTLFNGFETPDKAEPPFYVGSNG------------------------------------   196
sp|Q9NS39|RED2_HUMAN     PDTLFQEFEPPAPR-PGLAGGRPG------------------------------------   242
sp|Q96M93|ADAD1_HUMAN    NNHWFQSSQVPSFA--QMLK------------------------KNLPVQPATK-T---I   33
sp|Q8NCV1|ADAD2_HUMAN    PRPWRPL---PAQ-----AQ------------------------SAWGPAPAPA-T---Y   52

sp|Q9BUB4|ADAT1_HUMAN    ------------------------------------------------------------   0
sp|P55265|DSRAD_HUMAN    VGAQTFPSVSAPSKKVAKQMAAEEAMKALHGEATNSMASDNQPEGMISESLDNLESMMPN   711
sp|P78563|RED1_HUMAN     --DDSFSSSG-----------------------DLSLSASPVPASLAQPPLPVLPPF---   228
sp|Q9NS39|RED2_HUMAN     --DAALLSAAYG---------------------RRRLLCRAL--D-LVGPTPAT--P---   271
sp|Q96M93|ADAD1_HUMAN    TTPTGWSSESYGLSKMASK------VTQVTGNFPEPL----LSKNLSSISNPVLPPKKI-   82
sp|Q8NCV1|ADAD2_HUMAN    RAEGGWPQVSVLRDSGP-G------AGAGVGELGAARAWENLGEQMGKAPRVPVPPAGL-   104
```

FIG. 9B

```
sp|Q9BUB4|ADAT1_HUMAN     ------------------------------------------------------------   0
sp|P55265|DSRAD_HUMAN     KVRKIGELVRYLNTNPVGGLLEYARSHGFAAEFKLVDQSGPPHEPKFVYQ--AKVGGRWF   769
sp|P78563|RED1_HUMAN      --------PPPSGKNPVMILNE----LRPGLKYDFLSESGESHAKSFVMS--VVVDGQFF   274
sp|Q9NS39|RED2_HUMAN      --------AAPGERNPVVLLNR----LRAGLRYVCLAEPAERRARSFVMA--VSVDGRTF   317
sp|Q96M93|ADAD1_HUMAN     PKEFIMKYKR-GEINPVSALHQFAQMQRVQLDLKETVTTGNVMGPYFAFC--AVVDGIQY   139
sp|Q8NCV1|ADAD2_HUMAN     S----LPLKDPPASQAVSLLTEYAASLGIFLLFR----EDQPPGPCFPFSVSAELDGVVC   156

sp|Q9BUB4|ADAT1_HUMAN     ------------------------------------------------------------   0
sp|P55265|DSRAD_HUMAN     PAVCAHSKKQGKQEAADAALRVLIGENEKAE--RMGFTEVTPVTGASLRRTMLLLSRSPE   827
sp|P78563|RED1_HUMAN      EGSGRN-KKLAKARAAQSALAAIFNLHLD------QTPSRQPIPSEGLQ-----------   316
sp|Q9NS39|RED2_HUMAN      EGSGRS-KKLARGQAAQAALQELFDIQMP------GH-----APGRARR-----------   354
sp|Q96M93|ADAD1_HUMAN     KTGLGQNKKESRSNAAKLALDEL-LQLDEPEPRILETSGPPPFPAEPVVLSELAYVSKV-   197
sp|Q8NCV1|ADAD2_HUMAN     PAGTANSKTEAKQQAALSALCYIRSQLENPE--SPQTSSRPPLAP--LSV----------   202

sp|Q9BUB4|ADAT1_HUMAN     ----------MWTADEIAQLCYEHYGIRLPKKGKPEPNHEWTLLAAVVKIQSPADKACDT   50
sp|P55265|DSRAD_HUMAN     AQPKTLPLTGSTFHDQIAMLSHRCFNTLTNSFQPS--LLGRKILAAIIM-----KKDSE-   879
sp|P78563|RED1_HUMAN      -----L-HLPQVLADAVSRLVLGKFGDLTDNFSSP--HARRKVLAGVVM-----TTGTD-   362
sp|Q9NS39|RED2_HUMAN      -----T-PMPQEFADSISQLVTQKFREVTTDLTPM--HARHKALAGIVM-----TKGLD-   400
sp|Q96M93|ADAD1_HUMAN     -----HYEGRHIQYAKISQIVKERFNQLISNRSEY--LKYSSSLAAFII-----ERAG--   243
sp|Q8NCV1|ADAD2_HUMAN     -------ENILTHEQRCAALVSAGFDLLLDERSPY--WACKGTVAGVIL-----EREIPR   248
                                           : :    :     .            :*..:

sp|Q9BUB4|ADAT1_HUMAN     PDKPVQVTKEVVSMGTGTKCIGQSKMRKNGDILNDSHAEVIARRSFQRYLLHQLQLAATL   110
sp|P55265|DSRAD_HUMAN     -----D-MGVVVSLGTGNRCVKGDSLSLKGETVNDCHAEIISRRGFIRFLYSELMKYNSQ   933
sp|P78563|RED1_HUMAN      -----VKDAKVISVSTGTKCINGEYMSDRGLALNDCHAEIISRRSLLRFLYTQLELYLNN   417
sp|Q9NS39|RED2_HUMAN      -----ARQAQVVALSSGTKCISGEHLSDQGLVVNDCHAEVVARRAFLHFLYTQLELHLSK   455
sp|Q96M93|ADAD1_HUMAN     -------QHEVVAIGTGEYNYSQD-IKPDGRVLHDTHAVVTARRSLLRYFYRQLLLFYSK   295
sp|Q8NCV1|ADAD2_HUMAN     ARGHVKEIYKLVALGTGSSCCAGW-LEFSGQQLHDCHGLVIARRALLRFLFRQLLLATQG   307
                                    ::::.:*        :   *  ::* *. : :**.: :::  :*
```

FIG. 9B(Cont.)

```
sp|Q9BUB4|ADAT1_HUMAN      ----KEDSIFVPGTQKG-VWKLRRDLIFVFFSSHTPCGDASIIPMLEFEDQP---CCPVF    162
sp|P55265|DSRAD_HUMAN      T---AKDSIFEPAKG-GEKLQIKKTVSFHLYISTAPCGDGALFDKSCSDRAM--------    981
sp|P78563|RED1_HUMAN       -KDDQKRSIFQKSER-G-GFRLKENVQFHLYISTSPCGDARIFSPHEPILEGSRSYTQAG    474
sp|Q9NS39|RED2_HUMAN       RREDSERSIFVRLKE-G-GYRLRENILFHLYVSTSPCGDARLHSPYEITTD---------    504
sp|Q96M93|ADAD1_HUMAN      NPAMMEKSIFCTEPTS-NLLTLKQNINICLYMNQLPKGSAQIKSQLRLNPHSI-------    347
sp|Q8NCV1|ADAD2_HUMAN      GPKGKEQSVLAPQPGPGPPFTLKPRVFLHLYISNTPKGAARD---IYLPPTSE-------    357
                                : *::           ::  : : :: .  * * .
```

FIG. 9B(Cont.)

```
sp|Q9BUB4|ADAT1_HUMAN    RNWAHNSSVEASSNLEAPGNERKCEDPDSPVTKKMRLEPGTAAREVTNGAAHHQSFGKQK  222
sp|P55265|DSRAD_HUMAN    ----------ES----------------------------T-------ESRHYPVFENPK  996
sp|P78563|RED1_HUMAN     VQWCNHGSLQPRPP----G---LLSDPSTSTF----QGAGT-------TEPADRHPNRKA  516
sp|Q9NS39|RED2_HUMAN     -------------------------------------------------LHSSKHLVRKF  515
sp|Q96M93|ADAD1_HUMAN    ------SAFEANEE---------------------------------------LCLHVAV  362
sp|Q8NCV1|ADAD2_HUMAN    ------GGLPHSPP---------------------------------------MRLQAHV  372

sp|Q9BUB4|ADAT1_HUMAN    SGPISPGIHSCDLTVEGLATVTRIAPGSAKVIDVYRTGAKCVPGEAGDSGKPGAAFHQVG  282
sp|P55265|DSRAD_HUMAN    QGKLRTKVEN---------------------------GEGTIPVESS---------DIVP  1020
sp|P78563|RED1_HUMAN     RGQLRTKIES---------------------------GEGTIPVRSN---------ASIQ  540
sp|Q9NS39|RED2_HUMAN     RGHLRTKIES---------------------------GEGTVPVRGP---------SAVQ  539
sp|Q96M93|ADAD1_HUMAN    EGKIYLT-----------------------------------------------------  369
sp|Q8NCV1|ADAD2_HUMAN    LGQLKPV-----------------------------------------------------  379
                          * :

sp|Q9BUB4|ADAT1_HUMAN    LLRVKPGRGDRTRSMSCSDKMARWNVLGCQGALLMHLLEEPIYLSAVVIGK-CPYSQEAM  341
sp|P55265|DSRAD_HUMAN    TW-DGIRLGERLRTMSCSDKILRWNVLGLQGALLTHFL-QPIYLKSVTLGY--LFSQGHL  1076
sp|P78563|RED1_HUMAN     TW-DGVLQGERLLTMSCSDKIARWNVVGIQGSLLSIFV-EPIYFSSIILGS--LYHGDHL  596
sp|Q9NS39|RED2_HUMAN     TW-DGVLLGEQLITMSCTDKIARWNVLGLQGALLSHFV-EPVYLQSIVVGS--LHHTGHL  595
sp|Q96M93|ADAD1_HUMAN    VY-CPKDGVNRISSMSSSDKLTRWEVLGVQGALLSHFI-QPVYISSILIGDGNCSDTRGL  427
sp|Q8NCV1|ADAD2_HUMAN    CYVAPSLCDTHVGCLSASDKLARWAVLGLGGALLAHLV-SPLYSTSLILAD-SCHDPPTL  437
                                   :   :*.:**: ** *:*  *:**  :: .*:*  :: :.         :

sp|Q9BUB4|ADAT1_HUMAN    QRALIGRCQNVSA-----LPKGFGVQELKILQSDLLFEQSRSAVQAKRADSPGRLVPCGA  396
sp|P55265|DSRAD_HUMAN    TRAICCRVTRDGSAFEDGLRHPFIVNHPKVGRVS-IYDSK---------RQSGK--TKET  1124
sp|P78563|RED1_HUMAN     SRAMYQRISNIED-----LPPLYTLNKPLLSGIS-N-AEA---------RQPGK--APNF  638
sp|Q9NS39|RED2_HUMAN     ARVMSHRMEGVGQ-----LPASYRHNRPLLSGVS-D-AEA---------RQPGK--SPPF  637
sp|Q96M93|ADAD1_HUMAN    EIAIKQ---RVDDALTSKLPMFYLVNRPHISLVPSAYPL----------QMNLE--YKFL  472
sp|Q8NCV1|ADAD2_HUMAN    SRAIHTRP-CLDSVLGPCLPPPYVRTALHLFAGPPVAPSE---------PTPDT--CRGL  485
                           .:              *   :      :
```

FIG. 9C

```
sp|Q9BUB4|ADAT1_HUMAN     AISWSAVPEQPLDVTANGFPQGTTKKTIG------SLQARSQISKVELFRSFQKLLSRIA   450
sp|P55265|DSRAD_HUMAN     SVNWCLADGYDLEIL-----DGTRGTVDG------PRNELSRVSKKNIFLLFKKL----C   1169
sp|P78563|RED1_HUMAN      SVNWTVGDS-AIEVI-----NATTGKDEL------G--RASRLCKHALYCRWMRVHGKVP   684
sp|Q9NS39|RED2_HUMAN      SMNWVVGSA-DLEII-----NATTGRRSC------G--GPSRLCKHVLSARWARLYGRLS   683
sp|Q96M93|ADAD1_HUMAN     SLNWAQGDV-SLEIV-----DGLSGKITESSPFKSGMSMASRLCKAAMLSRFNLLAKEAK   526
sp|Q8NCV1|ADAD2_HUMAN     SLNWSLGDP-GIEVV-----DVATGRVKANA----ALGPPSRLCKASFLRAFHQAARAVG   535
                          ::.*       :::      :                   *::.*  :   :

sp|Q9BUB4|ADAT1_HUMAN     RDKWPHSLRVQKLDTYQEYKEAASSYQEAWS----TLRKQVFGSWIRNPPDYHQFK----   502
sp|P55265|DSRAD_HUMAN     SFRYR---RDLLRLSYGEAKKAARDYETAKNYFKKGLKDMGYGNWISKPQEEKNFYLCPV   1226
sp|P78563|RED1_HUMAN      SHLLRS--KITKPNVYHESKLAAKEYQAAKARLFTAFIKAGLGAWVEKPTEQDQFSLTP-   741
sp|Q9NS39|RED2_HUMAN      TRT-PS--PGDTPSMYCEAKLGAHTYQSVKQQLFKAFQKAGLGTWVRKPPEQQQFLLTL-   739
sp|Q96M93|ADAD1_HUMAN     K----E---LLEAGTYHAAKCMSASYQEAKCKLKSYLQQHGYGSWIVKSPCIEQFNM---   576
sp|Q8NCV1|ADAD2_HUMAN     K----P--YLLALKTYEAAK--AGPYQEARRQLSLLLDQQGLGAWPSKPLV-GKFRN---   583
                                         *   *  :  *: .       : .   * *  :     :*
```

FIG. 9C(Cont.)

sp|Q9BUB4|ADAT1_HUMAN 0.35074
sp|P55265|DSRAD_HUMAN 0.34445
sp|P78563|RED1_HUMAN 0.22818
sp|Q9NS39|RED2_HUMAN 0.23156
sp|Q96M93|ADAD1_HUMAN 0.33847
sp|Q8NCV1|ADAD2_HUMAN 0.34751

| CMV | MCP | Linker | ADAR2-DD (316-468) | Protein A | ADAR2-DD (469-700) | Protein B | TagBFP |

| NAME | SID | AMINO ACID SEQUENCE |
|---|---|---|
| MCP-<br>linker-<br>ADAR2-<br>DDN-<br>Bad(L)-<br>ADAR2(E488Q)<br>-<br>DDC-<br>TagRFP<br><br>Also<br>known as<br>"nDD-<br>BAD-<br>cDD" or<br>"BAD(L)<br>Only" | 88 | MASNFTQFVLVDNGGTGDVTVAPSNFANGIAEWISSNSRSQA<br>YKVTCSVRQSSAQNRKYTIKVEVPKGAWRSYLNMELTIPIFA<br>TNSDCELIVKAMQGLLKDGNPIPSAIAANSGIYGGSGSGAGS<br>GSPAGGGAPGSGGGSQLHLPQVLADAVSRLVLGKFGDLTDN<br>FSSPHARRKVLAGVVMTTGTDVKDAKVISVSTGTKCINGEY<br>MSDRGLALNDCHAEIISRRSLLRFLYTQLELYLNNKDDQKRSI<br>FQKSERGGFRLKENVQFHLYISTSPCGDARIFSPHEPILEEPAA<br>SGSGTGAPPNLWAAQRYGRELRRMSDELVDRHPNRKARGQ<br>LRTKIESGQGTIPVRSNASIQTWDGVLQGERLLTMSCSDKIAR<br>WNVVGIQGSLLSIFVEPIYFSSIILGSLYHGDHLSRAMYQRISN<br>IEDLPPLYTLNKPLLSGISNAEARQPGKAPNFSVNWTVGDSAI<br>EVINATTGKDELGRASRLCKHALYCRWMRVHGKVPSHLLRS<br>KITKPNVYHESKLAAKEYQAAKARLFTAFIKAGLGAWVEKP<br>TEQDQFSLTGSGSSELIKENMHMKLYMEGTVDNHHFKCTSE<br>GEGKPYEGTQTMRIKVVEGGPLPFAFDILATSFLYGSKTFINH<br>TQGIPDFFKQSFPEGFTWERVTTYEDGGVLTATQDTSLQDGC<br>LIYNVKIRGVNFTSNGPVMQKKTLGWEAFTETLYPADGGLE<br>GRNDMALKLVGGSHLIANIKTTYRSKKPAKNLKMPGVYYV<br>DYRLERIKEANNETYVEQHEVAVARYCDLPSKLGHKLN* |

FIG. 14A

| NAME | SID | AMINO ACID SEQUENCE |
|---|---|---|
| MCP-<br>linker-<br>BclxL -<br>linker -<br>ADAR2-<br>DDN-<br>Bad(L)-<br>ADAR2(E488Q)<br>-<br>DDC-<br>TagBFP<br><br><br><br>Also<br>known as<br>"BclxL-<br>nDD-<br>BAD-<br>cDD" | 89 | MASNFTQFVLVDNGGTGDVTVAPSNFANGIAEWISSNSRSQA<br>YKVTCSVRQSSAQNRKYTIKVEVPKGAWRSYLNMELTIPIFA<br>TNSDCELIVKAMQGLLKDGNPIPSAIAANSGIYGGSGSGAGS<br>GSPAGGGAPGSGGGSQSNRELVVDFLSYKLSQKGYSWSQFS<br>DVEENRTEAPEGTESEMETPSAINGNPSWHLADSPAVNGATG<br>HSSSLDAREVIPMAAVKQALREAGDEFELRYRRAFSDLTSQL<br>HITPGTAYQSFEQVVNELFRDGVNWGRIVAFFSFGGALCVES<br>VDKEMQVLVSRIAAWMATYLNDHLEPWIQENGGWDTFVEL<br>YGNNAAGGSGGSGGSGGSAAAQLHLPQVLADAVSRLVLGK<br>FGDLTDNFSSPHARRKVLAGVVMTTGTDVKDAKVISVSTGT<br>KCINGEYMSDRGLALNDCHAEIISRRSLLRFLYTQLELYLNN<br>KDDQKRSIFQKSERGGFRLKENVQFHLYISTSPCGDARIFSPH<br>EPILEEPAASGSGTGAPPNLWAAQRYGRELRRMSDELVDRHP<br>NRKARGQLRTKIESGQGTIPVRSNASIQTWDGVLQGERLLTM<br>SCSDKIARWNVVGIQGSLLSIFVEPIYFSSIILGSLYHGDHLSR<br>AMYQRISNIEDLPPLYTLNKPLLSGISNAEARQPGKAPNFSVN<br>WTVGDSAIEVINATTGKDELGRASRLCKHALYCRWMRVHG<br>KVPSHLLRSKITKPNVYHESKLAAKEYQAAKARLFTAFIKAG<br>LGAWVEKPTEQDQFSLTGSGSSELIKENMHMKLYMEGTVDN<br>HHFKCTSEGEGKPYEGTQTMRIKVVEGGPLPFAFDILATSFLY<br>GSKTFINHTQGIPDFFKQSFPEGFTWERVTTYEDGGVLTATQD<br>TSLQDGCLIYNVKIRGVNFTSNGPVMQKKTLGWEAFTETLYP<br>ADGGLEGRNDMALKLVGGSHLIANIKTTYRSKKPAKNLKMP<br>GVYYVDYRLERIKEANNETYVEQHEVAVARYCDLPSKL GHK<br>LN* |

FIG. 14A(Cont.)

| NAME | SID | AMINO ACID SEQUENCE |
|---|---|---|
| MCP-linker-<br>ADAR2-<br>DDN -<br>Bad(L)-<br>ADAR2(E488Q)<br>-DDC-<br>Bcl-xL-<br>TagBFP<br><br>Also known as "nDD-BAD-cDD-Bcl-xL" and "BAD(L)" | 90 | MASNFTQFVLVDNGGTGDVTVAPSNFANGIAEWISSNSRSQAYKVTC<br>SVRQSSAQNRKYTIKVEVPKGAWRSYLNMELTIPIFATNSDCELIVKA<br>MQGLLKDGNPIPSAIAANSGIYGGSGSGAGSGSPAGGGAPGSGGGSQL<br>HLPQVLADAVSRLVLGKFGDLTDNFSSPHARRKVLAGVVMTTGTDV<br>KDAKVISVSTGTKCINGEYMSDRGLALNDCHAEIISRRSLLRFLYTQLE<br>LYLNNKDDQKRSIFQKSERGGFRLKENVQFHLYISTSPCGDARIFSPHE<br>PILEEPAASGSGTGAPPNLWAAQRYGRELRRMSDELVDRHPNRKARG<br>QLRTKIESGQGTIPVRSNASIQTWDGVLQGERLLTMSCSDKIARWNVV<br>GIQGSLLSIFVEPIYFSSIILGSLYHGDHLSRAMYQRISNIEDLPPLYTLN<br>KPLLSGISNAEARQPGKAPNFSVNWTVGDSAIEVINATTGKDELGRAS<br>RLCKHALYCRWMRVHGKVPSHLLRSKITKPNVYHESKLAAKEYQAA<br>KARLFTAFIKAGLGAWVEKPTEQDQFSLTGSAAGGSGGSAAASSNRE<br>LVVDFLSYKLSQKGYSWSQFSDVEENRTEAPEGTESEMETPSAINGNP<br>SWHLADSPAVNGATGHSSSLDAREVIPMAAVKQALREAGDEFELRYR<br>RAFSDLTSQLHITPGTAYQSFEQVVNELFRDGVNWGRIVAFFSFGGAL<br>CVESVDKEMQVLVSRIAAWMATYLNDHLEPWIQENGGWDTFVELYG<br>NNGSSELIKENMHMKLYMEGTVDNHHFKCTSEGEGKPYEGTQTMRIK<br>VVEGGPLPFAFDILATSFLYGSKTFINHTQGIPDFFKQSFPEGFTWERVT<br>TYEDGGVLTATQDTSLQDGCLIYNVKIRGVNFTSNGPVMQKKTLGWE<br>AFTETLYPADGGLEGRNDMALKLVGGSHLIANIKTTYRSKKPAKNLK<br>MPGVYYVDYRLERIKEANNETYVEQHEVAVARYCDLPSKLGHKLN* |

FIG. 14B

| NAME | SID | AMINO ACID SEQUENCE |
|---|---|---|
| MCP-linker-BAD-ADAR2-DD(E488Q)-TagBFP<br><br>Also known as "BAD-DD" | 91 | MASNFTQFVLVDNGGTGDVTVAPSNFANGIAEWISSNSRSQAYKVTC<br>SVRQSSAQNRKYTIKVEVPKGAWRSYLNMELTIPIFATNSDCELIVKA<br>MQGLLKDGNPIPSAIAANSGIYGGSGSGAGSGSPAGGGAPGSGGGSTG<br>APPNLWAAQRYGRELRRMSDEFVDSFKKASQLHLPQVLADAVSRLVL<br>GKFGDLTDNFSSPHARRKVLAGVVMTTGTDVKDAKVISVSTGTKCIN<br>GEYMSDRGLALNDCHAEIISRRSLLRFLYTQLELYLNNKDDQKRSIFQ<br>KSERGGFRLKENVQFHLYISTSPCGDARIFSPHEPILEEPADRHPNRKAR<br>GQLRTKIESGQGTIPVRSNASIQTWDGVLQGERLLTMSCSDKIARWNV<br>VGIQGSLLSIFVEPIYFSSIILGSLYHGDHLSRAMYQRISNIEDLPPLYTL<br>NKPLLSGISNAEARQPGKAPNFSVNWTVGDSAIEVINATTGKDELGRA<br>SRLCKHALYCRWMRVHGKVPSHLLRSKITKPNVYHESKLAAKEYQA<br>AKARLFTAFIKAGLGAWVEKPTEQDQFSLTGSGSSELIKENMHMKLY<br>MEGTVDNHHFKCTSEGEGKPYEGTQTMRIKVVEGGPLPFAFDILATSF<br>LYGSKTFINHTQGIPDFFKQSFPEGFTWERVTTYEDGGVLTATQDTSLQ<br>DGCLIYNVKIRGVNFTSNGPVMQKKTLGWEAFTETLYPADGGLEGRN<br>DMALKLVGGSHLIANIKTTYRSKKPAKNLKMPGVYYVDYRLERIKEA<br>NNETYVEQHEVAVARYCDLPSKLGHKLN* |

FIG. 14B(Cont.)

| NAME | SID | AMINO ACID SEQUENCE |
|---|---|---|
| MCP-<br>linker-<br>BAD-<br>ADAR2-<br>DD(E488Q)<br>-Bcl-<br>xL-<br>TagRFP<br><br>Also<br>known as<br>"BAD-<br>DD-<br>BclxL"<br>and "WT" | 92 | MASNFTQFVLVDNGGTGDVTVAPSNFANGIAEWISSNSRSQ<br>AYKVTCSVRQSSAQNRKYTIKVEVPKGAWRSYLNMELTIPI<br>FATNSDCELIVKAMQGLLKDGNPIPSAIAANSGIYGGSGSG<br>AGSGSPAGGGAPGSGGGSTGAPPNLWAAQRYGRELRRMS<br>DEFVDSFKKASQLHLPQVLADAVSRLVLGKFGDLTDNFSSP<br>HARRKVLAGVVMTTGTDVKDAKVISVSTGTKCINGEYMS<br>DRGLALNDCHAEIISRRSLLRFLYTQLELYLNNKDDQKRSIF<br>QKSERGGFRLKENVQFHLYISTSPCGDARIFSPHEPILEEPAD<br>RHPNRKARGQLRTKIESGQGTIPVRSNASIQTWDGVLQGE<br>RLLTMSCSDKIARWNVVGIQGSLLSIFVEPIYFSSIILGSLYH<br>GDHLSRAMYQRISNIEDLPPLYTLNKPLLSGISNAEARQPG<br>KAPNFSVNWTVGDSAIEVINATTGKDELGRASRLCKHALY<br>CRWMRVHGKVPSHLLRSKITKPNVYHESKLAAKEYQAAK<br>ARLFTAFIKAGLGAWVEKPTEQDQFSLTGSAAAS SNRELVV<br>DFLSYKLSQKGYSWSQFSDVEENRTEAPEGTESEMETPSAI<br>NGNPSWHLADSPAVNGATGHSSSLDAREVIPMAAVKQALR<br>EAGDEFELRYRRAFSDLTSQLHITPGTAYQSFEQVVNELFR<br>DGVNWGRIVAFFSFGGALCVESVDKEMQVLVSRIAAWMA<br>TYLNDHLEPWIQENGGWDTFVELYGNNGSSELIKENMHM<br>KLYMEGTVDNHHFKCTSEGEGKPYEGTQTMRIKVVEGGP<br>LPFAFDILATSFLYGSKTFINHTQGIPDFFKQSFPEGFTWERV<br>TTYEDGGVLTATQDTSLQDGCLIYNVKIRGVNFTSNGPVM<br>QKKTLGWEAFTETLYPADGGLEGRNDMALKLVGGSHLIA<br>NIKTTYRSKKPAKNLKMPGVYYVDYRLERIKEANNETYVE<br>QHEVAVARYCDLPSKLGHKLN* |

FIG. 14C

| NAME | SID | AMINO ACID SEQUENCE |
|---|---|---|
| MCP-linker-ADAR2-DDN-Bad(F)-ADAR2 (E488Q)-DDC-Bcl-xL-mCherry-P2A-T2A-UAG-UAG-MS2-P2A-T2A-HA-mNeonGreen(M10K) | 93 | MASNFTQFVLVDNGGTGDVTVAPSNFANGIAEWISSNSRSQA YKVTCSVRQSSAQNRKYTIKVEVPKGAWRSYLNMELTIPIFA TNSDCELIVKAMQGLLKDGNPIPSAIAANSGIYGGSGSGAGS GSPAGGGAPGSGGGSQLHLPQVLADAVSRLVLGKFGDLTDN FSSPHARRKVLAGVVMTTGTDVKDAKVISVSTGTKCINGEY MSDRGLALNDCHAEIISRRSLLRFLYTQLELYLNNKDDQKRSI FQKSERGGFRLKENVQFHLYISTSPCGDARIFSPHEPILEEPAA SGSGTGAPPNLWAAQRYGRELRRMSDEFVDRHPNRKARGQL RTKIESGQGTIPVRSNASIQTWDGVLQGERLLTMSCSDKIAR WNVVGIQGSLLSIFVEPIYFSSIILGSLYHGDHLSRAMYQRISN IEDLPPLYTLNKPLLSGISNAEARQPGKAPNFSVNWTVGDSAI EVINATTGKDELGRASRLCKHALYCRWMRVHGKVPSHLLRS KITKPNVYHESKLAAKEYQAAKARLFTAFIKAGLGAWVEKP TEQDQFSLTGSGGTENLYFQSAASSNRELVVDFLSYKLSQKG YSWSQFSDVEENRTEAPEGTESEMETPSAINGNPSWHLADSP AVNGATGHSSSLDAREVIPMAAVKQALREAGDEFELRYRRAF SDLTSQLHITPGTAYQSFEQVVNELFRDGVNWGRIVAFFSFGG ALCVESVDKEMQVLVSRIAAWMATYLNDHLEPWIQENGGW DTFVELYGNNGSSELIKENMHMKRPSVATMVSKGEEDNMAII KEFMRFKVHMEGSVNGHEFEIEGEGEGRPYEGTQTAKLKVT KGGPLPFAWDILSPQFMYGSKAYVKHPADIPDYLKLSFPEGF KWERVMNFEDGGVVTVTQDSSLQDGEFIYKVKLRGTNFPSD GPVMQKKTMGWEASSERMYPEDGALKGEIKQRLKLKDGG HYDAEVKTTYKAKKPVQLPGAYNVNIKLDITSHNEDYTIVE QYERAEGRHSTGGMDELYKDYKDDDDKGSGATNFSLLKQA GDVEENPGPASAGSGEGRGSLLTCGDVEENPGPATGNSA*R* LCQRHAKHEDHPCTSATNFSLLKQAGDVEENPGPGGSEGRG SLLTCGDVEENPGPSGYPYDVPDYAIDVSKGEEDNKASLPAT HELHIFGSINGVDFDMVGQGTGNPNDGYEELNLKSTKGDLQ FSPWILVPHIGYGFHQYLPYPDGMSPFQAAMVDGSGYQVHR TMQFEDGASLTVNYRYTYEGSHIKGEAQVKGTGFPADGPVM TNSLTAADWCRSKKTYPNDKTIISTFKWSYTTGNGKRYRSTA RTTYTFAKPMAANYLKNQPMYVFRKTELKHSKTELNFKEW QKAFTDVMGMDELYKAS* |

FIG. 15A

| NAME | SID | AMINO ACID SEQUENCE |
|---|---|---|
| MCP-linker-ADAR2-DDN-Bad(F)-ADAR2 (E488Q)-DDC-Bcl-xL-mCherry-P2A-T2A-UAG-UAG-MS2-HaloTag-UAG-UAG-MS2-P2A-T2A-HA-mNeonGreen(M10K) | 94 | MASNFTQFVLVDNGGTGDVTVAPSNFANGIAEWISSNSRSQ<br>AYKVTCSVRQSSAQNRKYTIKVEVPKGAWRSYLNMELTIPI<br>FATNSDCELIVKAMQGLLKDGNPIPSAIAANSGIYGGSGSGA<br>GSGSPAGGGAPGSGGGSQLHLPQVLADAVSRLVLGKFGDLT<br>DNFSSPHARRKVLAGVVMTTGTDVKDAKVISVSTGTKCIN<br>GEYMSDRGLALNDCHAEIISRRSLLRFLYTQLELYLNNKDD<br>QKRSIFQKSERGGFRLKENVQFHLYISTSPCGDARIFSPHEPI<br>LEEPAASGSGTGAPPNLWAAQRYGRELRRMSDEFVDRHFN<br>RKARGQLRTKIESGQGTIPVRSNASIQTWDGVLQGERLLTM<br>SCSDKIARWNVVGIQGSLLSIFVEPIYFSSIILGSLYHGDHLSR<br>AMYQRISNIEDLPPLYTLNKPLLSGISNAEARQPGKAPNFSV<br>NWTVGDSAIEVINATTGKDELGRASRLCKHALYCRWMRVH<br>GKVPSHLLRSKITKPNVYHESKLAAKEYQAAKARLFTAFIK<br>AGLGAWVEKPTEQDQFSLTGSGGTENLYFQSAASSNRELVV<br>DFLSYKLSQKGYSWSQFSDVEENRTEAPEGTESEMETPSAI<br>NGNPSWHLADSPAVNGATGHSSSLDAREVIPMAAVKQALR<br>EAGDEFELRYRRAFSDLTSQLHITPGTAYQSFEQVVNELFRD<br>GVNWGRIVAFFSFGGALCVESVDKEMQVLVSRIAAWMATY<br>LNDHLEPWIQENGGWDTFVELYGNNGSSELIKENMHMKRP<br>SVATMVSKGEEDNMAIIKEFMRFKVHMEGSVNGHEFEIEGE<br>GEGRPYEGTQTAKLKVTKGGPLPFAWDILSPQFMYGSKAY<br>VKHPADIPDYLKLSFPEGFKWERVMNFEDGGVVTVTQDSS<br>LQDGEFIYKVKLRGTNFPSDGPVMQKKTMGWEASSERMY<br>PEDGALKGEIKQRLKLKDGGHYDAEVKTTYKAKKPVQLP<br>GAYNVNIKLDITSHNEDYTIVEQYERAEGRHSTGGMDELYK<br>DYKDDDDKGSGATNFSLLKQAGDVEENPGPASAGSGEGRG<br>SLLTCGDVEENPGPATGNSA*R*LCQRHAKHEDHPCAAMA<br>EIGTGFPFDPHYVEVLGERMHYVDVGPRDGTPVLFLHGNP<br>TSSYVWRNIIPHVAPTHRCIAPDLIGMGKSDKPDLGYFFDD<br>HVRFMDAFIEALGLEEVVLVIHDWGSALGFHWAKRNPERV<br>KGIAFMEFIRPIPTWDEWPEFARETFQAFRTTDVGRKLIIDQ<br>NVFIEGTLPMGVVRPLTEVEMDHYREPFLNPVDREPLWRFP<br>NELPIAGEPANIVALVEEYMDWLHQSPVPKLLFWGTPGVLI<br>PPAEAARLAKSLPNCKAVDIGPGLNLLQEDNPDLIGSEIARW<br>LSTLEISGTGMASMTGGQQMGPATGNSA*R*LCQRHAKHE<br>DHPCTSATNFSLLKQAGDVEENPGPGGSEGRGSLLTCGDVE<br>ENPGPSGYPYDVPDYAIDVSKGEEDNKASLPATHELHIFGSI<br>NGVDFDMVGQGTGNPNDGYEELNLKSTKGDLQFSPWILVP<br>HIGYGFHQYLPYPDGMSPFQAAMVDGSGYQVHRTMQFED<br>GASLTVNYRYTYEGSHIKGEAQVKGTGFPADGPVMTNSLT<br>AADWCRSKKTYPNDKTIISTFKWSYTTGNGKRYRSTARTT<br>YTFAKPMAANYLKNQPMYVFRKTELKHSKTELNFKEWQK<br>AFTDVMGMDELYKAS* |

FIG. 15B

Modified ADAR (E488Q)

Inducible ADAR (iADAR)

| Inducer +/- | Binding Pair status | ADAR status | Transcript construct | GOI expression |
|---|---|---|---|---|
| - | Binds | OFF | ACTIVATION construct | OFF |
| + | Not bound | ON | ACTIVATION construct | ON |
| - | Binds | OFF | INACTIVATION construct | ON |
| + | Not bound | ON | INACTIVATION construct | OFF |

SEQ ID NO:168, tdMCP_ADAR2-DDN-CP5-46-4D5E_ADAR2-DDC(E488Q)_mTagBFP(AD-Pep-AD)

MASNFTQFVLVDNGGTGDVTVAPSNFANGIAEWISSNSRSQAYKVTCSVRQSSAQNRKYTIKVEVPKGAW
RSYLNMELTIPIFATNSDCELIVKAMQGLLKDGNPIPSAIAANSGIYANFTQFVLVDNGGTGDVTVAPSNFAN
GIAEWISSNSRSQAYKVTCSVRQSSAQNRKYTIKVEVPKGAWRSYLNMELTIPIFATNSDCELIVKAMQGLLK
DGNPIPSAIAANSGIYGGSGSGAGSGSPAGGGAPGSGGGSQLHLPQVLADAVSRLVLGKFGDLTDNFSSPH
ARRKVLAGVVMTTGTDVKDAKVISVSTGTKCINGEYMSDRGLALNDCHAEIISRRSLLRFLYTQLELYLNNKD
DQKRSIFQKSERGGFRLKENVQFHLYISTSPCGDARIFSPHEPILEEPASSGGELDELVYLLDGPGYDPIHCDVV
TRGGSHLFNFDRHPNRKARGQLRTKIESGQGTIPVRSNASIQTWDGVLQGERLLTMSCSDKIARWNVVGIQ
GSLLSIFVEPIYFSSIILGSLYHGDHLSRAMYQRISNIEDLPPLYTLNKPLLSGISNAEARQPGKAPNFSVNWTVG
DSAIEVINATTGKDELGRASRLCKHALYCRWMRVHGKVPSHLLRSKITKPNVYHESKLAAKEYQAAKARLFTA
FIKAGLGAWVEKPTEQDQFSLTGSGSSELIKENMHMKLYMEGTVDNHHFKCTSEGEGKPYEGTQTMRIKVV
EGGPLPFAFDILATSFLYGSKTFINHTQGIPDFFKQSFPEGFTWERVTTYEDGGVLTATQDTSLQDGCLIYNVKI
RGVNFTSNGPVMQKKTLGWEAFTETLYPADGGLEGRNDMALKLVGGSHLIANIKTTYRSKKPAKNLKMPG
VYYVDYRLERIKEANNETYVEQHEVAVARYCDLPSKLGHKLN*

FIG. 18

SEQ ID NO:169, tdMCP_ADAR2-DDN-CP5-46-4D5E_ADAR2-DDC(E488Q)_NS4A/NS3(Genotype 1B)_mTagBFP MASNFTQFVLVDNGGTGDVTVAPSNFANGIAEWISSNSRSQAYKVTCSVRQSSAQNRKYTIKVEVPKGAW
RSYLNMELTIPIFATNSDCELIVKAMQGLLKDGNPIPSAIAANSGIYANFTQFVLVDNGGTGDVTVAPSNFAN
GIAEWISSNSRSQAYKVTCSVRQSSAQNRKYTIKVEVPKGAWRSYLNMELTIPIFATNSDCELIVKAMQGLLK
DGNPIPSAIAANSGIYGGSGSGAGSGSPAGGGAPGSGGGSQLHLPQVLADAVSRLVLGKFGDLTDNFSSPH
ARRKVLAGVVMTTGTDVKDAKVISVSTGTKCINGEYMSDRGLALNDCHAEIISRRSLLRFLYTQLELYLNNKD
DQKRSIFQKSERGGFRLKENVQFHLYISTSPCGDARIFSPHEPILEEPASSGGELDELVYLLDGPGYDPIHCDVV
TRGGSHLFNFDRHPNRKARGQLRTKIESGQGTIPVRSNASIQTWDGVLQGERLLTMSCSDKIARWNVVGIQ
GSLLSIFVEPIYFSSIILGSLYHGDHLSRAMYQRISNIEDLPPLYTLNKPLLSGISNAEARQPGKAPNFSVNWTVG
DSAIEVINATTGKDELGRASRLCKHALYCRWMRVHGKVPSHLLRSKITKPNVYHESKLAAKEYQAAKARLFTA
FIKAGLGAWVEKPTEQDQFSLTGSAAGGSGGSAAAQGSVVIVGRIILSGSGSITAYSQQTRGLLGCIITSLTGR
DKNQVEGEVQVVSTATQSFLATCVNGVCWTVYHGAGSKTLAGPKGPITQMYTNVDQDLVGWQAPPGAR
SLTPCTCGSSDLYLVTRHADVIPVRRRGDSRGSLLSPRPVSYLKGSSGGPLLCPSGHAVGIFRAAVCTRGVAKA
VDFVPVESMETTMRSESGSGTMSELIKENMHMKLYMEGTVDNHHFKCTSEGEGKPYEGTQTMRIKVVEG
GPLPFAFDILATSFLYGSKTFINHTQGIPDFFKQSFPEGFTWERVTTYEDGGVLTATQDTSLQDGCLIYNVKIRG
VNFTSNGPVMQKKTLGWEAFTETLYPADGGLEGRNDMALKLVGGSHLIANIKTTYRSKKPAKNLKMPGVYY
VDYRLERIKEANNETYVEQHEVAVARYCDLPSKLGHKLN*

FIG. 18(Cont.)

SEQ ID NO: 198, MCP-linker-BclxL -linker-ADAR2-DDN-Bad(L)-
ADAR2(E488Q)-DDC -TagRFP Also known as "BclxL-nDD-BAD-cDD"

MASNFTQFVLVDNGGTGDVTVAPSNFANGIAEWISSNSRSQAYKVTCSVRQSSAQNRKYTIKVEVPKGAW
RSYLNMELTIPIFATNSDCELIVKAMQGLLKDGNPIPSAIAANSGIYGGSGSGAGSGSPAGGGAPGSGGG
SQSNRELVVDFLSYKLSQKGYSWSQFSDVEENRTEAPEGTESEMETPSAINGNPSWHLADSPAVNGATGH
SSSLDAREVIPMAAVKQALREAGDEFELRYRRAFSDLTSQLHITPGTAYQSFEQVVNELFRDGVNWGRIV
AFFSFGGALCVESVDKEMQVLVSRIAAWMATYLNDHLEPWIQENGGWDTFVELYGNNAAGGSGGSGGSGG
SAAAQLHLPQVLADAVSRLVLGKFGDLTDNFSSPHARRKVLAGVVMTTGTDVKDAKVISVSTGTKCINGE
YMSDRGLALNDCHAEIISRRSLLRFLYTQLELYLNNKDDQKRSIFQKSERGGFRLKENVQFHLYISTSPC
GDARIFSPHEPILEEPAASGSGTGAPPNLWAAQRYGRELRRMSDELVDRHPNRKARGQLRTKIESGQGTI
PVRSNASIQTWDGVLQGERLLTMSCSDKIARWNVVGIQGSLLSIFVEPIYFSSIILGSLYHGDHLSRAMY
QRISNIEDLPPLYTLNKPLLSGISNAEARQPGKAPNFSVNWTVGDSAIEVINATTGKDELGRASRLCKHA
LYCRWMRVHGKVPSHLLRSKITKPNVYHESKLAAKEYQAAKARLFTAFIKAGLGAWVEKPTEQDQFSLTG
SGSSELIKENMHMKLYMEGTVDNHHFKCTSEGEGKPYEGTQTMRIKVVEGGPLPFAFDILATSFLYGSKT
FINHTQGIPDFFKQSFPEGFTWERVTTYEDGGVLTATQDTSLQDGCLIYNVKIRGVNFTSNGPVMQKKTL
GWEAFTETLYPADGGLEGRNDMALKLVGGSHLIANIKTTYRSKKPAKNLKMPGVYYVDYRLERIKEANNE
TYVEQHEVAVARYCDLPSKLGHKLN*

FIG. 21A

SEQ ID NO:200, MCP-linker-BAD-ADAR2-DD(E488Q)-TagBFP

Also known as "BAD-DD"

MASNFTQFVLVDNGGTGDVTVAPSNFANGIAEWISSNSRSQAYKVTCSVRQSSAQNRKYTIKVEVPKGAWRSY
LNMELTIPIFATNSDCELIVKAMQGLLKDGNPIPSAIAANSGIYGGSGSGAGSGSPAGGGAPGSGGGSTGAPP
NLWAAQRYGRELRRMSDEFVDSFKKASQLHLPQVLADAVSRLVLGKFGDLTDNFSSPHARRKVLAGVVMTTGT
DVKDAKVISVSTGTKCINGEYMSDRGLALNDCHAEIISRRSLLRFLYTQLELYLNNKDDQKRSIFQKSERGGF
RLKENVQFHLYISTSPCGDARIFSPHEPILEEPADRHPNRKARGQLRTKIESGQGTIPVRSNASIQTWDGVLQ
GERLLTMSCSDKIARWNVVGIQGSLLSIFVEPIYFSSIILGSLYHGDHLSRAMYQRISNIEDLPPLYTLNKPL
LSGISNAEARQPGKAPNFSVNWTVGDSAIEVINATTGKDELGRASRLCKHALYCRWMRVHGKVPSHLLRSKIT
KPNVYHESKLAAKEYQAAKARLFTAFIKAGLGAWVEKPTEQDQFSLTGSGSSELIKENMHMKLYMEGTVDNHH
FKCTSEGEGKPYEGTQTMRIKVVEGGPLPFAFDILATSFLYGSKTFINHTQGIPDFFKQSFPEGFTWERVTTY
EDGGVLTATQDTSLQDGCLIYNVKIRGVNFTSNGPVMQKKTLGWEAFTETLYPADGGLEGRNDMALKLVGGSH
LIANIKTTYRSKKPAKNLKMPGVYYVDYRLERIKEANNETYVEQHEVAVARYCDLPSKLGHKLN*

FIG. 21B

SEQ ID NO: 202, MCP-linker-BAD- ADAR2-DD(E488Q)-Bcl-xL-TagRFP

Also known as "BAD-DD-BclxL" and "WT"

MASNFTQFVLVDNGGTGDVTVAPSNFANGIAEWISSNSRSQAYKVTCSVRQSSAQNRKYTIKVEVPKGAW
RSYLNMELTIPIFATNSDCELIVKAMQGLLKDGNPIPSAIAANSGIYGGSGSGAGSGSPAGGGAPGSGGG
STGAPPNLWAAQRYGRELRRMSDEFVDSFKKASQLHLPQVLADAVSRLVLGKFGDLTDNFSSPHARRKVL
AGVVMTTGTDVKDAKVISVSTGTKCINGEYMSDRGLALNDCHAEIISRRSLLRFLYTQLELYLNNKDDQK
RSIFQKSERGGFRLKENVQFHLYISTSPCGDARIFSPHEPILEEPADRHPNRKARGQLRTKIESGQGTIP
VRSNASIQTWDGVLQGERLLTMSCSDKIARWNVVGIQGSLLSIFVEPIYFSSIILGSLYHGDHLSRAMYQ
RISNIEDLPPLYTLNKPLLSGISNAEARQPGKAPNFSVNWTVGDSAIEVINATTGKDELGRASRLCKHAL
YCRWMRVHGKVPSHLLRSKITKPNVYHESKLAAKEYQAAKARLFTAFIKAGLGAWVEKPTEQDQFSLTGS
AAASSNRELVVDFLSYKLSQKGYSWSQFSDVEENRTEAPEGTESEMETPSAINGNPSWHLADSPAVNGAT
GHSSSLDAREVIPMAAVKQALREAGDEFELRYRRAFSDLTSQLHITPGTAYQSFEQVVNELFRDGVNWGR
IVAFFSFGGALCVESVDKEMQVLVSRIAAWMATYLNDHLEPWIQENGGWDTFVELYGNNGSSELIKENMH
MKLYMEGTVDNHHFKCTSEGEGKPYEGTQTMRIKVVEGGPLPFAFDILATSFLYGSKTFINHTQGIPDFF
KQSFPEGFTWERVTTYEDGGVLTATQDTSLQDGCLIYNVKIRGVNFTSNGPVMQKKTLGWEAFTETLYPA
DGGLEGRNDMALKLVGGSHLIANIKTTYRSKKPAKNLKMPGVYYVDYRLERIKEANNETYVEQHEVAVAR
YCDLPSKLGHKLN*

FIG. 21C

SEQ ID NO: 204, tdMCP_ADAR2-DDN-CP5-46-4D5E_ADAR2-DDC(E488Q)_[redacted]
(AD-Pep-AD)

MASNFTQFVLVDNGGTGDVTVAPSNFANGIAEWISSNSRSQAYKVTCSVRQSSAQNRKYTIKVEVPKGAW
RSYLNMELTIPIFATNSDCELIVKAMQGLLKDGNPIPSAIAANSGIYANFTQFVLVDNGGTGDVTVAPSN
FANGIAEWISSNSRSQAYKVTCSVRQSSAQNRKYTIKVEVPKGAWRSYLNMELTIPIFATNSDCELIVKA
MQGLLKDGNPIPSAIAANSGIYGGSGSGAGSGSPAGGGAPGSGGGSQLHLPQVLADAVSRLVLGKFGDLT
DNFSSPHARRKVLAGVVMTTGTDVKDAKVISVSTGTKCINGEYMSDRGLALNDCHAEIISRRSLLRFLYT
QLELYLNNKDDQKRSIFQKSERGGFRLKENVQFHLYISTSPCGDARIFSPHEPILEEPASSGGELDELVY
LLDGPGYDPIHCDVVTRGGSHLFNFDRHPNRKARGQLRTKIESGQGTIPVRSNASIQTWDGVLQGERLLT
MSCSDKIARWNVVGIQGSLLSIFVEPIYFSSIILGSLYHGDHLSRAMYQRISNIEDLPPLYTLNKPLLSG
ISNAEARQPGKAPNFSVNWTVGDSAIEVINATTGKDELGRASRLCKHALYCRWMRVHGKVPSHLLRSKIT
KPNVYHESKLAAKEYQAAKARLFTAFIKAGLGAWVEKPTEQDQFSLTGSGS[redacted]*

FIG. 21D

SEQ ID NO: 206, tdMCP_ADAR2-DDN-CP5-46-4D5E _ADAR2-DDC(E488Q)_NS4A/NS3(Genotype 1B)_mTagBFP MASNFTQFVLVDNGGTGDVTVAPSNFANGIAEWISSNSRSQAYKVTC
SVRQSSAQNRKYTIKVEVPKGAWRSYLNMELTIPIFATNSDCELIVK
AMQGLLKDGNPIPSAIAANSGIYANFTQFVLVDNGGTGDVTVAPSNF
ANGIAEWISSNSRSQAYKVTCSVRQSSAQNRKYTIKVEVPKGAWRSY
LNMELTIPIFATNSDCELIVKAMQGLLKDGNPIPSAIAANSGIYGGS
GSGAGSGSPAGGGAPGSGGGSQLHLPQVLADAVSRLVLGKFGDLTDN
FSSPHARRKVLAGVVMTTGTDVKDAKVISVSTGTKCINGEYMSDRGL
ALNDCHAEIISRRSLLRFLYTQLELYLNNKDDQKRSIFQKSERGGFR
LKENVQFHLYISTSPCGDARIFSPHEPILEEPASSGGELDELVYLLD
GPGYDPIHCDVVTRGGSHLFNFDRHPNRKARGQLRTKIESGQGTIPV
RSNASIQTWDGVLQGERLLTMSCSDKIARWNVVGIQGSLLSIFVEPI
YFSSIILGSLYHGDHLSRAMYQRISNIEDLPPLYTLNKPLLSGISNA
EARQPGKAPNFSVNWTVGDSAIEVINATTGKDELGRASRLCKHALYC
RWMRVHGKVPSHLLRSKITKPNVYHESKLAAKEYQAAKARLFTAFIK
AGLGAWVEKPTEQDQFSLTGSAAGGSGGSAAAQGSVVIVGRIILSGS
GSITAYSQQTRGLLGCIITSLTGRDKNQVEGEVQVVSTATQSFLATC
VNGVCWTVYHGAGSKTLAGPKGPITQMYTNVDQDLVGWQAPPGARSL
TPCTCGSSDLYLVTRHADVIPVRRRGDSRGSLLSPRPVSYLKGSSGG
PLLCPSGHAVGIFRAAVCTRGVAKAVDFVPVESMETTMRSESGSGTM
SELIKENMHMKLYMEGTVDNHHFKCTSEGEGKPYEGTQTMRIKVVEG
GPLPFAFDILATSFLYGSKTFINHTQGIPDFFKQSFPEGFTWERVTT
YEDGGVLTATQDTSLQDGCLIYNVKIRGVNFTSNGPVMQKKTLGWEA
FTETLYPADGGLEGRNDMALKLVGGSHLIANIKTTYRSKKPAKNLKM
PGVYYVDYRLERIKEANNETYVEQHEVAVARYCDLPSKLGHKLN*

FIG. 21E

| NAME | SID | AMINO ACID SEQUENCE |
|---|---|---|
| MCP-<br>linker-<br>ADAR2-DDN-<br>Bad(F)-<br>ADAR2(E488Q)<br>-DDC-<br>Bcl-xL-<br>TagRFP | 287 | MASNFTQFVLVDNGGTGDVTVAPSNFANGIAEWISSNSRSQAYKVT<br>CSVRQSSAQNRKYTIKVEVPKGAWRSYLNMELTIPIFATNSDCELI<br>VKAMQGLLKDGNPIPSAIAANSGIYGGSGSGAGSGSPAGGGAPGSG<br>GGSQLHLPQVLADAVSRLVLGKFGDLTDNFSSPHARRKVLAGVVMT<br>TGTDVKDAKVISVSTGTKCINGEYMSDRGLALNDCHAEIISRRSLL<br>RFLYTQLELYLNNKDDQKRSIFQKSERGGFRLKENVQFHLYISTSP<br>CGDARIFSPHEPILEEPAASGSGTGAPPNLWAAQRYGRELRRMSDE<br>FVDRHPNRKARGQLRTKIESGQGTIPVRSNASIQTWDGVLQGERLL<br>TMSCSDKIARWNVVGIQGSLLSIFVEPIYFSSIILGSLYHGDHLSR<br>AMYQRISNIEDLPPLYTLNKPLLSGISNAEARQPGKAPNFSVNWTV<br>GDSAIEVINATTGKDELGRASRLCKHALYCRWMRVHGKVPSHLLRS<br>KITKPNVYHESKLAAKEYQAAKARLFTAFIKAGLGAWVEKPTEQDQ<br>FSLTGSAAGGSGGSAAASSNRELVVDFLSYKLSQKGYSWSQFSDVE<br>ENRTEAPEGTESEMETPSAINGNPSWHLADSPAVNGATGHSSSLDA<br>REVIPMAAVKQALREAGDEFELRYRRAFSDLTSQLHITPGTAYQSF<br>EQVVNELFRDGVNWGRIVAFFSFGGALCVESVDKEMQVLVSRIAAW<br>MATYLNDHLEPWIQENGGWDTFVELYGNNGSSELIKENMHMKLYME<br>GTVDNHHFKCTSEGEGKPYEGTQTMRIKVVEGGPLPFAFDILATSF<br>LYGSKTFINHTQGIPDFFKQSFPEGFTWERVTTYEDGGVLTATQDT<br>SLQDGCLIYNVKIRGVNFTSNGPVMQKKTLGWEAFTETLYPADGGL<br>EGRNDMALKLVGGSHLIANIKTTYRSKKPAKNLKMPGVYYVDYRLE<br>RIKEANNETYVEQHEVAVARYCDLPSKLGHKLN* |

FIG. 25A

| NAME | SID | AMINO ACID SEQUENCE |
| --- | --- | --- |
| MCP-<br>linker-<br>ADAR2-DDN-<br>Bad(F)-<br>ADAR2(E488Q)<br>-DDC-<br>Bcl-xL-<br>TagBFP | 288 | MASNFTQFVLVDNGGTGDVTVAPSNFANGIAEWISSNSRSQAYKVT<br>CSVRQSSAQNRKYTIKVEVPKGAWRSYLNMELTIPIFATNSDCELI<br>VKAMQGLLKDGNPIPSAIAANSGIYGGSGSGAGSGSPAGGGAPGSG<br>GGSQLHLPQVLADAVSRLVLGKFGDLTDNFSSPHARRKVLAGVVMT<br>TGTDVKDAKVISVSTGTKCINGEYMSDRGLALNDCHAEIISRRSLL<br>RFLYTQLELYLNNKDDQKRSIFQKSERGGFRLKENVQFHLYISTSP<br>CGDARIFSPHEPILEEPAASGSGTGAPPNLWAAQRYGRELRRMSDE<br>**V**VDRHPNRKARGQLRTKIESGQGTIPVRSNASIQTWDGVLQGERLL<br>TMSCSDKIARWNVVGIQGSLLSIFVEPIYFSSIILGSLYHGDHLSR<br>AMYQRISNIEDLPPLYTLNKPLLSGISNAEARQPGKAPNFSVNWTV<br>GDSAIEVINATTGKDELGRASRLCKHALYCRWMRVHGKVPSHLLRS<br>KITKPNVYHESKLAAKEYQAAKARLFTAFIKAGLGAWVEKPTEQDQ<br>FSLTGSAAGGSGGSAAASSNRELVVDFLSYKLSQKGYSWSQFSDVE<br>ENRTEAPEGTESEMETPSAINGNPSWHLADSPAVNGATGHSSSLDA<br>REVIPMAAVKQALREAGDEFELRYRRAFSDLTSQLHITPGTAYQSF<br>EQVVNELFRDGVNWGRIVAFFSFGGALCVESVDKEMQVLVSRIAAW<br>MATYLNDHLEPWIQENGGWDTFVELYGNNGSSELIKENMHMKLYME<br>GTVDNHHFKCTSEGEGKPYEGTQTMRIKVVEGGPLPFAFDILATSF<br>LYGSKTFINHTQGIPDFFKQSFPEGFTWERVTTYEDGGVLTATQDT<br>SLQDGCLIYNVKIRGVNFTSNGPVMQKKTLGWEAFTETLYPADGGL<br>EGRNDMALKLVGGSHLIANIKTTYRSKKPAKNLKMPGVYYVDYRLE<br>RIKEANNETYVEQHEVAVARYCDLPSKLGHKLN* |

FIG. 25A(Cont.)

| NAME | SID | AMINO ACID SEQUENCE |
| --- | --- | --- |
| MCP-<br>linker-<br>ADAR2-<br>DDN-<br>Bad(F)-<br>ADAR2(E488Q)<br>-DDC-<br>Bcl-xL-<br>TagBFP | 289 | MASNFTQFVLVDNGGTGDVTVAPSNFANGIAEWISSNSRSQAY<br>KVTCSVRQSSAQNRKYTIKVEVPKGAWRSYLNMELTIPIFATN<br>SDCELIVKAMQGLLKDGNPIPSAIAANSGIYGGSGSGAGSGSP<br>AGGGAPGSGGGSQLHLPQVLADAVSRLVLGKFGDLTDNFSSPH<br>ARRKVLAGVVMTTGTDVKDAKVISVSTGTKCINGEYMSDRGLA<br>LNDCHAEIISRRSLLRFLYTQLELYLNNKDDQKRSIFQKSERG<br>GFRLKENVQFHLYISTSPCGDARIFSPHEPILEEPAASGSGTG<br>APPNLWAAQRYGRELRRMSDE**G**VDRHPNRKARGQLRTKIESG**Q**<br>GTIPVRSNASIQTWDGVLQGERLLTMSCSDKIARWNVVGIQGS<br>LLSIFVEPIYFSSIILGSLYHGDHLSRAMYQRISNIEDLPPLY<br>TLNKPLLSGISNAEARQPGKAPNFSVNWTVGDSAIEVINATTG<br>KDELGRASRLCKHALYCRWMRVHGKVPSHLLRSKITKPNVYHE<br>SKLAAKEYQAAKARLFTAFIKAGLGAWVEKPTEQDQFSLTGSA<br>AGGSGGSAAASSNRELVVDFLSYKLSQKGYSWSQFSDVEENRT<br>EAPEGTESEMETPSAINGNPSWHLADSPAVNGATGHSSSLDAR<br>EVIPMAAVKQALREAGDEFELRYRRAFSDLTSQLHITPGTAYQ<br>SFEQVVNELFRDGVNWGRIVAFFSFGGALCVESVDKEMQVLVS<br>RIAAWMATYLNDHLEPWIQENGGWDTFVELYGNNGSSELIKEN<br>MHMKLYMEGTVDNHHFKCTSEGEGKPYEGTQTMRIKVVEGGPL<br>PFAFDILATSFLYGSKTFINHTQGIPDFFKQSFPEGFTWERVT<br>TYEDGGVLTATQDTSLQDGCLIYNVKIRGVNFTSNGPVMQKKT<br>LGWEAFTETLYPADGGLEGRNDMALKLVGGSHLIANIKTTYRS<br>KKPAKNLKMPGVYYVDYRLERIKEANNETYVEQHEVAVARYCD<br>LPSKLGHKLN* |

FIG. 25B

| NAME | SID | AMINO ACID SEQUENCE |
| --- | --- | --- |
| MCP-<br>linker-<br>ADAR2-<br>DDN-<br>MS1(A)-<br>ADAR2(E488Q)<br>-DDC-<br>TagBFP | 290 | MASNFTQFVLVDNGGTGDVTVAPSNFANGIAEWISSNSRSQAY<br>KVTCSVRQSSAQNRKYTIKVEVPKGAWRSYLNMELTIPIFATN<br>SDCELIVKAMQGLLKDGNPIPSAIAANSGIYGGSGSGAGSGSP<br>AGGGAPGSGGGSQLHLPQVLADAVSRLVLGKFGDLTDNFSSPH<br>ARRKVLAGVVMTTGTDVKDAKVISVSTGTKCINGEYMSDRGLA<br>LNDCHAEIISRRSLLRFLYTQLELYLNNKDDQKRSIFQKSERG<br>GFRLKENVQFHLYISTSPCGDARIFSPHEPILEEPAASGGSGG<br>SGRPEIWMTQGLRRLGDE**A**NAYYARRTGDRHPNRKARGQLRTK<br>IESG**Q**GTIPVRSNASIQTWDGVLQGERLLTMSCSDKIA**R**WNVV<br>GIQGSLLSIFVEPIYFSSIILGSLYHGDHLSRAMYQRISNIED<br>LPPLYTLNKPLLSGISNAEARQPGKAPNFSVNWTVGDSAIEVI<br>NATTGKDELGRASRLCKHALYCRWMRVHGKVPSHLLRSKITKP<br>NVYHESKLAAKEYQAAKARLFTAFIKAGLGAWVEKPTEQDQFS<br>**L**IGSGSSELIKENMHMKLYMEGTVDNHHFKCTSEGEGKPYEGT<br>QTMRIKVVEGGPLPFAFDILATSFLYGSKTFINHTQGIPDFFK<br>QSFPEGFTWERVTTYEDGGVLTATQDTSLQDGCLIYNVKIRGV<br>NFTSNGPVMQKKTLGWEAFTETLYPADGGLEGRNDMALKLVGG<br>SHLIANIKTTYRSKKPAKNLKMPGVYYVDYRLERIKEANNETY<br>VEQHEVAVARYCDLPSKLGHKLN* |

FIG. 25B(Cont.)

| NAME | SID | AMINO ACID SEQUENCE |
|---|---|---|
| MCP-linker-ADAR2-DDN-MS1(G)-ADAR2 (E488Q)-DDC-TagBFP | 291 | MASNFTQFVLVDNGGTGDVTVAPSNFANGIAEWISSN SRSQAYKVTCSVRQSSAQNRKYTIKVEVPKGAWRSYL NMELTIPIFATNSDCELIVKAMQGLLKDGNPIPSAIA ANSGIYGGSGSGAGSGSPAGGGAPGSGGGSQLHLPQV LADAVSRLVLGKFGDLTDNFSSPHARRKVLAGVVMTT GTDVKDAKVISVSTGTKCINGEYMSDRGLALNDCHAE IISRRSLLRFLYTQLELYLNNKDDQKRSIFQKSERGG FRLKENVQFHLYISTSPCGDARIFSPHEPILEEPAAS GGSGGSGRPEIWMTQGLRRLGDE**G**NAYYARRTGDRHP NRKARGQLRTKIESG**Q**GTIPVRSNASIQTWDGVLQGE RLLTMSCSDKIA**R**WNVVGIQGSLLSIFVEPIYFSSII LGSLYHGDHLSRAMYQRISNIEDLPPLYTLNKPLLSG ISNAEARQPGKAPNFSVNWTVGDSAIEVINATTGKDE LGRASRLCKHALYCRWMRVHGKVPSHLLRSKITKPNV YHESKLAAKEYQAAKARLFTAFIKAGLGAWVEKPTEQ DQFS**L**TGSGSSELIKENMHMKLYMEGTVDNHHFKCTS EGEGKPYEGTQTMRIKVVEGGPLPFAFDILATSFLYG SKTFINHTQGIPDFFKQSFPEGFTWERVTTYEDGGVL TATQDTSLQDGCLIYNVKIRGVNFTSNGPVMQKKTLG WEAFTETLYPADGGLEGRNDMALKLVGGSHLIANIKT TYRSKKPAKNLKMPGVYYVDYRLERIKEANNETYVEQ HEVAVARYCDLPSKLGHKLN* |

FIG. 25C

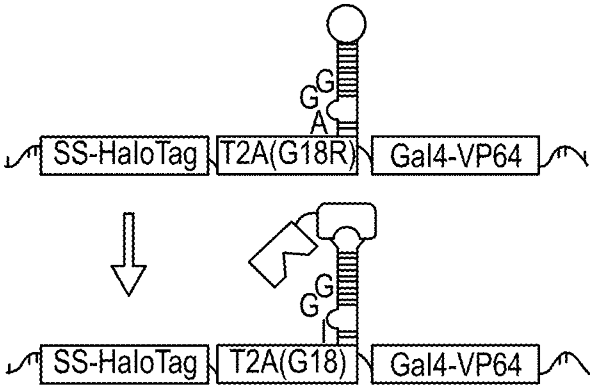
FIG. 29A
P2A : ---ATNFSLLKQAGDVEENPGP
T2A : ---EGRGSLLT-CGDVEENPGP
E2A : --QCTNYALLKLAGDVESNPGP
F2A : VKQTLNFDLLKLAGDVESNPGP
FIG. 29B
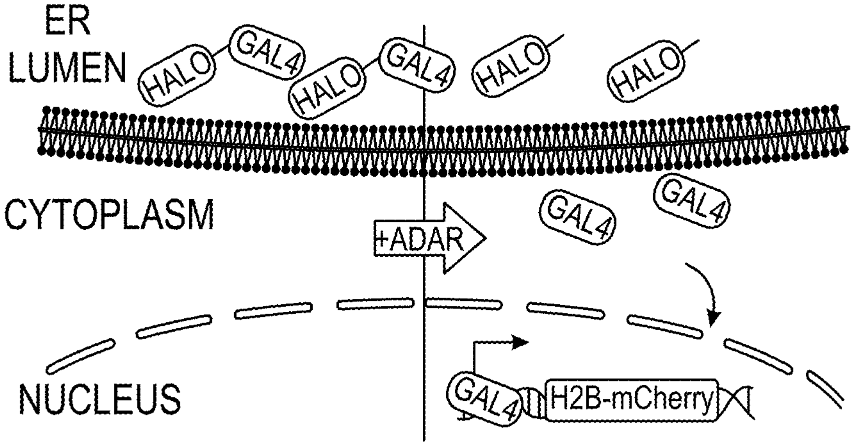
FIG. 29C

| mCherry-FLAG | UAG-UAG MS2-C | HaloTag | UAG-UAG MS2-C | HA-mNeonGreen |
|---|---|---|---|---|

| mCherry-FLAG | UAG-UAG MS2-C | HaloTag | UAG-UAG PP7 | HA-mNeonGreen |
|---|---|---|---|---|

| mCherry-FLAG | UAG-UAG MS2-C | HaloTag | UAG-UAG BoxB | HA-mNeonGreen |
|---|---|---|---|---|

| mCherry-FLAG | UAG-UAG MS2-C | HaloTag | UAG-UAG HIV TAR | HA-mNeonGreen |
|---|---|---|---|---|

| Protein Sequence A | STOP RBM | Protein Sequence B |
|---|---|---|

| mCherry-FLAG | UAG-UAG MS2-C | HA-mNeonGreen (1-166) | UAG MS2-C | HA-mNeonGreen (174-236) |
|---|---|---|---|---|

| MCP | linker | ADAR2-DD (316-468) | ALFA Var | ADAR2-DD (469-700) | ALFA Nanobody | TagBFP |
|-----|--------|--------------------|----------|--------------------|---------------|--------|

| MCP | linker | ADAR2-DD (316-468) | ALFA Var | ADAR2-DD (469-700)* | ALFA Nanobody | GFP Nanobody | TagBFP |
|-----|--------|--------------------|----------|---------------------|---------------|--------------|--------|

| MCP | linker | ADAR2-DD (316-468) | Pep | ADAR2-DD (469-700) | TagBFP |
|-----|--------|--------------------|-----|--------------------|--------|

| MCP | linker | ADAR2-DD (316-468) | Pep | ADAR2-DD (469-700) | NS3(1B) protease | TagBFP |
|-----|--------|--------------------|-----|--------------------|------------------|--------|

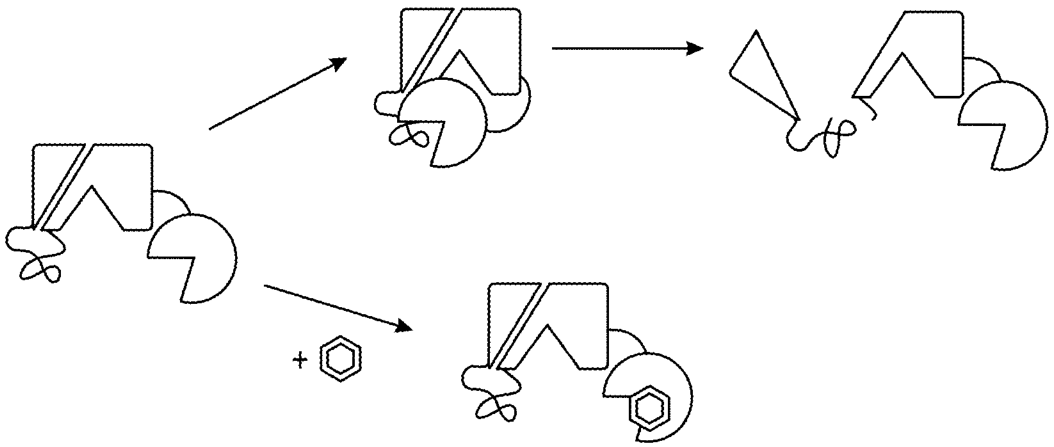
FIG. 35A
| | | | | | | |
|---|---|---|---|---|---|---|
| MCP | linker | ADAR2-DD (316-468) | 5A/5B | ADAR2-DD (469-700) | NS3(1B) protease | TagBFP |
| | | | | | | |
|---|---|---|---|---|---|---|
| MCP | linker | ADAR2-DD (316-468) | 5A/5B | ADAR2-DD (469-700) | dNS3(1B) protease | TagBFP |
FIG. 35B
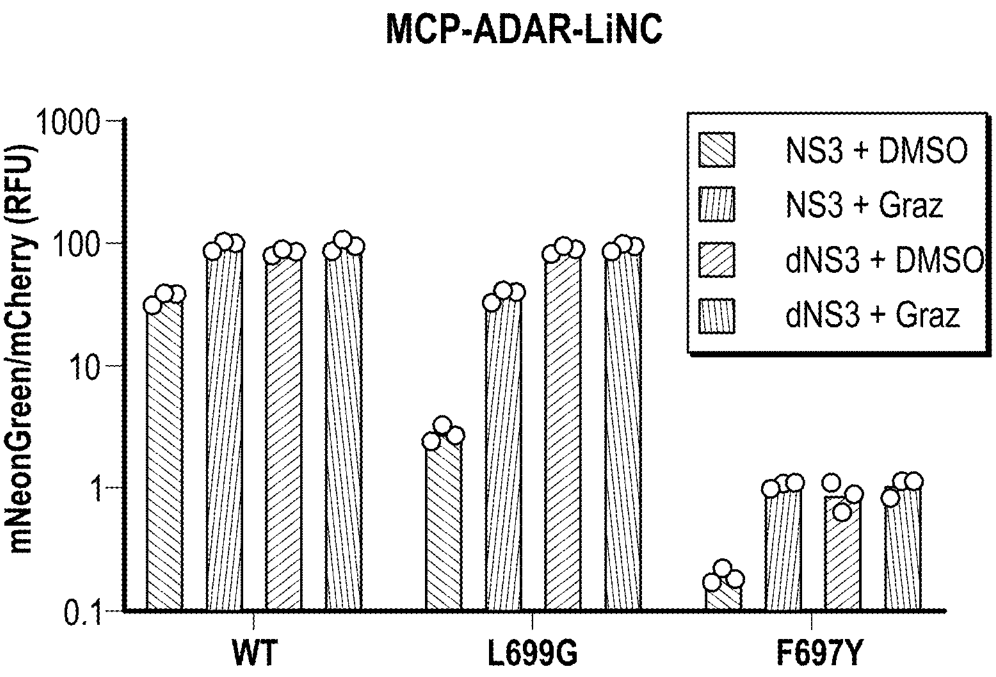
FIG. 35C

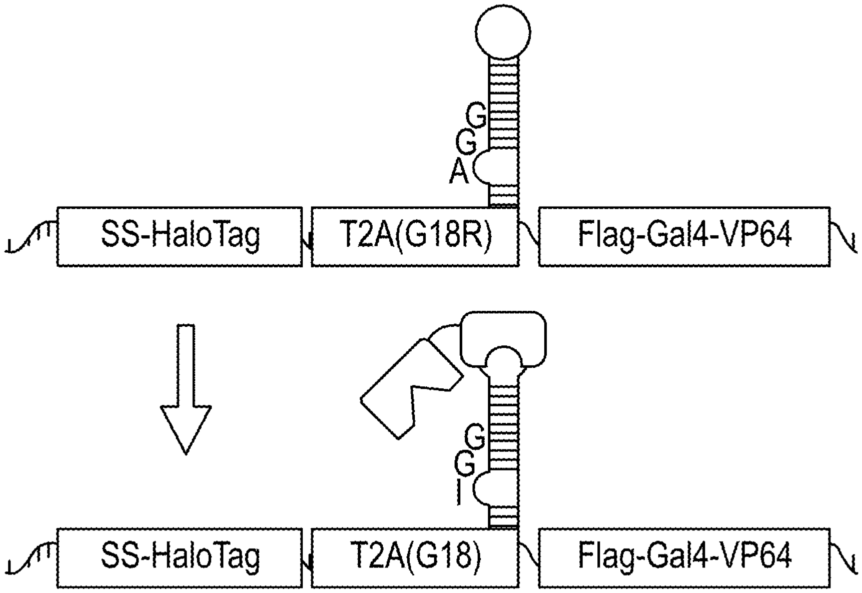
FIG. 37A
P2A : ---ATNFSLLKQAGDVEENPGP
T2A : ---EGRGSLLT-CGDVEENPGP
E2A : --QCTNYALLKLAGDVESNPGP
F2A : VKQTLNFDLLKLAGDVESNPGP
FIG. 37B
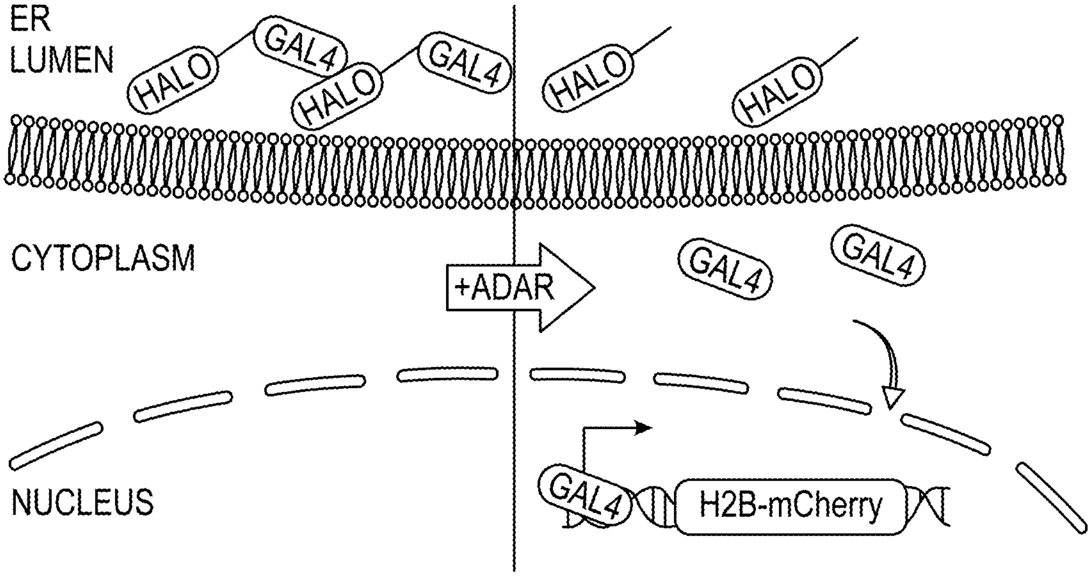
FIG. 37C

**SEQ ID NO: 292, dTomato BiCMV MS2-C AUG *EGFPd2*:**

ctctagactgcagcctcaggagatctgggcccctacttgtacagctcgtccatgccgtacaggaacaggtggtggcggccc
tcggagcgctcgtactgttccacgatggtgtagtcctcgttgtgggaggtgatgtccagcttggtgtccacgtagtagtagccg
ggcagttgcacgggcttcttggccatgtagatggtcttgaactccaccaggtagtggccgccgtccttcagcttcagggcctg
gtggatctcgcccttcagcacgccgtcgcgggggtacaggcgctcggtggaggcctcccagcccatggtcttcttctgcatta
cggggccgtcggggggggaagttggtgccgcgcatcttcaccttgtagatcagcgtgccgtcctgcagggaggagtcctggg
tcacggtcaccagaccgccgtcctcgaagttcatcacgcgctcccacttgaagccctcggggaaggacagcttcttgtaatc
ggggatgtcggcggggtgcttcacgtacgccttggagccgtacatgaactggggggacaggatgtcccaggcgaagggc
agggggccgcccttggtcaccttcagcttggcggtctgggtgccctcgtaggggcggccctcgccctcgccctcgatctcga
actcgtggccgttcatggagccctccatgcgcaccttgaagcgcatgaactctttgatgacctcctcgcccttgctcaccatgg
tggcgaattctccaggcgatctgacggttcactaaacgagctctgcttatataggcctcccaccgtacacgccacctcgacat
actcgagtagttattaatagtaatcaattacggggtcattagttcatagcccatatatggagttccgcgttacataacttacggta
aatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagt
acgccccctattgacgtcaatgacggtaaatggcccgcctggcattatgcccagtacatgaccttatgggactttcctacttgg
cagtacatctacgtattagtcatcgctattaccatggtgatgcggttttggcagtacatcaatgggcgtggatagcggtttgactc
acggggatttccaagtctccaccccattgacgtcaatgggagtttgttttggcaccaaaatcaacgggactttccaaaatgtc
gtaacaactccgccccattgacgcaaatgggcggtaggcgtgtacggtgggaggtctatataagcagagctggtttagtga
accgtcagatccgctagggatcctctagtcagctgacgcgtgctagcgatatcggcgcgccagcactcacCaTCgtcc
**CGCTGAGGATcACCCAGCGgccacG*atGgtgag***_caagggcgaggagctgttcaccggggtggtgcccat_
_cctggtcgagctggacggcgacgtaaacggccacaagttcagcgtgtccggcgagggcgagggcgatgccacctacgg_
_caagctgaccctgaagttcatctgcaccaccggcaagctgcccgtgccctggcccaccctcgtgaccaccctgacctacg_
_gcgtgcagtgcttcagccgctaccccgaccacatgaagcagcacgacttcttcaagtccgccatgcccgaaggctacgtc_
_caggagcgcaccatcttcttcaaggacgacggcaactacaagacccgcgccgaggtgaagttcgagggcgacaccctg_
_gtgaaccgcatcgagctgaagggcatcgacttcaaggaggacggcaacatcctggggcacaagctggagtacaactac_
_aacagccacaacgtctatatcatggccgacaagcagaagaacggcatcaaggtgaacttcaagatccgccacaacatc_
_gaggacggcagcgtgcagctcgccgaccactaccagcagaacacccccatcggcgacggccccgtgctgctgcccga_
_caaccactacctgagcacccagtccgccctgagcaaagaccccaacgagaagcgcgatcacatggtcctgctggagttc_
_gtgaccgccgccgggatcactctcggcatggacgagctgtacaagaagcttagccatggcttcccgccggaggtggagg_
_agcaggatgatggcacgctgcccatgtcttgtgcccaggagagcgggatggaccgtcaccctgcagcctgtgcttctgcta_
_ggatcaatgtg_TAGgcggccgcactcctcaggtgcaggctgcctatcagaaggtggtggctggtgtggccaatgccctgg
ctcacaaataccactgagatctttttccctctgccaaaa

FIG. 38A

**SEQ ID NO: 293, dTomato BiCMV MS2-C AUA *EGFPd2*:**

ctctagactgcagcctcaggagatctgggcccctacttgtacagctcgtccatgccgtacaggaacaggtggtggcggccc
tcggagcgctcgtactgttccacgatggtgtagtcctcgttgtgggaggtgatgtccagcttggtgtccacgtagtagtagccg
ggcagttgcacgggcttcttggccatgtagatggtcttgaactccaccaggtagtggccgccgtccttcagcttcagggcctg
gtggatctcgcccttcagcacgccgtcgcgggggtacaggcgctcggtggaggcctcccagcccatggtcttcttctgcatta
cggggccgtcgggggggaagttggtgccgcgcatcttcaccttgtagatcagcgtgccgtcctgcagggaggagtcctggg
tcacggtcaccagaccgccgtcctcgaagttcatcacgcgctcccacttgaagccctcggggaaggacagcttcttgtaatc
ggggatgtcggcggggtgcttcacgtacgccttggagccgtacatgaactgggggacaggatgtcccaggcgaagggc
agggggccgcccttggtcaccttcagcttggcggtctgggtgccctcgtaggggcggccctcgccctcgccctcgatctcga
actcgtggccgttcatggagccctccatgcgcaccttgaagcgcatgaactctttgatgacctcctcgcccttgctcaccatgg
tggcgaattctccaggcgatctgacggttcactaaacgagctctgcttatataggcctcccaccgtacacgccacctcgacat
actcgagtagttattaatagtaatcaattacggggtcattagttcatagcccatatatggagttccgcgttacataacttacggta
aatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagt
acgccccctattgacgtcaatgacggtaaatggcccgcctggcattatgcccagtacatgaccttatgggactttcctacttgg
cagtacatctacgtattagtcatcgctattaccatggtgatgcggttttggcagtacatcaatgggcgtggatagcggtttgactc
acggggatttccaagtctccaccccattgacgtcaatgggagtttgttttggcaccaaaatcaacgggactttccaaaatgtc
gtaacaactccgccccattgacgcaaatgggcggtaggcgtgtacggtgggaggtctatataagcagagctggtttagtga
accgtcagatccgctagggatcctctagtcagctgacgcgtgctagcgatatcggcgcgccagcactcacCaTCgtcc
**CGCTGAGGATcACCCAGCGgccacG*atAgtgag***caagggcgaggagctgttcaccggggtggtgcccat

FIG. 38B

*cctggtcgagctggacggcgacgtaaacggccacaagttcagcgtgtccggcgagggcgagggcgatgccacctacgg*
*caagctgaccctgaagttcatctgcaccaccggcaagctgcccgtgccctggcccaccctcgtgaccaccctgacctacg*
*gcgtgcagtgcttcagccgctaccccgaccacatgaagcagcacgacttcttcaagtccgccatgcccgaaggctacgtc*
*caggagcgcaccatcttcttcaaggacgacggcaactacaagacccgcgccgaggtgaagttcgagggcgacaccctg*
*gtgaaccgcatcgagctgaagggcatcgacttcaaggaggacggcaacatcctggggcacaagctggagtacaactac*
*aacagccacaacgtctatatcatggccgacaagcagaagaacggcatcaaggtgaacttcaagatccgccacaacatc*
*gaggacggcagcgtgcagctcgccgaccactaccagcagaacacccccatcggcgacggccccgtgctgctgcccga*
*caaccactacctgagcacccagtccgccctgagcaaagaccccaacgagaagcgcgatcacatggtcctgctggagttc*
*gtgaccgccgccgggatcactctcggcatggacgagctgtacaagaagcttagccatggcttcccgccggaggtggagg*
*agcaggatgatggcacgctgcccatgtcttgtgcccaggagagcgggatggaccgtcaccctgcagcctgtgcttctgcta*
*ggatcaatgtg*TAGgcggccgcactcctcaggtgcaggctgcctatcagaaggtggtggctggtgtggccaatgccctgg
ctcacaaataccactgagatctttttccctctgccaaaa

FIG. 38B(Cont.)

**SEQ ID NO: 294, dTomato BiCMV MS2-A AUG *EGFPd2*:**

ctctagactgcagcctcaggagatctgggcccctacttgtacagctcgtccatgccgtacaggaacaggtggtggcggccc
tcggagcgctcgtactgttccacgatggtgtagtcctcgttgtgggaggtgatgtccagcttggtgtccacgtagtagtagccg
ggcagttgcacgggcttcttggccatgtagatggtcttgaactccaccaggtagtggccgccgtccttcagcttcagggcctg
gtggatctcgcccttcagcacgccgtcgcgggggtacaggcgctcggtggaggcctcccagcccatggtcttcttctgcatta
cggggccgtcgggggggaagttggtgccgcgcatcttcaccttgtagatcagcgtgccgtcctgcagggaggagtcctggg
tcacggtcaccagaccgccgtcctcgaagttcatcacgcgctcccacttgaagccctcggggaaggacagcttcttgtaatc
ggggatgtcggcggggtgcttcacgtacgccttggagccgtacatgaactggggggacaggatgtcccaggcgaagggc
agggggccgcccttggtcaccttcagcttggcggtctgggtgccctcgtaggggcggccctcgccctcgccctcgatctcga
actcgtggccgttcatggagccctccatgcgcaccttgaagcgcatgaactctttgatgacctcctcgcccttgctcaccatgg
tggcgaattctccaggcgatctgacggttcactaaacgagctctgcttatataggcctcccaccgtacacgccacctcgacat
actcgagtagttattaatagtaatcaattacggggtcattagttcatagcccatatatggagttccgcgttacataacttacggta
aatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagt
acgccccctattgacgtcaatgacggtaaatggcccgcctggcattatgcccagtacatgaccttatgggactttcctacttgg
cagtacatctacgtattagtcatcgctattaccatggtgatgcggttttggcagtacatcaatgggcgtggatagcggtttgactc
acggggatttccaagtctccaccccattgacgtcaatgggagtttgttttggcaccaaaatcaacgggactttccaaaatgtc
gtaacaactccgccccattgacgcaaatgggcggtaggcgtgtacggtgggaggtctatataagcagagctggtttagtga
accgtcagatccgctagggatcctctagtcagctgacgcgtgctagcgatatcggcgcgccagcactcacCaTCgtcc
**CGCTGAGGATAACCCAGCGgccacG*atGgtgag***_caagggcgaggagctgttcaccggggtggtgccca_
*tcctggtcgagctggacggcgacgtaaacggccacaagttcagcgtgtccggcgagggcgagggcgatgccacctacg*
*gcaagctgaccctgaagttcatctgcaccaccggcaagctgcccgtgccctggcccaccctcgtgaccaccctgacctac*
*ggcgtgcagtgcttcagccgctaccccgaccacatgaagcagcacgacttcttcaagtccgccatgcccgaaggctacgt*
*ccaggagcgcaccatcttcttcaaggacgacggcaactacaagacccgcgccgaggtgaagttcgagggcgacaccct*
*ggtgaaccgcatcgagctgaagggcatcgacttcaaggaggacggcaacatcctggggcacaagctggagtacaacta*
*caacagccacaacgtctatatcatggccgacaagcagaagaacggcatcaaggtgaacttcaagatccgccacaacat*
*cgaggacggcagcgtgcagctcgccgaccactaccagcagaacacccccatcggcgacggccccgtgctgctgcccg*
*acaaccactacctgagcacccagtccgccctgagcaaagaccccaacgagaagcgcgatcacatggtcctgctggagtt*
*cgtgaccgccgccgggatcactctcggcatggacgagctgtacaagaagcttagccatggcttcccgccggaggtggag*
*gagcaggatgatggcacgctgcccatgtcttgtgcccaggagagcgggatggaccgtcaccctgcagcctgtgcttctgct*
*aggatcaatgtg*TAGgcggccgcactcctcaggtgcaggctgcctatcagaaggtggtggctggtgtggccaatgccctg
gctcacaaataccactgagatctttttccctctgccaaaa

FIG. 38C

**SEQ ID NO: 295, dTomato BiCMV MS2-A AUA *EGFPd2*:**

ctctagactgcagcctcaggagatctgggcccctacttgtacagctcgtccatgccgtacaggaacaggtggtggcggccc
tcggagcgctcgtactgttccacgatggtgtagtcctcgttgtgggaggtgatgtccagcttggtgtccacgtagtagtagccg
ggcagttgcacgggcttcttggccatgtagatggtcttgaactccaccaggtagtggccgccgtccttcagcttcagggcctg
gtggatctcgcccttcagcacgccgtcgcgggggtacaggcgctcggtggaggcctcccagcccatggtcttcttctgcatta
cggggccgtcgggggggaagttggtgccgcgcatcttcaccttgtagatcagcgtgccgtcctgcagggaggagtcctggg
tcacggtcaccagaccgccgtcctcgaagttcatcacgcgctcccacttgaagccctcggggaaggacagcttcttgtaatc
ggggatgtcggcggggtgcttcacgtacgccttggagccgtacatgaactggggggacaggatgtcccaggcgaagggc
agggggccgcccttggtcaccttcagcttggcggtctgggtgccctcgtaggggcggccctcgccctcgccctcgatctcga
actcgtggccgttcatggagccctccatgcgcaccttgaagcgcatgaactctttgatgacctcctcgcccttgctcaccatgg
tggcgaattctccaggcgatctgacggttcactaaacgagctctgcttatataggcctcccaccgtacacgccacctcgacat
actcgagtagttattaatagtaatcaattacggggtcattagttcatagcccatatatggagttccgcgttacataacttacggta
aatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagt
acgccccctattgacgtcaatgacggtaaatggcccgcctggcattatgcccagtacatgaccttatgggactttcctacttgg
cagtacatctacgtattagtcatcgctattaccatggtgatgcggttttggcagtacatcaatgggcgtggatagcggtttgactc
acggggatttccaagtctccaccccattgacgtcaatgggagtttgttttggcaccaaaatcaacgggactttccaaaatgtc
gtaacaactccgccccattgacgcaaatgggcggtaggcgtgtacggtgggaggtctatataagcagagctggtttagtga
accgtcagatccgctagggatcctctagtcagctgacgcgtgctagcgatatcggcgcgccagcactcacCaTCgtcc
**CGCTGAGGATAACCCAGCGgccacG*atAgtgag****caagggcgaggagctgttcaccggggtggtgccca*
*tcctggtcgagctggacggcgacgtaaacggccacaagttcagcgtgtccggcgagggcgagggcgatgccacctacg*
*gcaagctgaccctgaagttcatctgcaccaccggcaagctgcccgtgccctggcccaccctcgtgaccaccctgacctac*
*ggcgtgcagtgcttcagccgctaccccgaccacatgaagcagcacgacttcttcaagtccgccatgcccgaaggctacgt*
*ccaggagcgcaccatcttcttcaaggacgacggcaactacaagacccgcgccgaggtgaagttcgagggcgacaccct*
*ggtgaaccgcatcgagctgaagggcatcgacttcaaggaggacggcaacatcctggggcacaagctggagtacaacta*
*caacagccacaacgtctatatcatggccgacaagcagaagaacggcatcaaggtgaacttcaagatccgccacaacat*
*cgaggacggcagcgtgcagctcgccgaccactaccagcagaacacccccatcggcgacggccccgtgctgctgcccg*
*acaaccactacctgagcacccagtccgccctgagcaaagaccccaacgagaagcgcgatcacatggtcctgctggagtt*
*cgtgaccgccgccgggatcactctcggcatggacgagctgtacaagaagcttagccatggcttcccgccggaggtggag*
*gagcaggatgatggcacgctgcccatgtcttgtgcccaggagagcgggatggaccgtcaccctgcagcctgtgcttctgct*
*aggatcaatgtg*TAGgcggccgcactcctcaggtgcaggctgcctatcagaaggtggtggctggtgtggccaatgccctg
gctcacaaataccactgagatctttttccctctgccaaaa

FIG. 38D

**SEQ ID NO: 296, AUG-signal-sequence-HA-*GFP*-GPI**

TAATACGACTCACTATAGGGAGACCCAAGCTGGCTAGCGgtacc
gccaccATGGAGACCGACACCCTGCTCCTGTGGGTGTTGTTGC
TCTGGGTCCCAGGTTCTACCGGCGACGGAGGAGGCGGCTAT
CCCTATGACGTACCGGATTATGCCGGTgaacttgatgaattggtatactta
ctagatgggccaggttatgaccctatacatagtggcggtagtgggggacgtacg*atggtga*
*gcaagggcgaggagctgttcaccggggtggtgcccatcctggtcgagctggacggcgac*
*gtaaacggccacaagttcagcgtgtccggcgagggcgagggcgatgccacctacggca*
*agctgaccctgaagttcatctgcaccaccggcaagctgcccgtgccctggcccaccctcgt*
*gaccaccctgacctacggcgtgcagtgcttcagccgctaccccgaccacatgaagcagc*
*acgacttcttcaagtccgccatgcccgaaggctacgtccaggagcgcaccatcttcttcaa*
*ggacgacggcaactacaagacccgcgccgaggtgaagttcgagggcgacaccctggt*
*gaaccgcatcgagctgaagggcatcgacttcaaggaggacggcaacatcctggggcac*
*aagctggagtacaactacaacagccacaacgtctatatcatggccgacaagcagaaga*
*acggcatcaaggtgaacttcaagatccgccacaacatcgaggacggcagcgtgcagct*
*cgccgaccactaccagcagaacacccccatcggcgacggccccgtgctgctgcccgac*
*aaccactacctgagcacccagtccgccctgagcaaagaccccaacgagaagcgcgat*
*cacatggtcctgctggagttcgtgaccgccgccgggatcactctcggcatggatgaacta*t
accaactcgagaatggcggcataagcctgctggttcagaacacatcctggatgctgctgct
gctgctttccctctccctcctccaagccctggacttcatttctctgtaaTCTAGAGGGCC
CGTTTAAACCCGCTGATCAGCCTCGACTGTGCCTTCTAGTTGC
CAGCCATCTGT

FIG. 39A

**SEQ ID NO: 297, MS2-C-AUA-signal-sequence-HA-*GFP*-GPI**

TTATCGAAATTAATACGACTCACTATAGGGAGACCCAAGCTGG
CTAGCtGGTCTCCATcgtgccCGCTGAGGATcACCCAGCGgccac
gATaGAGACCGACACCCTGCTCCTGTGGGTGTTGTTGCTCTG
GGTCCCAGGTTCTACCGGCGACGGAGGAGGCGGCTATCCCT
ACGACGTACCGGATTACGCCGGTggcggtagtgggggacgtacg*atggt*
*gagcaagggcgaggagctgttcaccggggtggtgcccatcctggtcgagctggacggcg*
*acgtaaacggccacaagttcagcgtgtccggcgagggcgagggcgatgccacctacgg*
*caagctgaccctgaagttcatctgcaccaccggcaagctgcccgtgccctggcccaccct*
*cgtgaccaccctgacctacggcgtgcagtgcttcagccgctaccccgaccacatgaagc*
*agcacgacttcttcaagtccgccatgcccgaaggctacgtccaggagcgcaccatcttctt*
*caaggacgacggcaactacaagacccgcgccgaggtgaagttcgagggcgacaccct*
*ggtgaaccgcatcgagctgaagggcatcgacttcaaggaggacggcaacatcctgggg*
*cacaagctggagtacaactacaacagccacaacgtctatatcatggccgacaagcaga*
*agaacggcatcaaggtgaacttcaagatccgccacaacatcgaggacggcagcgtgca*
*gctcgccgaccactaccagcagaacacccccatcggcgacggccccgtgctgctgccc*
*gacaaccactacctgagcacccagtccgccctgagcaaagaccccaacgagaagcgc*
*gatcacatggtcctgctggagttcgtgaccgccgccgggatcactctcggcatggatgaac*
*ta*taccaactcgagaatggcggcataagcctgctggttcagaacacatcctggatgctgct
gctgctgctttccctctccctcctccaagccctggacttcatttctctgtaaTCTAGAGGG
CCCGTTTAAACCCGCTGATCAGCCT

FIG. 39B

**SEQ ID NO: 298, MS2-A-AUA-signal-sequence-HA-*GFP*-GPI**

TTATCGAAATTAATACGACTCACTATAGGGAGACCCAAGCTGG
CTAGCtGGTCTCCATcgtgccCGCTGAGGATaACCCAGCGgccac
gATaGAGACCGACACCCTGCTCCTGTGGGTGTTGTTGCTCTG
GGTCCCAGGTTCTACCGGCGACGGAGGAGGCGGCTATCCCT
ACGACGTACCGGATTACGCCGGTggcggtagtgggggacgtacg*atggt*
*gagcaagggcgaggagctgttcaccggggtggtgcccatcctggtcgagctggacggcg*
*acgtaaacggccacaagttcagcgtgtccggcgagggcgagggcgatgccacctacgg*
*caagctgaccctgaagttcatctgcaccaccggcaagctgcccgtgccctggcccaccct*
*cgtgaccaccctgacctacggcgtgcagtgcttcagccgctaccccgaccacatgaagc*
*agcacgacttcttcaagtccgccatgcccgaaggctacgtccaggagcgcaccatcttctt*
*caaggacgacggcaactacaagacccgcgccgaggtgaagttcgagggcgacaccct*
*ggtgaaccgcatcgagctgaagggcatcgacttcaaggaggacggcaacatcctgggg*
*cacaagctggagtacaactacaacagccacaacgtctatatcatggccgacaagcaga*
*agaacggcatcaaggtgaacttcaagatccgccacaacatcgaggacggcagcgtgca*
*gctcgccgaccactaccagcagaacacccccatcggcgacggccccgtgctgctgccc*
*gacaaccactacctgagcacccagtccgccctgagcaaagaccccaacgagaagcgc*
*gatcacatggtcctgctggagttcgtgaccgccgccgggatcactctcggcatggatgaac*
*ta*taccaactcgagaatggcggcataagcctgctggttcagaacacatcctggatgctgct
gctgctgctttccctctccctcctccaagccctggacttcatttctctgtaaTCTAGAGGG
CCCGTTTAAACCCGCTGATCAGCCT

FIG. 39C

**SEQ ID NO: 299, dTomato BiCMV MS2-C AUG-OFF *EGFPd2*:**

ctctagactgcagcctcaggagatctgggcccctacttgtacagctcgtccatgccgtacaggaacaggtggtggcggccc
tcggagcgctcgtactgttccacgatggtgtagtcctcgttgtgggaggtgatgtccagcttggtgtccacgtagtagtagccg
ggcagttgcacgggcttcttggccatgtagatggtcttgaactccaccaggtagtggccgccgtccttcagcttcagggcctg
gtggatctcgcccttcagcacgccgtcgcgggggtacaggcgctcggtggaggcctcccagcccatggtcttcttctgcatta
cggggccgtcgggggggaagttggtgccgcgcatcttcaccttgtagatcagcgtgccgtcctgcagggaggagtcctggg
tcacggtcaccagaccgccgtcctcgaagttcatcacgcgctcccacttgaagccctcggggaaggacagcttcttgtaatc
ggggatgtcggcggggtgcttcacgtacgccttggagccgtacatgaactggggggacaggatgtcccaggcgaagggc
agggggccgcccttggtcaccttcagcttggcggtctgggtgccctcgtaggggcggccctcgccctcgccctcgatctcga
actcgtggccgttcatggagccctccatgcgcaccttgaagcgcatgaactctttgatgacctcctcgcccttgctcaccatgg
tggcgaattctccaggcgatctgacggttcactaaacgagctctgcttatataggcctcccaccgtacacgccacctcgacat
actcgagtagttattaatagtaatcaattacggggtcattagttcatagcccatatatggagttccgcgttacataacttacggta
aatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagt
acgccccctattgacgtcaatgacggtaaatggcccgcctggcattatgcccagtacatgaccttatgggactttcctacttgg
cagtacatctacgtattagtcatcgctattaccatggtgatgcggttttggcagtacatcaatgggcgtggatagcggtttgactc
acggggatttccaagtctccaccccattgacgtcaatgggagtttgttttggcaccaaaatcaacgggactttccaaaatgtc
gtaacaactccgccccattgacgcaaatgggcggtaggcgtgtacggtgggaggtctatataagcagagctggtttagtga
accgtcagatccgctagggatcctctagtcagctgacgcgtgctagcgatatcggcgcgccagcactcacCaCCgtcc
CGCTGAGGATCACCCAGCGgccacGatGgtgag*caagggcgaggagctgttcaccggggtggtgccca*
*tcctggtcgagctggacggcgacgtaaacggccacaagttcagcgtgtccggcgagggcgagggcgatgccacctacg*
*gcaagctgaccctgaagttcatctgcaccaccggcaagctgcccgtgccctggcccaccctcgtgaccaccctgacctac*
*ggcgtgcagtgcttcagccgctaccccgaccacatgaagcagcacgacttcttcaagtccgccatgcccgaaggctacgt*
*ccaggagcgcaccatcttcttcaaggacgacggcaactacaagacccgcgccgaggtgaagttcgagggcgacaccct*
*ggtgaaccgcatcgagctgaagggcatcgacttcaaggaggacggcaacatcctggggcacaagctggagtacaacta*
*caacagccacaacgtctatatcatggccgacaagcagaagaacggcatcaaggtgaacttcaagatccgccacaacat*
*cgaggacggcagcgtgcagctcgccgaccactaccagcagaacacccccatcggcgacggccccgtgctgctgcccg*
*acaaccactacctgagcacccagtccgccctgagcaaagaccccaacgagaagcgcgatcacatggtcctgctggagtt*
*cgtgaccgccgccgggatcactctcggcatggacgagctgtacaagaagcttagccatggcttcccgccggaggtggag*
*gagcaggatgatggcacgctgcccatgtcttgtgcccaggagagcgggatggaccgtcaccctgcagcctgtgcttctgct*
*aggatcaatgtg*TAGgcggccgcactcctcaggtgcaggctgcctatcagaaggtggtggctggtgtggccaatgccctg
gctcacaaataccactgagatctttttccctctgccaaaa

FIG. 40A

**SEQ ID NO: 300, dTomato BiCMV MS2-A AUG-OFF *EGFPd2*:**

ctctagactgcagcctcaggagatctgggcccctacttgtacagctcgtccatgccgtacaggaacaggtggtggcggccc
tcggagcgctcgtactgttccacgatggtgtagtcctcgttgtgggaggtgatgtccagcttggtgtccacgtagtagtagccg
ggcagttgcacgggcttcttggccatgtagatggtcttgaactccaccaggtagtggccgccgtccttcagcttcagggcctg
gtggatctcgcccttcagcacgccgtcgcgggggtacaggcgctcggtggaggcctcccagcccatggtcttcttctgcatta
cggggccgtcgggggggaagttggtgccgcgcatcttcaccttgtagatcagcgtgccgtcctgcagggaggagtcctggg
tcacggtcaccagaccgccgtcctcgaagttcatcacgcgctcccacttgaagccctcggggaaggacagcttcttgtaatc
ggggatgtcggcggggtgcttcacgtacgccttggagccgtacatgaactggggggacaggatgtcccaggcgaagggc
agggggccgcccttggtcaccttcagcttggcggtctgggtgccctcgtaggggcggccctcgccctcgccctcgatctcga
actcgtggccgttcatggagccctccatgcgcaccttgaagcgcatgaactctttgatgacctcctcgcccttgctcaccatgg
tggcgaattctccaggcgatctgacggttcactaaacgagctctgcttatataggcctcccaccgtacacgccacctcgacat
actcgagtagttattaatagtaatcaattacggggtcattagttcatagcccatatatggagttccgcgttacataacttacggta
aatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagt
acgccccctattgacgtcaatgacggtaaatggcccgcctggcattatgcccagtacatgaccttatgggactttcctacttgg
cagtacatctacgtattagtcatcgctattaccatggtgatgcggttttggcagtacatcaatgggcgtggatagcggtttgactc
acggggatttccaagtctccaccccattgacgtcaatgggagtttgttttggcaccaaaatcaacgggactttccaaaatgtc
gtaacaactccgccccattgacgcaaatgggcggtaggcgtgtacggtgggaggtctatataagcagagctggtttagtga
accgtcagatccgctagggatcctctagtcagctgacgcgtgctagcgatatcggcgcgccagcactcacCaCCgtcc
**CGCTGAGGATAACCCAGCGgccacG*atGgtgag***_caagggcgaggagctgttcaccggggtggtgccca_
_tcctggtcgagctggacggcgacgtaaacggccacaagttcagcgtgtccggcgagggcgagggcgatgccacctacg_
_gcaagctgaccctgaagttcatctgcaccaccggcaagctgcccgtgccctggcccaccctcgtgaccaccctgacctac_
_ggcgtgcagtgcttcagccgctaccccgaccacatgaagcagcacgacttcttcaagtccgccatgcccgaaggctacgt_
_ccaggagcgcaccatcttcttcaaggacgacggcaactacaagacccgcgccgaggtgaagttcgagggcgacaccct_
_ggtgaaccgcatcgagctgaagggcatcgacttcaaggaggacggcaacatcctggggcacaagctggagtacaacta_
_caacagccacaacgtctatatcatggccgacaagcagaagaacggcatcaaggtgaacttcaagatccgccacaacat_
_cgaggacggcagcgtgcagctcgccgaccactaccagcagaacacccccatcggcgacggccccgtgctgctgcccg_
_acaaccactacctgagcacccagtccgccctgagcaaagaccccaacgagaagcgcgatcacatggtcctgctggagtt_
_cgtgaccgccgccgggatcactctcggcatggacgagctgtacaagaagcttagccatggcttcccgccggaggtggag_
_gagcaggatgatggcacgctgcccatgtcttgtgcccaggagagcgggatggaccgtcaccctgcagcctgtgcttctgct_
_aggatcaatgtg_TAGgcggccgcactcctcaggtgcaggctgcctatcagaaggtggtggctggtgtggccaatgccctg
gctcacaaataccactgagatctttttccctctgccaaaa

FIG. 40B

SEQ ID NO: 301, CD8signal-HA-HaloTag-T2A(G18R)-loop-MS2C-3xFLAG-Gal4VP64-T2A-TagBFP

TAATACGACTCACTATAGGGAGACCCAAGCTGGCTAGCGT TTAAACTTAAGCTTgccaccatggc
attgcccgtgaccgccctgctgctgccactggccttgttgctccacgccgcgcggccaTATCC CTACGATGTGCCCGATT
ACGCTaccggtATGGCAGAAATCGGTACTGGCTTTCCATTCGACCCCCATTATGTGGAAGTCC
TGGGCGAGCGCATGCACTACGTCGATGTT GGTCCGCGCGATGGCACCCCTGTGCTGTTCC
TGCACGGTAACCCGACCTCCTCCTACGTGTGGCGCAACATCATCCCGCATGTTGCACCGA
CCCATCGCTGCATTGCTCCAGACCTGATCGGTATGGGCAAATCCGACAAACCAGACCTGG
GTTATTTCTTCGACGACCACGTCCGCTTCATGGATGCCTTCATCGAAGCCCTGGGTCTGGA
AGAGGTCGTCCTGGTCATTCACGACTGGGGCTCCGCTCTGGGTTTCCACTGGGCCAAGCG
CAATCCAGAGCGCGTCAAAGGTATTGCATTTATGGAGTTCATCCGCCCTATCCCGACCTGG
GACGAATGGCCAGAATTTGCCCGCGAGACCT TCCAGGCCTTCCGCACCACCGACGTCGGC
CGCAAGCTGATCATCGATCAGAACGTTTTTATCGAGGGTACGCTGCCGATGGGTGTCGTCC
GCCCGCTGACTGAAGTCGAGATGGACCATTACCGCGAGCCGTTCCTGAATCCTGTTGACC
GCGAGCCACTGTGGCGCTTCCCAAACGAGCTGCCAATCGCCGGTGAGCCAGCGAACATCG
TCGCGCTGGTCGAAGAATACATGGACTGGCTGCACCAGTCCCCTGTCCCGAAGCTGCTGT
TCTGGGGCACCCCAGGCGTTCTGATCCCACCGGCCGAAGCCGCTCGCCTGGCCAAAAGC
CTGCCTAACTGCAAGGCTGTGGACATCGGCCCGGGTCTGAATCTGCTGCAAGAAGACAAC
CCGGACCTGATCGGCAGCGAGATCGCGCGCTGGCTGTCCACGCTCGAGATTTCCGGCggc
ggaGGAAGTGGCGAGGGCAGGGGAAGTCTCCTAACATGCGGGGACGTGGAGGAAAACCCT

FIG. 41 aGGCCTTACATGAGGATCACCCATGTTAGGCCcAGGGTTgactacaaagaccatgacggtgattataaag
atcatgacatcgactacaaggacgacgatgacaagGGTACCatgaagctgctgagcagcatcgagcaggcctgtgacatctgc
cggctgaagaaactgaagtgcagcaaagaaaagcccaagtgcgccaagtgcctgaagaacaactgggagtgccggtacagccc
caagaccaagagaagcccccctgaccagagcccacctgaccgaggtggaaagccggctggaaagactggaacagctgtttctgctg
atcttcccacgcgaggacctggacatgatcctgaagatggacagcctgcaggacatcaaggccctgctgaccggcctgttcgtgcag
gacaacgtgaacaaggacgccgtgaccgacagactggccagcgtggaaaccgacatgcccctgaccctgcggcagcacagaat
cagcgccaccagcagcagcgaggaaagcagcaacaagggccagcggcagctgacagtgtctgctgctgcaggcggaagcgga
ggctctggcggatctgatgccctggacgacttcgacctggatatgctgggcagcgacgccctggatgatttgatctggacatgctggga
tctgacgctctggacgatttcgatctcgacatgttgggatcagatgcactggatgactttgacctggacatgctcggatcaATGGAGG
GCAGAGGAAGTCTTCTAACATGCGGTGACGTGGAGGAGAATCCCGGCCCTGGATCCAGCG
AGCTGATTAAGGAGAACATGCACATGAAGCTGTACATGGAGGGCACCGTGGACAACCATCA
CTTCAAGTGCACATCCGAGGGCGAAGGCAAGCCCTACGAGGGCACCCAGACCATGAGAAT
CAAGGTGGTCGAGGGCGGCCCTCTCCCCTTCGCCTTCGACATCCTGGCTACTAGCTTCCT
CTACGGCAGCAAGACCTTCATCAACCACACCCAGGGCATCCCCGACTTCTTCAAGCAGTCC
TTCCCTGAGGGCTTCACATGGGAGAGAGTCACCACATACGAAGACGGGGGCGTGCTGACC
GCTACCCAGGACACCAGCCTCCAGGACGGCTGCCTCATCTACAACGTCAAGATCAGAGGG
GTGAACTTCACATCCAACGGCCCTGTGATG CAGAAGAAAACACTCGGCTGGGAGGCCTTC
ACCGAGACGCTGTACCCCGCTGACGGCGGCCTGGAAGGCAGAAACGACATGGCCCTGAA
GCTCGTGGGCGGGAGCCATCTGATCGCAAACATCAAGACCACATATAGATCCAAGAAACCC
GCTAAGAACCTCAAGATGCCTGGCGTCTACTATGTGGACTACAGACTGGAAAGAATCAAGG
AGGCCAACAACGAGACCTACGTCGAGCAGCACGAGGTGGCAGTGGCCAGATACTGCGACC
TCCCTAGCAAACTGGGGCACAAGCTTAATtgaTCTAGAGGGCCCGTTTAAACCCGCTGATCA
GCCTCGACTGTGCCTTCTA

FIG. 41(Cont.)

**SEQ ID NO: 302, mCherry-FLAG-P2A/T2A-Loop-MS2-HaloTag-T7-Loop-PP7-P2A/T2A-*HA-mNeonGreen(M10K)*:**

TAATACGACTCACTATAGGGAGACCCAAGCTGGCTAGGTAAGCTTGGTACCGAGCTCGGATCCa
ccggtcgccaccatggtgagcaagggcgaggaggataacatggccatcatcaaggagttcatgcgcttcaaggtgcacatggagggctcc
gtgaacggccacgagttcgagatcgagggcgagggcgagggccgcccctacgagggcacccagaccgccaagctgaaggtgaccaa
gggtggcccctgcccttcgcctgggacatcctgtcccctcagttcatgtacggctccaaggcctacgtgaagcaccccgccgacatccccga
ctacttgaagctgtccttccccgagggcttcaagtgggagcgcgtgatgaacttcgaggacggcggcgtggtgaccgtgacccaggactcct
ccctgcaggacggcgagttcatctacaaggtgaagctgcgcggcaccaacttcccctccgacggccccgtaatgcagaagaagaccatgg
gctgggaggcctcctccgagcggatgtaccccgaggacggcgccctgaagggcgagatcaagcagaggctgaagctgaaggacggcg
gccactacgacgctgaggtcaagaccacctacaaggccaagaagcccgtgcagctgcccggcgcctacaacgtcaacatcaagttggac
atcacctcccacaacgaggactacaccatcgtggaacagtacgaacgcgccgagggccgccactccaccggcggcatggacgagctgT
ACaaggattacaaggatgacgatgacaaaGGTAGCGGGGCAACTAATTTTAGCTTACTCAAACAGGCTGG
GGACGTCGAGGAGAATCCAGGCCCTGCATCCGCT GGCTCTGGAGAAGGACGAGGCTCCTTGCT
CACCTGTGGAGATGTCGAAGAGAACCCAGGTCCTGCAACCGGGAATTCCGCGTAGCGCTAGCT
TTGCCAGCGCCACGCGaaACATGAGGATcACCCATGTGCCGCTATGGCAGAAATCGGTACTGGC
TTTCCATTCGACCCCCATTATGTGGAAGTCCTGGGC GAGCGCATGCACTACGTCGATGTTGGTC
CGCGCGATGGCACCCCTGTGCTGTTCCTGCACGGTAACCCGACCTCCTCCTACGTGTGGCGCA
ACATCATCCCGCATGTTGCACCGACCCATCGC TGCATTGCTCCAGACCTGATCGGTATGGGCAA
ATCCGACAAACCAGACCTGGGTTATTTCTTCGACGACCACGTCCGCTTCATGGATGCCTTCATC
GAAGCCCTGGGTCTGGAAGAGGTCGTCCTGGTCATTCACGACTGGGGCTCCGCTCTGGGTTTC
CACTGGGCCAAGCGCAATCCAGAGCGCGTCAAAGGTATTGCATTTATGGAGTTCATCCGCCCTA

FIG. 42A

TCCCGACCTGGGACGAATGGCCAGAATTTGCCCGCGAGACCTTCCAGGCCTTCCGCACCACCG
ACGTCGGCCGCAAGCTGATCATCGATCAGAACGTTTTTATCGAGGGTACGCTGCCGATGGGTGT
CGTCCGCCCGCTGACTGAAGTCGAGATGGACCATTACCGCGAGCCGTTCCTGAATCCTGTTGAC
CGCGAGCCACTGTGGCGCTTCCCAAACGAGCTGCCAATCGCCGGTGAGCCAGCGAACATCGTC
GCGCTGGTCGAAGAATACATGGACTGGCTGCACCAGTCCCCTGTCCCGAAGCTGCTGTTCTGG
GGCACCCCAGGCGTTCTGATCCCACCGGCCGAAGCCGCTCGCCTGGCCAAAAGCCTGCCTAAC
TGCAAGGCTGTGGACATCGGCCCGGGTCTGAATCTGCTGCAAGAAGACAACCCGGACCTGATC
GGCAGCGAGATCGCGCGCTGGCTGTCGACGCTCGAGATTTCTGGCACCGGTATGGCATCTATG
ACTGGAGGCCAACAGATGgGTCCTGCAACCGGGAATTCCGCGTAGCGCTAGCTTTGCCAGCGC
CACGCGaaggagcagacgatatggcgtcgctccaaTACTAGTGCCACAAACTTCTCTCTGCTA AAGCAAGCA
GGTGATGTTGAAGAAAACCCAGGGCCTGGAGGGTCCGAGGGCAGGGGAAGTCTCCTAACATGC
GGGGACGTGGAGGAAAATCCCGGCCCATCCGGA *TATCCCTACGATGTGCCCGATTACGCTATC*
*GATgtgagcaagggcgaAgaAgataacaAggcctctcccagcgacacatgagttacacatctttggctccatcaacggtgtggactttg*
*acatggtgggtcagggcaccggcaatccaaatgatggttatgaggagttaaacctgaagtccaccaagggtgacctccagttctcccctgg*
*attctggtccctcatatcgggtatggcttccatcagtacctgccctaccctgacgggatgtcgcctttccaggccgccatggtagatggcAGCg*
*gataccaagtccatcgcacaatgcagtttgaagatggtgcctcccttactgttaactaccgctacacctacgagggaagccacatcaaagga*
*gaggcccaggtgaaggggactggtttccctgctgacggtcctgtgatgaccaactcgctgaccgctgcggactggtgcaggtcgaagaaga*
*cttaccccaacgacaaaaccatcatcagtacctttaagtggagttacaccactggaaatggcaagAGAtaccggagcactgcgcggacc*
*acctacacctttgccaagccaatggcggctaactatctgaagaaccagccgatgtacgtgttccgtaagacggagctcaagcactccaaga*
*ccgagctcaacttcaaggagtggcaaaaggcctttaccgatgtgatgGGAatggacGAGCTGTATaag*GCTAGC TAAGCG
GCCGCTCGAGTCTAGAGGGCCCGCGGTTCGAAGGTAAGCCTATCCCTAACCCTCTCCTCGGTC
TCGATTCTACGCGTACCGGTCATCATCACCATCACCATTGAGTTTAAACCCGCTGATCAGCCTCG
ACTGTGCCTTCTA

FIG. 42A(Cont.)

**SEQ ID NO: 303, mCherry-FLAG-P2A/T2A-Loop-MS2-HaloTag-T7-Loop-BoxB-P2A/T2A-*HA-mNeonGreen(M10K)***

TAATACGACTCACTATAGGGAGACCCAAGCTGGCTAGGTAAGCTTGGTACCGAGCTCGGATCCa
ccggtcgccaccatggtgagcaagggcgaggaggataacatggccatcatcaaggagttcatgcgcttcaaggtgcacatggagggctcc
gtgaacggccacgagttcgagatcgagggcgagggcgagggccgcccctacgagggcacccagaccgccaagctgaaggtgaccaa
gggtggcccctgcccttcgcctgggacatcctgtcccctcagttcatgtacggctccaaggcctacgtgaagcaccccgccgacatccccga
ctacttgaagctgtccttccccgagggcttcaagtgggagcgcgtgatgaacttcgaggacggcggcgtggtgaccgtgacccaggactcct
ccctgcaggacggcgagttcatctacaaggtgaagctgcgcggcaccaacttcccctccgacggccccgtaatgcagaagaagaccatgg
gctgggaggcctcctccgagcggatgtaccccgaggacggcgccctgaagggcgagatcaagcagaggctgaagctgaaggacggcg
gccactacgacgctgaggtcaagaccacctacaaggccaagaagcccgtgcagctgcccggcgcctacaacgtcaacatcaagttggac
atcacctcccacaacgaggactacaccatcgtggaacagtacgaacgcgccgagggccgccactccaccggcggcatggacgagctgT
ACaaggattacaaggatgacgatgacaaaGGTAGCGGGCAACTAATTTTAGCTTACTCAAACAGGCTGG
GGACGTCGAGGAGAATCCAGGCCCTGCATCCGCT GGCTCTGGAGAAGGACGAGGCTCCTTGCT
CACCTGTGGAGATGTCGAAGAGAACCCAGGTCCTGCAACCGGGAATTCCGCGTAGCGCTAGCT
TTGCCAGCGCCACGCGaaACATGAGGATcACCCATGTGCCGCTATGGCAGAAATCGGTACTGGC
TTTCCATTCGACCCCCATTATGTGGAAGTCCTGGGC GAGCGCATGCACTACGTCGATGTTGGTC
CGCGCGATGGCACCCCTGTGCTGTTCCTGCACGGTAACCCGACCTCCTCCTACGTGTGGCGCA
ACATCATCCCGCATGTTGCACCGACCCATCGC TGCATTGCTCCAGACCTGATCGGTATGGGCAA
ATCCGACAAACCAGACCTGGGTTATTTCTTCGACGACCACGTCCGCTTCATGGATGCCTTCATC
GAAGCCCTGGGTCTGGAAGAGGTCGTCCTGGTCATTCACGACTGGGGCTCCGCTCTGGGTTTC
CACTGGGCCAAGCGCAATCCAGAGCGCGTCAAAGGTATTGCATTTATGGAGTTCATCCGCCCTA

FIG. 42B

TCCCGACCTGGGACGAATGGCCAGAATTTGCCCGCGAGACCTTCCAGGCCTTCCGCACCACCG
ACGTCGGCCGCAAGCTGATCATCGATCAGAACGTTTTTATCGAGGGTACGCTGCCGATGGGTGT
CGTCCGCCCGCTGACTGAAGTCGAGATGGACCATTACCGCGAGCCGTTCCTGAATCCTGTTGA C
CGCGAGCCACTGTGGCGCTTCCCAAACGAGCTGCCAATCGCCGGTGAGCCAGCGAACATCGTC
GCGCTGGTCGAAGAATACATGGACTGGCTGCACCAGTCCCCTGTCCCGAAGCTGCTGTTCTGG
GGCACCCCAGGCGTTCTGATCCCACCGGCCGAAGCCGCTCGCCTGGCCAAAAGCCTGCCTAAC
TGCAAGGCTGTGGACATCGGCCCGGGTCTGAATCTGCTGCAAGAAGACAACCCGGACCTGATC
GGCAGCGAGATCGCGCGCTGGCTGTCGACGCTCGAGATTTCTGGCACCGGTATGGCATCTATG
ACTGGAGGCCAACAGATGgGTCCTGCAACCGGgAATTCCGCGTAGCGCTAGCTTTGCCAGCGC
CACGCGgtaagggccctgaagaagggcccaACTAGTGCCACAAACTTCTCTCTGCTAAAGCAAGCAGGTG
ATGTTGAAGAAAACCCAGGGCCTGGAGGGTCCGAGGGCAGGGGAAGTCTCCTAACATGCGGG
GACGTGGAGGAAAATCCCGGCCCATCCGGA TATCCCTACGATGTGCCCGATTACGCTATCGATgt
gagcaagggcgaAgaAgataacaAggcctctctcccagcgacacatgagttacacatctttggctccatcaacggtgtggactttgacatg
gtgggtcagggcaccggcaatccaaatgatggttatgaggagttaaacctgaagtccaccaagggtgacctccagttctccccctggattctg
gtccctcatatcgggtatggcttccatcagtacctgccctaccctgacgggatgtcgcctttccaggccgccatggtagatggcAGCggatac
caagtccatcgcacaatgcagtttgaagatggtgcctcccttactgttaactaccgctacacctacgagggaagccacatcaaaggagaggc
ccaggtgaaggggactggtttccctgctgacggtcctgtgatgaccaactcgctgaccgctgcggactggtgcaggtcgaagaagacttacc
ccaacgacaaaaccatcatcagtacctttaagtggagttacaccactggaaatggcaagAGAtaccggagcactgcgcggaccacctac
acctttgccaagccaatggcggctaactatctgaagaaccagccgatgtacgtgttccgtaagacggagctcaagcactccaagaccgagc
tcaacttcaaggagtggcaaaaggcctttaccgatgtgatgGGAatggacGAGCTGTATaagGCTAGCTAAGCGGCCG
CTCGAGTCTAGAGGGCCCGCGGTTCGAAGGTAAGCCTATCCCTAACCCTCTCCTCGGTCTCGAT
TCTACGCGTACCGGTCATCATCACCATCACCATTGAGTTTAAACCCGCTGATCAGCCTCGACTGT
GCCTTCTA

FIG. 42B(Cont.)

**SEQ ID NO: 304, mCherry-FLAG-P2A/T2A-Loop-MS2-HaloTag-T7-Loop-TAR-P2A/T2A-*HA-mNeonGreen(M10K)***

TAATACGACTCACTATAGGGAGACCCAAGCTGGCTAGGTAAGCTTGGTACCGAGCTCGGATCCa
ccggtcgccaccatggtgagcaagggcgaggaggataacatggccatcatcaaggagttcatgcgcttcaaggtgcacatggagggctcc
gtgaacggccacgagttcgagatcgagggcgagggcgagggccgcccctacgagggcacccagaccgccaagctgaaggtgaccaa
gggtggcccctgcccttcgcctgggacatcctgtcccctcagttcatgtacggctccaaggcctacgtgaagcaccccgccgacatccccga
ctacttgaagctgtccttccccgagggcttcaagtgggagcgcgtgatgaacttcgaggacggcggcgtggtgaccgtgacccaggactcct
ccctgcaggacggcgagttcatctacaaggtgaagctgcgcggcaccaacttcccctccgacggccccgtaatgcagaagaagaccatgg
gctgggaggcctcctccgagcggatgtaccccgaggacggcgccctgaagggcgagatcaagcagaggctgaagctgaaggacggcg
gccactacgacgctgaggtcaagaccacctacaaggccaagaagcccgtgcagctgcccggcgcctacaacgtcaacatcaagttggac
atcacctcccacaacgaggactacaccatcgtggaacagtacgaacgcgccgagggccgccactccaccggcggcatggacgagctgT
ACaaggattacaaggatgacgatgacaaaGGTAGCGGGGCAACTAATTTTAGCTTACTCAAACAGGCTGG
GGACGTCGAGGAGAATCCAGGCCCTGCATCCGCT GGCTCTGGAGAAGGACGAGGCTCCTTGCT
CACCTGTGGAGATGTCGAAGAGAACCCAGGTCCTGCAACCGGGAATTCCGCGTAGCGCTAGCT
TTGCCAGCGCCACGCGaaACATGAGGATcACCCATGTGCCGCTATGGCAGAAATCGGTACTGGC
TTTCCATTCGACCCCCATTATGTGGAAGTCCTGGGC GAGCGCATGCACTACGTCGATGTTGGTC
CGCGCGATGGCACCCCTGTGCTGTTCCTGCACGGTAACCCGACCTCCTCCTACGTGTGGCGCA
ACATCATCCCGCATGTTGCACCGACCCATCGC TGCATTGCTCCAGACCTGATCGGTATGGGCAA
ATCCGACAAACCAGACCTGGGTTATTTCTTCGACGACCACGTCCGCTTCATGGATGCCTTCATC
GAAGCCCTGGGTCTGGAAGAGGTCGTCCTGGTCATTCACGACTGGGGCTCCGCTCTGGGTTTC
CACTGGGCCAAGCGCAATCCAGAGCGCGTCAAAGGTATTGCATTTATGGAGTTCATCCGCCCTA

FIG. 42C

TCCCGACCTGGGACGAATGGCCAGAATTTGCCCGCGAGACCTTCCAGGCCTTCCGCACCACCG
ACGTCGGCCGCAAGCTGATCATCGATCAGAACGTTTTTATCGAGGGTACGCTGCCGATGGGTGT
CGTCCGCCCGCTGACTGAAGTCGAGATGGACCATTACCGCGAGCCGTTCCTGAATCCTGTTGA C
CGCGAGCCACTGTGGCGCTTCCCAAACGAGCTGCCAATCGCCGGTGAGCCAGCGAACATCGTC
GCGCTGGTCGAAGAATACATGGACTGGCTGCACCAGTCCCCTGTCCCGAAGCTGCTGTTCTGG
GGCACCCCAGGCGTTCTGATCCCACCGGCCGAAGCCGCTCGCCTGGCCAAAAGCCTGCCTAAC
TGCAAGGCTGTGGACATCGGCCCGGGTCTGAATCTGCTGCAAGAAGACAACCCGGACCTGATC
GGCAGCGAGATCGCGCGCTGGCTGTCGACGCTCGAGATTTCTGGCACCGGTATGGCATCTATG
ACTGGAGGCCAACAGATGgGTCCTGCAACCGGgAATTCCGCGTAGCGCTAGCTTTGCCAGCGC
CACGCGgtaggctcgtctgagctcattagctccgagccaACTA GTGCCACAAACTTCTCTCTGCTAAAGCAAGCA
GGTGATGTTGAAGAAAACCCAGGGCCTGGAGGGTCCGAGGGCAGGGGAAGTCTCCTAACATGC
GGGGACGTGGAGGAAAATCCCGGCCCATCCGGATA TCCCTACGATGTGCCCGATTACGCTATC
GATgtgagcaagggcgaAgaAgataacaAggcctctcccagcgacacatgagttacacatctttggctccatcaacggtgtggactttg
acatggtgggtcagggcaccggcaatccaaatgatggttatgaggagttaaacctgaagtccaccaagggtgacctccagttctccccctgg
attctggtccctcatatcgggtatggcttccatcagtacctgccctaccctgacgggatgtcgcctttccaggccgccatggtagatggcAGCg
gataccaagtccatcgcacaatgcagtttgaagatggtgcctcccttactgttaactaccgctacacctacgagggaagccacatcaaagga
gaggcccaggtgaaggggactggtttccctgctgacggtcctgtgatgaccaactcgctgaccgctgcggactggtgcaggtcgaagaaga
cttaccccaacgacaaaaccatcatcagtacctttaagtggagttacaccactggaaatggcaagAGAtaccggagcactgcgcggacc
acctacacctttgccaagccaatggcggctaactatctgaagaaccagccgatgtacgtgttccgtaagacggagctcaagcactccaaga
ccgagctcaacttcaaggagtggcaaaaggcctttaccgatgtgatgGGAatggacGAGCTGTATaagGCTAGC TAA GCG
GCCGCTCGAGTCTAGAGGGCCCGCGGTTCGAAGGTAAGCCTATCCCTAACCCTCTCCTCGGTC
TCGATTCTACGCGTACCGGTCATCATCACCATCACCATTGAGTTTAAACCCGCTGATCAGCCTCG
ACTGTGCCTTCTA

FIG. 42C(Cont.)

SEQ ID NO: 305, mCherry-FLAG-P2A/T2A-Loop-MS2-P2A/T2A-HA-mNeonGreen(1-166)-STOPloop-MS2-mNeonGreen(174-236)

TAATACGACTCACTATAGGGAGACCCAAGCTGGCTAGGTAAGCTTGGTACCGAGCTC

GGATCCaccggtcgccaccatggtgagcaagggcgaggaggataacatggccatcatcaaggagttcatgcgcttc aaggtgcacatggagggctccgtgaacggccacgagttcgagatcgagggcgagggcgagggccgcccctacgagg gcacccagaccgccaagctgaaggtgaccaagggtggccccctgcccttcgcctgggacatcctgtcccctcagttcatgt acggctccaaggcctacgtgaagcaccccgccgacatccccgactacttgaagctgtccttccccgagggcttcaagtgg gagcgcgtgatgaacttcgaggacggcggcgtggtgaccgtgacccaggactcctccctgcaggacggcgagttcatcta caaggtgaagctgcgcggcaccaacttcccctccgacggccccgtaatgcagaagaagaccatgggctgggaggcctc ctccgagcggatgtaccccgaggacggcgccctgaagggcgagatcaagcagaggctgaagctgaaggacggcggc cactacgacgctgaggtcaagaccacctacaaggccaagaagcccgtgcagctgcccggcgcctacaacgtcaacatc aagttggacatcacctcccacaacgaggactacaccatcgtggaacagtacgaacgcgccgagggccgccactccacc ggcggcatggacgagctgTACaaggattacaaggatgacgatgacaaaGGTAGCGGGGCAACTAATT

TTAGCTTACTCAAACAGGCTGGGGACGTCGAGGAGAATCCAGGCCCTGCATCCGCT

GGCTCTGGAGAAGGACGAGGCTCCTTGCTCACCTGTGGAGATGTCGAAGAGAACC

CAGGTCCTGCAACCGGGAATTCCGCGTAGCGCTAGCTTTGCCAGCGCCACGCGaaA

CATGAGGATcACCCATGTACTAGTGCCACAAACTTCTCTCTGCTAAAGCAAGCAGGT

GATGTTGAAGAAAACCCAGGGCCTGGAGGGTCCGAGGGCAGGGGAAGTCTCCTAA

CATGCGGGGACGTGGAGGAAAATCCCGGCCCATCCGGATATCCCTACGATGTGCCC

GATTACGCTCATatggtgagcaagggcgaggaggataacatggcctctctcccagcgacacatgagttacacatct ttggctccatcaacggtgtggactttgacatggtgggtcagggcaccggcaatccaaatgatggttatgaggagttaaacct gaagtccaccaagggtgacctccagttctcccctggattctggtccctcatatcgggtatggcttccatcagtacctgcccta ccctgacgggatgtcgcctttccaggccgccatggtagatggcAGCggataccaagtccatcgcacaatgcagtttgaag atggtgcctcccttactgttaactaccgctacacctacgagggaagccacatcaaaggagaggcccaggtgaaggggact ggtttccctgctgacggtcctgtgatgaccaactcgctgaccgctgcggactggtgcaggtcgaagaagacttaccccaac gacaaaaccatcatcagtaccttcaagTAGagctacaccactggtgtaGctccacttGATaCCATGAGGATc ACCCATGGCaagAGAtaccggagcactgcgcggaccacctacacctttgccaagccaatggcggctaactatctg aagaaccagccgatgtacgtgttccgtaagacggagctcaagcactccaagaccgagctcaacttcaaggagtggcaaa aggcctttaccgatgtgatgGGAatggacGAGCTGTATaagGCTAGCTAAGCGGCCGCTCGAGTC

TAGAGGGCCCGCGGTTCGAAGGTAAGCCTATCCCTAACCCTCTCCTCGGTCTCGAT

TCTACGCGTACCGGTCATCATCACCATCACCATTGAGTTTAAACCCGCTGATCAGCC

TCGACTGTGCCTTCTA

FIG. 43

**SEQ ID NO: 306, tdMCP-Nadar2-DD(316-468)-*ALFA*-Cadar2-DD(469-700)(E488Q & L699V)-AlfaNb-VHH9-*TagBFP***

TAATACGACTCACTATAGGGAGACCCAAGCT GGctagaggatcgaacccttaaggccaccatgGCGAGCAATTTTA
CCCAGTTTGTGCTTGTGGACAACGGCGGCACCGGGGACGTGACGGTGGCCCCCTCCAATTTTGCCA
ATGGCATTGCAGAATGGATAAGCTCTAACAGCAGGAGCCAGGCATACAAGGTGACCTGCAGCG TGAG
GCAGTCAAGCGCTCAAAACAGGAAGTACACCATTAAGGTCGAAGTGCCCAAAGGAGCTTGGAGGTCT
TACCTGAACATGGAACTGACAATTCCTATCTTCGCGACCAATAGCGACTGTGAGCTGATCGTG AAGGC
CATGCAAGGCCTGCTGAAAGACGGGAATCCCATACCCAGCGCCATCGCCGCTAACTCAGGCAT TTAC
GCTAATTTCACTCAGTTCGTACTGGTTGACAATGGGGGAACCGGCGACGTTACCGTGGCTCCA AGCA
ACTTCGCTAACGGGATCGCCGAGTGGATCAGCAGTAATTCACGCTCCCAAGCCTACAAAGTAA CCTG
CTCTGTACGGCAGAGTTCAGCCCAGAACCGAAAGTATACCATCAAAGTGGAGGTGCCGAAGGG CGC
CTGGCGGAGCTATCTGAATATGGAGCTGACCATCCCCATCTTTGCCACGAACAGCGATTGCGA GCTC
ATCGTCAAGGCGATGCAGGGCTTGCTGAAGGAT GGCAACCCTATCCCGAGCGCAATAGCAGCC AAC
AGCGGCATCTATgggggcagtgggagcggtgcaggatctggtagtccagctgggggaggagcaccgggtagcggtgggggtct cagct
gcacctgccccaggttctcgcagacgccgtatcccgccttgtactgggcaagtttggtgatcttactgacaattttcatctcctcatgcgaggcggaaagt
actcgcaggcgtcgtcatgacgaccggaactgacgtgaaagacgccaaagtcatctctgtctccacgggcacaaagtgcataaacggggagtacat
gagcgaccgggggctggcactgaatgattgtcacgctgaaataatatctaggcgatctctgcttagatttctctacactcaactcgaattgtaccttaaca
acaaagatgaccagaaacgcagtatatttcagaaatcagaacgcggcggatttcgacttaaggaaaacgttcagttccacttgtatatcagcacatcc
ccttgcggtgacgcccgaatcttttccccgcacgagccgatattggaggagcccgcgGCTAGC CCA*TCCCGCCTGGAGGAAGAA*
*CTTCGGAGGAGACTTACTGAG*CCTACCGGctccggagccggT GACagacatcctaataggaaggctagaggccaacttcgg
acgaagattgaaagtggccagggtactatcccggtgcggtccaacgctagtattcaaacgtgggacggagtccttcaaggtgaacggctgttgacaat
gagctgctcagacaaaatcgcgATGtggaatgtagtgggaatccaaggcagcctcttgagcatattcgtagaacccatatatttctcatccattatttg

FIG. 44A ggctctctgtatcatggtgaccatctgtcaagggctatgtaccaacgaatttctaatatcgaggatcttcctccactctatacactcaataagcctctcttgtc
cgggatatcaaacgctgaggcccgccagccagggaaagctcctaacttcagtgttaactggaccgttggtgattctgcgatagaggtcatcaacgcca
cgacaggtaaggatgagctcggtagagcctcacgcctgtgtaaacacgcgttgtattgtagatggatgagagtacatgggaaggtcccatctcacttgc
tccgaagcaagatcactaagcctaatgtgtatcatgagtcaaaactcgcggctaaagaataccaggcagccaaagctcgacttttacagcttttattaa
ggcagggctcggggcatgggtcgagaagccgaccgagcaggaccaattctctGTGacggggagcGGAGGTACCGCCGAAGTTC
AATTACAGGAATCGGGTGGAGGTCTGGTACAACCTGGGGGCTCTCTTCGCCTGAGTTGCACTG CCAG
TGGAGTTACGATTTCTGCACTTAATGCTAT GGCGATGGGTTGGTAT CGTCAGGCCCCAGGGGAACGT
CGCGTCATGGTCGCTGCCGTTTCCGAACGTGGCAATGCTATGTACCGCGAGTCTGTTCAGGGC CGCT
TCACGGTTACCCGCGATTTTACAAATAAAATGGTATCGTTGCAAATGGACAACTTAAAGCCAG AGGAC
ACTGCTGTGTACTACTGTCACGTCCTTGAAGATCGTGTGGATTCCTTTCATGATTATTGGGGG CAGGG
GACTCAGGTCACTGTATCCTCAGGaGCTGGATCCGGAGGTGGAGGCTCCggcaccatgatggatcaagtccaact
ggtggagtctggtggcgctttggtgcagccaggtggctctctgcgtttgtcctgtgccgcttdggcttcccagtgaaccgctattccatgcgctggtatcgc
caggctccaggcaaagagcgtgagtgggtagccggtatgtccagcgcgggtgatcgtagctcctatgaagactccgtgaagggccgtttcaccatca
gccgtgacgatgcccgtaacacggtgtatctgcaaatgaacagcttgaaacctgaagatacggccgtgtattactgtaatgtgaacgtgggcttcgagt
attggggccaaggcacccaggtcaccgtctccagcATGCATAGCGAGCTGATTAAGGAGAACATGCACATGAAGCTGT
ACATGGAGGGCACCGTGGACAACCATCACTTCAA GTGCACATCCGAGGGCGAAGGCAAGCCCTACG
AGGGCACCCAGACCATGAGAATCAAGGTGGTCGAGGGCGGCCCTCTCCCCTTCGCCTTCGACATCC
TGGCTACTAGCTTCCTCTACGGCAGCAAGACCTTCATCAACCACACCCAGGGCATCCCCGACTTCTT
CAAGCAGTCCTTCCCTGAGGGCTTCACATGGGAGAGAGTCACCACATACGAAGACGGGGGCGTGCT
GACCGCTACCCAGGACACCAGCCTCCAGGACGGCTGCCTCATCTACAACGTCAAGATCAGAGGGGT
GAACTTCACATCCAACGGCCCTGTGATGCAGAAGAAAACACTCGGCTGGGAGGCCTTCACCGAGAC
GCTGTACCCCGCTGACGGCGGCCTGGAAGGCAGAAACGACATGGCCCTGAAGCTCGTGGGCGGGA
GCCATCTGATCGCAAACATCAAGACCACATATAGATCCAAGAAACCCGCTAAGAACCTCAAGATGCCT
GGCGTCTACTATGTGGACTACAGACTGGAAAGAATCAAGGAGGCCAACAACGAGACCTACGTCGAGC
AGCACGAGGTGGCAGTGGCCAGATACTGCGACCTCCCTAGCAAACTGGGGCACAAGCTTAAT tAAGG
GCCCGTTTAAACCCGCTGATCAGCCTCGACTGTGCCTTCTA

FIG. 44A(Cont.)

**SEQ ID NO: 307, tdMCP-nADAR2-DD(316-468)-*ALFA*-cADAR2-DD(469-700)(E488Q & L699G)-AlfaNb-VHH9-*TagBFP***

*TAATACGACTCACTATAGGGAGACCCAAGCTGGctaga ggatcgaacccttaaggccaccatgGCGAGCAATTTTA*
*CCCAGTTTGTGCTTGTGGACAACGGCGGCACCGGGGACGTGACGGTGGCCCCCTCCAATTTTGCCA*
*ATGGCATTGCAGAATGGATAAGCTCTAACAGCAGGAGCCAGGCATACAAGGTGACCTGCAGCGTGAG*
*GCAGTCAAGCGCTCAAAACAGGAAGTACACCATTAAGGTCGAAGTGCCCAAAGGAGCTTGGAGGTCT*
*TACCTGAACATGGAACTGACAATTCCTATCTTCGCGACCAATAGCGACTGTGAGCTGATCGTGAAGGC*
*CATGCAAGGCCTGCTGAAAGACGGGAATCCCATA CCCAGCGCCATCGCCGCTAACTCAGGCATTTAC*
*GCTAATTTCACTCAGTTCGTACTGGTTGACAATGGGGGAACCGGCGACGTTACCGTGGCTCCAAGCA*
*ACTTCGCTAACGGGATCGCCGAGTGGATCAGCAGTAATTCACGCTCCCAAGCCTACAAAGTAACCTG*
*CTCTGTACGGCAGAGTTCAGCCCAGAACCGAAAGTATACCATCAAAGTGGAGGTGCCGAAGGGCGC*
*CTGGCGGAGCTATCTGAATATGGAGCTGACCATCCCCATCTTTGCCACGAACAGCGATTGCGAGCTC*
*ATCGTCAAGGCGATGCAGGGCTTGCTGAAGGAT GGCAACCCTATCCCGAGCG CAATAGCAGCCAAC*
*AGCGGCATCTATgggggcagtgggagcggtgcaggatctggtagtccagctgggggaggagcaccgggtagcggtgggggtct cagct*
*gcacctgccccaggttctcgcagacgccgtatcccgccttgtactgggcaagtttggtgatcttactgacaattttcatctcctcatgcgaggcggaaagt*
*actcgcaggcgtcgtcatgacgaccggaactgacgtgaaagacgccaaagtcatctctgtctccacgggcacaaagtgcataaacggggagtacat*
*gagcgaccgggggctggcactgaatgattgtcacgctgaaataatatctaggcgatctctgcttagatttctctacactcaactcgaattgtaccttaaca*
*acaaagatgaccagaaacgcagtatatttcagaaatcagaacgcggcggatttcgacttaaggaaaacgttcagttccacttgtatatcagcacatcc*
*ccttgcggtgacgcccgaatcttttccccgcacgagccgatattggaggagcccgcgGCTAGCCCATCCCGCCTGGAGGAAGAA*
*CTTCGGAGGAGACTTACTGAGCCTACCGGctccggagccggT GACagacatcctaataggaaggctagaggccaacttcgg*
*acgaagattgaaagtggccagggtactatcccggtgcggtccaacgctagtattcaaacgtgggacggagtccttcaaggtgaacggctgttgacaat*
*gagctgctcagacaaaatcgcgATGtggaatgtagtgggaatccaaggcagcctcttgagcatattcgtagaacccatatattctcatccattatttg*

FIG. 44B ggctctctgtatcatggtgaccatctgtcaagggctatgtaccaacgaatttctaatatcgaggatcttcctccactctatacactcaataagcctctcttgtc
cgggatatcaaacgctgaggcccgccagccagggaaagctcctaacttcagtgttaactggaccgttggtgattctgcgatagaggtcatcaacgcca
cgacaggtaaggatgagctcggtagagcctcacgcctgtgtaaacacgcgttgtattgtagatggatgagagtacatgggaaggtcccatctcacttgc
tccgaagcaagatcactaagcctaatgtgtatcatgagtcaaaactcgcggctaaagaataccaggcagccaaagctcgactttttacagcttttattaa
ggcagggctcggggcatgggtcgagaagccgaccgagcaggaccaattctctGGGacggggagcGGAGGTACCGCCGAAGTTC
AATTACAGGAATCGGGTGGAGGTCTGGTACAACCTGGGGGCTCTCTTCGCCTGAGTTGCACTGCCAG
TGGAGTTACGATTTCTGCACTTAATGCTAT GGCGATGGGTTGGTATCG TCAGGCCCCAGGGGAACGT
CGCGTCATGGTCGCTGCCGTTTCCGAACGTGGCAATGCTATGTACCGCGAGTCTGTTCAGGGCCGCT
TCACGGTTACCCGCGATTTTACAAATAAAATGGTATCGTTGCAAATGGACAACTTAAAGCCAGAGGAC
ACTGCTGTGTACTACTGTCACGTCCTTGAAGATCGTGTGGATTCCTTTCATGATTATTGGGGGCAGGG
GACTCAGGTCACTGTATCCTCAGGaGCTGGATCCGGAGGTGGAGGCTCCggcaccatgatggatcaagtccaact
ggtggagtctggtggcgctttggtgcagccaggtggctctctgcgtttgtcctgtgccgcttctggcttcccagtgaaccgctattccatgcgctggtatcgc
caggctccaggcaaagagcgtgagtgggtagccggtatgtccagcgcgggtgatcgtagctcctatgaagactccgtgaagggccgtttcaccatca
gccgtgacgatgcccgtaacacggtgtatctgcaaatgaacagcttgaaacctgaagatacggccgtgtattactgtaatgtgaacgtgggcttcgagt
attggggccaaggcacccaggtcaccgtctccagcATGCATAGCGAGCTGATTAAGGAGAACATGCACATGAAGCTGT
ACATGGAGGGCACCGTGGACAACCATCACTTCAA GTGCACATCCGAGGGCGAAGGCAAGCCCTACG
AGGGCACCCAGACCATGAGAATCAAGGTGGTCGAGGGCGGCCCTCTCCCCTTCGCCTTCGACATCC
TGGCTACTAGCTTCCTCTACGGCAGCAAGACCTTCATCAACCACACCCAGGGCATCCCCGACTTCTT
CAAGCAGTCCTTCCCTGAGGGCTTCACATGGGAGAGAGTCACCACATACGAAGACGGGGGCGTGCT
GACCGCTACCCAGGACACCAGCCTCCAGGACGGCTGCCTCATCTACAACGTCAAGATCAGAGGGGT
GAACTTCACATCCAACGGCCCTGTGATGCAGAAGAAAACACTCGGCTGGGAGGCCTTCACCGAGAC
GCTGTACCCCGCTGACGGCGGCCTGGAAGGCAGAAACGACATGGCCCTGAAGCTCGTGGGCGGGA
GCCATCTGATCGCAAACATCAAGACCACATATAGATCCAAGAAACCCGCTAAGAACCTCAAGATGCCT
GGCGTCTACTATGTGGACTACAGACTGGAAAGAATCAAGGAGGCCAACAACGAGACCTACGTCGAGC
AGCACGAGGTGGCAGTGGCCAGATACTGCGACCTCCCTAGCAAACTGGGGCACAAGCTTAAT tAAGG
GCCCGTTTAAACCCGCTGATCAGCCTCGACTGTGCCTTCTA

FIG. 44B(Cont.)

**SEQ ID NO: 308, tdMCP-nADAR2-DD(316-468)-*ALFA*-cADAR2-DD(469-700)(E488Q & F697Y)-AlfaNb-VHH9-*TagBFP***

TAATACGACTCACTATAGGGAGACCCAAGCT GGctagaggatcgaacccttaaggccaccatgGCGAGCAATTTTA
CCCAGTTTGTGCTTGTGGACAACGGCGGCACCGGGGACGTGACGGTGGCCCCCTCCAATTTTGCCA
ATGGCATTGCAGAATGGATAAGCTCTAACAGCAGGAGCCAGGCATACAAGGTGACCTGCAGCG TGAG
GCAGTCAAGCGCTCAAAACAGGAAGTACACCATTAAGGTCGAAGTGCCCAAAGGAGCTTGGAGGTCT
TACCTGAACATGGAACTGACAATTCCTATCTTCGCGACCAATAGCGACTGTGAGCTGATCGTG AAGGC
CATGCAAGGCCTGCTGAAAGACGGGAATCCCATACCCAGCGCCATCGCCGCTAACTCAGGCAT TTAC
GCTAATTTCACTCAGTTCGTACTGGTTGACAATGGGGGAACCGGCGACGTTACCGTGGCTCCA AGCA
ACTTCGCTAACGGGATCGCCGAGTGGATCAGCAGTAATTCACGCTCCCAAGCCTACAAAGTAA CCTG
CTCTGTACGGCAGAGTTCAGCCCAGAACCGAAAGTATACCATCAAAGTGGAGGTGCCGAAGGG CGC
CTGGCGGAGCTATCTGAATATGGAGCTGACCATCCCCATCTTTGCCACGAACAGCGATTGCGA GCTC
ATCGTCAAGGCGATGCAGGGCTTGCTGAAGGAT GGCAACCCTATCCCGAGCGCAATAGCAGCC AAC
AGCGGCATCTATgggggcagtgggagcggtgcaggatctggtagtccagctgggggaggagcaccgggtagcggtgggggtct cagct
gcacctgccccaggttctcgcagacgccgtatcccgccttgtactgggcaagtttggtgatcttactgacaatttttcatctcctcatgcgaggcggaaagt
actcgcaggcgtcgtcatgacgaccggaactgacgtgaaagacgccaaagtcatctctgtctccacgggcacaaagtgcataaacggggagtacat
gagcgaccgggggctggcactgaatgattgtcacgctgaaataatatctaggcgatctctgcttagatttctctacactcaactcgaattgtaccttaaca
acaaagatgaccagaaacgcagtatatttcagaaatcagaacgcggcggatttcgacttaaggaaaacgttcagttccacttgtatatcagcacatcc
ccttgcggtgacgcccgaatcttttccccgcacgagccgatattggaggagcccgcgGCTAGC CCA*TCCCGCCTGGAGGAAGAA*
*CTTCGGAGGAGACTTACTGAG*CCTACCGGctccggagccggT GACagacatcctaataggaaggctagaggccaacttcgg
acgaagattgaaagtggccagggtactatcccggtgcggtccaacgctagtattcaaacgtgggacggagtccttcaaggtgaacggctgttgacaat
gagctgctcagacaaaatcgcgATGtggaatgtagtgggaatccaaggcagcctcttgagcatattcgtagaacccatatatttctcatccattatttg

FIG. 44C ggctctctgtatcatggtgaccatctgtcaagggctatgtaccaacgaatttctaatatcgaggatcttcctccactctatacactcaataagcctctcttgtc cgggatatcaaacgctgaggcccgccagccagggaaagctcctaacttcagtgttaactggaccgttggtgattctgcgatagaggtcatcaacgcca cgacaggtaaggatgagctcggtagagcctcacgcctgtgtaaacacgcgttgtattgtagatggatgagagtacatgggaaggtcccatctcacttgc tccgaagcaagatcactaagcctaatgtgtatcatgagtcaaaactcgcggctaaagaataccaggcagccaaagctcgactttttacagcttttattaa ggcagggctcggggcatgggtcgagaagccgaccgagcaggaccaaTACtctctgacggggagcGGAGGTACCGCCGAAGTTC

AATTACAGGAATCGGGTGGAGGTCTGGTACAACCTGGGGGCTCTCTTCGCCTGAGTTGCACTG CCAG

TGGAGTTACGATTTCTGCACTTAATGCTAT GGCGATGGGTTGGTAT CGTCAGGCCCCAGGGGAACGT

CGCGTCATGGTCGCTGCCGTTTCCGAACGTGGCAATGCTATGTACCGCGAGTCTGTTCAGGGC CGCT

TCACGGTTACCCGCGATTTTACAAATAAAATGGTATCGTTGCAAATGGACAACTTAAAGCCAG AGGAC

ACTGCTGTGTACTACTGTCACGTCCTTGAAGATCGTGTGGATTCCTTTCATGATTATTGGGGG CAGGG

GACTCAGGTCACTGTATCCTCAGGaGCTGGATCCGGAGGTGGAGGCTCCggcaccatgatggatcaagtccaact ggtggagtctggtggcgctttggtgcagccaggtggctctctgcgtttgtcctgtgccgcttctggcttcccagtgaaccgctattccatgcgctggtatcgc caggctccaggcaaagagcgtgagtgggtagccggtatgtccagcgcgggtgatcgtagctcctatgaagactccgtgaagggccgtttcaccatca gccgtgacgatgcccgtaacacggtgtatctgcaaatgaacagcttgaaacctgaagatacggccgtgtattactgtaatgtgaacgtgggcttcgagt attggggccaaggcacccaggtcaccgtctccagcATGCATAGCGAGCTGATTAAGGAGAACATGCACATGAAGCTGT

ACATGGAGGGCACCGTGGACAACCATCACTTCAA GTGCACATCCGAGGGCGAAGGCAAGCCCTACG

AGGGCACCCAGACCATGAGAATCAAGGTGGTCGAGGGCGGCCCTCTCCCCTTCGCCTTCGACATCC

TGGCTACTAGCTTCCTCTACGGCAGCAAGACCTTCATCAACCACACCCAGGGCATCCCCGACTTCTT

CAAGCAGTCCTTCCCTGAGGGCTTCACATGGGAGAGAGTCACCACATACGAAGACGGGGGCGTGCT

GACCGCTACCCAGGACACCAGCCTCCAGGACGGCTGCCTCATCTACAACGTCAAGATCAGAGGGGT

GAACTTCACATCCAACGGCCCTGTGATGCAGAAGAAAACACTCGGCTGGGAGGCCTTCACCGAGAC

GCTGTACCCCGCTGACGGCGGCCTGGAAGGCAGAAACGACATGGCCCTGAAGCTCGTGGGCGGGA

GCCATCTGATCGCAAACATCAAGACCACATATAGATCCAAGAAACCCGCTAAGAACCTCAAGATGCCT

GGCGTCTACTATGTGGACTACAGACTGGAAAGAATCAAGGAGGCCAACAACGAGACCTACGTCGAGC

AGCACGAGGTGGCAGTGGCCAGATACTGCGACCTCCCTAGCAAACTGGGGCACAAGCTTAAT tAAGG

GCCCGTTTAAACCCGCTGATCAGCCTCGACTGTGCCTTCTA

FIG. 44C(Cont.)

**SEQ ID NO: 309, tdMCP-nADAR2-DD(316-468)-*ALFA-PE*-cADAR2-DD(469-700)(E488Q & L699V)-AlfaNb-VHH9-*TagBFP***

TAATACGACTCACTATAGGGAGACCCAAGCT GGctagaggatcgaacccttaaggccaccatgGCGAGCAATTTTA
CCCAGTTTGTGCTTGTGGACAACGGCGGCACCGGGGACGTGACGGTGGCCCCCTCCAATTTTGCCA
ATGGCATTGCAGAATGGATAAGCTCTAACAGCAGGAGCCAGGCATACAAGGTGACCTGCAGCG TGAG
GCAGTCAAGCGCTCAAAACAGGAAGTACACCATTAAGGTCGAAGTGCCCAAAGGAGCTTGGAGGTCT
TACCTGAACATGGAACTGACAATTCCTATCTTCGCGACCAATAGCGACTGTGAGCTGATCGTG AAGGC
CATGCAAGGCCTGCTGAAAGACGGGAATCCCATACCCAGCGCCATCGCCGCTAACTCAGGCAT TTAC
GCTAATTTCACTCAGTTCGTACTGGTTGACAATGGGGGAACCGGCGACGTTACCGTGGCTCCA AGCA
ACTTCGCTAACGGGATCGCCGAGTGGATCAGCAGTAATTCACGCTCCCAAGCCTACAAAGTAA CCTG
CTCTGTACGGCAGAGTTCAGCCCAGAACCGAAAGTATACCATCAAAGTGGAGGTGCCGAAGGG CGC
CTGGCGGAGCTATCTGAATATGGAGCTGACCATCCCCATCTTTGCCACGAACAGCGATTGCGA GCTC
ATCGTCAAGGCGATGCAGGGCTTGCTGAAGGAT GGCAACCCTATCCCGAGCGCAATAGCAGCC AAC
AGCGGCATCTATgggggcagtgggagcggtgcaggatctggtagtccagctgggggaggagcaccgggtagcggtggggggtct cagct
gcacctgccccaggttctcgcagacgccgtatcccgccttgtactgggcaagtttggtgatcttactgacaattttcatctcctcatgcgaggcggaaagt
actcgcaggcgtcgtcatgacgaccggaactgacgtgaaagacgccaaagtcatctctgtctccacgggcacaaagtgcataaacggggagtacat
gagcgaccgggggctggcactgaatgattgtcacgctgaaataatatctaggcgatctctgcttagatttctctacactcaactcgaattgtaccttaaca
acaaagatgaccagaaacgcagtatatttcagaaatcagaacgcggcggatttcgacttaaggaaaacgttcagttccacttgtatatcagcacatcc
ccttgcggtgacgcccgaatcttttccccgcacgagccgatattggaggagcccgcgGCTAGC GGATCAGGTCCA *GGACGCCTG*
*GAGGAAGAACTTCGGAGGAGACTTTCTCCT*GGAACCGGTGACagacatcctaataggaaggctagaggccaacttcg
gacgaagattgaaagtggccagggtactatcccggtgcggtccaacgctagtattcaaacgtgggacggagtccttcaaggtgaacggctgttgaca
atgagctgctcagacaaaatcgcgATGtggaatgtagtgggaatccaaggcagcctcttgagcatattcgtagaacccatatatttctcatccattattt

FIG. 44D gggctctctgtatcatggtgaccatctgtcaagggctatgtaccaacgaatttctaatatcgaggatcttcctccactctatacactcaataagcctctcttgt
ccgggatatcaaacgctgaggcccgccagccagggaaagctcctaacttcagtgttaactggaccgttggtgattctgcgatagaggtcatcaacgcc
acgacaggtaaggatgagctcggtagagcctcacgcctgtgtaaacacgcgttgtattgtagatggatgagagtacatgggaaggtcccatctcacttg
ctccgaagcaagatcactaagcctaatgtgtatcatgagtcaaaactcgcggctaaagaatacaggcagccaaagctcgacttttacagcttttatta
aggcagggctcggggcatgggtcgagaagccgaccgagcaggaccaattctctGTGacggggagcGGAGGTACCGCCGAAGTTC
AATTACAGGAATCGGGTGGAGGTCTGGTACAACCTGGGGGCTCTCTTCGCCTGAGTTGCACTG CCAG
TGGAGTTACGATTTCTGCACTTAATGCTAT GGCGATGGGTTGGTAT CGTCAGGCCCCAGGGGAACGT
CGCGTCATGGTCGCTGCCGTTTCCGAACGTGGCAATGCTATGTACCGCGAGTCTGTTCAGGGC CGCT
TCACGGTTACCCGCGATTTTACAAATAAAATGGTATCGTTGCAAATGGACAACTTAAAGCCAG AGGAC
ACTGCTGTGTACTACTGTCACGTCCTTGAAGATCGTGTGGATTCCTTTCATGATTATTGGGGG CAGGG
GACTCAGGTCACTGTATCCTCAGGaGCTGGATCCGGAGGTGGAGGCTCCggcaccatgatggatcaagtccaact
ggtggagtctggtggcgctttggtgcagccaggtggctctctgcgtttgtcctgtgccgcttctggcttcccagtgaaccgctattccatgcgctggtatcgc
caggctccaggcaaagagcgtgagtgggtagccggtatgtccagcgcgggtgatcgtagctcctatgaagactccgtgaagggccgtttcaccatca
gccgtgacgatgcccgtaacacggtgtatctgcaaatgaacagcttgaaacctgaagatacggccgtgtattactgtaatgtgaacgtgggcttcgagt
attggggccaaggcacccaggtcaccgtctccagcATGCAT*AGCGAGCTGATTAAGGAGAACATGCACATGAAGCTGT*
*ACATGGAGGGCACCGTGGACAACCATCACTTCAA GTGCACATCCGAGGGCGAAGGCAAGCCCTACG*
*AGGGCACCCAGACCATGAGAATCAAGGTGGTCGAGGGCGGCCCTCTCCCCTTCGCCTTCGACATCC*
*TGGCTACTAGCTTCCTCTACGGCAGCAAGACCTTCATCAACCACACCCAGGGCATCCCCGACTTCTT*
*CAAGCAGTCCTTCCCTGAGGGCTTCACATGGGAGAGAGTCACCACATACGAAGACGGGGGCGTGCT*
*GACCGCTACCCAGGACACCAGCCTCCAGGACGGCTGCCTCATCTACAACGTCAAGATCAGAGGGGT*
*GAACTTCACATCCAACGGCCCTGTGATGCAGAAGAAAACACTCGGCTGGGAGGCCTTCACCGAGAC*
*GCTGTACCCCGCTGACGGCGGCCTGGAAGGCAGAAACGACATGGCCCTGAAGCTCGTGGGCGGGA*
*GCCATCTGATCGCAAACATCAAGACCACATATAGATCCAAGAAACCCGCTAAGAACCTCAAGATGCCT*
*GGCGTCTACTATGTGGACTACAGACTGGAAAGAATCAAGGAGGCCAACAACGAGACCTACGTCGAGC*
*AGCACGAGGTGGCAGTGGCCAGATACTGCGACCTCCCTAGCAAACTGGGGCACAAGCTTAAT* tAAGG
GCCCGTTTAAACCCGCTGATCAGCCTCGACTGTGCCTTCTA

FIG. 44D(Cont.)

**SEQ ID NO: 310, tdMCP-nADAR2-DD(316-468)-*ALFA-PE*-cADAR2-DD(469-700)(E488Q & L699G)-AlfaNb-VHH9-*TagBFP***

TAATACGACTCACTATAGGGAGACCCAAGCT GGctagaggatcgaacccttaaggccaccatgGCGAGCAATTTTA
CCCAGTTTGTGCTTGTGGACAACGGCGGCACCGGGGACGTGACGGTGGCCCCCTCCAATTTTGCCA
ATGGCATTGCAGAATGGATAAGCTCTAACAGCAGGAGCCAGGCATACAAGGTGACCTGCAGCG TGAG
GCAGTCAAGCGCTCAAAACAGGAAGTACACCATTAAGGTCGAAGTGCCCAAAGGAGCTTGGAGGTCT
TACCTGAACATGGAACTGACAATTCCTATCTTCGCGACCAATAGCGACTGTGAGCTGATCGTG AAGGC
CATGCAAGGCCTGCTGAAAGACGGGAATCCCATACCCAGCGCCATCGCCGCTAACTCAGGCAT TTAC
GCTAATTTCACTCAGTTCGTACTGGTTGACAATGGGGGAACCGGCGACGTTACCGTGGCTCCA AGCA
ACTTCGCTAACGGGATCGCCGAGTGGATCAGCAGTAATTCACGCTCCCAAGCCTACAAAGTAA CCTG
CTCTGTACGGCAGAGTTCAGCCCAGAACCGAAAGTATACCATCAAAGTGGAGGTGCCGAAGGG CGC
CTGGCGGAGCTATCTGAATATGGAGCTGACCATCCCCATCTTTGCCACGAACAGCGATTGCGA GCTC
ATCGTCAAGGCGATGCAGGGCTTGCTGAAGGAT GGCAACCCTATCCCGAGCGCAATAGCAGCC AAC
AGCGGCATCTATgggggcagtgggagcggtgcaggatctggtagtccagctgggggaggagca ccgggtagcggtgggggtctcagct
gcacctgccccaggttctcgcagacgccgtatcccgccttgtactgggcaagtttggtgatcttactgacaattttcatctcctcatgcgaggcggaaagt
actcgcaggcgtcgtcatgacgaccggaactgacgtgaaagacgccaaagtcatctctgtctccacgggcacaaagtgcataaacggggagtacat
gagcgaccgggggctggcactgaatgattgtcacgctgaaataatatctaggcgatctctgcttagatttctctacactcaactcgaattgtaccttaaca
acaaagatgaccagaaacgcagtatatttcagaaatcagaacgcggcggatttcgacttaaggaaaacgttcagttccacttgtatatcagcacatcc
ccttgcggtgacgcccgaatcttttccccgcacgagccgatattggaggagcccgcgGCTAGC GGATCAGGTCCA*GGACGCCTG*
*GAGGAAGAACTTCGGAGGAGACTTTCTCCT*GGAACCGGTGACagacatcctaataggaaggctagaggccaacttcg
gacgaagattgaaagtggccagggtactatcccggtgcggtccaacgctagtattcaaacgtgggacggagtccttcaaggtgaacggctgttgaca
atgagctgctcagacaaaatcgcgATGtggaatgtagtgggaatccaaggcagcctcttgagcatattcgtagaacccatatatttctcatccattatttt

FIG. 44E gggctctctgtatcatggtgaccatctgtcaagggctatgtaccaacgaatttctaatatcgaggatcttcctccactctatacactcaataagcctctcttgt
ccgggatatcaaacgctgaggcccgccagccagggaaagctcctaacttcagtgttaactggaccgttggtgattctgcgatagaggtcatcaacgcc
acgacaggtaaggatgagctcggtagagcctcacgcctgtgtaaacacgcgttgtattgtagatggatgagagtacatgggaaggtcccatctcacttg
ctccgaagcaagatcactaagcctaatgtgtatcatgagtcaaaactcgcggctaaagaatacaggcagccaaagctcgacttttacagctttatta
aggcagggctcggggcatgggtcgagaagccgaccgagcaggaccaattctctGGGacggggagcGGAGGTACCGCCGAAGTT
CAATTACAGGAATCGGGTGGAGGTCTGGTACAACCTGGGGGCTCTCTTCGCCTGAGTTGCACT GCCA
GTGGAGTTACGATTTCTGCACTTAATGCTATGGCGATGGGTTGGTATCGTCAGGCCCCAGGGG AACG
TCGCGTCATGGTCGCTGCCGTTTCCGAACGTGGCAATGCTATGTACCGCGAGTCTGTTCAGGG CCGC
TTCACGGTTACCCGCGATTTTACAAATAAAATGGTATCGTTGCAAATGGACAACTTAAAGCCA GAGGA
CACTGCTGTGTACTACTGTCACGTCCTTGAAGATCGTGTGGATTCCTTTCATGATTATTGGGG GCAGG
GGACTCAGGTCACTGTATCCTCAGGaGCTGGATCCGGAGGTGGAGGCTCCggcaccatgatgg atcaagtccaa
ctggtggagtctggtggcgctttggtgcagccaggtggctctctgcgtttgtcctgtgccgcttctggcttcccagtgaaccgctattccatgcgctggtatcg
ccaggctccaggcaaagagcgtgagtgggtagccggtatgtccagcgcgggtgatcgtagctcctatgaagactccgtgaagggccgtttcaccatc
agccgtgacgatgcccgtaacacggtgtatctgcaaatgaacagcttgaaacctgaagatacggccgtgtattactgtaatgtgaacgtgggcttcgag
tattggggccaaggcacccaggtcaccgtctccagcATGCAT *AGCGAGCTGATTAAGGAGAACATGCACATGAAGCTG*
*TACATGGAGGGCACCGTGGACAACCATCACTTCAAGTGCACATCCGAGGGCGAAGGCAAGCCCTAC*
*GAGGGCACCCAGACCATGAGAATCAAGGTGGTCGAGGGCGGCCCTCTCCCCTTCGCCTTCGACATC*
*CTGGCTACTAGCTTCCTCTACGGCAGCAAGACCTTCATCAACCACACCCAGGGCATCCCCGACTTCT*
*TCAAGCAGTCCTTCCCTGAGGGCTTCACATGGGAGAGAGTCACCACATACGAAGACGGGGGCGTGC*
*TGACCGCTACCCAGGACACCAGCCTCCAGGACGGCTGCCTCATCTACAACGTCAAGATCAGAGGGG*
*TGAACTTCACATCCAACGGCCCTGTGATGCAGAAGAAAACACTCGGCTGGGAGGCCTTCACCGAGAC*
*GCTGTACCCCGCTGACGGCGGCCTGGAAGGCAGAAACGACATGGCCCTGAAGCTCGTGGGCGGGA*
*GCCATCTGATCGCAAACATCAAGACCACATATAGATCCAAGAAACCCGCTAAGAACCTCAAGATGCCT*
*GGCGTCTACTATGTGGACTACAGACTGGAAAGAATCAAGGAGGCCAACAACGAGACCTACGTCGAGC*
*AGCACGAGGTGGCAGTGGCCAGATACTGCGACCTCCCTAGCAAACTGGGGCACAAGCTTAAT* tAAGG
GCCCGTTTAAACCCGCTGATCAGCCTCGACTGTGCCTTCTA

FIG. 44E(Cont.)

**SEQ ID NO: 311, tdMCP-nADAR2-DD(316-468)-*ALFA-PE*-cADAR2-DD(469-700)(E488Q & F697Y)-AlfaNb-VHH9-*TagBFP***

TAATACGACTCACTATAGGGAGACCCAAGCT GGctagaggatcgaacccttaaggccaccatgGCGAGCAATTTTA
CCCAGTTTGTGCTTGTGGACAACGGCGGCACCGGGGACGTGACGGTGGCCCCCTCCAATTTTGCCA
ATGGCATTGCAGAATGGATAAGCTCTAACAGCAGGAGCCAGGCATACAAGGTGACCTGCAGCG TGAG
GCAGTCAAGCGCTCAAAACAGGAAGTACACCATTAAGGTCGAAGTGCCCAAAGGAGCTTGGAGGTCT
TACCTGAACATGGAACTGACAATTCCTATCTTCGCGACCAATAGCGACTGTGAGCTGATCGTG AAGGC
CATGCAAGGCCTGCTGAAAGACGGGAATCCCATACCCAGCGCCATCGCCGCTAACTCAGGCAT TTAC
GCTAATTTCACTCAGTTCGTACTGGTTGACAATGGGGGAACCGGCGACGTTACCGTGGCTCCA AGCA
ACTTCGCTAACGGGATCGCCGAGTGGATCAGCAGTAATTCACGCTCCCAAGCCTACAAAGTAA CCTG
CTCTGTACGGCAGAGTTCAGCCCAGAACCGAAAGTATACCATCAAAGTGGAGGTGCCGAAGGG CGC
CTGGCGGAGCTATCTGAATATGGAGCTGACCATCCCCATCTTTGCCACGAACAGCGATTGCGA GCTC
ATCGTCAAGGCGATGCAGGGCTTGCTGAAGGAT GGCAACCCTATCCCGAGCGCAATAGCAGCC AAC
AGCGGCATCTATgggggcagtgggagcggtgcaggatctggtagtccagctgggggaggagca ccgggtagcggtgggggtct*cagct*
*gcacctgccccaggttctcgcagacgccgtatcccgccttgtactgggcaagtttggtgatcttactgacaattttcatctcctcatgcgaggcggaaagt*
*actcgcaggcgtcgtcatgacgaccggaactgacgtgaaagacgccaaagtcatctctgtctccacgggcacaaagtgcataaacggggagtacat*
*gagcgaccgggggctggcactgaatgattgtcacgctgaaataatatctaggcgatctctgcttagatttctctacactcaactcgaattgtaccttaaca*
*acaaagatgaccagaaacgcagtatatttcagaaatcagaacgcggcggatttcgacttaaggaaaacgttcagttccacttgtatatcagcacatcc*
*ccttgcggtgacgcccgaatcttttccccgcacgagccgatattggaggagcccgcg*GCTAGCGGATCAGGTCCA*GGACGCCTG*
*GAGGAAGAACTTCGGAGGAGACTTTCTCCT*GGAACCGGTGACagacatcctaataggaaggctagaggccaacttcg
gacgaagattgaaagtggccagggtactatcccggtgcggtccaacgctagtattcaaacgtgggacggagtccttcaaggtgaacggctgttgaca
atgagctgctcagacaaaatcgcgATGtggaatgtagtgggaatccaaggcagcctcttgagcatattcgtagaacccatatatttctcatccattattt

FIG. 44F gggctctctgtatcatggtgaccatctgtcaagggctatgtaccaacgaatttctaatatcgaggatcttcctccactctatacactcaataagcctctcttgt
ccgggatatcaaacgctgaggcccgccagccagggaaagctcctaacttcagtgttaactggaccgttggtgattctgcgatagaggtcatcaacgcc
acgacaggtaaggatgagctcggtagagcctcacgcctgtgtaaacacgcgttgtattgtagatggatgagagtacatgggaaggtcccatctcacttg
ctccgaagcaagatcactaagcctaatgtgtatcatgagtcaaaactcgcggctaaagaatacaggcagccaaagctcgacttttacagcttttatta
aggcagggctcggggcatgggtcgagaagccgaccgagcaggaccaaTACtctctgacggggagcGGAGGTACCGCCGAAGTT
CAATTACAGGAATCGGGTGGAGGTCTGGTACAACCTGGGGGCTCTCTTCGCCTGAGTTGCACT GCCA
GTGGAGTTACGATTTCTGCACTTAATGCTATGGCGATGGGTTGGTATCGTCAGGCCCCAGGGG AACG
TCGCGTCATGGTCGCTGCCGTTTCCGAACGTGGCAATGCTATGTACCGCGAGTCTGTTCAGGG CCGC
TTCACGGTTACCCGCGATTTTACAAATAAAATGGTATCGTTGCAAATGGACAACTTAAAGCCA GAGGA
CACTGCTGTGTACTACTGTCACGTCCTTGAAGATCGTGTGGATTCCTTTCATGATTATTGGGG GCAGG
GGACTCAGGTCACTGTATCCTCAGGaGCTGGATCCGGAGGTGGAGGCTCCggcaccatgatgg atcaagtccaa
ctggtggagtctggtggcgctttggtgcagccaggtggctctctgcgtttgtcctgtgccgcttctggcttcccagtgaaccgctattccatgcgctggtatcg
ccaggctccaggcaaagagcgtgagtgggtagccggtatgtccagcgcgggtgatcgtagctcctatgaagactccgtgaagggccgtttcaccatc
agccgtgacgatgcccgtaacacggtgtatctgcaaatgaacagcttgaaacctgaagatacggccgtgtattactgtaatgtgaacgtgggcttcgag
tattggggccaaggcacccaggtcaccgtctccagcATGCAT *AGCGAGCTGATTAAGGAGAACATGCACATGAAGCTG*
*TACATGGAGGGCACCGTGGACAACCATCACTTCAAGTGCACATCCGAGGGCGAAGGCAAGCCCTAC*
*GAGGGCACCCAGACCATGAGAATCAAGGTGGTCGAGGGCGGCCCTCTCCCCTTCGCCTTCGACATC*
*CTGGCTACTAGCTTCCTCTACGGCAGCAAGACCTTCATCAACCACACCCAGGGCATCCCCGACTTCT*
*TCAAGCAGTCCTTCCCTGAGGGCTTCACATGGGAGAGAGTCACCACATACGAAGACGGGGGCGTGC*
*TGACCGCTACCCAGGACACCAGCCTCCAGGACGGCTGCCTCATCTACAACGTCAAGATCAGAGGGG*
*TGAACTTCACATCCAACGGCCCTGTGATGCAGAAGAAAACACTCGGCTGGGAGGCCTTCACCGAGAC*
*GCTGTACCCCGCTGACGGCGGCCTGGAAGGCAGAAACGACATGGCCCTGAAGCTCGTGGGCGGGA*
*GCCATCTGATCGCAAACATCAAGACCACATATAGATCCAAGAAACCCGCTAAGAACCTCAAGATGCCT*
*GGCGTCTACTATGTGGACTACAGACTGGAAAGAATCAAGGAGGCCAACAACGAGACCTACGTCGAGC*
*AGCACGAGGTGGCAGTGGCCAGATACTGCGACCTCCCTAGCAAACTGGGGCACAAGCTTAAT* tAAGG
GCCCGTTTAAACCCGCTGATCAGCCTCGACTGTGCCTTCTA

FIG. 44F(Cont.)

**SEQ ID NO: 312, *EGFP(R96M)*** agctcgtttagtgaaccgtcagatcgcctggagacgccatccacgctgttttgacctccatagaagacac
cgggaccgatccagcctccggactctagcgtttaaacttaagcttgccaccatg*gtgagcaagggcgag*
*gagctgttcaccggggtggtgcccatcctggtcgagctggacggcgacgtaaacggccacaagttcag*
*cgtgtccggcgagggcgagggcgatgccacctacggcaagctgaccctgaagttcatctgcaccaccg*
*gcaagctgcccgtgccctggcccaccctcgtgaccaccctgacctacggcgtgcagtgcttcagccgct*
*accccgaccacatgaagcagcacgacttcttcaagtccgccatgcccgaaggctacgtccaggaAAT*
*Gaccatcttcttcaaggacgacggcaactacaagacccgcgccgaggtgaagttcgagggcgacac*
*cctggtgaaccgcatcgagctgaagggcatcgacttcaaggaggacggcaacatcctggggcacaag*
*ctggagtacaactacaacagccacaacgtctatatcatggccgacaagcagaagaacggcatcaagg*
*tgaacttcaagatccgccacaacatcgaggacggcagcgtgcagctcgccgaccactaccagcagaa*
*cacccccatcggcgacggccccgtgctgctgcccgacaaccactacctgagcacccagtccgccctga*
*gcaaagaccccaacgagaagcgcgatcacatggtcctgctggagttcgtgaccgccgccgggatcac*
*tctcggcatggacgagctgtacaag*GGATCCTAAtctagagggccctattctatagtgtcacctaaat
gctagagctcgctgatcagcctcgactgtgccttcta

FIG. 44G

**SEQ ID NO: 313, *EGFP(R96M)*-ALFA** agctcgtttagtgaaccgtcagatcgcctggagacgccatccacgctgttttgacctccatagaagacac
cgggaccgatccagcctccggactctagcgtttaaacttaagcttgccaccatg*gtgagcaagggcgag*
*gagctgttcaccggggtggtgcccatcctggtcgagctggacggcgacgtaaacggccacaagttcag*
*cgtgtccggcgagggcgagggcgatgccacctacggcaagctgaccctgaagttcatctgcaccaccg*
*gcaagctgcccgtgccctggcccaccctcgtgaccaccctgacctacggcgtgcagtgcttcagccgct*
*accccgaccacatgaagcagcacgacttcttcaagtccgccatgcccgaaggctacgtccaggaAAT*
*Gaccatcttcttcaaggacgacggcaactacaagacccgcgccgaggtgaagttcgagggcgacac*
*cctggtgaaccgcatcgagctgaagggcatcgacttcaaggaggacggcaacatcctggggcacaag*
*ctggagtacaactacaacagccacaacgtctatatcatggccgacaagcagaagaacggcatcaagg*
*tgaacttcaagatccgccacaacatcgaggacggcagcgtgcagctcgccgaccactaccagcagaa*
*cacccccatcggcgacggccccgtgctgctgcccgacaaccactacctgagcacccagtccgccctga*
*gcaaagaccccaacgagaagcgcgatcacatggtcctgctggagttcgtgaccgccgccgggatcac*
*tctcggcatggacgagctgtacaag*GGATCCCGCCTGGAGGAAGAACTTCGGAGG
AGACTTACTGAGtaatctagagggccctattctatagtgtcacctaaatgctagagctcgctgatca
gcctcgactgtgccttcta

FIG. 44G(Cont.)

**SEQ ID NO: 314, MCP-*BAD*-nADAR2-DD-*AlfaPE*-cADAR2-DD(E488Q & F697Y)-AlfaNb-Bcl-xL-*mTagBFP***

TAATACGACTCACTATAGGGAGACCC AAGCTGGctagaggatcgaacccttaaggccaccatggcgtccaatttcact
cagtttgtgctggttgacaacggcgggaccggggacgttacggtagccccctcaaactttgccaacggtatagcggagtggataagcagca
attctaggagtcaagcatacaaagttacatgcagcgtgcgccaatctagcgctcagaatcgcaagtacaccattaaagtagaggtccccaa
gggagcctggagaagctatcttaacatggagttgaccataccaatcttcgctaccaactctgactgtgaactcattgtgaaagccatgcaaggt
ctgctcaaggatggtaacccaattccgtccgctatcgctgccaactctgggatttacgggggcagtgggagcggtgcaggatctggtagtcca
gctgggggaggagcaccgggtagcggtgggggtct*ACCGGTGCTCCACCCAATCTCTGGGCAGCGCAGCGCT*
*ACGGCCGTGAGCTCAGAAGGATGTCCGATGAGTTCGTCGATTCCTTCAAAAAGGCTAGC* cagctgc
acctgccccaggttctcgcagacgccgtatcccgccttgtactgggcaagtttggtgatcttactgacaatttttcatctcctcatgcgaggcggaa
agtactcgcaggcgtcgtcatgacgaccggaactgacgtgaaagacgccaaagtcatctctgtctccacgggcacaaagtgcataaacgg
ggagtacatgagcgaccgggggctggcactgaatgattgtcacgctgaaataatatctaggcgatctctgcttagatttctctacactcaactcg
aattgtaccttaacaacaaagatgaccagaaacgcagtatatttcagaaatcagaacgcggcggatttcgacttaaggaaaacgttcagttcc
acttgtatatcagcacatccccttgcggtgacgcccgaatcttttccccgcacgagccgatattggaggagcccgcgGCTAGCGGATC
AGGTCCA*GGACGCCTGGAGGAAGAACTTCGGAGGAGACTTTCTCCT*GGAACCGGTGACagacatc
ctaataggaaggctagaggccaacttcggacgaagattgaaagtggccagggtactatcccggtgcggtccaacgctagtattcaaacgtg
ggacggagtccttcaaggtgaacggctgttgacaatgagctgctcagacaaaatcgcgcgctggaatgtagtgggaatccaaggcagcctc
ttgagcatattcgtagaacccatatatttctcatccattatttgggctctctgtatcatggtgaccatctgtcaagggctatgtaccaacgaatttcta
atatcgaggatcttcctccactctatacactcaataagcctctcttgtccgggatatcaaacgctgaggcccgccagccagggaaagctcctaa
cttcagtgttaactggaccgttggtgattctgcgatagaggtcatcaacgccacgacaggtaaggatgagctcggtagagcctcacgcctgtgt
aaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgacttttacagcttttattaaggcagggctcggggcatgggtcgagaag
ccgaccgagcaggaccaaTACtctctgacggggagcGGAGGTACCGCCGAAGTTCAATTACAG GAATCGGGT
GGAGGTCTGGTACAACCTGGGGGCTCTCTTCGCCTGAGTTGCACTGCCAGTGGAGTTACGATT T

FIG. 45

CTGCACTTAATGCTATGGCGATGGGTTGGT ATCGTCAGGCCCCAGGGGAACGTCGCGTCATGG
TCGCTGCCGTTTCCGAACGTGGCAATGCTATGTACCGCGAGTCTGTTCAGGGCCGCTTCACGGT
TACCCGCGATTTTACAAATAAAATGGTATCGTT GCAAATGGACAACTTAAAGCCAGAGGACAC TG
CTGTGTACTACTGTCACGTCCTTGAAGATCGTGTGGATTCCTTTCATGATTATTGGGGGCAGG GG
ACTCAGGTCACTGTATCCTCAGGaGCTggaTCTGGAgccTCA AGTAACCGGGAGCTGGTGGTTGA
CTTTCTCTCCTACAAGCTTTCCCAGAAAGGATACA GCTGGAGTCAGTTTAGTGATGTGGAAGAGA
ACAGGACTGAGGCCCCAGAAGGGACTGAATC GGAGATGGAGACCCCCAGTGCCATCAATGGCA
ACCCATCCTGGCACCTGGCAGACAGCCCCGCGGTGAATGGAGCCACTGGCCACAGCAGCAGTT
TGGATGCCCGGGAGGTGATCCCCATGGCAGCAGTAAAGCAAGCGCTGAGGGAGGCAGGCGAC
GAGTTTGAACTGCGGTACCGGCGGGCATTCAG TGACCTGACATCCCAGCTCCACATCACCCCA
GGGACAGCATATCAGAGCTTTGAACAGGTAGTG AATGAACTCTTCCGGGATGGGGTAAACTGGG
GTCGCATTGTGGCCTTTTTCTCCTTCGGCGGGGCACTGTGCGTGGAAAGCGTAGACAAGGAGAT
GCAGGTATTGGTGAGTCGGATCGCAGCTTG GATGGCCACTTACCTGAATGACCACCTAGAGCCT
TGGATCCAGGAGAACGGCGGCTGGGATAC TTTTGTGGAACTCTATGGGAACAAT ggatccAGCGA
GCTGATTAAGGAGAACATGCACATGAAGCTGTACATGGAGGGCACCGTGGACAACCATCACTTC
AAGTGCACATCCGAGGGCGAAGGCAAGCCCTAC GAGGGCACCCAGACCATGAGAATCAAGGTG
GTCGAGGGCGGCCCTCTCCCCTTCGCCTTCGACATCCTGGCTACTAGCTTCCTCTACGGCAGC
AAGACCTTCATCAACCACACCCAGGGCATCCCC GACTTCTTCAAGCAGTCCTTCCCTGAGGGCT
TCACATGGGAGAGAGTCACCACATACGAAG ACGGGGGCGTGCTGACCGCTACCCAGGACACCA
GCCTCCAGGACGGCTGCCTCATCTACAACGTC AAGATCAGAGGGGTGAACTTCACATCCAACG
GCCCTGTGATGCAGAAGAAAACACTCGGCTGGGAGGCCTTCACCGAGACGCTGTACCCCGCTG
ACGGCGGCCTGGAAGGCAGAAACGACATGGCCCTGAAGCTCGTGGGCGGGAGCCATCTGATC
GCAAACATCAAGACCACATATAGATCCAAGAAACCCGCTAAGAACCTCAAGATGCCTGGCGTCT
ACTATGTGGACTACAGACTGGAAAGAATCAAG GAGGCCAACAACGAGACCTACGTCGAGCAGCA
CGAGGTGGCAGTGGCCAGATACTGCGACCTCCCTAGCAAACTGGGGCACAAGCTTAAT tAAGGG
CCCGTTTAAACCCGCTGATCAGCCTCGACTGTGCCTTCTA

FIG. 45(Cont.)

**SEQ ID NO: 315, tdMCP-nADAR2-DD-*NS3PepHI*-cADAR2-DD(E488Q)-*TagBFP***

TAATACGACTCACTATAGGGAGACCCAAGCTGGctagaggatcgaacccttaaggccaccatg GCGAGC
AATTTTACCCAGTTTGTGCTTGTGGACAAC GGCGGCACCGGGGACGTGACGGTGGCCCCC
TCCAATTTTGCCAATGGCATTGCAGAATGGATAAGCTCTAACAGCAGGAGCCAGGCATACA
AGGTGACCTGCAGCGTGAGGCAGTCAAGCGCTCAAAACAGGAAGTACACCATTAAGGTCG
AAGTGCCCAAAGGAGCTTGGAGGTCTTACCTGAACATGGAACTGACAATTCCTATCTTCGC
GACCAATAGCGACTGTGAGCTGATCGTGAAGGCCATGCAAGGCCTGCTGAAAGACGGGAA
TCCCATACCCAGCGCCATCGCCGCTAACTCAGGCATTTACGCTAATTTCACTCAGTTCGTA
CTGGTTGACAATGGGGGAACCGGCGACGTTACCGTGGCTCCAAGCAACTTCGCTAACGGG
ATCGCCGAGTGGATCAGCAGTAATTCACGCTCCCAAGCCTACAAAGTAACCTGCTCTGTAC
GGCAGAGTTCAGCCCAGAACCGAAAGTATACCATCAAAGTGGAGGTGCCGAAGGGCGCCT
GGCGGAGCTATCTGAATATGGAGCTGACCAT CCCCATCTTTGCCACGAACAGCGATTGCGA
GCTCATCGTCAAGGCGATGCAGGGCTTGCTGAAGGATGGCAACCCTATCCCGAGCGCAAT
AGCAGCCAACAGCGGCATCTATggggc agtgggagcggtgcaggatctggtagtccagctgggggaggagcacc
gggtagcggtgggggtctcagctgcacctgccccaggttctcgcagacgccgtatcccgccttgtactgggcaagtttggtgatcttact
gacaatttttcatctcctcatgcgaggcggaaagtactcgcaggcgtcgtcatgacgaccgga actgacgtgaaagacgccaaagtca
tctctgtctccacgggcacaaagtgcataaacggggagtacatgagcgaccgggggctggcactgaatgattgtcacgctgaaataat
atctaggcgatctctgcttagatttctctacactcaactcgaattgtaccttaacaacaaagatgaccagaaacgcagtatatttcagaaat
cagaacgcggcggatttcgacttaaggaaaacgttcagttccacttgtatatcagcacatccccttgcggtgacgcccgaatcttttcccc
gcacgagccgatattggaggagcccgcgTCGTCCGgt*ggagaacttgatgaattggtatacttactagatgggccaggttatgac*

FIG. 46A cctatacatTGCGATGTAGTGACAAGGGGCGGCAGCCACCTTTTCAATTTTGACagacatcctaatagg
aaggctagaggccaacttcggacgaagattgaaagtggccagggtactatcccggtgcggtccaacgctagtattcaaacgtgggac
ggagtccttcaaggtgaacggctgttgacaatgagctgctcagacaaaatcgcgcgctggaatgtagtgggaatccaaggcagcctct
tgagcatattcgtagaacccatatatttctcatccattatttgggctctctgtatcatggtgaccatctgtcaagggctatgtaccaacgaattt
ctaatatcgaggatcttcctccactctatacactcaataagcctctcttgtccgggatatcaaacgctgaggcccgccagccagggaaag
ctcctaacttcagtgttaactggaccgttggtgattctgcgatagaggtcatcaacgccacgacaggtaaggatgagctcggtagagcct
cacgcctgtgtaaacacgcgttgtattgtagatggatgagagtacatgggaaggtcccatctcacttgctccgaagcaagatcactaag
cctaatgtgtatcatgagtcaaaactcgcggctaaagaataccaggcagccaaagctcgactttttacagcttttattaaggcagggctc
ggggcatgggtcgagaagccgaccgagcaggaccaattctctctgacggggagcggatccAGCGAGCTGATTAAGGA
GAACATGCACATGAAGCTGTACATGGAGGGCACCGTGGACAACCATCACTTCAAGTGCACA
TCCGAGGGCGAAGGCAAGCCCTACGAGGGCACCCAGACCATGAGAATCAAGGTGGTCGA
GGGCGGCCCTCTCCCCTTCGCCTTCGACATCCTGGCTACTAGCTTCCTCTACGGCAGCAA
GACCTTCATCAACCACACCCAGGGCATCCCCGACTTCTTCAAGCAGTCCTTCCCTGAGGGC
TTCACATGGGAGAGAGTCACCACATACGAAGACGGGGGCGTGCTGACCGCTACCCAGGAC
ACCAGCCTCCAGGACGGCTGCCTCATCTACAACGTCAAGATCAGAGGGGTGAACTTCACAT
CCAACGGCCCTGTGATGCAGAAGAAAACACTCGGCTGGGAGGCCTTCACCGAGACGCTGT
ACCCCGCTGACGGCGGCCTGGAAGGCAGAAACGACATGGCCCTGAAGCTCGTGGGCGGG
AGCCATCTGATCGCAAACATCAAGACCACATATAGATCCAAGAAACCCGCTAAGAACCTCA
AGATGCCTGGCGTCTACTATGTGGACTACAGACTGGAAAGAATCAAGGAGGCCAACAACGA
GACCTACGTCGAGCAGCACGAGGTGGCAGTGGCCAGATACTGCGACCTCCCTAGCAAACT
GGGGCACAAGCTTAATtAAGGGCCCGTTTAAACCCGCTGATCAGCCTCGACTGTGCCTTCT

FIG. 46A(Cont.)

**SEQ ID NO: 316, tdMCP-nADAR2-DD-*NS3PepHI*-cADAR2-DD(E488Q)-NS3(1B)-*TagBFP***

TAATACGACTCACTATAGGGAGACCCAAGCT GGctagaggatcgaacccttaaggccaccatgGCGAGCAATTTTA
CCCAGTTTGTGCTTGTGGACAACGGCGGCACCGGGGACGTGACGGTGGCCCCCTCCAATTTTGCCA
ATGGCATTGCAGAATGGATAAGCTCTAACAGCAGGAGCCAGGCATACAAGGTGACCTGCAGCG TGAG
GCAGTCAAGCGCTCAAAACAGGAAGTACACCATTAAGGTCGAAGTGCCCAAAGGAGCTTGGAGGTCT
TACCTGAACATGGAACTGACAATTCCTATCTTCGCGACCAATAGCGACTGTGAGCTGATCGTG AAGGC
CATGCAAGGCCTGCTGAAAGACGGGAATCCCATACCCAGCGCCATCGCCGCTAACTCAGGCAT TTAC
GCTAATTTCACTCAGTTCGTACTGGTTGACAATGGGGGAACCGGCGACGTTACCGTGGCTCCA AGCA
ACTTCGCTAACGGGATCGCCGAGTGGATCAGCAGTAATTCACGCTCCCAAGCCTACAAAGTAA CCTG
CTCTGTACGGCAGAGTTCAGCCCAGAACCGAAAGTATACCATCAAAGTGGAGGTGCCGAAGGG CGC
CTGGCGGAGCTATCTGAATATGGAGCTGACCATCCCCATCTTTGCCACGAACAGCGATTGCGA GCTC
ATCGTCAAGGCGATGCAGGGCTTGCTGAAGGAT GGCAACCCTATCCCGAGCGCAATAGCAGCC AAC
AGCGGCATCTATgggggcagtgggagcggtgcaggatctggtagtccagctgggggaggagca ccgggtagcggtgggggtctcagct
gcacctgccccaggttctcgcagacgccgtatcccgccttgtactgggcaagtttggtgatcttactgacaatttttcatctcctcatgcgaggcggaaagt
actcgcaggcgtcgtcatgacgaccggaactgacgtgaaagacgccaaagtcatctctgtctccacgggcacaaagtgcataaacggggagtacat
gagcgaccgggggctggcactgaatgattgtcacgctgaaataatatctaggcgatctctgcttagatttctctacactcaactcgaattgtaccttaaca
acaaagatgaccagaaacgcagtatatttcagaaatcagaacgcggcggatttcgacttaaggaaaacgttcagttccacttgtatatcagcacatcc
ccttgcggtgacgcccgaatcttttccccgcacgagccgatattggaggagcccgcgTCGTCCGgt*ggagaacttgatgaattggtatacttacta*
*gatgggccaggttatgaccctatacatTGCGATGTAGTGACAAGGGGCGGCAGCCACCTTTTCAATTTT*GACagacat
cctaataggaaggctagaggccaacttcggacgaagattgaaagtggccagggtactatcccggtgcggtccaacgctagtattcaaacgtgggac
ggagtccttcaaggtgaacggctgttgacaatgagctgctcagacaaaatcgcgcgctggaatgtagtgggaatccaaggcagcctcttgagcatatt
cgtagaacccatatatttctcatccattatttgggctctctgtatcatggtgaccatctgtcaagggctatgtaccaacgaatttctaatatcgaggatcttcct

FIG. 46B ccactctatacactcaataagcctctcttgtccgggatatcaaacgctgaggcccgccagccagggaaagctcctaacttcagtgttaactggaccgttg
gtgattctgcgatagaggtcatcaacgccacgacaggtaaggatgagctcggtagagcctcacgcctgtgtaaacacgcgttgtattgtagatggatga
gagtacatgggaaggtcccatctcacttgctccgaagcaagatcactaagcctaatgtgtatcatgagtcaaaactcgcggctaaagaataccaggc
agccaaagctcgactttttacagcttttattaaggcagggctcggggcatgggtcgagaagccgaccgagcaggaccaattctctctgacgggggg
agcGCGGCCGGAGGTAGCGGCGGAAGCGCGGCCGCTcaggggtctgttgttattgttggtagaattattttatctggtagtggta
gtatcacggcctactcccaacagacgcggggcctacttggttgcatcatcactagcctcacaggccgggacaagaaccaggtcgaaggggaggttc
aagtggtttctaccgcaacacaatctttcctggcgacctgcgtcaacggcgtgtgctggactgtctaccatggcgctggctcgaagaccctagccggtcc
aaaaggtccaatcacccaaatgtacaccaatgtagaccaggacctcgtcggctggcaggcgcctccaggggcgcgctccttgacaccatgcacctg
tggcagctcggacctttacttggtcacgagacatgctgatgtcattccggtgcgccggcgaggcgacagcaggggaagtctactctcccccaggcccg
tctcctacctgaaaggctccTCAggtggtccattgctttgcccttcggggcacgctgtgggcatcttccgggctgctgtgtgcacccggggggtcgcga
aggcggtggacttcgtgcccgttgagtctatggaaactaccatgcggtctGAGAGTGGATCAGGTACCATGAGCGAGCTGATT
AAGGAGAACATGCACATGAAGCTGTACATGGAGGGCACCGTGGACAACCATCACTTCAAGTGCACAT
CCGAGGGCGAAGGCAAGCCCTACGAGGGCACCCAGACCATGAGAATCAAGGTGGTCGAGGGCGGC
CCTCTCCCCTTCGCCTTCGACATCCTGGCTACTAGCTTCCTCTACGGCAGCAAGACCTTCATCAACCA
CACCCAGGGCATCCCCGACTTCTTCAAGCAGTCCTTCCCTGAGGGCTTCACATGGGAGAGAGTCACC
ACATACGAAGACGGGGGCGTGCTGACCGCTACCCAGGACACCAGCCTCCAGGACGGCTGCCTCATC
TACAACGTCAAGATCAGAGGGGTGAACTTCACATCCAACGGCCCTGTGATGCAGAAGAAAACACTCG
GCTGGGAGGCCTTCACCGAGACGCTGTACCCCGCTGACGGCGGCCTGGAAGGCAGAAACGACATG
GCCCTGAAGCTCGTGGGCGGGAGCCATCTGATCGCAAACATCAAGACCACATATAGATCCAAGAAAC
CCGCTAAGAACCTCAAGATGCCTGGCGTCTACTATGTGGACTACAGACTGGAAAGAATCAAGGAGGC
CAACAACGAGACCTACGTCGAGCAGCACGAGGTGGCAGTGGCCAGATACTGCGACCTCCCTAGCAA
ACTGGGGCACAAGCTTAATtAAGGGCCCGTTTAAACCCGCTGATCAGCCTCGACTGTGCCTTCTA

FIG. 46B(Cont.)

**SEQ ID NO: 317, tdMCP-nADAR2-DD-*NS3PepHI*-cADAR2-DD(E488Q, K690R, & L699V)-NS3(1B)-*TagBFP***

TAATACGACTCACTATAGGGAGACCC AAGCTGGctagaggatcgaacccttaaggccaccatgGCGAGCAATT
TTACCCAGTTTGTGCTTGTGGACAACGGCGGCACCGGGGACGTGACGGTGGCCCCCTCCAATT
TTGCCAATGGCATTGCAGAATGGATAAGCTCTAACAGCAGGAGCCAGGCATACAAGGTGACCTG
CAGCGTGAGGCAGTCAAGCGCTCAAAACAGGAAGTACACCATTAAGGTCGAAGTGCCCAAAGG
AGCTTGGAGGTCTTACCTGAACATGGAACTGACAATTCCTATCTTCGCGACCAATAGCGACTGTG
AGCTGATCGTGAAGGCCATGCAAGGCCTGC TGAAAGACGGGAATCCCATACCCAGCGCCATCG
CCGCTAACTCAGGCATTTACGCTAATTTCACTCAGTTCGTACTGGTTGACAATGGGGGAACCGG
CGACGTTACCGTGGCTCCAAGCAACTTCGCTAACGGGATCGCCGAGTGGATCAGCAGTAATTCA
CGCTCCCAAGCCTACAAAGTAACCTGCTCTGTACGGCAGAGTTCAGCCCAGAACCGAAAGTATA
CCATCAAAGTGGAGGTGCCGAAGGGCGCCTGGCGGAGCTATCTGAATATGGAGCTGACCATCC
CCATCTTTGCCACGAACAGCGATTGCGAGCTCATCGTCAAGGCGATGCAGGGCTTGCTGAAGG
ATGGCAACCCTATCCCGAGCGCAATAGCAGCC AACAGCGGCATCTATgggggcagtgggagcg gtgcag
gatctggtagtccagctgggggaggagcaccgggtagcggtgggggtctcagctgcacctgccccaggttctcgcagacgccgtatcccg
ccttgtactgggcaagtttggtgatcttactgacaatttttcatctcctcatgcgaggcggaaagtactcgcaggcgtcgtcatgacgaccggaac
tgacgtgaaagacgccaaagtcatctctgtctccacgggcacaaagtgcataaacggggagtacatgagcgaccgggggctggcactga
atgattgtcacgctgaaataatatctaggcgatctctgcttagatttctctacactcaactcgaattgtaccttaacaacaaagatgaccagaaac
gcagtatatttcagaaatcagaacgcggcggatttcgacttaaggaaaacgttcagttccacttgtatatcagcacatccccttgcggtgacgcc
cgaatcttttccccgcacgagccgatattggaggagcccgcgTCGTCCGgt*ggagaacttgatgaattggtatacttactagatgggcca*
*ggttatgaccctatacat*TGCGATGTAGTGACAAGGGGCGGCAGCCACCTTTTCAATTTT GACagacatcctaa
taggaaggctagaggccaacttcggacgaagattgaaagtggccagggtactatcccggtgcggtccaacgctagtattcaaacgtgggac
ggagtccttcaaggtgaacggctgttgacaatgagctgctcagacaaaatcgcgcgctggaatgtagtgggaatccaaggcagcctcttgag
catattcgtagaacccatatatttctcatccattatttgggctctctgtatcatggtgaccatctgtcaagggctatgtaccaacgaatttctaatatcg

FIG. 46C aggatcttcctccactctatacactcaataagcctctcttgtccgggatatcaaacgctgaggcccgccagccagggaaagctcctaacttcag
tgttaactggaccgttggtgattctgcgatagaggtcatcaacgccacgacaggtaaggatgagctcggtagagcctcacgcctgtgtaaaca
cgcgttgtattgtagatggatgagagtacatgggaaggtcccatctcacttgctccgaagcaagatcactaagcctaatgtgtatcatgagtcaa
aactcgcggctaaagaataccaggcagccaaagctcgacttttacagcttttattaaggcagggctcggggcatgggtcgagAGGccga
ccgagcaggaccaattctctgtgacgggggggagcGCGGCCGGAGGTAGCGGCGGAAGCGCGGCCGCTcaggg
gtctgttgttattgttggtagaattattttatctggtagtggtagtatcacggcctactcccaacagacgcggggcctacttggttgcatcatcactag
cctcacaggccgggacaagaaccaggtcgaaggggaggttcaagtggtttctaccgcaacacaatctttcctggcgacctgcgtcaacggc
gtgtgctggactgtctaccatggcgctggctcgaagaccctagccggtccaaaaggtccaatcacccaaatgtacaccaatgtagaccagg
acctcgtcggctggcaggcgcctccaggggcgcgctccttgacaccatgcacctgtggcagctcggacctttacttggtcacgagacatgctg
atgtcattccggtgcgccggcgaggcgacagcaggggaagtctactctcccccaggcccgtctcctacctgaaaggctccTCAggtggtcc
attgctttgcccttcggggcacgctgtgggcatcttccgggctgctgtgtgcacccggggggtcgcgaaggcggtggacttcgtgcccgttgagt
ctatggaaactaccatgcggtctGAGAGTGGATCAGGTACCATG *AGCGAGCTGATTAAGGAGAACATGCAC*
*ATGAAGCTGTACATGGAGGGCACCGTGGAC AACCATCACTTCAAGTGCACATCCGAGGGCGAA*
*GGCAAGCCCTACGAGGGCACCCAGACCATGAGAAT CAAGGTGGTCGAGGGCGGCCCTCTCCC*
*CTTCGCCTTCGACATCCTGGCTACTAGCTTCCT CTACGGCAGCAAGACCTTCATCAACCACACC*
*CAGGGCATCCCCGACTTCTTCAAGCAGTCCTTCCCTGAGGGCTTCACATGGGAGAGAGTCACCA*
*CATACGAAGACGGGGGCGTGCTGACCGCTACCCA GGACACCAGCCTCCAGGACGGCTGCCTC*
*ATCTACAACGTCAAGATCAGAGGGGTGAACTTCACATCCAACGGCCCTGTGATGCAGAAGAAAA*
*CACTCGGCTGGGAGGCCTTCACCGAGACGCTGTACCCCGCTGACGGCGGCCTGGAAGGCAGA*
*AACGACATGGCCCTGAAGCTCGTGGGCGGGAGCCATCTGATCGCAAACATCAAGACCACATATA*
*GATCCAAGAAACCCGCTAAGAACCTCAAGATGCCT GGCGTCTACTATGTGGACTACAGACTGGA*
*AAGAATCAAGGAGGCCAACAACGAGACCTACGT CGAGCAGCACGAGGTGGCAGTGGCCAGATA*
*CTGCGACCTCCCTAGCAAACTGGGGCACAAGCTTAAT*tAAGGGCCCGTTTAAACCCGCTGATCA
GCCTCGACTGTGCCTTCTA

FIG. 46C(Cont.)

**SEQ ID NO: 318, MCP-nADAR2-DD-*5A/5B*-cADAR2-DD(E488Q)-solNS3(1B)-*TagBFP***

TAATACGACTCACTATAGGGAGACCCAAGCTGGctagaggatcgaacccttaaggccaccatggcgtccaattt
cactcagtttgtgctggttgacaacggcgggaccggggacgttacggtagcccctcaaactttgccaacggtatagcggagtggata
agcagcaattctaggagtcaagcatacaaagttacatgcagcgtgcgccaatctagcgctcagaatcgcaagtacaccattaaagta
gaggtccccaagggagcctggagaagctatcttaacatggagttgaccataccaatcttcgctaccaactctgactgtgaactcattgtg
aaagccatgcaaggtctgctcaaggatggtaacccaattccgtccgctatcgctgccaactctgggatttacgggggcagtgggagcg
gtgcaggatctggtagtccagctgggggaggagcaccgggtagcggtggggggtctcagctgcacctgccccaggttctcgcagac
gccgtatcccgccttgtactgggcaagtttggtgatcttactgacaatttttcatctcctcatgcgaggcggaaagtactcgcaggcgtcgtc
atgacgaccggaactgacgtgaaagacgccaaagtcatctctgtctccacgggcacaaagtgcataaacggggagtacatgagcg
accgggggctggcactgaatgattgtcacgctgaaataatatctaggcgatctctgcttagatttctctacactcaactcgaattgtacctta
acaacaaagatgaccagaaacgcagtatatttcagaaatcagaacgcggcggatttcgacttaaggaaaacgttcagttccacttgtat
atcagcacatccccttgcggtgacgcccgaatcttttccccgcacgagccgatattggaggagcccgcgGCTAGCGGA*GAAG*
*ATGTTGTCTGCTGTCATTCAATCTAC* GGCACCGGTGACagacatcctaataggaaggctagaggccaactt
cggacgaagattgaaagtggccagggtactatcccggtgcggtccaacgctagtattcaaacgtgggacggagtccttcaaggtgaa
cggctgttgacaatgagctgctcagacaaaatcgcgcgctggaatgtagtgggaatccaaggcagcctcttgagcatattcgtagaac
ccatatatttctcatccattatttgggctctctgtatcatggtgaccatctgtcaagggctatgtaccaacgaatttctaatatcgaggatcttcc
tccactctatacactcaataagcctctcttgtccgggatatcaaacgctgaggcccgccagccagggaaagctcctaacttcagtgttaa
ctggaccgttggtgattctgcgatagaggtcatcaacgccacgacaggtaaggatgagctcggtagagcctcacgcctgtgtaaacac
gcgttgtattgtagatggatgagagtacatgggaaggtcccatctcacttgctccgaagcaagatcactaagcctaatgtgtatcatgagt
caaaactcgcggctaaagaataccaggcagccaaagctcgacttttacagcttttattaaggcagggctcggggcatgggtcgagaa

FIG. 47A gccgaccgagcaggaccaattctctctgacggggagcGGTACCATGAAAAAGAAAggttctgt tgttattgttggtagaattA
ATttatctggtGACacggcctactcccaacagacgcggggcctaGAAggttgcCAAGAGacta gcCAAacaggccgggac
aagaaccaggtcgaaggggaggttcaagtggtttctaccgcaacacaatctttcctggcgaccTCCATCaacggcgtgCTTtgg
actgtctaccatggcgctggcaccagaaccATTgccAGCccaaaaggtccaGTGacccaaatg tacaccaatgtagacAAG
gacctcgtcggctggcaggcgcctCAAgggTCAcgctccttgacaccatgcacctgtggcagctcggacctttacttggtcacgaga
catgctgatgtcattccggtgcgccggcgaggcgacagcaggggaagtctactctcccccaggcccATCtcctacctgaaaggctcc
TCAggtggtccattgctttgccctGCTgggcacgctgtgggcatcttccgggctgctgtgAGTacccggggggtcgcgaaggcggt
ggacttcATTcccgttgagtctCTGgaaactaccatgcggtctCCAggatcc *AGCGAGCTGATTAAGGAGAACAT*
*GCACATGAAGCTGTACATGGAGGGCACCGTGGACAACCATCACTTCAAGTGCACATCCGA*
*GGGCGAAGGCAAGCCCTACGAGGGCACCCAGACCATGAGAATCAAGGTGGTCGAGGGCG*
*GCCCTCTCCCCTTCGCCTTCGACATCCTGGCTACTAGCTTCCTCTACGGCAGCAAGACCTT*
*CATCAACCACACCCAGGGCATCCCCGACTTCTT CAAGCAGTCCTTCCCTGAGGGCTTCACA*
*TGGGAGAGAGTCACCACATACGAAGACGGGGGCGTGCTGACCGCTACCCAGGACACCAG*
*CCTCCAGGACGGCTGCCTCATCTACAACGTCAAGATCAGAGGGGTGAACTTCACATCCAAC*
*GGCCCTGTGATGCAGAAGAAAACACTCGGCTGGGAGGCCTTCACCGAGACGCTGTACCCC*
*GCTGACGGCGGCCTGGAAGGCAGAAACGACATGGCCCTGAAGCTCGTGGGCGGGAGCCA*
*TCTGATCGCAAACATCAAGACCACATATAGATCCAAGAAACCCGCTAAGAACCTCAAGATG*
*CCTGGCGTCTACTATGTGGACTACAGACTGGAAAGAATCAAGGAGGCCAACAACGAGACCT*
*ACGTCGAGCAGCACGAGGTGGCAGTGGCCAGATACTGCGACCTCCCTAGCAAACTGGGGC*
*ACAAGCTTAAT*tAAGGGCCCGTTTAAACCCGCTGATCAGCCTCGACTGTGCCTTCTA

FIG. 47A(Cont.)

**SEQ ID NO: 319, MCP-nADAR2-DD-*5A/5B*-cADAR2-DD(E488Q)-soldNS3(1B)(S139A)-*TagBFP***

TAATACGACTCACTATAGGGAGACCCAAGCTGGctagaggatcgaacccttaaggccaccatggcgtccaattt
cactcagtttgtgctggttgacaacggcgggaccggggacgttacggtagccccctcaaactttgccaacggtatagcggagtggata
agcagcaattctaggagtcaagcatacaaagttacatgcagcgtgcgccaatctagcgctcagaatcgcaagtacaccattaaagta
gaggtccccaagggagcctggagaagctatcttaacatggagttgaccataccaatcttcgctaccaactctgactgtgaactcattgtg
aaagccatgcaaggtctgctcaaggatggtaacccaattccgtccgctatcgctgccaactctgggatttacgggggcagtgggagcg
gtgcaggatctggtagtccagctgggggaggagcaccgggtagcggtggggggtctcagctgcacctgccccaggttctcgcagac
gccgtatcccgccttgtactgggcaagtttggtgatcttactgacaattttcatctcctcatgcgaggcggaaagtactcgcaggcgtcgtc
atgacgaccggaactgacgtgaaagacgccaaagtcatctctgtctccacgggcacaaagtgcataaacggggagtacatgagcg
accgggggctggcactgaatgattgtcacgctgaaataatatctaggcgatctctgcttagatttctctacactcaactcgaattgtacctta
acaacaaagatgaccagaaacgcagtatatttcagaaatcagaacgcggcggatttcgacttaaggaaaacgttcagttccacttgtat
atcagcacatccccttgcggtgacgcccgaatcttttccccgcacgagccgatattggaggagcccgcgGCTAGCGGA*GAAG*
*ATGTTGTCTGCTGTCATTCAATCTAC* GGCACCGGTGACagacatcctaataggaaggctagaggccaactt
cggacgaagattgaaagtggccagggtactatcccggtgcggtccaacgctagtattcaaacgtgggacggagtccttcaaggtgaa
cggctgttgacaatgagctgctcagacaaaatcgcgcgctggaatgtagtgggaatccaaggcagcctcttgagcatattcgtagaac
ccatatatttctcatccattatttgggctctctgtatcatggtgaccatctgtcaagggctatgtaccaacgaatttctaatatcgaggatcttcc
tccactctatacactcaataagcctctcttgtccgggatatcaaacgctgaggcccgccagccagggaaagctcctaacttcagtgttaa
ctggaccgttggtgattctgcgatagaggtcatcaacgccacgacaggtaaggatgagctcggtagagcctcacgcctgtgtaaacac
gcgttgtattgtagatggatgagagtacatgggaaggtcccatctcacttgctccgaagcaagatcactaagcctaatgtgtatcatgagt

FIG. 47B caaaactcgcggctaaagaataccaggcagccaaagctcgacttttacagctttattaaggcagggctcggggcatgggtcgagaa
gccgaccgagcaggaccaattctctctgacggggagcGGTACCATGAAAAAGAAAggttctgt tgttattgttggtagaattA
ATttatctggtGACacggcctactcccaacagacgcggggcctaGAAggttgcCAAGAGacta gcCAAacaggccgggac
aagaaccaggtcgaaggggaggttcaagtggtttctaccgcaacacaatctttcctggcgaccTCCATCaacggcgtgCTTtgg
actgtctaccatggcgctggcaccagaaccATTgccAGCccaaaaggtccaGTGacccaaatg tacaccaatgtagacAAG
gacctcgtcggctggcaggcgcctCAAgggTCAcgctccttgacaccatgcacctgtggcagctcggacctttacttggtcacgaga
catgctgatgtcattccggtgcgccggcgaggcgacagcaggggaagtctactctcccccaggcccATCtcctacctgaaaggctcc
GCAggtggtccattgctttgccctGCTgggcacgctgtgggcatcttccgggctgctgtgAGTacc cgggggtcgcgaaggcgg
tggacttcATTcccgttgagtctCTGgaaactaccatgcggtctCCAggatcc AGCGAGCTGATTAAGGAGAACAT
GCACATGAAGCTGTACATGGAGGGCACCGTGGACAACCATCACTTCAAGTGCACATCCGA
GGGCGAAGGCAAGCCCTACGAGGGCACCCAGACCATGAGAATCAAGGTGGTCGAGGGCG
GCCCTCTCCCCTTCGCCTTCGACATCCTGGCTACTAGCTTCCTCTACGGCAGCAAGACCTT
CATCAACCACACCCAGGGCATCCCCGACTTCTT CAAGCAGTCCTTCCCTGAGGGCTTCACA
TGGGAGAGAGTCACCACATACGAAGACGGGGGCGTGCTGACCGCTACCCAGGACACCAG
CCTCCAGGACGGCTGCCTCATCTACAACGTCAAGATCAGAGGGGTGAACTTCACATCCAAC
GGCCCTGTGATGCAGAAGAAAACACTCGGCTGGGAGGCCTTCACCGAGACGCTGTACCCC
GCTGACGGCGGCCTGGAAGGCAGAAACGACATGGCCCTGAAGCTCGTGGGCGGGAGCCA
TCTGATCGCAAACATCAAGACCACATATAGATCCAAGAAACCCGCTAAGAACCTCAAGATG
CCTGGCGTCTACTATGTGGACTACAGACTGGAAAGAATCAAGGAGGCCAACAACGAGACCT
ACGTCGAGCAGCACGAGGTGGCAGTGGCCAGATACTGCGACCTCCCTAGCAAACTGGGGC
ACAAGCTTAATtAAGGGCCCGTTTAAACCCGCTGATCAGCCTCGACTGTGCCTTCTA

FIG. 47B(Cont.)

**SEQ ID NO: 320, MCP-nADAR2-DD-*5A/5B*-cADAR2-DD(E488Q & L699G)-solNS3(1B)-*TagBFP***

TAATACGACTCACTATAGGGAGACCCAAGCTGGctagaggatcgaacccttaaggccaccatggcgtccaattt
cactcagtttgtgctggttgacaacggcgggaccggggacgttacggtagcccctcaaactttgccaacggtatagcggagtggata
agcagcaattctaggagtcaagcatacaaagttacatgcagcgtgcgccaatctagcgctcagaatcgcaagtacaccattaaagta
gaggtccccaagggagcctggagaagctatcttaacatggagttgaccataccaatcttcgctaccaactctgactgtgaactcattgtg
aaagccatgcaaggtctgctcaaggatggtaacccaattccgtccgctatcgctgccaactctgggatttacgggggcagtgggagcg
gtgcaggatctggtagtccagctgggggaggagcaccgggtagcggtgggggtctcagctgcacctgccccaggttctcgcagac
gccgtatcccgccttgtactgggcaagtttggtgatcttactgacaattttcatctcctcatgcgaggcggaaagtactcgcaggcgtcgtc
atgacgaccggaactgacgtgaaagacgccaaagtcatctctgtctccacgggcacaaagtgcataaacggggagtacatgagcg
accgggggctggcactgaatgattgtcacgctgaaataatatctaggcgatctctgcttagatttctctacactcaactcgaattgtacctta
acaacaaagatgaccagaaacgcagtatatttcagaaatcagaacgcggcggatttcgacttaaggaaaacgttcagttccacttgtat
atcagcacatccccttgcggtgacgcccgaatcttttccccgcacgagccgatattggaggagcccgcgGCTAGCGGA*GAAG*
*ATGTTGTCTGCTGTCATTCAATCTAC* GGCACCGGTGACagacatcctaataggaaggctagaggccaactt
cggacgaagattgaaagtggccagggtactatcccggtgcggtccaacgctagtattcaaacgtgggacggagtccttcaaggtgaa
cggctgttgacaatgagctgctcagacaaaatcgcgcgctggaatgtagtgggaatccaaggcagcctcttgagcatattcgtagaac
ccatatatttctcatccattatttgggctctctgtatcatggtgaccatctgtcaagggctatgtaccaacgaatttctaatatcgaggatcttcc
tccactctatacactcaataagcctctcttgtccgggatatcaaacgctgaggcccgccagccagggaaagctcctaacttcagtgttaa
ctggaccgttggtgattctgcgatagaggtcatcaacgccacgacaggtaaggatgagctcggtagagcctcacgcctgtgtaaacac

FIG. 47C gcgttgtattgtagatggatgagagtacatgggaaggtcccatctcacttgctccgaagcaagatcactaagcctaatgtgtatcatgagt
caaaactcgcggctaaagaataccaggcagccaaagctcgactttttacagcttttattaaggcagggctcggggcatgggtcgagaa
gccgaccgagcaggaccaattctctGGGacggggagcGGTACCATGAAAAAGAAAggttctgttgttattgttggtagaat
tAATttatctggtGACacggcctactcccaacagacgcggggcctaGAAggttgcCAAGAGactagcCAAacaggccggg
acaagaaccaggtcgaaggggaggttcaagtggtttctaccgcaacacaatctttcctggcgaccTCCATCaacggcgtgCTTt
ggactgtctaccatggcgctggcaccagaaccATTgccAGCccaaaaggtccaGTGacccaaatgtacaccaatgtagacA
AGgacctcgtcggctggcaggcgcctCAAgggTCAcgctccttgacaccatgcacctgtggcagctcggacctttacttggtcacg
agacatgctgatgtcattccggtgcgccggcgaggcgacagcaggggaagtctactctcccccaggcccATCtcctacctgaaagg
ctccTCAggtggtccattgctttgccctGCTgggcacgctgtgggcatcttccgggctgctgtgAGTacccggggggtcgcgaagg
cggtggacttcATTcccgttgagtctCTGgaaactaccatgcggtctCCAggatcc AGCGAGCTGATTAAGGAGAA
CATGCACATGAAGCTGTACATGGAGGGCACCGTGGACAACCATCACTTCAAGTGCACATCC
GAGGGCGAAGGCAAGCCCTACGAGGGCACCCAGACCATGAGAATCAAGGTGGTCGAGGG
CGGCCCTCTCCCCTTCGCCTTCGACATCCTGGCTACTAGCTTCCTCTACGGCAGCAAGACC
TTCATCAACCACACCCAGGGCATCCCCGACTTC TTCAAGCAGTCCTTCCCTGAGGGCTTCA
CATGGGAGAGAGTCACCACATACGAAGACGGGGGCGTGCTGACCGCTACCCAGGACACCA
GCCTCCAGGACGGCTGCCTCATCTACAACGTCAAGATCAGAGGGGTGAACTTCACATCCAA
CGGCCCTGTGATGCAGAAGAAAACACTCGGCTGGGAGGCCTTCACCGAGACGCTGTACCC
CGCTGACGGCGGCCTGGAAGGCAGAAACGACATGGCCCTGAAGCTCGTGGGCGGGAGCC
ATCTGATCGCAAACATCAAGACCACATATA GATCCAAGAAACCCGCTAAGAACCTCAAGAT
GCCTGGCGTCTACTATGTGGACTACAGACTGGAAAGAATCAAGGAGGCCAACAACGAGAC
CTACGTCGAGCAGCACGAGGTGGCAGTGGCCAGATACTGCGACCTCCCTAGCAAACTGGG
GCACAAGCTTAATtAAGGGCCCGTTTAAACCCGCTGATCAGCCTCGACTGTGCCTTCTA

FIG. 47C(Cont.)

**SEQ ID NO: 321, MCP-nADAR2-DD-*5A/5B*-cADAR2-DD(E488Q & L699G)-soldNS3(1B)(S139A)-*TagBFP***

TAATACGACTCACTATAGGGAGACCCAAGCTGGctagaggatcgaacccttaaggccaccatggcgtccaattt
cactcagtttgtgctggttgacaacggcgggaccggggacgttacggtagcccctcaaactttgccaacggtatagcggagtggata
agcagcaattctaggagtcaagcatacaaagttacatgcagcgtgcgccaatctagcgctcagaatcgcaagtacaccattaaagta
gaggtccccaagggagcctggagaagctatcttaacatggagttgaccataccaatcttcgctaccaactctgactgtgaactcattgtg
aaagccatgcaaggtctgctcaaggatggtaacccaattccgtccgctatcgctgccaactctgggatttacgggggcagtgggagcg
gtgcaggatctggtagtccagctgggggaggagcaccgggtagcggtgggggtctcagctgcacctgccccaggttctcgcagac
gccgtatcccgccttgtactgggcaagtttggtgatcttactgacaattttcatctcctcatgcgaggcggaaagtactcgcaggcgtcgtc
atgacgaccggaactgacgtgaaagacgccaaagtcatctctgtctccacgggcacaaagtgcataaacggggagtacatgagcg
accgggggctggcactgaatgattgtcacgctgaaataatatctaggcgatctctgcttagatttctctacactcaactcgaattgtacctta
acaacaaagatgaccagaaacgcagtatatttcagaaatcagaacgcggcggatttcgacttaaggaaaacgttcagttccacttgtat
atcagcacatccccttgcggtgacgcccgaatcttttccccgcacgagccgatattggaggagcccgcgGCTAGCGGA*GAAG*
*ATGTTGTCTGCTGTCATTCAATCTAC* GGCACCGGTGACagacatcctaataggaaggctagaggccaactt
cggacgaagattgaaagtggccagggtactatcccggtgcggtccaacgctagtattcaaacgtgggacggagtccttcaaggtgaa
cggctgttgacaatgagctgctcagacaaaatcgcgcgctggaatgtagtgggaatccaaggcagcctcttgagcatattcgtagaac
ccatatatttctcatccattatttgggctctctgtatcatggtgaccatctgtcaagggctatgtaccaacgaatttctaatatcgaggatcttcc
tccactctatacactcaataagcctctcttgtccgggatatcaaacgctgaggcccgccagccagggaaagctcctaacttcagtgttaa
ctggaccgttggtgattctgcgatagaggtcatcaacgccacgacaggtaaggatgagctcggtagagcctcacgcctgtgtaaacac

FIG. 47D gcgttgtattgtagatggatgagagtacatgggaaggtcccatctcacttgctccgaagcaagatcactaagcctaatgtgtatcatgagt
caaaactcgcggctaaagaataccaggcagccaaagctcgacttttacagcttttattaaggcagggctcggggcatgggtcgagaa
gccgaccgagcaggaccaattctctGGGacggggagcGGTACCATGAAAAAGAAAggttctgttgttattgttggtagaat
tAATttatctggtGACacggcctactcccaacagacgcggggcctaGAAggttgcCAAGAGactagcCAAacaggccggg
acaagaaccaggtcgaaggggaggttcaagtggtttctaccgcaacacaatctttcctggcgaccTCCATCaacggcgtgCTTt
ggactgtctaccatggcgctggcaccagaaccATTgccAGCccaaaaggtccaGTGacccaaatgtacaccaatgtagacA
AGgacctcgtcggctggcaggcgcctCAAgggTCAcgctccttgacaccatgcacctgtggcagctcggacctttacttggtcacg
agacatgctgatgtcattccggtgcgccggcgaggcgacagcaggggaagtctactctcccccaggcccATCtcctacctgaaagg
ctccGCAggtggtccattgctttgccctGCTgggcacgctgtgggcatcttccgggctgctgtgAGTacccgggggtcgcgaagg
cggtggacttcATTcccgttgagtctCTGgaaactaccatgcggtctCCAggatcc *AGCGAGCTGATTAAGGAGAA*
*CATGCACATGAAGCTGTACATGGAGGGCACCGTGGACAACCATCACTTCAAGTGCACATCC*
*GAGGGCGAAGGCAAGCCCTACGAGGGCACCCAGACCATGAGAATCAAGGTGGTCGAGGG*
*CGGCCCTCTCCCCTTCGCCTTCGACATCCTGGCTACTAGCTTCCTCTACGGCAGCAAGACC*
*TTCATCAACCACACCCAGGGCATCCCCGACTTC TTCAAGCAGTCCTTCCCTGAGGGCTTCA*
*CATGGGAGAGAGTCACCACATACGAAGACGGGGGCGTGCTGACCGCTACCCAGGACACCA*
*GCCTCCAGGACGGCTGCCTCATCTACAACGTCAAGATCAGAGGGGTGAACTTCACATCCAA*
*CGGCCCTGTGATGCAGAAGAAAACACTCGGCTGGGAGGCCTTCACCGAGACGCTGTACCC*
*CGCTGACGGCGGCCTGGAAGGCAGAAACGACATGGCCCTGAAGCTCGTGGGCGGGAGCC*
*ATCTGATCGCAAACATCAAGACCACATATA GATCCAAGAAACCCGCTAAGAACCTCAAGAT*
*GCCTGGCGTCTACTATGTGGACTACAGACTGGAAAGAATCAAGGAGGCCAACAACGAGAC*
*CTACGTCGAGCAGCACGAGGTGGCAGTGGCCAGATACTGCGACCTCCCTAGCAAACTGGG*
*GCACAAGCTTAAT*tAAGGGCCCGTTTAAACCCGCTGATCAGCCTCGACTGTGCCTTCTA

FIG. 47D(Cont.)

**SEQ ID NO: 322, MCP-nADAR2-DD-*5A/5B*-cADAR2-DD(E488Q & F697Y)-soINS3(1B)-*TagBFP***

TAATACGACTCACTATAGGGAGACCCAAGCTGGctagaggatcgaacccttaaggccaccatggcgtccaattt
cactcagtttgtgctggttgacaacggcgggaccggggacgttacggtagcccctcaaactttgccaacggtatagcggagtggata
agcagcaattctaggagtcaagcatacaaagttacatgcagcgtgcgccaatctagcgctcagaatcgcaagtacaccattaaagta
gaggtccccaagggagcctggagaagctatcttaacatggagttgaccataccaatcttcgctaccaactctgactgtgaactcattgtg
aaagccatgcaaggtctgctcaaggatggtaacccaattccgtccgctatcgctgccaactctgggatttacgggggcagtgggagcg
gtgcaggatctggtagtccagctgggggaggagcaccgggtagcggtgggggtctcagctgcacctgccccaggttctcgcagac
gccgtatcccgccttgtactgggcaagtttggtgatcttactgacaatttttcatctcctcatgcgaggcggaaagtactcgcaggcgtcgtc
atgacgaccggaactgacgtgaaagacgccaaagtcatctctgtctccacgggcacaaagtgcataaacggggagtacatgagcg
accgggggctggcactgaatgattgtcacgctgaaataatatctaggcgatctctgcttagatttctctacactcaactcgaattgtacctta
acaacaaagatgaccagaaacgcagtatatttcagaaatcagaacgcggcggatttcgacttaaggaaaacgttcagttccacttgtat
atcagcacatccccttgcggtgacgcccgaatcttttccccgcacgagccgatattggaggagcccgcgGCTAGCGGA *GAAG*
*ATGTTGTCTGCTGTCATTCAATCTAC* GGCACCGGTGACagacatcctaataggaaggctagaggccaactt
cggacgaagattgaaagtggccagggtactatcccggtgcggtccaacgctagtattcaaacgtgggacggagtccttcaaggtgaa
cggctgttgacaatgagctgctcagacaaaatcgcgcgctggaatgtagtgggaatccaaggcagcctcttgagcatattcgtagaac
ccatatatttctcatccattatttgggctctctgtatcatggtgaccatctgtcaagggctatgtaccaacgaatttctaatatcgaggatcttcc
tccactctatacactcaataagcctctcttgtccgggatatcaaacgctgaggcccgccagccagggaaagctcctaacttcagtgttaa
ctggaccgttggtgattctgcgatagaggtcatcaacgccacgacaggtaaggatgagctcggtagagcctcacgcctgtgtaaacac

FIG. 47E gcgttgtattgtagatggatgagagtacatgggaaggtcccatctcacttgctccgaagcaagatcactaagcctaatgtgtatcatgagt
caaaactcgcggctaaagaataccaggcagccaaagctcgacttttacagctttattaaggcagggctcggggcatgggtcgagaa
gccgaccgagcaggaccaaTACtctctgacggggagcGGTACCATGAAAAAGAAAggttctgttgttattgttggtagaat
tAATttatctggtGACacggcctactcccaacagacgcggggcctaGAAggttgcCAAGAGactagcCAAacaggccggg
acaagaaccaggtcgaaggggaggttcaagtggtttctaccgcaacacaatctttcctggcgaccTCCATCaacggcgtgCTTt
ggactgtctaccatggcgctggcaccagaaccATTgccAGCccaaaaggtccaGTGacccaaatgtacaccaatgtagacA
AGgacctcgtcggctggcaggcgcctCAAgggTCAcgctccttgacaccatgcacctgtggcagctcggacctttacttggtcacg
agacatgctgatgtcattccggtgcgccggcgaggcgacagcaggggaagtctactctcccccaggcccATCtcctacctgaaagg
ctccTCAggtggtccattgctttgccctGCTgggcacgctgtgggcatcttccgggctgctgtgAGTacccggggggtcgcgaagg
cggtggacttcATTcccgttgagtctCTGgaaactaccatgcggtctCCAggatcc *AGCGAGCTGATTAAGGAGAA*
*CATGCACATGAAGCTGTACATGGAGGGCACCGTGGACAACCATCACTTCAAGTGCACATCC*
*GAGGGCGAAGGCAAGCCCTACGAGGGCACCCAGACCATGAGAATCAAGGTGGTCGAGGG*
*CGGCCCTCTCCCCTTCGCCTTCGACATCCTGGCTACTAGCTTCCTCTACGGCAGCAAGACC*
*TTCATCAACCACACCCAGGGCATCCCCGACTTC TTCAAGCAGTCCTTCCCTGAGGGCTTCA*
*CATGGGAGAGAGTCACCACATACGAAGACGGGGGCGTGCTGACCGCTACCCAGGACACCA*
*GCCTCCAGGACGGCTGCCTCATCTACAACGTCAAGATCAGAGGGGTGAACTTCACATCCAA*
*CGGCCCTGTGATGCAGAAGAAAACACTCGGCTGGGAGGCCTTCACCGAGACGCTGTACCC*
*CGCTGACGGCGGCCTGGAAGGCAGAAACGACATGGCCCTGAAGCTCGTGGGCGGGAGCC*
*ATCTGATCGCAAACATCAAGACCACATATA GATCCAAGAAACCCGCTAAGAACCTCAAGAT*
*GCCTGGCGTCTACTATGTGGACTACAGACTGGAAAGAATCAAGGAGGCCAACAACGAGAC*
*CTACGTCGAGCAGCACGAGGTGGCAGTGGCCAGATACTGCGACCTCCCTAGCAAACTGGG*
*GCACAAGCTTAAT*tAAGGGCCCGTTTAAACCCGCTGATCAGCCTCGACTGTGCCTTCTA

FIG. 47E(Cont.)

**SEQ ID NO: 323, MCP-nADAR2-DD-*5A/5B*-cADAR2-DD(E488Q & F697Y)-soldNS3(1B)(S139A)-*TagBFP***

TAATACGACTCACTATAGGGAGACCCAAGCTGGctagaggatcgaacccttaaggccaccatggcgtccaattt
cactcagtttgtgctggttgacaacggcgggaccggggacgttacggtagcccctcaaactttgccaacggtatagcggagtggata
agcagcaattctaggagtcaagcatacaaagttacatgcagcgtgcgccaatctagcgctcagaatcgcaagtacaccattaaagta
gaggtccccaagggagcctggagaagctatcttaacatggagttgaccataccaatcttcgctaccaactctgactgtgaactcattgtg
aaagccatgcaaggtctgctcaaggatggtaacccaattccgtccgctatcgctgccaactctgggatttacgggggcagtgggagcg
gtgcaggatctggtagtccagctgggggaggagcaccgggtagcggtgggggtctcagctgcacctgccccaggttctcgcagac
gccgtatcccgccttgtactgggcaagtttggtgatcttactgacaatttttcatctcctcatgcgaggcggaaagtactcgcaggcgtcgtc
atgacgaccggaactgacgtgaaagacgccaaagtcatctctgtctccacgggcacaaagtgcataaacggggagtacatgagcg
accgggggctggcactgaatgattgtcacgctgaaataatatctaggcgatctctgcttagatttctctacactcaactcgaattgtacctta
acaacaaagatgaccagaaacgcagtatatttcagaaatcagaacgcggcggatttcgacttaaggaaaacgttcagttccacttgtat
atcagcacatccccttgcggtgacgcccgaatcttttccccgcacgagccgatattggaggagcccgcgGCTAGCGGA*GAAG*
*ATGTTGTCTGCTGTCATTCAATCTAC* GGCACCGGTGACagacatcctaataggaaggctagaggccaactt
cggacgaagattgaaagtggccagggtactatcccggtgcggtccaacgctagtattcaaacgtgggacggagtccttcaaggtgaa
cggctgttgacaatgagctgctcagacaaaatcgcgcgctggaatgtagtgggaatccaaggcagcctcttgagcatattcgtagaac
ccatatatttctcatccattatttgggctctctgtatcatggtgaccatctgtcaagggctatgtaccaacgaatttctaatatcgaggatcttcc
tccactctatacactcaataagcctctcttgtccgggatatcaaacgctgaggcccgccagccagggaaagctcctaacttcagtgttaa
ctggaccgttggtgattctgcgatagaggtcatcaacgccacgacaggtaaggatgagctcggtagagcctcacgcctgtgtaaacac

FIG. 47F gcgttgtattgtagatggatgagagtacatgggaaggtcccatctcacttgctccgaagcaagatcactaagcctaatgtgtatcatgagt
caaaactcgcggctaaagaataccaggcagccaaagctcgacttttacagcttttattaaggcagggctcggggcatgggtcgagaa
gccgaccgagcaggaccaaTACtctctgacggggagcGGTACCATGAAAAAGAAAggttctgttgttattgttggtagaat
tAATttatctggtGACacggcctactcccaacagacgcggggcctaGAAggttgcCAAGAGactagcCAAacaggccggg
acaagaaccaggtcgaaggggaggttcaagtggtttctaccgcaacacaatctttcctggcgaccTCCATCaacggcgtgCTTt
ggactgtctaccatggcgctggcaccagaaccATTgccAGCccaaaaggtccaGTGacccaaatgtacaccaatgtagacA
AGgacctcgtcggctggcaggcgcctCAAgggTCAcgctccttgacaccatgcacctgtggcagctcggacctttacttggtcacg
agacatgctgatgtcattccggtgcgccggcgaggcgacagcaggggaagtctactctcccccaggcccATCtcctacctgaaagg
ctccGCAggtggtccattgctttgccctGCTgggcacgctgtgggcatcttccgggctgctgtgAGTacccggggggtcgcgaagg
cggtggacttcATTcccgttgagtctCTGgaaactaccatgcggtctCCAggatcc *AGCGAGCTGATTAAGGAGAA*
*CATGCACATGAAGCTGTACATGGAGGGCACCGTGGACAACCATCACTTCAAGTGCACATCC*
*GAGGGCGAAGGCAAGCCCTACGAGGGCACCCAGACCATGAGAATCAAGGTGGTCGAGGG*
*CGGCCCTCTCCCCTTCGCCTTCGACATCCTGGCTACTAGCTTCCTCTACGGCAGCAAGACC*
*TTCATCAACCACACCCAGGGCATCCCCGACTTC TTCAAGCAGTCCTTCCCTGAGGGCTTCA*
*CATGGGAGAGAGTCACCACATACGAAGACGGGGGCGTGCTGACCGCTACCCAGGACACCA*
*GCCTCCAGGACGGCTGCCTCATCTACAACGTCAAGATCAGAGGGGTGAACTTCACATCCAA*
*CGGCCCTGTGATGCAGAAGAAAACACTCGGCTGGGAGGCCTTCACCGAGACGCTGTACCC*
*CGCTGACGGCGGCCTGGAAGGCAGAAACGACATGGCCCTGAAGCTCGTGGGCGGGAGCC*
*ATCTGATCGCAAACATCAAGACCACATATA GATCCAAGAAACCCGCTAAGAACCTCAAGAT*
*GCCTGGCGTCTACTATGTGGACTACAGACTGGAAAGAATCAAGGAGGCCAACAACGAGAC*
*CTACGTCGAGCAGCACGAGGTGGCAGTGGCCAGATACTGCGACCTCCCTAGCAAACTGGG*
*GCACAAGCTTAAT*tAAGGGCCCGTTTAAACCCGCTGATCAGCCTCGACTGTGCCTTCTA

FIG. 47F(Cont.)

**SEQ ID NO: 324, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-MCP-nADAR2-DD-*BAD(F22)*-cADAR2(E488Q & R522M)-*BclxL*-*TagBFP***

TAATACGACTCACTATAGGGAGACCCAAGCTGGCTAGGTAAGCTTGGTACCGAGCTCGGATCC accggt
cgccaccatggtgagcaagggcgaggaggataacatggccatcatcaaggagttcatgcgcttcaaggtgcacatggagggctccgtg
aacggccacgagttcgagatcgagggcgagggcgagggccgcccctacgagggcacccagaccgccaagctgaaggtgaccaag
ggtggccccctgcccttcgcctgggacatcctgtcccctcagttcatgtacggctccaaggcctacgtgaagcaccccgccgacatccc
cgactacttgaagctgtccttccccgagggcttcaagtgggagcgcgtgatgaacttcgaggacggcggcgtggtgaccgtgacccag
gactcctccctgcaggacggcgagttcatctacaaggtgaagctgcgcggcaccaacttcccctccgacggccccgtaatgcagaaga
agaccatgggctgggaggcctcctccgagcggatgtaccccgaggacggcgccctgaagggcgagatcaagcagaggctgaagct
gaaggacggcggccactacgacgctgaggtcaagaccacctacaaggccaagaagcccgtgcagctgcccggcgcctacaacgtc
aacatcaagttggacatcacctcccacaacgaggactacaccatcgtggaacagtacgaacgcgccgagggccgccactccaccggc
ggcatggacgagctgTACaaggattacaaggatgacgatgacaaaGGTAGCGGGGCAACTAATTTTAGCTTACTCAA
ACAGGCTGGGGACGTCGAGGAGAATCCAGGCCCTGCATCCGCTGGCTCTGGAGAAGGACGAGG CT
CCTTGCTCACCTGTGGAGATGTCGAAGAGAACCCAGGTCCTGCAACCGGGAATTCCGCGTAGCGCTA
GCTTTGCCAGCGCCACGCGaaACATGAGGATcACCCATGTGCCGCTATGGCAGAAATCGGTACTGGC
TTTCCATTCGACCCCCATTATGTGGAAGTCCTGGGCGAGCGCATGCACTACGTCGATGTTGGT CCG
CGCGATGGCACCCCTGTGCTGTTCCTGCACGGTAACCCGACCTCCTCCTACGTGTGGCGCAACATC
ATCCCGCATGTTGCACCGACCCATCGCTGCATTGCTCCAGACCTGATCGGTATGGGCAAATCCGAC
AAACCAGACCTGGGTTATTTCTTCGACGACCACGTCCGCTTCATGGATGCCTTCATCGAAGCCCTG
GGTCTGGAAGAGGTCGTCCTGGTCATTCACGACTGGGGCTCCGCTCTGGGTTTCCACTGGGCCAA
GCGCAATCCAGAGCGCGTCAAAGGTATTGCA TTTATGGAGTTCATCCGCCCTATCCCGACCTGGGA

FIG. 48A

CGAATGGCCAGAATTTGCCCGCGAGACCTTCCAGGCCTTCCGCACCACCGACGTCGGCCGCAAGC
TGATCATCGATCAGAACGTTTTTATCGAGGGTACGCTGCCGATGGGTGTCGTCCGCCCGCTGACTG
AAGTCGAGATGGACCATTACCGCGAGCCGTTCCTGAATCCTGTTGACCGCGAGCCACTGTGGCGC
TTCCCAAACGAGCTGCCAATCGCCGGTGAGCCAGCGAACATCGTCGCGCTGGTCGAAGAATACAT
GGACTGGCTGCACCAGTCCCCTGTCCCGAAGCTGCTGTTCTGGGGCACCCCAGGCGTTCTGATCC
CACCGGCCGAAGCCGCTCGCCTGGCCAAAAGCCTGCCTAACTGCAAGGCTGTGGACATCGGCCC
GGGTCTGAATCTGCTGCAAGAAGACAACCCGGACCTGATCGGCAGCGAGATCGCGCGCTGGCTGT
CGACGCTCGAGATTTCTGGCACCGGTATGGCATCTATGACTGGAGGCCAACAGATGgGTCCTGCAAC
CGGGAATTCCGCGTAGCGCTAGCTTTGCCAGCGCCACGCGaaACATGAGGATcACCCATGTACTAGT
GCCACAAACTTCTCTCTGCTAAAGCAAGCAGGTGATGTTGAAGAAAACCCAGGGCCTGGAGGGTCCG
AGGGCAGGGGAAGTCTCCTAACATGCGGGGACGTGGAGGAAAATCCCGGCCCATCCGGA*TATCCCT*
*ACGATGTGCCCGATTACGCTATCGATgtgagcaagggcgaAgaAgataacaAggcctctcccagcgacacatgagttacac*
*atctttggctccatcaacggtgtggactttgacatggtgggtcagggcaccggcaatccaaatgatggttatgaggagttaaacctgaagtccaccaag*
*ggtgacctccagttctccccctggattctggtccctcatatcgggtatggcttccatcagtacctgccctaccctgacgggatgtcgcctttccaggccgcc*
*atggtagatggcAGCggataccaagtccatcgcacaatgcagtttgaagatggtgcctcccttactgttaactaccgctacacctacgagggaagcc*
*acatcaaaggagaggcccaggtgaaggggactggtttccctgctgacggtcctgtgatgaccaactcgctgaccgctgcggactggtgcaggtcgaa*
*gaagacttaccccaacgacaaaaccatcatcagtacctttaagtggagttacaccactggaaatggcaagAGAtaccggagcactgcgcggacc*
*acctacacctttgccaagccaatggcggctaactatctgaagaaccagccgatgtacgtgttccgtaagacggagctcaagcactccaagaccgag*
*ctcaacttcaaggagtggcaaaaggcctttaccgatgtgatgGGAatggacGAGCTGTATaag*GCTAGCTAAgcggccgctctagagt
cgacgggccgcggtaacaattgttaactaacttaagctagcaacggtttccctctagcgggatcaattccgccccccccctaacgttactggccgaa
gccgcttggaataaggccggtgtgcgtttgtctatatgttattttccaccatattgccgtcttttggcaatgtgagggcccggaaacctggccctgtcttcttga
cgagcattcctaggggtctttcccctctcgccaaaggaatgcaaggtctgttgaatgtcgtgaaggaagcagttcctctggaagcttcttgaagacaaac
aacgtctgtagcgaccctttgcaggcagcggaaccccccacctggcgacaggtgcctctgcggccaaaagccacgtgtataagatacacctgcaaa
ggcggcacaaccccagtgccacgttgtgagttggatagttgtggaaagagtcaaatggctctcctcaagcgtattcaacaaggggctgaaggatgcc
cagaaggtaccccattgtatgggatctgatctggggcctcggtgcacatgctttacatgtgtttagtcgaggttaaaaaaacgtctaggccccccgaacc
acggggacgtggtttcctttgaaaaacacgataatacc

FIG. 48A(Cont.)

**SEQ ID NO: 324, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-MCP-nADAR2-DD-*BAD(F22)*-cADAR2(E488Q & R522M)-*BclxL*-*TagBFP*** atggcgtccaatttcactcagtttgtgctggttgacaacggcgggaccggggacgttacggtagccccctcaaactttgccaacggtatagcggagtgg
ataagcagcaattctaggagtcaagcatacaaagttacatgcagcgtgcgccaatctagcgctcagaatcgcaagtacaccattaaagtagaggtcc
ccaagggagcctggagaagctatcttaacatggagttgaccataccaatcttcgctaccaactctgactgtgaactcattgtgaaagccatgcaaggtct
gctcaaggatggtaacccaattccgtccgctatcgctgccaactctgggatttacgggggcagtgggagcggtgcaggatctggtagtccagctgggg
gaggagcaccgggtagcggtggggggtctcagctgcacctgccccaggttctcgcagacgccgtatcccgccttgtactgggcaagtttggtgatctta
ctgacaattttcatctcctcatgcgaggcggaaagtactcgcaggcgtcgtcatgacgaccggaactgacgtgaaagacgccaaagtcatctctgtct
ccacgggcacaaagtgcataaacggggagtacatgagcgaccgggggctggcactgaatgattgtcacgctgaaataatatctaggcgatctctgct
tagatttctctacactcaactcgaattgtaccttaacaacaaagatgaccagaaacgcagtatatttcagaaatcagaacgcggcggatttcgacttaag
gaaaacgttcagttccacttgtatatcagcacatccccttgcggtgacgcccgaatcttttccccgcacgagccgatattggaggagcccgcgGCTA
GCGGGTCGGGCACCGGT*GCTCCACCCAATCTCTGGGCAGCGCAGCGCTACGGCCGTGAGCTCAGA*
*AGGATGTCCGATGAGttcGTC*GACagacatcctaataggaaggctagaggccaacttcggacgaagattgaaagtggccagggtact
atcccggtgcggtccaacgctagtattcaaacgtgggacggagtccttcaaggtgaacggctgttgacaatgagctgctcagacaaaatcgcgATGt
ggaatgtagtgggaatccaaggcagcctcttgagcatattcgtagaacccatatatttctcatccattatttgggctctctgtatcatggtgaccatctgtca
agggctatgtaccaacgaatttctaatatcgaggatcttcctccactctatacactcaataagcctctcttgtccgggatatcaaacgctgaggcccgcca
gccagggaaagctcctaacttcagtgttaactggaccgttggtgattctgcgatagaggtcatcaacgccacgacaggtaaggatgagctcggtagag
cctcacgcctgtgtaaacacgcgttgtattgtagatggatgagagtacatgggaaggtcccatctcacttgctccgaagcaagatcactaagcctaatgt
gtatcatgagtcaaaactcgcggctaaagaataccaggcagccaaagctcgacttttacagctttattaaggcagggctcggggcatggtcgaga

FIG. 48A(Cont.)

agccgaccgagcaggaccaattctctctgacggggagcGGAGGTACGGAGAATTTGTATTTTCAGAGCGGCTCGAGTG
GTGGATCAGGGAGCGCCGCTTCA*AGTAACCGGGAGCTGGTGGTTGACTTTCTCTCCTACAAGCTTTC*
*CCAGAAAGGATACAGCTGGAGTCAGTTTAGTGATGTGGAAGAGAACAGGACTGAGGCCCCAGAAGG*
*GACTGAATCGGAGATGGAGACCCCCAGTGCCATCAATGGCAACCCATCCTGGCACCTGGCAGACAG*
*CCCCGCGGTGAATGGAGCCACTGGCCACAGCAGCAGTTTGGATGCCCGGGAGGTGATCCCCATGGC*
*AGCAGTAAAGCAAGCGCTGAGGGAGGCAGGCGACGAGTTTGAACTGCGGTACCGGCGGGCATTCAG*
*TGACCTGACATCCCAGCTCCACATCACCCCAGGGACAGCATATCAGAGCTTTGAACAGGTAGTGAAT*
*GAACTCTTCCGGGATGGGGTAAACTGGGGTCGCATTGTGGCCTTTTTCTCCTTCGGCGGGGCACTGT*
*GCGTGGAAAGCGTAGACAAGGAGATGCAGGTATTGGTGAGTCGGATCGCAGCTTGGATGGCCACTT*
*ACCTGAATGACCACCTAGAGCCTTGGATCCAGGAGAACGGCGGCTGGGATACTTTTGTGGAACTCTA*
*TGGGAACAAT*ggatcc*AGCGAGCTGATTAAGGAGAACATGCACATGAAGCTGTACATGGAGGGCACCGT*
*GGACAACCATCACTTCAAGTGCACATCCGAGGGCGAAGGCAAGCCCTACGAGGGCACCCAGACCAT*
*GAGAATCAAGGTGGTCGAGGGCGGCCCTCTCCCCTTCGCCTTCGACATCCTGGCTACTAGCTTCCTC*
*TACGGCAGCAAGACCTTCATCAACCACACCCAGGGCATCCCCGACTTCTTCAAGCAGTCCTTCCCTG*
*AGGGCTTCACATGGGAGAGAGTCACCACATACGAAGACGGGGGCGTGCTGACCGCTACCCAGGACA*
*CCAGCCTCCAGGACGGCTGCCTCATCTACAACGTCAAGATCAGAGGGGTGAACTTCACATCCAACGG*
*CCCTGTGATGCAGAAGAAAACACTCGGCTGGGAGGCCTTCACCGAGACGCTGTACCCCGCTGACGG*
*CGGCCTGGAAGGCAGAAACGACATGGCCCTGAAGCTCGTGGGCGGGAGCCATCTGATCGCAAACAT*
*CAAGACCACATATAGATCCAAGAAACCCGCTAAGAACCTCAAGATGCCTGGCGTCTACTATGTGGACT*
*ACAGACTGGAAAGAATCAAGGAGGCCAACAACGAGACCTACGTCGAGCAGCACGAGGTGGCAGTGG*
*CCAGATACTGCGACCTCCCTAGCAAACTGGGGCACAAGCTTAAT*tAAGGGCCCGTTTAAACCCGCTGA
TCAGCCTCGACTGTGCCTTCTA

FIG. 48A(Cont.)

**SEQ ID NO: 325, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-MCP-nADAR2-DD-*BAD(F22L)*-cADAR2(E488Q & R522M)-*BclxL*-*TagBFP***

TAATACGACTCACTATAGGGAGACCCAAGCTGGCTAGGTAAGCTTGGTACCGAGCTCGGATCCaccggt
cgccaccatggtgagcaagggcgaggaggataacatggccatcatcaaggagttcatgcgcttcaaggtgcacatggagggctccgtg
aacggccacgagttcgagatcgagggcgagggcgagggccgcccctacgagggcacccagaccgccaagctgaaggtgaccaag
ggtggccccctgcccttcgcctgggacatcctgtcccctcagttcatgtacggctccaaggcctacgtgaagcaccccgccgacatccc
cgactacttgaagctgtccttccccgagggcttcaagtgggagcgcgtgatgaacttcgaggacggcggcgtggtgaccgtgacccag
gactcctccctgcaggacggcgagttcatctacaaggtgaagctgcgcggcaccaacttcccctccgacggccccgtaatgcagaaga
agaccatgggctgggaggcctcctccgagcggatgtaccccgaggacggcgccctgaagggcgagatcaagcagaggctgaagct
gaaggacggcggccactacgacgctgaggtcaagaccacctacaaggccaagaagcccgtgcagctgcccggcgcctacaacgtc
aacatcaagttggacatcacctcccacaacgaggactacaccatcgtggaacagtacgaacgcgccgagggccgccactccaccggc
ggcatggacgagctgTACaaggattacaaggatgacgatgacaaaGGTAGCGGGGCAACTAATTTTAGCTTACTCAA
ACAGGCTGGGGACGTCGAGGAGAATCCAGGCCCTGCATCCGCTGGCTCTGGAGAAGGACGAGGCT
CCTTGCTCACCTGTGGAGATGTCGAAGAGAACCCAGGTCCTGCAACCGGGAATTCCGCGTAGCGCTA
GCTTTGCCAGCGCCACGCGaaACATGAGGATcACCCATGTGCCGCTATGGCAGAAATCGGTACTGGC
TTTCCATTCGACCCCCATTATGTGGAAGTCCTGGGCGAGCGCATGCACTACGTCGATGTTGGTCCG
CGCGATGGCACCCCTGTGCTGTTCCTGCACGGTAACCCGACCTCCTCCTACGTGTGGCGCAACATC
ATCCCGCATGTTGCACCGACCCATCGCTGCATTGCTCCAGACCTGATCGGTATGGGCAAATCCGAC
AAACCAGACCTGGGTTATTTCTTCGACGACCACGTCCGCTTCATGGATGCCTTCATCGAAGCCCTG
GGTCTGGAAGAGGTCGTCCTGGTCATTCACGACTGGGGCTCCGCTCTGGGTTTCCACTGGGCCAA
GCGCAATCCAGAGCGCGTCAAAGGTATTGCATTTATGGAGTTCATCCGCCCTATCCCGACCTGGGA
CGAATGGCCAGAATTTGCCCGCGAGACCTTCCAGGCCTTCCGCACCACCGACGTCGGCCGCAAGC
TGATCATCGATCAGAACGTTTTTATCGAGGGTACGCTGCCGATGGGTGTCGTCCGCCCGCTGACTG

FIG. 48B

AAGTCGAGATGGACCATTACCGCGAGCCGTTCCTGAATCCTGTTGACCGCGAGCCACTGTGGCGC
TTCCCAAACGAGCTGCCAATCGCCGGTGAGCCAGCGAACATCGTCGCGCTGGTCGAAGAATACAT
GGACTGGCTGCACCAGTCCCCTGTCCCGAAGCTGCTGTTCTGGGGCACCCCAGGCGTTCTGATCC
CACCGGCCGAAGCCGCTCGCCTGGCCAAAAGCCTGCCTAACTGCAAGGCTGTGGACATCGGCCC
GGGTCTGAATCTGCTGCAAGAAGACAACCCGGACCTGATCGGCAGCGAGATCGCGCGCTGGCTGT
CGACGCTCGAGATTTCTGGCACCGGTATGGCATCTATGACTGGAGGCCAACAGATGgGTCCTGCAAC
CGGGAATTCCGCGTAGCGCTAGCTTTGCCAGCGCCACGCGaaACATGAGGATcACCCATGTACTAGT
GCCACAAACTTCTCTCTGCTAAAGCAAGCAGGTGATGTTGAAGAAAACCCAGGGCCTGGAGGGTCCG
AGGGCAGGGGAAGTCTCCTAACATGCGGGGACGTGGAGGAAAATCCCGGCCCATCCGGA*TATCCCT*
*ACGATGTGCCCGATTACGCTATCGATgtgagcaagggcgaAgaAgataacaAggcctctctcccagcgacacatgagttacac*
*atctttggctccatcaacggtgtggactttgacatggtgggtcagggcaccggcaatccaaatgatggttatgaggagttaaacctgaagtccaccaag*
*ggtgacctccagttctcccctggattctggtccctcatatcgggtatggcttccatcagtacctgccctaccctgacgggatgtcgcctttccaggccgcc*
*atggtagatggcAGCggataccaagtccatcgcacaatgcagtttgaagatggtgcctcccttactgttaactaccgctacacctacgagggaagcc*
*acatcaaaggagaggcccaggtgaaggggactggtttccctgctgacggtcctgtgatgaccaactcgctgaccgctgcggactggtgcaggtcgaa*
*gaagacttaccccaacgacaaaaccatcatcagtacctttaagtggagttacaccactggaaatggcaagAGAtaccggagcactgcgcggacc*
*acctacacctttgccaagccaatggcggctaactatctgaagaaccagccgatgtacgtgttccgtaagacggagctcaagcactccaagaccgag*
*ctcaacttcaaggagtggcaaaaggcctttaccgatgtgatgGGAatggacGAGCTGTATaag*GCTAGCTAAgcggccgctctagagt
cgacgggccgcggtaacaattgttaactaacttaagctagcaacggtttccctctagcgggatcaattccgcccccccccctaacgttactggccgaa
gccgcttggaataaggccggtgtgcgtttgtctatatgttattttccaccatattgccgtcttttggcaatgtgagggcccggaaacctggccctgtcttcttga
cgagcattcctaggggtctttcccctctcgccaaaggaatgcaaggtctgttgaatgtcgtgaaggaagcagttcctctggaagcttcttgaagacaaac
aacgtctgtagcgaccctttgcaggcagcggaaccccccacctggcgacaggtgcctctgcggccaaaagccacgtgtataagatacacctgcaaa
ggcggcacaaccccagtgccacgttgtgagttggatagttgtggaaagagtcaaatggctctcctcaagcgtattcaacaaggggctgaaggatgcc
cagaaggtaccccattgtatgggatctgatctggggcctcggtgcacatgctttacatgtgtttagtcgaggttaaaaaaacgtctaggccccccgaacc
acggggacgtggttttcctttgaaaaacacgataatacc

FIG. 48B(Cont.)

**SEQ ID NO: 325, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-MCP-nADAR2-DD-*BAD(F22L)*-cADAR2(E488Q & R522M)-*BclxL*-*TagBFP*** atggcgtccaatttcactcagtttgtgctggttgacaacggcgggaccggggacgttacggtagcccctcaaactttgccaacggtatagcggagtgg
ataagcagcaattctaggagtcaagcatacaaagttacatgcagcgtgcgccaatctagcgctcagaatcgcaagtacaccattaaagtagaggtcc
ccaagggagcctggagaagctatcttaacatggagttgaccataccaatcttcgctaccaactctgactgtgaactcattgtgaaagccatgcaaggtct
gctcaaggatggtaacccaattccgtccgctatcgctgccaactctgggatttacgggggcagtgggagcggtgcaggatctggtagtccagctgggg
gaggagcaccgggtagcggtgggggtctcagctgcacctgccccaggttctcgcagacgccgtatcccgccttgtactgggcaagtttggtgatctta
ctgacaattttcatctcctcatgcgaggcggaaagtactcgcaggcgtcgtcatgacgaccggaactgacgtgaaagacgccaaagtcatctctgtct
ccacgggcacaaagtgcataaacggggagtacatgagcgaccgggggctggcactgaatgattgtcacgctgaaataatatctaggcgatctctgct
tagatttctctacactcaactcgaattgtaccttaacaacaaagatgaccagaaacgcagtatatttcagaaatcagaacgcggcggatttcgacttaag
gaaaacgttcagttccacttgtatatcagcacatccccttgcggtgacgcccgaatcttttccccgcacgagccgatattggaggagcccgcgGCTA
GCGGGTCGGGCACCGGT*GCTCCACCCAATCTCTGGGCAGCGCAGCGCTACGGCCGTGAGCTCAGA*
*AGGATGTCCGATGAG* *CTG**GTC*GACagacatcctaataggaaggctagaggccaacttcggacgaagattgaaagtggccagggt
actatcccggtgcggtccaacgctagtattcaaacgtgggacggagtccttcaaggtgaacggctgttgacaatgagctgctcagacaaaatcgcgA
TGtggaatgtagtgggaatccaaggcagcctcttgagcatattcgtagaacccatatatttctcatccattatttgggctctctgtatcatggtgaccatctg
tcaagggctatgtaccaacgaatttctaatatcgaggatcttcctccactctatacactcaataagcctctcttgtccgggatatcaaacgctgaggcccg
ccagccagggaaagctcctaacttcagtgttaactggaccgttggtgattctgcgatagaggtcatcaacgccacgacaggtaaggatgagctcggta
gagcctcacgcctgtgtaaacacgcgttgtattgtagatggatgagagtacatgggaaggtcccatctcacttgctccgaagcaagatcactaagccta
atgtgtatcatgagtcaaaactcgcggctaaagaataccaggcagccaaagctcgacttttacagcttttattaaggcagggctcggggcatgggtcg
agaagccgaccgagcaggaccaattctctctgacggggagcGGAGGTACGGAGAATTTGTATTTTCAGAGCGGCTCGAG
TGGTGGATCAGGGAGCGCCGCTTCA*AGTAACCGGGAGCTGGTGGTTGACTTTCTCTCCTACAAGCTT*
*TCCCAGAAAGGATACAGCTGGAGTCAGTTTAGTGATGTGGAAGAGAACAGGACTGAGGCCCCAGAAG*

FIG. 48B(Cont.)

GGACTGAATCGGAGATGGAGACCCCCAGTGCCATCAATGGCAACCCATCCTGGCACCTGGCAGACA
GCCCCGCGGTGAATGGAGCCACTGGCCACAGCAGCAGTTTGGATGCCCGGGAGGTGATCCCCATG
GCAGCAGTAAAGCAAGCGCTGAGGGAGGCAGGCGACGAGTTTGAACTGCGGTACCGGCGGGCATTC
AGTGACCTGACATCCCAGCTCCACATCACCCCAGGGACAGCATATCAGAGCTTTGAACAGGTAGTGA
ATGAACTCTTCCGGGATGGGGTAAACTGGGGTCGCATTGTGGCCTTTTTCTCCTTCGGCGGGGCACT
GTGCGTGGAAAGCGTAGACAAGGAGATGCAGGTATTGGTGAGTCGGATCGCAGCTTGGATGGCCAC
TTACCTGAATGACCACCTAGAGCCTTGGATCCAGGAGAACGGCGGCTGGGATACTTTTGTGGAACTC
TATGGGAACAATggatccAGCGAGCTGATTAAGGAGAACATGCACATGAAGCTGTACATGGAGGGCACC
GTGGACAACCATCACTTCAAGTGCACATCCGAGGGCGAAGGCAAGCCCTACGAGGGCACCCAGACC
ATGAGAATCAAGGTGGTCGAGGGCGGCCCTCTCCCCTTCGCCTTCGACATCCTGGCTACTAGCTTCC
TCTACGGCAGCAAGACCTTCATCAACCACACCCAGGGCATCCCCGACTTCTTCAAGCAGTCCTTCCC
TGAGGGCTTCACATGGGAGAGAGTCACCACATA CGAAGACGGGGGCGTGCTGACCGCTACCCAGGA
CACCAGCCTCCAGGACGGCTGCCTCATCTACAACGTCAAGATCAGAGGGGTGAACTTCACATCCAAC
GGCCCTGTGATGCAGAAGAAAACACTCGGCTGGGAGGCCTTCACCGAGACGCTGTACCCCGCTGAC
GGCGGCCTGGAAGGCAGAAACGACATGGCCCTGAAGCTCGTGGGCGGGAGCCATCTGATCGCAAAC
ATCAAGACCACATATAGATCCAAGAAACCCGCTAAGAACCTCAAGATGCCTGGCGTCTACTATGTGGA
CTACAGACTGGAAAGAATCAAGGAGGCCAACAACGAGACCTACGTCGAGCAGCACGAGGTGGCAGT
GGCCAGATACTGCGACCTCCCTAGCAAACTGGGGCACAAGCTTAATtAAGGGCCCGTTTAAACCCGC
TGATCAGCCTCGACTGTGCCTTCTA

FIG. 48B(Cont.)

**SEQ ID NO: 326, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-MCP-nADAR2-DD-*BAD(F22V)*-cADAR2(E488Q & R522M)-*BclxL*-*TagBFP***

TAATACGACTCACTATAGGGAGACCCAAGCTGGCTAGGTAAGCTTGGTACCGAGCTCGGATCCaccggt
cgccaccatggtgagcaagggcgaggaggataacatggccatcatcaaggagttcatgcgcttcaaggtgcacatggagggctccgtg
aacggccacgagttcgagatcgagggcgagggcgagggccgcccctacgagggcacccagaccgccaagctgaaggtgaccaag
ggtggccccctgcccttcgcctgggacatcctgtcccctcagttcatgtacggctccaaggcctacgtgaagcaccccgccgacatccc
cgactacttgaagctgtccttccccgagggcttcaagtgggagcgcgtgatgaacttcgaggacggcggcgtggtgaccgtgacccag
gactcctccctgcaggacggcgagttcatctacaaggtgaagctgcgcggcaccaacttcccctccgacggccccgtaatgcagaaga
agaccatgggctgggaggcctcctccgagcggatgtaccccgaggacggcgccctgaagggcgagatcaagcagaggctgaagct
gaaggacggcggccactacgacgctgaggtcaagaccacctacaaggccaagaagcccgtgcagctgcccggcgcctacaacgtc
aacatcaagttggacatcacctcccacaacgaggactacaccatcgtggaacagtacgaacgcgccgagggccgccactccaccggc
ggcatggacgagctgTACaaggattacaaggatgacgatgacaaaGGTAGCGGGGCAACTAATTTTAGCTTACTCAA
ACAGGCTGGGGACGTCGAGGAGAATCCAGGCCCTGCATCCGCTGGCTCTGGAGAAGGACGAGGCT
CCTTGCTCACCTGTGGAGATGTCGAAGAGAACCCAGGTCCTGCAACCGGGAATTCCGCGTAGCGCTA
GCTTTGCCAGCGCCACGCGaaACATGAGGATcACCCATGTGCCGCTATGGCAGAAATCGGTACTGGC
TTTCCATTCGACCCCCATTATGTGGAAGTCCTGGGCGAGCGCATGCACTACGTCGATGTTGGTCCG
CGCGATGGCACCCCTGTGCTGTTCCTGCACGGTAACCCGACCTCCTCCTACGTGTGGCGCAACATC
ATCCCGCATGTTGCACCGACCCATCGCTGCATTGCTCCAGACCTGATCGGTATGGGCAAATCCGAC
AAACCAGACCTGGGTTATTTCTTCGACGACCACGTCCGCTTCATGGATGCCTTCATCGAAGCCCTG
GGTCTGGAAGAGGTCGTCCTGGTCATTCACGACTGGGGCTCCGCTCTGGGTTTCCACTGGGCCAA
GCGCAATCCAGAGCGCGTCAAAGGTATTGCATTTATGGAGTTCATCCGCCCTATCCCGACCTGGGA
CGAATGGCCAGAATTTGCCCGCGAGACCTTCCAGGCCTTCCGCACCACCGACGTCGGCCGCAAGC

FIG. 48C

TGATCATCGATCAGAACGTTTTTATCGAGGGTACGCTGCCGATGGGTGTCGTCCGCCCGCTGACTG
AAGTCGAGATGGACCATTACCGCGAGCCGTTCCTGAATCCTGTTGACCGCGAGCCACTGTGGCGC
TTCCCAAACGAGCTGCCAATCGCCGGTGAGCCAGCGAACATCGTCGCGCTGGTCGAAGAATACAT
GGACTGGCTGCACCAGTCCCCTGTCCCGAAGCTGCTGTTCTGGGGCACCCCAGGCGTTCTGATCC
CACCGGCCGAAGCCGCTCGCCTGGCCAAAAGCCTGCCTAACTGCAAGGCTGTGGACATCGGCCC
GGGTCTGAATCTGCTGCAAGAAGACAACCCGGACCTGATCGGCAGCGAGATCGCGCGCTGGCTGT
CGACGCTCGAGATTTCTGGCACCGGTATGGCATCTATGACTGGAGGCCAACAGATGgGTCCTGCAAC
CGGGAATTCCGCGTAGCGCTAGCTTTGCCAGCGCCACGCGaaACATGAGGATcACCCATGTACTAGT
GCCACAAACTTCTCTCTGCTAAAGCAAGCAGGTGATGTTGAAGAAAACCCAGGGCCTGGAGGGTCCG
AGGGCAGGGGAAGTCTCCTAACATGCGGGGACGTGGAGGAAAATCCCGGCCCATCCGGA*TATCCCT*
*ACGATGTGCCCGATTACGCTATCGATgtgagcaagggcgaAgaAgataacaAggcctctcccagcgacacatgagttacac*
*atctttggctccatcaacggtgtggactttgacatggtgggtcagggcaccggcaatccaaatgatggttatgaggagttaaacctgaagtccaccaag*
*ggtgacctccagttctcccctggattctggtccctcatatcgggtatggcttccatcagtacctgccctaccctgacgggatgtcgcctttccaggccgcc*
*atggtagatggcAGCggataccaagtccatcgcacaatgcagtttgaagatggtgcctcccttactgttaactaccgctacacctacgagggaagcc*
*acatcaaaggagaggcccaggtgaaggggactggtttccctgctgacggtcctgtgatgaccaactcgctgaccgctgcggactggtgcaggtcgaa*
*gaagacttaccccaacgacaaaaccatcatcagtacctttaagtggagttacaccactggaaatggcaagAGAtaccggagcactgcgcggacc*
*acctacacctttgccaagccaatggcggctaactatctgaagaaccagccgatgtacgtgttccgtaagacggagctcaagcactccaagaccgag*
*ctcaacttcaaggagtggcaaaaggcctttaccgatgtgatgGGAatggacGAGCTGTATaag*GCTAGCTAAgcggccgctctagagt
cgacgggccgcggtaacaattgttaactaacttaagctagcaacggtttccctctagcgggatcaattccgccccccccctaacgttactggccgaa
gccgcttggaataaggccggtgtgcgtttgtctatatgttattttccaccatattgccgtcttttggcaatgtgagggcccggaaacctggccctgtcttcttga
cgagcattcctaggggtctttcccctctcgccaaaggaatgcaaggtctgttgaatgtcgtgaaggaagcagttcctctggaagcttcttgaagacaaac
aacgtctgtagcgaccctttgcaggcagcggaaccccccacctggcgacaggtgcctctgcggccaaaagccacgtgtataagatacacctgcaaa
ggcggcacaaccccagtgccacgttgtgagttggatagttgtggaaagagtcaaatggctctcctcaagcgtattcaacaaggggctgaaggatgcc
cagaaggtaccccattgtatgggatctgatctggggcctcggtgcacatgctttacatgtgtttagtcgaggttaaaaaaacgtctaggccccccgaacc
acggggacgtggttttcctttgaaaaacacgataatacc

FIG. 48C(Cont.)

**SEQ ID NO: 326, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-MCP-nADAR2-DD-*BAD(F22V)*-cADAR2(E488Q & R522M)-*BclxL*-*TagBFP*** atggcgtccaatttcactcagtttgtgctggttgacaacggcgggaccggggacgttacggtagccccctcaaactttgccaacggtatagcggagtgg
ataagcagcaattctaggagtcaagcatacaaagttacatgcagcgtgcgccaatctagcgctcagaatcgcaagtacaccattaaagtagaggtcc
ccaagggagcctggagaagctatcttaacatggagttgaccataccaatcttcgctaccaactctgactgtgaactcattgtgaaagccatgcaaggtct
gctcaaggatggtaacccaattccgtccgctatcgctgccaactctgggatttacgggggcagtgggagcggtgcaggatctggtagtccagctgggg
gaggagcaccgggtagcggtgggggtctcagctgcacctgccccaggttctcgcagacgccgtatcccgccttgtactgggcaagtttggtgatctta
ctgacaatttttcatctcctcatgcgaggcggaaagtactcgcaggcgtcgtcatgacgaccggaactgacgtgaaagacgccaaagtcatctctgtct
ccacgggcacaaagtgcataaacggggagtacatgagcgaccgggggctggcactgaatgattgtcacgctgaaataatatctaggcgatctctgct
tagatttctctacactcaactcgaattgtaccttaacaacaaagatgaccagaaacgcagtatatttcagaaatcagaacgcggcggatttcgacttaag
gaaaacgttcagttccacttgtatatcagcacatccccttgcggtgacgcccgaatcttttccccgcacgagccgatattggaggagcccgcgGCTA
GCGGGTCGGGCACCGGT*GCTCCACCCAATCTCTGGGCAGCGCAGCGCTACGGCCGTGAGCTCAGA*
*AGGATGTCCGATGAGGTGGTC*GACagacatcctaataggaaggctagaggccaacttcggacgaagattgaaagtggccagggt
actatcccggtgcggtccaacgctagtattcaaacgtgggacggagtccttcaaggtgaacggctgttgacaatgagctgctcagacaaaatcgcgA
TGtggaatgtagtgggaatccaaggcagcctcttgagcatattcgtagaacccatatatttctcatccattatttgggctctctgtatcatggtgaccatctg
tcaagggctatgtaccaacgaatttctaatatcgaggatcttcctccactctatacactcaataagcctctcttgtccgggatatcaaacgctgaggcccg
ccagccagggaaagctcctaacttcagtgttaactggaccgttggtgattctgcgatagaggtcatcaacgccacgacaggtaaggatgagctcggta
gagcctcacgcctgtgtaaacacgcgttgtattgtagatggatgagagtacatgggaaggtcccatctcacttgctccgaagcaagatcactaagccta
atgtgtatcatgagtcaaaactcgcggctaaagaataccaggcagccaaagctcgacttttacagctttattaaggcagggctcggggcatgggtcg
agaagccgaccgagcaggaccaattctctctgacggggagcGGAGGTACGGAGAATTTGTATTTTCAGAGCGGCTCGAG

FIG. 48C(Cont.)

TGGTGGATCAGGGAGCGCCGCTTCAAGTAACCGGGAGCTGGTGGTTGACTTTCTCTCCTACAAGCTT
TCCCAGAAAGGATACAGCTGGAGTCAGTTTAGTGATGTGGAAGAGAACAGGACTGAGGCCCCAGAAG
GGACTGAATCGGAGATGGAGACCCCCAGTGCCATCAATGGCAACCCATCCTGGCACCTGGCAGACA
GCCCCGCGGTGAATGGAGCCACTGGCCACAGCAGCAGTTTGGATGCCCGGGAGGTGATCCCCATG
GCAGCAGTAAAGCAAGCGCTGAGGGAGGCAGGCGACGAGTTTGAACTGCGGTACCGGCGGGCATTC
AGTGACCTGACATCCCAGCTCCACATCACCCCAGGGACAGCATATCAGAGCTTTGAACAGGTAGTGA
ATGAACTCTTCCGGGATGGGGTAAACTGGGGTCGCATTGTGGCCTTTTTCTCCTTCGGCGGGGCACT
GTGCGTGGAAAGCGTAGACAAGGAGATGCAGGTATTGGTGAGTCGGATCGCAGCTTGGATGGCCAC
TTACCTGAATGACCACCTAGAGCCTTGGATCCAGGAGAACGGCGGCTGGGATACTTTTGTGGAACTC
TATGGGAACAATggatccAGCGAGCTGATTAAGGAGAACATGCACATGAAGCTGTACATGGAGGGCACC
GTGGACAACCATCACTTCAAGTGCACATCCGAGGGCGAAGGCAAGCCCTACGAGGGCACCCAGACC
ATGAGAATCAAGGTGGTCGAGGGCGGCCCTCTCCCCTTCGCCTTCGACATCCTGGCTACTAGCTTCC
TCTACGGCAGCAAGACCTTCATCAACCACACCCAGGGCATCCCCGACTTCTTCAAGCAGTCCTTCCC
TGAGGGCTTCACATGGGAGAGAGTCACCACATA CGAAGACGGGGGCGTGCTGACCGCTACCCAGGA
CACCAGCCTCCAGGACGGCTGCCTCATCTACAACGTCAAGATCAGAGGGGTGAACTTCACATCCAAC
GGCCCTGTGATGCAGAAGAAAACACTCGGCTGGGAGGCCTTCACCGAGACGCTGTACCCCGCTGAC
GGCGGCCTGGAAGGCAGAAACGACATGGCCCTGAAGCTCGTGGGCGGGAGCCATCTGATCGCAAAC
ATCAAGACCACATATAGATCCA AGAAACCCGCTAAGAACCTCAAGATGCCTGGCGTCTACTATGTGGA
CTACAGACTGGAAAGAATCAAGGAGGCCAACAACGAGACCTACGTCGAGCAGCACGAGGTGGCAGT
GGCCAGATACTGCGACCTCCCTAGCAAACTGGGGCACAAGCTTAATtAAGGGCCCGTTTAAACCCGC
TGATCAGCCTCGACTGTGCCTTCTA

FIG. 48C(Cont.)

**SEQ ID NO: 327, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-tdMCP-*BAD*-ADAR2-DD(E488Q & F697Y)-TEVcs-*BclxL*-*TagBFP***

TAATACGACTCACTATAGGGAGACCCAAGCTGGCTAGGTAAGCTTGGTACCGAGCTCGGATCCaccggt
cgccaccatggtgagcaagggcgaggaggataacatggccatcatcaaggagttcatgcgcttcaaggtgcacatggagggctccgtg
aacggccacgagttcgagatcgagggcgagggcgagggccgcccctacgagggcacccagaccgccaagctgaaggtgaccaag
ggtggcccccctgcccttcgcctgggacatcctgtcccctcagttcatgtacggctccaaggcctacgtgaagcaccccgccgacatccc
cgactacttgaagctgtccttccccgagggcttcaagtgggagcgcgtgatgaacttcgaggacggcggcgtggtgaccgtgacccag
gactcctccctgcaggacggcgagttcatctacaaggtgaagctgcgcggcaccaacttcccctccgacggccccgtaatgcagaaga
agaccatgggctgggaggcctcctccgagcggatgtaccccgaggacggcgccctgaagggcgagatcaagcagaggctgaagct
gaaggacggcggccactacgacgctgaggtcaagaccacctacaaggccaagaagcccgtgcagctgcccggcgcctacaacgtc
aacatcaagttggacatcacctcccacaacgaggactacaccatcgtggaacagtacgaacgcgccgagggccgccactccaccggc
ggcatggacgagctgTACaaggattacaaggatgacgatgacaaaGGTAGCGGGGCAACTAATTTTAGCTTACTCAA
ACAGGCTGGGGACGTCGAGGAGAATCCAGGCCCTGCATCCGCTGGCTCTGGAGAAGGACGAGGCT
CCTTGCTCACCTGTGGAGATGTCGAAGAGAACCCAGGTCCTGCAACCGGGAATTCCGCGTAGCGCTA
GCTTTGCCAGCGCCACGCGaaACATGAGGATcACCCATGTGCCGCTATGGCAGAAATCGGTACTGGC
TTTCCATTCGACCCCCATTATGTGGAAGTCCTGGGCGAGCGCATGCACTACGTCGATGTTGGTCCG
CGCGATGGCACCCCTGTGCTGTTCCTGCACGGTAACCCGACCTCCTCCTACGTGTGGCGCAACATC
ATCCCGCATGTTGCACCGACCCATCGCTGCATTGCTCCAGACCTGATCGGTATGGGCAAATCCGAC
AAACCAGACCTGGGTTATTTCTTCGACGACCACGTCCGCTTCATGGATGCCTTCATCGAAGCCCTG
GGTCTGGAAGAGGTCGTCCTGGTCATTCACGACTGGGGCTCCGCTCTGGGTTTCCACTGGGCCAA
GCGCAATCCAGAGCGCGTCAAAGGTATTGCATTTATGGAGTTCATCCGCCCTATCCCGACCTGGGA
CGAATGGCCAGAATTTGCCCGCGAGACCTTCCAGGCCTTCCGCACCACCGACGTCGGCCGCAAGC
TGATCATCGATCAGAACGTTTTTATCGAGGGTACGCTGCCGATGGGTGTCGTCCGCCCGCTGACTG

FIG. 49

AAGTCGAGATGGACCATTACCGCGAGCCGTTCCTGAATCCTGTTGACCGCGAGCCACTGTGGCGC
TTCCCAAACGAGCTGCCAATCGCCGGTGAGCCAGCGAACATCGTCGCGCTGGTCGAAGAATACAT
GGACTGGCTGCACCAGTCCCCTGTCCCGAAGCTGCTGTTCTGGGGCACCCCAGGCGTTCTGATCC
CACCGGCCGAAGCCGCTCGCCTGGCCAAAAGCCTGCCTAACTGCAAGGCTGTGGACATCGGCCC
GGGTCTGAATCTGCTGCAAGAAGACAACCCGGACCTGATCGGCAGCGAGATCGCGCGCTGGCTGT
CGACGCTCGAGATTTCTGGCACCGGTATGGCATCTATGACTGGAGGCCAACAGATGgGTCCTGCAAC
CGGGAATTCCGCGTAGCGCTAGCTTTGCCAGCGCCACGCGaaACATGAGGATcACCCATGTACTAGT
GCCACAAACTTCTCTCTGCTAAAGCAAGCAGGTGATGTTGAAGAAAACCCAGGGCCTGGAGGGTCCG
AGGGCAGGGGAAGTCTCCTAACATGCGGGGACGTGGAGGAAAATCCCGGCCCATCCGGA*TATCCCT*
*ACGATGTGCCCGATTACGCTATCGATgtgagcaagggcgaAgaAgataacaAggcctctcccagcgacacatgagttacac*
*atctttggctccatcaacggtgtggactttgacatggtgggtcagggcaccggcaatccaaatgatggttatgaggagttaaacctgaagtccaccaag*
*ggtgacctccagttctccccctggattctggtccctcatatcgggtatggcttccatcagtacctgccctaccctgacgggatgtcgcctttccaggccgcc*
*atggtagatggcAGCggataccaagtccatcgcacaatgcagtttgaagatggtgcctcccttactgttaactaccgctacacctacgagggaagcc*
*acatcaaaggagaggcccaggtgaaggggactggtttccctgctgacggtcctgtgatgaccaactcgctgaccgctgcggactggtgcaggtcgaa*
*gaagacttaccccaacgacaaaaccatcatcagtacctttaagtggagttacaccactggaaatggcaagAGAtaccggagcactgcgcggacc*
*acctacacctttgccaagccaatggcggctaactatctgaagaaccagccgatgtacgtgttccgtaagacggagctcaagcactccaagaccgag*
*ctcaacttcaaggagtggcaaaaggcctttaccgatgtgatgGGAatggacGAGCTGTATaag*GCTAGCTAAgcggccgctctagagt
cgacgggccgcggtaacaattgttaactaacttaagctagcaacggtttccctctagcgggatcaattccgcccccccccctaacgttactggccgaa
gccgcttggaataaggccggtgtgcgtttgtctatatgttattttccaccatattgccgtcttttggcaatgtgagggcccggaaacctggccctgtcttcttga
cgagcattcctaggggtctttcccctctcgccaaaggaatgcaaggtctgttgaatgtcgtgaaggaagcagttcctctggaagcttcttgaagacaaac
aacgtctgtagcgaccctttgcaggcagcggaaccccccacctggcgacaggtgcctctgcggccaaaagccacgtgtataagatacacctgcaaa
ggcggcacaaccccagtgccacgttgtgagttggatagttgtggaaagagtcaaatggctctcctcaagcgtattcaacaaggggctgaaggatgcc
cagaaggtaccccattgtatgggatctgatctggggcctcggtgcacatgctttacatgtgtttagtcgaggttaaaaaaacgtctaggccccccgaacc
acggggacgtggttttcctttgaaaaacacgataatacc

FIG. 49(Cont.)

**SEQ ID NO: 327, mCherry-FLAG-P2A-T2A-(UAG)2x-MS2(C)-HaloTag-(UAG)2x-MS2(C)-P2A-T2A-*HA-mNeonGreen(M10K)*-EMCV-IRES-tdMCP-*BAD*-ADAR2-DD(E488Q & F697Y)-TEVcs-*BclxL*-*TagBFP*** atgGCGAGCAATTTTACCCAGTTTGTGCTTGTGGACAACGGCGGCACCGGGGACGTGACGGTG GCCC
CCTCCAATTTTGCCAATGGCATTGCAGAATGGATAAGCTCTAACAGCAGGAGCCAGGCATACA AGGT
GACCTGCAGCGTGAGGCAGTCAAGCGCTCAAAACAGGAAGTACACCATTAAGGTCGAAGTGCC CAAA
GGAGCTTGGAGGTCTTACCTGAACATGGAACTGACAATTCCTATCTTCGCGACCAATAGCGACTGTGA
GCTGATCGTGAAGGCCATGCAAGGCCTGCTGAAAGACGGGAATCCCATACCCAGCGCCATCGCCGC
TAACTCAGGCATTTACGCTAATTTCACTCAGTTCGTACTGGTTGACAATGGGGGAACCGGCGACGTTA
CCGTGGCTCCAAGCAACTTCGCTAACGGGATCGCCGAGTGGATCAGCAGTAATTCACGCTCCCAAGC
CTACAAAGTAACCTGCTCTGTACGGCAGAGTTC AGCCCAGAACCGAAAGTATACCATCAAAGTGGAG
GTGCCGAAGGGCGCCTGGCGGAGCTATCTGAATATGGAGCTGACCATCCCCATCTTTGCCACGAACA
GCGATTGCGAGCTCATCGTCAAGGCGATG CAGGGCTTGCTGAAGGATGGCAACCCTATCCCGAGCG
CAATAGCAGCCAACAGCGGCATCTATgggggcagtgggagcggtgcaggatctggtagtccagctgggggaggagcaccgggt
agcggtggggggtctACCGGT*GCTCCACCCAATCTCTGGGCAGCGCAGCGCTACGGCCGTGAGCTCAGAA*
*GGATGTCCGATGAGTTCGTCGATTCCTTCAAAAAG*GCTAGCcagctgcacctgccccaggttctcgcagacgccgtatcc
cgccttgtactgggcaagtttggtgatcttactgacaatttttcatctcctcatgcgaggcggaaagtactcgcaggcgtcgtcatgacgaccggaactga
cgtgaaagacgccaaagtcatctctgtctccacgggcacaaagtgcataaacggggagtacatgagcgaccgggggctggcactgaatgattgtca
cgctgaaataatatctaggcgatctctgcttagatttctctacactcaactcgaattgtaccttaacaacaaagatgaccagaaacgcagtatatttcaga
aatcagaacgcggcggatttcgacttaaggaaaacgttcagttccacttgtatatcagcacatccccttgcggtgacgcccgaatcttttccccgcacga
gccgatattggaggagcccgcggacagacatcctaataggaaggctagaggccaacttcggacgaagattgaaagtggccagggtactatcccgg
tgcggtccaacgctagtattcaaacgtgggacggagtccttcaaggtgaacggctgttgacaatgagctgctcagacaaaatcgcgcgctggaatgta

FIG. 49(Cont.)

gtgggaatccaaggcagcctcttgagcatattcgtagaacccatatattctcatccattatttgggctctctgtatcatggtgaccatctgtcaagggctat
gtaccaacgaatttctaatatcgaggatcttcctccactctatacactcaataagcctctctgtccgggatatcaaacgctgaggcccgccagccaggg
aaagctcctaacttcagtgttaactggaccgttggtgattctgcgatagaggtcatcaacgccacgacaggtaaggatgagctcggtagagcctcacg
cctgtgtaaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgacttttacagcttttattaaggcagggctcggggcatgggtcgagaagccgac
cgagcaggaccaatActctctgacggggagcGGAGGTACGGAGAATTTGTATTTTCAGAGCGC CGCTTCAAGTAAC
CGGGAGCTGGTGGTTGACTTTCTCTCCTACAAGCTTTCCCAGAAAGGATACAGCTGGAGTCAGTTTA
GTGATGTGGAAGAGAACAGGACTGAGGCCCCAGAAGGGACTGAATCGGAGATGGAGACCCCCAGTG
CCATCAATGGCAACCCATCCTGGCACCTGGCAGACAGCCCCGCGGTGAATGGAGCCACTGGCCACA
GCAGCAGTTTGGATGCCCGGGAGGTGATCCCCATGGCAGCAGTAAAGCAAGCGCTGAGGGAGGCAG
GCGACGAGTTTGAACTGCGGTACCGGCGGGCATTCAGTGACCTGACATCCCAGCTCCACATCACCC
CAGGGACAGCATATCAGAGCTTTGAACAGGTAGTGAATGAACTCTTCCGGGATGGGGTAAACTGGGG
TCGCATTGTGGCCTTTTTCTCCTTCGGCGGGGCACTGTGCGTGGAAAGCGTAGACAAGGAGATGCAG
GTATTGGTGAGTCGGATCGCAGCTTGGATGGCCACTTACCTGAATGACCACCTAGAGCCTTGGATCC
AGGAGAACGGCGGCTGGGATACTTTTGTGGAACTCTATGGGAACAATggatccAGCGAGCTGATTAAGG
AGAACATGCACATGAAGCTGTACATGGAGGGCACCGTGGACAACCATCACTTCAAGTGCACAT CCGA
GGGCGAAGGCAAGCCCTACGAGGGCACCCAGACCATGAGAATCAAGGTGGTCGAGGGCGGCCCTC
TCCCCTTCGCCTTCGACATCCTGGCTACTAGCTTCCTCTACGGCAGCAAGACCTTCATCAACC ACACC
CAGGGCATCCCCGACTTCTTCAAGCAGTCCTTCCCTGAGGGCTTCACATGGGAGAGAGTCACCACAT
ACGAAGACGGGGGCGTGCTGACCGCTACCCAGGACACCAGCCTCCAGGACGGCTGCCTCATCTACA
ACGTCAAGATCAGAGGGGTGAACTTCACATCCAACGGCCCTGTGATGCAGAAGAAAACACTCG GCTG
GGAGGCCTTCACCGAGACGCTGTACCCCGCTGACGGCGGCCTGGAAGGCAGAAACGACATGGC CC
TGAAGCTCGTGGGCGGGAGCCATCTGATCGCAAACATCAAGACCACATATAGATCCAAGAAAC CCGC
TAAGAACCTCAAGATGCCTGGCGTCTACTATGTGGACTACAGACTGGAAAGAATCAAGGAGGC CAAC
AACGAGACCTACGTCGAGCAGCACGAGGTGGCAGTGGCCAGATACTGCGACCTCCCTAGCAAA CTG
GGGCACAAGCTTAATtAAGGGCCCGTTTAAACCC GCTGATCAGCCTCGACTGTGCCTTCTA

FIG. 49(Cont.)

**SEQ ID NO: 328, AUG-signal-sequence-HA-*GFP*-GPI**

METDTLLLWVLLLWVPGSTGDGGGGYPYDVPDYAG ELDELVYLLDGPGYDPIHSGGSGGRT*MVSK*
*GEELFTGVVPILVELDGDVNGHKFSVSGEGEGDATYGKLTLKFICTTGKLPVPWPTLVTTLTYGVQCF*
*SRYPDHMKQHDFFKSAMPEGYVQERTIFFKDDGNYKTRAEVKFEGDTLVNRIELKGIDFKEDGNILG*
*HKLEYNYNSHNVYIMADKQKNGIKVNFKIRHNIEDGSVQLADHYQQNTPIGDGPVLLPDNHYLSTQS*
*ALSKDPNEKRDHMVLLEFVTAAGITLGMDEL*YQLENGGISLLVQNTSWMLLLLLSLSLLQALDFISL*

**SEQ ID NO: 329, AUA-signal-sequence-HA-*GFP*-GPI**

IETDTLLLWVLLLWVPGSTGDGGGGYPYDVPDYAGGGSGGRT*M**VSKGEELFTGVVPILVELDGDVN*
*GHKFSVSGEGEGDATYGKLTLKFICTTGKLPVPWPTLVTTLTYGVQCFSRYPDHMKQHDFFKSAMP*
*EGYVQERTIFFKDDGNYKTRAEVKFEGDTLVNRIELKGIDFKEDGNILGHKLEYNYNSHNVYIMADKQ*
*KNGIKVNFKIRHNIEDGSVQLADHYQQNTPIGDGPVLLPDNHYLSTQSALSKDPNEKRDHMVLLEFVT*
*AAGITLGMDEL*YQLENGGISLLVQNTSWMLLLLLSLSLLQALDFISL*

FIG. 50

SEQ ID NO: 330, CD8signal-HA-HaloTag-T2A(G18R)-loop-MS2C-3xFLAG-Gal4VP64-T2A-TagBFP MALPVTALLLPLALLLHAARPYPYDVPDYATG MAEIGTGFPFDPHYVEVLGERMHYVDVGPRDGTPV
LFLHGNPTSSYVWRNIIPHVAPTHRCIAPDLIGMGKSDKPDLGYFFDDHVRFMDAFIEALGLEEVVL
VIHDWGSALGFHWAKRNPERVKGIAFMEFIRPIPTWDEWPEFARETFQAFRTTDVGRKLIIDQNVFI
EGTLPMGVVRPLTEVEMDHYREPFLNPVDREPLWRFPNELPIAGEPANIVALVEEYMDWLHQS PV
PKLLFWGTPGVLIPPAEAARLAKSLPNCKAVDIGPGLNLLQEDNPDLIGSEIARWLSTLEISGGGGS
GEGRGSLLTCGDVEENP(R)PYMRITHVRPRVDYKDHDGDYKDHDIDYKDDDDKGTMKLLSSIEQAC
DICRLKKLKCSKEKPKCAKCLKNNWECRYSPKTKRSPLTRAHLTEVESRLERLEQLFLLIFPREDLDM
ILKMDSLQDIKALLTGLFVQDNVNKDAVTDRLASVETDMPLTLRQHRISATSSSEESSNKGQRQLTVS
AAAGGSGGSGGSDALDDFDLDMLGSDALDDFDLDMLGSDALDDFDLDMLGSDALDDFDLDMLGSM
EGRGSLLTCGDVEENPGPGSSELIKENMHMKLYMEGTVDNHHFKCTSEGEGKPYEGTQTMRIKVVE
GGPLPFAFDILATSFLYGSKTFINHTQGIPDFFKQSFPEGFTWERVTTYEDGGVLTATQDTSLQDGCLI
YNVKIRGVNFTSNGPVMQKKTLGWEAFTETLYPADGGLEGRNDMALKLVGGSHLIANIKTTYRSKKP
AKNLKMPGVYYVDYRLERIKEANNETYVEQHEVAVARYCDLPSKLGHKLN*

FIG. 51

SEQ ID NOs: 331-333, mCherry-FLAG-P2A/T2A-Loop-MS2-P2A/T2A-*HA-mNeonGreen(1-166)-STOPloop*-MS2-*mNeonGreen(174-236)*

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYKDYKDDDDKGSGATNFSLLKQAGDVEENPGPASAGSGEGRGSL
LTCGDVEENPGPATGNSA* R*
LCQRHAKHEDHPCTSATNFSLLKQAGDVEENPGPGGSEGRGSLLTCGDVEENPGPSG*YPYDVPDYAHM*
*VSKGEEDNMASLPATHELHIFGSINGVDFDMVGQGTGNPNDGYEELNLKSTKGDLQFSPWILVPHIGYGF*
*HQYLPYPDGMSPFQAAMVDGSGYQVHRTMQFEDGASLTVNYRYTYEGSHIKGEAQVKGTGFPADGPVM*
*TNSLTAADWCRSKKTYPNDKTIIST* *FK**
*SYTTG*VAPLDTMRITH *GKRYRSTARTTYTFAKPMAANYLKNQPMYVFRKTELKHSKTELNFKEWQKAFTD*
*VMGMDELYKAS**

FIG. 52

**SEQ ID NO: 334, tdMCP-nADAR2-DD(316-468)-*ALFA*-cADAR2-DD(469-700)(E488Q & L699V)-AlfaNb-VHH9-*TagBFP***

MASNFTQFVLVDNGGTGDVTVAPSNFANGIAEWISSNSRSQAYKVTCSVRQSSAQNRKYTIKVEVPKGA
WRSYLNMELTIPIFATNSDCELIVKAMQGLLKDGNPIPSAIAANSGIYANFTQFVLVDNGGTGDVTVAPSNF
ANGIAEWISSNSRSQAYKVTCSVRQSSAQNRKYTIKVEVPKGAWRSYLNMELTIPIFATNSDC ELIVKAMQ
GLLKDGNPIPSAIAANSGIYGGSGSGAGSGSPAGGGAPGSGGGSQLHLPQVLADAVSRLVLGKFGDLTDN
FSSPHARRKVLAGVVMTTGTDVKDAKVISVSTGTKCINGEYMSDRGLALNDCHAEIISRRSLLRFLYTQLEL
YLNNKDDQKRSIFQKSERGGFRLKENVQFHLYISTSPCGDARIFSPHEPILEEPAASP*SRLEEELRRRLTE*P
TGSGAGDRHPNRKARGQLRTKIESGQGTIPVRSNASIQTWDGVLQGERLLTMSCSDKIAMWNVVGIQGSL
LSIFVEPIYFSSIILGSLYHGDHLSRAMYQRISNIEDLPPLYTLNKPLLSGISNAEARQPGKA PNFSVNWTVGD
SAIEVINATTGKDELGRASRLCKHALYCRWMRVHGKVPSHLLRSKITKPNVYHESKLAAKEYQ AAKARLFT
AFIKAGLGAWVEKPTEQDQFSVTGSGGTAEVQLQESGGGLVQPGGSLRLSCTASGVTISALNAMAMGWY
RQAPGERRVMVAAVSERGNAMYRESVQGRFTVTRDFTNKMVSLQMDNLKPEDTAVYYCHVLED RVDSF
HDYWGQGTQVTVSSGAGSGGGGSGTMMDQVQLVESGGALVQPGGSLRLSCAASGFPVNRYSMRWYR
QAPGKEREWVAGMSSAGDRSSYEDSVKGRFTISRDDARNTVYLQMNSLKPEDTAVYYCNVNVG FEYWG
QGTQVTVSSMH*SELIKENMHMKLYMEGTVDNHHFKCTSEGEGKPYEGTQTMRIKVVEGGPLPFAFDILAT*
*SFLYGSKTFINHTQGIPDFFKQSFPEGFTWERVTTYEDGGVLTATQDTSLQDGCLIYNVKIRGVNFTSNGP*
*VMQKKTLGWEAFTETLYPADGGLEGRNDMALKLVGGSHLIANIKTTYRSKKPAKNLKMPGVYYVDYRLERI*
*KEANNETYVEQHEVAVARYCDLPSKLGHKLN**

FIG. 53A

**SEQ ID NO: 335, tdMCP-nADAR2-DD(316-468)-*ALFA*-cADAR2-DD(469-700)(E488Q & L699G)-AlfaNb-VHH9-*TagBFP***

MASNFTQFVLVDNGGTGDVTVAPSNFANGIAEWISSNSRSQAYKVTCSVRQSSAQNRKYTIKVEVPKGA
WRSYLNMELTIPIFATNSDCELIVKAMQGLLKDGNPIPSAIAANSGIYANFTQFVLVDNGGTGDVTVAPSNF
ANGIAEWISSNSRSQAYKVTCSVRQSSAQNRKYTIKVEVPKGAWRSYLNMELTIPIFATNSDC ELIVKAMQ
GLLKDGNPIPSAIAANSGIYGGSGSGAGSGSPAGGGAPGSGGGSQLHLPQVLADAVSRLVLGKFGDLTDN
FSSPHARRKVLAGVVMTTGTDVKDAKVISVSTGTKCINGEYMSDRGLALNDCHAEIISRRSLLRFLYTQLEL
YLNNKDDQKRSIFQKSERGGFRLKENVQFHLYISTSPCGDARIFSPHEPILEEPAASP*SRLEEELRRRLTE*P
TGSGAGDRHPNRKARGQLRTKIESGQGTIPVRSNASIQTWDGVLQGERLLTMSCSDKIAMWNVVGIQGSL
LSIFVEPIYFSSIILGSLYHGDHLSRAMYQRISNIEDLPPLYTLNKPLLSGISNAEARQPGKAPNFSVNWTVGD
SAIEVINATTGKDELGRASRLCKHALYCRWMRVHGKVPSHLLRSKITKPNVYHESKLAAKEYQAAKARLFT
AFIKAGLGAWVEKPTEQDQFSGTGSGGTAEVQLQESGGGLVQPGGSLRLSCTASGVTISALNAMAMGWY
RQAPGERRVMVAAVSERGNAMYRESVQGRFTVTRDFTNKMVSLQMDNLKPEDTAVYYCHVLEDRVDSF
HDYWGQGTQVTVSSGAGSGGGGSGTMMDQVQLVESGGALVQPGGSLRLSCAASGFPVNRYSMRWYR
QAPGKEREWVAGMSSAGDRSSYEDSVKGRFTISRDDARNTVYLQMNSLKPEDTAVYYCNVNVG FEYWG
QGTQVTVSSMH*SELIKENMHMKLYMEGTVDNHHFKCTSEGEGKPYEGTQTMRIKVVEGGPLPFAFDILAT*
*SFLYGSKTFINHTQGIPDFFKQSFPEGFTWERVTTYEDGGVLTATQDTSLQDGCLIYNVKIRGVNFTSNGP*
*VMQKKTLGWEAFTETLYPADGGLEGRNDMALKLVGGSHLIANIKTTYRSKKPAKNLKMPGVYYVDYRLERI*
*KEANNETYVEQHEVAVARYCDLPSKLGHKLN**

FIG. 53A(Cont.)

**SEQ ID NO: 336, tdMCP-nADAR2-DD(316-468)-*ALFA*-cADAR2-DD(469-700)(E488Q & F697Y)-AlfaNb-VHH9-TagBFP**

MASNFTQFVLVDNGGTGDVTVAPSNFANGI AEWISSNSRSQAYKVTCSVRQSSAQNRKYTIKVEVP
KGAWRSYLNMELTIPIFATNSDCELIVKAMQG LLKDGNPIPSAIAANSGIYANFTQFVLVDNGGTGDVT
VAPSNFANGIAEWISSNSRSQAYKVTCSVRQSSAQ NRKYTIKVEVPKGAWRSYLNMELTIPIF ATNSD
CELIVKAMQGLLKDGNPIPSAIAANSGIYGGSGSGAGSGSPAGGGAPGSGGGSQLHLPQVLADAVS
RLVLGKFGDLTDNFSSPHARRKVLAGVVMTTG TDVKDAKVISVSTGTKCINGEYMSDRGLALNDCHA
EIISRRSLLRFLYTQLELYLNNKDDQKRSIFQKSERGGFRLKENVQFHLYISTSPCGDARIFSPHEPILE
EPAASP *SRLEEELRRRLTE*PTGSGAGDRHPNRKARGQLRTKIESGQGTIPVRSNASIQTWDGVLQG
ERLLTMSCSDKIAMWNVVGIQGSLLSIFVEPIYFSSIILGSLYHGDHLSRAMYQRISNIEDLP PLYTLNK
PLLSGISNAEARQPGKAPNFSVNWTVGDSAIEVINATTGKDELGRASRLCKHALYCRWMRVHG KVP
SHLLRSKITKPNVYHESKLAAKEYQAAKARLFTAFIKAGLGAWVEKPTEQDQYSLTGSGGTAEVQLQ
ESGGGLVQPGGSLRLSCTASGVTISALNAMAMGWYRQAPGERRVMVAAVSERGNAMYRESVQGR
FTVTRDFTNKMVSLQMDNLKPEDTAVYYCHVLEDRVDSFHDYWGQGTQVTVSSGAGSGGGGSG T
MMDQVQLVESGGALVQPGGSLRLSCAASGFPV NRYSMRWYRQAPGKEREWVAGMSSAGDRSSY
EDSVKGRFTISRDDARNTVYLQMNSLKPEDTAVYYCNVNVGFEYWGQGTQVTVSSMH *SELIKENMH*
*MKLYMEGTVDNHHFKCTSEGEGKPYEGTQTMRIKVVEGGPLPFAFDILATSFLYGSKTFINHTQGIPD*
*FFKQSFPEGFTWERVTTYEDGGVLTATQDTSLQDGCLIYNVKIRGVNFTSNGPVMQKKTLGWEAFT*
*ETLYPADGGLEGRNDMALKLVGGSHLIANIK TTYRSKKPAKNLKMPGVYYVDYRLERIKEANNETYV*
*EQHEVAVARYCDLPSKLGHKLN* *

FIG. 53B

**SEQ ID NO: 337, tdMCP-nADAR2-DD(316-468)-*ALFA-PE*-cADAR2-DD(469-700)(E488Q & L699V)-AlfaNb-VHH9-*TagBFP***

MASNFTQFVLVDNGGTGDVTVAPSNFANGI AEWISSNSRSQAYKVTCSVRQSSAQNRKYTIKVEVP
KGAWRSYLNMELTIPIFATNSDCELIVKAMQG LLKDGNPIPSAIAANSGIYANFTQFVLVDNG GTGDVT
VAPSNFANGIAEWISSNSRSQAYKVTCSVRQSSAQ NRKYTIKVEVPKGAWRSYLNMELTIPIF ATNSD
CELIVKAMQGLLKDGNPIPSAIAANSGIYGGSGSGAGSGSPAGGGAPGSGGGSQLHLPQVLADAVS
RLVLGKFGDLTDNFSSPHARRKVLAGVVMTTG TDVKDAKVISVSTGTKCINGEYMSDRGLALNDCHA
EIISRRSLLRFLYTQLELYLNNKDDQKRSIFQKSERGGFRLKENVQFHLYISTSPCGDARIFSPHEPILE
EPAASGSGP*GRLEEELRRRLSP*GTGDRHPNRKARGQLRTKIESGQGTIPVRSNASIQTWDGVLQGE
RLLTMSCSDKIAMWNVVGIQGSLLSIFVEPIYFSSIILGSLYHGDHLSRAMYQRISNIEDLPP LYTLNKPL
LSGISNAEARQPGKAPNFSVNWTVGDSAIEVINATTGKDELGRASRLCKHALYCRWMRVHGKV PSH
LLRSKITKPNVYHESKLAAKEYQAAKARLFTA FIKAGLGAWVEKPTEQDQFSVTGSGGTAEVQLQES
GGGLVQPGGSLRLSCTASGVTISALNAMAMG WYRQAPGERRVMVAAVSERGNAMYRESVQGRF T
VTRDFTNKMVSLQMDNLKPEDTAVYYCHVLEDRVDSFHDYWGQGTQVTVSSGAGSGGGGSGTM M
DQVQLVESGGALVQPGGSLRLSCAASGFPV NRYSMRWYRQAPGKEREWVAGMSSAGDRSSYED
SVKGRFTISRDDARNTVYLQMNSLKPEDTAVYYCNVNVGFEYWGQGTQVTVSSMH *SELIKENMHM*
*KLYMEGTVDNHHFKCTSEGEGKPYEGTQTMRIKVVEG GPLPFAFDILATSFLYGSKTFINHTQGIPDF*
*FKQSFPEGFTWERVTTYEDGGVLTATQDTSLQDGCLIYNVKIRGVNFTSNGPVMQKKTLGWEAFTE*
*TLYPADGGLEGRNDMALKLVGGSHLIANIKTTY RSKKPAKNLKMPGVYYVDYRLERIKEANNETYVE*
*QHEVAVARYCDLPSKLGHKLN* *

FIG. 53B(Cont.)

**SEQ ID NO: 338, tdMCP-nADAR2-DD(316-468)-*ALFA*-cADAR2-DD(469-700)(E488Q & L699G)-AlfaNb-VHH9-*TagBFP***

MASNFTQFVLVDNGGTGDVTVAPSNFANGI AEWISSNSRSQAYKVTCSVRQSSAQNRKYTIKVEVP
KGAWRSYLNMELTIPIFATNSDCELIVKAMQG LLKDGNPIPSAIAANSGIYANFTQFVLVDNGGTGDVT
VAPSNFANGIAEWISSNSRSQAYKVTCSVRQSSAQ NRKYTIKVEVPKGAWRSYLNMELTIPIF ATNSD
CELIVKAMQGLLKDGNPIPSAIAANSGIYGGSGSGAGSGSPAGGGAPGSGGGSQLHLPQVLADAVS
RLVLGKFGDLTDNFSSPHARRKVLAGVVMTTG TDVKDAKVISVSTGTKCINGEYMSDRGLALNDCHA
EIISRRSLLRFLYTQLELYLNNKDDQKRSIFQKSERGGFRLKENVQFHLYISTSPCGDARIFSPHEPILE
EPAASGSGP *GRLEEELRRRLSP*GTGDRHPNRKARGQLRTKIESGQGTIPVRSNASIQTWDGVLQGE
RLLTMSCSDKIAMWNVVGIQGSLLSIFVEPIYFSSIILGSLYHGDHLSRAMYQRISNIEDLPP LYTLNKPL
LSGISNAEARQPGKAPNFSVNWTVGDSAIEVINATTGKDELGRASRLCKHALYCRWMRVHGKVPSH
LLRSKITKPNVYHESKLAAKEYQAAKARLFTAFIKAGLGAWVEKPTEQDQFSGTGSGGTAEVQLQES
GGGLVQPGGSLRLSCTASGVTISALNAMAMG WYRQAPGERRVMVAAVSERGNAMYRESVQGRF T
VTRDFTNKMVSLQMDNLKPEDTAVYYCHVLEDRVDSFHDYWGQGTQVTVSSGAGSGGGGSGTM M
DQVQLVESGGALVQPGGSLRLSCAASGFPV NRYSMRWYRQAPGKEREWVAGMSSAGDRSSYED
SVKGRFTISRDDARNTVYLQMNSLKPEDTAVYYCNVNVGFEYWGQGTQVTVSSMH *SELIKENMHM*
*KLYMEGTVDNHHFKCTSEGEGKPYEGTQTMRIKVVEG GPLPFAFDILATSFLYGSKTFINHTQGIPDF*
*FKQSFPEGFTWERVTTYEDGGVLTATQDTSLQDGCLIYNVKIRGVNFTSNGPVMQKKTLGWEAFTE*
*TLYPADGGLEGRNDMALKLVGGSHLIANIKTTY RSKKPAKNLKMPGVYYVDYRLERIKEANNETYVE*
*QHEVAVARYCDLPSKLGHKLN* *

FIG. 53C

**SEQ ID NO: 339, tdMCP-nADAR2-DD(316-468)-*ALFA*-cADAR2-DD(469-700)(E488Q & F697Y)-AlfaNb-VHH9-*TagBFP***

MASNFTQFVLVDNGGTGDVTVAPSNFANGIAEWISSNSRSQAYKVTCSVRQSSAQNRKYTIKVEVP
KGAWRSYLNMELTIPIFATNSDCELIVKAMQGLLKDGNPIPSAIAANSGIYANFTQFVLVDNGGTGDVT
VAPSNFANGIAEWISSNSRSQAYKVTCSVRQSSAQNRKYTIKVEVPKGAWRSYLNMELTIPIFATNSD
CELIVKAMQGLLKDGNPIPSAIAANSGIYGGSGSGAGSGSPAGGGAPGSGGGSQLHLPQVLADAVS
RLVLGKFGDLTDNFSSPHARRKVLAGVVMTTGTDVKDAKVISVSTGTKCINGEYMSDRGLALNDCHA
EIISRRSLLRFLYTQLELYLNNKDDQKRSIFQKSERGGFRLKENVQFHLYISTSPCGDARIFSPHEPILE
EPAASGSGP*GRLEEELRRRLSP*GTGDRHPNRKARGQLRTKIESGQGTIPVRSNASIQTWDGVLQGE
RLLTMSCSDKIAMWNVVGIQGSLLSIFVEPIYFSSIILGSLYHGDHLSRAMYQRISNIEDLPPLYTLNKPL
LSGISNAEARQPGKAPNFSVNWTVGDSAIEVINATTGKDELGRASRLCKHALYCRWMRVHGKVPSH
LLRSKITKPNVYHESKLAAKEYQAAKARLFTAFIKAGLGAWVEKPTEQDQYSLTGSGGTAEVQLQES
GGGLVQPGGSLRLSCTASGVTISALNAMAMGWYRQAPGERRVMVAAVSERGNAMYRESVQGRFT
VTRDFTNKMVSLQMDNLKPEDTAVYYCHVLEDRVDSFHDYWGQGTQVTVSSGAGSGGGGSGTMM
DQVQLVESGGALVQPGGSLRLSCAASGFPVNRYSMRWYRQAPGKEREWVAGMSSAGDRSSYED
SVKGRFTISRDDARNTVYLQMNSLKPEDTAVYYCNVNVGFEYWGQGTQVTVSSMH*SELIKENMHM*
*KLYMEGTVDNHHFKCTSEGEGKPYEGTQTMRIKVVEGGPLPFAFDILATSFLYGSKTFINHTQGIPDF*
*FKQSFPEGFTWERVTTYEDGGVLTATQDTSLQDGCLIYNVKIRGVNFTSNGPVMQKKTLGWEAFTE*
*TLYPADGGLEGRNDMALKLVGGSHLIANIKTTYRSKKPAKNLKMPGVYYVDYRLERIKEANNETYVE*
*QHEVAVARYCDLPSKLGHKLN* *

FIG. 53C(Cont.)

**SEQ ID NO: 340, *EGFP(R96M)***

*MVSKGEELFTGVVPILVELDGDVNGHKFSVSGEGEGDATYGKLTLKFICTTGKLPVPWPTLVTT*
*LTYGVQCFSRYPDHMKQHDFFKSAMPEGYVQEMTIFFKDDGNYKTRAEVKFEGDTLVNRIELK*
*GIDFKEDGNILGHKLEYNYNSHNVYIMADKQKNGIKVNFKIRHNIEDGSVQLADHYQQNTPIGDG*
*PVLLPDNHYLSTQSALSKDPNEKRDHMVLLEFVTAAGITLGMDELYK*GS*

SEQ ID NO: 341, EGFP(R96M)-ALFA

M*VSKGEELFTGVVPILVELDGDVNGHKFSVSGEGEGDATYGKLTLKFICTTGKLPVPWPTLVTT*
*LTYGVQCFSRYPDHMKQHDFFKSAMPEGYVQEMTIFFKDDGNYKTRAEVKFEGDTLVNRIELK*
*GIDFKEDGNILGHKLEYNYNSHNVYIMADKQKNGIKVNFKIRHNIEDGSVQLADHYQQNTPIGDG*
*PVLLPDNHYLSTQSALSKDPNEKRDHMVLLEFVTAAGITLGMDELYK*GSRLEEELRRRLTE*

FIG. 53D

**SEQ ID NO: 342, MCP-*BAD*-nADAR2-DD-*AlfaPE*-cADAR2-DD(E488Q & F697Y)-AlfaNb-*Bcl-xL-mTagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYGGSGSGAGS GS
PAGGGAPGSGGGSTG*APPNLWAAQRYGRELRRMSDEFVDSFKKAS*QLHLPQVLADAVSRLV
LGKFGDLTDNFSSPHARRKVLAGVVMTTGTDVKDAKVISVSTGTKCINGEYMSDRGLALNDCH
AEIISRRSLLRFLYTQLELYLNNKDDQKRSIFQKSERGGFRLKENVQFHLYISTSPCGDARIF SPH
EPILEEPAASGSGP*GRLEEELRRRLSP*GTGDRHPNRKARGQLRTKIESGQGTIPVRSNASIQTW
DGVLQGERLLTMSCSDKIARWNVVGIQGSLLSIFVEPIYFSSIILGSLYHGDHLSRAMYQRISNIE
DLPPLYTLNKPLLSGISNAEARQPGKAPNFSVNWTVGDSAIEVINATTGKDELGRASRLCKHALY
CRWMRVHGKVPSHLLRSKITKPNVYHESKLAAKEYQAAKARLFTAFIKAGLGAWVEKPTEQDQ
YSLTGSGGTAEVQLQESGGGLVQPGGSLRLSCTASGVTISALNAMAMGWYRQAPGERRVMV
AAVSERGNAMYRESVQGRFTVTRDFTNKMVSLQMDNLKPEDTAVYYCHVLEDRVDSFHDYW
GQGTQVTVSSGAGSGASSNRELVVDFLSYKLSQKGYSWSQFSDVEENRTEAPEGTESEMET
PSAINGNPSWHLADSPAVNGATGHSSSLDAREVIPMAAVKQALREAGDEFELRYRRAFSDLT
SQLHITPGTAYQSFEQVVNELFRDGVNWGRIVAFFSFGGALCVESVDKEMQVLVSRIAAWMA
TYLNDHLEPWIQENGGWDTFVELYGNNGS*SELIKENMHMKLYMEGTVDNHHFKCTSEGEGKP*
*YEGTQTMRIKVVEGGPLPFAFDILATSFLYGSKTFINHTQGIPDFFKQSFPEGFTWERVTTYEDG*
*GVLTATQDTSLQDGCLIYNVKIRGVNFTSNGPVMQKKTLGWEAFTETLYPADGGLEGRNDMAL*
*KLVGGSHLIANIKTTYRSKKPAKNLKMPGVYYVDYRLERIKEANNETYVEQHEVAVARYCDLPS*
*KLGHKLN**

FIG. 54

**SEQ ID NO: 343, tdMCP-nADAR2-DD-*NS3PepHI*-cADAR2-DD(E488Q)-*TagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYANFTQFVLVDNG
GTGDVTVAPSNFANGIAEWISSNSRSQAYKVTCSVRQSSAQNRKYTIKVEVPKGAWRSYLNME
LTIPIFATNSDCELIVKAMQGLLKDGNPIPSAIAANSGIYGGSGSGAGSGSPAGGGAPGSGGG S
QLHLPQVLADAVSRLVLGKFGDLTDNFSSPHARRKVLAGVVMTTGTDVKDAKVISVSTGTKCI N
GEYMSDRGLALNDCHAEIISRRSLLRFLYTQLELYLNNKDDQKRSIFQKSERGGFRLKENVQFH
LYISTSPCGDARIFSPHEPILEEPASSG *GELDELVYLLDGPGYDPIHCDVVTRGGSHLFNF*DRHP
NRKARGQLRTKIESGQGTIPVRSNASIQTWDGVLQGERLLTMSCSDKIARWNVVGIQGSLLSIFV
EPIYFSSIILGSLYHGDHLSRAMYQRISNIEDLPPLYTLNKPLLSGISNAEARQPGKAPNFSVNWT
VGDSAIEVINATTGKDELGRASRLCKHALYCRWMRVHGKVPSHLLRSKITKPNVYHESKLAAKE
YQAAKARLFTAFIKAGLGAWVEKPTEQDQFSLTGSGS *SELIKENMHMKLYMEGTVDNHHFKCT*
*SEGEGKPYEGTQTMRIKVVEGGPLPFAFDILATSFLYGSKTFINHTQGIPDFFKQSFPEGFTWER*
*VTTYEDGGVLTATQDTSLQDGCLIYNVKIRGVNFTSNGPVMQKKTLGWEAFTETLYPADGGLE*
*GRNDMALKLVGGSHLIANIKTTYRSKKPAKNLKMPGVYYVDYRLERIKEANNETYVEQHEVAVA*
*RYCDLPSKLGHKLN**

FIG. 55A

**SEQ ID NO: 344, tdMCP-nADAR2-DD-*NS3PepHI*-cADAR2-DD(E488Q)-NS3(1B)-*TagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYANFTQFVLVDNG
GTGDVTVAPSNFANGIAEWISSNSRSQAYKVTCSVRQSSAQNRKYTIKVEVPKGAWRSYLNME
LTIPIFATNSDCELIVKAMQGLLKDGNPIPSAIAANSGIYGGSGSGAGSGSPAGGGAPGSGGG S
QLHLPQVLADAVSRLVLGKFGDLTDNFSSPHARRKVLAGVVMTTGTDVKDAKVISVSTGTKCI N
GEYMSDRGLALNDCHAEIISRRSLLRFLYTQLELYLNNKDDQKRSIFQKSERGGFRLKENVQFH
LYISTSPCGDARIFSPHEPILEEPASSG *GELDELVYLLDGPGYDPIHCDVVTRGGSHLFNF*DRHP
NRKARGQLRTKIESGQGTIPVRSNASIQTWDGVLQGERLLTMSCSDKIARWNVVGIQGSLLSIFV
EPIYFSSIILGSLYHGDHLSRAMYQRISNIEDLPPLYTLNKPLLSGISNAEARQPGKAPNFSVNWT
VGDSAIEVINATTGKDELGRASRLCKHALYCRWMRVHGKVPSHLLRSKITKPNVYHESKLAAKE
YQAAKARLFTAFIKAGLGAWVEKPTEQDQFSLTGSAAGGSGGSAAAQGSVVIVGRIILSGSGSIT
AYSQQTRGLLGCIITSLTGRDKNQVEGEVQVVSTATQSFLATCVNGVCWTVYHGAGSKTLAGP
KGPITQMYTNVDQDLVGWQAPPGARSLTPCTCGSSDLYLVTRHADVIPVRRRGDSRGSLLSPR
PVSYLKGSSGGPLLCPSGHAVGIFRAAVCTRGVAKAVDFVPVESMETTMRSESGSGTM*SELIK*
*ENMHMKLYMEGTVDNHHFKCTSEGEGKPYEGTQTMRIKVVEGGPLPFAFDILATSFLYGSKTFI*
*NHTQGIPDFFKQSFPEGFTWERVTTYEDGGVLTATQDTSLQDGCLIYNVKIRGVNFTSNGPVM*
*QKKTLGWEAFTETLYPADGGLEGRNDMALKLVGGSHLIANIKTTYRSKKPAKNLKMPGVYYVD*
*YRLERIKEANNETYVEQHEVAVARYCDLPSKLGHKLN**

FIG. 55A(Cont.)

**SEQ ID NO: 345, tdMCP-nADAR2-DD-*NS3PepHI*-cADAR2-DD(E488Q, K690R, & L699V)-NS3(1B)-*TagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYANFTQFVLVDNG
GTGDVTVAPSNFANGIAEWISSNSRSQAYKVTCSVRQSSAQNRKYTIKVEVPKGAWRSYLNME
LTIPIFATNSDCELIVKAMQGLLKDGNPIPSAIAANSGIYGGSGSGAGSGSPAGGGAPGSGGG S
QLHLPQVLADAVSRLVLGKFGDLTDNFSSPHARRKVLAGVVMTTGTDVKDAKVISVSTGTKCI N
GEYMSDRGLALNDCHAEIISRRSLLRFLYTQLELYLNNKDDQKRSIFQKSERGGFRLKENVQFH
LYISTSPCGDARIFSPHEPILEEPASSG *GELDELVYLLDGPGYDPIHCDVVTRGGSHLFNF*DRHP
NRKARGQLRTKIESGQGTIPVRSNASIQTWDGVLQGERLLTMSCSDKIARWNVVGIQGSLLSIFV
EPIYFSSIILGSLYHGDHLSRAMYQRISNIEDLPPLYTLNKPLLSGISNAEARQPGKAPNFSV NWT
VGDSAIEVINATTGKDELGRASRLCKHALYCRWMRVHGKVPSHLLRSKITKPNVYHESKLAAKE
YQAAKARLFTAFIKAGLGAWVERPTEQDQFSVTGSAAGGSGGSAAAQGSVVIVGRIILSGSGSI
TAYSQQTRGLLGCIITSLTGRDKNQVEGEVQVVSTATQSFLATCVNGVCWTVYHGAGSKTLAG
PKGPITQMYTNVDQDLVGWQAPPGARSLTPCTCGSSDLYLVTRHADVIPVRRRGDSRGSLLSP
RPVSYLKGSSGGPLLCPSGHAVGIFRAAVCTRGVAKAVDF VPVESMETTMRSESGSGTM*SELI*
*KENMHMKLYMEGTVDNHHFKCTSEGEGKPYEGTQTMRIKVVEGGPLPFAFDILATSFLYGSKT*
*FINHTQGIPDFFKQSFPEGFTWERVTTYEDGGVLTATQDTSLQDGCLIYNVKIRGVNFTSNGPV*
*MQKKTLGWEAFTETLYPADGGLEGRNDMALKLVGGSHLIANIKTTYRSKKPAKNLKMPGVYYV*
*DYRLERIKEANNETYVEQHEVAVARYCDLPSKLGHKLN* *

FIG. 55B

**SEQ ID NO: 346, MCP-nADAR2-DD-*5A/5B*-cADAR2-DD(E488Q)-solNS3(1B)-*TagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYGGSGSGAGS GS
PAGGGAPGSGGGSQLHLPQVLADAVSRLVLGKFGDLTDNFSSPHARRKVLAGVVMTTGTDVK
DAKVISVSTGTKCINGEYMSDRGLALNDCHAEIISRRSLLRFLYTQLELYLNNKDDQKRSIFQKSE
RGGFRLKENVQFHLYISTSPCGDARIFSPHEPILEEPAASG*EDVVCCHSIY*GTGDRHPNRKARG
QLRTKIESGQGTIPVRSNASIQTWDGVLQGERLLTMSCSDKIARWNVVGIQGSLLSIFVEPIYFSS
IILGSLYHGDHLSRAMYQRISNIEDLPPLYTLNKPLLSGISNAEARQPGKAPNFSVNWTVGDSAIE
VINATTGKDELGRASRLCKHALYCRWMRVHGKVPSHLLRSKITKPNVYHESKLAAKEYQAAKA
RLFTAFIKAGLGAWVEKPTEQDQFSLTGSGTMKKKGSVVIVGRINLSGDTAYSQQTRGLEGCQ
ETSQTGRDKNQVEGEVQVVSTATQSFLATSINGVLWTVYHGAGTRTIASPKGPVTQMYTNVDK
DLVGWQAPQGSRSLTPCTCGSSDLYLVTRHADVIPVRRRGDSRGSLLSPRPISYLKGSSGGPL
LCPAGHAVGIFRAAVSTRGVAKAVDFIPVESLETTMRSPGS *SELIKENMHMKLYMEGTVDNHHF*
*KCTSEGEGKPYEGTQTMRIKVVEGGPLPFAFDILATSFLYGSKTFINHTQGIPDFFKQSFPEGFT*
*WERVTTYEDGGVLTATQDTSLQDGCLIYNVKIRGVNFTSNGPVMQKKTLGWEAFTETLYPADG*
*GLEGRNDMALKLVGGSHLIANIKTTYRSKKPAKNLKMPGVYYVDYRLERIKEANNETYVEQHEV*
*AVARYCDLPSKLGHKLN**

FIG. 56A

**SEQ ID NO: 347, MCP-nADAR2-DD-*5A/5B*-cADAR2-DD(E488Q)-soldNS3(1B)(S139A)-TagBFP**

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYGGSGSGAGS GS
PAGGGAPGSGGGSQLHLPQVLADAVSRLVLGKFGDLTDNFSSPHARRKVLAGVVMTTGTDVK
DAKVISVSTGTKCINGEYMSDRGLALNDCHAEIISRRSLLRFLYTQLELYLNNKDDQKRSIFQKSE
RGGFRLKENVQFHLYISTSPCGDARIFSPHEPILEEPAASG*EDVVCCHSIY*GTGDRHPNRKARG
QLRTKIESGQGTIPVRSNASIQTWDGVLQGERLLTMSCSDKIARWNVVGIQGSLLSIFVEPIY FSS
IILGSLYHGDHLSRAMYQRISNIEDLPPLYTLNKPLLSGISNAEARQPGKAPNFSVNWTVGDS AIE
VINATTGKDELGRASRLCKHALYCRWMRVHGKVPSHLLRSKITKPNVYHESKLAAKEYQAAKA
RLFTAFIKAGLGAWVEKPTEQDQFSLTGSGTMKKKGSVVIVGRINLSGD TAYSQQTRGLEGCQ
ETSQTGRDKNQVEGEVQVVSTATQSFLATSINGVLWTVYHGAGTRTIASPKGPVTQMYTNVDK
DLVGWQAPQGSRSLTPCTCGSSDLYLVTR HADVIPVRRRGDSRGSLLSPRPISYLKGSAGGPL
LCPAGHAVGIFRAAVSTRGVAKAVDFIPVESLETTMRSPGS *SELIKENMHMKLYMEGTVDNHHF*
*KCTSEGEGKPYEGTQTMRIKVVEGGPLPFAFDILATSFLYGSKTFINHTQGIPDFFKQSFPEGFT*
*WERVTTYEDGGVLTATQDTSLQDGCLIYNVKIRGVNFTSNGPVMQKKTLGWEAFTETLYPADG*
*GLEGRNDMALKLVGGSHLIANIKTTYRSKKPAKNLKMPGVYYVD YRLERIKEANNETYVEQHEV*
*AVARYCDLPSKLGHKLN**

FIG. 56A(Cont.)

**SEQ ID NO: 348, MCP-nADAR2-DD-*5A/5B*-cADAR2-DD(E488Q & L699G)-solNS3(1B)-*TagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYGGSGSGAGS GS
PAGGGAPGSGGGS*QLHLPQVLADAVSRLVLGKFGDLTDNFSSPHARRKVLAGVVMTTGTDVK*
*DAKVISVSTGTKCINGEYMSDRGLALNDCHAEIISRRSLLRFLYTQLELYLNNKDDQKRSIFQKSE*
*RGGFRLKENVQFHLYISTSPCGDARIFSPHEPILEEPA*ASG*EDVVCCHSIY*GTGDRHPNRKARG
QLRTKIESGQGTIPVRSNASIQTWDGVLQGERLLTMSCSDKIARWNVVGIQGSLLSIFVEPIY FSS
IILGSLYHGDHLSRAMYQRISNIEDLPPLYTLNKPLLSGISNAEARQPGKAPNFSVNWTVGDS AIE
VINATTGKDELGRASRLCKHALYCRWMRVHGKVPSHLLRSKITKPNVYHESKLAAKEYQAAKA
RLFTAFIKAGLGAWVEKPTEQDQFSGTGSGTMKKKGSVVIVGRINLSGDTAYSQQTRGLEGCQ
ETSQTGRDKNQVEGEVQVVSTATQSFLATSINGVLWTVYHGAGTRTIASPKGPVTQMYTNVDK
DLVGWQAPQGSRSLTPCTCGSSDLYLVTRHADV IPVRRRGDSRGSLLSPRPISYLKGSSGGPL
LCPAGHAVGIFRAAVSTRGVAKAVDFIPVESLETTMRSPGS *SELIKENMHMKLYMEGTVDNHHF*
*KCTSEGEGKPYEGTQTMRIKVVEGGPLPFAFDILATSFLYGSKTFINHTQGIPDFFKQSFPEGFT*
*WERVTTYEDGGVLTATQDTSLQDGCLIYNVKIRGVNFTSNGPVMQKKTLGWEAFTETLYPADG*
*GLEGRNDMALKLVGGSHLIANIKTTYRSKKPAKNLKMPGVYYVDYRLERIKEANNETYVEQHEV*
*AVARYCDLPSKLGHKLN**

FIG. 56B

**SEQ ID NO: 349, MCP-nADAR2-DD-*5A/5B*-cADAR2-DD(E488Q & L699G)-soldNS3(1B)(S139A)-*TagBFP***

MASNFTQFVLVDNGGTGDVTVAPSNFANGIAEWISSNSRSQAYKVTCSVRQSSAQNRKYTIKV
EVPKGAWRSYLNMELTIPIFATNSDCELIVKAMQGLLKDGNPIPSAIAANSGIYGGSGSGAGS GS
PAGGGAPGSGGGSQLHLPQVLADAVSRLVLGKFGDLTDNFSSPHARRKVLAGVVMTTGTDVK
DAKVISVSTGTKCINGEYMSDRGLALNDCHAEIISRRSLLRFLYTQLELYLNNKDDQKRSIFQKSE
RGGFRLKENVQFHLYISTSPCGDARIFSPHEPILEEPAASG*EDVVCCHSIY*GTGDRHPNRKARG
QLRTKIESGQGTIPVRSNASIQTWDGVLQGERLLTMSCSDKIARWNVVGIQGSLLSIFVEPIYFSS
IILGSLYHGDHLSRAMYQRISNIEDLPPLYTLNKPLLSGISNAEARQPGKAPNFSVNWTVGDSAIE
VINATTGKDELGRASRLCKHALYCRWMRVHGKVPSHLLRSKITKPNVYHESKLAAKEYQAAKA
RLFTAFIKAGLGAWVEKPTEQDQFSGTGSGTMKKKGSVVIVGRINLSGDTAYSQQTRGLEGCQ
ETSQTGRDKNQVEGEVQVVSTATQSFLATSINGVLWTVYHGAGTRTIASPKGPVTQMYTNVDK
DLVGWQAPQGSRSLTPCTCGSSDLYLVTR HADVIPVRRRGDSRGSLLSPRPISYLKGSAGGPL
LCPAGHAVGIFRAAVSTRGVAKAVDFIPVESLETTMRSPGS *SELIKENMHMKLYMEGTVDNHHF*
*KCTSEGEGKPYEGTQTMRIKVVEGGPLPFAFDILATSFLYGSKTFINHTQGIPDFFKQSFPEGFT*
*WERVTTYEDGGVLTATQDTSLQDGCLIYNVKIRGVNFTSNGPVMQKKTLGWEAFTETLYPADG*
*GLEGRNDMALKLVGGSHLIANIKTTYRSKKPAKNLKMPGVYYVDYRLERIKEANNETYVEQHEV*
*AVARYCDLPSKLGHKLN**

FIG. 56B(Cont.)

**SEQ ID NO: 350, MCP-nADAR2-DD-*5A/5B*-cADAR2-DD(E488Q & F697Y)-solNS3(1B)-*TagBFP***

MASNFTQFVLVDNGGTGDVTVAPSNFANGIAEWISSNSRSQAYKVTCSVRQSSAQNRK
YTIKVEVPKGAWRSYLNMELTIPIFATNSDCELIVKAMQGLLKDGNPIPSAIAANSGIYGG
SGSGAGSGSPAGGGAPGSGGGSQLHLPQVLADAVSRLVLGKFGDLTDNFSSPHARRK
VLAGVVMTTGTDVKDAKVISVSTGTKCINGEYMSDRGLALNDCHAEIISRRSLLRFLYTQ
LELYLNNKDDQKRSIFQKSERGGFRLKENVQFHLYISTSPCGDARIFSPHEPILEEPAAS
G*EDVVCCHSIY*GTGDRHPNRKARGQLRTKIESGQGTIPVRSNASIQTWDGVLQGERLL
TMSCSDKIARWNVVGIQGSLLSIFVEPIYFSSIILGSLYHGDHLSRAMYQRISNIEDLPPLY
TLNKPLLSGISNAEARQPGKAPNFSVNWTVGDSAIEVINATTGKDELGRASRLCKHALY
CRWMRVHGKVPSHLLRSKITKPNVYHESKLAAKEYQAAKARLFTAFIKAGLGAWVEKPT
EQDQYSLTGSGTMKKKGSVVIVGRINLSGDTAYSQQTRGLEGCQETSQTGRDKNQVE
GEVQVVSTATQSFLATSINGVLWTVYHGAGTRTIASPKGPVTQMYTNVDKDLVGWQAP
QGSRSLTPCTCGSSDLYLVTRHADVIPVRRRGDSRGSLLSPRPISYLKGSSGGPLLCPA
GHAVGIFRAAVSTRGVAKAVDFIPVESLETTMRSPGS*SELIKENMHMKLYMEGTVDNHH*
*FKCTSEGEGKPYEGTQTMRIKVVEGGPLPFAFDILATSFLYGSKTFINHTQGIPDFFKQS*
*FPEGFTWERVTTYEDGGVLTATQDTSLQDGCLIYNVKIRGVNFTSNGPVMQKKTLGWE*
*AFTETLYPADGGLEGRNDMALKLVGGSHLIANIKTTYRSKKPAKNLKMPGVYYVDYRLE*
*RIKEANNETYVEQHEVAVARYCDLPSKLGHKLN**

FIG. 56C

**SEQ ID NO: 351, MCP-nADAR2-DD-*5A/5B*-cADAR2-DD(E488Q & F697Y)-soldNS3(1B)(S139A)-*TagBFP***

MASNFTQFVLVDNGGTGDVTVAPSNFANGIAEWISSNSRSQAYKVTCSVRQSSAQNRK
YTIKVEVPKGAWRSYLNMELTIPIFATNSDCELIVKAMQGLLKDGNPIPSAIAANSGIYGG
SGSGAGSGSPAGGGAPGSGGGSQLHLPQVLADAVSRLVLGKFGDLTDNFSSPHARRK
VLAGVVMTTGTDVKDAKVISVSTGTKCINGEYMSDRGLALNDCHAEIISRRSLLRFLYTQ
LELYLNNKDDQKRSIFQKSERGGFRLKENVQFHLYISTSPCGDARIFSPHEPILEEPAAS
G*EDVVCCHSIY*GTGDRHPNRKARGQLRTKIESGQGTIPVRSNASIQTWDGVLQGERLL
TMSCSDKIARWNVVGIQGSLLSIFVEPIYFSSIILGSLYHGDHLSRAMYQRISNIEDLPPLY
TLNKPLLSGISNAEARQPGKAPNFSVNWTVGDSAIEVINATTGKDELGRASRLCKHALY
CRWMRVHGKVPSHLLRSKITKPNVYHESKLAAKEYQAAKARLFTAFIKAGLGAWVEKPT
EQDQYSLTGSGTMKKKGSVVIVGRINLSGDTAYSQQTRGLEGCQETSQTGRDKNQVE
GEVQVVSTATQSFLATSINGVLWTVYHGAGTRTIASPKGPVTQMYTNVDKDLVGWQAP
QGSRSLTPCTCGSSDLYLVTRHADVIPVRRRGDSRGSLLSPRPISYLKGSAGGPLLCPA
GHAVGIFRAAVSTRGVAKAVDFIPVESLETTMRSPGS*SELIKENMHMKLYMEGTVDNHH*
*FKCTSEGEGKPYEGTQTMRIKVVEGGPLPFAFDILATSFLYGSKTFINHTQGIPDFFKQS*
*FPEGFTWERVTTYEDGGVLTATQDTSLQDGCLIYNVKIRGVNFTSNGPVMQKKTLGWE*
*AFTETLYPADGGLEGRNDMALKLVGGSHLIANIKTTYRSKKPAKNLKMPGVYYVDYRLE*
*RIKEANNETYVEQHEVAVARYCDLPSKLGHKLN**

FIG. 56C(Cont.)

**SEQ ID NO: 352, MCP-nADAR2-DD-*BAD(F22)*-cADAR2(E488Q & R522M)-BclxL-*TagBFP***

MASNFTQFVLVDNGGTGDVTVAPSNFANGIAEWISSNSRSQAYKVTCSVRQSSAQNRKYTI
KVEVPKGAWRSYLNMELTIPIFATNSDCELIVKAMQGLLKDGNPIPSAIAANSGIYGGSGSGA
GSGSPAGGGAPGSGGGSQLHLPQVLADAVSRLVLGKFGDLTDNFSSPHARRKVLAGVVM
TTGTDVKDAKVISVSTGTKCINGEYMSDRGLALNDCHAEIISRRSLLRFLYTQLELYLNNKDD
QKRSIFQKSERGGFRLKENVQFHLYISTSPCGDARIFSPHEPILEEPAASGSGTG*APPNLWA*
*AQRYGRELRRMSDEF*VDRHPNRKARGQLRTKIESGQGTIPVRSNASIQTWDGVLQGERLL
TMSCSDKIAMWNVVGIQGSLLSIFVEPIYFSSIILGSLYHGDHLSRAMYQRISNIEDLPPLYTL
NKPLLSGISNAEARQPGKAPNFSVNWTVGDSAIEVINATTGKDELGRASRLCKHALYCRWM
RVHGKVPSHLLRSKITKPNVYHESKLAAKEYQAAKARLFTAFIKAGLGAWVEKPTEQDQFSL
TGSGGTENLYFQSGSSGGSGSAASSNRELVVDFLSYKLSQKGYSWSQFSDVEENRTEAPE
GTESEMETPSAINGNPSWHLADSPAVNGATGHSSSLDAREVI PMAAVKQALREAGDEFELR
YRRAFSDLTSQLHITPGTAYQSFEQVVNELFRDGVNWGRIVAFFSFGGALCVESVDKEMQV
LVSRIAAWMATYLNDHLEPWIQENGGWDTFVELYGNNGS*SELIKENMHMKLYMEGTVDNH*
*HFKCTSEGEGKPYEGTQTMRIKVVEGGPLPFAFDILATSFLYGSKTFINHTQGIPDFFKQSFP*
*EGFTWERVTTYEDGGVLTATQDTSLQDGCLIYNVKIRGVNFTSNGPVMQKKTLGWEAFTET*
*LYPADGGLEGRNDMALKLVGGSHLIANIKTTYRSKKPAKNLKMPGVYYVDYRLERIKEANNE*
*TYVEQHEVAVARYCDLPSKLGHKLN*

FIG. 57A

**SEQ ID NO: 353, MCP-nADAR2-DD-*BAD(F22L)*-cADAR2(E488Q & R522M)-BclxL-*TagBFP***

MASNFTQFVLVDNGGTGDVTVAPSNFANGIAEWISSNSRSQAYKVTCSVRQSSAQNRKYTI
KVEVPKGAWRSYLNMELTIPIFATNSDCELIVKAMQGLLKDGNPIPSAIAANSGIYGGSGSGA
GSGSPAGGGAPGSGGGSQLHLPQVLADAVSRLVLGKFGDLTDNFSSPHARRKVLAGVVM
TTGTDVKDAKVISVSTGTKCINGEYMSDRGLALNDCHAEIISRRSLLRFLYTQLELYLNNKDD
QKRSIFQKSERGGFRLKENVQFHLYISTSPCGDARIFSPHEPILEEPAASGSGTG*APPNLWA*
*AQRYGRELRRMSDELV*DRHPNRKARGQLRTKIESGQGTIPVRSNASIQTWDGVLQGERLL
TMSCSDKIAMWNVVGIQGSLLSIFVEPIYFSSIILGSLYHGDHLSRAMYQRISNIEDLPPLYTL
NKPLLSGISNAEARQPGKAPNFSVNWTVGDSAIEVINATTGKDELGRASRLCKHALYCRWM
RVHGKVPSHLLRSKITKPNVYHESKLAAKEYQAAKARLFTAFIKAGLGAWVEKPTEQDQFSL
TGSGGTENLYFQSGSSGGSGSAASSNRELVVDFLSYKLSQKGYSWSQFSDVEENRTEAPE
GTESEMETPSAINGNPSWHLADSPAVNGATGHSSSLDAREVIPMAAVKQALREAGDEFELR
YRRAFSDLTSQLHITPGTAYQSFEQVVNELFRDGVNWGRIVAFFSFGGALCVESVDKEMQV
LVSRIAAWMATYLNDHLEPWIQENGGWDTFVELYGNNGS*SELIKENMHMKLYMEGTVDNH*
*HFKCTSEGEGKPYEGTQTMRIKVVEGGPLPFAFDILATSFLYGSKTFINHTQGIPDFFKQSFP*
*EGFTWERVTTYEDGGVLTATQDTSLQDGCLIYNVKIRGVNFTSNGPVMQKKTLGWEAFTET*
*LYPADGGLEGRNDMALKLVGGSHLIANIKTTYRSKKPAKNLKMPGVYYVDYRLERIKEANNE*
*TYVEQHEVAVARYCDLPSKLGHKLN*

FIG. 57A(Cont.)

**SEQ ID NO: 354, MCP-nADAR2-DD-*BAD(F22V)*-cADAR2(E488Q & R522M)-BclxL-TagBFP**

MASNFTQFVLVDNGGTGDVTVAPSNFANGIAEWISSNSRSQAYKVTCSVRQSSAQNRKYTI
KVEVPKGAWRSYLNMELTIPIFATNSDCELIVKAMQGLLKDGNPIPSAIAANSGIYGGSGSGA
GSGSPAGGGAPGSGGGSQLHLPQVLADAVSRLVLGKFGDLTDNFSSPHARRKVLAGVVM
TTGTDVKDAKVISVSTGTKCINGEYMSDRGLALNDCHAEIISRRSLLRFLYTQLELYLNNKDD
QKRSIFQKSERGGFRLKENVQFHLYISTSPCGDARIFSPHEPILEEPAASGSGTG*APPNLWA*
*AQRYGRELRRMSDEV*VDRHPNRKARGQLRTKIESGQGTIPVRSNASIQTWDGVLQGERLL
TMSCSDKIAMWNVVGIQGSLLSIFVEPIYFSSIILGSLYHGDHLSRAMYQRISNIEDLPPLYTL
NKPLLSGISNAEARQPGKAPNFSVNWTVGDSAIEVINATTGKDELGRASRLCKHALYCRWM
RVHGKVPSHLLRSKITKPNVYHESKLAAKEYQAAKARLFTAFIKAGLGAWVEKPTEQDQFSL
TGSGGTENLYFQSGSSGGSGSAASSNRELVVDFLSYKLSQKGYSWSQFSDVEENRTEAPE
GTESEMETPSAINGNPSWHLADSPAVNGATGHSSSLDAREVIPMAAVKQALREAGDEFELR
YRRAFSDLTSQLHITPGTAYQSFEQVVNELFRDGVNWGRIVAFFSFGGALCVESVDKEMQV
LVSRIAAWMATYLNDHLEPWIQENGGWDTFVELYGNNGS*SELIKENMHMKLYMEGTVDNH*
*HFKCTSEGEGKPYEGTQTMRIKVVEGGPLPFAFDILATSFLYGSKTFINHTQGIPDFFKQSFP*
*EGFTWERVTTYEDGGVLTATQDTSLQDGCLIYNVKIRGVNFTSNGPVMQKKTLGWEAFTET*
*LYPADGGLEGRNDMALKLVGGSHLIANIKTTYRSKKPAKNLKMPGVYYVDYRLERIKEANNE*
*TYVEQHEVAVARYCDLPSKLGHKLN*

FIG. 57B

**SEQ ID NO: 355, tdMCP-*BAD*-ADAR2-DD(E488Q & F697Y)-TEVcs-BclxL-*TagBFP***

MASNFTQFVLVDNGGTGDVTVAPSNFANGIAEWISSNSRSQAYKVTCSVRQSSAQNRKYTI
KVEVPKGAWRSYLNMELTIPIFATNSDCELIVKAMQGLLKDGNPIPSAIAANSGIYANFTQFV
LVDNGGTGDVTVAPSNFANGIAEWISSNSRSQAYKVTCSVRQSSAQNRKYTIKVEVPKGA
WRSYLNMELTIPIFATNSDCELIVKAMQGLLKDGNPIPSAIAANSGIYGGSGSGAGSGSPAG
GGAPGSGGGSTG*APPNLWAAQRYGRELRRMSDEFVDSFKK*ASQLHLPQVLADAVSRLVL
GKFGDLTDNFSSPHARRKVLAGVVMTTGTDVKDAKVISVSTGTKCINGEYMSDRGLALNDC
HAEIISRRSLLRFLYTQLELYLNNKDDQKRSIFQKSERGGFRLKENVQFHLYISTSPCGDARIF
SPHEPILEEPADRHPNRKARGQLRTKIESGQGTIPVRSNASIQTWDGVLQGERLLTMSCSD
KIARWNVVGIQGSLLSIFVEPIYFSSIILGSLYHGDHLSRAMYQRISNIEDLPPLYTLNKPLLSGI
SNAEARQPGKAPNFSVNWTVGDSAIEVINATTGKDELGRASRLCKHALYCRWMRVHGKVP
SHLLRSKITKPNVYHESKLAAKEYQAAKARLFTAFIKAGLGAWVEKPTEQDQYSLTGSGGTE
NLYFQSAASSNRELVVDFLSYKLSQKGYSWSQFSDVEENRTEAPEGTESEMETPSAINGNP
SWHLADSPAVNGATGHSSSLDAREVIPMAAVKQALREAGDEFELRYRRAFSDLTSQLHITP
GTAYQSFEQVVNELFRDGVNWGRIVAFFSFGGALCVESVDKEMQVLVSRIAAWMATYLND
HLEPWIQENGGWDTFVELYGNNGS*SELIKENMHMKLYMEGTVDNHHFKCTSEGEGKPYE*
*GTQTMRIKVVEGGPLPFAFDILATSFLYG SKTFINHTQGIPDFFKQSFPEGFTWERVTTYED*
*GGVLTATQDTSLQDGCLIYNVKIRGVNFTSNGPVMQKKTLGWEAFTETLYPADGGLEGRN*
*DMALKLVGGSHLIANIKTTYRSKKPAKNLKMPGVYYVDYRLERIKEANNETYVEQHEVAVAR*
*YCDLPSKLGHKLN**

FIG. 58

**SEQ ID NO: 356, CD8signal-HA-*HaloTag*-T2A(G18R)-loop-MS2C-3xFLAG-*Gal4VP64*-T2A-*TagBFP***

TAATACGACTCACTAT AGGGAGACCCAAGCTGGCTAGCGTTTAAACTTAAGCTTgccaccatg gc
attgcccgtgaccgccctgctgctgccactggccttgttgctccacgccgcgcggccaTATCC CTACGATGTGCCCGATT
ACGCTaccggt*ATGGCAGAAATCGGTACTGGCTTTCCATTCGACCCCCATTATGTGGAAGTCC*
*TGGGCGAGCGCATGCACTACGTCGATGTT GGTCCGCGCGATGGCACCCCTGTGCTGTTCC*
*TGCACGGTAACCCGACCTCCTCCTACGTGTGGCGCAACATCATCCCGCATGTTGCACCGA*
*CCCATCGCTGCATTGCTCCAGACCTGATC GGTATGGGCAAATCCGACAAACCAGACCTGG*
*GTTATTTCTTCGACGACCACGTCCGCTTCATGGATGCCTTCATCGAAGCCCTGGGTCTGGA*
*AGAGGTCGTCCTGGTCATTCACGACTGGGGCTCCGCTCTGGGTTTCCACTGGGCCAAGCG*
*CAATCCAGAGCGCGTCAAAGGTATTGCATT TATGGAGTTCATCCGCCCTATCCCGACCTGG*
*GACGAATGGCCAGAATTTGCCCGCGAGACCT TCCAGGCCTTCCGCACCACCGACGTCGGC*
*CGCAAGCTGATCATCGATCAGAACGTTTTTATCGAGGGTACGCTGCCGATGGGTGTCGTCC*
*GCCCGCTGACTGAAGTCGAGATGGACCATTACCGCGAGCCGTTCCTGAATCCTGTTGACC*
*GCGAGCCACTGTGGCGCTTCCCAAACGAGCTGCCAATCGCCGGTGAGCCAGCGAACATCG*
*TCGCGCTGGTCGAAGAATACATGGACTGGCTGCACCAGTCCCCTGTCCCGAAGCTGCTGT*
*TCTGGGGCACCCCAGGCGTTCTGATCCCACCGGCCGAAGCCGCTCGCCTGGCCAAAAGC*
*CTGCCTAACTGCAAGGCTGTGGACATCGGCCCGGGTCTGAATCTGCTGCAAGAAGACAAC*
*CCGGACCTGATCGGCAGCGAGATCGCGCGCTGGCTGTCCACGCTCGAGATTTCCGGC*ggc
ggaGGAAGTGGCGAGGGCAGGGGAAGTCTCCTAACATGCGGGGACGTGGAGGAAAACCCT

FIG. 59A aGGCCTTACATGAGGATCACCCATGTTAGGCCcAGGGTTgactacaaagaccatgacggtgattataaag
atcatgacatcgactacaaggacgacgatgacaagGGTACC*atgaagctgctgagcagcatcgagcaggcctgtgacatctgc*
*cggctgaagaaactgaagtgcagcaaagaaaagcccaagtgcgccaagtgcctgaagaacaactgggagtgccggtacagccc*
*caagaccaagagaagcccctgaccagagcccacctgaccgaggtggaaagccggctggaaagactggaacagctgtttctgctg*
*atcttcccacgcgaggacctggacatgatcctgaagatggacagcctgcaggacatcaaggccctgctgaccggcctgttcgtgcag*
*gacaacgtgaacaaggacgccgtgaccgacagactggccagcgtggaaaccgacatgcccctgaccctgcggcagcacagaat*
*cagcgccaccagcagcagcgaggaaagcagcaacaagggccagcggcagctgacagtgtctgctgctgcaggcggaagcgga*
*ggctctggcggatctgatgccctggacgacttcgacctggatatgctgggcagcgacgccctggatgatttgatctggacatgctggga*
*tctgacgctctggacgatttcgatctcgacatgttgggatcagatgcactggatgactttgacctggacatgctcggatca*ATGGAGG
GCAGAGGAAGTCTTCTAACATGCGGTGACGTGGAGGAGAATCCCGGCCCTGGATCC *AGCG*
*AGCTGATTAAGGAGAACATGCACATGAAGCTGTACATGGAGGGCACCGTGGACAACCATCA*
*CTTCAAGTGCACATCCGAGGGCGAAGGCAAGCCCTACGAGGGCACCCAGACCATGAGAAT*
*CAAGGTGGTCGAGGGCGGCCCTCTCCCCTTCGCCTTCGACATCCTGGCTACTAGCTTCCT*
*CTACGGCAGCAAGACCTTCATCAACCACACCCAGGGCATCCCCGACTTCTTCAAGCAGTCC*
*TTCCCTGAGGGCTTCACATGGGAGAGAGTCACCACATACGAAGACGGGGGCGTGCTGACC*
*GCTACCCAGGACACCAGCCTCCAGGACGGCTGCCTCATCTACAACGTCAAGATCAGAGGG*
*GTGAACTTCACATCCAACGGCCCTGTGATGCAGAAGAAAACACTCGGCTGGGAGGCCTTC*
*ACCGAGACGCTGTACCCCGCTGACGGCGGCCTGGAAGGCAGAAACGACATGGCCCTGAA*
*GCTCGTGGGCGGGAGCCATCTGATCGCAAACATCAAGACCACATATAGATCCAAGAAACCC*
*GCTAAGAACCTCAAGATGCCTGGCGTCTACTATGTGGACTACAGACTGGAAAGAATCAAGG*
*AGGCCAACAACGAGACCTACGTCGAGCAGCACGAGGTGGCAGTGGCCAGATACTGCGACC*
*TCCCTAGCAAACTGGGGCACAAGCTTAAT*tgaTCTAGAGGGCCCGTTTAAACCCGCTGATCA
GCCTCGACTGTGCCTTCTA

FIG. 59A(Cont.)

**SEQ ID NO: 357, TagBFP-P2A-T2A-*Gal4-VP64*** taatacgactcactatagggagacccaagcttggtaccATGagcgagctgattaaggagaacatg
cacatgaagctgtacatggagggcaccgtggacaaccatcacttcaagtgcacatccgagggc
gaaggcaagccctacgagggcacccagaccatgagaatcaaggtggtcgagggcggccctc
tccccttcgccttcgacatcctggctactagcttcctctacggcagcaagaccttcatcaacaca
cccagggcatccccgacttcttcaagcagtccttccctgagggcttcacatgggagagagtcac
cacatacgaagacgggggcgtgctgaccgctacccaggacaccagcctccaggacggctgc
ctcatctacaacgtcaagatcagaggggtgaacttcacatccaacggccctgtgatgcagaaga
aaacactcggctgggaggccttcaccgagacgctgtaccccgctgacggcggcctggaaggc
agaaacgacatggccctgaagctcgtgggcgggagccatctgatcgcaaacatcaagaccac
atatagatccaagaaacccgctaagaacctcaagatgcctggcgtctactatgtggactacaga
ctggaaagaatcaaggaggccaacaacgagacctacgtcgagcagcacgaggtggcagtgg
ccagatactgcgacctccctagcaaactggggcacaagcttaatACTAGTGCCACAAAC
TTCTCTCTGCTAAAGCAAGCAGGTGATGTTGAAGAAAACCCAGGGCCT
GGAGGGTCCGAGGGCAGGGGAAGTCTCCTAACATGCGGGGACGTGG
AGGAAAATCCCGGACCAgaattcgccacc*atgaagctgctgagcagcatcgagcaggcctg*
*tgacatctgccggctgaagaaactgaagtgcagcaaagaaaagcccaagtgcgccaagtgcctgaa*
*gaacaactgggagtgccggtacagccccaagaccaagagaagccccctgaccagagcccacctga*
*ccgaggtggaaagccggctggaaagactggaacagctgtttctgctgatcttcccacgcgaggacctgg*
*acatgatcctgaagatggacagcctgcaggacatcaaggccctgctgaccggcctgttcgtgcaggac*
*aacgtgaacaaggacgccgtgaccgacagactggccagcgtggaaaccgacatgcccctgaccctg*
*cggcagcacagaatcagcgccaccagcagcagcgaggaaagcagcaacaagggccagcggcag*
*ctgacagtgtctgctgctgcaggcggaagcggaggctctggcggatctgatgccctggacgacttcgac*
*ctggatatgctgggcagcgacgccctggatgatttgatctggacatgctgggatctgacgctctggacga*
*tttcgatctcgacatgttgggatcagatgcactggatgactttgacctggacatgctcggatca*tgatctaga
gggccctattctatagtgtcacctaaatgctagagctcgctgatcagcctcgactgtgccttcta

FIG. 59B

**SEQ ID NO: 358, CD8signal-HA-*HaloTag*-T2A(G18R)-loop-MS2C-3xFLAG-*Gal4VP64*-T2A-*TagBFP***

MALPVTALLLPLALLLHAARPYPYDVPDYATG*MAEIGTGFPFDPHYVEVLG*
*ERMHYVDVGPRDGTPVLFLHGNPTSSYVWRNIIPHVAPTHRCIAPDLIGM*
*GKSDKPDLGYFFDDHVRFMDAFIEALGLEEVVLVIHDWGSALGFHWAKRN*
*PERVKGIAFMEFIRPIPTWDEWPEFARETFQAFRTTDVGRKLIIDQNVFIEG*
*TLPMGVVRPLTEVEMDHYREPFLNPVDREPLWRFPNELPIAGEPANIVALV*
*EEYMDWLHQSPVPKLLFWGTPGVLIPPAEAARLAKSLPNCKAVDIGPGLN*
*LLQEDNPDLIGSEIARWLSTLEIS*GGGGSGEGRGSLLTCGDVEENP(R)PY
MRITHVRPRVDYKDHDGDYKDHDIDYKDDDDKGT*MKLLSSIEQACDICRL*
*KKLKCSKEKPKCAKCLKNNWECRYSPKTKRSPLTRAHLTEVESRLERLEQ*
*LFLLIFPREDLDMILKMDSLQDIKALLTGLFVQDNVNKDAVTDRLASVETDM*
*PLTLRQHRISATSSSEESSNKGQRQLTVSAAAGGSGGSGGSDALDDFDLD*
*MLGSDALDDFDLDMLGSDALDDFDLDMLGSDALDDFDLDMLGS*MEGRG
SLLTCGDVEENPGPGS*SELIKENMHMKLYMEGTVDNHHFKCTSEGEGKP*
*YEGTQTMRIKVVEGGPLPFAFDILATSFLYGSKTFINHTQGIPDFFKQSFPE*
*GFTWERVTTYEDGGVLTATQDTSLQDGCLIYNVKIRGVNFTSNGPVMQKK*
*TLGWEAFTETLYPADGGLEGRNDMALKLVGGSHLIANIKTTYRSKKPAKNL*
*KMPGVYYVDYRLERIKEANNETYVEQHEVAVARYCDLPSKLGHKLN**

FIG. 60

**SEQ ID NO: 359, TagBFP-P2A-T2A-*Gal4-VP64***

MSELIKENMHMKLYMEGTVDNHHFKCTSEGEGKPYEGTQTMRIKVVEG
GPLPFAFDILATSFLYGSKTFINHTQGIPDFFKQSFPEGFTWERVTTYEDG
GVLTATQDTSLQDGCLIYNVKIRGVNFTSNGPVMQKKTLGWEAFTETLYP
ADGGLEGRNDMALKLVGGSHLIANIKTTYRSKKPAKNLKMPGVYYVDYR
LERIKEANNETYVEQHEVAVARYCDLPSKLGHKLNTSATNFSLLKQAGDV
EENPGPGGSEGRGSLLTCGDVEENPGPEFAT*MKLLSSIEQACDICRLKK*
*LKCSKEKPKCAKCLKNNWECRYSPKTKRSPLTRAHLTEVESRLERLEQL*
*FLLIFPREDLDMILKMDSLQDIKALLTGLFVQDNVNKDAVTDRLASVETDM*
*PLTLRQHRISATSSSEESSNKGQRQLTVSAAAGGSGGSGGSDALDDFDL*
*DMLGSDALDDFDLDMLGSDALDDFDLDMLGSDALDDFDLDMLGS**

FIG. 60(Cont.)

COMPOSITIONS AND METHODS FOR CONTROLLED mRNA TRANSLATION AND STABILITY

CROSS-REFERENCE TO RELATED APPLICATIONS

This application claims benefit under 35 U.S.C. § 119(e) of U.S. Provisional Application No. 63/434,275 filed Dec. 21, 2022, the contents of which are incorporated herein by reference in their entirety.

GOVERNMENT SUPPORT

This invention was made with government support under contract No. R35-GM128859 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Mar. 22, 2024, is named 701586-000107USPT_SL.xml and is 718,305 bytes in size.

TECHNICAL FIELD

The technology described herein relates to methods and compositions for editing RNAs using an engineered inducible Adenosine Deaminase enzymes, including an Adenosine Deaminase Acting on RNA (iADAR) enzyme that is capable, in the presence of an inducer, to deaminate one or more adenosines in target RNAs, where the target RNA comprises a target codon, to regulate gene expression of a gene of interest.

BACKGROUND

Nucleic acid editing carries enormous potential for biological research and the development of therapeutics. Current tools for DNA or RNA editing rely on introducing exogenous proteins into living organisms, which is subject to potential risks or technical barriers due to possible aberrant effector activity, delivery limits and immunogenicity. Moreover, nucleic acid based medicines, including messenger RNA (mRNA) based vaccines and therapeutics have rapidly developed in the past several years and have emerged as a promising technology with many potential applications in both medicine and basic science research. Instead of producing and delivering a protein directly to cells/organisms/patients, nucleic acids (including mRNAs) are delivered to cells via lipid nanoparticles (LNP) or other agents. Upon entry, ribosome mediated-translation results in the production of proteins encoded by the delivered nucleic acid sequences. A limitation of mRNA-based agents is that uptake of the mRNA to any human cell type will result in its translation and thus expression of the encoded protein. Thus, a limitation of mRNA based medicines is the limited control over translation of an encoded protein sequence.

Genome editing is a powerful tool for biomedical research and development of therapeutics for diseases. Editing technologies using engineered nucleases, such as zinc finger nucleases (ZFNs), transcription activator-like effector nucleases (TALENs), and Cas proteins of CRISPR system have been applied to manipulate the genome in a myriad of organisms. Recently, taking advantage of the deaminase proteins, such as Adenosine Deaminase Acting on RNA (ADAR), new tools were developed for RNA editing. In mammalian cells, there are three types of ADAR proteins, Adar1 (two isoforms, p110 and p150), Adar2 and Adar3 (catalytically inactive). The catalytic substrate of ADAR protein is double-stranded RNA, and ADAR can remove the —NH2 group from an adenosine (A) nucleobase, changing A to inosine (I). Inosine preferentially base pairs with cytosine, and therefore the cell's transcriptional and translational machinery interprets inosine as guanosine. To achieve targeted RNA editing, the ADAR protein or its catalytic domain was fused with a λN peptide, a SNAP-tag or a Cas protein (dCas13b), and a guide RNA was designed to recruit the chimeric ADAR protein to the target site. Alternatively, overexpressing ADAR1 or ADAR2 proteins together with an R/G motif-bearing guide RNA was also reported to enable targeted RNA editing.

However, currently available ADAR-mediated RNA editing technologies have certain limitations. Over-expression of ADAR1 has recently been reported to confer oncogenicity in multiple myelomas due to aberrant hyper-editing on RNAs, and to generate substantial global off-targeting edits. In addition, ectopic expression of proteins or their domains of non-human origin has potential risk of eliciting immunogenicity.

There is a need for control of the translation of nucleic acid based therapeutics. In particular, there is a need for an inducible ADAR system that avoids overexpression of ADARs and can rapidly activate ADAR to tailor the adenosine deaminase activity in a rapid and controlled manner.

SUMMARY

Provided herein are compositions, kits, systems and methods related to an engineered, inducible adenosine deaminase (iAD) enzymes, including but not limited to, an engineered inducible adenosine deaminase acting on RNA (ADAR) enzyme, which can be activated in the presence of an inducer. Without wishing to be limited to theory, ADAR is used as an exemplary engineered inducible adenosine deaminase (iAD), but it is envisioned that the methods, compositions and systems disclosed herein are applicable to other adenosine deaminase enzymes, including but not limited to ADAR, ADAD and ADAT. Disclosed herein are inducible AR (iAR) proteins, e.g., inducible ADAR (iADAR) enzymes that can transition from an OFF ("iADAR-OFF") to an ON ("iADAR-ON") state in the presence of an inducer, therefore enabling rapid and controllable regulation of the adenosine deaminase activity. Also described are synthetic RNA molecules, to which the iAD can be specifically recruited to edit at least one stop codon into a non-stop codon, leading to decreased or increased translation of the RNA molecules depending on the specific construct. For example, when the iADAR is ON state, it can affect the translation of a gene of interest (GOI), depending on the target nucleic acid construct that the iADAR acts on, resulting in translation of a GOI being turned ON or OFF. By way of example only, an iADAR in the on state (iADAR-ON) can edit A→I, therefore changing a STOP (UAG) codon to UIG, therefore eliminating the STOP codon.

In one embodiment, if the STOP codon, which is present in a double stranded transcript region, herein referred to as a "ds-STOP region" is upstream (e.g., 5') of an open reading frame (ORF), such as a GOI (referred to herein as an "target activation construct" or "TAC"), the iADAR-ON can remove the STOP codon resulting in translation of the downstream GOI. Thus, in this embodiment, in the presence of an inducer, gene translation is ON. That is—in the presence of the inducer, the translation of the GOI is switched from OFF→ON. In another embodiment, if the ds-STOP region comprising the STOP codon is located between a 5' GOI and a 3' polyA signal (referred to herein as an "inactivation construct" or "TIC"), an iADAR-ON can edit and remove the STOP codon, resulting in translation of the polyA tail, stalling of the ribosome, and leading to NON-STOP decay of the mRNA GOI. Thus, in this embodiment, in the presence of an inducer, gene translation is OFF. That is, in the presence of an inducer, the translation of the GOI is switched from ON→OFF. In some embodiments, the mRNA encoding the GOI is also destroyed by the cell.

In other aspects described herein are synthetic RNA molecules, to which the iAD can be specifically recruited to edit at least one start codon into a non-start codon, leading to decreased translation of the RNA molecules and/or altered translation initiation sites depending on the specific construct.

In other aspects described herein are synthetic RNA molecules, to which the iAD can be specifically recruited to edit at least one non-start codon into a start codon, leading to increased translation of the RNA molecules.

In other aspects described herein are synthetic RNA molecules, to which the iAD can be specifically recruited to edit at least one sense codon into a mutated sense codon, leading to an alteration of the structure and/or function of the RNA and/or encoded polypeptide, depending on the specific construct.

One aspect of the technology relates to an inducible adenosine deaminase enzymes (iAD), for example, but not limited to inducible ADAR (IADAR) enzymes. Other aspects disclosed herein relates to another inducible aminase enzyme, such as an inducible ADAR, ADAD or ADAT.

The technology described herein is also directed to systems comprising the iAD and synthetic RNA molecule, nucleic acids and vectors encoding the iAD and synthetic RNA molecule, and methods of using such systems, nucleic acids, and vectors.

Another aspect of the technology relates to synthetic nucleic acid constructs that iADAR effectuates.

Another aspect of the technology relates to systems and cells comprising an iADAR and a nucleic effector construct, e.g., an activation construct or inactivation construct as disclosed herein.

Another aspect relates to nucleic acid constructs that function as an activation construct or inactivation construct. Another aspect relates to nucleic acid encoding an iADAR and one or more of a target activation construct (TA-construct or TAC) or target inactivation construct (TI-construct or TIC).

BRIEF DESCRIPTION OF THE DRAWINGS

FIG. 1A) Stop codon editing reporter composed of a single mRNA transcript encoding for mCherry-FLAG (red) and HA-mNeonGreen (green) separated by a dsRNA hairpin containing a UAG stop codon (dark gray) and an RNA-binding element (light gray). In the absence of recoding, only mCherry is translated by host ribosomes. Figure discloses "AAAAAAAAAAA" as SEQ ID NO: 407. FIG. 1B) Co-expression of a fusion protein containing an RNA binding domain and a hyperactive ADAR-deaminase domain (orange and yellow) leads to colocalization of substrate & enzyme, editing of UAG stop codon to UIG, read-through by ribosome of RNA elements, and expression of mNeonGreen. Figure discloses "AAAAAAAAAAA" as SEQ ID NO: 407. FIG. 1C) Representative images of HEK293FT cells co-transfected with a UAG-MS2 editing reporter and MCP-ADAR2(E488Q)-TagBFP or catalytically inactive ADAR2(E396A). Scale-bar=250 μm. FIG. 1D) Stop codon editing assay by Western blot analysis of HEK293FT cells transfected with mRNA reporters containing different number of stop codons and/or MS2 elements. FIG. 1E) Orthogonality of ADAR2 editing of reporters with different RNA-binding domains and RNA elements observed by representative micrographs of HEK293FT cells co-transfected with reporters and ADAR variants. Images are overlays of mCherry (magenta) and m NeonGreen (green) fluorescence. Control lane were transfected only with the reporter. Scale bar=500 μm.

FIG. 2A) Stop codon editing reporter composed of a single mRNA transcript encoding for a destabilized EGFP variant (EGFPd2—green), UAG stop codon in a dsRNA hairpin (dark gray), an RNA-binding element (light gray), and polyA tail. No other stop codons are present outside of the loop. In the absence of editing, EGFPd2 is translated by the host ribosome. Figure discloses "AAAAAAAAAAA" as SEQ ID NO: 407. FIG. 2B) Plasmid architecture of a reporter than turns off EGFPd2 with RNA editing. Bidirectional CMV (BiCMV) drives expression of a constitutive dTomato (red) and an editable EGFPd2 construct via separate transcripts. Figure discloses "AAAAAAAAAAA" as SEQ ID NO: 407. FIG. 2C) ADAR-DD leads to editing of all reporter stop codons, translation and ribosome stalling at the polyA tail, recruitment of proteins associated with non-stop decay (Ski7), and mRNA degradation by exonucleases/exosome. FIG. 2D) HEK293FT cells were transfected with inactive and active ADAR variants with the Non-Stop-Decay reporter construct and fluorescent images were collected 48 hours later. Overlay of dTomato and EGFPd2 shows relative extent of expression. Scale bar=200 μm.

FIG. 3A) Crystal structure of ADAR2-DD bound to dsRNA (PDB-5ED2). RNA shown in orange, ADAR2-DD shown in cyan, 5' Binding Loop residues amenable to insertions shown in green and the C-terminus shown in red. FIG. 3B) A model of an autoinhibitory ADAR: an insertion is made in the 5' Binding loop (green) that does not disturb catalytic activity. Subsequent fusion of a high affinity binding partner (gray) to the C-terminus (red) leads to an equilibrium shift towards an inhibited state. The addition of a small-molecule drug that can disrupt that interaction (orange) leads to an active ADAR-DD state. FIG. 3C) Architecture of the drug-inducible ADAR proteins using BH3 derived peptides and Bcl-2 Homologs as the interaction domains. FIG. 3D) Representative fluorescent micrographs showing the relative expression of mCherry and mNeonGreen from the ADAR-editing reporter when HEK293FT cells were co-transfected with different ADAR variants. Merged channels show overlay of mCherry (magenta) and mNconGreen (green). Table below micrographs identify the ADAR variant by BH3-peptide insertion at 5' Binding Loop (Bad, Bim, or MS1(117A)) and Bcl-2 Homolog fused at the C-terminus (Bcl-xL or Mcl-1), and displays whether inhibitory drugs were added. Scale bar=200 μm. FIG. 3E) Flow cytometry analysis of HEK293FT cells transfected with reporter and ADAR variants. ADAR2-BclxL represents Bad insertion variant. Drug added for BclxL was 500 nM of A-1331852 at the time of transfection, and for Mcl-I was 2 μM of S63845. Cells were gated for ADAR transfection via BFP fluorescence, and relative fluorescence was quantified by the median of the ratio of mNeonGreen to mCherry. Bars represent mean fluorescence of three independent transfections (n=3). FIG. 3F) Drug response titration of Bad-BclxL system using A-1331852. Bad point mutant was also tested (F121L). Drug added at the time of transfection (other than Cntrl condition, where no drug was added). Relative fluorescence quantified via flow cytometry 48 hours after transfection. Mean relative fluorescence for three independent transfections (n=3) is plotted±s.d. per drug concentration. FIG. 3G) Drug response titration of MS1-Mcl-1 system using S63845. Original MS1 (117) and destabilized binding mutant MS1 (117A) were both tested. Drug added at the time of transfection (other than Cntrl condition, where no drug was added). Relative fluorescence quantified for transfected cells via flow cytometry 48 hours later. Mean relative fluorescence for three independent transfections (n=3) is plotted #s.d. per drug concentration. FIG. 3H) Flow cytometry analysis of HEK293FT cells transfected with variants of ADAR and with the EGFPd2/dTomato reporter, where editing leads to destruction of fluorescent signal. If indicated, 2 μM of S63845 was added at the time of transfection. Mean relative fluorescence for three independent transfections (n=3) is plotted and P-values that were derived from a 2-way ANOVA (groups were ADAR variant and drug) are shown for certain comparisons.

FIG. 4A-4E—Autoinhibited ADAR Variants Utilizing Repressive Epitope-Antibody Fragment Interactions Can Activate via Antigen Binding. FIG. 4A) A model of allosteric ADAR activation via competitive antigen binding. An inserted epitope at the 5' binding loop (green) and a C-terminally (red) fused antibody fragment (gray) bind and make the ADAR adopt an inhibited state. Soluble antigen (purple) that can compete with the intramolecular interaction due to high concentration or affinity shifts the equilibrium towards an active ADAR, allosterically activating the ADAR. FIG. 4B) Crystal structure of the ALFA epitope tag and anti-ALFA nanobody (NbALFA) (PDB—612G). FIG. 4C) Protein architecture of ALFA-based allosteric ADAR and soluble ALFA antigen fused to miRFP. Also displayed are the amino acid sequences of ALFA variants with lowering affinity (ALFA: SRLEEELRRRLTE, SEQ ID NO: 85; AFLA-PE: GRLEEELRRRLSP, SEQ ID NO: 86; ALFA-78: GRLEQEIRARLSP, SEQ ID NO: 87). FIG. 4D) Two-dimensional contour plots of mNeonGreen vs mCherry fluorescence derived from flow-cytometry analysis of transfected HEK293FT cells (gated by BFP and mCherry). Each contour-group contains 10% of the population. Original full length ADAR-DD and catalytically inactive E396A mutant shown on left (blue and red), and ALFA insertion with NbALFA fusion without and with soluble ALFA shown on right (green and purple). Each population displays an individual replicate representative of an experiment done in triplicate. FIG. 4E) Representative fluorescent micrographs showing the relative expression of mCherry and mNeonGreen from the ADAR-editing reporter when HEK293FT cells were co-transfected with different ALFA-ADAR variants with and without soluble ALFA co-transfection. Merged channels show overlay of mCherry (magenta) and mNeonGreen (green). The table below the micrographs identify the ADAR variant by ALFA variant insertion at 5' Binding Loop (ALFA, ALFA-PE, or ALFA-78) and whether NbALFA was fused to the C-terminus, and displays whether miRFP670-ALFA was co-transfected. Scale bar=500 μm.

FIG. 5A) A model of proteolytic cleavage based induction of ADAR activity. In this scheme, a cut site (yellow) is inserted in the linker between the C-terminus of ADAR (red) and the N-terminus of a protein domain (gray) that constitutively binds a peptide/protein inserted at the 5' Binding Loop (green). Irreversible proteolytic cleavage does not interfere with protein interactions but leads to relaxation of the autoinhibited state and therefore catalytically active ADAR. FIG. 5B) Crystal structure of the SpyTag (green) and SpyCatcher (gray) covalent complex (PDB—4MLI). FIG. 5C) Architecture of the ADAR that can be activated by TEV protease used in subsequent experiments. FIG. 5D) Flow cytometry analysis of HEK293FT cells transfected with editing reporter and SpyTag based ADAR variants. Conditions related to ADAR variant and TEV addition shown below (2A refers to SpyCatcher being co-expressed via 2A self-cleaving peptides and not C-terminally fused like the others). Cells were gated for ADAR transfection via BFP fluorescence, and relative fluorescence was quantified by the median of the ratio of mNeonGreen to mCherry. Bars represent mean fluorescence of three independent transfections (n=3)±s.d., and P-Values displayed were derived from one-way ANOVA. FIG. 5E) Two-dimensional contour plots of mNeonGreen vs mCherry fluorescence derived from flow-cytometry analysis of ADAR-TEVcs transfected HEK293FT cells gated by BFP and mCherry (right two columns from D). Each contour-group contains 10% of the population. Co-transfected with a plasmid encoding TEV protease shown in red, whereas transfected without TEV protease is shown in blue. Each population displays an individual replicate representative of an experiment done in triplicate. FIG. 5F) A model for photolytic activation of ADAR variants. Similar to model A, but a photocleavable domain (i.e., PhoCl) is inserted between ADAR and the binding domain instead of a protease cleavage site. Irreversible photocleavage via purple light does not interfere with protein interactions but leads to relaxation of the autoinhibited state and therefore catalytically active ADAR. FIG. 5G) Fluorescence micrographs showing an increase in relative fluorescence of mNeonGreen (green) and mCherry (magenta) over time in cells that were transfected with the editing reporter and a PhoCl integrated Bad-BelxL construct. At time 0, cells were imaged and then illuminated with violet light from a BFP filter for 10s. 2 hours later, the same spot was recorded and illuminated again with 10s of violet light before being recorded for a final time 4 hours from the first illumination event. Scale bar=500μ.

FIG. 6A-60 are tables showing the domains of the polypeptides of SEQ ID NOs: 1-37. "SID" indicate the SEQ ID NO. See also Table 1 in Example 3.

FIG. 7A-7B shows a sequence alignment of ADAR1 (DSRAD; SEQ ID NO: 79), ADAR2 (RED1; SEQ ID NO: 80), and ADAR3 (RED2; SEQ ID NO: 81).

FIG. 8A-8C shows a sequence alignment of ADAR1 (DSRAD; SEQ ID NO: 79), ADAR2 (RED1; SEQ ID NO: 80), ADAR3 (RED2; SEQ ID NO: 81), ADAD1 (SEQ ID NO: 82), and ADAD2 (SEQ ID NO: 83).

FIG. 9A-9C shows a sequence alignment of ADAT1 (SEQ ID NO: 84), ADAR1 (DSRAD; SEQ ID NO: 79), ADAR2 (RED1; SEQ ID NO: 80), ADAR3 (RED2; SEQ ID NO: 81), ADAD1 (SEQ ID NO: 82), and ADAD2 (SEQ ID NO: 83).

FIG. 11A) General map of previous topology for creating autoinhibited ADAR enzymes. Here two heterodimeric protein components (A and B) are inserted at a specific loop and fused to the C-terminus. FIG. 11B) Quantification of fluorescent micrographs demonstrating that the second protein partner must be fused to the C-terminus. HEK cells were transfected with 50 ng of both a reporter construct and of an ADAR construct and treated with A-1331852, and two days later images were taken on an epifluorescent microscope. The images were then analyzed by the following-background was subtracted, a mask was created of transfected cells using the BFP channel, and the ratio of m NeonGreen to mCherry of the corresponding region was computed with ImageJ. FIG. 11C) ADAR2-DD crystal structure (PDB 5ED2). The C-terminus is shown in red and the insertion loop is shown in green. The distance between the two is greater than 50 Å. FIG. 11D) Map of new autoinhibited ADAR constructs with the heterodimeric protein components fused to the N and C termini. FIG. 11E) Crystal structure showing the distance between the C (red) and N (green) termini is greater than 50 Å when folded. FIG. 11F) Quantification of fluorescent micrographs demonstrating that using both termini can lead to an allosterically activated ADAR construct. HEK cells were transfected with 50 ng of both a reporter construct and of an ADAR construct and treated with A-1331852, and two days later images were taken on an epifluorescent microscope. The images were then analyzed by the following-background was subtracted, a mask was created of transfected cells using the BFP channel, and the ratio of mNeonGreen to mCherry of the corresponding region was computed with ImageJ. Please note that this experiment was done with the experiment for FIG. 11B, and that some data points are the same. All data shown is n=1.

FIG. 12A) General schematic for how to create a self-editing, ADAR-encoding mRNA. Upstream of an editable stop codon, an allosteric ADAR is fused to an RNA-binding protein that recognized a motif adjacent to the first stop codon. Downstream of the stop codon is a gene of interest. FIG. 12B) Schematics for testing self-editing mRNA used in subsequent experiments. BAD (F)-Bcl-xL were used as the pair, and either 1 or 2 editable stop codon loops (each containing two UAG stop codons) were downstream. FIG. 12C) Fluorescent micrographs of HEK cells which were transfected two days prior with each construct listed above (corresponding to whether the ADAR was mutated and whether there were one or two editable stop codon loops) with or without 1 μM of A-1331852. mCherry is shown in red and mNeonGreen is shown in green as a single image. Robust editing as seen by m NeonGreen fluorescent is apparent in both configurations. FIG. 12D) Quantification of the images shown in FIG. 12C. The images were then analyzed by the following-background was subtracted, a mask was created of transfected cells using the mCherry channel, and the value of mNeonGreen of the corresponding region was computed with ImageJ. All data shown is n=1.

FIG. 13A shows that a Ribonucleoprotein complex can comprise a pre-assembled engineered ADAR sensor with mRNA. FIG. 13B shows that a single, self-editing mRNA construct can encode the ADAR component upstream in the first open reading frame and a downstream product (e.g., an effector protein such as a reporter, interferon, caspase, etc.) in the second open reading frame of the RNA.

FIG. 14A-14C are tables showing the domains of the polypeptides of SEQ ID NOs: 88-92. "SID" indicate the SEQ ID NO. See also Table 2 in Example 7.

FIG. 15A-15B are tables showing the domains of the polypeptides of SEQ ID NOs: 93-94. "SID" indicate the SEQ ID NO. See also Table 3 in Example 8.

FIG. 16A is a schematic of one embodiment, showing modification of the Deaminase domain (DD) so that the adenosine deaminase activity is constitutively on. In the embodiment shown, the DD is a heterodimer of two fragments or portions, e.g., AD-DDn and AD-DDc, however, it is envisioned that the DD can be a single polypeptide that is not split. The Table in FIG. 16A shows that when the constitutively active modified AD, e.g., ADAR is coupled with an affinity binding pair as disclosed herein, it becomes an inducible AD (iAD) or inducible ADAR (IADAR), and depending on the location of the ds-STOP region, will result in activation of a GOI or deactivation (e.g., mRNA decay) of a GOI. FIG. 16B is a schematic illustration of the iADAR fusion protein that comprises an affinity binding pair (e.g., BP1 and BP2), that when in the absence of an inducer prevents the co-factor IP6 from activating the adenosine deaminase activity. In the presence of an inducer, the binding between the affinity binding pair (e.g., BP1 and BP2) is interrupted or inhibited, thereby allowing IP6 to bind to the DD and changing the iADAR from the OFF to ON state, and adenosine deaminase activity can occur. Depending on the location of the ds-STOP region in a target construct, e.g., a target activation construct (TAC) or a target inactivation construct (TIC), the GOI expression is turned ON or OFF respectively. Depending on the affinity binding pair of the iADAR, inducers can be, but are not limited to, small molecules, proteases, light-inducible control, sound inducible control, cell cycle dependent, ultrasound or other wavelength dependent, antibodies, endogenous triggers, disease triggers, external triggers and cell-specific marker triggers, and the like.

FIG. 18 shows SEQ ID NO: 168 (AD-Pep-AD) and SEQ ID NO: 169, exemplary iADARs using NS3 and NS3 peptide.

In FIG. 20A-20G, the yellow loop is the dsRNA stop loop, and the blue loop is the dsRNA binding motif (e.g., MS2, PP7, HIV tar, BoxB loops), which are capable of being bound by an RNA-binding domain. FIG. 20A shows UAG-UAG Stop Loop w/ MS2 Loop (SEQ ID NO: 395), FIG. 20B shows UAG-UGG Stop Loop w/ MS2 Loop (SEQ ID NO: 396). FIG. 20C shows UGG-UAG Stop Loop w/ MS2 Loop (SEQ ID NO: 397). FIG. 20D shows UAG-UAG Stop Loop w/ Internal MS2 Loop (SEQ ID NO: 398). FIG. 20E shows UAG-UAG Stop Loop w/PP7 Loop (SEQ ID NO: 399). FIG. 20F shows UAG-UAG Stop Loop w/ HIV Tar Loop (SEQ ID NO: 400). FIG. 20G shows UAG-UAG Stop Loop w/ BoxB Loop (SEQ ID NO: 401). FIG. 20H shows the General Secondary Structure of dsRNA Stop Loop; the dashed lines represent hydrogen bonding between base pairs, and w, x, y & z represent variables. It should be noted that not necessarily every hydrogen bond/base pairing depicted in the diagram below needs to be maintained, but enough to become a substrate for ADAR deaminase domains. Figure discloses SEQ ID NO: 408.

FIG. 21A-21E show exemplary sequences described herein (see e.g., Example 17). FIG. 21A shows CP-linker-BelxL-linker-ADAR2-DDN-Bad(L)-ADAR2(E488Q)-DDC-TagBFP (see e.g., SEQ ID NO: 198). FIG. 21B shows MCP-linker-BAD-ADAR2-DD (E488Q)-TagBFP (see e.g., SEQ ID NO: 200). FIG. 21C shows MCP-linker-BAD-ADAR2-DD (E488Q)-Bcl-XL-TagBFP (see e.g., SEQ ID NO: 202). FIG. 21D shows tdMCP_ADAR2-DDN-CP5-46-4D5E_ADAR2-DDC (E488Q)_mTagBFP (AD-Pep-AD) (see e.g., SEQ ID NO: 204) FIG. 21E shows tdMCP_A-DAR2-DDN-CP5-46-4D5E ADAR2-DDC (E488Q) NS4A/NS3 (Genotype 1B)_mTagBFP (see e.g., SEQ ID NO: 206).

FIG. 22A) A thermodynamic model showing the competition between IP6 binding and cis-heterodimerization. ADAR is shown in blue, with the C-terminus shown in brighter blue. Each dimer component is shown in green and red. IP6 is shown in magenta. The affinity of each component shifts the equilibrium accordingly. FIG. 22B) Residues that contact IP6 and/or stabilize the C-terminus are shown in the crystal structure (left) or as a LigPlot (right). FIG. 22C) A plasmid map of the construct that was used in the mutational screen. BAD(V), a mutant with lowered affinity to Bcl-xL, was used because of its leakiness. FIG. 22D) Flow cytometry data of HEK cells that were co-transfected with an ADAR reporter and ADAR mutant variants of BAD(V)-BclxL in the presence of A-1331852. Two days after transfection, cells were lifted and analyzed via flow cytometry. Using FLOWJO, cells were gated by 1% of BFP fluorescence and the median of the ratio of mNeonGreen to mCherry is plotted. All data shown is n=1.

FIG. 23A) Plasmid map of MS1(117A)/MS1 (117G)-Mcl1 ADAR variants. FIG. 23B) Quantification of fluorescent micrographs of MS1(117A)-Mell ADAR mutants. HEK cells were transfected with 50 ng of both a reporter construct and different ADAR mutant constructs and treated with S63845 (an Mcl-1 inhibitor), and two days later images were taken on an epifluorescent microscope. The images were then analyzed by the following-background was subtracted, a mask was created of transfected cells using the BFP channel, and the ratio of mNeonGreen to mCherry of the corresponding region was computed with ImageJ. FIG. 23C) Quantification of fluorescent micrographs of MS1(I17G)-Mcl1 ADAR mutants. HEK cells were transfected with 50 ng of both a reporter construct and different ADAR mutant constructs and treated with S63845 (an Mcl-1 inhibitor), and two days later images were taken on an epifluorescent microscope. The images were then analyzed by the following-background was subtracted, a mask was created of transfected cells using the BFP channel, and the ratio of m NeonGreen to mCherry of the corresponding region was computed with ImageJ. FIG. 23D) Plasmid map of N-terminal BAD fusion construct. FIG. 23E) Quantification of fluorescent micrographs of nBAD-ADAR-cBcl-xL mutants. HEK cells were transfected with 50 ng of both a reporter construct and different ADAR mutant constructs and treated with A-1331852 (a Bcl-xL inhibitor), and two days later images were taken on an epifluorescent microscope. The images were then analyzed by the following-background was subtracted, a mask was created of transfected cells using the BFP channel, and the ratio of mNeonGreen to mCherry of the corresponding region was computed with ImageJ. All data shown is n=1.

FIG. 25A-25C show exemplary sequences described herein (see e.g., Example 17). FIG. 25A shows MCP-linker-ADAR2-DDN-Bad(F)-ADAR2(E488Q)-DDC-Bcl-XL (see e.g., SEQ ID NO: 287) and MCP-linker-ADAR2-DDN-Bad (F)-ADAR2(E488Q)-DDC-Bcl-XL-TagBFP (see e.g., SEQ ID NO: 288). FIG. 25B shows MCP-linker-ADAR2-DDN-Bad(F)-ADAR2(E488Q)-DDC-Bcl-xL-TagBFP (see e.g., SEQ ID NO: 289) and MCP-linker-ADAR2-DDN-MS1(A)-ADAR2(E488Q)-DDC-TagBFP (see e.g., SEQ ID NO: 290). FIG. 25C shows MCP-linker-ADAR2-DDN-MS1(G)-ADAR2(E488Q)-DDC-TagBFP (see e.g., SEQ ID NO: 291).

FIG. 26A) General schematic for ADAR-editing creation of a novel start codon. An RNA target substrate in the 5'UTR of a transcript contains an editable AUA target positioned in frame with a downstream ORF (EGFPd2. Co-expression of RBP-ADAR-DD leads to editing of the AUA into AUI, generating a start codon that can be interpreted as "AUG. " FIG. 26B; SEQ ID NO: 409) Sequence and secondary structure prediction of an example editable substrate as predicted by RNAfold. An MS2 motif for interaction with an MCP based RBP is highlighted. The AUA editing target is also highlighted. Conversion of this AUA into AUI generates a new start site and ORF. FIG. 26C) General plasmid map of the tested design. FIGS. 26D&26E) HEK cells were co-transfected with a plasmid encoding a bidirectional CMV promoter encoding an editing target in combination with dTomato as a transfection marker. Two editing target constructs are compared, which contain either a high-affinity "MS2-C" (FIG. 26D) or modest affinity "MS2-A" (FIG. 26E) MCP/RBP sequence[4]. Editable sequences containing "AUA" targets within the RNA motifs were tested in combination with active or inactive iADAR constructs. Levels of editing were determined by measuring EGFPd2/dTomato ratios. The AUA-containing "editable" targets were compared to control sequences containing the intended editing product ("AUG") as a positive control. Control cells expressing the reporter without transfected iADAR constructs ("NT"—white); cells expressing the reporter in combination with an inactive MCP-ADAR (E396A) ("dA-DAR"—striped); cells expressing reporter in combination with active MCP-ADAR ("ADAR"-black) deaminase domains. Cells were analyzed by flow cytometry with quantification of dTomato and EGFP2 levels in single cells; plotted values represent median emission value intensities of the analyzed populations (EGFPd2: dTomato). Positively transfected cells were gated based on dTomato expression. Statistical significance determined using Prism: Two-way ANOVA (n=3 separate transfections). **-P<0.0001, *-P<0.001, **-P<0.01, *-P<0.05.

FIG. 27A) General schematic of iADAR-mediated editing of a non-coding AUA target for creation of a new (AUI) start codon and ORF. Conversion of the target AUA into AUI results in the in-frame fusion of target protein with a signal sequence (SS) for ER-mediated protein secretion in combination with an HA epitope tag. A RNA target in the 5'UTR contains an editable AUA sequence which is positioned in frame with the original start codon encoding a cytoplasmically localized GFP protein. Co-expression of an RBD-ADAR-DD leads to the creation of an upstream start codon (AUI) that leads to an ORF expansion and the encoding of a protein product containing an N-terminally fused signal peptide. Note that upon creation of the AUI new start codon, the original AUG start codon becomes read as an elongator AUG/methionine. Note also that the editing-mediated ORF expansion results in the secretion of the encoded protein into the ER lumen via the translated signal sequence. Secretion of this protein also permits the post-translational modification of GFP which contains a C-terminal site for GPI (glycosylphosphatidylinositol) linkage. GPI modification is not expected to occur for the non-edited cytoplasmic GFP, as modification with this lipid does not generally occur cytoplasmically. Thus the net result of the editing event produces a new protein product with i) higher mass, ii) altered localization, iii) altered recognition (HA tag), and iv) altered post-translational modification susceptibility. FIG. 27B) Schematic for the cell-based detection of editing-mediate protein relocation. Non-transfected cells (left) do not express any GFP, transfected cells without ADAR-editing of new start codon express GFP intracellularly (middle). Upon ADAR editing of the targeted AUA, a new start codon is generated and the ORF is expanded. The protein product of the expanded ORF encodes a secretory pathway-targeted, HA-tagged, and GPI modified protein. Thus, following editing, GFP could be localized to luminal and extracellular positions in combination with intracellular localized GFP translated from unedited or pre-edited transcripts (right). FIG. 27C) Imaging of live HEK293FT cells transfected with plasmids encoding the edit-target containing GFP-GPI encoding transcript. Cells co-transfected with plasmids encoding editing inactive (top) or active MCP-ADAR (bottom) constructs are shown. AUA-SS-GFP-GPI co-transfected with inactive dADAR showed primarily cytoplasmic localization of GFP, whereas active ADAR showed membrane and ER localization (white arrows). Scale bar is 100 μm. FIG. 27D) Confirmation of the editing-induced altered GFP localization and HA-fusion by antibody staining of the HA epitope occurs only in active MCP-ADAR transfected cells. Transfected cells were fixed and stained for HA epitope tag using an anti-HA antibody and fluorescent AF647 conjugated secondary antibody. The constitutively exported SS-HA-GFP-GPI control and MCP-ADAR conditions had anti-HA AF647 signal that colocalized with GFP signal at the plasma membrane. In contrast, cells transfected with inactive MCP-dADAR contained minimal anti-HA signal. Scale bar-50 μm.

FIG. 28A) General schematic for iADAR mediated elimination of a start codon. An editable RNA motif containing a targeted start codon (AUG) is positioned within the 5" region of a EGFPd2-encoding ORF. Upon editing, the AUG target is converted to IUG, eliminating its recognition by translation initiation machinery and thereby altering/eliminating the EGFPd2-encoding ORF. In cells without iADAR, or prior to/in the absence of editing EGFPd2 will be translated in full; following editing by RBP-ADAR-DD translation of full length EGFPd2 is blocked. FIG. 28B) Secondary structure prediction of an editable loop by RNAfold. MS2 motif is shown in yellow and the AUG start codon is shown in green. Figure discloses SEQ ID NO: 410. FIG. 28C) General plasmid map depicting the reporter scheme. FIG. 28D) Transfection of HEK cells with editable AUG reporters containing MS2-C or MS2-A motifs and active ADAR leads to a significant decrease in translational efficiency of downstream EGFPd2 compared to inactive MCP-dADAR. Cells were transfected with the two reporters and either non-ADAR encoding DNA (NT-white), inactive MCP-dADAR (dADAR-striped), or active MCP-ADAR (ADAR-black). 48 hours post-transfection, cells were trypsinized and analyzed by flow cytometry. Values are plotted as median levels of relative EGFPd2-to-dTomato emissions. Transfected cells were identified based on dTomato gating. Statistical analysis for significance performed via Prism: Two-way ANOVA (n=3 separate transfections). **-$P<0.0001$, *-$P<0.001$, **-$P<0.01$. *-$P<0.05$.

FIG. 29A-29C show Sense Codon Editing for altering the localization, fusion state, and activity of an mRNA encoded protein (AGG to IGG). Sense codon editing of RNA regions encoding a 2A "skipping" peptide results in altered protein targeting, localization, and activity. FIG. 29A) Schematic of sense codon ADAR editing DNA construct. A dsRNA hairpin is inserted at the C-terminus of a skipping deficient T2A-G18R mutant with a MS2-C loop. In the presence of ADAR activity, the Gly 18 is rescued by deamination of the AGG codon to IGG. FIG. 29B) Multiple-sequence alignment of various known 2A "self-cleaving" or "skipping" peptides. Sequences from different viruses are shown, including: P2A, porcine teschovirus-1 (SEQ ID NO: 360); T2A, thosea asigna virus (SEQ ID NO: 361); E2A, equine rhinitis A virus (SEQ ID NO: 362); F2A, foot-and-mouth disease virus (SEQ ID NO: 363). Conserved residues that are needed for the "skipping" activity of these 2A peptides are highlighted. Mutation of these residues eliminates self-cleavage/skipping activity, resulting in the translation of an unskipped (intact) fusion protein. FIG. 29C) Reporter design for editing-induced formation of a skipping peptide. In this design, iADAR activity is utilized to convert a mutated 2A sequence into a skipping active 2A peptide. In the absence of ADAR editing/prior to editing (left), an N-terminal secretion/signal-sequence targets the intact full-length protein into the ER, including the Gal4-VP64 transcription factor sequence. Upon ending of a target codon an active 2A peptide is generated, resulting in the skipping and release of a cytoplasmic Gal4-VP64, which can then be translocated to the nucleus to activate a target gene. Generation of the active 2A peptide is mediated by base editing of an arginine encoding send codon (AGG) to a sense codon that is interpreted as a glycine (IGG). IGG (right), which is read as a glycine, the Gal4-VP64 is now expressed in the cytoplasm where it can translocate into the nucleus and turn on an H2B-mCherry reporter that is integrated with upstream UAS elements.

FIG. 30A) Schematic of 4×UAG MS2-C ADAR-dependent reporter construct. FIG. 30B) Schematic of novel dual-input mRNA reporters. 2 upstream, editable stop codons have an MS2 motif, and the subsequent 2 stop codons have a different RNA motif (PP7, BoxB or HIV-TAR). FIG. 30C) 4×UAG-MS2-C reporter expression of mNeonGreen is dependent on active ADAR. HEK cells co-transfected with the reporter and either non-ADAR coding DNA or MCP-ADAR. FIG. 30D-30F) 2×UAG-MS2 and 2×UAG-PP7 reporter (FIG. 30D) has full expression when co-transfected with MCP-ADAR and PCP-ADAR. However, BoxB (FIG. 30E) and HIV-TAR (FIG. 30F) constructs did not show significant improvement in dual transfection compared to MCP-ADAR transfection. HEK cells co-transfected with the different reporters and different RBD-ADAR constructs. 48 hours post-transfection, cells were lifted, flow cytometry was performed and median relative mNeonGreen-to-mCherry fluorescence was computed for transfected cells based on mCherry gating. Statistical analysis for significance performed via Prism: One-way ANOVA (n=3 separate transfections). **-P<0.0001, *-P<0.001, **-P<0.01, *-P<0.05.

FIG. 31A) General schematic of an internal STOP iADAR product. Here, two polypeptide sequences (red and green) whose sequences must be fused to be functional are separated by a STOP codon and RNA binding motif (RBM). This scheme can be used for split-proteins like a split fluorescent protein (left) or multi-domain proteins like transcription factors (middle) or membrane receptors (right). FIG. 31B) Plasmid map of internal STOP codon reporter construct tested. There are two upstream, editable STOP codons, and one STOP-MS2 loop inserted in the mNeonGreen protein. Editing of all 3 STOP codons would be necessary for rescue of mNeonGreen fluorescence. FIG. 31C) The Internal STOP reporter construct functions as expected, where mNeonGreen expression is stimulated by co-transfection with active MCP-ADAR. HEK293FT cells were co-transfected with the original 4×UAG-MS2 reporter or the Internal STOP reporter and either non-coding DNA, inactive MCP-dADAR (dADAR), or active MCP-ADAR (ADAR). Relative fluorescence is diminished for the Internal-STOP compared to the 4×UAG-MS2 reporter, but is significantly increased when co-expressed with active ADAR. 48 hours post-transfection, cells were lifted, flow cytometry was performed and median relative mNeonGreen-to-mCherry fluorescence was computed for transfected cells based on m Cherry gating.

FIG. 32A) Map of previously tested ALFAtag iADAR, where the intramolecular interaction between ALFA epitope variants and the AlfaNb autoinhibit the deaminase activity. FIG. 32B) Map of newly tested constructs, which contain mutations to the ADAR2-DD and also include a GFP nanobody to improve co-localization of the activating EGFP(R96M)-ALFAtag. FIG. 32C& FIG. 32D) HEK293FT cells were transfected with 4×UAG MS2 Reporter, either EGFP(R96M) or EGFP (R96M)-ALFAtag, and ADAR2-DD mutants for the high affinity ALFA insertion (FIG. 32C) or lower affinity ALFA-PE peptide variant (FIG. 32D). Increasing the strength of the mutation in ALFA-PE constructs leads to an increased fold change. Fluorescence was measured via microscopy and relative fluorescence per cell was computed in ImageJ. Each point represents a single cell (n=1 transfection).

FIG. 33A) Schematic of dual input iADAR proteins. One deaminase domain contains two intramolecular interactions (gray and green, dark gray and dark green) which can lead to autoinhibition of the ADAR independently. Adding antigen (purple) or drug (orange) alone relieves one set of autoinhibitory domains, but addition of both is necessary to activate the protein. FIG. 33B) Plasmid map of ALFA-Bel dual input iADAR. BAD peptide (dark green) is fused to the N-terminus of the ADAR2-DD (F697Y), whereas ALFA-PE is inserted at the 5' RNA binding site (green). There is also a tandem fusion of the AlfaNb and Bcl-xL at the C-terminus. FIG. 33C) The dual input of antigen and drug leads to highest translational efficiency. HEK293FT cells were transfected with the ALFA-Bel iADAR and the 4×UAG MS2 reporter with either EGFP(R96M) or EGFP(R96M)-ALFA and treated with either 1 μM of A-1331852 or DMSO. Significantly, the highest expression of mNeonGreen is seen with dual addition of drug and antigen. 48 hours post-transfection, cells were lifted, flow cytometry was performed and median relative mNeonGreen-to-m Cherry fluorescence was computed for transfected cells based on mCherry gating. Statistical analysis for significance performed via Prism: One-way ANOVA (n=3 separate transfections). **-P<0.0001, -P<0.001, **-P<0.01, *-P<0.05.

FIG. 34A) Drug inducible iADAR scheme based on intramolecular interactions. FIG. 34B) Construct maps for tested iADAR variants. Pep is inserted at the 5' RNA binding site (green) and the NS3 (1B) protease domain (red) is fused to the C-terminus of the deaminase domain.

FIG. 34C) Grazoprevir can induce iADAR constructs. HEK293FT cells were transfected with the NS3 iADAR variants and the 4×UAG MS2 reporter with either 2 μM of grazoprevir or DMSO added at the time of transfection. Increased repression is seen in the K690R mutant, leading to slightly elevated fold-change. 48 hours post-transfection, cells were lifted, flow cytometry was performed and median relative mNeonGreen-to-mCherry fluorescence was computed for transfected cells based on mCherry gating. Statistical analysis for significance performed via Prism: Two-way ANOVA (n=3 separate transfections). **-P<0.0001, *-P<0.001, **-P<0.01, *-P<0.05.

FIG. 35A-35C show Grazoprevir-Inducible ADAR by Active Proteolysis. Ligand Inducible Connection (LiNC) of cleavage labile ADAR domain creates a functional iADAR. FIG. 35A) Schematic of ADAR-LiNC. The NS5A/5B protease cut site (green) is inserted in the ADAR2-DD (blue) at the 5' RNA binding site, and NS3 protease domain (red) is fused to the C-terminus. In the absence of drug (top), cis-proteolysis leads to inactivation of ADAR by dissociation of the two halves of ADAR2-DD. Protease inhibitor addition (bottom) ablates cleavage, leading to correct folding of ADAR-DD and deaminase activity. FIG. 35B) Construct maps of ADAR-LiNC system. dNS3 represents a catalytically inactive protease domain as a control, which is achieved through a S139A mutation. FIG. 35C) ADAR-LiNC leads to another mechanism of grazoprevir-inducible ADAR activity. A higher fold change between the uninduced and induced condition is observed for ADAR2-DD mutants (L699G and F697Y). HEK293FT cells were transfected with the LiNC iADAR variants and the 4×UAG MS2 reporter with either 2 μM of grazoprevir or DMSO added at the time of transfection. 48 hours post-transfection, cells were lifted, flow cytometry was performed and median relative mNeonGreen-to-mCherry fluorescence was computed for transfected cells based on mCherry gating.

FIG. 36A) Map of previous iterations of single-construct designs where the iADAR sensor (blue) is translated upstream of the editable STOP codons before a regulatable payload (green). FIG. 36B) Map of novel single-construct design where the iADAR sensor is driven by a downstream IRES element. Canonical translation leads to the production of a constitutive component (red) and a regulatable downstream component. FIG. 36C) HEK293FT cells were transfected with the IRES IADAR constructs expressing Bcl-XL-BAD variants with 1 μM of A-1331852 or DMSO added at the time of transfection. FIG. 36D) Map of Drug/Protease OR-gate IRES iADAR utilizing Bcl-xL, BAD, and TEVcs. Addition of drug or proteolysis will lead to release of autoinhibition. FIG. 36E) HEK293FT cells were transfected with the Bcl-TEV IRES iADAR and either filler DNA or a plasmid encoding TEV protease (TEVp), and treated with either 1 μM of A-1331852 or DMSO at the time of transfection. The addition of TEV protease or A-1331852 led to higher iADAR activity and mNeonGreen expression. 48 hours post transfection, cells were imaged and the mean mNeonGreen-to-mCherry ratio was computed for transfected cells (gated by mCherry expression) by ImageJ. Each dot represents a single cell (n=1 transfection).

FIG. 37A-37G show Sense Codon Editing for altering the localization, fusion state, and activity of an mRNA encoded protein (AGG to IGG). Sense codon editing of RNA regions encoding a 2A "skipping" peptide results in altered protein targeting, localization, and activity. FIG. 37A) Schematic of sense codon ADAR editing DNA construct. A dsRNA hairpin is inserted at the C-terminus of a skipping deficient T2A-G18R mutant with a MS2-C loop. In the presence of ADAR activity, the Gly 18 is rescued by deamination of the AGG codon to IGG. FIG. 37B) Multiple-sequence alignment of various known 2A "self-cleaving" or "skipping" peptides. Sequences from different viruses are shown, including: P2A, porcine teschovirus-1 (SEQ ID NO: 360); T2A, thosea asigna virus (SEQ ID NO: 361); E2A, equine rhinitis A virus (SEQ ID NO: 362); F2A, foot-and-mouth disease virus (SEQ ID NO: 363). Conserved residues that are needed for the "skipping" activity of these 2A peptides are highlighted. Mutation of these residues eliminates self-cleavage/skipping activity, resulting in the translation of an unskipped (intact) fusion protein. FIG. 37C) Reporter design for editing-induced formation of a skipping peptide. In this design, iADAR activity is utilized to convert a mutated 2A sequence into a skipping active 2A peptide. In the absence of ADAR editing/prior to editing (left), an N-terminal secretion/signal-sequence targets the intact full-length protein into the ER, including the Gal4-VP64 transcription factor sequence. Upon ending of a target codon an active 2A peptide is generated, resulting in the skipping and release of a cytoplasmic Gal4-VP64, which can then be translocated to the nucleus to activate a target gene. Generation of the active 2A peptide is mediated by base editing of an arginine encoding send codon (AGG) to a sense codon that is interpreted as a glycine (IGG). IGG (right), which is read as a glycine, the Gal4-VP64 is now expressed in the cytoplasm where it can translocate into the nucleus and turn on an H2B-mCherry reporter that is integrated with upstream UAS elements. FIG. 37D) Active ADAR-editing of T2A (G18R) and release of Gal4-VP64 in HEK293FT-UAS-H2B-mCherry cells leads to an increase in the median H2B-mCherry fluorescence intensity. Cells were co-transfected with 3 ng of SS-Halo-T2A *-FLAG-Gal4-VP64 and 30 ng of MCP-ADAR or MCP-dADAR. FIG. 37E & FIG. 37F) Active ADAR-editing of T2A (G18R) and release of Gal4-VP64 in HEK293FT-UAS-H2B-mCherry cells leads to an increase in the population of H2B-mCherry positive cells. Cells were co-transfected with 0.3 ng (FIG. 37E) or 0.03 ng (FIG. 37F) of SS-Halo-T2A *-FLAG-Gal4-VP64 and 30 ng of MCP-ADAR or MCP-dADAR. Characteristic H2B-mcherry histograms of TagBFP-positive cells that are expressing inactive dADAR (black) or active ADAR (gray). The dotted lines represent the threshold for calling a cell mCherry-positive, determined by the top 0.5% of non-transfected cells. FIG. 37G) Western blot of HEK293FT-UAS-H2B-mCherry cells co-transfected with the T2A* construct and MCP-ADAR constructs stained for FLAG epitope and GAPDH loading control. Blank squares were transfected with filler DNA and the square with the d represents dADAR. Predicted masses of FLAG-fusion proteins: Halo-T2A *-FLAG-Gal4VP64-67 kDa (skipping incompetent) and FLAG-Gal4VP64-30 kDa (skipping competent). Additional potential bands due to incomplete skipping of C-terminal T2A-TagBFP: Halo-T2A *-FLAG-Gal4VP64-T2A-TagBFP-93 kDa and FLAG-Gal4VP64-T2A-TagBFP-56 kDa. FIG. 37D-37F) 24 hours post-transfection, cells were trypsinized and analyzed by flow cytometry. Transfected cells were identified based on gating for Tag BFP (0.5% of non-transfected cells), and H2B-mCherry positive cells were identified based on gating for mCherry (0.5% of non-transfected cells). Values in FIG. 37D are plotted as median levels of H2B-mCherry in transfected cells. Values in FIG. 37E and FIG. 37F are plotted as percentage of mCherry-positive cells in transfected cells. The histograms shown in FIG. 37E and FIG. 37F are representative of T2A* transfected cells with MCP-ADAR or MCP-dADAR. Statistical analysis for significance performed via Prism: multiple student t-tests (n=3 separate transfections). *-P<0.0001. *-P<0.001, -P<0.01, *-P<0.05.

FIG. 38A-38D show exemplary START-Codon Editing AUA to AUI nucleic acid Constructs (see e.g., FIG. 26), SEQ ID NOs: 292-295.

FIG. 39A-39C show exemplary START-Codon Editing AUA to AUI nucleic acid Constructs (signal sequence & HA), SEQ ID NOs: 296-298.

FIG. 40A-40B show exemplary START-Codon Editing AUG to AUI nucleic acid Constructs (see e.g., FIG. 27), SEQ ID NOs: 299-300.

FIG. 41 shows an exemplary In-Frame Protein Sequence Editing nucleic acid construct, see e.g., . SEQ ID NO: 301.

FIG. 42A-42C show exemplary Two-Input AND-Gate with Multiple STOP codons nucleic acid constructs, SEQ ID NOs: 302-304.

FIG. 43 shows an exemplary nucleic acid construct with Internal STOP Codon Substrates, see e.g., SEQ ID NO: 305.

FIG. 44A-44G show exemplary nucleic acid constructs with Inclusion of ADAR Mutations and Localization Domain for Antigen Sensing, SEQ ID NOs: 306-313.

FIG. 45 shows an exemplary Multi-Input iADAR nucleic acid construct, SEQ ID NO: 314.

FIG. 46A-46C show exemplary Mutation of NS3-peptide based system nucleic acid constructs, SEQ ID NOs: 315-317.

FIG. 47A-47F show exemplary Ligand-Inducible Connection Based iADAR nucleic acid Constructs, SEQ ID NOs: 318-323.

FIG. 48A-48C show exemplary BAD-BclxL IRES nucleic acid Constructs, SEQ ID NOs: 324-326.

FIG. 49 shows an exemplary BAD-AD-BclxL IRES nucleic acid Construct, SEQ ID NO: 327.

FIG. 50 shows exemplary AUA to AUI (signal sequence & HA) amino acid Constructs, SEQ ID NOs: 328-329.

FIG. 51 shows an exemplary In-Frame Protein Sequence Editing amino acid Construct, SEQ ID NO: 330.

FIG. 52 shows an exemplary Internal STOP Codon Substrates amino acid Construct, SEQ ID NOs: 331-333.

FIG. 53A-53D show exemplary amino acid constructs with Inclusion of ADAR Mutations and Localization Domain for Antigen Sensing, SEQ ID NOs: 334-341.

FIG. 54 shows an exemplary Multi-Input iADAR Protein amino acid Construct, SEQ ID NO: 342.

FIG. 55A-55B show exemplary Mutation of NS3-peptide based system amino acid constructs, SEQ ID NOs: 343-345.

FIG. 56A-56C show exemplary Ligand-Inducible Connection Based iADAR amino acid Constructs, SEQ ID NOs: 346-351.

FIG. 57A-57B show exemplary BAD-BelxL IRES amino acid Constructs, SEQ ID NOs: 352-354.

FIG. 58 shows an exemplary BAD-AD-BclxL IRES amino acid Construct, SEQ ID NO: 355.

FIG. 59A-59B show exemplary In-Frame Protein Sequence Editing nucleic acid constructs, SEQ ID NOs: 356-357.

FIG. 60 shows exemplary In-Frame Protein Sequence Editing amino acid constructs, SEQ ID NOs: 358-359.

FIG. 61A) Schematic of in vitro transcribed mRNA constructs. FIG. 61B) Schematic of IADAR mRNA that is delivered by lipofectamine and is dependent on drug to turn on fluorescent protein expression. FIG. 61C) HEK293FT cells either non-transfected (NT) or transfected with catalytically inactive ADAR (dADAR), constitutively active ADAR (ADAR), or conditionally active iADAR (BAD(V)) mRNA circuits. 48 hours post-transfection, cells were analyzed for expression of downstream mNeonGreen, as determined as having a value greater than 1% of non-transfected cells.

DETAILED DESCRIPTION

Figure 1A:
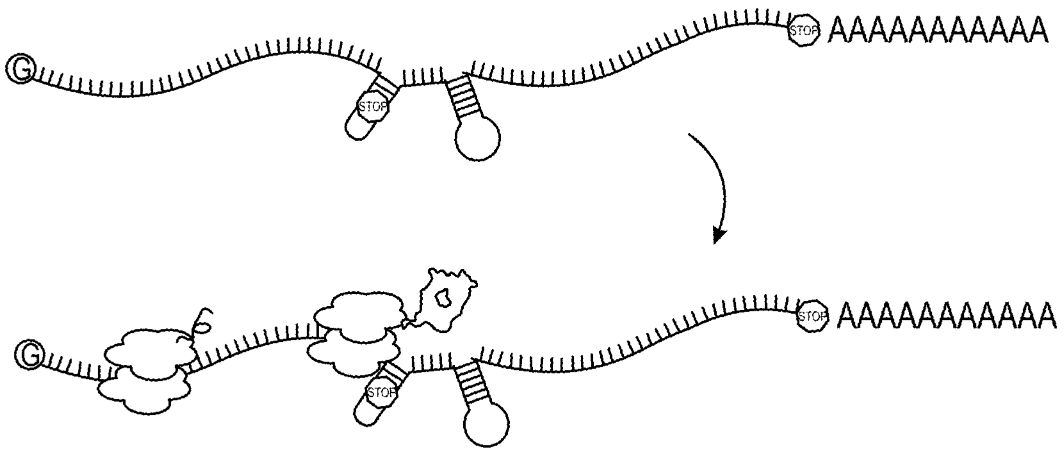
FIG. 1A-1E—ADAR2-DD Can Edit Reporter UAG Stop Codons in dsRNA Hairpins.

Provided herein are compositions, kits, systems and methods related to an inducible adenosine deaminase acting on RNA (ADAR) enzyme, which can be activated in the presence of an inducer. These inducible ADAR (iADAR) enzymes can transition from an OFF ("IADAR-OFF") to an ON ("IADAR-ON") state in the presence of an inducer. When the iADAR is ON state, it can effect the translation of a gene of interest (GOI), depending on the nucleic acid construct that the iADAR acts on, resulting in translation of a GOI being turned ON or OFF. In some embodiments, an iADAR in the on state (iADAR-ON) can edit a target codon. As used herein the term "target codon" refers to a three base pair codon (e.g., a stop codon, a start codon, a non-start codon, or a sense codon) comprising at least one adenosine nucleotide in a double-stranded region of an RNA construct, which is targeted by the activated IADAR (iADAR "ON"), and the activated iADAR deaminates the at least one adenosine nucleotide in the target codon into an inosine nucleotide. By way of example only, an iADAR in the on state (IADAR-ON) can edit a STOP (UAG) codon to UIG, therefore eliminating the STOP codon.

In one embodiment, if the STOP codon is upstream (e.g., 5') of a GOI (referred to herein as an "activation construct"), the iADAR-ON can remove the STOP codon resulting in translation of the downstream GOI. Thus, in this embodiment, in the presence of an inducer, gene translation is ON. That is—in the presence of the inducer, the translation of the GOI is switched from OFF→ON. In another embodiment, if the STOP codon is located 5' of a GOI and a 3' polyA signal (referred to herein as an "inactivation construct"), an iADAR-ON can edit and remove the STOP codon, resulting in translation of the poly A tail and leading to mRNA GOI decay. Thus, in this embodiment, in the presence of an inducer, gene translation is OFF. That is, in the presence of an inducer, the translation of the GOI is switched from ON→OFF. In some embodiments, the mRNA encoding the GOI is also destroyed by the cell.

As disclosed herein, the technology described herein relates to engineered human ADAR deaminase domains (DD), such that the ADAR is modified to be in a constitutively inactive state. Normally ADAR is constitutively active in the presence of its co-factor IP6. This engineering of the DDs of the ADAR enables the ADAR to be inducible, e.g., it is an engineered inducible ADAR (IADAR) that needs an inducer to turn it on. For iADAR to become activated i.e., to be turned ON, it is allosterically modulated from an inactive (iADAR-OFF) to an active state (iADAR-ON) in response to an inducer, e.g., without limitation, a small molecule drug, target antigen-binding, protease activity, and light, or any combination of these stimuli. For illustrative purposes only, and as disclosed herein, the pairing the engineered iADAR with a synthetic mRNA transcripts that comprise a target codon (e.g., STOP, START, non-START, or SENSE codon) located in a double-stranded region of the transcript (e.g., a ds-STOP, ds-START, or ds-SENSE region or loop) that localize the iADAR to an editable target codon enables the iADAR-ON to edit the target codon, therefore, in effect remove/eliminate or mutate the target codon, to change the protein expression of, or mRNA stability of a GOI in a synthetic construct. Accordingly, the technology disclosed herein enables the selective editing of target codons (e.g., STOP, START, non-START, or SENSE codons) in synthetic mRNA transcripts based on user defined and potentially endogenous inputs.

It is envisioned that the use of the iADAR as disclosed herein is not limited to acting on the synthetic constructs defined herein, rather, the inducible iADAR can be used in any gene editing method that uses an ADAR, including but not limited to gene therapy methods, such as, but not limited to, a viral or non-viral delivery of a nucleic acid to a subject that has a target codon (e.g., a STOP, START, non-START, or SENSE codon). Uses of an iADAR as disclosed herein in gene therapy applications enables a system for improved control and/or regulation of a GOI being delivered by the viral vector or non-viral vector, for example, for safety methods enabling GOI expression only when the inducer of the iADAR is present, and/or degradation of the GOI if the delivered GOI needed to be eliminated.

Moreover, in some embodiments, the IADAR can be used in any gene editing method where the target codon (e.g., STOP, START, non-START, or SENSE codon) is inserted into a target nucleic acid sequence, for example, using gene editing methodologies such as CRISPR systems.

I. IADAR

Deaminase proteins, such as, but not limited to, Adenosine Deaminase Acting on RNA (ADAR) have recently been developed as novel tools for RNA editing. In mammalian cells, there are three types of ADAR proteins, Adar1 (two isoforms, p110 and p150), Adar2 and Adar3 (catalytically inactive). The catalytic substrate of ADAR protein is double-stranded RNA, and it can remove the-NH 2 group from an adenosine (A) nucleobase, changing A to inosine (I), which is recognized as guanosine (G) and paired with cytidine (C) during subsequent cellular transcription and translation processes. Previous modifications to ADAR have been reported, where λN peptide is fused to human Adar1 or Adar2 deaminase domain to construct the λN-ADARDD system, which could be guided to bind specific RNA targets by a fusion RNA consisting of BoxB stem loop and antisense RNA. Such a modified λN-ADARDD can edit and change a target A to I by introducing an A-C mismatch at the target A base, resulting in A to G RNA base editing. Other methods for RNA editing include fusing antisense RNA to R/G motif (ADAR-recruiting RNA scaffold) to edit target RNA by overexpressing Adar1 or Adar2 proteins in mammalian cells, and using dCas13-ADAR to precisely target and edit RNA. Additionally, reports of engineered RNA that is partially complementary to the target transcript to recruit native ADAR1 or ADAR2 to change adenosine to inosine at a specific site in a target RNA have been reported, and are referred to as "LEAPER" (Leveraging Endogenous ADAR for Programmable Editing on RNA) and the ADAR-recruiting RNAs are referred to interchangeably as "dRNA" or "arRNA", which is disclosed in UA application No. 20210355494, which is incorporated herein in its entirety reference.

The technology disclosed herein is directed to an inducible ADAR (IADAR), where ADAR has been engineered to be active only in the presence of an inducer, and where the iADAR can edit target codons (e.g., stop, start, non-start, or sense codons) in a synthetic mRNA transcript comprising a ds-target codon (ds-TC) region as disclosed herein, wherein the ds-TC region comprises a target codon located in a double stranded region and a binding motif (BM) for a RNA binding domain, as disclosed herein. As an exemplary example, an iADAR that is ADAR2-DD (E488Q) that is fused to the C-terminus of bacteriophage-derived MS2 coat protein (MCP), which serves as a RNA binding domain and binds a specific RNA motif. While the fusion of MCP to ADAR has previously been reported to have editing activity on dsRNA duplex between a substrate strand and a guide strand, it was for targeting the adenosine deaminase activity to a specific RNA target sequence. Herein, the inventors further engineered and improved the ADAR in that the deaminase domain (DD) has been modified to be inducible, so that adenosine deaminase activity is only ON or functional in the presence of a specific inducer, enabling inducer-dependent adenosine deaminase activity, e.g., editing a target codon (e.g., STOP, START, non-START, or SENSE codon) present on the short hairpin motif in the presence of an inducer. More specifically, the inventors have modified the deaminase domain of the AR to include (1) a RNA binding domain (RBD) that binds to a specific binding motif on a ds-TC region (e.g., ds-STOP, ds-START, or ds-SENSE region) disclosed herein, and (ii) an affinity binding pair that activates the DD in the presence of an inducer, and (iii) specific modifications to the DD polypeptide that enables the function of the adenosine deaminase to be activated only by the presence of an inducer (i.e., the DD is modified to be constitutively active so that the affinity binding pair controls the adenosine deaminase activity) therefore resulting in an inducible ADAR that is capable of target codon (e.g., stop, start, non-start, or sense codon) editing on the same strand to a target transcript or GOI when it expressed in human cells.

In some embodiments, the iAD or iADAR comprises the amino acid sequences of one of SEQ ID NOs: 1-37, 88-94, 168, 169, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 1-37, 88-94, 168, 169, that maintains the same function.

A. iADAR Fusion Protein Components

One aspect of the technology relates to an inducible ADAR (IADAR). In some embodiments, an iADAR is a fusion protein comprising, in brief, two deaminase domains (DD) or two portions of a deaminase domain, each deaminase domain, or portion thereof, attached to, or associated with, a binding protein of a binding pair, where each of the binding proteins bind to each other in the absence of an inducer. When the two binding proteins of the binding pair bind to each other (e.g., in the absence of an inducer), it deforms the IP6-binding pocket and sterically inhibits access of the cofactor IP6 to activate ADAR, therefore the iADAR is in the inactivated or OFF state (IADAR-OFF). Without wishing to be bound by theory, deformation of the IP6 binding pocket prevents stable/ordered IP6 binding and folding of the IP6 binding pocket. "Access" of IP6 to the binding site residues may be impeded (e.g., in a solvent, IP6 may transiently interact with a couple of residues). The coordination of the IP6 interacting residues into the active, folded state of ADAR is impaired. When the inducer is present, the binding pair no-longer bind to each other, enabling access of the IP6 to the binding site in the ADAR, and activating the iADAR to the ON state (i.e., iADAR-ON).

In particular embodiments, the fusion protein comprises: (a) a first portion of a deaminase domain (DD) of an adenosine deaminase; (b) a first member of a binding pair associated with the first portion of the DD; (c) a second portion of the DD; and (d) a second member of a binding pair associated with the second portion of the DD, wherein the first member of the binding pair binds to the second member of the binding pair in the absence of an inducer, resulting in allosteric inhibition of the first and second portions of the DD, and wherein the first member of the binding pair does not bind to the second member of the binding pair in the presence of the inducer, resulting in activation of the first and second portions of the DD.

In some embodiments, in the absence of an inducer, the first and second portions of the DD allosterically inhibit the IP6 binding pocket, e.g., by deformation of the inositol hexaphosphate (IP6) binding pocket, and/or by preventing access of IP6 to a IP6 binding pocket.

In some embodiments, the iADAR fusion protein is a modified adenosine deaminase (AD) selected from any of: Adenosine Deaminase Acting on RNA (ADAR), Adenosine Deaminase TRNA Specific (ADAT), or Adenosine Deaminase Domain Containing (ADAD).

In exemplary embodiments, the iADAR is an engineered Adenosine Deaminase Acting on RNA (ADAR) fusion protein. In some embodiments, the iADAR is selected from an engineered ADAR1, ADAR2, or ADAR3 molecule. In some embodiments, the iADAR is an engineered ADAR1 polypeptide or engineered ADAR2 polypeptide.

In certain embodiments, the iADAR is engineered from a natural or endogenously ADAR present in the host cell, for example, naturally or endogenously present in the eukaryotic cell. In some embodiments, the IADAR is modified based on an iADAR that is endogenously expressed by the host cell. In certain embodiments, the iADAR is exogenous to the host cell. In some embodiments, the iADAR is encoded by a nucleic acid (e.g., DNA or RNA) as disclosed herein. In some embodiments, the method comprises introducing the iADAR or a nucleic acid construct encoding the iADAR into the host cell. In some embodiments, the method does not comprise introducing any protein into the host cell. In some embodiments, the method comprises delivery of ribonucleoprotein comprising an RNA molecule as described herein. In some embodiments, the method comprises co-delivery of the iADAR (or nucleic encoding it) and an RNA molecule as described herein. In certain embodiments, the iADAR is iADAR1 and/or iADAR 2. In some embodiments, the iADAR is one or more iADARs selected from the group consisting of hiADAR1, hiADAR2, murine iADAR1 and murine iADAR2.

In some embodiments, an iADAR2 fusion protein comprises the DD of ADAR2 and comprises residues of SEQ ID NO: 95, or a polypeptide having at least about 85%, or about 85%, or about 90%, or about 95%, or about 98% homology to SEQ ID NO: 95, where SEQ ID NO: 95 comprises E488Q modification for a constitutively active deaminase activity of ADAR2. The E488Q modification of ADAR2 increases the catalytic efficiency and rate of the enzyme as compared to the non-modified ADAR2 enzyme, which is also constitutively active. In some embodiments the iADAR2 can comprise a single polypeptide, or be split into two DD portions, e.g., a DDN and DDC fragments as disclosed herein.

RNA-Binding Domain of the iADAR

In some embodiments, the iADAR fusion protein comprises a RNA-binding domain (RBD) that binds to a binding motif for RBD, which in some embodiments, is located in the ds-TC region (e.g., ds-STOP, ds-START, or ds-SENSE region) of an RNA molecule.

In some embodiments, the RNA-binding domain is selected from the group consisting of MCP, PCP, λN, and HIV tat. In some embodiments, the RNA-binding domain comprises MCP which binds to the Binding motif for RBD (BM) that comprises MS2. In some embodiments, the RNA-binding domain comprises tandem dimers of MCP (tdMCP), which bind to the Binding motif for RBD (BM) that comprises MS2. In some embodiments, the RNA-binding domain comprises PCP which binds to the Binding motif for RBD (BM) that comprises PP7. In some embodiments, the RNA-binding domain comprises tandem dimers of PCP (tdPCP), which bind to the Binding motif for RBD (BM) that comprises PP7. In some embodiments, the RNA-binding domain comprises AN which binds to a ds-TC region (e.g., ds-STOP, ds-START, or ds-SENSE region) that comprises the Binding motif for RBD (BM) that comprises BoxB. In some embodiments, the RNA-binding domain comprises HIV Tat, which binds to a ds-TC region (e.g., ds-STOP, ds-START, or ds-SENSE region) that comprises the Binding motif for RBD (BM) that comprises TAR.

In some embodiments, the RNA-binding domain (RBD) is MCP having an amino acid sequence comprising:

(SEQ ID NO: 100)
MASNFTQFVLVDNGGTGDVTVAPSNFANGIAEWISSNSRSQAYKVTCSV
RQSSAQNRKYTIKVEVPKGAWRSYLNMELTIPIFATNSDCELIVKAMQG
LLKDGNPIPSAIAANSGIY.

In some embodiments of any of the aspects, the RNA-binding domain is MCP that comprises an amino acid of SEQ ID NO: 100. In some embodiments of any of the aspects, the sequence of the RNA-binding domain is MCP comprising SEQ ID NO: 100 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 100 that maintains the same functions as SEQ ID NO: 100 (e.g., where the RNA-binding domain MCP binds to the Binding motif for RBD (BM) MS2).

In some embodiments, the RNA-binding domain (RBD) is PCP having an amino acid sequence comprising:

(SEQ ID NO: 101)
MSKTIVLSVGEATRTLTEIQSTADRQIFEEKVGPLVGRLRLTASLRQNG
AKTAYRVNLKLDQADVVDSGLPKVRYTQVWSHDVTIVANSTEASRKSLY
DLTKSLVATSQVEDLVVNLVPLG.

In some embodiments of any of the aspects, the RNA-binding domain is PCP that comprises an amino acid of SEQ ID NO: 101. In some embodiments of any of the aspects, the sequence of the RNA-binding domain is PCP comprising SEQ ID NO: 101 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 101 that maintains the same functions as SEQ ID NO: 101 (e.g., where the RNA-binding domain PCP binds to the Binding motif for RBD (BM) PP7).

In some embodiments, the RNA-binding domain (RBD) is a mutated RBD, e.g., as disclosed in U.S. Provisional application 63/578,836, filed Aug. 25, 2023, the contents of which are incorporated herein by reference in its entirety. The mutated RBD can be derived from MCP or PCP to create a destabilized MCP or PCP. In some embodiments, the destabilized MCP or PCP comprises at least one degron domain that leads to degradation of any polypeptide comprising it when the polypeptide is not bound to its cognate binding motif in the RNA.

In some embodiments, the RNA-binding domain (RBD) is AN having an amino acid sequence comprising: MADAQTRRRERRAEKQAQWKAAN (SEQ ID NO: 102). In some embodiments of any of the aspects, the RNA-binding domain is AN that comprises an amino acid of SEQ ID NO: 102. In some embodiments of any of the aspects, the sequence of the RNA-binding domain is AN comprising SEQ ID NO: 102 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 102 that maintains the same functions as SEQ ID NO: 102 (e.g., where the RNA-binding domain λN binds to the Binding motif for RBD (BM) BoxB).

In some embodiments, the RNA-binding domain (RBD) is HIV tat having an amino acid sequence comprising: MASGPRPRGTRGKGRRIRR (SEQ ID NO: 103). In some embodiments of any of the aspects, the RNA-binding domain is HIV tat that comprises an amino acid of SEQ ID NO: 103. In some embodiments of any of the aspects, the sequence of the RNA-binding domain is HIV tat comprising SEQ ID NO: 103 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 103 that maintains the same functions as SEQ ID NO: 103 (e.g., where the RNA-binding domain HIV tat binds to the Binding motif for RBD (BM) HIV TAR).

In some embodiments the RBD is located at the N-terminal of the iAD fusion protein. In some embodiments, the iAD fusion protein comprises a RBD attached to the C-terminus of a DD, or DDN, as disclosed herein. In some embodiments, there is a linker located between the RBD and the DD or DDN. In some embodiments, the RBD is located at the most C-terminal end of the iAD fusion protein. In some embodiments, the RBD is located at an internal position of the iAD fusion protein.

B. Deaminase Domain (DD) of Adenosine Deaminase (AD)

Without wishing to be bound by theory, the deaminase domain (DD) of an adenosine deaminase enzyme as disclosed herein, e.g., ADAR, ADAT, or ADAD, can be fused to 2 members of a binding pair, where the binding pair bind to each other in the absence of an inducer, preventing the activation of the AD enzyme, as disclosed herein. In some embodiments each member of the binding pair binds to different portions of the DD, there the DD is a single polypeptide, e.g., for example, see FIG. 11E. In alternative embodiments, the DD is split into two fragments or portions, where the two fragments of the DD form a heterodimer, and each member of the binding pair is fused to each of the DD-split fragments, for example, see FIG. 11A.

In some embodiments, the iADAR comprises a deaminase domain of adenosine deaminase (referred to herein as "AD-DD" or "AD-deaminase domain") that is split into at least two fragments; (i) a first portion of the deaminase domain (AD-DDN or nDD) and (ii) a second portion of a deaminase domain (AD-DDC or cDD), Stated differently, the deaminase domain of the adenosine deaminase (AR-DD), such as but not limited to ADAR, is split into two fragments or polypeptide portions, referred to herein as AD-DDN and AD-DDC, referring to a N-terminal portion of the DD and a C-terminal portion of the DD, respectively. In some embodiments, the two polypeptide portions of DD (i.e., AD-DDN and AD-DDC), together have deaminase activity—that is, both the AD-DDN and AD-DDC are required for deaminase activity. In some embodiments, the AD-DDN has adenosine deaminase activity that is blocked or inhibited by the binding pair, BP1 and BP2 in the absence of an inducer. In some embodiments, the AD-DDC has adenosine deaminase activity that is blocked or inhibited by the binding pair, BP1 and BP2 in the absence of an inducer.

In some embodiments, the two polypeptide fragments of the deaminase domain (e.g., AD-DDN and AD-DDC) of the iADAR fusion protein are capable of converting at least one stop codon into at least one non-stop codon. In some embodiments, the AD-deaminase domain (that is split into two polypeptide fragments; AD-DDN and AD-DDC) is modified so that the adenosine deaminase is constitutively active—that is, if the binding protein pair was not associated, the AD-deaminase domain would be constitutively active (however, as it is part of the iADAR, the adenosine deaminase activity is inhibited in the absence of an inducer). In some embodiments, the AD-deaminase domain, which is split into 2 or more fragments, is a constitutively active AD-deaminase domain, and can, for example comprise one of: an E1008Q mutation in ADAR1; an E488Q mutation in ADAR2; or an E527Q mutation in ADAR3. The E1008Q, E488Q, and E527Q modifications of ADAR1, ADAR2, and ADAR3, respectively, increase the catalytic efficiency and rate of the enzyme as compared to the non-modified enzyme, which is also constitutively active.

In some embodiments, the AD-deaminase domain is from Adenosine Deaminase TRNA Specific (ADAT), for example, ADAT1. In some embodiments, the AD-deaminase domain is from Adenosine Deaminase Domain Containing (ADAD), for example, but not limited to, ADAD1 or ADAD2. In some embodiments, the AD-deaminase domain is from ADAR, ADAT, or ADAD that is a mammalian adenosine deaminase. In some embodiments, the ADAR, ADAT, or ADAD is a human adenosine deaminase.

In some embodiments, the iADAR as disclosed herein comprises a AR-deaminase domain that is split into two or more fragments at the location of a RNA binding loop, e.g., wherein the RNA binding loop is the 5' RNA binding loop (RBL) of ADAR1, ADAR2, ADAR3, ADAD1, or ADAD2. In some embodiments, the AD-deaminase domain is split into two polypeptide fragments (e.g., AD-DDN and AD-DDC) at a 5' RNA binding loop (RBL), where the RBL is selected from any of: residues G969 to K999 of ADAR1: GALFDKSCSDRAMESTESRHYPVFENPKQGK (SEQ ID NO: 134) of ADAR1; residues A454 to Q479 of ADAR2: ARIFSPHEPILEEPADRHPNRKARGQ (SEQ ID NO: 135); residues A493 to H518 of ADAR3: ARLHSPYEITTDLHSSKHLVRKFRGH (SEQ ID NO: 136); residues A334 to K365 of ADAD1: AQIKSQLRLNPHSISAFEANEELCLHVAVEGK (SEQ ID NO: 137); residues A347 to Q375 of ADAD2: AARDIYLPPTSEGGLPHSPPMRLQAHVLGQ (SEQ ID NO: 138); residues K974 to S986 of ADAR1: KSCSDRAMES (SEQ ID NO: 139) of ADAR1; residues F457 to D469 of ADAR2: FSPHEPILEEPAD (SEQ ID NO: 140); residues P498 to S508 of ADAR3: PYEITTDLHSS (SEQ ID NO: 141); residues Q339 to P344 of ADAD1: QLRLNP (SEQ ID NO: 142); or residues P352 to P360 of ADAD2: PPTSEGGLP (SEQ ID NO: 143).

In some embodiments, where the iADAR comprises a AD-deaminase domain from ADAR1, the AD-deaminase domain is split between any of the following: residues S977 and D978 of ADAR1 or residues T984 and E985 of ADAR1, or residues L340 and R341 of ADAD1. In some embodiments, where the iADAR comprises a AD-deaminase domain from ADAR2, the AD-deaminase domain is split between residues A468 and D469 of ADAR2 residues G357 and G358 of ADAD2. In some embodiments, where the iADAR comprises a AD-deaminase domain from ADAR3, the AD-deaminase domain is split between residues S507 and S508 of ADAR3.

In some embodiments, where the DD is a single polypeptide, it comprises amino acids 316-700 of ADAR2, for example, it comprises the amino acid residues of the following sequence:

```
                                          (SEQ ID NO: 95)
QLHLPQVLADAVSRLVLGKFGDLTDNFSSPHARRKVLAGVVMTTGTDVK

DAKVISVSTGTKCINGEYMSDRGLALNDCHAEIISRRSLLRFLYTQLEL

YLNNKDDQKRSIFQKSERGGFRLKENVQFHLYISTSPCGDARIFSPHEP

ILEEPADRHPNRKARGQLRTKIESGQGTIPVRSNASIQTWDGVLQGERL

LTMSCSDKIARWNVVGIQGSLLSIFVEPIYFSSIILGSLYHGDHLSRAM

YQRISNIEDLPPLYTLNKPLLSGISNAEARQPGKAPNFSVNWTVGDSAI

EVINATTGKDELGRASRLCKHALYCRWMRVHGKVPSHLLRSKITKPNVY

HESKLAAKEYQAAKARLFTAFIKAGLGAWVEKPTEQDQFSLT,
```

where E488Q is present.

In some embodiments of any of the aspects, the DD of ADAR2 comprises an amino acid of SEQ ID NO: 95. In some embodiments of any of the aspects, the sequence of the DD of ADAR2 comprises SEQ ID NO: 95 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 95 that maintains the same functions as SEQ ID NO: 95 (e.g., ADAR2-DD that comprises the E488Q modification).

In some embodiments of the aspects, the sequence of the DD of ADAR 2 (e.g., ADAR2-DDC) comprises SEQ ID NO: 95 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 95 and comprises the E448Q modification (i.e., which correspond to a Q residue at position 173 in SEQ ID NO: 95), and that maintains the same functions as SEQ ID NO: 95 (e.g., ADAR2-DD, which comprises the E488Q modifications).

In some embodiments, where the DD of ADAR2 is a single polypeptide, it comprises amino acids 316-700 of ADAR2, for example, it comprises the amino acid residues of the following sequence:

(SEQ ID NO: 96)
QLHLPQVLADAVSRLVLGKFGDLTDNFSSPHARRKVLAGVVMTTG

TDVKDAKVISVSTGTKCINGEYMSDRGLALNDCHAAIISRRSLLR

FLYTQLELYLNNKDDQKRSIFQKSERGGFRLKENVQFHLYISTSP

CGDARIFSPHEPILEEPADRHPNRKARGQLRTKIESGQGTIPVRS

NASIQTWDGVLQGERLLTMSCSDKIARWNVVGIQGSLLSIFVEPI

YFSSIILGSLYHGDHLSRAMYQRISNIEDLPPLYTLNKPLLSGIS

NAEARQPGKAPNFSVNWTVGDSAIEVINATTGKDELGRASRLCKH

ALYCRWMRVHGKVPSHLLRSKITKPNVYHESKLAAKEYQAAKARL

FTAFIKAGLGAWVEKPTEQDQFSLT, where E396A and E488Q modifications are present.

In some embodiments of any of the aspects, the DD of ADAR2 comprises an amino acid of SEQ ID NO: 96. In some embodiments of any of the aspects, the sequence of the DD of ADAR2 comprises SEQ ID NO: 96 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 96 that maintains the same functions as SEQ ID NO: 96 (e.g., ADAR2-DD that comprises E396A and E488Q modification).

In some embodiments of the aspects, the sequence of the DD of ADAR 2 (e.g., .ADAR2-DDC) comprises SEQ ID NO: 96 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 96 and comprises E396A and E448Q modifications (i.e., which correspond to an A residue at position 81 in SEQ ID NO: 96 (E96A) a Q residue at position 173 in SEQ ID NO: 96), and that maintains the same functions as SEQ ID NO: 96 (e.g., ADAR2-DD, which comprises both E396A and E488Q modifications).

In some embodiments, where the DD of ADAR2 is split into two portions, for example (i) a N-terminal portion (ADAR2-DDN) and (ii) a C-terminal portion (ADAR2-DDC), the N-terminal portion comprises amino acids 316-486 of ADAR2. In some embodiments, the C-terminal portion of the AD-DD of ADAR2 comprises amino acids 469-700 of ADAR2.

In some embodiments, ADAR2-DDN comprises the amino acids of (SEQ ID NO: 97)
QLHLPQVLADAVSRLVLGKFGDLTDNFSSPHARRKVLAGVVMTTG

TDVKDAKVISVSTGTKCINGEYMSDRGLALNDCHAEIISRRSLLR

FLYTQLELYLNNKDDQKRSIFQKSERGGFRLKENVQFHLYISTSP

CGDARIFSPHEPILEEPA.

In some embodiments of any of the aspects, the ADAR2-DDN comprises an amino acid of SEQ ID NO: 97. In some embodiments of any of the aspects, the sequence of the ADAR2-DDN comprises SEQ ID NO: 97 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 97 that maintains the same functions as SEQ ID NO: 97 (e.g., ADAR2-DDN).

In some embodiments, the ADAR-DDC comprises the amino acids of:

(SEQ ID NO: 98)
DRHPNRKARGQLRTKIESGQGTIPVRSNASIQTWDGVLQGERLLT

MSCSDKIARWNVVGIQGSLLSIFVEPIYFSSIILGSLYHGDHLSR

AMYQRISNIEDLPPLYTLNKPLLSGISNAEARQPGKAPNFSVNWT

VGDSAIEVINATTGKDELGRASRLCKHALYCRWMRVHGKVPSHLL

RSKITKPNVYHESKLAAKEYQAAKARLFTAFIKAGLGAWVEKPTE

QDQFSLT, where E488Q is present. In some embodiments of any of the aspects, the ADAR2-DDC comprises an amino acid of SEQ ID NO: 98. In some embodiments of any of the aspects, the sequence of the ADAR2-DDC comprises SEQ ID NO: 98 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 98 that maintains the same functions as SEQ ID NO: 98 (e.g., ADAR2-DDC, which comprises E488Q modification).

In some embodiments of any of the aspects, the sequence of the ADAR2-DDC comprises SEQ ID NO: 98 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 98 and comprises E448Q modification (i.e., which corresponds to a Q residue at position 20 in SEQ ID NO: 98), and that maintains the same functions as SEQ ID NO: 98 (e.g., ADAR2-DDC, which comprises E488Q modification).

In some embodiments, the AD-deaminase domain (e.g., ADAR) comprises at least one mutation that decreases the background activity of the enzyme (e.g., activity on non-target RNAs; e.g., off-target activity). In some embodiments, the at least one mutation in the AD-deaminase domain (e.g., ADAR) is in the IP6 binding pocket (see e.g., FIG. 22-24, Example 12). In some embodiments, the at least one mutation in the AD-deaminase domain (e.g., ADAR; e.g., SEQ ID NO: 80) is in an amino acid residue selected from the group consisting of: R400, R522, S531, Y658, K662, Y668, K672, K690, F697, and L699 (see e.g., FIG. 24). In some embodiments, the at least one mutation in the AD-deaminase domain (e.g., ADAR; e.g., SEQ ID NO: 80) is in an amino acid residue selected from the group consisting of: T375, R400, R522, Y658, K662, Y668, K672, K690, F697, and L699. In some embodiments, the at least one mutation in the AD-deaminase domain (e.g., ADAR; e.g., SEQ ID NO: 80) is in an amino acid residue selected from the group consisting of: T375, R400, R522, K662, K672, V688, K690, F697, and L699 (see e.g., Table 11). In some embodiments, the at least one mutation in the AD-deaminase domain (e.g., ADAR; e.g., SEQ ID NO: 80) is selected from the group consisting of: T375G, R400K, R522M, K662R, K662M, K672R, K672M, V688A, V688G, K690R, K690M, F697Y, F697L, F6971, F697V, F697A, F697G, L699V, L699A, and L699G. In some embodiments, the at least one mutation in the AD-deaminase domain (e.g., ADAR; e.g., SEQ ID NO: 80) is selected from the group consisting of: R400K, R522M, K690R, and L699G. In some embodiments, the at least one mutation in the AD-deaminase domain (e.g., ADAR; e.g., SEQ ID NO: 80) is R522M and/or L699G.

In some embodiments, the fusion protein comprising at least one mutation in the AD-deaminase domain comprises one of SEQ ID NOs: 287-291 or an amino acid sequence that is at least at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 287-291, that maintains the same function.

C. Affinity Binding Pairs

As disclosed herein, the first and second binding proteins of an affinity binding pair bind or interact, in the absence of an inducer, to allosterically and/or sterically inhibit the activation of the iADAR by the IP6 co-factor, therefore the iADAR is in the OFF state (iADAR-OFF). In some embodiments, in the absence of an inducer, the binding protein pair allosteric inhibit of the first and second portions of the DD (deaminase domain), where the inhibition is any one or more of: deformation of the inositol hexaphosphate (IP6) binding pocket of first and second portions of the DD, preventing access of IP6 to a IP6 binding pocket.

The affinity binding pair can comprise of two protein or polypeptides that, in the absence of an inducer, engage in protein-protein interaction with each other that link the first and the second portion of the DD together. For example, the fusion protein can comprise a first portion of a DD (AD-DDN) associated with a binding protein 1 (BP1), where the BP1 associates with BP2, where BP2 is fused to the second portion of the DD (AD-DDC). That is, in the absence of an inducer, the fusion protein comprises, not in any particular order, [AD-DDN]-[BP1]-[BP2]-[AD-DDC], where BP1 and BP2 binding pair link AD-DDN and AD-DDC and prevent IP6 access to the binding pocket. When an inducer is present, the AD-DDN and AD-DDC no longer interact and/or prevent IP6 from accessing the binding pocket and AD-DDN and AD-DDC together, have deaminase activity.

In some embodiments, BP1 and BP2 are switched positions, such that BP2 is associated with the first portion of the DD, and BP1 is associated with the second portion of the DD.

In some embodiments, the binding pair can be any linkage protein pairs or moieties that reversibly interact. As disclosed herein, there are different classes of binding pairs that can be used, for example but not limited to, simple ligand and ligand binding protein pair, antibody or antigen binding domain and peptide antigen, a repressible protease activation domain, a Degron domain, a induced-degradation domain, a induced-proximity domains, or a cytosolie sequestering domains, e.g., as disclosed in U.S. Pat. No. 11,530,246, which is incorporated herein in its entirety by reference.

In some embodiments, the first and second members of the binding pair are Bad and Bcl-xL, and the inducer of the first and second binding pairs is A-1331852. In some embodiments, the first and second members of the binding pair are Bad and Bcl-xL, and the inducer of the first and second binding pairs is ABT-737. In alternative embodiments, the first and second members of the binding pair are Bim and Bcl-xL, and the inducer of the first and second binding pairs is A-1331852. In alternative embodiments, the first and second members of the binding pair are Bim and Bcl-xL, and the inducer of the first and second binding pairs is ABT-737. In some embodiments, the first and second members of the binding pair are MS1 and MCL-1, and the inducer of the first and second binding pairs is S63845.

In alternative embodiments, the first member (BP1) of the binding pair comprises an antigen-binding domain, and the second member (BP2) of the binding pair comprises a first antigen, and the inducer comprises a second antigen, where the antigen-binding domain binds to the second antigen with a higher affinity than to the first antigen. That is, the inducer functions as a competitive inhibitor, and BP1 binds with greater affinity to the inducer than to the second antigen of BP2, thereby disrupting the interaction between BP1 and BP2.

In alternative embodiments, the first member (BP1) of the binding pair comprises an antigen-binding domain, and the second member (BP2) of the binding pair comprises a first antigen, and the inducer comprises a second antigen, where the antigen-binding domain binds to the second antigen with a similar affinity than to the first antigen. That is, the inducer functions as a competitive inhibitor, and BP1 binds with similar affinity to the inducer than to the second antigen of BP2, thereby disrupting the interaction between BP1 and BP2.

In some embodiments, the first member (BP1) of the binding pair comprises an anti-ALFA antigen binding domain, and the second member (BP2) of the binding pair comprises a first ALFA antigen, and the inducer of the first and second binding pairs comprises a second ALFA antigen, where anti-ALFA antigen binding domain binds to the second ALFA antigen with a higher affinity than to the first ALFA antigen.

In some embodiments, the first member (BP1) of the binding pair comprises an anti-ALFA antigen binding domain, and the second member (BP2) of the binding pair comprises a first ALFA antigen, and the inducer of the first and second binding pairs comprises a second ALFA antigen, where anti-ALFA antigen binding domain binds to the second ALFA antigen with a similar affinity compared to the first ALFA antigen.

In alternative embodiments, there is a cleavable linkage located either between the AD-DDN and BP1 or AD-DDC and BP2. That is, in the absence of the inducer, the BP1 and BP2 interact preventing activation of iADAR. When the inducer is present, it can cleave and separate cither AD-DDN from BP1 and/or AD-DDC from BP2, therefore while BP1 and BP2 may still interact they no longer sterically inhibit access of IP6 to the binding pocket.

Accordingly, in one embodiment, the iADAR comprises a first member of the binding pair (BP1) that is associated with the AD-DDN, and a second member of the binding pair (BP2) that is associated with the AD-DDC, and where there is a cleavable linker located between the BP2 and AD-DDC. In such an embodiment, in the absence of an inducer, the BP2 is associated with the AD-DDC, therefore the BP1 and BP2 members of the binding pair interact and sterically hinder access of the IP6 cofactor to its binding site (therefore the iADAR is in the iADAR-OFF state or configuration). In the presence of an inducer that is a protease that specifically cleaves the cleavable linker, the association between BP2 and AD-DDC is broken, therefore removing or preventing the steric hindrance by the binding pair, therefore resulting in the iADAR in the iADAR-ON state.

In some embodiments, the cleavable linker is cleaved by an inducer that is a signal, e.g., light signal or sound signal. In some embodiments, the cleavable linker is cleaved by a protease or enzymatic cleavage signal, and the inducer is a protease.

TABLE 4A

List of Exemplary Binding pairs, with the Binding Protein 1 (BP1) and cognate Binding Protein 2 (BP2)

| BP1 | BP2 |
|---|---|
| Bim ((SEQ ID NO: 118) | Bcl-XL (SEQ ID NO: 117) |
| MS1(I)(SEQ ID NO: 119) | Mcl-1 (SEQ ID NO: 120) |
| Bad(L) (SEQ ID NO: 121) or BAD (SEQ ID NO: 116) or Bad(F) ((SEQ ID NO: 115) | Bcl-XL (SEQ ID NO: 117) |
| ALFA (SEQ ID NO: 122) or ALFA-PE ((SEQ ID NO: 124) or ALFA-78 ((SEQ ID NO: 125) | NbALFA (SEQ ID NO: 123) |
| SpyTag (SEQ ID NO: 126) | SpyCatcher (SEQ ID NO: 127) |

TABLE 4B

Exemplary Affinity Binding pairs are selected from any of:

| SEQ ID NO: | Binding Pair (BP1) | Sequence |
|---|---|---|
| 115 | Bad(F) | ASGSGTGAPPNLWAAQRYGRELRRMSDEFV |
| 116 | Bad | APPNLWAAQRYGRELRRMSDEFVDSFKK |
| 117 | Bcl-XL | SNRELVVDFLSYKLSQKGYSWSQFSDVEENRTEAPEGTESEMETPSAINGNPSWHLADSPAVNGATGHSSSLDAREVIPMAAVKQALREAGDEFELRYRRAFSDLTSQLHITPGTAYQSFEQVVNELFRDGVNWGRIVAFFSFGGALCVESVDKEMQVLVSRIAAWMATYLNDHLEPWIQENGGWDTFVELYGNN |
| 118 | Bim | ASGSGSGDMRPEIWIAQELRRIGDEFNAYYARRTG |
| 119 | MS(1)A | ASGGSGGSGRPEIWMTQGLRRLGDEANAYYARRTG |
| 120 | Mcl1 | DELYRQSLEIISRYLREQATGAKDTKPMGRSGATSRKALETLRRVGDGVQRNHETAFQGMLRKLDIKNEDDVKSLSRVMIHVFSDGVTNWGRIVTLISFGAFVAKHLKTINQESCIEPLAESITDVLVRTKRDWLVKQRGWDGFVEFFHVEDLEGG |
| 121 | Bad(L) | ASGSGTGAPPNLWAAQRYGRELRRMSDELV |
| 122 | ALFA | **SRLEEELRRRLTE**P |
| 123 | NbALFA | EVQLQESGGGLVQPGGSLRLSCTASGVTISALNAMAMGWYRQAPGERRVMVAAVSERGNAMYRESVQGRFTVTRDFTNKMVSLQMDNLKPEDTAVYYCHVLEDRVDSFHDYWGQGTQVTVSS |
| 124 | ALFA-PE | GSGP**GRLEEELRRRLSP**G |
| 125 | ALFA-78 | ASGSGP**GRLEQEIRARLSP**GT |
| 126 | Spy Tag | ASGGSGA**HIVMVDAYKPTK**GTG |
| 127 | SpyCatcher | MVDTLSGLSSEQGQSGDMTIEEDSATHIKFSKRDEDGKELAGATMELRDSSGKTISTWISDGQVKDFYLYPGKYTFVETAAPDGYEVATAITFTVNEQGQVTVNGKATKGDAHIG* |

TABLE 4B-continued

| Exemplary Affinity Binding pairs are selected from any of: | | |
|---|---|---|
| SEQ ID NO: | Binding Pair (BP1) | Sequence |
| 128 | PoC1 | VIPDYFKQSFPEGYSWERSMTYEDGGICIATNDITMEGDSFINKIH FKGTNFPPNGPVMQKRTVGWEASTEKMYERDGVLKGDVKMKLLLKG GGHYRCDYRTTYKVKQKPVKLPDYHFVDHRIEILSHDKDYNKVKLY EHAVARNSTDSMDELYKGGSGGMVSKGEETITSVIKPDMKNKLRME GNVNGHAFVIEGEGSGKPFEGIQTIDLEVKEGAPLPFAYDILTTAF HYGNRVFTKYPR |
| 129 | TEV (tobacco Etch Virus) cleavage site | GTENLYFQS |
| 130 | Linker comprising a TEV | GSGGTENLYFQSGTSGGA |

In some embodiments, an iAD, e.g., iADAR fusion protein comprises an AD-DDN associated with a first member of the binding pair (e.g., BP1), and an AD-DDC associated with a second member of the binding pair (e.g., BP2). In some embodiments, the BP1 is a SpyCatcher domain (e.g., SEQ ID NO: 127, or a polypeptide that that is at least 85% sequence identity to SEQ ID NO: 127. In some embodiments, where BP1 is a SpyCatcher domain, the BP2 is a Spy Tag which is associated with the AD-DDC, where the Spy Tag comprised amino acids of SEQ ID NO: 126 or a polypeptide that that is at least 85% sequence identity to SEQ ID NO: 126. In some embodiments, there is a cleavable linker located between the AD-DDN and the BP1. In alternative embodiments, there is a cleavable linker located between the AD-DDC and BP2. In some embodiments, there is a cleavable linker located between the BP1 and its attachment to the AD-DD or AD-DDN, and/or a cleavable linker located between BP2 and its attachment to AD-DD or AD-DDC.

In some embodiments the cleavable linkage comprises a Tobacco Etch Virus cleavage site (e.g., SEQ ID NO: 129). In some embodiments, the cleavable linker located between the AD-DDC and the BP2 (e.g., a SpyCatcher domain or other BP2 as disclosed herein) comprises SEQ ID NO: 130, or a linker that is at least 85% sequence identity to SEQ ID NO: 130. In some embodiments, the cleavable linker is cleaved by TEV protease (SEQ ID NO: 36)

In some embodiments, a cleavable linker located between the BP2 (e.g., Spy Catcher domain) and AD-DDC is a cleavable linker that is cleaved by light at a specific wavelength. In some embodiments, a cleavable linker that is cleaved by light at a specific wavelength and is located between the AD-DDC and the BP2 (e.g. a SpyCatcher domain) is PhoCl comprises SEQ ID NO: 130, or a linker that is at least 85% sequence identity to SEQ ID NO: 130.

Figure 19A:
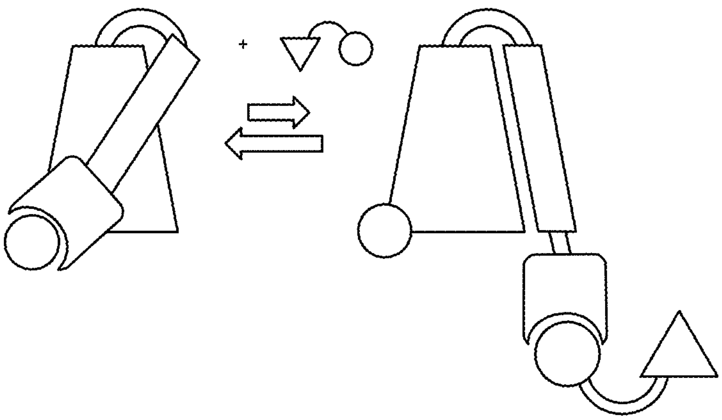
FIG. 19A-19B shows that fusion of an additional binding domain localizes inducer to iADAR and increases sensitivity.
Figure 19B:
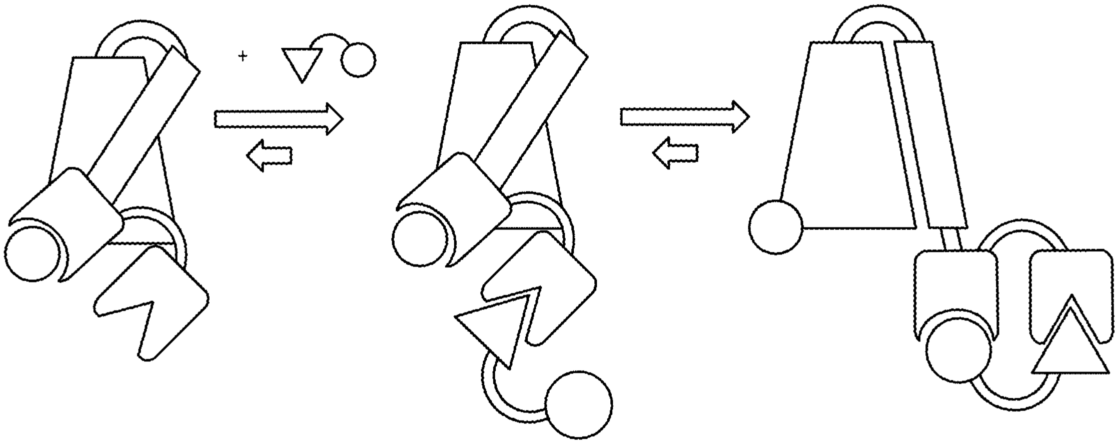

In some embodiments, the iADAR comprises a binding domain (BP1'), which is in addition to the first binding domain (BP1); the additional binding domain can localize the inducer to iADAR and increase sensitivity (see e.g., Example 10, FIG. 19A-19B). Such an additional protein binding domain can increase the local concentration of inducers and reduce the amount of inducer necessary to activate an iADAR.

As a non-limiting example, in antigen activating iADAR systems, fusing an additional antigen binding domain (BP1') that binds a distinct epitope (BP2') from the other antigen binding domain (BP1, which binds to the epitope BP2) serves to bind the antigen (BP2') and increase the local concentration of the inducer, leading to increased sensitivity.

As a non-limiting example, in protease activating iADAR systems, an antigen binding domain (BP1') would bring the protease (BP1) in close proximity to its substrate (BP2) and increase the efficiency and catalytic rate of the cleavage.

The additional binding domain (BP1') can be any of the binding domains described herein, as long as the additional binding domain (BP1') and its cognate antigen (BP2') is different and distinct from the first affinity binding pair (e.g., BP1 and BP2). Non-limiting examples of the additional binding domain (BP1') include: Bcl-XL (SEQ ID NO: 117), Mcl-1 (SEQ ID NO: 120), Bcl-XL (SEQ ID NO: 117), NbALFA (SEQ ID NO: 123), SpyCatcher (SEQ ID NO: 127).

The additional binding domain (BP1') binds to its cognate binding domain (BP2'), non-limiting examples of which include Bim ((SEQ ID NO: 118), MS1(I) (SEQ ID NO: 119), Bad(L) (SEQ ID NO: 121), BAD (SEQ ID NO: 116), Bad(F) ((SEQ ID NO: 115), ALFA (SEQ ID NO: 122), ALFA-PE ((SEQ ID NO: 124), ALFA-78 ((SEQ ID NO: 125), SpyTag (SEQ ID NO: 126) (see e.g., Tables 4A-4B).

In some embodiments, the additional binding domain (BP1') is a repressible protease as described further herein (e.g., NS3), and its cognate antigen (BP2') is a peptide (e.g., an NS3-binding peptide such as ANR) as described further herein.

In some embodiments, the additional binding domain (BP1') is linked to the first binding domain (BP1) directly or indirectly via a linker. In some embodiments, the cognate antigen (BP2', which binds to the additional binding domain, BP1') is linked to the inducer (for the BP1 and BP2 binding pair), directly or indirectly via a linker.

i. Inducers of the Affinity Binding Pair

Depending on the affinity binding pair of the iADAR, inducers can be, but are not limited to, small molecules, proteases, light-inducible control, sound inducible control, cell cycle dependent, ultrasound or other wavelength dependent, heat-activated triggers, antibodies, endogenous triggers, disease triggers, external triggers and cell-specific marker triggers, and the like.

Non-limiting examples of small molecule inducers include A-1331852, ABT-737, and S63845 as described further herein. In embodiments using a repressible protease and its cognate protease domain as the binding pair of the iADAR, the inducer can be a protease inhibitor, e.g., selected from grazoprevir, danoprevir, simeprevir, asunaprevir, ciluprevir, boceprevir, sovaprevir, paritaprevir, ombitasvir, paritaprevir, ritonavir, dasabuvir, and telaprevir or Table 9.

ii. Repressible Protease

In some embodiments, the affinity binding pair comprises a repressible protease, such as NS3, that binds to a peptide domain. See e.g., US20230159600A1 and US20220098246A1, which are incorporated herein by reference in their entireties.

Figure 34A:
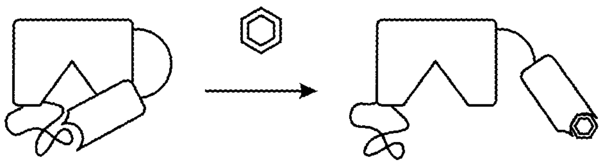
FIG. 34A-34C show Grazoprevir-Inducible iADAR by High Affinity Peptide Based Autoinhibition. The high affinity interaction between HCV NS3 (1B) protease and a binding peptide leads to antiviral drug induced iADAR.
Figure 34B:
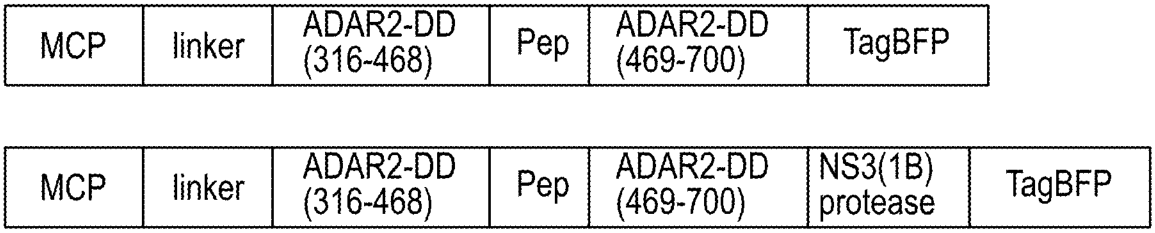

In one aspect described herein is a fusion protein comprising: (a) a first portion of a deaminase domain (DD) of an adenosine deaminase; (b) a repressible protease associated with the first portion of the DD; (c) a second portion of the DD; and (d) a protease-binding peptide associated with the second portion of the DD (see e.g., FIG. 34A-34C). In some embodiments, the repressible protease is capable of binding to the protease-binding peptide in the absence of an inhibitor for the repressible protease, resulting in allosteric inhibition of the first and second portions of the DD. In some embodiments, the repressible protease is not capable of binding to the protease-binding peptide in the presence of the inhibitor for the repressible protease, resulting in activation of the first and second portions of the DD.

In one aspect described herein is a fusion protein comprising: (a) a first portion of a deaminase domain (DD) of an adenosine deaminase; (b) a repressible protease associated with the first portion of the DD; (c) a second portion of the DD; and (d) a protease cleavage site associated with the first and second portions of the DD (see e.g., FIG. 35A-35C). In some embodiments, the repressible protease is capable of binding to the protease cleavage site in the absence of an inhibitor for the repressible protease, resulting in cleavage of the protease cleavage site and inactivation of the first and second portions of the DD. In some embodiments, the repressible protease is not capable of binding to the protease cleavage site in the presence of the inhibitor for the repressible protease, resulting in activation of the first and second portions of the DD.

As used herein, the term "repressible protease" refers to a protease that can be inactivated by the presence or absence of a specific agent (e.g., that specifically binds to the protease). In some embodiments, a repressible protease is active (e.g., binds to a peptide domain) in the absence of the specific agent and is inactive (e.g., does not bind to a peptide domain) in the presence of the specific agent. In some embodiments, the specific agent is a protease inhibitor. In some embodiments, the protease inhibitor specifically inhibits a given repressible protease as described herein.

In some embodiments of any of the aspects, an iAD polypeptide as described herein (or an iADAR polypeptide system collectively) comprises 1, 2, 3, 4, 5, or more repressible protease(s). In some embodiments of any of the aspects, the iAD polypeptide or system comprises one repressible protease. In embodiments comprising multiple repressible proteases, the multiple repressible proteases can be different individual repressible proteases or multiple copies of the same repressible protease, or a combination of the foregoing.

Non-limiting examples of repressible proteases include hepatitis C virus proteases (e.g., NS3 and NS2-3); HIV protease; HIV1 protease; coronavirus (main) protease; SARS-CoV2 protease; Tobacco etch virus (TEV) protease; signal peptidase; proprotein convertases of the subtilisin/kexin family (furin, PC1, PC2, PC4, PACE4, PC5, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N; insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; T F alpha secretase; FAS ligand secretase; TNF receptor-I and -II secretases; CD30 secretase; KL1 and KL2 secretases; IL6 receptor secretase; CD43, CD44 secretase; CD 16-1 and CD 16-11 secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H. For a discussion of proteases, see, e.g., V. Y. H. Hook, Proteolytic and cellular mechanisms in prohormone and proprotein processing, RG Landes Company, Austin, Tex., USA (1998); N. M. Hooper et al., Biochem. J. 321:265-279 (1997); Z. Werb, Cell 9 1:439-442 (1997); T. G. Wolfsberg et al., J. Cell Biol. 131:275-278 (1995); K. Murakami and J. D. Etlinger, Biochem. Biophys. Res. Comm. 146:1249-1259 (1987); T. Berg et al., Biochem. J. 307:313-326 (1995); M. J. Smyth and J. A. Trapani, Immunology Today 16:202-206 (1995); R. V. Talanian et al., J. Biol. Chem. 272:9677-9682 (1997); and N. A. Thomberry et a, J. Biol. Chem. 272: 17907-1791 1 (1997); International Patent Application WO2019118518; Rajakuberan et al., Methods Mol Biol. 2012; 903:393-405; Gao et al. Science 21 Sep. 2018: Vol. 361, Issue 6408, pp. 1252-1258; Tague et al., Nat Methods. 2018 July; 15 (7): 519-522; Lin et al. PNAS Jun. 3, 2008 105 (22) 7744-7749; U.S. patent application Ser. No. 16/832,751 filed Mar. 27, 2020; the contents of each of which are incorporated herein by reference in their entireties.

In some embodiments of any of the aspects, the repressible protease is hepatitis C virus (HCV) nonstructural protein 3 (NS3). NS3, also known as p-70, is a viral nonstructural protein that is a 70 kDa cleavage product of the hepatitis C virus polyprotein. The 631-residue HCV NS3 protein is a dual-function protein, containing the trypsin/chymotrypsin-like serine protease in the N-terminal region and a helicase and nucleoside triphosphatase in the C-terminal region. The minimal sequences required for a functional serine protease activity comprise the N-terminal 180 amino acids of the NS3 protein, which can also be referred to as "NS3a". Deletion of up to 14 residues from the N terminus of the NS3 protein is tolerated while maintaining the serine protease activity. Accordingly, the repressible proteases described herein comprise at the least residues 14-180 of the wildtype NS3 protein.

HCV has at least seven genotypes, labeled 1 through 7, which can also be further designated with "a" and "b" subtypes. Accordingly, the repressible protease can be an HCV genotype 1 NS3, an HCV genotype 1a NS3, an HCV genotype 1b NS3, an HCV genotype 2 NS3, an HCV genotype 2a NS3, an HCV genotype 2b NS3, an HCV genotype 3 NS3, an HCV genotype 3a NS3, an HCV genotype 3b NS3, an HCV genotype 4 NS3, an HCV genotype 4a NS3, an HCV genotype 4b NS3, an HCV genotype 5 NS3, an HCV genotype 5a NS3, an HCV genotype 5b NS3, an HCV genotype 6 NS3, an HCV genotype 6a NS3, an HCV genotype 6b NS3, an HCV genotype 7 NS3, an HCV genotype 7a NS3, or an HCV genotype 7b NS3. In some embodiments of any of the aspects, the repressible protease can be any known HCV NS3 genotype, variant, or mutant, e.g., that maintains the same function. In some embodiments of any of the aspects, the NS3 sequence comprises residues 1-180 of the NS3 protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin, Chapter 6: HCV NS3-4A Serine Protease, Hepatitis C Viruses: Genomes and Molecular Biology, Editor: Tan SL, Norfolk (UK): Horizon Bioscience, 2006; the content of which is incorporated herein by reference in its entirety). In some embodiments of any of the aspects, the repressible protease is a chimera of 2, 3, 4, 5, or more different NS3 genotypes, variants, or mutants as described herein, such that the protease maintains its cleavage and/or binding functions.

In some embodiments of any of the aspects, the repressible protease of an iAD polypeptide as described herein comprises SEQ ID NOs: 208-224 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 208-224 that maintains the same function.

In some embodiments of any of the aspects, the repressible protease of an iAD polypeptide as described herein does not comprise at most the first (i.e., N-terminal) residues of SEQ ID NOs: 208-224. In some embodiments of any of the aspects, the repressible protease of an iAD polypeptide as described herein comprises residues 1-180, 2-180, 3-180, 4-180, 5-180, 6-180, 7-180, 8-180, 9-180, 10-180, 11-180, 12-180, 13-180, 14-180, 15-180, 16-180, 17-180, 18-180, 19-180, 20-180, 21-180, 22-180, 23-180, 24-180, 25-180, 26-180, 27-180, 28-180, 29-180, or 30-180 of SEQ ID NOs: 208-224.

NS3 (genotype 1A), 189 aa; bold text indicates His-57 of the catalytic triad; italicized double underlined text indicates Asp-81 of the catalytic triad; bold italicized indicates Ser-139 of the catalytic triad; double underlined text indicates Asp-168.

SEQ ID NO: 208

APITAYAQQTRGLLGCIITSLTGRDKNQVEGEVQIVSTAT

QTFLATCINGVCWAVYHGAGTRTIASPKGPVIQMYTNVD

Q*D*LVGWPAPQGSRSLTPCTCGSSDLYLVTRHADVIPVRR

RGDSRGSLLSPRPISYLKGS*S*GGPLLCPAGHAVGLFRAA

VCTRGVAKAVDFIPVENLETTMRSPVFTDNSS,

NS3 protease domain (genotype 1A)

SEQ ID NO: 209

APITAYAQQTRGLLGCIITSLTGRDKNQVEGEVQIVSTATQTFLA

TCINGVCWAVYHGAGTRTIASPKGPVIQMYTNVDQDLVGWPAPQG

SRSLTPCTCGSSDLYLVTRHADVIPVRRRGDSRGSLLSPRPISYL

KGSSGGPLLCPAGHAVGLFRAAVCTRGVAKAVDFIPVENLETTMR

SPVFTD,

-continued

NS3 (genotype 1A), 180 aa (see e.g., residues 1027-1206 of Hepatitis C virus genotype 1 polyprotein, NCBI Reference Sequence: NP_671491.1.

SEQ ID NO: 210

APITAYAQQTRGLLGCIITSLTGRDKNQVEGEVQIVSTATQTFLA

TCINGVCWTVYHGAGTRTIASPKGPVIQMYTNVDQDLVGWPAPQG

SRSLTPCTCGSSDLYLVTRHADVIPVRRRGDSRGSLLSPRPISYL

KGSSGGPLLCPAGHAVGLFRAAVCTRGVAKAVDFIPVENLETTMR,

NS3 (genotype 1B), 180 aa (see e.g., residues 1-180 Chain A, Ns3 Protease, PDB: 4K8B_A)

SEQ ID NO: 211

APITAYSQQTRGLLGCIITSLTGRDKNQVEGEVQVVSTATQSFLA

TCVNGVCWTVYHGAGSKTLAGPKGPITQMYTNVDQDLVGWQAPPG

ARSLTPCTCGSSDLYLVTRHADVIPVRRRGDSRGSLLSPRPVSYL

KGSSGGPLLCPSGHAVGIFRAAVCTRGVAKAVDFVPVESMETTMR,

NS3 (genotype 2), 180 aa (see e.g., residues 1031-1210 of Hepatitis C virus genotype 2 polyprotein, NCBI Reference Sequence: YP_001469630.1

SEQ ID NO: 212

APITAYAQQTRGLLGTIVVSMTGRDKTEQAGEIQVLSTVTQSFLG

TSISGVLWTVYHGAGNKTLAGSRGPVTQMYSSAEGDLVGWPSPPG

TKSLEPCTCGAVDLYLVTRNADVIPARRRGDKRGALLSPRPLSTL

KGSSGGPVLCPRGHAVGVFRAAVCSRGVAKSIDFIPVETLDIVTR,

NS3 (genotype 3), 180 aa (see e.g., residues 1033-1212 of Hepatitis C virus genotype 3 polyprotein, NCBI Reference Sequence: YP_001469631.1)

SEQ ID NO: 213

APITAYAQQTRGLLGTIVTSLTGRDKNVVTGEVQVLSTATQTFLG

TTVGGVIWTVYHGAGSRTLAGAKHPALQMYTNVDQDLVGWPAPPG

AKSLEPCACGSSDLYLVTRDADVIPARRRGDSTASLLSPRPLACL

KGSSGGPVMCPSGHVAGIFRAAVCTRGVAKSLQFIPVETLSTQAR,

NS3 (genotype 4), 180 aa (see e.g., residues 1027-1206 of Hepatitis C virus genotype 4 polyprotein, NCBI Reference Sequence: YP_001469632.1)

SEQ ID NO: 214

APITAYAQQTRGLFSTIVTSLTGRDTNENCGEVQVLSTATQSFLG

TAVNGVMWTVYHGAGAKTISGPKGPVNQMYTNVDQDLVGWPAPPG

VRSLAPCTCGSADLYLVTRHADVIPVRRRGDTRGALLSPRPISIL

KGSSGGPLLCPMGHRAGIFRAAVCTRGVAKAVDFVPVESLETTMR,

NS3 (genotype 5), 180 aa (see e.g., residues 1028-1207 of Hepatitis C virus genotype 5 polyprotein, NCBI Reference Sequence: YP_001469633.1)

SEQ ID NO: 215

APITAYAQQTRGVLGAIVLSLTGRDKNEAEGEVQFLSTATQTFLG

ICINGVMWTLFHGAGSKTLAGPKGPVVQMYTNVDKDLVGWPSPPG

-continued

KGSLTRCTCGSADLYLVTRHADVIPARRRGDTRASLLSPRPISYL

KGSSGGPIMCPSGHVVGVFRAAVCTRGVAKALEFVPVENLETTMR,

NS3 (genotype 6), 180 aa (see e.g., residues 1032-1211 of Hepatitis C virus genotype 6 polyprotein, NCBI Reference Sequence: YP_001469634.1)

SEQ ID NO: 216

APITAYAQQTRGLVGTIVTSLTGRDKNEAEGEVQVVSTATQSFLA

TTINGVLWTVYHGAGSKNLAGPKGPVCQMYTNVDQDLVGWPAPLG

ARSLAPCTCGSSDLYLVTRGADVIPARRRGDTRAALLSPRPISTL

KGSSGGPLMCPSGHVVGLFRAAVCTRGVAKALDFIPVENMDTTMR,

NS3 (genotype 7), 180 aa (see e.g., residues 1031-1210 of Hepatitis C virus genotype 7 polyprotein, NCBI Reference Sequence: YP_009272536.1)

SEQ ID NO: 217

APISAYAQQTRGLISTLVVSLTGRDKNETAGEVQVLSTSTQTFLG

TNVGGVMWGPYHGAGTRTVAGRGGPVLQMYTSVSDDLVGWPAPPG

SKSLEPCSCGSADLYLVTRNADVLPLRRKGDGTASLLSPRPVSSL

KGSSGGPVLCPQSHCVGIFRAAVCTRGVAKAVQFVPIEKMQVAQR,

NS3 genotype 1a (HCV-H), 180 aa

SEQ ID NO: 218

APITAYAQQTRGLLGCIITSLTGRDKNQVEGEVQIVSTATQTFLA

TCINGVCWTVYHGAGTRTIASPKGPVIQMYTNVDQDLVGWPAPQG

SRSLTPCTCGSSDLYLVTRHADVIPVRRRGDSRGSLLSPRPISYL

KGSSGGPLLCPAGHAVGLFRAAVCTRGVTKAVDFIPVENLETTMR,

NS3 genotype 1b (HCV-BK), 180 aa

SEQ ID NO: 219

APITAYSQQTRGLLGCIITSLTGRDKNQVEGEVQVVSTATQSFLA

TCVNGVCWTVYHGAGSKTLAAPKGPITQMYTNVDQDLVGWPKPPG

ARSLTPCTCGSSDLYLVTRHADVIPVRRRGDSRGSLLSPRPVSYL

KGSSGGPLLCPFGHAVGIFRAAVCTRGVAKAVDFVPVESMETTMR,

NS3 genotype 2a (HCV-J6), 180 aa

SEQ ID NO: 220

APITAYAQQTRGLLGTIVVSMTGRDKTEQAGEIQVLSTVTQSFLG

TTISGVLWTVYHGAGNKTLAGSRGPVTQMYSSAEGDLVGWPSPPG

TKSLEPCTCGAVDLYLVTRNADVIPARRRGDKRGALLSPRPLSTL

KGSSGGPVLCPRGHAVGVFRAAVCSRGVAKSIDFIPVETLDIVTR,

NS3 genotype 2b (HCV-J8), 180 aa

SEQ ID NO: 221

APITAYTQQTRGLLGAIVVSLTGRDKNEQAGQVQVLSSVTQTFLG

TSISGVLWTVYHGAGNKTLAGPKGPVTQMYTSAEGDLVGWPSPPG

TKSLDPCTCGAVDLYLVTRNADVIPVRRKDDRRGALLSPRPLSTL

KGSSGGPVLCSRGHAVGLFRAAVCARGVAKSIDFIPVESLDVATR,

-continued

NS3 genotype 3a (HCV-Nz11), 180 aa

SEQ ID NO: 222

APITAYAQQTRGLLGTIVTSLTGRDKNVVTGEVQVLSTATQTFLG

TTVGGVIWTVYHGAGSRTLAGAKHPALQMYTNVDQDLVGWPAPPG

AKSLEPCACGSSDLYLVTRDADVIPARRRGDSTASLLSPRPLACL

KGSSGGPVMCPSGHVAGIFRAAVCTRGVAKSLQFIPVETLSTQAR,

In some embodiments of any of the aspects, a repressible protease as described herein is resistant to 1, 2, 3, 4, 5, or more different protease inhibitors as described herein. Non-limiting examples of NS3 amino acid substitutions conferring resistance to HCV NS3 protease inhibitors include: V36L (e.g., genotype 1b), V36M (e.g., genotype 2a), T54S (e.g., genotype 1b), Y56F (e.g., genotype 1b), Q80L (e.g., genotype 1b), Q80R (e.g., genotype 1b), Q80K (e.g., genotype 1a, 1b, 6a), Y1321 (e.g., genotype 1b), A156S (e.g., genotype 2a), A156G, A156T, A156V, D168A (e.g., genotype 1b), 1170V (e.g., genotype 1b), S20N, R26K, Q28R, A39T, Q41R, 171V, Q80R, Q86R, P89L, P89S, S10IN, A111S, P115S, S122R, R155Q, L144F, A150V, R155W, V158L, D168A, D168G, D168H, D168N, D168V, D168E, D168Y, E176K, T178S, M179I, M179V, and M179T. See e.g., Sun et al., Gene Expr. 2018, 18 (1): 63-69; Kliemann et al., World J Gastroenterol. 2016 Oct. 28, 22 (40): 8910-8917; U.S. Pat. Nos. 7,208,309; 7,494,660; the contents of each of which are incorporated herein by reference in their entireties.

In some embodiments of any of the aspects, an iAD polypeptide as described herein comprises an NS3 protease comprising at least one resistance mutation as described herein or any combination thereof. In some embodiments of any of the aspects, an iAD polypeptide as described herein comprises an NS3 protease that is resistant to one protease inhibitor but responsive to at least one other protease inhibitor. In some embodiments of any of the aspects, an iAD system comprises: (a) a first iAD polypeptide comprising a repressible protease (e.g., NS3) that is resistant to a first protease inhibitor and that is susceptible to a second protease inhibitor; and (b) a second iAD polypeptide comprising a repressible protease (e.g., NS3) that is susceptible to a first protease inhibitor and that is resistant to a second protease inhibitor. Accordingly, presence of the first protease inhibitor can modulate the activity of the second iAD polypeptide but not the first iAD polypeptide, while the presence of the second protease inhibitor can modulate the activity of the first iAD polypeptide but not the second iAD polypeptide.

In some embodiments of any of the aspects, a repressible protease as described herein is sensitive to 1, 2, 3, 4, 5, or more different protease inhibitors as described herein. In some embodiments of any of the aspects, the NS3 protease comprises at least one of the following mutations: V36M, TS4A, S122G, F43L, Q80K, S122R, D168Y, or any combination thereof. In some embodiments of any of the aspects, the NS3 protease comprises at least one of the following mutations: V36M, T54A, S122G, or any combination thereof; such a protease is also referred to herein as $NS3^{AI}$, as these mutations increase its sensitivity to asunaprevir (see e.g., SEQ ID NO: 223). In some embodiments of any of the aspects, the NS3 protease comprises at least one of the following mutations: F43L, Q80K, S122R, D168Y, or any combination thereof; such a protease is also referred to herein as $NS3^{TI}$, as these mutations increase its sensitivity to telaprevir (see e.g., SEQ ID NO: 224). See e.g., WO2019023164; Jacobs et al., StaPLs: versatile genetically encoded modules for engineering drug-inducible proteins, Nat Methods. 2018 July; 15(7): 523-526; the contents of each of each are incorporated herein by reference in their entireties.

NS3$^{AI}$; the V36M, T54A, S122G mutations are shown in bold double underlined text, respectively

SEQ ID NO: 223

APITAYAQQTRGLLGCIITSLTGRDKNQVEGEVQIMSTATQTFLA

TCINGVCWAVYHGAGTRTIASPKGPVIQMYTNVDQDLVGWPAPQG

SRSLTPCTCGSSDLYLVTRHADVIPVRRRGDGRGSLLSPRPISYL

KGSSGGPLLCPAGHAVGLFRAAVCTRGVAKAVDFIPVENLETTMR

SPVFTD,

NS3$^{TI}$; the F43L, Q80K, S122R, D168Y mutations are shown in bold double underlined text, respectively

SEQ ID NO: 224

APITAYAQQTRGLLGCIITSLTGRDKNQVEGEVQIVSTATQTLLA

TCINGVCWAVYHGAGTRTIASPKGPVIQMYTNVDKDLVGWPAPQG

SRSLTPCTCGSSDLYLVTRHADVIPVRRRGDRRGSLLSPRPISYL

KGSSGGPLLCPAGHAVGLFRAAVCTRGVAKAVYFIPVENLETTMR

SPVFTD,

In some embodiments of any of the aspects, the polypeptide further comprising a cofactor for the repressible protease. As used herein the term "cofactor for the repressible protease" refers to a molecule that increases the activity of the repressible protease. In some embodiments of any of the aspects, an iAD polypeptide as described herein comprises 1, 2, 3, 4, 5, or more cofactors for the repressible protease. In some embodiments of any of the aspects, the iAD polypeptide comprises one cofactor for each repressible protease. In embodiments comprising multiple cofactors for the repressible protease, the multiple cofactors for the repressible protease can be different individual cofactors or multiple copies of the same cofactor, or a combination of the foregoing.

In some embodiments of any of the aspects, the cofactor is an HSV NS4A domain, and the repressible protease is HSV NS3. The nonstructural protein 4a (NS4A) is the smallest of the nonstructural HCV proteins. The NS4A protein has multiple functions in the HCV life cycle, including (1) anchoring the NS3-4A complex to the outer leaflet of the endoplasmic reticulum and mitochondrial outer membrane, (2) serving as a cofactor for the NS3A serine protease, (3) augmenting NS3A helicase activity, and (4) regulating NS5A hyperphosphorylation and viral replication. The interactions between NS4A and NS4B control genome replication and between NS3 and NS4A play a role in virus assembly.

In some embodiments of any of the aspects, an iAD polypeptide as described herein comprises the portion of the NS4a polypeptide that serves as a cofactor for NS3. Deletion analysis has shown that the central region (approximately residues 21 to 34) of the 54-residue NS4A protein is essential and sufficient for the cofactor function of the NS3 serine protease. Accordingly, in some embodiments of any of the aspects, the repressible protease cofactor comprises a 14-residue region of the wildtype NS4A protein.

In some embodiments of any of the aspects, the cofactor for the repressible protease can be an HCV genotype 1 NS4A, an HCV genotype 1a NS4A, an HCV genotype 1b NS4A, an HCV genotype 2 NS4A, an HCV genotype 2a NS4A, an HCV genotype 2b NS4A, an HCV genotype 3 NS4A, an HCV genotype 3a NS4A, an HCV genotype 3b NS4A, an HCV genotype 4 NS4A, an HCV genotype 4a NS4A, an HCV genotype 4b NS4A, an HCV genotype 5 NS4A, an HCV genotype 5a NS4A, an HCV genotype 5b NS4A, an HCV genotype 6 NS4A, an HCV genotype 6a NS4A, an HCV genotype 6b NS4A, an HCV genotype 7 NS4A, an HCV genotype 7a NS4A, or an HCV genotype 7b NS4A. In some embodiments of any of the aspects, the cofactor for the repressible protease can be any known NS4A genotype, variant, or mutant, e.g., that maintains the same function. In some embodiments of any of the aspects, the NS4A sequence comprises residues 21-31 of the NS4A protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin 2006 supra; see e.g., Table 8).

In some embodiments of any of the aspects, the cofactor for a repressible protease of an iAD polypeptide as described herein comprises SEQ ID NOs: 48, 98, 137-156, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 48, 98, 137-156 that maintains the same functions as one of SEQ ID NOs: 48, 98, 137-156. In some embodiments of any of the aspects, the cofactor for a repressible protease of an iAD polypeptide as described herein comprises SEQ ID NOs: 81, 93, 96, 255-276, or an amino acid sequence that is at least 95% identical to the sequence of one of SEQ ID NOs: 81, 93, 96, 255-276 that maintains the same function.

In some embodiments of any of the aspects, the cofactor for the repressible protease of an iAD polypeptide as described herein comprises residues 1-14, 1-13, 1-12, 1-11, 1-10, 2-14, 2-13, 2-12, 2-11, 2-10, 3-14, 3-13, 3-12, 3-11, 3-10, 4-14, 4-13, 4-12, 4-11, or 4-10 of any of SEQ ID NOs: 225-249.

SEQ ID NO: 225, NS4A (genotype 1A), 13 aa,
GCVVIVGRIVLSG

SEQ ID NO: 226, NS4A domain (genotype 1a)
STWVLVGGVLAALAAYCLSTGCVVIVGRIVLSGKPAIIPDREVLY SEQ ID NO: 227, NS4
(with L6 linker in bold text)
STWVLVGGVLAALAAYCLSTGCVVIVGRIVLSGKP

AGSSGSSIIPDREVLY

SEQ ID NO: 228, NS4A domain,
IDTKYIMTCMSADLEVVTSTWVLVGGVLAALAAY

CLSTGCVVIVGRIVLSGKPAIIPDREVLY

SEQ ID NO: 229, NS4A (genotype 1B), 12 aa,
GSVVIVGRIILS;
see e.g., Chain C,
Nonstructural Protein, PDB: 4K8B C.

SEQ ID NO: 230, NS4A (genotype 1), 14 aa
(see e.g., residues 1678-1691 of Hepatitis C virus genotype 1 polyprotein, NCBI Reference Sequence: NP_671491.1):
GCVVIVGRIVLSGK -continued SEQ ID NO: 231, NS4A (genotype 2), 14 aa (see e.g., residues 1682-1695 of Hepatitis C virus genotype 2 polyprotein, NCBI Reference Sequence: YP_001469630.1:
GCVCIIGRLHINQR SEQ ID NO: 232, NS4A (genotype 3), 14 aa (see e.g., residues 1684-1697 of Hepatitis C virus genotype 3 polyprotein, NCBI Reference Sequence: YP_001469631.1):
GCVVIVGHIELEGK SEQ ID NO: 233, NS4A (genotype 4), 14 aa (see e.g., residues 1678-1691 of Hepatitis C virus genotype 4 polyprotein, NCBI Reference Sequence: YP_001469632.1):
GSVVIVGRVVLSGQ SEQ ID NO: 234, NS4A (genotype 5), 14 aa (see e.g., residues 1679-1692 of Hepatitis C virus genotype 5 polyprotein, NCBI Reference Sequence: YP_001469633.1):
GSVAIVGRIILSGR SEQ ID NO: 235, NS4A (genotype 6), 14 aa (see e.g., residues 1683-1696 of Hepatitis C virus genotype 6 polyprotein, NCBI Reference Sequence: YP_001469634.1):
GCVVICGRIVTSGK SEQ ID NO: 236, NS4A (genotype 7), 14 aa (see e.g., residues 1682-1695 of Hepatitis C virus genotype 7 polyprotein, NCBI Reference Sequence: YP_009272536.1):
GSVVVVGRVVLGSN In some embodiments of any of the aspects, the NS4A sequence is selected from Table 5. In one embodiment, the NS4A comprises residues 21-31 of SEQ ID NO: 237-249 or a sequence that is at least 70% identical.

TABLE 8

Exemplary NS4A sequences (see e.g., Chao Lin 2006 *supra*). Residues 21-31 are bolded.

| SEQ ID NO | Genotype (strain) | Sequence |
|---|---|---|
| 237 | 1a (HCV-H) | STWVL VGGVL AALAA YCLST **GCVVI VGRIV LS**GKP AIIPD REVLY QEFDE MEEC |
| 238 | 1a (HCV-1) | STWVL VGGVL AALAA YCLST **GCVVI VGRVV LS**GKP AIIPD REVLY REFDE MEEC |
| 239 | 1a (HCV-J1) | STWVL VGGVL AALAA YCLST GCVVI VGRIV LSGRP AIIPD REVLY REFDE MEEC |
| 240 | 1b (HCV-BK) | STWVL VGGVL AALAA YCLTT **GSVVI VGRII LS**GRP AIVPD RELLY QEFDE MEEC |
| 241 | 1b (HCV-JK1) | STWVL VGGVL AALAA YCLTT **GSVVI VGRII LS**GRP AIIPD RELLY QEFDE MEEC |
| 242 | 1b (HCV-J4) | STWVL VGGVL AALAA YCLTT **GSVVI VGRII LS**GKP AVVPD RELLY QEFDE MEEC |
| 243 | 1b (HCV-J) | STWVL VGGVL AALAA YCLTT **GSVVI VGRII LS**GRP AVIPD RELLY REFDE MEEC |

TABLE 8-continued

Exemplary NS4A sequences (see e.g., Chao Lin 2006 *supra*). Residues 21-31 are bolded.

| SEQ ID NO | Genotype (strain) | Sequence |
|---|---|---|
| 244 | 2a (HCV-J6) | STWVL AGGVL AAVAA YCLAT **GCVCI IGRLH VN**QRA VVAPD KEVLY EAFDE MEEC |
| 245 | 2a (D14112) | STWVL AGGVL AAVAA YCLAT **GCVSI IGRLH IN**GRA VVAPD KEVLY EAFDE MEEC |
| 246 | 2b (HCV-J8) | SSWVL AGGVL AAVAA YCLAT **GCISI IGRLH LN**DRV VVAPD KEILY EAFDE MEEC |
| 247 | 2b (D14114) | STWVL AGGVL AAVAA YCLAT **GCVSI IGRLH LN**DQV VVTPD KEILY EAFDE MEEC |
| 248 | 3a (HCV-Nz11) | STWVL LGGVL AALAA YCLSV **GCVVI VGHIE LE**GKP ALVPD KEVLY QQYDE MEEC |
| 249 | 3a (HCV-K3a) | STWVL LGGVL AAVAA YCLSV **GCVVI VGHIE LG**GKP ALVPD KEVLY QQYDE MEEC |

In some embodiments of any of the aspects, an iAD polypeptide as described herein can comprise any combination of NS3 and NS4A genotypes, variants, or mutants as described herein. In one embodiment, the NS3 and NS4A are selected from selected from the same genotype as each other. In some embodiments of any of the aspects, the NS3 is genotype 1a and the NS4A is genotype 1b. In some embodiments of any of the aspects, the NS3 is genotype 1b and the NS4A is genotype 1a.

In some embodiments of any of the aspects, an iAD polypeptide as described herein comprises an HSV NS4A domain adjacent to the NS3 repressible protease. In some embodiments of any of the aspects, the NS4A domain is N-terminal of the NS3 repressible protease. In some embodiments of any of the aspects, the NS4A domain is C-terminal of the NS3 repressible protease. In some embodiments of any of the aspects, the iAD polypeptide comprises a peptide linker between the NS4A domain and the NS3 repressible protease. Non-limiting examples of linker (e.g., between the NS4A domain and the NS3 repressible protease) include: SGTS (SEQ ID NO: 250) and GSGS (SEQ ID NO: 251).

In some embodiments of any of the aspects, any two domains as described herein in an iAD polypeptide can be joined into a single polypeptide by positioning a peptide linker, e.g., a flexible linker between them. As used herein "peptide linker" refers to an oligo- or polypeptide region from about 2 to 100 amino acids in length, which links together any of the sequences of the polypeptides as described herein. In some embodiments, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable.

In some embodiments of any of the aspects, the iAD comprises a TimeSTAMP domain (a time-specific tag for the age measurement of proteins). In some embodiments of any of the aspects, the TimeSTAMP comprises a repressible protease, at least one protease cleavage site, and a detectable marker. The detectable marker is removed from the iAD immediately after translation by the activity of the repressible protease until the time a protease inhibitor is added, after which newly synthesized iAD polypeptides retain their markers. TimeSTAMP allows for time-specific tagging of the age measurement of proteins, and allows sensitive and nonperturbative visualization and quantification of newly synthesized proteins of interest with exceptionally tight temporal control.

In some embodiments of any of the aspects, the repressible protease exhibits increased solubility compared to the wild-type protease. As a non-limiting example, the NS3 protease can comprise at least one of the following mutations or any combination thereof: Leu13 is substituted to Glu; Leu 14 is substituted to Glu; Ile17 is substituted to Gln; Ile18 is substituted to Glu; and/or Leu21 is substituted to Gln. In some embodiments of any of the aspects, an iAD polypeptide as described herein comprises a repressible protease comprising SEQ ID NOs: 252-260, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 307-315 that maintains the same functions (e.g., serine protease; increased solubility) as SEQ ID NOs: -252-260; see e.g., US Patent 6333186 and US Patent Publication US20020106642, the contents of each are incorporated herein by reference in their entireties.

```
soluble NS3, 182 aa
                                        SEQ ID NO: 252
MAPITAYAQQTRGLLGCIITSLTGRDKNQVEGEVQIVSTAAQTFL

ATCINGVCWTVYHGAGTRTIASPKGPVIQMYTNVDKDLVGWPAPQ

GSRSLTPCTCGSSDLYLVTRHADVIPVRRRGDSRGSLLSPRPISY

LKGSSGGPLLCPAGHAVGIFRAAVCTRGVAKAVDFIPVESLETTM

RS,

soluble NS3/NS4A, 195 aa
                                        SEQ ID NO: 253
MKKKGSVVIVGRIVLNGAYAQQTRGLLGCIITSLTGRDKNQVEGE

VQIVSTAAQTFLATCINGVCWTVYHGAGTRTIASPKGPVIQMYTN

VDKDLVGWPAPQGSRSLTPCTCGSSDLYLVTRHADVIPVRRRGDS

RGSLLSPRPISYLKGSSGGPLLCPAGHAVGIFRAAVCTRGVAKAV

DFIPVESLETTMRSP,

soluble NS3/NS4A, 195 aa
                                        SEQ ID NO: 254
MKKKGSVVIVGRIVLNGAYAQQTRGEEGCQETSQTGRDKNQVEGE

VQIVSTAAQTFLATCINGVCWTVYHGAGTRTIASPKGPVIQMYTN

VDKDLVGWPAPQGSRSLTPCTCGSSDLYLVTRHADVIPVRRRGDS

RGSLLSPRPISYLKGSSGGPLLCPAGHAVGIFRAAVCTRGVAKAV

DFIPVESLETTMRSP,

soluble NS3/NS4A, 197 aa
                                        SEQ ID NO: 255
MKKKGSVVIVGRINLSGDTAYAQQTRGEEGCQETSQTGRDKNQVE

GEVQIVSTAAQTFLATCINGVCWTVYHGAGTRTIASPKGPVIQMY
```

-continued

```
TNVDKDLVGWPAPQGSRSLTPCTCGSSDLYLVTRHADVIPVRRRG

DSRGSLLSPRPISYLKGSSGGPLLCPAGHAVGIFRAAVCTRGVAK

AVDFIPVESLETTMRSP,

soluble NS3/NS4A, 197 aa
                                        SEQ ID NO: 256
MKKKGSVVIVGRINLSGDTAYAQQTRGEEGCQETSQTGRDKNQVE

GEVQIVSTATQTFLATCINGVCWTVYHGAGTRTIASPKGPVTQMY

TNVDKDLVGWQAPQGSRSLTPCTCGSSDLYLVTRHADVIPVRRRG

DSRGSLLSPRPISYLKGSSGGPLLCPAGHAVGIFRAAVCTRGVAK

AVDFIPVESLETTMRSP

soluble NS3/NS4A, 197 aa
                                        SEQ ID NO: 257
MKKKGSVVIVGRINLSGDTAYAQQTRGEEGCQETSQTGRDKNQVE

GEVQIVSTATQTFLATSINGVLWTVYHGAGTRTIASPKGPVTQMY

TNVDKDLVGWQAPQGSRSLTPCTCGSSDLYLVTRHADVIPVRRRG

DSRGSLLSPRPISYLKGSSGGPLLCPAGHAVGIFRAAVSTRGVAK

AVDFIPVESLETTMRSP

soluble NS3/NS4A, 197 aa
                                        SEQ ID NO: 258
MKKKGSVVIVGRINLSGDTAYAQQTRGEQGCQKTSHTGRDKNQVE

GEVQIVSTATQTFLATSINGVLWTVYHGAGTRTIASPKGPVTQMY

TNVDKDLVGWQAPQGSRSLTPCTCGSSDLYLVTRHADVIPVRRRG

DSRGSLLSPRPISYLKGSSGGPLLCPAGHAVGIFRAAVSTRGVAK

AVDFIPVESLETTMRSP

soluble NS3/NS4A, 197 aa
                                        SEQ ID NO: 259
MKKKGSVVIVGRINLSGDTAYAQQTRGEQGTQKTSHTGRDKNQVE

GEVQIVSTATQTFLATSINGVLWTVYHGAGTRTIASPKGPVTQMY

TNVDKDLVGWQAPQGSRSLTPCTCGSSDLYLVTRHADVIPVRRRG

DSRGSLLSPRPISYLKGSSGGPLLCPAGHAVGIFRAAVSTRGVAK

AVDFIPVESLETTMRSP

NS3aH1, soluble NS3/NS4A (S139A), 196 aa
                                        SEQ ID NO: 260
KKKGSVVIVGRINLSGDTAYAQQTRGEEGCQETSQTGRDKNQVEG

EVQIVSTATQTFLATSINGVLWTVYHGAGTRTIASPKGPVTQMYT

NVDKDLVGWQAPQGSRSLTPCTCGSSDLYLVTRHADVIPVRRRGD

SRGSLLSPRPISYLKGSAGGPLLCPAGHAVGIFRAAVSTRGVAKA

VDFIPVESLETTMRSP,
```

In some embodiments of any of the aspects, the repressible protease comprises mutations to increase binding affinity for a specific ligand. As a non-limiting example, NS3aH1 (e.g., SEQ ID NO: 260) comprises four mutations needed for interaction with the ANR peptide (e.g., SEQ ID NO: 261, GELDELVYLLDGPGYDPIHSD): A7S, E13L, 135V and T42S. Accordingly, in some embodiments of any of the aspects, a repressible protease as described herein comprises at least one of the following mutations: A7S, E13L, 135V and T42S, or any combination thereof.

In some embodiments of any of the aspects, an iAD polypeptide as described herein comprises a repressible protease that is catalytically active. For HCV NS3, the catalytic triad comprises His-57, Asp-81, and Ser-139. In regard to a repressible protease, "catalytically active" refers to the ability to cleave at a protease cleavage site. In some embodiments of any of the aspects, the catalytically active repressible protease can be any repressible protease as described further herein that maintains the catalytic triad, i.e., comprises no non-synonymous substitutions at His-57, Asp-81, and/or Ser-139.

In some embodiments of any of the aspects, an iAD polypeptide as described herein comprises a repressible protease that is catalytically inactive, i.e., dead. In regard to a repressible protease, "catalytically inactive" refers to the inability to cleave at a protease cleavage site. Accordingly, a catalytically inactive NS3 protease can comprise a non-synonymous mutation at any one of His-57, Asp-81, and Ser-139. Non-limiting examples of NS3 inactivating mutations include H57A, D81A, S139A, or any combination thereof. As such, any one of SEQ ID NOs: 208-224 or SEQ ID NOs: 252-260 can comprise a H57A mutation; a D81A mutation; a S139A mutation; any nonsynonymous mutation to His-57, Asp-81, and Ser-139; or any combination thereof. In some embodiments of any of the aspects, any one of SEQ ID NOs: 208-224 or SEQ ID NOs: 252-260 can comprise a S139A mutation. In some embodiments of any of the aspects, a mutation to the catalytic triad does not disrupt other functions of the repressible protease, e.g., binding to a protease inhibitor, and/or binding to a peptide domain.

In some embodiments of any of the aspects, a catalytically-inactive repressible protease of an iAD polypeptide as described herein comprises SEQ ID NOs: 99 or 103, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NOs: 99 or 103 that maintains the same functions as SEQ ID NOS: 262 or 263 (e.g., catalytically inactive). In some embodiments of any of the aspects, a catalytically-inactive repressible protease of an iAD polypeptide as described herein comprises SEQ ID NOs: 262 or 263, or an amino acid sequence that is at least 95% identical to the sequence of SEQ ID NOs: 262 or 263 that maintains the same functions as SEQ ID NOs: 262 or 263 (e.g., catalytically inactive, but maintaining functions of the repressible protease, e.g., binding to a protease inhibitor, and/or binding to a peptide domain).

In some embodiments of any of the aspects, a catalytically-inactive repressible protease is encoded by a nucleic acid sequence comprising SEQ ID NOs: 264 or 265 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NOs: 264 or 265 that maintains the same function, or a codon-optimized version thereof. In some embodiments of any of the aspects, a catalytically-inactive repressible protease is encoded by a nucleic acid sequence comprising SEQ ID NOs: 75, 79 or a sequence that is at least 95% identical to SEQ ID NOs: 264 or 265 that maintains the same function.

NS3 (genotype 1B; S139A), 537 nt; bold text (e.g., nt 409-411 of SEQ ID NO: 75) indicates the conserved S139 residue mutated to alanine, i.e., S139A.

SEQ ID NO: 262

ATCACGGCCTACTCCCAACAGACGCGGGGCCTACTTGGTTGCATCATCACTAGCCTCACAGG

CCGGGACAAGAACCAGGTCGAAGGGGAGGTTCAAGTGGTTTCTACCGCAACACAATCTTTC

CTGGCGACCTGCGTCAACGGCGTGTGCTGGACTGTCTACCATGGCGCTGGCTCGAAGACCCT

AGCCGGTCCAAAAGGTCCAATCACCCAAATGTACACCAATGTAGACCAGGACCTCGTCGGC

TGGCAGGCGCCTCCAGGGGCGCGCTCCTTGACACCATGCACCTGTGGCAGCTCGGACCTTTA

CTTGGTCACGAGACATGCTGATGTCATTCCGGTGCGCCGGCGAGGCGACAGCAGGGGAAGT

CTACTCTCCCCCAGGCCCGTCTCCTACCTGAAAGGCTCCGCAGGTGGTCCATTGCTTTGCCCT

TCGGGGCACGCTGTGGGCATCTTCCGGGCTGCTGTGTGCACCCGGGGGGTCGCGAAGGCGGT

GGACTTCGTGCCCGTTGAGTCTATGGAAACTACCATGCGGTCT

NS3 (genotype 1A; S139A), 567 nt; bold dotted underlined text indicates His-57 of the catalytic triad; italicized double underlined text indicates Asp-81 of the catalytic triad; bold italicized dotted underlined text indicates Ser-139 of the catalytic triad mutated to alanine (S139A); zig zag underlined text indicates Asp-168.

SEQ ID NO: 264

GCGCCCATCACGGCGTACGCCCAGCAGACGAGAGGCCTCCTAGGGTGTATAATCACCAGCC

TGACTGGCCGGGACAAAAACCAAGTGGAGGGTGAGGTCCAGATCGTGTCAACTGCTACCCA

AACCTTCCTGGCAACGTGCATCAATGGGGTATGCTGGGCAGTCTACCACGGGGCCGGAACG

AGGACCATCGCATCACCCAAGGGTCCTGTCATCCAGATGTATACCAATGTGGACCAA*GAC*CT

TGTGGGCTGGCCCGCTCCTCAAGGTTCCCGCTCATTGACACCCTGTACCTGCGGCTCCTCGGA

CCTTTACCTGGTCACGAGGCACGCCGATGTCATTCCCGTGCGCCGGCGAGGTGATAGCAGGG

GTAGCCTGCTTTCGCCCCGGCCCATTTCCTACTTGAAAGGCTCC*GCG*GGGGGTCCGCTGTTGT

-continued

GCCCCGCGGGACACGCCGTGGGCCTATTCAGGGCCGCGGTGTGCACCCGTGGAGTGGCTAA

AGCGGTGGACTTTATCCCTGTGGAGAACCTAGAGACAACCATGAGATCCCCGGTGTTCACGG

ACAACTCCTCT

NS3 (genotype 1B; S139A), 179 aa; bold text (e.g., nt 409-411 of SEQ ID NO: 262) indicates S139A.

SEQ ID NO: 263

ITAYSQQTRGLLGCIITSLTGRDKNQVEGEVQVVSTATQSFLATCVNGVCWTVYHGAGSKTLAG

PKGPITQMYTNVDQDLVGWQAPPGARSLTPCTCGSSDLYLVTRHADVIPVRRRGDSRGSLLSPRP

VSYLKGSAGGPLLCPSGHAVGIFRAAVCTRGVAKAVDFVPVESMETTMRS

NS3 (genotype 1A; S139A), 189 aa; bold dotted underlined text indicates His-57 of the catalytic triad; italicized double underlined text (e.g., nt 241-243 of SEQ ID NO: 264) indicates Asp-81 of the catalytic triad; bold italicized dotted underlined text (e.g., nt 415-417 of SEQ ID NO: 264) indicates Ser-139 of the catalytic triad mutated to alanine (S139A); zig zag underlined text (e.g., nt 502-504 of SEQ ID NO: 264) indicates Asp-168.

SEQ ID NO: 265

APITAYAQQTRGLLGCIITSLTGRDKNQVEGEVQIVSTATQTFLATCINGVCWAVYHGAGTRTIA

SPKGPVIQMYTNVDQ*D*LVGWPAPQGSRSLTPCTCGSSDLYLVTRHADVIPVRRRGDSRGSLLSPR

PISYLKGS*A*GGPLLCPAGHAVGLFRAAVCTRGVAKAVDFIPVENLETTMRSPVFTDNSS

In some embodiments of any of the aspects, the binding between the repressible protease and its cognate peptide domain can be disrupted by an inducer, such as a protease inhibitor. In some embodiments of any of the aspects, an iAD polypeptide as described herein is in combination with a protease inhibitor. As used herein, "in combination with" refers to two or more substances being present in the same formulation in any molecular or physical arrangement, e.g., in an admixture, in a solution, in a mixture, in a suspension, in a colloid, in an emulsion. The formulation can be a homogeneous or heterogeneous mixture. In some embodiments of any of the aspects, the active compound(s) can be comprised by a superstructure, e.g., nanoparticles, liposomes, vectors, cells, scaffolds, or the like, said superstructure is which in solution, mixture, admixture, suspension, etc., with the iAD polypeptide or iAD polypeptide system. In some embodiments of any of the aspects, the iAD polypeptide is bound to a protease inhibitor bound to the repressible protease. In some embodiments of any of the aspects, the iAD polypeptide is bound specifically to a protease inhibitor bound to the repressible protease.

In some embodiments of any of the aspects, the iAD polypeptide is in combination with 1, 2, 3, 4, 5, or more protease inhibitors. In some embodiments of any of the aspects, the iAD polypeptide is in combination with one protease inhibitor. In embodiments comprising multiple protease inhibitors, the multiple protease inhibitors can be different individual protease inhibitors or multiple copies of the same protease inhibitor, or a combination of the foregoing.

In some embodiments of any of the aspects, the protease inhibitor is grazoprevir (abbreviated as GZV or GZP; see e.g., PubChem CID: 44603531). In some embodiments of any of the aspects, the protease inhibitor is danoprevir (DNV; see e.g., PubChem CID: 11285588). In some embodiments of any of the aspects, the protease inhibitor is an approved NS3 protease inhibitor, such as but not limited to grazoprevir, danoprevir, simeprevir, asunaprevir, ciluprevir, boceprevir, sovaprevir, paritaprevir, ombitasvir, paritaprevir, ritonavir, dasabuvir, and telaprevir. Additional non-limiting examples of NS3 protease inhibitors are listed in Table 9 (see e.g., McCauley and Rudd, Hepatitis C virus NS3/4a protease inhibitors, Current Opinion in Pharmacology 2016, 30:84-92; the content of which is incorporated herein by reference in its entirety).

TABLE 9

Exemplary NS3/NS4A protease inhibitors

| Description or Name(s) | Structure |
|---|---|
| The N-terminal hexapeptide product of substrate cleavage (e.g., DDIVPC-OH (SEQ ID NO: 404)) | 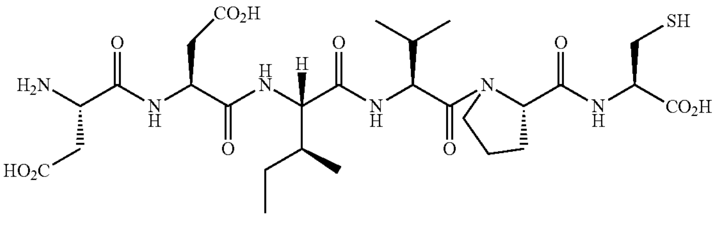 [SMILES: CC[C@H](C)[C@H](NC(=O)[C@H](CC(=O)O)NC(=O)[C@@H](N)CC(=O)O)C(=O)N[C@H](C(=O)N1CCC[C@H]1C(=O)N[C@@H](CS)C(=O)O)C(C)C] 1 |

TABLE 9-continued
| Exemplary NS3/NS4A protease inhibitors | |
|---|---|
| Description or Name(s) | Structure |
| One of the products of cleavage of the NS4a-NS4b peptide (e.g., Ac-DEMEEC-OH (SEQ ID NO: 405)) | 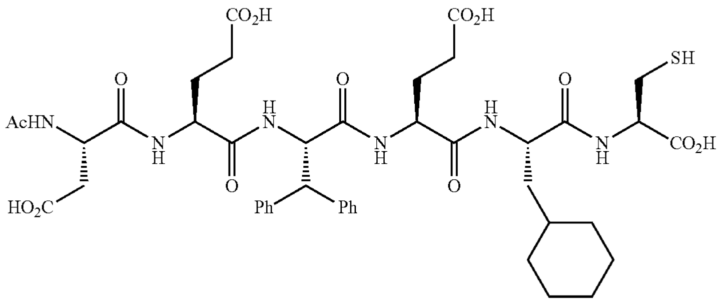 [SMILES: CC(=O)N[C@@H](CC(=O)O)C(=O)N[C@@H](CCC(=O)O)C(=O)N[C@H](C(=O)N[C@@H](CCC(=O)O)C(=O)N[C@@H](CC1CCCCC1)C(=O)N[C@@H](CS)C(=O)O)C(c1ccccc1)c1ccccc1] 2 |
| VICTRELIS ™ boceprevir SCH503034 | 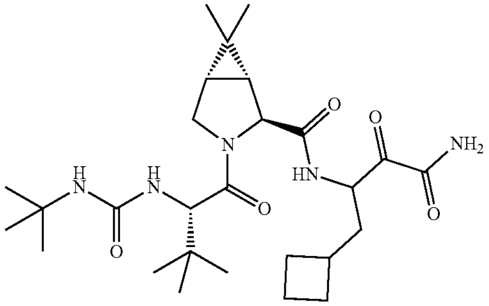 [SMILES: CC(C)(C)NC(=O)N[C@H](C(=O)N1C[C@H]2[C@@H]([C@H]1C(=O)NC(CC1CCC1)C(=O)C(N)=O)C2(C)C)C(C)(C)C] |
| INCIVEK ™, INCIVIO ™, telaprevir, VX-950 | 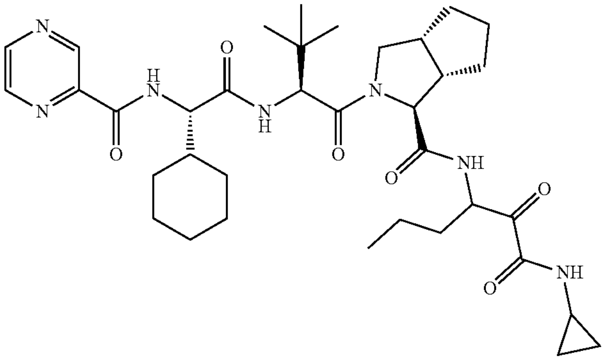 [SMILES: CCCC(NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1] |
| Ciluprevir; BILN-2061 | 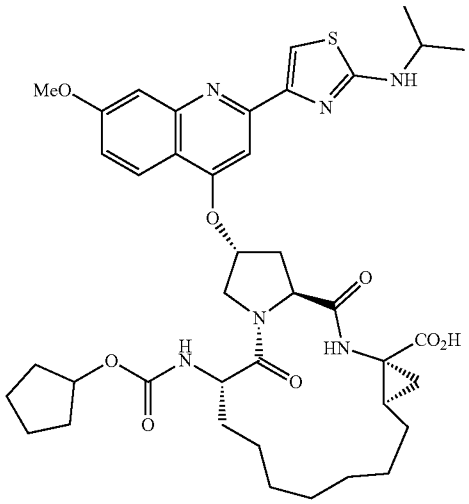 |

TABLE 9-continued
| Exemplary NS3/NS4A protease inhibitors | |
|---|---|
| Description or Name(s) | Structure |
| BMS-605339 | 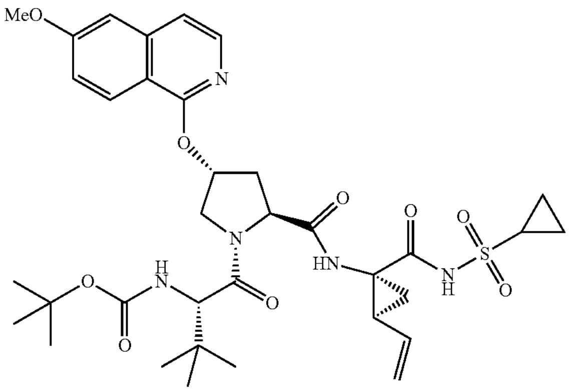 |
| MK-4519 | 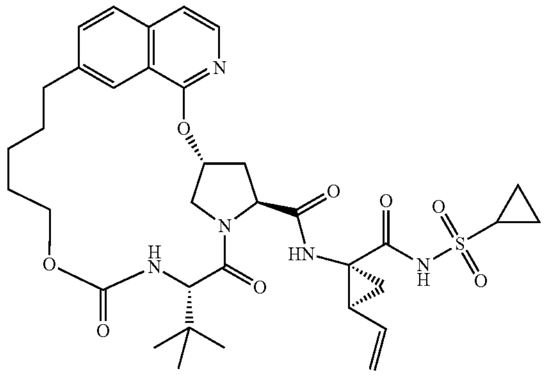 [SMILES: C=C[C@@H]1C[C@]1(NC(=O)[C@@H]1C[C@@H]2CN1C(=O)[C@H](C(C)(C)C)NC(=O)OCCCCCc1ccc3ccnc(c3c1)O2)C(=O)NS(=O)(=O)C1CC1] |
| faldaprevir, BI-201335 | 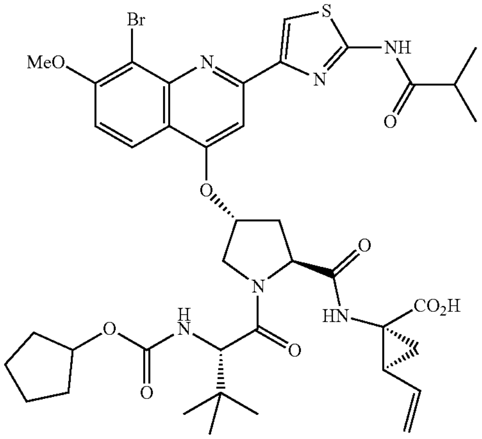 [SMILES: C=C[C@@H]1C[C@]1(NC(=O)[C@@H]1C[C@@H](Oc2cc(-c3csc(NC(=O)C(C)C)n3)nc3c(Br)c(OC)ccc23)CN1C(=O)[C@@H](NC(=O)OC1CCCC1)C(C)(C)C)C(=O)O] |

TABLE 9-continued
| Exemplary NS3/NS4A protease inhibitors | |
|---|---|
| Description or Name(s) | Structure |
| Danoprevir, ITMN-191, R7227 | 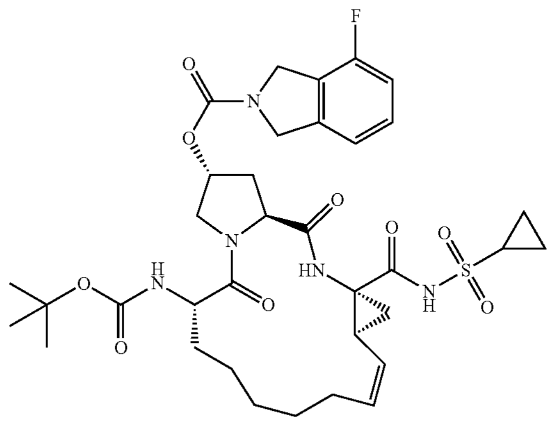 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](OC(=O)N3Cc4cccc(F)c4C3)CN2C1=O] |
| SUNVEPRA ™ asunaprevir, BMS-650032 | 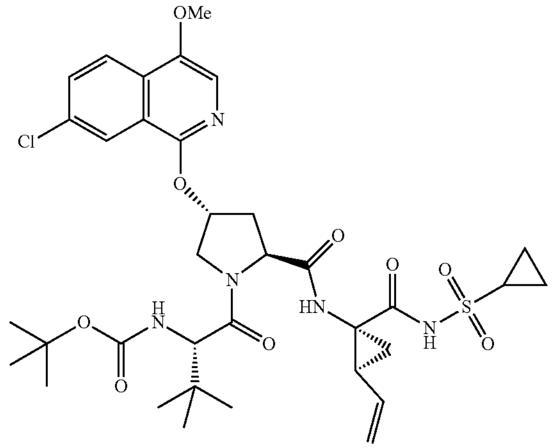 [SMILES: C=C[C@@H]1C[C@]1(NC(=O)[C@@H]1C[C@@H](Oc2ncc(OC)c3ccc(Cl)cc23)CN1C(=O)[C@@H](NC(=O)OC(C)(C)C)C(C)(C)C)C(=O)NS(=O)(=O)C1CC1] |
| VANIHEP ™ vaniprevir, MK-7009 | 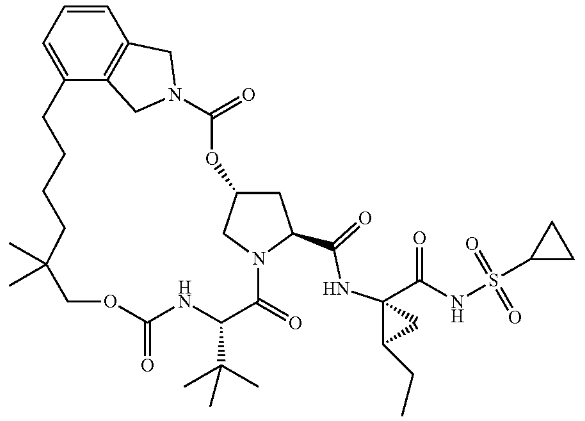 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1CN(C3)C(=O)O2)C(=O)NS(=O)(=O)C1CC1] |

TABLE 9-continued
| Exemplary NS3/NS4A protease inhibitors | |
|---|---|
| Description or Name(s) | Structure |
| OLYSIO ™ simeprevir, TMC-435350 | 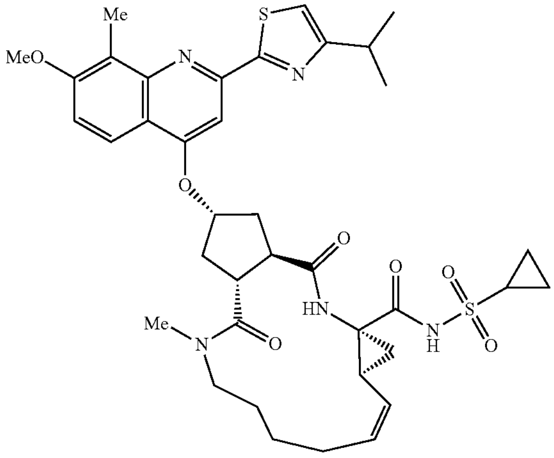 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C] |
| Sovaprevir, ACH-1625 | 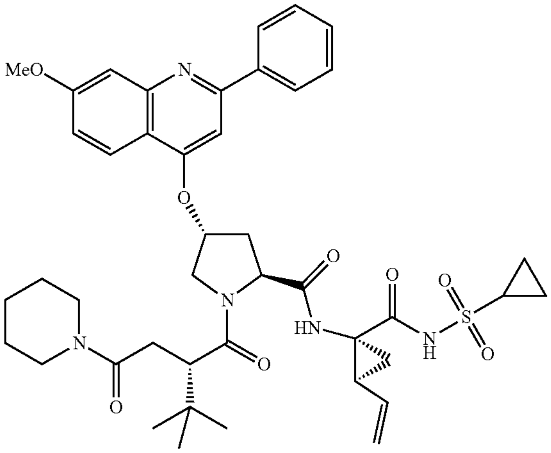 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] |
| Deldeprevir/neceprevir, ACH-2684 | 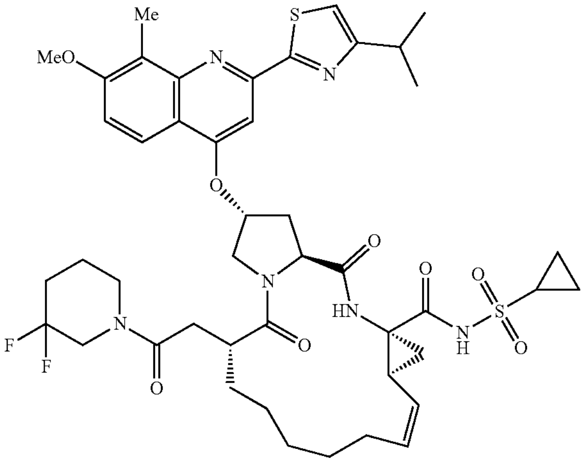 [SMILES: COc1ccc2c(O[C@@H]3C[C@H]4C(=O)N[C@]5(C(=O)NS(=O)(=O)C6CC6)C[C@H]5/C=C\CCCCC[C@H](CC(=O)N5CCCC(F)(F)C5)C(=O)N4C3)cc(-c3nc(C(C)C)cs3)nc2c1C] |

TABLE 9-continued
| Exemplary NS3/NS4A protease inhibitors | |
|---|---|
| Description or Name(s) | Structure |
| IDX320 | 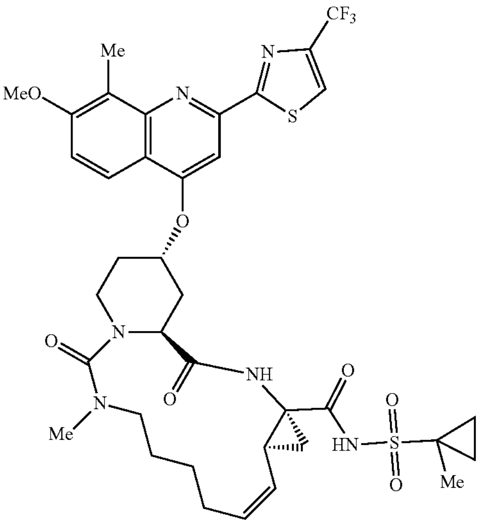 [SMILES: COc1ccc2c(O[C@H]3CCN4C(=O)N(C)CCCC/C=C\[C@@H]5C[C@@]5(C(=O)NS(=O)(=O)C5(C)CC5)NC(=O)[C@@H]4C3)cc(-c3nc(C(F)(F)F)cs3)nc2c1C] |
| GS-9256 | 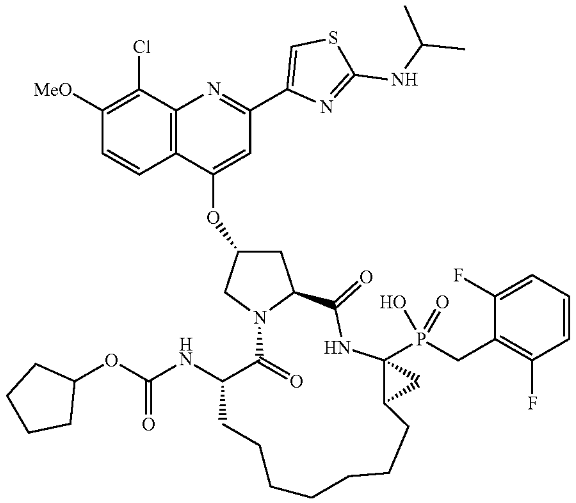 |
| PHX1766 | 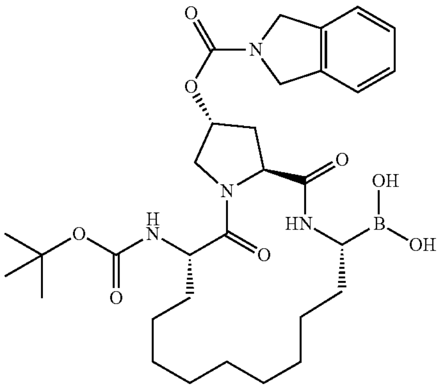 [SMILES: CC(C)(C)OC(=O)N[C@H]1CCCCCCCCC[C@@H](B(O)O)NC(=O)[C@@H]2C[C@@H](OC(=O)N3Cc4ccccc4C3)CN2C1=O] |

TABLE 9-continued
| Exemplary NS3/NS4A protease inhibitors | |
|---|---|
| Description or Name(s) | Structure |
| MK-2748 | 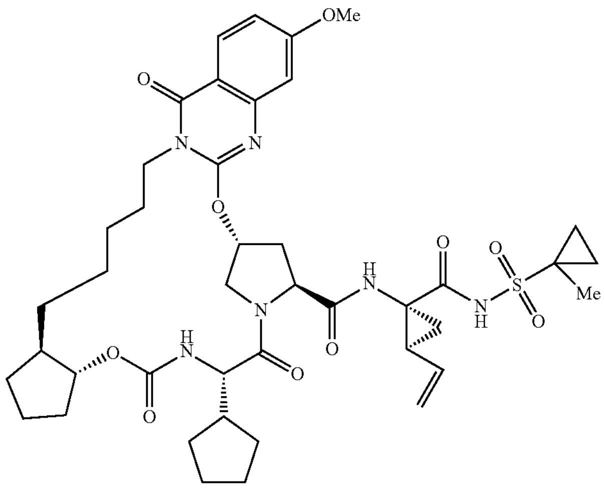 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(OC)ccc3c1=O)O2)C(=O)NS(=O)(=O)C1(C)CC1] |
| Vedrorevir, GS-9451, GS-9451 | 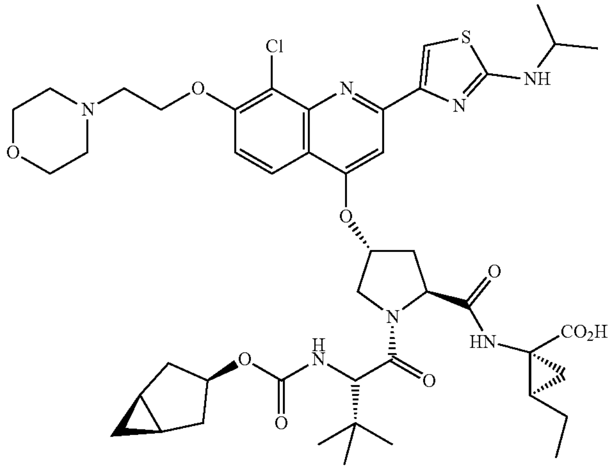 |
| MK-6325 | 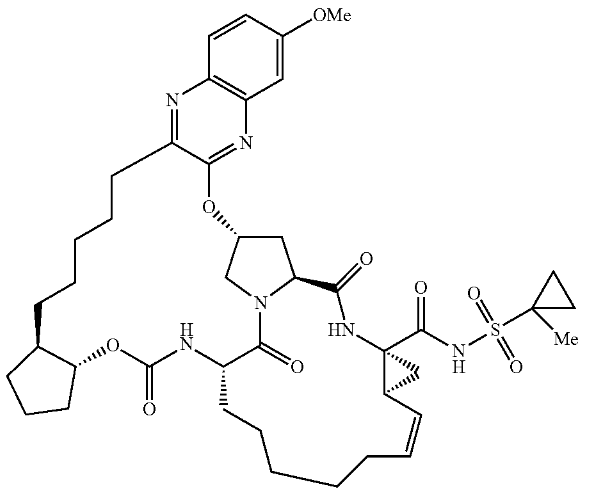 [SMILES: COc1ccc2nc3c(nc2c1)O[C@@H]1C[C@H]2C(=O)N[C@]4(C(=O)NS(=O)(=O)C5(C)CC5)C[C@H]4/C=C\CCCCC[C@H](NC(=O)O[C@@H]4CCC[C@H]4CCCCC3)C(=O)N2C1] |

TABLE 9-continued
| Exemplary NS3/NS4A protease inhibitors | |
|---|---|
| Description or Name(s) | Structure |
| MK-8831 | 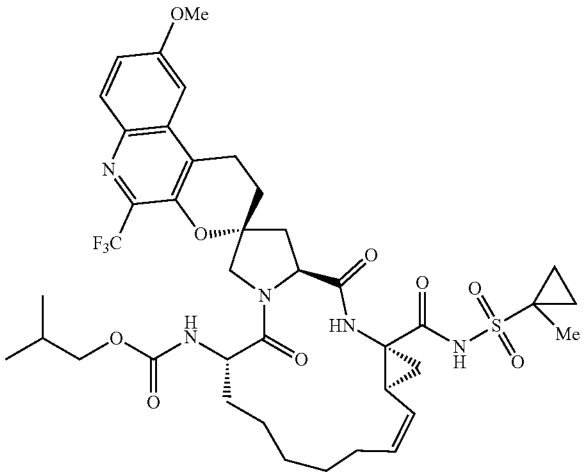 [SMILES: COc1ccc2nc(C(F)(F)F)c3c(c2c1)CC[C@]1(C[C@H]2C(=O)N[C@]4(C(=O)NS(=O)(=O)C5(C)CC5)C[C@H]4/C=C\CCCCC[C@H](NC(=O)OCC(C)C)C(=O)N2C1)O3] |
| VIKERA PAK ™ paritaprevir, ABT-450 | 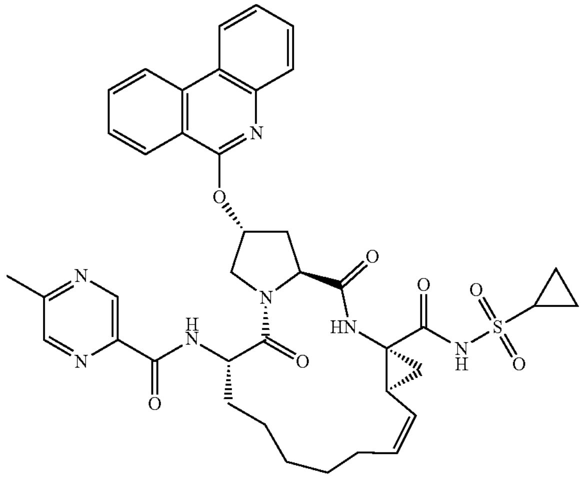 |
| ZEPATIER ™ grazoprevir, MK-5172 | 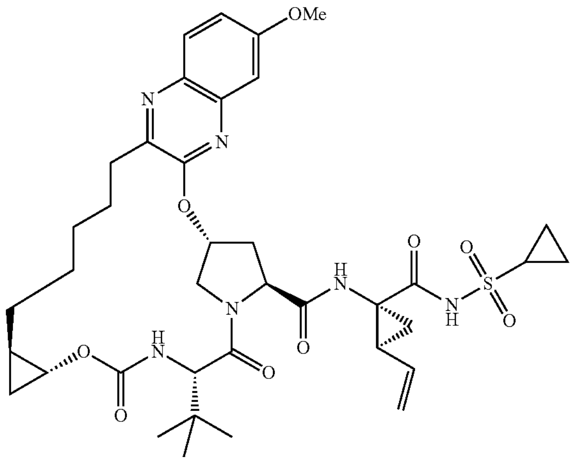 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1] |

TABLE 9-continued

| Exemplary NS3/NS4A protease inhibitors | |
|---|---|
| Description or Name(s) | Structure |
| Glecaprevir, ABT-493 | 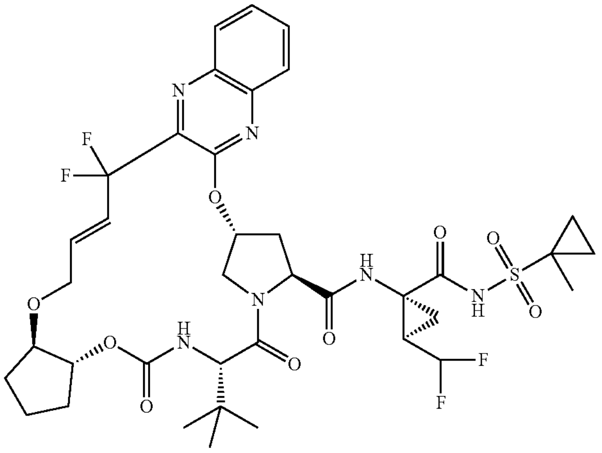 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O] |
| Voxilaprevir, GS-9857 | 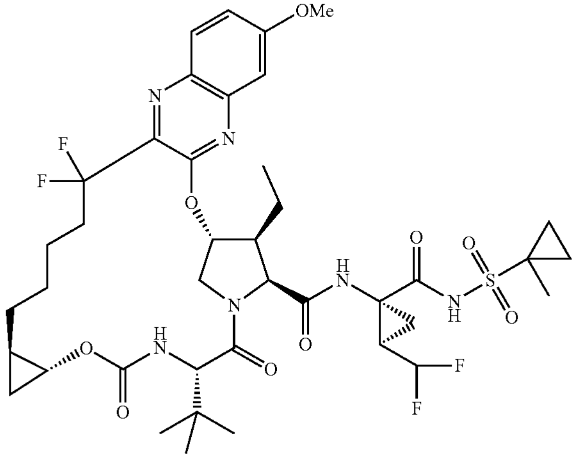 [SMILES: CC[C@@H]1[C@@H]2CN(C(=O)[C@H](C(C)(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F] |

In several aspects, described herein are iAD polypeptides comprising a peptide domain. As used herein, the term "peptide domain" refers to a short polypeptide domain that can specifically bind to a repressible protease as described herein (e.g., NS3 protease). The peptide domain can also be referred to herein as a "protease-binding domain". In some embodiments of any of the aspects, any peptide that can bind to the repressible protease can be used. In some embodiments of any of the aspects, the peptide domain comprises a protease cleavage site as described herein and is a substrate peptidomimetic. In some embodiments of any of the aspects, the peptide domain is specifically bound by but not cleaved by the repressible protease. In some embodiments of any of the aspects, an iAD polypeptide as described herein (or an iAD polypeptide system collectively) comprises 1, 2, 3, 4, 5, or more peptide domains. In some embodiments of any of the aspects, the iAD polypeptide or system comprises one peptide domain. In embodiments comprising multiple peptide domains, the multiple peptide domains can be different individual peptide domains or multiple copies of the same peptide domain, or a combination of the foregoing.

Table 10 lists non-limiting examples of peptide domains (e.g., for NS3 protease), Such inhibitory peptides cap the active site and bind via a "tyrosine" finger at an alternative NS3-4A site. The peptides are not cleaved due to a combination of geometrical constraints and impairment of the oxyanion hole function. Negligible susceptibility to known (e.g., A156V and R155K) resistance mutations of the NS3-4A protease have been observed. Accordingly, non-limiting examples of peptide domains include: K5-66, K5-66-A, K5-66-B, K6-10, K6-10A, K6-10B K5-66-R, CP5-46, CP5-46-4D5E, CP5-46-A, CP5- 46A-4D5E, Ant-CP5-46A-4D5E, and apo NS3a reader (ANR) peptides (see e.g., Kugler et al., High Affinity Peptide Inhibitors of the Hepatitis C Virus NS3-4A Protease Refractory to Common Resistant Mutants, J Biol Chem. 2012 Nov. 9; 287 (46): 39224-39232; Cunningham-Bryant et al., J Am Chem Soc. 2019 Feb. 27; 141(8):3352-3355).

TABLE 10

| Exemplary Peptide Domains | | |
|---|---|---|
| SEQ ID NO: | Peptide | Sequence |
| 266 | K5-66 | GELGRLVYLLDGPGYDPIHC SLAYGDASTLVVF |
| 267 | K5-66-A | GELGRLVYLLDGPGYDPI |
| 268 | K5-66-B | HCSLAYGDASTLVVF |
| 269 | K6-10 | GELGRPVYVLGDPGYYA THCIYATTNDALIFSV |
| 270 | K6-10-A | GELGRPVYVLGDPGYYAT |
| 271 | K6-10-B | HCIYATTNDALIFSV |
| 272 | K5-66-R | GELGRIPSDTYDLAVGA LHCPFYLVSGLVYLDG |
| 273 | CP5-46 | GELGRLVYLLDGPGYDP IHCDVVTRGGSHLFNF |
| 274 | CP5-46-4D5E | GELDELVYLLDGPGYDP IHCDVVTRGGSHLFNF |
| 275 | CP5-46-A | GELGRLVYLLDGPGYDPIHCD |
| 276 | CP5-46A-4D5E | GELDELVYLLDGPGYDPIHS |
| 277 | Ant-CP5-46A-4D5E | RQIK IWFQNRRMKWKKGEL DELVYLLDGPGYDPIHS |
| 261 | ANR | GELDELVYLLDGPGYDPIHSD |

In some embodiments of any of the aspects, the peptide domain of an iAD polypeptide as described herein comprises SEQ ID NOs: 261, 266-277, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 261, 266-277, that maintains the same functions as one of SEQ ID NOs: 261, 266-277 (e.g., binding to a repressible protease). In some embodiments of any of the aspects, the peptide domain of an iAD polypeptide as described herein comprises SEQ ID NOs: 261, 266-277, or an amino acid sequence that is at least 95% identical to the sequence of one of SEQ ID NOs: 261, 266-277, that maintains the same functions as one of SEQ ID NOs: 261, 266-277.

In some embodiments of any of the aspects, the peptide domain of an iAD polypeptide as described herein is encoded by a nucleic acid sequence comprising SEQ ID NO: 278 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 278 that maintains the same function or a codon-optimized version of SEQ ID NO: 278. In some embodiments of any of the aspects, the peptide domain of an iAD polypeptide as described herein is encoded by a nucleic acid sequence comprising SEQ ID NO: 278 or a sequence that is at least 95% identical to SEQ ID NO: 278 that maintains the same function.

```
CP5-46-5D5E, 99 nt
                                  SEQ ID NO: 278
GGAGAACTTGATGAATTGGTATACTTACTAG

ATGGGCCAGGTTATGACCCTATACATTGCGA

TGTAGTGACAAGGGGCGGCAGCCACCTTTTC

AATTTT,
```

In some embodiments of any of the aspects, a peptide domain is specific for a certain genotype of repressible protease. As a non-limiting example, the peptide ANR (e.g., SEQ ID NO: 261) was selected to interact with genotype 1b NS3a (e.g., SEQ ID NO: 211) or an NS3 comprising the following mutations: A7S, E13L, 135V and T42S (e.g., SEQ ID NO: 260). Apo NS3a reader (ANR) forms a basal complex with NS3a-genotype 1b with an affinity of 10 nM, which is disrupted by NS3a-targeting drugs. Accordingly, described herein are iAD systems comprising a peptide domain (e.g., SEQ ID NO: 261, 266-277) and a repressible protease (e.g., SEQ ID NO: 211, 260).

Described herein are iAD polypeptides comprising protease cleavage sites. As used herein, the term "protease cleavage site" refers to a specific sequence or sequence motif recognized by and cleaved by the repressible protease. A cleavage site for a protease includes the specific amino acid sequence or motif recognized by the protease during proteolytic cleavage and typically includes the surrounding one to six amino acids on either side of the scissile bond, which bind to the active site of the protease and are used for recognition as a substrate. In some embodiments of any of the aspects, the protease cleavage site can be any site specifically bound by and cleaved by the repressible protease. In some embodiments of any of the aspects, an iAD polypeptide as described herein comprises 1, 2, 3, 4, 5, or more protease cleavage sites. In some embodiments of any of the aspects, the iAD polypeptide comprises one protease cleavage site. In some embodiments of any of the aspects, the iAD polypeptide comprises two protease cleavage sites. In embodiments comprising multiple protease cleavage sites, the multiple protease cleavage sites can be different individual protease cleavage sites or multiple copies of the same protease cleavage sites, or a combination of the foregoing.

As a non-limiting example, during HCV replication, the NS3-4A serine protease is responsible for the proteolytic cleavage at four junctions of the HCV polyprotein precursor: NS3/NS4A (self-cleavage), NS4A/NS4B, NS4B/NSSA, and NS5A/NS5B. Accordingly, the protease cleavage site of an iAD polypeptide as described herein can be a NS3/NS4A cleavage site, a NS4A/NS4B cleavage site, a NS4B/NS5A cleavage site, or a NS5A/NS5B cleavage site. The protease cleavage site can be a protease cleavage sites from HCV genotype 1, genotype 1a, genotype 1b, genotype 2, genotype 2a, genotype 2b, genotype 3, genotype 3a, genotype 3b, genotype 4, genotype 4a, genotype 4b, genotype 5, genotype 5a, genotype 5b, genotype 6, genotype 6a, genotype 6b, genotype 7, genotype 7a NS4A, or genotype 7b. In some embodiments of any of the aspects, the protease cleavage site can be any known NS3/NS4A protease cleavage site or variant or mutant thereof, e.g., that maintains the same function. In some embodiments of any of the aspects, the NS4A sequence comprises residues 21-31 of the NS4A protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin 2006 supra).

In some embodiments of any of the aspects, the protease cleavage site of an iAD polypeptide as described herein comprises SEQ ID NOs: 364-389, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 364-389 that maintains the same function.

In some embodiments of any of the aspects, the protease cleavage site of an iAD polypeptide as described herein comprises residues 1-20, 1-19, 1-18, 1-17, 1-16, 1-15, 2-20, 2-19, 2-18, 2-17, 2-16, 2-15, 3-20, 3-19, 3-18, 3-17, 3-16, 3-15, 4-20, 4-19, 4-18, 4-17, 4-16, 4-15, 5-20, 5-19, 5-18, 5-17, 5-16, or 5-15, of any of SEQ ID NOs: 208-224.

```
NS5A/5B cut site (CC), 10 aa,
                                SEQ ID NO: 364
EDVVCCHSIY,

NS4A/4B cut site (CS), 14 aa,
                                SEQ ID NO: 365
LYQEFDEMEECSQH,

N3 cleavage site (NS4A/4B cut site),
                                SEQ ID NO: 366
DEMEECSQHL,

                                SEQ ID NO: 367
QEFEDVVPCSMGS,

NS5A/5B cut site,
                                SEQ ID NO: 368
EDVVCCHSI,

NS4A/4B cut site,
                                SEQ ID NO: 369
DEMEECSQH,
```

TABLE 13

Exemplary NS3/NS4A protease cleavage sites (see e.g., Chao Lin 2006 *supra*).

| Cleavage Site Type | SEQ ID NO | Genotype (Strain) | Sequence (cleavage site shown with space) |
|---|---|---|---|
| NS3/NS4A | 370 | 1a (HCV-H) | CMSADLEVVT STWVLVGGVL |
| | 371 | 1b (HCV-BK) | CMSADLEVVT STWVLVGGVL |
| | 372 | 2a (HCV-J6) | CMQADLEVMT STWVLAGGVL |
| | 373 | 2b (HCV-J8) | CMQADLEIMT SSWVLAGGVL |
| | 374 | 3a (HCV-Nz11) | CMSADLEVTT STWVLLGGVL |
| NS4A/NS4B | 375 | 1a (HCV-H) | YQEFDEMEEC SQHLPYIEQG |
| | 376 | 1b (HCV-BK) | YQEFDEMEEC ASHLPYIEQG |
| | 377 | 2a (HCV-J6) | YEAFDEMEEC ASRAALIEEG |
| | 378 | 2b (HCV-J8) | YEAFDEMEEC ASKAALIEEG |
| | 379 | 3a (HCV-Nz11) | YQQYDEMEEC SQAAPYIEQA |
| NS4B/NS5A | 380 | 1a (HCV-H) | WISSECTTPC SGSWLRDVWD |
| | 381 | 1b (HCV-BK) | WINEDCSTPC SGSWLRDVWD |
| | 382 | 2a (HCV-J6) | WITEDCPIPC SGSWLRDVWD |
| | 383 | 2b (HCV-J8) | WITEDCPVPC SGSWLQDIWD |
| | 384 | 3a (HCV-Nz11) | WINEDYPSPC SDDWLRTIWD |
| NS5A/NS5B | 385 | 1a (HCV-H) | GADTEDVVCC SMSYSWTGAL |
| | 386 | 1b (HCV-BK) | EEASEDVVCC SMSYTWTGAL |
| | 387 | 2a (HCV-J6) | SEEDDSVVCC SMSYSWTGAL |
| | 388 | 2b (HCV-J8) | SDQEDSVICC SMSYSWTGAL |
| | 389 | 3a (HCV-Nz11) | DSEEQSVVCC SMSYSWTGAL |

In some embodiments of any of the aspects, an iAD polypeptide as described herein comprises two protease cleavage sites, with one N-terminal of the NS3-NS4A complex, and the other C-terminal of the NS3-NS4A complex (see e.g., Table 14). In some embodiments of any of the aspects, the two protease cleavage sites can be the same cleavage sites or different cleavage sites.

TABLE 14

Exemplary Protease Cleavage Site Combinations.

| | | | | | | | | |
|---|---|---|---|---|---|---|---|---|
| N | 3/4A | | | | 4A/4B | | | |
| C | 3/4A | 4A/4B | 4B/5A | 5A/5B | 3/4A | 4A/4B | 4B/5A | 5A/5B |
| N | 4B/5A | | | | 5A/5B | | | |
| C | 3/4A | 4A/4B | 4B/5A | 5A/5B | 3/4A | 4A/4B | 4B/5A | 5A/5B |

"N" indicates N-terminal of the NS3-NS4A complex.

"C" indicates C-terminal of the NS3-NS4A complex.

"3/4A" indicates the NS3/NS4A cleavage site.

"4A/4B" indicates the NS4A/NS4B cleavage site.

"4B/5A" indicates the NS4B/NS5A cleavage site.

"5A/5B" indicates the NS5A/NS5B cleavage site.

In some embodiments of any of the aspects, an iAD polypeptide as described herein comprise any known genotypes, variants, or mutants of NS3/NS4A, NS4A/NS4B, NS4B/NSSA, and NS5A/NS5B cleavage sites. In one embodiment, the two protease cleavage sites are selected from selected from the same genotype as each other.

D. Exemplary iADAR Fusion Proteins.

TABLE 5

Exemplary fusion proteins are disclosed in the following table:

| | SEQ ID NO: | | Corresponding sequence including TagBFP |
|---|---|---|---|
| MCP-linker-ADAR2-DDN-Bad(F)-ADAR2(E488Q)-DDC | 150 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGT GAPPNLWAAQRYGRELRRMSDEFVDRHPNR KARGQLRTKIESGQGTIPVRSNASIQTWDG VLQGERLLTMSCSDKIARWNVVGIQGSLLS IFVEPIYFSSIILGSLYHGDHLSRAMYQRI SNIEDLPPLYTLNKPLLSGISNAEARQPGK APNFSVNWTVGDSAIEVINATTGKDELGRA SRLCKHALYCRWMRVHGKVPSHLLRSKITK PNVYHESKLAAKEYQAAKARLFTAFIKAGL GAWVEKPTEQDQFSLT | 17 |
| MCP-linker-ADAR2-DDN-Bad(F)-ADAR2(E488Q)-DDC-Bcl-XL-T | 151 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGT GAPPNLWAAQRYGRELRRMSDEFVDRHPNR KARGQLRTKIESGQGTIPVRSNASIQTWDG VLQGERLLTMSCSDKIARWNVVGIQGSLLS IFVEPIYFSSIILGSLYHGDHLSRAMYQRI SNIEDLPPLYTLNKPLLSGISNAEARQPGK APNFSVNWTVGDSAIEVINATTGKDELGRA SRLCKHALYCRWMRVHGKVPSHLLRSKITK PNVYHESKLAAKEYQAAKARLFTAFIKAGL GAWVEKPTEQDQFSLTGSAAGGSGGSAAAS SNRELVVDFLSYKLSQKGYSWSQFSDVEEN RTEAPEGTESEMETPSAINGNPSWHLADSP AVNGATGHSSSLDAREVIPMAAVKQALREA GDEFELRYRRAFSDLTSQLHITPGTAYQSF EQVVNELFRDGVNWGRIVAFFSFGGALCVE SVDKEMQVLVSRIAAWMATYLNDHLEPWIQ ENGGWDTFVELYGNN | 18 |
| MCP-linker-ADAR2-DDN-Bim-ADAR2(E488Q)-DDC | 152 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGS GDMRPEIWIAQELRRIGDEFNAYYARRTGD RHPNRKARGQLRTKIESGQGTIPVRSNASI QTWDGVLQGERLLTMSCSDKIARWNVVGIQ GSLLSIFVEPIYFSSIILGSLYHGDHLSRA MYQRISNIEDLPPLYTLNKPLLSGISNAEA RQPGKAPNFSVNWTVGDSAIEVINATTGKD | 20 |

TABLE 5-continued

| Exemplary fusion proteins are disclosed in the following table: | SEQ ID NO: | | Corresponding sequence including TagBFP |
|---|---|---|---|
| | | ELGRASRLCKHALYCRWMRVHGKVPSHLLR SKITKPNVYHESKLAAKEYQAAKARLFTAF IKAGLGAWVEKPTEQDQFSLT | |
| MCP-linker-ADAR2-DDN-MS1(A)-ADAR2(E488Q)-DDC | 153 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGGSG GSGRPEIWMTQGLRRLGDEANAYYARRTGD RHPNRKARGQLRTKIESGQGTIPVRSNASI QTWDGVLQGERLLTMSCSDKIARWNVVGIQ GSLLSIFVEPIYFSSIILGSLYHGDHLSRA MYQRISNIEDLPPLYTLNKPLLSGISNAEA RQPGKAPNFSVNWTVGDSAIEVINATTGKD ELGRASRLCKHALYCRWMRVHGKVPSHLLR SKITKPNVYHESKLAAKEYQAAKARLFTAF IKAGLGAWVEKPTEQDQFSLT | 22 |
| MCP-linker-ADAR2-DDN-Bad(L)-ADAR2(E488Q)-DDC-Bcl-xL | 154 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGT GAPPNLWAAQRYGRELRRMSDELVDRHPNR KARGQLRTKIESGQGTIPVRSNASIQTWDG VLQGERLLTMSCSDKIARWNVVGIQGSLLS IFVEPIYFSSIILGSLYHGDHLSRAMYQRI SNIEDLPPLYTLNKPLLSGISNAEARQPGK APNFSVNWTVGDSAIEVINATTGKDELGRA SRLCKHALYCRWMRVHGKVPSHLLRSKITK PNVYHESKLAAKEYQAAKARLFTAFIKAGL GAWVEKPTEQDQFSLTGSAAGGSGGSAAAS SNRELVVDFLSYKLSQKGYSWSQFSDVEEN RTEAPEGTESEMETPSAINGNPSWHLADSP AVNGATGHSSSLDAREVIPMAAVKQALREA GDEFELRYRRAFSDLTSQLHITPGTAYQSF EQVVNELFRDGVNWGRIVAFFSFGGALCVE SVDKEMQVLVSRIAAWMATYLNDHLEPWIQ ENGGWDTFVELYGNN | 23 |
| MCP-linker-ADAR2-DDN-MS1(I)-ADAR2(E488Q)-DDC-Mcl-1 | 155 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGGSG GSGRPEIWMTQGLRRLGDEINAYYARRTGD RHPNRKARGQLRTKIESGQGTIPVRSNASI QTWDGVLQGERLLTMSCSDKIARWNVVGIQ GSLLSIFVEPIYFSSIILGSLYHGDHLSRA MYQRISNIEDLPPLYTLNKPLLSGISNAEA RQPGKAPNFSVNWTVGDSAIEVINATTGKD ELGRASRLCKHALYCRWMRVHGKVPSHLLR SKITKPNVYHESKLAAKEYQAAKARLFTAF IKAGLGAWVEKPTEQDQFSLTGSGTGGPGD ELYRQSLEIISRYLREQATGAKDTKPMGRS GATSRKALETLRRVGDGVQRNHETAFQGML | 24 |

TABLE 5-continued

Exemplary fusion proteins are disclosed in the following table:

| | SEQ ID NO: | | Corresponding sequence including TagBFP |
|---|---|---|---|
| | | RKLDIKNEDDVKSLSRVMIHVFSDGVTNWG RIVTLISFGAFVAKHLKTINQESCIEPLAE SITDVLVRTKRDWLVKQRGWDGFVEFFHVE DLEGG | |
| MCP-linker-ADAR2-DDN-ALFA-ADAR2(E 488Q)-DDC | 156 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASP**SRL EEELRRRLTE**PTGDRHPNRKARGQLRTKIE SG**Q**GTIPVRSNASIQTWDGVLQGERLLTMS CSDKIARWNVVGIQGSLLSIFVEPIYFSSI ILGSLYHGDHLSRAMYQRISNIEDLPPLYT LNKPLLSGISNAEARQPGKAPNFSVNWTVG DSAIEVINATTGKDELGRASRLCKHALYCR WMRVHGKVPSHLLRSKITKPNVYHESKLAA KEYQAAKARLFTAFIKAGLGAWVEKPTEQD QFSLT | 25 |
| MCP-linker-ADAR2-DDN-ALFA-ADAR2(E 488Q)-DDC-NbALFA | 157 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASP**SRL EEELRRRLTE**PTGDRHPNRKARGQLRTKIE SG**Q**GTIPVRSNASIQTWDGVLQGERLLTMS CSDKIARWNVVGIQGSLLSIFVEPIYFSSI ILGSLYHGDHLSRAMYQRISNIEDLPPLYT LNKPLLSGISNAEARQPGKAPNFSVNWTVG DSAIEVINATTGKDELGRASRLCKHALYCR WMRVHGKVPSHLLRSKITKPNVYHESKLAA KEYQAAKARLFTAFIKAGLGAWVEKPTEQD QFSLTGSGGTAEVQLQESGGGLVQPGGSLR LSCTASGVTISALNAMAMGWYRQAPGERRV MVAAVSERGNAMYRESVQGRFTVTRDFTNK MVSLQMDNLKPEDTAVYYCHVLEDRVDSFH DYWGQGTQVTVSS | 26 |
| MCP-linker-ADAR2-DDN-ALFA-PE-ADAR2(E 488Q)-DDC | 158 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGP **GRLEEELRRRLSP**GTGDRHPNRKARGQLRT KIESG**Q**GTIPVRSNASIQTWDGVLQGERLL TMSCSDKIARWNVVGIQGSLLSIFVEPIYF SSIILGSLYHGDHLSRAMYQRISNIEDLPP LYTLNKPLLSGISNAEARQPGKAPNFSVNW TVGDSAIEVINATTGKDELGRASRLCKHAL YCRWMRVHGKVPSHLLRSKITKPNVYHESK LAAKEYQAAKARLFTAFIKAGLGAWVEKPT EQDQFSLT | 27 |

TABLE 5-continued

Exemplary fusion proteins are disclosed in the following table:

| | SEQ ID NO: | | Corresponding sequence including TagBFP |
|---|---|---|---|
| MCP-linker-ADAR2-DDN-ALFA-PE-ADAR2(E488Q)-DDC-NbALFA | 159 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGP **GRLEEELRRRLSP**GTGDRHPNRKARGQLRT KIESG**Q**GTIPVRSNASIQTWDGVLQGERLL TMSCSDKIARWNVVGIQGSLLSIFVEPIYF SSIILGSLYHGDHLSRAMYQRISNIEDLPP LYTLNKPLLSGISNAEARQPGKAPNFSVNW TVGDSAIEVINATTGKDELGRASRLCKHAL YCRWMRVHGKVPSHLLRSKITKPNVYHESK LAAKEYQAAKARLFTAFIKAGLGAWVEKPT EQDQFSLTGSGGTAEVQLQESGGGLVQPGG SLRLSCTASGVTISALNAMAMGWYRQAPGE RRVMVAAVSERGNAMYRESVQGRFTVTRDF TNKMVSLQMDNLKPEDTAVYYCHVLEDRVD SFHDYWGQGTQVTVSS | 28 |
| MCP-linker-ADAR2-DDN-SpyTag-ADAR2(E488Q)-DDC --P2A-T2A-SpyCatcher | 160 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGGSG A**HIVMVDAYKPTK**GTGDRHPNRKARGQLRT KIESG**Q**GTIPVRSNASIQTWDGVLQGERLL TMSCSDKIARWNVVGIQGSLLSIFVEPIYF SSIILGSLYHGDHLSRAMYQRISNIEDLPP LYTLNKPLLSGISNAEARQPGKAPNFSVNW TVGDSAIEVINATTGKDELGRASRLCKHAL YCRWMRVHGKVPSHLLRSKITKPNVYHESK LAAKEYQAAKARLFTAFIKAGLGAWVEKPT EQDQFSLTGSGSTSATNFSLLKQAGDVEEN PGPGGSEGRGSLLTCGDVEENPGPGTSGGA MVDTLSGLSSEQGQSGDMTIEEDSATHIKF SKRDEDGKELAGATMELRDSSGKTISTWIS DGQVKDFYLYPGKYTFVETAAPDGYEVATA ITFTVNEQGQVTVNGKATKGDAHIG* | 34 |
| MCP-linker-ADAR2-DDN-Spy Tag-ADAR2(E488Q)-DDC-TEVcs-SpyCatcher | 161 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGGSG A**HIVMVDAYKPTK**GTGDRHPNRKARGQLRT KIESG**Q**GTIPVRSNASIQTWDGVLQGERLL TMSCSDKIARWNVVGIQGSLLSIFVEPIYF SSIILGSLYHGDHLSRAMYQRISNIEDLPP LYTLNKPLLSGISNAEARQPGKAPNFSVNW TVGDSAIEVINATTGKDELGRASRLCKHAL YCRWMRVHGKVPSHLLRSKITKPNVYHESK LAAKEYQAAKARLFTAFIKAGLGAWVEKPT EQDQFSLTGSGGTENLYFQSGTSGGAMVDT | 35 |

TABLE 5-continued

Exemplary fusion proteins are disclosed in the following table:

| | SEQ ID NO: | | Corresponding sequence including TagBFP |
|---|---|---|---|
| | | LSGLSSEQGQSGDMTIEEDSATHIKFSKRD EDGKELAGATMELRDSSGKTISTWISDGQV KDFYLYPGKYTFVETAAPDGYEVATAITFT VNEQGQVTVNGKATKGDAHI | |
| MCP-linker-ADAR2-DDN-Bad(L)-ADAR2(E488Q)-DDC-PhoCl-Bcl-XL | 162 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGT GAPPNLWAAQRYGRELRRMSDELVDRHPNR KARGQLRTKIESGQGTIPVRSNASIQTWDG VLQGERLLTMSCSDKIARWNVVGIQGSLLS IFVEPIYFSSIILGSLYHGDHLSRAMYQRI SNIEDLPPLYTLNKPLLSGISNAEARQPGK APNFSVNWTVGDSAIEVINATTGKDELGRA SRLCKHALYCRWMRVHGKVPSHLLRSKITK PNVYHESKLAAKEYQAAKARLFTAFIKAGL GAWVEKPTEQDQFSLTGSGSGGVIPDYFKQ SFPEGYSWERSMTYEDGGICIATNDITMEG DSFINKIHFKGTNFPPNGPVMQKRTVGWEA STEKMYERDGVLKGDVKMKLLLKGGGHYRC DYRTTYKVKQKPVKLPDYHFVDHRIEILSH DKDYNKVKLYEHAVARNSTDSMDELYKGGS GGMVSKGEETITSVIKPDMKNKLRMEGNVN GHAFVIEGEGSGKPFEGIQTIDLEVKEGAP LPFAYDILTTAFHYGNRVFTKYPRSGSGSS NRELVVDFLSYKLSQKGYSWSQFSDVEENR TEAPEGTESEMETPSAINGNPSWHLADSPA VNGATGHSSSLDAREVIPMAAVKQALREAG DEFELRYRRAFSDLTSQLHITPGTAYQSFE QVVNELFRDGVNWGRIVAFFSFGGALCVES VDKEMQVLVSRIAAWMATYLNDHLEPWIQE NGGWDTFVELYGNN | 37 |
| MCP-linker-ADAR2-DDN-Bad(L)-ADAR2(E488Q)-DDC Also known as "nDD-BAD-cDD" or "BAD(L) Only" | 163 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQLHLPQVLA DAVSRLVLGKFGDLTDNFSSPHARRKVLAG VVMTTGTDVKDAKVISVSTGTKCINGEYMS DRGLALNDCHAEIISRRSLLRFLYTQLELY LNNKDDQKRSIFQKSERGGFRLKENVQFHL YISTSPCGDARIFSPHEPILEEPAASGSGT GAPPNLWAAQRYGRELRRMSDELVDRHPNR KARGQLRTKIESGQGTIPVRSNASIQTWDG VLQGERLLTMSCSDKIARWNVVGIQGSLLS IFVEPIYFSSIILGSLYHGDHLSRAMYQRI SNIEDLPPLYTLNKPLLSGISNAEARQPGK APNFSVNWTVGDSAIEVINATTGKDELGRA SRLCKHALYCRWMRVHGKVPSHLLRSKITK PNVYHESKLAAKEYQAAKARLFTAFIKAGL GAWVEKPTEQDQFSLT | 88 |
| MCP-linker-BclxL - linker - ADAR2-DDN-Bad(L)-ADAR2(E488Q)-DDC - Also known as | 164 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSQSNRELVVD FLSYKLSQKGYSWSQFSDVEENRTEAPEGT ESEMETPSAINGNPSWHLADSPAVNGATGH SSSLDAREVIPMAAVKQALREAGDEFELRY RRAFSDLTSQLHITPGTAYQSFEQVVNELF RDGVNWGRIVAFFSFGGALCVESVDKEMQV LVSRIAAWMATYLNDHLEPWIQENGGWDTF VELYGNNAAGGSGGSGGSGGSAAAQLHLPQ | 89 |

TABLE 5-continued

| | | | Corresponding |
| | SEQ | | sequence |
| | ID | | including |
| | NO: | | TagBFP |
|---|---|---|---|
| "BclxL-<br>nDD-BAD-<br>cDD" | | VLADAVSRLVLGKFGDLTDNFSSPHARRKV<br>LAGVVMTTGTDVKDAKVISVSTGTKCINGE<br>YMSDRGLALNDCHAEIISRRSLLRFLYTQL<br>ELYLNNKDDQKRSIFQKSERGGFRLKENVQ<br>FHLYISTSPCGDARIFSPHEPILEEPAASG<br>SGTGAPPNLWAAQRYGRELRRMSDELVDRH<br>PNRKARGQLRTKIESGQGTIPVRS<br>NASIQTWDGVLQGERLLTMSCSDKIARWNV<br>VGIQGSLLSIFVEPIYFSSIILGSLYHGDH<br>LSRAMYQRISNIEDLPPLYTLNKPLLSGIS<br>NAEARQPGKAPNFSVNWTVGDSAIEVINAT<br>TGKDELGRASRLCKHALYCRWMRVHGKVPS<br>HLLRSKITKPNVYHESKLAAKEYQAAKARL<br>FTAFIKAGLGAWVEKPTEQDQFSLT | |
| nDD-BAD-<br>cDD-Bcl-<br>XL (MCP-<br>linker-<br>ADAR2-<br>DDN-<br>Bad(L)-<br>ADAR2(E<br>488Q)-<br>DDC-Bcl-<br>xL<br>(or Bad(L) | 165 | MASNFTQFVLVDNGGTGDVTVAPSNFANGI<br>AEWISSNSRSQAYKVTCSVRQSSAQNRKYT<br>IKVEVPKGAWRSYLNMELTIPIFATNSDCE<br>LIVKAMQGLLKDGNPIPSAIAANSGIYGGS<br>GSGAGSGSPAGGGAPGSGGGSQLHLPQVLA<br>DAVSRLVLGKFGDLTDNFSSPHARRKVLAG<br>VVMTTGTDVKDAKVISVSTGTKCINGEYMS<br>DRGLALNDCHAEIISRRSLLRFLYTQLELY<br>LNNKDDQKRSIFQKSERGGFRLKENVQFHL<br>YISTSPCGDARIFSPHEPILEEPAASGSGT<br>GAPPNLWAAQRYGRELRRMSDELVDRHPNR<br>KARGQLRTKIESGQGTIPVRSNAS<br>IQTWDGVLQGERLLTMSCSDKIARWNVVGI<br>QGSLLSIFVEPIYFSSIILGSLYHGDHLSR<br>AMYQRISNIEDLPPLYTLNKPLLSGISNAE<br>ARQPGKAPNFSVNWTVGDSAIEVINATTGK<br>DELGRASRLCKHALYCRWMRVHGKVPSHLL<br>RSKITKPNVYHESKLAAKEYQAAKARLFTA<br>FIKAGLGAWVEKPTEQDQFSLTGSAAGGSG<br>GSAAASSNRELVVDFLSYKLSQKGYSWSQF<br>SDVEENRTEAPEGTESEMETPSAINGNPSW<br>HLADSPAVNGATGHSSSLDAREVIPMAAVK<br>QALREAGDEFELRYRRAFSDLTSQLHITPG<br>TAYQSFEQVVNELFRDGVNWGRIVAFFSFG<br>GALCVESVDKEMQVLVSRIAAWMATYLNDH<br>LEPWIQENGGWDTFVELYGNNG | 90 |
| MCP-<br>linker-<br>BAD-<br>ADAR2-<br>DD(E488Q<br>)<br>Also<br>known as<br>"BAD-<br>DD" | 166 | MASNFTQFVLVDNGGTGDVTVAPSNFANGI<br>AEWISSNSRSQAYKVTCSVRQSSAQNRKYT<br>IKVEVPKGAWRSYLNMELTIPIFATNSDCE<br>LIVKAMQGLLKDGNPIPSAIAANSGIYGGS<br>GSGAGSGSPAGGGAPGSGGGSTGAPPNLWA<br>AQRYGRELRRMSDEFVDSFKKASQLHLPQV<br>LADAVSRLVLGKFGDLTDNFSSPHARRKVL<br>AGVVMTTGTDVKDAKVISVSTGTKCINGEY<br>MSDRGLALNDCHAEIISRRSLLRFLYTQLE<br>LYLNNKDDQKRSIFQKSERGGFRLKENVQF<br>HLYISTSPCGDARIFSPHEPILEEPADRHP<br>NRKARGQLRTKIESGQGTIPVRSN<br>ASIQTWDGVLQGERLLTMSCSDKIARWNVV<br>GIQGSLLSIFVEPIYFSSIILGSLYHGDHL<br>SRAMYQRISNIEDLPPLYTLNKPLLSGISN<br>AEARQPGKAPNFSVNWTVGDSAIEVINATT<br>GKDELGRASRLCKHALYCRWMRVHGKVPSH<br>LLRSKITKPNVYHESKLAAKEYQAAKARLF<br>TAFIKAGLGAWVEKPTEQDQFSLT | 91 |
| MCP-<br>linker-<br>BAD-<br>ADAR2-<br>DD(E488Q<br>)-Bcl-xL<br>Also<br>known as<br>"BAD-DD-<br>BclxL" and | 167 | MASNFTQFVLVDNGGTGDVTVAPSNFANGI<br>AEWISSNSRSQAYKVTCSVRQSSAQNRKYT<br>IKVEVPKGAWRSYLNMELTIPIFATNSDCE<br>LIVKAMQGLLKDGNPIPSAIAANSGIYGGS<br>GSGAGSGSPAGGGAPGSGGGSTGAPPNLWA<br>AQRYGRELRRMSDEFVDSFKKASQLHLPQV<br>LADAVSRLVLGKFGDLTDNFSSPHARRKVL<br>AGVVMTTGTDVKDAKVISVSTGTKCINGEY<br>MSDRGLALNDCHAEIISRRSLLRFLYTQLE<br>LYLNNKDDQKRSIFQKSERGGFRLKENVQF | 92 |

TABLE 5-continued

Exemplary fusion proteins are disclosed in the following table:

| | SEQ ID NO: | | Corresponding sequence including TagBFP |
|---|---|---|---|
| "WT" | | HLYISTSPCGDARIFSPHEPILEEPADRHP NRKARGQLRTKIESGQGTIPVRSN ASIQTWDGVLQGERLLTMSCSDKIARWNVV GIQGSLLSIFVEPIYFSSIILGSLYHGDHL SRAMYQRISNIEDLPPLYTLNKPLLSGISN AEARQPGKAPNFSVNWTVGDSAIEVINATT GKDELGRASRLCKHALYCRWMRVHGKVPSH LLRSKITKPNVYHESKLAAKEYQAAKARLF TAFIKAGLGAWVEKPTEQDQFSLTGSAAAS SNRELVVDFLSYKLSQKGYSWSQFSDVEEN RTEAPEGTESEMETPSAINGNPSWHLADSP AVNGATGHSSSLDAREVIPMAAVKQALREA GDEFELRYRRAFSDLTSQLHITPGTAYQSF EQVVNELFRDGVNWGRIVAFFSFGGALCVE SVDKEMQVLVSRIAAWMATYLNDHLEPWIQ ENGGWDTFVELYGNN | |
| tdMCP AD AR2-DDN-CP5-46-4D5E AD AR2-DDC(E488 Q)_(AD-Pep-AD) | 279 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYANF TQFVLVDNGGTGDVTVAPSNFANGIAEWIS SNSRSQAYKVTCSVRQSSAQNRKYTIKVEV PKGAWRSYLNMELTIPIFATNSDCELIVKA MQGLLKDGNPIPSAIAANSGIYGGSGSGAG SGSPAGGGAPGSGGGSQLHLPQVLADAVSR LVLGKFGDLTDNFSSPHARRKVLAGVVMTT GTDVKDAKVISVSTGTKCINGEYMSDRGLA LNDCHAEIISRRSLLRFLYTQLELYLNNKD DQKRSIFQKSERGGFRLKENVQFHLYISTS PCGDARIFSPHEPILEEPASSGGELDELVY LLDGPGYDPIHCDVVTRGGSHLFNFDRHPN RKARGQLRTKIESGQGTIPVRSNASIQTWD GVLQGERLLTMSCSDKIARWNVVGIQGSLL SIFVEPIYFSSIILGSLYHGDHLSRAMYQR ISNIEDLPPLYTLNKPLLSGISNAEARQPG KAPNFSVNWTVGDSAIEVINATTGKDELGR ASRLCKHALYCRWMRVHGKVPSHLLRSKIT KPNVYHESKLAAKEYQAAKARLFTAFIKAG LGAWVEKPTEQDQFSLT | 168 |
| tdMCP AD AR2-DDN-CP5-46-4D5E ADAR2-DDC(E488 Q)_NS4A/ NS3 (Genotype 1B) | 280 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYANF TQFVLVDNGGTGDVTVAPSNFANGIAEWIS SNSRSQAYKVTCSVRQSSAQNRKYTIKVEV PKGAWRSYLNMELTIPIFATNSDCELIVKA MQGLLKDGNPIPSAIAANSGIYGGSGSGAG SGSPAGGGAPGSGGGSQLHLPQVLADAVSR LVLGKFGDLTDNFSSPHARRKVLAGVVMTT GTDVKDAKVISVSTGTKCINGEYMSDRGLA LNDCHAEIISRRSLLRFLYTQLELYLNNKD DQKRSIFQKSERGGFRLKENVQFHLYISTS PCGDARIFSPHEPILEEPASSGGELDELVY LLDGPGYDPIHCDVVTRGGSHLFNFDRHPN RKARGQLRTKIESGQGTIPVRSNASIQTWD GVLQGERLLTMSCSDKIARWNVVGIQGSLL SIFVEPIYFSSIILGSLYHGDHLSRAMYQR ISNIEDLPPLYTLNKPLLSGISNAEARQPG KAPNFSVNWTVGDSAIEVINATTGKDELGR ASRLCKHALYCRWMRVHGKVPSHLLRSKIT KPNVYHESKLAAKEYQAAKARLFTAFIKAG LGAWVEKPTEQDQFSLTGSAAGGSGGSAAA QGSVVIVGRIILSGSGSITAYSQQTRGLLG CIITSLTGRDKNQVEGEVQVVSTATQSFLA TCVNGVCWTVYHGAGSKTLAGPKGPITQMY TNVDQDLVGWQAPPGARSLTPCTCGSSDLY LVTRHADVIPVRRRGDSRGSLLSPRPVSYL KGSSGGPLLCPSGHAVGIFRAAVCTRGVAK AVDFVPVESMETTMRSESMASNFTQFVLVD NGGTGDVTVAPSNFANGIAEWISSNSRSQA | 169 |

TABLE 5-continued

Exemplary fusion proteins are disclosed in the following table:

| | SEQ ID NO: | | Corresponding sequence including TagBFP |
|---|---|---|---|
| | | YKVTCSVRQSSAQNRKYTIKVEVPKGAWRS YLNMELTIPIFATNSDCELIVKAMQGLLKD GNPIPSAIAANSGIYGGSGSGAGSGSPAGG GAPGSGGGSQSNRELVVDFLSYKLSQKGYS WSQFSDVEENRTEAPEGTESEMETPSAING | |
| MCP-linker-BclxL - linker - ADAR2-DDN-Bad(L)-ADAR2(E488Q)-DDC; Also known as "BclxL-nDD-BAD-CDD" | 281 | NPSWHLADSPAVNGATGHSSSLDAREVIPM AAVKQALREAGDEFELRYRRAFSDLTSQLH ITPGTAYQSFEQVVNELFRDGVNWGRIVAF FSFGGALCVESVDKEMQVLVSRIAAWMATY LNDHLEPWIQENGGWDTFVELYGNNAAGGS GGSGGSGGSAAAQLHLPQVLADAVSRLVLG KFGDLTDNFSSPHARRKVLAGVVMTTGTDV KDAKVISVSTGTKCINGEYMSDRGLALNDC HAEIISRRSLLRFLYTQLELYLNNKDDQKR SIFQKSERGGFRLKENVQFHLYISTSPCGD ARIFSPHEPILEEPAASGSGTGAPPNLWAA QRYGRELRRMSDELVDRHPNRKARGQLRTK IESG**Q**GTIPVRSNASIQTWDGVLQ GERLLT MSCSDKIARWNVVGIQGSLLSIFVEPIYFS SIILGSLYHGDHLSRAMYQRISNIEDLPPL YTLNKPLLSGISNAEARQPGKAPNFSVNWT VGDSAIEVINATTGKDELGRASRLCKHALY CRWMRVHGKVPSHLLRSKITKPNVYHESKL AAKEYQAAKARLFTAFIKAGLGAWVEKPTE QDQFSLT | 198 |
| MCP-linker-BAD-ADAR2-DD (E488Q) Also known as "BAD-DD" | 282 | ASNFTQFVLVDNGGTGDVTVAPSNFANGIA EWISSNSRSQAYKVTCSVRQSSAQNRKYTI KVEVPKGAWRSYLNMELTIPIFATNSDCEL IVKAMQGLLKDGNPIPSAIAANSGIYGGSG SGAGSGSPAGGGAPGSGGGSTGAPPNLWAA QRYGRELRRMSDEFVDSFKKASQLHLPQVL ADAVSRLVLGKFGDLTDNFSSPHARRKVLA GVVMTTGTDVKDAKVISVSTGTKCINGEYM SDRGLALNDCHAEIISRRSLLRFLYTQLEL YLNNKDDQKRSIFQKSERGGFRLKENVQFH LYISTSPCGDARIFSPHEPILEEPADRHPN RKARGQLRTKIESG**Q**GTIPVRSNA SIQTWD GVLQGERLLTMSCSDKIARWNVVGIQGSLL SIFVEPIYFSSIILGSLYHGDHLSRAMYQR ISNIEDLPPLYTLNKPLLSGISNAEARQPG KAPNFSVNWTVGDSAIEVINATTGKDELGR ASRLCKHALYCRWMRVHGKVPSHLLRSKIT KPNVYHESKLAAKEYQAAKARLFTAFIKAG LGAWVEKPTEQDQFSLT | 200 |
| MCP-linker-BAD-ADAR2-DD(E488Q)-Bcl-xL Also known as "BAD-DD-BclxL" and "WT" | 283 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYGGS GSGAGSGSPAGGGAPGSGGGSTGAPPNLWA AQRYGRELRRMSDEFVDSFKKASQLHLPQV LADAVSRLVLGKFGDLTDNFSSPHARRKVL AGVVMTTGTDVKDAKVISVSTGTKCINGEY MSDRGLALNDCHAEIISRRSLLRFLYTQLE LYLNNKDDQKRSIFQKSERGGFRLKENVQF HLYISTSPCGDARIFSPHEPILEEPADRHP NRKARGQLRTKIESGQGTIPVRSNASIQTW DGVLQGERLLTMSCSDKIA**R**WNVV GIQGSL LSIFVEPIYFSSIILGSLYHGDHLSRAMYQ RISNIEDLPPLYTLNKPLLSGISNAEARQP GKAPNFSVNWTVGDSAIEVINATTGKDELG RASRLCKHALYCRWMRVHGKVPSHLLRSKI TKPNVYHESKLAAKEYQAAKARLFTAFIKA GLGAWVEKPTEQDQFSLTGSAAASSNRELV VDFLSYKLSQKGYSWSQFSDVEENRTEAPE GTESEMETPSAINGNPSWHLADSPAVNGAT GHSSSLDAREVIPMAAVKQALREAGDEFEL | 202 |

TABLE 5-continued

Exemplary fusion proteins are disclosed in the following table:

| | SEQ ID NO: | | Corresponding sequence including TagBFP |
|---|---|---|---|
| | | RYRRAFSDLTSQLHITPGTAYQSFEQVVNE LFRDGVNWGRIVAFFSFGGALCVESVDKEM QVLVSRIAAWMATYLNDHLEPWIQENGGWD TFVELYGNN | |
| tdMCP_ADAR2-DDN-CP5-46-4D5E_ADAR2-DDC(E488Q) (AD-Pep-AD) | 284 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYANF TQFVLVDNGGTGDVTVAPSNFANGIAEWIS SNSRSQAYKVTCSVRQSSAQNRKYTIKVEV PKGAWRSYLNMELTIPIFATNSDCELIVKA MQGLLKDGNPIPSAIAANSGIYGGSGSGAG SGSPAGGGAPGSGGGSQLHLPQVLADAVSR LVLGKFGDLTDNFSSPHARRKVLAGVVMTT GTDVKDAKVISVSTGTKCINGEYMSDRGLA LNDCHAEIISRRSLLRFLYTQLELYLNNKD DQKRSIFQKSERGGFRLKENVQFHLYISTS PCGDARIFSPHEPILEEPASSGGELDELVY LLDGPGYDPIHCDVVTRGGSHLFNFDRHPN RKARGQLRTKIESGQGTIPVRSNASIQTWD GVLQGERLLTMSCSDKIARWNVVGIQGSLL SIFVEPIYFSSIILGSLYHGDHLSRAMYQR ISNIEDLPPLYTLNKPLLSGISNAEARQPG KAPNFSVNWTVGDSAIEVINATTGKDELGR ASRLCKHALYCRWMRVHGKVPSHLLRSKIT KPNVYHESKLAAKEYQAAKARLFTAFIKAG LGAWVEKPTEQDQFSLT | 204 |
| tdMCP_ADAR2-DDN-CP5-46-4D5E ADAR2-DDC(E488Q)_NS4A/NS3 (Genotype 1B) | 285 | MASNFTQFVLVDNGGTGDVTVAPSNFANGI AEWISSNSRSQAYKVTCSVRQSSAQNRKYT IKVEVPKGAWRSYLNMELTIPIFATNSDCE LIVKAMQGLLKDGNPIPSAIAANSGIYANF TQFVLVDNGGTGDVTVAPSNFANGIAEWIS SNSRSQAYKVTCSVRQSSAQNRKYTIKVEV PKGAWRSYLNMELTIPIFATNSDCELIVKA MQGLLKDGNPIPSAIAANSGIYGGSGSGAG SGSPAGGGAPGSGGGSQLHLPQVLADAVSR LVLGKFGDLTDNFSSPHARRKVLAGVVMTT GTDVKDAKVISVSTGTKCINGEYMSDRGLA LNDCHAEIISRRSLLRFLYTQLELYLNNKD DQKRSIFQKSERGGFRLKENVQFHLYISTS PCGDARIFSPHEPILEEPASSGGELDELVY LLDGPGYDPIHCDVVTRGGSHLFNFDRHPN RKARGQLRTKIESGQGTIPVRSNASIQTWD GVLQGERLLTMSCSDKIARWNVVGIQGSLL SIFVEPIYFSSIILGSLYHGDHLSRAMYQR ISNIEDLPPLYTLNKPLLSGISNAEARQPG KAPNFSVNWTVGDSAIEVINATTGKDELGR ASRLCKHALYCRWMRVHGKVPSHLLRSKIT KPNVYHESKLAAKEYQAAKARLFTAFIKAG LGAWVEKPTEQDQFSLTGSAAGGSGGSAAA QGSVVIVGRIILSGSGSITAYSQQTRGLLG CIITSLTGRDKNQVEGEVQVVSTATQSFLA TCVNGVCWTVYHGAGSKTLAGPKGPITQMY TNVDQDLVGWQAPPGARSLTPCTCGSSDLY LVTRHADVIPVRRRGDSRGSLLSPRPVSYL KGSSGGPLLCPSGHAVGIFRAAVCTRGVAK AVDFVPVESMETTMRSES | 206 |

In some embodiments, the methods, compositions and systems disclosed herein relate to an iAD which is an iADAR2. Exemplary iADAR2 are disclosed in Table 5.

In some embodiments of the aspects, an iADAR2 fusion protein for use in the methods and compositions as disclosed herein is selected from any of SEQ ID NO: 150-167, SEQ ID NO: 279-285 or a sequence that has at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% sequence identity to an amino acid sequence selected from any of SEQ ID NO: 150-167 or SEQ ID NO: 279-285, and that maintains the same functions as the sequence from which is it derived.

In some embodiments, an exemplary iADAR2 has the ADAR2-DD in one polypeptide, and is selected from any of SEQ ID NO: 166 or 167, or a polypeptide that has at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% sequence identity to an amino acid sequence selected from SEQ ID NO: 166 or 167, and that maintains the same functions as the sequence from which is it derived.

In some embodiments, an exemplary iADAR2 has the ADAR2-DD in one polypeptide in combination with NS3 and its cognate peptide domain (e.g., CP5-46-4D5E). Such an iADAR2 can comprise one of SEQ ID NO: 169, 206, 280, or 285, or a polypeptide that has at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% sequence identity to one of SEQ ID NO: 169, 206, 280, or 285, and that maintains the same functions as the sequence from which is it derived.

Figure 33A:
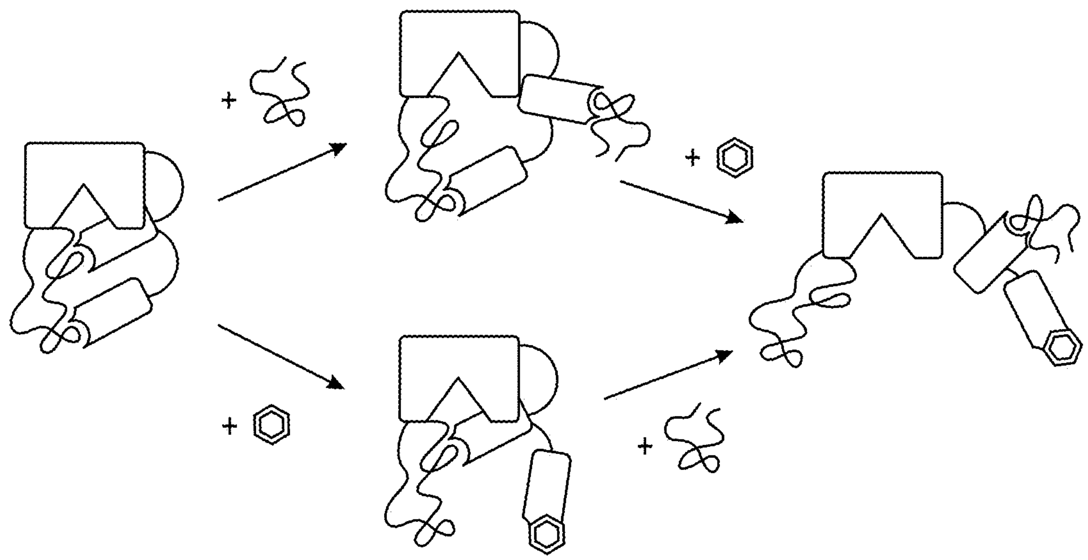
FIG. 33A-33C show iADAR Based Antigen AND Drug Logic. Antigen, Drug AND-Gates can be constructed using dual repressed iADAR proteins.

In one aspect, described herein is a fusion protein comprising: (a) a first portion of a deaminase domain (DD) of an adenosine deaminase; (b) a first member of a first binding pair associated with the first portion of the DD; (c) a second portion of the DD; (d) a second member of a first binding pair associated with the second portion of the DD; (e) a first member of a second binding pair associated with the first member of the first binding pair; and (f) a second member of the second binding pair associated with the second member of the first binding pair (see e.g., FIG. 33A-33C). In some embodiments, the first member of the first binding pair is capable of binding to the second member of the first binding pair in the absence of a first inducer, resulting in allosteric inhibition of the first and second portions of the DD. In some embodiments, the first member of the first binding pair is not capable of binding to the second member of the first binding pair in the presence of the first inducer, resulting in activation of the first and second portions of the DD. In some embodiments, the first member of the second binding pair is capable of binding to the second member of the second binding pair in the absence of a second inducer, resulting in allosteric inhibition of the first and second portions of the DD. In some embodiments, the first member of the second binding pair is not capable of binding to the second member of the second binding pair in the presence of the second inducer, resulting in activation of the first and second portions of the DD. In some embodiments, the fusion protein further comprises a third, fourth, fifth, sixth, seventh, eighth, ninth, tenth or more binding pairs.

In some embodiments, an iAD polypeptide can comprise one of SEQ ID NO: 334-339 or 342-355 or a polypeptide that has at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% sequence identity to one of SEQ ID NO: SEQ ID NO: 334-339 or 342-355, and that maintains the same functions as the sequence from which is it derived.

In some embodiments, an AD polypeptide can be encoded by a nucleic acid comprising one of SEQ ID NO: 390-392 or a nucleic acid that has at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% sequence identity to one of SEQ ID NO: 390-392, and that maintains the same functions when expressed as a polypeptide as the sequence from which is it derived.

II. Synthetic Effector Constructs

As disclosed herein in the Examples, the iADAR was demonstrated to edit stop codons in a synthetic mRNA transcript, where the synthetic construct comprises the STOP codon located in a small hair-pin, referred to herein as "ds-STOP" region. In particular, as disclosed herein the iADAR2 is specifically modified and engineered so it could edit a STOP by using a short hairpin motif, thereby enabling the stop codon editing on the same nucleic acid strand that GOI is expressed, and that is bound to by the DD. In some embodiments, a ds-TC region (e.g., ds-STOP, ds-START, or ds-SENSE region) is in a synthetic construct as disclosed herein, e.g., a TIC or TAC as disclosed herein.

Another aspect of the technology relates to synthetic nucleic acid constructs the IADAR effectuates. In particular, another aspect of the technology described herein relates to synthetic nucleic acid constructs that function as a target activation construct (TAC) or target inactivation construct (TIC), where the synthetic TAC comprises a hairpin loop comprising a STOP codon located upstream (i.e., 5') of a nucleic acid encoding Gene of Interest (GOI), and where a synthetic TIC comprises a hairpin loop comprising a STOP codon located downstream (i.e., 3') of a GOI and upstream (i.e., 5') of a nucleic acid poly A sequence. Another aspect relates to nucleic acid encoding an iADAR and/or a nucleic acid encoding one or more of an activation construct (TAC) or inactivation construct (TIC).

In some embodiments, synthetic constructs, referred to herein as Target Activation Constructs (TAC) or Target inactivation constructs (TIC) are exemplary mRNA transcripts that can be edited by iADAR when it is in the active state (iADAR-ON).

It is envisioned that the iADAR can edit any synthetic construct comprising a hairpin loop with a STOP codon located within the hairpin loop, which are referred to herein as "ds-STOP" regions. Such synthetic constructs comprising a ds-TC region (e.g., ds-STOP, ds-START, or ds-SENSE region) as defined herein, can be delivered to a cell, e.g., a human cell by any means, including but not limited to using viral vectors and non-viral vectors as described herein, and/or use of CRISPR/Cas systems.

Accordingly, in some embodiments, the ds-TC region (e.g., ds-STOP, ds-START, or ds-SENSE region) can be inserted into a nucleic acid sequence in the genome of a cell using gene editing technologies, including but not limited to CRISPR or other gene-editing technologies. Depending where the ds-STOP is inserted into the nucleic acid sequence, e.g., genome of a cell, if it is inserted upstream of a polyA sequence to a particular transcript, such embodiment could enable IADAR mediated mRNA decay of a particular gene or transcript in a cell, which could be turned on by the presence of an inducer.

In some embodiments, the synthetic effector constructs described herein comprise synthetic RNA. In some embodiments, the synthetic effector constructs described herein comprise synthetic mRNA. In some embodiments, the synthetic effector constructs described herein comprise synthetic circular RNA.

In some embodiments, the synthetic RNA molecule comprises one of SEQ ID NOs: 292-327 or 356-357 or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 292-327 or 356-357, that maintains the same function.

A. Double-Stranded Region of the RNA

Described herein are RNA molecules comprising at least one double-stranded region. In some embodiments, the double-stranded region of the RNA comprises (i) at least one target codon; and (ii) an RNA binding motif capable of being bound by an RNA-binding domain (e.g., of an iAD polypeptide as described further herein). In some embodiments, the double-stranded region comprises secondary structure of the RNA. In some embodiments, the double-stranded region comprises at least one hairpin. In some embodiments, the double-stranded region comprises at least two hairpins.

In some embodiments, the double-stranded region is at least 10 nucleotides long, at least 20 nucleotides long, at least 30 nucleotides long, at least 40 nucleotides long, at least 50 nucleotides long, at least 60 nucleotides long, at least 70 nucleotides long, at least 80 nucleotides long, at least 90 nucleotides long, at least 100 nucleotides long, or more. In some embodiments, the double-stranded region is at most 10 nucleotides long, at most 20 nucleotides long, at most 30 nucleotides long, at most 40 nucleotides long, at most 50 nucleotides long, at most 60 nucleotides long, at most 70 nucleotides long, at most 80 nucleotides long, at most 90 nucleotides long, or at most 100 nucleotides long. In some embodiments, the double-stranded region is about 10 nucleotides long, about 20 nucleotides long, about 30 nucleotides long, about 40 nucleotides long, about 50 nucleotides long, about 60 nucleotides long, about 70 nucleotides long, about 80 nucleotides long, about 90 nucleotides long, or about 100 nucleotides long. In some embodiments, the double-stranded region is about 55-65 nucleotides long, about 50-70 nucleotides long, about 45-75 nucleotides long, or about 40-80 nucleotides long.

i. Target Codons

Described herein are RNA molecules comprising at least one target codon. In some embodiments, the RNA molecule comprises 1, 2, 3, 4, 5, 6, 7, 8, 9, 10, or more target codons. In some embodiments, the at least one target codon is present in a double-stranded region of the RNA molecule. In some embodiments, the target codon is a double-stranded target codon (dsTC). In some embodiments, the at least one target codon is in close proximity to at least one RNA binding motif capable of being bound by an RNA-binding domain (e.g., of an iAD polypeptide as described further herein). In some embodiments, the target codon is a stop codon (e.g., a double-stranded stop codon, ds-STOP). In some embodiments, the target codon is a start codon (e.g., a double-stranded start codon, ds-START), In some embodiments, the target codon is a non-start codon (e.g., a double-stranded non-start codon, ds-non-START). In some embodiments, the target codon is a sense codon (e.g., a double-stranded sense codon, ds-SENSE).

In some embodiments, the target codon is upstream of at least one open reading frame. In some embodiments, the target codon is downstream of at least one open reading frame. In some embodiments, the target codon is within at least one open reading frame. In some embodiments, action of the induced iAD on the target codon results in activation, deactivation, or alteration to translation of an associated open reading, depending on the structure of the RNA molecule. Table 16 contains non-limiting examples of target codons in RNA molecules and their effect on RNA structure and/or function.

TABLE 16

Exemplary RNA molecule types

| double-stranded target codon (ds-TC) change by induced iAD | Location of ds-TC in RNA molecule | Type of RNA construct (activity in presence of induced iAD) |
|---|---|---|
| STOP → non-STOP | 5' of ORF or middle of ORF | Activation construct (OFF → ON) |
| STOP → non-STOP | 3' of ORF | Inactivation construct (ON → OFF) |
| START → non-START | 5' of ORF | Inactivation construct (ON → OFF) |
| START → non-START | 5' of ORF or middle of ORF | Altered initiation site → protein length variants |
| non-START → START | 5' of ORF or middle of ORF | Activation construct (OFF → ON) |
| sense 1 → sense 2 | Any sense codon in ORF | Altered codon → RNA functional variants (e.g., splicing, translation, degradation, etc.) and/or Altered amino acid → protein mutation variants |

a. ds-STOP regions

As disclosed herein, an iADAR in the ON state can edit a STOP codon in a RNA transcript, where the STOP codon is located a double stranded region in the transcript, and where the iADAR can bind to the double stranded region to eliminate the STOP signal. Accordingly, in some embodiments, the STOP codon is located in double stranded region, herein referred to as "ds-STOP" region. In some embodiments, the ds-STOP region is a short hairpin loop, where the short hairpin loop is RNA or mRNA.

In some embodiments, the ds-STOP region is a double stranded RNA transcript that comprises (i) a STOP codon as disclosed herein, and (ii) a Binding motif for RBD (BM), where the Binding motif for RBD (BM) binds to a RNA-binding domain (RBD) of the iADAR. In some embodiments, the Binding motif for RBD (BM) is capable of being bound by an RNA-binding domain of the DD.

In some embodiments, the ds-STOP region comprises at least one hairpin. In some embodiments, the ds-STOP region comprises at least one hairpin comprising the at least one stop codon and the Binding motif for RBD (BM). In some embodiments, the ds-STOP region comprises a first hairpin comprising the at least one stop codon and a second hairpin comprising the Binding motif for RBD (BM).

As disclosed herein, in the presence of an inducer the iADAR changes an A to an I in mRNA. In some embodiments, the ds-STOP region comprises a stop codon UAG, which is edited to a UIG codon in the presence of an inducer. In some embodiments, the mRNA STOP codon present in the ds-STOP region is selected from any of: UAA, UAG, or UGA, Accordingly, in the presence of an inducer, the iADAR-ON edits the STOP codon UAA to UII, or STOP codon UAG to UIG or STOP codon UGA to UGI, therefore eliminating the STOP codon in each case.

In some embodiments, the ds-STOP region comprises at least one stop codon, where the Stop codon comprises UAG. In some embodiments, the ds-STOP region comprises at least one non-stop codon, for example, where the non-stop codon comprises at least one tryptophan codon, e.g., a tryptophan codon comprises UGG.

In some embodiments, the ds-STOP region comprises a STOP sequence selected from any of SEQ ID NO: 105-110, 170, 174, 178, 182, 186, 190, or 194, or a nucleic acid sequence comprising at least 10 consecutive nucleotides selected from SEQ ID NO: 105-110, 170, 174, 178, 182, 186, 190, or 194, or a nucleic acid sequence having at least 70%, or about 75%, or about 80%, or about 85%, or about 90%, or about 92%, or about 94% or about 96% or about 98%, or about 99% or 100% sequence identity to any of SEQ ID NO: 105-110, 170, 174, 178, 182, 186, 190, or 194.

TABLE 6

Exemplary STOP sequences comprising stop Codons in a ds-STOP region:

| SEQ ID | Stop Codon sequence in ds-STOP region | |
|---|---|---|
| 105 | UAG-UAG-MS2 | CGCGTAGCGCTAGCTTTGCCAGCGCCACGCGaaACATGAGGATcACCCATGT |
| 106 | UGG-UGG | CGCGTGGCGCTGGCTTCCTTGCCAGCGCCACGCG |
| 107 | UAG-UGG | CGCGTAGCGCTGGCTTCCTTGCCAGCGCCACGCG |
| 108 | UAG-UAG | CGCGTAGCGCTAGCTTCCTTGCCAGCGCCACGCG |
| 109 | UAG-UAG-PP7 | CGCGTAGCGCTAGCTTTGCCAGCGCCACGCGaaggagcagacgatatggcgtcgctcc |
| 110 | UAG-UAG-BoxB | CGCGTAGCGCTAGCTTTGCCAGCGCCACGCGgtaagggccctgaagaagggccc |
| 111 | UAG-UAG-HIV TAR | CGCGTAGCGCTAGCTTTGCCAGCGCCACGCGgtaggctcgtctgagctcattagctccgagcc |
| 170 | UAG-UAG Stop Loop (bolded) w/ MS2 Loop (italicized) | AATTC**CGCGTAGCGCTAGCTTTGCCAGCGCCACGCG**aa*ACATGAGGATcACCCATGT*ACTAGT |
| 174 | UAG-UGG Stop Loop (bolded) w/ MS2 Loop (italicized) | AATTC**CGCGTAGCGCTGGCTTTGCCAGCGCCACGCG**aa*ACATGAGGATcACCCATGT*ACTAGT |
| 178 | UGG-UAG Stop Loop (bolded) w/ MS2 Loop (italicized) | AATTC**CGCGTGGCGCTAGCTTTGCCAGCGCCACGCG**aa*ACATGAGGATcACCCATGT*ACTAGT |
| 182 | UAG-UAG Stop Loop (bolded) w/Internal MS2 Loop (italicized) | AATTC**CGCGTAGCGCTAGC**T_ACATGAGGATcACCCATGT_**TGCCAGCGCCACGCG**ACTAGT |
| 186 | UAG-UAG Stop Loop (bolded) w/ PP7 Loop (italicized) | AATTC**CGCGTAGCGCTAGCTTTGCCAGCGCCACGCG**aa*ggagcagacgatatggcgtcgctccaa*TACTAGT |
| 190 | UAG-UAG Stop Loop (bolded) w/ HIV Tar Loop (italicized) | AATT**CCGCGTAGCGCTAGCTTTGCCAGCGCCACGCGG**t*aggctcgtctgagctcattagctccgagcca*ACTAGT |
| 194 | UAG-UAG Stop Loop (bolded) w/ BoxB Loop | AATT**CCGCGTAGCGCTAGCTTTGCCAGCGCCACGCGG**t*aagggccctgaagaagggccca*ACTAGT |

In some embodiments, the STOP sequence comprises a P2A-T2A sequence 5' and/or 3' of any stop sequence, e.g., a stop sequence selected from any of SEQ ID NO: 105-110, or a sequence having at least 85% sequence identity to any of SEQ ID NO: 105-110. In some embodiments, a P2A-T2A sequence encodes an amino acid comprising the sequence of: ATNFSLLKQAGDVEEN-PGPASAGSGEGRGSLLTCGDVEENPGP (SEQ ID NO: 112). In some embodiments, the ds-STOP region comprises a sequence selected from SEQ ID NO: 112 or a sequence at least 85% sequence identity to SEQ ID NO: 112.

b. ds-START or ds-Non-START Regions

As disclosed herein, an iADAR in the ON state can edit a START codon in a RNA transcript, where the START codon is located a double stranded region in the transcript, and where the iADAR can bind to the double stranded region to eliminate the START signal. Accordingly, in some embodiments, the START codon is located in double stranded region, herein referred to as "ds-START" region. In some embodiments, the ds-START region is a short hairpin loop, where the short hairpin loop is RNA or mRNA.

In some embodiments, the ds-START region is a double stranded RNA transcript that comprises (i) a START codon as disclosed herein, and (ii) a Binding motif for RBD (BM), where the Binding motif for RBD (BM) binds to a RNA-binding domain (RBD) of the iADAR. In some embodiments, the Binding motif for RBD (BM) is capable of being bound by an RNA-binding domain of the DD.

In some embodiments, the ds-START region comprises at least one hairpin. In some embodiments, the ds-START region comprises at least one hairpin comprising the at least one start codon and the Binding motif for RBD (BM). In some embodiments, the ds-START region comprises a first hairpin comprising the at least one START codon and a second hairpin comprising the Binding motif for RBD (BM).

As disclosed herein, in the presence of an inducer the iADAR changes an A to an I in mRNA. In some embodiments, the ds-non-START region comprises a non-start codon AUA, which is edited to a AUI start codon in the presence of an inducer. In some embodiments, the ds-START region comprises a start codon AUG, which is edited to a IUG non-start codon in the presence of an inducer. In some embodiments, the mRNA START codon present in the ds-START region is selected from any of: AUI or AUG. Accordingly, in the presence of an inducer, the iADAR-ON edits the START codon AUG to IUG, therefore eliminating the START codon and deactivating translation. In other embodiments, in the presence of an inducer, the iADAR-ON edits the non-START codon AUA to START codon AUI, therefore adding a START codon and activating translation.

In some embodiments, the ds-START region comprises at least one start codon, where the start codon comprises AUI or AUG. In some embodiments, the ds-non-START region comprises at least one non-start codon, including but not limited to AUA or IUG.

In some embodiments, the ds-START region comprises a start or non-start sequence as tested in any of FIGS. 26-28, as shown in any of FIGS. 38-40, or included in any of SEQ ID NO: 292-300 or a nucleic acid sequence comprising at least 10 consecutive nucleotides selected from SEQ ID NO: 292-300, or a nucleic acid sequence having at least 70%, or about 75%, or about 80%, or about 85%, or about 90%, or about 92%, or about 94% or about 96% or about 98%, or about 99% or 100% sequence identity to any of SEQ ID NO: 292-300.

c. ds-SENSE Regions

As disclosed herein, an iADAR in the ON state can edit a SENSE codon in a RNA transcript, where the SENSE codon is located a double stranded region in the transcript, and where the iADAR can bind to the double stranded region to mutate the SENSE codon encoding a first amino acid into a mutated sense codon encoding a second amino acid. In some embodiments, the iADAR can bind to the double stranded region to mutate the SENSE codon encoding an amino acid into a mutated sense codon encoding the same amino acid. In some embodiments, the mutated sense codon can affect the activity of the RNA, e.g., splicing, translation, degradation, etc. Accordingly, in some embodiments, the SENSE codon is located in double stranded region, herein referred to as "ds-SENSE" region. In some embodiments, the ds-SENSE region is a short hairpin loop, where the short hairpin loop is RNA or mRNA.

In some embodiments, the ds-SENSE region is a double stranded RNA transcript that comprises (i) a SENSE codon as disclosed herein, and (ii) a Binding motif for RBD (BM), where the Binding motif for RBD (BM) binds to a RNA-binding domain (RBD) of the iADAR. In some embodiments, the Binding motif for RBD (BM) is capable of being bound by an RNA-binding domain of the DD.

In some embodiments, the ds-SENSE region comprises at least one hairpin. In some embodiments, the ds-SENSE region comprises at least one hairpin comprising the at least one sense codon and the Binding motif for RBD (BM). In some embodiments, the ds-SENSE region comprises a first hairpin comprising the at least one SENSE codon and a second hairpin comprising the Binding motif for RBD (BM).

As disclosed herein, in the presence of an inducer the iADAR changes an A to an I in mRNA. In some embodiments, the ds-SENSE region comprises a codon selected from Table 15, which is edited to a mutated sense codon in the presence of an inducer, as shown in Table 15. In some embodiments, the sense codon comprises an adenosine nucleotide in the first position of the codon. In some embodiments, the sense codon comprises an adenosine nucleotide in the second position of the codon. In some embodiments, the sense codon comprises an adenosine nucleotide in the third position of the codon. In some embodiments, the sense codon comprises an adenosine nucleotide in the first and second positions of the codon. In some embodiments, the sense codon comprises an adenosine nucleotide in the second and third positions of the codon. In some embodiments, the sense codon comprises an adenosine nucleotide in the first and third positions of the codon. In some embodiments, the sense codon comprises an adenosine nucleotide in the first, second, and third positions of the codon.

In some embodiments, the sense codon is within a self-cleaving peptide sequence. In some embodiments, mutation of the sense codon to the mutated codon results in increased or decreased cleavage of the self-cleaving peptide when in the translated protein. In some embodiments, the self-cleaving peptide belongs to the 2A peptide family, which can also be referred to as a 2A Ribosomal Skip Sequence. Non-limiting examples of 2A peptides include P2A, E2A, F2A and T2A (see e.g., SEQ ID NOs 360-363). F2A is derived from foot-and-mouth disease virus 18; E2A is derived from equine rhinitis A virus; P2A is derived from porcine teschovirus-1 2A; T2A is derived from thosea asigna virus 2A. In some embodiments of any of the aspects, the N-terminal of the 2A peptide comprises the sequence "GSG" (Gly-Ser-Gly). In some embodiments of any of the aspects, the N-terminal of the 2A peptide does not comprise the sequence "GSG" (Gly-Ser-Gly).

In some embodiments, the ds-SENSE region comprises a sense sequence as tested in any of FIG. 29 or 37, as shown in any of FIG. 41, 59, or 60, as shown in Table 15, or included in any of SEQ ID NO: 301, 356, or 357 or a nucleic acid sequence comprising at least 10 consecutive nucleotides selected from SEQ ID NO: 301, 356, or 357, or a nucleic acid sequence having at least 70%, or about 75%, or about 80%, or about 85%, or about 90%, or about 92%, or about 94% or about 96% or about 98%, or about 99% or 100% sequence identity to any of SEQ ID NO: 301, 356, or 357.

ii. Binding Motifs

Described herein are RNA molecules comprising at least one binding motif that can bind to an RNA binding domain (RBD) (e.g., of an iAD polypeptide as described further herein). In some embodiments, the RNA molecule comprises 1, 2, 3, 4, 5, 6, 7, 8, 9, 10, or more binding motifs. In some embodiments, the at least one binding motif is present in a double-stranded region of the RNA molecule.

In some embodiments, the double-stranded region (e.g., ds-STOP, ds-START, or ds-SENSE) region comprises at least one binding motif that binds to the RNA binding domain (RBD) selected from the group consisting of MS2, PP7, BoxB, and HIV TAR, as disclosed in Table 7.

In some embodiments, the double-stranded region (e.g., ds-STOP, ds-START, or ds-SENSE) region comprises at least one MS2 RBD binding motif comprising ACATGAGGATcACCCATGT (SEQ ID NO: 403) or a sequence at least 80%, or at least about 85%, or at least about 90% or at least about 95% sequence identity to SEQ ID NO: 130. It is contemplated herein that a sequence variant of MS2 RBD binding motif can be used, that maintains its binding function.

In some embodiments, the double-stranded region (e.g., ds-STOP, ds-START, or ds-SENSE) region comprises at least one PP7 RBD binding motif comprising ggagcagacgatatggcgtcgctcc (SEQ ID NO: 131) or a sequence at least 80%, or at least about 85%, or at least about 90% or at least about 95% sequence identity to SEQ ID NO: 131. It is contemplated herein that a sequence variant of PP7 RBD binding motif can be used, that maintains its binding function; for example, Lim and Peabody, "RNA recognition site of PP7 coat protein" Nucleic Acids Research 30(19):4138-44 (2002), the contents of which are incorporated herein by reference in its entirety, describes non-limiting examples of PP7 sequence variants.

In some embodiments, the double-stranded region (e.g., ds-STOP, ds-START, or ds-SENSE) region comprises at least one BoxB RBD binding motif comprising gggccctgaagaagggccc (SEQ ID NO: 132) or a sequence at least 80%, or at least about 85%, or at least about 90% or at least about 95% sequence identity to SEQ ID NO: 132. It is contemplated herein that a sequence variant of BoxB RBD binding motif can be used, that maintains its binding function.

In some embodiments, the double-stranded region (e.g., ds-STOP, ds-START, or ds-SENSE) region comprises at least one HIV Tar RBD binding motif comprising ggctcgtctgagctcattagctccgagcc (SEQ ID NO: 133) or a sequence at least 80%, or at least about 85%, or at least about 90% or at least about 95% sequence identity to SEQ ID NO: 133. It is contemplated herein that a sequence variant of HIV Tar RBD binding motif can be used, that maintains its binding function.

TAC can comprise upstream of the ds-STOP region, a first open reading frame (1st ORF). In some embodiments, the 1st ORF comprises a nucleic acid sequence that encodes for a first polypeptide, and the second reading frame encodes for a second polypeptide. In some embodiments, the first open reading frame encodes for a first portion of a polypeptide, and the second reading frame encodes for a second portion of the polypeptide. In some embodiments, the first open reading frame comprises a nucleic acid sequence that encodes for the iADAR fusion protein as described herein.

In some embodiments, the second ORF, e.g., the nucleic acid sequence located 3' of the ds-STOP region encodes an effector molecule or effector protein, as disclosed herein.

Figure 1B:
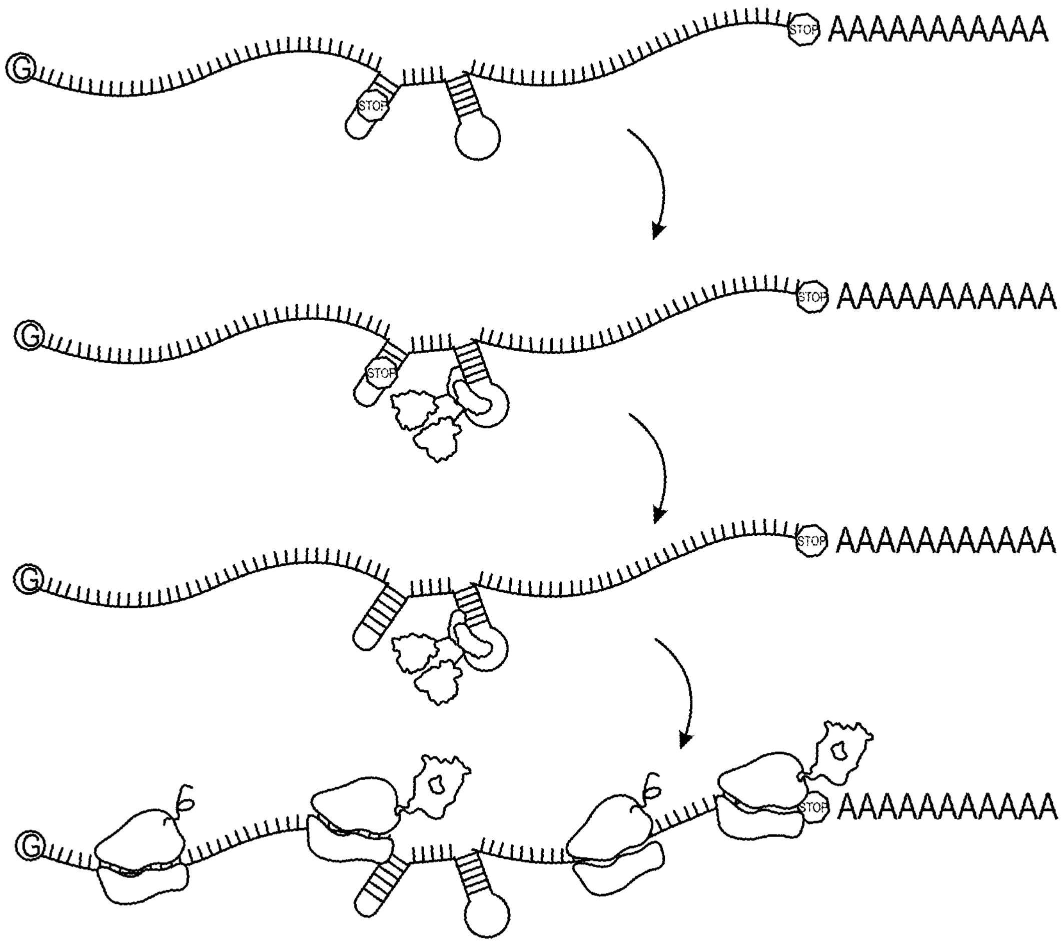

In some embodiments, the TAC comprises a synthetic RNA construct as exemplified by FIG. 1A-1B: an upstream coding region, a short hairpin that contains 1 or more stop codons, an RBD binding motif, and a downstream coding region.

C. Target Inactivation Construct (TIC)

In some embodiments, an exemplary Target iNactivation construct (TIC) is a synthetic RNA molecule, that comprises, in the following order: (i) a first open reading frame that is operatively linked to the double-stranded STOP region, (ii) as least a ds-STOP region, as defined herein, for example, but not limited to, a hairpin loop, where the ds-STOP region comprises, at least one stop codon; and a binding motif for RBD capable of being bound by an RNA-binding domain of the DD; and (iii) a poly A region. In some embodiments, the first ORF comprises a nucleic

TABLE 7

Binding motif for RBD (BM)

| SEQ ID NO: | Binding motif for RBD (BM) | Sequence | Is bound by RNA Binding Domain (RBD) of the iAD | SEQ ID NO: of the RBD |
|---|---|---|---|---|
| 403 | MS2 | ACATGAGGATcACCCATGT | MCP | 100 |
| 131 | PP7 | ggagcagacgatatggcgtcgctcc | PCP | 101 |
| 132 | BoxB | gggccctgaagaagggccc | λN | 102 |
| 133 | HIV TAR | ggctcgtctgagctcattagctccgagcc | HIV Tat | 103 |

In some embodiments, the Binding motif for RBD (BM) can be located after the stop codon sequence. In some embodiments, the Binding motif for RBD (BM) can be located before a stop codon sequence, e.g., a stop codon sequence disclosed in Table 6.

B. Target Activation Construct (TAC)

In some embodiments, an exemplary Target Activation construct (TAC) is a synthetic RNA molecule, that comprises at least (i) a double stranded region, referred to herein as "ds-STOP" region, for example, but not limited to, a hairpin loop, where the ds-STOP region comprises, at least one stop codon; and a binding motif for RBD capable of being bound by an RNA-binding domain of the DD; and (ii) a second open reading frame, wherein the second open reading frame (2nd ORF) is operatively linked to the double-stranded region. In some embodiments, the second ORF comprises a nucleic acid encoding a GOI of interest. The GOI is a nucleic acid transcript, can encode, for example but not limited to; a protein of interest to be expressed, mRNA, miRNA, antisense, and the like. In some embodiments, the acid encoding a GOI of interest. The GOI is a nucleic acid transcript, can encode, for example but not limited to; a protein of interest to be expressed, mRNA, miRNA, antisense, and the like. In some embodiments, in place of or in addition to the polyA region, the synthetic RNA molecule comprises a ribosome stalling sequence, which can lead to RNA degradation. Non-limiting examples of ribosome stalling sequences are known in the art, see e.g., Yip and Shao, "Detecting and Rescuing Stalled Ribosomes," Trends in Biochemical Sciences, Volume 46, Issue 9, P731-743, September 2021, the contents of which are incorporated herein by reference in their entirety.

In some aspects of embodiments disclosed herein, an RNA molecule can comprise: (a) an open reading frame; (b) a ds-STOP region, comprising (i) at least one stop codon; and (ii) a binding motif for RBD capable of being bound by an RNA-binding domain; and (c) a poly-A tail.

In some aspects of embodiments disclosed herein, an RNA molecule (e.g., a TIC) can comprise: (a) a ds-START region, comprising (i) at least one start codon; and (ii) a binding motif for RBD capable of being bound by an RNA-binding domain; and (b) an open reading frame.

In some embodiments of any of the aspects, the RNA-binding domain comprises MCP, and the Binding motif for RBD (BM) comprises MS2. In some embodiments of any of the aspects, the RNA-binding domain comprises PCP, and the Binding motif for RBD (BM) comprises PP7. In some embodiments of any of the aspects, the RNA-binding domain comprises AN, and the Binding motif for RBD (BM) comprises BoxB. In some embodiments of any of the aspects, the RNA-binding domain comprises HIV Tat, and the Binding motif for RBD (BM) comprises TAR.

In some embodiments of any of the aspects, the double-stranded region of the RNA molecule comprises at least one hairpin. In some embodiments of any of the aspects, the double-stranded region of the RNA molecule comprises one hairpin comprising the at least one stop codon and the Binding motif for RBD (BM). In some embodiments of any of the aspects, the double-stranded region of the RNA molecule comprises a first hairpin comprising the at least one stop codon and a second hairpin comprising the Binding motif for RBD (BM).

Figure 2A:
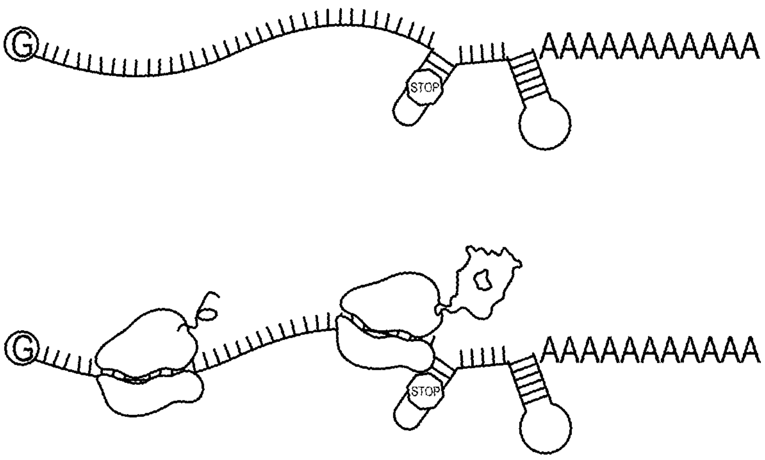
FIG. 2A-2D—Final Stop Codon Editing Leads to Reduced Protein Expression.
Figure 2B:
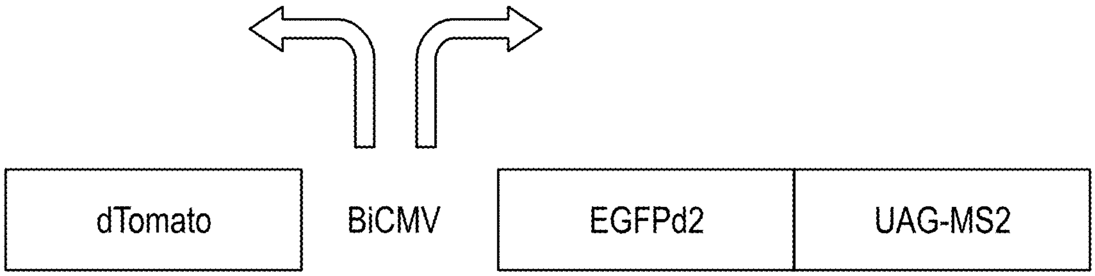
Figure 2C:
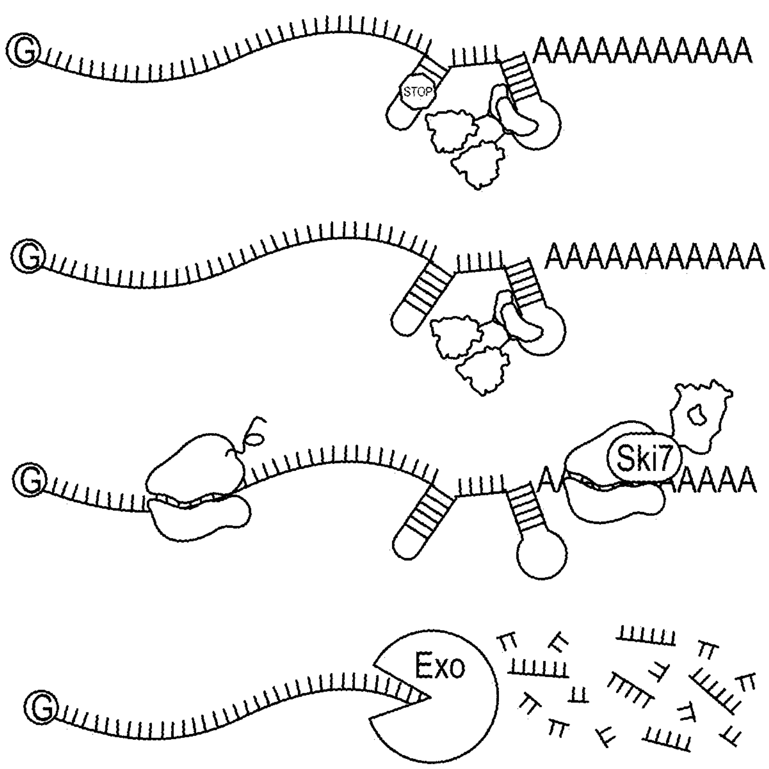

In some embodiments, the TiC comprises a synthetic RNA construct as exemplified by FIG. 2A-2C: an upstream coding region, a short hairpin that contains 1 or more stop codons, an RBD binding motif, and a polyA tail or ribosome stalling sequence.

D. Synthetic Construct Comprising Both a TAC and TIC

In some embodiments, a synthetic construct comprises both a TAC and TIC. Such a construct enables switching of the translation of one GOI to another GOI. For exemplary purposes only, in one embodiment, a synthetic construct comprises, in the following order, a first ORF, a first ds-STOP region, a polyA sequence, a second ds-STOP region, and a second ORF. In such an embodiment, when the inducer is absent, the iADAR-OFF enables the translation of the first ORF only (1-ORF expressed only). When the inducer is present, e.g., the iADAR is in ON state (IADAR-ON) the first ds-STOP is edited and therefore the polyA sequence is translation and results in the transcript for the first ORF undergoing mRNA decay (e.g., $1^{st}$-ORF decay/OFF) and the second ds-STOP is edited therefore enabling translation of the second ORF (e.g., $2^{nd}$-ORF is expressed). In some embodiments, such a transcript comprising a TAC and TIN can comprise an IRES located between the first and second ds-STOP regions. In some embodiments, the first ORF encodes an effector molecule, and the second ORF encodes a second effector molecule, where the second effector molecule is a second or alternative version of the first effector molecule. Stated differently, using such a system, in the presence of the inducer, one can easily switch the expression from the first ORF (e.g., transcript A) to the second ORF (e.g., transcript B).

E. Effector Protein.

In some embodiments, the GOI is a nucleic acid transcript, which can encode, for example but not limited to: a protein of interest to be expressed as an effector protein, and the like. Effector molecules are well known in the art and can include, but are not limited to, antibodies, enzymes, chimeric antigen receptors (CARs). In some embodiments, the effector protein comprises an antigen-binding domain for a cancer antigen. In some embodiments, the effector protein comprises an antigen-binding domain for a microbial antigen.

In some embodiments the effector protein comprises a detectable marker or a reporter molecule, including but not limited to a fluorescent protein or a detectable tag (e.g., c-Myc, HA, VSV-G, HSV, FLAG, V5, HIS, or biotin). In some embodiments of any of the aspects, an effector protein as described herein, especially those that are administered to a subject or those that are part of a pharmaceutical composition, do not comprise detectable markers that are immunogenic. In some embodiments of any of the aspects, an effector protein as described herein do not comprise GFP, mCherry, HAI, or any other immunogenic markers. In some embodiments of any of the aspects, an effector protein described herein that comprises a detectable marker can have the detectable marker removed at a later time, e.g., a removable (e.g., cleavable) detectable marker. In some embodiments of any of the aspects, an effector protein described herein that comprises a detectable marker can have the detectable marker replaced with a different detectable marker, as known in the art or described herein, e.g., a replaceable (e.g., interchangeable) detectable marker.

III. Systems

Another aspect of the technology relates to systems and cells comprising an iADAR and a nucleic effector construct, e.g., an activation construct or inactivation construct as disclosed herein.

In certain embodiments, the iADAR is naturally or endogenously present in the host cell, for example, naturally or endogenously present in the eukaryotic cell. In some embodiments, the ADAR is endogenously expressed by the host cell. In certain embodiments, the iADAR is exogenous to the host cell. In some embodiments, the iADAR is encoded by a nucleic acid (e.g., DNA or RNA). In some embodiments, the method comprises introducing the iADAR or a construct encoding the iADAR into the host cell. In some embodiments, the method does not comprise introducing any protein into the host cell. In certain embodiments, the iADAR is iADAR1 and/or iADAR2. In some embodiments, the iADAR is one or more iADARs selected from the group consisting of hiADAR1, hiADAR2, murine iADAR1 and murine iADAR2.

In one aspect described herein is a system for modulating RNA translation comprising: (a) a fusion protein comprising an RNA-binding domain linked to a deaminase domain of an adenosine deaminase; and (b) an RNA molecule comprising: (i) an open reading frame; (ii) a double-stranded region comprising: (A) at least one target codon (e.g., stop, start, non-start, or sense codon); and (B) a binding motif for RBD capable of being bound by the RNA-binding domain of the fusion protein; and (iii) a poly-A tail.

In one aspect described herein is a system for modulating RNA translation comprising: (a) a fusion protein comprising: (i) an RNA-binding domain; (ii) a first portion of a deaminase domain (DD) of an adenosine deaminase; (iii) a first member of a binding pair associated with the first portion of the DD; (iv) a second portion of the DD; and (v) a second member of a binding pair associated with the second portion of the DD; and (b) an RNA molecule as described herein.

In one aspect described herein is a system for modulating RNA translation comprising: (a) a fusion protein comprising: (i) an RNA-binding domain; (ii) a first portion of a deaminase domain (DD) of an adenosine deaminase; (iii) a first member of a binding pair associated with the first portion of the DD; (iv) a second portion of the DD; and (v) a second member of a binding pair associated with the second portion of the DD; and (b) an RNA molecule comprising: (i) a first open reading frame; (ii) a double-stranded region comprising: (A) at least one target codon (stop, start, non-start, or sense codon); and (B) a binding motif for RBD capable of being bound by the RNA-binding domain of the fusion protein; and (iii) a second open reading frame.

In one aspect described herein is a system for modulating RNA translation comprising: (a) a fusion protein comprising: (i) an RNA-binding domain; (ii) a first portion of a deaminase domain (DD) of an adenosine deaminase; (iii) a first member of a binding pair associated with the first portion of the DD; (iv) a second portion of the DD; and (v) a second member of a binding pair associated with the second portion of the DD; and (b) an RNA molecule comprising: (i) an open reading frame; (ii) a double-stranded region comprising: (A) at least one target codon (stop, start, non-start, or sense codon); and (B) a binding motif for RBD capable of being bound by the RNA-binding domain of the fusion protein; and (iii) a poly-A tail.

In one aspect described herein is a system for modulating RNA translation comprising: (a) a fusion protein comprising: (i) an RNA-binding domain; (ii) a first portion of a deaminase domain (DD) of an adenosine deaminase; (iii) a first member of a binding pair associated with the first portion of the DD; (iv) a second portion of the DD; (v) a cleavable linker; and (vi) a second member of a binding pair associated with the cleavable linker; and (b) an RNA molecule as described herein.

In one aspect described herein is a system for modulating RNA translation comprising: (a) a fusion protein comprising: (1) an RNA-binding domain; (ii) a first portion of a deaminase domain (DD) of an adenosine deaminase; (iii) a first member of a binding pair associated with the first portion of the DD; (iv) a second portion of the DD; (v) a cleavable linker; and (vi) a second member of a binding pair associated with the cleavable linker; and (b) an RNA molecule comprising: (i) a first open reading frame; (ii) a double-stranded region comprising: (A) at least one target codon (stop, start, non-start, or sense codon); and (B) a binding motif for RBD capable of being bound by the RNA-binding domain of the fusion protein; and (iii) a second open reading frame.

In one aspect described herein is a system for modulating RNA translation comprising: (a) a fusion protein comprising: (1) an RNA-binding domain; (ii) a first portion of a deaminase domain (DD) of an adenosine deaminase; (iii) a first member of a binding pair associated with the first portion of the DD; (iv) a second portion of the DD; (v) a cleavable linker; and (vi) a second member of a binding pair associated with the cleavable linker; and (b) an RNA molecule comprising: (i) an open reading frame; (ii) a double-stranded region comprising: (A) at least one target codon (stop, start, non-start, or sense codon); and (B) a binding motif for RBD capable of being bound by the RNA-binding domain of the fusion protein; and (iii) a poly-A tail.

In some embodiments, the deaminase domain is capable of converting the at least one stop codon into at least one non-stop codon. In some embodiments, the first reading frame is translated when the at least one stop codon is present in the double-stranded region of the RNA molecule. In some embodiments, the RNA molecule is degraded when the at least one stop codon is converted into the at least one non-stop codon.

In some embodiments, the deaminase domain is capable of converting the at least one start codon into at least one non-start codon. In some embodiments, the reading frame is translated when the at least one start codon is present in the double-stranded region of the RNA molecule. In some embodiments, the RNA molecule is not translated when the at least one start codon is converted into the at least one non-start codon.

In some embodiments, the deaminase domain is capable of converting the at least one non-start codon into at least one start codon. In some embodiments, the RNA molecule is translated when the at least one non-start codon is converted into the at least one start codon. In some embodiments, the reading frame is not translated when the at least one non-start codon is present in the double-stranded region of the RNA molecule.

In some embodiments, the deaminase domain is capable of converting the at least one sense codon into at least one mutated sense codon. In some embodiments, the structure and/or function of the RNA and/or encoded polypeptide is altered when the at least one sense codon is converted into the at least one mutated sense codon.

In some embodiments, the system further comprising an inducer of the first and second binding pairs. Depending on the affinity binding pair of the iADAR, inducers can be, but are not limited to, small molecules, proteases, light-inducible control, sound inducible control, cell cycle dependent, ultrasound or other wavelength dependent triggers, chemically cleavable linkers, heat-activated triggers, antibodies, endogenous triggers, disease triggers, external triggers and cell-specific marker triggers, and the like. Non-limiting examples of small molecule inducers include A-1331852, ABT-737, and S63845 as described further herein. Non-limiting examples of chemically cleavable linkers include click-release based chemistry, see e.g., van Onzen et al., "Bioorthogonal Tetrazine Carbamate Cleavage by Highly Reactive trans-Cyclooctene, J. Am. Chem. Soc. 2020, 142, 25, 10955-10963, the content of which is incorporated herein by reference in its entirety. Non-limiting examples of ultrasound dependent triggers can use chemical means or gas vesicles, see e.g., Berkowski et al., "Ultrasound-Induced Site-Specific Cleavage of Azo-Functionalized Poly(ethylene glycol)," Macromolecules 2005, 38, 22, 8975-8978; Farhadi et al., "Ultrasound Imaging of Gene Expression in Mammalian Cells," Science. 2019 Sep. 27; 365(6460): 1469-1475; the contents of each of which are incorporated herein by reference in their entireties.

In embodiments using a repressible protease and its cognate protease domain as the binding pair of the IADAR, the inducer can be a protease inhibitor, e.g., selected from grazoprevir, danoprevir, simeprevir, asunaprevir, ciluprevir, boceprevir, sovaprevir, paritaprevir, ombitasvir, paritaprevir, ritonavir, dasabuvir, and telaprevir or Table 9.

In some embodiments, the first and second members of the binding pair of the fusion protein bind to each other in the absence of an inducer of the first and second binding pairs. Binding of the first and second members of the binding pair can reduce or prevent at least one of the following: the formation of the inositol hexaphosphate (IP6) binding pocket of first and second portions of the deaminase domain; deaminase activity of the first and second portions of the deaminase domain; conversion by the deaminase domain of the at least one target codon of the RNA molecule into at least one inosine-comprising codon; conversion by the deaminase domain of the at least one stop codon of the RNA molecule into at least one non-stop codon; conversion by the deaminase domain of the at least one start codon of the RNA molecule into at least one non-start codon; conversion by the deaminase domain of the at least one non-start codon of the RNA molecule into at least one start codon; conversion by the deaminase domain of the at least one sense codon of the RNA molecule encoding for a first amino acid into at least one mutated sense codon encoding for a second amino acid; translation of a reading frame (e.g., the second reading frame of the RNA molecule); and/or degradation of the RNA molecule.

In some embodiments, the first and second members of the binding pair of the fusion protein do not bind to each other in the presence of an inducer of the first and second binding pairs, allowing for or increasing at least one of the following outcomes: the formation of the inositol hexaphosphate (IP6) binding pocket of first and second portions of the deaminase domain; deaminase activity of the first and second portions of the deaminase domain; conversion by the deaminase domain of the at least one target codon of the RNA molecule into at least one inosine-comprising codon; conversion by the deaminase domain of the at least one stop codon of the RNA molecule into at least one non-stop codon; conversion by the deaminase domain of the at least one start codon of the RNA molecule into at least one non-start codon; conversion by the deaminase domain of the at least one non-start codon of the RNA molecule into at least one start codon; conversion by the deaminase domain of the at least one sense codon of the RNA molecule encoding for a first amino acid into at least one mutated sense codon encoding for a second amino acid; translation of a reading frame (e.g., the second reading frame) of the RNA molecule; and/or degradation of the RNA molecule.

In systems comprising a cleavable linker in the iADAR, the system can further comprise a cleavage inducer. Depending on the cleavable linker used in the iADAR, the cleavage inducer can be light, sound, ultrasound, chemical, heat, endogenous triggers, disease triggers, external triggers and cell-specific marker triggers, and the like.

In some embodiments, the cleavable linker is not cleaved in the absence of a cleavage inducer. Lack of cleavage of the cleavable linker can reduce or prevent at least one of the following outcomes: the formation of the inositol hexaphosphate (IP6) binding pocket of first and second portions of the deaminase domain; deaminase activity of the first and second portions of the deaminase domain; conversion by the deaminase domain of the at least one target codon of the RNA molecule into at least one inosine-comprising codon; conversion by the deaminase domain of the at least one stop codon of the RNA molecule into at least one non-stop codon; conversion by the deaminase domain of the at least one start codon of the RNA molecule into at least one non-start codon; conversion by the deaminase domain of the at least one non-start codon of the RNA molecule into at least one start codon; conversion by the deaminase domain of the at least one sense codon of the RNA molecule encoding for a first amino acid into at least one mutated sense codon encoding for a second amino acid; translation of a reading frame (e.g., the second reading frame) of the RNA molecule; and/or degradation of the RNA molecule.

In some embodiments, the cleavable linker is cleaved in the presence of a cleavage inducer, which can allow or increase one of the following outcomes: the formation of the inositol hexaphosphate (IP6) binding pocket of first and second portions of the deaminase domain; deaminase activity of the first and second portions of the deaminase domain; conversion by the deaminase domain of the at least one target codon of the RNA molecule into at least one inosine-comprising codon; conversion by the deaminase domain of the at least one stop codon of the RNA molecule into at least one non-stop codon; conversion by the deaminase domain of the at least one start codon of the RNA molecule into at least one non-start codon; conversion by the deaminase domain of the at least one non-start codon of the RNA molecule into at least one start codon; conversion by the deaminase domain of the at least one sense codon of the RNA molecule encoding for a first amino acid into at least one mutated sense codon encoding for a second amino acid; translation of a reading frame (e.g., the second reading frame) of the RNA molecule; and/or degradation of the RNA molecule.

In some embodiments, the at least one stop codon of the synthetic RNA molecule comprises UAG. In some embodiments, the at least one non-stop codon of the synthetic RNA molecule comprises at least one tryptophan codon. In some embodiments, the at least one tryptophan codon of the synthetic RNA molecule comprises UGG.

In some embodiments, the RNA-binding domain comprises MCP, and the Binding motif for RBD (BM) comprises MS2. In some embodiments, the RNA-binding domain comprises PCP, and the Binding motif for RBD (BM) comprises PP7. In some embodiments, the RNA-binding domain comprises AN, and the Binding motif for RBD (BM) comprises BoxB. In some embodiments, the RNA-binding domain comprises HIV Tat, and the Binding motif for RBD (BM) comprises TAR.

In some embodiments, the double-stranded region of the RNA molecule comprises at least one hairpin. In some embodiments, the double-stranded region of the RNA molecule comprises one hairpin comprising the at least one target codon (stop, start, non-start, or sense codon) and the Binding motif for RBD (BM). In some embodiments, the double-stranded region of the RNA molecule comprises a first hairpin comprising the at least one target codon (stop, start, non-start, or sense codon) and a second hairpin comprising the Binding motif for RBD (BM).

IV. Nucleic Acids

Described herein are various nucleic acids. In one aspect, described herein is a nucleic acid encoding a fusion protein (e.g., iAD, iADAR) as described herein. In one aspect, described herein is a nucleic acid encoding a synthetic RNA molecule as described herein. In one aspect, described herein is a nucleic acid encoding a fusion protein and a synthetic RNA molecule as described herein.

In some embodiments, the nucleic acid encoding the fusion protein and the nucleic acid encoding the RNA molecule are operably linked to a single promoter. In some embodiments, the nucleic acid encoding the fusion protein and the nucleic acid encoding the RNA molecule are each operably linked to a separate promoter. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule. In some embodiments, the nucleic acid encoding the fusion protein is linked to and 5' of the nucleic acid encoding the RNA molecule. In some embodiments, the nucleic acid encoding the fusion protein is linked to and 3' of the nucleic acid encoding the RNA molecule.

In some embodiments, the nucleic acid comprises DNA. In some embodiments, the nucleic acid comprises RNA. In some embodiments, the nucleic acid comprises RNA and DNA.

In some embodiments, the nucleic acid is one of SEQ ID NOs: 38-73, 95, 99, 173, 177, 181, 185, 189, 193, 197, 199, 201, 203, 205, or 207, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 38-73, 95, 99, 173, 177, 181, 185, 189, 193, 197, 199, 201, 203, 205, or 207, that maintains the same function, or a codon-optimized version thereof.

In some embodiments of any of the aspects, a nucleic acid (e.g. DNA, or RNA transcript disclosed herein) is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of nucleic acid compounds useful in the embodiments described herein include, but are not limited to nucleic acids containing modified backbones or no natural internucleoside linkages. nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In some embodiments of any of the aspects, the modified nucleic acid will have a phosphorus atom in its internucleoside backbone.

Modified nucleic acid backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2-[wherein the native phosphodiester backbone is represented as —O—P—O—CH2-].

In other nucleic acid mimetics, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The nucleic acid can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R, et al., (2007) Mol. Canc. Ther. 6(3):833-843; Grunweller, A. et al., (2003) Nucleic Acids Research 31(12):3185-3193).

Modified nucleic acids can also contain one or more substituted sugar moieties. The nucleic acids described herein can include one of the following at the 2' position: OH; F; O—, S—, or N-alkyl; O—, S-, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O [(CH2)nO] mCH3, O(CH2)nOCH3, O(CH2)nNH2, O(CH2)nCH3, O(CH2)nONH2, and O(CH2)nON[(CH2)nCH3)]2, where n and m are from 1 to about 10. In some embodiments of any of the aspects, nucleic acids include one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleic acid, or a group for improving the pharmacodynamic properties of a nucleic acid, and other substituents having similar properties. In some embodiments of any of the aspects, the modification includes a 2' methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'—OCH3), 2'-aminopropoxy (2'-OCH2CH2$CH_2$NH2) and 2'-fluoro (2'-F). Similar modifications can also be made at other positions on the nucleic acid, particularly the 3' position of the sugar on the 3' terminal nucleotide or in 2'-5' linked dsRNAs and the 5' position of 5' terminal nucleotide. Nucleic acids may also have sugar mimetics such as cyclobutyl moieties in place of the pentofuranosyl sugar.

A nucleic acid can also include nucleobase (often referred to in the art simply as "base") modifications or substitutions. As used herein, "unmodified" or "natural" or "canonical" nucleobases include the purine bases adenine (A) and guanine (G), and the pyrimidine bases thymine (T), cytosine (C) and uracil (U). Modified or "non-canonical" nucleobases can include other synthetic and natural nucleobases including but not limited to as inosine, isocytosine, isoguanine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. In some embodiments of any of the aspects, modified nucleobases can include d5SICS and dNAM, which are a non-limiting example of unnatural nucleobases that can be used separately or together as base pairs (see e.g., Leconte et. al. J. Am. Chem. Soc.2008, 130, 7, 2336-2343; Malyshev et. al. PNAS. 2012. 109 (30) 12005-12010). In some embodiments of any of the aspects, the nucleic acid comprises any modified nucleobases known in the art, i.e., any nucleobase that is modified from an unmodified and/or natural nucleobase.

The preparation of the modified nucleic acids, backbones, and nucleobases described above are well known in the art.

Another modification of a nucleic acid featured in the invention involves chemically linking to the nucleic acid to one or more ligands, moieties or conjugates that enhance the activity, cellular distribution, pharmacokinetic properties, or cellular uptake of the nucleic acid. Such moieties include but are not limited to lipid moieties such as a cholesterol moiety (Letsinger et al., Proc. Natl. Acid. Sci. USA, 1989, 86:6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

V. Vectors

In some embodiments, one or more of the nucleic acids encoding a synthetic STOP region that is operatively linked to a GOI or transcript of interest as disclosed herein is expressed in a recombinant expression vector or plasmid. In some embodiments, a synthetic target activation construct (TAC) or target inactivation construct (TIC), or both, as disclosed herein, are expressed in a recombinant expression vector or plasmid. In some embodiments, a TIC or TAC can comprise one or more nucleic acids encoding an iAD, e.g., iADAR as disclosed herein is expressed in a recombinant expression vector or plasmid. In some embodiments, a vector (e.g., a lentivirus) express (A) iADAR and TAC RNA, (B) iADAR and TIC, or (C) at least one iADAR, TAC RNA, and TIC RNA, for example one iADAR that acts on the TAC RNA and another iADAR that acts on the TIC RNA. In some embodiments, one or more of the nucleic acids encoding an iAD, e.g., iADAR can be as disclosed herein is expressed in a recombinant expression vector or plasmid. In some embodiments, the TIC or TAC RNA (e.g., comprising a GOI) is delivered by lentivirus or non-viral constructs, e.g., closed ended DNA (ceDNA), etc.

As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., B-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the polypeptides described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

In some embodiments, one or more of the recombinantly expressed gene can be integrated into the genome of the cell.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

VI. Cells and Compositions

In one aspect, described herein is a cell comprising at least one fusion protein (e.g., iAD, iADAR) as described herein. In one aspect, described herein is a cell comprising at least one synthetic RNA molecule (e.g., TIC, TAC) as described herein. In one aspect, described herein is a cell comprising at least one nucleic acid as described herein. In one aspect, described herein is a cell comprising at least one vector as described herein. In one aspect, described herein is a cell comprising at least one system (e.g., iADAR and synthetic TIC or TAC RNA) as described herein.

In some embodiments, the cell is selected from the group consisting of a fibroblast, a hematopoietic cell, a neuron, a pancreatic cell, a muscle cell, a bone cell, a hepatocyte, a pancreatic cell, an epithelial cell, an endothelial cell, a cardiomyocyte, an immune cell (e.g., a T cell, a B cell), a liver cell, an osteocyte, and the like.

In one aspect, described herein is a composition comprising at least one fusion protein (e.g., iAD, iADAR) as described herein. In one aspect, described herein is a composition comprising at least one synthetic RNA molecule (e.g., TIC, TAC) as described herein. In one aspect, described herein is a composition comprising at least one nucleic acid as described herein. In one aspect, described herein is a composition comprising at least one vector as described herein. In one aspect, described herein is a composition comprising at least one system (e.g., iADAR and synthetic TIC or TAC RNA) as described herein. In one aspect, described herein is a composition comprising at least one cell as described herein. In some embodiments, the composition further comprises at least one inducer of the first and second binding pairs. In some embodiments, the composition further comprises at least one cleavage inducer. The composition can be in the form of a liquid, gel solid, powder, and the like.

In one aspect, described herein is a pharmaceutical composition comprising at least one a pharmaceutically compatible carrier at least one fusion protein (e.g., iAD, IADAR) as described herein. In one aspect, described herein is a pharmaceutical composition comprising at least one a pharmaceutically compatible carrier at least one synthetic RNA molecule (e.g., TIC, TAC) as described herein. In one aspect, described herein is a pharmaceutical composition comprising at least one a pharmaceutically compatible carrier at least one nucleic acid as described herein. In one aspect, described herein is a pharmaceutical composition comprising at least one a pharmaceutically compatible carrier at least one vector as described herein. In one aspect, described herein is a pharmaceutical composition comprising at least one a pharmaceutically compatible carrier at least one system (e.g., iADAR and synthetic TIC or TAC RNA) as described herein. In one aspect, described herein is a pharmaceutical composition comprising at least one a pharmaceutically compatible carrier at least one cell as described herein. In some embodiments, the composition further comprises at least one inducer of the first and second binding pairs. In some embodiments, the composition further comprises at least one cleavage inducer. The composition can be in the form of a liquid, gel solid, powder, and the like.

In some embodiments, the technology described herein relates to a pharmaceutical composition comprising at least one of (a) fusion protein, (b) RNA molecule, (c) nucleic acid, (d) vector, (e) system, (f) cell, and/or (g) composition, as described herein, and optionally a pharmaceutically acceptable carrier. In some embodiments, the active ingredients of the pharmaceutical composition comprise (a) fusion protein, (b) RNA molecule, (c) nucleic acid, (d) vector, (e) system, (f) cell, and/or (g) composition as described herein. In some embodiments, the active ingredients of the pharmaceutical composition consist essentially of (a) fusion protein, (b) RNA molecule, (c) nucleic acid, (d) vector, (e) system, (f) cell, and/or (g) composition as described herein. In some embodiments, the active ingredients of the pharmaceutical composition consist of (a) fusion protein, (b) RNA molecule, (c) nucleic acid, (d) vector, (c) system, (f) cell, and/or (g) composition as described herein.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; (24) C2-C12 alcohols; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. (a) fusion protein, (b) RNA molecule, (c) nucleic acid, (d) vector, (e) system, (f) cell, and/or (g) composition as described herein.

In some embodiments, the pharmaceutical composition comprising at least one (a) fusion protein, (b) RNA molecule, (c) nucleic acid, (d) vector, (e) system, (f) cell, and/or (g) composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Pharmaceutical compositions comprising at least one (a) fusion protein, (b) RNA molecule, (c) nucleic acid, (d) vector. (e) system, (f) cell, and/or (g) composition as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the pharmaceutical composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591, 767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropyl methylcellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the at least one (a) fusion protein, (b) RNA molecule, (c) nucleic acid, (d) vector, (e) system, (f) cell, and/or (g) composition as described herein described herein is administered as a monotherapy, e.g., another treatment for the disease or disorder is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include a cancer therapy selected from the group consisting of: radiation therapy, surgery, gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylmelamines including altretamine, triethylenemelamine, trietylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omegaI1 (see, e.g., Agnew, Chem. Intl. Ed. Engl., 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomycins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, III.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In addition, the methods of treatment can further include the use of radiation or radiation therapy. Further, the methods of treatment can further include the use of surgical treatments.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs-such as aspirin, ibuprofen, or naproxen);

corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition comprising at least one (a) fusion protein, (b) RNA molecule, (c) nucleic acid, (d) vector, (e) system, and/or (f) cell as described herein can be administered to a patient once. In certain embodiments, an effective dose of a composition comprising at least one (a) fusion protein, (b) RNA molecule, (c) nucleic acid, (d) vector, (e) system, and/or (f) cell as described herein can be administered to a patient repeatedly. For systemic administration, subjects can be administered a therapeutic amount of a composition comprising at least one (a) fusion protein, (b) RNA molecule, (c) nucleic acid, (d) vector, (e) system, and/or (f) cell as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g., by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the (a) fusion protein, (b) RNA molecule, (c) nucleic acid, (d) vector, (e) system, and/or (f) cell as described herein. The desired dose or amount can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition as described herein can be administered over a period of time, such as over a 5 minute, 10 minute, 15 minute, 20 minute, or 25 minute period.

The dosage ranges for the administration of a composition as described herein, according to the methods described herein depend upon, for example, the form of the composition, its potency, and the extent to which symptoms, markers, or indicators of a condition described herein are desired to be reduced, for example the percentage reduction desired for the disease or disorder or the extent to which, for example, immune reactions, are desired to be induced. The dosage should not be so large as to cause adverse side effects, such as autoimmunity. Generally, the dosage will vary with the age, condition, and sex of the patient and can be determined by one of skill in the art. The dosage can also be adjusted by the individual physician in the event of any complication.

The efficacy of a composition as described herein in, e.g. the treatment of a condition described herein, or to induce a response as described herein can be determined by the skilled clinician. However, a treatment is considered "effective treatment." as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer or infectious disease. When using an experimental animal model, efficacy of treatment is evidenced when a statistically significant change in a marker is observed.

VII. Uses

In certain embodiments, the method using the iADAR can be used for editing on a target RNA to generate point mutation and/or misfolding of the protein encoded by the target RNA, and/or generating an early stop codon, an aberrant splice site, and/or an alternative splice site in the target RNA.

In certain embodiments, the iADAR-ON results in the deamination of a target (e.g., the target A) in the target RNA and results in a missense mutation, an early stop codon, aberrant splicing, or alternative splicing in the target RNA.

In certain embodiments, the iADAR-ON results in the deamination of a target (e.g., the target A) in the target RNA and results in deactivating or eliminating a STOP codon.

In some embodiments, the target RNA encodes a protein, and the deamination of a target (e.g., the target A) in the target RNA results in a point mutation, truncation, elongation and/or misfolding of the protein. In some embodiments, the iADAR-ON results in the deamination of a target (e.g., the target A) in the target RNA, and results in reversal of a missense mutation, an early stop codon, aberrant splicing, or alternative splicing in the target RNA. In some embodiments, wherein the target RNA encodes a truncated, elongated, mutated, or misfolded protein, the iADAR-ON can deaminate the target A in the target RNA, and result in a functional, full-length, correctly-folded and/or wild-type protein by reversal of a missense mutation, an early stop codon, aberrant splicing, or alternative splicing in the target RNA. In some embodiments, the iADAR-ON acts on a target RNA that is a regulatory RNA, and the iADAR-ON results in the deamination of the target A to effectuate a change in the expression of a downstream molecule regulated by the target RNA. For example, as disclosed herein, where the STOP codon is eliminated, the downstream GOI to the STOP codon is expressed (e.g., target activation construct or TAC), or alternatively, where the STOP is downstream of a GOI and upstream (e.g., 5') of a polyA tail, the mRNA of the GOI is degraded.

In some embodiments, the iADAR can be used in any gene editing method where the at least one stop codon (e.g., ds-STOP codon) is inserted into a target nucleic acid sequence, for example, using gene editing methodologies such as CRISPR systems. While examples herein show exemplary RNA Target inactivation constructs (TIC) and RNA target activation constructs (TAC), it is contemplated herein that iADAR can be used in natural systems, circular RNA systems, ceDNA, etc. e.g., in which the at least one stop codon (e.g., ds-STOP codon) is inserted into the target nucleic acid sequence using gene editing methodologies. In some embodiments, there is provided an edited RNA or a host cell having an edited RNA produced by any one of the methods of RNA editing as described above.

In one aspect, described herein is a method of modulating RNA expression (e.g., RNA translation) in a cell, the method comprising contacting the cell with at least one fusion protein (e.g., iAD, iADAR) as described herein. In one aspect, described herein is a method of modulating RNA expression (e.g., RNA translation) in a cell, the method comprising contacting the cell with at least one synthetic RNA molecule (e.g., TIC, TAC) as described herein. In one aspect, described herein is a method of modulating RNA expression (e.g., RNA translation) in a cell, the method comprising contacting the cell with at least one nucleic acid as described herein. In one aspect, described herein is a method of modulating RNA expression (e.g., RNA translation) in a cell, the method comprising contacting the cell with at least one vector as described herein. In one aspect, described herein is a method of modulating RNA expression (e.g., RNA translation) in a cell, the method comprising contacting the cell with at least one system (e.g., iADAR and synthetic TIC or TAC RNA) as described herein. In one aspect, described herein is a method of modulating RNA expression (e.g., RNA translation) in a cell, the method comprising contacting the cell with at least one composition as described herein. In one aspect, described herein is a method of modulating RNA expression (e.g., RNA translation) in a cell, the method comprising contacting the cell with at least one pharmaceutical composition as described herein.

In some embodiments, the method further comprises contacting the cell with at least one inducer of the first and second binding pairs. In some embodiments, the method further comprises contacting the cell with at least one cleavage inducer.

In some embodiments, the methods described herein relate to treating a subject having or diagnosed as having a disease or disorder, such as cancer or an infectious disease. Subjects having cancer can be identified by a physician using current methods of diagnosing cancer. Symptoms and/or complications of cancer which characterize these conditions and aid in diagnosis are well known in the art. A family history of cancer, or exposure to risk factors for cancer can also aid in determining if a subject is likely to have cancer or in making a diagnosis of cancer.

Subjects having an infectious disease can be identified by a physician using current methods of an infectious disease. Symptoms and/or complications of an infectious disease which characterize these conditions and aid in diagnosis are well known in the art. A family history of infectious disease, or exposure to risk factors for infectious disease can also aid in determining if a subject is likely to have an infectious disease or in making a diagnosis of an infectious disease.

In one aspect, the present application provides a method for treating or preventing a disease or condition in an individual, comprising editing a target RNA associated with the disease or condition in a cell of the individual according to any one of the methods for RNA editing as described above. In some embodiments, the method comprises editing the target RNA in the cell ex vivo. In some embodiments, the method comprises administering a cell comprised the edited target RNA to the individual. In some embodiments, the method comprises administering to the individual an effective amount of the ADAR-recruiting RNA (dRNA) or construct encoding the dRNA. In some embodiments, the method further comprises introducing to the cell the ADAR or a construct (e.g., viral vector, a nucleic acid) encoding the ADAR. In some embodiments, the method further comprises administering to the individual the ADAR or a construct (e.g., viral vector, a nucleic acid) encoding the ADAR. In some embodiments, the disease or condition is a hereditary genetic disease. In some embodiments, the disease or condition is associated with one or more acquired genetic mutations, e.g., drug resistance. In some embodiments, the disease or condition is cancer. In some embodiments, the disease or condition is an infectious disease, such a viral, bacterial, or fungal infection.

The compositions described herein can be administered to a subject having or diagnosed as having a disease or disorder, such as cancer or an infectious disease. In some embodiments, the methods described herein comprise administering an effective amount of compositions described herein to a subject in order to alleviate a symptom of a disease or disorder, such as cancer or an infectious disease. As used herein, "alleviating a symptom" is ameliorating any condition or symptom associated with the a disease or disorder, such as cancer or an infectious disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration, Administration can be local or systemic.

In one aspect, described herein is a method of treating a cancer or microbial infection in a subject in need thereof, the method comprising administering an effective amount of at least one fusion protein (e.g., iAD, iADAR) as described herein. In one aspect, described herein is a method of treating a cancer or microbial infection in a subject in need thereof, the method comprising administering an effective amount of at least one synthetic RNA molecule (e.g., TIC, TAC) as described herein. In one aspect, described herein is a method of treating a cancer or microbial infection in a subject in need thereof, the method comprising administering an effective amount of at least one nucleic acid as described herein. In one aspect, described herein is a method of treating a cancer or microbial infection in a subject in need thereof, the method comprising administering an effective amount of at least one vector as described herein. In one aspect, described herein is a method of treating a cancer or microbial infection in a subject in need thereof, the method comprising administering an effective amount of at least one system (e.g., IADAR and synthetic TIC or TAC RNA) as described herein. In one aspect, described herein is a method of treating a cancer or microbial infection in a subject in need thereof, the method comprising administering an effective amount of at least one composition as described herein. In one aspect, described herein is a method of treating a cancer or microbial infection in a subject in need thereof, the method comprising administering an effective amount of at least one pharmaceutical composition as described herein.

In some embodiments, the treatment method further comprises administering at least one inducer of the first and second binding pairs. In some embodiments, the treatment method further comprises administering at least one cleavage inducer. In some embodiments, the inducer or cleavage inducer is administered after the nucleic acid encoding the fusion protein and/or the nucleic acid encoding the RNA molecule.

In one aspect, described herein is a method for treating a cancer or microbial infection in a subject in need thereof, the method comprising administering an effective amount of: (a) a nucleic acid encoding for an RNA molecule comprising: (i) a first open reading frame encoding for a fusion protein; (ii) a double-stranded region comprising: (A) at least one stop codon; and (B) a binding motif for RBD capable of being bound by an RNA-binding domain; and (iii) a second open reading frame encoding for an effector protein.

In one aspect, described herein is a method for treating a cancer or microbial infection in a subject in need thereof, the method comprising administering an effective amount of: (a) a nucleic acid encoding a fusion protein comprising an RNA-binding domain linked to a deaminase domain of an adenosine deaminase; and (b) a nucleic acid encoding for an RNA molecule comprising: (i) an open reading frame encoding for an effector protein; (ii) a double-stranded region comprising: (A) at least one stop codon; and (B) a binding motif for RBD capable of being bound by an RNA-binding domain; and (iii) a poly-A tail.

In some embodiments, the effector protein comprises an antigen-binding domain for a cancer antigen. In some embodiments, the effector protein comprises an antigen-binding domain for microbial antigen.

In some embodiments, the fusion protein administered in a treatment method comprises an RNA-binding domain linked to a deaminase domain of an adenosine deaminase. In some embodiments, the fusion protein comprises: (a) an RNA-binding domain; (b) a first portion of a deaminase domain of an adenosine deaminase; (c) a first member of a binding pair; (d) a second portion of the deaminase domain; and/or (e) a second member of a binding pair. In some embodiments, the fusion protein administered in a treatment method comprises (a) an RNA-binding domain; (b) a first portion of a deaminase domain of an adenosine deaminase; (c) a first member of a binding pair; (d) a second portion of the deaminase domain; (e) a cleavable linker; and/or (f) a second member of a binding pair.

VIII. Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or disorder. A subject can be male or female.

A subject can be one who has been previously diagnosed with or identified as suffering from or having a condition in need of treatment or one or more complications related to such a condition, and optionally, have already undergone treatment for a condition to be treated, or the one or more complications related to a condition to be treated.

A "subject in need" of treatment for a particular condition can be a subject having that condition, diagnosed as having that condition, or at risk of developing that condition.

The term "effective amount" as used herein refers to the amount of (a) fusion protein, (b) RNA molecule, (c) nucleic acid, (d) vector, (e) system, (f) cell, (g) composition, and/or (g) pharmaceutical composition needed to alleviate at least one or more symptom of a disease or disorder in a subject in need thereof, and relates to a sufficient amount to provide the desired effect. The term "therapeutically effective amount" therefore refers to an amount of (a) fusion protein, (b) RNA molecule, (c) nucleic acid, (d) vector, (e) system, (f) cell, (g) composition, and/or (g) pharmaceutical composition that is sufficient to provide a particular effect, e.g., anti-cancer, e.g., anti-infectious disease, effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested by one of ordinary skill in the art to confirm that a desired activity, e.g. elimination of a STOP codon and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q): (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a polypeptide which retains at least 50% of the wild-type reference polypeptide's activity. A functional fragment can comprise conservative substitutions of the sequences disclosed herein.

In some embodiments, the polypeptide described herein can be a variant of a polypeptide sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a protein or fragment thereof that retains activity of the native or reference polypeptide. A wide variety of, for example, PCR-based, site-specific mutagenesis approaches are known in the art and can be applied by the ordinarily skilled artisan to generate and test artificial variants.

A variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

A variant amino acid sequence can be at least 50%, at least 60%, at least 70%, at least 80%, at least 90%, at least 91%, at least 92%, at least 93%, at least 94%, at least 95%, at least 96%, at least 97%, at least 98%, at least 99%, or more, similar to a native or reference sequence. As used herein, "similarity" refers to an identical amino acid or a conservatively substituted amino acid, as described herein. Accordingly, the percentage of "sequence similarity" is the percentage of amino acids which is either identical or conservatively changed; e.g., "sequence similarity"=(% sequence identity)+(% conservative changes). It should be understood that a sequence that has a specified percent similarity to a reference sequence necessarily encompasses a sequence with the same specified percent identity to that reference sequence. The skilled person will be aware of various computer programs, using different mathematical algorithms, that are available to determine the identity or similarity between two sequences. For instance, use can be made of a computer program employing the Needleman and Wunsch algorithm (Needleman et al. (1970)); the GAP program in the Accelrys GCG software package (Accelerys Inc., San Diego U.S.A.); the algorithm of E. Meyers and W. Miller (Meyers et al. (1989)) which has been incorporated into the ALIGN program (version 2.0); or more preferably the BLAST (Basic Local Alignment Tool using default parameters); see e.g., U.S. Pat. No. 10,023,890, the content of which is incorporated by reference herein in its entirety.

As used herein, the phrase "maintains the same function", when used in reference to an enzyme, catalyzes the same reaction as a reference enzyme. When used in reference to an ADAR or AR, it changes an A to an I in the same molecule, substance, or factor.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. A wide variety of, site-specific mutagenesis approaches, e.g., Kunkel's method, cassette mutagenesis, PCR site-directed mutagenesis (e.g., traditional PCR, primer extension, or inverse PCR), whole plasmid mutagenesis, in vivo site-directed mutagenesis, CRISPR/Cas-guided mutagenesis, are known in the art and can be applied by the ordinarily skilled artisan to introduce mutations into specific nucleic acid loci. Techniques for making such alterations are very well established and include, for example, those disclosed by Walder et al. (Gene 42:133, 1986); Bauer et al. (Gene 37:73, 1985); Craik (Bio Techniques, January 1985, 12-19); Smith et al. (Genetic Engineering: Principles and Methods, Plenum Press, 1981); Braman, Jeff, ed. (2002) In Vitro Mutagenesis Protocols, Methods in Molecular Biology, Vol. 182 (2nd ed.); Khudyakov and Fields (2002), Artificial DNA: Methods and Applications, CRC Press; Hsu et al. (2014), Cell 157 (6): 1262-78; Cerchione et al. (2020) PLOS ONE 15 (4): e0231716; and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA, including closed ended DNA (ceDNA) or other circular DNA systems. Suitable RNA can include, e.g., mRNA and circular RNA constructs, The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" refers to the nucleic acid sequence which is transcribed (DNA) to RNA in vitro or in vivo when operably linked to appropriate regulatory sequences. The gene may or may not include regions preceding and following a coding region, e.g. 5' untranslated (5'UTR) or "leader" sequences and 3' UTR or "trailer" sequences, as well as intervening sequences (introns) between individual coding segments (exons).

"In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the iAD, e.g., iADAR described herein is exogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount, An ectopic substance can be one that is normally found in a given cell, but at a much lower amount and/or at a different time. Ectopic also includes a substance, such as a polypeptide or nucleic acid that is not naturally found or expressed in a given cell in its natural environment.

In some embodiments of any of the aspects, the iAD, e.g., iADAR2 comprises at least one functional heterologous gene. As used herein, the term "heterologous" refers to that which is not endogenous to, or naturally occurring in, a referenced sequence, molecule (including e.g., a protein), virus, cell, tissue, or organism. For example, a heterologous sequence of the present disclosure can be derived from a different species, or from the same species but substantially modified from an original form. Also for example, a nucleic acid sequence that is not normally expressed in a cell or a virus is a heterologous nucleic acid sequence with regard to that cell or virus. The term "heterologous" can refer to DNA, RNA, or protein that does not occur naturally as part of the organism in which it is present or which is found in a location or locations in the genome that differ from that in which it occurs in nature. It is DNA, RNA, or protein that is not endogenous to the virus or cell and has been artificially introduced into the virus or cell.

In some embodiments, a nucleic acid encoding a polypeptide as described herein (e.g. an iAD, e.g., iADAR2 polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine.

In some embodiments of any of the aspects, the cells can be maintained in culture. As used herein, "maintaining" refers to continuing the viability of a cell or population of cells. A maintained population of cells will have at least a subpopulation of metabolically active cells.

As used herein, the term "specific binding" refers to a chemical or physical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways.

In some embodiments, an analog is a substance that can be generated from the reference substance, e.g., by chemical manipulation of the reference substance.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John B. Coligan (ed.), John Wiley and Sons, Inc., 2005; and Current Protocols in Immunology (CPI) (John E. Coligan, ADA M Kruisbeek, David H Margulies, Ethan M. Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure of the iAD, e.g., iADAR2 without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A fusion protein comprising:
   (a) a first portion of a deaminase domain (DD) of an adenosine deaminase;
   (b) a first member of a binding pair associated with the first portion of the DD;
   (c) a second portion of the DD; and
   (d) a second member of a binding pair associated with the second portion of the DD,
   wherein the first member of the binding pair is capable of binding to the second member of the binding pair in the absence of an inducer, resulting in allosteric inhibition of the first and second portions of the DD, and
   wherein the first member of the binding pair is not capable of binding to the second member of the binding pair in the presence of the inducer, resulting in activation of the first and second portions of the DD.
2. The fusion protein of paragraph 1, wherein in the allosteric inhibition of the first and second portions of the DD comprises deformation of the inositol hexaphosphate (IP6) binding pocket of first and second portions of the DD.
3. The fusion protein of paragraph 1, wherein in the activation of the first and second portions of the DD comprises deaminase activity.
4. The fusion protein of paragraph 1, further comprising an RNA-binding domain.
5. The fusion protein of paragraph 1, wherein the RNA-binding domain (RBD) is capable of binding to a binding motif for the RBD on an RNA molecule.
6. The fusion protein of paragraph 1, wherein the deaminase domain is capable of deamination of an adenosine nucleotide into an inosine nucleotide in an RNA molecule.
7. The fusion protein of paragraph 1, wherein the deaminase domain is capable of converting at least one stop codon into at least one non-stop codon.
8. The fusion protein of paragraph 1, wherein the deaminase domain is capable of converting UAG, UGA, or UAA stop codons to UIG, UGI, or UII non-stop codons, respectively.
9. The fusion protein of paragraph 1, wherein the deaminase domain is capable of converting at least one start codon into at least one non-start codon.
10. The fusion protein of paragraph 1, wherein the deaminase domain is capable of converting an AUG start codon to an IUG non-start codon.
11. The fusion protein of paragraph 1, wherein the deaminase domain is capable of converting at least one start codon into at least one non-start codon.
12. The fusion protein of paragraph 1, wherein the deaminase domain is capable of converting an AUA non-start codon to an AUI start codon.
13. The fusion protein of paragraph 1, wherein the deaminase domain is capable of converting at least one sense codon encoding a first amino acid into at least one mutated sense codon encoding a second amino acid.
14. The fusion protein of paragraph 1, wherein the deaminase domain is capable of converting at least one sense codon into at least one mutated sense codon, as selected from Table 15.
15. The fusion protein of paragraph 1, wherein the adenosine deaminase comprises Adenosine Deaminase Acting on RNA (ADAR), Adenosine Deaminase TRNA Specific (ADAT), or Adenosine Deaminase Domain Containing (ADAD).
16. The fusion protein of paragraph 1, wherein the adenosine deaminase comprises Adenosine Deaminase Acting on RNA (ADAR).
17. The fusion protein of paragraph 16, wherein the ADAR is ADAR1, ADAR2, or ADAR3.
18. The fusion protein of paragraph 16, wherein the ADAR is ADAR1 or ADAR2.
19. The fusion protein of paragraph 16, wherein the ADAR is ADAR2.
20. The fusion protein of paragraph 1, wherein in the presence of the inducer, the DD is constitutively active.
21. The fusion protein of paragraph 1, wherein in the presence of the inducer, the ADAR deaminase domain is constitutively active.
22. The fusion protein of paragraph 20 or 21, wherein the constitutively active deaminase domain comprises: an E1008Q mutation in ADAR1; an E488Q mutation in ADAR2; or an E527Q mutation in ADAR3.
23. The fusion protein of paragraph 1, wherein the DD comprises at least one mutation in the IP6 binding pocket that decreases background activity.
24. The fusion protein of paragraph 1, wherein the ADAR comprises at least one mutation in the IP6 binding pocket that decreases background activity.
25. The fusion protein of paragraph 23 or 24, wherein the at least one mutation is in an amino acid residue selected from the group consisting of: T375, R400, R522, Y658, K662, Y668, K672, V688, K690, F697, and L699.
26. The fusion protein of paragraph 23 or 24, wherein the at least one mutation is selected from the group consisting of: T375G, R400K, R522M, K662R, K662M, K672R, K672M, V688A, V688G, K690R, K690M, F697Y, F697L, F6971, F697V, F697A, F697G, L699V, L699A, and L699G.
27. The fusion protein of paragraph 1, wherein the adenosine deaminase comprises Adenosine Deaminase TRNA Specific (ADAT).

28. The fusion protein of paragraph 27, wherein the ADAT is ADAT1.
29. The fusion protein of paragraph 1, wherein the adenosine deaminase comprises Adenosine Deaminase Domain Containing (ADAD).
30. The fusion protein of paragraph 29, wherein the ADAD is ADAD1 or ADAD2.
31. The fusion protein of any one of paragraphs 1-30, wherein the ADAR, ADAT, or ADAD is a mammalian adenosine deaminase.
32. The fusion protein of any one of paragraphs 1-31, wherein the ADAR, ADAT, or ADAD is a human adenosine deaminase.
33. The fusion protein of paragraph 4, wherein the RNA-binding domain is selected from the group consisting of MCP, PCP, λN, and HIV tat.
34. The fusion protein of any one of paragraphs 1-33, comprising from N-terminus to C-terminus:
(a) the RNA-binding domain;
(b) the first portion of the deaminase domain;
(c) the first member of the binding pair;
(d) the second portion of the deaminase domain; and
(c) the second member of the binding pair.
35. The fusion protein of any one of paragraphs 1-34, wherein the first and second portions of the deaminase domain are split at an RNA binding loop.
36. The fusion protein of paragraph 35, wherein the RNA binding loop is the 5' RNA binding loop (RBL) of ADAR1, ADAR2, ADAR3, ADAD1, or ADAD2.
37. The fusion protein of paragraph 35, wherein the RNA binding loop comprises:

```
(a) residues G969 to K999 of ADAR1:
                                   (SEQ ID NO: 134)
GALFDKSCSDRAMESTESRHYPVFENPKQGK of ADAR1;

(b) residues A454 to Q479 of ADAR2:
                                   (SEQ ID NO: 135)
ARIFSPHEPILEEPADRHPNRKARGQ;

(c) residues A493 to H518 of ADAR3:
                                   (SEQ ID NO: 136)
ARLHSPYEITTDLHSSKHLVRKFRGH;

(d) residues A334 to K365 of ADAD1:
                                   (SEQ ID NO: 137)
AQIKSQLRLNPHSISAFEANEELCLHVAVEGK;
or

(e) residues A347 to Q375 of ADAD2:
                                   (SEQ ID NO: 138)
AARDIYLPPTSEGGLPHSPPMRLQAHVLGQ.
```

38. The fusion protein of paragraph 35, wherein the RNA binding loop comprises:

```
                                            (SEQ ID NO: 139)
(a) residues K974 to S986 of ADAR1: KSCSDRAMES;

                                            (SEQ ID NO: 140)
(b) residues F457 to D469 of ADAR2: FSPHEPILEEPAD;

                                            (SEQ ID NO: 141)
(c) residues P498 to S508 of ADAR3: PYEITTDLHSS;

                                            (SEQ ID NO: 142)
(d) residues Q339 to P344 of ADADI: QLRLNP;
or

                                            (SEQ ID NO: 143)
(e) residues P352 to P360 of ADAD2: PPTSEGGLP
```

39. The fusion protein of paragraph 35, wherein the first and second portions of the deaminase domain are split between:
(a) residues S977 and D978 of ADAR1;
(b) residues T984 and E985 of ADAR1;
(c) residues A468 and D469 of ADAR2;
(d) residues S507 and S508 of ADAR3;
(e) residues L340 and R341 of ADAD1; or
(f) residues G357 and G358 of ADAD2.
40. The fusion protein of any one of paragraphs 1-39, comprising from N-terminus to C-terminus:
(a) the RNA-binding domain;
(b) the first member of the binding pair;
(c) the first portion of deaminase domain;
(d) the second portion of the deaminase domain; and
(e) the second member of the binding pair.
41. The fusion protein of any one of paragraphs 1-40, wherein the first and second members of the binding pair are Bad and Bcl-xL, and the inducer of the first and second binding pairs is A-1331852 or ABT-737.
42. The fusion protein of any one of paragraphs 1-40, wherein the first and second members of the binding pair are Bim and Bcl-xL, and the inducer of the first and second binding pairs is A-1331852.
43. The fusion protein of any one of paragraphs 1-40, wherein the first and second members of the binding pair are MS1 and MCL-1, and the inducer of the first and second binding pairs is S63845.
44. The fusion protein of any one of paragraphs 1-43, wherein the first and second members of the binding pair are a repressible protease and a protease-binding peptide, and the inducer of the first and second binding pairs is an inhibitor of the repressible protease.
45. The fusion protein of paragraph 44, wherein the repressible protease is selected from the group consisting of: HIV protease, HCV protease, and SARS-CoV2 protease.
46. The fusion protein of paragraph 44, wherein the protease-binding peptide comprises a domain that specifically binds to the HIV protease, HCV protease, or SARS-CoV2 protease.
47. The fusion protein of any one of paragraphs 44-46, wherein the repressible protease is NS3 protease from Hepatitis C virus (HCV).
48. The fusion protein of any one of paragraphs 44-47, wherein the protease-binding peptide is selected from the group consisting of: K5-66 peptide, K5-66-A peptide, K5-66-B peptide, K6-10 peptide, K6-10-A peptide, K6-10-B peptide, K5-66-R peptide, CP5-46 peptide, CP5-46-4D5E peptide, CP5-46-A peptide, CP5-46A-4D5E peptide, Ant-CP5-46A-4D5E peptide, and ANR peptide.
49. The fusion protein of any one of paragraphs 44-48, wherein the protease inhibitor is selected from the group consisting of: grazoprevir, danoprevir, simeprevir, asunaprevir, ciluprevir, boceprevir, sovaprevir, paritaprevir, ombitasvir, paritaprevir, ritonavir, dasabuvir, and telaprevir.
50. The fusion protein of any one of paragraphs 44-49, wherein the repressible protease is NS3 protease from Hepatitis C virus (HCV); the protease-binding peptide is CP5-46-4D5E, and/or the protease inhibitor is grazoprevir.
51. The fusion protein of any one of paragraphs 44-50, wherein the repressible protease is NS3 protease from Hepatitis C virus (HCV) type 1b.

52. The fusion protein of any one of paragraphs 1-51, wherein:
(a) the first member of the binding pair comprises an antigen-binding domain,
(b) the second member of the binding pair comprises a first antigen, and
(c) the inducer of the first and second binding pairs comprises a second antigen;
wherein the antigen-binding domain is capable of binding to the second antigen with a similar or higher affinity than to the first antigen.
53. The fusion protein of any one of paragraphs 1-52, wherein:
(a) the first member of the binding pair comprises an anti-ALFA antigen binding domain,
(b) the second member of the binding pair comprises a first ALFA antigen, and
(c) the inducer of the first and second binding pairs comprises a second ALFA antigen;
wherein the anti-ALFA antigen binding domain is capable of binding to the second ALFA antigen or variants thereof.
54. The fusion protein of paragraph 53, wherein the anti-ALFA antigen binding domain is capable of binding to the second ALFA antigen or variants thereof with a similar or higher affinity than to the first ALFA antigen.
55. The fusion protein of any one of paragraphs 1-54, wherein the fusion protein further comprises a cleavable linker between the second portion of the deaminase domain the second member of the binding pair.
56. The fusion protein of paragraph 55, wherein the cleavable linker comprises at least one protease cleavage site.
57. A fusion protein comprising:
(a) a first portion of a deaminase domain (DD) of an adenosine deaminase;
(b) a first member of a binding pair associated with the first portion of the DD;
(c) a second portion of the DD;
(d) a cleavable linker; and
(e) a second member of a binding pair associated with the cleavable linker;
wherein the first member of the binding pair is capable of binding to the second member of the binding pair in the absence of a cleavage inducer, resulting in allosteric inhibition of the first and second portions of the DD, and
wherein the cleavable linker is cleaved in the presence of the cleavage inducer, resulting in activation of the first and second portions of the DD.
58. The fusion protein of paragraph 57, wherein in the allosteric inhibition comprises deformation of the inositol hexaphosphate (IP6) binding pocket of first and second portions of the DD.
59. The fusion protein of paragraph 57, wherein in the activation of the first and second portions of the DD comprises deaminase activity.
60. The fusion protein of paragraph 57, wherein the cleavage inducer for the cleavable linker is light, sound, chemical, or an enzyme.
61. The fusion protein of paragraph 57, further comprising an RNA-binding domain (RBD).
62. The fusion protein of paragraph 61, wherein the RNA-binding domain (RBD) is capable of binding to a binding motif for the RBD on an RNA molecule.
63. The fusion protein of any one of paragraphs 57-62, wherein:
(a) the first member of the binding pair comprises a SpyCatcher domain,
(b) the second member of the binding pair comprises a Spy tag,
(c) the cleavable linker comprises Tobacco Etch Virus (TEV) cut site cleavable by a TEV protease, and
(d) the cleavage inducer comprises light.
64. A fusion protein comprising an RNA-binding domain linked to a deaminase domain of an adenosine deaminase.
65. The fusion protein of paragraph 64, wherein the RNA-binding domain is N-terminal of the deaminase domain.
66. The fusion protein of paragraph 65, wherein the RNA-binding domain is C-terminal of the deaminase domain.
67. A fusion protein comprising:
(a) a first portion of a deaminase domain (DD) of an adenosine deaminase;
(b) a first member of a first binding pair associated with the first portion of the DD;
(c) a second portion of the DD;
(d) a second member of a first binding pair associated with the second portion of the DD;
(e) a first member of a second binding pair associated with the first member of the first binding pair; and
(f) a second member of the second binding pair associated with the second member of the first binding pair;
wherein the first member of the first binding pair is capable of binding to the second member of the first binding pair in the absence of a first inducer, resulting in allosteric inhibition of the first and second portions of the DD;
wherein the first member of the first binding pair is not capable of binding to the second member of the first binding pair in the presence of the first inducer, resulting in activation of the first and second portions of the DD;
wherein the first member of the second binding pair is capable of binding to the second member of the second binding pair in the absence of a second inducer, resulting in allosteric inhibition of the first and second portions of the DD; and
wherein the first member of the second binding pair is not capable of binding to the second member of the second binding pair in the presence of the second inducer, resulting in activation of the first and second portions of the DD.
68. A fusion protein comprising:
(a) a first portion of a deaminase domain (DD) of an adenosine deaminase;
(b) a repressible protease associated with the first portion of the DD;
(c) a second portion of the DD; and
(d) a protease-binding peptide associated with the second portion of the DD,
wherein the repressible protease is capable of binding to the protease-binding peptide in the absence of an inhibitor for the repressible protease, resulting in allosteric inhibition of the first and second portions of the DD, and
wherein the repressible protease is not capable of binding to the protease-binding peptide in the presence of the inhibitor for the repressible protease, resulting in activation of the first and second portions of the DD.

69. A fusion protein comprising:
(a) a first portion of a deaminase domain (DD) of an adenosine deaminase;
(b) a repressible protease associated with the first portion of the DD;
(c) a second portion of the DD; and
(d) a protease cleavage site associated with the first and second portions of the DD;
wherein the repressible protease is capable of binding to the protease cleavage site in the absence of an inhibitor for the repressible protease, resulting in cleavage of the protease cleavage site and inactivation of the first and second portions of the DD; and
wherein the repressible protease is not capable of binding to the protease cleavage site in the presence of the inhibitor for the repressible protease, resulting in activation of the first and second portions of the DD.

70. The fusion protein of paragraph 68 or 69, wherein the repressible protease is selected from the group consisting of: HIV protease, HCV protease, and SARS-CoV2 protease.

71. The fusion protein of any one of paragraphs 68-70, wherein the protease-binding peptide comprises a domain that is capable of specifically binding to the HIV protease, HCV protease, or SARS-CoV2 protease, 72. The fusion protein of any one of paragraphs 68-71, wherein the repressible protease is NS3 protease from Hepatitis C virus (HCV).

73. The fusion protein of any one of paragraphs 68-72, wherein the protease-binding peptide is selected from the group consisting of: K5-66 peptide, K5-66-A peptide, K5-66-B peptide, K6-10 peptide, K6-10-A peptide, K6-10-B peptide, K5-66-R peptide, CP5-46 peptide, CP5-46-4D5E peptide, CP5-46-A peptide, CP5-46A-4D5E peptide, Ant-CP5-46A-4D5E peptide, and ANR peptide.

74. The fusion protein of any one of paragraphs 68-73, wherein the protease inhibitor is selected from the group consisting of: grazoprevir, danoprevir, simeprevir, asunaprevir, ciluprevir, boceprevir, sovaprevir, paritaprevir, ombitasvir, paritaprevir, ritonavir, dasabuvir, and telaprevir.

75. The fusion protein of any one of paragraphs 68-74, wherein the repressible protease is NS3 protease from Hepatitis C virus (HCV); the protease-binding peptide is CP5-46-4D5E, and/or the protease inhibitor is grazoprevir.

76. The fusion protein of any one of paragraphs 68-75, wherein the repressible protease is NS3 protease from Hepatitis C virus (HCV) type 1b.

77. The fusion protein of any one of paragraphs 68-76, wherein the protease cleavage site is a NS3/NS4A cleavage site, a NS4A/NS4B cleavage site, a NS4B/NS5A cleavage site, or a NS5A/NS5B cleavage site.

78. A fusion protein comprising from N terminus to C terminus;
a) ADAR2-DDN;
b) NS3 binding peptide;
c) ADAR2-DDC; and
d) HCV NS3 protease from genotype 1B.

79. The fusion protein of paragraph 78, wherein the ADAR2-DDN comprises residues Q316 to A568 of ADAR2.

80. The fusion protein of paragraph 78, wherein the NS3 binding peptide comprises CP5-46-4D5E.

81. The fusion protein of paragraph 78, wherein the ADAR2-DDC comprises residues D569 to T700 of ADAR2.

82. The fusion protein of paragraph 78, wherein the fusion protein further comprises a tandem-dimer MS2 coat protein (tdMCP) at the N-terminus.

83. An RNA molecule comprising:
(a) a double-stranded region comprising:
(i) at least one target codon; and
(ii) an RNA binding motif capable of being bound by an RNA-binding domain; and
(b) at least one open reading frame, wherein the at least one open reading frame is operatively linked to the double-stranded region.

84. The RNA molecule of paragraph 83, wherein the at least one open reading frame encodes for the fusion protein of any one of paragraphs 1-82.

85. The RNA molecule of paragraph 83, wherein the at least one open reading frame encodes for at least one effector protein.

86. An RNA molecule comprising:
(a) a first open reading frame;
(b) a double-stranded region comprising:
(i) at least one target codon; and
(ii) an RNA binding motif capable of being bound by an RNA-binding domain; and
(c) a second open reading frame, wherein the second open reading frame is operatively linked to the double-stranded region.

87. The RNA molecule of paragraph 86, wherein the first open reading frame encodes for a first polypeptide, and the second reading frame encodes for a second polypeptide.

88. The RNA molecule of paragraph 86, wherein the first open reading frame encodes for a first portion of a polypeptide, and the second reading frame encodes for a second portion of the polypeptide.

89. The RNA molecule of paragraph 86, wherein the first open reading frame encodes for the fusion protein of any one of paragraphs 1-82.

90. The RNA molecule of paragraph 86, wherein the second open reading frame encodes for at least one effector protein.

91. The RNA molecule of paragraph 86, wherein the second open reading frame encodes for the fusion protein of any one of paragraphs 1-82.

92. The RNA molecule of paragraph 86, wherein the first open reading frame encodes for at least one effector protein.

93. The RNA molecule of paragraph 86, wherein an internal ribosome entry site (IRES) is located between the first and second open reading frames.

94. An RNA molecule comprising:
(a) an open reading frame;
(b) a double-stranded region comprising:
(i) at least one target codon; and
(ii) an RNA binding motif capable of being bound by an RNA-binding domain; and
(c) a poly-A tail.

95. The RNA molecule of paragraph 94, wherein the open reading frame encodes for the fusion protein of any one of paragraphs 1-82.

96. The RNA molecule of paragraph 94, wherein the open reading frame encodes for an effector protein.
97. The RNA molecule of any one of paragraphs 83-96, wherein the effector protein comprises an antigen-binding domain for a cancer antigen or a microbial antigen.
98. The RNA of any one of paragraphs 83-97, wherein the target codon comprises at least one adenosine nucleotide.
99. The RNA of any one of paragraphs 83-98, wherein the target codon is a stop codon, a start codon, a non-start codon, or a sense codon.
100. The RNA of paragraph 99, wherein the stop codon is capable of being converted into a non-stop codon.
101. The RNA molecule of paragraph 99 or 100, wherein the at least one stop codon comprises UAG.
102. The RNA molecule of paragraph 100, wherein the at least one non-stop codon comprises at least one tryptophan codon.
103. The RNA molecule of paragraph 102, wherein the at least one tryptophan codon comprises UGG.
104 The RNA of any one of paragraphs 99-103, wherein the stop codon is UAG, UGA, or UAA, and the non-stop codon is UIG, UGI, or UII, respectively.
105 The RNA of paragraph 99, wherein the start codon is capable of being converted into a non-start codon.
106. The RNA of paragraph 105, wherein the start codon is AUG, and the non-start codon is IUG.
107. The RNA of paragraph 99, wherein the non-start codon is capable of being converted into a non-start codon.
108. The RNA of paragraph 107, wherein the non-start codon is AUA, and the start codon is AUI.
109 The RNA of paragraph 99, wherein the sense codon encoding a first amino acid is capable of being converted into a mutated sense codon encoding a second amino acid.
110. The RNA of paragraph 109, wherein the sense codon and mutated sense codon are selected from Table 15.
111 The RNA molecule of paragraph 83-110, the RNA-binding domain comprises the RNA-binding domain of the fusion protein of any one of paragraphs 1-82.
112. The RNA molecule of paragraph 83-111, wherein the RNA binding motif is selected from the group consisting of MS2, PP7, BoxB, and TAR.
113. The RNA molecule of paragraph 83-112, wherein the RNA-binding domain is selected from the group consisting of MCP, PCP, λN, and HIV tat.
114. The RNA molecule of paragraph 83-113, wherein:
  (a) the RNA-binding domain comprises MCP, and the RNA binding motif comprises MS2;
  (b) the RNA-binding domain comprises PCP, and the RNA binding motif comprises PP7;
  (c) the RNA-binding domain comprises AN, and the RNA binding motif comprises BoxB; or
  (d) the RNA-binding domain comprises HIV Tat, and the RNA binding motif comprises TAR.
115. The RNA molecule of paragraph 83-114, wherein the double-stranded region of the RNA molecule comprises at least one hairpin.
116. The RNA molecule of paragraph 83-115, wherein the double-stranded region of the RNA molecule comprises one hairpin comprising the at least one target codon and the RNA binding motif.
117. The RNA molecule of paragraph 83-116, wherein the double-stranded region of the RNA molecule comprises a first hairpin comprising the at least one target codon and a second hairpin comprising the RNA binding motif.
118. A nucleic acid encoding the fusion protein of any one of paragraphs 1-82.
119. A nucleic acid encoding the RNA molecule of any one of paragraphs 83-117.
120. A nucleic acid encoding the fusion protein of any one of paragraphs 1-82 and the RNA molecule of any one of paragraphs 83-117.
121. The nucleic acid of paragraph 120, wherein the nucleic acid encoding the fusion protein and the nucleic acid encoding the RNA molecule are operably linked to a single promoter.
122 The nucleic acid of paragraph 120, wherein the nucleic acid encoding the fusion protein and the nucleic acid encoding the RNA molecule are each operably linked to a separate promoter.
123 The nucleic acid of any one of paragraphs 120-122, wherein the nucleic acid encoding the fusion protein is 5' of the nucleic acid encoding the RNA molecule.
124. The nucleic acid of any one of paragraphs 120-122, wherein the nucleic acid encoding the fusion protein is 3' of the nucleic acid encoding the RNA molecule.
125 The nucleic acid of any one of paragraphs 118-124, wherein the nucleic acid comprises DNA.
126. The nucleic acid of any one of paragraphs 118-125, wherein the nucleic acid comprises RNA.
127. A vector comprising the nucleic acid of any one of paragraphs 118-126.
128. A system for modulating RNA translation comprising the fusion protein of any one of paragraphs 1-82 and the RNA molecule of any one of paragraphs 83-117.
129. A system for modulating RNA translation comprising a first fusion protein of any one of paragraphs 1-82 and a second fusion protein of any one of paragraphs 1-82.
130. A system for modulating RNA translation comprising at least one fusion protein of any one of paragraphs 1-82 and at least one RNA molecule of any one of paragraphs 83-117.
131. A system for modulating RNA translation comprising
  (a) a fusion protein comprising an RNA-binding domain linked to a deaminase domain of an adenosine deaminase; and
  (b) an RNA molecule comprising:
    (i) a double-stranded region comprising:
      (A) at least one target codon; and
      (B) an RNA binding motif capable of being bound by an RNA-binding domain; and
    (ii) at least one open reading frame, wherein the at least one open reading frame is operatively linked to the double-stranded region.
132 The system of any one of paragraphs 131, wherein the target codon is a stop codon, a start codon, a non-start codon, or a sense codon.
133. The system of paragraph 131 or 132, wherein the deaminase domain is capable of converting the at least one stop codon into at least one non-stop codon.
134. The system of any one of paragraphs 131-133, wherein the reading frame is not translated when the at least one stop codon is present in the double-stranded region of the RNA molecule.

135. The system of any one of paragraphs 131-134, wherein the reading frame is translated when the at least one stop codon is converted into the at least one non-stop codon.

136. The system of any one of paragraphs 131-135, wherein the deaminase domain is capable of converting the at least one start codon into at least one non-start codon.

137. The system of any one of paragraphs 131-136, wherein the reading frame is translated when the at least one start codon is present in the double-stranded region of the RNA molecule.

138 The system of any one of paragraphs 131-137, wherein the reading frame is not translated when the at least one start codon is converted into the at least one non-start codon.

139. The system of any one of paragraphs 131-138, wherein the deaminase domain is capable of converting the at least one non-start codon into at least one start codon.

140. The system of any one of paragraphs 131-139, wherein the reading frame is not translated when the at least one non-start codon is present in the double-stranded region of the RNA molecule.

141. The system of any one of paragraphs 131-140, wherein the reading frame is translated when the at least one non-start codon is converted into the at least one start codon.

142. The system of any one of paragraphs 131-141, wherein the deaminase domain is capable of converting the at least one sense stop codon encoding a first amino acid into at least one mutated sense codon encoding a second amino acid.

143. A system for modulating RNA translation comprising:
- (a) a fusion protein comprising an RNA-binding domain linked to a deaminase domain of an adenosine deaminase; and
- (b) an RNA molecule comprising:
  - (i) a first open reading frame;
  - (ii) a double-stranded region comprising:
    - (A) at least one target codon; and
    - (B) an RNA binding motif capable of being bound by the RNA-binding domain of the fusion protein; and
  - (iii) a second open reading frame.

144. The RNA of paragraph 143, wherein the target codon is a stop codon, a start codon, a non-start codon, or a sense codon.

145. The system of paragraph 143 or 144, wherein the deaminase domain is capable of converting the at least one stop codon into at least one non-stop codon.

146. The system of any one of paragraphs 143-145, wherein the second reading frame is not translated when the at least one stop codon is present in the double-stranded region of the RNA molecule.

147. The system of any one of paragraphs 143-146, wherein the second reading frame is translated when the at least one stop codon is converted into the at least one non-stop codon. 148. The system of any one of paragraphs 143-147, wherein the first open reading frame is translated when the at least one stop codon or the at least one non-stop codon is present in the double-stranded region of the RNA molecule.

149 The system of any one of paragraphs 143-148, wherein the deaminase domain is capable of converting the at least one start codon into at least one non-start codon.

150. The system of any one of paragraphs 143-149, wherein the second reading frame is translated when the at least one start codon is present in the double-stranded region of the RNA molecule.

151. The system of any one of paragraphs 143-150, wherein the second reading frame is not translated when the at least one start codon is converted into the at least one non-start codon.

152. The system of any one of paragraphs 143-151, wherein the first open reading frame is translated when the at least one start codon or the at least one non-start codon is present in the double-stranded region of the RNA molecule.

153 The system of any one of paragraphs 143-152, wherein the deaminase domain is capable of converting the at least one non-start codon into at least one start codon.

154 The system of any one of paragraphs 143-153, wherein the second reading frame is not translated when the at least one non-start codon is present in the double-stranded region of the RNA molecule.

155. The system of any one of paragraphs 143-154, wherein the second reading frame is translated when the at least one non-start codon is converted into the at least one start codon.

156. The system of any one of paragraphs 143-155, wherein the deaminase domain is capable of converting the at least one sense stop codon encoding a first amino acid into at least one mutated sense codon encoding a second amino acid.

157. The system of any one of paragraphs 143-156, wherein the first open reading frame encodes for a first polypeptide, and the second reading frame encodes for a second polypeptide.

158. The system of any one of paragraphs 143-157, wherein the first open reading frame encodes for a first portion of a polypeptide, and the second reading frame encodes for a second portion of the polypeptide.

159. The system of any one of paragraphs 143-158, wherein the first open reading frame encodes for the fusion protein of any one of paragraphs 1-82.

160. The system of any one of paragraphs 143-159, wherein the second open reading frame encodes for an effector protein.

161. The system of any one of paragraphs 143-160, wherein the effector protein comprises an antigen-binding domain for a cancer antigen or a microbial antigen.

162. A system for modulating RNA translation comprising:
- (a) a fusion protein comprising an RNA-binding domain linked to a deaminase domain of an adenosine deaminase; and
- (b) an RNA molecule comprising:
  - (i) an open reading frame;
  - (ii) a double-stranded region comprising:
    - (A) at least one target codon; and
    - (B) an RNA binding motif capable of being bound by the RNA-binding domain of the fusion protein; and
  - (iii) a poly-A tail.

163. The RNA of paragraph 162, wherein the target codon is a stop codon, a start codon, a non-start codon, or a sense codon.
164. The system of paragraph 162 or 163, wherein the deaminase domain is capable of converting the at least one stop codon into at least one non-stop codon.
165. The system of any one of paragraphs 162-164, wherein the first open reading frame is translated when the at least one stop codon is present in the double-stranded region of the RNA molecule.
166 The system of any one of paragraphs 162-165, wherein the RNA molecule is degraded when the at least one stop codon is converted into the at least one non-stop codon.
167. A system for modulating RNA translation comprising:
  (a) a fusion protein comprising:
    (i) an RNA-binding domain;
    (ii) a first portion of a deaminase domain (DD) of an adenosine deaminase;
    (iii) a first member of a binding pair associated with the first portion of the DD;
    (iv) a second portion of the DD; and
    (v) a second member of a binding pair associated with the second portion of the DD; and
  (b) the RNA molecule of any one of paragraphs 83-117.
168. A system for modulating RNA translation comprising:
  (a) a fusion protein comprising:
    (i) an RNA-binding domain;
    (ii) a first portion of a deaminase domain (DD) of an adenosine deaminase;
    (iii) a first member of a binding pair associated with the first portion of the DD;
    (iv) a second portion of the DD; and
    (v) a second member of a binding pair associated with the second portion of the DD; and
  (b) an RNA molecule comprising:
    (i) a first open reading frame;
    (ii) a double-stranded region comprising:
      (A) at least one target codon; and
      (B) an RNA binding motif capable of being bound by the RNA-binding domain of the fusion protein; and
    (iii) a second open reading frame.
169. A system for modulating RNA translation comprising:
  (a) a fusion protein comprising:
    (i) an RNA-binding domain;
    (ii) a first portion of a deaminase domain (DD) of an adenosine deaminase;
    (iii) a first member of a binding pair associated with the first portion of the DD;
    (iv) a second portion of the DD; and
    (v) a second member of a binding pair associated with the second portion of the DD; and
  (b) an RNA molecule comprising:
    (i) an open reading frame;
    (ii) a double-stranded region comprising:
      (A) at least one target codon; and
      (B) an RNA binding motif capable of being bound by the RNA-binding domain of the fusion protein; and
    (iii) a poly-A tail.
170. The system of any one of paragraphs 167-169, wherein the target codon is a stop codon, a start codon, a non-start codon, or a sense codon,
171. The system of any one of paragraphs 128-170, the system further comprising an inducer of the first and second binding pairs.
172. The system of any one of paragraphs 128-171, wherein the first and second members of the binding pair of the fusion protein are capable of binding to each other in the absence of an inducer of the first and second binding pairs and reduce or prevent:
  (a) the formation of the inositol hexaphosphate (IP6) binding pocket of first and second portions of the deaminase domain;
  (b) deaminase activity of the first and second portions of the deaminase domain;
  (c) conversion by the deaminase domain of the at least one target codon of the RNA molecule into at least one inosine-comprising codon;
  (d) conversion by the deaminase domain of the at least one stop codon of the RNA molecule into at least one non-stop codon;
  (e) conversion by the deaminase domain of the at least one start codon of the RNA molecule into at least one non-start codon;
  (f) conversion by the deaminase domain of the at least one non-start codon of the RNA molecule into at least one start codon; and/or
  (g) conversion by the deaminase domain of the at least one sense codon of the RNA molecule encoding for a first amino acid into at least one mutated codon encoding for a second amino acid.
173. The system of any one of paragraphs 128-172, wherein the first and second members of the binding pair of the fusion protein are not capable of binding to each other in the presence of an inducer of the first and second binding pairs, allowing for:
  (a) the formation of the inositol hexaphosphate (IP6) binding pocket of first and second portions of the deaminase domain;
  (b) deaminase activity of the first and second portions of the deaminase domain;
  (c) conversion by the deaminase domain of the at least one target codon of the RNA molecule into at least one inosine-comprising codon;
  (d) conversion by the deaminase domain of the at least one stop codon of the RNA molecule into at least one non-stop codon;
  (e) conversion by the deaminase domain of the at least one start codon of the RNA molecule into at least one non-start codon;
  (f) conversion by the deaminase domain of the at least one non-start codon of the RNA molecule into at least one start codon; and/or
  (g) conversion by the deaminase domain of the at least one sense codon of the RNA molecule encoding for a first amino acid into at least one mutated sense codon encoding for a second amino acid.
174. The system of any one of paragraphs 128-173, wherein conversion by the deaminase domain of at least one target codon in the RNA molecule into at least one inosine-comprising codon increases or decreases:
  (a) translation of the reading frame of the RNA molecule;
  (b) translation of the second reading frame of the RNA molecule;
  (c) degradation of the RNA molecule; and/or
  (d) translation of a variant polypeptide encoded by the RNA molecule.

175. A system for modulating RNA translation comprising:
(a) a fusion protein comprising:
(i) an RNA-binding domain;
(ii) a first portion of a deaminase domain (DD) of an adenosine deaminase;
(iii) a first member of a binding pair associated with the first portion of the DD;
(iv) a second portion of the DD;
(v) a cleavable linker; and
(vi) a second member of a binding pair associated with the cleavable linker; and
(b) the RNA molecule of any one of paragraphs 83-117.

176. A system for modulating RNA translation comprising:
(a) a fusion protein comprising:
(i) an RNA-binding domain;
(ii) a first portion of a deaminase domain (DD) of an adenosine deaminase;
(iii) a first member of a binding pair associated with the first portion of the DD;
(iv) a second portion of the DD;
(v) a cleavable linker; and
(vi) a second member of a binding pair associated with the cleavable linker; and
(b) an RNA molecule comprising:
(i) a first open reading frame;
(ii) a double-stranded region comprising:
(A) at least one target codon; and
(B) an RNA binding motif capable of being bound by the RNA-binding domain of the fusion protein; and
(iii) a second open reading frame.

177. A system for modulating RNA translation comprising:
(a) a fusion protein comprising:
(i) an RNA-binding domain;
(ii) a first portion of a deaminase domain (DD) of an adenosine deaminase;
(iii) a first member of a binding pair associated with the first portion of the DD;
(iv) a second portion of the DD;
(v) a cleavable linker; and
(vi) a second member of a binding pair associated with the cleavable linker; and
(b) an RNA molecule comprising:
(i) an open reading frame;
(ii) a double-stranded region comprising:
(A) at least one target codon; and
(B) an RNA binding motif capable of being bound by the RNA-binding domain of the fusion protein; and
(iii) a poly-A tail.

178. The system of any one of paragraphs 175-177, the system further comprising a cleavage inducer.

179. The system of any one of paragraphs 175-178, wherein the cleavable linker is not cleaved in the absence of a cleavage inducer and reduces or prevents:
(a) the formation of the inositol hexaphosphate (IP6) binding pocket of first and second portions of the deaminase domain;
(b) deaminase activity of the first and second portions of the deaminase domain;
(c) conversion by the deaminase domain of the at least one target codon of the RNA molecule into at least one inosine-comprising codon;
(d) conversion by the deaminase domain of the at least one stop codon of the RNA molecule into at least one non-stop codon;
(e) conversion by the deaminase domain of the at least one start codon of the RNA molecule into at least one non-start codon;
(f) conversion by the deaminase domain of the at least one non-start codon of the RNA molecule into at least one start codon; and/or
(g) conversion by the deaminase domain of the at least one sense codon of the RNA molecule encoding for a first amino acid into at least one mutated sense codon encoding for a second amino acid.

180. The system of any one of paragraphs 175-179, wherein the cleavable linker is cleaved in the presence of a cleavage inducer and allows for:
(a) the formation of the inositol hexaphosphate (IP6) binding pocket of first and second portions of the deaminase domain;
(b) deaminase activity of the first and second portions of the deaminase domain;
(c) conversion by the deaminase domain of the at least one target codon of the RNA molecule into at least one inosine-comprising codon;
(d) conversion by the deaminase domain of the at least one stop codon of the RNA molecule into at least one non-stop codon;
(e) conversion by the deaminase domain of the at least one start codon of the RNA molecule into at least one non-start codon;
(f) conversion by the deaminase domain of the at least one non-start codon of the RNA molecule into at least one start codon; and/or
(g) conversion by the deaminase domain of the at least one sense codon of the RNA molecule encoding for a first amino acid into at least one mutated sense codon encoding for a second amino acid.

181. The system of any one of paragraphs 175-180, wherein conversion by the deaminase domain of at least one target codon in the RNA molecule into at least one inosine-comprising codon increases or decreases:
(a) translation of the reading frame of the RNA molecule;
(b) translation of the second reading frame of the RNA molecule;
(c) degradation of the RNA molecule; and/or
(d) translation of a variant polypeptide encoded by the RNA molecule.

182 The system of any one of paragraphs 175-181, wherein the target codon is a stop codon, a start codon, a non-start codon, or a sense codon.

183. The system of any one of paragraphs 128-182, wherein the at least one stop codon comprises UAG.

184. The system of any one of paragraphs 128-183, wherein the at least one non-stop codon comprises at least one tryptophan codon.

185. The system of any one of paragraphs 128-184, wherein the at least one tryptophan codon comprises UGG.

186. The system of any one of paragraphs 128-185, wherein the stop codon is UAG, UGA, or UAA, and the non-stop codon is UIG, UGI, or UII, respectively.

187. The system of any one of paragraphs 128-186, wherein the start codon is capable of being converted into a non-start codon.

188. The system of any one of paragraphs 128-187, wherein the start codon is AUG, and the non-start codon is IUG.

189. The system of any one of paragraphs 128-188, wherein the non-start codon is capable of being converted into a start codon.

190 The system of any one of paragraphs 128-189, wherein the non-start codon is AUA, and the start codon is AUI.

191. The system of any one of paragraphs 128-190, wherein the sense codon encoding a first amino acid is capable of being converted into a mutated sense codon encoding a second amino acid.

192. The system of any one of paragraphs 128-191, wherein the sense codon and mutated sense codon are selected from Table 15.

193. The system of any one of paragraphs 128-192, wherein:
- (a) the RNA-binding domain comprises MCP, and the RNA binding motif comprises MS2;
- (b) the RNA-binding domain comprises PCP, and the RNA binding motif comprises PP7;
- (c) the RNA-binding domain comprises AN, and the RNA binding motif comprises BoxB; or
- (d) the RNA-binding domain comprises HIV Tat, and the RNA binding motif comprises TAR.

194. The system of any one of paragraphs 128-193, wherein the double-stranded region of the RNA molecule comprises at least one hairpin.

195. The system of any one of paragraphs 128-194, wherein the double-stranded region of the RNA molecule comprises one hairpin comprising the at least one stop codon and the RNA binding motif.

196. The system of any one of paragraphs 128-195, wherein the double-stranded region of the RNA molecule comprises a first hairpin comprising the at least one stop codon and a second hairpin comprising the RNA binding motif.

197. A cell comprising:
- (a) the fusion protein of any one of paragraphs 1-82;
- (b) the RNA molecule of any one of paragraphs 83-117;
- (c) the nucleic acid of any one of paragraphs 118-126;
- (d) the vector of paragraph 127; and/or
- (e) the system of any one of paragraphs 128-196.

198. A composition comprising at least one of:
- (a) the fusion protein of any one of paragraphs 1-82;
- (b) the RNA molecule of any one of paragraphs 83-117;
- (c) the nucleic acid of any one of paragraphs 118-126;
- (d) the vector of paragraph 127;
- (e) the system of any one of paragraphs 128-196; and/or
- (f) the cell of paragraph 197.

199 The composition of paragraph 198, the composition further comprising:
- (a) an inducer of the first and second binding pairs;
- (b) a cleavage inducer; and/or
- (c) a protease inhibitor.

200. A pharmaceutical composition comprising a pharmaceutically compatible carrier and at least one of:
- (a) the fusion protein of any one of paragraphs 1-82;
- (b) the RNA molecule of any one of paragraphs 83-117;
- (c) the nucleic acid of any one of paragraphs 118-126;
- (d) the vector of paragraph 127;
- (c) the system of any one of paragraphs 128-196; and/or
- (f) the cell of paragraph 197.

201. The pharmaceutical composition of paragraph 200, the pharmaceutical composition further comprising:
- (a) an inducer of the first and second binding pairs;
- (b) a cleavage inducer; and/or
- (c) a protease inhibitor.

202. A method of modulating RNA translation in a cell, the method comprising contacting the cell with;
- (a) the fusion protein of any one of paragraphs 1-82;
- (b) the RNA molecule of any one of paragraphs 83-117;
- (c) the nucleic acid of any one of paragraphs 118-126;
- (d) the vector of paragraph 127;
- (e) the system of any one of paragraphs 128-196;
- (f) the composition of any one of paragraphs 198-199; and/or
- (g) the pharmaceutical composition of any one of paragraphs 200-201.

203. The method of paragraph 202, the method further comprising contacting the cell with:
- (a) an inducer of the first and second binding pairs;
- (b) a cleavage inducer; and/or
- (c) a protease inhibitor.

204. A method for treating a cancer or microbial infection in a subject in need thereof, the method comprising administering an effective amount of:
- (a) the fusion protein of any one of paragraphs 1-82;
- (b) the RNA molecule of any one of paragraphs 83-117;
- (c) the nucleic acid of any one of paragraphs 118-126;
- (d) the vector of paragraph 127;
- (e) the system of any one of paragraphs 128-196;
- (f) the cell of paragraph 197;
- (g) the composition of any one of paragraphs 198-199; and/or
- (h) the pharmaceutical composition of any one of paragraphs 200-201.

205. The method of paragraph 204, the method further comprising contacting the cell with:
- (a) an inducer of the first and second binding pairs;
- (b) a cleavage inducer; and/or
- (c) a protease inhibitor.

206. A method for treating a cancer or microbial infection in a subject in need thereof, the method comprising administering an effective amount of:
- (a) a nucleic acid encoding for an RNA molecule comprising:
  - (i) a first open reading frame encoding for a fusion protein;
  - (ii) a double-stranded region comprising:
    - (A) at least one target codon; and
    - (B) an RNA binding motif capable of being bound by an RNA-binding domain; and
  - (iii) a second open reading frame encoding for an effector protein.

207. A method for treating a cancer or microbial infection in a subject in need thereof, the method comprising administering an effective amount of:
- (a) a nucleic acid encoding a fusion protein comprising an RNA-binding domain linked to a deaminase domain of an adenosine deaminase; and
- (b) a nucleic acid encoding for an RNA molecule comprising:
  - (i) an open reading frame encoding for an effector protein;
  - (ii) a double-stranded region comprising:
    - (A) at least one target codon; and
    - (B) an RNA binding motif capable of being bound by an RNA-binding domain; and
  - (iii) a poly-A tail.

208. The method of paragraph 207, wherein the fusion protein comprises the fusion protein of any one of paragraphs 1-82.
209. The method of paragraph 207 or 208, wherein the fusion protein comprises an RNA-binding domain linked to a deaminase domain of an adenosine deaminase.
210. The method of any one of paragraphs 207-209, wherein the fusion protein comprises:
   (a) an RNA-binding domain;
   (b) a first portion of a deaminase domain of an adenosine deaminase;
   (c) a first member of a binding pair;
   (d) a second portion of the deaminase domain; and
   (e) a second member of a binding pair.
211. The method of paragraph any one of paragraphs 207-209, wherein the fusion protein comprises:
   (a) an RNA-binding domain;
   (b) a first portion of a deaminase domain of an adenosine deaminase;
   (c) a first member of a binding pair;
   (d) a second portion of the deaminase domain;
   (e) a cleavable linker; and
   (f) a second member of a binding pair.
212. The method of paragraph any one of paragraphs 207-211, wherein the effector protein comprises an antigen-binding domain for a cancer antigen or a microbial antigen.
213. The method of paragraph any one of paragraphs 207-212, the method further comprising administering to the subject an effective amount of:
   (a) an inducer of the first and second binding pairs of the fusion protein;
   (b) a cleavage inducer of the cleavable linker; and/or
   (c) a protease inhibitor
214. The method of paragraph 213, wherein the inducer, cleavage inducer, or protease inhibitor is administered after the nucleic acid encoding the fusion protein and/or the nucleic acid encoding the RNA molecule.

Some embodiments of the technology described herein can be defined according to any of the following numbered paragraphs:

1. A fusion protein comprising:
   (a) a first portion of a deaminase domain (DD) of an adenosine deaminase;
   (b) a first member of a binding pair associated with the first portion of the DD;
   (c) a second portion of the DD; and
   (d) a second member of a binding pair associated with the second portion of the DD,
   wherein the first member of the binding pair is capable of binding to the second member of the binding pair in the absence of an inducer, resulting in allosteric inhibition of the first and second portions of the DD, and
   wherein the first member of the binding pair is not capable of binding to the second member of the binding pair in the presence of the inducer, resulting in activation of the first and second portions of the DD.
2. The fusion protein of paragraph 1, wherein in the allosteric inhibition of the first and second portions of the DD comprises deformation of the inositol hexaphosphate (IP6) binding pocket of first and second portions of the DD.
3. The fusion protein of paragraph 1, wherein in the activation of the first and second portions of the DD comprises deaminase activity.
4. The fusion protein of paragraph 1, further comprising an RNA-binding domain, wherein the RNA-binding domain (RBD) is capable of binding to a binding motif for the RBD on an RNA molecule.
5. The fusion protein of paragraph 4, wherein the RNA-binding domain is selected from the group consisting of MCP, PCP, λN, and HIV tat.
6. The fusion protein of paragraph 1, wherein the deaminase domain is capable of:
   (a) deamination of an adenosine nucleotide into an inosine nucleotide in an RNA molecule;
   (b) converting at least one stop codon into at least one non-stop codon;
   (c) converting at least one start codon into at least one non-start codon;
   (d) converting at least one non-start codon into at least one start codon;
   and/or
   (d) converting at least one sense codon encoding a first amino acid into at least one mutated sense codon encoding a second amino acid.
7. The fusion protein of paragraph 1, wherein the adenosine deaminase comprises Adenosine Deaminase Acting on RNA (ADAR), Adenosine Deaminase TRNA Specific (ADAT), or Adenosine Deaminase Domain Containing (ADAD).
8. The fusion protein of paragraph 7, wherein the ADAR is ADAR1, ADAR2, or ADAR3; the ADAT is ADAT1; or the ADAD is ADAD1 or ADAD2.
9. The fusion protein of paragraph 1, wherein in the presence of the inducer, the DD is constitutively active.
10. The fusion protein of paragraph 9, wherein the constitutively active deaminase domain comprises: an E1008Q mutation in ADAR1; an E488Q mutation in ADAR2; or an E527Q mutation in ADAR3.
11. The fusion protein of paragraph 1, wherein the DD comprises at least one mutation in the IP6 binding pocket that decreases background activity.
12. The fusion protein of paragraph 11, wherein the at least one mutation is in ADAR2 in an amino acid residue selected from the group consisting of: T375, R400, R522, Y658, K662, Y668, K672, V688, K690, F697, and L699.
13. The fusion protein of paragraph 4, comprising from N-terminus to C-terminus:
   (a) the RNA-binding domain;
   (b) the first portion of the deaminase domain;
   (c) the first member of the binding pair;
   (d) the second portion of the deaminase domain; and
   (e) the second member of the binding pair; or comprising from N-terminus to C-terminus
   (f) the RNA-binding domain;
   (g) the first member of the binding pair;
   (h) the first portion of deaminase domain;
   (i) the second portion of the deaminase domain; and
   (j) the second member of the binding pair.
14. The fusion protein of paragraph 1, wherein the first and second portions of the deaminase domain are split at an RNA binding loop.

15. The fusion protein of paragraph 14, wherein the RNA binding loop comprises:
(a) residues G969 to K999 of ADAR1:

```
(a) residues G969 to K999 of ADAR1:
                                  (SEQ ID NO: 134)
GALFDKSCSDRAMESTESRHYPVFENPKQGK of ADAR1;

(b) residues A454 to Q479 of ADAR2:
                                  (SEQ ID NO: 135)
ARIFSPHEPILEEPADRHPNRKARGQ;

(c) residues A493 to H518 of ADAR3:
                                  (SEQ ID NO: 136)
ARLHSPYEITTDLHSSKHLVRKFRGH;

(d) residues A334 to K365 of ADAD1:
                                  (SEQ ID NO: 137)
AQIKSQLRLNPHSISAFEANEELCLHVAVEGK;

(e) residues A347 to Q375 of ADAD2:
                                  (SEQ ID NO: 138)
AARDIYLPPTSEGGLPHSPPMRLQAHVLGQ;

(f) residues K974 to S986 of ADAR1:
                                  (SEQ ID NO: 139)
KSCSDRAMES;

(g) residues F457 to D469 of ADAR2:
                                  (SEQ ID NO: 140)
FSPHEPILEEPAD;

(h) residues P498 to S508 of ADAR3:
                                  (SEQ ID NO: 141)
PYEITTDLHSS;

(i) residues Q339 to P344 of ADADI:
                                  (SEQ ID NO: 142)
QLRLNP;
or

(j) residues P352 to P360 of ADAD2:
                                  (SEQ ID NO: 143)
PPTSEGGLP.
```

16. The fusion protein of paragraph 14, wherein the first and second portions of the deaminase domain are split between:
(a) residues S977 and D978 of ADAR1;
(b) residues T984 and E985 of ADAR1;
(c) residues A468 and D469 of ADAR2;
(d) residues S507 and S508 of ADAR3;
(e) residues L340 and R341 of ADAD1; or
(f) residues G357 and G358 of ADAD2.

17. The fusion protein of paragraph 1, wherein the first and second members of the binding pair are:
(a) Bad and Bcl-xL, and the inducer of the first and second binding pairs is A-1331852 or ABT-737;
(b) Bim and Bcl-xL, and the inducer of the first and second binding pairs is A-1331852;
(c) MS1 and MCL-1, and the inducer of the first and second binding pairs is $63845; or
(d) a repressible protease and a protease-binding peptide, and the inducer of the first and second binding pairs is an inhibitor of the repressible protease.

18. The fusion protein of paragraph 1, wherein:
(a) the first member of the binding pair comprises an antigen-binding domain,
(b) the second member of the binding pair comprises a first antigen, and
(c) the inducer of the first and second binding pairs comprises a second antigen;
wherein the antigen-binding domain is capable of binding to the second antigen with a similar or higher affinity than to the first antigen.

19. The fusion protein of paragraph 1, wherein the fusion protein further comprises a cleavable linker between the second portion of the deaminase domain the second member of the binding pair.

20. A fusion protein comprising:
(a) a first portion of a deaminase domain (DD) of an adenosine deaminase;
(b) a repressible protease associated with the first portion of the DD;
(c) a second portion of the DD; and
(d) a protease cleavage site associated with the first and second portions of the DD;
wherein the repressible protease is capable of binding to the protease cleavage site in the absence of an inhibitor for the repressible protease, resulting in cleavage of the protease cleavage site and inactivation of the first and second portions of the DD; and
wherein the repressible protease is not capable of binding to the protease cleavage site in the presence of the inhibitor for the repressible protease, resulting in activation of the first and second portions of the DD.

21. An RNA molecule comprising:
(I)
(a) a double-stranded region comprising:
(i) at least one target codon; and
(ii) an RNA binding motif capable of being bound by an RNA-binding domain; and
(b) at least one open reading frame, wherein the at least one open reading frame is operatively linked to the double-stranded region; or
(II)
(a) a first open reading frame;
(b) a double-stranded region comprising:
(i) at least one target codon; and
(ii) an RNA binding motif capable of being bound by an RNA-binding domain; and
(c) a second open reading frame, wherein the second open reading frame is operatively linked to the double-stranded region; or
(III)
(a) an open reading frame;
(b) a double-stranded region comprising:
(i) at least one target codon; and
(ii) an RNA binding motif capable of being bound by an RNA-binding domain; and
(c) a poly-A tail.

22. The RNA molecule of paragraph 21,
wherein the open reading frame encodes for a fusion protein or an effector protein;
wherein the first open reading frame encodes for a first polypeptide and the second open reading frame encodes for a second polypeptide;
wherein the first open reading frame encodes for a first portion of a polypeptide, and the second open reading frame encodes for a second portion of the polypeptide;
wherein the first or second open reading frame encodes for a fusion protein; or
wherein the first or second open reading frame encodes for at least one effector protein.

23. The RNA of paragraph 21, wherein the target codon is a stop codon, a start codon, a non-start codon, or a sense codon; and wherein the target codon comprises at least one adenosine nucleotide.

24. The RNA molecule of paragraph 21, wherein:
   (a) the RNA-binding domain comprises MCP, and the RNA binding motif comprises MS2;
   (b) the RNA-binding domain comprises PCP, and the RNA binding motif comprises PP7;
   (c) the RNA-binding domain comprises AN, and the RNA binding motif comprises BoxB; or
   (d) the RNA-binding domain comprises HIV Tat, and the RNA binding motif comprises TAR.
25. The RNA molecule of paragraph 21, wherein the double-stranded region of the RNA molecule comprises:
   at least one hairpin.
   one hairpin comprising the at least one target codon and the RNA binding motif, or a first hairpin comprising the at least one target codon and a second hairpin comprising the RNA binding motif.
26. A system for modulating RNA translation comprising:
   (a) a fusion protein comprising:
      (i) an RNA-binding domain;
      (ii) a first portion of a deaminase domain (DD) of an adenosine deaminase;
      (iii) a first member of a binding pair associated with the first portion of the DD;
      (iv) a second portion of the DD; and
      (v) a second member of a binding pair associated with the second portion of the DD; and
   (b) the RNA molecule of paragraph 21.
27. The system of paragraph 26, further comprising an inducer of the first and second binding pairs.
28. The system of paragraph 26, wherein the first and second members of the binding pair of the fusion protein are capable of binding to each other in the absence of an inducer of the first and second binding pairs and reduce or prevent:
   (a) the formation of the inositol hexaphosphate (IP6) binding pocket of first and second portions of the deaminase domain;
   (b) deaminase activity of the first and second portions of the deaminase domain;
   (c) conversion by the deaminase domain of the at least one target codon of the RNA molecule into at least one inosine-comprising codon;
   (d) conversion by the deaminase domain of the at least one stop codon of the RNA molecule into at least one non-stop codon;
   (e) conversion by the deaminase domain of the at least one start codon of the RNA molecule into at least one non-start codon;
   (f) conversion by the deaminase domain of the at least one non-start codon of the RNA molecule into at least one start codon; and/or
   (g) conversion by the deaminase domain of the at least one sense codon of the RNA molecule encoding for a first amino acid into at least one mutated codon encoding for a second amino acid.
29. The system of paragraph 26, wherein the first and second members of the binding pair of the fusion protein are not capable of binding to each other in the presence of an inducer of the first and second binding pairs, allowing for:
   (a) the formation of the inositol hexaphosphate (IP6) binding pocket of first and second portions of the deaminase domain;
   (b) deaminase activity of the first and second portions of the deaminase domain;
   (c) conversion by the deaminase domain of the at least one target codon of the RNA molecule into at least one inosine-comprising codon;
   (d) conversion by the deaminase domain of the at least one stop codon of the RNA molecule into at least one non-stop codon;
   (e) conversion by the deaminase domain of the at least one start codon of the RNA molecule into at least one non-start codon;
   (f) conversion by the deaminase domain of the at least one non-start codon of the RNA molecule into at least one start codon; and/or
   (g) conversion by the deaminase domain of the at least one sense codon of the RNA molecule encoding for a first amino acid into at least one mutated sense codon encoding for a second amino acid.
30. The system of paragraph 29, wherein conversion by the deaminase domain of at least one target codon in the RNA molecule into at least one inosine-comprising codon increases or decreases:
   (a) translation of the reading frame of the RNA molecule;
   (b) translation of the second reading frame of the RNA molecule;
   (c) degradation of the RNA molecule; and/or
   (d) translation of a variant polypeptide encoded by the RNA molecule.

The technology described herein is further illustrated by the following examples which in no way should be construed as being further limiting.

EXAMPLES

Example 1

Brief Summary of the Embodiment

Nucleic acid based medicines, including messenger RNA (mRNA) based vaccines and therapeutics have emerged as a promising technology with many applications in both medicine and basic science research. Instead of producing and delivering a protein directly to cells/organisms/patients, nucleic acids (including mRNAs) are delivered to cells via lipid nanoparticles (LNP) or other agents. Upon entry, ribosome mediated-translation results in the production of proteins encoded by the delivered nucleic acid sequences. A limitation of mRNA-based agents is that uptake of the mRNA to any human cell type will result in its translation and thus expression of the encoded protein. Thus, a limitation of mRNA based medicines is the limited control over translation of an encoded protein sequence. To overcome this limitation, described herein is a set of technologies that permit programmable control over the translation state and stability of mRNAs in a way that can be regulated via exogenous inducers (e.g., drugs, light, etc.) based on presence of intracellular signals and components (including proteins, enzymes, antigens, and cell-type markers, etc.). The technology described herein relates to compositions, systems and methods that permit control over mRNA modification and subsequent translational decoding (e.g., protein expression) through stop-codon editing and read-through of an mRNA transcript. RNA editing can be mediated by an engineered human adenosine deaminase acting on RNA (ADAR) enzyme domains possessing engineered conditional activity, which can be regulated via exposure to drugs or light, or activated in response to post-translational modifications (e.g., proteolysis or through the binding of a specified target proteins/antigens of interest.

ADAR proteins catalyze the deamination of adenosine into inosine, and this modification is among the most prevalent post-transcriptional modifications in mammalian cells. ADAR proteins are conserved across phyla, with humans containing three homologues, two of which are catalytically active (ADAR1 & ADAR2). ADAR can be used to edit UAG stop codons to UIG in the presence of a complimentary strand of RNA to form dsRNA in trans and cis. Inosine's hydrogen bonding profile closely resembles guanine, and a UIG codon typically base-pairs with the tryptophan tRNA anticodon, allowing for the incorporation of tryptophan instead of the recruitment of release factors, and translation continues. ADAR can also be used to edit endogenous transcripts, correct deleterious mutations, and to turn on protein expression upon hybridization of an endogenous transcript to synthetic transcripts.

The current technology utilizes a site near the RNA binding loop on hADAR2 and hADAR1 deaminase domains that can accommodate insertions of small protein domains and/or peptides without substantially affecting editing activity. Fusion of a protein domain or peptide on the C-terminus of the deaminase domain that forms a hetero/homodimer to its cognate partner in the RNA binding loop greatly reduces the editing activity of ADAR. The use of protein-peptide interaction partners and/or cleavable linkers that can be disassociated and/or separated upon drug, light, protease, or ligand addition restores deaminase activity of the enzymatic domain. By complexing and localizing this engineered deaminase downstream of an editable stop codon, a user-defined input leads to the editing of the stop codon and readthrough to the protein cargo. Conversely, if the editable stop codon is the final stop codon before the mRNA polyA tail, then readthrough leads to the recruitment of endogenous Skip7, the initiation of non-stop decay, and the destruction of both the protein via the host proteasome and the mRNA via host exonucleases. The implementation of stop-codon editing to turn on protein expression or lead to mRNA turnover can be used in tandem in single-transcript circuits to lead to multi-input or complex logic, including but not limited to rapid induction with signal A (e.g., drug, light, protease, or ligand) and rapid mRNA decay via signal B (e.g., if the editable stop codon is the final stop codon before the mRNA polyA tail).

Exemplary applications include, but are not limited to, the development of dose-able and time-resolved mRNA therapeutics. In this scheme, mRNA can be delivered to a patient, and a physician can control the timing, degree and duration of protein expression by using a drug. Additionally, this technology can be applied to make therapeutics that produce protein only in certain cells that have a specific protein expression profile (e.g., virally infected cells, senescent cells, or cancerous cells). In this scheme, the inactive ADAR can be activated only in response to the binding of a specific protein partner or upon specific protease activity. This application reduces off-target effects if a user is looking to apply protein expression to only a certain subset of cells. Finally, this technology can be used for the development of sensitive in-vitro sensors and/or diagnostics through the coupling of ADAR-editing activity to cell-free translation systems.

Without wishing to be bound by theory, the following variations of the system are contemplated herein.

Alternative manufacturing methods can be used.

As described herein, some embodiments use DNA-encoded elements and transient transfection with plasmid DNA, which permits the complexing of purified ADAR protein with in vitro transcribed RNA. Exemplary applications include RNA vaccines and therapeutics. As such, in some embodiments, the compositions and methods described herein can be performed with bases used in mRNA vaccines to evade innate immune response, such as NI-methyl-pseudouridine containing transcripts.

In some embodiments, the ADAR protein can be produced in the absence of inositol hexaphosphate (IP6), which is a required cofactor for RNA editing by ADAR. Thus, pre-complexing of RNA and ADAR in the absence of IP6 prior to delivery to a subject ensures that ADAR cannot edit the RNA. The ADAR can gain activity only when administered to a subject either by adding IP6 to the complex prior to administration to the subject or relying on host IP6 to serve as ADAR's co-factor.

In some embodiments, the ADAR-RNA system can be used in an in-vitro/cell-free context as a sensor. In this context, the enzymatic activity of ADAR upon addition of a stimulus of interest can be coupled to cell-free translation of a reporter gene on the RNA to get sensitive detection of the stimulus.

Alternative chemistry can be used.

As described herein, the readout can be the translation of a downstream protein or the turnover of a synthetic transcript. An alternative readout that can be useful in pure biological contexts or in sensing applications is the actual base that is edited (e.g., adenine turning to hypoxanthine). This change can be detected by cDNA sequencing or fluorescence in situ hybridization (FISH) assays as inosine preferentially base pairs with cytosine and can be read out that way. In this context, bulk RNAseq can be coupled to ADAR based sensing to produce a readout of a population of cells.

As described herein, the constrained state of the ADAR by self-binding domains can be relieved by competitive binding or cleavage of a linker; however, an alternative method can be done by physical/chemical deformation of the binding/chemical interface by post-translational modifications. In this method, one of the binding components also has sites for post-translational modifications (e.g., phosphorylation by kinases, ubiquitination by ubiquitin ligases, methylation, etc.) that interfere with the intramolecular binding affinity. In this case the activity of a host enzyme interferes directly with the binding interface between the two autoinhibitory components and leads to relaxation of the constrained ADAR.

Another variation of the work described above is the use of non-genetically encoded components. Everything described above utilized genetically encoded ADAR variants relying on cellular synthesis of the repressed ADAR-DDs. However, it is useful to instead use other chemistry to link the RBL to the C-terminus and use other chemical means to open such a linkage. As an example, the two parts of the protein can be linked together in-vitro with a linker that contains azobenzene, dialkoxydiphenylsilane, or other chemically, bio-orthogonally cleavable linkers. Additionally, the use of other chemistries can be useful for the photo-dissociative/photocleavable component of the patent, as there are a host of photocleavable linkers which can be inserted between the domains in vitro.

Another variation that was tested was inserting tandem ligand-binding protein pairs in tandem in the 5' RNA binding loop. Bcl-xL and BAD peptide insertions were tested at that site, and it was found that the resulting ADAR-DD was drug-inducible in a manner analogous, though lower extent of editing was found, to the C-terminal fusion of Bcl-xL and BAD insertion at the 5' RNA binding loop. Other variations tested were inserting PhoCl and AsLOV2 domains in the S' RNA binding loop. Other variations include inserting tandem antibody-antigen pairs and other chemically or light disrupted protein interaction pairs.

Alternative Constructs

ADAR-DDs orthologs from other organisms can be considered as well as the paralogous ADAR1 protein from humans. There is a high degree of conserved sequence identity between these two. Without wishing to be bound by theory, it was hypothesized that the same mechanism and homologous sites can function similarly to ADAR2-DD. Secondly, additional work was done utilizing different BH3 and Bcl-2 family domains and different point mutants of these peptides. Third, NS3 inhibitor (e.g., grazoprevir, etc.) inducible ADAR2-DD construct were created using NS3/4A and NS3 binding peptide as the autoinhibitory domains.

It is contemplated herein that any antibody-fragment and antigen pairing can be used in the iADAR construct. There are many examples of antibody-antigen, ligand-receptor, and ligand-binding protein interactions (therapeutic and otherwise) known in the art that can be utilized. Additionally, proteolytic activation can use the synthetic TEV protease, an HIV protease, HCV protease, SARS-CoV2 protease, or other protease-inducible version (also referred to herein as repressible proteases).

On the synthetic transcript side, fluorescent protein reporters can be substituted with any protein of interest upstream (e.g., the ADAR itself, a sensing component of the ADAR domain, etc.) and/or the fluorescent protein reporters downstream of the editable stop codon can be substituted with any protein of interest (e.g., suicide genes such as caspases for a kill switch, different cytokines for inflammatory or anti-inflammatory effects, etc.).

One example is encoding an ADAR-DD with a chemically-inducible dimerization domain (CID) next to its repressive domain and encoding upstream on the RNA the same binding partner fused to the other CID domain. When drug is added, the repressed ADAR-DD-CID fusion colocalizes with the second CID-peptide component that is soluble and expressed in the cell, and the increased local concentration leads to trans binding and activation of ADAR.

Additionally, the specific RNA sequences used in the RNA hairpin, RNA binding element, and 3'UTR/polyA tail are only exemplary, and minor or major changes in the primary, secondary, or tertiary structure of these RNA elements can be done.

Another variation is the modulation of C-terminal linker length by exogenous addition. In this scenario, there is a certain linker length between the ADAR-DD and the dimerization domain whereby the ADAR-DD is spontaneously active. By placing domains that functionally change radius with stimuli (e.g., LOV domain J alpha helix with light or HCV NS3-NS3-binding peptide with drug) then the ADAR can be turned from an inactive to an active state. Another variation to make a light or protease inducible ADAR2 can be by inducing the availability of a cryptic protease site (e.g., hiding a cut site in a LOV domain).

Additional Alternatives

The constructs described herein can be administered using virus-mediated delivery.

The constructs described herein can be used to detect viral antigens in infected cells, including the expression of viral proteases.

Instead of alternating translation or transcript stability, modifications can be used to alter different aspects of regulation, including trafficking or subcellular localization.

The constructs described herein can be used combined with self-replication mechanisms to mediate amplification within specific cell types.

Example 2

Technical Description for iADAR-DD Editing

Adenosine deaminase acting on RNA (ADAR) enzymes are conserved across phyla and are responsible for the conversion of adenosine to inosine in eukaryotic messenger RNA (mRNA), a common and critical post-transcriptional modification. Inosine has a different hydrogen bonding pairing than adenine, and although it is capable of base pairing with cytosine, uracil, and adenine, it has been shown to preferentially base pair with cytosine. This change in base-pairing preference allows for a phenomenon called recoding, where a codon that previously encoded one amino-acid/release-factor is changed to base-pair to a different codon during translation. Previous groups have utilized ADAR editing of the amber stop codon UAG to UIG to allow for read-through and downstream translation of a protein of interest from a synthetic transcript.

As disclosed herein, the technology described herein relates to protein engineering of adenosine deaminase (AD), e.g., human ADAR deaminase domains (DD), such that the ADAR is in the constitutively inactive state. This engineering of the DDs of the ADAR enables the ADAR to be inducible, e.g., it is an engineered inducible ADAR (IADAR). For iADAR to become activated i.e., turned ON, it is allosterically modulated from an inactive to an active state in response to small molecule drugs, target antigen-binding, protease activity, and light. As disclosed herein, in one embodiment, pairing the engineered iADAR with a synthetic mRNA transcript that localize the iADAR to an editable stop codon allows for enzyme activity to be coupled to a change in synthetic, user-defined protein expression and/or mRNA stability. Therefore, this invention enables the selective editing of synthetic mRNA transcripts based on user defined and potentially endogenous inputs.

Applicants disclosed herein an exemplary proof of principal synthetic constructs are generated, which are referred to herein as Target Activation Constructs (TAC) or Target inactivation constructs (TIC), that demonstrate and validate as exemplary mRNA transcripts that can be edited by iADAR in the active state (iADAR-ON). The inventors first tested whether they could edit stop codons in a synthetic mRNA transcript with a constitutively active ADAR2-DD (E488Q) fused to the C-terminus of bacteriophage-derived MS2 coat protein (MCP), a protein which binds a specific RNA motif. Previous groups have demonstrated the editing activity of this protein construct on dsRNA duplex between a substrate strand and a guide strand. However, the inventors were interested in testing whether by using a short hairpin motif, they could get stop codon editing on the same strand that they directed the DD to when expressed in human cells.

The inventors demonstrate use of a first Target Activation construct (TAC), which is a synthetic transcript that contains 4 parts (FIG. 1A): an upstream coding region (red), a short hairpin that contains 1 or more stop codons (black), an RBD binding motif (gray), and a downstream coding region (green). For the reporter system, the inventors used the fluorescent protein-epitope tag tandem fusions of mCherry-FLAG and HA-mNeonGreen as the upstream and downstream coding regions. Without DD editing activity, translation is terminated after mCherry-FLAG. Coexpression with MCP-ADAR2-DD was hypothesized to lead to binding of MCP-DD, stop codon UAG editing to UIG, and expression of mNeonGreen (FIG. 1B).

Figure 1C:
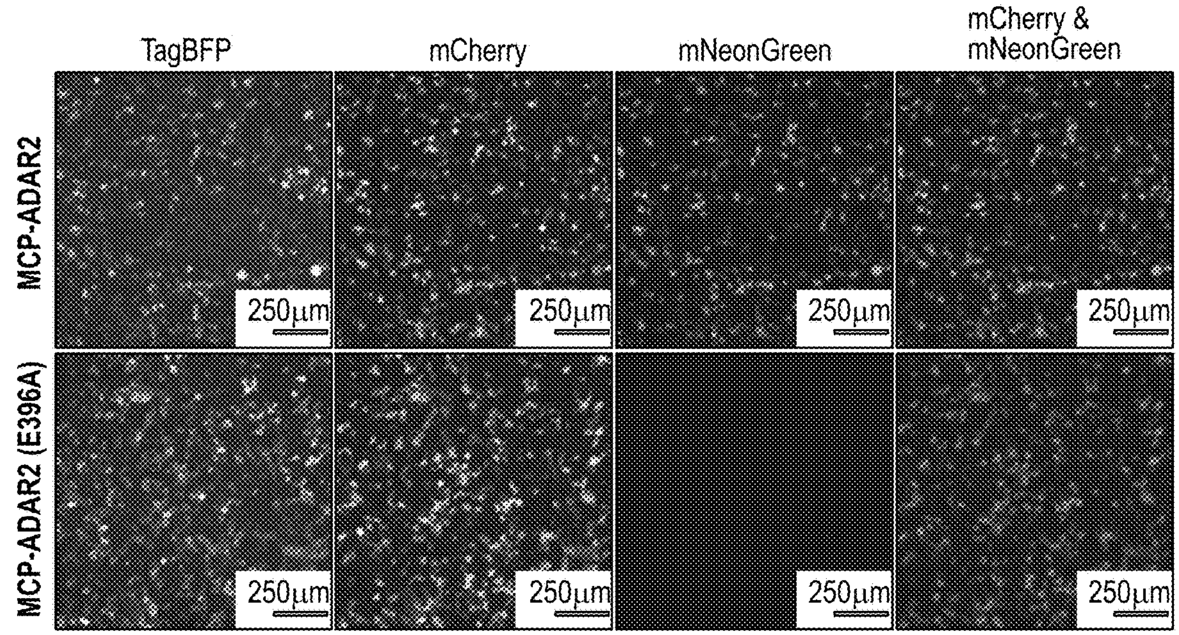
Figure 1D:
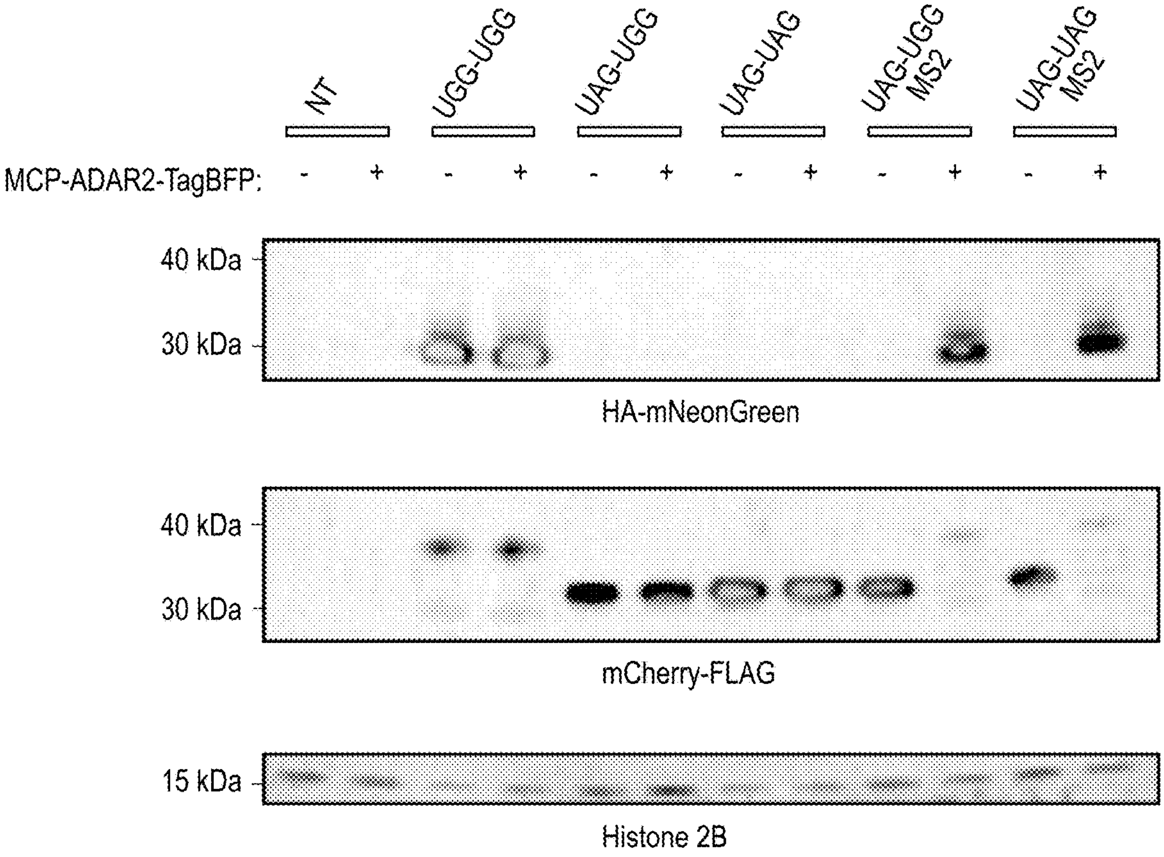

HEK 293 FT cells were co-transfected with plasmids expressing the reporter containing 2 UAG stop codons in the hairpin and a pcDNA3 construct encoding a fusion protein composed of MCP, ADAR2-DD (E488Q), and TagBFP. As a control, they also co-transfected a catalytically inactive DD containing the mutation E396A. Two days after transfection, fluorescence microscopy showed that mNeonGreen robustly expressed in the population co-transfected with active ADAR-DD whereas there was minimal mNeonGreen fluorescence in the catalytically inactive condition (FIG. 1C). They further confirmed this result by performing a Western blot on HEK293FT cells co-transfected with MCP-ADAR-DD and reporter constructs containing different numbers of stop codons and RNA elements (FIG. 1D). The Western blot showed HA-mNeonGreen expression in non-trivial, control conditions only when MCP-ADAR and a reporter containing an MS2 operator were co-transfected. Almost no off-target editing was observed in stop-codon reporters with the downstream MS2 operator, demonstrating that the ADAR is relatively specific to transcripts containing an RNA encoded RBD binding motif.

Figure 1E:
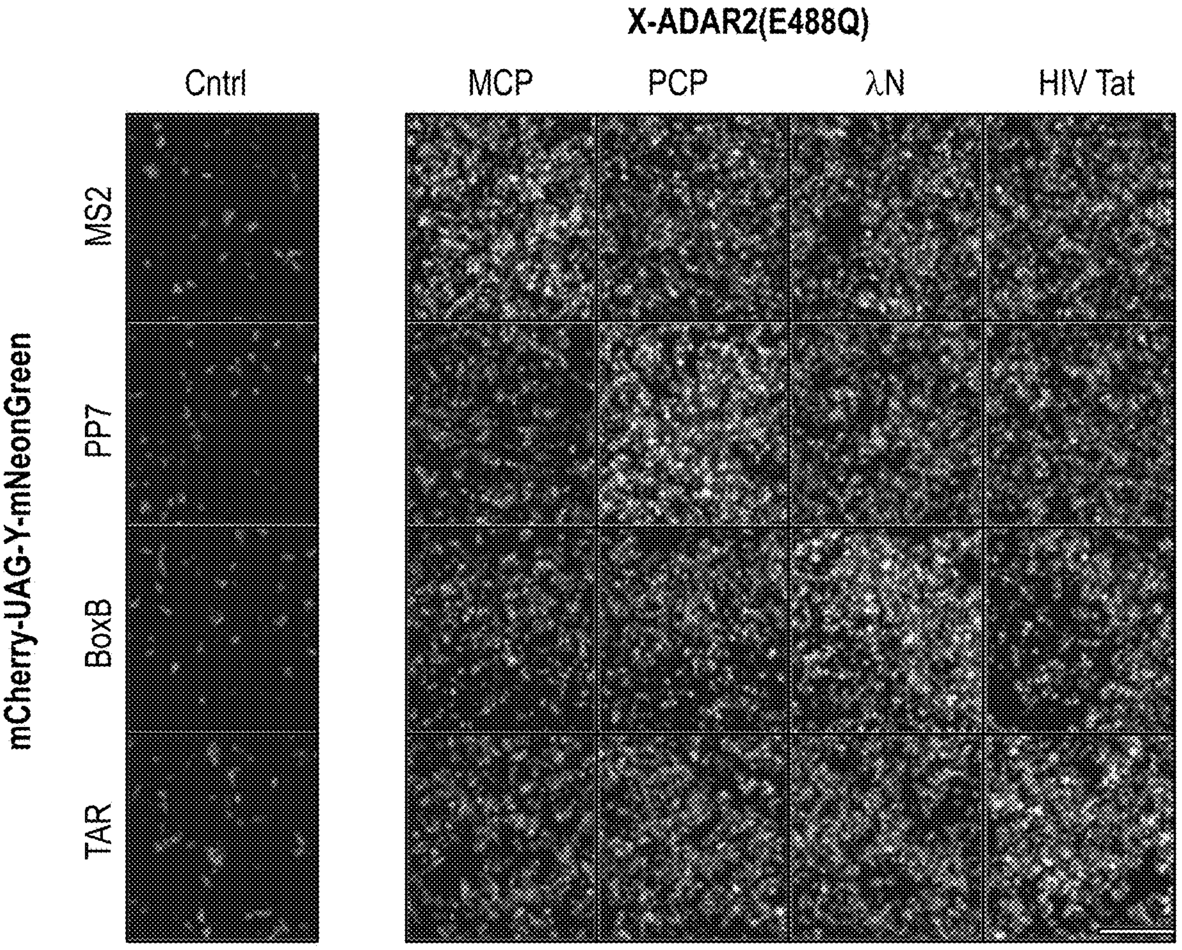

The inventors sought to test the modularity of the RNA-binding-domain (RBD) and RNA-elements by swapping out the MCP and MS2 operator with other RBDs and RNA elements: PP7 coat protein (PCP) and PP7 operator, HIV Tat peptide and trans-activation response element (TAR), and A bacteriophage N peptide (AN) and BoxB operator. mNeonGreen expression was strongly observed by fluorescent microscopy when the correct RBD and RNA element were co-transfected into HEK293FT cells, and the mNeonGreen-to-mCherry ratio is similar across RBD-element pairs demonstrating similar relative editing efficiencies (FIG. 1E).

In addition to testing a synthetic transcript which utilizes stop-codon editing to turn on a downstream protein product, which has been previously demonstrated, the inventors sought to create an original way to couple enzymatic ADAR activity to protein and mRNA degradation: an OFF-switch. In order to do so, the inventors designed a synthetic transcript (FIG. 2A) where there is an open reading frame (green), 1 or more stop codons in an RNA-hairpin (dark gray), a specific RNA element (light gray), and a 3'UTR with no downstream stop codons prior to the polyadenylate (polyA) tail. The inventors created a reporter plasmid that contained a bidirectional CMV driving the expression dTomato on one transcript and EGFPd2, an editable stop codon, an MS2 operator, and a mutated rabbit-β-globin 3'UTR/poly A signal sequence lacking additional stop codons on the other transcript (FIG. 2B). In the absence of ADAR-DD activity, both dTomato and EGFPd2 should be translated and expressed. However, coexpression of MCP-ADAR2 should lead to editing of the only in-frame stop codon and the initiation of an endogenous process called non-stop decay, whereby the translating ribosome stalls on the polyA-tail and recruits Ski7 followed by exonucleases to destroy the mRNA (FIG. 2C). In this process, proteosomal degradation of the nascent, unreleased polypeptide also occurs.

Figure 2D:
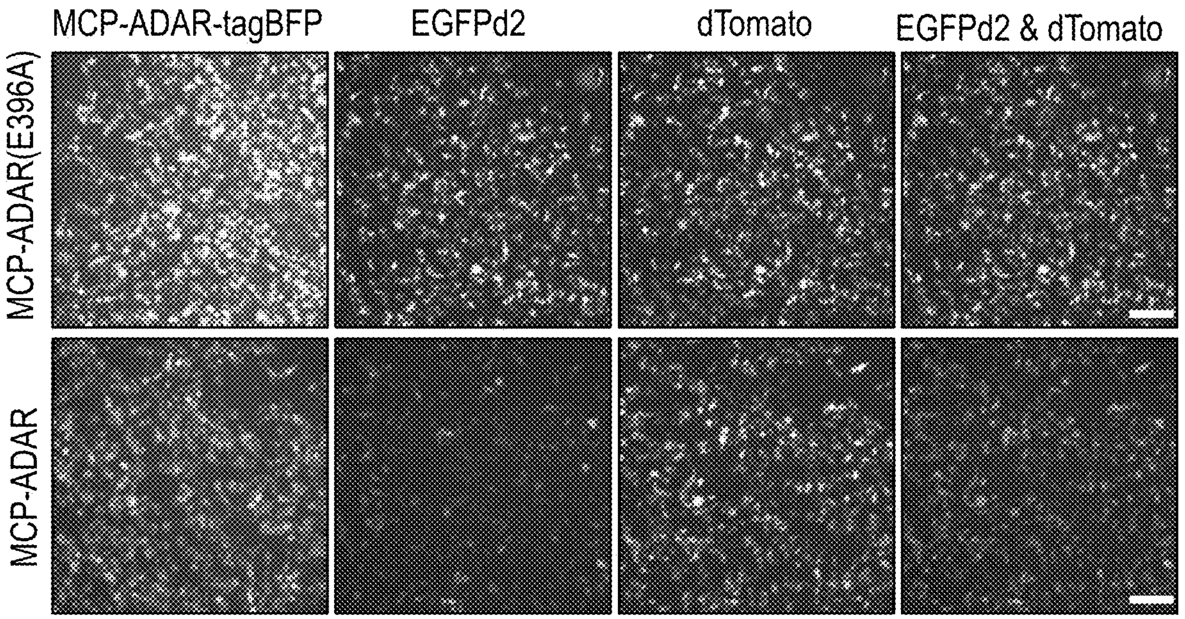

In order to test this, HEK 293 FT cells were co-transfected with plasmids encoding the biCMV reporter with 2 UAG stop codons in the hairpin and a pcDNA3 construct encoding an MCP fusion to catalytically active and inactive ADAR2-DD (FIG. 2D). Analysis by fluorescence microscopy 48-hours post-transfection demonstrated that coexpression of the catalytically active DD leads to greatly decreased EGFPd2 expression levels relative to the catalytically inactive DD. This is the first example of ADAR's being used to downregulate protein translation and lead to mRNA degradation via non-stop decay.

The previous section demonstrates the ability of ADAR activity to lead to increased or decreased protein expression and/or mRNA stability, but all of this work was carried out using a constitutively active ADAR-DD. The second of this work is the engineering of ADAR-DD's to be allosterically regulated by small-molecule drugs, competitive antigen binding, protease, and light.

Figure 3A:
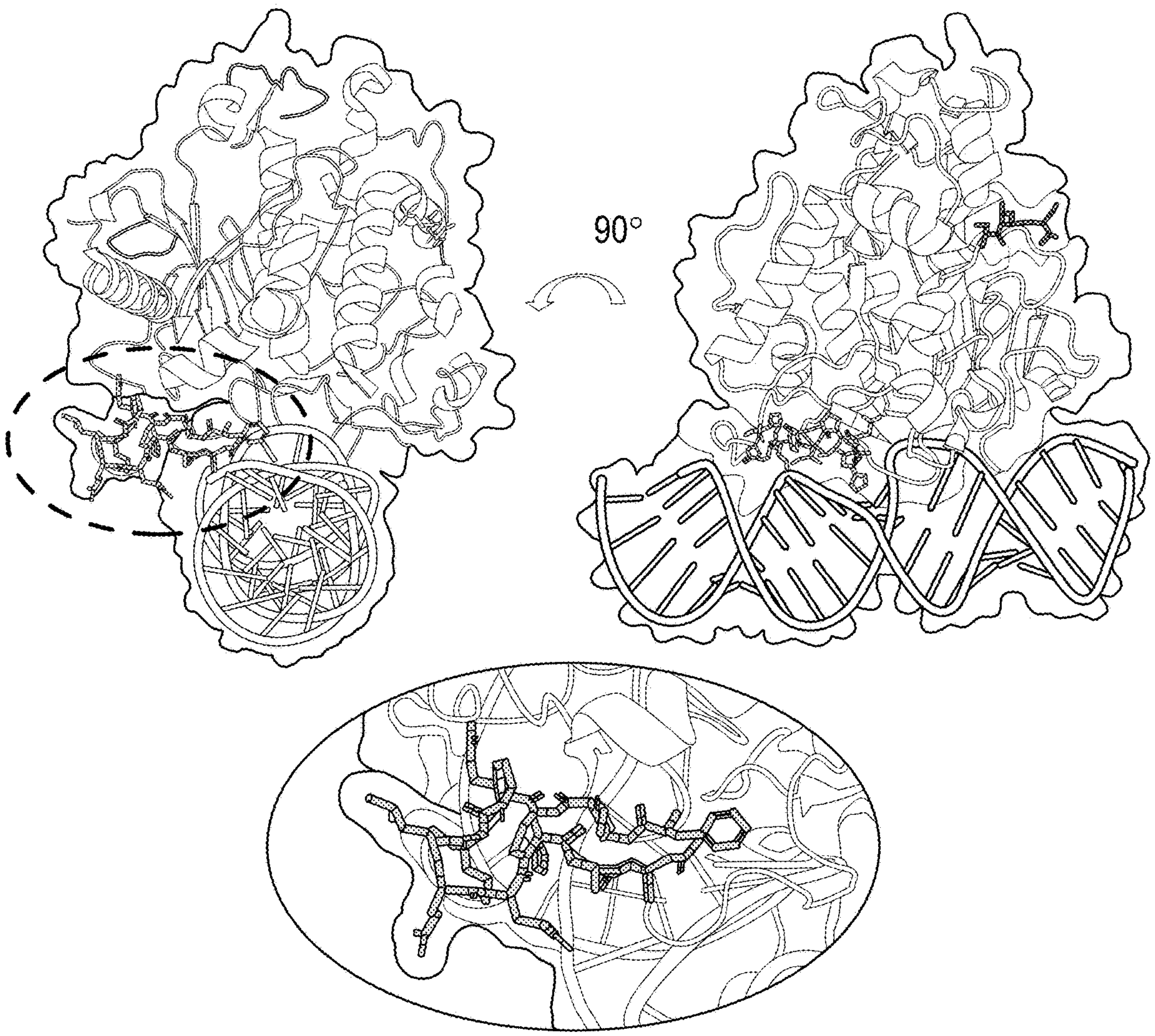
FIG. 3A-3H—Engineered, Drug-Inducible ADAR2-DD by Chemical Disruption of Intramolecular Binding Domains.
Figure 3B:
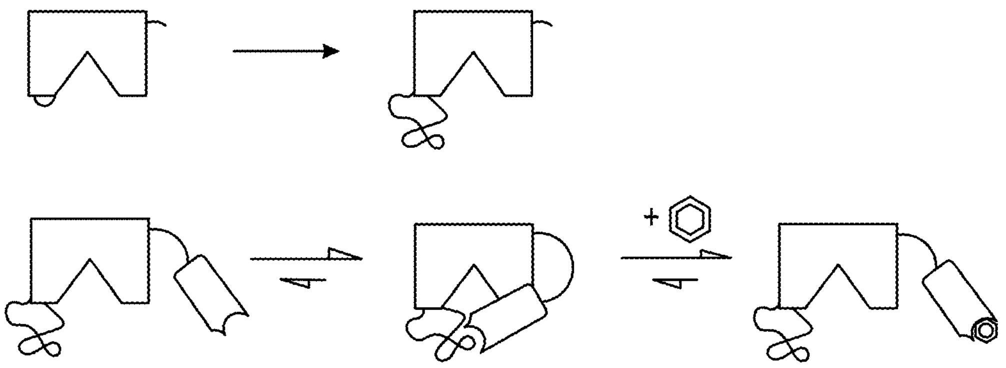

In order to accomplish this, the inventors investigated whether sites on the 5' RNA binding loop (RBL) of human ADAR2-DD between residues F457 and D469 (green in FIG. 3A) can accommodate peptide/protein insertions without serious decreases in catalytic activity. Previous work has demonstrated that this loop is non-conserved between paralogs (with ADAR1 having a large insertion at this cite relative to ADAR2), that the residue identity in this loop can be mutated, and that splitting ADAR2 at this position results in halves that have modest activity when reconstituted. Inspired by work on engineered drug-inducible enzymes via terminal or internal fusion of drug-dissociative protein domains, the inventors sought to insert a peptide/protein into the 5' loop (FIG. 3B top) that can reversibly bind to a peptide/protein partner at the C-terminus (FIG. 3B bottom). The addition of a small-molecule drug that competitively binds the same site as the inserted peptide/protein shifts the equilibrium away from the bound, repressed conformation and towards the open, catalytically active conformation (FIG. 3B bot).

Figure 3C:
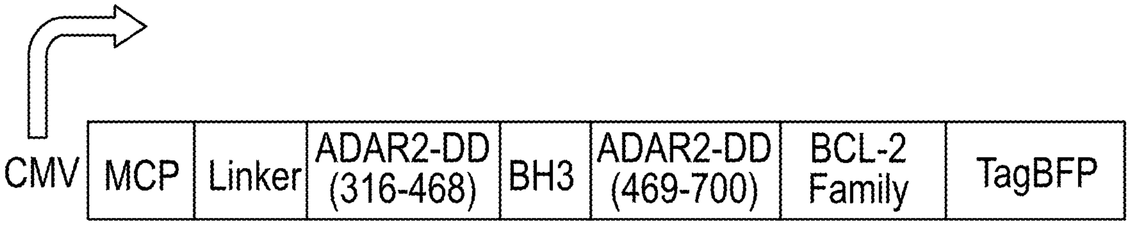

As a demonstration of this principle, the inventors designed and constructed ADAR2-DD variants with B-cell lymphoma-2 (Bcl-2) homology-3 (BH3) proteins, which are peptides which bind reversibly to Bcl-2 family proteins, inserted into the RBL (FIG. 3C). The inventors also fused cognate Bcl-2 family binding partners to the C-terminus to create a reversible, autoinhibited ADAR-DD. As BH3-Bel-2 family interactions regulate apoptosis and are dysregulated in various diseases including cancer, there are a host of small molecule drugs which can ablate BH3-Bcl2 binding. The inventors constructed ADAR2-DD variants with only the BH3 peptides Bad and Bim inserted at the RBL between A469 and D470 (with a 7 amino acid linker between A469 and the start of the BH3 peptides), and autoinhibited variants with Bad and Bim insertions and human Bcl-xL fused to the C-Terminus of ADAR2-DD. The inventors also constructed a DD variant with a synthetic, mutated Mcl-1 binding peptide MS1(117A), and a variant with MS1(117A) and human Mcl-1 (AA 171-326) fused to the RBL and C-terminus respectively.

Figure 3D:
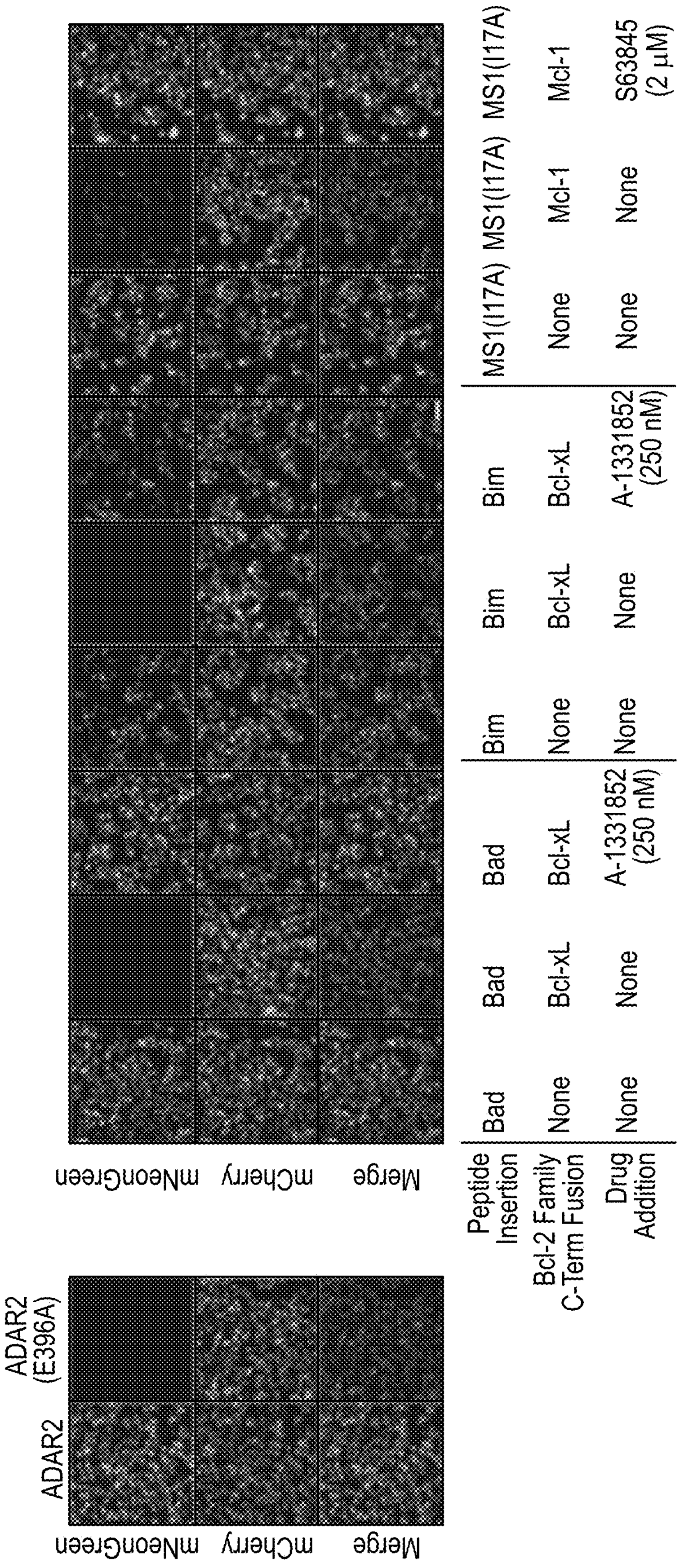
Figure 3E:
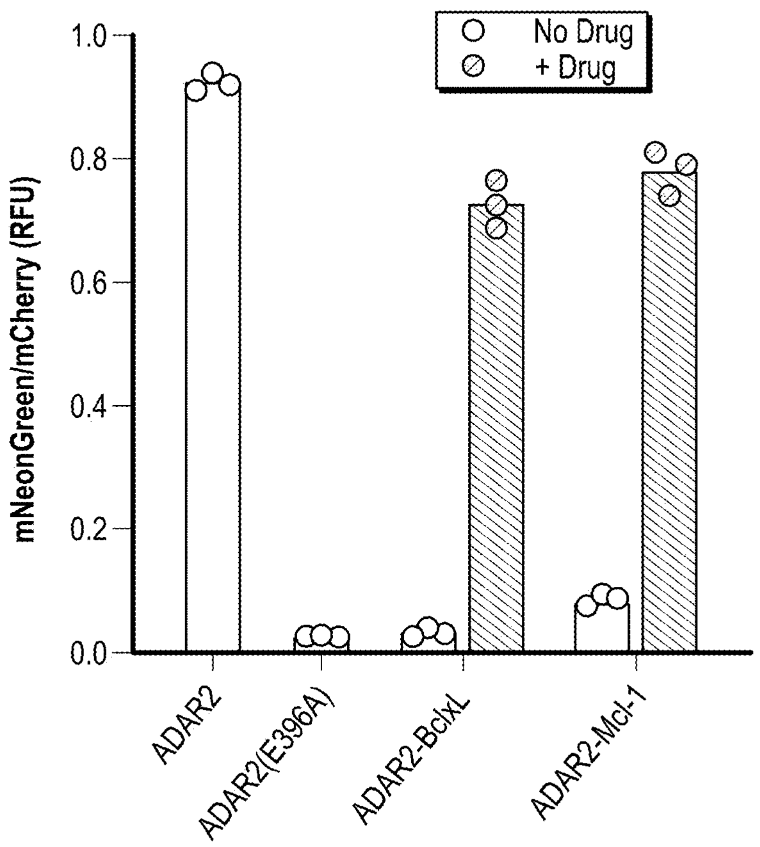

To investigate whether these ADAR variants were functional and drug-responsive, the inventors co-transfected HEK293FT with the mCherry-mNeonGreen reporter construct and the MCP-ADAR-DD variants described above with inhibitors added at the time of transfection (250 nM of A-1331852 for Bcl-xL and 2 μM of S63845 for Mcl-1 containing proteins). Two days later, fluorescence microscopy images were taken of the cell populations. The inventors saw that BH3 peptide insertions on their own did not greatly affect the enzymatic activity of ADAR2 (FIG. 3D), that C-terminal fusion of Bcl-2 binding partners greatly inhibited ADAR editing activity, and that treatment with drug was able to rescue editing activity. The inventors repeated the experiment and analyzed the samples by flow-cytometry. The relative fluorescence of mNeonGreen to mCherry in transfected cells mirrored the microscopy results and showed that the inventors were able to successfully create allosteric and drug-responsive ADAR2 variants with a similar dynamic range to native and catalytically inactive ADAR2-DD by fusing chemically disruptable heterodimeric protein partners at the RBL and C-terminus (FIG. 3E).

Figure 3F:
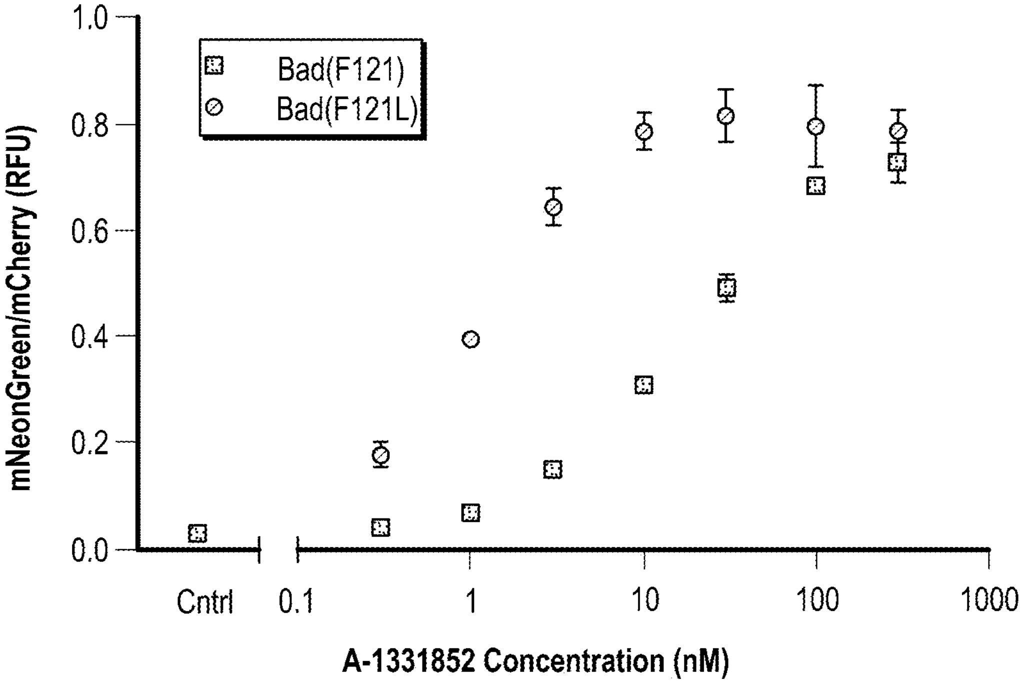
Figure 3G:
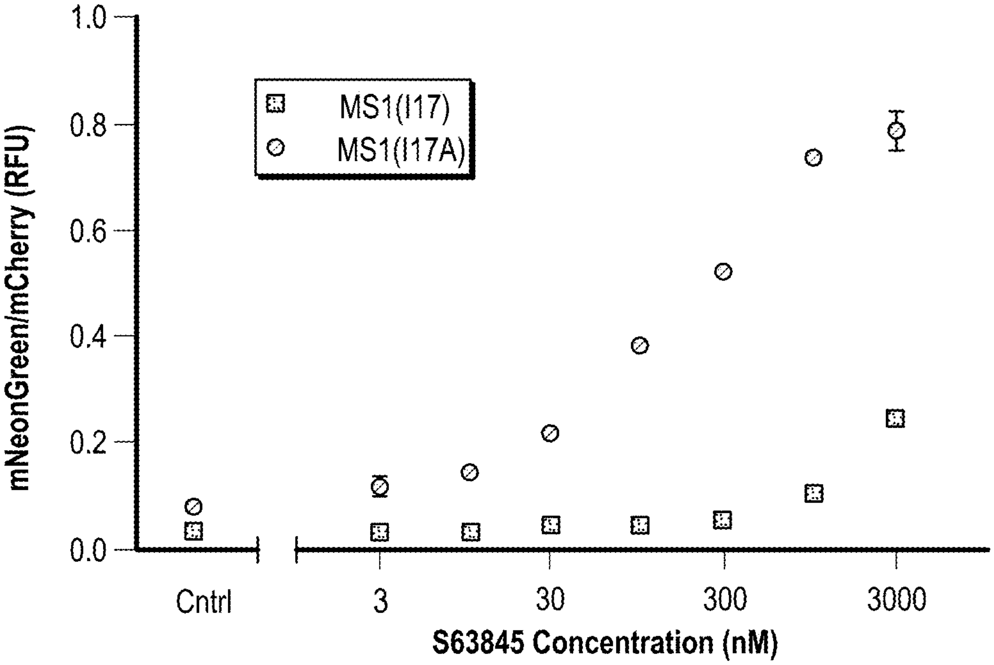

The inventors investigated whether the allosteric ADAR-DD activity was dose responsive by performing a titration with A-1331852 for the ADAR-Bad-BelxL variant and with a variant containing a single point mutation (F121L) (FIG. 3F). The point mutant variant was more drug responsive that the original Bad-peptide variant, and activated at concentrations as low as 1 nM and maxed out at ~30 nM of A-1331852. The inventors also performed a titration of S63845 on the ADAR-MS1(A)-Mcl-1 variant and compared it to an ADAR variant with the original MS1 peptide, and found that the MS1(A) variant is far more drug-responsive than the original MS1 peptide, with mNeonGreen activation beginning to be seen at ~100 nM (FIG. 3G).

Figure 3H:
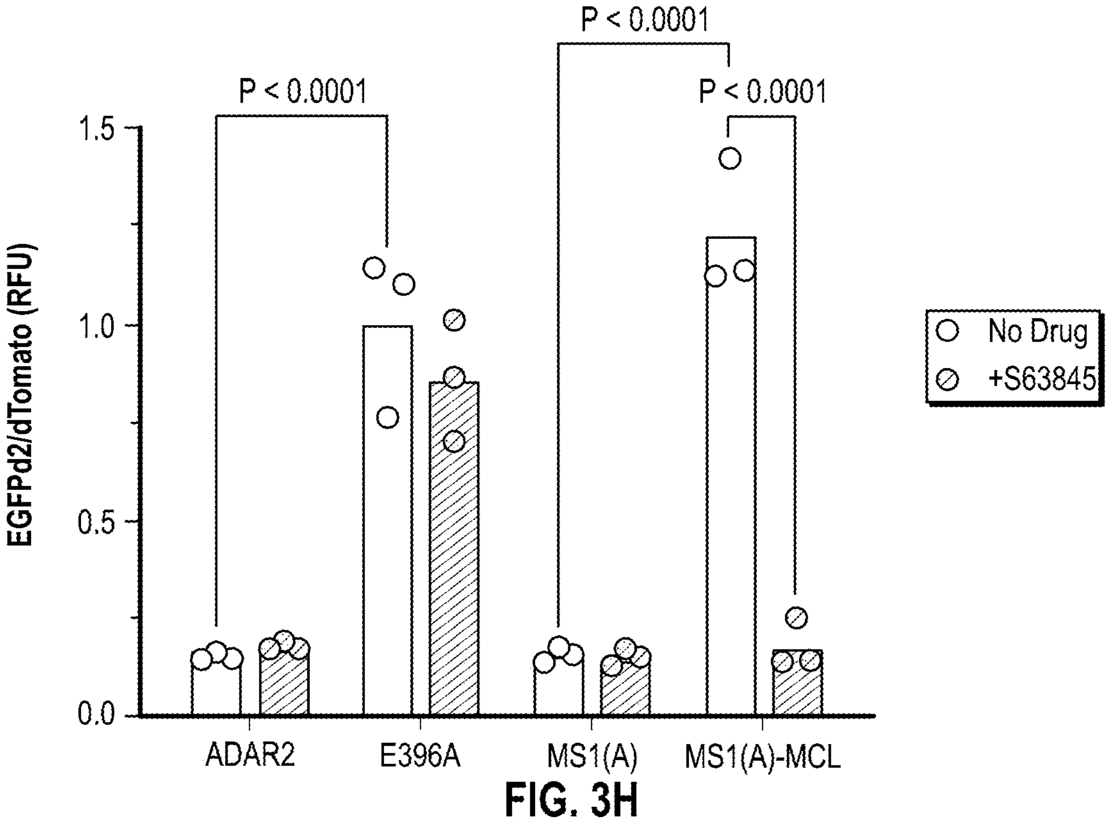

As a final test, the inventors used the MS1(117A)/Mcl-1 variant with the dTomato-BiCMV-EGFPd2 reporter plasmid (FIG. 2B), which should lose EGFPd2 fluorescence with ADAR editing of the final stop codon. The inventors transfected HEK293FT cells with both constructs, added 2 μM of S63845 at the time of transfection, and 48 hours later assessed relative fluorescent levels of transfected cells by flow cytometry, taking the median of EGFPd2/dTomato for that population of cells (FIG. 3H). The inventors found that the MS1(117A) peptide insertion and the drug treated MS1 (117A)/Mcl-1 ADAR-DDs reduced EGFPd2/dTomato fluorescence levels to similar extents as original ADAR-DD, and that the MS1(117A)/Mcl-1 variant without drug had similar levels as the catalytically inactive variant. The inventors therefore demonstrated a general mechanism to create a drug-inducible ADAR-DD that can function in human cells and in a variety of different contexts.

Figure 4A:
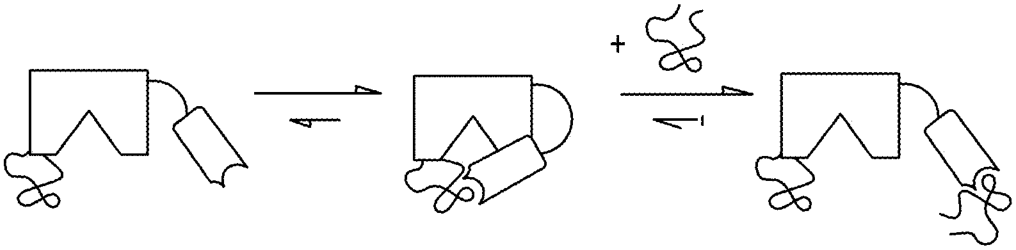

The inventors further sought to investigate whether this same allosteric mechanism of competitive-binding leading to the dissociation of a repressive intramolecular interaction between RBL and C-terminal domains could be applied more generally to make an ADAR that is activated by binding to any epitope (FIG. 4A). In this system, a peptide/protein/epitope insertion at the RBL (green) and an antibody fragment (gray) fused to the C-terminus (red) interact and inhibit ADAR2 enzyme activity (blue). However, the addition of another antigen that can bind the same antibody fragment (purple) leads to the dissociation of the inhibitory intramolecular interaction and to ADAR-DD activity. This would be a broadly useful development and create a sensing mechanism that can enable the specific targeting of mRNA translation to cell types with a specific proteomic profile (e.g., oncogenes or viral proteins).

Figure 4B:
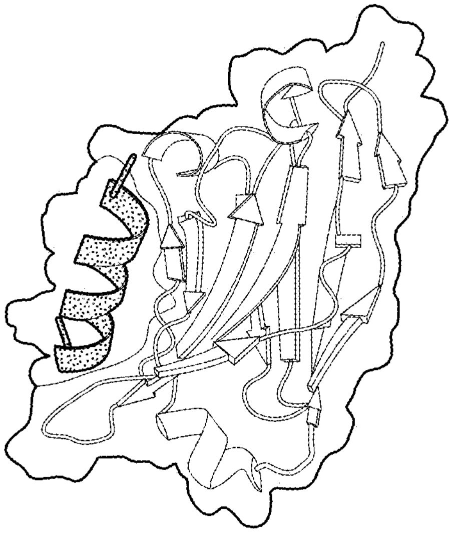
Figure 4C:
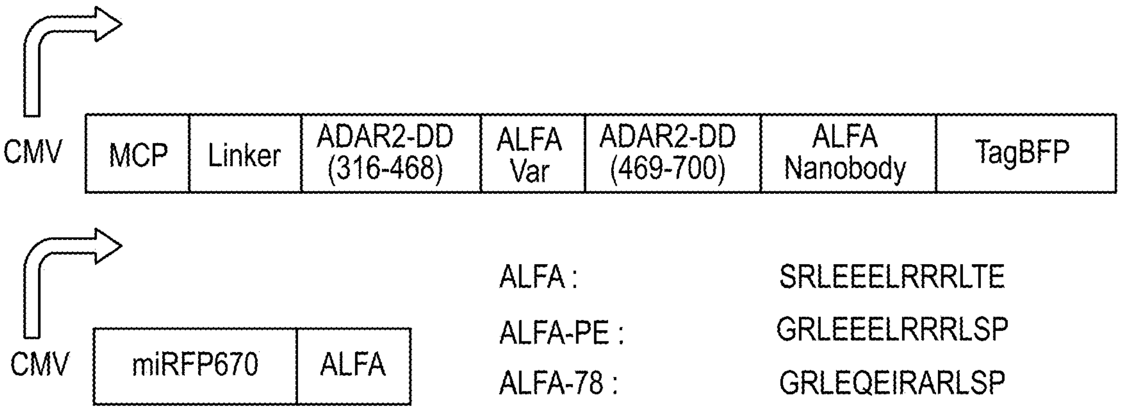

Seeking a model antigen-antibody fragment pair, the inventors used the ALFA epitope tag and anti-ALFA nanobody (NbALFA) due to it being a well-characterized interaction pair that works in the cytosol of living cells and has a number of described, weaker variants (FIG. 4B). The inventors constructed ADAR-DDs with three variants of the ALFA epitope tag of differing nanobody binding affinities inserted between residues A469 and D470 (ALFA, ALFA-PE, & ALFA-78) (FIG. 4C). The inventors also constructed ADAR-DD variants with the NbALFA fused to the C-terminus (FIG. 4C), which should lead to an intramolecular, inhibitory interaction between the ALFA and NbALFA that can be relieved by the binding of an ALFA tag fused to a second construct (FIG. 4A).

The inventors transiently co-transfected HEK 293 FT cells with the mCherry-mNeonGreen reporter, MCP-ADAR2-DD variants containing different configurations of ALFA-tag insertions and NbALFA fusions, and uncaging constructs containing miRFP670 fused to ALFA. Without wishing to be bound by theory, it was hypothesized that the intramolecular interaction would inhibit the ADAR2-DD, but that the ALFA tag on the miRFP670 would displace the lower strength ALFA variants (PE and 78), and perhaps at high enough concentrations displace the intramolecular ALFA, and lead to increased editing.

Figure 4E:
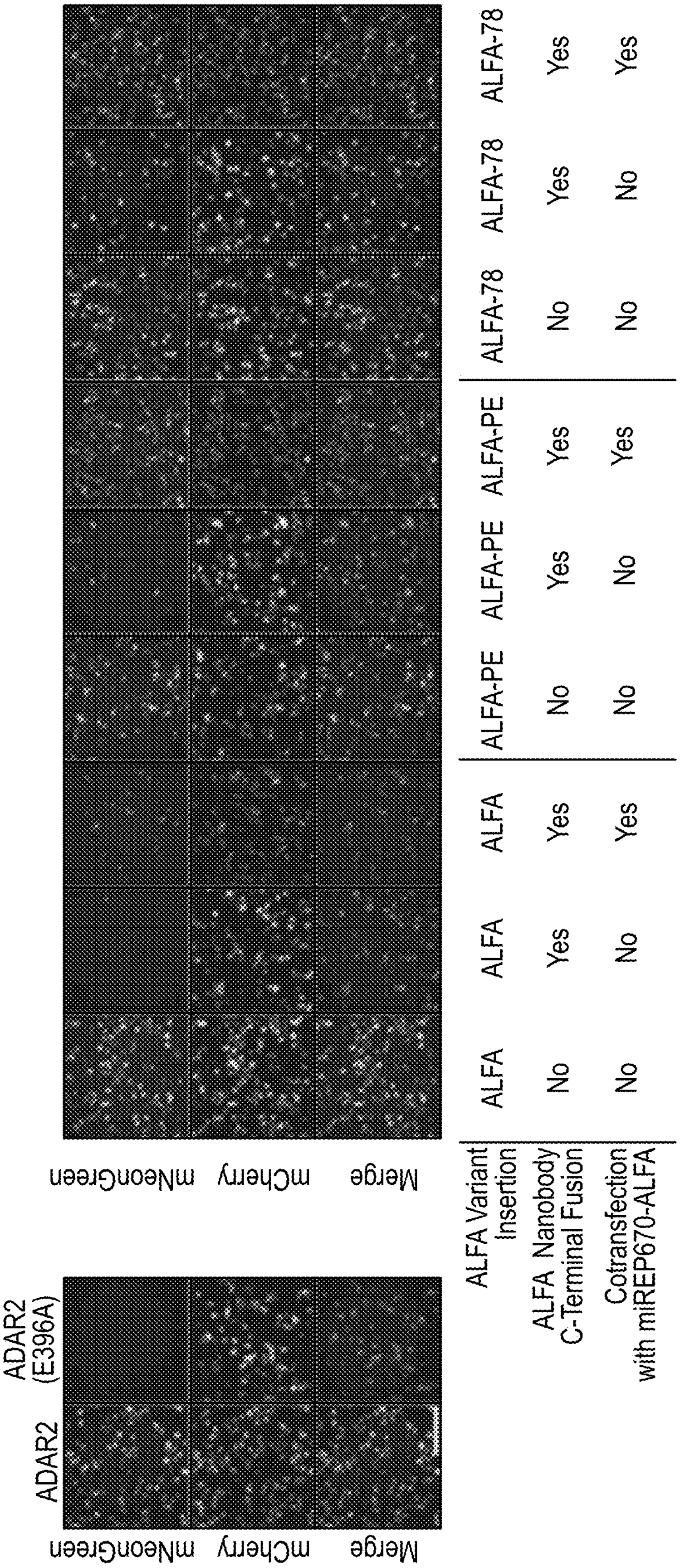

The inventors analyzed the cells by flow cytometry (FIG. 4D) and by microscopy (FIG. 4E) after 48 hours. The ADAR-DD's with ALFA variants inserted were all active and lead to mNeonGreen expression when alone (FIG. 4E), and the fusion of the NbALFA to the C-terminus decreased mNeonGreen fluorescence in all ALFA variants though more strongly according to the interaction affinity (ALFA>ALFA-PE>ALFA-78). The co-transfection with miRFP670-ALFA lead to elevated mNeonGreen expression levels in all cases, even with ADAR-ALFA-Nb where the competitive antigen is the same as the intramolecular antigen (FIGS. 4D and E). The lower affinity ALFA-PE and ALFA-78 variants however showed higher editing rates when co-transfected when compared to ALFA, which was expected. This clearly demonstrates an allosteric ADAR2-DD that is activated by binding of a user defined antigen.

The final component of the constructs detailed here is an ADAR-DD that can be activated by proteolytic and/or photolytic cleavage of the linker between the C-terminus of ADAR-DD and the N-terminus of the fused intramolecular binding domain. The inventors previously found that Bcl-xL fusion to ADAR2-DD with Bad inserted at the RBL was only inactive with a C-terminal fusion, and that soluble co-expression or N-terminal fusion did not lead to an auto-inhibited ADAR2-DD (data not shown). This implied that Bcl-xL binding to the Bad peptide at the RBL was not by itself inhibitory, but that its fusion to the C-terminus was causing the protein to adopt an inhibited state/conformation. Without wishing to be bound by theory, it was hypothesized that as opposed to inducing an active conformation by competitive binding, the inventors could induce an active ADAR-DD state by changing whether one component is fused/associated to the C-terminus of the DD.

Figure 5A:
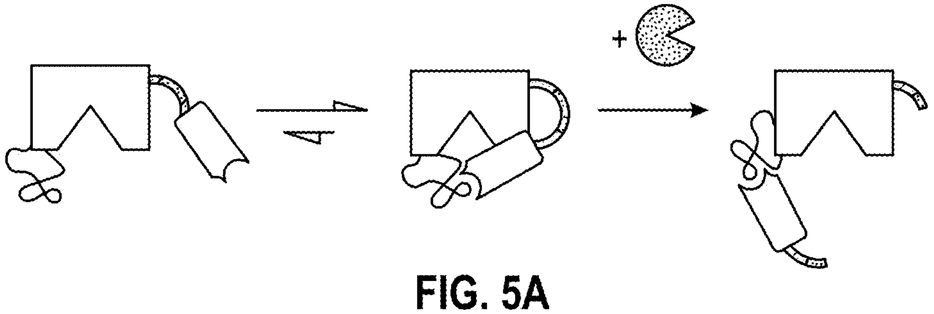
FIG. 5A-5G—Autoinhibited ADAR Can Be Activated Through Proteolytic and Photolytic Cleavage.
Figure 5B:
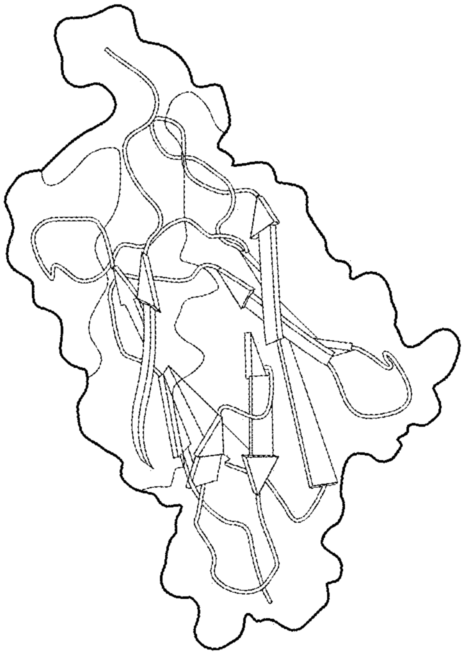

The first method that the inventors tested was activation through proteolytic cleavage. In this scheme (FIG. 5A), a protein/peptide is inserted at the RBL, its protein/peptide binding partner is fused to the C-terminus of ADAR-DD, and a protease cut site (polypeptide sequence prone to proteolytic cleavage) is inserted between ADAR-DD and the C-terminal fusion. When a protease that can cleave the specific cut site is present, the cleavage relieves the inhibitory conformation. For this scheme, the inventors used the engineered SpyTag and SpyCatcher which forms a covalent isopeptide bond between the domains (FIG. 5B), making the interaction irreversible. The inventors constructed an MCP-ADAR-DD variant that contained SpyTag inserted at the RBL, a variant containing SpyTag and SpyCatcher fused to the C-terminus, and a construct that co-expressed ADAR-Spy Tag and SpyCatcher separated by the "self-cleaving-peptides" P2A and T2A. Without wishing to be bound by theory, it was hypothesized that the SpyTag-SpyCatcher interaction would only inhibit ADAR activity when the SpyCatcher was fused to the C-terminus and not when separated from the ADAR-DD (T2A construct).

Figure 5C:
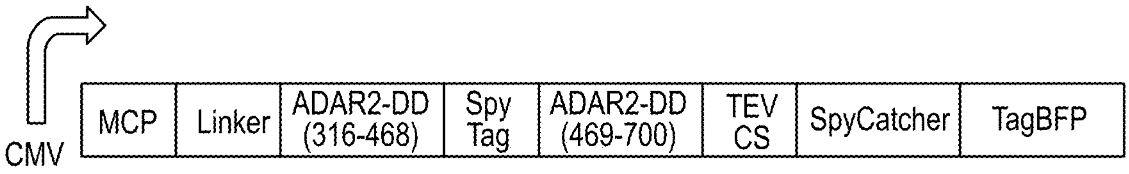
Figure 5D:
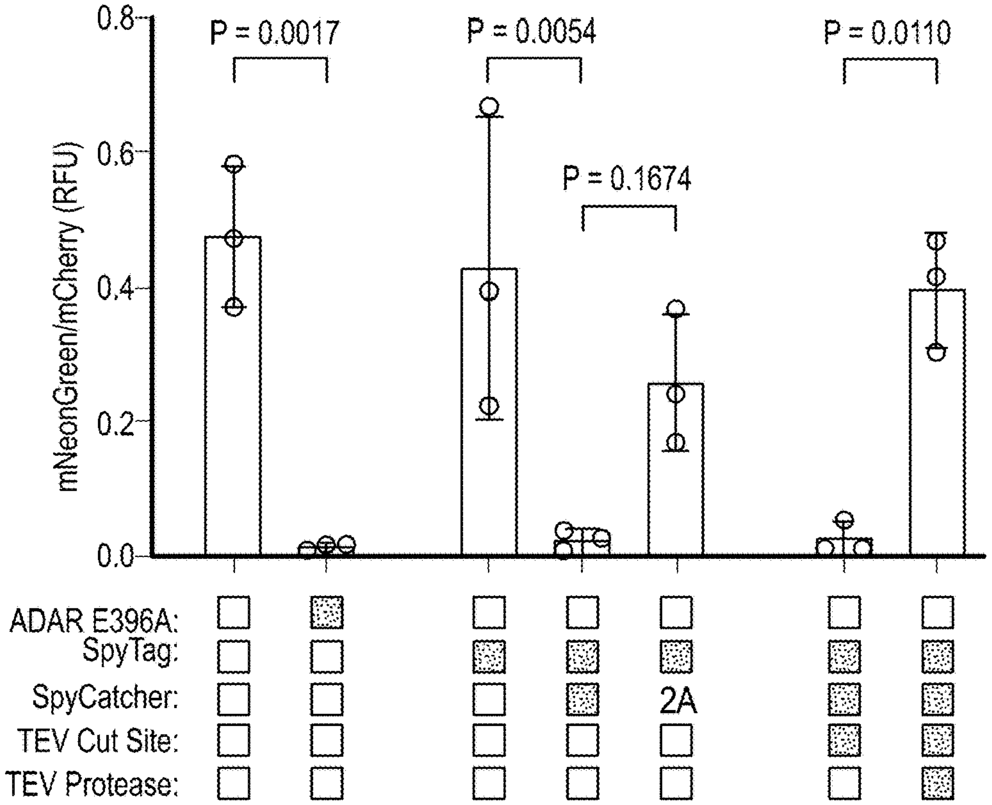
Figure 5E:
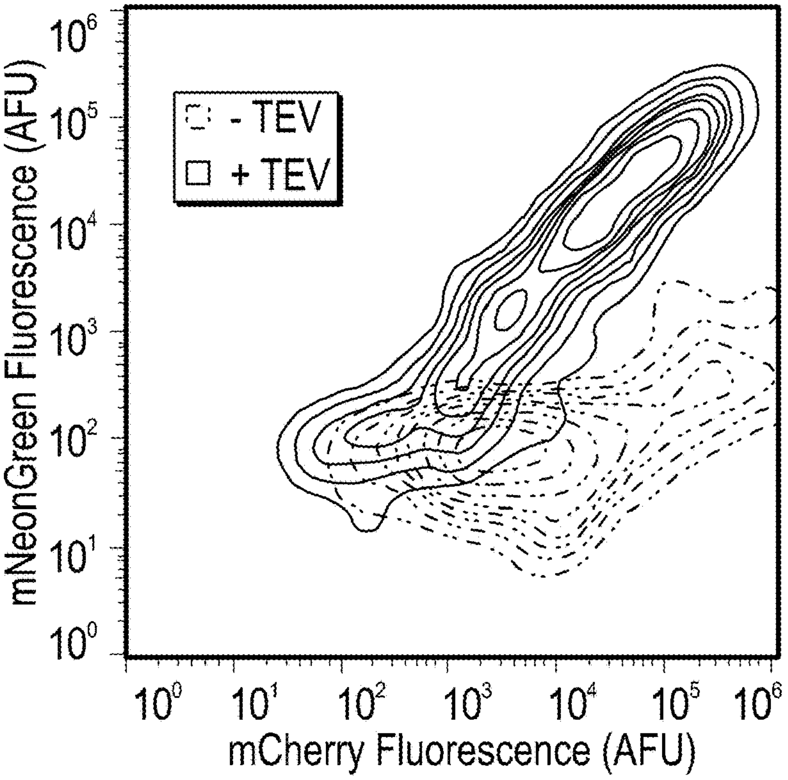

When cotransfected with the mCherry-mNeonGreen reporter, activity was seen in the SpyTag variant and with the T2A-SpyCatcher variant, but not with the C-Terminal fusion, confirming that association alone did not inhibit ADAR2-DD (FIG. 5D). The inventors then made an ADAR-DD variant with an inserted TEV protease cut site (amino acids ENLYFQG, SEQ ID NO: 286) between the C-terminus of ADAR2-DD and the N-terminus of SpyCatcher (FIG. 5C). The inventors co-transfected HEK 293 FT cells with the reporter construct, the ADAR-DD TEVcs variant, and the TEV protease and 48 hours later analyzed the transfected cells via flow cytometry (FIG. 5D-5E). The ADAR-DD variant with SpyTag at the RBL and a TEVes separating the DD and SpyCatcher was only active with the addition of TEV protease, and its induced activity was close to that of the non-engineered ADAR2-DD.

This demonstrates that the technology can be adapted to make other ADAR variants that are responsive to other proteases, as only the cut-site in the linker needs to change. This technology can be applied to make a system that turns on translation of a therapeutic protein in response to viral or other disease-associated proteases, or can be paired with other systems to make sensitive protease sensors.

Figure 5F:
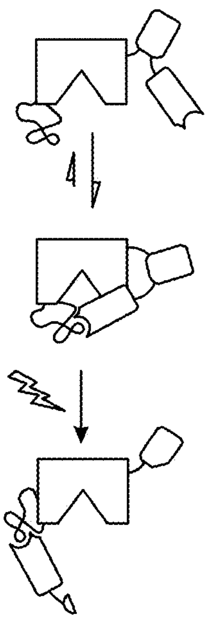

With proteolytic-based induction demonstrated, the inventors sought to create an ADAR-DD variant that could instead undergo photocleavage induction. In order to achieve this, the inventors constructed an ADAR-DD variant using Bad inserted at the RBL, PhoCl—an engineered photocleavable protein based on a circularly permuted mMaple fluorescent protein—fused to the C-terminus of ADAR-DD, and Bcl-xL fused to the C-terminus of PhoCl. In this configuration (FIG. 5F), PhoCl serves as a linker between the C-terminus of ADAR and the N-terminus of a protein/peptide binding domain that can be cleaved by violet (~405 nm) light.

Figure 5G:
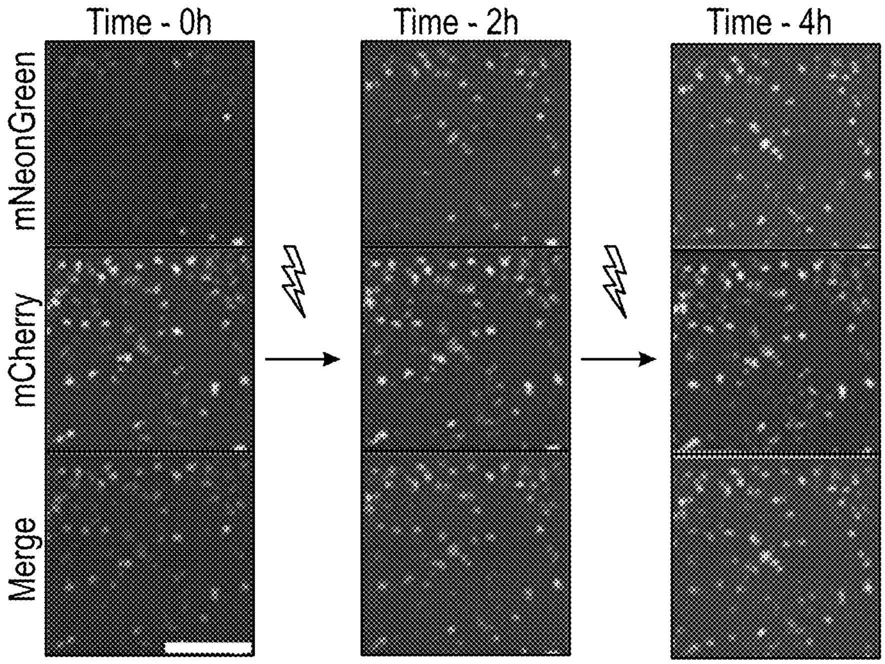
Figure 10:
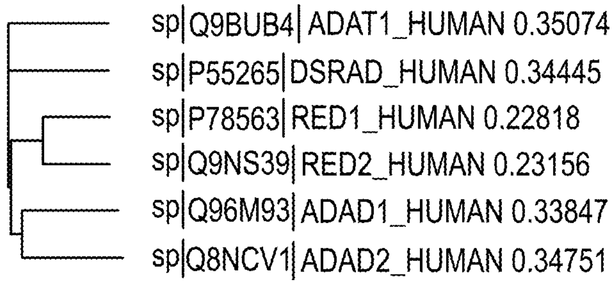
FIG. 10 shows a phylogenetic tree of ADAT1 (SEQ ID NO: 84), ADAR1 (DSRAD; SEQ ID NO: 79), ADAR2 (RED1; SEQ ID NO: 80), ADAR3 (RED2; SEQ ID NO: 81), ADAD1 (SEQ ID NO: 82), and ADAD2 (SEQ ID NO: 83).

This ADAR-DD variant was fused to MCP and was subsequently co-transfected into HEK 293 FT cells with the m Cherry-mNeonGreen reporter plasmid. 48 hours after transfection, the media was replaced with OptiMEM and the sample was moved to an epifluorescent microscope to be imaged and tracked over time. Subsequent to the first image being captured, the sample was illuminated with violet light for 10s using an HXP 120V light source with an EBFP filter. Two hours later, fluorescent images were recorded, and the same sample underwent another 10s of violet light illumination. A final image was captured two hours after this event (four hours after the first illumination event). The inventors observed that mNeonGreen fluorescence greatly increased post-illumination relative to mCherry fluorescence, which remained relatively constant, implying that the photocleavage of the PhoCl linker lead to the production of a more active ADAR2-DD (FIG. 5G).

Example 3

TABLE 1

Amino Acid Sequence Table (see e.g., FIG. 6)

| NAME | SEQ ID NO | See e.g., FIGS. | AMINO ACID SEQUENCE |
|---|---|---|---|
| MS2 On Reporter: mCherry-FLAG P2A-T2A-UAG-UAG-MS2-P2A-T2A-HA-mNeonGreen | 1 & 104 | 1C, 1E, 3D-G, 4D-E, 5D-E, 5G | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKGSGATNFSLLKQAGDVEENPGPASAG SGEGRGSLLTCGDVEENPGPATGNSA*R*LCQRHAKHED HPCTSATNFSLLKQAGDVEENPGPGGSEGRGSLLTCGDV EENPGPSGYPYDVPDYAHMVSKGEEDNMASLPATHELHI FGSINGVDFDMVGQGTGNPNDGYEELNLKSTKGDLQFSP WILVPHIGYGFHQYLPYPDGMSPFQAAMVDGSGYQVHR TMQFEDGASLTVNYRYTYEGSHIKGEAQVKGTGFPADGP VMTNSLTAADWCRSKKTYPNDKTIISTFKWSYTTGNGKR YRSTARTTYTFAKPMAANYLKNQPMYVFRKTELKHSKT ELNFKEWQKAFTDVMGMDELYKAS* |
| MCP-linker-ADAR2(E488Q)-TagBFP | 2 | 1C-E, 2D 3D-H, 4D-E, 5D-E | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPADRHPNRKARGQLRTKIESGQGT IPVRSNASIQTWDGVLQGERLLTMSCSDKIARWNVVGIQ GSLLSIFVEPIYFSSIILGSLYHGDHLSRAMYQRISNIEDLPP LYTLNKPLLSGISNAEARQPGKAPNFSVNWTVGDSAIEVI NATTGKDELGRASRLCKHALYCRWMRVHGKVPSHLLRS KITKPNVYHESKLAAKEYQAAKARLFTAFIKAGLGAWVE KPTEQDQFSLTGSGSSELIKENMHMKLYMEGTVDNHHFK CTSEGEVTTYEDGGVLTATQDTSLQDGCLIYNVKIRGVN FTSNGPVMQKKTLGWEAFTETLYPADGGLEGRNDMALK LVGGSHLIANIKTTYRSKKPAKNLKMPGVYYVDYRLERI KEANNETYVEQHEVAVARYCDLPSKLGHKLN* |

TABLE 1-continued

Amino Acid Sequence Table (see e.g., FIG. 6)

| NAME | SEQ ID NO | See e.g., FIGS. | AMINO ACID SEQUENCE |
|---|---|---|---|
| MCP-linker-ADAR2(E396A & E488Q)-TagBFP | 3 | 1C-E, 2D, 3D-H, 4D-E, 5D-E | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAAIISRRSLLRFLYT QLELYLNNKDDQKRSIFQKSERGGFRLKENVQFHLYISTS PCGDARIFSPHEPILEEPADRHPNRKARGQLRTKIESGQGT IPVRSNASIQTWDGVLQGERLLTMSCSDKIARWNVVGIQ GSLLSIFVEPIYFSSIILGSLYHGDHLSRAMYQRISNIEDLPP LYTLNKPLLSGISNAEARQPGKAPNFSVNWTVGDSAIEVI NATTGKDELGRASRLCKHALYCRWMRVHGKVPSHLLRS KITKPNVYHESKLAAKEYQAAKARLFTAFIKAGLGAWVE KPTEQDQFSLTGSGSSELIKENMHMKLYMEGTVDNHHFK CTSEGEVTTYEDGGVLTATQDTSLQDGCLIYNVKIRGVN FTSNGPVMQKKTLGWEAFTETLYPADGGLEGRNDMALK LVGGSHLIANIKTTYRSKKPAKNLKMPGVYYVDYRLERI KEANNETYVEQHEVAVARYCDLPSKLGHKLN* |
| mCherry-FLAG-UGG-UGG-P2A-T2A-HA-mNeonGreen | 4 | 1D | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKNSAWRWLPCQRHATSATNFSLLKQA GDVEENPGPGGSEGRGSLLTCGDVEENPGPSGYPYDVPD YAHMVSKGEEDNMASLPATHELHIFGSINGVDFDMVGQ GTGNPNDGYEELNLKSTKGDLQFSPWILVPHIGYGFHQY LPYPDGMSPFQAAMVDGSGYQVHRTMQFEDGASLTVNY RYTYEGSHIKGEAQVKGTGFPADGPVMTNSLTAADWCR SKKTYPNDKTIISTFKWSYTTGNGKRYRSTARTTYTFAKP MAANYLKNQPMYVFRKTELKHSKTELNFKEWQKAFTD VMGMDELYKAS* |
| mCherry-FLAG-UAG-UGG-P2A-T2A-HA-mNeonGreen | 5 & 113 | 1D | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKNSA*RWLPCQRHATSATNFSLLKQAG DVEENPGPGGSEGRGSLLTCGDVEENPGPSGYPYDVPDY AHMVSKGEEDNMASLPATHELHIFGSINGVDFDMVGQG TGNPNDGYEELNLKSTKGDLQFSPWILVPHIGYGFHQYLP YPDGMSPFQAAMVDGSGYQVHRTMQFEDGASLTVNYR YTYEGSHIKGEAQVKGTGFPADGPVMTNSLTAADWCRS KKTYPNDKTIISTFKWSYTTGNGKRYRSTARTTYTFAKP MAANYLKNQPMYVFRKTELKHSKTELNFKEWQKAFTD VMGMDELYKAS* |
| mCherry-FLAG-UAG-UAG-P2A-T2A-HA-mNeonGreen | 6 & 114 | 1D | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKNSA*R*LPCQRHATSATNFSLLKQAGD VEENPGPGGSEGRGSLLTCGDVEENPGPSGYPYDVPDYA HMVSKGEEDNMASLPATHELHIFGSINGVDFDMVGQGT GNPNDGYEELNLKSTKGDLQFSPWILVPHIGYGFHQYLP YPDGMSPFQAAMVDGSGYQVHRTMQFEDGASLTVNYR YTYEGSHIKGEAQVKGTGFPADGPVMTNSLTAADWCRS KKTYPNDKTIISTFKWSYTTGNGKRYRSTARTTYTFAKP MAANYLKNQPMYVFRKTELKHSKTELNFKEWQKAFTD VMGMDELYKAS* |
| mCherry-FLAG-UAG-UGG-MS2-P2A-T2A-HA-mNeonGreen | 7 & 144 | 1D | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD |

TABLE 1-continued

| Amino Acid Sequence Table (see e.g., FIG. 6) | | | |
|---|---|---|---|
| NAME | SEQ ID NO | See e.g., FIGS. | AMINO ACID SEQUENCE |
| | | | ELYKDYKDDDDKNSAWR*LCQRHAKHEDHPCTSATNFS LLKQAGDVEENPGPGGSEGRGSLLTCGDVEENPGPSGYP YDVPDYAHMVSKGEEDNMASLPATHELHIFGSINGVDFD MVGQGTGNPNDGYEELNLKSTKGDLQFSPWILVPHIGYG FHQYLPYPDGMSPFQAAMVDGSGYQVHRTMQFEDGASL TVNYRYTYEGSHIKGEAQVKGTGFPADGPVMTNSLTAA DWCRSKKTYPNDKTIISTFKWSYTTGNGKRYRSTARTTY TFAKPMAANYLKNQPMYVFRKTELKHSKTELNFKEWQK AFTDVMGMDELYKAS* |
| mCherry-FLAG-UAG-UAG-MS2-P2A-T2A-HA-mNeonGreen | 8 & 145 | 1D | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKNSA*R*LCQRHAKHEDHPCTSATNFSL LKQAGDVEENPGPGGSEGRGSLLTCGDVEENPGPSGYPY DVPDYAHMVSKGEEDNMASLPATHELHIFGSINGVDFD MVGQGTGNPNDGYEELNLKSTKGDLQFSPWILVPHIGYG FHQYLPYPDGMSPFQAAMVDGSGYQVHRTMQFEDGASL TVNYRYTYEGSHIKGEAQVKGTGFPADGPVMTNSLTAA DWCRSKKTYPNDKTIISTFKWSYTTGNGKRYRSTARTTY TFAKPMAANYLKNQPMYVFRKTELKHSKTELNFKEWQK AFTDVMGMDELYKAS* |
| mCherry-FLAG P2A-T2A-UAG-UAG-PP7-P2A-T2A-HA-mNeonGreen | 9 & 146 | 1E | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKGSGATNFSLLKQAGDVEENPGPASAG SGEGRGSLLTCGDVEENPGPATGNSA*R*LCQRHAKEQTI WRRSNTSATNFSLLKQAGDVEENPGPGGSEGRGSLLTCG DVEENPGPSGYPYDVPDYAHMVSKGEEDNMASLPATHE LHIFGSINGVDFDMVGQGTGNPNDGYEELNLKSTKGDLQ FSPWILVPHIGYGFHQYLPYPDGMSPFQAAMVDGSGYQV HRTMQFEDGASLTVNYRYTYEGSHIKGEAQVKGTGFPA DGPVMTNSLTAADWCRSKKTYPNDKTIISTFKWSYTTGN GKRYRSTARTTYTFAKPMAANYLKNQPMYVFRKTELKH SKTELNFKEWQKAFTDVMGMDELYKAS* |
| mCherry-FLAG P2A-T2A-UAG-UAG-BoxB-P2A-T2A-HA-mNeonGreen | 10 & 147 | 1E | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKGSGATNFSLLKQAGDVEENPGPASAG SGEGRGSLLTCGDVEENPGPATGNSA*R*LCQRHAVRAL KKGPTSATNFSLLKQAGDVEENPGPGGSEGRGSLLTCGD VEENPGPSGYPYDVPDYAHMVSKGEEDNMASLPATHEL HIFGSINGVDFDMVGQGTGNPNDGYEELNLKSTKGDLQF SPWILVPHIGYGFHQYLPYPDGMSPFQAAMVDGSGYQV HRTMQFEDGASLTVNYRYTYEGSHIKGEAQVKGTGFPA DGPVMTNSLTAADWCRSKKTYPNDKTIISTFKWSYTTGN GKRYRSTARTTYTFAKPMAANYLKNQPMYVFRKTELKH SKTELNFKEWQKAFTDVMGMDELYKAS* |
| mCherry-FLAG P2A-T2A-UAG-UAG-HIV TAR-P2A-T2A-HA-mNeonGreen | 11 & 148 | 1E | MVSKGEEDNMAIIKEFMRFKVHMEGSVNGHEFEIEGEGE GRPYEGTQTAKLKVTKGGPLPFAWDILSPQFMYGSKAYV KHPADIPDYLKLSFPEGFKWERVMNFEDGGVVTVTQDSS LQDGEFIYKVKLRGTNFPSDGPVMQKKTMGWEASSERM YPEDGALKGEIKQRLKLKDGGHYDAEVKTTYKAKKPVQ LPGAYNVNIKLDITSHNEDYTIVEQYERAEGRHSTGGMD ELYKDYKDDDDKGSGATNFSLLKQAGDVEENPGPASAG SGEGRGSLLTCGDVEENPGPATGNSA*R*LCQRHAVGSSE LISSEPTSATNFSLLKQAGDVEENPGPGGSEGRGSLLTCG DVEENPGPSGYPYDVPDYAHMVSKGEEDNMASLPATHE LHIFGSINGVDFDMVGQGTGNPNDGYEELNLKSTKGDLQ FSPWILVPHIGYGFHQYLPYPDGMSPFQAAMVDGSGYQV HRTMQFEDGASLTVNYRYTYEGSHIKGEAQVKGTGFPA DGPVMTNSLTAADWCRSKKTYPNDKTIISTFKWSYTTGN |

TABLE 1-continued

| Amino Acid Sequence Table (see e.g., FIG. 6) | | | |
|---|---|---|---|
| NAME | SEQ ID NO | See e.g., FIGS. | AMINO ACID SEQUENCE |
| | | | GKRYRSTARTTYTFAKPMAANYLKNQPMYVFRKTELKH SKTELNFKEWQKAFTDVMGMDELYKAS* |
| PCP-linker-ADAR2 (E488Q) DD-TagBFP | 12 | 1E | MSKTIVLSVGEATRTLTEIQSTADRQIFEEKVGPLVGRLRL TASLRQNGAKTAYRVNLKLDQADVVDSGLPKVRYTQV WSHDVTIVANSTEASRKSLYDLTKSLVATSQVEDLVVNL VPLGRASTGSGIYGGSGSGAGSGSPAGGGAPGSGGGSQL HLPQVLADAVSRLVLGKFGDLTDNFSSPHARRKVLAGV VMTTGTDVKDAKVISVSTGTKCINGEYMSDRGLALNDC HAEIISRRSLLRFLYTQLELYLNNKDDQKRSIFQKSERGGF RLKENVQFHLYISTSPCGDARIFSPHEPILEEPADRHPNRK ARG**Q**LRTKIESGQGTIPVRSNASIQTWDGVLQGERLLTMS CSDKIARWNVVGIQGSLLSIFVEPIYFSSIILGSLYHGDHLS RAMYQRISNIEDLPPLYTLNKPLLSGISNAEARQPGKAPN FSVNWTVGDSAIEVINATTGKDELGRASRLCKHALYCRW MRVHGKVPSHLLRSKITKPNVYHESKLAAKEYQAAKAR LFTAFIKAGLGAWVEKPTEQDQFSLTGSGSSELIKENMH MKLYMEGTVDNHHFKCTSEGEVTTYEDGGVLTATQDTS LQDGCLIYNVKIRGVNFTSNGPVMQKKTLGWEAFTETLY PADGGLEGRNDMALKLVGGSHLIANIKTTYRSKKPAKNL KMPGVYYVDYRLERIKEANNETYVEQHEVAVARYCDLP SKLGHKLN* |
| λN-linker-ADAR2 (E488Q) DD-TagBFP | 13 | 1E | MADAQTRRRERRAEKQAQWKAANTGSGIYGGSGSGAG SGSPAGGGAPGSGGGSQLHLPQVLADAVSRLVLGKFGDL TDNFSSPHARRKVLAGVVMTTGTDVKDAKVISVSTGTKC INGEYMSDRGLALNDCHAEIISRRSLLRFLYTQLELYLNN KDDQKRSIFQKSERGGFRLKENVQFHLYISTSPCGDARIFS PHEPILEEPADRHPNRKARGQLRTKIESG**Q**GTIPVRSNASI QTWDGVLQGERLLTMSCSDKIARWNVVGIQGSLLSIFVE PIYFSSIILGSLYHGDHLSRAMYQRISNIEDLPPLYTLNKPL LSGISNAEARQPGKAPNFSVNWTVGDSAIEVINATTGKDE LGRASRLCKHALYCRWMRVHGKVPSHLLRSKITKPNVY HESKLAAKEYQAAKARLFTAFIKAGLGAWVEKPTEQDQ FSLTGSGSSELIKENMHMKLYMEGTVDNHHFKCTSEGEV TTYEDGGVLTATQDTSLQDGCLIYNVKIRGVNFTSNGPV MQKKTLGWEAFTETLYPADGGLEGRNDMALKLVGGSH LIANIKTTYRSKKPAKNLKMPGVYYVDYRLERIKEANNE TYVEQHEVAVARYCDLPSKLGHKLN* |
| HIV-tat-linker-ADAR2 (E488Q) DD-TagBFP | 14 | 1E | MASGPRPRGTRGKGRRIRRTGSGIYGGSGSGAGSGSPAG GGAPGSGGGSQLHLPQVLADAVSRLVLGKFGDLTDNFSS PHARRKVLAGVVMTTGTDVKDAKVISVSTGTKCINGEY MSDRGLALNDCHAEIISRRSLLRFLYTQLELYLNNKDDQ KRSIFQKSERGGFRLKENVQFHLYISTSPCGDARIFSPHEPI LEEPADRHPNRKARGQLRTKIESG**Q**GTIPVRSNASIQTWD GVLQGERLLTMSCSDKIARWNVVGIQGSLLSIFVEPIYFSS IILGSLYHGDHLSRAMYQRISNIEDLPPLYTLNKPLLSGISN AEARQPGKAPNFSVNWTVGDSAIEVINATTGKDELGRAS RLCKHALYCRWMRVHGKVPSHLLRSKITKPNVYHESKL AAKEYQAAKARLFTAFIKAGLGAWVEKPTEQDQFSLTGS GSSELIKENMHMKLYMEGTVDNHHFKCTSEGEVTTYED GGVLTATQDTSLQDGCLIYNVKIRGVNFTSNGPVMQKKT LGWEAFTETLYPADGGLEGRNDMALKLVGGSHLIANIKT TYRSKKPAKNLKMPGVYYVDYRLERIKEANNETYVEQH EVAVARYCDLPSKLGHKLN* |
| dTomato | 15 | 2B, 2D, 3H | MVSKGEEVIKEFMRFKVRMEGSMNGHEFEIEGEGEGRPY EGTQTAKLKVTKGGPLPFAWDILSPQFMYGSKAYVKHP ADIPDYKKLSFPEGFKWERVMNFEDGGLVTVTQDSSLQD GTLIYKVKMRGTNFPPDGPVMQKKTMGWEASTERLYPR DGVLKGEIHQALKLKDGGHYLVEFKTIYMAKKPVQLPG YYYVDTKLDITSHNEDYTIVEQYERSEGRHHLFLYGMDE LYK |
| EGFPd2-UAG-UAG-MS2-polyA | 16 & 149 | 2B, 2D, 3H | MVSKGEELFTGVVPILVELDGDVNGHKFSVSGEGEGDAT YGKLTLKFICTTGKLPVPWPTLVTTLTYGVQCFSRYPDH MKQHDFFKSAMPEGYVQERTIFFKDDGNYKTRAEVKFE GDTLVNRIELKGIDFKEDGNILGHKLEYNYNSHNVYIMA DKQKNGIKVNFKIRHNIEDGSVQLADHYQQNTPIGDGPV LLPDNHYLSTQSALSKDPNEKRDHMVLLEFVTAAGITLG MDELYKKLSHGFPPEVEEQDDGTLPMSCAQESGMDRHP |

TABLE 1-continued

| Amino Acid Sequence Table (see e.g., FIG. 6) | | | |
|---|---|---|---|
| NAME | SEQ ID NO | See e.g., FIGS. | AMINO ACID SEQUENCE |
| | | | AACASARINV*R*LCQRHTKHEDHPCRPHSSGAGCLSEG<br>GGWCGQCPGSQIPLRSFSLCQKLWGHHEAPWASDFWLIK<br>EIYF . . . |
| MCP-linker-ADAR2-DDN-Bad(F)-ADAR2 (E488Q)-DDC-TagBFP | 17 | 3D | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGTGAPPNLWAAQRYGRE<br>LRRMSDEFVDRHPNRKARGQLRTKIESG**Q**GTIPVRSNASI<br>QTWDGVLQGERLLTMSCSDKIARWNVVGIQGSLLSIFVE<br>PIYFSSIILGSLYHGDHLSRAMYQRISNIEDLPPLYTLNKPL<br>LSGISNAEARQPGKAPNFSVNWTVGDSAIEVINATTGKDE<br>LGRASRLCKHALYCRWMRVHGKVPSHLLRSKITKPNVY<br>HESKLAAKEYQAAKARLFTAFIKAGLGAWVEKPTEQDQ<br>FSLTGSGSSELIKENMHMKLYMEGTVDNHHFKCTSEGEG<br>KPYEGTQTMRIKVVEGGPLPFAFDILATSFLYGSKTFINHT<br>QGIPDFFKQSFPEGFTWERVTTYEDGGVLTATQDTSLQD<br>GCLIYNVKIRGVNFTSNGPVMQKKTLGWEAFTETLYPAD<br>GGLEGRNDMALKLVGGSHLIANIKTTYRSKKPAKNLKM<br>PGVYYVDYRLERIKEANNETYVEQHEVAVARYCDLPSK<br>LGHKLN* |
| MCP-linker-ADAR2-DDN-Bad(F)-ADAR2 88Q)-DDC-(E4Bcl-xL-TagBFP | 18 | 3D-F | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGTGAPPNLWAAQRYGRE<br>LRRMSDEFVDRHPNRKARGQLRTKIESG**Q**GTIPVRSNASI<br>QTWDGVLQGERLLTMSCSDKIARWNVVGIQGSLLSIFVE<br>PIYFSSIILGSLYHGDHLSRAMYQRISNIEDLPPLYTLNKPL<br>LSGISNAEARQPGKAPNFSVNWTVGDSAIEVINATTGKDE<br>LGRASRLCKHALYCRWMRVHGKVPSHLLRSKITKPNVY<br>HESKLAAKEYQAAKARLFTAFIKAGLGAWVEKPTEQDQ<br>FSLTGSAAGGSGGSAAASSNRELVVDFLSYKLSQKGYSW<br>SQFSDVEENRTEAPEGTESEMETPSAINGNPSWHLADSPA<br>VNGATGHSSSLDAREVIPMAAVKQALREAGDEFELRYRR<br>AFSDLTSQLHITPGTAYQSFEQVVNELFRDGVNWGRIVAF<br>FSFGGALCVESVDKEMQVLVSRIAAWMATYLNDHLEPW<br>IQENGGWDTFVELYGNNGSSELIKENMHMKLYMEGTVD<br>NHHFKCTSEGEGKPYEGTQTMRIKVVEGGPLPFAFDILAT<br>SFLYGSKTFINHTQGIPDFFKQSFPEGFTWERVTTYEDGG<br>VLTATQDTSLQDGCLIYNVKIRGVNFTSNGPVMQKKTLG<br>WEAFTETLYPADGGLEGRNDMALKLVGGSHLIANIKTTY<br>RSKKPAKNLKMPGVYYVDYRLERIKEANNETYVEQHEV<br>AVARYCDLPSKLGHKLN* |
| MCP-linker-ADAR2-DDN-Bim-ADAR2 (E488Q)-DDC-TagBFP | 19 | 3D | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGSGDMRPEIWIAQELRRI<br>GDEFNAYYARRTGDRHPNRKARGQLRTKIESG**Q**GTIPVR<br>SNASIQTWDGVLQGERLLTMSCSDKIARWNVVGIQGSLL<br>SIFVEPIYFSSIILGSLYHGDHLSRAMYQRISNIEDLPPLYTL<br>NKPLLSGISNAEARQPGKAPNFSVNWTVGDSAIEVINATT<br>GKDELGRASRLCKHALYCRWMRVHGKVPSHLLRSKITK<br>PNVYHESKLAAKEYQAAKARLFTAFIKAGLGAWVEKPT<br>EQDQFSLTGSGSSELIKENMHMKLYMEGTVDNHHFKCTS<br>EGEGKPYEGTQTMRIKVVEGGPLPFAFDILATSFLYGSKT<br>FINHTQGIPDFFKQSFPEGFTWERVTTYEDGGVLTATQDT<br>SLQDGCLIYNVKIRGVNFTSNGPVMQKKTLGWEAFTETL<br>YPADGGLEGRNDMALKLVGGSHLIANIKTTYRSKKPAKN<br>LKMPGVYYVDYRLERIKEANNETYVEQHEVAVARYCDL<br>PSKLGHKLN* |

TABLE 1-continued

Amino Acid Sequence Table (see e.g., FIG. 6)

| NAME | SEQ ID NO | See e.g., FIGS. | AMINO ACID SEQUENCE |
|---|---|---|---|
| MCP-linker-ADAR2-DDN-Bim-ADAR2 (E488Q)-DDC-Bcl-xL-TagBFP | 20 | 3D | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGSGSGDMRPEIWIAQELRRI GDEFNAYYARRTGDRHPNRKARGQLRTKIESG**Q**GTIPVR SNASIQTWDGVLQGERLLTMSCSDKIARWNVVGIQGSLL SIFVEPIYFSSIILGSLYHGDHLSRAMYQRISNIEDLPPLYTL NKPLLSGISNAEARQPGKAPNFSVNWTVGDSAIEVINATT GKDELGRASRLCKHALYCRWMRVHGKVPSHLLRSKITK PNVYHESKLAAKEYQAAKARLFTAFIKAGLGAWVEKPT EQDQFSLTGSAAGGSGGSAAASSNRELVVDFLSYKLSQK GYSWSQFSDVEENRTEAPEGTESEMETPSAINGNPSWHL ADSPAVNGATGHSSSLDAREVIPMAAVKQALREAGDEFE LRYRRAFSDLTSQLHITPGTAYQSFEQVVNELFRDGVNW GRIVAFFSFGGALCVESVDKEMQVLVSRIAAWMATYLN DHLEPWIQENGGWDTFVELYGNNGSSELIKENMHMKLY MEGTVDNHHFKCTSEGEGKPYEGTQTMRIKVVEGGPLPF AFDILATSFLYGSKTFINHTQGIPDFFKQSFPEGFTWERVT TYEDGGVLTATQDTSLQDGCLIYNVKIRGVNFTSNGPVM QKKTLGWEAFTETLYPADGGLEGRNDMALKLVGGSHLI ANIKTTYRSKKPAKNLKMPGVYYVDYRLERIKEANNETY VEQHEVAVARYCDLPSKLGHKLN* |
| MCP-linker-ADAR2-DDN-MS1(A)-ADAR2 (E488Q)-DDC-TagBFP | 21 | 3D,3H | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSGGSGRPEIWMTQGLRRL GDEANAYYARRTGDRHPNRKARGQLRTKIESG**Q**GTIPVR SNASIQTWDGVLQGERLLTMSCSDKIARWNVVGIQGSLL SIFVEPIYFSSIILGSLYHGDHLSRAMYQRISNIEDLPPLYTL NKPLLSGISNAEARQPGKAPNFSVNWTVGDSAIEVINATT GKDELGRASRLCKHALYCRWMRVHGKVPSHLLRSKITK PNVYHESKLAAKEYQAAKARLFTAFIKAGLGAWVEKPT EQDQFSLTGSGSSELIKENMHMKLYMEGTVDNHHFKCTS EGEGKPYEGTQTMRIKVVEGGPLPFAFDILATSFLYGSKT FINHTQGIPDFFKQSFPEGFTWERVTTYEDGGVLTATQDT SLQDGCLIYNVKIRGVNFTSNGPVMQKKTLGWEAFTETL YPADGGLEGRNDMALKLVGGSHLIANIKTTYRSKKPAKN LKMPGVYYVDYRLERIKEANNETYVEQHEVAVARYCDL PSKLGHKLN* |
| MCP-linker-ADAR2-DDN-MS1(A)-ADAR2 (E488Q)-DDC-Mcl-1-TagBFP | 22 | 3D-E, 3G-H | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSGGSGRPEIWMTQGLRRL GDEANAYYARRTGDRHPNRKARGQLRTKIESG**Q**GTIPVR SNASIQTWDGVLQGERLLTMSCSDKIARWNVVGIQGSLL SIFVEPIYFSSIILGSLYHGDHLSRAMYQRISNIEDLPPLYTL NKPLLSGISNAEARQPGKAPNFSVNWTVGDSAIEVINATT GKDELGRASRLCKHALYCRWMRVHGKVPSHLLRSKITK PNVYHESKLAAKEYQAAKARLFTAFIKAGLGAWVEKPT EQDQFSLTGSGTGGPGDELYRQSLEIISRYLREQATGAKD TKPMGRSGATSRKALETLRRVGDGVQRNHETAFQGMLR KLDIKNEDDVKSLSRVMIHVFSDGVTNWGRIVTLISFGAF VAKHLKTINQESCIEPLAESITDVLVRTKRDWLVKQRGW DGFVEFFHVEDLEGGGSSELIKENMHMKLYMEGTVDNH HFKCTSEGEGKPYEGTQTMRIKVVEGGPLPFAFDILATSF LYGSKTFINHTQGIPDFFKQSFPEGFTWERVTTYEDGGVL TATQDTSLQDGCLIYNVKIRGVNFTSNGPVMQKKTLGWE |

TABLE 1-continued

Amino Acid Sequence Table (see e.g., FIG. 6)

| NAME | SEQ ID NO | See e.g., FIGS. | AMINO ACID SEQUENCE |
|---|---|---|---|
| | | | AFTETLYPADGGLEGRNDMALKLVGGSHLIANIKTTYRS<br>KKPAKNLKMPGVYYVDYRLERIKEANNETYVEQHEVAV<br>ARYCDLPSKLGHKLN* |
| MCP-linker-<br>ADAR2-<br>DDN-<br>Bad(L)-<br>ADAR2<br>(E488Q)-DDC-<br>Bcl-xL-<br>TagBFP | 23 | 3F | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGTGAPPNLWAAQRYGRE<br>LRRMSDE**L**VDRHPNRKARGQLRTKIESG**Q**GTIPVRSNASI<br>QTWDGVLQGERLLTMSCSDKIARWNVVGIQGSLLSIFVE<br>PIYFSSIILGSLYHGDHLSRAMYQRISNIEDLPPLYTLNKPL<br>LSGISNAEARQPGKAPNFSVNWTVGDSAIEVINATTGKDE<br>LGRASRLCKHALYCRWMRVHGKVPSHLLRSKITKPNVY<br>HESKLAAKEYQAAKARLFTAFIKAGLGAWVEKPTEQDQ<br>FSLTGSAAGGSGGSAAASSNRELVVDFLSYKLSQKGYSW<br>SQFSDVEENRTEAPEGTESEMETPSAINGNPSWHLADSPA<br>VNGATGHSSSLDAREVIPMAAVKQALREAGDEFELRYRR<br>AFSDLTSQLHITPGTAYQSFEQVVNELFRDGVNWGRIVAF<br>FSFGGALCVESVDKEMQVLVSRIAAWMATYLNDHLEPW<br>IQENGGWDTFVELYGNNGSSELIKENMHMKLYMEGTVD<br>NHHFKCTSEGEGKPYEGTQTMRIKVVEGGPLPFAFDILAT<br>SFLYGSKTFINHTQGIPDFFKQSFPEGFTWERVTTYEDGG<br>VLTATQDTSLQDGCLIYNVKIRGVNFTSNGPVMQKKTLG<br>WEAFTETLYPADGGLEGRNDMALKLVGGSHLIANIKTTY<br>RSKKPAKNLKMPGVYYVDYRLERIKEANNETYVEQHEV<br>AVARYCDLPSKLGHKLN* |
| MCP-linker-<br>ADAR2-<br>DDN-<br>MS1(I)-<br>ADAR2<br>(E488Q)-DDC-<br>Mcl-1-<br>TagBFP | 24 | 3G | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGGSGGSGRPEIWMTQGLRRL<br>GDE**I**NAYYARRTGDRHPNRKARGQLRTKIESGQGTIPVR<br>SNASIQTWDGVLQGERLLTMSCSDKIARWNVVGIQGSLL<br>SIFVEPIYFSSIILGSLYHGDHLSRAMYQRISNIEDLPPLYTL<br>NKPLLSGISNAEARQPGKAPNFSVNWTVGDSAIEVINATT<br>GKDELGRASRLCKHALYCRWMRVHGKVPSHLLRSKITK<br>PNVYHESKLAAKEYQAAKARLFTAFIKAGLGAWVEKPT<br>EQDQFSLTGSGTGGPGDELYRQSLEIISRYLREQATGAKD<br>TKPMGRSGATSRKALETLRRVGDGVQRNHETAFQGMLR<br>KLDIKNEDDVKSLSRVMIHVFSDGVTNWGRIVTLISFGAF<br>VAKHLKTINQESCIEPLAESITDVLVRTKRDWLVKQRGW<br>DGFVEFFHVEDLEGGGSSELIKENMHMKLYMEGTVDNH<br>HFKCTSEGEGKPYEGTQTMRIKVVEGGPLPFAFDILATSF<br>LYGSKTFINHTQGIPDFFKQSFPEGFTWERVTTYEDGGVL<br>TATQDTSLQDGCLIYNVKIRGVNFTSNGPVMQKKTLGWE<br>AFTETLYPADGGLEGRNDMALKLVGGSHLIANIKTTYRS<br>KKPAKNLKMPGVYYVDYRLERIKEANNETYVEQHEVAV<br>ARYCDLPSKLGHKLN* |
| MCP-linker-<br>ADAR2-<br>DDN-<br>ALFA-<br>ADAR2<br>(E488Q)-DDC-<br>TagBFP | 25 | 4C, 4E | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASP**SRLEEELRRRLTE**PTGDRH<br>PNRKARGQLRTKIESG**Q**GTIPVRSNASIQTWDGVLQGERL<br>LTMSCSDKIARWNVVGIQGSLLSIFVEPIYFSSIILGSLYHG<br>DHLSRAMYQRISNIEDLPPLYTLNKPLLSGISNAEARQPG<br>KAPNFSVNWTVGDSAIEVINATTGKDELGRASRLCKHAL<br>YCRWMRVHGKVPSHLLRSKITKPNVYHESKLAAKEYQA<br>AKARLFTAFIKAGLGAWVEKPTEQDQFSLTGSGSSELIKE<br>NMHMKLYMEGTVDNHHFKCTSEGEGKPYEGTQTMRIK<br>VVEGGPLPFAFDILATSFLYGSKTFINHTQGIPDFFKQSFPE<br>GFTWERVTTYEDGGVLTATQDTSLQDGCLIYNVKIRGVN |

TABLE 1-continued

| Amino Acid Sequence Table (see e.g., FIG. 6) | | | |
|---|---|---|---|
| NAME | SEQ ID NO | See e.g., FIGS. | AMINO ACID SEQUENCE |
| | | | FTSNGPVMQKKTLGWEAFTETLYPADGGLEGRNDMALK<br>LVGGSHLIANIKTTYRSKKPAKNLKMPGVYYVDYRLERI<br>KEANNETYVEQHEVAVARYCDLPSKLGHKLN* |
| MCP-linker-<br>ADAR2-<br>DDN-<br>ALFA-<br>ADAR2<br>(E488Q)-DDC-<br>NbALFA-<br>TagBFP | 26 | 4C-E | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASP**SRLEEELRRRLTE**PTGDRH<br>PNRKARGQLRTKIESG**Q**GTIPVRSNASIQTWDGVLQGERL<br>LTMSCSDKIARWNVVGIQGSLLSIFVEPIYFSSIILGSLYHG<br>DHLSRAMYQRISNIEDLPPLYTLNKPLLSGISNAEARQPG<br>KAPNFSVNWTVGDSAIEVINATTGKDELGRASRLCKHAL<br>YCRWMRVHGKVPSHLLRSKITKPNVYHESKLAAKEYQA<br>AKARLFTAFIKAGLGAWVEKPTEQDQFSLTGSGGTAEVQ<br>LQESGGGLVQPGGSLRLSCTASGVTISALNAMAMGWYR<br>QAPGERRVMVAAVSERGNAMYRESVQGRFTVTRDFTNK<br>MVSLQMDNLKPEDTAVYYCHVLEDRVDSFHDYWGQGT<br>QVTVSSGAGSSELIKENMHMKLYMEGTVDNHHFKCTSE<br>GEGKPYEGTQTMRIKVVEGGPLPFAFDILATSFLYGSKTFI<br>NHTQGIPDFFKQSFPEGFTWERVTTYEDGGVLTATQDTSL<br>QDGCLIYNVKIRGVNFTSNGPVMQKKTLGWEAFTETLYP<br>ADGGLEGRNDMALKLVGGSHLIANIKTTYRSKKPAKNL<br>KMPGVYYVDYRLERIKEANNETYVEQHEVAVARYCDLP<br>SKLGHKLN* |
| MCP-linker-<br>ADAR2-<br>DDN-<br>ALFA-PE-<br>ADAR2<br>(E488Q)-DDC-<br>TagBFP | 27 | 4C, 4E | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGP**GRLEEELRRRLSP**GT<br>GDRHPNRKARGQLRTKIESG**Q**GTIPVRSNASIQTWDGVL<br>QGERLLTMSCSDKIARWNVVGIQGSLLSIFVEPIYFSSIILG<br>SLYHGDHLSRAMYQRISNIEDLPPLYTLNKPLLSGISNAE<br>ARQPGKAPNFSVNWTVGDSAIEVINATTGKDELGRASRL<br>CKHALYCRWMRVHGKVPSHLLRSKITKPNVYHESKLAA<br>KEYQAAKARLFTAFIKAGLGAWVEKPTEQDQFSLTGSGS<br>SELIKENMHMKLYMEGTVDNHHFKCTSEGEGKPYEGTQ<br>TMRIKVVEGGPLPFAFDILATSFLYGSKTFINHTQGIPDFF<br>KQSFPEGFTWERVTTYEDGGVLTATQDTSLQDGCLIYNV<br>KIRGVNFTSNGPVMQKKTLGWEAFTETLYPADGGLEGR<br>NDMALKLVGGSHLIANIKTTYRSKKPAKNLKMPGVYYV<br>DYRLERIKEANNETYVEQHEVAVARYCDLPSKLGHKLN* |
| MCP-linker-<br>ADAR2-<br>DDN-<br>ALFA-PE-<br>ADAR2<br>(E488Q)-DDC-<br>NbALFA-<br>TagBFP | 28 | 4C, 4E | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGIYG<br>GSGSGAGSGSPAGGGAPGSGGGSQLHLPQVLADAVSRLV<br>LGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGP**GRLEEELRRRLSP**GT<br>GDRHPNRKARGQLRTKIESG**Q**GTIPVRSNASIQTWDGVL<br>QGERLLTMSCSDKIARWNVVGIQGSLLSIFVEPIYFSSIILG<br>SLYHGDHLSRAMYQRISNIEDLPPLYTLNKPLLSGISNAE<br>ARQPGKAPNFSVNWTVGDSAIEVINATTGKDELGRASRL<br>CKHALYCRWMRVHGKVPSHLLRSKITKPNVYHESKLAA<br>KEYQAAKARLFTAFIKAGLGAWVEKPTEQDQFSLTGSGG<br>TAEVQLQESGGGLVQPGGSLRLSCTASGVTISALNAMAM<br>GWYRQAPGERRVMVAAVSERGNAMYRESVQGRFTVTR<br>DFTNKMVSLQMDNLKPEDTAVYYCHVLEDRVDSFHDY<br>WGQGTQVTVSSGAGSSELIKENMHMKLYMEGTVDNHH<br>FKCTSEGEGKPYEGTQTMRIKVVEGGPLPFAFDILATSFL<br>YGSKTFINHTQGIPDFFKQSFPEGFTWERVTTYEDGGVLT<br>ATQDTSLQDGCLIYNVKIRGVNFTSNGPVMQKKTLGWE<br>AFTETLYPADGGLEGRNDMALKLVGGSHLIANIKTTYRS<br>KKPAKNLKMPGVYYVDYRLERIKEANNETYVEQHEVAV<br>ARYCDLPSKLGHKLN* |

TABLE 1-continued

Amino Acid Sequence Table (see e.g., FIG. 6)

| NAME | SEQ ID NO | See e.g., FIGS. | AMINO ACID SEQUENCE |
| --- | --- | --- | --- |
| MCP-linker-ADAR2-DDN-ALFA-78-ADAR2 (E488Q)-DDC-TagBFP | 29 | 4C, 4E | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGSGP**GRLEQEIRARLSP**GTG DRHPNRKARGQLRTKIESG**Q**GTIPVRSNASIQTWDGVLQ GERLLTMSCSDKIARWNVVGIQGSLLSIFVEPIYFSSIILGS LYHGDHLSRAMYQRISNIEDLPPLYTLNKPLLSGISNAEA RQPGKAPNFSVNWTVGDSAIEVINATTGKDELGRASRLC KHALYCRWMRVHGKVPSHLLRSKITKPNVYHESKLAAK EYQAAKARLFTAFIKAGLGAWVEKPTEQDQFSLTGSGSS ELIKENMHMKLYMEGTVDNHHFKCTSEGEGKPYEGTQT MRIKVVEGGPLPFAFDILATSFLYGSKTFINHTQGIPDFFK QSFPEGFTWERVTTYEDGGVLTATQDTSLQDGCLIYNVK IRGVNFTSNGPVMQKKTLGWEAFTETLYPADGGLEGRN DMALKLVGGSHLIANIKTTYRSKKPAKNLKMPGVYYVD YRLERIKEANNETYVEQHEVAVARYCDLPSKLGHKLN* |
| MCP-linker-ADAR2-DDN-ALFA-PE-ADAR2 (E488Q)-DDC-NbALFA-TagBFP | 30 | 4C, 4E | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGSGP**GRLEQEIRARLSP**GTG DRHPNRKARGQLRTKIESG**Q**GTIPVRSNASIQTWDGVLQ GERLLTMSCSDKIARWNVVGIQGSLLSIFVEPIYFSSIILGS LYHGDHLSRAMYQRISNIEDLPPLYTLNKPLLSGISNAEA RQPGKAPNFSVNWTVGDSAIEVINATTGKDELGRASRLC KHALYCRWMRVHGKVPSHLLRSKITKPNVYHESKLAAK EYQAAKARLFTAFIKAGLGAWVEKPTEQDQFSLTGSGGT AEVQLQESGGGLVQPGGSLRLSCTASGVTISALNAMAMG WYRQAPGERRVMVAAVSERGNAMYRESVQGRFTVTRD FTNKMVSLQMDNLKPEDTAVYYCHVLEDRVDSFHDYW GQGTQVTVSSGAGSSELIKENMHMKLYMEGTVDNHHFK CTSEGEGKPYEGTQTMRIKVVEGGPLPFAFDILATSFLYG SKTFINHTQGIPDFFKQSFPEGFTWERVTTYEDGGVLTAT QDTSLQDGCLIYNVKIRGVNFTSNGPVMQKKTLGWEAFT ETLYPADGGLEGRNDMALKLVGGSHLIANIKTTYRSKKP AKNLKMPGVYYVDYRLERIKEANNETYVEQHEVAVARY CDLPSKLGHKLN* |
| miRFP670-ALFA | 31 | 4C-E | MVAGHASGSPAFGTASHSNCEHEEIHLAGSIQPHGALLV VSEHDHRVIQASANAAEFLNLGSVLGVPLAEIDGDLLIKI LPHLDPTAEGMPVAVRCRIGNPSTEYCGLMHRPPEGGLII ELERAGPSIDLSGTLAPALERIRTAGSLRALCDDTVLLFQQ CTGYDRVMVYRFDEQGHGLVFSECHVPGLESYFGNRYP SSTVPQMARQLYVRQRVRVLVDVTYQPVPLEPRLSPLTG RDLDMSGCFLRSMSPCHLQFLKDMGVRATLAVSLVVGG KLWGLVVCHHYLPRFIRFELRAICKRLAERIATRITALESL ESRLEEELRRRLTE* |
| MCP-linker-ADAR2-DDN-SpyTag-ADAR2 (E488Q)-DDC-TagBFP | 32 | 5D | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSG**AHIVMVDAYKPTK**GT GDRHPNRKARGQLRTKIESG**Q**GTIPVRSNASIQTWDGVL QGERLLTMSCSDKIARWNVVGIQGSLLSIFVEPIYFSSIILG SLYHGDHLSRAMYQRISNIEDLPPLYTLNKPLLSGISNAE ARQPGKAPNFSVNWTVGDSAIEVINATTGKDELGRASRL CKHALYCRWMRVHGKVPSHLLRSKITKPNVYHESKLAA KEYQAAKARLFTAFIKAGLGAWVEKPTEQDQFSLTGSGS SELIKENMHMKLYMEGTVDNHHFKCTSEGEGKPYEGTQ TMRIKVVEGGPLPFAFDILATSFLYGSKTFINHTQGIPDFF KQSFPEGFTWERVTTYEDGGVLTATQDTSLQDGCLIYNV |

TABLE 1-continued

Amino Acid Sequence Table (see e.g., FIG. 6)

| NAME | SEQ ID NO | See e.g., FIGS. | AMINO ACID SEQUENCE |
|---|---|---|---|
| | | | KIRGVNFTSNGPVMQKKTLGWEAFTETLYPADGGLEGR NDMALKLVGGSHLIANIKTTYRSKKPAKNLKMPGVYYV DYRLERIKEANNETYVEQHEVAVARYCDLPSKLGHKLN* |
| MCP-linker-ADAR2-DDN-SpyTag-ADAR2 (E488Q)-DDC-SpyCatcher-TagBFP | 33 | 5D | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSG**AHIVMVDAYKPTK**GT GDRHPNRKARGQLRTKIESG**Q**GTIPVRSNASIQTWDGVL QGERLLTMSCSDKIARWNVVGIQGSLLSIFVEPIYFSSIILG SLYHGDHLSRAMYQRISNIEDLPPLYTLNKPLLSGISNAE ARQPGKAPNFSVNWTVGDSAIEVINATTGKDELGRASRL CKHALYCRWMRVHGKVPSHLLRSKITKPNVYHESKLAA KEYQAAKARLFTAFIKAGLGAWVEKPTEQDQFSLTGSGT SGGAMVDTLSGLSSEQGQSGDMTIEEDSATHIKFSKRDE DGKELAGATMELRDSSGKTISTWISDGQVKDFYLYPGKY TFVETAAPDGYEVATAITFTVNEQGQVTVNGKATKGDA HIGSSELIKENMHMKLYMEGTVDNHHFKCTSEGEGKPYE GTQTMRIKVVEGGPLPFAFDILATSFLYGSKTFINHTQGIP DFFKQSFPEGFTWERVTTYEDGGVLTATQDTSLQDGCLI YNVKIRGVNFTSNGPVMQKKTLGWEAFTETLYPADGGL EGRNDMALKLVGGSHLIANIKTTYRSKKPAKNLKMPGV YYVDYRLERIKEANNETYVEQHEVAVARYCDLPSKLGH KLN* |
| MCP-linker-ADAR2-DDN-Spy Tag-ADAR2 (E488Q)-DDC-TagBFP - P2A-T2A-SpyCatcher | 34 | 5D | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSG**AHIVMVDAYKPTK**GT GDRHPNRKARGQLRTKIESG**Q**GTIPVRSNASIQTWDGVL QGERLLTMSCSDKIARWNVVGIQGSLLSIFVEPIYFSSIILG SLYHGDHLSRAMYQRISNIEDLPPLYTLNKPLLSGISNAE ARQPGKAPNFSVNWTVGDSAIEVINATTGKDELGRASRL CKHALYCRWMRVHGKVPSHLLRSKITKPNVYHESKLAA KEYQAAKARLFTAFIKAGLGAWVEKPTEQDQFSLTGSGS SELIKENMHMKLYMEGTVDNHHFKCTSEGEGKPYEGTQ TMRIKVVEGGPLPFAFDILATSFLYGSKTFINHTQGIPDFF KQSFPEGFTWERVTTYEDGGVLTATQDTSLQDGCLIYNV KIRGVNFTSNGPVMQKKTLGWEAFTETLYPADGGLEGR NDMALKLVGGSHLIANIKTTYRSKKPAKNLKMPGVYYV DYRLERIKEANNETYVEQHEVAVARYCDLPSKLGHKLNT SATNFSLLKQAGDVEENPGPGGSEGRGSLLTCGDVEENP GPGTSGGAMVDTLSGLSSEQGQSGDMTIEEDSATHIKFSK RDEDGKELAGATMELRDSSGKTISTWISDGQVKDFYLYP GKYTFVETAAPDGYEVATAITFTVNEQGQVTVNGKATK GDAHIG* |
| MCP-linker-ADAR2-DDN-Spy Tag-ADAR2 (E488Q)-DDC-TEVcs-SpyCatcher-TagBFP | 35 | 5D-E | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSG**AHIVMVDAYKPTK**GT GDRHPNRKARGQLRTKIESG**Q**GTIPVRSNASIQTWDGVL QGERLLTMSCSDKIARWNVVGIQGSLLSIFVEPIYFSSIILG SLYHGDHLSRAMYQRISNIEDLPPLYTLNKPLLSGISNAE ARQPGKAPNFSVNWTVGDSAIEVINATTGKDELGRASRL CKHALYCRWMRVHGKVPSHLLRSKITKPNVYHESKLAA KEYQAAKARLFTAFIKAGLGAWVEKPTEQDQFSLTGSGG TENLYFQSGTSGGAMVDTLSGLSSEQGQSGDMTIEEDSA THIKFSKRDEDGKELAGATMELRDSSGKTISTWISDGQVK DFYLYPGKYTFVETAAPDGYEVATAITFTVNEQGQVTVN GKATKGDAHIGSSELIKENMHMKLYMEGTVDNHHFKCT SEGEGKPYEGTQTMRIKVVEGGPLPFAFDILATSFLYGSK |

TABLE 1-continued

Amino Acid Sequence Table (see e.g., FIG. 6)

| NAME | SEQ ID NO | See e.g., FIGS. | AMINO ACID SEQUENCE |
|---|---|---|---|
| | | | TFINHTQGIPDFFKQSFPEGFTWERVTTYEDGGVLTATQD TSLQDGCLIYNVKIRGVNFTSNGPVMQKKTLGWEAFTET LYPADGGLEGRNDMALKLVGGSHLIANIKTTYRSKKPAK NLKMPGVYYVDYRLERIKEANNETYVEQHEVAVARYCD LPSKLGHKLN* |
| TEV Protease | 36 | 5D-E | MGESLFKGPRDYNPISSTICHLTNESDGHTTSLYGIGFGPFI ITNKHLFRRNNGTLLVQSLHGVFKVKNTTTLQQHLIDGR DMIIIRMPKDFPPFPQKLKFREPQREERICLVTTNFQTKSM SSMVSDTSCTFPSSDGIFWKHWIQTKDGQCGSPLVSTRDG FIVGIHSASNFTNTNNYFTSVPKNFMELLTNQEAQQWVS GWRLNADSVLWGGHKVFMVKPEEPFQPVKEATQL* |
| MCP-linker-ADAR2-DDN-Bad(L)-ADAR2 (E488Q)-DDC-PhoCl-Bcl-xL-TagBFP | 37 | 5G | MASNFTQFVLVDNGGTGDVTVAPSNFANGIAEWISSNSR SQAYKVTCSVRQSSAQNRKYTIKVEVPKGAWRSYLNME LTIPIFATNSDCELIVKAMQGLLKDGNPIPSAIAANSGIYG GSGSGAGSGSPAGGGAPGSGGGSQLHLPQVLADAVSRLV LGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGSGTGAPPNLWAAQRYGRE LRRMSDELVDRHPNRKARGQLRTKIESGQGTIPVRSNASI QTWDGVLQGERLLTMSCSDKIARWNVVGIQGSLLSIFVE PIYFSSIILGSLYHGDHLSRAMYQRISNIEDLPPLYTLNKPL LSGISNAEARQPGKAPNFSVNWTVGDSAIEVINATTGKDE LGRASRLCKHALYCRWMRVHGKVPSHLLRSKITKPNVY HESKLAAKEYQAAKARLFTAFIKAGLGAWVEKPTEQDQ FSLTGSGSGGVIPDYFKQSFPEGYSWERSMTYEDGGICIA TNDITMEGDSFINKIHFKGTNFPPNGPVMQKRTVGWEAS TEKMYERDGVLKGDVKMKLLLKGGGHYRCDYRTTYKV KQKPVKLPDYHFVDHRIEILSHDKDYNKVKLYEHAVAR NSTDSMDELYKGGSGGMVSKGEETITSVIKPDMKNKLR MEGNVNGHAFVIEGEGSGKPFEGIQTIDLEVKEGAPLPFA YDILTTAFHYGNRVFTKYPRSGSGSSNRELVVDFLSYKLS QKGYSWSQFSDVEENRTEAPEGTESEMETPSAINGNPSW HLADSPAVNGATGHSSSLDAREVIPMAAVKQALREAGD EFELRYRRAFSDLTSQLHITPGTAYQSFEQVVNELFRDGV NWGRIVAFFSFGGALCVESVDKEMQVLVSRIAAWMATY LNDHLEPWIQENGGWDTFVELYGNNGSSELIKENMHMK LYMEGTVDNHHFKCTSEGEGKPYEGTQTMRIKVVEGGP LPFAFDILATSFLYGSKTFINHTQGIPDFFKQSFPEGFTWER VTTYEDGGVLTATQDTSLQDGCLIYNVKIRGVNFTSNGP VMQKKTLGWEAFTETLYPADGGLEGRNDMALKLVGGS HLIANIKTTYRSKKPAKNLKMPGVYYVDYRLERIKEANN ETYVEQHEVAVARYCDLPSKLGHKLN* |

Example 4

DNA Sequences of Relevant Plasmids (Sequences Given are Between Promoter and Terminator)

RNA features are highlighted accordingly.

SEQ ID NO: 38 (see e.g., polypeptide in SEQ ID NO: 1) - mCherry-FLAG-P2A-T2A-UAG-
UAG-MS2-P2A-T2A-HA-mNeonGreen; UAG-UAG is bolded; MS2 is bold italicized.
AGGTAAGCTTGGTACCGAGCTCGGATCCaccggtcgccaccatggtgagcaagggcgaggaggataacatggccatcatca
aggagttcatgcgcttcaaggtgcacatggagggctccgtgaacggccacgagttcgagatcgagggcgagggcgagggccgcccctacgagggc
acccagaccgccaagctgaaggtgaccaagggtggccccctgcccttcgcctgggacatcctgtcccctcagttcatgtacggctccaaggcctacgtg
aagcaccccgccgacatccccgactacttgaagctgtccttccccgagggcttcaagtgggagcgcgtgatgaacttcgaggacggcggcgtggtgac
cgtgacccaggactcctccctgcaggacggcgagttcatctacaaggtgaagctgcgcggcaccaacttcccctccgacggccccgtaatgcagaaga
agaccatgggctgggaggcctcctccgagcggatgtaccccgaggacggcgccctgaagggcgagatcaagcagaggctgaagctgaaggacgg
cggccactacgacgctgaggtcaagaccacctacaaggccaagaagcccgtgcagctgcccggcgcctacaacgtcaacatcaagttggacatcacc
tcccacaacgaggactacaccatcgtggaacagtacgaacgcgccgagggccgccactccaccggcggcatggacgagctgTACaaggattaca
aggatgacgatgacaaaGGTAGCGGGGCAACTAATTTTAGCTTACTCAAACAGGCTGGGGACGTCGA
GGAGAATCCAGGCCCTGCATCCGCTGGCTCTGGAGAAGGACGAGGCTCCTTGCTCACCTGTG
GAGATGTCGAAGAGAACCCAGGTCCTGCAACCGGGAATTCCGCGTAGCGCTAGCTTTGCC
AGCGCCACGCGaaACATGAGGATcACCCATGTACTAGTGCCACAAACTTCTCTCTGCTAAA
GCAAGCAGGTGATGTTGAAGAAAACCCAGGGCCTGGAGGGTCCGAGGGCAGGGGAAGTCTC
CTAACATGCGGGGACGTGGAGGAAAATCCCGGCCCATCCGGATATCCCTACGATGTGCCCG
ATTACGCTCATatggtgagcaagggcgaggaggataacatggcctctctcccagcgacacatgagttacacatctttggctccatcaacggtgt
ggactttgacatggtgggtcagggcaccggcaatccaaatgatggttatgaggagttaaacctgaagtccaccaagggtgacctccagttctcccccctgg
attctggtccctcatatcgggtatggcttccatcagtacctgccctaccctgacgggatgtcgcctttccaggccgccatggtagatggcAGCggatacc
aagtccatcgcacaatgcagtttgaagatggtgcctcccttactgttaactaccgctacacctacgagggaagccacatcaaaggagaggcccaggtga
aggggactggtttccctgctgacggtcctgtgatgaccaactcgctgaccgctgcggactggtgcaggtcgaagaagacttaccccaacgacaaaacca
tcatcagtacctttaagtggagttacaccactggaaatggcaagAGAtaccggagcactgcgcggaccacctacacctttgccaagccaatggcggct
aactatctgaagaaccagccgatgtacgtgttccgtaagacggagctcaagcactccaagaccgagctcaacttcaaggagtggcaaaaggcctttacc
gatgtgatgGGAatggacGAGCTGTATaagGCTAGCTAAGCGGCCGCTCGAGTCTAGAGGGCCCGCGG
TTCGAAGGTA SEQ ID NO: 39 (see e.g., polypeptide in SEQ ID NO: 2) - MCP-linker-ADAR2(E488Q)-
TagBFP
gatcgaaccccttaaggccaccatggcgtccaatttcactcagtttgtgctggttgacaacggcgggaccggggacgttacggtagccccctcaaactttgc
caacggtatagcggagtggataagcagcaattctaggagtcaagcatacaaagttacatgcagcgtgcgccaatctagcgctcagaatcgcaagtacac
cattaaagtagaggtccccaagggagcctggagaagctatcttaacatggagttgaccataccaatcttcgctaccaactctgactgtgaactcattgtgaa
agccatgcaaggtctgctcaaggatggtaacccaattccgtccgctatcgctgccaactctgggatttacgggggcagtgggagcggtgcaggatctgg
tagtccagctgggggaggagcaccgggtagcggtgggggtctcagctgcacctgccccaggttctcgcagacgccgtatcccgccttgtactgggca
agtttggtgatcttactgacaatttttcatctcctcatgcgaggcggaaagtactcgcaggcgtcgtcatgacgaccggaactgacgtgaaagacgccaaa
gtcatctctgtctccacgggcacaaagtgcataaacggggagtacatgagcgaccgggggctggcactgaatgattgtcacgctgaaataatatctaggc
gatctctgcttagatttctctacactcaactcgaattgtaccttaacaacaaagatgaccagaaacgcagtatatttcagaaatcagaacgcggcggatttcg
acttaaggaaaacgttcagttccacttgtatatcagcacatccccttgcggtgacgcccgaatcttttccccgcacgagccgatattggaggagcccgcgg
acagacatcctaataggaaggctagaggccaacttcggacgaagattgaaagtggccagggtactatcccggtgcggtccaacgctagtattcaaacgt
gggacggagtccttcaaggtgaacggctgttgacaatgagctgctcagacaaaatcgcgcgctggaatgtagtgggaatccaaggcagcctcttgagc
atattcgtagaacccatatatttctcatccattattttgggctctctgtatcatggtgaccatctgtcaagggctatgtaccaacgaatttctaatatcgaggatctt
cctccactctatacactcaataagcctctcttgtccgggatatcaaacgctgaggcccgccagccagggaaagctcctaacttcagtgttaactggaccgtt
ggtgattctgcgatagaggtcatcaacgccacgacaggtaaggatgagctcggtagagcctcacgcctgtgtaaacacgcgttgtattgtagatggatga
gagtacatgggaaggtcccatctcacttgctccgaagcaagatcactaagcctaatgtgtatcatgagtcaaaactcgcggctaaagaataccaggcagc
caaagctcgactttttacagcttttattaaggcagggctcggggcatgggtcgagaagccgaccgagcaggaccaattctctctgacggggagcggatc
cAGCGAGCTGATTAAGGAGAACATGCACATGAAGCTGTACATGGAGGGCACCGTGGACAAC
CATCACTTCAAGTGCACATCCGAGGGCGAAGGCAAGCCCTACGAGGGCACCCAGACCATGA
GAATCAAGGTGGTCGAGGGCGGCCCTCTCCCCTTCGCCTTCGACATCCTGGCTACTAGCTTC
CTCTACGGCAGCAAGACCTTCATCAACCACACCCAGGGCATCCCCGACTTCTTCAAGCAGTC
CTTCCCTGAGGGCTTCACATGGGAGAGAGTCACCACATACGAAGACGGGGGCGTGCTGACC
GCTACCCAGGACACCAGCCTCCAGGACGGCTGCCTCATCTACAACGTCAAGATCAGAGGGG
TGAACTTCACATCCAACGGCCCTGTGATGCAGAAGAAAACACTCGGCTGGGAGGCCTTCACC
GAGACGCTGTACCCCGCTGACGGCGGCCTGGAAGGCAGAAACGACATGGCCCTGAAGCTCG -continued TGGGCGGGAGCCATCTGATCGCAAACATCAAGACCACATATAGATCCAAGAAACCCGCTAA
GAACCTCAAGATGCCTGGCGTCTACTATGTGGACTACAGACTGGAAAGAATCAAGGAGGCC
AACAACGAGACCTACGTCGAGCAGCACGAGGTGGCAGTGGCCAGATACTGCGACCTCCCTA
GCAAACTGGGGCACAAGCTTAATtAAGGGCCCGTTTAAACCCGC SEQ ID NO: 40 (see e.g., polypeptide in SEQ ID NO: 3) - MCP-linker-ADAR2(E396A &
E488Q)-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctGCCataatatctaggcgatctctgcttagatttctctacactcaactcgaattgta
ccttaacaacaaagatgaccagaaacgcagtatatttcagaaatcagaacgcggcggatttcgacttaaggaaaacgttcagttccacttgtatatcagcac
atccccttgcggtgacgcccgaatcttttccccgcacgagccgatattggaggagcccgcggacagacatcctaataggaaggctagaggccaacttcg
gacgaagattgaaagtggccagggtactatcccggtgcggtccaacgctagtattcaaacgtgggacggagtccttcaaggtgaacggctgttgacaat
gagctgctcagacaaaatcgcgcgctggaatgtagtgggaatccaaggcagcctcttgagcatattcgtagaacccatatatttctcatccattattttgggc
tctctgtatcatggtgaccatctgtcaagggctatgtaccaacgaatttctaatatcgaggatcttcctccactctatacactcaataagcctctcttgtccggg
atatcaaacgctgaggcccgccagccagggaaagctcctaacttcagtgttaactggaccgttggtgattctgcgatagaggtcatcaacgccacgacag
gtaaggatgagctcggtagagcctcacgcctgtgtaaacacgcgttgtattgtagatggatgagagtacatgggaaggtcccatctcacttgctccgaagc
aagatcactaagcctaatgtgtatcatgagtcaaaactcgcggctaaagaataccaggcagccaaagctcgactttttacagcttttattaaggcagggctc
ggggcatgggtcgagaagccgaccgagcaggaccaattctctctgacggggagcggatccAGCGAGCTGATTAAGGAGAACA
TGCACATGAAGCTGTACATGGAGGGCACCGTGGACAACCATCACTTCAAGTGCACATCCGA
GGGCGAAGGCAAGCCCTACGAGGGCACCCAGACCATGAGAATCAAGGTGGTCGAGGGCGG
CCCTCTCCCCTTCGCCTTCGACATCCTGGCTACTAGCTTCCTCTACGGCAGCAAGACCTTCAT
CAACCACACCCAGGGCATCCCCGACTTCTTCAAGCAGTCCTTCCCTGAGGGCTTCACATGGG
AGAGAGTCACCACATACGAAGACGGGGGCGTGCTGACCGCTACCCAGGACACCAGCCTCCA
GGACGGCTGCCTCATCTACAACGTCAAGATCAGAGGGGTGAACTTCACATCCAACGGCCCTG
TGATGCAGAAGAAAACACTCGGCTGGGAGGCCTTCACCGAGACGCTGTACCCCGCTGACGG
CGGCCTGGAAGGCAGAAACGACATGGCCCTGAAGCTCGTGGGCGGGAGCCATCTGATCGCA
AACATCAAGACCACATATAGATCCAAGAAACCCGCTAAGAACCTCAAGATGCCTGGCGTCT
ACTATGTGGACTACAGACTGGAAAGAATCAAGGAGGCCAACAACGAGACCTACGTCGAGCA
GCACGAGGTGGCAGTGGCCAGATACTGCGACCTCCCTAGCAAACTGGGGCACAAGCTTAATt
AAGGGCCCGTTTAAACCCGCTGATCAGCCTCGACTGTGCCTTCTA SEQ ID NO: 41 (see e.g., polypeptide in SEQ ID NO: 4) - mCherry-FLAG-UGG-UGG-P2A-
T2A-HA-mNeonGreen; UGG-UGG is bolded
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaagAATTCCGCGTGGCG
CTGGCTTCCTTGCCAGCGCCACGCGACTAGTGCCACAAACTTCTCTCTGCTAAAGCAAGC
AGGTGATGTTGAAGAAAACCCAGGGCCTGGAGGGTCCGAGGGCAGGGGAAGTCTCCTAACA
TGCGGGGACGTGGAGGAAAATCCCGGCCCATCCGGATATCCCTACGATGTGCCCGATTACGC
TCATatggtgagcaagggcgaggaggataacatggcctctctcccagcgacacatgagttacacatctttggctccatcaacggtgtggactttgaca
tggtgggtcagggcaccggcaatccaaatgatggttatgaggagttaaacctgaagtccaccaagggtgacctccagttctcccccctggattctggtccct
catatcgggtatggcttccatcagtacctgccctaccctgacgggatgtcgcctttccaggccgccatggtagatggcAGCggataccaagtccatcgc -continued acaatgcagtttgaagatggtgcctcccttactgttaactaccgctacacctacgagggaagccacatcaaaggagaggcccaggtgaaggggactggt
ttccctgctgacggtcctgtgatgaccaactcgctgaccgctgcggactggtgcaggtcgaagaagacttaccccaacgacaaaaccatcatcagtacct
ttaagtggagttacaccactggaaatggcaagAGAtaccggagcactgcgcggaccacctacacctttgccaagccaatggcggctaactatctgaa
gaaccagccgatgtacgtgttccgtaagacggagctcaagcactccaagaccgagctcaacttcaaggagtggcaaaaggcctttaccgatgtgatgG
GAatggacGAGCTGTATaagGCTAGCTAAGCGGCCGCTCGAGTCTAGAGGGCCCGCGGTTCGAA
GGTAAGCCTATCCCTAACCCTCTCCTCGGTCTCGATTCTACGCGTACCGGTCATCATCACCAT
CACCATTGAGTTTAAACCCGCTGATCAGCCTCGACTGTGCCTTCTA SEQ ID NO: 42 (see e.g., polypeptide in SEQ ID NO: 5) - mCherry-FLAG-UAG-UGG-P2A-T2A-HA-mNeonGreen; UAG-UGG is bolded TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggcccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaagAATTCCGCGTAGCG
CTGGCTTCCTTGCCAGCGCCACGCGACTAGTGCCACAAACTTCTCTCTGCTAAAGCAAGC
AGGTGATGTTGAAGAAAACCCAGGGCCTGGAGGGTCCGAGGGCAGGGGAAGTCTCCTAACA
TGCGGGGACGTGGAGGAAAATCCCGGCCCATCCGGATATCCCTACGATGTGCCCGATTACGC
TCATatggtgagcaagggcgaggaggataacatggcctctctcccagcgacacatgagttacacatctttggctccatcaacggtgtggactttgaca
tggtgggtcagggcaccggcaatccaaatgatggttatgaggagttaaacctgaagtccaccaagggtgacctccagttctcccccctggattctggtccct
catatcgggtatggcttccatcagtacctgccctaccctgacgggatgtcgcctttccaggccgccatggtagatggcAGCggataccaagtccatcgc
acaatgcagtttgaagatggtgcctcccttactgttaactaccgctacacctacgagggaagccacatcaaaggagaggcccaggtgaaggggactggt
ttccctgctgacggtcctgtgatgaccaactcgctgaccgctgcggactggtgcaggtcgaagaagacttaccccaacgacaaaaccatcatcagtacct
ttaagtggagttacaccactggaaatggcaagAGAtaccggagcactgcgcggaccacctacacctttgccaagccaatggcggctaactatctgaa
gaaccagccgatgtacgtgttccgtaagacggagctcaagcactccaagaccgagctcaacttcaaggagtggcaaaaggcctttaccgatgtgatgG
GAatggacGAGCTGTATaagGCTAGCTAAGCGGCCGCTCGAGTCTAGAGGGCCCGCGGTTCGAA
GGTAAGCCTATCCCTAACCCTCTCCTCGGTCTCGATTCTACGCGTACCGGTCATCATCACCAT
CACCATTGAGTTTAAACCCGCTGATCAGCCTCGACTGTGCCTTCTA SEQ ID NO: 43 (see e.g., polypeptide in SEQ ID NO: 6) - mCherry-FLAG-UAG-UAG-P2A-T2A-HA-mNeonGreen; UAG-UAG is bolded TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggcccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaagAATTCCGCGTAGCG
CTAGCTTCCTTGCCAGCGCCACGCGACTAGTGCCACAAACTTCTCTCTGCTAAAGCAAGC
AGGTGATGTTGAAGAAAACCCAGGGCCTGGAGGGTCCGAGGGCAGGGGAAGTCTCCTAACA
TGCGGGGACGTGGAGGAAAATCCCGGCCCATCCGGATATCCCTACGATGTGCCCGATTACGC
TCATatggtgagcaagggcgaggaggataacatggcctctctcccagcgacacatgagttacacatctttggctccatcaacggtgtggactttgaca
tggtgggtcagggcaccggcaatccaaatgatggttatgaggagttaaacctgaagtccaccaagggtgacctccagttctcccccctggattctggtccct
catatcgggtatggcttccatcagtacctgccctaccctgacgggatgtcgcctttccaggccgccatggtagatggcAGCggataccaagtccatcgc
acaatgcagtttgaagatggtgcctcccttactgttaactaccgctacacctacgagggaagccacatcaaaggagaggcccaggtgaaggggactggt
ttccctgctgacggtcctgtgatgaccaactcgctgaccgctgcggactggtgcaggtcgaagaagacttaccccaacgacaaaaccatcatcagtacct
ttaagtggagttacaccactggaaatggcaagAGAtaccggagcactgcgcggaccacctacacctttgccaagccaatggcggctaactatctgaa
gaaccagccgatgtacgtgttccgtaagacggagctcaagcactccaagaccgagctcaacttcaaggagtggcaaaaggcctttaccgatgtgatgG -continued GAatggacGAGCTGTATaagGCTAGCTAAGCGGCCGCTCGAGTCTAGAGGGCCCGCGGTTCGAA
GGTAAGCCTATCCCTAACCCTCTCCTCGGTCTCGATTCTACGCGTACCGGTCATCATCACCAT
CACCATTGAGTTTAAACCCGCTGATCAGCCTCGACTGTGCCTTCTA SEQ ID NO: 44 (see e.g., polypeptide in SEQ ID NO: 7) - mCherry-FLAG-UAG-UGG-
MS2-P2A-T2A-HA-mNeonGreen; UAG-UGG is bolded; MS2 is bold italicized
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaagAATTCCGCGTAGCG
CTGGCTTTGCCAGCGCCACGCGaa*ACATGAGGATcACCCATGT*ACTAGTGCCACAAACTTCT
CTCTGCTAAAGCAAGCAGGTGATGTTGAAGAAAACCCAGGGCCTGGAGGGTCCGAGGGCAG
GGGAAGTCTCCTAACATGCGGGGACGTGGAGGAAAATCCCGGCCCATCCGGATATCCCTAC
GATGTGCCCGATTACGCTCATatggtgagcaagggcgaggaggataacatggcctctctcccagcgacacatgagttacacatcttt
ggctccatcaacggtgtggactttgacatggtgggtcagggcaccggcaatccaaatgatggttatgaggagttaaacctgaagtccaccaagggtgac
ctccagttctccccctggattctggtccctcatatcgggtatggcttccatcagtacctgccctaccctgacgggatgtcgcctttccaggccgccatggtag
atggcAGCggataccaagtccatcgcacaatgcagtttgaagatggtgcctcccttactgttaactaccgctacacctacgagggaagccacatcaaa
ggagaggcccaggtgaaggggactggtttccctgctgacggtcctgtgatgaccaactcgctgaccgctgcggactggtgcaggtcgaagaagactta
ccccaacgacaaaaccatcatcagtacctttaagtggagttacaccactggaaatggcaagAGAtaccggagcactgcgcggaccacctacaccttt
gccaagccaatggcggctaactatctgaagaaccagccgatgtacgtgttccgtaagacggagctcaagcactccaagaccgagctcaacttcaagga
gtggcaaaaggcctttaccgatgtgatgGGAatggacGAGCTGTATaagGCTAGCTAAGCGGCCGCTCGAGTCTAG
AGGGCCCGCGGTTCGAAGGTAAGCCTATCCCTAACCCTCTCCTCGGTCTCGATTCTACGCGT
ACCGGTCATCATCACCATCACCATTGAGTTTAAACCCGCTGATCAGCCTCGACTGTGCCTTCT
A SEQ ID NO: 45 (see e.g., polypeptide in SEQ ID NO: 8) - mCherry-FLAG-UAG-UAG-
MS2-P2A-T2A-HA-mNeonGreen; UAG-UAG is bolded; MS2 is bold italicized
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaagAATTCCGCGTAGCG
CTAGCTTTGCCAGCGCCACGCGaa*ACATGAGGATcACCCATGT*ACTAGTGCCACAAACTTCT
CTCTGCTAAAGCAAGCAGGTGATGTTGAAGAAAACCCAGGGCCTGGAGGGTCCGAGGGCAG
GGGAAGTCTCCTAACATGCGGGGACGTGGAGGAAAATCCCGGCCCATCCGGATATCCCTAC
GATGTGCCCGATTACGCTCATatggtgagcaagggcgaggaggataacatggcctctctcccagcgacacatgagttacacatcttt
ggctccatcaacggtgtggactttgacatggtgggtcagggcaccggcaatccaaatgatggttatgaggagttaaacctgaagtccaccaagggtgac
ctccagttctccccctggattctggtccctcatatcgggtatggcttccatcagtacctgccctaccctgacgggatgtcgcctttccaggccgccatggtag
atggcAGCggataccaagtccatcgcacaatgcagtttgaagatggtgcctcccttactgttaactaccgctacacctacgagggaagccacatcaaa
ggagaggcccaggtgaaggggactggtttccctgctgacggtcctgtgatgaccaactcgctgaccgctgcggactggtgcaggtcgaagaagactta
ccccaacgacaaaaccatcatcagtacctttaagtggagttacaccactggaaatggcaagAGAtaccggagcactgcgcggaccacctacaccttt
gccaagccaatggcggctaactatctgaagaaccagccgatgtacgtgttccgtaagacggagctcaagcactccaagaccgagctcaacttcaagga
gtggcaaaaggcctttaccgatgtgatgGGAatggacGAGCTGTATaagGCTAGCTAAGCGGCCGCTCGAGTCTAG -continued AGGGCCCGCGGTTCGAAGGTAAGCCTATCCCTAACCCTCTCCTCGGTCTCGATTCTACGCGT
ACCGGTCATCATCACCATCACCATTGAGTTTAAACCCGCTGATCAGCCTCGACTGTGCCTTCT
A SEQ ID NO: 46 (see e.g., polypeptide in SEQ ID NO: 9) - mCherry-FLAG-P2A-T2A-UAG-UAG-PP7-P2A-T2A-HA-mNeonGreen; UAG-UAG is bolded; PP7 is bold italicized.
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGGAATTCCGCGTAG**CGCTAGCTTTGCCAGCGCCACGCG*aaggagcagacgatatggcgtc***
*gctcc*aaTACTAGTGCCACAAACTTCTCTCTGCTAAAGCAAGCAGGTGATGTTGAAGAAAACCC
AGGGCCTGGAGGGTCCGAGGGCAGGGGAAGTCTCCTAACATGCGGGGACGTGGAGGAAAA
TCCCGGCCCATCCGGATATCCCTACGATGTGCCCGATTACGCTCATatggtgagcaagggcgaggaggata
acatggcctctctcccagcgacacatgagttacacatctttggctccatcaacggtgtggactttgacatggtgggtcagggcaccggcaatccaaatgat
ggttatgaggagttaaacctgaagtccaccaagggtgacctccagttctcccccctggattctggtccctcatatcgggtatggcttccatcagtacctgccct
accctgacgggatgtcgcctttccaggccgccatggtagatggcAGCggataccaagtccatcgcacaatgcagtttgaagatggtgcctcccttactg
ttaactaccgctacacctacgagggaagccacatcaaaggagaggcccaggtgaaggggactggtttccctgctgacggtcctgtgatgaccaactcgc
tgaccgctgcggactggtgcaggtcgaagaagacttaccccaacgacaaaaccatcatcagtacctttaagtggagttacaccactggaaatggcaag
AGAtaccggagcactgcgcggaccacctacacctttgccaagccaatggggctaactatctgaagaaccagccgatgtacgtgttccgtaagacgg
agctcaagcactccaagaccgagctcaacttcaaggagtggcaaaaggcctttaccgatgtgatgGGAatggacGAGCTGTATaagGCT
AGCTAAGCGGCCGCTCGAGTCTAGAGGGCCCGCGGTTCGAAGGTAAGCCTATCCCTAACCCT
CTCCTCGGTCTCGATTCTACGCGTACCGGTCATCATCACCATCACCATTGAGTTTAAACCCGC
TGATCAGCCTCGACTGTGCCTTCTA SEQ ID NO: 47 (see e.g., polypeptide in SEQ ID NO: 10) - mCherry-FLAG-P2A-T2A-UAG-UAG-BoxB-P2A-T2A-HA-mNeonGreen; UAG-UAG is bolded; BoxB is bold italicized.
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGGAACCCAGGTCCT
GCAACCGGgAATTC**CGCGTAGCGCTAGCTTTGCCAGCGCCACGCG*gtaagggccctgaagaagggcc***
*c*aACTAGTGCCACAAACTTCTCTCTGCTAAAGCAAGCAGGTGATGTTGAAGAAAACCCAGGG
CCTGGAGGGTCCGAGGGCAGGGGAAGTCTCCTAACATGCGGGGACGTGGAGGAAAATCCCG
GCCCATCCGGATATCCCTACGATGTGCCCGATTACGCTCATatggtgagcaagggcgaggaggataacatggcc
tctctcccagcgacacatgagttacacatctttggctccatcaacggtgtggactttgacatggtgggtcagggcaccggcaatccaaatgatggttatgag
gagttaaacctgaagtccaccaagggtgacctccagttctcccccctggattctggtccctcatatcgggtatggcttccatcagtacctgccctaccctgac
gggatgtcgcctttccaggccgccatggtagatggcAGCggataccaagtccatcgcacaatgcagtttgaagatggtgcctcccttactgttaactac
cgctacacctacgagggaagccacatcaaaggagaggcccaggtgaaggggactggtttccctgctgacggtcctgtgatgaccaactcgctgaccgc
tgcggactggtgcaggtcgaagaagacttaccccaacgacaaaaccatcatcagtacctttaagtggagttacaccactggaaatggcaagAGAtac -continued cggagcactgcgcggaccacctacacctttgccaagccaatggcggctaactatctgaagaaccagccgatgtacgtgttccgtaagacggagctcaa
gcactccaagaccgagctcaacttcaaggagtggcaaaaggcctttaccgatgtgatgGGAatggacGAGCTGTATaagGCTAGCTA
AGCGGCCGCTCGAGTCTAGAGGGCCCGCGGTTCGAAGGTAAGCCTATCCCTAACCCTCTCCT
CGGTCTCGATTCTACGCGTACCGGTCATCATCACCATCACCATTGAGTTTAAACCCGCTGATC
AGCCTCGACTGTGCCTTCTA SEQ ID NO: 48 (see e.g., polypeptide in SEQ ID NO: 11) - mCherry-FLAG-P2A-T2A-
UAG-UAG-HIV TAR-P2A-T2A-HA-mNeonGreen; UAG-UAG is bolded; HIV TAR is bold italicized
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtacccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGgAATTCCGCGTAGCGCTAGCTTTGCCAGCGCCACGCGgta*ggctcgtctgagctcattagct*
*ccgagcc*aACTAGTGCCACAAACTTCTCTCTGCTAAAGCAAGCAGGTGATGTTGAAGAAAACCC
AGGGCCTGGAGGGTCCGAGGGCAGGGGAAGTCTCCTAACATGCGGGGACGTGGAGGAAAA
TCCCGGCCCATCCGGATATCCCTACGATGTGCCCGATTACGCTCATatggtgagcaagggcgaggaggata
acatggcctctctcccagcgacacatgagttacacatctttggctccatcaacggtgtggactttgacatggtgggtcagggcaccggcaatccaaatgat
ggttatgaggagttaaacctgaagtccaccaagggtgacctccagttctcccccctggattctggtccctcatatcgggtatggcttccatcagtacctgccct
accctgacgggatgtcgcctttccaggccgccatggtagatggcAGCggataccaagtccatcgcacaatgcagtttgaagatggtgcctcccttactg
ttaactaccgctacacctacgagggaagccacatcaaaggagaggcccaggtgaaggggactggtttccctgctgacggtcctgtgatgaccaactcgc
tgaccgctgcggactggtgcaggtcgaagaagacttaccccaacgacaaaaccatcatcagtacctttaagtggagttacaccactggaaatggcaag
AGAtaccggagcactgcgcggaccacctacacctttgccaagccaatggcggctaactatctgaagaaccagccgatgtacgtgttccgtaagacgg
agctcaagcactccaagaccgagctcaacttcaaggagtggcaaaaggcctttaccgatgtgatgGGAatggacGAGCTGTATaagGCT
AGCTAAGCGGCCGCTCGAGTCTAGAGGGCCCGCGGTTCGAAGGTAAGCCTATCCCTAACCCT
CTCCTCGGTCTCGATTCTACGCGTACCGGTCATCATCACCATCACCATTGAGTTTAAACCCGC
TGATCAGCCTCGACTGTGCCTTCTA SEQ ID NO: 49 (see e.g., polypeptide in SEQ ID NO: 12) - PCP-linker-ADAR2(E488Q)
DD-TagBFP
TAATACGACTCACTATAGGGAGACCCAAGCTGGctagaggatcgaacccggtaccgccaccATGtccAAGACA
ATCGTGCTTAGCGTGGGAGAAGCAACTCGAACCCTCACAGAAATCCAATCAACAGCCGACC
GACAGATTTTTGAAGAGAAAGTGGGTCCCTTGGTTGGCCGGCTCAGGCTCACAGCCAGCTTG
AGACAGAACGGAGCCAAGACTGCCTATCGAGTGAATCTCAAGCTGGACCAGGCCGATGTAG
TGGACAGTGGTTTGCCCAAGGTTAGATACACGCAAGTGTGGTCACACGATGTCACTATTGTG
GCAAACTCCACCGAGGCAAGCAGGAAGTCCCTGTATGACCTGACCAAATCTTTGGTGGCGA
CGAGCCAAGTAGAGGATCTGGTGGTAAACCTGGTGCCCCTGGGAAGAGCCTCAACCGGTtctg
ggatttacgggggcagtgggagcggtgcaggatctggtagtccagctgggggaggagcaccgggtagcggtggggggtctcagctgcacctgcccc
aggttctcgcagacgccgtatcccgccttgtactgggcaagtttggtgatcttactgacaatttttcatctcctcatgcgaggcggaaagtactcgcaggcgt
cgtcatgacgaccggaactgacgtgaaagacgccaaagtcatctctgtctccacgggcacaaagtgcataaacggggagtacatgagcgaccggggg
ctggcactgaatgattgtcacgctgaaataatatctaggcgatctctgcttagatttctctacactcaactcgaattgtaccttaacaacaaagatgaccagaa
acgcagtatatttcagaaatcagaacgcggcggatttcgacttaaggaaaacgttcagttccacttgtatatcagcacatccccttgcggtgacgcccgaat
cttttccccgcacgagccgatattggaggagcccgcggacagacatcctaataggaaggctagaggccaacttcggacgaagattgaaagtggccagg
gtactatcccggtgcggtccaacgctagtattcaaacgtgggacggagtccttcaaggtgaacggctgttgacaatgagctgctcagacaaaatcgcgcg
ctggaatgtagtgggaatccaaggcagcctcttgagcatattcgtagaacccatatatttctcatccattattttgggctctctgtatcatggtgaccatctgtca
agggctatgtaccaacgaatttctaatatcgaggatcttcctccactctatacactcaataagcctctcttgtccgggatatcaaacgctgaggcccgccagc
cagggaaagctcctaacttcagtgttaactggaccgttggtgattctgcgatagaggtcatcaacgccacgacaggtaaggatgagctcggtagagcctc
acgcctgtgtaaacacgcgttgtattgtagatggatgagagtacatgggaaggtcccatctcacttgctccgaagcaagatcactaagcctaatgtgtatca -continued tgagtcaaaactcgcggctaaagaataccaggcagccaaagctcgactttttacagcttttattaaggcagggctcggggcatgggtcgagaagccgac
cgagcaggaccaattctctctgacggggagcggatccAGCGAGCTGATTAAGGAGAACATGCACATGAAGCTGTA
CATGGAGGGCACCGTGGACAACCATCACTTCAAGTGCACATCCGAGGGCGAAGGCAAGCCC
TACGAGGGCACCCAGACCATGAGAATCAAGGTGGTCGAGGGCGGCCCTCTCCCCTTCGCCTT
CGACATCCTGGCTACTAGCTTCCTCTACGGCAGCAAGACCTTCATCAACCACACCCAGGGCA
TCCCCGACTTCTTCAAGCAGTCCTTCCCTGAGGGCTTCACATGGGAGAGAGTCACCACATAC
GAAGACGGGGGCGTGCTGACCGCTACCCAGGACACCAGCCTCCAGGACGGCTGCCTCATCT
ACAACGTCAAGATCAGAGGGGTGAACTTCACATCCAACGGCCCTGTGATGCAGAAGAAAAC
ACTCGGCTGGGAGGCCTTCACCGAGACGCTGTACCCCGCTGACGGCGGCCTGGAAGGCAGA
AACGACATGGCCCTGAAGCTCGTGGGCGGGAGCCATCTGATCGCAAACATCAAGACCACAT
ATAGATCCAAGAAACCCGCTAAGAACCTCAAGATGCCTGGCGTCTACTATGTGGACTACAG
ACTGGAAAGAATCAAGGAGGCCAACAACGAGACCTACGTCGAGCAGCACGAGGTGGCAGT
GGCCAGATACTGCGACCTCCCTAGCAAACTGGGGCACAAGCTTAATtAAGGGCCCGTTTAAA
CCCGCTGATCAGCCTCGACTGTGCCTTCTA SEQ ID NO: 50 (see e.g., polypeptide in SEQ ID NO: 13) - λN-linker-ADAR2(E488Q) DD-TagBFP
TAATACGACTCACTATAGGGAGACCCAAGCTGGctagaggatcgaacccggtaccgccaccATGGCCgacgcac
aaacacgacgacgtgagcgtcgcgctgagaaacaagctcaatggaaagctgcaaacACCGGTtctgggatttacgggggcagtgggagcggtg
caggatctggtagtccagctgggggaggagcaccgggtagcggtgggggtctcagctgcacctgccccaggttctcgcagacgccgtatcccgcctt
gtactgggcaagtttggtgatcttactgacaatttttcatctcctcatgcgaggcggaaagtactcgcaggcgtcgtcatgacgaccggaactgacgtgaaa
gacgccaaagtcatctctgtctccacgggcacaaagtgcataaacggggagtacatgagcgaccgggggctggcactgaatgattgtcacgctgaaat
aatatctaggcgatctctgcttagatttctctacactcaactcgaattgtaccttaacaacaaagatgaccagaaacgcagtatatttcagaaatcagaacgc
ggcggatttcgacttaaggaaaacgttcagttccacttgtatatcagcacatccccttgcggtgacgcccgaatcttttccccgcacgagccgatattggag
gagcccgcggacagacatcctaataggaaggctagaggccaacttcggacgaagattgaaagtggccagggtactatcccggtgcggtccaacgcta
gtattcaaacgtgggacggagtccttcaaggtgaacggctgttgacaatgagctgctcagacaaaatcgcgcgctggaatgtagtgggaatccaaggca
gcctcttgagcatattcgtagaacccatatatttctcatccattatttgggctctctgtatcatggtgaccatctgtcaagggctatgtaccaacgaatttctaat
atcgaggatcttcctccactctatacactcaataagcctctcttgtccgggatatcaaacgctgaggcccgccagccagggaaagctcctaacttcagtgtt
aactggaccgttggtgattctgcgatagaggtcatcaacgccacgacaggtaaggatgagctcggtagagcctcacgcctgtgtaaacacgcgttgtatt
gtagatggatgagagtacatgggaaggtcccatctcacttgctccgaagcaagatcactaagcctaatgtgtatcatgagtcaaaactcgcggctaaaga
ataccaggcagccaaagctcgactttttacagcttttattaaggcagggctcggggcatgggtcgagaagccgaccgagcaggaccaattctctctgacg
gggagcggatccAGCGAGCTGATTAAGGAGAACATGCACATGAAGCTGTACATGGAGGGCACCGT
GGACAACCATCACTTCAAGTGCACATCCGAGGGCGAAGGCAAGCCCTACGAGGGCACCCAG
ACCATGAGAATCAAGGTGGTCGAGGGCGGCCCTCTCCCCTTCGCCTTCGACATCCTGGCTAC
TAGCTTCCTCTACGGCAGCAAGACCTTCATCAACCACACCCAGGGCATCCCCGACTTCTTCA
AGCAGTCCTTCCCTGAGGGCTTCACATGGGAGAGAGTCACCACATACGAAGACGGGGGCGT
GCTGACCGCTACCCAGGACACCAGCCTCCAGGACGGCTGCCTCATCTACAACGTCAAGATCA
GAGGGGTGAACTTCACATCCAACGGCCCTGTGATGCAGAAGAAAACACTCGGCTGGGAGGC
CTTCACCGAGACGCTGTACCCCGCTGACGGCGGCCTGGAAGGCAGAAACGACATGGCCCTG
AAGCTCGTGGGCGGGAGCCATCTGATCGCAAACATCAAGACCACATATAGATCCAAGAAAC
CCGCTAAGAACCTCAAGATGCCTGGCGTCTACTATGTGGACTACAGACTGGAAAGAATCAA
GGAGGCCAACAACGAGACCTACGTCGAGCAGCACGAGGTGGCAGTGGCCAGATACTGCGAC
CTCCCTAGCAAACTGGGGCACAAGCTTAATtAAGGGCCCGTTTAAACCCGCTGATCAGCCTC
GACTGTGCCTTCTA SEQ ID NO: 51 (see e.g., polypeptide in SEQ ID NO: 14) - HIV-tat-linker-ADAR2(E488Q) DD-TagBFP
TAATACGACTCACTATAGGGAGACCCAAGCTGGctagaggatcgaacccggtaccgccaccATGGCCtctggtcc
tcgtccccgtggtactcgtggtaaaggtcgccgtattcgtcgcACCGGTtctgggatttacgggggcagtgggagcggtgcaggatctggtagtcc
agctgggggaggagcaccgggtagcggtgggggtctcagctgcacctgccccaggttctcgcagacgccgtatcccgccttgtactgggcaagtttg
gtgatcttactgacaatttttcatctcctcatgcgaggcggaaagtactcgcaggcgtcgtcatgacgaccggaactgacgtgaaagacgccaaagtcatc
tctgtctccacgggcacaaagtgcataaacggggagtacatgagcgaccgggggctggcactgaatgattgtcacgctgaaataatatctaggcgatctc
tgcttagatttctctacactcaactcgaattgtaccttaacaacaaagatgaccagaaacgcagtatatttcagaaatcagaacgcggcggatttcgacttaa
ggaaaacgttcagttccacttgtatatcagcacatccccttgcggtgacgcccgaatcttttccccgcacgagccgatattggaggagcccgcggacaga -continued catcctaataggaaggctagaggccaacttcggacgaagattgaaagtggccagggtactatcccggtgcggtccaacgctagtattcaaacgtgggac
ggagtccttcaaggtgaacggctgttgacaatgagctgctcagacaaaatcgcgcgctggaatgtagtgggaatccaaggcagcctcttgagcatattcg
tagaacccatatatttctcatccattatttgggctctctgtatcatggtgaccatctgtcaagggctatgtaccaacgaatttctaatatcgaggatcttcctcca
ctctatacactcaataagcctctcttgtccgggatatcaaacgctgaggcccgccagccagggaaagctcctaacttcagtgttaactggaccgttggtgat
tctgcgatagaggtcatcaacgccacgacaggtaaggatgagctcggtagagcctcacgcctgtgtaaacacgcgttgtattgtagatggatgagagtac
atgggaaggtcccatctcacttgctccgaagcaagatcactaagcctaatgtgtatcatgagtcaaaactcgcggctaaagaataccaggcagccaaagc
tcgacttttttacagcttttattaaggcagggctcggggcatgggtcgagaagccgaccgagcaggaccaattctctctgacggggagcggatccAGC
GAGCTGATTAAGGAGAACATGCACATGAAGCTGTACATGGAGGGCACCGTGGACAACCATC
ACTTCAAGTGCACATCCGAGGGCGAAGGCAAGCCCTACGAGGGCACCCAGACCATGAGAAT
CAAGGTGGTCGAGGGCGGCCCTCTCCCCTTCGCCTTCGACATCCTGGCTACTAGCTTCCTCTA
CGGCAGCAAGACCTTCATCAACCACACCCAGGGCATCCCCGACTTCTTCAAGCAGTCCTTCC
CTGAGGGCTTCACATGGGAGAGAGTCACCACATACGAAGACGGGGGCGTGCTGACCGCTAC
CCAGGACACCAGCCTCCAGGACGGCTGCCTCATCTACAACGTCAAGATCAGAGGGGTGAAC
TTCACATCCAACGGCCCTGTGATGCAGAAGAAAACACTCGGCTGGGAGGCCTTCACCGAGA
CGCTGTACCCCGCTGACGGCGGCCTGGAAGGCAGAAACGACATGGCCCTGAAGCTCGTGGG
CGGGAGCCATCTGATCGCAAACATCAAGACCACATATAGATCCAAGAAACCCGCTAAGAAC
CTCAAGATGCCTGGCGTCTACTATGTGGACTACAGACTGGAAAGAATCAAGGAGGCCAACA
ACGAGACCTACGTCGAGCAGCACGAGGTGGCAGTGGCCAGATACTGCGACCTCCCTAGCAA
ACTGGGGCACAAGCTTAATAAGGGCCCGTTTAAACCCGCTGATCAGCCTCGACTGTGCCTTC
TA SEQ ID NO: 52 (see e.g., polypeptide in SEQ ID NO: 15 & 16) - dTomato-BiCMV-EGFPd2-UAG-UAG-MS2-polyA; UAG-UAG is bolded; MS2 is bold italicized; polyA is bold double-underlined.

cggcagtgaaaaaaatgctttatttgtgaaatttgtgatgctattgctttatttgtaaccattataagctgcaataaacaagttaacaacaacaattgcattcatttt
atgtttcaggttcaggggggaggtgtgggaggttttttaaagcaagtaaaacctctacaaatgtggtatggctgattatgatcctctagactgcagcctcagga
gatctgggcccctacttgtacagctcgtccatgccgtacaggaacaggtggtggcggccctcggagcgctcgtactgttccacgatggtgtagtcctcgtt
gtgggaggtgatgtccagcttggtgtccacgtagtagtagccgggcagttgcacgggcttcttggccatgtagatggtcttgaactccaccaggtagtggc
cgccgtccttcagcttcagggcctggtggatctcgcccttcagcacgccgtcgcgggggtacaggcgctcggtggaggcctcccagcccatggtcttctt
ctgcattacggggccgtcggggggggaagttggtgccgcgcatcttcaccttgtagatcagcgtgccgtcctgcagggaggagtcctgggtcacggtcac
cagaccgccgtcctcgaagttcatcacgcgctcccacttgaagccctcggggaaggacagcttcttgtaatcggggatgtcggcggggtgcttcacgta
cgccttggagccgtacatgaactggggggacaggatgtcccaggcgaagggcagggggccgcccttggtcaccttcagcttggcggtctgggtgccc
tcgtaggggcggccctcgccctcgccctcgatctcgaactcgtggccgttcatggagccctccatgcgcaccttgaagcgcatgaactctttgatgacctc
ctcgcccttgctcaccatggtggcgaattctccaggcgatctgacggttcactaaacgagctctgcttatataggcctcccaccgtacacgccacctcgac
atactcgagtagttattaatagtaatcaattacggggtcattagttcatagcccatatatggagttccgcgttacataacttacggtaaatggcccgcctggct
gaccgcccaacgacccccgcccattgacgtcaataatgacgtatgttcccatagtaacgccaatagggactttccattgacgtcaatgggtggagtatttac
ggtaaactgcccacttggcagtacatcaagtgtatcatatgccaagtacgccccctattgacgtcaatgacggtaaatggcccgcctggcattatgcccag
tacatgaccttatgggactttcctacttggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgggactttccaaaatgtcgtaacaact
ccgccccattgacgcaaatgggcggtaggcgtgtacggtgggaggtctatataagcagagctggtttagtgaaccgtcagatccgctagggatcctcta
gtcagctgacgcgtgctagcgatatcggcgcgccagcatttaaatctgtacagaccggtcgccaccatggtgagcaagggcgaggagctgttcaccgg
ggtggtgcccatcctggtcgagctggacggcgacgtaaacggccacaagttcagcgtgtccggcgagggcgagggcgatgccacctacggcaagct
gaccctgaagttcatctgcaccaccggcaagctgcccgtgccctggcccaccctcgtgaccaccctgacctacggcgtgcagtgcttcagccgctaccc
cgaccacatgaagcagcacgacttcttcaagtccgccatgcccgaaggctacgtccaggagcgcaccatcttcttcaaggacgacggcaactacaaga
cccgcgccgaggtgaagttcgagggcgacaccctggtgaaccgcatcgagctgaagggcatcgacttcaaggaggacggcaacatcctggggcaca
agctggagtacaactacaacagccacaacgtctatatcatggccgacaagcagaagaacggcatcaaggtgaacttcaagatccgccacaacatcgag
gacggcagcgtgcagctcgccgaccactaccagcagaacacccccatcggcgacggccccgtgctgctgcccgacaaccactacctgagcacccag
tccgccctgagcaaagaccccaacgagaagcgcgatcacatggtcctgctggagttcgtgaccgccgccgggatcactctcggcatggacgagctgta
caagaagcttagccatggcttcccgccggaggtggaggagcaggatgatggcacgctgcccatgtcttgtgcccaggagagcgggatggaccgtcac
cctgcagcctgtgcttctgcCCggAtcAACgtgTAGCGCTAGCTTTGCCAGCGCCACACGaa*ACATGAGGA*
*TcACCCATGT*cggccgcactcctcaggtgcaggctgcctatcagaaggtggtggctggtgtggccaatgccctggctcacaaataccactgaga
tctttttccctctgccaaaaattatggggacatcatgaagccccttgGgcatctgacttctggctaataaaggaaatttattttcattgcaatagtgtgttgg
aatttttttgtgtctctcactcggaaggacatatgggagggcaaatcatttaaaacatcagaatgagt -continued SEQ ID NO: 53 (see e.g., polypeptide in SEQ ID NO: 17) - MCP-linker-ADAR2-DDN-
Bad(F)- ADAR2(E488Q)-DDC-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGGTCGGGCACCGGTGCTC
CACCCAATCTCTGGGCAGCGCAGCGCTACGGCCGTGAGCTCAGAAGGATGTCCGATGAGttcG
TCGACagacatcctaataggaaggctagaggccaacttcggacgaagattgaaagtggccagggtactatcccggtgcggtccaacgctagtattc
aaacgtgggacggagtccttcaaggtgaacggctgttgacaatgagctgctcagacaaaatcgcgcgctggaatgtagtgggaatccaaggcagcctct
tgagcatattcgtagaacccatatatttctcatccattattttgggctctctgtatcatggtgaccatctgtcaagggctatgtaccaacgaatttctaatatcgag
gatcttcctccactctatacactcaataagcctctcttgtccgggatatcaaacgctgaggcccgccagccagggaaagctcctaacttcagtgttaactgg
accgttggtgattctgcgatagaggtcatcaacgccacgacaggtaaggatgagctcggtagagcctcacgcctgtgtaaacacgcgttgtattgtagatg
gatgagagtacatgggaaggtcccatctcacttgctccgaagcaagatcactaagcctaatgtgtatcatgagtcaaaactcgcggctaaagaataccag
gcagccaaagctcgacttttacagcttttattaaggcagggctcggggcatgggtcgagaagccgaccgagcaggaccaattctctctgacggggagc
ggatccAGCGAGCTGATTAAGGAGAACATGCACATGAAGCTGTACATGGAGGGCACCGTGGAC
AACCATCACTTCAAGTGCACATCCGAGGGCGAAGGCAAGCCCTACGAGGGCACCCAGACCA
TGAGAATCAAGGTGGTCGAGGGCGGCCCTCTCCCCTTCGCCTTCGACATCCTGGCTACTAGC
TTCCTCTACGGCAGCAAGACCTTCATCAACCACACCCAGGGCATCCCCGACTTCTTCAAGCA
GTCCTTCCCTGAGGGCTTCACATGGGAGAGAGTCACCACATACGAAGACGGGGGCGTGCTG
ACCGCTACCCAGGACACCAGCCTCCAGGACGGCTGCCTCATCTACAACGTCAAGATCAGAG
GGGTGAACTTCACATCCAACGGCCCTGTGATGCAGAAGAAAACACTCGGCTGGGAGGCCTT
CACCGAGACGCTGTACCCCGCTGACGGCGGCCTGGAAGGCAGAAACGACATGGCCCTGAAG
CTCGTGGGCGGGAGCCATCTGATCGCAAACATCAAGACCACATATAGATCCAAGAAACCCG
CTAAGAACCTCAAGATGCCTGGCGTCTACTATGTGGACTACAGACTGGAAAGAATCAAGGA
GGCCAACAACGAGACCTACGTCGAGCAGCACGAGGTGGCAGTGGCCAGATACTGCGACCTC
CCTAGCAAACTGGGGCACAAGCTTAATtAAGGGCCCGTTTAAACCCGCTGATCAGCCTCGAC
TGTGCCTTCTA SEQ ID NO: 54 (see e.g., polypeptide in SEQ ID NO: 18) - MCP-linker-ADAR2-DDN-
Bad(F)- ADAR2(E488Q)-DDC-Bcl-xL-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGGTCGGGCACCGGTGCTC
CACCCAATCTCTGGGCAGCGCAGCGCTACGGCCGTGAGCTCAGAAGGATGTCCGATGAGttcG
TCGACagacatcctaataggaaggctagaggccaacttcggacgaagattgaaagtggccagggtactatcccggtgcggtccaacgctagtattc
aaacgtgggacggagtccttcaaggtgaacggctgttgacaatgagctgctcagacaaaatcgcgcgctggaatgtagtgggaatccaaggcagcctct
tgagcatattcgtagaacccatatatttctcatccattattttgggctctctgtatcatggtgaccatctgtcaagggctatgtaccaacgaatttctaatatcgag
gatcttcctccactctatacactcaataagcctctcttgtccgggatatcaaacgctgaggcccgccagccagggaaagctcctaacttcagtgttaactgg
accgttggtgattctgcgatagaggtcatcaacgccacgacaggtaaggatgagctcggtagagcctcacgcctgtgtaaacacgcgttgtattgtagatg
gatgagagtacatgggaaggtcccatctcacttgctccgaagcaagatcactaagcctaatgtgtatcatgagtcaaaactcgcggctaaagaataccag
gcagccaaagctcgacttttacagcttttattaaggcagggctcggggcatgggtcgagaagccgaccgagcaggaccaattctctctgacggggagc -continued GCGGCCGGAGGTAGCGGCGGAAGCGCGGCCGCTTCAAGTAACCGGGAGCTGGTGGTTGACT
TTCTCTCCTACAAGCTTTCCCAGAAAGGATACAGCTGGAGTCAGTTTAGTGATGTGGAAGAG
AACAGGACTGAGGCCCCAGAAGGGACTGAATCGGAGATGGAGACCCCCAGTGCCATCAATG
GCAACCCATCCTGGCACCTGGCAGACAGCCCCGCGGTGAATGGAGCCACTGGCCACAGCAG
CAGTTTGGATGCCCGGGAGGTGATCCCCATGGCAGCAGTAAAGCAAGCGCTGAGGGAGGCA
GGCGACGAGTTTGAACTGCGGTACCGGCGGGCATTCAGTGACCTGACATCCCAGCTCCACAT
CACCCCAGGGACAGCATATCAGAGCTTTGAACAGGTAGTGAATGAACTCTTCCGGGATGGG
GTAAACTGGGGTCGCATTGTGGCCTTTTTCTCCTTCGGCGGGGCACTGTGCGTGGAAAGCGT
AGACAAGGAGATGCAGGTATTGGTGAGTCGGATCGCAGCTTGGATGGCCACTTACCTGAAT
GACCACCTAGAGCCTTGGATCCAGGAGAACGGCGGCTGGGATACTTTTGTGGAACTCTATGG
GAACAATggatccAGCGAGCTGATTAAGGAGAACATGCACATGAAGCTGTACATGGAGGGCAC
CGTGGACAACCATCACTTCAAGTGCACATCCGAGGGCGAAGGCAAGCCCTACGAGGGCACC
CAGACCATGAGAATCAAGGTGGTCGAGGGCGGCCCTCTCCCCTTCGCCTTCGACATCCTGGC
TACTAGCTTCCTCTACGGCAGCAAGACCTTCATCAACCACACCCAGGGCATCCCCGACTTCT
TCAAGCAGTCCTTCCCTGAGGGCTTCACATGGGAGAGAGTCACCACATACGAAGACGGGGG
CGTGCTGACCGCTACCCAGGACACCAGCCTCCAGGACGGCTGCCTCATCTACAACGTCAAGA
TCAGAGGGGTGAACTTCACATCCAACGGCCCTGTGATGCAGAAGAAAACACTCGGCTGGGA
GGCCTTCACCGAGACGCTGTACCCCGCTGACGGCGGCCTGGAAGGCAGAAACGACATGGCC
CTGAAGCTCGTGGGCGGGAGCCATCTGATCGCAAACATCAAGACCACATATAGATCCAAGA
AACCCGCTAAGAACCTCAAGATGCCTGGCGTCTACTATGTGGACTACAGACTGGAAAGAAT
CAAGGAGGCCAACAACGAGACCTACGTCGAGCAGCACGAGGTGGCAGTGGCCAGATACTGC
GACCTCCCTAGCAAACTGGGGCACAAGCTTAATAAGGGCCCGTTTAAACCCGCTGATCAGC
CTCGACTGTGCCTTCTA SEQ ID NO: 55 (see e.g., polypeptide in SEQ ID NO: 19) - MCP-linker-ADAR2-DDN-Bim-
ADAR2(E488Q)-DDC-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGGTCGGGCTCTGGAGAC
ATGCGGCCAGAGATTTGGATCGCACAGGAACTGAGGCGCATTGGCGATGAGTTCAATGCAT
ACTATGCCCGAAGAACCGGTGACagacatcctaataggaaggctagaggccaacttcggacgaagattgaaagtggccagggta
ctatcccggtgcggtccaacgctagtattcaaacgtgggacggagtccttcaaggtgaacggctgttgacaatgagctgctcagacaaaatcgcgcgctg
gaatgtagtgggaatccaaggcagcctcttgagcatattcgtagaacccatatatttctcatccattattttgggctctctgtatcatggtgaccatctgtcaag
ggctatgtaccaacgaatttctaatatcgaggatcttcctccactctatacactcaataagcctctcttgtccgggatatcaaacgctgaggcccgccagcca
gggaaagctcctaacttcagtgttaactggaccgttggtgattctgcgatagaggtcatcaacgccacgacaggtaaggatgagctcggtagagcctcac
gcctgtgtaaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgactttttacagcttttattaaggcagggctcggggcatgggtcgagaagccgaccg
agcaggaccaattctctctgacggggagcggatccAGCGAGCTGATTAAGGAGAACATGCACATGAAGCTGTAC
ATGGAGGGCACCGTGGACAACCATCACTTCAAGTGCACATCCGAGGGCGAAGGCAAGCCCT
ACGAGGGCACCCAGACCATGAGAATCAAGGTGGTCGAGGGCGGCCCTCTCCCCTTCGCCTTC
GACATCCTGGCTACTAGCTTCCTCTACGGCAGCAAGACCTTCATCAACCACACCCAGGGCAT
CCCCGACTTCTTCAAGCAGTCCTTCCCTGAGGGCTTCACATGGGAGAGAGTCACCACATACG
AAGACGGGGGCGTGCTGACCGCTACCCAGGACACCAGCCTCCAGGACGGCTGCCTCATCTA
CAACGTCAAGATCAGAGGGGTGAACTTCACATCCAACGGCCCTGTGATGCAGAAGAAAACA
CTCGGCTGGGAGGCCTTCACCGAGACGCTGTACCCCGCTGACGGCGGCCTGGAAGGCAGAA
ACGACATGGCCCTGAAGCTCGTGGGCGGGAGCCATCTGATCGCAAACATCAAGACCACATA
TAGATCCAAGAAACCCGCTAAGAACCTCAAGATGCCTGGCGTCTACTATGTGGACTACAGAC -continued TGGAAAGAATCAAGGAGGCCAACAACGAGACCTACGTCGAGCAGCACGAGGTGGCAGTGG
CCAGATACTGCGACCTCCCTAGCAAACTGGGGCACAAGCTTAATtAAGGGCCCGTTTAAACC
CGCTGATCAGCCTCGACTGTGCCTTCTA SEQ ID NO: 56 (see e.g., polypeptide in SEQ ID NO: 20) - MCP-linker-ADAR2-DDN-Bim-
ADAR2(E488Q)-DDC-Bcl-xL-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGGTCGGGCTCTGGAGAC
ATGCGGCCAGAGATTTGGATCGCACAGGAACTGAGGCGCATTGGCGATGAGTTCAATGCAT
ACTATGCCCGAAGAACCGGTGACagacatcctaataggaaggctagaggccaacttcggacgaagattgaaagtggccagggta
ctatcccggtgcggtccaacgctagtattcaaacgtgggacggagtccttcaaggtgaacggctgttgacaatgagctgctcagacaaaatcgcgcgctg
gaatgtagtgggaatccaaggcagcctcttgagcatattcgtagaacccatatatttctcatccattattttgggctctctgtatcatggtgaccatctgtcaag
ggctatgtaccaacgaatttctaatatcgaggatcttcctccactctatacactcaataagcctctcttgtccgggatatcaaacgctgaggcccgccagcca
gggaaagctcctaacttcagtgttaactggaccgttggtgattctgcgatagaggtcatcaacgccacgacaggtaaggatgagctcggtagagcctcac
gcctgtgtaaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgactttttacagcttttattaaggcagggctcggggcatgggtcgagaagccgaccg
agcaggaccaattctctctgacggggagcGCGGCCGGAGGTAGCGGCGGAAGCGCGGCCGCTTCAAGTAACC
GGGAGCTGGTGGTTGACTTTCTCTCCTACAAGCTTTCCCAGAAAGGATACAGCTGGAGTCAG
TTTAGTGATGTGGAAGAGAACAGGACTGAGGCCCCAGAAGGGACTGAATCGGAGATGGAGA
CCCCCAGTGCCATCAATGGCAACCCATCCTGGCACCTGGCAGACAGCCCCGCGGTGAATGG
AGCCACTGGCCACAGCAGCAGTTTGGATGCCCGGGAGGTGATCCCCATGGCAGCAGTAAAG
CAAGCGCTGAGGGAGGCAGGCGACGAGTTTGAACTGCGGTACCGGCGGGCATTCAGTGACC
TGACATCCCAGCTCCACATCACCCCAGGGACAGCATATCAGAGCTTTGAACAGGTAGTGAAT
GAACTCTTCCGGGATGGGGTAAACTGGGGTCGCATTGTGGCCTTTTTCTCCTTCGGCGGGGC
ACTGTGCGTGGAAAGCGTAGACAAGGAGATGCAGGTATTGGTGAGTCGGATCGCAGCTTGG
ATGGCCACTTACCTGAATGACCACCTAGAGCCTTGGATCCAGGAGAACGGCGGCTGGGATA
CTTTTGTGGAACTCTATGGGAACAATggatccAGCGAGCTGATTAAGGAGAACATGCACATGAA
GCTGTACATGGAGGGCACCGTGGACAACCATCACTTCAAGTGCACATCCGAGGGCGAAGGC
AAGCCCTACGAGGGCACCCAGACCATGAGAATCAAGGTGGTCGAGGGCGGCCCTCTCCCCT
TCGCCTTCGACATCCTGGCTACTAGCTTCCTCTACGGCAGCAAGACCTTCATCAACCACACCC
AGGGCATCCCCGACTTCTTCAAGCAGTCCTTCCCTGAGGGCTTCACATGGGAGAGAGTCACC
ACATACGAAGACGGGGGCGTGCTGACCGCTACCCAGGACACCAGCCTCCAGGACGGCTGCC
TCATCTACAACGTCAAGATCAGAGGGGTGAACTTCACATCCAACGGCCCTGTGATGCAGAA
GAAAACACTCGGCTGGGAGGCCTTCACCGAGACGCTGTACCCCGCTGACGGCGGCCTGGAA
GGCAGAAACGACATGGCCCTGAAGCTCGTGGGCGGGAGCCATCTGATCGCAAACATCAAGA
CCACATATAGATCCAAGAAACCCGCTAAGAACCTCAAGATGCCTGGCGTCTACTATGTGGAC
TACAGACTGGAAAGAATCAAGGAGGCCAACAACGAGACCTACGTCGAGCAGCACGAGGTG
GCAGTGGCCAGATACTGCGACCTCCCTAGCAAACTGGGGCACAAGCTTAATtAAGGGCCCGT
TTAAACCCGCTGATCAGCCTCGACTGTGCCTTCTA SEQ ID NO: 57 (see e.g., polypeptide in SEQ ID NO: 21) - MCP-linker-ADAR2-DDN-
MS1(A)- ADAR2(E488Q)-DDC-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg -continued tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCGGCGGATCT
GGGCGACCAGAAATCTGGATGACACAAGGTTTACGCAGACTCGGAGATGAGGCAAATGCTT
ACTATGCTAGACGGACCGGTGACagacatcctaataggaaggctagaggccaacttcggacgaagattgaaagtggccagggta
ctatcccggtgcggtccaacgctagtattcaaacgtgggacggagtccttcaaggtgaacggctgttgacaatgagctgctcagacaaaatcgcgcgctg
gaatgtagtgggaatccaaggcagcctcttgagcatattcgtagaacccatatatttctcatccattattttgggctctctgtatcatggtgaccatctgtcaag
ggctatgtaccaacgaatttctaatatcgaggatcttcctccactctatacactcaataagcctctcttgtccgggatatcaaacgctgaggcccgccagcca
gggaaagctcctaacttcagtgttaactggaccgttggtgattctgcgatagaggtcatcaacgccacgacaggtaaggatgagctcggtagagcctcac
gcctgtgtaaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgactttttacagcttttattaaggcagggctcggggcatgggtcgagaagccgaccg
agcaggaccaattctctctgacggggagcggatccAGCGAGCTGATTAAGGAGAACATGCACATGAAGCTGTAC
ATGGAGGGCACCGTGGACAACCATCACTTCAAGTGCACATCCGAGGGCGAAGGCAAGCCCT
ACGAGGGCACCCAGACCATGAGAATCAAGGTGGTCGAGGGCGGCCCTCTCCCCTTCGCCTTC
GACATCCTGGCTACTAGCTTCCTCTACGGCAGCAAGACCTTCATCAACCACACCCAGGGCAT
CCCCGACTTCTTCAAGCAGTCCTTCCCTGAGGGCTTCACATGGGAGAGAGTCACCACATACG
AAGACGGGGGCGTGCTGACCGCTACCCAGGACACCAGCCTCCAGGACGGCTGCCTCATCTA
CAACGTCAAGATCAGAGGGGTGAACTTCACATCCAACGGCCCTGTGATGCAGAAGAAAACA
CTCGGCTGGGAGGCCTTCACCGAGACGCTGTACCCCGCTGACGGCGGCCTGGAAGGCAGAA
ACGACATGGCCCTGAAGCTCGTGGGCGGGAGCCATCTGATCGCAAACATCAAGACCACATA
TAGATCCAAGAAACCCGCTAAGAACCTCAAGATGCCTGGCGTCTACTATGTGGACTACAGAC
TGGAAAGAATCAAGGAGGCCAACAACGAGACCTACGTCGAGCAGCACGAGGTGGCAGTGG
CCAGATACTGCGACCTCCCTAGCAAACTGGGGCACAAGCTTAATtAAGGGCCCGTTTAAACC
CGCTGATCAGCCTCGACTGTGCCTTCTA SEQ ID NO: 58 (see e.g., polypeptide in SEQ ID NO: 22) - MCP-linker-ADAR2-DDN-MS1(A)- ADAR2(E488Q)-DDC-Mcl-1-TagBFP TAATACGACTCACTATAGGGAGACCCAAGCTGGctagaggatcgaacccttaaggccaccatggcgtccaatttcactca
gtttgtgctggttgacaacggcgggaccggggacgttacggtagccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCGGCGGATCT
GGGCGACCAGAAATCTGGATGACACAAGGTTTACGCAGACTCGGAGATGAGGCAAATGCTT
ACTATGCTAGACGGACCGGTGACagacatcctaataggaaggctagaggccaacttcggacgaagattgaaagtggccagggta
ctatcccggtgcggtccaacgctagtattcaaacgtgggacggagtccttcaaggtgaacggctgttgacaatgagctgctcagacaaaatcgcgcgctg
gaatgtagtgggaatccaaggcagcctcttgagcatattcgtagaacccatatatttctcatccattattttgggctctctgtatcatggtgaccatctgtcaag
ggctatgtaccaacgaatttctaatatcgaggatcttcctccactctatacactcaataagcctctcttgtccgggatatcaaacgctgaggcccgccagcca
gggaaagctcctaacttcagtgttaactggaccgttggtgattctgcgatagaggtcatcaacgccacgacaggtaaggatgagctcggtagagcctcac
gcctgtgtaaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgactttttacagcttttattaaggcagggctcggggcatgggtcgagaagccgaccg
agcaggaccaattctctctgacggggagcGGTACCGgCGgTccaggggacgagttgtaccggcagtcgctggagattatctctCGCtacctt
cgggagcaggccaccGGAgccaaggacacaaagccaatgggcaggtctggggccaccagcaggaaggcgctgGAAaccttacgacgggttg
gggatggcgtgcagcgcaaccacgagACTgccttccaaggcatgcttcggaaactggacatcaaaaacgaaGATgatgtgaaatcgttgtctAG
GgtgatgatccatgttttcagcgacggcgtaacaaactggggcaggattgtgactctcatttcttttggtgcctttgtggctaaacacttgAAAaccataa
accaagaaagctgcatcgaaccattagcagaaagtatcacagacgttctcgtaaggacaaaacgggactggctagttaaacaaagaggctgggatggg
tttgtggagttcttccatgtagaggacctagaaggtggcggatccAGCGAGCTGATTAAGGAGAACATGCACATGAAGC -continued TGTACATGGAGGGCACCGTGGACAACCATCACTTCAAGTGCACATCCGAGGGCGAAGGCAA
GCCCTACGAGGGCACCCAGACCATGAGAATCAAGGTGGTCGAGGGCGGCCCTCTCCCCTTC
GCCTTCGACATCCTGGCTACTAGCTTCCTCTACGGCAGCAAGACCTTCATCAACCACACCCA
GGGCATCCCCGACTTCTTCAAGCAGTCCTTCCCTGAGGGCTTCACATGGGAGAGAGTCACCA
CATACGAAGACGGGGGCGTGCTGACCGCTACCCAGGACACCAGCCTCCAGGACGGCTGCCT
CATCTACAACGTCAAGATCAGAGGGGTGAACTTCACATCCAACGGCCCTGTGATGCAGAAG
AAAACACTCGGCTGGGAGGCCTTCACCGAGACGCTGTACCCCGCTGACGGCGGCCTGGAAG
GCAGAAACGACATGGCCCTGAAGCTCGTGGGCGGGAGCCATCTGATCGCAAACATCAAGAC
CACATATAGATCCAAGAAACCCGCTAAGAACCTCAAGATGCCTGGCGTCTACTATGTGGACT
ACAGACTGGAAAGAATCAAGGAGGCCAACAACGAGACCTACGTCGAGCAGCACGAGGTGG
CAGTGGCCAGATACTGCGACCTCCCTAGCAAACTGGGGCACAAGCTTAATtAAGGGCCCGTT
TAAACCCGCTGATCAGCCTCGACTGTGCCTTCTA SEQ ID NO: 59 (see e.g., polypeptide in SEQ ID NO: 23) - MCP-linker-ADAR2-DDN-
Bad(L)- ADAR2(E488Q)-DDC-Bcl-xL-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGGTCGGGCACCGGTGCTC
CACCCAATCTCTGGGCAGCGCAGCGCTACGGCCGTGAGCTCAGAAGGATGTCCGATGAGcTG
GTCGACagacatcctaataggaaggctagaggccaacttcggacgaagattgaaagtggccagggtactatcccggtgcggtccaacgctagtatt
caaacgtgggacggagtccttcaaggtgaacggctgttgacaatgagctgctcagacaaaatcgcgcgctggaatgtagtgggaatccaaggcagcct
cttgagcatattcgtagaacccatatatttctcatccattattttgggctctctgtatcatggtgaccatctgtcaagggctatgtaccaacgaatttctaatatcg
aggatcttcctccactctatacactcaataagcctctcttgtccgggatatcaaacgctgaggcccgccagccagggaaagctcctaacttcagtgttaact
ggaccgttggtgattctgcgatagaggtcatcaacgccacgacaggtaaggatgagctcggtagagcctcacgcctgtgtaaacacgcgttgtattgtag
atggatgagagtacatgggaaggtcccatctcacttgctccgaagcaagatcactaagcctaatgtgtatcatgagtcaaaactcgcggctaaagaatacc
aggcagccaaagctcgacttttacagcttttattaaggcagggctcggggcatgggtcgagaagccgaccgagcaggaccaattctctctgacgggga
gcGCGGCCGGAGGTAGCGGCGGAAGCGCGGCCGCTTCAAGTAACCGGGAGCTGGTGGTTGA
CTTTCTCTCCTACAAGCTTTCCCAGAAAGGATACAGCTGGAGTCAGTTTAGTGATGTGGAAG
AGAACAGGACTGAGGCCCCAGAAGGGACTGAATCGGAGATGGAGACCCCCAGTGCCATCAA
TGGCAACCCATCCTGGCACCTGGCAGACAGCCCCGCGGTGAATGGAGCCACTGGCCACAGC
AGCAGTTTGGATGCCCGGGAGGTGATCCCCATGGCAGCAGTAAAGCAAGCGCTGAGGGAGG
CAGGCGACGAGTTTGAACTGCGGTACCGGCGGGCATTCAGTGACCTGACATCCCAGCTCCAC
ATCACCCCAGGGACAGCATATCAGAGCTTTGAACAGGTAGTGAATGAACTCTTCCGGGATG
GGGTAAACTGGGGTCGCATTGTGGCCTTTTTCTCCTTCGGCGGGGCACTGTGCGTGGAAAGC
GTAGACAAGGAGATGCAGGTATTGGTGAGTCGGATCGCAGCTTGGATGGCCACTTACCTGA
ATGACCACCTAGAGCCTTGGATCCAGGAGAACGGCGGCTGGGATACTTTTGTGGAACTCTAT
GGGAACAATggatccAGCGAGCTGATTAAGGAGAACATGCACATGAAGCTGTACATGGAGGGC
ACCGTGGACAACCATCACTTCAAGTGCACATCCGAGGGCGAAGGCAAGCCCTACGAGGGCA
CCCAGACCATGAGAATCAAGGTGGTCGAGGGCGGCCCTCTCCCCTTCGCCTTCGACATCCTG
GCTACTAGCTTCCTCTACGGCAGCAAGACCTTCATCAACCACACCCAGGGCATCCCCGACTT
CTTCAAGCAGTCCTTCCCTGAGGGCTTCACATGGGAGAGAGTCACCACATACGAAGACGGG
GGCGTGCTGACCGCTACCCAGGACACCAGCCTCCAGGACGGCTGCCTCATCTACAACGTCAA
GATCAGAGGGGTGAACTTCACATCCAACGGCCCTGTGATGCAGAAGAAAACACTCGGCTGG
GAGGCCTTCACCGAGACGCTGTACCCCGCTGACGGCGGCCTGGAAGGCAGAAACGACATGG
CCCTGAAGCTCGTGGGCGGGAGCCATCTGATCGCAAACATCAAGACCACATATAGATCCAA
GAAACCCGCTAAGAACCTCAAGATGCCTGGCGTCTACTATGTGGACTACAGACTGGAAAGA -continued ATCAAGGAGGCCAACAACGAGACCTACGTCGAGCAGCACGAGGTGGCAGTGGCCAGATACT
GCGACCTCCCTAGCAAACTGGGGCACAAGCTTAATtAAGGGCCCGTTTAAACCCGCTGATCA
GCCTCGACTGTGCCTTCTA SEQ ID NO: 60 (see e.g., polypeptide in SEQ ID NO: 24) - MCP-linker-ADAR2-DDN-
MS1(I)- ADAR2(E488Q)-DDC-Mcl-1-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCGGCGGATCT
GGGCGACCAGAAATCTGGATGACACAAGGTTTACGCAGACTCGGAGATGAGATAAATGCTT
ACTATGCTAGACGGACCGGTGACagacatcctaataggaaggctagaggccaacttcggacgaagattgaaagtggccagggta
ctatcccggtgcggtccaacgctagtattcaaacgtgggacggagtccttcaaggtgaacggctgttgacaatgagctgctcagacaaaatcgcgcgctg
gaatgtagtgggaatccaaggcagcctcttgagcatattcgtagaacccatatatttctcatccattattttgggctctctgtatcatggtgaccatctgtcaag
ggctatgtaccaacgaatttctaatatcgaggatcttcctccactctatacactcaataagcctctcttgtccgggatatcaaacgctgaggcccgccagcca
gggaaagctcctaacttcagtgttaactggaccgttggtgattctgcgatagaggtcatcaacgccacgacaggtaaggatgagctcggtagagcctcac
gcctgtgtaaacacgcgttgtattgtagatggatgagagtacatgggaaggtcccatctcacttgctccgaagcaagatcactaagcctaatgtgtatcatg
agtcaaaactcgcggctaaagaataccaggcagccaaagctcgactttttacagcttttattaaggcagggctcggggcatgggtcgagaagccgaccg
agcaggaccaattctctctgacggggagcGGTACCGgCGgTccaggggacgagttgtaccggcagtcgctggagattatctctCGCtacctt
cgggagcaggccaccGGAgccaaggacacaaagccaatgggcaggtctggggccaccagcaggaaggcgctgGAAaccttacgacgggttg
gggatggcgtgcagcgcaaccacgagACTgccttccaaggcatgcttcggaaactggacatcaaaaacgaaGATgatgtgaaatcgttgtctAG
GgtgatgatccatgttttcagcgacggcgtaacaaactggggcaggattgtgactctcatttcttttggtgcctttgtggctaaacacttgAAAaccataa
accaagaaagctgcatcgaaccattagcagaaagtatcacagacgttctcgtaaggacaaaacgggactggctagttaaacaaagaggctgggatggg
tttgtggagttcttccatgtagaggacctagaaggtggcggatccAGCGAGCTGATTAAGGAGAACATGCACATGAAGC
TGTACATGGAGGGCACCGTGGACAACCATCACTTCAAGTGCACATCCGAGGGCGAAGGCAA
GCCCTACGAGGGCACCCAGACCATGAGAATCAAGGTGGTCGAGGGCGGCCCTCTCCCCTTC
GCCTTCGACATCCTGGCTACTAGCTTCCTCTACGGCAGCAAGACCTTCATCAACCACACCCA
GGGCATCCCCGACTTCTTCAAGCAGTCCTTCCCTGAGGGCTTCACATGGGAGAGAGTCACCA
CATACGAAGACGGGGGCGTGCTGACCGCTACCCAGGACACCAGCCTCCAGGACGGCTGCCT
CATCTACAACGTCAAGATCAGAGGGGTGAACTTCACATCCAACGGCCCTGTGATGCAGAAG
AAAACACTCGGCTGGGAGGCCTTCACCGAGACGCTGTACCCCGCTGACGGCGGCCTGGAAG
GCAGAAACGACATGGCCCTGAAGCTCGTGGGCGGGAGCCATCTGATCGCAAACATCAAGAC
CACATATAGATCCAAGAAACCCGCTAAGAACCTCAAGATGCCTGGCGTCTACTATGTGGACT
ACAGACTGGAAAGAATCAAGGAGGCCAACAACGAGACCTACGTCGAGCAGCACGAGGTGG
CAGTGGCCAGATACTGCGACCTCCCTAGCAAACTGGGGCACAAGCTTAATtAAGGGCCCGTT
TAAACCCGCTGATCAGCCTCGACTGTGCCTTCTA SEQ ID NO: 61 (see e.g., polypeptide in SEQ ID NO: 25) - MCP-linker-ADAR2-DDN-
ALFA-ADAR2(E488Q)-DDC-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat -continued ccccttgcggtgacgcccgaatcttttccccgcacgagccgatattggaggagcccgcgGCTAGCCCATCCCGCCTGGAGGAAG
AACTTCGGAGGAGACTTACTGAGCCTACCGGTGACagacatcctaataggaaggctagaggccaacttcggacgaag
attgaaagtggccagggtactatcccggtgcggtccaacgctagtattcaaacgtgggacggagtccttcaaggtgaacggctgttgacaatgagctgct
cagacaaaatcgcgcgctggaatgtagtgggaatccaaggcagcctcttgagcatattcgtagaacccatatatttctcatccattattttgggctctctgtat
catggtgaccatctgtcaagggctatgtaccaacgaatttctaatatcgaggatcttcctccactctatacactcaataagcctctcttgtccgggatatcaaa
cgctgaggcccgccagccagggaaagctcctaacttcagtgttaactggaccgttggtgattctgcgatagaggtcatcaacgccacgacaggtaagga
tgagctcggtagagcctcacgcctgtgtaaacacgcgttgtattgtagatggatgagagtacatgggaaggtcccatctcacttgctccgaagcaagatca
ctaagcctaatgtgtatcatgagtcaaaactcgcggctaaagaataccaggcagccaaagctcgactttttacagcttttattaaggcagggctcggggcat
gggtcgagaagccgaccgagcaggaccaattctctctgacggggagcggatccAGCGAGCTGATTAAGGAGAACATGCAC
ATGAAGCTGTACATGGAGGGCACCGTGGACAACCATCACTTCAAGTGCACATCCGAGGGCG
AAGGCAAGCCCTACGAGGGCACCCAGACCATGAGAATCAAGGTGGTCGAGGGCGGCCCTCT
CCCCTTCGCCTTCGACATCCTGGCTACTAGCTTCCTCTACGGCAGCAAGACCTTCATCAACCA
CACCCAGGGCATCCCCGACTTCTTCAAGCAGTCCTTCCCTGAGGGCTTCACATGGGAGAGAG
TCACCACATACGAAGACGGGGGCGTGCTGACCGCTACCCAGGACACCAGCCTCCAGGACGG
CTGCCTCATCTACAACGTCAAGATCAGAGGGGTGAACTTCACATCCAACGGCCCTGTGATGC
AGAAGAAAACACTCGGCTGGGAGGCCTTCACCGAGACGCTGTACCCCGCTGACGGCGGCCT
GGAAGGCAGAAACGACATGGCCCTGAAGCTCGTGGGCGGGAGCCATCTGATCGCAAACATC
AAGACCACATATAGATCCAAGAAACCCGCTAAGAACCTCAAGATGCCTGGCGTCTACTATGT
GGACTACAGACTGGAAAGAATCAAGGAGGCCAACAACGAGACCTACGTCGAGCAGCACGA
GGTGGCAGTGGCCAGATACTGCGACCTCCCTAGCAAACTGGGGCACAAGCTTAATtAAGGGC
CCGTTTAAACCCGCTGATCAGCCTCGACTGTGCCTTCTA SEQ ID NO: 62 (see e.g., polypeptide in SEQ ID NO: 26) - MCP-linker-ADAR2-DDN-
ALFA-ADAR2(E488Q)-DDC-NbALFA-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCCCATCCCGCCTGGAGGAAG
AACTTCGGAGGAGACTTACTGAGCCTACCGGTGACagacatcctaataggaaggctagaggccaacttcggacgaag
attgaaagtggccagggtactatcccggtgcggtccaacgctagtattcaaacgtgggacggagtccttcaaggtgaacggctgttgacaatgagctgct
cagacaaaatcgcgcgctggaatgtagtgggaatccaaggcagcctcttgagcatattcgtagaacccatatatttctcatccattattttgggctctctgtat
catggtgaccatctgtcaagggctatgtaccaacgaatttctaatatcgaggatcttcctccactctatacactcaataagcctctcttgtccgggatatcaaa
cgctgaggcccgccagccagggaaagctcctaacttcagtgttaactggaccgttggtgattctgcgatagaggtcatcaacgccacgacaggtaagga
tgagctcggtagagcctcacgcctgtgtaaacacgcgttgtattgtagatggatgagagtacatgggaaggtcccatctcacttgctccgaagcaagatca
ctaagcctaatgtgtatcatgagtcaaaactcgcggctaaagaataccaggcagccaaagctcgactttttacagcttttattaaggcagggctcggggcat
gggtcgagaagccgaccgagcaggaccaattctctctgacggggagcGGAGGTACCGCCGAAGTTCAATTACAGGAAT
CGGGTGGAGGTCTGGTACAACCTGGGGGCTCTCTTCGCCTGAGTTGCACTGCCAGTGGAGTT
ACGATTTCTGCACTTAATGCTATGGCGATGGGTTGGTATCGTCAGGCCCCAGGGGAACGTCG
CGTCATGGTCGCTGCCGTTTCCGAACGTGGCAATGCTATGTACCGCGAGTCTGTTCAGGGCC
GCTTCACGGTTACCCGCGATTTTACAAATAAAATGGTATCGTTGCAAATGGACAACTTAAAG
CCAGAGGACACTGCTGTGTACTACTGTCACGTCCTTGAAGATCGTGTGGATTCCTTTCATGAT
TATTGGGGGCAGGGGACTCAGGTCACTGTATCCTCAGGaGCTggatccAGCGAGCTGATTAAGG
AGAACATGCACATGAAGCTGTACATGGAGGGCACCGTGGACAACCATCACTTCAAGTGCAC
ATCCGAGGGCGAAGGCAAGCCCTACGAGGGCACCCAGACCATGAGAATCAAGGTGGTCGAG
GGCGGCCCTCTCCCCTTCGCCTTCGACATCCTGGCTACTAGCTTCCTCTACGGCAGCAAGACC
TTCATCAACCACACCCAGGGCATCCCCGACTTCTTCAAGCAGTCCTTCCCTGAGGGCTTCAC
ATGGGAGAGAGTCACCACATACGAAGACGGGGGCGTGCTGACCGCTACCCAGGACACCAGC
CTCCAGGACGGCTGCCTCATCTACAACGTCAAGATCAGAGGGGTGAACTTCACATCCAACGG -continued CCCTGTGATGCAGAAGAAAACACTCGGCTGGGAGGCCTTCACCGAGACGCTGTACCCCGCT
GACGGCGGCCTGGAAGGCAGAAACGACATGGCCCTGAAGCTCGTGGGCGGGAGCCATCTGA
TCGCAAACATCAAGACCACATATAGATCCAAGAAACCCGCTAAGAACCTCAAGATGCCTGG
CGTCTACTATGTGGACTACAGACTGGAAAGAATCAAGGAGGCCAACAACGAGACCTACGTC
GAGCAGCACGAGGTGGCAGTGGCCAGATACTGCGACCTCCCTAGCAAACTGGGGCACAAGC
TTAATtAAGGGCCCGTTTAAACCCGCTGATCAGCCTCGACTGTGCCTTCTA SEQ ID NO: 63 (see e.g., polypeptide in SEQ ID NO: 27) - MCP-linker-ADAR2-DDN-
ALFA-PE- ADAR2(E488Q)-DDC-TagBFP
TAATACGACTCACTATAGGGAGACCCAAGCTGGctagaggatcgaacccttaaggccaccatggcgtccaatttcactca
gtttgtgctggttgacaacgggggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGATCAGGTCCAGGACGC
CTGGAGGAAGAACTTCGGAGGAGACTTTCTCCTGGAACCGGTGACagacatcctaataggaaggctagagg
ccaacttcggacgaagattgaaagtggccagggtactatcccggtgcggtccaacgctagtattcaaacgtgggacggagtccttcaaggtgaacggct
gttgacaatgagctgctcagacaaaatcgcgcgctggaatgtagtgggaatccaaggcagcctcttgagcatattcgtagaacccatatatttctcatccatt
atttgggctctctgtatcatggtgaccatctgtcaagggctatgtaccaacgaatttctaatatcgaggatcttcctccactctatacactcaataagcctctctt
gtccgggatatcaaacgctgaggcccgccagccagggaaagctcctaacttcagtgttaactggaccgttggtgattctgcgatagaggtcatcaacgcc
acgacaggtaaggatgagctcggtagagcctcacgcctgtgtaaacacgcgttgtattgtagatggatgagagtacatgggaaggtcccatctcacttgct
ccgaagcaagatcactaagcctaatgtgtatcatgagtcaaaactcgcggctaaagaataccaggcagccaaagctcgactttttacagcttttattaaggc
agggctcggggcatgggtcgagaagccgaccgagcaggaccaattctctctgacggggagcggatccAGCGAGCTGATTAAGGAG
AACATGCACATGAAGCTGTACATGGAGGGCACCGTGGACAACCATCACTTCAAGTGCACAT
CCGAGGGCGAAGGCAAGCCCTACGAGGGCACCCAGACCATGAGAATCAAGGTGGTCGAGG
GCGGCCCTCTCCCCTTCGCCTTCGACATCCTGGCTACTAGCTTCCTCTACGGCAGCAAGACCT
TCATCAACCACACCCAGGGCATCCCCGACTTCTTCAAGCAGTCCTTCCCTGAGGGCTTCACA
TGGGAGAGAGTCACCACATACGAAGACGGGGGCGTGCTGACCGCTACCCAGGACACCAGCC
TCCAGGACGGCTGCCTCATCTACAACGTCAAGATCAGAGGGGTGAACTTCACATCCAACGGC
CCTGTGATGCAGAAGAAAACACTCGGCTGGGAGGCCTTCACCGAGACGCTGTACCCCGCTG
ACGGCGGCCTGGAAGGCAGAAACGACATGGCCCTGAAGCTCGTGGGCGGGAGCCATCTGAT
CGCAAACATCAAGACCACATATAGATCCAAGAAACCCGCTAAGAACCTCAAGATGCCTGGC
GTCTACTATGTGGACTACAGACTGGAAAGAATCAAGGAGGCCAACAACGAGACCTACGTCG
AGCAGCACGAGGTGGCAGTGGCCAGATACTGCGACCTCCCTAGCAAACTGGGGCACAAGCT
TAATtAAGGGCCCGTTTAAACCCGCTGATCAGCCTCGACTGTGCCTTCTA SEQ ID NO: 64 (see e.g., polypeptide in SEQ ID NO: 28) - MCP-linker-ADAR2-DDN-
ALFA-PE- ADAR2(E488Q)-DDC-NbALFA-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGATCAGGTCCAGGACGC
CTGGAGGAAGAACTTCGGAGGAGACTTTCTCCTGGAACCGGTGACagacatcctaataggaaggctagagg
ccaacttcggacgaagattgaaagtggccagggtactatcccggtgcggtccaacgctagtattcaaacgtgggacggagtccttcaaggtgaacggct -continued gttgacaatgagctgctcagacaaaatcgcgcgctggaatgtagtgggaatccaaggcagcctcttgagcatattcgtagaacccatatatttctcatccatt
attttgggctctctgtatcatggtgaccatctgtcaagggctatgtaccaacgaatttctaatatcgaggatcttcctccactctatacactcaataagcctctctt
gtccgggatatcaaacgctgaggcccgccagccagggaaagctcctaacttcagtgttaactggaccgttggtgattctgcgatagaggtcatcaacgcc
acgacaggtaaggatgagctcggtagagcctcacgcctgtgtaaacacgcgttgtattgtagatggatgagagtacatgggaaggtcccatctcacttgct
ccgaagcaagatcactaagcctaatgtgtatcatgagtcaaaactcgcggctaaagaataccaggcagccaaagctcgactttttacagcttttattaaggc
agggctcggggcatgggtcgagaagccgaccgagcaggaccaattctctctgacggggagcGGAGGTACCGCCGAAGTTCAAT
TACAGGAATCGGGTGGAGGTCTGGTACAACCTGGGGGCTCTCTTCGCCTGAGTTGCACTGCC
AGTGGAGTTACGATTTCTGCACTTAATGCTATGGCGATGGGTTGGTATCGTCAGGCCCCAGG
GGAACGTCGCGTCATGGTCGCTGCCGTTTCCGAACGTGGCAATGCTATGTACCGCGAGTCTG
TTCAGGGCCGCTTCACGGTTACCCGCGATTTTACAAATAAAATGGTATCGTTGCAAATGGAC
AACTTAAAGCCAGAGGACACTGCTGTGTACTACTGTCACGTCCTTGAAGATCGTGTGGATTC
CTTTCATGATTATTGGGGGCAGGGGACTCAGGTCACTGTATCCTCAGGaGCTggatccAGCGAG
CTGATTAAGGAGAACATGCACATGAAGCTGTACATGGAGGGCACCGTGGACAACCATCACT
TCAAGTGCACATCCGAGGGCGAAGGCAAGCCCTACGAGGGCACCCAGACCATGAGAATCAA
GGTGGTCGAGGGCGGCCCTCTCCCCTTCGCCTTCGACATCCTGGCTACTAGCTTCCTCTACGG
CAGCAAGACCTTCATCAACCACACCCAGGGCATCCCCGACTTCTTCAAGCAGTCCTTCCCTG
AGGGCTTCACATGGGAGAGAGTCACCACATACGAAGACGGGGGCGTGCTGACCGCTACCCA
GGACACCAGCCTCCAGGACGGCTGCCTCATCTACAACGTCAAGATCAGAGGGGTGAACTTC
ACATCCAACGGCCCTGTGATGCAGAAGAAAACACTCGGCTGGGAGGCCTTCACCGAGACGC
TGTACCCCGCTGACGGCGGCCTGGAAGGCAGAAACGACATGGCCCTGAAGCTCGTGGGCGG
GAGCCATCTGATCGCAAACATCAAGACCACATATAGATCCAAGAAACCCGCTAAGAACCTC
AAGATGCCTGGCGTCTACTATGTGGACTACAGACTGGAAAGAATCAAGGAGGCCAACAACG
AGACCTACGTCGAGCAGCACGAGGTGGCAGTGGCCAGATACTGCGACCTCCCTAGCAAACT
GGGGCACAAGCTTAATtAAGGGCCCGTTTAAACCCGCTGATCAGCCTCGACTGTGCCTTCTA SEQ ID NO: 65 (see e.g., polypeptide in SEQ ID NO: 29) - MCP-linker-ADAR2-DDN-ALFA-78- ADAR2(E488Q)-DDC-TagBFP TAATACGACTCACTATAGGGAGACCCAAGCTGGctagaggatcgaacccttaaggccaccatggcgtccaatttcactca
gtttgtgctggttgacaacggcgggaccggggacgttacggtagcccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGATCAGGTCCAGGCCGCC
TGGAGCAGGAAATTCGGGCAAGACTTTCTCCTGGAACCGGTGACagacatcctaataggaaggctagaggcc
aacttcggacgaagattgaaagtggccagggtactatcccggtgcggtccaacgctagtattcaaacgtgggacggagtccttcaaggtgaacggctgtt
gacaatgagctgctcagacaaaatcgcgcgctggaatgtagtgggaatccaaggcagcctcttgagcatattcgtagaacccatatatttctcatccattatt
ttgggctctctgtatcatggtgaccatctgtcaagggctatgtaccaacgaatttctaatatcgaggatcttcctccactctatacactcaataagcctctcttgt
ccgggatatcaaacgctgaggcccgccagccagggaaagctcctaacttcagtgttaactggaccgttggtgattctgcgatagaggtcatcaacgcca
cgacaggtaaggatgagctcggtagagcctcacgcctgtgtaaacacgcgttgtattgtagatggatgagagtacatgggaaggtcccatctcacttgctc
cgaagcaagatcactaagcctaatgtgtatcatgagtcaaaactcgcggctaaagaataccaggcagccaaagctcgactttttacagcttttattaaggca
gggctcggggcatgggtcgagaagccgaccgagcaggaccaattctctctgacggggagcggatccAGCGAGCTGATTAAGGAGA
ACATGCACATGAAGCTGTACATGGAGGGCACCGTGGACAACCATCACTTCAAGTGCACATC
CGAGGGCGAAGGCAAGCCCTACGAGGGCACCCAGACCATGAGAATCAAGGTGGTCGAGGG
CGGCCCTCTCCCCTTCGCCTTCGACATCCTGGCTACTAGCTTCCTCTACGGCAGCAAGACCTT
CATCAACCACACCCAGGGCATCCCCGACTTCTTCAAGCAGTCCTTCCCTGAGGGCTTCACAT
GGGAGAGAGTCACCACATACGAAGACGGGGGCGTGCTGACCGCTACCCAGGACACCAGCCT
CCAGGACGGCTGCCTCATCTACAACGTCAAGATCAGAGGGGTGAACTTCACATCCAACGGC
CCTGTGATGCAGAAGAAAACACTCGGCTGGGAGGCCTTCACCGAGACGCTGTACCCCGCTG
ACGGCGGCCTGGAAGGCAGAAACGACATGGCCCTGAAGCTCGTGGGCGGGAGCCATCTGAT
CGCAAACATCAAGACCACATATAGATCCAAGAAACCCGCTAAGAACCTCAAGATGCCTGGC -continued GTCTACTATGTGGACTACAGACTGGAAAGAATCAAGGAGGCCAACAACGAGACCTACGTCG
AGCAGCACGAGGTGGCAGTGGCCAGATACTGCGACCTCCCTAGCAAACTGGGGCACAAGCT
TAATtAAGGGCCCGTTTAAACCCGCTGATCAGCCTCGACTGTGCCTTCTA SEQ ID NO: 66 (see e.g., polypeptide in SEQ ID NO: 30) - MCP-linker-ADAR2-DDN-
ALFA-PE- ADAR2(E488Q)-DDC-NbALFA-TagBFP
TAATACGACTCACTATAGGGAGACCCAAGCTGGctagaggatcgaacccttaaggccaccatggcgtccaatttcactca
gtttgtgctggttgacaacgggggaccggggacgttacggtagccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGATCAGGTCCAGGCCGCC
TGGAGCAGGAAATTCGGGCAAGACTTTCTCCTGGAACCGGTGACagacatcctaataggaaggctagaggcc
aacttcggacgaagattgaaagtggccagggtactatcccggtgcggtccaacgctagtattcaaacgtgggacggagtccttcaaggtgaacggctgtt
gacaatgagctgctcagacaaaatcgcgcgctggaatgtagtgggaatccaaggcagcctcttgagcatattcgtagaacccatatatttctcatccattatt
ttgggctctctgtatcatggtgaccatctgtcaagggctatgtaccaacgaatttctaatatcgaggatcttcctccactctatacactcaataagcctctcttgt
ccgggatatcaaacgctgaggcccgccagccagggaaagctcctaacttcagtgttaactggaccgttggtgattctgcgatagaggtcatcaacgcca
cgacaggtaaggatgagctcggtagagcctcacgcctgtgtaaacacgcgttgtattgtagatggatgagagtacatgggaaggtcccatctcacttgctc
cgaagcaagatcactaagcctaatgtgtatcatgagtcaaaactcgcggctaaagaataccaggcagccaaagctcgactttttacagcttttattaaggca
gggctcggggcatgggtcgagaagccgaccgagcaggaccaattctctctgacggggagcGGAGGTACCGCCGAAGTTCAATT
ACAGGAATCGGGTGGAGGTCTGGTACAACCTGGGGGCTCTCTTCGCCTGAGTTGCACTGCCA
GTGGAGTTACGATTTCTGCACTTAATGCTATGGCGATGGGTTGGTATCGTCAGGCCCCAGGG
GAACGTCGCGTCATGGTCGCTGCCGTTTCCGAACGTGGCAATGCTATGTACCGCGAGTCTGT
TCAGGGCCGCTTCACGGTTACCCGCGATTTTACAAATAAAATGGTATCGTTGCAAATGGACA
ACTTAAAGCCAGAGGACACTGCTGTGTACTACTGTCACGTCCTTGAAGATCGTGTGGATTCC
TTTCATGATTATTGGGGGCAGGGGACTCAGGTCACTGTATCCTCAGGaGCTggatccAGCGAGCT
GATTAAGGAGAACATGCACATGAAGCTGTACATGGAGGGCACCGTGGACAACCATCACTTC
AAGTGCACATCCGAGGGCGAAGGCAAGCCCTACGAGGGCACCCAGACCATGAGAATCAAG
GTGGTCGAGGGCGGCCCTCTCCCCTTCGCCTTCGACATCCTGGCTACTAGCTTCCTCTACGGC
AGCAAGACCTTCATCAACCACACCCAGGGCATCCCCGACTTCTTCAAGCAGTCCTTCCCTGA
GGGCTTCACATGGGAGAGAGTCACCACATACGAAGACGGGGGCGTGCTGACCGCTACCCAG
GACACCAGCCTCCAGGACGGCTGCCTCATCTACAACGTCAAGATCAGAGGGGTGAACTTCA
CATCCAACGGCCCTGTGATGCAGAAGAAAACACTCGGCTGGGAGGCCTTCACCGAGACGCT
GTACCCCGCTGACGGCGGCCTGGAAGGCAGAAACGACATGGCCCTGAAGCTCGTGGGCGGG
AGCCATCTGATCGCAAACATCAAGACCACATATAGATCCAAGAAACCCGCTAAGAACCTCA
AGATGCCTGGCGTCTACTATGTGGACTACAGACTGGAAAGAATCAAGGAGGCCAACAACGA
GACCTACGTCGAGCAGCACGAGGTGGCAGTGGCCAGATACTGCGACCTCCCTAGCAAACTG
GGGCACAAGCTTAATtAAGGGCCCGTTTAAACCCGCTGATCAGCCTCGACTGTGCCTTCTA SEQ ID NO: 67 (see e.g., polypeptide in SEQ ID NO: 31) - miRFP670-ALFA
TAATACGACTCACTATAGGGAGACCCAAGCTGGCTAGCGTTTAAACTTAAGCTTatggtagcaggtc
atgcctctggcagccccgcattcgggaccgcctctcattcgaattgcgaacatgaagagatccacctcgccggctcgatccagccgcatggcgcgcttct
ggtcgtcagcgaacatgatcatcgcgtcatccaggccagcgccaacgccgcggaatttctgaatctcggaagcgtactcggcgttccgctcgccgagat
cgacggcgatctgttgatcaagatcctgccgcatctcgatcccaccgccgaaggcatgccggtcgcggtgcgctgccggatcggcaatccctctacgg
agtactgcggtctgatgcatcggcctccggaaggcgggctgatcatcgaactcgaacgtgccggcccgtcgatcgatctgtcaggcacgctggcgccg
gcgctggagcggatccgcacggcgggttcactgcgcgcgctgtgcgatgacaccgtgctgctgtttcagcagtgcaccggctacgaccgggtgatggt
gtatcgtttcgatgagcaaggccacggcctggtattctccgagtgccatgtgcctgggctcgaatcctatttcggcaaccgctatccgtcgtcgactgtccc
gcagatggcgcggcagctgtacgtgcggcagcgcgtccgcgtgctggtcgacgtcacctatcagccggtgccgctggagccgcggctgtcgccgctg -continued accgggcgcgatctcgacatgtcgggctgcttcctgcgctcgatgtcgccgtgccatctgcagttcctgaaggacatgggcgtgcgcgccaccctggcg
gtgtcgctggtggtcggcggcaagctgtggggcctggttgtctgtcaccattatctgccgcgcttcatccgtttcgagctgcgggcgatctgcaaacggct
cgccgaaaggatcgcgacgcggatcaccgcgcttgagagcCTCGAGTCCCGCCTGGAGGAAGAACTTCGGAGGAG
ACTTACTGAGtaatctagagggccctattctatagtgtcacctaaatgctagagctcgctgatcagcctcgactgtgccttcta SEQ ID NO: 68 (see e.g., polypeptide in SEQ ID NO: 32) - MCP-linker-ADAR2-DDN-
SpyTag- ADAR2(E488Q)-DDC-TagBFP
TAATACGACTCACTATAGGGAGACCCAAGCTGGctagaggatcgaacccttaaggccaccatggcgtccaatttcactca
gtttgtgctggttgacaacgggggaccggggacgttacggtagcccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCggagcccacatcgtg
atggtggacgcctacaagccgacgaagGGAACCGGTGACagacatcctaataggaaggctagaggccaacttcggacgaagattgaaagt
ggccagggtactatcccggtgcggtccaacgctagtattcaaacgtgggacggagtccttcaaggtgaacggctgttgacaatgagctgctcagacaaa
atcgcgcgctggaatgtagtgggaatccaaggcagcctcttgagcatattcgtagaacccatatatttctcatccattattttgggctctctgtatcatggtgac
catctgtcaagggctatgtaccaacgaatttctaatatcgaggatcttcctccactctatacactcaataagcctctcttgtccgggatatcaaacgctgaggc
ccgccagccagggaaagctcctaacttcagtgttaactggaccgttggtgattctgcgatagaggtcatcaacgccacgacaggtaaggatgagctcggt
agagcctcacgcctgtgtaaacacgcgttgtattgtagatggatgagagtacatgggaaggtcccatctcacttgctccgaagcaagatcactaagcctaa
tgtgtatcatgagtcaaaactcgcggctaaagaataccaggcagccaaagctcgactttttacagcttttattaaggcagggctcggggcatgggtcgaga
agccgaccgagcaggaccaattctctctgacggggagcggatccAGCGAGCTGATTAAGGAGAACATGCACATGAAG
CTGTACATGGAGGGCACCGTGGACAACCATCACTTCAAGTGCACATCCGAGGGCGAAGGCA
AGCCCTACGAGGGCACCCAGACCATGAGAATCAAGGTGGTCGAGGGCGGCCCTCTCCCCTT
CGCCTTCGACATCCTGGCTACTAGCTTCCTCTACGGCAGCAAGACCTTCATCAACCACACCC
AGGGCATCCCCGACTTCTTCAAGCAGTCCTTCCCTGAGGGCTTCACATGGGAGAGAGTCACC
ACATACGAAGACGGGGGCGTGCTGACCGCTACCCAGGACACCAGCCTCCAGGACGGCTGCC
TCATCTACAACGTCAAGATCAGAGGGGTGAACTTCACATCCAACGGCCCTGTGATGCAGAA
GAAAACACTCGGCTGGGAGGCCTTCACCGAGACGCTGTACCCCGCTGACGGCGGCCTGGAA
GGCAGAAACGACATGGCCCTGAAGCTCGTGGGGGGAGCCATCTGATCGCAAACATCAAGA
CCACATATAGATCCAAGAAACCCGCTAAGAACCTCAAGATGCCTGGCGTCTACTATGTGGAC
TACAGACTGGAAAGAATCAAGGAGGCCAACAACGAGACCTACGTCGAGCAGCACGAGGTG
GCAGTGGCCAGATACTGCGACCTCCCTAGCAAACTGGGGCACAAGCTTAATtAAGGGCCCGT
TTAAACCCGCTGATCAGCCTCGACTGTGCCTTCTA SEQ ID NO: 69 (see e.g., polypeptide in SEQ ID NO: 33) - MCP-linker-ADAR2-DDN-
SpyTag- ADAR2(E488Q)-DDC-SpyCatcher-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCggagcccacatcgtg
atggtggacgcctacaagccgacgaagGGAACCGGTGACagacatcctaataggaaggctagaggccaacttcggacgaagattgaaagt
ggccagggtactatcccggtgcggtccaacgctagtattcaaacgtgggacggagtccttcaaggtgaacggctgttgacaatgagctgctcagacaaa
atcgcgcgctggaatgtagtgggaatccaaggcagcctcttgagcatattcgtagaacccatatatttctcatccattattttgggctctctgtatcatggtgac
catctgtcaagggctatgtaccaacgaatttctaatatcgaggatcttcctccactctatacactcaataagcctctcttgtccgggatatcaaacgctgaggc -continued ccgccagccagggaaagctcctaacttcagtgttaactggaccgttggtgattctgcgatagaggtcatcaacgccacgacaggtaaggatgagctcggt
agagcctcacgcctgtgtaaacacgcgttgtattgtagatggatgagagtacatgggaaggtcccatctcacttgctccgaagcaagatcactaagcctaa
tgtgtatcatgagtcaaaactcgcggctaaagaataccaggcagccaaagctcgactttttacagcttttattaaggcagggctcggggcatgggtcgaga
agccgaccgagcaggaccaattctctctgacggggagcGGTACCagcggaggcgccatggttgataccttatcaggtttatcaagtgagcaaggt
cagtccggtgatatgacaattgaagaagatagtgctacccatattaaattctcaaaacgtgatgaggacggcaaagagttagctggtgcaactatggagtt
gcgtgattcatctggtaaaactattagtacatggatttcagatggacaagtgaaagatttctacctgtatccaggaaaatatacatttgtcgaaaccgcagcac
cagacggttatgaggtagcaactgctattacctttacagttaatgagcaaggtcaggttactgtaaatggcaaagcaactaaaggtgacgctcatattggat
ccAGCGAGCTGATTAAGGAGAACATGCACATGAAGCTGTACATGGAGGGCACCGTGGACAA
CCATCACTTCAAGTGCACATCCGAGGGCGAAGGCAAGCCCTACGAGGGCACCCAGACCATG
AGAATCAAGGTGGTCGAGGGCGGCCCTCTCCCCTTCGCCTTCGACATCCTGGCTACTAGCTT
CCTCTACGGCAGCAAGACCTTCATCAACCACACCCAGGGCATCCCCGACTTCTTCAAGCAGT
CCTTCCCTGAGGGCTTCACATGGGAGAGAGTCACCACATACGAAGACGGGGGCGTGCTGAC
CGCTACCCAGGACACCAGCCTCCAGGACGGCTGCCTCATCTACAACGTCAAGATCAGAGGG
GTGAACTTCACATCCAACGGCCCTGTGATGCAGAAGAAAACACTCGGCTGGGAGGCCTTCA
CCGAGACGCTGTACCCCGCTGACGGCGGCCTGGAAGGCAGAAACGACATGGCCCTGAAGCT
CGTGGGCGGGAGCCATCTGATCGCAAACATCAAGACCACATATAGATCCAAGAAACCCGCT
AAGAACCTCAAGATGCCTGGCGTCTACTATGTGGACTACAGACTGGAAAGAATCAAGGAGG
CCAACAACGAGACCTACGTCGAGCAGCACGAGGTGGCAGTGGCCAGATACTGCGACCTCCC
TAGCAAACTGGGGCACAAGCTTAATtAAGGGCCCGTTTAAACCCGCTGATCAGCCTCGACTG
TGCCTTCTA SEQ ID NO: 70 (see e.g., polypeptide in SEQ ID NO: 34) - MCP-linker-ADAR2-DDN-
SpyTag- ADAR2(E488Q)-DDC-TagBFP -P2A-T2A-SpyCatcher
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCggagcccacatcgtg
atggtggacgcctacaagccgacgaagGGAACCGGTGACagacatcctaataggaaggctagaggccaacttcggacgaagattgaaagt
ggccagggtactatcccggtgcggtccaacgctagtattcaaacgtgggacggagtccttcaaggtgaacggctgttgacaatgagctgctcagacaaa
atcgcgcgctggaatgtagtgggaatccaaggcagcctcttgagcatattcgtagaacccatatatttctcatccattattttggctctctgtatcatggtgac
catctgtcaagggctatgtaccaacgaatttctaatatcgaggatcttcctccactctatacactcaataagcctctcttgtccgggatatcaaacgctgaggc
ccgccagccagggaaagctcctaacttcagtgttaactggaccgttggtgattctgcgatagaggtcatcaacgccacgacaggtaaggatgagctcggt
agagcctcacgcctgtgtaaacacgcgttgtattgtagatggatgagagtacatgggaaggtcccatctcacttgctccgaagcaagatcactaagcctaa
tgtgtatcatgagtcaaaactcgcggctaaagaataccaggcagccaaagctcgactttttacagcttttattaaggcagggctcggggcatgggtcgaga
agccgaccgagcaggaccaattctctctgacggggagcggatccAGCGAGCTGATTAAGGAGAACATGCACATGAAG
CTGTACATGGAGGGCACCGTGGACAACCATCACTTCAAGTGCACATCCGAGGGCGAAGGCA
AGCCCTACGAGGGCACCCAGACCATGAGAATCAAGGTGGTCGAGGGCGGCCCTCTCCCCTT
CGCCTTCGACATCCTGGCTACTAGCTTCCTCTACGGCAGCAAGACCTTCATCAACCACACCC
AGGGCATCCCCGACTTCTTCAAGCAGTCCTTCCCTGAGGGCTTCACATGGGAGAGAGTCACC
ACATACGAAGACGGGGGCGTGCTGACCGCTACCCAGGACACCAGCCTCCAGGACGGCTGCC
TCATCTACAACGTCAAGATCAGAGGGGTGAACTTCACATCCAACGGCCCTGTGATGCAGAA
GAAAACACTCGGCTGGGAGGCCTTCACCGAGACGCTGTACCCCGCTGACGGCGGCCTGGAA
GGCAGAAACGACATGGCCCTGAAGCTCGTGGGCGGGAGCCATCTGATCGCAAACATCAAGA
CCACATATAGATCCAAGAAACCCGCTAAGAACCTCAAGATGCCTGGCGTCTACTATGTGGAC
TACAGACTGGAAAGAATCAAGGAGGCCAACAACGAGACCTACGTCGAGCAGCACGAGGTG
GCAGTGGCCAGATACTGCGACCTCCCTAGCAAACTGGGGCACAAGCTTAATACTAGTGCCAC
AAACTTCTCTCTGCTAAAGCAAGCAGGTGATGTTGAAGAAAACCCAGGGCCTGGAGGGTCC
GAGGGCAGGGGAAGTCTCCTAACATGCGGGGACGTGGAGGAAAATCCCGGACCAGGTACCa -continued gcggaggcgccatggttgataccttatcaggtttatcaagtgagcaaggtcagtccggtgatatgacaattgaagaagatagtgctacccatattaaattctc
aaaacgtgatgaggacggcaaagagttagctggtgcaactatggagttgcgtgattcatctggtaaaactattagtacatggatttcagatggacaagtga
aagatttctacctgtatccaggaaaatatacatttgtcgaaaccgcagcaccagacggttatgaggtagcaactgctattacctttacagttaatgagcaagg
tcaggttactgtaaatggcaaagcaactaaaggtgacgctcatattggatAAGGGCCCGTTTAAACCCGCTGATCAGCCTCG
ACTGTGCCTTCTA SEQ ID NO: 71 (see e.g., polypeptide in SEQ ID NO: 35) - MCP-linker-ADAR2-DDN-
SpyTag- ADAR2(E488Q)-DDC-TEVcs-SpyCatcher-TagBFP
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccggggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGAGGTAGCggagcccacatcgtg
atggtggacgcctacaagccgacgaagGGAACCGGTGACagacatcctaataggaaggctagaggccaacttcggacgaagattgaaagt
ggccagggtactatcccggtgcggtccaacgctagtattcaaacgtgggacggagtccttcaaggtgaacggctgttgacaatgagctgctcagacaaa
atcgcgcgctggaatgtagtgggaatccaaggcagcctcttgagcatattcgtagaacccatatatttctcatccattatttgggctctctgtatcatggtgac
catctgtcaagggctatgtaccaacgaatttctaatatcgaggatcttcctccactctatacactcaataagcctctcttgtccgggatatcaaacgctgaggc
ccgccagccagggaaagctcctaacttcagtgttaactggaccgttggtgattctgcgatagaggtcatcaacgccacgacaggtaaggatgagctcggt
agagcctcacgcctgtgtaaacacgcgttgtattgtagatggatgagagtacatgggaaggtcccatctcacttgctccgaagcaagatcactaagcctaa
tgtgtatcatgagtcaaaactcgcggctaaagaataccaggcagccaaagctcgactttttacagcttttattaaggcagggctcggggcatgggtcgaga
agccgaccgagcaggaccaattctctctgacggggagcGGAGGTACGGAGAATTTGTATTTTCAGAGCGGTACCag
cggaggcgccatggttgataccttatcaggtttatcaagtgagcaaggtcagtccggtgatatgacaattgaagaagatagtgctacccatattaaattctca
aaacgtgatgaggacggcaaagagttagctggtgcaactatggagttgcgtgattcatctggtaaaactattagtacatggatttcagatggacaagtgaa
agatttctacctgtatccaggaaaatatacatttgtcgaaaccgcagcaccagacggttatgaggtagcaactgctattacctttacagttaatgagcaaggt
caggttactgtaaatggcaaagcaactaaaggtgacgctcatattggatccAGCGAGCTGATTAAGGAGAACATGCACATG
AAGCTGTACATGGAGGGCACCGTGGACAACCATCACTTCAAGTGCACATCCGAGGGCGAAG
GCAAGCCCTACGAGGGCACCCAGACCATGAGAATCAAGGTGGTCGAGGGCGGCCCTCTCCC
CTTCGCCTTCGACATCCTGGCTACTAGCTTCCTCTACGGCAGCAAGACCTTCATCAACCACAC
CCAGGGCATCCCCGACTTCTTCAAGCAGTCCTTCCCTGAGGGCTTCACATGGGAGAGAGTCA
CCACATACGAAGACGGGGGCGTGCTGACCGCTACCCAGGACACCAGCCTCCAGGACGGCTG
CCTCATCTACAACGTCAAGATCAGAGGGGTGAACTTCACATCCAACGGCCCTGTGATGCAGA
AGAAAACACTCGGCTGGGAGGCCTTCACCGAGACGCTGTACCCCGCTGACGGCGGCCTGGA
AGGCAGAAACGACATGGCCCTGAAGCTCGTGGGCGGGAGCCATCTGATCGCAAACATCAAG
ACCACATATAGATCCAAGAAACCCGCTAAGAACCTCAAGATGCCTGGCGTCTACTATGTGGA
CTACAGACTGGAAAGAATCAAGGAGGCCAACAACGAGACCTACGTCGAGCAGCACGAGGT
GGCAGTGGCCAGATACTGCGACCTCCCTAGCAAACTGGGGCACAAGCTTAATtAAGGGCCCG
TTTAAACCCGCTGATCAGCCTCGACTGTGCCTTCTA SEQ ID NO: 72 (see e.g., polypeptide in SEQ ID NO: 36) - TEV Protease
Taatacgactcactatagggagacccaagctggctagttaagcttgccaccatgggcgagagccttttcaagggcccgagggactacaacccgatctcc
agcaccatctgtcacctgaccaacgagagcgacggtcacaccactagtctgtacggcatcggcttcggccccttcatcatcaccaacaagcatctgttca
ggaggaataacggcacactgctggtgcaaagcctgcacggcgtgttcaaagtgaagaacacaaccaccctgcaacagcacctgatcgacggcaggg
acatgattatcatcaggatgcccaaggacttcccccccctttccccagaaactgaagttcagggagccacaaagggaggagcgaatctgcctggtgacca
ccaacttccagaccaagtccatgagcagcatggtctctgataccagctgcaccttccccagcagcgacggcatcttctggaagcactggattcagacgaa
ggatggccaatgcggcagcccattggtgagcactagggacggcttcatcgtgggcatccacagcgccagcaattttaccaataccaacaactacttcac
gagcgtgccgaaaaacttcatggagctgttgaccaatcaagaggcgcagcagtgggtgagcggctggaggctgaacgccgacagcgttctttggggc
ggacataaggtgttcatggtcaagcccgaggaacccttccagcccgttaaggaagccactcagctttgataactcgagtctagagggcccgcggttcga
acaaaaactcatctcagaagaggatctgaatatgcataccggtcatcatcaccatcaccattgagtttaaacccgctgatcagcctcgactgtgccttcta -continued SEQ ID NO: 73 (see e.g., polypeptide in SEQ ID NO: 37) - MCP-linker-ADAR2-DDN-
Bad(L)- ADAR2(E488Q)-DDC-PhoCl-Bcl-xL-TagBFP

```
TAATACGACTCACTATAGGGAGACCCAAGCTGGctagaggatcgaacccttaaggccaccatggcgtccaatttcactca
gtttgtgctggttgacaacggcgggaccggggacgttacggtagcccctcaaactttgccaacggtatagcggagtggataagcagcaattctaggag
tcaagcatacaaagttacatgcagcgtgcgccaatctagcgctcagaatcgcaagtacaccattaaagtagaggtccccaagggagcctggagaagcta
tcttaacatggagttgaccataccaatcttcgctaccaactctgactgtgaactcattgtgaaagccatgcaaggtctgctcaaggatggtaacccaattccg
tccgctatcgctgccaactctgggatttacgggggcagtgggagcggtgcaggatctggtagtccagctgggggaggagcaccgggtagcggtgggg
ggtctcagctgcacctgccccaggttctcgcagacgccgtatcccgccttgtactgggcaagtttggtgatcttactgacaatttttcatctcctcatgcgag
gcggaaagtactcgcaggcgtcgtcatgacgaccggaactgacgtgaaagacgccaaagtcatctctgtctccacgggcacaaagtgcataaacggg
gagtacatgagcgaccgggggctggcactgaatgattgtcacgctgaaataatatctaggcgatctctgcttagatttctctacactcaactcgaattgtacc
ttaacaacaaagatgaccagaaacgcagtatatttcagaaatcagaacgcggcggatttcgacttaaggaaaacgttcagttccacttgtatatcagcacat
ccccttgcggtgacgcccgaatcttttccccgcacgagccgatattggaggagcccgcgGCTAGCGGGTCGGGCACCGGTGCTC
CACCCAATCTCTGGGCAGCGCAGCGCTACGGCCGTGAGCTCAGAAGGATGTCCGATGAGcTG
GTCGACagacatcctaataggaaggctagaggccaacttcggacgaagattgaaagtggccagggtactatcccggtgcggtccaacgctagtatt
caaacgtgggacggagtccttcaaggtgaacggctgttgacaatgagctgctcagacaaaatcgcgcgctggaatgtagtgggaatccaaggcagcct
cttgagcatattcgtagaacccatatatttctcatccattattttgggctctctgtatcatggtgaccatctgtcaagggctatgtaccaacgaatttctaatatcg
aggatcttcctccactctatacactcaataagcctctcttgtccgggatatcaaacgctgaggcccgccagccagggaaagctcctaacttcagtgttaact
ggaccgttggtgattctgcgatagaggtcatcaacgccacgacaggtaaggatgagctcggtagagcctcacgcctgtgtaaacacgcgttgtattgtag
atggatgagagtacatgggaaggtcccatctcacttgctccgaagcaagatcactaagcctaatgtgtatcatgagtcaaaactcgcggctaaagaatacc
aggcagccaaagctcgacttttttacagcttttattaaggcagggctcggggcatgggtcgagaagccgaccgagcaggaccaattctctctgacgggga
gcGGAAGTGGTggtGTGATCCCTGACTACTTCAAGCAGAGCTTCCCCGAGGGCTACAGCTGGG
AGCGCAGCATGACCTACGAGGACGGCGGCATCTGCATCGCCACCAACGACATCACAATGGA
GGGGGACAGCTTCATCAACAAGATCCACTTCAAGGGCACGAACTTCCCCCCCAACGGCCCC
GTGATGCAGAAGAGGACCGTGGGCTGGGAGGCCAGCACCGAGAAGATGTACGAGCGCGAC
GGCGTGCTGAAGGGCGACGTGAAGATGAAGCTGCTGCTGAAGGGCGGCGGCCACTATCGCT
GCGACTACCGCACCACCTACAAGGTCAAGCAGAAGCCCGTAAAGCTGCCCGACTACCACTT
CGTGGACCACCGCATCGAGATCCTGAGCCACGACAAGGACTACAACAAGGTGAAGCTGTAC
GAGCACGCCGTGGCCCGCAACTCCACCGACAGCATGGACGAGCTGTACAAGGGTGGCAGCG
GTGGCATGGTGAGCAAGGGCGAGGAGACCATTACAAGCGTGATCAAGCCTGACATGAAGAA
CAAGCTGCGCATGGAGGGCAACGTGAACGGCCACGCCTTCGTGATCGAGGGCGAGGGCAGC
GGCAAGCCCTTCGAGGGCATCCAGACGATTGATTTGGAGGTGAAGGAGGGCGCCCCGCTGC
CCTTCGCCTACGACATCCTGACCACCGCCTTCCACTACGGCAACCGCGTGTTCACCAAGTAC
CCACGGTCGGGAAGTGGCTCAAGTAACCGGGAGCTGGTGGTTGACTTTCTCTCCTACAAGCT
TTCCCAGAAAGGATACAGCTGGAGTCAGTTTAGTGATGTGGAAGAGAACAGGACTGAGGCC
CCAGAAGGGACTGAATCGGAGATGGAGACCCCCAGTGCCATCAATGGCAACCCATCCTGGC
ACCTGGCAGACAGCCCCGCGGTGAATGGAGCCACTGGCCACAGCAGCAGTTTGGATGCCCG
GGAGGTGATCCCCATGGCAGCAGTAAAGCAAGCGCTGAGGGAGGCAGGCGACGAGTTTGAA
CTGCGGTACCGGCGGGCATTCAGTGACCTGACATCCCAGCTCCACATCACCCCAGGGACAGC
ATATCAGAGCTTTGAACAGGTAGTGAATGAACTCTTCCGGGATGGGGTAAACTGGGGTCGC
ATTGTGGCCTTTTTCTCCTTCGGCGGGGCACTGTGCGTGGAAAGCGTAGACAAGGAGATGCA
GGTATTGGTGAGTCGGATCGCAGCTTGGATGGCCACTTACCTGAATGACCACCTAGAGCCTT
GGATCCAGGAGAACGGCGGCTGGGATACTTTTGTGGAACTCTATGGGAACAATggatccAGCG
AGCTGATTAAGGAGAACATGCACATGAAGCTGTACATGGAGGGCACCGTGGACAACCATCA
CTTCAAGTGCACATCCGAGGGCGAAGGCAAGCCCTACGAGGGCACCCAGACCATGAGAATC
AAGGTGGTCGAGGGCGGCCCTCTCCCCTTCGCCTTCGACATCCTGGCTACTAGCTTCCTCTAC
GGCAGCAAGACCTTCATCAACCACACCCAGGGCATCCCCGACTTCTTCAAGCAGTCCTTCCC
TGAGGGCTTCACATGGGAGAGAGTCACCACATACGAAGACGGGGGCGTGCTGACCGCTACC
CAGGACACCAGCCTCCAGGACGGCTGCCTCATCTACAACGTCAAGATCAGAGGGGTGAACT
TCACATCCAACGGCCCTGTGATGCAGAAGAAAACACTCGGCTGGGAGGCCTTCACCGAGAC
```

-continued

```
GCTGTACCCCGCTGACGGCGGCCTGGAAGGCAGAAACGACATGGCCCTGAAGCTCGTGGGC
GGGAGCCATCTGATCGCAAACATCAAGACCACATATAGATCCAAGAAACCCGCTAAGAACC
TCAAGATGCCTGGCGTCTACTATGTGGACTACAGACTGGAAAGAATCAAGGAGGCCAACAA
CGAGACCTACGTCGAGCAGCACGAGGTGGCAGTGGCCAGATACTGCGACCTCCCTAGCAAA
CTGGGGCACAAGCTTAATtAAGGGCCCGTTTAAACCCGCTGATCAGCCTCGACTGTGCCTTCT
A
```

Example 5

Homologous ADAR Sequences

The iAD approach described herein can work for other ADAR2 isoforms and homologous proteins such as ADAR1 and ADAR3 (although ADAR3 is a catalytically inactive). Without wishing to be bound by theory, it is hypothesized that all 3 ADARs bind IP6 and take on a similar structure.

In addition to these proteins, there are three other homologues encoded in mammalian genome which can be susceptible to a similar engineering: ADAT1, ADAD1, and ADAD2. ADAT1 is a tRNA-specific adenosine deaminase which is known to require IP6 and catalyzes the deamination of adenosine in the anticodon loop of tRNAs. ADAD1 and ADAD2 are two proteins with expression limited to male testis and are important for germ cell differentiation. They are thought to be catalytically inactive and mutation of them does not affect male germ cell RNA editing.

ADAR3, ADAD1, and ADAD2 are thought to be catalytically inactive; it is contemplated here that ADAR3, ADAD1, and/or ADAD2 can be engineered to be catalytically active (e.g., by inserting regions of or mutating residues to that of ADAR1, ADAR2, and/or ADAT1 that allow for such catalytic deaminase activity). ADAT1 edits conserved loop structures in tRNA; it is contemplated here that ADAT1 can be engineered to target dsRNA regions of mRNA (e.g., by inserting regions of or mutating residues to that of ADAR1, ADAR2, ADAR3, ADAD1, and/or ADAD2 that allow for such binding to dsRNA regions of mRNA). The ADAR2 constructs described herein can at least be adapted using ADAR1 or the engineered versions of ADAR3, ADAD1, ADAD2, and/or ADAT1.

Based on multiple sequence alignments and other groups' research, annotated in bold below is the deaminase domain of ADAR1 (E1008Q) and bold-double-underlined is the 5' RNA binding loop residues that can be amenable to insertion and the predicted insertion site with//(based on Park, S., Doherty, E. E., Xie, Y., Padyana, A. K., Fang, F., Zhang, Y., Karki, A., Lebrilla, C. B., Siegel, J. B. & Beal, P. A. High-throughput mutagenesis reveals unique structural features of human ADAR1. *Nat Commun* 11, 5130 (2020).). Additionally, bolded and italicized are residues that may not be necessary on each terminus.

ADAR1-DD(E1008Q) (834-1226)

SEQ ID NO: 74,

*PLT*GSTFHDQIAMLSHRCFNTLTNSFQPSLLGRKILAAIIMKKDSED

MGVVVSLGTGNRCVKGDSLSLKGETVNDCHAEIISRRGFIRFLYSEL

MKYNSQTAKDSIFEPAKGGEKLQIKKTVSFHLYISTAPCGDGALFD

KSCS//DRAMEST//ESRHYPVFENPKQGKL

RTKVENGQGTIPVESSDIVPTWDGIRLGERLRTMSCSDKILRWNVLG

LQGALLTHFLQPIYLKSVTLGYLFSQGHLTRAICCRVTRDGSAFEDG

LRHPFIVNHPKVGRVSIYDSKRQSGKTKETSVNWCLADGYDLEILDG

TRGTVDGPRNELSRVSKKNIFLLFKKLCSFRYRRDLLRLSYGEAKKA

ARDYETAKNYFKKGLKDMGYGNWISKPQEEKNFYL*CPV*

Based on multiple sequence alignment (ADAR2 and ADAR3 are closely related), this is the deaminase domain for ADAR3.

ADAR3-DD(E527Q) (354-738)

SEQ ID NO: 75,

RTPMPQEFADSISQLVTQKFREVTTDLTPMHARHKALAGIVMTKGL

DARQAQVVALSSGTKCISGEHLSDQGLVVNDCHAEVVARRAFLHFL

YTQLELHLSKRREDSERSIFVRLKEGGYRLRENILFHLYVSTSPCG

DARLHSPYEITTDLHS//SKHLVRKFRGHLRTKIESGQGTVPVRGP

SAVQTWDGVLLGEQLITMSCTDKIARWNVLGLQGALLSHFVEPVYL

QSIVVGSLHHTGHLARVMSHRMEGVGQLPASYRHNRPLLSGVSDTE

ARQPGKSPPFSMNWVVGSADLEIINATTGRRSCGGPSRLCKHVLSA

RWARLYGRLSTRTPSPGDTPSMYCEAKLGAHTYQSVKQQLFKAFQK

AGLGTWVRKPPEQQQFLLT

Predicted RNA binding loop shown are in bold-double-underlined text below. The termini of the deaminase domains can also work for heterodimer domains using N and C terminal fusions.

ADAD1-DD (198-576)

SEQ ID NO: 76,

HYEGRHIQYAKISQIVKERFNQLISNRSEYLKYSSSLAAF

IIERAGQHEVVAIGTGEYNYSQDIKPDGRVLHDTHAVVTA

RRSLLRYFYRQLLLFYSKNPAMMEKSIFCTEPTSNLLTLK

QNINICLYMNQLPKGSAQIKSQL//RLNPHSISAFEANEE

LCLHVAVEGKIYLTVYCPKDGVNRISSMSSSDKLTRWEVL

GVQGALLSHFIQPVYISSILIGDGNCSDTRGLEIAIKQRV

DDALTSKLPMFYLVNRPHISLVPSAYPLQMNLEYKFLSLN

WAQGDVSLEIVDGLSGKITESSPFKSGMSMASRLCKAAML

SRFNLLAKEAKKELLEAGTYHAAKCMSASYQEAKCKLKSY

LQQHGYGSWIVKSPCIEQFNM

ADAD2-DD (200-583)

SEQ ID NO: 77,

SVENILTHEQRCAALVSAGFDLLLDERSPYWACKGTVAGV

ILEREIPRARGHVKEIYKLVALGTGSSCCAGWLEFSGQQL

HDCHGLVIARRALLRFLFRQLLLATQGGPKGKEQSVLAPQ

PGPGPPFTLKPRVFLHLYISNTPKGAARDIYL

PPTSEG//GLPHSPPMRLQAHVLGQLKPVCYVAPSLCDTH

VGCLSASDKLARWAVLGLGGALLAHLVSPLYSTSLILADS

CHDPPTLSRAIHTRPCLDSVLGPCLPPPYVRTALHLFAGP

PVAPSEPTPDTCRGLSLNWSLGDPGIEVVDVATGRVKANA

ALGPPSRLCKASFLRAFHQAARAVGKPYLLALKTYEAAKA

GPYQEARRQLSLLLDQQGLGAWPSKPLVGKFRN

For ADAT1, a non-homologous stretch in annotated in bold

ADAT1-DD (1-502)

SEQ ID NO: 78,

MWTADEIAQLCYEHYGIRLPKKGKPEPNHEWTLLAAVVKIQSPADKACDTPDKPVQVTKEVVS

MGTGTKCIGQSKMRKNGDILNDSHAEVIARRSFQRYLLHQLQLAATLKEDSIFVPGTQKGV

WKLRRDLIFVFFSSHTPCGDASIIPMLEFEDQPCCPVFRNWAHNSSVEASSNLEAPGNERKC

EDPDSPVTKKMRLEPGTAAREVTNGAAHHQSFGKQKSGPISPGIHSCDLTVEGLATVTRIAP

GSAKVIDVYRTGAKCVPGEAGDSGKPGAAFHQVGLLRVKPGRGDRTRSMSCSDKMARWNV

LGCQGALLMHLLEEPIYLSAVVIGKCPYSQEAMQRALIGRCQNVSALPKGFGVQELKILQSDLLF

EQSRSAVQAKRADSPGRLVPCGAAISWSAVPEQPLDVTANGFPQGTTKKTIGSLQARSQISKVEL

FRSFQKLLSRIARDKWPHSLRVQKLDTYQEYKEAASSYQEAWSTLRKQVFGSWIRNPPDYHQFK

P55265|DSRAD_HUMAN, ADAR1, 1226 amino acids (aa)

SEQ ID NO: 79,

MNPRQGYSLSGYYTHPFQGYEHRQLRYQQPGPGSSPSSFLLKQIEFLKGQLPEAPVIGKQTPSLPP

SLPGLRPRFPVLLASSTRGRQVDIRGVPRGVHLRSQGLQRGFQHPSPRGRSLPQRGVDCLSSHFQE

LSIYQDQEQRILKFLEELGEGKATTAHDLSGKLGTPKKEINRVLYSLAKKGKLQKEAGTPPLWKI

AVSTQAWNQHSGVVRPDGHSQGAPNSDPSLEPEDRNSTSVSEDLLEPFIAVSAQAWNQHSGVVR

PDSHSQGSPNSDPGLEPEDSNSTSALEDPLEFLDMAEIKEKICDYLFNVSDSSALNLAKNIGLTKA

RDINAVLIDMERQGDVYRQGTTPPIWHLTDKKRERMQIKRNTNSVPETAPAAIPETKRNAEFLTC

NIPTSNASNNMVTTEKVENGQEPVIKLENRQEARPEPARLKPPVHYNGPSKAGYVDFENGQWAT

DDIPDDLNSIRAAPGEFRAIMEMPSFYSHGLPRCSPYKKLTECQLKNPISGLLEYAQFASQTCEFN

MIEQSGPPHEPRFKFQVVINGREFPPAEAGSKKVAKQDAAMKAMTILLEEAKAKDSGKSEESSH

YSTEKESEKTAESQTPTPSATSFFSGKSPVTTLLECMHKLGNSCEFRLLSKEGPAHEPKFQYCVAV

GAQTFPSVSAPSKKVAKQMAAEEAMKALHGEATNSMASDNQPEGMISESLDNLESMMPNKVR

KIGELVRYLNTNPVGGLLEYARSHGFAAEFKLVDQSGPPHEPKFVYQAKVGGRWFPAVCAHSK

KQGKQEAADAALRVLIGENEKAERMGFTEVTPVTGASLRRTMLLLSRSPEAQPKTLPLTGSTFH

DQIAMLSHRCFNTLTNSFQPSLLGRKILAAIIMKKDSEDMGVVVSLGTGNRCVKGDSLSLKGETV

NDCHAEIISRRGFIRFLYSELMKYNSQTAKDSIFEPAKGGEKLQIKKTVSFHLYISTAPCGDGALFD

KSCSDRAMESTESRHYPVFENPKQGKLRTKVENGEGTIPVESSDIVPTWDGIRLGERLRTMSCSD

KILRWNVLGLQGALLTHFLQPIYLKSVTLGYLFSQGHLTRAICCRVTRDGSAFEDGLRHPFIVNHP

KVGRVSIYDSKRQSGKTKETSVNWCLADGYDLEILDGTRGTVDGPRNELSRVSKKNIFLLFKKL

CSFRYRRDLLRLSYGEAKKAARDYETAKNYFKKGLKDMGYGNWISKPQEEKNFYLCPV

P78563-2|RED1_HUMAN, ADAR2, 701 aa

SEQ ID NO: 80,

MDIEDEENMSSSSTDVKENRNLDNVSPKDGSTPGPGEGSQLSNGGGGGPGRKRPLEEGSNGHSK

YRLKKRRKTPGPVLPKNALMQLNEIKPGLQYTLLSQTGPVHAPLFVMSVEVNGQVFEGSGPTKK

KAKLHAAEKALRSFVQFPNASEAHLAMGRTLSVNTDFTSDQADFPDTLFNGFETPDKAEPPFYV

GSNGDDSFSSSGDLSLSASPVPASLAQPPLPVLPPFPPPSGKNPVMILNELRPGLKYDFLSESGESH

AKSFVMSVVVDGQFFEGSGRNKKLAKARAAQSALAAIFNLHLDQTPSRQPIPSEGLQLHLPQVL

ADAVSRLVLGKFGDLTDNFSSPHARRKVLAGVVMTTGTDVKDAKVISVSTGTKCINGEYMSDR

GLALNDCHAEIISRRSLLRFLYTQLELYLNNKDDQKRSIFQKSERGGFRLKENVQFHLYISTSPCG

DARIFSPHEPILEEPADRHPNRKARGQLRTKIESGEGTIPVRSNASIQTWDGVLQGERLLTMSCSD

KIARWNVVGIQGSLLSIFVEPIYFSSIILGSLYHGDHLSRAMYQRISNIEDLPPLYTLNKPLLSGISN

-continued

AEARQPGKAPNFSVNWTVGDSAIEVINATTGKDELGRASRLCKHALYCRWMRVHGKVPSHLLR

SKITKPNVYHESKLAAKEYQAAKARLFTAFIKAGLGAWVEKPTEQDQFSLTP

Q9NS39|RED2_HUMAN, ADAR3, 739 aa

SEQ ID NO: 81,

MASVLGSGRGSGGLSSQLKCKSKRRRRRRSKRKDKVSILSTFLAPFKHLSPGITNTEDDDTLSTSS

AEVKENRNVGNLAARPPPSGDRARGGAPGAKRKRPLEEGNGGHLCKLQLVWKKLSWSVAPKN

ALVQLHELRPGLQYRTVSQTGPVHAPVFAVAVEVNGLTFEGTGPTKKKAKMRAAELALRSFVQ

FPNACQAHLAMGGGPGPGTDFTSDQADFPDTLFQEFEPPAPRPGLAGGRPGDAALLSAAYGRRR

LLCRALDLVGPTPATPAAPGERNPVVLLNRLRAGLRYVCLAEPAERRARSFVMAVSVDGRTFEG

SGRSKKLARGQAAQAALQELFDIQMPGHAPGRARRTPMPQEFADSISQLVTQKFREVTTDLTPM

HARHKALAGIVMTKGLDARQAQVVALSSGTKCISGEHLSDQGLVVNDCHAEVVARRAFLHFLY

TQLELHLSKRREDSERSIFVRLKEGGYRLRENILFHLYVSTSPCGDARLHSPYEITTDLHSSKHLVR

KFRGHLRTKIESGEGTVPVRGPSAVQTWDGVLLGEQLITMSCTDKIARWNVLGLQGALLSHFVE

PVYLQSIVVGSLHHTGHLARVMSHRMEGVGQLPASYRHNRPLLSGVSDAEARQPGKSPPFSMN

WVVGSADLEIINATTGRRSCGGPSRLCKHVLSARWARLYGRLSTRTPSPGDTPSMYCEAKLGAH

TYQSVKQQLFKAFQKAGLGTWVRKPPEQQQFLLTL

Q96M93|ADAD1_HUMAN, 576 aa

SEQ ID NO: 82,

MASNNHWFQSSQVPSFAQMLKKNLPVQPATKTITTPTGWSSESYGLSKMASKVTQVTGNFPEPL

LSKNLSSISNPVLPPKKIPKEFIMKYKRGEINPVSALHQFAQMQRVQLDLKETVTTGNVMGPYFA

FCAVVDGIQYKTGLGQNKKESRSNAAKLALDELLQLDEPEPRILETSGPPPFPAEPVVLSELAYVS

KVHYEGRHIQYAKISQIVKERFNQLISNRSEYLKYSSSLAAFIIERAGQHEVVAIGTGEYNYSQDIK

PDGRVLHDTHAVVTARRSLLRYFYRQLLLFYSKNPAMMEKSIFCTEPTSNLLTLKQNINICLYMN

QLPKGSAQIKSQLRLNPHSISAFEANEELCLHVAVEGKIYLTVYCPKDGVNRISSMSSSDKLTRWE

VLGVQGALLSHFIQPVYISSILIGDGNCSDTRGLEIAIKQRVDDALTSKLPMFYLVNRPHISLVPSA

YPLQMNLEYKFLSLNWAQGDVSLEIVDGLSGKITESSPFKSGMSMASRLCKAAMLSRFNLLAKE

AKKELLEAGTYHAAKCMSASYQEAKCKLKSYLQQHGYGSWIVKSPCIEQFNM

Q8NCV1|ADAD2_HUMAN, 583 aa

SEQ ID NO: 83,

MASASQGADDDGSRRKPRLAASLQISPQPRPWRPLPAQAQSAWGPAPAPATYRAEGGWPQVSV

LRDSGPGAGAGVGELGAARAWENLGEQMGKAPRVPVPPAGLSLPLKDPPASQAVSLLTEYAAS

LGIFLLFREDQPPGPCFPFSVSAELDGVVCPAGTANSKTEAKQQAALSALCYIRSQLENPESPQTSS

RPPLAPLSVENILTHEQRCAALVSAGFDLLLDERSPYWACKGTVAGVILEREIPRARGHVKEIYKL

VALGTGSSCCAGWLEFSGQQLHDCHGLVIARRALLRFLFRQLLLATQGGPKGKEQSVLAPQPGP

GPPFTLKPRVFLHLYISNTPKGAARDIYLPPTSEGGLPHSPPMRLQAHVLGQLKPVCYVAPSLCDT

HVGCLSASDKLARWAVLGLGGALLAHLVSPLYSTSLILADSCHDPPTLSRAIHTRPCLDSVLGPC

LPPPYVRTALHLFAGPPVAPSEPTPDTCRGLSLNWSLGDPGIEVVDVATGRVKANAALGPPSRLC

KASFLRAFHQAARAVGKPYLLALKTYEAAKAGPYQEARRQLSLLLDQQGLGAWPSKPLVGKFR

N

Q9BUB4|ADAT1_HUMAN, 502 aa

SEQ ID NO: 84,

MWTADEIAQLCYEHYGIRLPKKGKPEPNHEWTLLAAVVKIQSPADKACDTPDKPVQVTKEVVS

MGTGTKCIGQSKMRKNGDILNDSHAEVIARRSFQRYLLHQLQLAATLKEDSIFVPGTQKGVWKL

RRDLIFVFFSSHTPCGDASIIPMLEFEDQPCCPVFRNWAHNSSVEASSNLEAPGNERKCEDPDSPV

TKKMRLEPGTAAREVTNGAAHHQSFGKQKSGPISPGIHSCDLTVEGLATVTRIAPGSAKVIDVYR

-continued

TGAKCVPGEAGDSGKPGAAFHQVGLLRVKPGRGDRTRSMSCSDKMARWNVLGCQGALLMHL

LEEPIYLSAVVIGKCPYSQEAMQRALIGRCQNVSALPKGFGVQELKILQSDLLFEQSRSAVQAKR

ADSPGRLVPCGAAISWSAVPEQPLDVTANGFPQGTTKKTIGSLQARSQISKVELFRSFQKLLSRIA

RDKWPHSLRVQKLDTYQEYKEAASSYQEAWSTLRKQVFGSWIRNPPDYHQFK

Example 6

Use Cases of ADAR Technology

Diagnostic/Detection of Antigens in Vitro.

The modularity of the allosteric ADAR platform allows for rapid detection of antigens of interest via cell-free translation. In this case, the cis-heterodimerizing components are composed of an antibody fragment and an epitope (peptide or protein) of equal or lower affinity than that of the natural antigen. The allosteric-ADAR is either already present in the cell-free translation mixture, or is encoded as DNA and is added to a cell-free transcription and translation mixture. Additionally, the stop-codon editing reporter (fluorescent, luminescent, or colorimetric) is encoded by DNA and is also added by the user (along with a variable concentration of IP6). A sample of interest, the reporter DNA, IP6, and the ADAR DNA is mixed at time zero. If the sample contains the antigen of interest, the ADAR enzyme will become active due to the antibody fragment binding the soluble antigen, edit the reporter mRNA and lead to translation of a protein which can be read out (e.g., fluorescently, luminescently, or colorimetrically). In this way, signal can accumulate relatively rapidly.

One advantage that this system has is that by exogenously controlling the IP6 concentration added, one can shift the equilibrium of active vs. inactive ADAR and therefore tune the stringency of detection. One can use low affinity heterodimer pairs without necessarily increasing background if one also adds low concentrations of IP6. With this, it can be easier to adapt to different antibody fragments and it can be possible to detect low concentrations of antigen.

As well, because the reporter can be configured in a ratiometric way (upstream translation of one component vs. the downstream translation of another after editing), it can serve as an internal control and be easier to get an estimate of ADAR activity/antigen concentration.

It can be possible to increase the sensitivity of this system by encoding two antibody fragments which bind distinct epitopes of the same antigen. In this case, the sensor is autoinhibited only by one antibody-epitope pair, allowing the free antibody fragment to bind and concentrate the antigen. This increase in local concentration would lead to increased activation (and more sensitive detection). This can also be configured in a way to detect protease activity in a sample, or can be coupled with inducible proteolytic activity as another way to activate this cell-free circuit.

Therapeutic Applications Via Antigen/Protease/Enzyme Activated RNA Circuits

The allosteric ADAR platform enables the ability for a single, easily deliverable mRNA to sense the intracellular environment and turn on or off a therapeutic payload accordingly. In this case, an mRNA encoding both the sensor and the actuator is delivered systemically (or specifically via a decorated LNP), and the therapeutic protein is translated only in diseased cells. The allosteric ADAR(s) that the mRNA encodes can be activated by disease-associated antigens, proteases, and/or protein activity.

For disease associated antigens, the ADAR is autoinhibited due to a cis-interacting heterodimeric pair consisting of an antibody-fragment and an epitope/epitope mimic with equal or lesser affinity than the natural antigen. When translated in host cells, the ADAR can remain in an inactive state unless the antigen of interest is present in cells. In this case, the higher affinity antigen preferentially binds to the antibody fragment, relieving the autoinhibition. This leads to the editing of the stop-codon and delivery of the therapeutic payload.

In this case, the use of two antibody fragments can increase the sensitivity of the system.

For example, such a construct can comprise an autoinhibited ADAR comprising a heterodimeric nanobody-epitope pair specific for the HIV protein p24. In this case, the construct comprises an N-terminal fusion of an attenuated p24 fragment and C-terminal fusion of two nanobodies specific for distinct epitopes (one of which is mutated so that the nanobody cannot bind). This can only turn on in HIV producing cells.

Alternative examples include encoding antibody-epitope pairs that recognize/mimic oncogenic proteins such as the HPV protein E6.

For disease associated proteases, the ADAR is autoinhibited due to a constitutively interacting heterodimer pair where one component contains a protease cut site in the linker between the ADAR C-terminus and the dimer component N-terminus. This ADAR can be repressed unless there is a cleavage event, at which point it can spontaneously activate and turn on the translation of the payload.

An example, such a construct can comprise the ALFA nanobody/epitope pair with an HIV PR cut site in the linker between the nanobody and the ADAR. In this case, only in cells where there is active HIV PR can the ADAR turn on, limiting payload delivery to HIV producing/receiving cells.

For disease associated protein activity, the ADAR is autoinhibited due to a heterodimeric pair that be dissociated by competitive binding to the product of a disease associated enzyme.

As an example, the heterodimer can comprise a phosphotyrosine binding (PTB) domain and a peptide with moderate affinity for the phosphotyrosine domain. In the absence of cancer-associated constitutive signaling, the ADAR is repressed. However, in cancer cells where there is increased activity of receptor tyrosine kinases (RTKs), the ADAR is activated by the higher affinity interaction between the PTB and cancer-associated receptor.

See following reference for examples of circuit that exploits PTB; the contents of which are incorporated herein by reference in its entirety. Chung, H. K. et al. A compact synthetic pathway rewires cancer signaling to therapeutic effector release. Science eaat6982 (2019) doi:10.1126/science.aat6982.

An additional PTB or SH2 domain can be added to localize autoinhibited ADAR to RTK.

In each of the preceding cases, the opposite logic can be applied using the ADAR-OFF circuit design to ensure that the ADAR activity leads to degradation of mRNA in the wrong cell type.

Additionally, one can combine multiple ADAR sensors and RNA circuit types into a single mRNA circuit. In this case, the presence of multiple factors would be necessary to turn on (or off) a payload. For example, a redundant circuit using p24-antigen sensing AND HIV PR sensing can ensure the expression is confined to the correct cells.

Precision Control of Timing and Extent of mRNA Translation or Degradation

Another exemplary use case outlined here is the ability to use the chemogenetically activated ADAR domains to precisely control when a therapeutic mRNA is translated or destroyed. In this case, instead of the ADAR sensor reacting to the cellular environment, it is reacting to an exogenously added small molecule drug. In this case, the ADAR is repressed by a heterodimer pair that can be dissociated by a small molecule, leading to an active ADAR domain.

The ADAR-OFF circuit can be implemented to quickly turn-off protein translation and destroy mRNA transcripts.

This can be a safety measure.

The ADAR-ON circuit can be implemented to tune the expression levels of a protein dependent on dosing in a small molecule drug.

These systems can also be used in tandem with two different drug-responsive ADARs: ADAR-ON allows dosage based control. ADAR-OFF allows quick turnover after initial.

Example 7

N-Terminal Fusion Site Works as an Alternative to Loop Insertion

Figure 11A:
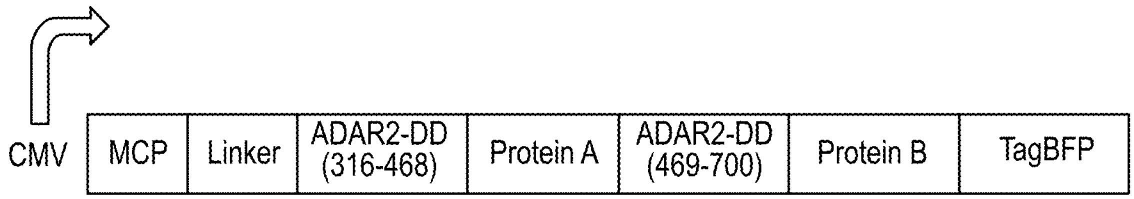
FIG. 11A-11F—Fusion of heterodimers to the N and C termini leads to allosteric ADARs.
Figure 11B:
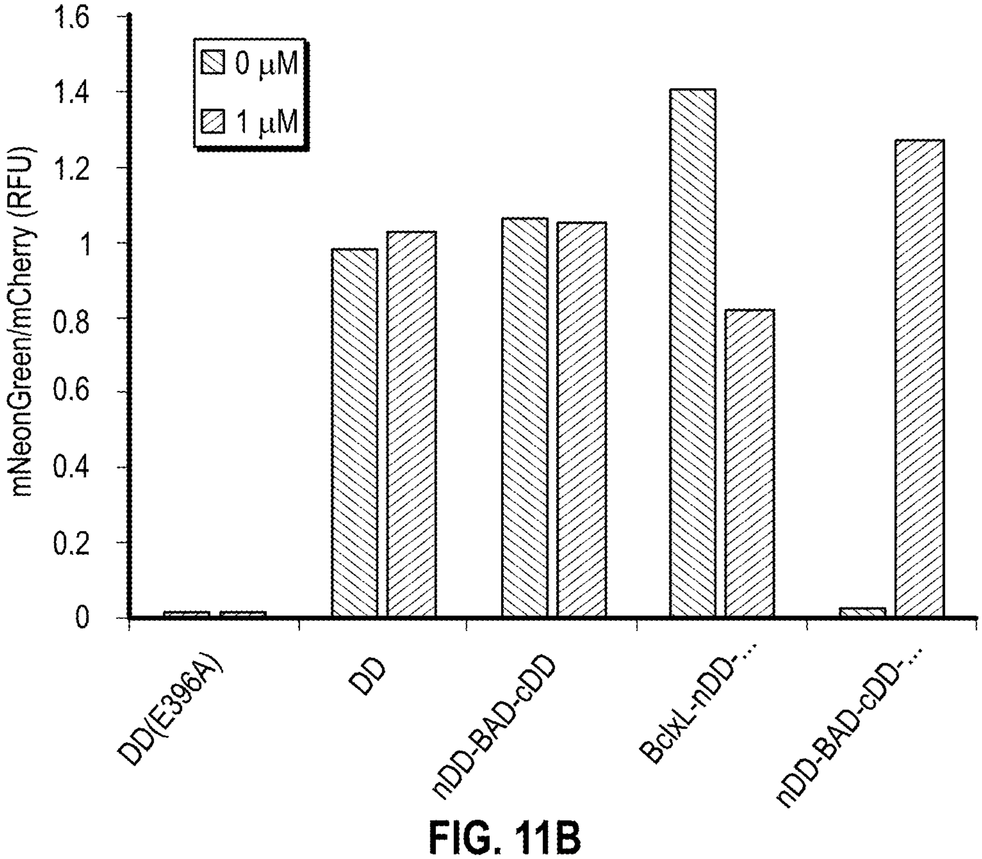
Figure 11C:
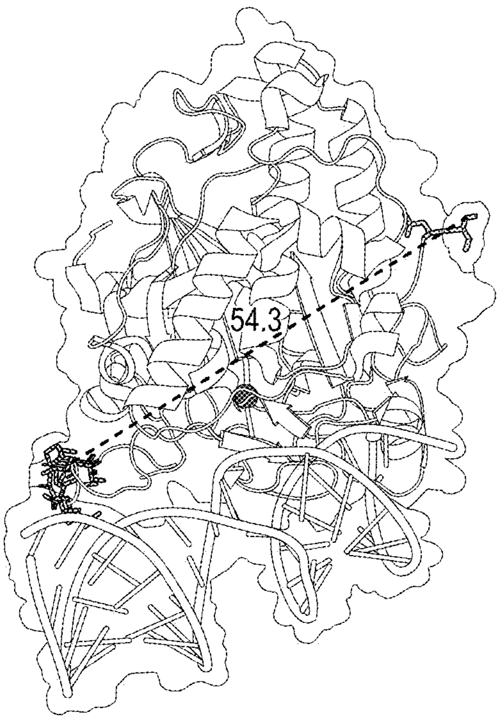

The constructs described in above examples used engineered ADAR2 deaminase domains that all contained the same basic topology (FIG. 11*a*). In short, one component of a protein-based heterodimer was fused to the C-terminus of ADAR2-DD and one component (commonly a peptide) was inserted between residues A468 and D469. The inventors sought to determine the mechanism of autoinhibition. When the inventors inserted the BAD peptide into the ADAR deaminase domain (DD), they found that fusing its heterodimeric partner to the C-terminus was required for autoinhibition and that fusion to the N-terminus with a suitable linker did not inhibit the enzymatic activity (FIG. 11*b*). Based on the crystal structure of ADAR2-DD (FIG. 11*c*), the distance between the C-terminus and the insertion loop for the folded enzyme should be greater than 50 Å and should be incompatible with the domains interacting in cis.

The C-terminal portion of the deaminase domain is involved in binding the cofactor inositol hexaphosphate (IP6). This cofactor is required for the proper folding of catalytically active ADAR domains. Without wishing to be bound by theory, it was hypothesized that the autoinhibition seen in the engineered ADAR domains is due to the cis-interaction between the dimerization domains constraining the formation of the C-terminal IP6 binding pocket. In this hypothesis, the cis-interactions are more thermodynamically favorable than the formation and binding of IP6; drug addition interferes with the cis-heterodimer and shifts the equilibrium back towards the IP6-bound state.

Figure 11D:
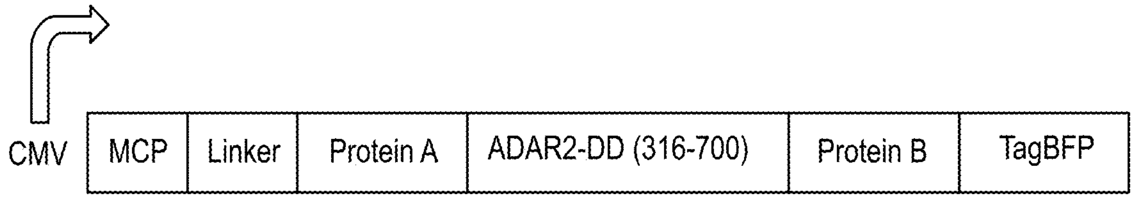
Figure 11E:
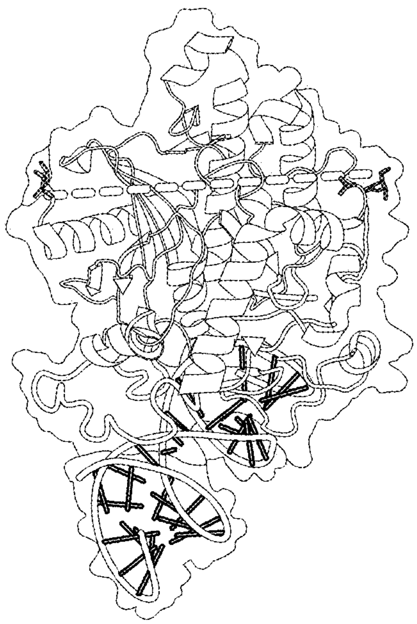
Figure 11F:
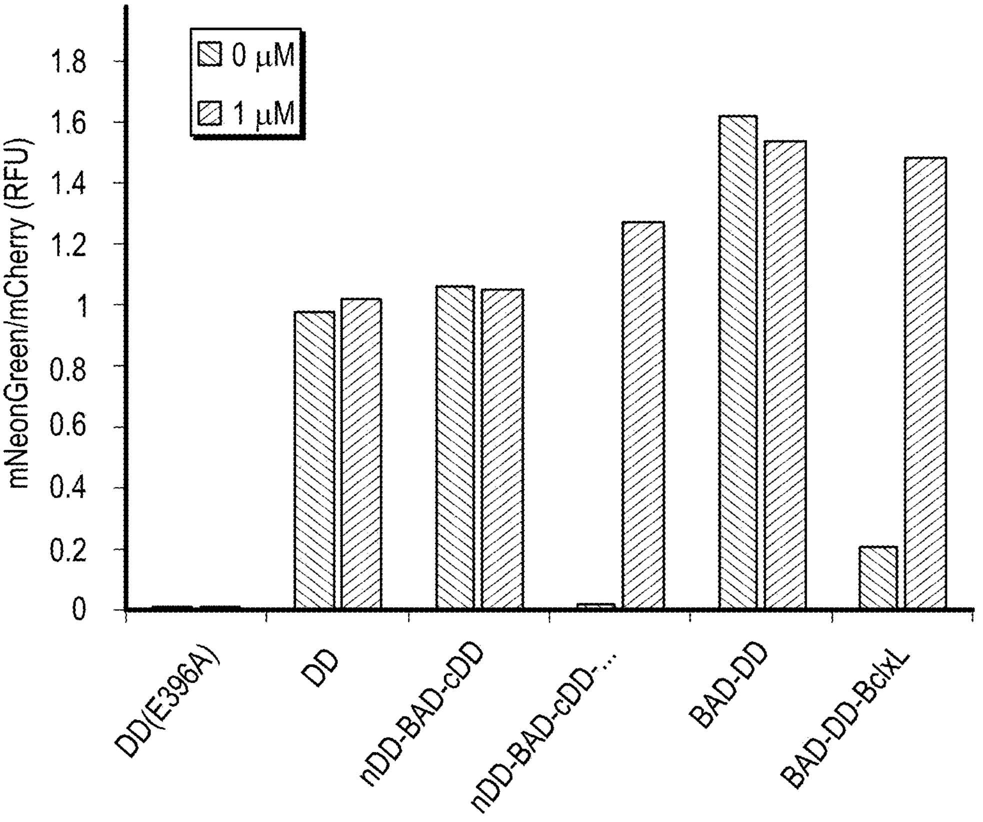

A consequence of this hypothesis is that the fusion/insertion position of one of the dimer components may be variable, e.g., the only requirements are that one component is fused to the C-terminus and the other component is fused to a position far enough away to make the cis-interaction and IP6 binding mutually exclusive. Towards that end, the inventors tested if fusion to the N-terminus can substitute for the insertion site (FIG. 11*d*). The N-terminal Q316 residue is located on the opposite side of the folded ADAR domain and is over 50 Å away from the C-terminal T700 residue (FIG. 11*e*). The inventors found that the fusion of the N-terminal BAD peptide did not affect ADAR editing of the reporter construct on its own, but that Bcl-xL fusion to the C-terminus led to drug-dependent allostery (FIG. 11*f*). The background in the absence of drug was significantly higher in this conformation than in the previously described conformation, but the N-terminal site can serve as a more modular fusion site and can accommodate folded/globular heterodimeric protein partners more readily than the insertion site previously described. As well, this provides evidence for the IP6-competition model.

TABLE 2

Amino Acid Sequence Table
(see e.g., FIG. 11, 14)

| NAME | SEQ ID NO | See e.g., FIGS. | AMINO ACID SEQUENCE |
|---|---|---|---|
| MCP-linker-ADAR2-DDN-Bad(L)-ADAR2(E488Q)-DDC-TagBFP Also known as "nDD-BAD-CDD" or "BAD(L) Only" | 88 | 11b, 11f | MASNFTQFVLVDNGGTGDVT VAPSNFANGIAEWISSNSRS QAYKVTCSVRQSSAQNRKYT IKVEVPKGAWRSYLNMELTI PIFATNSDCELIVKAMQGLL KDGNPIPSAIAANSGIYGGS GSGAGSGSPAGGGAPGSGGG SQLHLPQVLADAVSRLVLGK FGDLTDNFSSPHARRKVLAG VVMTTGTDVKDAKVISVSTG TKCINGEYMSDRGLALNDCH AEIISRRSLLRFLYTQLELY LNNKDDQKRSIFQKSERGGF RLKENVQFHLYISTSPCGDA RIFSPHEPILEEPAASGSGT GAPPNLWAAQRYGRELRRMS DELVDRHPNRKARGQLRTKI ESGQGTIPVRSNASIQTWDG VLQGERLLTMSCSDKIARWN VVGIQGSLLSIFVEPIYFSS IILGSLYHGDHLSRAMYQRI SNIEDLPPLYTLNKPLLSGI SNAEARQPGKAPNFSVNWTV GDSAIEVINATTGKDELGRA SRLCKHALYCRWMRVHGKVP SHLLRSKITKPNVYHESKLA AKEYQAAKARLFTAFIKAGL GAWVEKPTEQDQFSLTGSGS SELIKENMHMKLYMEGTVDN HHFKCTSEGEGKPYEGTQTM RIKVVEGGPLPFAFDILATS FLYGSKTFINHTQGIPDFFK QSFPEGFTWERVTTYEDGGV LTATQDTSLQDGCLIYNVKI RGVNFTSNGPVMQKKTLGWE AFTETLYPADGGLEGRNDMA LKLVGGSHLIANIKTTYRSK KPAKNLKMPGVYYVDYRLER IKEANNETYVEQHEVAVARY CDLPSKLGHKLN* |
| MCP-linker-BclxL-linker-ADAR2-DDN-Bad(L)-ADAR2(E488Q)-DDC-TagBFP Also known as "BclxL-nDD-BAD-CDD" | 89 | 11b | MASNFTQFVLVDNGGTGDVT VAPSNFANGIAEWISSNSRS QAYKVTCSVRQSSAQNRKYT IKVEVPKGAWRSYLNMELTI PIFATNSDCELIVKAMQGLL KDGNPIPSAIAANSGIYGGS GSGAGSGSPAGGGAPGSGGG SQSNRELVVDFLSYKLSQKG YSWSQFSDVEENRTEAPEGT ESEMETPSAINGNPSWHLAD SPAVNGATGHSSSLDAREVI PMAAVKQALREAGDEFELRY RRAFSDLTSQLHITPGTAYQ SFEQVVNELFRDGVNWGRIV |

TABLE 2-continued

Amino Acid Sequence Table (see e.g., FIG. 11, 14)

| NAME | SEQ ID NO | See e.g., FIGS. | AMINO ACID SEQUENCE |
|---|---|---|---|
| | | | AFFSFGGALCVESVDKEMQVLVSRIAAWMATYLNDHLEPWIQENGGWDTFVELYGNNAAGGSGGSGGSGGSAAAQLHLPQVLADAVSRLVLGKFGDLTDNFSSPHARRKVLAGVVMTTGTDVKDAKVISVSTGTKCINGEYMSDRGLALNDCHAEIISRRSLLRFLYTQLELYLNNKDDQKRSIFQKSERGGFRLKENVQFHLYISTSPCGDARIFSPHEPILEEPAASGSGTGAPPNLWAAQRYGRELRRMSDELVDRHPNRKARGQLRTKIESG**Q**GTIPVRSNASIQTWDGVLQGERLLTMSCSDKIARWNVVGIQGSLLSIFVEPIYFSSIILGSLYHGDHLSRAMYQRISNIEDLPPLYTLNKPLLSGISNAEARQPGKAPNFSVNWTVGDSAIEVINATTGKDELGRASRLCKHALYCRWMRVHGKVPSHLLRSKITKPNVYHESKLAAKEYQAAKARLFTAFIKAGLGAWVEKPTEQDQFSLTGSGSSELIKENMHMKLYMEGTVDNHHFKCTSEGEGKPYEGTQTMRIKVVEGGPLPFAFDILATSFLYGSKTFINHTQGIPDFFKQSFPEGFTWERVTTYEDGGVLTATQDTSLQDGCLIYNVKIRGVNFTSNGPVMQKKTLGWEAFTETLYPADGGLEGRNDMALKLVGGSHLIANIKTTYRSKKPAKNLKMPGVYYVDYRLERIKEANNETYVEQHEVAVARYCDLPSKLGHKLN* |
| MCP-linker-ADAR2-DDN-Bad(L)-ADAR2(E488Q)-DDC-Bcl-xL-TagBFP Also known as “nDD-BAD-CDD-Bcl-xL” and “BAD(L)” | 90 | 11b, 11f | MASNFTQFVLVDNGGTGDVTVAPSNFANGIAEWISSNSRSQAYKVTCSVRQSSAQNRKYTIKVEVPKGAWRSYLNMELTIPIFATNSDCELIVKAMQGLLKDGNPIPSAIAANSGIYGGSGSGAGSGSPAGGGAPGSGGGSQLHLPQVLADAVSRLVLGKFGDLTDNFSSPHARRKVLAGVVMTTGTDVKDAKVISVSTGTKCINGEYMSDRGLALNDCHAEIISRRSLLRFLYTQLELYLNNKDDQKRSIFQKSERGGFRLKENVQFHLYISTSPCGDARIFSPHEPILEEPAASGSGTGAPPNLWAAQRYGRELRRMSDELVDRHPNRKARGQLRTKIESG**Q**GTIPVRSNASIQTWDGVLQGERLLTMSCSDKIARWNVVGIQGSLLSIFVEPIYFSSIILGSLYHGDHLSRAMYQRISNIEDLPPLYTLNKPLLSGISNAEARQPGKAPNFSVNWTVGDSAIEVINATTGKDELGRASRLCKHALYCRWMRVHGKVPSHLLRSKITKPNVYHESKLAAKEYQAAKARLFTAFIKAGLGAWVEKPTEQDQFSLTGSAAGGSGGSAAASSNRELVVDFLSYKLSQKGYSWSQFSDVEENRTEAPEGTESEMETPSAINGNPSWHLADSPAVNGATGHSSSLDAREVIPMAAVKQALREAGDEFELRYRRAFSDLTSQLHITPGTAYQSFEQVVNELFRD |

TABLE 2-continued

Amino Acid Sequence Table (see e.g., FIG. 11, 14)

| NAME | SEQ ID NO | See e.g., FIGS. | AMINO ACID SEQUENCE |
|---|---|---|---|
| | | | GVNWGRIVAFFSFGGALCVESVDKEMQVLVSRIAAWMATYLNDHLEPWIQENGGWDTFVELYGNNGSSELIKENMHMKLYMEGTVDNHHFKCTSEGEGKPYEGTQTMRIKVVEGGPLPFAFDILATSFLYGSKTFINHTQGIPDFFKQSFPEGFTWERVTTYEDGGVLTATQDTSLQDGCLIYNVKIRGVNFTSNGPVMQKKTLGWEAFTETLYPADGGLEGRNDMALKLVGGSHLIANIKTTYRSKKPAKNLKMPGVYYVDYRLERIKEANNETYVEQHEVAVARYCDLPSKLGHKLN* |
| MCP-linker-BAD-ADAR2-DD(E488Q)-TagBFP Also known as “BAD-DD” | 91 | 11f | MASNFTQFVLVDNGGTGDVTVAPSNFANGIAEWISSNSRSQAYKVTCSVRQSSAQNRKYTIKVEVPKGAWRSYLNMELTIPIFATNSDCELIVKAMQGLLKDGNPIPSAIAANSGIYGGSGSGAGSGSPAGGGAPGSGGGSTGAPPNLWAAQRYGRELRRMSDEFVDSFKKASQLHLPQVLADAVSRLVLGKFGDLTDNFSSPHARRKVLAGVVMTTGTDVKDAKVISVSTGTKCINGEYMSDRGLALNDCHAEIISRRSLLRFLYTQLELYLNNKDDQKRSIFQKSERGGFRLKENVQFHLYISTSPCGDARIFSPHEPILEEPADRHPNRKARGQLRTKIESG**Q**GTIPVRSNASIQTWDGVLQGERLLTMSCSDKIARWNVVGIQGSLLSIFVEPIYFSSIILGSLYHGDHLSRAMYQRISNIEDLPPLYTLNKPLLSGISNAEARQPGKAPNFSVNWTVGDSAIEVINATTGKDELGRASRLCKHALYCRWMRVHGKVPSHLLRSKITKPNVYHESKLAAKEYQAAKARLFTAFIKAGLGAWVEKPTEQDQFSLTGSGSSELIKENMHMKLYMEGTVDNHHFKCTSEGEGKPYEGTQTMRIKVVEGGPLPFAFDILATSFLYGSKTFINHTQGIPDFFKQSFPEGFTWERVTTYEDGGVLTATQDTSLQDGCLIYNVKIRGVNFTSNGPVMQKKTLGWEAFTETLYPADGGLEGRNDMALKLVGGSHLIANIKTTYRSKKPAKNLKMPGVYYVDYRLERIKEANNETYVEQHEVAVARYCDLPSKLGHKLN* |
| MCP-linker-BAD-ADAR2-DD(E488Q)-Bcl-xL-TagBFP Also known as “BAD-DD-BclxL” and “WT” | 92 | 11f | MASNFTQFVLVDNGGTGDVTVAPSNFANGIAEWISSNSRSQAYKVTCSVRQSSAQNRKYTIKVEVPKGAWRSYLNMELTIPIFATNSDCELIVKAMQGLLKDGNPIPSAIAANSGIYGGSGSGAGSGSPAGGGAPGSGGGSTGAPPNLWAAQRYGRELRRMSDEFVDSFKKASQLHLPQVLADAVSRLVLGKFGDLTDNFSSPHARRKVLAGVVMTTGTDVKDAKVISVSTGTKCINGEYMSDRGLALNDCHAEIISRRSLLRFLYTQLELYLNNKDDQKRSIFQKSERGGFRLKENVQFHLYISTSPCGDARIFSPHEP |

TABLE 2-continued

Amino Acid Sequence Table (see e.g., FIG. 11, 14)

| NAME | SEQ ID NO | See e.g., FIGS. | AMINO ACID SEQUENCE |
|---|---|---|---|
| | | | ILEEPADRHPNRKARGQLRT<br>KIESG**Q**GTIPVRSNASIQTW<br>DGVLQGERLLTMSCSDKIAR<br>WNVVGIQGSLLSIFVEPIYF<br>SSIILGSLYHGDHLSRAMYQ<br>RISNIEDLPPLYTLNKPLLS<br>GISNAEARQPGKAPNFSVNW<br>TVGDSAIEVINATTGKDELG<br>RASRLCKHALYCRWMRVHGK<br>VPSHLLRSKITKPNVYHESK<br>LAAKEYQAAKARLFTAFIKA<br>GLGAWVEKPTEQDQFSLTGS<br>AAASSNRELVVDFLSYKLSQ<br>KGYSWSQFSDVEENRTEAPE<br>GTESEMETPSAINGNPSWHL<br>ADSPAVNGATGHSSSLDARE<br>VIPMAAVKQALREAGDEFEL<br>RYRRAFSDLTSQLHITPGTA<br>YQSFEQVVNELFRDGVNWGR<br>IVAFFSFGGALCVESVDKEM<br>QVLVSRIAAWMATYLNDHLE<br>PWIQENGGWDTFVELYGNNG<br>SSELIKENMHMKLYMEGTVD<br>NHHFKCTSEGEGKPYEGTQT<br>MRIKVVEGGPLPFAFDILAT<br>SFLYGSKTFINHTQGIPDFF<br>KQSFPEGFTWERVTTYEDGG<br>VLTATQDTSLQDGCLIYNVK<br>IRGVNFTSNGPVMQKKTLGW<br>EAFTETLYPADGGLEGRNDM<br>ALKLVGGSHLIANIKTTYRS<br>KKPAKNLKMPGVYYVDYRLE<br>RIKEANNETYVEQHEVAVAR<br>YCDLPSKLGHKLN* |

Example 8

Figure 12A:
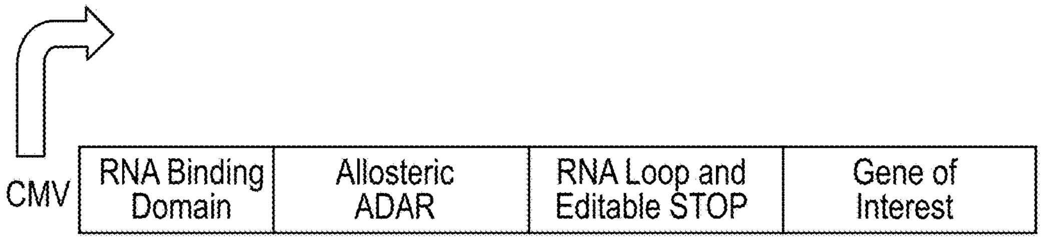
FIG. 12A-12D—Single plasmid constructs which encode a self-editing mRNA leads to efficient activation.

Self-Editing mRNA Encoding Allosteric ADAR Enables Single Construct Delivery Also described herein is a single mRNA construct that encodes an upstream allosteric ADAR-DD, an editable stop codon, and a downstream gene of interest (see e.g., FIG. 12*a*). This configuration can be easier to deliver than two separate constructs (e.g., ADAR and mRNA transcript) and can be easier to manufacture than purifying the allosteric ADAR and delivering as an RNA-protein complex.

Figure 12B:
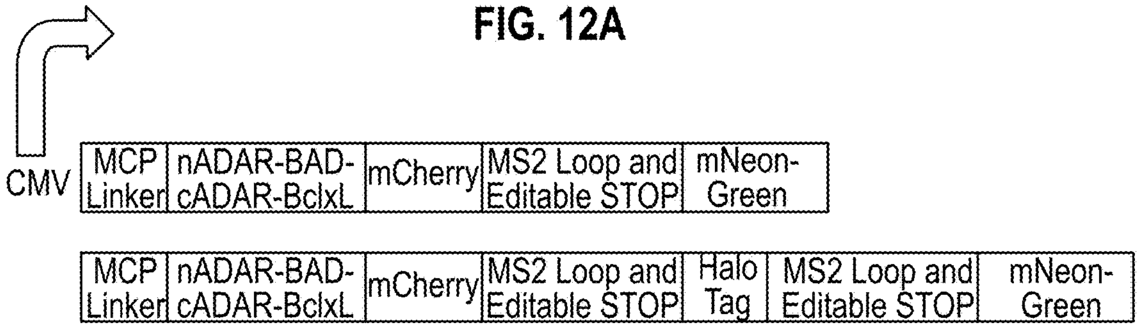
Figure 12C:
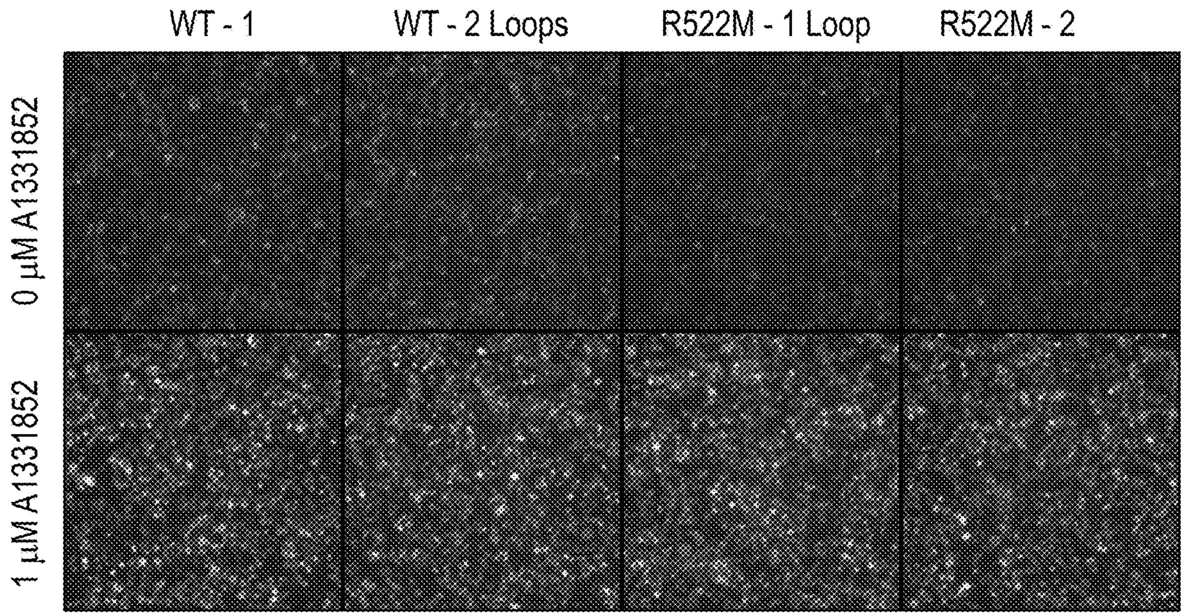
Figure 12D:
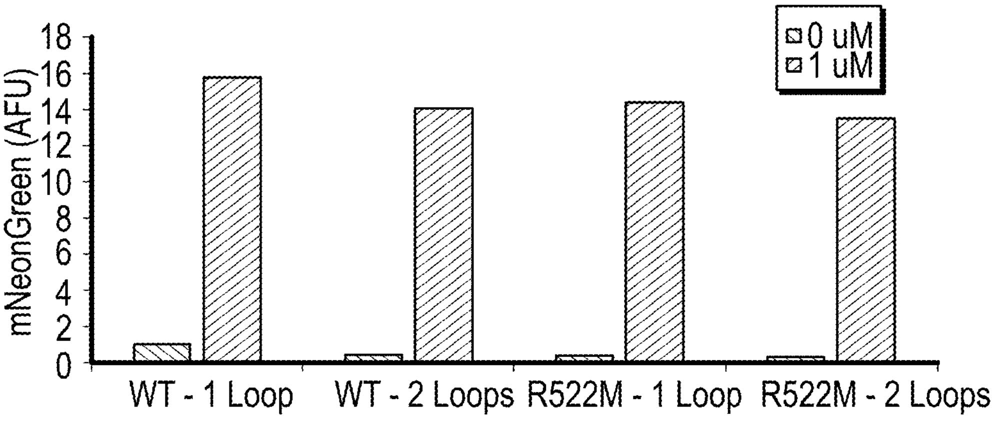
Figure 13A:
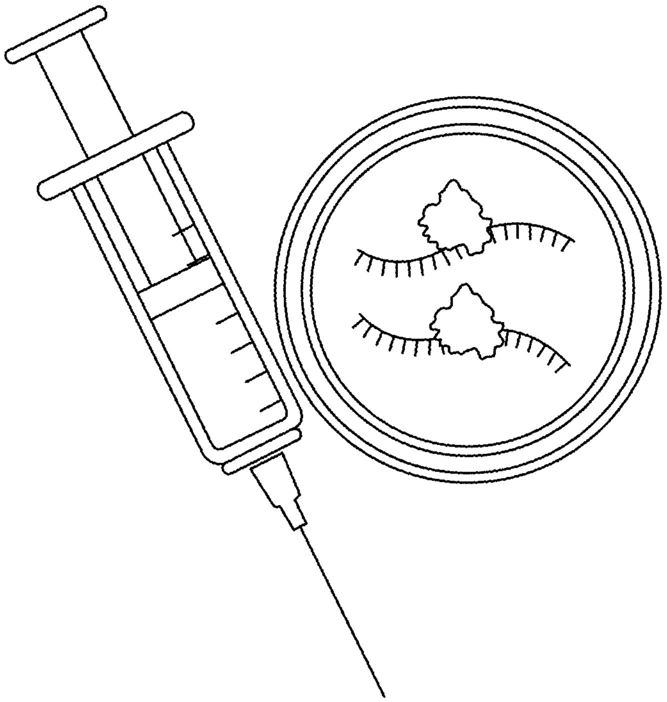
FIG. 13A-13B show schematics of embodiments that can be delivered as a single mRNA therapeutic. For example, the RNA molecule and fusion protein components can be combined into a single deliverable.
Figure 13B:
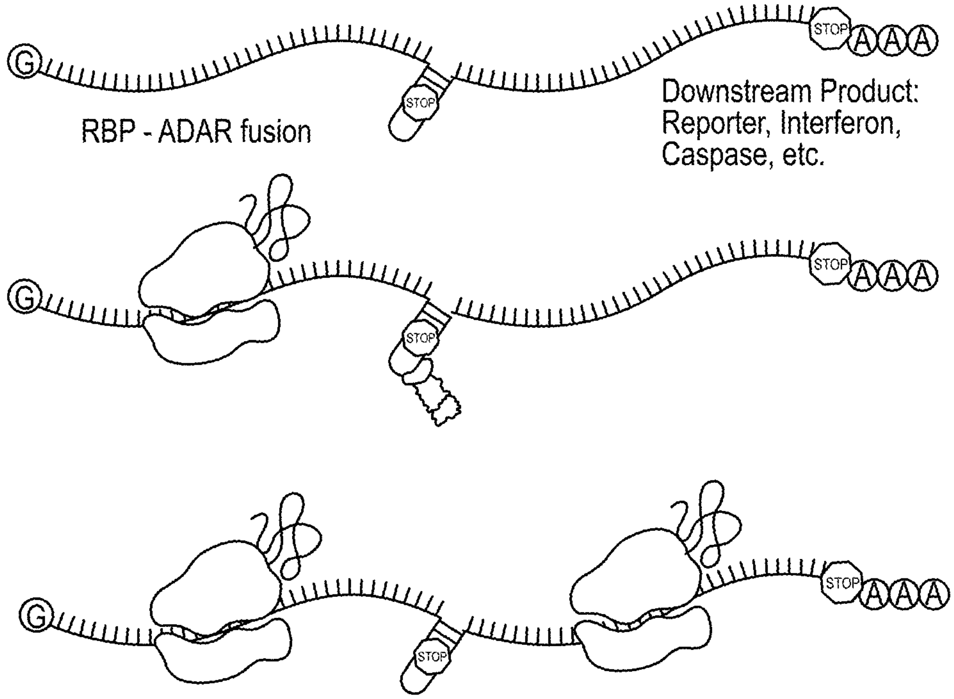
Figure 16A:
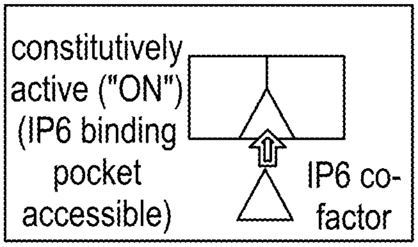
FIG. 16A-16B are schematic illustrations to show the modification of the deaminase domain of adenosine deaminases, including ADAR, into an inducible system and function to change a stop codon on exemplary synthetic activation or inactivation constructs.
Figure 16B:
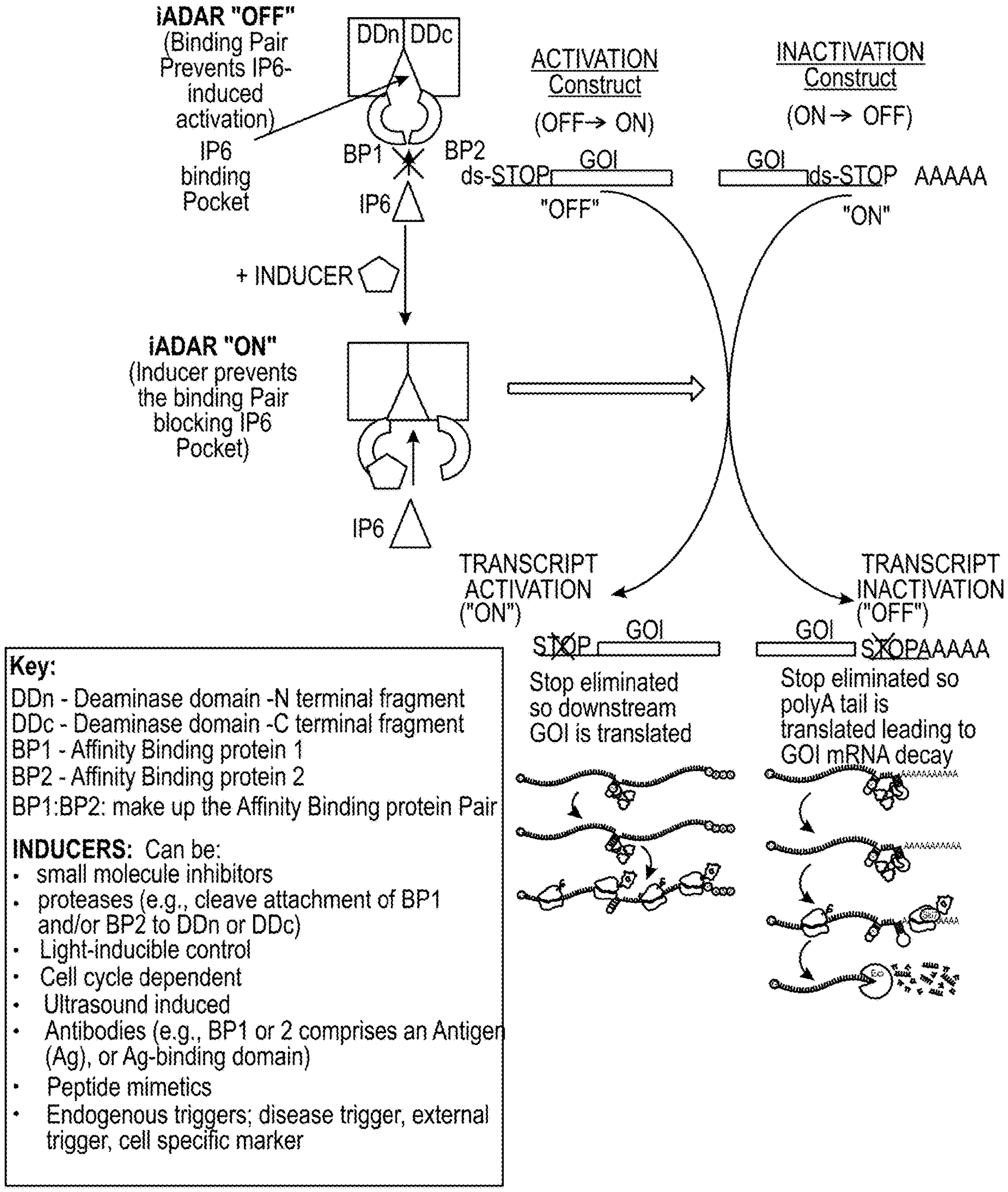
Figure 16C:
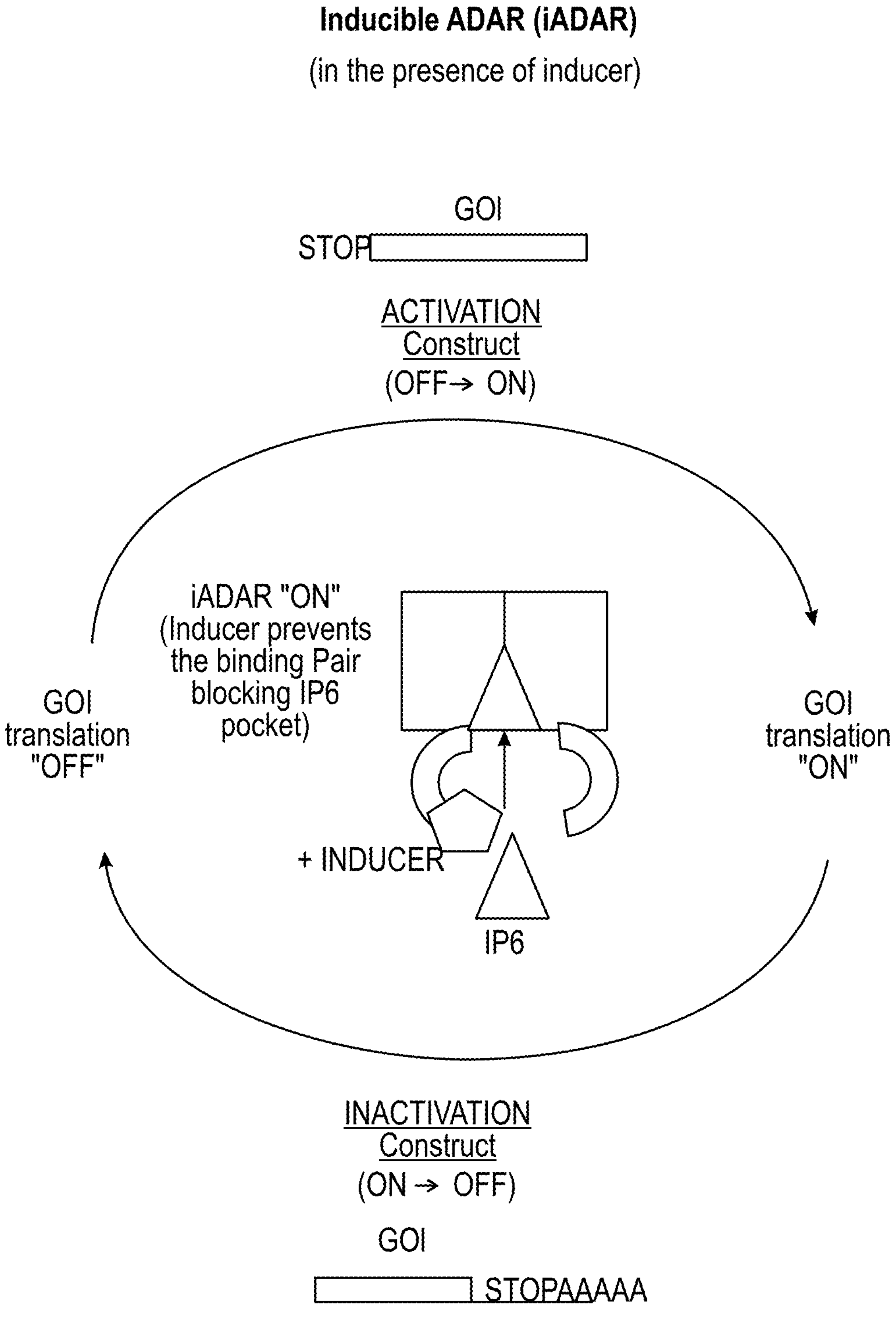

To test this, plasmids were created encoding an MS2 coat protein, BAD/Bcl-xL autoinhibited ADAR-DD (WT), and mCherry fusion protein upstream of either 1 or 2 editable STOP codon loops, with a downstream m NeonGreen as a readout (see e.g., FIG. 12*b*). HEK cells were then transfected with each of the constructs with and without 1 uM of A-1331852 and imaged the cells two days post transfection. An overlay of the mCherry (red channel) and mNeonGreen (green channel) channels shows that there is minimal translation of mNeonGreen in the absence of drug, and that all constructs lead to efficient translation of mNeonGreen with drug addition (see e.g., FIG. 12*c*). By quantifying the extent of mNeonGreen translation in transfected cells (see e.g., FIG. 12*d*), it is evident that background was reduced slightly by adding an additional editable-STOP loop (setting WT-1 Loop as 1 AFU, WT-2 Loops had background values of 0.5 AFU).

This data demonstrates the ability to administer a single, self-regulating mRNA, which can be used as a diagnostic or therapeutic.

TABLE 3

Amino Acid Sequence Table (see e.g., FIG. 12, 15)

| NAME | SEQ ID NO | See e.g., FIGS. | AMINO ACID SEQUENCE |
|---|---|---|---|
| MCP-linker-ADAR2-DDN-Bad(F)-ADAR2(E488Q)-DDC-Bcl-xL-mCherry-P2A-T2A-UAG-UAG-MS2-P2A-T2A-HA-mNeonGreen (M10K) | 93 & 411 | 12c, 12d "WT - 1 Loop" Note mutation site R522M is bolded | MASNFTQFVLVDNGGTGDVTVAPSNFANGIAEWISSNSRS<br>QAYKVTCSVRQSSAQNRKYTIKVEVPKGAWRSYLNMELTI<br>PIFATNSDCELIVKAMQGLLKDGNPIPSAIAANSGIYGGSGS<br>GAGSGSPAGGGAPGSGGGSQLHLPQVLADAVSRLVLGKFG<br>DLTDNFSSPHARRKVLAGVVMTTGTDVKDAKVISVSTGTK<br>CINGEYMSDRGLALNDCHAEIISRRSLLRFLYTQLELYLNN<br>KDDQKRSIFQKSERGGFRLKENVQFHLYISTSPCGDARIFSP<br>HEPILEEPAASGSGTGAPPNLWAAQRYGRELRRMSDEFVD<br>RHPNRKARGQLRTKIESGQGTIPVRSNASIQTWDGVLQGER<br>LLTMSCSDKIARWNVVGIQGSLLSIFVEPIYFSSIILGSLYHG<br>DHLSRAMYQRISNIEDLPPLYTLNKPLLSGISNAEARQPGKA<br>PNFSVNWTVGDSAIEVINATTGKDELGRASRLCKHALYCR<br>WMRVHGKVPSHLLRSKITKPNVYHESKLAAKEYQAAKAR<br>LFTAFIKAGLGAWVEKPTEQDQFSLTGSGGTENLYFQSAAS<br>SNRELVVDFLSYKLSQKGYSWSQFSDVEENRTEAPEGTESE<br>METPSAINGNPSWHLADSPAVNGATGHSSSLDAREVIPMA<br>AVKQALREAGDEFELRYRRAFSDLTSQLHITPGTAYQSFEQ<br>VVNELFRDGVNWGRIVAFFSFGGALCVESVDKEMQVLVSR<br>IAAWMATYLNDHLEPWIQENGGWDTFVELYGNNGSSELIK<br>ENMHMKRPSVATMVSKGEEDNMAIIKEFMRFKVHMEGSV<br>NGHEFEIEGEGEGRPYEGTQTAKLKVTKGGPLPFAWDILSP<br>QFMYGSKAYVKHPADIPDYLKLSFPEGFKWERVMNFEDG<br>GVVTVTQDSSLQDGEFIYKVKLRGTNFPSDGPVMQKKTMG<br>WEASSERMYPEDGALKGEIKQRLKLKDGGHYDAEVKTTY<br>KAKKPVQLPGAYNVNIKLDITSHNEDYTIVEQYERAEGRHS<br>TGGMDELYKDYKDDDDKGSGATNFSLLKQAGDVEENPGP<br>ASAGSGEGRGSLLTCGDVEENPGPATGNSA*R*LCQRHAK<br>HEDHPCTSATNFSLLKQAGDVEENPGPGGSEGRGSLLTCG |

TABLE 3-continued

| Amino Acid Sequence Table (see e.g., FIG. 12, 15) | | | |
|---|---|---|---|
| NAME | SEQ ID NO | See e.g., FIGS. | AMINO ACID SEQUENCE |
| | | | DVEENPGPSGYPYDVPDYAIDVSKGEEDNKASLPATHELHI<br>FGSINGVDFDMVGQGTGNPNDGYEELNLKSTKGDLQFSPW<br>ILVPHIGYGFHQYLPYPDGMSPFQAAMVDGSGYQVHRTM<br>QFEDGASLTVNYRYTYEGSHIKGEAQVKGTGFPADGPVMT<br>NSLTAADWCRSKKTYPNDKTIISTFKWSYTTGNGKRYRST<br>ARTTYTFAKPMAANYLKNQPMYVFRKTELKHSKTELNFK<br>EWQKAFTDVMGMDELYKAS* |
| MCP-linker-<br>ADAR2-<br>DDN-<br>Bad(F)-<br>ADAR2(E488Q)-<br>DDC-<br>Bcl-XL-<br>mCherry-<br>P2A-T2A-<br>UAG-UAG-<br>MS2-<br>HaloTag-<br>UAG-UAG-<br>MS2-P2A-<br>T2A-HA-<br>mNeonGreen<br>(M10K) | 94,<br>393,<br>and<br>411 | 12c, 12d<br>"WT - 2<br>Loop"<br>Note<br>mutation<br>site R522M<br>is bolded | MASNFTQFVLVDNGGTGDVTVAPSNFANGIAEWISSNSRS<br>QAYKVTCSVRQSSAQNRKYTIKVEVPKGAWRSYLNMELTI<br>PIFATNSDCELIVKAMQGLLKDGNPIPSAIAANSGIYGGSGS<br>GAGSGSPAGGGAPGSGGGSQLHLPQVLADAVSRLVLGKFG<br>DLTDNFSSPHARRKVLAGVVMTTGTDVKDAKVISVSTGTK<br>CINGEYMSDRGLALNDCHAEIISRRSLLRFLYTQLELYLNN<br>KDDQKRSIFQKSERGGFRLKENVQFHLYISTSPCGDARIFSP<br>HEPILEEPAASGSGTGAPPNLWAAQRYGRELRRMSDEFVD<br>RHPNRKARGQLRTKIESGQGTIPVRSNASIQTWDGVLQGER<br>LLTMSCSDKIARWNVVGIQGSLLSIFVEPIYFSSIILGSLYHG<br>DHLSRAMYQRISNIEDLPPLYTLNKPLLSGISNAEARQPGKA<br>PNFSVNWTVGDSAIEVINATTGKDELGRASRLCKHALYCR<br>WMRVHGKVPSHLLRSKITKPNVYHESKLAAKEYQAAKAR<br>LFTAFIKAGLGAWVEKPTEQDQFSLTGSGGTENLYFQSAAS<br>SNRELVVDFLSYKLSQKGYSWSQFSDVEENRTEAPEGTESE<br>METPSAINGNPSWHLADSPAVNGATGHSSSLDAREVIPMA<br>AVKQALREAGDEFELRYRRAFSDLTSQLHITPGTAYQSFEQ<br>VVNELFRDGVNWGRIVAFFSFGGALCVESVDKEMQVLVSR<br>IAAWMATYLNDHLEPWIQENGGWDTFVELYGNNGSSELIK<br>ENMHMKRPSVATMVSKGEEDNMAIIKEFMRFKVHMEGSV<br>NGHEFEIEGEGEGRPYEGTQTAKLKVTKGGPLPFAWDILSP<br>QFMYGSKAYVKHPADIPDYLKLSFPEGFKWERVMNFEDG<br>GVVTVTQDSSLQDGEFIYKVKLRGTNFPSDGPVMQKKTMG<br>WEASSERMYPEDGALKGEIKQRLKLKDGGHYDAEVKTTY<br>KAKKPVQLPGAYNVNIKLDITSHNEDYTIVEQYERAEGRHS<br>TGGMDELYKDYKDDDDKGSGATNFSLLKQAGDVEENPGP<br>ASAGSGEGRGSLLTCGDVEENPGPATGNSA*R*LCQRHAK<br>HEDHPCAAMAEIGTGFPFDPHYVEVLGERMHYVDVGPRD<br>GTPVLFLHGNPTSSYVWRNIIPHVAPTHRCIAPDLIGMGKSD<br>KPDLGYFFDDHVRFMDAFIEALGLEEVVLVIHDWGSALGF<br>HWAKRNPERVKGIAFMEFIRPIPTWDEWPEFARETFQAFRT<br>TDVGRKLIIDQNVFIEGTLPMGVVRPLTEVEMDHYREPFLN<br>PVDREPLWRFPNELPIAGEPANIVALVEEYMDWLHQSPVPK<br>LLFWGTPGVLIPPAEAARLAKSLPNCKAVDIGPGLNLLQED<br>NPDLIGSEIARWLSTLEISGTGMASMTGGQQMGPATGNSA*<br>R*LCQRHAKHEDHPCTSATNFSLLKQAGDVEENPGPGGSE<br>GRGSLLTCGDVEENPGPSGYPYDVPDYAIDVSKGEEDNKA<br>SLPATHELHIFGSINGVDFDMVGQGTGNPNDGYEELNLKST<br>KGDLQFSPWILVPHIGYGFHQYLPYPDGMSPFQAAMVDGS<br>GYQVHRTMQFEDGASLTVNYRYTYEGSHIKGEAQVKGTG<br>FPADGPVMTNSLTAADWCRSKKTYPNDKTIISTFKWSYTT<br>GNGKRYRSTARTTYTFAKPMAANYLKNQPMYVFRKTELK<br>HSKTELNFKEWQKAFTDVMGMDELYKAS* |

Below are DNA sequences of interest, e.g., for Table 3.

SEQ ID NO: 402, MCP-linker-ADAR2-DDN-Bad(F)-ADAR2(E488Q)-DDC-Bcl-XL-mCherry-P2A-T2A-UAG-UAG-MS2-P2A-T2A-HA-mNeonGreen(M10K), see e.g., polypeptide in SEQ ID NO: 93; UAG-UAG-MS2 domain is bold-italicized CTTATCGAAATTAATACGACTCACTATAGGGAGACCCAAGCTGGc tagaggatcgaacccttaaggccaccatggcgtccaatttcactc agtttgtgctggttgacaacggcgggaccggggacgttacggtag ccccctcaaactttgccaacggtatagcggagtggataagcagca attctaggagtcaagcatacaaagttacatgcagcgtgcgccaat ctagcgctcagaatcgcaagtacaccattaaagtagaggtcccca -continued agggagcctggagaagctatcttaacatggagttgaccataccaa tcttcgctaccaactctgactgtgaactcattgtgaaagccatgc aaggtctgctcaaggatggtaacccaattccgtccgctatcgctg ccaactctgggatttacgggggcagtgggagcggtgcaggatctg gtagtccagctgggggaggagcaccgggtagcggtgggggtctc agctgcacctgccccaggttctcgcagacgccgtatcccgccttg tactgggcaagtttggtgatcttactgacaatttttcatctcctc atgcgaggcggaaagtactcgcaggcgtcgtcatgacgaccggaa ctgacgtgaaagacgccaaagtcatctctgtctccacgggcacaa -continued agtgcataaacggggagtacatgagcgaccgggggctggcactga
atgattgtcacgctgaaataatatctaggcgatctctgcttagat
ttctctacactcaactcgaattgtaccttaacaacaaagatgacc
agaaacgcagtatatttcagaaatcagaacgcggcggatttcgac
ttaaggaaaacgttcagttccacttgtatatcagcacatcccctt
gcggtgacgcccgaatcttttccccgcacgagccgatattggagg
agcccgcgGCTAGCGGGTCGGGCACCGGTGCTCCACCCAATCTCT
GGGCAGCGCAGCGCTACGGCCGTGAGCTCAGAAGGATGTCCGATG
AGttcGTCGACagacatcctaataggaaggctagaggccaacttc
ggacgaagattgaaagtggccagggtactatcccggtgcggtcca
acgctagtattcaaacgtgggacggagtccttcaaggtgaacggc
tgttgacaatgagctgctcagacaaaatcgcgcgctggaatgtag
tgggaatccaaggcagcctcttgagcatattcgtagaacccatat
atttctcatccattattttgggctctctgtatcatggtgaccatc
tgtcaagggctatgtaccaacgaatttctaatatcgaggatcttc
ctccactctatacactcaataagcctctcttgtccgggatatcaa
acgctgaggcccgccagccagggaaagctcctaacttcagtgtta
actggaccgttggtgattctgcgatagaggtcatcaacgccacga
caggtaaggatgagctcggtagagcctcacgcctgtgtaaacacg
cgttgtattgtagatggatgagagtacatgggaaggtcccatctc
acttgctccgaagcaagatcactaagcctaatgtgtatcatgagt
caaaactcgcggctaaagaataccaggcagccaaagctcgacttt
ttacagcttttattaaggcagggctcggggcatgggtcgagaagc
cgaccgagcaggaccaattctctctgacggggagcGGAGGTACGG
AGAATTTGTATTTTCAGAGCGCCGCTTCAAGTAACCGGGAGCTGG
TGGTTGACTTTCTCTCCTACAAGCTTTCCCAGAAAGGATACAGCT
GGAGTCAGTTTAGTGATGTGGAAGAGAACAGGACTGAGGCCCCAG
AAGGGACTGAATCGGAGATGGAGACCCCCAGTGCCATCAATGGCA
ACCCATCCTGGCACCTGGCAGACAGCCCCGCGGTGAATGGAGCCA
CTGGCCACAGCAGCAGTTTGGATGCCCGGGAGGTGATCCCCATGG
CAGCAGTAAAGCAAGCGCTGAGGGAGGCAGGCGACGAGTTTGAAC
TGCGGTACCGGCGGGCATTCAGTGACCTGACATCCCAGCTCCACA
TCACCCCAGGGACAGCATATCAGAGCTTTGAACAGGTAGTGAATG
AACTCTTCCGGGATGGGGTAAACTGGGGTCGCATTGTGGCCTTTT
TCTCCTTCGGCGGGGCACTGTGCGTGGAAAGCGTAGACAAGGAGA
TGCAGGTATTGGTGAGTCGGATCGCAGCTTGGATGGCCACTTACC
TGAATGACCACCTAGAGCCTTGGATCCAGGAGAACGGCGGCTGGG
ATACTTTTGTGGAACTCTATGGGAACAATggatccAGCGAGCTGA
TTAAGGAGAACATGCACATGAAGCGCCCatcggtcgccaccatgg
tgagcaagggcgaggaggataacatggccatcatcaaggagttca
tgcgcttcaaggtgcacatggagggctccgtgaacggccacgagt -continued tcgagatcgagggcgagggcgagggccgcccctacgagggcaccc
agaccgccaagctgaaggtgaccaagggtggcccccctgcccttcg
cctgggacatcctgtcccctcagttcatgtacggctccaaggcct
acgtgaagcaccccgccgacatccccgactacttgaagctgtcct
tccccgagggcttcaagtgggagcgcgtgatgaacttcgaggacg
gcggcgtggtgaccgtgacccaggactcctccctgcaggacggcg
agttcatctacaaggtgaagctgcgcggcaccaacttccccctccg
acggccccgtaatgcagaagaagaccatgggctgggaggcctcct
ccgagcggatgtaccccgaggacggcgccctgaagggcgagatca
agcagaggctgaagctgaaggacggcggccactacgacgctgagg
tcaagaccacctacaaggccaagaagcccgtgcagctgcccggcg
cctacaacgtcaacatcaagttggacatcacctcccacaacgagg
actacaccatcgtggaacagtacgaacgcgccgagggccgccact
ccaccggcggcatggacgagctgTACaaggattacaaggatgacg
atgacaaaGGTAGCGGGGCAACTAATTTTAGCTTACTCAAACAGG
CTGGGGACGTCGAGGAGAATCCAGGCCCTGCATCCGCTGGCTCTG
GAGAAGGACGAGGCTCCTTGCTCACCTGTGGAGATGTCGAAGAGA
ACCCAGGTCCTGCAACCGGGAATTC*CGCGTAGCGCTAGCTTTGCC*
*AGCGCCACGCGaaACATGAGGATcACCCATGT*ACTAGTGCCACAA
ACTTCTCTCTGCTAAAGCAAGCAGGTGATGTTGAAGAAAACCCAG
GGCCTGGAGGGTCCGAGGGCAGGGGAAGTCTCCTAACATGCGGGG
ACGTGGAGGAAAATCCCGGCCCATCCGGATATCCCTACGATGTGC
CCGATTACGCTATCGATgtgagcaagggcgaAgaAgataacaAgg
cctctctcccagcgacacatgagttacacatctttggctccatca
acggtgtggactttgacatggtgggtcagggcaccggcaatccaa
atgatggttatgaggagttaaacctgaagtccaccaagggtgacc
tccagttctcccccctggattctggtccctcatatcgggtatggct
tccatcagtacctgccctaccctgacgggatgtcgcctttccagg
ccgccatggtagatggcAGCggataccaagtccatcgcacaatgc
agtttgaagatggtgcctcccttactgttaactaccgctacacct
acgagggaagccacatcaaaggagaggcccaggtgaaggggactg
gtttccctgctgacggtcctgtgatgaccaactcgctgaccgctg
cggactggtgcaggtcgaagaagacttaccccaacgacaaaacca
tcatcagtacctttaagtggagttacaccactggaaatggcaagA
GAtaccggagcactgcgcggaccacctacacctttgccaagccaa
tggcggctaactatctgaagaaccagccgatgtacgtgttccgta
agacggagctcaagcactccaagaccgagctcaacttcaaggagt
ggcaaaaggcctttaccgatgtgatgGGAatggacGAGCTGTATa -continued agGCTAGCTAAGCGGCCGCTCGAGTCTAGAGGGCCCGCGGTTCGA

AGGTAAGCCTATCCCTAACCCTCTCCTCGGTCTCGATTCTACGCG

TACCGGTCATCATCACCATCACCATTGAGTTTAAACCCGCTGATC

AG

SEQ ID NO: 99, MCP-linker-ADAR2-DDN-Bad(F)-ADAR2(E488Q)-DDC-Bcl-xL-mCherry-P2A-T2A-UAG-UAG-MS2-HaloTag-UAG-UAG-MS2-P2A-T2A-HA-mNeonGreen(M10K);
see e.g., polypeptide in SEQ ID NO: 94;
UAG-UAG-MS2 domains are bold-italicized
CTTATCGAAATTAATACGACTCACTATAGGGAGACCCAAGCTGGc tagaggatcgaacccttaaggccaccatggcgtccaatttcactc agtttgtgctggttgacaacggcgggaccggggacgttacggtag cccccctcaaactttgccaacggtatagcggagtggataagcagca attctaggagtcaagcatacaaagttacatgcagcgtgcgccaat ctagcgctcagaatcgcaagtacaccattaaagtagaggtcccca agggagcctggagaagctatcttaacatggagttgaccataccaa tcttcgctaccaactctgactgtgaactcattgtgaaagccatgc aaggtctgctcaaggatggtaacccaattccgtccgctatcgctg ccaactctgggatttacgggggcagtgggagcggtgcaggatctg gtagtccagctgggggaggagcaccgggtagcggtggggggtctc agctgcacctgccccaggttctcgcagacgccgtatcccgccttg tactgggcaagtttggtgatcttactgacaatttttcatctcctc atgcgaggcggaaagtactcgcaggcgtcgtcatgacgaccggaa ctgacgtgaaagacgccaaagtcatctctgtctccacgggcacaa agtgcataaacggggagtacatgagcgaccgggggctggcactga atgattgtcacgctgaaataatatctaggcgatctctgcttagat ttctctacactcaactcgaattgtaccttaacaacaaagatgacc agaaacgcagtatatttcagaaatcagaacgcggcggatttcgac ttaaggaaaacgttcagttccacttgtatatcagcacatcccctt gcggtgacgcccgaatcttttccccgcacgagccgatattggagg agcccgcgGCTAGCGGGTCGGGCACCGGTGCTCCACCCAATCTCT

GGGCAGCGCAGCGCTACGGCCGTGAGCTCAGAAGGATGTCCGATG

AGttcGTCGACagacatcctaataggaaggctagaggccaacttc ggacgaagattgaaagtggccagggtactatcccggtgcggtcca acgctagtattcaaacgtgggacggagtccttcaaggtgaacggc tgttgacaatgagctgctcagacaaaatcgcgcgctggaatgtag tgggaatccaaggcagcctcttgagcatattcgtagaacccatat atttctcatccattattttgggctctctgtatcatggtgaccatc tgtcaagggctatgtaccaacgaatttctaatatcgaggatcttc ctccactctatacactcaataagcctctcttgtccgggatatcaa acgctgaggcccgccagccagggaaagctcctaacttcagtgtta actggaccgttggtgattctgcgatagaggtcatcaacgccacga -continued caggtaaggatgagctcggtagagcctcacgcctgtgtaaacacg cgttgtattgtagatggatgagagtacatgggaaggtcccatctc acttgctccgaagcaagatcactaagcctaatgtgtatcatgagt caaaactcgcggctaaagaataccaggcagccaaagctcgacttt ttacagcttttattaaggcagggctcggggcatgggtcgagaagc cgaccgagcaggaccaattctctctgacggggagcGGAGGTACGG

AGAATTTGTATTTTCAGAGCGCCGCTTCAAGTAACCGGGAGCTGG

TGGTTGACTTTCTCTCCTACAAGCTTTCCCAGAAAGGATACAGCT

GGAGTCAGTTTAGTGATGTGGAAGAGAACAGGACTGAGGCCCCAG

AAGGGACTGAATCGGAGATGGAGACCCCCAGTGCCATCAATGGCA

ACCCATCCTGGCACCTGGCAGACAGCCCCGCGGTGAATGGAGCCA

CTGGCCACAGCAGCAGTTTGGATGCCCGGGAGGTGATCCCCATGG

CAGCAGTAAAGCAAGCGCTGAGGGAGGCAGGCGACGAGTTTGAAC

TGCGGTACCGGCGGGCATTCAGTGACCTGACATCCCAGCTCCACA

TCACCCCAGGGACAGCATATCAGAGCTTTGAACAGGTAGTGAATG

AACTCTTCCGGGATGGGGTAAACTGGGGTCGCATTGTGGCCTTTT

TCTCCTTCGGCGGGGCACTGTGCGTGGAAAGCGTAGACAAGGAGA

TGCAGGTATTGGTGAGTCGGATCGCAGCTTGGATGGCCACTTACC

TGAATGACCACCTAGAGCCTTGGATCCAGGAGAACGGCGGCTGGG

ATACTTTTGTGGAACTCTATGGGAACAATggatccAGCGAGCTGA

TTAAGGAGAACATGCACATGAAGCGCCCatcggtcgccaccatgg tgagcaagggcgaggaggataacatggccatcatcaaggagttca tgcgcttcaaggtgcacatggagggctccgtgaacggccacgagt tcgagatcgagggcgagggcgagggccgcccctacgagggcaccc agaccgccaagctgaaggtgaccaagggtggcccccctgcccttcg cctgggacatcctgtcccctcagttcatgtacggctccaaggcct acgtgaagcaccccgccgacatccccgactacttgaagctgtcct tccccgagggcttcaagtgggagcgcgtgatgaacttcgaggacg gcggcgtggtgaccgtgacccaggactcctccctgcaggacggcg agttcatctacaaggtgaagctgcgcggcaccaacttcccctccg acggccccgtaatgcagaagaagaccatgggctgggaggcctcct ccgagcggatgtaccccgaggacggcgccctgaagggcgagatca agcagaggctgaagctgaaggacggcggccactacgacgctgagg tcaagaccacctacaaggccaagaagcccgtgcagctgcccggcg cctacaacgtcaacatcaagttggacatcacctcccacaacgagg actacaccatcgtggaacagtacgaacgcgccgagggccgccact ccaccggcggcatggacgagctgTACaaggattacaaggatgacg atgacaaaGGTAGCGGGGCAACTAATTTTAGCTTACTCAAACAGG

CTGGGGACGTCGAGGAGAATCCAGGCCCTGCATCCGCTGGCTCTG

GAGAAGGACGAGGCTCCTTGCTCACCTGTGGAGATGTCGAAGAGA

ACCCAGGTCCTGCAACCGGGAATTC*CGCGTAGCGCTAGCTTTGCC*

-continued

*AGCGCCACGCGaaACATGAGGATcACCCATGT*GCCGCTATGGCAG
AAATCGGTACTGGCTTTCCATTCGACCCCCATTATGTGGAAGTCC
TGGGCGAGCGCATGCACTACGTCGATGTTGGTCCGCGCGATGGCA
CCCCTGTGCTGTTCCTGCACGGTAACCCGACCTCCTCCTACGTGT
GGCGCAACATCATCCCGCATGTTGCACCGACCCATCGCTGCATTG
CTCCAGACCTGATCGGTATGGGCAAATCCGACAAACCAGACCTGG
GTTATTTCTTCGACGACCACGTCCGCTTCATGGATGCCTTCATCG
AAGCCCTGGGTCTGGAAGAGGTCGTCCTGGTCATTCACGACTGGG
GCTCCGCTCTGGGTTTCCACTGGGCCAAGCGCAATCCAGAGCGCG
TCAAAGGTATTGCATTTATGGAGTTCATCCGCCCTATCCCGACCT
GGGACGAATGGCCAGAATTTGCCCGCGAGACCTTCCAGGCCTTCC
GCACCACCGACGTCGGCCGCAAGCTGATCATCGATCAGAACGTTT
TTATCGAGGGTACGCTGCCGATGGGTGTCGTCCGCCCGCTGACTG
AAGTCGAGATGGACCATTACCGCGAGCCGTTCCTGAATCCTGTTG
ACCGCGAGCCACTGTGGCGCTTCCCAAACGAGCTGCCAATCGCCG
GTGAGCCAGCGAACATCGTCGCGCTGGTCGAAGAATACATGGACT
GGCTGCACCAGTCCCCTGTCCCGAAGCTGCTGTTCTGGGGCACCC
CAGGCGTTCTGATCCCACCGGCCGAAGCCGCTCGCCTGGCCAAAA
GCCTGCCTAACTGCAAGGCTGTGGACATCGGCCCGGGTCTGAATC
TGCTGCAAGAAGACAACCCGGACCTGATCGGCAGCGAGATCGCGC
GCTGGCTGTCGACGCTCGAGATTTCTGGCACCGGTATGGCATCTA
TGACTGGAGGCCAACAGATGgGTCCTGCAACCGGGAATTC*CGCGT*
*AGCGCTAGCTTTGCCAGCGCCACGCGaaACATGAGGATcACCCAT*
*GT*ACTAGTGCCACAAACTTCTCTCTGCTAAAGCAAGCAGGTGATG
TTGAAGAAAACCCAGGGCCTGGAGGGTCCGAGGGCAGGGGAAGTC
TCCTAACATGCGGGGACGTGGAGGAAAATCCCGGCCCATCCGGAT
ATCCCTACGATGTGCCCGATTACGCTATCGATgtgagcaagggcg
aAgaAgataacaAggcctctctcccagcgacacatgagttacaca
tctttggctccatcaacggtgtggactttgacatggtgggtcagg
gcaccggcaatccaaatgatggttatgaggagttaaacctgaagt
ccaccaagggtgacctccagttctcccccctggattctggtccctc
atatcgggtatggcttccatcagtacctgccctaccctgacggga
tgtcgcctttccaggccgccatggtagatggcAGCggataccaag
tccatcgcacaatgcagtttgaagatggtgcctcccttactgtta
actaccgctacacctacgagggaagccacatcaaaggagaggccc
aggtgaaggggactggtttccctgctgacggtcctgtgatgacca
actcgctgaccgctgcggactggtgcaggtcgaagaagacttacc
ccaacgacaaaaccatcatcagtacctttaagtggagttacacca
ctggaaatggcaagAGAtaccggagcactgcgcggaccacctaca
cctttgccaagccaatggggctaactatctgaagaaccagccgat -continued gtacgtgttccgtaagacggagctcaagcactccaagaccgagct
caacttcaaggagtggcaaaaggcctttaccgatgtgatgGGAat
ggacGAGCTGTATaagGCTAGCTAAGCGGCCGCTCGAGTCTAGAG
GGCCCGCGGTTCGAAGGTAAGCCTATCCCTAACCCTCTCCTCGGT
CTCGATTCTACGCGTACCGGTCATCATCACCATCACCATTGAGTT
TAAACCCGCTGATCAG

Example 9

Development of Grazoprevir Activated ADAR

Described in other examples is a drug responsivity (small molecule) based upon the heterodimerization of Bcl-2 family proteins and BH3 peptides (BclxL & Mcl-1 along with Bad, Bid, & MS1 peptides). Described in Example 9 is a system based upon the drug induced dissociation of an antiviral peptide with a viral protease (e.g., CP5-46-4D5E & HCV protease NS3 from genotype 1B). This peptide binds with high affinity to the HCV protease, and can be dissociated by adding protease inhibitors like grazoprevir. Furthermore, there are no mutations and the protein utilizes the insertion site).

Figure 17:
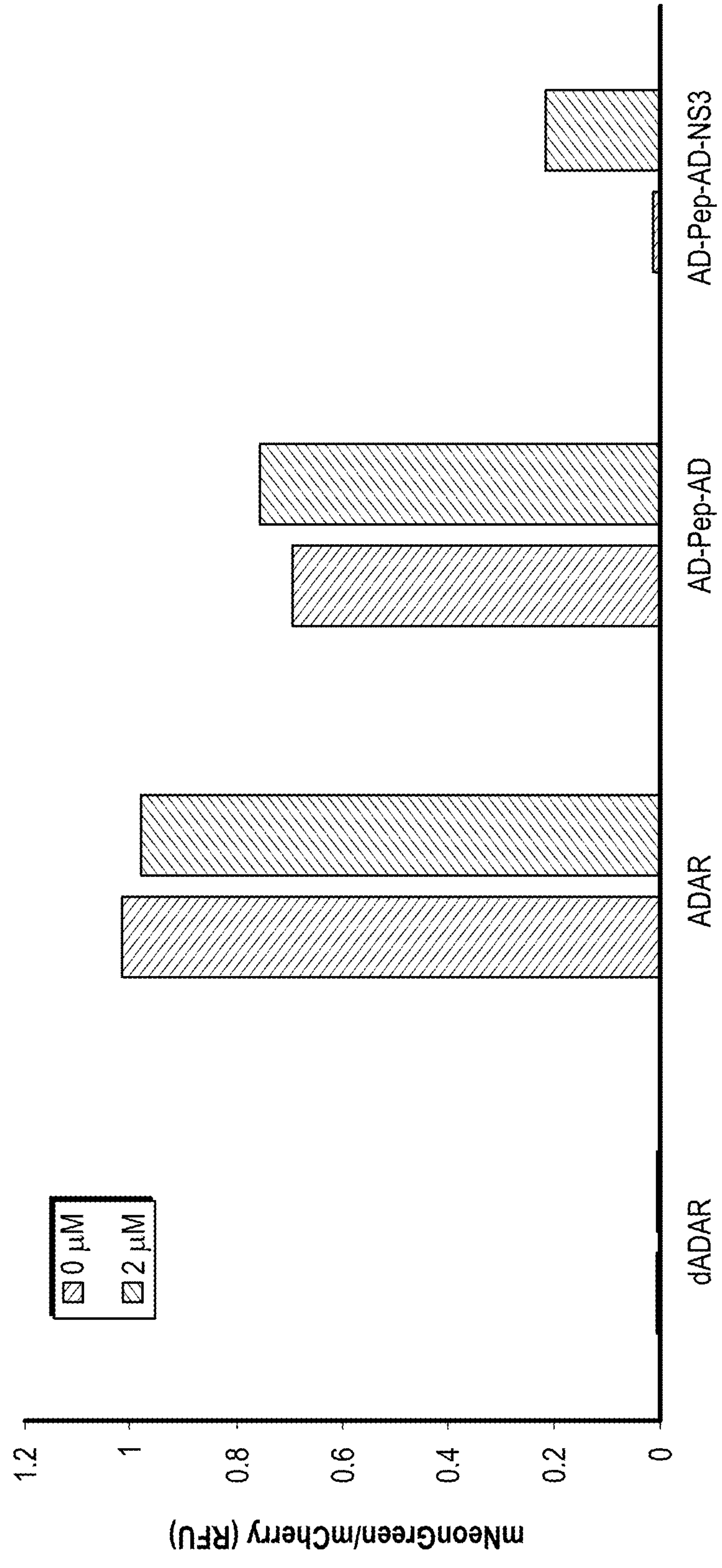
FIG. 17 shows activity of a Grazoprevir Activated ADAR ("AD-Pep-AD-NS3").

This drug-dissociative pair was utilized to engineer a NS3-inhibitor activated ADAR by fusing the peptide in the 5' binding loop and the NS3 protease to the C-terminus of ADAR2-DD. In some embodiments, a monomeric, tandem-dimer form of MS2 coat protein (tdMCP) can be used. Inserting the CP5-46-4D5E peptide into ADAR2-DD does not greatly influence editing activity, but fusing NS3 to the C-terminus leads to a drug-dependent reduction in editing efficiency (~18× higher mNG/mCh with grazoprevir) (see e.g., FIG. 17: HEK cells, transiently transfected with 2 μM grazoprevir added at the time of transfection, imaged 48 hours later, data processed by IMAGEJ to get the median value of the ratio of mNeonGreen to mCherry, gated by BFP for transfection).

SEQ ID NO: 168, tdMCP_ADAR2-DDN-CP5-46-4D5E_ADAR2-DDC(E488Q)_mTagBFP (AD-Pep-AD) (see e.g., FIG. 18)

MASNFTQFVLVDNGGTGDVTVAPSNFANGIAEWISSNSRSQAYKV
TCSVRQSSAQNRKYTIKVEVPKGAWRSYLNMELTIPIFATNSDCE
LIVKAMQGLLKDGNPIPSAIAANSGIYANFTQFVLVDNGGTGDVT
VAPSNFANGIAEWISSNSRSQAYKVTCSVRQSSAQNRKYTIKVEV
PKGAWRSYLNMELTIPIFATNSDCELIVKAMQGLLKDGNPIPSAI
AANSGIYGGSGSGAGSGSPAGGGAPGSGGGSQLHLPQVLADAVSR
LVLGKFGDLTDNFSSPHARRKVLAGVVMTTGTDVKDAKVISVSTG
TKCINGEYMSDRGLALNDCHAEIISRRSLLRFLYTQLELYLNNKD
DQKRSIFQKSERGGFRLKENVQFHLYISTSPCGDARIFSPHEPIL
EEPASSGGELDELVYLLDGPGYDPIHCDVVTRGGSHLFNFDRHPN
RKARGQLRTKIESGQGTIPVRSNASIQTWDGVLQGERLLTMSCSD
KIARWNVVGIQGSLLSIFVEPIYFSSIILGSLYHGDHLSRAMYQR
ISNIEDLPPLYTLNKPLLSGISNAEARQPGKAPNFSVNWTVGDSA
IEVINATTGKDELGRASRLCKHALYCRWMRVHGKVPSHLLRSKIT

-continued

KPNVYHESKLAAKEYQAAKARLFTAFIKAGLGAWVEKPTEQDQFS

LTGSGSSELIKENMHMKLYMEGTVDNHHFKCTSEGEGKPYEGTQT

MRIKVVEGGPLPFAFDILATSFLYGSKTFINHTQGIPDFFKQSFP

EGFTWERVTTYEDGGVLTATQDTSLQDGCLIYNVKIRGVNFTSNG

PVMQKKTLGWEAFTETLYPADGGLEGRNDMALKLVGGSHLIANIK

TTYRSKKPAKNLKMPGVYYVDYRLERIKEANNETYVEQHEVAVAR

YCDLPSKLGHKLN*

SEQ ID NO: 169, tdMCP_ADAR2-
DDN-CP5-46-4D5E ADAR2-
DDC(E488Q)_NS4A/NS3(Genotype 1B)_
mTagBFP (see e.g., FIG. 18)
MASNFTQFVLVDNGGTGDVTVAPSNFANGIAEWISSNSRSQAYKV

TCSVRQSSAQNRKYTIKVEVPKGAWRSYLNMELTIPIFATNSDCE

LIVKAMQGLLKDGNPIPSAIAANSGIYANFTQFVLVDNGGTGDVT

VAPSNFANGIAEWISSNSRSQAYKVTCSVRQSSAQNRKYTIKVEV

PKGAWRSYLNMELTIPIFATNSDCELIVKAMQGLLKDGNPIPSAI

AANSGIYGGSGSGAGSGSPAGGGAPGSGGGSQLHLPQVLADAVSR

LVLGKFGDLTDNFSSPHARRKVLAGVVMTTGTDVKDAKVISVSTG

TKCINGEYMSDRGLALNDCHAEIISRRSLLRFLYTQLELYLNNKD

DQKRSIFQKSERGGFRLKENVQFHLYISTSPCGDARIFSPHEPIL

EEPASSGGELDELVYLLDGPGYDPIHCDVVTRGGSHLFNFDRHPN

RKARGQLRTKIESGQGTIPVRSNASIQTWDGVLQGERLLTMSCSD

KIARWNVVGIQGSLLSIFVEPIYFSSIILGSLYHGDHLSRAMYQR

ISNIEDLPPLYTLNKPLLSGISNAEARQPGKAPNFSVNWTVGDSA

IEVINATTGKDELGRASRLCKHALYCRWMRVHGKVPSHLLRSKIT

KPNVYHESKLAAKEYQAAKARLFTAFIKAGLGAWVEKPTEQDQFS

LTGSAAGGSGGSAAAQGSVVIVGRIILSGSGSITAYSQQTRGLLG

CIITSLTGRDKNQVEGEVQVVSTATQSFLATCVNGVCWTVYHGAG

SKTLAGPKGPITQMYTNVDQDLVGWQAPPGARSLTPCTCGSSDLY

LVTRHADVIPVRRRGDSRGSLLSPRPVSYLKGSSGGPLLCPSGHA

VGIFRAAVCTRGVAKAVDFVPVESMETTMRSESGSGTMSELIKEN

MHMKLYMEGTVDNHHFKCTSEGEGKPYEGTQTMRIKVVEGGPLPF

AFDILATSFLYGSKTFINHTQGIPDFFKQSFPEGFTWERVTTYED

GGVLTATQDTSLQDGCLIYNVKIRGVNFTSNGPVMQKKTLGWEAF

TETLYPADGGLEGRNDMALKLVGGSHLIANIKTTYRSKKPAKNLK

MPGVYYVDYRLERIKEANNETYVEQHEVAVARYCDLPSKLGHKLN*

Example 10

Fusion of an Additional Binding Domain to Localize Inducer to iADAR and Increase Sensitivity In some embodiments, an antigen activated iADAR system can be relatively insensitive to low concentrations of inducer, as the intramolecular interaction is more likely to form, especially if the inducer binding is of similar affinity, due to high local concentration (see e.g., FIG. 19A).

In order to increase the sensitivity of the antigen-activated iADAR system, described herein is a system where there are 2 or more antigen binding domains (see e.g., FIG. 19B): (1) One antigen-binding domain is bound to the intramolecular epitope mimic, leading to inactivation of ADAR (green figures). (2) The other antigen-binding domain (which binds a distinct epitope) is unbound and therefore free to bind its epitope (blue figures).

In this system, the free antigen binding domain is able to bind to the inducer and localize the activating epitope closer to the iADAR.

This system is thermodynamically more likely to open and activate the ADAR at lower concentrations, and should be more sensitive to intracellular antigen.

This second antigen binding domain can be located at any position in the fusion protein relative to the other domains.

Example 11

Non-Limiting Examples of dsRNA Stop Loops with RNA Motifs

UAG-UAG Stop Loop w/ MS2 Loop

Figure 20A:
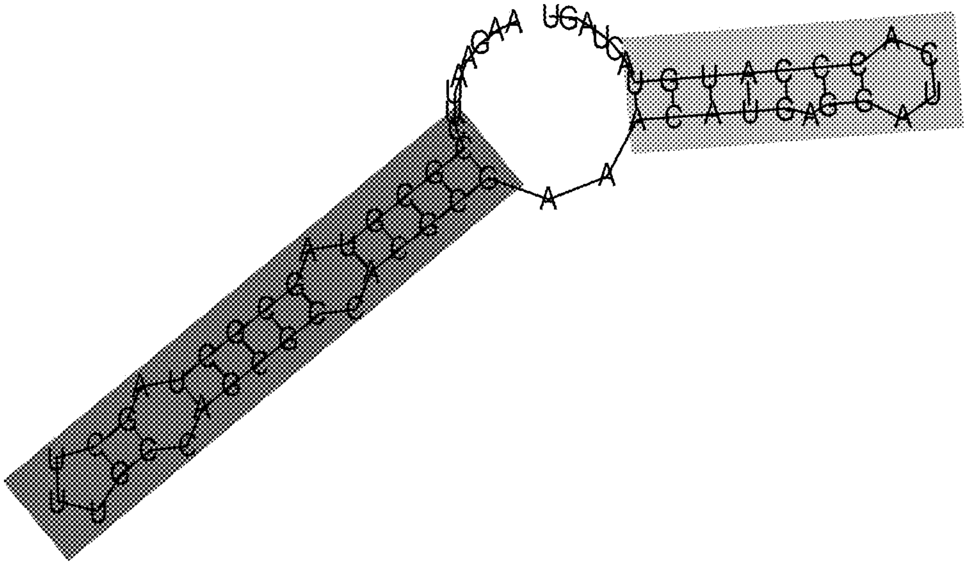
FIG. 20A-20H show non-limiting examples of dsRNA stop loops with RNA motifs; see also Example 1. The RNA secondary structures were generated by RNAFold™.

UAG-UAG Stop Loop (bolded) w/ MS2 Loop (italicized); this is the loop used most frequently and for most/all of the data with MS2 loops; see e.g., FIG. 20A:

SEQ ID NO: 170, DNA-
AATTCCGCGTAGCGCTAGCTTTGCCAGCGCCACGCGaa*ACA*

*TGAGGATcACCCATGT*ACTAGT

SEQ ID NO: 171, RNA-
AAUUCCGCGUAGCGCUAGCUUUGCCAGCGCCACGCGaa*ACA*

*UGAGGAUcACCCAUGU*ACUAGU

SEQ ID NO: 172, Protein-
NSA*R*LCQRHAKHEDHPCTS

SEQ ID NO: 173, Full DNA Sequence of
mCherry_FLAG_P2A_T2A_loop
(UAG-UAG)_MS2(C)_P2A_T2A_HA_
mNeonGreen (BOLD IS ORF); bold double
underlined is UAG-UAG Stop Loop w/ MS2
Loop, SEQ ID NO: 170 above:
TAATACGACTCACTATAGGGAGACC

CAAGCTGGCTAGGTAAGCTTGGTACCGAGCTCGGATC

Caccggtcgccaccatggtgagcaagggcgaggaggata acatggccatcatcaaggagttcatgcgcttcaaggtgca catggagggctccgtgaacggccacgagttcgagatcgag ggcgagggcgagggccgcccctacgagggcacccagaccg ccaagctgaaggtgaccaagggtggccccctgcccttcgc ctgggacatcctgtcccctcagttcatgtacggctccaag gcctacgtgaagcaccccgccgacatccccgactacttga agctgtccttccccgagggcttcaagtgggagcgcgtgat gaacttcgaggacggcggcgtggtgaccgtgacccaggac tcctccctgcaggacggcgagttcatctacaaggtgaagc tgcgcggcaccaacttcccctccgacggccccgtaatgca gaagaagaccatgggctgggaggcctcctccgagcggatg taccccgaggacggcgccctgaagggcgagatcaagcaga

-continued ggctgaagctgaaggacggcggccactacgacgctgaggt caagaccacctacaaggccaagaagcccgtgcagctgccc ggcgcctacaacgtcaacatcaagttggacatcacctccc acaacgaggactacaccatcgtggaacagtacgaacgcgc cgagggccgccactccaccggcggcatggacgagctgTAC aaggattacaaggatgacgatgacaaaGGTAGCGGGGCAA

CTAATTTTAGCTTACTCAAACAGGCTGGGGACGTCGAGGA

GAATCCAGGCCCTGCATCCGCTGGCTCTGGAGAAGGACGA

GGCTCCTTGCTCACCTGTGGAGATGTCGAAGAGAACCCAG

GTCCTGCAACCGGGAATTCCGCGTAGCGCTAGCTTTGCCA

GCGCCACGCGaaACATGAGGATcACCCATGTACTAGTGCC

ACAAACTTCTCTCTGCTAAAGCAAGCAGGTGATGTTGAAG

AAAACCCAGGGCCTGGAGGGTCCGAGGGCAGGGGAAGTCT

CCTAACATGCGGGGACGTGGAGGAAAATCCCGGCCCATCC

GGATATCCCTACGATGTGCCCGATTACGCTCATatggtga gcaagggcgaggaggataacatggcctctctcccagcgac acatgagttacacatctttggctccatcaacggtgtggac tttgacatggtgggtcagggcaccggcaatccaaatgatg gttatgaggagttaaacctgaagtccaccaagggtgacct ccagttctcccccctggattctggtccctcatatcgggtat ggcttccatcagtacctgccctaccctgacgggatgtcgc ctttccaggccgccatggtagatggcAGCggataccaagt ccatcgcacaatgcagtttgaagatggtgcctcccttact gttaactaccgctacacctacgagggaagccacatcaaag gagaggcccaggtgaaggggactggtttccctgctgacgg tcctgtgatgaccaactcgctgaccgctgcggactggtgc aggtcgaagaagacttaccccaacgacaaaaccatcatca gtacctttaagtggagttacaccactggaaatggcaagAG

Ataccggagcactgcgcggaccacctacacctttgccaag ccaatggcggctaactatctgaagaaccagccgatgtacg tgttccgtaagacggagctcaagcactccaagaccgagct caacttcaaggagtggcaaaaggcctttaccgatgtgatg

GGAatggacGAGCTGTATaagGCTAGCTAAGCGGCCGCTC

GAGTCTAGAGGGCCCGCGGTTCGAAGGTAAGCCTATCCCT

AACCCTCTCCTCGGTCTCGATTCTACGCGTACCGGTCATC

ATCACCATCACCATTGAGTTTAAACCCGCTGATCAGCCTC

GACTGTGCCTTCTA

UAG-UGG Stop Loop w/ MS2 Loop

Figure 20B:
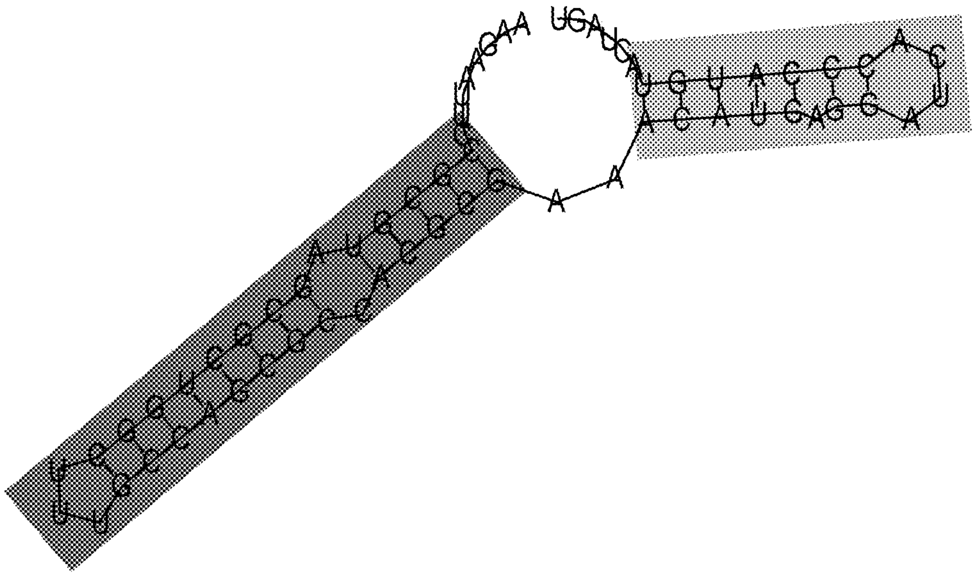

UAG-UGG Stop Loop (bolded) w/ MS2 Loop (italicized); see e.g., FIG. 20B:

SEQ ID NO: 174, DNA-
AATTCCGCGTAGCGCTGGCTTTGCCAGCGCCACGCG aa*ACATGAGGATcACCCATGTA*CTAGT

SEQ ID NO: 175, RNA-
AAUUCCGCGUAGCGCUGGCUUUGCCAGCGCCACGCG aa*ACAUGAGGAUcACCCAUGU*ACUAGU

SEQ ID NO: 176, Protein-
NSA*RWLCQRHAKHEDHPCTS

SEQ ID NO: 177, Full DNA Sequence of mCherry_FLAG_P2A_T2A_loop(UAG-UGG)_MS2(C)_P2A_T2A HA_mNeonGreen; bold is ORF; bold double underlined is UAG-UGG Stop Loop w/ MS2 Loop, SEQ ID NO: 174 from above:
TAATACGACTCACTATAGGGAGACCCAAGCTGGCTAGGTA AGCTTGGTACCGAGCTCGGATCCaccggtcgccaccatgg tgagcaagggcgaggaggataacatggccatcatcaagga gttcatgcgcttcaaggtgcacatggagggctccgtgaac ggccacgagttcgagatcgagggcgagggcgagggccgcc cctacgagggcacccagaccgccaagctgaaggtgaccaa gggtggccccctgcccttcgcctgggacatcctgtcccct cagttcatgtacggctccaaggcctacgtgaagcaccccg ccgacatccccgactacttgaagctgtccttccccgaggg cttcaagtgggagcgcgtgatgaacttcgaggacggcggc gtggtgaccgtgacccaggactcctccctgcaggacggcg agttcatctacaaggtgaagctgcgcggcaccaacttccc ctccgacggccccgtaatgcagaagaagaccatgggctgg gaggcctcctccgagcggatgtaccccgaggacggcgccc tgaagggcgagatcaagcagaggctgaagctgaaggacgg cggccactacgacgctgaggtcaagaccacctacaaggcc aagaagcccgtgcagctgcccggcgcctacaacgtcaaca tcaagttggacatcacctcccacaacgaggactacaccat cgtggaacagtacgaacgcgccgagggccgccactccacc ggcggcatggacgagctgTACaaggattacaaggatgacg atgacaaaGGTAGCGGGGCAACTAATTTTAGCTTACTCAA

ACAGGCTGGGGACGTCGAGGAGAATCCAGGCCCTGCATCC

GCTGGCTCTGGAGAAGGACGAGGCTCCTTGCTCACCTGTG

GAGATGTCGAAGAGAACCCAGGTCCTGCAACCGGGAATTC

CGCGTAGCGCTGGCTTTGCCAGCGCCACGCGaaACATGAG

GATcACCCATGTACTAGTGCCACAAACTTCTCTCTGCTAA

AGCAAGCAGGTGATGTTGAAGAAAACCCAGGGCCTGGAGG

GTCCGAGGGCAGGGGAAGTCTCCTAACATGCGGGGACGTG

GAGGAAAATCCCGGCCCATCCGGATATCCCTACGATGTGC

-continued

CCGATTACGCTCATatggtgagcaagggcgaggaggataa catggcctctctcccagcgacacatgagttacacatcttt ggctccatcaacggtgtggactttgacatggtgggtcagg gcaccggcaatccaaatgatggttatgaggagttaaacct gaagtccaccaagggtgacctccagttctcccccctggatt ctggtccctcatatcgggtatggcttccatcagtacctgc cctaccctgacgggatgtcgcctttccaggccgccatggt agatggcAGCggataccaagtccatcgcacaatgcagttt gaagatggtgcctcccttactgttaactaccgctacacct acgagggaagccacatcaaaggagaggcccaggtgaaggg gactggtttccctgctgacggtcctgtgatgaccaactcg ctgaccgctgcggactggtgcaggtcgaagaagacttacc ccaacgacaaaaccatcatcagtacctttaagtggagtta caccactggaaatggcaagAGAtaccggagcactgcgcgg accacctacacctttgccaagccaatggcggctaactatc tgaagaaccagccgatgtacgtgttccgtaagacggagct caagcactccaagaccgagctcaacttcaaggagtggcaa aaggcctttaccgatgtgatgGGAatggacGAGCTGTATa agGCTAGCTAAGCGGCCGCTCGAGTCTAGAGGGCCCGCGG

TTCGAAGGTAAGCCTATCCCTAACCCTCTCCTCGGTCTCG

ATTCTACGCGTACCGGTCATCATCACCATCACCATTGAGT

TTAAACCCGCTGATCAGCCTCGACTGTGCCTTCT

UGG-UAG Stop Loop w/ MS2 Loop

Figure 20C:
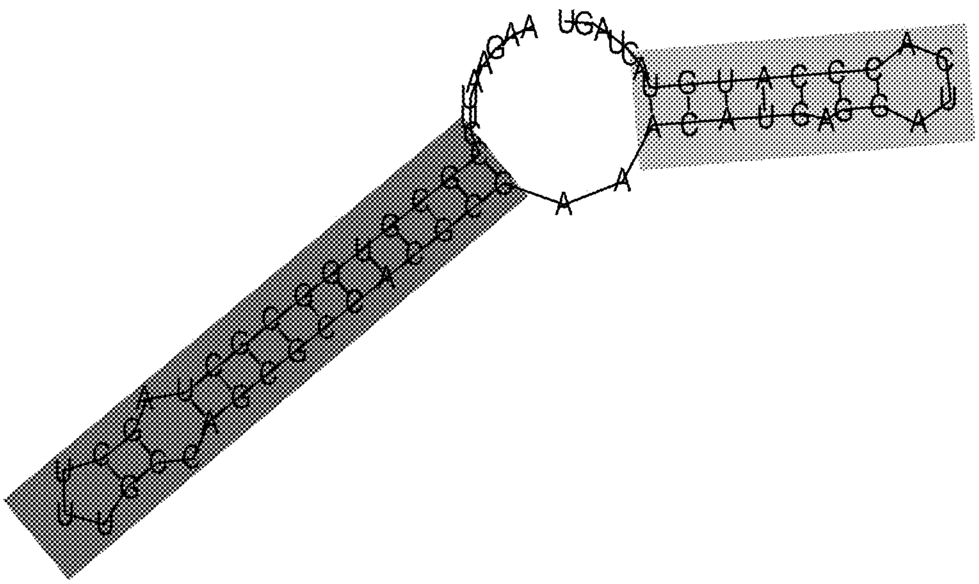

UGG-UAG Stop Loop (bolded) w/ MS2 Loop (italicized); see e.g., FIG. 20C:

SEQ ID NO: 178, DNA-
AATTCCGCGTGGCGCTAGCTTTGCCAGCGCCACGCG aa*ACATGAGGATcACCCATGT*ACTAGT

SEQ ID NO: 179, RNA-
AAUUCCGCGUGGCGCUAGCUUUGCCAGCGCCACGCG
aa*ACAUGAGGAUcACCCAUGU*ACUAGU

SEQ ID NO: 180 and SEQ ID NO: 394, Protein-
NSAWR*LCQRHAKHEDHPCTS

SEQ ID NO: 181, Full DNA Sequence of mCherry_FLAG_P2A_T2A_loop(UGG-UAG)_MS2(C)_P2A_T2A HA_mNeonGreen; bold is ORF; bold double underlined is UGG-UAG Stop Loop w/ MS2 Loop, SEQ ID NO: 178 from above:
TAATACGACTCACTATAGGGAGACCCAAGCTGGCTAGGTA AGCTTGGTACCGAGCTCGGATCCaccggtcgccaccatg gtgagcaagggcgaggaggataacatggccatcatcaagg agttcatgcgcttcaaggtgcacatggagggctccgtgaa cggccacgagttcgagatcgagggcgagggcgagggccgc ccctacgagggcacccagaccgccaagctgaaggtgacca agggtggcccccctgcccttcgcctgggacatcctgtcccc

-continued tcagttcatgtacggctccaaggcctacgtgaagcacccc gccgacatccccgactacttgaagctgtccttccccgagg gcttcaagtgggagcgcgtgatgaacttcgaggacggcgg cgtggtgaccgtgacccaggactcctccctgcaggacggc gagttcatctacaaggtgaagctgcgcggcaccaacttcc cctccgacggccccgtaatgcagaagaagaccatgggctg ggaggcctcctccgagcggatgtaccccgaggacggcgcc ctgaagggcgagatcaagcagaggctgaagctgaaggacg gcggccactacgacgctgaggtcaagaccacctacaaggc caagaagcccgtgcagctgcccggcgcctacaacgtcaac atcaagttggacatcacctcccacaacgaggactacacca tcgtggaacagtacgaacgcgccgagggccgccactccac cggcggcatggacgagctgTACaaggattacaaggatgac gatgacaaaGGTAGCGGGGCAACTAATTTTAGCTTACTCA

AACAGGCTGGGGACGTCGAGGAGAATCCAGGCCCTGCATC

CGCTGGCTCTGGAGAAGGACGAGGCTCCTTGCTCACCTGT

GGAGATGTCGAAGAGAACCCAGGTCCTGCAACCGGGAATT

CCGCGTGGCGCTAGCTTTGCCAGCGCCACGCGaaACATGA

GGATcACCCATGTACTAGTGCCACAAACTTCTCTCTGCTA

AAGCAAGCAGGTGATGTTGAAGAAAACCCAGGGCCTGGAG

GGTCCGAGGGCAGGGGAAGTCTCCTAACATGCGGGGACGT

GGAGGAAAATCCCGGCCCATCCGGATATCCCTACGATGTG

CCCGATTACGCTCATatggtgagcaagggcgaggaggata acatggcctctctcccagcgacacatgagttacacatctt tggctccatcaacggtgtggactttgacatggtgggtcag ggcaccggcaatccaaatgatggttatgaggagttaaacc tgaagtccaccaagggtgacctccagttctcccccctggat tctggtccctcatatcgggtatggcttccatcagtacctg ccctaccctgacgggatgtcgcctttccaggccgccatgg tagatggcAGCggataccaagtccatcgcacaatgcagtt tgaagatggtgcctcccttactgttaactaccgctacacc tacgagggaagccacatcaaaggagaggcccaggtgaagg ggactggtttccctgctgacggtcctgtgatgaccaactc gctgaccgctgcggactggtgcaggtcgaagaagacttac cccaacgacaaaaccatcatcagtacctttaagtggagtt acaccactggaaatggcaagAGAtaccggagcactgcgcg gaccacctacacctttgccaagccaatggcggctaactat ctgaagaaccagccgatgtacgtgttccgtaagacggagc tcaagcactccaagaccgagctcaacttcaaggagtggca aaaggcctttaccgatgtgatgGGAatggacGAGCTGTAT

-continued aagGCTAGCTAAGCGGCCGCTCGAGTCTAGAGGGCCCGCG

GTTCGAAGGTAAGCCTATCCCTAACCCTCTCCTCGGTCTC

GATTCTACGCGTACCGGTCATCATCACCATCACCATTGAG

TTTAAACCCGCTGATCAGCCTCGACTGTGCCTTCT

UAG-UAG Stop Loop w/ Internal MS2 Loop

Figure 20D:
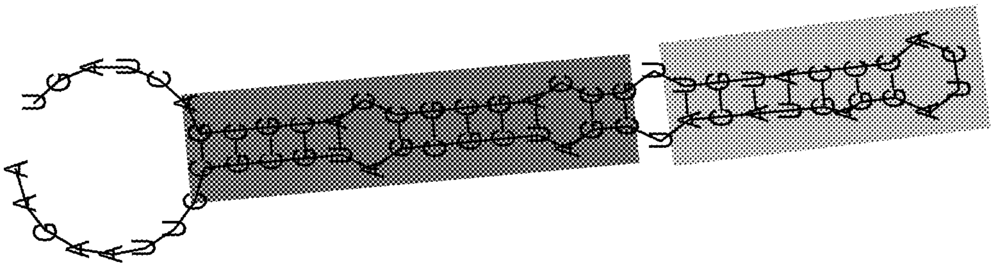

UAG-UAG Stop Loop (bolded) w/Internal MS2 Loop (italicized); see e.g., FIG. 20D:
SEQ ID NO: 182, DNA-
AATTCCGCGTAGCGCTAGCT*ACATGAGGATcA*

*CCCATGTT*GCCAGCGCCACGCGACTAGT

SEQ ID NO: 183, RNA-
AAUUCCGCGUAGCGCUAGCU*ACAUGAGGAUCA*

*CCCAUGUU*GCCAGCGCCACGCGACUAGU

SEQ ID NO: 184, Protein-
NSA*R*LHEDHPCCQRHATS

SEQ ID NO: 185, Full DNA Sequence of mCherry FLAG_P2A_T2A_loop((UAG-UAG) MS2(C))_P2A_T2A_HA_mNeonGreen; bold is ORF; bold double underlined is UAG-UAG Stop Loop w/Internal MS2 Loop, SEQ ID NO: 182 from above:
TAATACGACTCACTATAGGGAGACCCAAGCTGGCTAGGTA AGCTTGGTACCGAGCTCGGATCCaccggtcgccaccatgg tgagcaagggcgaggaggataacatggccatcatcaagga gttcatgcgcttcaaggtgcacatggagggctccgtgaac ggccacgagttcgagatcgagggcgagggcgagggccgcc cctacgagggcacccagaccgccaagctgaaggtgaccaa gggtggccccctgcccttcgcctgggacatcctgtcccct cagttcatgtacggctccaaggcctacgtgaagcaccccg ccgacatccccgactacttgaagctgtccttccccgaggg cttcaagtgggagcgcgtgatgaacttcgaggacggcggc gtggtgaccgtgacccaggactcctccctgcaggacggcg agttcatctacaaggtgaagctgcgcggcaccaacttccc ctccgacggccccgtaatgcagaagaagaccatgggctgg gaggcctcctccgagcggatgtaccccgaggacggcgccc tgaagggcgagatcaagcagaggctgaagctgaaggacgg cggccactacgacgctgaggtcaagaccacctacaaggcc aagaagcccgtgcagctgcccggcgcctacaacgtcaaca tcaagttggacatcacctcccacaacgaggactacaccat cgtggaacagtacgaacgcgccgagggccgccactccacc ggcggcatggacgagctgTACaaggattacaaggatgacg atgacaaaGGTAGCGGGGCAACTAATTTTAGCTTACTCAA

ACAGGCTGGGGACGTCGAGGAGAATCCAGGCCCTGCATCC

GCTGGCTCTGGAGAAGGACGAGGCTCCTTGCTCACCTGTG

GAGATGTCGAAGAGAACCCAGGTCCTGCAACCGGGAATTC

-continued

CGCGTAGCGCTAGCTACATGAGGATcACCCATGTTGCCAG

CGCCACGCGACTAGTGCCACAAACTTCTCTCTGCTAAAGC

AAGCAGGTGATGTTGAAGAAAACCCAGGGCCTGGAGGGTC

CGAGGGCAGGGGAAGTCTCCTAACATGCGGGGACGTGGAG

GAAAATCCCGGCCCATCCGGATATCCCTACGATGTGCCCG

ATTACGCTCATatggtgagcaagggcgaggaggataacat ggcctctctcccagcgacacatgagttacacatctttggc tccatcaacggtgtggactttgacatggtgggtcagggca ccggcaatccaaatgatggttatgaggagttaaacctgaa gtccaccaagggtgacctccagttctccccctggattctg gtccctcatatcgggtatggcttccatcagtacctgccct accctgacgggatgtcgcctttccaggccgccatggtaga tggcAGCggataccaagtccatcgcacaatgcagtttgaa gatggtgcctcccttactgttaactaccgctacacctacg agggaagccacatcaaaggagaggcccaggtgaaggggac tggtttccctgctgacggtcctgtgatgaccaactcgctg accgctgcggactggtgcaggtcgaagaagacttacccca acgacaaaaccatcatcagtacctttaagtggagttacac cactggaaatggcaagAGAtaccggagcactgcgcggacc acctacacctttgccaagccaatggcggctaactatctga agaaccagccgatgtacgtgttccgtaagacggagctcaa gcactccaagaccgagctcaacttcaaggagtggcaaaag gcctttaccgatgtgatgGGAatggacGAGCTGTATaagG

CTAGCTAAGCGGCCGCTCGAGTCTAGAGGGCCCGCGGTTC

GAAGGTAAGCCTATCCCTAACCCTCTCCTCGGTCTCGATT

CTACGCGTACCGGTCATCATCACCATCACCATTGAGTTTA

AACCCGCTGATCAGCCTCGACTGTGCCTTCT

UAG-UAG Stop Loop w/ PP7 Loop

Figure 20E:
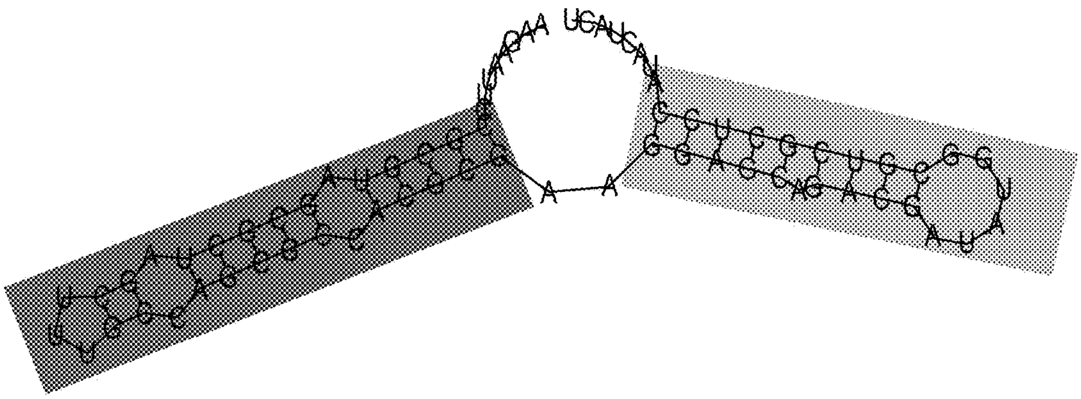

UAG-UAG Stop Loop (bolded) w/ PP7 Loop (italicized); see e.g., FIG. 20E:
SEQ ID NO: 186, DNA-
AATTCCGCGTAGCGCTAGCTTTGCCAGCGCCACGCG

*aaggagcagacgatatggcgtcgctccaa*TACTAGT

SEQ ID NO: 187, RNA-
AAUUCCGCGUAGCGCUAGCUUUGCCAGCGCCACGCG
*aaggagcagacgauauggcgucgcuccaa*UACUAGU SEQ ID NO: 188, Protein-
NSA*R*LCQRHAKEQTIWRRSNTS SEQ ID NO: 189, Full DNA Sequence of mCherry_FLAG_P2A_T2A_loop(UAG-UAG) PP7_P2A_T2A_HA_mNeonGreen; bold is ORF; bold double underlined is UAG-UAG Stop Loop w/ PP7 Loop, SEQ ID NO: 186 from above:
TAATACGACTCACTATAGGGAGACCCAAGCTGGCTAGGTA AGCTTGGTACCGAGCTCGGATCCaccggtcgccaccatg

Figure 20F:
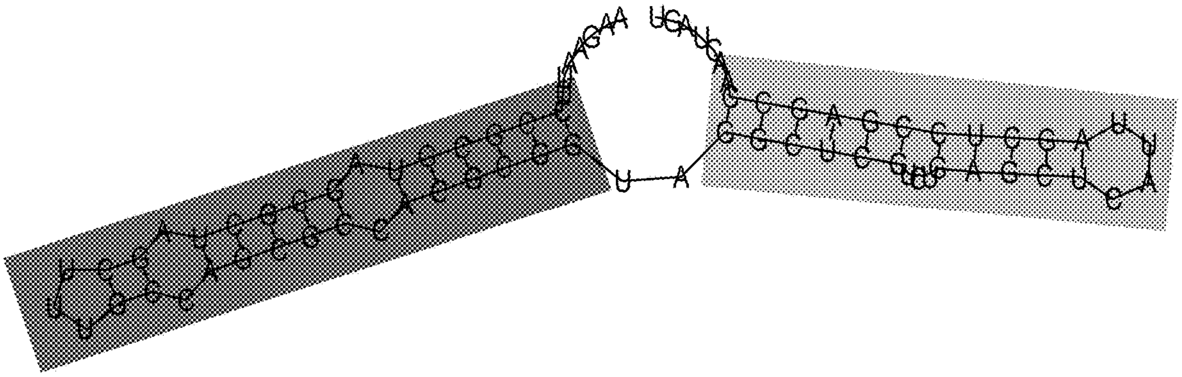

-continued gtgagcaagggcgaggaggataacatggccatcatcaagg
agttcatgcgcttcaaggtgcacatggagggctccgtgaa
cggccacgagttcgagatcgagggcgagggcgagggccgc
ccctacgagggcacccagaccgccaagctgaaggtgacca
agggtggcccctgcccttcgcctgggacatcctgtcccc
tcagttcatgtacggctccaaggcctacgtgaagcacccc
gccgacatccccgactacttgaagctgtccttccccgagg
gcttcaagtgggagcgcgtgatgaacttcgaggacggcgg
cgtggtgaccgtgacccaggactcctccctgcaggacggc
gagttcatctacaaggtgaagctgcgcggcaccaacttcc
cctccgacggccccgtaatgcagaagaagaccatgggctg
ggaggcctcctccgagcggatgtaccccgaggacggcgcc
ctgaagggcgagatcaagcagaggctgaagctgaaggacg
gcggccactacgacgctgaggtcaagaccacctacaaggc
caagaagcccgtgcagctgcccggcgcctacaacgtcaac
atcaagttggacatcacctcccacaacgaggactacacca
tcgtggaacagtacgaacgcgccgagggccgccactccac
cggcggcatggacgagctgTACaaggattacaaggatgac
gatgacaaaGGTAGCGGGGCAACTAATTTTAGCTTACTCA
AACAGGCTGGGGACGTCGAGGAGAATCCAGGCCCTGCATC
CGCTGGCTCTGGAGAAGGACGAGGCTCCTTGCTCACCTGT
GGAGATGTCGAAGAGAACCCAGGTCCTGCAACCGGGAATT
CCGCGTAGCGCTAGCTTTGCCAGCGCCACGCGaaggagca
gacgatatggcctcgctccaaTACTAGTGCCACAAACTTC
TCTCTGCTAAAGCAAGCAGGTGATGTTGAAGAAAACCCAG
GGCCTGGAGGGTCCGAGGGCAGGGGAAGTCTCCTAACATG
CGGGGACGTGGAGGAAAATCCCGGCCCATCCGGATATCCC
TACGATGTGCCCGATTACGCTCATatggtgagcaagggcg
aggaggataacatggcctctctcccagcgacacatgagtt
acacatctttggctccatcaacggtgtggactttgacatg
gtgggtcagggcaccggcaatccaaatgatggttatgagg
agttaaacctgaagtccaccaagggtgacctccagttctc
cccctggattctggtccctcatatcgggtatggcttccat
cagtacctgccctaccctgacgggatgtcgcctttccagg
ccgccatggtagatggcAGCggataccaagtccatcgcac
aatgcagtttgaagatggtgcctcccttactgttaactac
cgctacacctacgagggaagccacatcaaaggagaggccc
aggtgaaggggactggtttccctgctgacggtcctgtgat
gaccaactcgctgaccgctgcggactggtgcaggtcgaag
aagacttaccccaacgacaaaaccatcatcagtaccttta -continued agtggagttacaccactggaaatggcaagAGAtaccggag
cactgcgcggaccacctacacctttgccaagccaatggcg
gctaactatctgaagaaccagccgatgtacgtgttccgta
agacggagctcaagcactccaagaccgagctcaacttcaa
ggagtggcaaaaggcctttaccgatgtgatgGGAatggac
GAGCTGTATaagGCTAGCTAAGCGGCCGCTCGAGTCTAGA
GGGCCCGCGGTTCGAAGGTAAGCCTATCCCTAACCCTCTC
CTCGGTCTCGATTCTACGCGTACCGGTCATCATCACCATC
ACCATTGAGTTTAAACCCGCTGATCAGCCTCGACTGTGCC
TTCT UAG-UAG Stop Loop w/ HIV Tar Loop UAG-UAG Stop Loop (bolded) w/ HIV Tar Loop (italicized); see e.g., FIG. 20F:
SEQ ID NO: 190, DNA-
AATTCCGCGTAGCGCTAGCTTTGCCAGCGCCACGCGGt
*aggctcgtctgagctcattagctccgagcca*ACTAGT SEQ ID NO: 191, RNA-
AAUUCCGCGUAGCGCUAGCUUUGCCAGCGCCACGCGGua
*ggcucgucugagcucauuagcuccgagcca*ACUAGU SEQ ID NO: 192, Protein-
NSA*R*LCQRHAVGSSELISSEPTS SEQ ID NO: 193, Full DNA Sequence of mCherry FLAG_P2A_T2A loop(UAG-UAG) HIV Tar P2A T2A HA mNeonGreen; bold is ORF; bold double underlined is UAG-UAG Stop Loop w/ HIV Tar Loop, SEQ ID NO: 190 from above:
TAATACGACTCACTATAGGGAGACCCAAGCTGGCTAGGTAAGCTT
GGTACCGAGCTCGGATCCaccggtcgccaccatggtgagcaaggg
cgaggaggataacatggccatcatcaaggagttcatgcgcttcaa
ggtgcacatggagggctccgtgaacggccacgagttcgagatcga
gggcgagggcgagggccgcccctacgagggcacccagaccgccaa
gctgaaggtgaccaagggtggcccctgcccttcgcctgggacat
cctgtcccctcagttcatgtacggctccaaggcctacgtgaagca
ccccgccgacatccccgactacttgaagctgtccttccccgaggg
cttcaagtgggagcgcgtgatgaacttcgaggacggcggcgtggt
gaccgtgacccaggactcctccctgcaggacggcgagttcatcta
caaggtgaagctgcgcggcaccaacttcccctccgacggccccgt
aatgcagaagaagaccatgggctgggaggcctcctccgagcggat
gtaccccgaggacggcgccctgaagggcgagatcaagcagaggct
gaagctgaaggacggcggccactacgacgctgaggtcaagaccac
ctacaaggccaagaagcccgtgcagctgcccggcgcctacaacgt
caacatcaagttggacatcacctcccacaacgaggactacaccat
cgtggaacagtacgaacgcgccgagggccgccactccaccggcgg
catggacgagctgTACaaggattacaaggatgacgatgacaaaGG
TAGCGGGGCAACTAATTTTAGCTTACTCAAACAGGCTGGGGACGT -continued

CGAGGAGAATCCAGGCCCTGCATCCGCTGGCTCTGGAGAAGGACG

AGGCTCCTTGCTCACCTGTGGAGATGTCGAAGAGAACCCAGGTCC

TGCAACCGGGAATTCCGCGTAGCGCTAGCTTTGCCAGCGCCACGC

GGtaggctcgtctgagctcattagctccgagccaACTAGTGCCAC

AAACTTCTCTCTGCTAAAGCAAGCAGGTGATGTTGAAGAAAACCC

AGGGCCTGGAGGGTCCGAGGGCAGGGGAAGTCTCCTAACATGCGG

GGACGTGGAGGAAAATCCCGGCCCATCCGGATATCCCTACGATGT

GCCCGATTACGCTCATatggtgagcaagggcgaggaggataacat ggcctctctcccagcgacacatgagttacacatctttggctccat caacggtgtggactttgacatggtgggtcagggcaccggcaatcc aaatgatggttatgaggagttaaacctgaagtccaccaagggtga cctccagttctcccccctggattctggtccctcatatcgggtatgg cttccatcagtacctgccctaccctgacgggatgtcgcctttcca ggccgccatggtagatggcAGCggataccaagtccatcgcacaat gcagtttgaagatggtgcctcccttactgttaactaccgctacac ctacgagggaagccacatcaaaggagaggcccaggtgaaggggac tggtttccctgctgacggtcctgtgatgaccaactcgctgaccgc tgcggactggtgcaggtcgaagaagacttaccccaacgacaaaac catcatcagtacctttaagtggagttacaccactggaaatggcaa gAGAtaccggagcactgcgcggaccacctacacctttgccaagcc aatggcggctaactatctgaagaaccagccgatgtacgtgttccg taagacggagctcaagcactccaagaccgagctcaacttcaagga gtggcaaaaggcctttaccgatgtgatgGGAatggacGAGCTGTA TaagGCTAGCTAAGCGGCCGCTCGAGTCTAGAGGGCCCGCGGTTC

GAAGGTAAGCCTATCCCTAACCCTCTCCTCGGTCTCGATTCTACG

CGTACCGGTCATCATCACCATCACCATTGAGTTTAAACCCGCTGA

TCAGCCTCGACTGTGCCTTCT

UAG-UAG Stop Loop w/ BoxB Loop

Figure 20G:
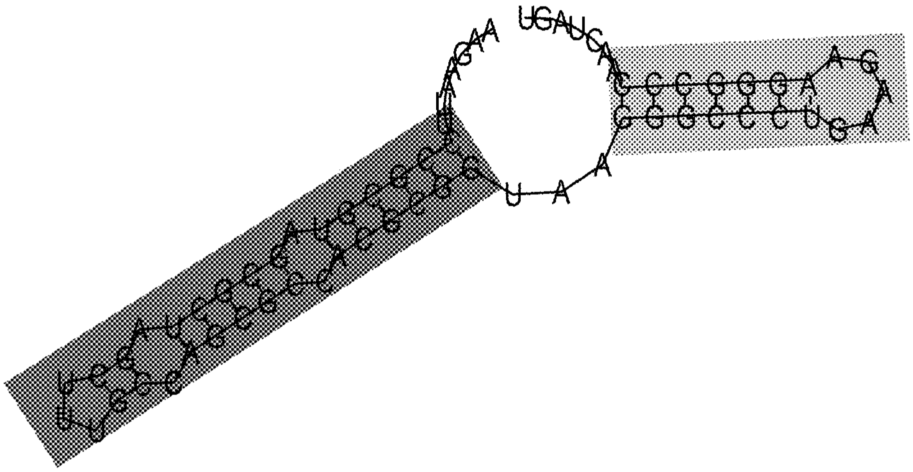
Figure 20H:
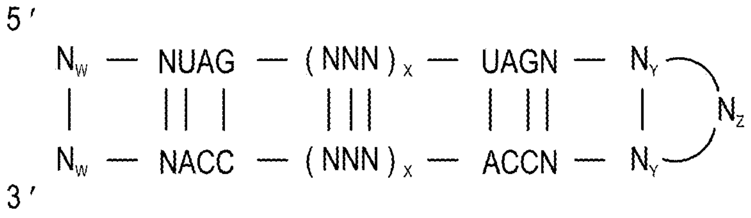

UAG-UAG Stop Loop (bolded) w/ BoxB Loop (italicized); see e.g., FIG. 20G:
SEQ ID NO: 194, DNA-
AATTCCGCGTAGCGCTAGCTTTGCCAGCGCCACGCGG taa*gggccctgaagaagggccc*aACTAGT

SEQ ID NO: 195, RNA-
AAUUCCGCGUAGCGCUAGCUUUGCCAGCGCCACGCGG uaagggcccugaagaagggcccaACUAGU SEQ ID NO: 196, Protein-NSA*R*LCQRHAVRALKKGPTS SEQ ID NO: 197, Full DNA Sequence of mCherry_FLAG_P2A_T2A_loop(UAG-UAG) BoxB_P2A_T2A HA mNeonGreen; bold is ORF; bold double underlined is UAG-UAG Stop -continued Loop w/ BoxB Loop, SEQ ID NO: 194 from above:
TAATACGACTCACTATAGGGAGACCCAAGCTGGCTAGGTAAGCTT GGTACCGAGCTCGGATCCaccggtcgccaccatggtgagcaaggg cgaggaggataacatggccatcatcaaggagttcatgcgcttcaa ggtgcacatggagggctccgtgaacggccacgagttcgagatcga gggcgagggcgagggccgcccctacgagggcacccagaccgccaa gctgaaggtgaccaagggtggccccctgcccttcgcctgggacat cctgtcccctcagttcatgtacggctccaaggcctacgtgaagca ccccgccgacatccccgactacttgaagctgtccttccccgaggg cttcaagtgggagcgcgtgatgaacttcgaggacggcggcgtggt gaccgtgacccaggactcctccctgcaggacggcgagttcatcta caaggtgaagctgcgcggcaccaacttcccctccgacggccccgt aatgcagaagaagaccatgggctgggaggcctcctccgagcggat gtaccccgaggacggcgccctgaagggcgagatcaagcagaggct gaagctgaaggacggcggccactacgacgctgaggtcaagaccac ctacaaggccaagaagcccgtgcagctgcccggcgcctacaacgt caacatcaagttggacatcacctcccacaacgaggactacaccat cgtggaacagtacgaacgcgccgagggccgccactccaccggcgg catggacgagctgTACaaggattacaaggatgacgatgacaaaGG

TAGCGGGGCAACTAATTTTAGCTTACTCAAACAGGCTGGGGACGT

CGAGGAGAATCCAGGCCCTGCATCCGCTGGCTCTGGAGAAGGACG

AGGCTCCTTGCTCACCTGTGGAGATGTCGAAGAGAACCCAGGTCC

TGCAACCGGGAATTCCGCGTAGCGCTAGCTTTGCCAGCGCCACGC

GGtaagggccctgaagaagggcccaACTAGTGCCACAAACTTCTC

TCTGCTAAAGCAAGCAGGTGATGTTGAAGAAAACCCAGGGCCTGG

AGGGTCCGAGGGCAGGGGAAGTCTCCTAACATGCGGGGACGTGGA

GGAAAATCCCGGCCCATCCGGATATCCCTACGATGTGCCCGATTA

CGCTCATatggtgagcaagggcgaggaggataacatggcctctct cccagcgacacatgagttacacatctttggctccatcaacggtgt ggactttgacatggtgggtcagggcaccggcaatccaaatgatgg ttatgaggagttaaacctgaagtccaccaagggtgacctccagtt ctcccccctggattctggtccctcatatcgggtatggcttccatca gtacctgccctaccctgacgggatgtcgcctttccaggccgccat ggtagatggcAGCggataccaagtccatcgcacaatgcagtttga agatggtgcctcccttactgttaactaccgctacacctacgaggg aagccacatcaaaggagaggcccaggtgaaggggactggtttccc tgctgacggtcctgtgatgaccaactcgctgaccgctgcggactg gtgcaggtcgaagaagacttaccccaacgacaaaaccatcatcag tacctttaagtggagttacaccactggaaatggcaagAGAtaccg gagcactgcgcggaccacctacacctttgccaagccaatggcggc taactatctgaagaaccagccgatgtacgtgttccgtaagacgga -continued gctcaagcactccaagaccgagctcaacttcaaggagtggcaaaa ggcctttaccgatgtgatgGGAatggacGAGCTGTATaagGCTAG

CTAAGCGGCCGCTCGAGTCTAGAGGGCCCGCGGTTCGAAGGTAAG

CCTATCCCTAACCCTCTCCTCGGTCTCGATTCTACGCGTACCGGT

CATCATCACCATCACCATTGAGTTTAAACCCGCTGATCAGCCTCG

ACTGTGCCTTCT

Example 12: Mutations to the IP6 Binding Pocket Reduce Background Activity

Figure 22A:
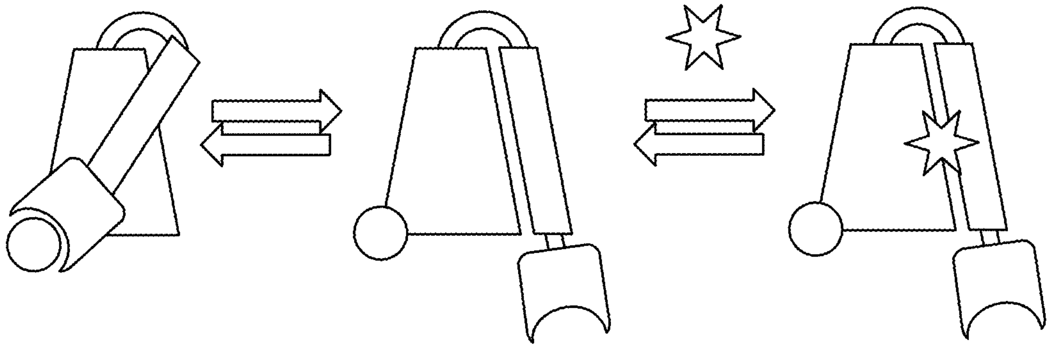
FIG. 22A-22D show that mutation of IP6 binding pocket reduces the background of allosteric ADAR.
Figure 22B:
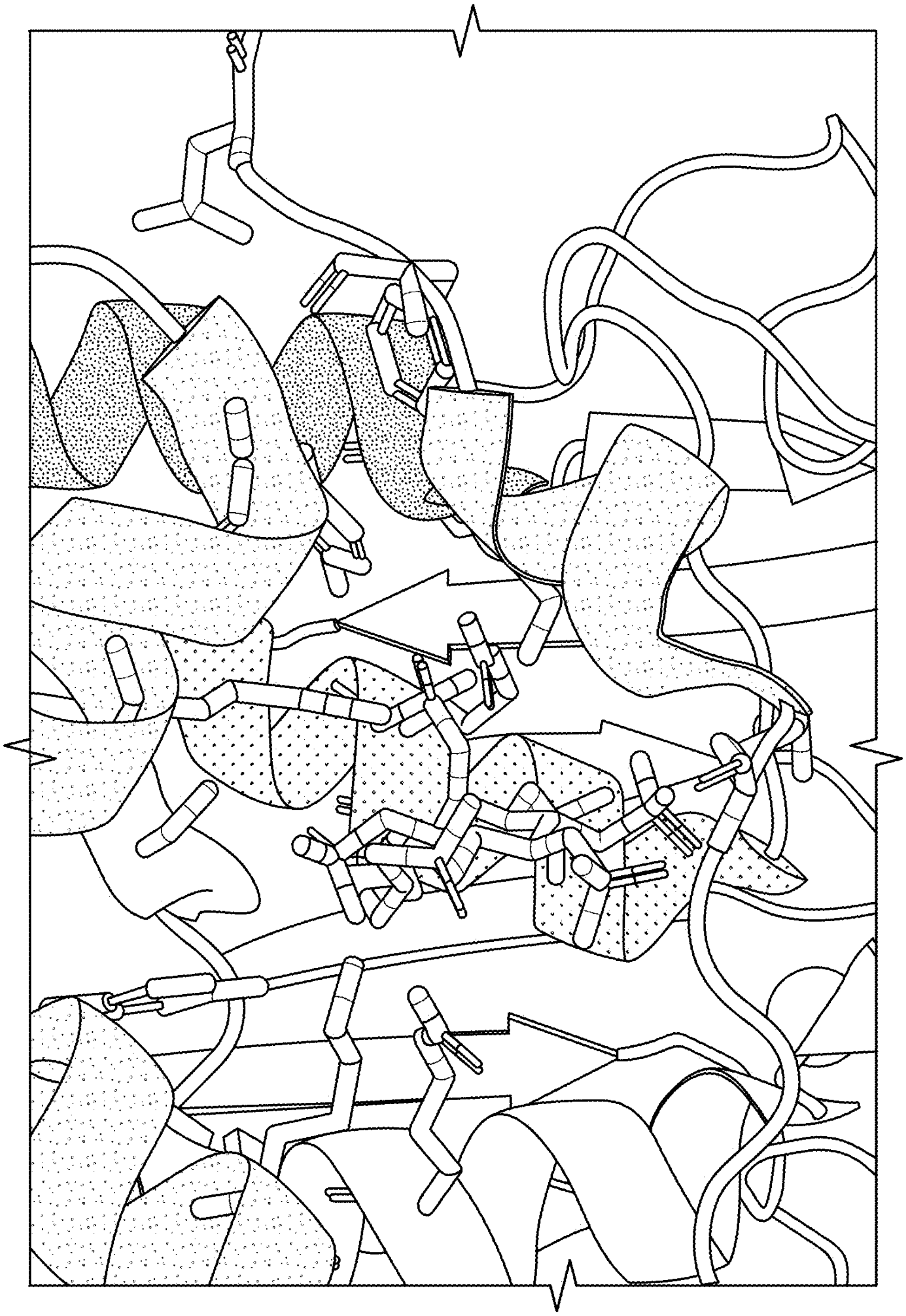
Figure 22B:
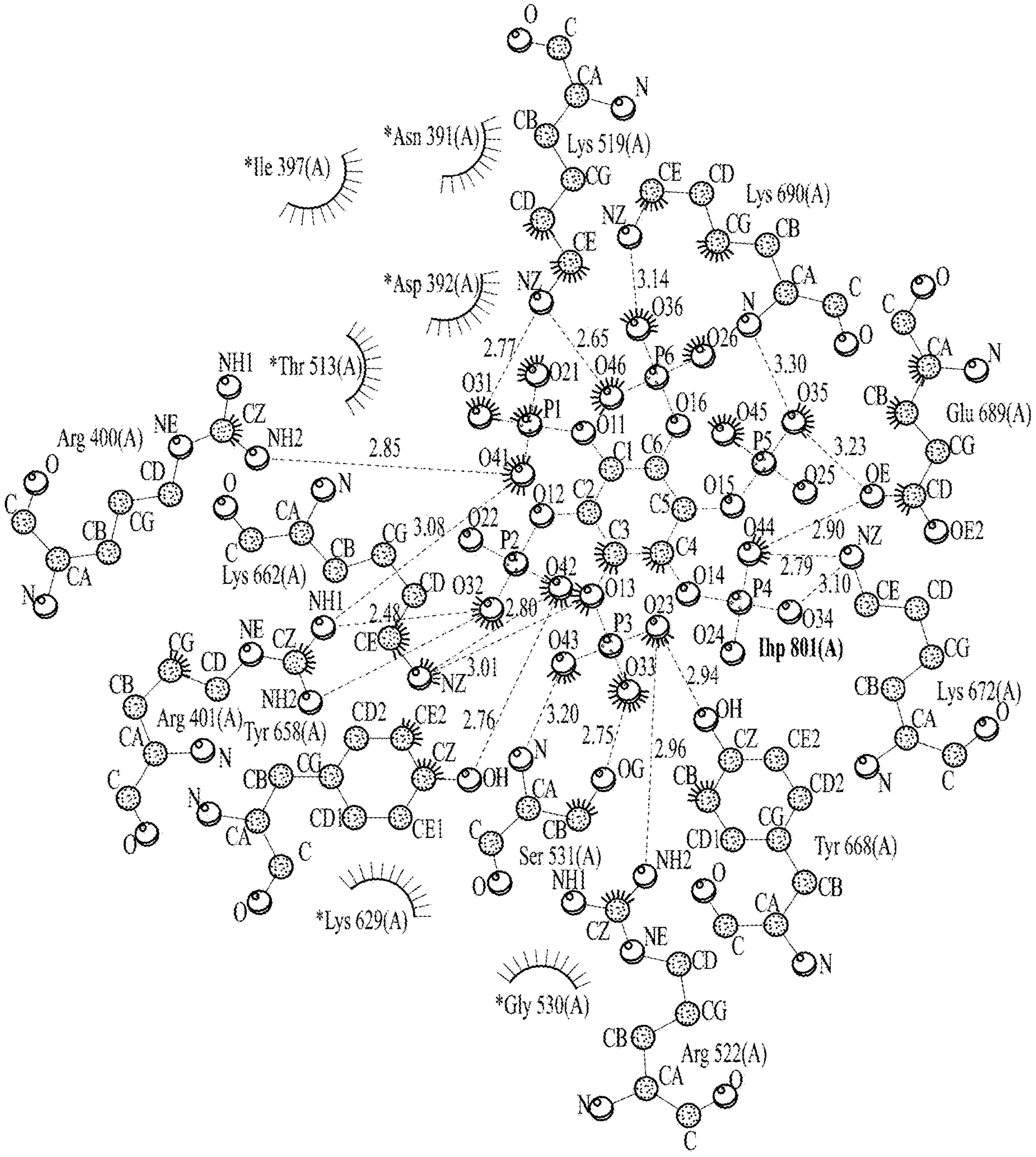

With the IP6-competition hypothesis previously outlined, the system should be in equilibrium between the cis-interaction (misfolded) state of ADAR and the IP6-bound (folded and active) state of ADAR (see e.g., FIG. 22*a*). In this model, the background in the system would be a result of the IP6 bound state. Background can be reduced by shifting the equilibrium towards the cis-interaction by either increasing the affinity of the heterodimers or by decreasing the affinity for the enzyme for IP6.

Towards this end, mutant variants of the ADAR2-DD were created and tested to see if the background could be reduced from a leaky system. The screen focused on conserved residues involved in IP6 binding or C-terminal tail folding (see e.g., FIG. 22*b*), as it was hypothesized that these would be the most likely to reduce the background of the system.

Figure 22C:
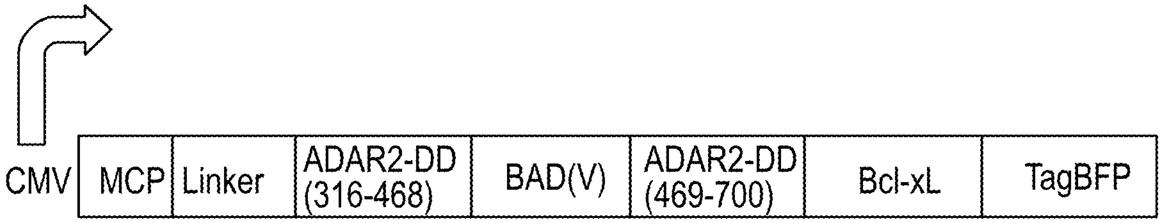
Figure 22D:
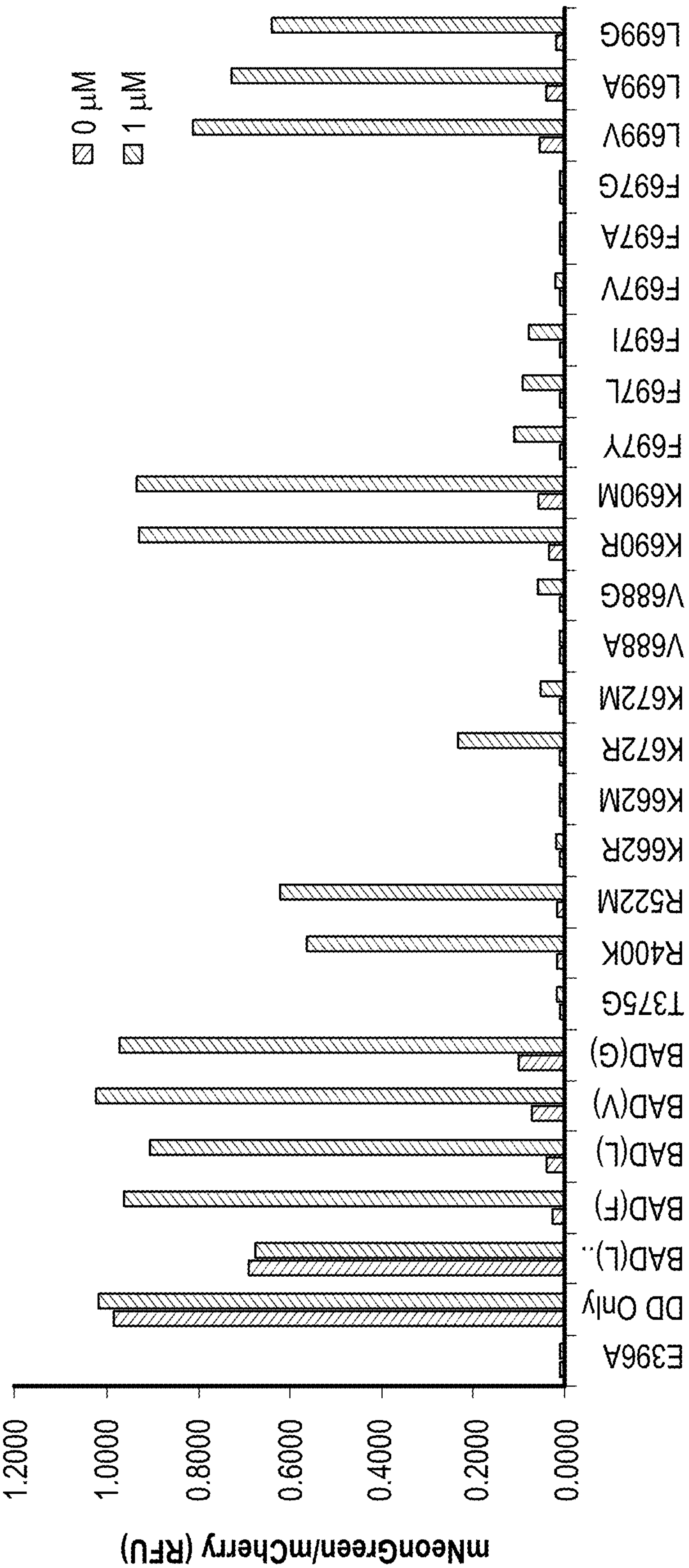

As a scaffold, a construct was used that displayed increased leakiness due to a mutation in the BAD peptide (F121V) which reduces affinity for Bcl-xL (see e.g., FIG. 22*c*). Mutated versions were then cloned and co-transfected with an editing reporter in the absence and presence of A-1331852, and absolute background and fold change upon drug addition were determined by flow cytometry (see e.g., FIG. 22*d* and table 11). In this assay, R522M, L699G, and R400K were found to yield the highest fold changes while other mutations had lower absolute background. Additional mutations and combinations were tested with different reporter constructs as well, and those are listed in table 12.

These mutations were then tested to see if they would be transferrable to other “leaky” systems. The MS1(117A)-Mcl1 interaction pair was previously found to lead to a drug (S63845) inducible ADAR, but there was substantial background in the absence of the drug (see e.g., FIG. 23*a*). The R522M and L699G mutations were then cloned into the ADAR-DD and the plasmids were co-transfected into HEK cells with and without S63845. Both R522M and L699G mutations substantially reduced the background of the MS1 (A)-Mell system while not seriously decreasing the activation (see e.g., FIG. 23*b*). This resulted in an increase in fold change from 12× for the WT DD to 67× and 140× for R522M and L699G respectively. These mutations were also tested in the even leaker MS1(117G) system and substantial reduction was found in background (see e.g., FIG. 23*c*). The fold change increased from 2.8× for the WT DD to 13× and 73× for R522M and L699G respectively. These data demonstrate that these mutations can be useful in multiple drug controlled systems.

Figure 23A:
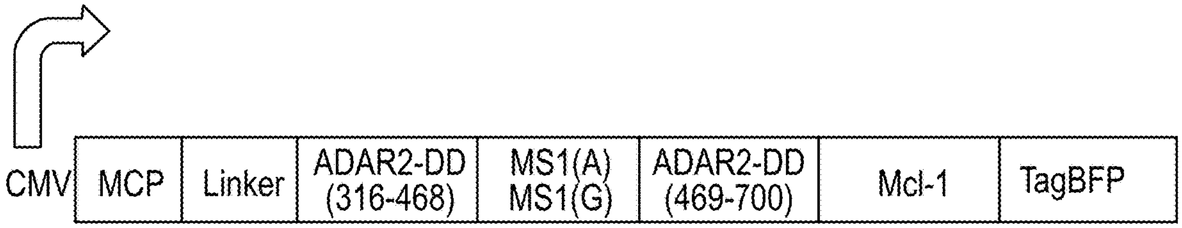
FIG. 23A-23E show that IP6 binding mutations decrease the background of MS1 and of N-terminal BAD ADAR variants.
Figure 23B:
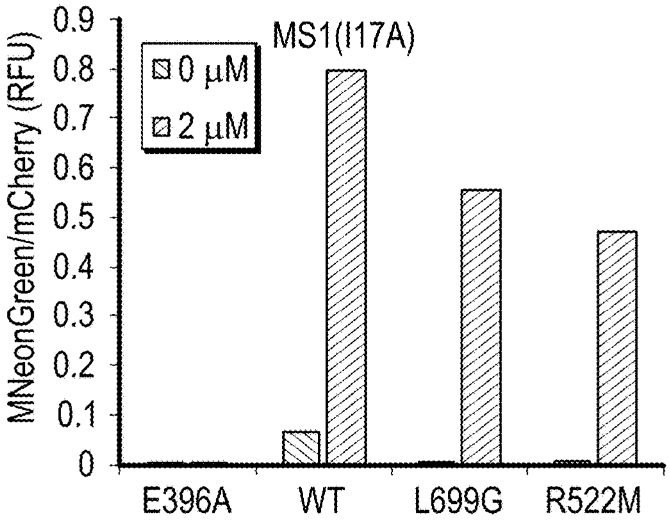
Figure 23C:
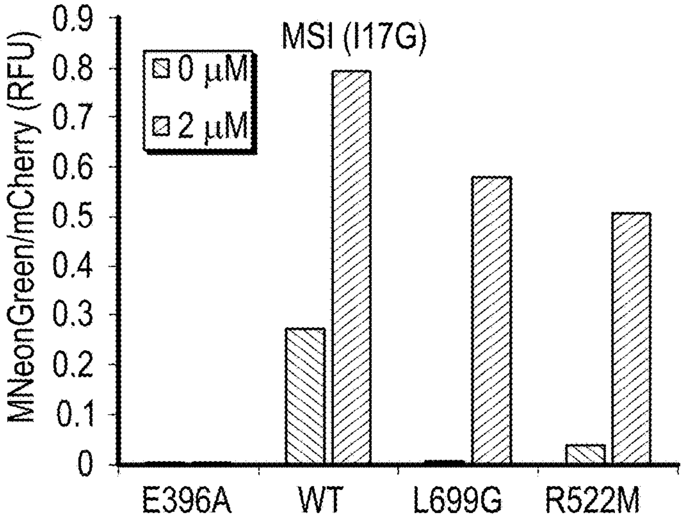
Figure 23D:
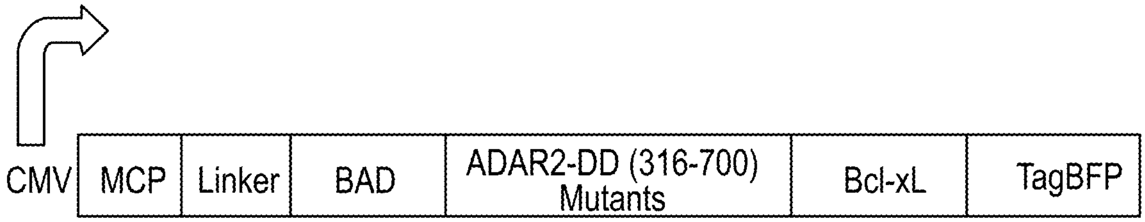
Figure 23E:
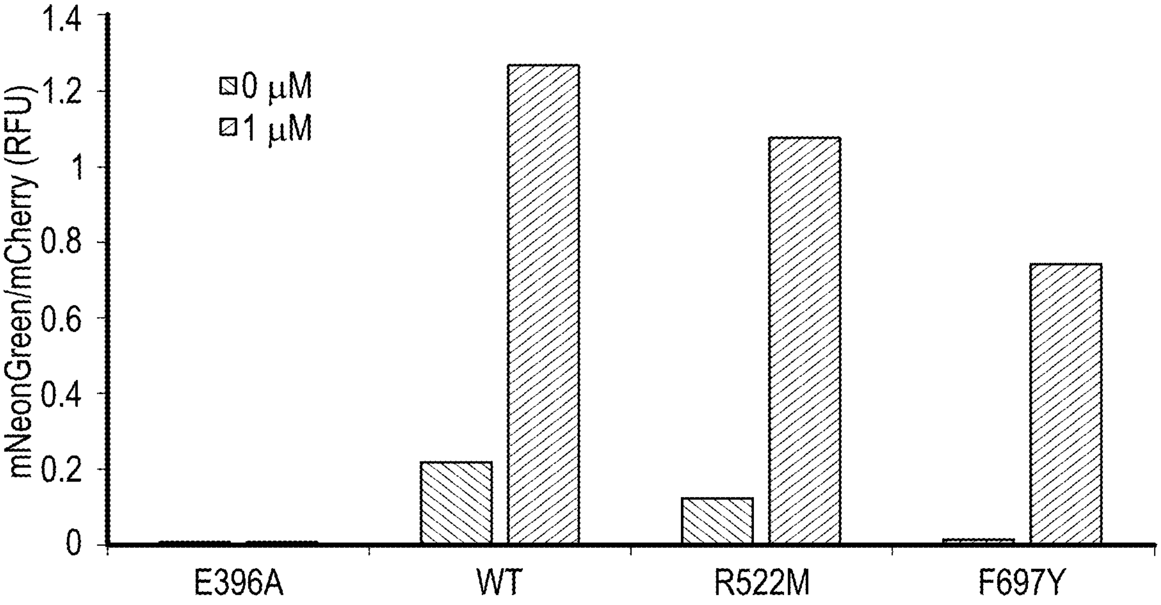
Figure 24:
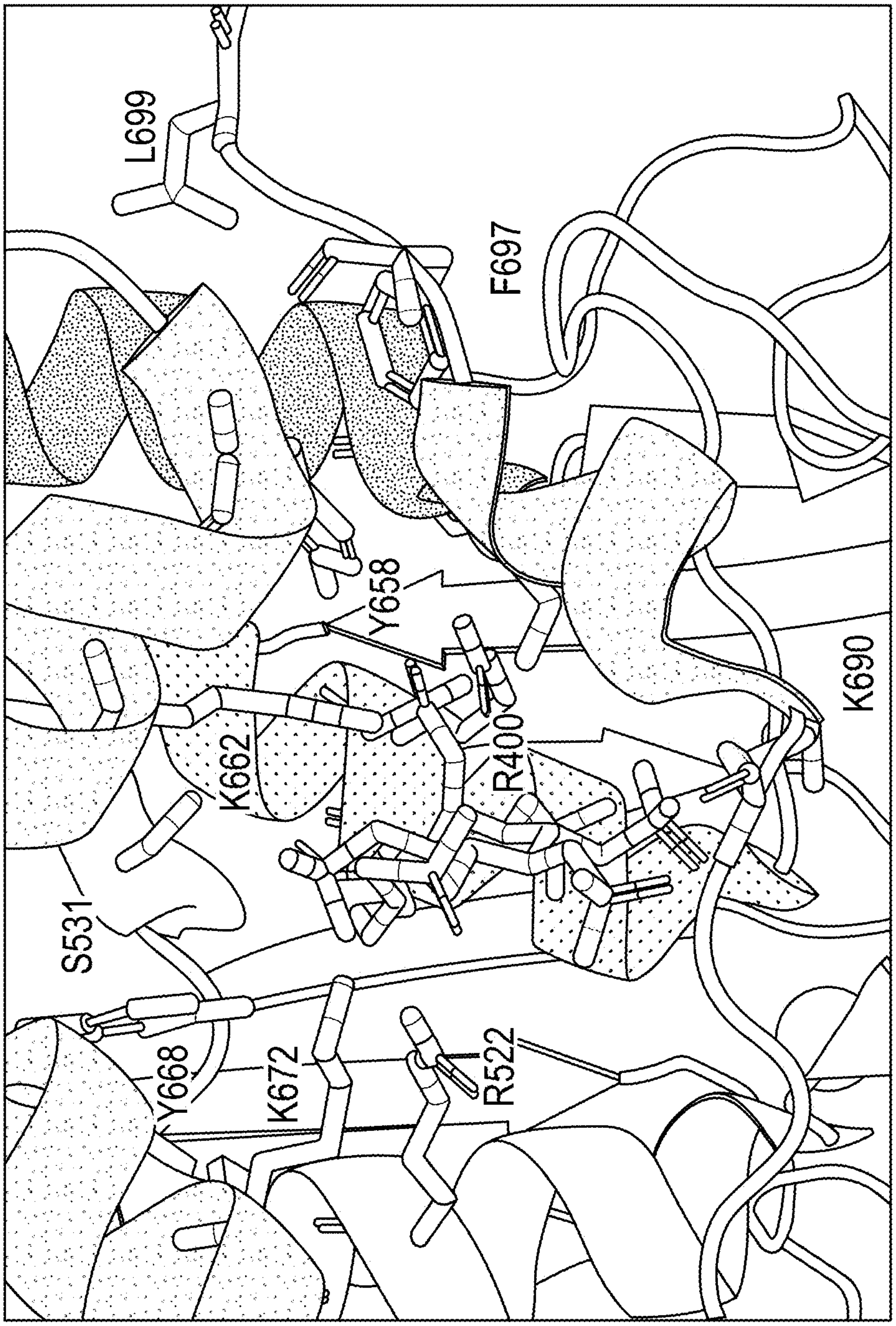
FIG. 24 shows amino acid residues in the IP6 binding pocket of ADAR.

These or other mutations were then tested to see if they could reduce the background in the N-terminal system (see e.g., FIG. 23*d*). HEK cells were co-transfected with both the ADAR-DD encoding plasmid and the reporter plasmid in the absence or presence of the Bcl-xL inhibitor A-1331852. The F697Y mutation substantially decreased the background of the system and therefore led to a substantial increase in fold change (5.9× for WT and 83× for F697Y). This improved N-terminal fusion scaffold is great utility for using globular/folded heterodimeric pairs (e.g., the use of an antibody fragment and its epitope for antigen sensing).

TABLE 11

Mutation List and Corresponding Flow Cytometry Values

| NAME | 0 μM | 1 μM | Fold Change |
|---|---|---|---|
| E396A | 0.0049 | 0.0047 | 0.964933 |
| DD Only | 0.9853 | 1.0147 | 1.02994 |
| BAD(L) Only | 0.690265 | 0.672566 | 0.974359 |
| BAD(F) | 0.025959 | 0.961652 | 37.04545 |
| BAD(L) | 0.038938 | 0.902655 | 23.18182 |
| BAD(V) | 0.070796 | 1.020649 | 14.41667 |
| BAD(G) | 0.100295 | 0.967552 | 9.647059 |
| Mutations | | | |
| T375G | 0.004454 | 0.016519 | 3.708609 |
| R400K | 0.015339 | 0.560472 | 36.53846 |
| R522M | 0.014749 | 0.619469 | 42 |
| K662R | 0.005457 | 0.016519 | 3.027027 |
| K662M | 0.004879 | 0.0059 | 1.20919 |
| K672R | 0.00885 | 0.230088 | 26 |
| K672M | 0.0059 | 0.049558 | 8.4 |
| V688A | 0.005481 | 0.00826 | 1.506997 |
| V688G | 0.00826 | 0.054867 | 6.642857 |
| K690R | 0.033038 | 0.926254 | 28.03571 |
| K690M | 0.057817 | 0.932153 | 16.12245 |
| F697Y | 0.00649 | 0.106195 | 16.36364 |
| F697L | 0.00708 | 0.088496 | 12.5 |
| F697I | 0.005552 | 0.076696 | 13.81509 |
| F697V | 0.005027 | 0.018879 | 3.755869 |
| F697A | 0.005528 | 0.00944 | 1.707577 |
| F697G | 0.00649 | 0.011209 | 1.727273 |
| L699V | 0.056047 | 0.80826 | 14.42105 |
| L699A | 0.038348 | 0.725664 | 18.92308 |
| L699G | 0.018289 | 0.637168 | 34.83871 |

TABLE 12

Additional mutations tested, but no data shown.

| Original Residue | Mutated Residues |
|---|---|
| S531 | S531A |
| F697 | F697M, F697W, F697H |
| Y658 | Y658F |
| Y668 | Y668F |

TABLE 13

Amino Acid Sequence Table (see e.g., FIG. 11, 14, 22, 23, 26); NOTE: ALL other mutants listed in FIG. 22d are of "BAD(V)" with the corresponding mutation

| NAME | SEQ ID NO | See e.g., FIGS. | AMINO ACID SEQUENCE |
|---|---|---|---|
| MCP-linker-BAD-ADAR2-DD(E488Q)-Bcl-xL-TagBFP | 92 | 11f, 14c, 23e Note Mutations in 23e are bolded | MASNFTQFVLVDNGGTGDVTVAPSNFANGIAEWISSNSR<br>SQAYKVTCSVRQSSAQNRKYTIKVEVPKGAWRSYLNME<br>LTIPIFATNSDCELIVKAMQGLLKDGNPIPSAIAANSGI<br>YGGSGSGAGSGSPAGGGAPGSGGGSTGAPPNLWAAQRYG<br>RELRRMSDEFVDSFKKASQLHLPQVLADAVSRLVLGKFG<br>DLTDNFSSPHARRKVLAGVVMTTGTDVKDAKVISVSTGTK<br>CINGEYMSDRGLALNDCHAEIISRRSLLRFLYTQLELYLN<br>NKDDQKRSIFQKSERGGFRLKENVQFHLYISTSPCGDARI<br>FSPHEPILEEPADRHPNRKARGQLRTKIESG**Q**GTIPVRSNA<br>SIQTWDGVLQGERLLTMSCSDKIA**R**WNVVGIQGSLLSIFV<br>EPIYFSSIILGSLYHGDHLSRAMYQRISNIEDLPPLYTLN<br>KPLLSGISNAEARQPGKAPNFSVNWTVGDSAIEVINATTG<br>KDELGRASRLCKHALYCRWMRVHGKVPSHLLRSKITKPNV<br>YHESKLAAKEYQAAKARLFTAFIKAGLGAWVEKPTEQD<br>Q**F**SLTGSAAASSNRELVVDFLSYKLSQKGYSWSQFSDVE<br>ENRTEAPEGTESEMETPSAINGNPSWHLADSPAVNGATG<br>HSSSLDAREVIPMAAVKQALREAGDEFELRYRRAFSDLT<br>SQLHITPGTAYQSFEQVVNELFRDGVNWGRIVAFFSFGG<br>ALCVESVDKEMQVLVSRIAAWMATYLNDHLEPWIQENG<br>GWDTFVELYGNNGSSELIKENMHMKLYMEGTVDNHHF<br>KCTSEGEGKPYEGTQTMRIKVVEGGPLPFAFDILATSFLY<br>GSKTFINHTQGIPDFFKQSFPEGFTWERVTTYEDGGVLTA<br>TQDTSLQDGCLIYNVKIRGVNFTSNGPVMQKKTLGWEAF<br>TETLYPADGGLEGRNDMALKLVGGSHLIANIKTTYRSKK<br>PAKNLKMPGVYYVDYRLERIKEANNETYVEQHEVAVAR<br>YCDLPSKLGHKLN* |
| Also known as "BAD-DD-BclxL" and "WT" MCP-linker-ADAR2-DDN-Bad(F)-ADAR2(E488Q)-DDC-Bcl-xL-TagBFP | 287 | 22d, 25a "BAD(F)" | MASNFTQFVLVDNGGTGDVTVAPSNFANGIAEWISSNSR<br>SQAYKVTCSVRQSSAQNRKYTIKVEVPKGAWRSYLNMEL<br>TIPIFATNSDCELIVKAMQGLLKDGNPIPSAIAANSGIY<br>GGSGSGAGSGSPAGGGAPGSGGGSQLHLPQVLADAVSRL<br>VLGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGTGAPPNLWAAQRYGRE<br>LRRMSDEFVDRHPNRKARGQLRTKIESG**Q**GTIPVRSNASI<br>QTWDGVLQGERLLTMSCSDKIARWNVVGIQGSLLSIFVEP<br>IYFSSIILGSLYHGDHLSRAMYQRISNIEDLPPLYTLNKP<br>LLSGISNAEARQPGKAPNFSVNWTVGDSAIEVINATTGKD<br>ELGRASRLCKHALYCRWMRVHGKVPSHLLRSKITKPNVY<br>HESKLAAKEYQAAKARLFTAFIKAGLGAWVEKPTEQDQ<br>FSLTGSAAGGSGGSAAASSNRELVVDFLSYKLSQKGYSW<br>SQFSDVEENRTEAPEGTESEMETPSAINGNPSWHLADSPA<br>VNGATGHSSSLDAREVIPMAAVKQALREAGDEFELRYRR<br>AFSDLTSQLHITPGTAYQSFEQVVNELFRDGVNWGRIVAF<br>FSFGGALCVESVDKEMQVLVSRIAAWMATYLNDHLEPW<br>IQENGGWDTFVELYGNNGSSELIKENMHMKLYMEGTVD<br>NHHFKCTSEGEGKPYEGTQTMRIKVVEGGPLPFAFDILAT<br>SFLYGSKTFINHTQGIPDFFKQSFPEGFTWERVTTYEDGG<br>VLTATQDTSLQDGCLIYNVKIRGVNFTSNGPVMQKKTLG<br>WEAFTETLYPADGGLEGRNDMALKLVGGSHLIANIKTTY<br>RSKKPAKNLKMPGVYYVDYRLERIKEANNETYVEQHEV<br>AVARYCDLPSKLGHKLN* |
| MCP-linker-ADAR2-DDN-Bad(F)-ADAR2(E488Q)-DDC- | 288 | 22d, 25a "BAD(V)" | MASNFTQFVLVDNGGTGDVTVAPSNFANGIAEWISSNSR<br>SQAYKVTCSVRQSSAQNRKYTIKVEVPKGAWRSYLNMEL<br>TIPIFATNSDCELIVKAMQGLLKDGNPIPSAIAANSGIY<br>GGSGSGAGSGSPAGGGAPGSGGGSQLHLPQVLADAVSRL<br>VLGKFGDLTDNFSSPHARRKVLAGVVMTTGTDVKDAKVI<br>SVSTGTKCINGEYMSDRGLALNDCHAEIISRRSLLRFLYT<br>QLELYLNNKDDQKRSIFQKSERGGFRLKENVQFHLYISTS<br>PCGDARIFSPHEPILEEPAASGSGTGAPPNLWAAQRYGRE<br>LRRMSDEVVDRHPNRKARGQLRTKIESG**Q**GTIPVRSNASI<br>QTWDGVLQGERLLTMSCSDKIARWNVVGIQGSLLSIFVE<br>PIYFSSIILGSLYHGDHLSRAMYQRISNIEDLPPLYTLNK<br>PLLSGISNAEARQPGKAPNFSVNWTVGDSAIEVINATTGK<br>DELGRASRLCKHALYCRWMRVHGKVPSHLLRSKITKPNVY<br>HESKLAAKEYQAAKARLFTAFIKAGLGAWVEKPTEQDQF<br>SLTGSAAGGSGGSAAASSNRELVVDFLSYKLSQKGYSWS<br>QFSDVEENRTEAPEGTESEMETPSAINGNPSWHLADSPA<br>VNGATGHSSSLDAREVIPMAAVKQALREAGDEFELRYRR |

TABLE 13-continued

Amino Acid Sequence Table (see e.g., FIG. 11, 14, 22, 23, 26); NOTE: ALL other mutants listed in FIG. 22d are of "BAD(V)" with the corresponding mutation

| NAME | SEQ ID NO | See e.g., FIGS. | AMINO ACID SEQUENCE |
|---|---|---|---|
| | | | AFSDLTSQLHITPGTAYQSFEQVVNELFRDGVNWGRIVA FFSFGGALCVESVDKEMQVLVSRIAAWMATYLNDHLEPW IQENGGWDTFVELYGNNGSSELIKENMHMKLYMEGTVDN HHFKCTSEGEGKPYEGTQTMRIKVVEGGPLPFAFDILAT SFLYGSKTFINHTQGIPDFFKQSFPEGFTWERVTTYEDGG VLTATQDTSLQDGCLIYNVKIRGVNFTSNGPVMQKKTLG WEAFTETLYPADGGLEGRNDMALKLVGGSHLIANIKTTY RSKKPAKNLKMPGVYYVDYRLERIKEANNETYVEQHEV AVARYCDLPSKLGHKLN* |
| Bcl-xL-TagBFP MCP-linker-ADAR2-DDN-Bad(F)-ADAR2(E488Q)-DDC-Bcl-xL-TagBFP | 289 | 22d, 25b "BAD(G)" | MASNFTQFVLVDNGGTGDVTVAPSNFANGIAEWISSNSR SQAYKVTCSVRQSSAQNRKYTIKVEVPKGAWRSYLNMEL TIPIFATNSDCELIVKAMQGLLKDGNPIPSAIAANSGIY GGSGSGAGSGSPAGGGAPGSGGGSQLHLPQVLADAVSRL VLGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGSGTGAPPNLWAAQRYGRE LRRMSDE**G**VDRHPNRKARGQLRTKIESG**Q**GTIPVRSNASI QTWDGVLQGERLLTMSCSDKIARWNVVGIQGSLLSIFVE PIYFSSIILGSLYHGDHLSRAMYQRISNIEDLPPLYTLNK PLLSGISNAEARQPGKAPNFSVNWTVGDSAIEVINATTGK DELGRASRLCKHALYCRWMRVHGKVPSHLLRSKITKPNVY HESKLAAKEYQAAKARLFTAFIKAGLGAWVEKPTEQDQF SLTGSAAGGSGGSAAASSNRELVVDFLSYKLSQKGYSWS QFSDVEENRTEAPEGTESEMETPSAINGNPSWHLADSPA VNGATGHSSSLDAREVIPMAAVKQALREAGDEFELRYRR AFSDLTSQLHITPGTAYQSFEQVVNELFRDGVNWGRIVA FFSFGGALCVESVDKEMQVLVSRIAAWMATYLNDHLEPW IQENGGWDTFVELYGNNGSSELIKENMHMKLYMEGTVDN HHFKCTSEGEGKPYEGTQTMRIKVVEGGPLPFAFDILAT SFLYGSKTFINHTQGIPDFFKQSFPEGFTWERVTTYEDGG VLTATQDTSLQDGCLIYNVKIRGVNFTSNGPVMQKKTLG WEAFTETLYPADGGLEGRNDMALKLVGGSHLIANIKTTY RSKKPAKNLKMPGVYYVDYRLERIKEANNETYVEQHEV AVARYCDLPSKLGHKLN* |
| MCP-linker-ADAR2-DDN-MS1(A)-ADAR2(E488Q)-DDC-TagBFP | 290 | 23b "WT" Note Other mutants are bolded 25b | MASNFTQFVLVDNGGTGDVTVAPSNFANGIAEWISSNSR SQAYKVTCSVRQSSAQNRKYTIKVEVPKGAWRSYLNMEL TIPIFATNSDCELIVKAMQGLLKDGNPIPSAIAANSGIY GGSGSGAGSGSPAGGGAPGSGGGSQLHLPQVLADAVSRL VLGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSGGSGRPEIWMTQGLRR LGDE**A**NAYYARRTGDRHPNRKARGQLRTKIESG**Q**GTIPVR SNASIQTWDGVLQGERLLTMSCSDKIA**R**WNVVGIQGSLLS IFVEPIYFSSIILGSLYHGDHLSRAMYQRISNIEDLPPLY TLNKPLLSGISNAEARQPGKAPNFSVNWTVGDSAIEVINA TTGKDELGRASRLCKHALYCRWMRVHGKVPSHLLRSKITK PNVYHESKLAAKEYQAAKARLFTAFIKAGLGAWVEKPTEQ DQFS**L**TGSGSSELIKENMHMKLYMEGTVDNHHFKCTSEGE GKPYEGTQTMRIKVVEGGPLPFAFDILATSFLYGSKTFI NHTQGIPDFFKQSFPEGFTWERVTTYEDGGVLTATQDTS LQDGCLIYNVKIRGVNFTSNGPVMQKKTLGWEAFTETL YPADGGLEGRNDMALKLVGGSHLIANIKTTYRSKKPAKN LKMPGVYYVDYRLERIKEANNETYVEQHEVAVARYCDL PSKLGHKLN* |
| MCP-linker-ADAR2-DDN-MS1(G)-ADAR2(E488Q)-DDC-TagBFP | 291 | 23c "WT" Note Other mutants are bolded 25c | MASNFTQFVLVDNGGTGDVTVAPSNFANGIAEWISSNSR SQAYKVTCSVRQSSAQNRKYTIKVEVPKGAWRSYLNMEL TIPIFATNSDCELIVKAMQGLLKDGNPIPSAIAANSGIY GGSGSGAGSGSPAGGGAPGSGGGSQLHLPQVLADAVSRL VLGKFGDLTDNFSSPHARRKVLAGVVMTTGTDVKDAKVI SVSTGTKCINGEYMSDRGLALNDCHAEIISRRSLLRFLYT QLELYLNNKDDQKRSIFQKSERGGFRLKENVQFHLYISTS PCGDARIFSPHEPILEEPAASGGSGGSGRPEIWMTQGLRR LGDE**G**NAYYARRTGDRHPNRKARGQLRTKIESG**Q**GTIPVR SNASIQTWDGVLQGERLLTMSCSDKIA**R**WNVVGIQGSLLS IFVEPIYFSSIILGSLYHGDHLSRAMYQRISNIEDLPPLY TLNKPLLSGISNAEARQPGKAPNFSVNWTVGDSAIEVINA |

TABLE 13-continued

Amino Acid Sequence Table (see e.g., FIG. 11, 14, 22, 23, 26); NOTE: ALL other mutants listed in FIG. 22d are of "BAD(V)" with the corresponding mutation

| NAME | SEQ ID NO | See e.g., FIGS. | AMINO ACID SEQUENCE |
|---|---|---|---|
| | | | TTGKDELGRASRLCKHALYCRWMRVHGKVPSHLLRSKITK PNVYHESKLAAKEYQAAKARLFTAFIKAGLGAWVEKPT EQDQFS**L**TGSGSSELIKENMHMKLYMEGTVDNHHFKCTS EGEGKPYEGTQTMRIKVVEGGPLPFAFDILATSFLYGSKT FINHTQGIPDFFKQSFPEGFTWERVTTYEDGGVLTATQDT SLQDGCLIYNVKIRGVNFTSNGPVMQKKTLGWEAFTETL YPADGGLEGRNDMALKLVGGSHLIANIKTTYRSKKPAKN LKMPGVYYVDYRLERIKEANNETYVEQHEVAVARYCDL PSKLGHKLN* |

Example 13: mRNA Variants

This section details different mRNA compositions that can be coupled with the iADAR technology to produce functional mRNA circuits that modulate the translation or function of a gene of interest. Prior compositions demonstrated the ADAR-based editing of a UAG-STOP codon contained within a hairpin to UIG, which is interpreted by the ribosome as the UGG-tryptophan codon. By encoding a unique RNA motif and a gene of interest downstream of the editable stop codon, translation of the gene of interest can be controlled with ADAR and iADAR constructs. The iADAR platform can be used to control any transcript that can accommodate a dsRNA loop and is sensitive to an A to I event. Additionally, using multiple editable sites on a single transcript can permit multi-input logic.

To expand the scope of the technology beyond single-input STOP codon editing, ADAR-sensitive reporters that function via distinct mechanisms were constructed and tested.

START-Codon Editing

Creation of a START Codon (AUA to AUI)

AUI Start Codon Changes Initiation (Out of Frame to in-Frame)

In most of biology, an AUG START codon is necessary for the initiation of proper translation, though there are exceptions. As inosine is typically interpreted by the cell as a guanine, it was tested whether an ADAR-generated AUI could serve as an initiation site for translation when in the 5'UTR of a gene of interest (see e.g., FIG. 26*a*). With this, it would be possible to generate novel initiation sites of translation to control a gene of interest, where the novel start codon leads to in-frame translation of the full gene.

Figure 26A:
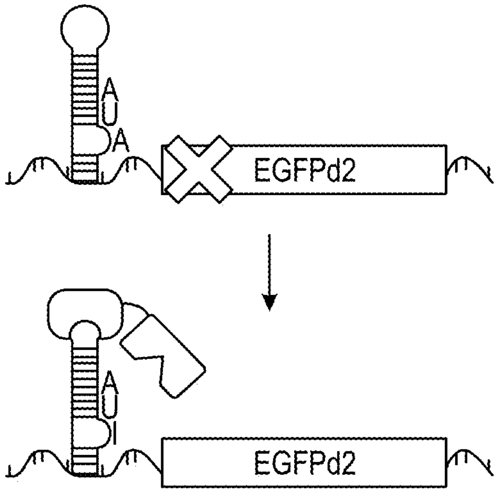
FIG. 26A-26E show editing of an upstream "AUA" to "AUI" for defining a new start codon and open reading frame (ORF). Creation of a new start codon and ORF by editing mediated conversion of a 5' non-ORF target site.
Figure 26B:
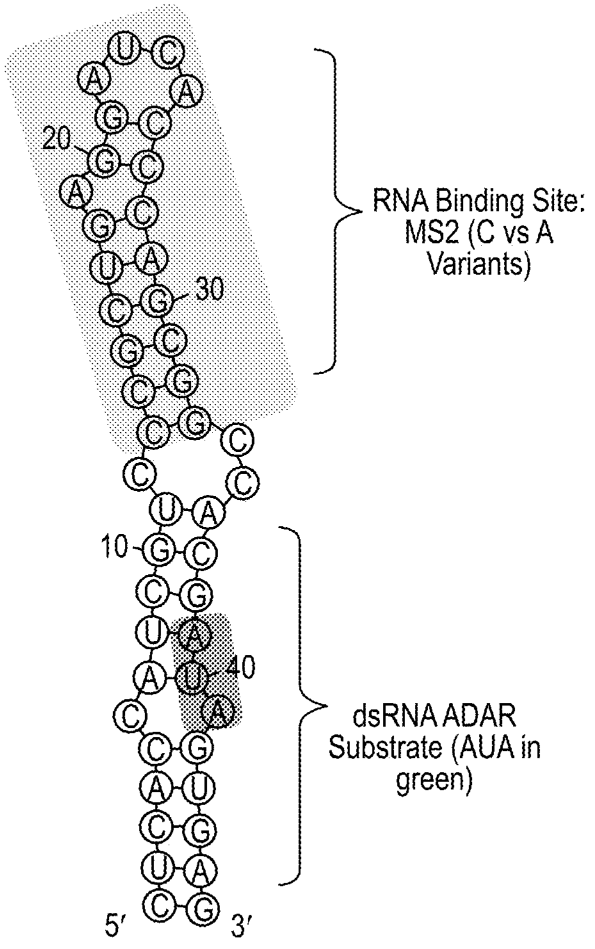

To test this, an ADAR substrate was designed composed of a dsRNA hairpin containing both an AUA-codon with a mismatch at the second adenine to promote specific deamination to AUI (as opposed to IUA or IUI) and an MS2 operator motif (see e.g., FIG. 26*b*). The design of one large dsRNA hairpin was chosen to promote correct folding of RNA secondary structures. Previous studies have shown that MS2 operators in the 5'UTR of eukaryotic mRNA can lead to decreased translational efficiency when co-expressed with its corresponding coat protein (MS2 coat protein, or MCP), so high and low affinity variants of the MS2 operator (called here MS2-C and MS2-A respectively for the base at the stem loop) were tested with the idea that the lower affinity MS2-A loop would be less likely to inhibit translation by coat protein alone. As positive controls, the same loops were also designed with the correct AUG start codon.

Figure 26C:
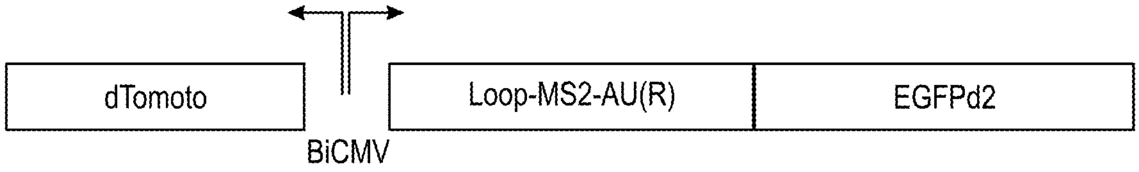

These designs were cloned into pcDNA3 vectors containing a bidirectional CMV promoter driving constitutive dTomato and EGFPd2 (see e.g., FIG. 26*c*). The S'UTR and start codon of EGFPd2 were replaced with the editable start codon designs so the translational efficiency could be measured by looking at the EGFPd2 fluorescence relative to dTomato when co-expressed with MCP-ADAR. In this construct, if the correct start codon is skipped, the next AUG codon leads to a short, out of frame translation product.

HEK293FT cells were co-transfected with each of the reporter constructs (MS2-C w/ AUG start, MS2-C w/ AUA start, MS2-A w/ AUG start, and MS2-A w/ AUA start) and either filler DNA, inactivated ADAR2-DD (E396A) fused to MCP (MCP-dADAR), or active ADAR2-DD (E488Q) fused to MCP (MCP-ADAR). 48 hours post-transfection, cells were lifted and analyzed by flow cytometry. Transfected cells were gated by dTomato, and the median EGFPd2-to-dTomato ratio for the population was calculated per replicate (n=3) by FLOWJO. 2-Way ANOVA was performed to determine significance.

Figure 26D:
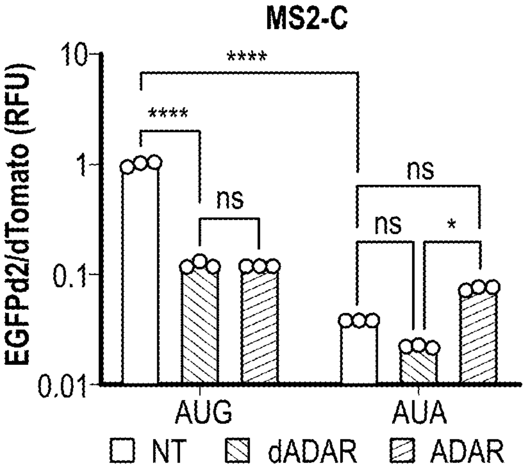
Figure 26E:
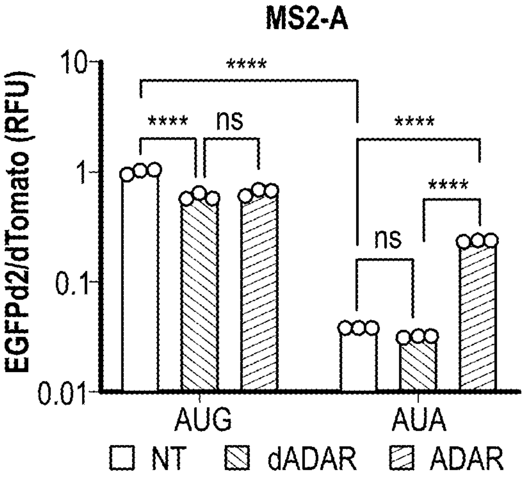

Co-transfection of the MS2-C reporters with MCP-dADAR and MCP-ADAR significantly decreased the relative fluorescence compared to transfecting with filler DNA (NT) (see e.g., FIG. 26*d*). While there was some increase of the relative fluorescence when co-transfecting the AUA reporter and the active MCP-ADAR, this increase was not significant relative to the non-cotransfected (NT) condition (see e.g., FIG. 26*d*).

Comparatively, co-transfection of MCP-dADAR and ADAR with the weaker affinity MS2-A substrate had a more modest negative effect on translational efficiency from a native AUG start codon. More importantly, co-transfection of the MS2-A w/ AUA substrate with MCP-ADAR led to a significant increase in the relative EGFPd2/dTomato fluorescence.

This data indicates that MCP-ADAR2-DD fusion proteins are capable of increasing the rate of translation initiation by converting some fraction of an initiation-deficient AUA codon in the 5'UTR to AUI.

Editing of an AUA Codon to Create an Upstream, in-Frame Motif

The previous schemes demonstrated the capability to turn on or off translation by editing the START codon, as the subsequent AUG codon in those constructs were out of frame with the EGFPd2. Subsequent tests focused on whether translation initiation could be shifted to another START codon that is in frame with the original START codon (see e.g., FIG. 27*a*). In this way, a polypeptide sequence can be added to the original translation product that would modify the activity or localization of the original translation product.

Figure 27A:
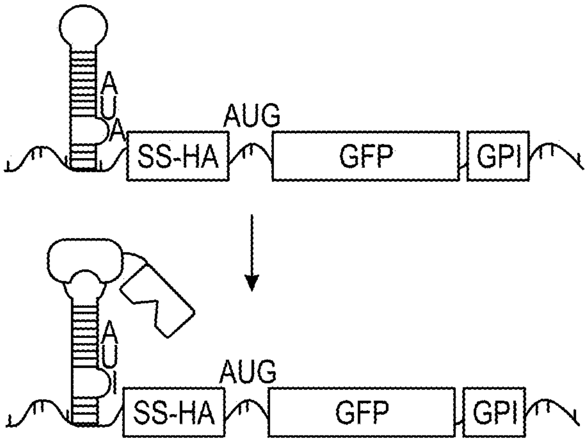
FIG. 27A-27D show upstream AUA to AUI editing to create an expanded ORF encoding a protein with an editing-dependent N-terminal fusion. ORF expansion was accomplished by editing of in-frame and upstream editing of AUA to an AUI.
Figure 27B:
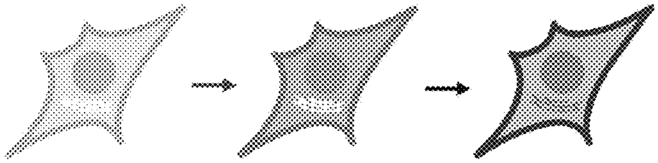

To test this, a reporter construct was designed that contained: an MS2-A editable AUA start codon upstream of the murine IgGκ signal sequence and HA epitope tag (SS-HA), an in frame AUG start codon, GFP, and the glycosylphosphatidylinositol (GPI) anchor sequence from Thymocyte differentiation antigen 1 (GPI in diagram) (see e.g., FIG. 27*a*). With this reporter, in the absence of editing, the majority of the translated product will be from the AUG codon directly upstream of GFP. This will lead to the translation product residing in the cytoplasm with a non-functional GPI anchor (as this post-translational modification (PTM) must occur in the endoplasmic reticulum (ER) lumen). Upon ADAR editing of the upstream AUA to AUI, translation will initiate upstream of the signal sequence, leading to co-translational translocation of HA-GFP-GPI into the ER lumen, the addition of the GPI anchor PTM, and presentation of HA-GFP on the plasma membrane (see e.g., FIG. 27*b*). With this construct, the editing can be monitored by either by microscopy (looking for ER & plasma membrane localization) or directly by immunostaining for the HA-tag.

HEK cells were co-transfected with the GFP-GPI reporter and either filler DNA, MCP-dADAR, or MCP-ADAR. A GFP-GPI with a functional start codon before the secretion signal was also transfected as a positive control (GFP-GPI Control). One day after transfection, HEK cells were imaged live, and then fixed and stained for HA tag with a primary anti-HA antibody and a secondary antibody that was conjugated to ALEXAFLUOR 647 (AF647).

Figure 27C:
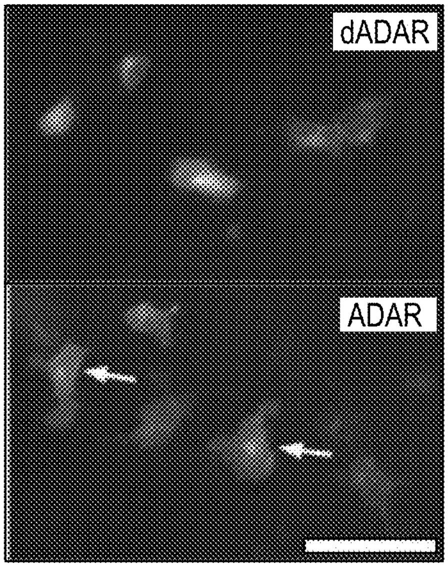
Figure 27D:
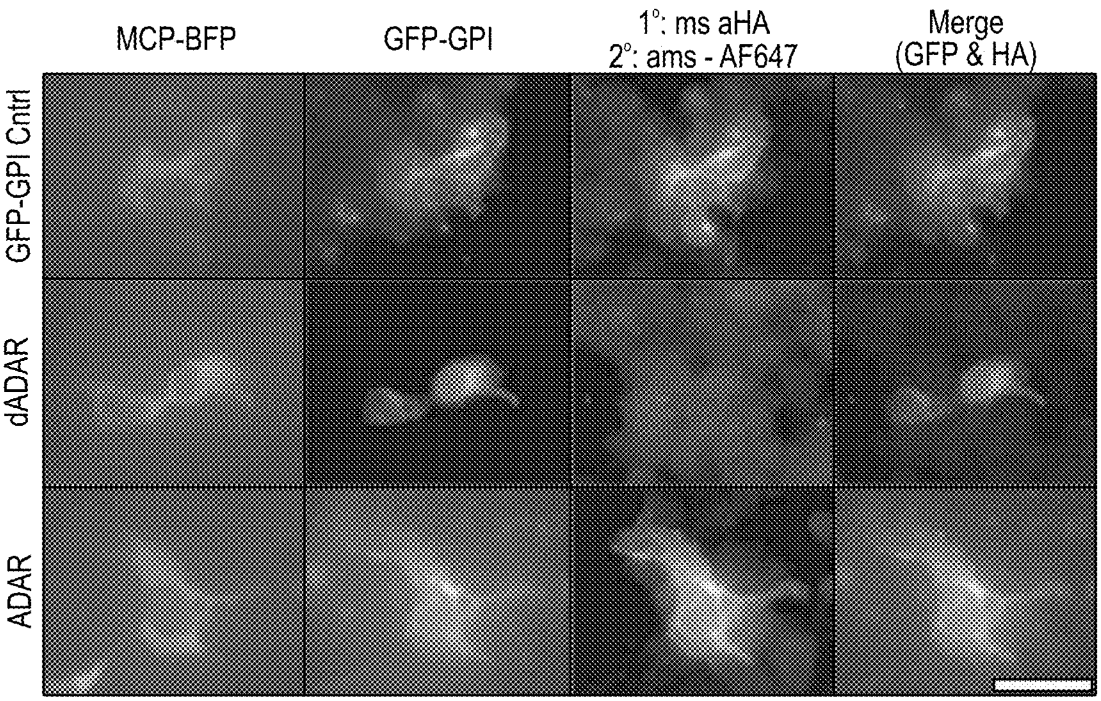

When imaging live cells, the subcellular GFP expression pattern for the AUA-START construct was found to be dependent on co-transfection of active MCP-ADAR (see e.g., FIG. 27*c*). The cellular distribution of GFP of the SS-GFP-GPI positive control and the AUA-SS-GFP-GPI co-transfected with MCP-ADAR looked very similar, whereas the AUA-SS-GFP-GPI construct co-transfected with inactive MCP-dADAR led to a different, more cytoplasmic distribution (see e.g., FIG. 27*c*). After imaging live, cells were fixed with paraformaldehyde, permeabilized using a light detergent, and stained for HA tag. With this, robust staining was observed for the GFP-GPI control and for AUA vectors co-transfected with active MCP-ADAR (see e.g., FIG. 27*d*). However, there was not much staining for cells co-transfected with the AUA construct and catalytically inactivated MCP-dADAR.

This data demonstrates that the AUA to AUI creation of a start codon can be used to add short motifs to existing proteins.

Destruction of an AUG Start Codon to IUG

Figure 28A:
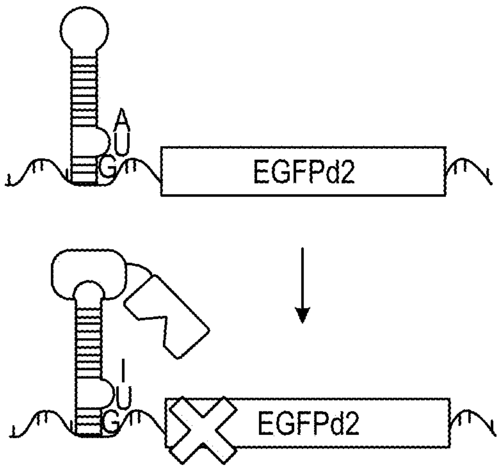
FIG. 28A-28D show AUG to IUG editing for start codon removal and ORF modification/elimination. Functional start codons were converted to non-functional start codons with cis-acting ADAR deaminase domains.

The inverse of the above scheme would be the destruction of an AUG start codon by deamination of the adenosine to IUG (see e.g., FIG. 28*a*). This edited codon would be most likely skipped by the pre-initiation complex (if read as GUG), leading to a decrease in the translation efficiency of a gene of interest. This can be used to make an "OFF" switch when there is no alternative start that leads to productive translation.

Figure 28B:
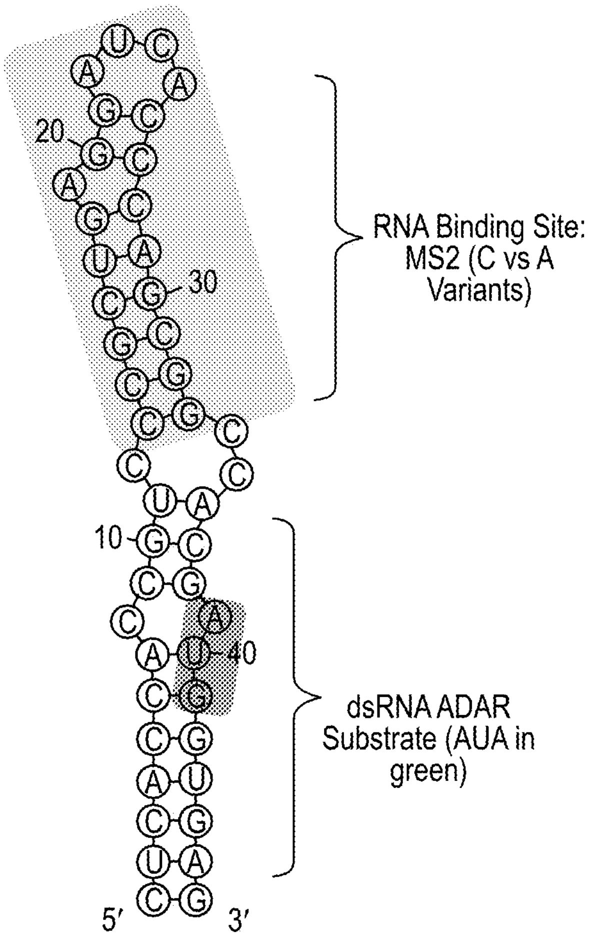
Figure 28C:
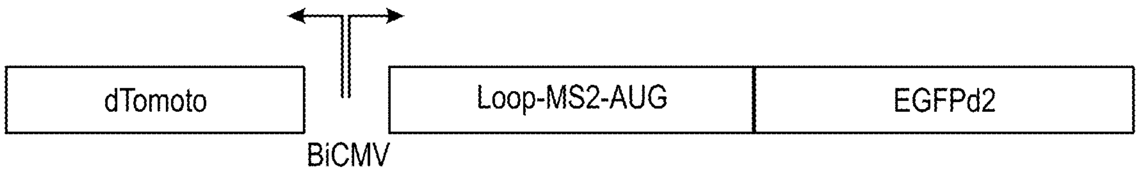

To test this, an ADAR substrate was designed similar to the substrates tested above, but with an AUG codon in a dsRNA hairpin with a mismatch to promote the deamination of the correct adenine (see e.g., FIG. 28*b*). This scheme was similarly tested with both the high affinity MS2-C and lower affinity MS2-A variants by cloning these substrates into a pcDNA3 vector with a bidirectional CMV driving the expression of dTomato and EGFPd2 (see e.g., FIG. 28*c*).

HEK cells were co-transfected with the two different reporter constructs (MS2-C and MS2-A) and either filler DNA, MCP-dADAR, or MCP-ADAR. 48 hours post-transfection, cells were lifted and analyzed by flow cytometry. Transfected cells were gated by dTomato, and the median EGFPd2-to-dTomato ratio for the population was calculated per replicate (n=3) by FLOWJO. 2-Way ANOVA was performed to determine significance.

Figure 28D:
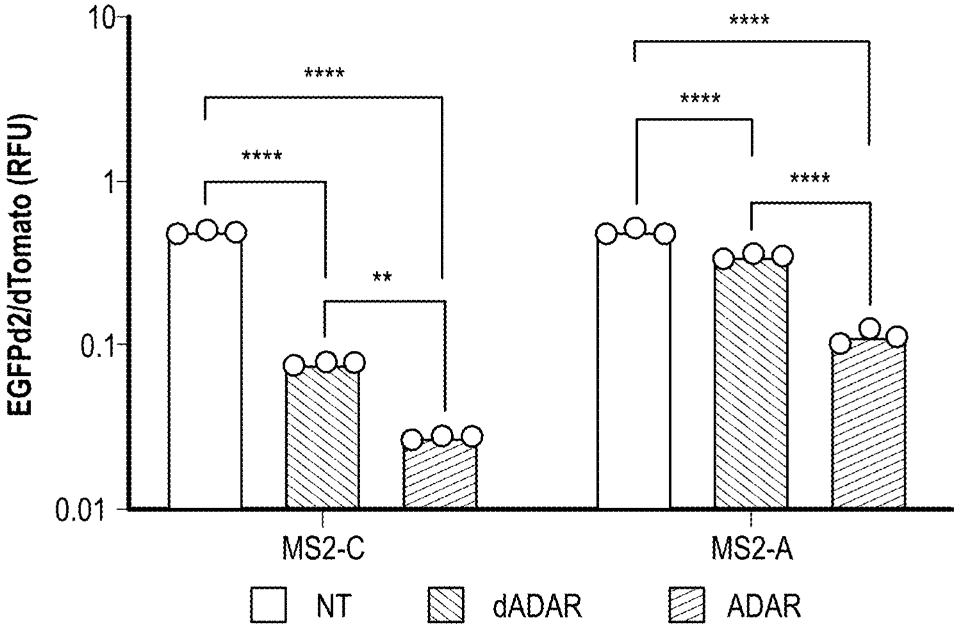

Co-transfection of the high affinity MS2-C based construct with either MCP fusion protein (active or inactive ADAR) led to a significant decrease in translational efficiency of EGFPd2 (see e.g., FIG. 28*d*). Additionally, there was a further significant difference between the active and inactive ADAR variants, indicating that the translational repression due to the protein-RNA interaction was further enhanced by the active ADAR (e.g., through deamination of the correct start codon). Similar to MS2-C, the MS2-A based construct also had a significant decrease in translational efficiency for both MCP-dADAR and MCP-ADAR (see e.g., FIG. 28*d*). Co-transfection with the active ADAR variant led to a further, significant decrease in relative EGFPd2 levels in the cells.

These experiments demonstrate that a start codon can be edited to increase or decrease expression of a gene of interest from the ADAR platform.

Sense Codon Editing

In addition to controlling gene activity by editing the initiation or termination of translation, this iADAR technology can be used to recode a protein by deamination of in-frame codons (e.g., to introduce mutations to specific sites). In order to do this, one would need to introduce a dsRNA loop and an RNA binding motif to an adjacent codon of interest (see e.g., FIG. 29*a*). The expression of active ADAR would lead to deamination of an adenine base to inosine, which would be interpreted as guanine and a different amino acid would be inserted into the growing polypeptide chain. The number of possible recoding permutations is constrained by the genetic code, e.g., in human cells, it is impossible to use adenosine deamination to convert from or to a proline, as the four proline codons are CCN (see e.g., Table 15 for possible functional recoding). However, there are still scenarios where this functionality may be desirable.

To show inducible ADAR recoding of a protein's amino acid composition, a construct was designed that contained: a CD8 signal peptide, an HA epitope tag, the self-labeling HaloTag, a mutant variant of the thosea asigna virus 2A self-cleaving peptide that is defective for ribosome skipping (Gly18Arg mutation), the DNA binding domain of Gal4, and a 4× repeat of the transcriptional activation domain from herpes virus (VP64) (see e.g., FIG. 29*a*). The penultimate glycine in 2A peptides is invariant (see e.g., FIG. 29*b*) and any mutation leads to defective ribosome skipping. The codon for the G18R residue (AGG) is in a dsRNA hairpin with the high affinity MS2-C motif, which acts as a substrate for targeted MCP-ADAR. In the absence of ADAR editing, the defective T2A sequence will lead to the topological sequestering of the Gal4-VP64 transcription factor in the ER lumen due to the fusion to the secreted HaloTag (see e.g., FIG. 29*c*). Upon ADAR editing of the Arg 18 codon to glycine (AGG to IGG), the T2A regains the function of ribosome skipping. This leads to the protein domains downstream of the T2A sequence to be translated as a separate polypeptide in the cytoplasm, whereby the GAL4-VP64 transcription factor will translocate to the nucleus and turn on the expression of a fluorescent H2B-mCherry reporter (see e.g., FIG. 29*c*). This demonstrates the ability of directed ADAR domains to edit and recode a protein sequence of interest to modulate protein function.

To test this, an in-house clonal HEK293FT cell line that contains an integrated UAS-H2B-mCherry reporter was co-transfected with the T2A (G18R) construct and either filler DNA, MCP-dADAR, or MCP-ADAR. A GAL4-VP64 positive control was also transfected into HEK cells. One day post transfection, cells were imaged via microscopy to check for transcriptional activation via H2B-mCherry expression (see e.g., Example 16).

Two-Input Logic

Two-Input AND-Gate by Using Multiple STOP Codons and RNA Motifs

Figure 30A:
FIG. 30A-30F show Two-Input, dual-editing, AND-gate mRNA editing substrates. Multiple stop codons and RNA-binding motifs enable multi-input logic.

In other reporter designs, adding additional STOP codons and RNA binding motifs (RBM) was found to lead to reduced background of the system without severely affecting the maximum editing efficiency (e.g., mCherry-2xSTOP-MS2-HaloTag-2xSTOP-MS2-mNeonGreen) (see e.g., FIG. 30*a*). In addition, the RBM of the reporter and the RNA binding domain (RBD) fused to ADAR2-DD can be swapped to get a level of orthogonal activation by editing.

Figure 30B:
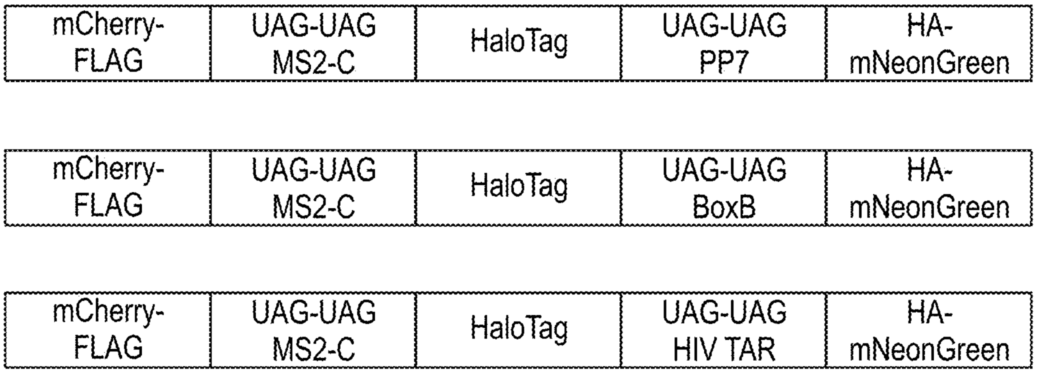

Multi-input logic gates can be constructed from different RBMs and RBDs and used in series on a single transcript (see e.g., FIG. 30*b*). The expression of one active RBD-ADAR fusion construct alone can lead to minimal editing of all 4 STOP codons, and expression of both RBD fusion proteins can allow get full editing and expression of the downstream gene. This can then be applied to make multi-input iADAR circuits on a single mRNA.

To test this, three reporters were constructed that were composed of an upstream m Cherry-FLAG-P2A-T2A, 2×UAG stop codon loop beside an MS2 RBM, a Halo Tag-T7 tag spacer, another 2×UAG stop codon loop with a different RBM (PP7, BoxB or HIV TAR), and a downstream HA-mNeonGreen (M10K) reporter (see e.g., FIG. 30*b*). 75,000 HEK293FT cells were then co-transfected with 50 ng of reporter DNA and either 30 ng of filler DNA, 15 ng of MCP-ADAR and 15 ng of filler DNA, 15 ng of the respective RBD-ADAR fusion (PCP, λN, or HIV-Tat) and 15 ng of filler DNA, or 15 ng of both MCP-ADAR and RBD-ADAR. 48 hours post-transfection, cells were analyzed by flow cytometry, gated for mCherry expression, and the median mNeonGreen to mCherry value per well was computed. One-way ANOVA statistical analysis was performed (n=3).

Figure 30C:
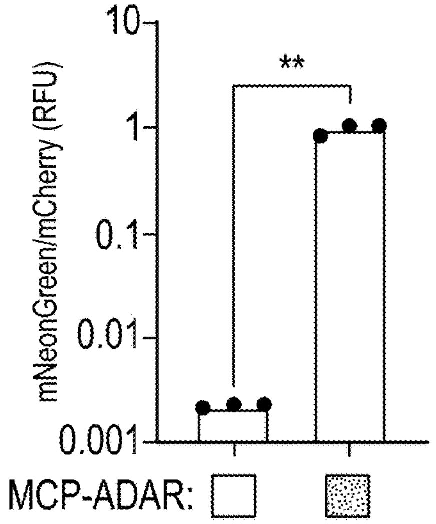
Figure 30D:
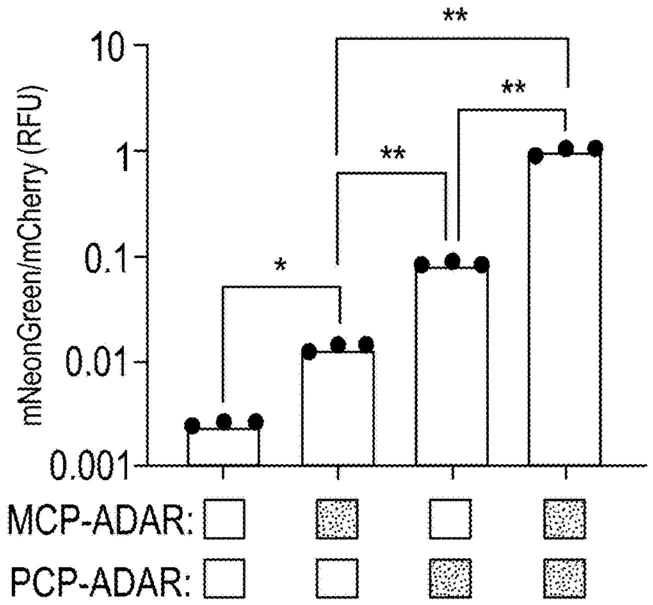
Figure 30E:
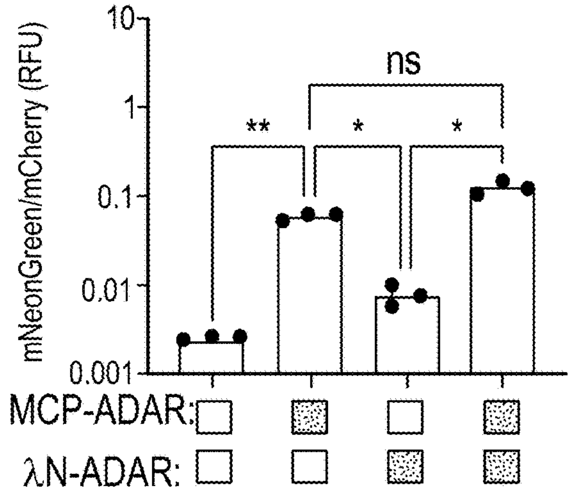
Figure 30F:
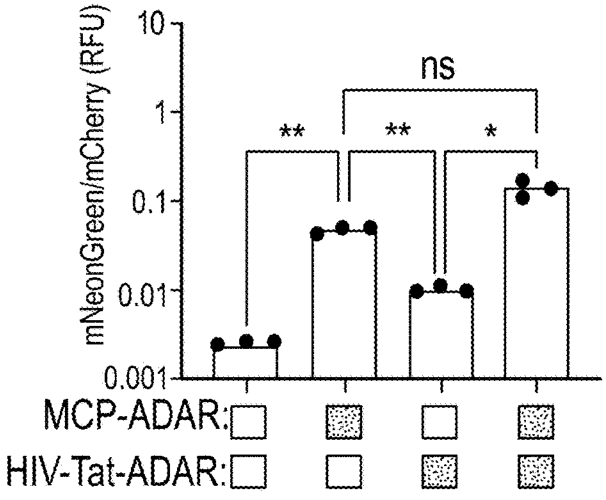

When compared to the reporter consisting of two MS2-C loops (see e.g., FIG. 30*c*), the background and maximal activation of the dual-input MS2 and PP7 reporter was very similar (see e.g., FIG. 30*d*). Co-transfection of both MCP-ADAR and PCP-ADAR led to significantly higher translational efficiency compared to cells that were singly transfected with MCP-ADAR or PCP-ADAR alone (see e.g., FIG. 30*d*). However, the same result was not observed for the dual-input reporters consisting of MS2 & BoxB (see e.g., FIG. 30*c*) or MS2 & HIV-TAR (see e.g., FIG. 30*f*).

This data demonstrates the capability of the system to be extended by encoding multiple ADAR substrates and RBMs on a single transcript.

STOP-Codon Insertion Between Functional Domains

In other iterations of the STOP codon editing iADAR reporters, the STOP codons were positioned between two polypeptides that were separated by self-cleaving 2A peptides, and functioned as distinct components. As an example, the reporter shown in FIG. 30*a* has three separate protein domains (mCherry, HaloTag, and mNeonGreen) that all operate independently of each other.

Figure 31A:
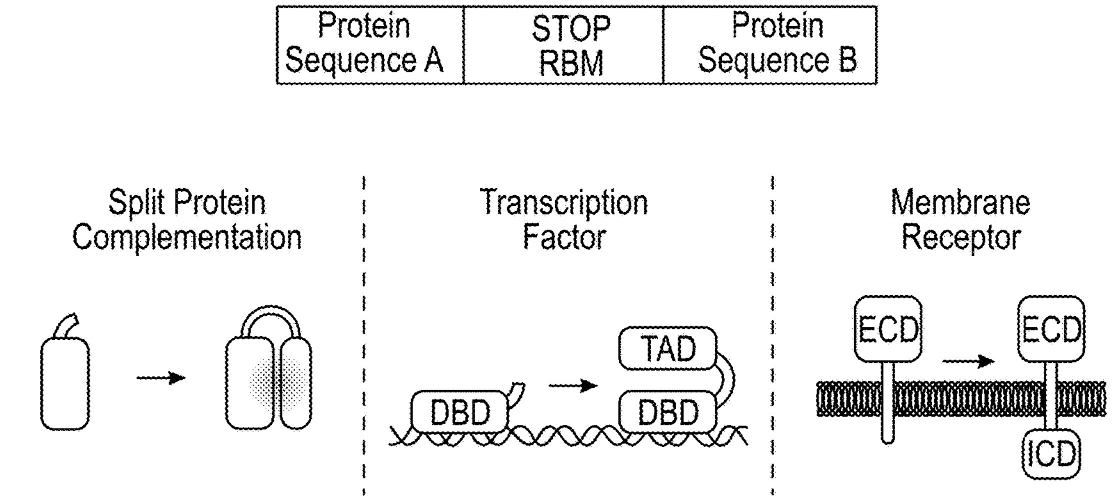
FIG. 31A-31C show editing of an internal STOP codon between fusion-dependent protein domains. Directed ADAR editing of internal STOP codons in a protein can rescue function.

In certain circumstances, it can be advantageous to have the recoding of a STOP codon to a tryptophan codon lead to the creation of a new fusion protein, where the upstream and downstream domains are fused together as a single, functional polypeptide chain (see e.g., FIG. 31*a*). Examples where this can be useful include split proteins of interest (N-terminal domain and C-terminal domain), transcription factors (DNA-binding domain (DBD) and transcriptional activation domain (TAD)), membrane receptors (extracellular domain, transmembrane domain and intracellular domain), or any multi-domain protein (see e.g., FIG. 31*a*). One advantage of this approach can be the ability to modulate protein effectors more sharply by having the pre-edited translation product have an opposing effect to the post-edited product. In the case of transcription factors, expressing the pre-edited DBD can act to repress transcription initially, and the post-edited DBD-TAD fusion protein will lead to transcription (see e.g., FIG. 31*a*). This is one example, but this can be a generally desirable feature.

Figure 31B:
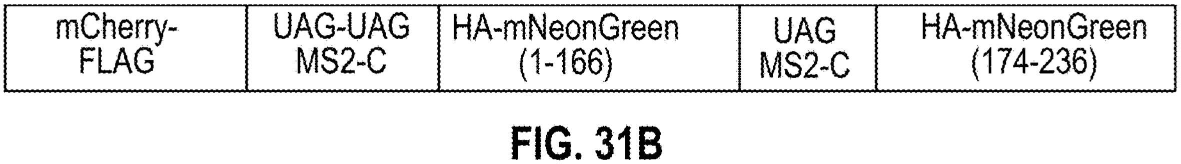

To demonstrate the capability of the iADAR platform to create functional fusion proteins post-editing, a reporter was designed and tested that contained an MS2-directed editable STOP codons between 2A peptides and in the middle of mNeonGreen (see e.g., FIG. 31*b*). The STOP codon loop inserted into mNeonGreen was designed adjacent to a flexible loop, and all amino acids outside of the loop were retained (other than the W167 position which was mutated to a STOP codon). In the case of this reporter, m NeonGreen fluorescence only occurs when editing of both sets of STOP codons occurs. This would therefore serve as a demonstration of STOP codon editing leading to a functional fusion protein.

To test this, 70,000 HEK293FT cells were co-transfected with 50 ng of either the 2×UAG-Internal-STOP-MS2 reporter or the previously tested 4×UAG-MS2 reporter plasmids, and 30 ng of either non-ADAR encoding DNA (NT), inactive MCP-dADAR (dADAR), and active MCP-ADAR (ADAR) plasmids. 48 hours post-transfection, cells were lifted and analyzed by flow cytometry, gated for mCherry expression, and the median mNeonGreen to mCherry value per well was computed. n=3 transfections.

Figure 31C:
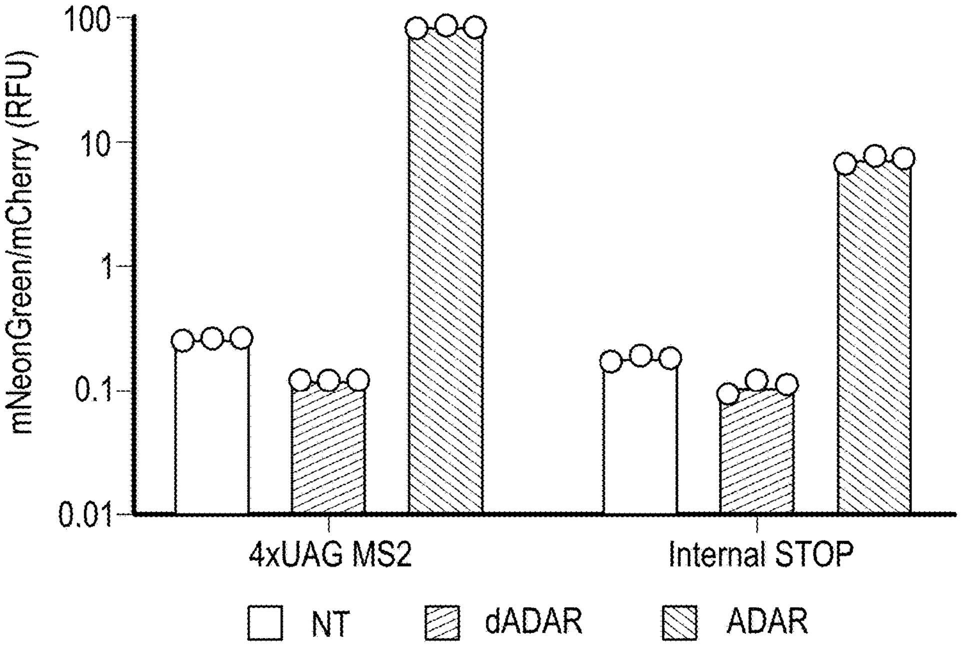

The insertion of the editable STOP codon and MS2 loop into the coding sequence for mNeonGreen (Internal STOP) led to editing dependent mNeonGreen expression (see e.g., FIG. 31*c*). Compared to the original 4×UAG-MS2 reporter, the induced fold change was reduced, but the background fluorescence was also lower.

Although the construct was initially designed to determine if there was a more sensitive iADAR reporter, this data demonstrates iADAR mRNA variants where the activity of the payload is dependent on the fusion of the pre-STOP and post-STOP components.

Example 14: IADAR Protein Variants

This section details new or enhanced designs of the protein components of the iADAR platform (i.e. the engineering of the enzymatic domain of adenosine deaminase).

Inclusion of ADAR Mutations and Localization Domain for Antigen Sensing

Figure 32A:
FIG. 32A-32D show ADAR2-DD Mutations with ALFA-Sensing iADAR. ADAR2 mutations increase fold change of weaker antigen sensing systems.

The AlfaTag epitope can be sensed by an AlfaTag inducible ADAR domain which contains: MS2 coat protein, N-ADAR2-DD (316-468), AlfaTag epitope or epitope variants, C-ADAR2-DD (469-700), and Alfa-Nanobody (AlfaNb) (see e.g., FIG. 32*a*). Lower affinity epitope variants (AlfaPE & Alfa78) can be used, however they had increased background activity independent of soluble AlfaTag expression. Introducing certain mutations into the ADAR2-DD led to decreased background and an increase in fold change in drug inducible iADAR systems (Bcl-xL and Mcl-1). The same mutations were introduced into the weaker AlfaTag epitope variants to reduce the background of the system.

Figure 32B:

To test this, constructs were created that were similar to those before but with the addition of the mutations to the ADAR2-DD (L699V, L699G & F697Y) and an additional single-domain antibody fragment capable of binding to GFP and its derivatives (VHH9) (see e.g., FIG. 32*b*). In addition, non-fluorescent EGFP(R96M) and EGFP(R96M)-AlfaTag fusion proteins were constructed as the control and experimental stimuli respectively. HEK293FT cells were then co-transfected with 4×UAG-MS2 iADAR reporter (see e.g., FIG. 32*a*), either EGFP(R96M) or EGFP(R96M)-AlfaTag, and the different mutations of the AlfaTag inducible iADAR. 48 hours after transfection, cells were imaged via microscopy and the mNconGreen-to-mCherry ratio was computed for individual iADAR-BFP-positive cells via ImageJ and the mean was computed by GRAPHPAD PRISM. n=1 replicate of transfected HEK.

Figure 32C:
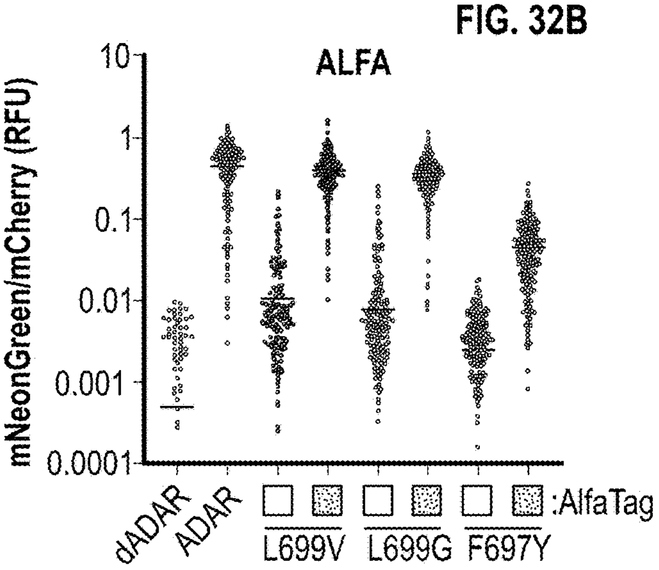
Figure 32D:
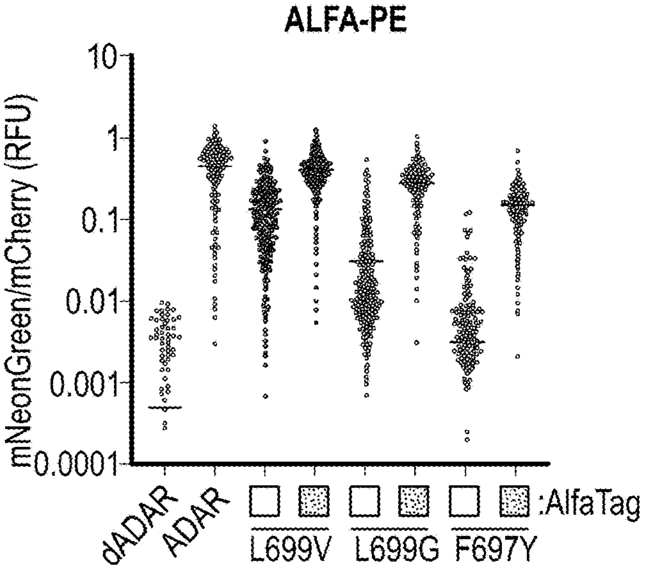

For the high-affinity ALFA variant of the iADAR, the addition of stronger mutations did not greatly reduce the mean background (L699V-0.010 RFU, L699G-0.0077 RFU, F697Y-0.0025 RFU) or increase the mean fold change of the uninduced to induced system (L699V-37x, L699G-46x, F697Y-18x) (see e.g., FIG. 32*c*). However, the insertion of the weaker variant, ALFA-PE, into the iADAR system did greatly affect the mean background level (L699V-0.13 RFU, L699G-0.030 RFU, F697Y-0.0031 RFU) and the mean fold change of the system (L699V-3.0x, L699G-9.1x, F697Y-47x) (see e.g., FIG. 32*d*).

This data demonstrates that the addition of mutations decreases the background and increases the fold-change for the lower-affinity nanobody-epitope pairs. While ALFA-AlfaNb interaction is reported to be picomolar, the ALFA-PE-AlfaNb interaction is reported to be nanomolar, which is similar to other intrabody-epitope interaction strengths.

Multi-Input IADAR Proteins

While the dual-input reporter data (Two-Input Logic) indicated that it is possible to construct multi-input logic using multiple RBD-iADAR fusion proteins with a single mRNA transcript, it is advantageous to be able to encode this multi-input logic with a single RBD-iADAR protein sensor. An auto-inhibited ADAR-DD can require two events (e.g., antigen, drug, protease, etc.) to fully relieve the autoinhibited state of a single enzymatic domain (see e.g., FIG. 33*a*).

Figure 33B:
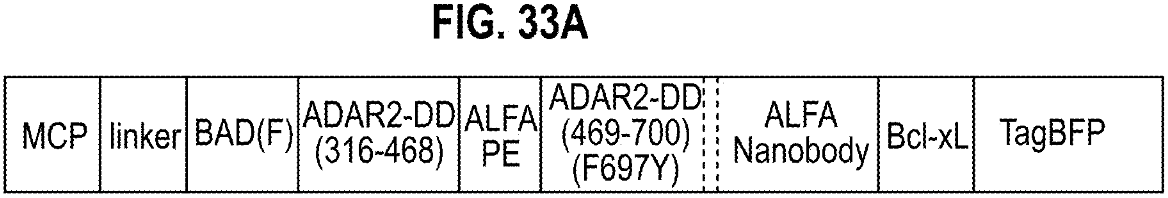
Figure 33C:
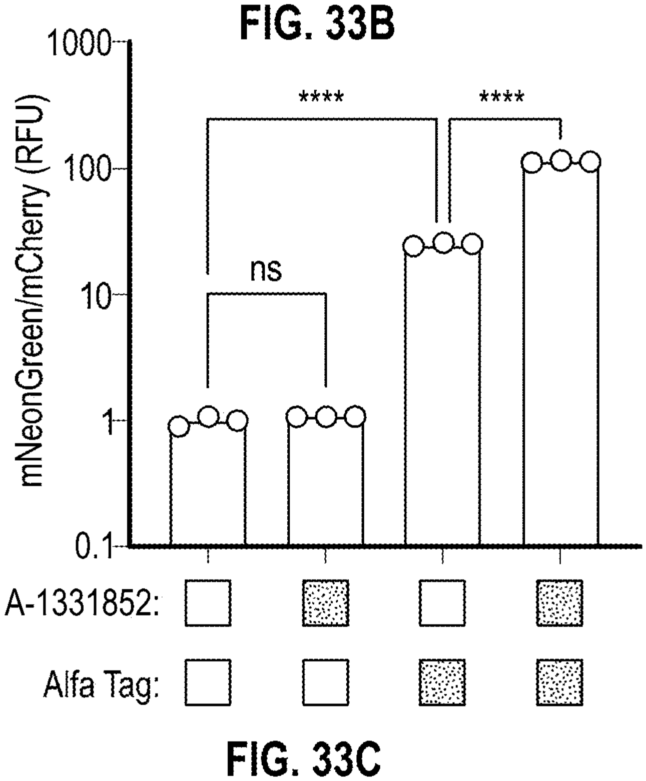

In order to test this, a plasmid was constructed that combined Bcl-XL-BAD and AlfaNb-ALFA iADARs into a single protein (see e.g., FIG. 33*b*). The BAD-peptide was fused to the N-terminus of ADAR2-DD and the ALFA-PE peptide was inserted at the 5' RNA binding site. On the C-terminus of ADAR2-DD, the AlfaNb and Bcl-xL were fused in tandem. The F697Y mutation was also used to decrease the potential of background.

With this system, iADAR activity only occurs when soluble AlfaTag (purple squiggle) was expressed and the Bcl-xL inhibitor A-1331852 (orange hexagon) was added, as the addition of either alone would not disturb the other intramolecular interaction (see e.g., FIG. 33*a*).

HEK293FT cells were co-transfected with the dual-input iADAR, the 4×UAG-MS2 reporter, and either EGFP (R96M) or EGFP(R96M)-AlfaTag on day 0. At the time of transfection, 500 nM of A-1331852 or DMSO was added to their respective conditions. 48 hours after transfection, cells were lifted and run via flow cytometry. The median mCherry to mNeonGreen ratio was computed for transfected cells were gated by BFP expression and mCherry expression. The experiment was then analyzed via one-way ANOVA (n=3 transfected cell populations per condition).

The highest median relative fluorescence was achieved when both A-1331852 and

EGFP(R96M)-AlfaTag were present (see e.g., FIG. 33*c*), and was significantly higher than either alone (~110× and ~4.6× greater than A-1331852 and AlfaTag respectively). Transfection with AlfaTag and treatment with DMSO was also significantly higher than the negative condition or A-1331852 treatment.

This data demonstrates capability of "daisy-chaining" protein components together under the iADAR platform to create dual-input logic. The utility of an optimized version of this system is that it allows for exogenous control (e.g., through small-molecule drugs) of antigen sensing, which can be used in therapeutic contexts.

Grazoprevir Inducible Systems Updates

Mutation of NS3-Peptide Based System

An iADAR was constructed and tested that was induced by approved antiviral drugs that relied on the NS3 HCV-protease and a high affinity peptide (see e.g., Development of Grazoprevir Activated ADAR). This system functioned by the same mechanism as the Bcl-xL and Mcl-1 systems, e.g., drug based displacement of a high-affinity intramolecular interaction (see e.g., FIG. 34*a*).

HEK293FT cells were co-transfected with the 4xUAG MS2 reporter and either an MCP-ADAR containing a peptide insertion at the 5' RNA binding site (see e.g., FIG. 34*b*, Pep), grazoprevir iADAR (Pep-NS3) or a mutant version of the iADAR (Pep-NS3 (K690R)). At the time of transfection, 3 μM of DMSO or grazoprevir was added. 48 hours after transfection, cells were lifted and run via flow cytometry. The median mCherry to mNeonGreen ratio was computed for transfected cells that were gated by BFP expression and mCherry expression. The experiment was then analyzed via two-way ANOVA (n=3 transfected cell populations per condition).

Figure 34C:
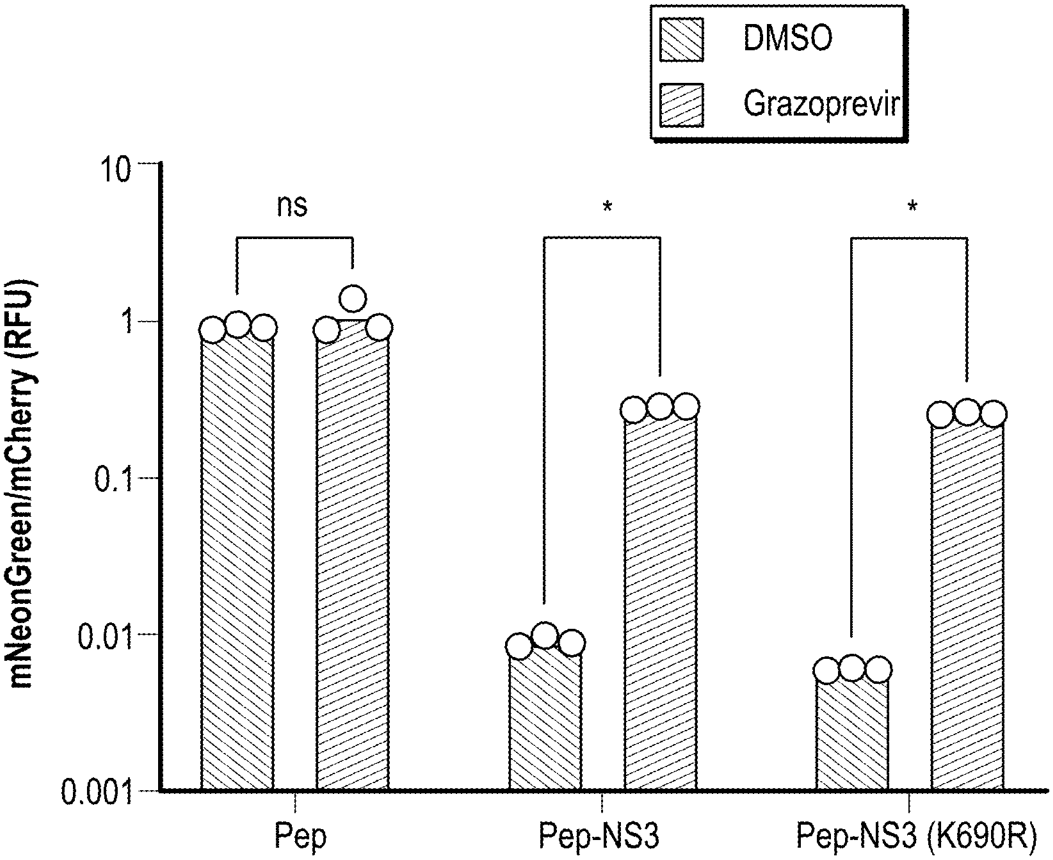

The fold change of the grazoprevir treated iADAR compared to DMSO treated was ~31× for the WT system and ~43× for the IADAR K690R (see e.g., FIG. 34*c*). This further demonstrates the utility of various mutations in developing more sensitive iADAR systems.

Ligand-INducible Connection Based iADAR

Catalytically active NS3 and protease inhibitors can be used to create conditional fusion proteins, termed Ligand-INducible Connections (LINCs). The scheme relies on fusion of the NS3 protease and its corresponding cut site(s) between separate or split domains of a protein that relies on both components to function (see e.g., FIG. 35*a*).

In the context of iADAR, the LiNC system was used to create a grazoprevir inducible ADAR by inserting the NS5A/5B cutsite in the 5' RNA binding loop (see e.g., FIG. 35*b*, green). When active NS3 protease is fused to the C-terminus, cleavage occurs and the two ADAR halves dissociates (see e.g., FIG. 35*a*). When the protease inhibitor grazoprevir is added or a catalytically inactive NS3 (dNS3) is used, the halves remain intact and the iADAR remains active.

To test this, LINC-ADAR constructs were created with WT, L699G, or F697Y mutations (see e.g., FIG. 35*b*) and HEK293FT cells were co-transfected with them and the 4×UAG-MS2 reporter in the presence of 2 μM grazoprevir or DMSO vehicle. 48 hours after transfection and drug treatment, cells were lifted and analyzed by flow cytometry.

The median mCherry to mNeonGreen ratio was computed for transfected cells that were gated by BFP expression and mCherry expression. (n=3 transfected cell populations per condition).

While the WT LiNC had only a modest drug dependent increase in ADAR editing activity, the L699G mutant had better drug dependent performance (~13× fold increase when grazoprevir is added) (see e.g., FIG. 35*c*). This data demonstrates the versatility of engineering ADAR and inserting different epitopes in the 5' RNA binding site.

Example 15: Combined Transcript and IADAR-IRES Control

Figure 36A:
FIG. 36A-36E show that IRES-based iADAR Constructs Enable Novel Single Construct Design. Use of the EMCV IRES leads to robust, single transcript circuits.

This section details single transcript designs that combine the iADAR-sensor and iADAR-substrate. The iADAR-sensor can be encoded before the first set of editable UAG stop codons to create a single construct capable of sensing and responding to stimuli (see e.g., FIG. 36*a*). This design is advantageous for linear mRNA therapeutics due to all components of the circuit being deliverable as a single transcript.

Figure 36B:
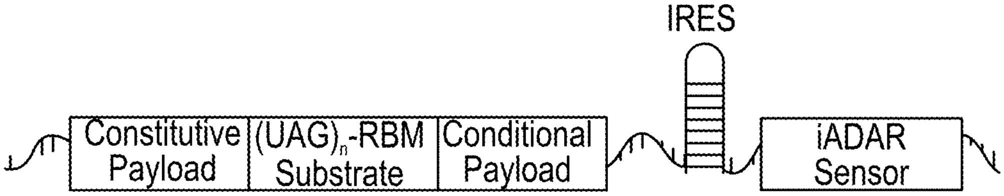

As an additional mechanism of achieving the same "all-in-one" design, an mRNA transcript was designed and constructed that encoded both a reporter construct (in this case, the 4×UAG reporter) whose translation is driven by canonical, cap-dependent translation and a downstream iADAR sensor driven by a virally-derived internal ribosome entry site (IRES) (see e.g., FIG. 36*b*). In this way, a single mRNA, in the absence of the iADAR inducer, would drive the translation of the iADAR sensor and protein of interest (in the case of the data, mCherry). Upon induction, a second, downstream protein (in this case, mNeonGreen) would be translated after stop codon editing. This design can offer the advantage of tunability of iADAR-sensor expression without affecting the expression of the payload after induction. This scheme can also be adaptable to circular mRNA or other modalities that rely on IRES driven expression in cells.

Figure 36C:
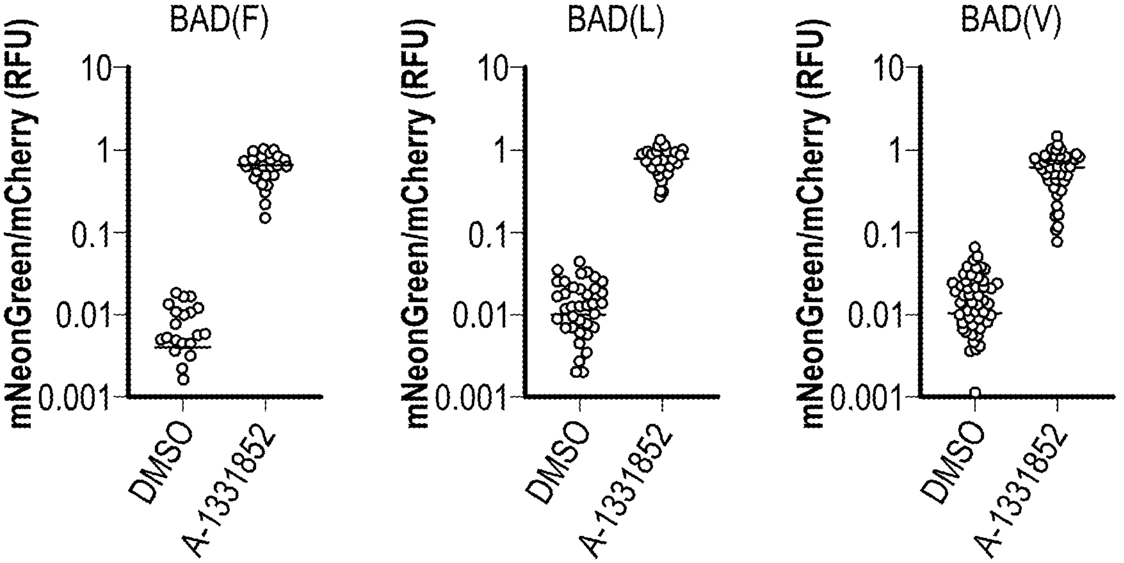

To test this, drug and protease inducible iADAR IRES circuits were constructed. For the drug-inducible iADAR IRES, low background BclXL-BAD pairs were used that contained variant BAD peptides (F22, F22L, & F22V) inserted between AA site 468/469 in the ADAR2-DD and the R522M mutation in the ADAR2-DD domain. The EMCV IRES and the BAD iADARs were placed in the 3'UTR of the 4×UAG reporter construct to create the single construct. 70,000 HEK cells were then transfected with 50 ng of the respective plasmids in the presence of 1 μM A-1331852 or DMSO, and cells were imaged 48 hours later via microscopy. Images were then analyzed by IMAGEJ, where the mNeonGreen-to-mCherry ratio was calculated for individual, transfected cells (gated by mCherry expression). All of the IRES-iADAR constructs were induced by A-1331852 addition relative to DMSO treatment, with fold changes of the mean RFU of 160× for BAD (F22), 80× for BAD (F22L), and 60× for BAD (F22V) (see e.g., FIG. 36*c*). This showed that this configuration worked as expected, and that using an IRES to drive the expression of iADAR is a viable strategy.

Figure 36D:
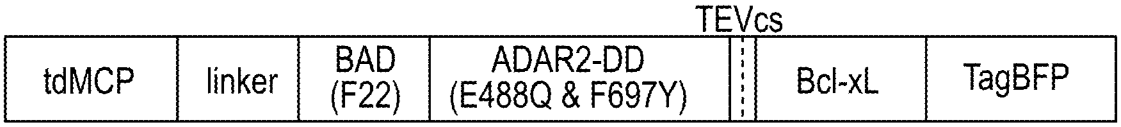

The construction of a protease-inducible iADAR was also tested with the IRES design. To do this, a TEV-inducible iADAR design was tested, composed of: a tandem-dimer MCP, BAD peptide fused to the N-terminus of ADAR2-DD (E488Q & F697Y), a TEV cut site, Bcl-xL, and TagBFP (see e.g., FIG. 36*d*). This protein functions as an OR-gate, as it can be induced by either dissociation of the BAD-BclxL by addition of A-1331852 or by TEV-based proteolysis of the linker between the C-terminus of the deaminase domain and Bcl-xL.

70,000 HEK cells were then transfected with 50 ng of the plasmid and 3 ng of either filler DNA or a plasmid encoding TEV protease. Each transfection condition was plated in the presence of 1 μM A-1331852 or DMSO. Cells were imaged 48 hours later via microscopy. Images were then analyzed by IMAGEJ, where the mNeonGreen-to-mCherry ratio was calculated for individual, transfected cells (gated by mCherry expression).

Figure 36E:
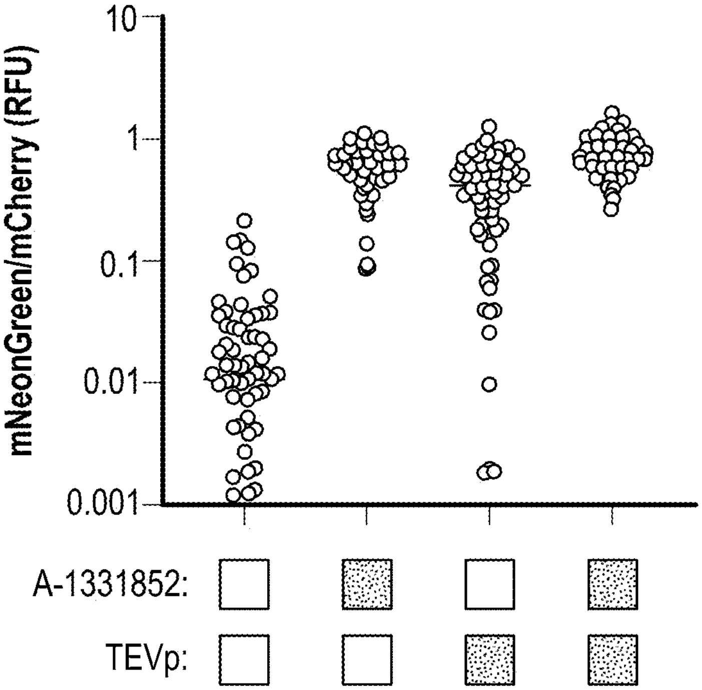

All of the IRES-iADAR construct was induced by either the A-1331852 drug or by TEV protease (see e.g., FIG. 36*e*). The fold change of the mean RFU was 27× for A-1331852 alone, 17× for TEV protease, and 32× for the dual addition of A-1331852 and TEV protease. This demonstrates both the versatility of the IRES based "all-in-one" scheme and the ability for a single iADAR protein to be activated by different stimuli (OR-gate compared to the previous AND-gate).

Example 16: Sense Codon Editing

In addition to controlling gene activity by editing the initiation or termination of translation, this iADAR technology can be used to recode a protein by deamination of in-frame codons (i.e. introduce mutations to specific sites). In order to do this, one can introduce a dsRNA loop and an RNA binding motif to an adjacent codon of interest (see e.g., FIG. 37*a*). The expression of active ADAR leads to deamination of an adenine base to inosine, which would be interpreted as guanine and a different amino acid would be inserted into the growing polypeptide chain. The number of possible recoding permutations is constrained by the genetic code, e.g., in human cells, it is impossible to use adenosine deamination to convert from or to a proline, as the four proline codons are CCN (see e.g., Table 15 for possible functional recoding). However, there are still scenarios where this functionality may be desirable.

To test inducible ADAR recoding of a protein's amino acid composition, a construct was designed that contained: a CD8 signal peptide, an HA epitope tag, the self-labeling Halo Tag, a mutant variant of the thosea asigna virus 2A self-cleaving peptide that is defective for ribosome skipping (Gly 18Arg mutation), the DNA binding domain of Gal4, and a 4× repeat of the transcriptional activation domain from herpes virus (VP64) (see e.g., FIG. 37*a*). The penultimate glycine in 2A peptides is invariant (see e.g., FIG. 37*b*) and any mutation leads to defective ribosome skipping. The codon for the G18R residue (AGG) is in a dsRNA hairpin with the high affinity MS2-C motif, which acts as a substrate for targeted MCP-ADAR. In the absence of ADAR editing, the defective T2A sequence will lead to the topological sequestering of the Gal4-VP64 transcription factor in the ER lumen due to the fusion to the secreted HaloTag (see e.g., FIG. 37*c*). Upon ADAR editing of the Arg18 codon to glycine (AGG to IGG), the T2A regains the function of ribosome skipping. This leads to the protein domains downstream of the T2A sequence to be translated as a separate polypeptide in the cytoplasm, whereby the GAL4-VP64 transcription factor translocate to the nucleus and turn on the expression of a fluorescent H2B-mCherry reporter (see e.g., FIG. 37*c*). This demonstrates the ability of directed ADAR domains to edit and recode a protein sequence of interest to modulate protein function.

To test this, an in-house clonal HEK293FT cell line that contains an integrated UAS-H2B-mCherry reporter was co-transfected with the editable T2A (also called T2A*) construct (3 ng, 0.3 ng and 0.03 ng) and either MCP-dADAR or MCP-ADAR (30 ng). A GAL4-VP64 positive control was also transfected into HEK cells. One day post-transfection, cells were lifted and analyzed by flow cytometry. Transfected cells were gated by TagBFP, the median H2B-mCherry fluorescence for the population was calculated and H2B-mCherry positive populations within the transfected cells were determined by the percentage of cells above 0.5% of non-transfected control cells per replicate (n=3) by FLOWJO.

Additionally, the clonal HEK line was co-transfected with 3 ng of the T2A* construct and 30 ng of either filler DNA, MCP-dADAR, or MCP-ADAR. 48 hours later lysates were collected with 1×LDS-PAGE loading buffer (THERMOFISHER) on ice. The samples were sonicated, centrifuged, and boiled at 70° C. for 10 min after the addition of 1×Reducing Agent (THERMOFISHER). The samples were run on a 4%-12% bis-tris polyacrylamide gel at 175V for 45 minutes, and the samples were transferred onto a nitrocellulose membrane using the IBLOT (THERMOFISHER). Samples were probed for FLAG tag (Direct-Blot™ HRP anti-DYKDDDDK Tag Antibody, “DYKDDDDK” is disclosed as SEQ ID NO: 406) and GAPDH-loading control (Direct-Blot™ HRP anti-GAPDH Antibody) respectively.

Figure 37D:
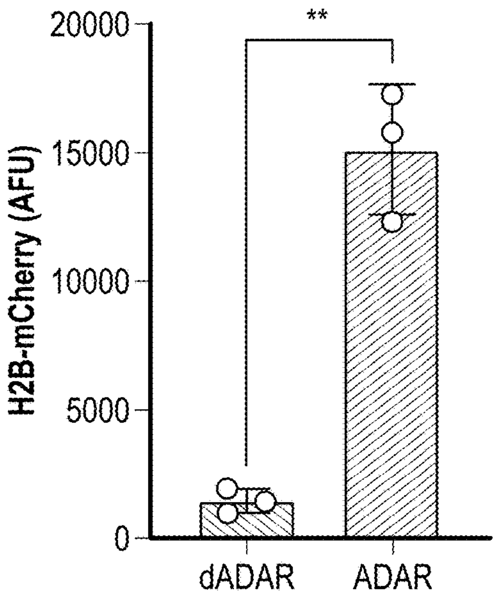
Figure 37E:
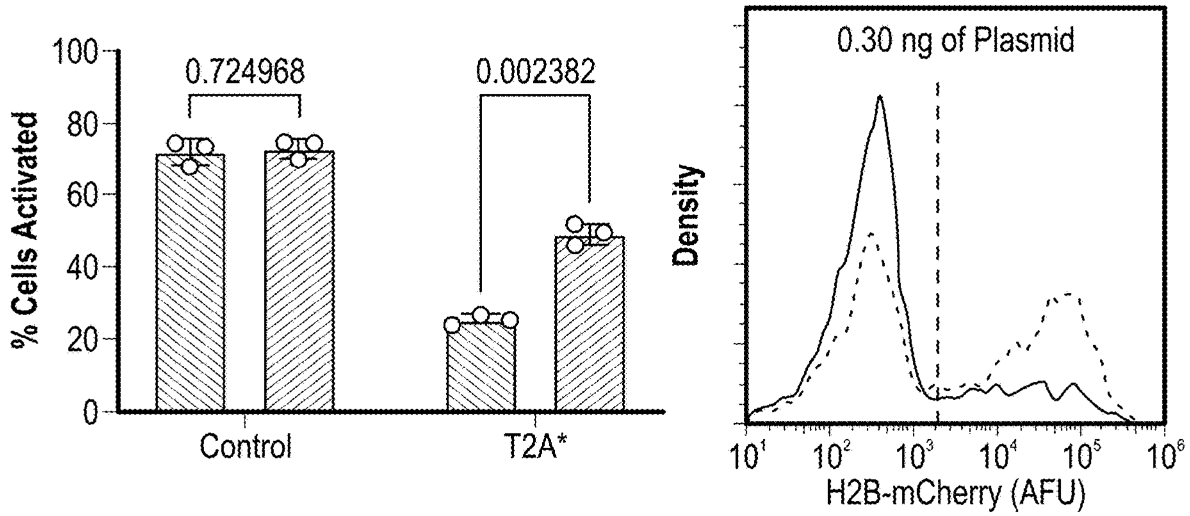
Figure 37F:
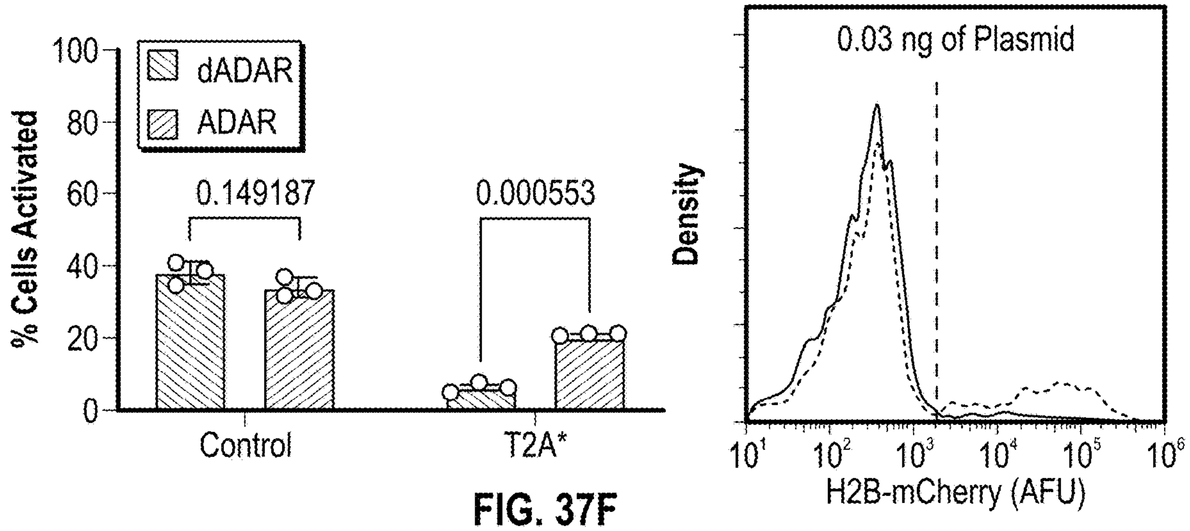

Co-transfecting 3 ng the editable T2A* with the active MCP-ADAR led to a significant increase in the median H2B-mCherry expression compared to the inactive MCP-dADAR control (see e.g., FIG. 37*d*). The population of the HEK293FT clonal lines that expressed any H2B-mCherry when co-transfected with 0.3 ng (see e.g., FIG. 37*e*) or 0.03 ng (see e.g., FIG. 37*f*) of the T2A* construct was significantly higher when co-transfected with MCP-ADAR compared to dADAR, though the percentage of activated cells were lower than the Gal4-VP64 positive control.

Figure 37G:
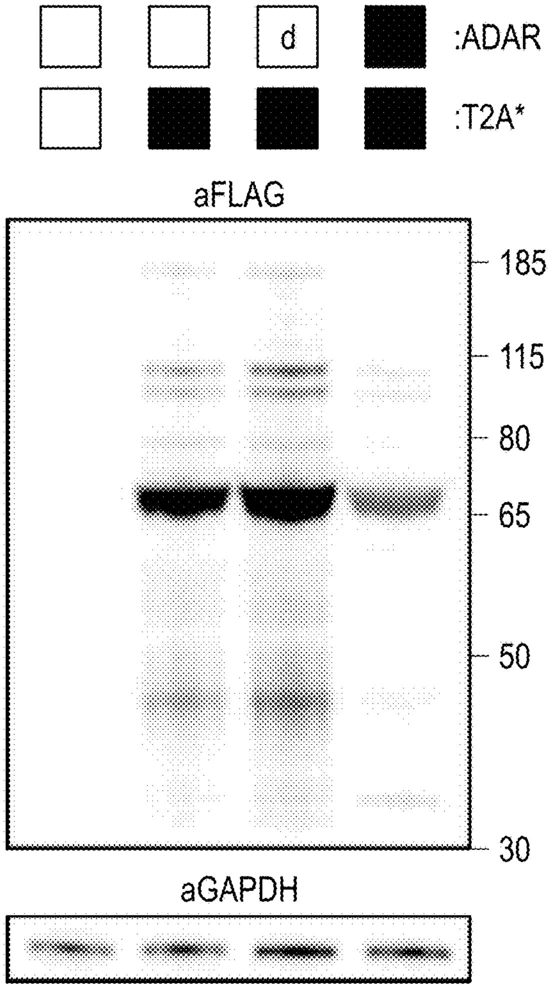

Cells that co-transfected with the T2A* construct and active MCP-ADAR had a reduced staining for the main HaloTag-T2A *-FLAG-Gal4-VP64 fusion product (predicted mass of ~67 kDa) compared to the control and dADAR conditions (see e.g., FIG. 37*g*). Additionally, the proportion of FLAG-Gal4-VP64 (predicted mass of ~30 kDa) relative to the main product was increased (although there appears to still be signal in the other conditions). Finally, additional bands corresponding to potential cleavage products are reduced.

These data combined demonstrate the capability of the iADAR system to lead to the functional recoding of a sense codon in a protein-encoding transcript to lead to a change in protein localization and activity.

Example 17: Exemplary Sequences

TABLE 15

| Functional Re-coding Events | | |
|---|---|---|
| | Unedited Codon and Amino Acid | Recoded Codon and Amino Acid |
| First Position—<br>**A**NN to **I**NN | AUH-ILE | IUH-VAL |
| | **AUG-MET** | **IUG-VAL** |
| | ACN-THR | GCN-ALA |
| | AAY-ASN | IAY-ASP |
| | AAR-LYS | IAR-GLU |
| | AGY-SER | IGY-GLY |
| | **AGR-ARG** | **IGR-GLY** |

TABLE 15-continued

| Functional Re-coding Events | | |
|---|---|---|
| | Unedited Codon and Amino Acid | Recoded Codon and Amino Acid |
| Second Position—<br>N**A**N to N**I**N | UAY-TYR | UIY-CYS |
| | **UAG-STOP** | **UIG-TRP** |
| | CAY-HIS | CIY-ARG |
| | CAR-GLN | CIR-ARG |
| | AAY-ASN | AIY-SER |
| | AAR-LYS | AIR-ARG |
| | GAY-ASP | GIY-GLY |
| | GAR-GLU | GIR-GLY |
| Third Position—<br>NN**A** to NN**I** | UGA-STOP | UGI-TRP |
| | **AUA-ILE** | **AUI-MET** |
| First & Second Position —<br>**AA**N to **II**N | AAY-ASN | IIY-GLY |
| | AAR-LYS | IIR-GLY |
| Second & Third Position—<br>N**AA** to N**II** | UAA-STOP | UII-TRP |

*Bold are the recoding events tested herein. Without wishing to be bound by theory, it is hypothesized that any of the above Unedited Codons can be edited into the corresponding Recoded Codon by the iAD polypeptides described herein.

Exemplary sequences (see e.g., FIG. 21A-21E).

```
SEQ ID NO: 198, MCP-linker-BclxL-
linker-ADAR2-DDN-Bad(L)-ADAR2(E488Q)-
DDC-TagBFP Also known as "BclxL-nDD-BAD-cDD"
(see e.g., FIG. 21A)
MASNFTQFVLVDNGGTGDVTVAPSNFANGIAEWISSNSRSQAYKV

TCSVRQSSAQNRKYTIKVEVPKGAWRSYLNMELTIPIFATNSDCE

LIVKAMQGLLKDGNPIPSAIAANSGIYGGSGSGAGSGSPAGGGAP

GSGGGSQSNRELVVDFLSYKLSQKGYSWSQFSDVEENRTEAPEGT

ESEMETPSAINGNPSWHLADSPAVNGATGHSSSLDAREVIPMAAV

KQALREAGDEFELRYRRAFSDLTSQLHITPGTAYQSFEQVVNELF

RDGVNWGRIVAFFSFGGALCVESVDKEMQVLVSRIAAWMATYLND

HLEPWIQENGGWDTFVELYGNNAAGGSGGSGGSGGSAAAQLHLPQ

VLADAVSRLVLGKFGDLTDNFSSPHARRKVLAGVVMTTGTDVKDA

KVISVSTGTKCINGEYMSDRGLALNDCHAEIISRRSLLRFLYTQL

ELYLNNKDDQKRSIFQKSERGGFRLKENVQFHLYISTSPCGDARI

FSPHEPILEEPAASGSGTGAPPNLWAAQRYGRELRRMSDELVDRH

PNRKARGQLRTKIESGQGTIPVRSNASIQTWDGVLQGERLLTMSC

SDKIARWNVVGIQGSLLSIFVEPIYFSSIILGSLYHGDHLSRAMY

QRISNIEDLPPLYTLNKPLLSGISNAEARQPGKAPNFSVNWTVGD

SAIEVINATTGKDELGRASRLCKHALYCRWMRVHGKVPSHLLRSK

ITKPNVYHESKLAAKEYQAAKARLFTAFIKAGLGAWVEKPTEQDQ

FSLTGSGSSELIKENMHMKLYMEGTVDNHHFKCTSEGEGKPYEGT

QTMRIKVVEGGPLPFAFDILATSFLYGSKTFINHTQGIPDFFKQS

FPEGFTWERVTTYEDGGVLTATQDTSLQDGCLIYNVKIRGVNFTS

NGPVMQKKTLGWEAFTETLYPADGGLEGRNDMALKLVGGSHLIAN

IKTTYRSKKPAKNLKMPGVYYVDYRLERIKEANNETYVEQHEVAV

ARYCDLPSKLGHKLN*
```

-continued

SEQ ID NO: 199,
TAATACGACTCACTATAGGGAGACCCAAGCTGGctagaggatcga
acccttaaggccaccatggcgtccaatttcactcagtttgtgctg
gttgacaacggcgggaccggggacgttacggtagccccctcaaac
tttgccaacggtatagcggagtggataagcagcaattctaggagt
caagcatacaaagttacatgcagcgtgcgccaatctagcgctcag
aatcgcaagtacaccattaaagtagaggtccccaagggagcctgg
agaagctatcttaacatggagttgaccataccaatcttcgctacc
aactctgactgtgaactcattgtgaaagccatgcaaggtctgctc
aaggatggtaacccaattccgtccgctatcgctgccaactctggg
atttacgggggcagtgggagcggtgcaggatctggtagtccagct
gggggaggagcaccgggtagcggtggggggtctcagAGTAACCGG
GAGCTGGTGGTTGACTTTCTCTCCTACAAGCTTTCCCAGAAAGGA
TACAGCTGGAGTCAGTTTAGTGATGTGGAAGAGAACAGGACTGAG
GCCCCAGAAGGGACTGAATCGGAGATGGAGACCCCCAGTGCCATC
AATGGCAACCCATCCTGGCACCTGGCAGACAGCCCCGCGGTGAAT
GGAGCCACTGGCCACAGCAGCAGTTTGGATGCCCGGGAGGTGATC
CCCATGGCAGCAGTAAAGCAAGCGCTGAGGGAGGCAGGCGACGAG
TTTGAACTGCGGTACCGGCGGGCATTCAGTGACCTGACATCCCAG
CTCCACATCACCCCAGGGACAGCATATCAGAGCTTTGAACAGGTA
GTGAATGAACTCTTCCGGGATGGGGTAAACTGGGGTCGCATTGTG
GCCTTTTTCTCCTTCGGCGGGGCACTGTGCGTGGAAAGCGTAGAC
AAGGAGATGCAGGTATTGGTGAGTCGGATCGCAGCTTGGATGGCC
ACTTACCTGAATGACCACCTAGAGCCTTGGATCCAGGAGAACGGC
GGCTGGGATACTTTTGTGGAACTCTATGGGAACAATGCGGCCGGA
GGTAGCGGCGGAAGCGGTGGCTCTGGAGGCTCAGCGGCCGCTCAA
TTAcacctgccccaggttctcgcagacgccgtatcccgccttgta
ctgggcaagtttggtgatcttactgacaatttttcatctcctcat
gcgaggcggaaagtactcgcaggcgtcgtcatgacgaccggaact
gacgtgaaagacgccaaagtcatctctgtctccacgggcacaaag
tgcataaacggggagtacatgagcgaccgggggctggcactgaat
gattgtcacgctgaaataatatctaggcgatctctgcttagattt
ctctacactcaactcgaattgtaccttaacaacaaagatgaccag
aaacgcagtatatttcagaaatcagaacgcggcggatttcgactt
aaggaaaacgttcagttccacttgtatatcagcacatccccttgc
ggtgacgcccgaatcttttccccgcacgagccgatattggaggag
cccgcgGCTAGCGGGTCGGGCACCGGTGCTCCACCCAATCTCTGG
GCAGCGCAGCGCTACGGCCGTGAGCTCAGAAGGATGTCCGATGAG
CTGGTCGACagacatcctaataggaaggctagaggccaacttcgg
acgaagattgaaagtggccagggtactatcccggtgcggtccaac
gctagtattcaaacgtgggacggagtccttcaaggtgaacggctg -continued ttgacaatgagctgctcagacaaaatcgcgcgctggaatgtagtg
ggaatccaaggcagcctcttgagcatattcgtagaacccatatat
ttctcatccattattttgggctctctgtatcatggtgaccatctg
tcaagggctatgtaccaacgaatttctaatatcgaggatcttcct
ccactctatacactcaataagcctctcttgtccgggatatcaaac
gctgaggcccgccagccagggaaagctcctaacttcagtgttaac
tggaccgttggtgattctgcgatagaggtcatcaacgccacgaca
ggtaaggatgagctcggtagagcctcacgcctgtgtaaacacgcg
ttgtattgtagatggatgagagtacatgggaaggtcccatctcac
ttgctccgaagcaagatcactaagcctaatgtgtatcatgagtca
aaactcgcggctaaagaataccaggcagccaaagctcgactttttt
acagcttttattaaggcagggctcggggcatgggtcgagaagccg
accgagcaggaccaattctctctgacggggagcggatccAGCGAG
CTGATTAAGGAGAACATGCACATGAAGCTGTACATGGAGGGCACC
GTGGACAACCATCACTTCAAGTGCACATCCGAGGGCGAAGGCAAG
CCCTACGAGGGCACCCAGACCATGAGAATCAAGGTGGTCGAGGGC
GGCCCTCTCCCCTTCGCCTTCGACATCCTGGCTACTAGCTTCCTC
TACGGCAGCAAGACCTTCATCAACCACACCCAGGGCATCCCCGAC
TTCTTCAAGCAGTCCTTCCCTGAGGGCTTCACATGGGAGAGAGTC
ACCACATACGAAGACGGGGGCGTGCTGACCGCTACCCAGGACACC
AGCCTCCAGGACGGCTGCCTCATCTACAACGTCAAGATCAGAGGG
GTGAACTTCACATCCAACGGCCCTGTGATGCAGAAGAAAACACTC
GGCTGGGAGGCCTTCACCGAGACGCTGTACCCCGCTGACGGCGGC
CTGGAAGGCAGAAACGACATGGCCCTGAAGCTCGTGGGCGGGAGC
CATCTGATCGCAAACATCAAGACCACATATAGATCCAAGAAACCC
GCTAAGAACCTCAAGATGCCTGGCGTCTACTATGTGGACTACAGA
CTGGAAAGAATCAAGGAGGCCAACAACGAGACCTACGTCGAGCAG
CACGAGGTGGCAGTGGCCAGATACTGCGACCTCCCTAGCAAACTG
GGGCACAAGCTTAATtAAGGGCCCGTTTAAACCCGCTGATCAGCC
TCGACTGTGCCTTCTA SEQ ID NO: 200,
MCP-linker-BAD-ADAR2-DD(E488Q)-TagBFP Also
known as “BAD-DD” (see e.g., FIG. 21B)
MASNFTQFVLVDNGGTGDVTVAPSNFANGIAEWISSNSRSQAYKV
TCSVRQSSAQNRKYTIKVEVPKGAWRSYLNMELTIPIFATNSDCE
LIVKAMQGLLKDGNPIPSAIAANSGIYGGSGSGAGSGSPAGGGAP
GSGGGSTGAPPNLWAAQRYGRELRRMSDEFVDSFKKASQLHLPQV
LADAVSRLVLGKFGDLTDNFSSPHARRKVLAGVVMTTGTDVKDAK
VISVSTGTKCINGEYMSDRGLALNDCHAEIISRRSLLRFLYTQLE
LYLNNKDDQKRSIFQKSERGGFRLKENVQFHLYISTSPCGDARIF
SPHEPILEEPADRHPNRKARGQLRTKIESGQGTIPVRSNASIQTW
DGVLQGERLLTMSCSDKIARWNVVGIQGSLLSIFVEPIYFSSIIL -continued GSLYHGDHLSRAMYQRISNIEDLPPLYTLNKPLLSGISNAEARQP
GKAPNFSVNWTVGDSAIEVINATTGKDELGRASRLCKHALYCRWM
RVHGKVPSHLLRSKITKPNVYHESKLAAKEYQAAKARLFTAFIKA
GLGAWVEKPTEQDQFSLTGSGSSELIKENMHMKLYMEGTVDNHHF
KCTSEGEGKPYEGTQTMRIKVVEGGPLPFAFDILATSFLYGSKTF
INHTQGIPDFFKQSFPEGFTWERVTTYEDGGVLTATQDTSLQDGC
LIYNVKIRGVNFTSNGPVMQKKTLGWEAFTETLYPADGGLEGRND
MALKLVGGSHLIANIKTTYRSKKPAKNLKMPGVYYVDYRLERIKE
ANNETYVEQHEVAVARYCDLPSKLGHKLN*

SEQ ID NO: 201,
TAATACGACTCACTATAGGGAGACCCAAGCTGGctagaggatcga
acccttaaggccaccatggcgtccaatttcactcagtttgtgctg
gttgacaacggcgggaccggggacgttacggtagccccctcaaac
tttgccaacggtatagcggagtggataagcagcaattctaggagt
caagcatacaaagttacatgcagcgtgcgccaatctagcgctcag
aatcgcaagtacaccattaaagtagaggtccccaagggagcctgg
agaagctatcttaacatggagttgaccataccaatcttcgctacc
aactctgactgtgaactcattgtgaaagccatgcaaggtctgctc
aaggatggtaacccaattccgtccgctatcgctgccaactctggg
atttacgggggcagtgggagcggtgcaggatctggtagtccagct
gggggaggagcaccgggtagcggtggggggtctACCGGTGCTCCA
CCCAATCTCTGGGCAGCGCAGCGCTACGGCCGTGAGCTCAGAAGG
ATGTCCGATGAGTTCGTCGATTCCTTCAAAAAGGCTAGCcagctg
cacctgccccaggttctcgcagacgccgtatcccgccttgtactg
ggcaagtttggtgatcttactgacaattttcatctcctcatgcg
aggcggaaagtactcgcaggcgtcgtcatgacgaccggaactgac
gtgaaagacgccaaagtcatctctgtctccacgggcacaaagtgc
ataaacggggagtacatgagcgaccgggggctggcactgaatgat
tgtcacgctgaaataatatctaggcgatctctgcttagatttctc
tacactcaactcgaattgtaccttaacaacaaagatgaccagaaa
cgcagtatatttcagaaatcagaacgcggcggatttcgacttaag
gaaaacgttcagttccacttgtatatcagcacatccccttgcggt
gacgcccgaatcttttccccgcacgagccgatattggaggagccc
gcggacagacatcctaataggaaggctagaggccaacttcggacg
aagattgaaagtggccagggtactatcccggtgcggtccaacgct
agtattcaaacgtgggacggagtccttcaaggtgaacggctgttg
acaatgagctgctcagacaaaatcgcgcgctggaatgtagtggga
atccaaggcagcctcttgagcatattcgtagaacccatatatttc
tcatccattatttgggctctctgtatcatggtgaccatctgtca
agggctatgtaccaacgaatttctaatatcgaggatcttcctcca
ctctatacactcaataagcctctcttgtccgggatatcaaacgct -continued gaggcccgccagccagggaaagctcctaacttcagtgttaactgg
accgttggtgattctgcgatagaggtcatcaacgccacgacaggt
aaggatgagctcggtagagcctcacgcctgtgtaaacacgcgttg
tattgtagatggatgagagtacatgggaaggtcccatctcacttg
ctccgaagcaagatcactaagcctaatgtgtatcatgagtcaaaa
ctcgcggctaaagaataccaggcagccaaagctcgactttttaca
gcttttattaaggcagggctcggggcatgggtcgagaagccgacc
gagcaggaccaattctctctgacggggagcggatccAGCGAGCTG
ATTAAGGAGAACATGCACATGAAGCTGTACATGGAGGGCACCGTG
GACAACCATCACTTCAAGTGCACATCCGAGGGCGAAGGCAAGCCC
TACGAGGGCACCCAGACCATGAGAATCAAGGTGGTCGAGGGCGGC
CCTCTCCCCTTCGCCTTCGACATCCTGGCTACTAGCTTCCTCTAC
GGCAGCAAGACCTTCATCAACCACACCCAGGGCATCCCCGACTTC
TTCAAGCAGTCCTTCCCTGAGGGCTTCACATGGGAGAGAGTCACC
ACATACGAAGACGGGGGCGTGCTGACCGCTACCCAGGACACCAGC
CTCCAGGACGGCTGCCTCATCTACAACGTCAAGATCAGAGGGGTG
AACTTCACATCCAACGGCCCTGTGATGCAGAAGAAAACACTCGGC
TGGGAGGCCTTCACCGAGACGCTGTACCCCGCTGACGGCGGCCTG
GAAGGCAGAAACGACATGGCCCTGAAGCTCGTGGGCGGGAGCCAT
CTGATCGCAAACATCAAGACCACATATAGATCCAAGAAACCCGCT
AAGAACCTCAAGATGCCTGGCGTCTACTATGTGGACTACAGACTG
GAAAGAATCAAGGAGGCCAACAACGAGACCTACGTCGAGCAGCAC
GAGGTGGCAGTGGCCAGATACTGCGACCTCCCTAGCAAACTGGGG
CACAAGCTTAATtAAGGGCCCGTTTAAACCCGCTGATCAGCCTCG
ACTGTGCCTTCTA SEQ ID NO: 202, MCP-linker-BAD-ADAR2-DD (E488Q)-Bcl-xL-TagBFP Also known as “BAD-DD-BclxL” and “WT” (see e.g., FIG. 21C)
MASNFTQFVLVDNGGTGDVTVAPSNFANGIAEWISSNSRSQAYKV
TCSVRQSSAQNRKYTIKVEVPKGAWRSYLNMELTIPIFATNSDCE
LIVKAMQGLLKDGNPIPSAIAANSGIYGGSGSGAGSGSPAGGGAP
GSGGGSTGAPPNLWAAQRYGRELRRMSDEFVDSFKKASQLHLPQV
LADAVSRLVLGKFGDLTDNFSSPHARRKVLAGVVMTTGTDVKDAK
VISVSTGTKCINGEYMSDRGLALNDCHAEIISRRSLLRFLYTQLE
LYLNNKDDQKRSIFQKSERGGFRLKENVQFHLYISTSPCGDARIF
SPHEPILEEPADRHPNRKARGQLRTKIESGQGTIPVRSNASIQTW
DGVLQGERLLTMSCSDKIARWNVVGIQGSLLSIFVEPIYFSSIIL
GSLYHGDHLSRAMYQRISNIEDLPPLYTLNKPLLSGISNAEARQP
GKAPNFSVNWTVGDSAIEVINATTGKDELGRASRLCKHALYCRWM
RVHGKVPSHLLRSKITKPNVYHESKLAAKEYQAAKARLFTAFIKA
GLGAWVEKPTEQDQFSLTGSAAASSNRELVVDFLSYKLSQKGYSW
SQFSDVEENRTEAPEGTESEMETPSAINGNPSWHLADSPAVNGAT -continued GHSSSLDAREVIPMAAVKQALREAGDEFELRYRRAFSDLTSQLHI TPGTAYQSFEQVVNELFRDGVNWGRIVAFFSFGGALCVESVDKEM QVLVSRIAAWMATYLNDHLEPWIQENGGWDTFVELYGNNGSSELI KENMHMKLYMEGTVDNHHFKCTSEGEGKPYEGTQTMRIKVVEGGP LPFAFDILATSFLYGSKTFINHTQGIPDFFKQSFPEGFTWERVTT YEDGGVLTATQDTSLQDGCLIYNVKIRGVNFTSNGPVMQKKTLGW EAFTETLYPADGGLEGRNDMALKLVGGSHLIANIKTTYRSKKPAK NLKMPGVYYVDYRLERIKEANNETYVEQHEVAVARYCDLPSKLGH KLN*

SEQ ID NO: 203,
TAATACGACTCACTATAGGGAGACCCAAGCTGGctagaggatcga acccttaaggccaccatggcgtccaatttcactcagtttgtgctg gttgacaacggcgggaccggggacgttacggtagcccccctcaaac tttgccaacggtatagcggagtggataagcagcaattctaggagt caagcatacaaagttacatgcagcgtgcgccaatctagcgctcag aatcgcaagtacaccattaaagtagaggtccccaagggagcctgg agaagctatcttaacatggagttgaccataccaatcttcgctacc aactctgactgtgaactcattgtgaaagccatgcaaggtctgctc aaggatggtaacccaattccgtccgctatcgctgccaactctggg atttacgggggcagtgggagcggtgcaggatctggtagtccagct gggggaggagcaccgggtagcggtggggggtctACCGGTGCTCCA CCCAATCTCTGGGCAGCGCAGCGCTACGGCCGTGAGCTCAGAAGG ATGTCCGATGAGTTCGTCGATTCCTTCAAAAAGGCTAGCcagctg cacctgccccaggttctcgcagacgccgtatcccgccttgtactg ggcaagtttggtgatcttactgacaatttttcatctcctcatgcg aggcggaaagtactcgcaggcgtcgtcatgacgaccggaactgac gtgaaagacgccaaagtcatctctgtctccacgggcacaaagtgc ataaacggggagtacatgagcgaccgggggctggcactgaatgat tgtcacgctgaaataatatctaggcgatctctgcttagatttctc tacactcaactcgaattgtaccttaacaacaaagatgaccagaaa cgcagtatatttcagaaatcagaacgcggcggatttcgacttaag gaaaacgttcagttccacttgtatatcagcacatccccttgcggt gacgcccgaatcttttccccgcacgagccgatattggaggagccc gcggacagacatcctaataggaaggctagaggccaacttcggacg aagattgaaagtggccagggtactatcccggtgcggtccaacgct agtattcaaacgtgggacggagtccttcaaggtgaacggctgttg acaatgagctgctcagacaaaatcgcgcgctggaatgtagtggga atccaaggcagcctcttgagcatattcgtagaacccatatatttc tcatccattatttgggctctctgtatcatggtgaccatctgtca agggctatgtaccaacgaatttctaatatcgaggatcttcctcca ctctatacactcaataagcctctcttgtccgggatatcaaacgct -continued gaggcccgccagccagggaaagctcctaacttcagtgttaactgg accgttggtgattctgcgatagaggtcatcaacgccacgacaggt aaggatgagctcggtagagcctcacgcctgtgtaaacacgcgttg tattgtagatggatgagagtacatgggaaggtcccatctcacttg ctccgaagcaagatcactaagcctaatgtgtatcatgagtcaaaa ctcgcggctaaagaataccaggcagccaaagctcgactttttaca gcttttattaaggcagggctcggggcatgggtcgagaagccgacc gagcaggaccaattctctctgacggggagcgcggccgccTCAAGT AACCGGGAGCTGGTGGTTGACTTTCTCTCCTACAAGCTTTCCCAG AAAGGATACAGCTGGAGTCAGTTTAGTGATGTGGAAGAGAACAGG ACTGAGGCCCCAGAAGGGACTGAATCGGAGATGGAGACCCCCAGT GCCATCAATGGCAACCCATCCTGGCACCTGGCAGACAGCCCCGCG GTGAATGGAGCCACTGGCCACAGCAGCAGTTTGGATGCCCGGGAG GTGATCCCCATGGCAGCAGTAAAGCAAGCGCTGAGGGAGGCAGGC GACGAGTTTGAACTGCGGTACCGGCGGGCATTCAGTGACCTGACA TCCCAGCTCCACATCACCCCAGGGACAGCATATCAGAGCTTTGAA CAGGTAGTGAATGAACTCTTCCGGGATGGGGTAAACTGGGGTCGC ATTGTGGCCTTTTTCTCCTTCGGCGGGGCACTGTGCGTGGAAAGC GTAGACAAGGAGATGCAGGTATTGGTGAGTCGGATCGCAGCTTGG ATGGCCACTTACCTGAATGACCACCTAGAGCCTTGGATCCAGGAG AACGGCGGCTGGGATACTTTTGTGGAACTCTATGGGAACAATgga tccAGCGAGCTGATTAAGGAGAACATGCACATGAAGCTGTACATG GAGGGCACCGTGGACAACCATCACTTCAAGTGCACATCCGAGGGC GAAGGCAAGCCCTACGAGGGCACCCAGACCATGAGAATCAAGGTG GTCGAGGGCGGCCCTCTCCCCTTCGCCTTCGACATCCTGGCTACT AGCTTCCTCTACGGCAGCAAGACCTTCATCAACCACACCCAGGGC ATCCCCGACTTCTTCAAGCAGTCCTTCCCTGAGGGCTTCACATGG GAGAGAGTCACCACATACGAAGACGGGGGCGTGCTGACCGCTACC CAGGACACCAGCCTCCAGGACGGCTGCCTCATCTACAACGTCAAG ATCAGAGGGGTGAACTTCACATCCAACGGCCCTGTGATGCAGAAG AAAACACTCGGCTGGGAGGCCTTCACCGAGACGCTGTACCCCGCT GACGGCGGCCTGGAAGGCAGAAACGACATGGCCCTGAAGCTCGTG GGCGGGAGCCATCTGATCGCAAACATCAAGACCACATATAGATCC AAGAAACCCGCTAAGAACCTCAAGATGCCTGGCGTCTACTATGTG GACTACAGACTGGAAAGAATCAAGGAGGCCAACAACGAGACCTAC GTCGAGCAGCACGAGGTGGCAGTGGCCAGATACTGCGACCTCCCT AGCAAACTGGGGCACAAGCTTAATtAAGGGCCCGTTTAAACCCGC TGATCAGCCTCGACTGTGCCTTCTA SEQ ID NO: 204, tdMCP_ADAR2-DDN-CP5-46-4D5E_
ADAR2-DDC(E488Q)_mTagBFP
(AD-Pep-AD) (see e.g., FIG. 21D)
MASNFTQFVLVDNGGTGDVTVAPSNFANGIAEWISSNSRSQAYKV
TCSVRQSSAQNRKYTIKVEVPKGAWRSYLNMELTIPIFATNSDCE
LIVKAMQGLLKDGNPIPSAIAANSGIYANFTQFVLVDNGGTGDVT
VAPSNFANGIAEWISSNSRSQAYKVTCSVRQSSAQNRKYTIKVEV
PKGAWRSYLNMELTIPIFATNSDCELIVKAMQGLLKDGNPIPSAI
AANSGIYGGSGSGAGSGSPAGGGAPGSGGGSQLHLPQVLADAVSR
LVLGKFGDLTDNFSSPHARRKVLAGVVMTTGTDVKDAKVISVSTG
TKCINGEYMSDRGLALNDCHAEIISRRSLLRFLYTQLELYLNNKD
DQKRSIFQKSERGGFRLKENVQFHLYISTSPCGDARIFSPHEPIL
EEPASSGGELDELVYLLDGPGYDPIHCDVVTRGGSHLFNFDRHPN
RKARGQLRTKIESGQGTIPVRSNASIQTWDGVLQGERLLTMSCSD
KIARWNVVGIQGSLLSIFVEPIYFSSIILGSLYHGDHLSRAMYQR
ISNIEDLPPLYTLNKPLLSGISNAEARQPGKAPNFSVNWTVGDSA
IEVINATTGKDELGRASRLCKHALYCRWMRVHGKVPSHLLRSKIT
KPNVYHESKLAAKEYQAAKARLFTAFIKAGLGAWVEKPTEQDQFS
LTGSGSSELIKENMHMKLYMEGTVDNHHFKCTSEGEGKPYEGTQT
MRIKVVEGGPLPFAFDILATSFLYGSKTFINHTQGIPDFFKQSFP
EGFTWERVTTYEDGGVLTATQDTSLQDGCLIYNVKIRGVNFTSNG
PVMQKKTLGWEAFTETLYPADGGLEGRNDMALKLVGGSHLIANIK
TTYRSKKPAKNLKMPGVYYVDYRLERIKEANNETYVEQHEVAVAR
YCDLPSKLGHKLN*

SEQ ID NO: 205, Nucleic Acid-
TAATACGACTCACTATAGGGAGACCCAAGCTGGctagaggatcga
acccttaaggccaccatgGCGAGCAATTTTACCCAGTTTGTGCTT
GTGGACAACGGCGGCACCGGGGACGTGACGGTGGCCCCCTCCAAT
TTTGCCAATGGCATTGCAGAATGGATAAGCTCTAACAGCAGGAGC
CAGGCATACAAGGTGACCTGCAGCGTGAGGCAGTCAAGCGCTCAA
AACAGGAAGTACACCATTAAGGTCGAAGTGCCCAAAGGAGCTTGG
AGGTCTTACCTGAACATGGAACTGACAATTCCTATCTTCGCGACC
AATAGCGACTGTGAGCTGATCGTGAAGGCCATGCAAGGCCTGCTG
AAAGACGGGAATCCCATACCCAGCGCCATCGCCGCTAACTCAGGC
ATTTACGCTAATTTCACTCAGTTCGTACTGGTTGACAATGGGGGA
ACCGGCGACGTTACCGTGGCTCCAAGCAACTTCGCTAACGGGATC
GCCGAGTGGATCAGCAGTAATTCACGCTCCCAAGCCTACAAAGTA
ACCTGCTCTGTACGGCAGAGTTCAGCCCAGAACCGAAAGTATACC
ATCAAAGTGGAGGTGCCGAAGGGCGCCTGGCGGAGCTATCTGAAT
ATGGAGCTGACCATCCCCATCTTTGCCACGAACAGCGATTGCGAG
CTCATCGTCAAGGCGATGCAGGGCTTGCTGAAGGATGGCAACCCT
ATCCCGAGCGCAATAGCAGCCAACAGCGGCATCTATgggggcagt gggagcggtgcaggatctggtagtccagctgggggaggagcaccg
ggtagcggtggggggtctcagctgcacctgccccaggttctcgca
gacgccgtatcccgccttgtactgggcaagtttggtgatcttact
gacaatttttcatctcctcatgcgaggcggaaagtactcgcaggc
gtcgtcatgacgaccggaactgacgtgaaagacgccaaagtcatc
tctgtctccacgggcacaaagtgcataaacggggagtacatgagc
gaccgggggctggcactgaatgattgtcacgctgaaataatatct
aggcgatctctgcttagatttctctacactcaactcgaattgtac
cttaacaacaaagatgaccagaaacgcagtatatttcagaaatca
gaacgcggcggatttcgacttaaggaaaacgttcagttccacttg
tatatcagcacatccccttgcggtgacgcccgaatcttttccccg
cacgagccgatattggaggagcccgcgTCGTCCGgtggagaactt
gatgaattggtatacttactagatgggccaggttatgaccctata
catTGCGATGTAGTGACAAGGGGCGGCAGCCACCTTTTCAATTTT
GACagacatcctaataggaaggctagaggccaacttcggacgaag
attgaaagtggccagggtactatcccggtgcggtccaacgctagt
attcaaacgtgggacggagtccttcaaggtgaacggctgttgaca
atgagctgctcagacaaaatcgcgcgctggaatgtagtgggaatc
caaggcagcctcttgagcatattcgtagaacccatatatttctca
tccattattttgggctctctgtatcatggtgaccatctgtcaagg
gctatgtaccaacgaatttctaatatcgaggatcttcctccactc
tatacactcaataagcctctcttgtccgggatatcaaacgctgag
gcccgccagccagggaaagctcctaacttcagtgttaactggacc
gttggtgattctgcgatagaggtcatcaacgccacgacaggtaag
gatgagctcggtagagcctcacgcctgtgtaaacacgcgttgtat
tgtagatggatgagagtacatgggaaggtcccatctcacttgctc
cgaagcaagatcactaagcctaatgtgtatcatgagtcaaaactc
gcggctaaagaataccaggcagccaaagctcgactttttacagct
tttattaaggcagggctcggggcatgggtcgagaagccgaccgag
caggaccaattctctctgacggggagcggatccAGCGAGCTGATT
AAGGAGAACATGCACATGAAGCTGTACATGGAGGGCACCGTGGAC
AACCATCACTTCAAGTGCACATCCGAGGGCGAAGGCAAGCCCTAC
GAGGGCACCCAGACCATGAGAATCAAGGTGGTCGAGGGCGGCCCT
CTCCCCTTCGCCTTCGACATCCTGGCTACTAGCTTCCTCTACGGC
AGCAAGACCTTCATCAACCACACCCAGGGCATCCCCGACTTCTTC
AAGCAGTCCTTCCCTGAGGGCTTCACATGGGAGAGAGTCACCACA
TACGAAGACGGGGGCGTGCTGACCGCTACCCAGGACACCAGCCTC
CAGGACGGCTGCCTCATCTACAACGTCAAGATCAGAGGGGTGAAC
TTCACATCCAACGGCCCTGTGATGCAGAAGAAAACACTCGGCTGG
GAGGCCTTCACCGAGACGCTGTACCCCGCTGACGGCGGCCTGGAA
GGCAGAAACGACATGGCCCTGAAGCTCGTGGGCGGGAGCCATCTG -continued

ATCGCAAACATCAAGACCACATATAGATCCAAGAAACCCGCTAAG

AACCTCAAGATGCCTGGCGTCTACTATGTGGACTACAGACTGGAA

AGAATCAAGGAGGCCAACAACGAGACCTACGTCGAGCAGCACGAG

GTGGCAGTGGCCAGATACTGCGACCTCCCTAGCAAACTGGGGCAC

AAGCTTAATtAAGGGCCCGTTTAAACCCGCTGATCAGCCTCGACT

GTGCCTTCTA

SEQ ID NO: 206, tdMCP_ADAR2-DDN-CP5-46-4D5E ADAR2-DDC(E488Q)_NS4A/NS3 (Genotype 1B)_mTagBFP (see e.g., FIG. 21E)
MASNFTQFVLVDNGGTGDVTVAPSNFANGIAEWISSNSRSQAYKV

TCSVRQSSAQNRKYTIKVEVPKGAWRSYLNMELTIPIFATNSDCE

LIVKAMQGLLKDGNPIPSAIAANSGIYANFTQFVLVDNGGTGDVT

VAPSNFANGIAEWISSNSRSQAYKVTCSVRQSSAQNRKYTIKVEV

PKGAWRSYLNMELTIPIFATNSDCELIVKAMQGLLKDGNPIPSAI

AANSGIYGGSGSGAGSGSPAGGGAPGSGGGSQLHLPQVLADAVSR

LVLGKFGDLTDNFSSPHARRKVLAGVVMTTGTDVKDAKVISVSTG

TKCINGEYMSDRGLALNDCHAEIISRRSLLRFLYTQLELYLNNKD

DQKRSIFQKSERGGFRLKENVQFHLYISTSPCGDARIFSPHEPIL

EEPASSGGELDELVYLLDGPGYDPIHCDVVTRGGSHLFNFDRHPN

RKARGQLRTKIESGQGTIPVRSNASIQTWDGVLQGERLLTMSCSD

KIARWNVVGIQGSLLSIFVEPIYFSSIILGSLYHGDHLSRAMYQR

ISNIEDLPPLYTLNKPLLSGISNAEARQPGKAPNFSVNWTVGDSA

IEVINATTGKDELGRASRLCKHALYCRWMRVHGKVPSHLLRSKIT

KPNVYHESKLAAKEYQAAKARLFTAFIKAGLGAWVEKPTEQDQFS

LTGSAAGGSGGSAAAQGSVVIVGRIILSGSGSITAYSQQTRGLLG

CIITSLTGRDKNQVEGEVQVVSTATQSFLATCVNGVCWTVYHGAG

SKTLAGPKGPITQMYTNVDQDLVGWQAPPGARSLTPCTCGSSDLY

LVTRHADVIPVRRRGDSRGSLLSPRPVSYLKGSSGGPLLCPSGHA

VGIFRAAVCTRGVAKAVDFVPVESMETTMRSESGSGTMSELIKEN

MHMKLYMEGTVDNHHFKCTSEGEGKPYEGTQTMRIKVVEGGPLPF

AFDILATSFLYGSKTFINHTQGIPDFFKQSFPEGFTWERVTTYED

GGVLTATQDTSLQDGCLIYNVKIRGVNFTSNGPVMQKKTLGWEAF

TETLYPADGGLEGRNDMALKLVGGSHLIANIKTTYRSKKPAKNLK

MPGVYYVDYRLERIKEANNETYVEQHEVAVARYCDLPSKLGHKLN

*

SEQ ID NO: 207,
TAATACGACTCACTATAGGGAGACCCAAGCTGGctagaggatcga acccttaaggccaccatgGCGAGCAATTTTACCCAGTTTGTGCTT

GTGGACAACGGCGGCACCGGGGACGTGACGGTGGCCCCCTCCAAT

TTTGCCAATGGCATTGCAGAATGGATAAGCTCTAACAGCAGGAGC

CAGGCATACAAGGTGACCTGCAGCGTGAGGCAGTCAAGCGCTCAA

AACAGGAAGTACACCATTAAGGTCGAAGTGCCCAAAGGAGCTTGG

-continued

AGGTCTTACCTGAACATGGAACTGACAATTCCTATCTTCGCGACC

AATAGCGACTGTGAGCTGATCGTGAAGGCCATGCAAGGCCTGCTG

AAAGACGGGAATCCCATACCCAGCGCCATCGCCGCTAACTCAGGC

ATTTACGCTAATTTCACTCAGTTCGTACTGGTTGACAATGGGGGA

ACCGGCGACGTTACCGTGGCTCCAAGCAACTTCGCTAACGGGATC

GCCGAGTGGATCAGCAGTAATTCACGCTCCCAAGCCTACAAAGTA

ACCTGCTCTGTACGGCAGAGTTCAGCCCAGAACCGAAAGTATACC

ATCAAAGTGGAGGTGCCGAAGGGCGCCTGGCGGAGCTATCTGAAT

ATGGAGCTGACCATCCCCATCTTTGCCACGAACAGCGATTGCGAG

CTCATCGTCAAGGCGATGCAGGGCTTGCTGAAGGATGGCAACCCT

ATCCCGAGCGCAATAGCAGCCAACAGCGGCATCTATgggggcagt gggagcggtgcaggatctggtagtccagctgggggaggagcaccg ggtagcggtggggggtctcagctgcacctgccccaggttctcgca gacgccgtatcccgccttgtactgggcaagtttggtgatcttact gacaatttttcatctcctcatgcgaggcggaaagtactcgcaggc gtcgtcatgacgaccggaactgacgtgaaagacgccaaagtcatc tctgtctccacgggcacaaagtgcataaacggggagtacatgagc gaccgggggctggcactgaatgattgtcacgctgaaataatatct aggcgatctctgcttagatttctctacactcaactcgaattgtac cttaacaacaaagatgaccagaaacgcagtatatttcagaaatca gaacgcggcggatttcgacttaaggaaaacgttcagttccacttg tatatcagcacatccccttgcggtgacgcccgaatcttttccccg cacgagccgatattggaggagcccgcgTCGTCCGGtggagaactt gatgaattggtatacttactagatgggccaggttatgaccctata catTGCGATGTAGTGACAAGGGGCGGCAGCCACCTTTTCAATTTT GACagacatcctaataggaaggctagaggccaacttcggacgaag attgaaagtggccagggtactatcccggtgcggtccaacgctagt attcaaacgtgggacggagtccttcaaggtgaacggctgttgaca atgagctgctcagacaaaatcgcgcgctggaatgtagtgggaatc caaggcagcctcttgagcatattcgtagaacccatatatttctca tccattattttgggctctctgtatcatggtgaccatctgtcaagg gctatgtaccaacgaatttctaatatcgaggatcttcctccactc tatacactcaataagcctctcttgtccgggatatcaaacgctgag gcccgccagccagggaaagctcctaacttcagtgttaactggacc gttggtgattctgcgatagaggtcatcaacgccacgacaggtaag gatgagctcggtagagcctcacgcctgtgtaaacacgcgttgtat tgtagatggatgagagtacatgggaaggtcccatctcacttgctc cgaagcaagatcactaagcctaatgtgtatcatgagtcaaaactc gcggctaaagaataccaggcagccaaagctcgactttttacagct tttattaaggcagggctcggggcatgggtcgagaagccgaccgag caggaccaattctctctgacggggagcGCGGCCGGAGGTAGCGGC -continued GGAAGCGCGGCCGCTcaggggtctgttgttattgttggtagaatt attttatctggtagtggtagtatcacggcctactcccaacagacg cggggcctacttggttgcatcatcactagcctcacaggccgggac aagaaccaggtcgaaggggaggttcaagtggtttctaccgcaaca caatctttcctggcgacctgcgtcaacggcgtgtgctggactgtc taccatggcgctggctcgaagaccctagccggtccaaaaggtcca atcacccaaatgtacaccaatgtagaccaggacctcgtcggctgg caggcgcctccaggggcgcgctccttgacaccatgcacctgtggc agctcggacctttacttggtcacgagacatgctgatgtcattccg gtgcgccggcgaggcgacagcaggggaagtctactctcccccagg cccgtctcctacctgaaaggctccTCAggtggtccattgctttgc ccttcggggcacgctgtgggcatcttccgggctgctgtgtgcacc cggggggtcgcgaaggcggtggacttcgtgcccgttgagtctatg gaaactaccatgcggtctGAGAGTGGATCAGGTACCATGAGCGAG

CTGATTAAGGAGAACATGCACATGAAGCTGTACATGGAGGGCACC

GTGAACAACCATCACTTCAAGTGCACATCCGAGGGCGAAGGCAAG

CCCTACGAGGGCACCCAGACCATGAGAATCAAGGTGGTCGAGGGC

GGCCCTCTCCCCTTCGCCTTCGACATCCTGGCTACTAGCTTCCTC

TACGGCAGCAAGACCTTCATCAACCACACCCAGGGCATCCCCGAC

TTCTTCAAGCAGTCCTTCCCTGAGGGCTTCACATGGGAGAGAGTC

ACCACATACGAAGACGGGGGCGTGCTGACCGCTACCCAGGACACC

AGCCTCCAGGACGGCTGCCTCATCTACAACGTCAAGATCAGAGGG

GTGAACTTCACATCCAACGGCCCTGTGATGCAGAAGAAAACACTC

GGCTGGGAGGCCTTCACCGAGACGCTGTACCCCGCTGACGGCGGC

CTGGAAGGCAGAAACGACATGGCCCTGAAGCTCGTGGGCGGGAGC

CATCTGATCGCAAACATCAAGACCACATATAGATCCAAGAAACCC

GCTAAGAACCTCAAGATGCCTGGCGTCTACTATGTGGACTACAGA

CTGGAAAGAATCAAGGAGGCCAACAACGAGACCTACGTCGAGCAG

CACGAGGTGGCAGTGGCCAGATACTGCGACCTCCCTAGCAAACTG

GGGCACAAGCTTAATTtAAGGGCCCGTTTAAACCCGCTGATCAGC

CTCGACTGTGCCTTCTA

Example 18: Transfection of In Vitro Transcribed mRNA

Figure 61A:
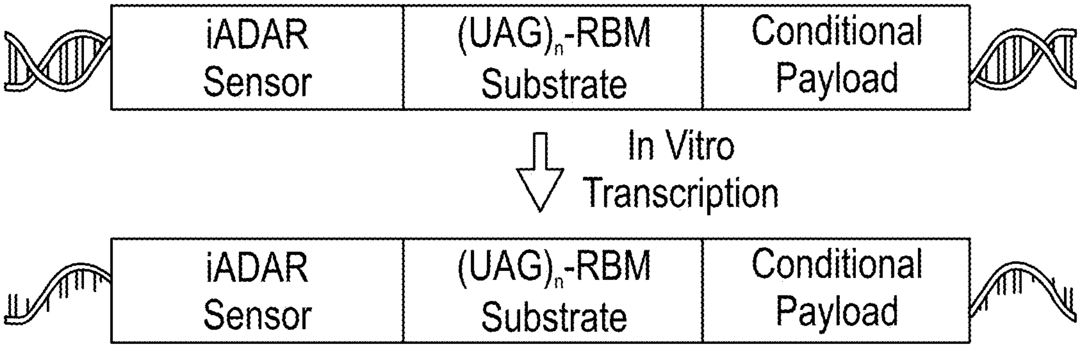
FIG. 61A-61C—In vitro transcribed iADAR sensors can be directly delivered to cells.
Figure 61B:
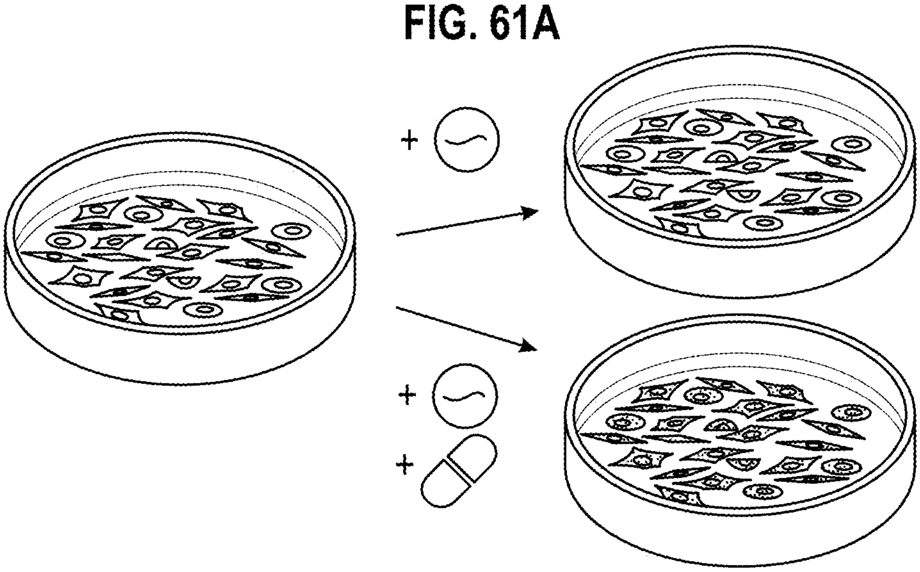

This example shows that constructs encoding an iADAR sensor and substrate on the same mRNA (see e.g., FIG. 61A) can be transcribed in vitro and delivered to cells as a single mRNA construct. To test this, iADAR constructs were cloned that contained the catalytically inactive ADAR2-DD (dADAR), constitutively active ADAR2-DD (ADAR), or conditionally active ADAR2-DD that is dependent on the addition of Bel inhibitor A-1331852 (BAD(V)) upstream of editable stop codons and an mNeonGreen fluorescent protein (see e.g., FIG. 61A). In this case, the dADAR and ADAR constructs serve as negative and positive controls respectively. For the BAD(V) construct, cells only express mNeonGreen if A-1331852 is present during the transfection (see e.g., FIG. 61B).

To test this, the 3' end of the plasmid was subsequently digested using PmeI, a DNA clean-up was performed, ARCA-capped mRNA was transcribed with T7 polymerase, the remaining DNA were digested with DNAse I, and a poly-A tail was added with *E. coli* Poly(A) Polymerase (all reagents and protocols from NEW ENGLAND BIO's HiScribe® T7 ARCA mRNA Kit (with tailing)). 70,000 HEK293FT cells were then transfected in suspension with 100 ng of each mRNA construct using Lipofectamine™ MessengerMAX™ Transfection Reagent. Cells were also treated with either DMSO or 1 μM of A-1331852. ~48 hours after transfection, cells were analyzed by flow cytometry. mNeonGreen positive cells were determined as greater than the top 1% of gated non-transfected HEK cells (NT).

Figure 61C:
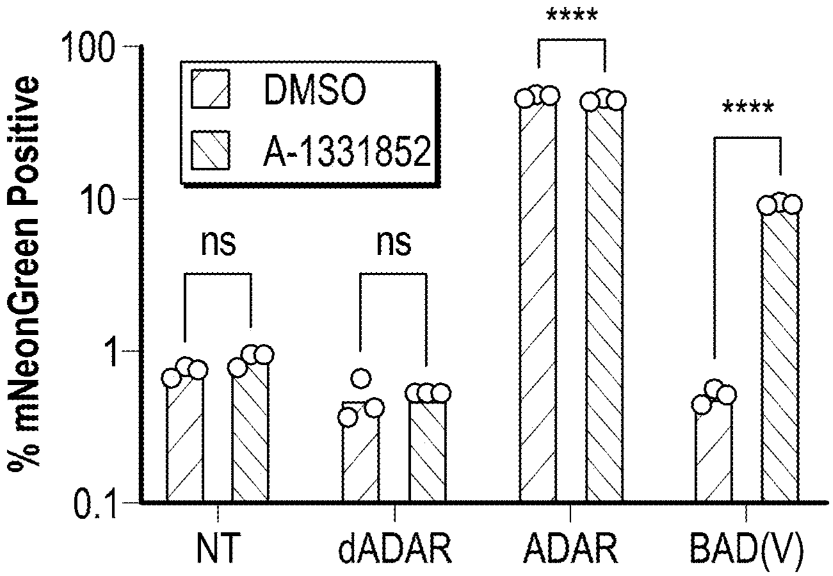

There was an insignificant population of m NeonGreen positive cells for the non-transfected cells (NT) or dADAR negative control, and a significant population of mNeonGreen positive cells for the active ADAR case (see e.g., FIG. 61C). The extent of mNeonGreen positive cells for the BAD(V) construct was dependent on the presence of A-1331852 (see e.g., FIG. 61C), with an increase of ~18× when A-1331852 was present.

Combined, these data demonstrate that the iADAR system is compatible with a delivery system where in-vitro transcribed mRNA is delivered directly to cells.

DNA Sequences

SEQ ID NO: 390, MCP_ADAR2-DD(E396A & E488Q)_mCherry_FLAG_P2A_T2A_loop(UAG-UAG)_MS2(C)_HaloTag_loop(UAG-UAG)_MS2(C)_P2A_T2A HA_mNeonGreen(M10K)

TAATACGACTCACTATAGGGAGACCCAAGCTGGctagaggatcga acccttaaggccaccatggcgtccaatttcactcagtttgtgctg gttgacaacggcgggaccggggacgttacggtagccccctcaaac tttgccaacggtatagcggagtggataagcagcaattctaggagt caagcatacaaagttacatgcagcgtgcgccaatctagcgctcag aatcgcaagtacaccattaaagtagaggtccccaagggagcctgg agaagctatcttaacatggagttgaccataccaatcttcgctacc aactctgactgtgaactcattgtgaaagccatgcaaggtctgctc aaggatggtaacccaattccgtccgctatcgctgccaactctggg atttacgggggcagtgggagcggtgcaggatctggtagtccagct gggggaggagcaccgggtagcggtgggggtctcagctgcacctg ccccaggttctcgcagacgccgtatcccgccttgtactgggcaag tttggtgatcttactgacaatttttcatctcctcatgcgaggcgg aaagtactcgcaggcgtcgtcatgacgaccggaactgacgtgaaa gacgccaaagtcatctctgtctccacgggcacaaagtgcataaac ggggagtacatgagcgaccgggggctggcactgaatgattgtcac gctGCCataatatctaggcgatctctgcttagatttctctacact caactcgaattgtaccttaacaacaaagatgaccagaaacgcagt atatttcagaaatcagaacgcggcggatttcgacttaaggaaaac -continued gttcagttccacttgtatatcagcacatccccttgcggtgacgcc cgaatcttttccccgcacgagccgatattggaggagcccgcggac agacatcctaataggaaggctagaggccaacttcggacgaagatt gaaagtggccagggtactatcccggtgcggtccaacgctagtatt caaacgtgggacggagtccttcaaggtgaacggctgttgacaatg agctgctcagacaaaatcgcgcgctggaatgtagtgggaatccaa ggcagcctcttgagcatattcgtagaacccatatatttctcatcc attattttgggctctctgtatcatggtgaccatctgtcaagggct atgtaccaacgaatttctaatatcgaggatcttcctccactctat acactcaataagcctctcttgtccgggatatcaaacgctgaggcc cgccagccagggaaagctcctaacttcagtgttaactggaccgtt ggtgattctgcgatagaggtcatcaacgccacgacaggtaaggat gagctcggtagagcctcacgcctgtgtaaacacgcgttgtattgt agatggatgagagtacatgggaaggtcccatctcacttgctccga agcaagatcactaagcctaatgtgtatcatgagtcaaaactcgcg gctaaagaataccaggcagccaaagctcgactttttacagctttt attaaggcagggctcggggcatgggtcgagaagccgaccgagcag gaccaattctctctgacggggagcggatccAGCGAGCTGATTAAG GAGAACATGCACATGAAGCGCCCatcggtcgccaccatggtgagc aagggcgaggaggataacatggccatcatcaaggagttcatgcgc ttcaaggtgcacatggagggctccgtgaacggccacgagttcgag atcgagggcgagggcgagggccgcccctacgagggcacccagacc gccaagctgaaggtgaccaagggtggccccctgcccttcgcctgg gacatcctgtcccctcagttcatgtacggctccaaggcctacgtg aagcaccccgccgacatccccgactacttgaagctgtccttcccc gagggcttcaagtgggagcgcgtgatgaacttcgaggacggcggc gtggtgaccgtgacccaggactcctccctgcaggacggcgagttc atctacaaggtgaagctgcgcggcaccaacttcccctccgacggc cccgtaatgcagaagaagaccatgggctgggaggcctcctccgag cggatgtaccccgaggacggcgccctgaagggcgagatcaagcag aggctgaagctgaaggacggcggccactacgacgctgaggtcaag accacctacaaggccaagaagcccgtgcagctgcccggcgcctac aacgtcaacatcaagttggacatcacctcccacaacgaggactac accatcgtggaacagtacgaacgcgccgagggccgccactccacc ggcggcatggacgagctgTACaaggattacaaggatgacgatga caaaGGTAGCGGGGCAACTAATTTTAGCTTACTCAAACAGGCTGG

GGACGTCGAGGAGAATCCAGGCCCTGCATCCGCTGGCTCTGGAGA

AGGACGAGGCTCCTTGCTCACCTGTGGAGATGTCGAAGAGAACCC

AGGTCCTGCAACCGGGAATTCCGCGTAGCGCTAGCTTTGCCAGCG

CCACGCGaaACATGAGGATcACCCATGTGCCGCTATGGCAGAAAT

CGGTACTGGCTTTCCATTCGACCCCCATTATGTGGAAGTCCTGGG

CGAGCGCATGCACTACGTCGATGTTGGTCCGCGCGATGGCACCCC

TGTGCTGTTCCTGCACGGTAACCCGACCTCCTCCTACGTGTGGCG

CAACATCATCCCGCATGTTGCACCGACCCATCGCTGCATTGCTCC

AGACCTGATCGGTATGGGCAAATCCGACAAACCAGACCTGGGTTA

TTTCTTCGACGACCACGTCCGCTTCATGGATGCCTTCATCGAAGC

CCTGGGTCTGGAAGAGGTCGTCCTGGTCATTCACGACTGGGGCTC

CGCTCTGGGTTTCCACTGGGCCAAGCGCAATCCAGAGCGCGTCAA

AGGTATTGCATTTATGGAGTTCATCCGCCCTATCCCGACCTGGGA

CGAATGGCCAGAATTTGCCCGCGAGACCTTCCAGGCCTTCCGCAC

CACCGACGTCGGCCGCAAGCTGATCATCGATCAGAACGTTTTTAT

CGAGGGTACGCTGCCGATGGGTGTCGTCCGCCCGCTGACTGAAGT

CGAGATGGACCATTACCGCGAGCCGTTCCTGAATCCTGTTGACCG

CGAGCCACTGTGGCGCTTCCCAAACGAGCTGCCAATCGCCGGTGA

GCCAGCGAACATCGTCGCGCTGGTCGAAGAATACATGGACTGGCT

GCACCAGTCCCCTGTCCCGAAGCTGCTGTTCTGGGGCACCCCAGG

CGTTCTGATCCCACCGGCCGAAGCCGCTCGCCTGGCCAAAAGCCT

GCCTAACTGCAAGGCTGTGGACATCGGCCCGGGTCTGAATCTGCT

GCAAGAAGACAACCCGGACCTGATCGGCAGCGAGATCGCGCGCTG

GCTGTCGACGCTCGAGATTTCTGGCACCGGTATGGCATCTATGAC

TGGAGGCCAACAGATGgGTCCTGCAACCGGGAATTCCGCGTAGCG

CTAGCTTTGCCAGCGCCACGCGaaACATGAGGATcACCCATGTAC

TAGTGCCACAAACTTCTCTCTGCTAAAGCAAGCAGGTGATGTTGA

AGAAAACCCAGGGCCTGGAGGGTCCGAGGGCAGGGGAAGTCTCCT

AACATGCGGGGACGTGGAGGAAAATCCCGGCCCATCCGGATATCC

CTACGATGTGCCCGATTACGCTATCGATgtgagcaagggcgaAga

AgataacaAggcctctctcccagcgacacatgagttacacatctt tggctccatcaacggtgtggactttgacatggtgggtcagggcac cggcaatccaaatgatggttatgaggagttaaacctgaagtccac caagggtgacctccagttctcccccctggattctggtccctcatat cgggtatggcttccatcagtacctgccctaccctgacgggatgtc gcctttccaggccgccatggtagatggcAGCggataccaagtcca tcgcacaatgcagtttgaagatggtgcctcccttactgttaacta ccgctacacctacgagggaagccacatcaaaggagaggcccaggt gaaggggactggtttccctgctgacggtcctgtgatgaccaactc gctgaccgctgcggactggtgcaggtcgaagaagacttaccccaa cgacaaaaccatcatcagtacctttaagtggagttacaccactgg aaatggcaagAGAtaccggagcactgcgcggaccacctacacctt tgccaagccaatggcggctaactatctgaagaaccagccgatgta cgtgttccgtaagacggagctcaagcactccaagaccgagctcaa cttcaaggagtggcaaaaggcctttaccgatgtgatgGGAatgga -continued cGAGCTGTATaagGCTAGCTAAGCGGCCGCTCGAGTCTAGAGGGC

CCGCGGTTCGAAGGTAAGCCTATCCCTAACCCTCTCCTCGGTCTC

GATTCTACGCGTACCGGTCATCATCACCATCACCATTGAGTTTAA

ACCCGCTGATCAGCCTCGACTGTGCCTTCTA

SEQ ID NO: 391, MCP_ADAR2-DD (E488Q)_mCherry_FLAG_P2A_T2A_loop(UAG-UAG)_MS2(C)_HaloTag_loop(UAG-UAG)_MS2(C)_P2A_T2A_HA_mNeonGreen(M10K)
TAATACGACTCACTATAGGGAGACCCAAGCTGGctagaggatcga acccttaaggccaccatggcgtccaatttcactcagtttgtgctg gttgacaacggcgggaccggggacgttacggtagcccccctcaaac tttgccaacggtatagcggagtggataagcagcaattctaggagt caagcatacaaagttacatgcagcgtgcgccaatctagcgctcag aatcgcaagtacaccattaaagtagaggtccccaagggagcctgg agaagctatcttaacatggagttgaccataccaatcttcgctacc aactctgactgtgaactcattgtgaaagccatgcaaggtctgctc aaggatggtaacccaattccgtccgctatcgctgccaactctggg atttacgggggcagtgggagcggtgcaggatctggtagtccagct gggggaggagcaccgggtagcggtggggggtctcagctgcacctg ccccaggttctcgcagacgccgtatcccgccttgtactgggcaag tttggtgatcttactgacaatttttcatctcctcatgcgaggcgg aaagtactcgcaggcgtcgtcatgacgaccggaactgacgtgaaa gacgccaaagtcatctctgtctccacgggcacaaagtgcataaac ggggagtacatgagcgaccgggggctggcactgaatgattgtcac gctgaaataatatctaggcgatctctgcttagatttctctacact caactcgaattgtaccttaacaacaaagatgaccagaaacgcagt atatttcagaaatcagaacgcggcggatttcgacttaaggaaaac gttcagttccacttgtatatcagcacatccccttgcggtgacgcc cgaatcttttccccgcacgagccgatattggaggagcccgcggac agacatcctaataggaaggctagaggccaacttcggacgaagatt gaaagtggccagggtactatcccggtgcggtccaacgctagtatt caaacgtgggacggagtccttcaaggtgaacggctgttgacaatg agctgctcagacaaaatcgcgcgctggaatgtagtgggaatccaa ggcagcctcttgagcatattcgtagaacccatatatttctcatcc attattttgggctctctgtatcatggtgaccatctgtcaagggct atgtaccaacgaatttctaatatcgaggatcttcctccactctat acactcaataagcctctcttgtccgggatatcaaacgctgaggcc cgccagccagggaaagctcctaacttcagtgttaactggaccgtt ggtgattctgcgatagaggtcatcaacgccacgacaggtaaggat gagctcggtagagcctcacgcctgtgtaaacacgcgttgtattgt agatggatgagagtacatgggaaggtcccatctcacttgctccga agcaagatcactaagcctaatgtgtatcatgagtcaaaactcgcg -continued gctaaagaataccaggcagccaaagctcgactttttacagctttt attaaggcagggctcggggcatgggtcgagaagccgaccgagcag gaccaattctctctgacggggagcggatccAGCGAGCTGATTAAG GAGAACATGCACATGAAGCGCCCatcggtcgccaccatggtgagc aagggcgaggaggataacatggccatcatcaaggagttcatgcgc ttcaaggtgcacatggagggctccgtgaacggccacgagttcgag atcgagggcgagggcgagggccgcccctacgagggcacccagacc gccaagctgaaggtgaccaagggtggcccccctgcccttcgcctgg gacatcctgtcccctcagttcatgtacggctccaaggcctacgtg aagcaccccgccgacatccccgactacttgaagctgtccttcccc gagggcttcaagtgggagcgcgtgatgaacttcgaggacggcggc gtggtgaccgtgacccaggactcctccctgcaggacggcgagttc atctacaaggtgaagctgcgcggcaccaacttcccctccgacggc cccgtaatgcagaagaagaccatgggctgggaggcctcctccgag cggatgtaccccgaggacggcgccctgaagggcgagatcaagcag aggctgaagctgaaggacggcggccactacgacgctgaggtcaag accacctacaaggccaagaagcccgtgcagctgcccggcgcctac aacgtcaacatcaagttggacatcacctcccacaacgaggactac accatcgtggaacagtacgaacgcgccgagggccgccactccacc ggcggcatggacgagctgTACaaggattacaaggatgacgatga caaaGGTAGCGGGGCAACTAATTTTAGCTTACTCAAACAGGCTGG

GGACGTCGAGGAGAATCCAGGCCCTGCATCCGCTGGCTCTGGAGA

AGGACGAGGCTCCTTGCTCACCTGTGGAGATGTCGAAGAGAACCC

AGGTCCTGCAACCGGGAATTCCGCGTAGCGCTAGCTTTGCCAGCG

CCACGCGaaACATGAGGATcACCCATGTGCCGCTATGGCAGAAAT

CGGTACTGGCTTTCCATTCGACCCCCATTATGTGGAAGTCCTGGG

CGAGCGCATGCACTACGTCGATGTTGGTCCGCGCGATGGCACCCC

TGTGCTGTTCCTGCACGGTAACCCGACCTCCTCCTACGTGTGGCG

CAACATCATCCCGCATGTTGCACCGACCCATCGCTGCATTGCTCC

AGACCTGATCGGTATGGGCAAATCCGACAAACCAGACCTGGGTTA

TTTCTTCGACGACCACGTCCGCTTCATGGATGCCTTCATCGAAGC

CCTGGGTCTGGAAGAGGTCGTCCTGGTCATTCACGACTGGGGCTC

CGCTCTGGGTTTCCACTGGGCCAAGCGCAATCCAGAGCGCGTCAA

AGGTATTGCATTTATGGAGTTCATCCGCCCTATCCCGACCTGGGA

CGAATGGCCAGAATTTGCCCGCGAGACCTTCCAGGCCTTCCGCAC

CACCGACGTCGGCCGCAAGCTGATCATCGATCAGAACGTTTTTAT

CGAGGGTACGCTGCCGATGGGTGTCGTCCGCCCGCTGACTGAAGT

CGAGATGGACCATTACCGCGAGCCGTTCCTGAATCCTGTTGACCG

CGAGCCACTGTGGCGCTTCCCAAACGAGCTGCCAATCGCCGGTGA

GCCAGCGAACATCGTCGCGCTGGTCGAAGAATACATGGACTGGCT

GCACCAGTCCCCTGTCCCGAAGCTGCTGTTCTGGGGCACCCCAGG

-continued

CGTTCTGATCCCACCGGCCGAAGCCGCTCGCCTGGCCAAAAGCCT
GCCTAACTGCAAGGCTGTGGACATCGGCCCGGGTCTGAATCTGCT
GCAAGAAGACAACCCGGACCTGATCGGCAGCGAGATCGCGCGCTG
GCTGTCGACGCTCGAGATTTCTGGCACCGGTATGGCATCTATGAC
TGGAGGCCAACAGATGgGTCCTGCAACCGGGAATTCCGCGTAGCG
CTAGCTTTGCCAGCGCCACGCGaaACATGAGGATcACCCATGTAC
TAGTGCCACAAACTTCTCTCTGCTAAAGCAAGCAGGTGATGTTGA
AGAAAACCCAGGGCCTGGAGGGTCCGAGGGCAGGGGAAGTCTCCT
AACATGCGGGGACGTGGAGGAAAATCCCGGCCCATCCGGATATCC
CTACGATGTGCCCGATTACGCTATCGATgtgagcaagggcgaAga
AgataacaAggcctctctcccagcgacacatgagttacacatctt
tggctccatcaacggtgtggactttgacatggtgggtcagggcac
cggcaatccaaatgatggttatgaggagttaaacctgaagtccac
caagggtgacctccagttctccccctggattctggtccctcatat
cgggtatggcttccatcagtacctgccctaccctgacgggatgtc
gcctttccaggccgccatggtagatggcAGCggataccaagtcca
tcgcacaatgcagtttgaagatggtgcctcccttactgttaacta
ccgctacacctacgagggaagccacatcaaaggagaggcccaggt
gaaggggactggtttccctgctgacggtcctgtgatgaccaactc
gctgaccgctgcggactggtgcaggtcgaagaagacttaccccaa
cgacaaaaccatcatcagtacctttaagtggagttacaccactgg
aaatggcaagAGAtaccggagcactgcgcggaccacctacacctt
tgccaagccaatggggctaactatctgaagaaccagccgatgtac
gtgtttccgtaagacggagctcaagcactccaagaccgagctcaac
ttcaaggagtggcaaaaggcctttaccgatgtgatgGGAatggac
GAGCTGTATaagGCTAGCTAAGCGGCCGCTCGAGTCTAGAGGGCC
CGCGGTTCGAAGGTAAGCCTATCCCTAACCCTCTCCTCGGTCTCG
ATTCTACGCGTACCGGTCATCATCACCATCACCATTGAGTTTAAA
CCCGCTGATCAGCCTCGACTGTGCCTTCTA SEQ ID NO: 392, MCP_ADAR2-DDN_BAD (V)_ADAR2-DDC(E488Q & K672R)_Bcl-xL_mCherry_FLAG_P2A_T2A_loop(UAG-UAG)_MS2(C)_HaloTag_loop(UAG-UAG)_MS2(C)_P2A_T2A HA_mNeonGreen(M10K)
TAATACGACTCACTATAGGGAGACCCAAGCTGGctagaggatcga
acccttaaggccaccatggcgtccaatttcactcagtttgtgctg
gttgacaacggcgggaccggggacgttacggtagccccctcaaac
tttgccaacggtatagcggagtggataagcagcaattctaggagt
caagcatacaaagttacatgcagcgtgcgccaatctagcgctcag
aatcgcaagtacaccattaaagtagaggtccccaagggagcctgg
agaagctatcttaacatggagttgaccataccaatcttcgctacc
aactctgactgtgaactcattgtgaaagccatgcaaggtctgctc
aaggatggtaacccaattccgtccgctatcgctgccaactctggg
atttacgggggcagtgggagcggtgcaggatctggtagtccagct
gggggaggagcaccgggtagcggtggggggtctcagctgcacctg
ccccaggttctcgcagacgccgtatcccgccttgtactgggcaag
tttggtgatcttactgacaatttttcatctcctcatgcgaggcgg
aaagtactcgcaggcgtcgtcatgacgaccggaactgacgtgaaa
gacgccaaagtcatctctgtctccacgggcacaaagtgcataaac
ggggagtacatgagcgaccgggggctggcactgaatgattgtcac
gctgaaataatatctaggcgatctctgcttagatttctctacact
caactcgaattgtaccttaacaacaaagatgaccagaaacgcagt
atatttcagaaatcagaacgcggcggatttcgacttaaggaaaac
gttcagttccacttgtatatcagcacatccccttgcggtgacgcc
cgaatcttttccccgcacgagccgatattggaggagcccgcgGCT
AGCGGGTCGGGCACCGGTGCTCCACCCAATCTCTGGGCAGCGCAG
CGCTACGGCCGTGAGCTCAGAAGGATGTCCGATGAGGTGGTCGAC
agacatcctaataggaaggctagaggccaacttcggacgaagatt
gaaagtggccagggtactatcccggtgcggtccaacgctagtatt
caaacgtgggacggagtccttcaaggtgaacggctgttgacaatg
agctgctcagacaaaatcgcgcgctggaatgtagtgggaatccaa
ggcagcctcttgagcatattcgtagaacccatatatttctcatcc
attattttgggctctctgtatcatggtgaccatctgtcaagggct
atgtaccaacgaatttctaatatcgaggatcttcctccactctat
acactcaataagcctctcttgtccgggatatcaaacgctgaggcc
cgccagccagggaaagctcctaacttcagtgttaactggaccgtt
ggtgattctgcgatagaggtcatcaacgccacgacaggtaaggat
gagctcggtagagcctcacgcctgtgtaaacacgcgttgtattgt
agatggatgagagtacatgggaaggtcccatctcacttgctccga
agcaagatcactaagcctaatgtgtatcatgagtcaaaactcgcg
gctaaagaataccaggcagccaGGctcgactttttacagctttt
attaaggcagggctcggggcatgggtcgagaagccgaccgagcag
gaccaattctctctgacggggagcGCGGCCGGAGGTAGCGGCGGA
AGCGCGGCCGCCTCAAGTAACCGGGAGCTGGTGGTTGACTTTCTC
TCCTACAAGCTTTCCCAGAAAGGATACAGCTGGAGTCAGTTTAGT
GATGTGGAAGAGAACAGGACTGAGGCCCCAGAAGGGACTGAATCG
GAGATGGAGACCCCCAGTGCCATCAATGGCAACCCATCCTGGCAC
CTGGCAGACAGCCCCGCGGTGAATGGAGCCACTGGCCACAGCAGC
AGTTTGGATGCCCGGGAGGTGATCCCCATGGCAGCAGTAAAGCAA
GCGCTGAGGGAGGCAGGCGACGAGTTTGAACTGCGGTACCGGCGG
GCATTCAGTGACCTGACATCCCAGCTCCACATCACCCCAGGGACA
GCATATCAGAGCTTTGAACAGGTAGTGAATGAACTCTTCCGGGAT
GGGGTAAACTGGGGTCGCATTGTGGCCTTTTTCTCCTTCGGCGGG -continued

GCACTGTGCGTGGAAAGCGTAGACAAGGAGATGCAGGTATTGGTG

AGTCGGATCGCAGCTTGGATGGCCACTTACCTGAATGACCACCTA

GAGCCTTGGATCCAGGAGAACGGCGGCTGGGATACTTTTGTGGAA

CTCTATGGGAACAATggatccAGCGAGCTGATTAAGGAGAACATG

CACATGAAGCGCCCatcggtcgccaccatggtgagcaagggcgag gaggataacatggccatcatcaaggagttcatgcgcttcaaggtg cacatggagggctccgtgaacggccacgagttcgagatcgagggc gagggcgagggccgcccctacgagggcacccagaccgccaagctg aaggtgaccaagggtggcccctgcccttcgcctgggacatcctg tcccctcagttcatgtacggctccaaggcctacgtgaagcacccc gccgacatccccgactacttgaagctgtccttccccgagggcttc aagtgggagcgcgtgatgaacttcgaggacggcggcgtggtgacc gtgacccaggactcctccctgcaggacggcgagttcatctacaag gtgaagctgcgcggcaccaacttcccctccgacggccccgtaatg cagaagaagaccatgggctgggaggcctcctccgagcggatgtac cccgaggacggcgccctgaagggcgagatcaagcagaggctgaag ctgaaggacggcggccactacgacgctgaggtcaagaccacctac aaggccaagaagcccgtgcagctgcccggcgcctacaacgtcaac atcaagttggacatcacctcccacaacgaggactacaccatcgtg gaacagtacgaacgcgccgagggccgccactccaccggcggcatg gacgagctgTACaaggattacaaggatgacgatgacaaaGGTAGC

GGGGCAACTAATTTTAGCTTACTCAAACAGGCTGGGGACGTCGAG

GAGAATCCAGGCCCTGCATCCGCTGGCTCTGGAGAAGGACGAGGC

TCCTTGCTCACCTGTGGAGATGTCGAAGAGAACCCAGGTCCTGCA

ACCGGGAATTCCGCGTAGCGCTAGCTTTGCCAGCGCCACGCGaaA

CATGAGGATcACCCATGTGCCGCTATGGCAGAAATCGGTACTGGC

TTTCCATTCGACCCCCATTATGTGGAAGTCCTGGGCGAGCGCATG

CACTACGTCGATGTTGGTCCGCGCGATGGCACCCCTGTGCTGTTC

CTGCACGGTAACCCGACCTCCTCCTACGTGTGGCGCAACATCATC

CCGCATGTTGCACCGACCCATCGCTGCATTGCTCCAGACCTGATC

GGTATGGGCAAATCCGACAAACCAGACCTGGGTTATTTCTTCGAC

GACCACGTCCGCTTCATGGATGCCTTCATCGAAGCCCTGGGTCTG

GAAGAGGTCGTCCTGGTCATTCACGACTGGGGCTCCGCTCTGGGT

TTCCACTGGGCCAAGCGCAATCCAGAGCGCGTCAAAGGTATTGCA

TTTATGGAGTTCATCCGCCCTATCCCGACCTGGGACGAATGGCCA

GAATTTGCCCGCGAGACCTTCCAGGCCTTCCGCACCACCGACGTC

GGCCGCAAGCTGATCATCGATCAGAACGTTTTTATCGAGGGTACG

CTGCCGATGGGTGTCGTCCGCCCGCTGACTGAAGTCGAGATGGAC

CATTACCGCGAGCCGTTCCTGAATCCTGTTGACCGCGAGCCACTG

TGGCGCTTCCCAAACGAGCTGCCAATCGCCGGTGAGCCAGCGAAC

ATCGTCGCGCTGGTCGAAGAATACATGGACTGGCTGCACCAGTCC

-continued

CCTGTCCCGAAGCTGCTGTTCTGGGGCACCCCAGGCGTTCTGATC

CCACCGGCCGAAGCCGCTCGCCTGGCCAAAAGCCTGCCTAACTGC

AAGGCTGTGGACATCGGCCCGGGTCTGAATCTGCTGCAAGAAGAC

AACCCGGACCTGATCGGCAGCGAGATCGCGCGCTGGCTGTCGACG

CTCGAGATTTCTGGCACCGGTATGGCATCTATGACTGGAGGCCAA

CAGATGgGTCCTGCAACCGGGAATTCCGCGTAGCGCTAGCTTTGC

CAGCGCCACGCGaaACATGAGGATcACCCATGTACTAGTGCCACA

AACTTCTCTCTGCTAAAGCAAGCAGGTGATGTTGAAGAAAACCCA

GGGCCTGGAGGGTCCGAGGGCAGGGGAAGTCTCCTAACATGCGGG

GACGTGGAGGAAAATCCCGGCCCATCCGGATATCCCTACGATGTG

CCCGATTACGCTATCGATgtgagcaagggcgaAgaAgataacaAg gcctctctcccagcgacacatgagttacacatctttggctccatc aacggtgtggactttgacatggtgggtcagggcaccggcaatcca aatgatggttatgaggagttaaacctgaagtccaccaagggtgac ctccagttctcccccctggattctggtccctcatatcgggtatggc ttccatcagtacctgccctaccctgacgggatgtcgcctttccag gccgccatggtagatggcAGCggataccaagtccatcgcacaatg cagtttgaagatggtgcctcccttactgttaactaccgctacacc tacgagggaagccacatcaaaggagaggcccaggtgaaggggact ggtttccctgctgacggtcctgtgatgaccaactcgctgaccgct gcggactggtgcaggtcgaagaagacttaccccaacgacaaaacc atcatcagtacctttaagtggagttacaccactggaaatggcaag AGAtaccggagcactgcgcggaccacctacacctttgccaagcca atggcggctaactatctgaagaaccagccgatgtacgtgttccgt aagacggagctcaagcactccaagaccgagctcaacttcaaggag tggcaaaaggcctttaccgatgtgatgGGAatggacGAGCTGTAT aagGCTAGCTAAGCGGCCGCTCGAGTCTAGAGGGCCCGCGGTTCG

AAGGTAAGCCTATCCCTAACCCTCTCCTCGGTCTCGATTCTACGC

GTACCGGTCATCATCACCATCACCATTGAGTTTAAACCCGCTGAT

CAGCCTCGACTGTGCCTTCTA

REFERENCES

The disclosures of all publications, patents, patent applications and published patent applications referred to herein are hereby incorporated herein by reference in their entirety.

US20210355494

WO2023020574

US20200263180

Kügler, J. et al. High Affinity Peptide Inhibitors of the Hepatitis C Virus NS3-4A Protease Refractory to Common Resistant Mutants. J Biol Chem 287, 39224-39232 (2012).

Tague, E. P., McMahan, J. B., Tague, N., Dunlop, M. J. & Ngo, J. T. Controlled Protein Activities with Viral Proteases, Antiviral Peptides, and Antiviral Drugs. Acs Chem Biol 18, 1228-1236 (2023).

D. Cunningham-Bryant, E. M. Dieter, G. W. Foight, J. C. Rose, D. E. Loutey, D. J. Maly, A Chemically Disrupted Proximity System for Controlling Dynamic Cellular Processes. J Am Chem Soc. 141, 3352-3355 (2019).

Jiang, K. et al. Programmable eukaryotic protein synthesis with RNA sensors by harnessing ADAR. Nat Biotechnol 1-10 (2022) doi: 10.1038/s41587-022-01534-5.

Katrekar, D. et al. In vivo RNA editing of point mutations via RNA-guided adenosine deaminases. Nat Methods 16, 239-242 (2019).

Klauer, A. A. & Hoof, A. van. Degradation of mRNAs that lack a stop codon: a decade of nonstop progress. Wiley Interdiscip Rev RNA 3, 649-660 (2012)

Matthews, M. M. et al. Structures of human ADAR2 bound to dsRNA reveal base-flipping mechanism and basis for site selectivity. Nat Struct Mol Biol 23, 426-433 (2016).

Park, S. et al. High-throughput mutagenesis reveals unique structural features of human ADAR1. Nat Commun 11, 5130 (2020).

Katrekar, D. et al. Comprehensive interrogation of the ADAR2 deaminase domain for engineering enhanced RNA editing activity and specificity. Elife 11, e75555 (2022).

Goreshnik, I. & Maly, D. J. A Small Molecule-Regulated Guanine Nucleotide Exchange Factor. J Am Chem Soc 132, 938-940 (2010).

Rose, J. C. et al. Rapidly inducible Cas9 and DSB-ddPCR to probe editing kinetics. Nat Methods 14, 891-896 (2017).

Wang, L. et al. Discovery of A 1331852, a First-in-Class, Potent, and Orally-Bioavailable BCL XL Inhibitor. Acs Med Chem Lett 11, 1829-1836 (2020).

Kotschy, A. et al. The MCLI inhibitor S63845 is tolerable and effective in diverse cancer models. Nature 538, 477-482 (2016).

Götzke, H. et al. The ALFA-tag is a highly versatile tool for nanobody-based bioscience applications. Nat Commun 10, 4403 (2019).

STEFFEN, F., HANSJOERG, G., FELIPE, O. D. L., GUSTAV, S. P. E. & MARKEL, M. C. EPITOPE TAGS RECOGNIZED BY SPECIFIC BINDERS.

Zakeri, B. et al. Peptide tag forming a rapid covalent bond to a protein, through engineering a bacterial adhesin. Proc National Acad Sci 109, E690-E697 (2012).

Li, L., Fierer, J. O., Rapoport, T. A. & Howarth, M. Structural Analysis and Optimization of the Covalent Association between SpyCatcher and a Peptide Tag. J Mol Biol 426, 309-317 (2014).

Liu, Z. et al. Systematic comparison of 2A peptides for cloning multi-genes in a polycistronic vector. Sci Repuk 7, 2193 (2017).

Zhang, W. et al. Optogenetic control with a photocleavable protein, PhoCl. Nat Methods 14, 391-394 (2017).

Chung, H. K. et al. A compact synthetic pathway rewires cancer signaling to therapeutic effector release. Science eaat6982 (2019) doi: 10.1126/science.aat6982.

Drabkin, H. J. & RajBhandary, U. L. Initiation of Protein Synthesis in Mammalian Cells with Codons Other Than AUG and Amino Acids Other Than Methionine. Mol. Cell. Biol. 18, 5140-5147 (1998).

Stripecke, R., Oliveira, C. C., Mccarthy, J. E. G. & Hentze, M. W. Proteins Binding to 5' Untranslated Region Sites: a General Mechanism for Translational Regulation of mRNAs in Human and Yeast Cells. Mol. Cell. Biol. 14, 5898-5909 (1994).

Buenrostro, J. D. et al. Quantitative analysis of RNA-protein interactions on a massively parallel array reveals biophysical and evolutionary landscapes. Nat Biotechnol 32, 562-568 (2014).

Johansson, H. E. et al. A thermodynamic analysis of the sequence-specific binding of RNA by bacteriophage MS2 coat protein. Proc National Acad Sci 95, 9244-9249 (1998).

Sharma, P. et al. 2A peptides provide distinct solutions to driving stop-carry on translational recoding. Nucleic Acids Res. 40, 3143-3151 (2012).

Feng, S. et al. Improved split fluorescent proteins for endogenous protein labeling. Nat Commun 8, 370 (2017).

Wood, T. I. et al. Defining the Role of Arginine 96 in Green Fluorescent Protein Fluorophore Biosynthesis †, ‡. Biochemistry 44, 16211-16220 (2005).

Götzke, H. et al. The ALFA-tag is a highly versatile tool for nanobody-based bioscience applications. Nat Commun 10, 4403 (2019).

STEFFEN, F., HANSJOERG, G., FELIPE, O. D. L., GUSTAV, S. P. E. & MARKEL, M. C. EPITOPE TAGS RECOGNIZED BY SPECIFIC BINDERS.

Tague, E. P., Dotson, H. L., Tunney, S. N., Sloas, D. C. & Ngo, J. T. Chemogenetic control of gene expression and cell signaling with antiviral drugs. Nat Methods 15, 519-522 (2018).

Jacobs, C. L., Badice, R. K. & Lin, M. Z. StaPLs: versatile genetically encoded modules for engineering drug-inducible proteins. Nat. Methods 15, 523-526 (2018).

SEQUENCE LISTING

```
Sequence total quantity: 411
SEQ ID NO: 1            moltype = AA  length = 296
FEATURE                 Location/Qualifiers
source                  1..296
                        mol_type = protein
                        organism = synthetic construct
SEQUENCE: 1
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKGSGATN FSLLKQAGDV EENPGPASAG SGEGRGSLLT CGDVEENPGP ATGNSA      296

SEQ ID NO: 2            moltype = AA  length = 701
FEATURE                 Location/Qualifiers
source                  1..701
                        mol_type = protein
```

```
                         organism = synthetic construct
SEQUENCE: 2
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPADRHPNR  300
KARGQLRTKI ESGQGTIPVR SNASIQTWDG VLQGERLLTM SCSDKIARWN VVGIQGSLLS  360
IFVEPIYFSS IILGSLYHGD HLSRAMYQRI SNIEDLPPLY TLNKPLLSGI SNAEARQPGK  420
APNFSVNWTV GDSAIEVINA TTGKDELGRA SRLCKHALYC RWMRVHGKVP SHLLRSKITK  480
PNVYHESKLA AKEYQAAKAR LFTAFIKAGL GAWVEKPTEQ DQFSLTGSGS SELIKENMHM  540
KLYMEGTVDN HHFKCTSEGE VTTYEDGGVL TATQDTSLQD GCLIYNVKIR GVNFTSNGPV  600
MQKKTLGWEA FTETLYPADG GLEGRNDMAL KLVGGSHLIA NIKTTYRSKK PAKNLKMPGV  660
YYVDYRLERI KEANNETYVE QHEVAVARYC DLPSKLGHKL N                     701

SEQ ID NO: 3             moltype = AA  length = 701
FEATURE                  Location/Qualifiers
source                   1..701
                         mol_type = protein
                         organism = synthetic construct
SEQUENCE: 3
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AAIISRRSLL RFLYTQLELY  240
LNNKDDQKRS IFQKSERGGF RLKENVQFHL YISTSPCGDA RIFSPHEPIL EEPADRHPNR  300
KARGQLRTKI ESGQGTIPVR SNASIQTWDG VLQGERLLTM SCSDKIARWN VVGIQGSLLS  360
IFVEPIYFSS IILGSLYHGD HLSRAMYQRI SNIEDLPPLY TLNKPLLSGI SNAEARQPGK  420
APNFSVNWTV GDSAIEVINA TTGKDELGRA SRLCKHALYC RWMRVHGKVP SHLLRSKITK  480
PNVYHESKLA AKEYQAAKAR LFTAFIKAGL GAWVEKPTEQ DQFSLTGSGS SELIKENMHM  540
KLYMEGTVDN HHFKCTSEGE VTTYEDGGVL TATQDTSLQD GCLIYNVKIR GVNFTSNGPV  600
MQKKTLGWEA FTETLYPADG GLEGRNDMAL KLVGGSHLIA NIKTTYRSKK PAKNLKMPGV  660
YYVDYRLERI KEANNETYVE QHEVAVARYC DLPSKLGHKL N                     701

SEQ ID NO: 4             moltype = AA  length = 549
FEATURE                  Location/Qualifiers
source                   1..549
                         mol_type = protein
                         organism = synthetic construct
SEQUENCE: 4
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKNSAWRW LPCQRHATSA TNFSLLKQAG DVEENPGPGG SEGRGSLLTC GDVEENPGPS  300
GYPYDVPDYA HMVSKGEEDN MASLPATHEL HIFGSINGVD FDMVGQGTGN PNDGYEELNL  360
KSTKGDLQFS PWILVPHIGY GFHQYLPYPD GMSPFQAAMV DGSGYQVHRT MQFEDGASLT  420
VNYRYTYEGS HIKGEAQVKG TGFPADGPVM TNSLTAADWC RSKKTYPNDK TIISTFKWSY  480
TTGNGKRYRS TARTTYTFAK PMAANYLKNQ PMYVFRKTEL KHSKTELNFK EWQKAFTDVM  540
GMDELYKAS                                                         549

SEQ ID NO: 5             moltype = AA  length = 247
FEATURE                  Location/Qualifiers
source                   1..247
                         mol_type = protein
                         organism = synthetic construct
SEQUENCE: 5
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKNSA                                                           247

SEQ ID NO: 6             moltype = AA  length = 247
FEATURE                  Location/Qualifiers
source                   1..247
                         mol_type = protein
                         organism = synthetic construct
SEQUENCE: 6
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKNSA                                                           247

SEQ ID NO: 7             moltype = AA  length = 249
FEATURE                  Location/Qualifiers
source                   1..249
                         mol_type = protein
```

```
                       organism = synthetic construct
SEQUENCE: 7
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKNSAWR                                                          249

SEQ ID NO: 8           moltype = AA  length = 247
FEATURE                Location/Qualifiers
source                 1..247
                       mol_type = protein
                       organism = synthetic construct
SEQUENCE: 8
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKNSA                                                            247

SEQ ID NO: 9           moltype = AA  length = 296
FEATURE                Location/Qualifiers
source                 1..296
                       mol_type = protein
                       organism = synthetic construct
SEQUENCE: 9
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKGSGATN FSLLKQAGDV EENPGPASAG SGEGRGSLLT CGDVEENPGP ATGNSA      296

SEQ ID NO: 10          moltype = AA  length = 296
FEATURE                Location/Qualifiers
source                 1..296
                       mol_type = protein
                       organism = synthetic construct
SEQUENCE: 10
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKGSGATN FSLLKQAGDV EENPGPASAG SGEGRGSLLT CGDVEENPGP ATGNSA      296

SEQ ID NO: 11          moltype = AA  length = 296
FEATURE                Location/Qualifiers
source                 1..296
                       mol_type = protein
                       organism = synthetic construct
SEQUENCE: 11
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKGSGATN FSLLKQAGDV EENPGPASAG SGEGRGSLLT CGDVEENPGP ATGNSA      296

SEQ ID NO: 12          moltype = AA  length = 714
FEATURE                Location/Qualifiers
source                 1..714
                       mol_type = protein
                       organism = synthetic construct
SEQUENCE: 12
MSKTIVLSVG EATRTLTEIQ STADRQIFEE KVGPLVGRLR LTASLRQNGA KTAYRVNLKL  60
DQADVVDSGL PKVRYTQVWS HDVTIVANST EASRKSLYDL TKSLVATSQV EDLVVNLVPL  120
GRASTGSGIY GGSGSGAGSG SPAGGGAPGS GGGSQLHLPQ VLADAVSRLV LGKFGDLTDN  180
FSSPHARRKV LAGVVMTTGT DVKDAKVISV STGTKCINGE YMSDRGLALN DCHAEIISRR  240
SLLRFLYTQL ELYLNNKDDQ KRSIFQKSER GGFRLKENVQ FHLYISTSPC GDARIFSPHE  300
PILEEPADRH PNRKARGQLR TKIESGQGTI PVRSNASIQT WDGVLQGERL LTMSCSDKIA  360
RWNVVGIQGS LLSIFVEPIY FSSIILGSLY HGDHLSRAMY QRISNIEDLP PLYTLNKPLL  420
SGISNAEARQ PGKAPNFSVN WTVGDSAIEV INATTGKDEL GRASRLCKHA LYCRWMRVHG  480
KVPSHLLRSK ITKPNVYHES KLAAKEYQAA KARLFTAFIK AGLGAWVEKP TEQDQFSLTG  540
SGSSELIKEN MHMKLYMEGT VDNHHFKCTS EGEVTTYEDG GVLTATQDTS LQDGCLIYNV  600
KIRGVNFTSN GPVMQKKTLG WEAFTETLYP ADGGLEGRND MALKLVGGSH LIANIKTTYR  660
SKKPAKNLKM PGVYYVDYRL ERIKEANNET YVEQHEVAVA RYCDLPSKLG HKLN        714

SEQ ID NO: 13          moltype = AA  length = 613
FEATURE                Location/Qualifiers
source                 1..613
                       mol_type = protein
```

```
                          organism = synthetic construct
SEQUENCE: 13
MADAQTRRRE RRAEKQAQWK AANTGSGIYG GSGSGAGSGS PAGGGAPGSG GGSQLHLPQV  60
LADAVSRLVL GKFGDLTDNF SSPHARRKVL AGVVMTTGTD VKDAKVISVS TGTKCINGEY  120
MSDRGLALND CHAEIISRRS LLRFLYTQLE LYLNNKDDQK RSIFQKSERG GFRLKENVQF  180
HLYISTSPCG DARIFSPHEP ILEEPADRHP NRKARGQLRT KIESGQGTIP VRSNASIQTW  240
DGVLQGERLL TMSCSDKIAR WNVVGIQGSL LSIFVEPIYF SSIILGSLYH GDHLSRAMYQ  300
RISNIEDLPP LYTLNKPLLS GISNAEARQP GKAPNFSVNW TVGDSAIEVI NATTGKDELG  360
RASRLCKHAL YCRWMRVHGK VPSHLLRSKI TKPNVYHESK LAAKEYQAAK ARLFTAFIKA  420
GLGAWVEKPT EQDQFSLTGS GSSELIKENM HMKLYMEGTV DNHHFKCTSE GEVTTYEDGG  480
VLTATQDTSL QDGCLIYNVK IRGVNFTSNG PVMQKKTLGW EAFTETLYPA DGGLEGRNDM  540
ALKLVGGSHL IANIKTTYRS KKPAKNLKMP GVYYVDYRLE RIKEANNETY VEQHEVAVAR  600
YCDLPSKLGH KLN                                                     613

SEQ ID NO: 14             moltype = AA  length = 609
FEATURE                   Location/Qualifiers
source                    1..609
                          mol_type = protein
                          organism = synthetic construct
SEQUENCE: 14
MASGPRPRGT RGKGRRIRRT GSGIYGGSGS GAGSGSPAGG GAPGSGGGSQ LHLPQVLADA  60
VSRLVLGKFG DLTDNFSSPH ARRKVLAGVV MTTGTDVKDA KVISVSTGTK CINGEYMSDR  120
GLALNDCHAE IISRRSLLRF LYTQLELYLN NKDDQKRSIF QKSERGGFRL KENVQFHLYI  180
STSPCGDARI FSPHEPILEE PADRHPNRKA RGQLRTKIES GQGTIPVRSN ASIQTWDGVL  240
QGERLLTMSC SDKIARWNVV GIQGSLLSIF VEPIYFSSII LGSLYHGDHL SRAMYQRISN  300
IEDLPPLYTL NKPLLSGISN AEARQPGKAP NFSVNWTVGD SAIEVINATT GKDELGRASR  360
LCKHALYCRW MRVHGKVPSH LLRSKITKPN VYHESKLAAK EYQAAKARLF TAFIKAGLGA  420
WVEKPTEQDQ FSLTGSGSSE LIKENMHMKL YMEGTVDNHH FKCTSEGEVT TYEDGGVLTA  480
TQDTSLQDGC LIYNVKIRGV NFTSNGPVMQ KKTLGWEAFT ETLYPADGGL EGRNDMALKL  540
VGGSHLIANI KTTYRSKKPA KNLKMPGVYY VDYRLERIKE ANNETYVEQH EVAVARYCDL  600
PSKLGHKLN                                                          609

SEQ ID NO: 15             moltype = AA  length = 234
FEATURE                   Location/Qualifiers
source                    1..234
                          mol_type = protein
                          organism = synthetic construct
SEQUENCE: 15
MVSKGEEVIK EFMRFKVRME GSMNGHEFEI EGEGEGRPYE GTQTAKLKVT KGGPLPFAWD  60
ILSPQFMYGS KAYVKHPADI PDYKKLSFPE GFKWERVMNF EDGGLVTVTQ DSSLQDGTLI  120
YKVKMRGTNF PPDGPVMQKK TMGWEASTER LYPRDGVLKG EIHQALKLKD GGHYLVEFKT  180
IYMAKKPVQL PGYYYVDTKL DITSHNEDYT IVEQYERSEG RHHLFLYGMD ELYK        234

SEQ ID NO: 16             moltype = AA  length = 281
FEATURE                   Location/Qualifiers
source                    1..281
                          mol_type = protein
                          organism = synthetic construct
SEQUENCE: 16
MVSKGEELFT GVVPILVELD GDVNGHKFSV SGEGEGDATY GKLTLKFICT TGKLPVPWPT  60
LVTTLTYGVQ CFSRYPDHMK QHDFFKSAMP EGYVQERTIF FKDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSALSK DPNEKRDHMV LLEFVTAAGI TLGMDELYKK  240
LSHGFPPEVE EQDDGTLPMS CAQESGMDRH PAACASARIN V                      281

SEQ ID NO: 17             moltype = AA  length = 792
FEATURE                   Location/Qualifiers
source                    1..792
                          mol_type = protein
                          organism = synthetic construct
SEQUENCE: 17
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEFVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGS SELIKENMHM KLYMEGTVDN HHFKCTSEGE GKPYEGTQTM  600
RIKVVEGGPL PFAFDILATS FLYGSKTFIN HTQGIPDFFK QSFPEGFTWE RVTTYEDGGV  660
LTATQDTSLQ DGCLIYNVKI RGVNFTSNGP VMQKKTLGWE AFTETLYPAD GGLEGRNDMA  720
LKLVGGSHLI ANIKTTYRSK KPAKNLKMPG VYYVDYRLER IKEANNETYV EQHEVAVARY  780
CDLPSKLGHK LN                                                      792

SEQ ID NO: 18             moltype = AA  length = 999
FEATURE                   Location/Qualifiers
source                    1..999
```

```
                        mol_type = protein
                        organism = synthetic construct
SEQUENCE: 18
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEFVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNGSSEL IKENMHMKLY  780
MEGTVDNHHF KCTSEGEGKP YEGTQTMRIK VVEGGPLPFA FDILATSFLY GSKTFINHTQ  840
GIPDFFKQSF PEGFTWERVT TYEDGGVLTA TQDTSLQDGC LIYNVKIRGV NFTSNGPVMQ  900
KKTLGWEAFT ETLYPADGGL EGRNDMALKL VGGSHLIANI KTTYRSKKPA KNLKMPGVYY  960
VDYRLERIKE ANNETYVEQH EVAVARYCDL PSKLGHKLN                        999

SEQ ID NO: 19           moltype = AA  length = 797
FEATURE                 Location/Qualifiers
source                  1..797
                        mol_type = protein
                        organism = synthetic construct
SEQUENCE: 19
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGS  300
GDMRPEIWIA QELRRIGDEF NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSGSSELIK ENMHMKLYME GTVDNHHFKC TSEGEGKPYE  600
GTQTMRIKVV EGGPLPFAFD ILATSFLYGS KTFINHTQGI PDFFKQSFPE GFTWERVTTY  660
EDGGVLTATQ DTSLQDGCLI YNVKIRGVNF TSNGPVMQKK TLGWEAFTET LYPADGGLEG  720
RNDMALKLVG GSHLIANIKT TYRSKKPAKN LKMPGVYYVD YRLERIKEAN NETYVEQHEV  780
AVARYCDLPS KLGHKLN                                                797

SEQ ID NO: 20           moltype = AA  length = 1004
FEATURE                 Location/Qualifiers
source                  1..1004
                        mol_type = protein
                        organism = synthetic construct
SEQUENCE: 20
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGS  300
GDMRPEIWIA QELRRIGDEF NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSAAGGSGG SAAASSNREL VVDFLSYKLS QKGYSWSQFS  600
DVEENRTEAP EGTESEMETP SAINGNPSWH LADSPAVNGA TGHSSSLDAR EVIPMAAVKQ  660
ALREAGDEFE LRYRRAFSDL TSQLHITPGT AYQSFEQVVN ELFRDGVNWG RIVAFFSFGG  720
ALCVESVDKE MQVLVSRIAA WMATYLNDHL EPWIQENGGW DTFVELYGNN GSSELIKENM  780
HMKLYMEGTV DNHHFKCTSE GEGKPYEGTQ TMRIKVVEGG PLPFAFDILA TSFLYGSKTF  840
INHTQGIPDF FKQSFPEGFT WERVTTYEDG GVLTATQDTS LQDGCLIYNV KIRGVNFTSN  900
GPVMQKKTLG WEAFTETLYP ADGGLEGRND MALKLVGGSH LIANIKTTYR SKKPAKNLKM  960
PGVYYVDYRL ERIKEANNET YVEQHEVAVA RYCDLPSKLG HKLN                  1004

SEQ ID NO: 21           moltype = AA  length = 797
FEATURE                 Location/Qualifiers
source                  1..797
                        mol_type = protein
                        organism = synthetic construct
SEQUENCE: 21
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEA NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
```

```
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSGSSELIK ENMHMKLYME GTVDNHHFKC TSEGEGKPYE  600
GTQTMRIKVV EGGPLPFAFD ILATSFLYGS KTFINHTQGI PDFFKQSFPE GFTWERVTTY  660
EDGGVLTATQ DTSLQDGCLI YNVKIRGVNF TSNGPVMQKK TLGWEAFTET LYPADGGLEG  720
RNDMALKLVG GSHLIANIKT TYRSKKPAKN LKMPGVYYVD YRLERIKEAN NETYVEQHEV  780
AVARYCDLPS KLGHKLN                                                 797

SEQ ID NO: 22          moltype = AA  length = 959
FEATURE                Location/Qualifiers
source                 1..959
                       mol_type = protein
                       organism = synthetic construct
SEQUENCE: 22
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEA NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSGTGGPGD ELYRQSLEII SRYLREQATG AKDTKPMGRS  600
GATSRKALET LRRVGDGVQR NHETAFQGML RKLDIKNEDD VKSLSRVMIH VFSDGVTNWG  660
RIVTLISFGA FVAKHLKTIN QESCIEPLAE SITDVLVRTK RDWLVKQRGW DGFVEFFHVE  720
DLEGGGSSEL IKENMHMKLY MEGTVDNHHF KCTSEGEGKP YEGTQTMRIK VVEGGPLPFA  780
FDILATSFLY GSKTFINHTQ GIPDFFKQSF PEGFTWERVT TYEDGGVLTA TQDTSLQDGC  840
LIYNVKIRGV NFTSNGPVMQ KKTLGWEAFT ETLYPADGGL EGRNDMALKL VGGSHLIANI  900
KTTYRSKKPA KNLKMPGVYY VDYRLERIKE ANNETYVEQH EVAVARYCDL PSKLGHKLN   959

SEQ ID NO: 23          moltype = AA  length = 999
FEATURE                Location/Qualifiers
source                 1..999
                       mol_type = protein
                       organism = synthetic construct
SEQUENCE: 23
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNGSSEL IKENMHMKLY  780
MEGTVDNHHF KCTSEGEGKP YEGTQTMRIK VVEGGPLPFA FDILATSFLY GSKTFINHTQ  840
GIPDFFKQSF PEGFTWERVT TYEDGGVLTA TQDTSLQDGC LIYNVKIRGV NFTSNGPVMQ  900
KKTLGWEAFT ETLYPADGGL EGRNDMALKL VGGSHLIANI KTTYRSKKPA KNLKMPGVYY  960
VDYRLERIKE ANNETYVEQH EVAVARYCDL PSKLGHKLN                         999

SEQ ID NO: 24          moltype = AA  length = 959
FEATURE                Location/Qualifiers
source                 1..959
                       mol_type = protein
                       organism = synthetic construct
SEQUENCE: 24
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEI NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSGTGGPGD ELYRQSLEII SRYLREQATG AKDTKPMGRS  600
GATSRKALET LRRVGDGVQR NHETAFQGML RKLDIKNEDD VKSLSRVMIH VFSDGVTNWG  660
RIVTLISFGA FVAKHLKTIN QESCIEPLAE SITDVLVRTK RDWLVKQRGW DGFVEFFHVE  720
DLEGGGSSEL IKENMHMKLY MEGTVDNHHF KCTSEGEGKP YEGTQTMRIK VVEGGPLPFA  780
FDILATSFLY GSKTFINHTQ GIPDFFKQSF PEGFTWERVT TYEDGGVLTA TQDTSLQDGC  840
LIYNVKIRGV NFTSNGPVMQ KKTLGWEAFT ETLYPADGGL EGRNDMALKL VGGSHLIANI  900
KTTYRSKKPA KNLKMPGVYY VDYRLERIKE ANNETYVEQH EVAVARYCDL PSKLGHKLN   959

SEQ ID NO: 25          moltype = AA  length = 781
```

-continued

```
FEATURE                Location/Qualifiers
source                 1..781
                       mol_type = protein
                       organism = synthetic construct
SEQUENCE: 25
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASPSRL  300
EEELRRRLTE PTGDRHPNRK ARGQLRTKIE SGQGTIPVRS NASIQTWDGV LQGERLLTMS  360
CSDKIARWNV VGIQGSLLSI FVEPIYFSSI ILGSLYHGDH LSRAMYQRIS NIEDLPPLYT  420
LNKPLLSGIS NAEARQPGKA PNFSVNWTVG DSAIEVINAT TGKDELGRAS RLCKHALYCR  480
WMRVHGKVPS HLLRSKITKP NVYHESKLAA KEYQAAKARL FTAFIKAGLG AWVEKPTEQD  540
QFSLTGSGSS ELIKENMHMK LYMEGTVDNH HFKCTSEGEG KPYEGTQTMR IKVVEGGPLP  600
FAFDILATSF LYGSKTFINH TQGIPDFFKQ SFPEGFTWER VTTYEDGGVL TATQDTSLQD  660
GCLIYNVKIR GVNFTSNGPV MQKKTLGWEA FTETLYPADG GLEGRNDMAL KLVGGSHLIA  720
NIKTTYRSKK PAKNLKMPGV YYVDYRLERI KEANNETYVE QHEVAVARYC DLPSKLGHKL  780
N                                                                 781

SEQ ID NO: 26          moltype = AA  length = 909
FEATURE                Location/Qualifiers
source                 1..909
                       mol_type = protein
                       organism = synthetic construct
SEQUENCE: 26
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASPSRL  300
EEELRRRLTE PTGDRHPNRK ARGQLRTKIE SGQGTIPVRS NASIQTWDGV LQGERLLTMS  360
CSDKIARWNV VGIQGSLLSI FVEPIYFSSI ILGSLYHGDH LSRAMYQRIS NIEDLPPLYT  420
LNKPLLSGIS NAEARQPGKA PNFSVNWTVG DSAIEVINAT TGKDELGRAS RLCKHALYCR  480
WMRVHGKVPS HLLRSKITKP NVYHESKLAA KEYQAAKARL FTAFIKAGLG AWVEKPTEQD  540
QFSLTGSGGT AEVQLQESGG GLVQPGGSLR LSCTASGVTI SALNAMAMGW YRQAPGERRV  600
MVAAVSERGN AMYRESVQGR FTVTRDFTNK MVSLQMDNLK PEDTAVYYCH VLEDRVDSFH  660
DYWGQGTQVT VSSGAGSSEL IKENMHMKLY MEGTVDNHHF KCTSEGEGKP YEGTQTMRIK  720
VVEGGPLPFA FDILATSFLY GSKTFINHTQ GIPDFFKQSF PEGFTWERVT TYEDGGVLTA  780
TQDTSLQDGC LIYNVKIRGV NFTSNGPVMQ KKTLGWEAFT ETLYPADGGL EGRNDMALKL  840
VGGSHLIANI KTTYRSKKPA KNLKMPGVYY VDYRLERIKE ANNETYVEQH EVAVARYCDL  900
PSKLGHKLN                                                         909

SEQ ID NO: 27          moltype = AA  length = 784
FEATURE                Location/Qualifiers
source                 1..784
                       mol_type = protein
                       organism = synthetic construct
SEQUENCE: 27
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGP  300
GRLEEELRRR LSPGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GSSELIKENM HMKLYMEGTV DNHHFKCTSE GEGKPYEGTQ TMRIKVVEGG  600
PLPFAFDILA TSFLYGSKTF INHTQGIPDF FKQSFPEGFT WERVTTYEDG GVLTATQDTS  660
LQDGCLIYNV KIRGVNFTSN GPVMQKKTLG WEAFTETLYP ADGGLEGRND MALKLVGGSH  720
LIANIKTTYR SKKPAKNLKM PGVYYVDYRL ERIKEANNET YVEQHEVAVA RYCDLPSKLG  780
HKLN                                                              784

SEQ ID NO: 28          moltype = AA  length = 912
FEATURE                Location/Qualifiers
source                 1..912
                       mol_type = protein
                       organism = synthetic construct
SEQUENCE: 28
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGP  300
GRLEEELRRR LSPGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
```

```
EQDQFSLTGS GGTAEVQLQE SGGGLVQPGG SLRLSCTASG VTISALNAMA MGWYRQAPGE  600
RRVMVAAVSE RGNAMYRESV QGRFTVTRDF TNKMVSLQMD NLKPEDTAVY YCHVLEDRVD  660
SFHDYWGQGT QVTVSSGAGS SELIKENMHM KLYMEGTVDN HHFKCTSEGE GKPYEGTQTM  720
RIKVVEGGPL PFAFDILATS FLYGSKTFIN HTQGIPDFFK QSFPEGFTWE RVTTYEDGGV  780
LTATQDTSLQ DGCLIYNVKI RGVNFTSNGP VMQKKTLGWE AFTETLYPAD GGLEGRNDMA  840
LKLVGGSHLI ANIKTTYRSK KPAKNLKMPG VYYVDYRLER IKEANNETYV EQHEVAVARY  900
CDLPSKLGHK LN                                                      912

SEQ ID NO: 29          moltype = AA  length = 784
FEATURE                Location/Qualifiers
source                 1..784
                       mol_type = protein
                       organism = synthetic construct
SEQUENCE: 29
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGP  300
GRLEQEIRAR LSPGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GSSELIKENM HMKLYMEGTV DNHHFKCTSE GEGKPYEGTQ TMRIKVVEGG  600
PLPFAFDILA TSFLYGSKTF INHTQGIPDF FKQSFPEGFT WERVTTYEDG GVLTATQDTS  660
LQDGCLIYNV KIRGVNFTSN GPVMQKKTLG WEAFTETLYP ADGGLEGRND MALKLVGGSH  720
LIANIKTTYR SKKPAKNLKM PGVYYVDYRL ERIKEANNET YVEQHEVAVA RYCDLPSKLG  780
HKLN                                                               784

SEQ ID NO: 30          moltype = AA  length = 912
FEATURE                Location/Qualifiers
source                 1..912
                       mol_type = protein
                       organism = synthetic construct
SEQUENCE: 30
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGP  300
GRLEQEIRAR LSPGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GGTAEVQLQE SGGGLVQPGG SLRLSCTASG VTISALNAMA MGWYRQAPGE  600
RRVMVAAVSE RGNAMYRESV QGRFTVTRDF TNKMVSLQMD NLKPEDTAVY YCHVLEDRVD  660
SFHDYWGQGT QVTVSSGAGS SELIKENMHM KLYMEGTVDN HHFKCTSEGE GKPYEGTQTM  720
RIKVVEGGPL PFAFDILATS FLYGSKTFIN HTQGIPDFFK QSFPEGFTWE RVTTYEDGGV  780
LTATQDTSLQ DGCLIYNVKI RGVNFTSNGP VMQKKTLGWE AFTETLYPAD GGLEGRNDMA  840
LKLVGGSHLI ANIKTTYRSK KPAKNLKMPG VYYVDYRLER IKEANNETYV EQHEVAVARY  900
CDLPSKLGHK LN                                                      912

SEQ ID NO: 31          moltype = AA  length = 330
FEATURE                Location/Qualifiers
source                 1..330
                       mol_type = protein
                       organism = synthetic construct
SEQUENCE: 31
MVAGHASGSP AFGTASHSNC EHEEIHLAGS IQPHGALLVV SEHDHRVIQA SANAAEFLNL  60
GSVLGVPLAE IDGDLLIKIL PHLDPTAEGM PVAVRCRIGN PSTEYCGLMH RPPEGGLIIE  120
LERAGPSIDL SGTLAPALER IRTAGSLRAL CDDTVLLFQQ CTGYDRVMVY RFDEQGHGLV  180
FSECHVPGLE SYFGNRYPSS TVPQMARQLY VRQRVRVLVD VTYQPVPLEP RLSPLTGRDL  240
DMSGCFLRSM SPCHLQFLKD MGVRATLAVS LVVGGKLWGL VVCHHYLPRF IRFELRAICK  300
RLAERIATRI TALESLESRL EEELRRRLTE                                   330

SEQ ID NO: 32          moltype = AA  length = 784
FEATURE                Location/Qualifiers
source                 1..784
                       mol_type = protein
                       organism = synthetic construct
SEQUENCE: 32
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
AHIVMVDAYK PTKGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
```

-continued

```
YCRWMRVHGK VPSHLLRSKI TKPNVYHESK LAAKEYQAAK ARLFTAFIKA GLGAWVEKPT  540
EQDQFSLTGS GSSELIKENM HMKLYMEGTV DNHHFKCTSE GEGKPYEGTQ TMRIKVVEGG  600
PLPFAFDILA TSFLYGSKTF INHTQGIPDF FKQSFPEGFT WERVTTYEDG GVLTATQDTS  660
LQDGCLIYNV KIRGVNFTSN GPVMQKKTLG WEAFTETLYP ADGGLEGRND MALKLVGGSH  720
LIANIKTTYR SKKPAKNLKM PGVYYVDYRL ERIKEANNET YVEQHEVAVA RYCDLPSKLG  780
HKLN                                                              784

SEQ ID NO: 33           moltype = AA  length = 904
FEATURE                 Location/Qualifiers
source                  1..904
                        mol_type = protein
                        organism = synthetic construct
SEQUENCE: 33
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
AHIVMVDAYK PTKGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GTSGGAMVDT LSGLSSEQGQ SGDMTIEEDS ATHIKFSKRD EDGKELAGAT  600
MELRDSSGKT ISTWISDGQV KDFYLYPGKY TFVETAAPDG YEVATAITFT VNEQGQVTVN  660
GKATKGDAHI GSSELIKENM HMKLYMEGTV DNHHFKCTSE GEGKPYEGTQ TMRIKVVEGG  720
PLPFAFDILA TSFLYGSKTF INHTQGIPDF FKQSFPEGFT WERVTTYEDG GVLTATQDTS  780
LQDGCLIYNV KIRGVNFTSN GPVMQKKTLG WEAFTETLYP ADGGLEGRND MALKLVGGSH  840
LIANIKTTYR SKKPAKNLKM PGVYYVDYRL ERIKEANNET YVEQHEVAVA RYCDLPSKLG  900
HKLN                                                              904

SEQ ID NO: 34           moltype = AA  length = 947
FEATURE                 Location/Qualifiers
source                  1..947
                        mol_type = protein
                        organism = synthetic construct
SEQUENCE: 34
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
AHIVMVDAYK PTKGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GSSELIKENM HMKLYMEGTV DNHHFKCTSE GEGKPYEGTQ TMRIKVVEGG  600
PLPFAFDILA TSFLYGSKTF INHTQGIPDF FKQSFPEGFT WERVTTYEDG GVLTATQDTS  660
LQDGCLIYNV KIRGVNFTSN GPVMQKKTLG WEAFTETLYP ADGGLEGRND MALKLVGGSH  720
LIANIKTTYR SKKPAKNLKM PGVYYVDYRL ERIKEANNET YVEQHEVAVA RYCDLPSKLG  780
HKLNTSATNF SLLKQAGDVE ENPGPGGSEG RGSLLTCGDV EENPGPGTSG GAMVDTLSGL  840
SSEQGQSGDM TIEEDSATHI KFSKRDEDGK ELAGATMELR DSSGKTISTW ISDGQVKDFY  900
LYPGKYTFVE TAAPDGYEVA TAITFTVNEQ GQVTVNGKAT KGDAHIG                947

SEQ ID NO: 35           moltype = AA  length = 914
FEATURE                 Location/Qualifiers
source                  1..914
                        mol_type = protein
                        organism = synthetic construct
SEQUENCE: 35
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
AHIVMVDAYK PTKGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GGTENLYFQS GTSGGAMVDT LSGLSSEQGQ SGDMTIEEDS ATHIKFSKRD  600
EDGKELAGAT MELRDSSGKT ISTWISDGQV KDFYLYPGKY TFVETAAPDG YEVATAITFT  660
VNEQGQVTVN GKATKGDAHI GSSELIKENM HMKLYMEGTV DNHHFKCTSE GEGKPYEGTQ  720
TMRIKVVEGG PLPFAFDILA TSFLYGSKTF INHTQGIPDF FKQSFPEGFT WERVTTYEDG  780
GVLTATQDTS LQDGCLIYNV KIRGVNFTSN GPVMQKKTLG WEAFTETLYP ADGGLEGRND  840
MALKLVGGSH LIANIKTTYR SKKPAKNLKM PGVYYVDYRL ERIKEANNET YVEQHEVAVA  900
RYCDLPSKLG HKLN                                                    914

SEQ ID NO: 36           moltype = AA  length = 235
FEATURE                 Location/Qualifiers
source                  1..235
```

```
                         mol_type = protein
                         organism = synthetic construct
SEQUENCE: 36
MGESLFKGPR DYNPISSTIC HLTNESDGHT TSLYGIGFGP FIITNKHLFR RNNGTLLVQS  60
LHGVFKVKNT TTLQQHLIDG RDMIIIRMPK DFPPFPQKLK FREPQREERI CLVTTNFQTK  120
SMSSMVSDTS CTFPSSDGIF WKHWIQTKDG QCGSPLVSTR DGFIVGIHSA SNFTNTNNYF  180
TSVPKNFMEL LTNQEAQQWV SGWRLNADSV LWGGHKVFMV KPEEPFQPVK EATQL       235

SEQ ID NO: 37            moltype = AA  length = 1238
FEATURE                  Location/Qualifiers
source                   1..1238
                         mol_type = protein
                         organism = synthetic construct
SEQUENCE: 37
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGS GGVIPDYFKQ SFPEGYSWER SMTYEDGGIC IATNDITMEG  600
DSFINKIHFK GTNFPPNGPV MQKRTVGWEA STEKMYERDG VLKGDVKMKL LLKGGGHYRC  660
DYRTTYKVKQ KPVKLPDYHF VDHRIEILSH DKDYNKVKLY EHAVARNSTD SMDELYKGGS  720
GGMVSKGEET ITSVIKPDMK NKLRMEGNVN GHAFVIEGEG SGKPFEGIQT IDLEVKEGAP  780
LPFAYDILTT AFHYGNRVFT KYPRSGSGSS NRELVVDFLS YKLSQKGYSW SQFSDVEENR  840
TEAPEGTESE METPSAINGN PSWHLADSPA VNGATGHSSS LDAREVIPMA AVKQALREAG  900
DEFELRYRRA FSDLTSQLHI TPGTAYQSFE QVVNELFRDG VNWGRIVAFF SFGGALCVES  960
VDKEMQVLVS RIAAWMATYL NDHLEPWIQE NGGWDTFVEL YGNNGSSELI KENMHMKLYM  1020
EGTVDNHHFK CTSEGEGKPY EGTQTMRIKV VEGGPLPFAF DILATSFLYG SKTFINHTQG  1080
IPDFFKQSFP EGFTWERVTT YEDGGVLTAT QDTSLQDGCL IYNVKIRGVN FTSNGPVMQK  1140
KTLGWEAFTE TLYPADGGLE GRNDMALKLV GGSHLIANIK TTYRSKKPAK NLKMPGVYYV  1200
DYRLERIKEA NNETYVEQHE VAVARYCDLP SKLGHKLN                         1238

SEQ ID NO: 38            moltype = DNA  length = 1895
FEATURE                  Location/Qualifiers
source                   1..1895
                         mol_type = other DNA
                         organism = synthetic construct
SEQUENCE: 38
aggtaagctt ggtaccgagc tcggatccac cggtcgccac catggtgagc aagggcgagg  60
aggataacat ggccatcatc aaggagttca tgcgcttcaa ggtgcacatg gagggctccg  120
tgaacggcca cgagttcgag atcgagggcg agggcgaggg ccgcccctac gagggcaccc  180
agaccgccaa gctgaaggtg accaagggtg gccccctgcc cttcgcctgg gacatcctgt  240
cccctcagtt catgtacggc tccaaggcct acgtgaagca ccccgccgac atccccgact  300
acttgaagct gtccttcccc gagggcttca agtgggagcg cgtgatgaac ttcgaggacg  360
gcggcgtggt gaccgtgacc caggactcct ccctgcagga cggcgagttc atctacaagg  420
tgaagctgcg cggcaccaac ttcccctccg acggccccgt aatgcagaag aagaccatgg  480
gctgggaggc ctcctccgag cggatgtacc ccgaggacgg cgccctgaag ggcgagatca  540
agcagaggct gaagctgaag gacggcggcc actacgacgc tgaggtcaag accacctaca  600
aggccaagaa gcccgtgcag ctgcccggcg cctacaacgt caacatcaag ttggacatca  660
cctcccacaa cgaggactac accatcgtgg aacagtacga acgcgccgag ggccgccact  720
ccaccggcgg catggacgag ctgtacaagg attacaagga tgacgatgac aaaggtagcg  780
gggcaactaa ttttagctta ctcaaacagg ctggggacgt cgaggagaat ccaggccctg  840
catccgctgg ctctggagaa ggacgaggct ccttgctcac ctgtggagat gtcgaagaga  900
acccaggtcc tgcaaccggg aattccgcgt agcgctagct ttgccagcgc cacgcgaaac  960
atgaggatca cccatgtact agtgccacaa acttctctct gctaaagcaa gcaggtgatg  1020
ttgaagaaaa cccagggcct ggagggtccg agggcagggg aagtctccta acatgcgggg  1080
acgtggagga aaatcccggc ccatccggat atccctacga tgtgcccgat tacgctcata  1140
tggtgagcaa gggcgaggag gataacatgg cctctctccc agcgacacat gagttacaca  1200
tctttggctc catcaacggt gtggactttg acatggtggg tcagggcacc ggcaatccaa  1260
atgatggtta tgaggagtta aacctgaagt ccaccaaggg tgacctccag ttctcccccct  1320
ggattctggt ccctcatatc gggtatggct tccatcagta cctgccctac cctgacggga  1380
tgtcgccttt ccaggccgcc atggtagatg gcagcggata ccaagtccat cgcacaatgc  1440
agtttgaaga tggtgcctcc cttactgtta actaccgcta cacctacgag ggaagccaca  1500
tcaaaggaga ggcccaggtg aaggggactg gtttccctgc tgacggtcct gtgatgacca  1560
actcgctgac cgctgcggac tggtgcaggt cgaagaagac ttaccccaac gacaaaacca  1620
tcatcagtac ctttaagtgg agttacacca ctggaaatgg caagagatac cggagcactg  1680
cgcggaccac ctacaccttt gccaagccaa tggcggctaa ctatctgaag aaccagccga  1740
tgtacgtgtt ccgtaagacg gagctcaagc actccaagac cgagctcaac ttcaaggagt  1800
ggcaaaaggc ctttaccgat gtgatgggaa tggacgagct gtataaggct agctaagcgg  1860
ccgctcgagt ctagagggcc cgcggttcga aggta                            1895

SEQ ID NO: 39            moltype = DNA  length = 2328
FEATURE                  Location/Qualifiers
source                   1..2328
                         mol_type = other DNA
```

```
                         organism = synthetic construct
SEQUENCE: 39
gatcgaaccc ttaaggccac catggcgtcc aatttcactc agtttgtgct ggttgacaac  60
ggcgggaccg gggacgttac ggtagccccc tcaaactttg ccaacggtat agcggagtgg  120
ataagcagca attctaggag tcaagcatac aaagttacat gcagcgtgcg ccaatctagc  180
gctcagaatc gcaagtacac cattaaagta gaggtcccca agggagcctg gagaagctat  240
cttaacatgg agttgaccat accaatcttc gctaccaact ctgactgtga actcattgtg  300
aaagccatgc aaggtctgct caaggatggt aacccaattc cgtccgctat cgctgccaac  360
tctgggattt acgggggcag tgggagcggt gcaggatctg gtagtccagc tgggggagga  420
gcaccgggta gcggtggggg gtctcagctg cacctgcccc aggttctcgc agacgccgta  480
tcccgccttg tactgggcaa gtttggtgat cttactgaca atttttcatc tcctcatgcg  540
aggcggaaag tactcgcagg cgtcgtcatg acgaccggaa ctgacgtgaa agacgccaaa  600
gtcatctctg tctccacggg cacaaagtgc ataaacgggg agtacatgag cgaccggggg  660
ctggcactga atgattgtca cgctgaaata atatctaggc gatctctgct tagatttctc  720
tacactcaac tcgaattgta ccttaacaac aaagatgacc agaaacgcag tatatttcag  780
aaatcagaac gcggcggatt tcgacttaag gaaaacgttc agttccactt gtatatcagc  840
acatcccctt gcggtgacgc ccgaatcttt tccccgcacg agccgatatt ggaggagccc  900
gcggacagac atcctaatag gaaggctaga ggccaacttc ggacgaagat tgaaagtggc  960
cagggtacta tcccggtgcg gtccaacgct agtattcaaa cgtgggacgg agtccttcaa  1020
ggtgaacggc tgttgacaat gagctgctca gacaaaatcg cgcgctggaa tgtagtggga  1080
atccaaggca gcctcttgag catattcgta gaacccatat atttctcatc cattattttg  1140
ggctctctgt atcatggtga ccatctgtca agggctatgt accaacgaat ttctaatatc  1200
gaggatcttc ctccactcta tacactcaat aagcctctct tgtccgggat atcaaacgct  1260
gaggcccgcc agccagggaa agctcctaac ttcagtgtta actggaccgt tggtgattct  1320
gcgatagagg tcatcaacgc cacgacaggt aaggatgagc tcggtagagc ctcacgcctg  1380
tgtaaacacg cgttgtattg tagatggatg agagtacatg ggaaggtccc atctcacttg  1440
ctccgaagca agatcactaa gcctaatgtg tatcatgagt caaaactcgc ggctaaagaa  1500
taccaggcag ccaaagctcg actttttaca gcttttatta aggcagggct cggggcatgg  1560
gtcgagaagc cgaccgagca ggaccaattc tctctgacgg ggagcggatc cagcgagctg  1620
attaaggaga acatgcacat gaagctgtac atggagggca ccgtggacaa ccatcacttc  1680
aagtgcacat ccgagggcga aggcaagccc tacgagggca cccagaccat gagaatcaag  1740
gtggtcgagg gcggccctct ccccttcgcc ttcgacatcc tggctactag cttcctctac  1800
ggcagcaaga ccttcatcaa ccacacccag ggcatccccg acttcttcaa gcagtccttc  1860
cctgagggct tcacatggga gagagtcacc acatacgaag acgggggcgt gctgaccgct  1920
acccaggaca ccagcctcca ggacggctgc ctcatctaca acgtcaagat cagaggggtg  1980
aacttcacat ccaacggccc tgtgatgcag aagaaaacac tcggctggga ggccttcacc  2040
gagacgctgt accccgctga cggcggcctg gaaggcagaa acgacatggc cctgaagctc  2100
gtgggcggga gccatctgat cgcaaacatc aagaccacat atagatccaa gaaacccgct  2160
aagaacctca agatgcctgg cgtctactat gtggactaca gactggaaag aatcaaggag  2220
gccaacaacg agacctacgt cgagcagcac gaggtggcag tggccagata ctgcgacctc  2280
cctagcaaac tggggcacaa gcttaattaa gggcccgttt aaacccgc               2328

SEQ ID NO: 40            moltype = DNA  length = 2392
FEATURE                  Location/Qualifiers
source                   1..2392
                         mol_type = other DNA
                         organism = synthetic construct
SEQUENCE: 40
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgccataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggacagaca tcctaatagg  960
aaggctagag gccaacttcg gacgaagatt gaaagtggcc agggtactat cccggtgcgg  1020
tccaacgcta gtattcaaac gtgggacgga gtccttcaag gtgaacggct gttgacaatg  1080
agctgctcag acaaaatcgc gcgctggaat gtagtgggaa tccaaggcag cctcttgagc  1140
atattcgtag aacccatata tttctcatcc attattttgg gctctctgta tcatggtgac  1200
catctgtcaa gggctatgta ccaacgaatt tctaatatcg aggatcttcc tccactctat  1260
acactcaata agcctctctt gtccgggata tcaaacgctg aggcccgcca gccagggaaa  1320
gctcctaact tcagtgttaa ctggaccgtt ggtgattctg cgatagaggt catcaacgcc  1380
acgacaggta aggatgagct cggtagagcc tcacgcctgt gtaaacacgc gttgtattgt  1440
agatggatga gagtacatgg gaaggtccca tctcacttgc tccgaagcaa gatcactaag  1500
cctaatgtgt atcatgagtc aaaactcgcg gctaaagaat accaggcagc caaagctcga  1560
ctttttacag cttttattaa ggcagggctc ggggcatggg tcgagaagcc gaccgagcag  1620
gaccaattct ctctgacggg gagcggatcc agcgagctga ttaaggagaa catgcacatg  1680
aagctgtaca tggagggcac cgtggacaac catcacttca agtgcacatc cgagggcgaa  1740
ggcaagccct acgagggcac ccagaccatg agaatcaagg tggtcgaggg cggccctctc  1800
cccttcgcct tcgacatcct ggctactagc ttcctctacg gcagcaagac cttcatcaac  1860
```

-continued

```
cacacccagg gcatccccga cttcttcaag cagtccttcc ctgagggctt cacatgggag  1920
agagtcacca catacgaaga cgggggcgtg ctgaccgcta cccaggacac cagcctccag  1980
gacggctgcc tcatctacaa cgtcaagatc agaggggtga acttcacatc caacggccct  2040
gtgatgcaga agaaaacact cggctgggag gccttcaccg agacgctgta ccccgctgac  2100
ggcggcctgg aaggcagaaa cgacatggcc ctgaagctcg tgggcgggag ccatctgatc  2160
gcaaacatca agaccacata tagatccaag aaacccgcta agaacctcaa gatgcctggc  2220
gtctactatg tggactacag actggaaaga atcaaggagg ccaacaacga gacctacgtc  2280
gagcagcacg aggtggcagt ggccagatac tgcgacctcc ctagcaaact ggggcacaag  2340
cttaattaag ggcccgttta aacccgctga tcagcctcga ctgtgccttc ta          2392

SEQ ID NO: 41          moltype = DNA  length = 1870
FEATURE                Location/Qualifiers
source                 1..1870
                       mol_type = other DNA
                       organism = synthetic construct
SEQUENCE: 41
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaagaa ttccgcgtgg cgctggcttc cttgccagcg  840
ccacgcgact agtgccacaa acttctctct gctaaagcaa gcaggtgatg ttgaagaaaa  900
cccagggcct ggagggtccg agggcagggg aagtctccta acatgcgggg acgtggagga  960
aaatcccggc ccatccggat atccctacga tgtgcccgat tacgctcata tggtgagcaa  1020
gggcgaggag gataacatgg cctctctccc agcgacacat gagttacaca tctttggctc  1080
catcaacggt gtggactttg acatggtggg tcagggcacc ggcaatccaa atgatggtta  1140
tgaggagtta aacctgaagt ccaccaaggg tgacctccag ttctcccccct ggattctggt  1200
ccctcatatc gggtatggct tccatcagta cctgccctac cctgacggga tgtcgccttt  1260
ccaggccgcc atggtagatg gcagcggata ccaagtccat cgcacaatgc agtttgaaga  1320
tggtgcctcc cttactgtta actaccgcta cacctacgag ggaagccaca tcaaaggaga  1380
ggcccaggtg aaggggactg gtttccctgc tgacggtcct gtgatgacca actcgctgac  1440
cgctgcggac tggtgcaggt cgaagaagac ttaccccaac gacaaaacca tcatcagtac  1500
ctttaagtgg agttacacca ctggaaatgg caagagatac cggagcactg cgcggaccac  1560
ctacaccttt gccaagccaa tggcggctaa ctatctgaag aaccagccga tgtacgtgtt  1620
ccgtaagacg gagctcaagc actccaagac cgagctcaac ttcaaggagt ggcaaaaggc  1680
ctttaccgat gtgatgggaa tggacgagct gtataaggct agctaagcgg ccgctcgagt  1740
ctagagggcc cgcggttcga aggtaagcct atccctaacc ctctcctcgg tctcgattct  1800
acgcgtaccg gtcatcatca ccatcaccat tgagtttaaa cccgctgatc agcctcgact  1860
gtgccttcta                                                         1870

SEQ ID NO: 42          moltype = DNA  length = 1870
FEATURE                Location/Qualifiers
source                 1..1870
                       mol_type = other DNA
                       organism = synthetic construct
SEQUENCE: 42
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaagaa ttccgcgtag cgctggcttc cttgccagcg  840
ccacgcgact agtgccacaa acttctctct gctaaagcaa gcaggtgatg ttgaagaaaa  900
cccagggcct ggagggtccg agggcagggg aagtctccta acatgcgggg acgtggagga  960
aaatcccggc ccatccggat atccctacga tgtgcccgat tacgctcata tggtgagcaa  1020
gggcgaggag gataacatgg cctctctccc agcgacacat gagttacaca tctttggctc  1080
catcaacggt gtggactttg acatggtggg tcagggcacc ggcaatccaa atgatggtta  1140
tgaggagtta aacctgaagt ccaccaaggg tgacctccag ttctcccccct ggattctggt  1200
ccctcatatc gggtatggct tccatcagta cctgccctac cctgacggga tgtcgccttt  1260
ccaggccgcc atggtagatg gcagcggata ccaagtccat cgcacaatgc agtttgaaga  1320
tggtgcctcc cttactgtta actaccgcta cacctacgag ggaagccaca tcaaaggaga  1380
ggcccaggtg aaggggactg gtttccctgc tgacggtcct gtgatgacca actcgctgac  1440
```

```
cgctgcggac tggtgcaggt cgaagaagac ttaccccaac gacaaaacca tcatcagtac  1500
ctttaagtgg agttacacca ctggaaatgg caagagatac cggagcactg cgcggaccac  1560
ctacaccttt gccaagccaa tggcggctaa ctatctgaag aaccagccga tgtacgtgtt  1620
ccgtaagacg gagctcaagc actccaagac cgagctcaac ttcaaggagt ggcaaaaggc  1680
ctttaccgat gtgatgggaa tggacgagct gtataaggct agctaagcgg ccgctcgagt  1740
ctagagggcc cgcggttcga aggtaagcct atccctaacc ctctcctcgg tctcgattct  1800
acgcgtaccg gtcatcatca ccatcaccat tgagtttaaa cccgctgatc agcctcgact  1860
gtgccttcta                                                          1870

SEQ ID NO: 43          moltype = DNA  length = 1870
FEATURE                Location/Qualifiers
source                 1..1870
                       mol_type = other DNA
                       organism = synthetic construct
SEQUENCE: 43
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaagaa ttccgcgtag cgctagcttc cttgccagcg  840
ccacgcgact agtgccacaa acttctctct gctaaagcaa gcaggtgatg ttgaagaaaa  900
cccagggcct ggagggtccg agggcagggg aagtctccta acatgcgggg acgtggagga  960
aaatcccggc ccatccggat atccctacga tgtgcccgat tacgctcata tggtgagcaa  1020
gggcgaggag gataacatgg cctctctccc agcgacacat gagttacaca tctttggctc  1080
catcaacggt gtggactttg acatggtggg tcagggcacc ggcaatccaa atgatggtta  1140
tgaggagtta aacctgaagt ccaccaaggg tgacctccag ttctccccct ggattctggt  1200
ccctcatatc gggtatggct tccatcagta cctgccctac cctgacggga tgtcgccttt  1260
ccaggccgcc atggtagatg gcagcggata ccaagtccat cgcacaatgc agtttgaaga  1320
tggtgcctcc cttactgtta actaccgcta cacctacgag ggaagccaca tcaaaggaga  1380
ggcccaggtg aaggggactg gtttccctgc tgacggtcct gtgatgacca actcgctgac  1440
cgctgcggac tggtgcaggt cgaagaagac ttaccccaac gacaaaacca tcatcagtac  1500
ctttaagtgg agttacacca ctggaaatgg caagagatac cggagcactg cgcggaccac  1560
ctacaccttt gccaagccaa tggcggctaa ctatctgaag aaccagccga tgtacgtgtt  1620
ccgtaagacg gagctcaagc actccaagac cgagctcaac ttcaaggagt ggcaaaaggc  1680
ctttaccgat gtgatgggaa tggacgagct gtataaggct agctaagcgg ccgctcgagt  1740
ctagagggcc cgcggttcga aggtaagcct atccctaacc ctctcctcgg tctcgattct  1800
acgcgtaccg gtcatcatca ccatcaccat tgagtttaaa cccgctgatc agcctcgact  1860
gtgccttcta                                                          1870

SEQ ID NO: 44          moltype = DNA  length = 1888
FEATURE                Location/Qualifiers
source                 1..1888
                       mol_type = other DNA
                       organism = synthetic construct
SEQUENCE: 44
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaagaa ttccgcgtag cgctggcttt gccagcgcca  840
cgcgaaacat gaggatcacc catgtactag tgccacaaac ttctctctgc taaagcaagc  900
aggtgatgtt gaagaaaacc cagggcctgg agggtccgag ggcaggggaa gtctcctaac  960
atgcggggac gtggaggaaa atcccggccc atccggatat ccctacgatg tgcccgatta  1020
cgctcatatg gtgagcaagg gcgaggagga taacatggcc tctctcccag cgacacatga  1080
gttacacatc tttggctcca tcaacggtgt ggactttgac atggtgggtc agggcaccgg  1140
caatccaaat gatggttatg aggagttaaa cctgaagtcc accaagggtg acctccagtt  1200
ctcccccctgg attctggtcc ctcatatcgg gtatggcttc catcagtacc tgccctaccc  1260
tgacgggatg tcgcctttcc aggccgccat ggtagatggc agcggatacc aagtccatcg  1320
cacaatgcag tttgaagatg gtgcctccct tactgttaac taccgctaca cctacgaggg  1380
aagccacatc aaaggagagg cccaggtgaa ggggactggt ttccctgctg acggtcctgt  1440
gatgaccaac tcgctgaccg ctgcggactg gtgcaggtcg aagaagactt accccaacga  1500
```

```
caaaaccatc atcagtacct ttaagtggag ttacaccact ggaaatggca agagataccg  1560
gagcactgcg cggaccacct acacctttgc caagccaatg gcggctaact atctgaagaa  1620
ccagccgatg tacgtgttcc gtaagacgga gctcaagcac tccaagaccg agctcaactt  1680
caaggagtgg caaaaggcct ttaccgatgt gatgggaatg gacgagctgt ataaggctag  1740
ctaagcggcc gctcgagtct agagggcccg cggttcgaag gtaagcctat ccctaaccct  1800
ctcctcggtc tcgattctac gcgtaccggt catcatcacc atcaccattg agtttaaacc  1860
cgctgatcag cctcgactgt gccttcta                                     1888

SEQ ID NO: 45          moltype = DNA  length = 1888
FEATURE                Location/Qualifiers
source                 1..1888
                       mol_type = other DNA
                       organism = synthetic construct
SEQUENCE: 45
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaagaa ttccgcgtag cgctagcttt gccagcgcca  840
cgcgaaacat gaggatcacc catgtactag tgccacaaac ttctctctgc taaagcaagc  900
aggtgatgtt gaagaaaacc cagggcctgg agggtccgag ggcaggggaa gtctcctaac  960
atgcggggac gtggaggaaa atcccggccc atccggatat ccctacgatg tgcccgatta  1020
cgctcatatg gtgagcaagg gcgaggagga taacatggcc tctctcccag cgacacatga  1080
gttacacatc tttggctcca tcaacggtgt ggactttgac atggtgggtc agggcaccgg  1140
caatccaaat gatggttatg aggagttaaa cctgaagtcc accaagggtg acctccagtt  1200
ctccccctgg attctggtcc ctcatatcgg gtatggcttc catcagtacc tgccctaccc  1260
tgacgggatg tcgcctttcc aggccgccat ggtagatggc agcggatacc aagtccatcg  1320
cacaatgcag tttgaagatg gtgcctccct tactgttaac taccgctaca cctacgaggg  1380
aagccacatc aaaggagagg cccaggtgaa ggggactggt ttccctgctg acggtcctgt  1440
gatgaccaac tcgctgaccg ctgcggactg gtgcaggtcg aagaagactt accccaacga  1500
caaaaccatc atcagtacct ttaagtggag ttacaccact ggaaatggca agagataccg  1560
gagcactgcg cggaccacct acacctttgc caagccaatg gcggctaact atctgaagaa  1620
ccagccgatg tacgtgttcc gtaagacgga gctcaagcac tccaagaccg agctcaactt  1680
caaggagtgg caaaaggcct ttaccgatgt gatgggaatg gacgagctgt ataaggctag  1740
ctaagcggcc gctcgagtct agagggcccg cggttcgaag gtaagcctat ccctaaccct  1800
ctcctcggtc tcgattctac gcgtaccggt catcatcacc atcaccattg agtttaaacc  1860
cgctgatcag cctcgactgt gccttcta                                     1888

SEQ ID NO: 46          moltype = DNA  length = 2044
FEATURE                Location/Qualifiers
source                 1..2044
                       mol_type = other DNA
                       organism = synthetic construct
SEQUENCE: 46
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaggagcag acgatatggc gtcgctccaa  1020
tactagtgcc acaaacttct ctctgctaaa gcaagcaggt gatgttgaag aaaacccagg  1080
gcctggaggg tccgagggca ggggaagtct cctaacatgc ggggacgtgg aggaaaatcc  1140
cggcccatcc ggatatccct acgatgtgcc cgattacgct catatggtga gcaagggcga  1200
ggaggataac atggcctctc tcccagcgac acatgagtta cacatctttg gctccatcaa  1260
cggtgtggac tttgacatgg tgggtcaggg caccggcaat ccaaatgatg gttatgagga  1320
gttaaacctg aagtccacca agggtgacct ccagttctcc ccctggattc tggtccctca  1380
tatcgggtat ggcttccatc agtacctgcc ctaccctgac gggatgtcgc ctttccaggc  1440
cgccatggta gatggcagcg gataccaagt ccatcgcaca atgcagtttg aagatggtgc  1500
ctcccttact gttaactacc gctacaccta cgagggaagc cacatcaaag gagaggccca  1560
```

```
ggtgaagggg actggtttcc ctgctgacgg tcctgtgatg accaactcgc tgaccgctgc  1620
ggactggtgc aggtcgaaga agacttaccc caacgacaaa accatcatca gtacctttaa  1680
gtggagttac accactggaa atggcaagag ataccggagc actgcgcgga ccacctacac  1740
ctttgccaag ccaatggcgg ctaactatct gaagaaccag ccgatgtacg tgttccgtaa  1800
gacggagctc aagcactcca agaccgagct caacttcaag gagtggcaaa aggcctttac  1860
cgatgtgatg ggaatggacg agctgtataa ggctagctaa gcggccgctc gagtctagag  1920
ggcccgcggt tcgaaggtaa gcctatccct aaccctctcc tcggtctcga ttctacgcgt  1980
accggtcatc atcaccatca ccattgagtt taaacccgct gatcagcctc gactgtgcct  2040
tcta                                                               2044
```

```
SEQ ID NO: 47           moltype = DNA  length = 2038
FEATURE                 Location/Qualifiers
source                  1..2038
                        mol_type = other DNA
                        organism = synthetic construct
SEQUENCE: 47
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc ggtaagggcc ctgaagaagg gcccaactag  1020
tgccacaaac ttctctctgc taaagcaagc aggtgatgtt gaagaaaacc cagggcctgg  1080
agggtccgag ggcaggggaa gtctcctaac atgcggggac gtggaggaaa atcccggccc  1140
atccggatat ccctacgatg tgcccgatta cgctcatatg gtgagcaagg gcgaggagga  1200
taacatggcc tctctcccag cgacacatga gttacacatc tttggctcca tcaacggtgt  1260
ggactttgac atggtgggtc agggcaccgg caatccaaat gatggttatg aggagttaaa  1320
cctgaagtcc accaagggtg acctccagtt ctccccctgg attctggtcc ctcatatcgg  1380
gtatggcttc catcagtacc tgccctaccc tgacgggatg tcgcctttcc aggccgccat  1440
ggtagatggc agcggatacc aagtccatcg cacaatgcag tttgaagatg gtgcctccct  1500
tactgttaac taccgctaca cctacgaggg aagccacatc aaaggagagg cccaggtgaa  1560
ggggactggt ttccctgctg acggtcctgt gatgaccaac tcgctgaccg ctgcggactg  1620
gtgcaggtcg aagaagactt accccaacga caaaaccatc atcagtacct ttaagtggag  1680
ttacaccact ggaaatggca agagataccg gagcactgcg cggaccacct acacctttgc  1740
caagccaatg gcggctaact atctgaagaa ccagccgatg tacgtgttcc gtaagacgga  1800
gctcaagcac tccaagaccg agctcaactt caaggagtgg caaaaggcct ttaccgatgt  1860
gatgggaatg gacgagctgt ataaggctag ctaagcggcc gctcgagtct agagggcccg  1920
cggttcgaag gtaagcctat ccctaaccct ctcctcggtc tcgattctac gcgtaccggt  1980
catcatcacc atcaccattg agtttaaacc cgctgatcag cctcgactgt gccttcta    2038
```

```
SEQ ID NO: 48           moltype = DNA  length = 2047
FEATURE                 Location/Qualifiers
source                  1..2047
                        mol_type = other DNA
                        organism = synthetic construct
SEQUENCE: 48
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc ggtaggctcg tctgagctca ttagctccga  1020
gccaactagt gccacaaact tctctctgct aaagcaagca ggtgatgttg aagaaaaccc  1080
agggcctgga gggtccgagg gcaggggaag tctcctaaca tgcggggacg tggaggaaaa  1140
tcccggccca tccggatatc cctacgatgt gcccgattac gctcatatgg tgagcaaggg  1200
cgaggaggat aacatggcct ctctcccagc gacacatgag ttacacatct ttggctccat  1260
caacggtgtg gactttgaca tggtgggtca gggcaccggc aatccaaatg atggttatga  1320
```

-continued

```
ggagttaaac ctgaagtcca ccaagggtga cctccagttc tccccctgga ttctggtccc  1380
tcatatcggg tatggcttcc atcagtacct gccctaccct gacgggatgt cgcctttcca  1440
ggccgccatg gtagatggca gcggatacca agtccatcgc acaatgcagt ttgaagatgg  1500
tgcctccctt actgttaact accgctacac ctacgaggga agccacatca aaggagaggc  1560
ccaggtgaag ggactggtt tccctgctga cggtcctgtg atgaccaact cgctgaccgc  1620
tgcggactgg tgcaggtcga agaagactta ccccaacgac aaaaccatca tcagtacctt  1680
taagtggagt tacaccactg gaaatggcaa gagataccgg agcactgcgc ggaccaccta  1740
cacctttgcc aagccaatgg cggctaacta tctgaagaac cagccgatgt acgtgttccg  1800
taagacggag ctcaagcact ccaagaccga gctcaacttc aaggagtggc aaaaggcctt  1860
taccgatgtg atgggaatgg acgagctgta taaggctagc taagcggccg ctcgagtcta  1920
gagggcccgc ggttcgaagg taagcctatc cctaaccctc tcctcggtct cgattctacg  1980
cgtaccggtc atcatcacca tcaccattga gtttaaaccc gctgatcagc ctcgactgtg  2040
ccttcta                                                            2047

SEQ ID NO: 49          moltype = DNA  length = 2432
FEATURE                Location/Qualifiers
source                 1..2432
                       mol_type = other DNA
                       organism = synthetic construct
SEQUENCE: 49
taatacgact cactataggg agacccaagc tggctagagg atcgaacccg gtaccgccac  60
catgtccaag acaatcgtgc ttagcgtggg agaagcaact cgaaccctca cagaaatcca  120
atcaacagcc gaccgacaga tttttgaaga gaaagtgggt cccttggttg gccggctcag  180
gctcacagcc agcttgagac agaacggagc caagactgcc tatcgagtga atctcaagct  240
ggaccaggcc gatgtagtgg acagtggttt gcccaaggtt agatacacgc aagtgtggtc  300
acacgatgtc actattgtgg caaactccac cgaggcaagc aggaagtccc tgtatgacct  360
gaccaaatct ttggtggcga cgagccaagt agaggatctg gtggtaaacc tggtgcccct  420
gggaagagcc tcaaccggtt ctgggattta cggggcagt gggagcggtg caggatctgg  480
tagtccagct gggggaggag caccgggtag cggtgggggg tctcagctgc acctgcccca  540
ggttctcgca gacgccgtat cccgccttgt actgggcaag tttggtgatc ttactgacaa  600
tttttcatct cctcatgcga ggcggaaagt actcgcaggc gtcgtcatga cgaccggaac  660
tgacgtgaaa gacgccaaag tcatctctgt ctccacgggc acaaagtgca taaacgggga  720
gtacatgagc gaccgggggc tggcactgaa tgattgtcac gctgaaataa tatctaggcg  780
atctctgctt agatttctct acactcaact cgaattgtac cttaacaaca aagatgacca  840
gaaacgcagt atatttcaga aatcagaacg cggcggattt cgacttaagg aaaacgttca  900
gttccacttg tatatcagca catccccttg cggtgacgcc cgaatctttt ccccgcacga  960
gccgatattg gaggagcccg cggacagaca tcctaatagg aaggctagag gccaacttcg  1020
gacgaagatt gaaagtggcc aggtactat cccggtgcgg tccaacgcta gtattcaaac  1080
gtgggacgga gtccttcaag gtgaacggct gttgacaatg agctgctcag acaaaatcgc  1140
gcgctggaat gtagtgggaa tccaaggcag cctcttggagc atattcgtag aacccatata  1200
tttctcatcc attattttgg gctctctgta tcatggtgac catctgtcaa gggctatgta  1260
ccaacgaatt tctaatatcg aggatcttcc tccactctat acactcaata agcctctctt  1320
gtccgggata tcaaacgctg aggcccgcca gccagggaaa gctcctaact tcagtgttaa  1380
ctggaccgtt ggtgattctg cgatagaggt catcaacgcc acgacaggta aggatgagct  1440
cggtagagcc tcacgcctgt gtaaacacgc gttgtattgt agatggatga gagtacatgg  1500
gaaggtccca tctcacttgc tccgaagcaa gatcactaag cctaatgtgt atcatgagtc  1560
aaaactcgcg gctaaagaat accaggcagc caaagctcga ctttttacag cttttattaa  1620
ggcagggctc ggggcatggg tcgagaagcc gaccgagcag gaccaattct ctctgacggg  1680
gagcggatcc agcgagctga ttaaggagaa catgcacatg aagctgtaca tggagggcac  1740
cgtggacaac catcacttca agtgcacatc cgagggcgaa ggcaagccct acgagggcac  1800
ccagaccatg agaatcaagg tggtcgaggg cggccctctc cccttcgcct tcgacatcct  1860
ggctactagc ttcctctacg gcagcaagac cttcatcaac cacacccagg gcatccccga  1920
cttcttcaag cagtccttcc ctgagggctt cacatgggag agagtcacca catacgaaga  1980
cgggggcgtg ctgaccgcta cccaggacac cagcctccag gacggctgcc tcatctacaa  2040
cgtcaagatc agaggggtga acttcacatc caacggccct gtgatgcaga agaaaacact  2100
cggctgggag gccttcaccg agacgctgta ccccgctgac ggcggcctgg aaggcagaaa  2160
cgacatggcc ctgaagctcg tgggcgggag ccatctgatc gcaaacatca agaccacata  2220
tagatccaag aaacccgcta agaacctcaa gatgcctggc gtctactatg tggactacag  2280
actggaaaga atcaaggagg ccaacaacga gacctacgtc gagcagcacg aggtggcagt  2340
ggccagatac tgcgacctcc ctagcaaact ggggcacaag cttaattaag ggcccgttta  2400
aacccgctga tcagcctcga ctgtgccttc ta                                2432

SEQ ID NO: 50          moltype = DNA  length = 2129
FEATURE                Location/Qualifiers
source                 1..2129
                       mol_type = other DNA
                       organism = synthetic construct
SEQUENCE: 50
taatacgact cactataggg agacccaagc tggctagagg atcgaacccg gtaccgccac  60
catggccgac gcacaaacac gacgacgtga gcgtcgcgct gagaaacaag ctcaatggaa  120
agctgcaaac accggttctg ggatttacgg gggcagtggg agcggtgcag gatctggtag  180
tccagctggg ggaggagcac cgggtagcgg tggggggtct cagctgcacc tgccccaggt  240
tctcgcagac gccgtatccc gccttgtact gggcaagttt ggtgatctta ctgacaattt  300
ttcatctcct catgcgaggc ggaaagtact cgcaggcgtc gtcatgacga ccggaactga  360
cgtgaaagac gccaaagtca tctctgtctc cacgggcaca aagtgcataa acggggagta  420
catgagcgac cgggggctgg cactgaatga ttgtcacgct gaaataatat ctaggcgatc  480
tctgcttaga tttctctaca ctcaactcga attgtacctt aacaacaaag atgaccagaa  540
acgcagtata tttcagaaat cagaacgcgg cggatttcga cttaaggaaa acgttcagtt  600
ccacttgtat atcagcacat ccccttgcgg tgacgcccga atcttttccc cgcacgagcc  660
```

```
gatattggag gagcccgcgg acagacatcc taataggaag gctagaggcc aacttcggac  720
gaagattgaa agtggccagg gtactatccc ggtgcggtcc aacgctagta ttcaaacgtg  780
ggacggagtc cttcaaggtg aacggctgtt gacaatgagc tgctcagaca aaatcgcgcg  840
ctggaatgta gtgggaatcc aaggcagcct cttgagcata ttcgtagaac ccatatattt  900
ctcatccatt attttgggct ctctgtatca tggtgaccat ctgtcaaggg ctatgtacca  960
acgaatttct aatatcgagg atcttcctcc actctataca ctcaataagc ctctcttgtc  1020
cgggatatca aacgctgagg cccgccagcc agggaaagct cctaacttca gtgttaactg  1080
gaccgttggt gattctgcga tagaggtcat caacgccacg acaggtaagg atgagctcgg  1140
tagagcctca cgcctgtgta aacacgcgtt gtattgtaga tggatgagag tacatgggaa  1200
ggtcccatct cacttgctcc gaagcaagat cactaagcct aatgtgtatc atgagtcaaa  1260
actcgcggct aaagaatacc aggcagccaa agctcgactt tttacagctt ttattaaggc  1320
agggctcggg gcatgggtcg agaagccgac cgagcaggac caattctctc tgacggggag  1380
cggatccagc gagctgatta aggagaacat gcacatgaag ctgtacatgg agggcaccgt  1440
ggacaaccat cacttcaagt gcacatccga gggcgaaggc aagccctacg agggcaccca  1500
gaccatgaga atcaaggtgg tcgagggcgg ccctctcccc ttcgccttcg acatcctggc  1560
tactagcttc ctctacggca gcaagacctt catcaaccac acccagggca tccccgactt  1620
cttcaagcag tccttccctg agggcttcac atgggagaga gtcaccacat acgaagacgg  1680
gggcgtgctg accgctaccc aggacaccag cctccaggac ggctgcctca tctacaacgt  1740
caagatcaga ggggtgaact tcacatccaa cggccctgtg atgcagaaga aaacactcgg  1800
ctgggaggcc ttcaccgaga cgctgtaccc cgctgacggc ggcctggaag gcagaaacga  1860
catggccctg aagctcgtgg gcgggagcca tctgatcgca aacatcaaga ccacatatag  1920
atccaagaaa cccgctaaga acctcaagat gcctggcgtc tactatgtgg actacagact  1980
ggaaagaatc aaggaggcca acaacgagac ctacgtcgag cagcacgagg tggcagtggc  2040
cagatactgc gacctcccta gcaaactggg gcacaagctt aattaagggc ccgtttaaac  2100
ccgctgatca gcctcgactg tgccttcta                                   2129
```

```
SEQ ID NO: 51          moltype = DNA  length = 2117
FEATURE                Location/Qualifiers
source                 1..2117
                       mol_type = other DNA
                       organism = synthetic construct
SEQUENCE: 51
taatacgact cactataggg agacccaagc tggctagagg atcgaacccg gtaccgccac  60
catggcctct ggtcctcgtc cccgtggtac tcgtggtaaa ggtcgccgta ttcgtcgcac  120
cggttctggg atttacgggg gcagtgggag cggtgcagga tctggtagtc cagctggggg  180
aggagcaccg ggtagcggtg gggggtctca gctgcacctg ccccaggttc tcgcagacgc  240
cgtatcccgc cttgtactgg gcaagtttgg tgatcttact gacaattttt catctcctca  300
tgcgaggcgg aaagtactcg caggcgtcgt catgacgacc ggaactgacg tgaaagacgc  360
caaagtcatc tctgtctcca cgggcacaaa gtgcataaac ggggagtaca tgagcgaccg  420
ggggctggca ctgaatgatt gtcacgctga aataatatct aggcgatctc tgcttagatt  480
tctctacact caactcgaat tgtaccttaa caacaaagat gaccagaaac gcagtatatt  540
tcagaaatca gaacgcggcg gatttcgact taaggaaaac gttcagttcc acttgtatat  600
cagcacatcc ccttgcggtg acgcccgaat cttttccccg cacgagccga tattggagga  660
gcccgcggac agacatccta ataggaaggc tagaggccaa cttcggacga agattgaaag  720
tggccagggt actatcccgg tgcggtccaa cgctagtatt caaacgtggg acggagtcct  780
tcaaggtgaa cggctgttga caatgagctg ctcagacaaa atcgcgcgct ggaatgtagt  840
gggaatccaa ggcagcctct tgagcatatt cgtagaaccc atatatttct catccattat  900
tttgggctct ctgtatcatg gtgaccatct gtcaagggct atgtaccaac gaatttctaa  960
tatcgaggat cttcctccac tctatacact caataagcct ctcttgtccg ggatatcaaa  1020
cgctgaggcc cgccagccag ggaaagctcc taacttcagt gttaactgga ccgttggtga  1080
ttctgcgata gaggtcatca acgccacgac aggtaaggat gagctcggta gagcctcacg  1140
cctgtgtaaa cacgcgttgt attgtagatg gatgagagta catgggaagg tcccatctca  1200
cttgctccga agcaagatca ctaagcctaa tgtgtatcat gagtcaaaac tcgcggctaa  1260
agaataccag gcagccaaag ctcgactttt tacagctttt attaaggcag ggctcggggc  1320
atgggtcgag aagccgaccg agcaggacca attctctctg acggggagcg gatccagcga  1380
gctgattaag gagaacatgc acatgaagct gtacatggag ggcaccgtgg acaaccatca  1440
cttcaagtgc acatccgagg gcgaaggcaa gccctacgag ggcacccaga ccatgagaat  1500
caaggtggtc gagggcggcc ctctcccctt cgccttcgac atcctggcta ctagcttcct  1560
ctacggcagc aagaccttca tcaaccacac ccagggcatc cccgacttct tcaagcagtc  1620
cttccctgag ggcttcacat gggagagagt caccacatac gaagacgggg gcgtgctgac  1680
cgctacccag gacaccagcc tccaggacgg ctgcctcatc tacaacgtca agatcagagg  1740
ggtgaacttc acatccaacg gccctgtgat gcagaagaaa acactcggct gggaggcctt  1800
caccgagacg ctgtaccccg ctgacggcgg cctggaaggc agaaacgaca tggccctgaa  1860
gctcgtgggc gggagccatc tgatcgcaaa catcaagacc acatatagat ccaagaaacc  1920
cgctaagaac ctcaagatgc ctggcgtcta ctatgtggac tacagactgg aaagaatcaa  1980
ggaggccaac aacgagacct acgtcgagca gcacgaggtg gcagtggcca gatactgcga  2040
cctccctagc aaactggggc acaagcttaa ttaagggccc gtttaaaccc gctgatcagc  2100
ctcgactgtg ccttcta                                                 2117
```

```
SEQ ID NO: 52          moltype = DNA  length = 2835
FEATURE                Location/Qualifiers
source                 1..2835
                       mol_type = other DNA
                       organism = synthetic construct
SEQUENCE: 52
cggcagtgaa aaaaatgctt tatttgtgaa atttgtgatg ctattgcttt atttgtaacc  60
attataagct gcaataaaca agttaacaac aacaattgca ttcattttat gtttcaggtt  120
cagggggagg tgtgggaggt tttttaaagc aagtaaaacc tctacaaatg tggtatggct  180
gattatgatc ctctagactg cagcctcagg agatctgggc ccctacttgt acagctcgtc  240
```

-continued

```
catgccgtac aggaacaggt ggtggcggcc ctcggagcgc tcgtactgtt ccacgatggt  300
gtagtcctcg ttgtgggagg tgatgtccag cttggtgtcc acgtagtagt agccgggcag  360
ttgcacgggc ttcttggcca tgtagatggt cttgaactcc accaggtagt ggccgccgtc  420
cttcagcttc agggcctggt ggatctcgcc cttcagcacg ccgtcgcggg ggtacaggcg  480
ctcggtggag gcctcccagc ccatggtctt cttctgcatt acggggccgt cgggggggaa  540
gttggtgccg cgcatcttca ccttgtagat cagcgtgccg tcctgcaggg aggagtcctg  600
ggtcacggtc accagaccgc cgtcctcgaa gttcatcacg cgctcccact tgaagccctc  660
ggggaaggac agcttcttgt aatcggggat gtcggcgggg tgcttcacgt acgccttgga  720
gccgtacatg aactgggggg acaggatgtc ccaggcgaag ggcagggggc cgcccttggt  780
caccttcagc ttggcggtct gggtgccctc gtaggggcgg ccctcgccct cgccctcgat  840
ctcgaactcg tggccgttca tggagccctc catgcgcacc ttgaagcgca tgaactcttt  900
gatgacctcc tcgcccttgc tcaccatggt ggcgaattct ccaggcgatc tgacggttca  960
ctaaacgagc tctgcttata taggcctccc accgtacacg ccacctcgac atactcgagt  1020
agttattaat agtaatcaat tacggggtca ttagttcata gcccatatat ggagttccgc  1080
gttacataac ttacggtaaa tggcccgcct ggctgaccgc ccaacgaccc ccgcccattg  1140
acgtcaataa tgacgtatgt tcccatagta acgccaatag ggactttcca ttgacgtcaa  1200
tgggtggagt atttacggta aactgcccac ttggcagtac atcaagtgta tcatatgcca  1260
agtacgcccc ctattgacgt caatgacggt aaatggcccg cctggcatta tgcccagtac  1320
atgaccttat gggactttcc tacttggcag tacatctacg tattagtcat cgctattacc  1380
atggtgatgc ggttttggca gtacatcaat gggcgtggat agcggtttga ctcacgggga  1440
tttccaagtc tccaccccat tgacgtcaat gggagtttgt tttggcacca aaatcaacgg  1500
gactttccaa aatgtcgtaa caactccgcc ccattgacgc aaatgggcgg taggcgtgta  1560
cggtgggagg tctatataag cagagctggt ttagtgaacc gtcagatccg ctagggatcc  1620
tctagtcagc tgacgcgtgc tagcgatatc ggcgcgccag catttaaatc tgtacagacc  1680
ggtcgccacc atggtgagca agggcgagga gctgttcacc ggggtggtgc ccatcctggt  1740
cgagctggac ggcgacgtaa acggccacaa gttcagcgtg tccggcgagg gcgagggcga  1800
tgccacctac ggcaagctga ccctgaagtt catctgcacc accggcaagc tgcccgtgcc  1860
ctggcccacc ctcgtgacca ccctgaccta cggcgtgcag tgcttcagcc gctaccccga  1920
ccacatgaag cagcacgact tcttcaagtc cgccatgccc gaaggctacg tccaggagcg  1980
caccatcttc ttcaaggacg acggcaacta caagacccgc gccgaggtga agttcgaggg  2040
cgacaccctg gtgaaccgca tcgagctgaa gggcatcgac ttcaaggagg acggcaacat  2100
cctggggcac aagctggagt acaactacaa cagccacaac gtctatatca tggccgacaa  2160
gcagaagaac ggcatcaagg tgaacttcaa gatccgccac aacatcgagg acggcagcgt  2220
gcagctcgcc gaccactacc agcagaacac ccccatcggc gacggccccg tgctgctgcc  2280
cgacaaccac tacctgagca cccagtccgc cctgagcaaa gaccccaacg agaagcgcga  2340
tcacatggtc ctgctggagt tcgtgaccgc cgccgggatc actctcggca tggacgagct  2400
gtacaagaag cttagccatg gcttcccgcc ggaggtggag gagcaggatg atggcacgct  2460
gcccatgtct tgtgcccagg agagcgggat ggaccgtcac cctgcagcct gtgcttctgc  2520
ccggatcaac gtgtagcgct agctttgcca gcgccacacg aaacatgagg atcacccatg  2580
tcggccgcac tcctcaggtg caggctgcct atcagaaggt ggtggctggt gtggccaatg  2640
ccctggctca caaataccac tgagatcttt ttccctctgc caaaaattat ggggacatca  2700
tgaagcccct tgggcatctg acttctggct aataaaggaa atttattttc attgcaatag  2760
tgtgttggaa ttttttgtgt ctctcactcg gaaggacata tgggagggca aatcatttaa  2820
aacatcagaa tgagt                                                  2835
```

```
SEQ ID NO: 53           moltype = DNA  length = 2482
FEATURE                 Location/Qualifiers
source                  1..2482
                        mol_type = other DNA
                        organism = synthetic construct
SEQUENCE: 53
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg gtcgggcacc  960
ggtgctccac ccaatctctg ggcagcgcag cgctacggcc gtgagctcag aaggatgtcc  1020
gatgagttcg tcgacagaca tcctaatagg aaggctagag gccaacttcg gacgaagatt  1080
gaaagtggcc agggtactat cccggtgcgg tccaacgcta gtattcaaac gtgggacgga  1140
gtccttcaag gtgaacggct gttgacaatg agctgctcag acaaaatcgc gcgctggaat  1200
gtagtgggaa tccaaggcag cctcttgagc atattcgtag aacccatata tttctcatcc  1260
attattttgg gctctctgta tcatggtgac catctgtcaa gggctatgta ccaacgaatt  1320
tctaatatcg aggatcttcc tccactctat acactcaata agcctctctt gtccgggata  1380
tcaaacgctg aggcccgcca gccagggaaa gctcctaact tcagtgttaa ctggaccgtt  1440
ggtgattctg cgatagaggt catcaacgcc acgacaggta aggatgagct cggtagagcc  1500
tcacgcctgt gtaaacacgc gttgtattgt agatggatga gagtacatgg gaaggtccca  1560
tctcacttgc tccgaagcaa gatcactaag cctaatgtgt atcatgagtc aaaactcgcg  1620
gctaaagaat accaggcagc caaagctcga ctttttacag cttttattaa ggcagggctc  1680
```

```
ggggcatggg tcgagaagcc gaccgagcag gaccaattct ctctgacggg gagcggatcc  1740
agcgagctga ttaaggagaa catgcacatg aagctgtaca tggagggcac cgtggacaac  1800
catcacttca agtgcacatc cgagggcgaa ggcaagccct acgagggcac ccagaccatg  1860
agaatcaagg tggtcgaggg cggccctctc cccttcgcct tcgacatcct ggctactagc  1920
ttcctctacg gcagcaagac cttcatcaac cacacccagg gcatccccga cttcttcaag  1980
cagtccttcc ctgagggctt cacatgggag agagtcacca catacgaaga cgggggcgtg  2040
ctgaccgcta cccaggacac cagcctccag gacggctgcc tcatctacaa cgtcaagatc  2100
agaggggtga acttcacatc caacggccct gtgatgcaga agaaaacact cggctgggag  2160
gccttcaccg agacgctgta ccccgctgac ggcggcctgg aaggcagaaa cgacatggcc  2220
ctgaagctcg tgggcgggag ccatctgatc gcaaacatca agaccacata tagatccaag  2280
aaacccgcta agaacctcaa gatgcctggc gtctactatg tggactacag actggaaaga  2340
atcaaggagg ccaacaacga gacctacgtc gagcagcacg aggtggcagt ggccagatac  2400
tgcgacctcc ctagcaaact ggggcacaag cttaattaag ggcccgttta aacccgctga  2460
tcagcctcga ctgtgccttc ta                                          2482

SEQ ID NO: 54          moltype = DNA  length = 3103
FEATURE                Location/Qualifiers
source                 1..3103
                       mol_type = other DNA
                       organism = synthetic construct
SEQUENCE: 54
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg gtcgggcacc  960
ggtgctccac ccaatctctg ggcagcgcag cgctacggcc gtgagctcag aaggatgtcc  1020
gatgagttcg tcgacagaca tcctaatagg aaggctagag gccaacttcg gacgaagatt  1080
gaaagtggcc agggtactat cccggtgcgg tccaacgcta gtattcaaac gtgggacgga  1140
gtccttcaag gtgaacggct gttgacaatg agctgctcag acaaaaatcgc gcgctggaat  1200
gtagtgggaa tccaaggcag cctcttgagc atattcgtag aacccatata tttctcatcc  1260
attattttgg gctctctgta tcatggtgac catctgtcaa gggctatgta ccaacgaatt  1320
tctaatatcg aggatcttcc tccactctat acactcaata agcctctctt gtccgggata  1380
tcaaacgctg aggcccgcca gccagggaaa gctcctaact tcagtgttaa ctggaccgtt  1440
ggtgattctg cgatagaggt catcaacgcc acgacaggta aggatgagct cggtagagcc  1500
tcacgcctgt gtaaacacgc gttgtattgt agatggatga gagtacatgg gaaggtccca  1560
tctcacttgc tccgaagcaa gatcactaag cctaatgtgt atcatgagtc aaaactcgcg  1620
gctaaagaat accaggcagc caaagctcga ctttttacag cttttattaa ggcagggctc  1680
ggggcatggg tcgagaagcc gaccgagcag gaccaattct ctctgacggg gagcgcggcc  1740
ggaggtagcg gcggaagcgc ggccgcttca agtaaccggg agctggtggt tgactttctc  1800
tcctacaagc tttcccagaa aggatacagc tggagtcagt ttagtgatgt ggaagagaac  1860
aggactgagg ccccagaagg gactgaatcg gagatggaga cccccagtgc catcaatggc  1920
aacccatcct ggcacctggc agacagcccc gcggtgaatg gagccactgg ccacagcagc  1980
agtttggatg cccgggaggt gatccccatg gcagcagtaa agcaagcgct gagggaggca  2040
ggcgacgagt ttgaactgcg gtaccggcgg gcattcagtg acctgacatc ccagctccac  2100
atcaccccag ggacagcata tcagagcttt gaacaggtag tgaatgaact cttccgggat  2160
ggggtaaact ggggtcgcat tgtggccttt ttctccttcg gcggggcact gtgcgtggaa  2220
agcgtagaca aggagatgca ggtattggtg agtcggatcg cagcttggat ggccacttac  2280
ctgaatgacc acctagagcc ttggatccag gagaacggcg gctgggatac ttttgtggaa  2340
ctctatggga acaatggatc cagcgagctg attaaggaga acatgcacat gaagctgtac  2400
atggagggca ccgtggacaa ccatcacttc aagtgcacat ccgagggcga aggcaagccc  2460
tacgagggca cccagaccat gagaatcaag gtggtcgagg gcggccctct ccccttcgcc  2520
ttcgacatcc tggctactag cttcctctac ggcagcaaga ccttcatcaa ccacacccag  2580
ggcatccccg acttcttcaa gcagtccttc cctgagggct tcacatggga gagagtcacc  2640
acatacgaag acgggggcgt gctgaccgct acccaggaca ccagcctcca ggacggctgc  2700
ctcatctaca acgtcaagat cagaggggtg aacttcacat ccaacggccc tgtgatgcag  2760
aagaaaacac tcggctggga ggccttcacc gagacgctgt accccgctga cggcggcctg  2820
gaaggcagaa acgacatggc cctgaagctc gtgggcggga gccatctgat cgcaaacatc  2880
aagaccacat atagatccaa gaaacccgct aagaacctca agatgcctgg cgtctactat  2940
gtggactaca gactggaaag aatcaaggag gccaacaacg agacctacgt cgagcagcac  3000
gaggtggcag tggccagata ctgcgacctc cctagcaaac tggggcacaa gcttaattaa  3060
gggcccgttt aaacccgctg atcagcctcg actgtgcctt cta                   3103

SEQ ID NO: 55          moltype = DNA  length = 2497
FEATURE                Location/Qualifiers
source                 1..2497
                       mol_type = other DNA
                       organism = synthetic construct
```

SEQUENCE: 55
taatacgact cactataggg agacccaagc tggctagagg atcgaaccct taaggccacc 60
atggcgtcca atttcactca gtttgtgctg gttgacaacg gcgggaccgg ggacgttacg 120
gtagccccct caaactttgc caacggtata gcggagtgga taagcagcaa ttctaggagt 180
caagcataca aagttacatg cagcgtgcgc caatctagcg ctcagaatcg caagtacacc 240
attaaagtag aggtccccaa gggagcctgg agaagctatc ttaacatgga gttgaccata 300
ccaatcttcg ctaccaactc tgactgtgaa ctcattgtga aagccatgca aggtctgctc 360
aaggatggta acccaattcc gtccgctatc gctgccaact ctgggattta cgggggcagt 420
gggagcggtg caggatctgg tagtccagct gggggaggag caccgggtag cggtgggggg 480
tctcagctgc acctgcccca ggttctcgca gacgccgtat cccgccttgt actgggcaag 540
tttggtgatc ttactgacaa tttttcatct cctcatgcga ggcggaaagt actcgcaggc 600
gtcgtcatga cgaccggaac tgacgtgaaa gacgccaaag tcatctctgt ctccacgggc 660
acaaagtgca taaacgggga gtacatgagc gaccgggggc tggcactgaa tgattgtcac 720
gctgaaataa tatctaggcg atctctgctt agatttctct acactcaact cgaattgtac 780
cttaacaaca aagatgacca gaaacgcagt atatttcaga aatcagaacg cggcggattt 840
cgacttaagg aaaacgttca gttccacttg tatatcagca catccccttg cggtgacgcc 900
cgaatctttt ccccgcacga gccgatattg gaggagcccg cggctagcgg gtcgggctct 960
ggagacatgc ggccagagat ttggatcgca caggaactga ggcgcattgg cgatgagttc 1020
aatgcatact atgcccgaag aaccggtgac agacatccta ataggaaggc tagaggccaa 1080
cttcggacga agattgaaag tggccagggt actatcccgg tgcggtccaa cgctagtatt 1140
caaacgtggg acggagtcct tcaaggtgaa cggctgttga caatgagctg ctcagacaaa 1200
atcgcgcgct ggaatgtagt gggaatccaa ggcagcctct tgagcatatt cgtagaaccc 1260
atatatttct catccattat tttgggctct ctgtatcatg gtgaccatct gtcaagggct 1320
atgtaccaac gaatttctaa tatcgaggat cttcctccac tctatacact caataagcct 1380
ctcttgtccg ggatatcaaa cgctgaggcc cgccagccag ggaaagctcc taacttcagt 1440
gttaactgga ccgttggtga ttctgcgata gaggtcatca acgccacgac aggtaaggat 1500
gagctcggta gagcctcacg cctgtgtaaa cacgcgttgt attgtagatg gatgagagta 1560
catgggaagg tcccatctca cttgctccga agcaagatca ctaagcctaa tgtgtatcat 1620
gagtcaaaac tcgcggctaa agaataccag gcagccaaag ctcgactttt tacagctttt 1680
attaaggcag ggctcggggc atgggtcgag aagccgaccg agcaggacca attctctctg 1740
acggggagcg gatccagcga gctgattaag gagaacatgc acatgaagct gtacatggag 1800
ggcaccgtgg acaaccatca cttcaagtgc acatccgagg gcgaaggcaa gccctacgag 1860
ggcacccaga ccatgagaat caaggtggtc gagggcggcc ctctcccctt cgccttcgac 1920
atcctggcta ctagcttcct ctacggcagc aagaccttca tcaaccacac ccagggcatc 1980
cccgacttct tcaagcagtc cttccctgag ggcttcacat gggagagagt caccacatac 2040
gaagacgggg gcgtgctgac cgctacccag gacaccagcc tccaggacgg ctgcctcatc 2100
tacaacgtca agatcagagg ggtgaacttc acatccaacg gccctgtgat gcagaagaaa 2160
acactcggct gggaggcctt caccgagacg ctgtaccccg ctgacggcgg cctggaaggc 2220
agaaacgaca tggccctgaa gctcgtgggc gggagccatc tgatcgcaaa catcaagacc 2280
acatatagat ccaagaaacc cgctaagaac ctcaagatgc ctggcgtcta ctatgtggac 2340
tacagactgg aaagaatcaa ggaggccaac aacgagacct acgtcgagca gcacgaggtg 2400
gcagtggcca gatactgcga cctccctagc aaactggggc acaagcttaa ttaagggccc 2460
gtttaaaccc gctgatcagc ctcgactgtg ccttcta 2497

SEQ ID NO: 56 moltype = DNA length = 3118
FEATURE Location/Qualifiers
source 1..3118
mol_type = other DNA
organism = synthetic construct SEQUENCE: 56
taatacgact cactataggg agacccaagc tggctagagg atcgaaccct taaggccacc 60
atggcgtcca atttcactca gtttgtgctg gttgacaacg gcgggaccgg ggacgttacg 120
gtagccccct caaactttgc caacggtata gcggagtgga taagcagcaa ttctaggagt 180
caagcataca aagttacatg cagcgtgcgc caatctagcg ctcagaatcg caagtacacc 240
attaaagtag aggtccccaa gggagcctgg agaagctatc ttaacatgga gttgaccata 300
ccaatcttcg ctaccaactc tgactgtgaa ctcattgtga aagccatgca aggtctgctc 360
aaggatggta acccaattcc gtccgctatc gctgccaact ctgggattta cgggggcagt 420
gggagcggtg caggatctgg tagtccagct gggggaggag caccgggtag cggtgggggg 480
tctcagctgc acctgcccca ggttctcgca gacgccgtat cccgccttgt actgggcaag 540
tttggtgatc ttactgacaa tttttcatct cctcatgcga ggcggaaagt actcgcaggc 600
gtcgtcatga cgaccggaac tgacgtgaaa gacgccaaag tcatctctgt ctccacgggc 660
acaaagtgca taaacgggga gtacatgagc gaccgggggc tggcactgaa tgattgtcac 720
gctgaaataa tatctaggcg atctctgctt agatttctct acactcaact cgaattgtac 780
cttaacaaca aagatgacca gaaacgcagt atatttcaga aatcagaacg cggcggattt 840
cgacttaagg aaaacgttca gttccacttg tatatcagca catccccttg cggtgacgcc 900
cgaatctttt ccccgcacga gccgatattg gaggagcccg cggctagcgg gtcgggctct 960
ggagacatgc ggccagagat ttggatcgca caggaactga ggcgcattgg cgatgagttc 1020
aatgcatact atgcccgaag aaccggtgac agacatccta ataggaaggc tagaggccaa 1080
cttcggacga agattgaaag tggccagggt actatcccgg tgcggtccaa cgctagtatt 1140
caaacgtggg acggagtcct tcaaggtgaa cggctgttga caatgagctg ctcagacaaa 1200
atcgcgcgct ggaatgtagt gggaatccaa ggcagcctct tgagcatatt cgtagaaccc 1260
atatatttct catccattat tttgggctct ctgtatcatg gtgaccatct gtcaagggct 1320
atgtaccaac gaatttctaa tatcgaggat cttcctccac tctatacact caataagcct 1380
ctcttgtccg ggatatcaaa cgctgaggcc cgccagccag ggaaagctcc taacttcagt 1440
gttaactgga ccgttggtga ttctgcgata gaggtcatca acgccacgac aggtaaggat 1500
gagctcggta gagcctcacg cctgtgtaaa cacgcgttgt attgtagatg gatgagagta 1560
catgggaagg tcccatctca cttgctccga agcaagatca ctaagcctaa tgtgtatcat 1620
gagtcaaaac tcgcggctaa agaataccag gcagccaaag ctcgactttt tacagctttt 1680
attaaggcag ggctcggggc atgggtcgag aagccgaccg agcaggacca attctctctg 1740

```
acggggagcg cggccggagg tagcggcgga agcgcggccg cttcaagtaa ccgggagctg  1800
gtggttgact ttctctccta caagctttcc cagaaaggat acagctggag tcagtttagt  1860
gatgtggaag agaacaggac tgaggcccca gaagggactg aatcggagat ggagaccccc  1920
agtgccatca atggcaaccc atcctggcac ctggcagaca gccccgcggt gaatggagcc  1980
actggccaca gcagcagttt ggatgcccgg gaggtgatcc ccatggcagc agtaaagcaa  2040
gcgctgaggg aggcaggcga cgagtttgaa ctgcggtacc ggcgggcatt cagtgacctg  2100
acatcccagc tccacatcac cccagggaca gcatatcaga gctttgaaca ggtagtgaat  2160
gaactcttcc gggatggggt aaactggggt cgcattgtgg cctttttctc cttcggcggg  2220
gcactgtgcg tggaaagcgt agacaaggag atgcaggtat tggtgagtcg gatcgcagct  2280
tggatggcca cttacctgaa tgaccaccta gagccttgga tccaggagaa cggcggctgg  2340
gatacttttg tggaactcta tgggaacaat ggatccagcg agctgattaa ggagaacatg  2400
cacatgaagc tgtacatgga gggcaccgtg gacaaccatc acttcaagtg cacatccgag  2460
ggcgaaggca agccctacga gggcacccag accatgagaa tcaaggtggt cgagggcggc  2520
cctctcccct tcgccttcga catcctggct actagcttcc tctacggcag caagaccttc  2580
atcaaccaca cccagggcat ccccgacttc ttcaagcagt ccttccctga gggcttcaca  2640
tgggagagag tcaccacata cgaagacggg ggcgtgctga ccgctaccca ggacaccagc  2700
ctccaggacg gctgcctcat ctacaacgtc aagatcagag ggtgaactt cacatccaac  2760
ggccctgtga tgcagaagaa aacactcggc tgggaggcct tcaccgagac gctgtacccc  2820
gctgacggcg gcctggaagg cagaaacgac atggccctga agctcgtggg cgggagccat  2880
ctgatcgcaa acatcaagac cacatataga tccaagaaac ccgctaagaa cctcaagatg  2940
cctggcgtct actatgtgga ctacagactg gaaagaatca aggaggccaa caacgagacc  3000
tacgtcgagc agcacgaggt ggcagtggcc agatactgcg acctccctag caaactgggg  3060
cacaagctta attaagggcc cgtttaaacc cgctgatcag cctcgactgt gccttcta    3118
```

```
SEQ ID NO: 57          moltype = DNA  length = 2497
FEATURE                Location/Qualifiers
source                 1..2497
                       mol_type = other DNA
                       organism = synthetic construct
SEQUENCE: 57
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcggc  960
ggatctgggc gaccagaaat ctggatgaca caaggtttac gcagactcgg agatgaggca  1020
aatgcttact atgctagacg gaccggtgac agacatccta ataggaaggc tagaggccaa  1080
cttcggacga agattgaaag tggccagggt actatcccgg tgcggtccaa cgctagtatt  1140
caaacgtggg acggagtcct tcaaggtgaa cggctgttga caatgagctg ctcagacaaa  1200
atcgcgcgct ggaatgtagt gggaatccaa ggcagcctct tgagcatatt cgtagaaccc  1260
atatatttct catccattat tttgggctct ctgtatcatg gtgaccatct gtcaagggct  1320
atgtaccaac gaatttctaa tatcgaggat cttcctccac tctatacact caataagcct  1380
ctcttgtccg ggatatcaaa cgctgaggcc cgccagccag ggaaagctcc taacttcagt  1440
gttaactgga ccgttggtga ttctgcgata gaggtcatca acgccacgac aggtaaggat  1500
gagctcggta gagcctcacg cctgtgtaaa cacgcgttgt attgtagatg gatgagagta  1560
catgggaagg tcccatctca cttgctccga agcaagatca ctaagcctaa tgtgtatcat  1620
gagtcaaaac tcgcggctaa agaataccag gcagccaaag ctcgactttt tacagctttt  1680
attaaggcag ggctcggggc atgggtcgag aagccgaccg agcaggacca attctctctg  1740
acggggagcg gatccagcga gctgattaag gagaacatgc acatgaagct gtacatggag  1800
ggcaccgtgg acaaccatca cttcaagtgc acatccgagg gcgaaggcaa gccctacgag  1860
ggcacccaga ccatgagaat caaggtggtc gagggcggcc ctctcccctt cgccttcgac  1920
atcctggcta ctagcttcct ctacggcagc aagaccttca tcaaccacac ccagggcatc  1980
cccgacttct tcaagcagtc cttccctgag ggcttcacat gggagagagt caccacatac  2040
gaagacgggg gcgtgctgac cgctacccag gacaccagcc tccaggacgg ctgcctcatc  2100
tacaacgtca agatcagagg ggtgaacttc acatccaacg gccctgtgat gcagaagaaa  2160
acactcggct gggaggcctt caccgagacg ctgtaccccg ctgacggcgg cctggaaggc  2220
agaaacgaca tggccctgaa gctcgtgggc gggagccatc tgatcgcaaa catcaagacc  2280
acatatagat ccaagaaacc cgctaagaac ctcaagatgc ctggcgtcta ctatgtggac  2340
tacagactgg aaagaatcaa ggaggccaac aacgagacct acgtcgagca gcacgaggtg  2400
gcagtggcca gatactgcga cctccctagc aaactggggc acaagcttaa ttaagggccc  2460
gtttaaaccc gctgatcagc ctcgactgtg ccttcta                           2497
```

```
SEQ ID NO: 58          moltype = DNA  length = 2983
FEATURE                Location/Qualifiers
source                 1..2983
                       mol_type = other DNA
                       organism = synthetic construct
SEQUENCE: 58
```

-continued

```
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcggc  960
ggatctgggc gaccagaaat ctggatgaca caaggtttac gcagactcgg agatgaggca  1020
aatgcttact atgctagacg gaccggtgac agacatccta ataggaaggc tagaggccaa  1080
cttcggacga agattgaaag tggccagggt actatcccgg tgcggtccaa cgctagtatt  1140
caaacgtggg acggagtcct tcaaggtgaa cggctgttga caatgagctg ctcagacaaa  1200
atcgcgcgct ggaatgtagt gggaatccaa ggcagcctct tgagcatatt cgtagaaccc  1260
atatatttct catccattat tttgggctct ctgtatcatg gtgaccatct gtcaagggct  1320
atgtaccaac gaatttctaa tatcgaggat cttcctccac tctatacact caataagcct  1380
ctcttgtccg ggatatcaaa cgctgaggcc cgccagccag ggaaagctcc taacttcagt  1440
gttaactgga ccgttggtga ttctgcgata gaggtcatca acgccacgac aggtaaggat  1500
gagctcggta gagcctcacg cctgtgtaaa cacgcgttgt attgtagatg gatgagagta  1560
catgggaagg tcccatctca cttgctccga agcaagatca ctaagcctaa tgtgtatcat  1620
gagtcaaaac tcgcggctaa agaataccag gcagccaaag ctcgactttt tacagctttt  1680
attaaggcag ggctcggggc atgggtcgag aagccgaccg agcaggacca attctctctg  1740
acggggagcg gtaccggcgg tccaggggac gagttgtacc ggcagtcgct ggagattatc  1800
tctcgctacc ttcgggagca ggccaccgga gccaaggaca caaagccaat gggcaggtct  1860
ggggccacca gcaggaaggc gctggaaacc ttacgacggg ttggggatgg cgtgcagcgc  1920
aaccacgaga ctgccttcca aggcatgctt cggaaactgg acatcaaaaa cgaagatgat  1980
gtgaaatcgt tgtctagggt gatgatccat gttttcagcg acggcgtaac aaactggggc  2040
aggattgtga ctctcatttc ttttggtgcc tttgtggcta aacacttgaa aaccataaac  2100
caagaaagct gcatcgaacc attagcagaa agtatcacag acgttctcgt aaggacaaaa  2160
cgggactggc tagttaaaca aagaggctgg gatgggtttg tggagttctt ccatgtagag  2220
gacctagaag gtggcggatc cagcgagctg attaaggaga acatgcacat gaagctgtac  2280
atggagggca ccgtggacaa ccatcacttc aagtgcacat ccgagggcga aggcaagccc  2340
tacgagggca cccagaccat gagaatcaag gtggtcgagg gcggccctct ccccttcgcc  2400
ttcgacatcc tggctactag cttcctctac ggcagcaaga ccttcatcaa ccacacccag  2460
ggcatccccg acttcttcaa gcagtccttc cctgagggct tcacatggga gagagtcacc  2520
acatacgaag acgggggcgt gctgaccgct acccaggaca ccagcctcca ggacggctgc  2580
ctcatctaca acgtcaagat cagaggggtg aacttcacat ccaacggccc tgtgatgcag  2640
aagaaaacac tcggctggga ggccttcacc gagacgctgt accccgctga cggcggcctg  2700
gaaggcagaa acgacatggc cctgaagctc gtgggcggga gccatctgat cgcaaacatc  2760
aagaccacat atagatccaa gaaacccgct aagaacctca agatgcctgg cgtctactat  2820
gtggactaca gactggaaag aatcaaggag gccaacaacg agacctacgt cgagcagcac  2880
gaggtggcag tggccagata ctgcgacctc cctagcaaac tggggcacaa gcttaattaa  2940
gggcccgttt aaacccgctg atcagcctcg actgtgcctt cta                    2983
```

```
SEQ ID NO: 59           moltype = DNA  length = 3103
FEATURE                 Location/Qualifiers
source                  1..3103
                        mol_type = other DNA
                        organism = synthetic construct
SEQUENCE: 59
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg gtcgggcacc  960
ggtgctccac ccaatctctg ggcagcgcag cgctacggcc gtgagctcag aaggatgtcc  1020
gatgagctgg tcgacagaca tcctaatagg aaggctagag gccaacttcg gacgaagatt  1080
gaaagtggcc agggtactat cccggtgcgg tccaacgcta gtattcaaac gtgggacgga  1140
gtccttcaag gtgaacggct gttgacaatg agctgctcag acaaaatcgc gcgctggaat  1200
gtagtgggaa tccaaggcag cctcttgagc atattcgtag aacccatata tttctcatcc  1260
attattttgg gctctctgta tcatggtgac catctgtcaa gggctatgta ccaacgaatt  1320
```

```
tctaatatcg aggatcttcc tccactctat acactcaata agcctctctt gtccgggata  1380
tcaaacgctg aggcccgcca gccagggaaa gctcctaact tcagtgttaa ctggaccgtt  1440
ggtgattctg cgatagaggt catcaacgcc acgacaggta aggatgagct cggtagagcc  1500
tcacgcctgt gtaaacacgc gttgtattgt agatggatga gagtacatgg gaaggtccca  1560
tctcacttgc tccgaagcaa gatcactaag cctaatgtgt atcatgagtc aaaactcgcg  1620
gctaaagaat accaggcagc caaagctcga ctttttacag cttttattaa ggcagggctc  1680
ggggcatggg tcgagaagcc gaccgagcag gaccaattct ctctgacggg gagcgcggcc  1740
ggaggtagcg gcggaagcgc ggccgcttca agtaaccggg agctggtggt tgactttctc  1800
tcctacaagc tttcccagaa aggatacagc tggagtcagt ttagtgatgt ggaagagaac  1860
aggactgagg ccccagaagg gactgaatcg gagatggaga cccccagtgc catcaatggc  1920
aacccatcct ggcacctggc agacagcccc gcggtgaatg gagccactgg ccacagcagc  1980
agtttggatg cccgggaggt gatccccatg gcagcagtaa agcaagcgct gagggaggca  2040
ggcgacgagt ttgaactgcg gtaccggcgg gcattcagtg acctgacatc ccagctccac  2100
atcaccccag ggacagcata tcagagcttt gaacaggtag tgaatgaact cttccgggat  2160
ggggtaaact ggggtcgcat tgtggccttt ttctccttcg gcggggcact gtgcgtggaa  2220
agcgtagaca aggagatgca ggtattggtg agtcggatcg cagcttggat ggccacttac  2280
ctgaatgacc acctagagcc ttggatccag gagaacggcg gctgggatac ttttgtggaa  2340
ctctatggga acaatggatc cagcgagctg attaaggaga acatgcacat gaagctgtac  2400
atggagggca ccgtggacaa ccatcacttc aagtgcacat ccgagggcga aggcaagccc  2460
tacgagggca cccagaccat gagaatcaag gtggtcgagg gcggccctct ccccttcgcc  2520
ttcgacatcc tggctactag cttcctctac ggcagcaaga ccttcatcaa ccacacccag  2580
ggcatccccg acttcttcaa gcagtccttc cctgagggct tcacatggga gagagtcacc  2640
acatacgaag acgggggcgt gctgaccgct acccaggaca ccagcctcca ggacggctgc  2700
ctcatctaca acgtcaagat cagaggggtg aacttcacat ccaacggccc tgtgatgcag  2760
aagaaaacac tcggctggga ggccttcacc gagacgctgt accccgctga cggcggcctg  2820
gaaggcagaa acgacatggc cctgaagctc gtgggcggga gccatctgat cgcaaacatc  2880
aagaccacat atagatccaa gaaacccgct aagaacctca agatgcctgg cgtctactat  2940
gtggactaca gactggaaag aatcaaggag gccaacaacg agacctacgt cgagcagcac  3000
gaggtggcag tggccagata ctgcgacctc cctagcaaac tggggcacaa gcttaattaa  3060
gggcccgttt aaacccgctg atcagcctcg actgtgcctt cta                   3103

SEQ ID NO: 60           moltype = DNA  length = 2983
FEATURE                 Location/Qualifiers
source                  1..2983
                        mol_type = other DNA
                        organism = synthetic construct
SEQUENCE: 60
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcggc  960
ggatctgggc gaccagaaat ctggatgaca caaggtttac gcagactcgg agatgagata  1020
aatgcttact atgctagacg gaccggtgac agacatccta ataggaaggc tagaggccaa  1080
cttcggacga agattgaaag tggccagggt actatcccgg tgcggtccaa cgctagtatt  1140
caaacgtggg acggagtcct tcaaggtgaa cggctgttga caatgagctg ctcagacaaa  1200
atcgcgcgct ggaatgtagt gggaatccaa ggcagcctct tgagcatatt cgtagaaccc  1260
atatatttct catccattat tttgggctct ctgtatcatg gtgaccatct gtcaagggct  1320
atgtaccaac gaatttctaa tatcgaggat cttcctccac tctatacact caataagcct  1380
ctcttgtccg ggatatcaaa cgctgaggcc cgccagccag ggaaagctcc taacttcagt  1440
gttaactgga ccgttggtga ttctgcgata gaggtcatca acgccacgac aggtaaggat  1500
gagctcggta gagcctcacg cctgtgtaaa cacgcgttgt attgtagatg gatgagagta  1560
catgggaagg tcccatctca cttgctccga agcaagatca ctaagcctaa tgtgtatcat  1620
gagtcaaaac tcgcggctaa agaataccag gcagccaaag ctcgactttt tacagctttt  1680
attaaggcag ggctcggggc atgggtcgag aagccgaccg agcaggacca attctctctg  1740
acggggagcg gtaccggcgg tccaggggac gagttgtacc ggcagtcgct ggagattatc  1800
tctcgctacc ttcgggagca ggccaccgga gccaaggaca caaagccaat gggcaggtct  1860
ggggccacca gcaggaaggc gctggaaacc ttacgacggg ttggggatgg cgtgcagcgc  1920
aaccacgaga ctgccttcca aggcatgctt cggaaactgg acatcaaaaa cgaagatgat  1980
gtgaaatcgt tgtctagggt gatgatccat gttttcagcg acggcgtaac aaactggggc  2040
aggattgtga ctctcatttc ttttggtgcc tttgtggcta aacacttgaa aaccataaac  2100
caagaaagct gcatcgaacc attagcagaa agtatcacag acgttctcgt aaggacaaaa  2160
cgggactggc tagttaaaca aagaggctgg gatgggtttg tggagttctt ccatgtagag  2220
gacctagaag gtggcggatc cagcgagctg attaaggaga acatgcacat gaagctgtac  2280
atggagggca ccgtggacaa ccatcacttc aagtgcacat ccgagggcga aggcaagccc  2340
tacgagggca cccagaccat gagaatcaag gtggtcgagg gcggccctct ccccttcgcc  2400
ttcgacatcc tggctactag cttcctctac ggcagcaaga ccttcatcaa ccacacccag  2460
ggcatccccg acttcttcaa gcagtccttc cctgagggct tcacatggga gagagtcacc  2520
```

-continued

```
acatacgaag acgggggcgt gctgaccgct acccaggaca ccagcctcca ggacggctgc  2580
ctcatctaca acgtcaagat cagaggggtg aacttcacat ccaacggccc tgtgatgcag  2640
aagaaaacac tcggctggga ggccttcacc gagacgctgt accccgctga cggcggcctg  2700
gaaggcagaa acgacatggc cctgaagctc gtgggcggga gccatctgat cgcaaacatc  2760
aagaccacat atagatccaa gaaacccgct aagaacctca agatgcctgg cgtctactat  2820
gtggactaca gactggaaag aatcaaggag gccaacaacg agacctacgt cgagcagcac  2880
gaggtggcag tggccagata ctgcgacctc cctagcaaac tggggcacaa gcttaattaa  2940
gggcccgttt aaacccgctg atcagcctcg actgtgcctt cta                    2983

SEQ ID NO: 61          moltype = DNA  length = 2449
FEATURE                Location/Qualifiers
source                 1..2449
                       mol_type = other DNA
                       organism = synthetic construct
SEQUENCE: 61
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagccc atcccgcctg  960
gaggaagaac ttcggaggag acttactgag cctaccggtg acagacatcc taataggaag  1020
gctagaggcc aacttcggac gaagattgaa agtggccagg gtactatccc ggtgcggtcc  1080
aacgctagta ttcaaacgtg ggacggagtc cttcaaggtg aacggctgtt gacaatgagc  1140
tgctcagaca aaatcgcgcg ctggaatgta gtgggaatcc aaggcagcct cttgagcata  1200
ttcgtagaac ccatatattt ctcatccatt attttgggct ctctgtatca tggtgaccat  1260
ctgtcaaggg ctatgtacca acgaatttct aatatcgagg atcttcctcc actctataca  1320
ctcaataagc ctctcttgtc cggatatca aacgctgagg cccgccagcc agggaaagct  1380
cctaacttca gtgttaactg gaccgttggt gattctgcga tagaggtcat caacgccacg  1440
acaggtaagg atgagctcgg tagagcctca cgcctgtgta aacacgcgtt gtattgtaga  1500
tggatgagag tacatgggaa ggtcccatct cacttgctcc gaagcaagat cactaagcct  1560
aatgtgtatc atgagtcaaa actcgcggct aaagaatacc aggcagccaa agctcgactt  1620
tttacagctt ttattaaggc agggctcggg gcatgggtcg agaagccgac cgagcaggac  1680
caattctctc tgacggggag cggatccagc gagctgatta aggagaacat gcacatgaag  1740
ctgtacatgg agggcaccgt ggacaaccat cacttcaagt gcacatccga gggcgaaggc  1800
aagccctacg agggcaccca gaccatgaga atcaaggtgg tcgagggcgg ccctctcccc  1860
ttcgccttcg acatcctggc tactagcttc ctctacggca gcaagacctt catcaaccac  1920
acccagggca tccccgactt cttcaagcag tccttccctg agggcttcac atgggagaga  1980
gtcaccacat acgaagacgg gggcgtgctg accgctaccc aggacaccag cctccaggac  2040
ggctgcctca tctacaacgt caagatcaga ggggtgaact tcacatccaa cggccctgtg  2100
atgcagaaga aaacactcgg ctgggaggcc ttcaccgaga cgctgtaccc cgctgacggc  2160
ggcctggaag gcagaaacga catggccctg aagctcgtgg gcgggagcca tctgatcgca  2220
aacatcaaga ccacatatag atccaagaaa cccgctaaga acctcaagat gcctggcgtc  2280
tactatgtgg actacagact ggaaagaatc aaggaggcca acaacgagac ctacgtcgag  2340
cagcacgagg tggcagtggc cagatactgc gacctcccta gcaaactggg gcacaagctt  2400
aattaagggc ccgtttaaac ccgctgatca gcctcgactg tgccttcta             2449

SEQ ID NO: 62          moltype = DNA  length = 2833
FEATURE                Location/Qualifiers
source                 1..2833
                       mol_type = other DNA
                       organism = synthetic construct
SEQUENCE: 62
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagccc atcccgcctg  960
```

-continued

```
gaggaagaac ttcggaggag acttactgag cctaccggtg acagacatcc taataggaag  1020
gctagaggcc aacttcggac gaagattgaa agtggccagg gtactatccc ggtgcggtcc  1080
aacgctagta ttcaaacgtg ggacggagtc cttcaaggtg aacggctgtt gacaatgagc  1140
tgctcagaca aaatcgcgcg ctggaatgta gtgggaatcc aaggcagcct cttgagcata  1200
ttcgtagaac ccatatattt ctcatccatt attttgggct ctctgtatca tggtgaccat  1260
ctgtcaaggg ctatgtacca acgaatttct aatatcgagg atcttcctcc actctataca  1320
ctcaataagc ctctcttgtc cgggatatca aacgctgagg cccgccagcc agggaaagct  1380
cctaacttca gtgttaactg gaccgttggt gattctgcga tagaggtcat caacgccacg  1440
acaggtaagg atgagctcgg tagagcctca cgcctgtgta aacacgcgtt gtattgtaga  1500
tggatgagag tacatgggaa ggtcccatct cacttgctcc gaagcaagat cactaagcct  1560
aatgtgtatc atgagtcaaa actcgcggct aaagaatacc aggcagccaa agctcgactt  1620
tttacagctt ttattaaggc agggctcggg gcatgggtcg agaagccgac cgagcaggac  1680
caattctctc tgacggggag cggaggtacc gccgaagttc aattacagga atcgggtgga  1740
ggtctggtac aacctggggg ctctcttcgc ctgagttgca ctgccagtgg agttacgatt  1800
tctgcactta atgctatggc gatgggttgg tatcgtcagg ccccagggga acgtcgcgtc  1860
atggtcgctg ccgtttccga acgtggcaat gctatgtacc gcgagtctgt tcagggccgc  1920
ttcacggtta cccgcgattt tacaaataaa atggtatcgt tgcaaatgga caacttaaag  1980
ccagaggaca ctgctgtgta ctactgtcac gtccttgaag atcgtgtgga ttcctttcat  2040
gattattggg ggcaggggac tcaggtcact gtatcctcag gagctggatc cagcgagctg  2100
attaaggaga acatgcacat gaagctgtac atggagggca ccgtggacaa ccatcacttc  2160
aagtgcacat ccgagggcga aggcaagccc tacgagggca cccagaccat gagaatcaag  2220
gtggtcgagg gcggccctct ccccttcgcc ttcgacatcc tggctactag cttcctctac  2280
ggcagcaaga ccttcatcaa ccacacccag ggcatccccg acttcttcaa gcagtccttc  2340
cctgagggct tcacatggga gagagtcacc acatacgaag acgggggcgt gctgaccgct  2400
acccaggaca ccagcctcca ggacggctgc ctcatctaca acgtcaagat cagaggggtg  2460
aacttcacat ccaacggccc tgtgatgcag aagaaaacac tcggctggga ggccttcacc  2520
gagacgctgt accccgctga cggcggcctg gaaggcagaa acgacatggc cctgaagctc  2580
gtgggcggga gccatctgat cgcaaacatc aagaccacat atagatccaa gaaacccgct  2640
aagaacctca agatgcctgg cgtctactat gtggactaca gactggaaag aatcaaggag  2700
gccaacaacg agacctacgt cgagcagcac gaggtggcag tggccagata ctgcgacctc  2760
cctagcaaac tggggcacaa gcttaattaa gggcccgttt aaacccgctg atcagcctcg  2820
actgtgcctt cta                                                2833

SEQ ID NO: 63           moltype = DNA  length = 2458
FEATURE                 Location/Qualifiers
source                  1..2458
                        mol_type = other DNA
                        organism = synthetic construct
SEQUENCE: 63
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg atcaggtcca  960
ggacgcctgg aggaagaact tcggaggaga ctttctcctg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggatccagcg agctgattaa ggagaacatg  1740
cacatgaagc tgtacatgga gggcaccgtg gacaaccatc acttcaagtg cacatccgag  1800
ggcgaaggca agccctacga gggcacccag accatgagaa tcaaggtggt cgagggcggc  1860
cctctcccct tcgccttcga catcctggct actagcttcc tctacggcag caagaccttc  1920
atcaaccaca cccagggcat ccccgacttc ttcaagcagt ccttccctga gggcttcaca  1980
tgggagagag tcaccacata cgaagacggg ggcgtgctga ccgctaccca ggacaccagc  2040
ctccaggacg gctgcctcat ctacaacgtc aagatcagag gggtgaactt cacatccaac  2100
ggccctgtga tgcagaagaa aacactcggc tgggaggcct tcaccgagac gctgtacccc  2160
gctgacggcg gcctggaagg cagaaacgac atggccctga agctcgtggg cgggagccat  2220
ctgatcgcaa acatcaagac cacatataga tccaagaaac ccgctaagaa cctcaagatg  2280
cctggcgtct actatgtgga ctacagactg gaaagaatca aggaggccaa caacgagacc  2340
tacgtcgagc agcacgaggt ggcagtggcc agatactgcg acctccctag caaactgggg  2400
```

```
cacaagctta attaagggcc cgtttaaacc cgctgatcag cctcgactgt gccttcta    2458

SEQ ID NO: 64          moltype = DNA  length = 2842
FEATURE                Location/Qualifiers
source                 1..2842
                       mol_type = other DNA
                       organism = synthetic construct
SEQUENCE: 64
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg atcaggtcca  960
ggacgcctgg aggaagaact tcggaggaga ctttctcctg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggaggtaccg ccgaagttca attacaggaa  1740
tcgggtggag gtctggtaca acctgggggc tctcttcgcc tgagttgcac tgccagtgga  1800
gttacgattt ctgcacttaa tgctatggcg atgggttggt atcgtcaggc cccaggggaa  1860
cgtcgcgtca tggtcgctgc cgtttccgaa cgtggcaatg ctatgtaccg cgagtctgtt  1920
cagggccgct tcacggttac ccgcgatttt acaaataaaa tggtatcgtt gcaaatggac  1980
aacttaaagc cagaggacac tgctgtgtac tactgtcacg tccttgaaga tcgtgtggat  2040
tcctttcatg attattgggg gcaggggact caggtcactg tatcctcagg agctggatcc  2100
agcgagctga ttaaggagaa catgcacatg aagctgtaca tggagggcac cgtggacaac  2160
catcacttca agtgcacatc cgagggcgaa ggcaagccct acgagggcac ccagaccatg  2220
agaatcaagg tggtcgaggg cggccctctc cccttcgcct tcgacatcct ggctactagc  2280
ttcctctacg gcagcaagac cttcatcaac cacacccagg gcatccccga cttcttcaag  2340
cagtccttcc ctgagggctt cacatgggag agagtcacca catacgaaga cgggggcgtg  2400
ctgaccgcta cccaggacac cagcctccag gacggctgcc tcatctacaa cgtcaagatc  2460
agaggggtga acttcacatc caacggccct gtgatgcaga agaaaacact cggctgggag  2520
gccttcaccg agacgctgta ccccgctgac ggcggcctgg aaggcagaaa cgacatggcc  2580
ctgaagctcg tgggcgggag ccatctgatc gcaaacatca agaccacata tagatccaag  2640
aaacccgcta agaacctcaa gatgcctggc gtctactatg tggactacag actggaaaga  2700
atcaaggagg ccaacaacga gacctacgtc gagcagcacg aggtggcagt ggccagatac  2760
tgcgacctcc ctagcaaact ggggcacaag cttaattaag ggcccgttta aacccgctga  2820
tcagcctcga ctgtgccttc ta                                          2842

SEQ ID NO: 65          moltype = DNA  length = 2458
FEATURE                Location/Qualifiers
source                 1..2458
                       mol_type = other DNA
                       organism = synthetic construct
SEQUENCE: 65
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg atcaggtcca  960
```

```
ggccgcctgg agcaggaaat tcgggcaaga ctttctcctg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggatccagcg agctgattaa ggagaacatg  1740
cacatgaagc tgtacatgga gggcaccgtg gacaaccatc acttcaagtg cacatccgag  1800
ggcgaaggca agccctacga gggcacccag accatgagaa tcaaggtggt cgagggcggc  1860
cctctcccct tcgccttcga catcctggct actagcttcc tctacggcag caagaccttc  1920
atcaaccaca cccagggcat ccccgacttc ttcaagcagt ccttccctga gggcttcaca  1980
tgggagagag tcaccacata cgaagacggg ggcgtgctga ccgctaccca ggacaccagc  2040
ctccaggacg gctgcctcat ctacaacgtc aagatcagag ggtgaactt cacatccaac  2100
ggccctgtga tgcagaagaa aacactcggc tgggaggcct tcaccgagac gctgtacccc  2160
gctgacggcg gcctggaagg cagaaacgac atggccctga agctcgtggg cgggagccat  2220
ctgatcgcaa acatcaaggac cacatataga tccaagaaac ccgctaagaa cctcaagatg  2280
cctggcgtct actatgtgga ctacagactg gaaagaatca aggaggccaa caacgagacc  2340
tacgtcgagc agcacgaggt ggcagtggcc agatactgcg acctccctag caaactgggg  2400
cacaagctta attaagggcc cgtttaaacc cgctgatcag cctcgactgt gccttcta    2458
```

```
SEQ ID NO: 66           moltype = DNA  length = 2842
FEATURE                 Location/Qualifiers
source                  1..2842
                        mol_type = other DNA
                        organism = synthetic construct
SEQUENCE: 66
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg atcaggtcca  960
ggccgcctgg agcaggaaat tcgggcaaga ctttctcctg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggaggtaccg ccgaagttca attacaggaa  1740
tcgggtggag gtctggtaca acctgggggc tctcttcgcc tgagttgcac tgccagtgga  1800
gttacgattt ctgcacttaa tgctatggcg atgggttggt atcgtcaggc cccaggggaa  1860
cgtcgcgtca tggtcgctgc cgtttccgaa cgtggcaatg ctatgtaccg cgagtctgtt  1920
cagggccgct tcacggttac ccgcgatttt acaaataaaa tggtatcgtt gcaaatggac  1980
aacttaaagc cagaggacac tgctgtgtac tactgtcacg tccttgaaga tcgtgtggat  2040
tcctttcatg attattgggg gcaggggact caggtcactg tatcctcagg agctggatcc  2100
agcgagctga ttaaggagaa catgcacatg aagctgtaca tggagggcac cgtggacaac  2160
catcacttca agtgcacatc cgagggcgaa ggcaagccct acgagggcac ccagaccatg  2220
agaatcaagg tggtcgaggg cggccctctc cccttcgcct tcgacatcct ggctactagc  2280
ttcctctacg gcagcaagac cttcatcaac cacacccagg gcatccccga cttcttcaag  2340
cagtccttcc ctgagggctt cacatgggag agagtcacca catacgaaga cgggggcgtg  2400
ctgaccgcta cccaggacac cagcctccag gacggctgcc tcatctacaa cgtcaagatc  2460
agaggggtga acttcacatc caacggccct gtgatgcaga agaaaacact cggctgggag  2520
gccttcaccg agacgctgta ccccgctgac ggcggcctgg aaggcagaaa cgacatggcc  2580
ctgaagctcg tgggcgggag ccatctgatc gcaaacatca agaccacata tagatccaag  2640
aaacccgcta agaacctcaa gatgcctggc gtctactatg tggactacag actggaaaga  2700
atcaaggagg ccaacaacga gacctacgtc gagcagcacg aggtggcagt ggccagatac  2760
tgcgacctcc ctagcaaact ggggcacaag cttaattaag ggcccgttta aacccgctga  2820
```

```
tcagcctcga ctgtgccttc ta                                           2842

SEQ ID NO: 67          moltype = DNA  length = 1118
FEATURE                Location/Qualifiers
source                 1..1118
                       mol_type = other DNA
                       organism = synthetic construct
SEQUENCE: 67
taatacgact cactataggg agacccaagc tggctagcgt ttaaacttaa gcttatggta  60
gcaggtcatg cctctggcag ccccgcattc gggaccgcct ctcattcgaa ttgcgaacat  120
gaagagatcc acctcgccgg ctcgatccag ccgcatggcg cgcttctggt cgtcagcgaa  180
catgatcatc gcgtcatcca ggccagcgcc aacgccgcgg aatttctgaa tctcggaagc  240
gtactcggcg ttccgctcgc cgagatcgac ggcgatctgt tgatcaagat cctgccgcat  300
ctcgatccca ccgccgaagg catgccggtc gcggtgcgct gccggatcgg caatccctct  360
acggagtact gcggtctgat gcatcggcct ccggaaggcg ggctgatcat cgaactcgaa  420
cgtgccggcc cgtcgatcga tctgtcaggc acgctggcgc cggcgctgga gcggatccgc  480
acggcgggtt cactgcgcgc gctgtgcgat gacaccgtgc tgctgtttca gcagtgcacc  540
ggctacgacc gggtgatggt gtatcgtttc gatgagcaag gccacggcct ggtattctcc  600
gagtgccatg tgcctgggct cgaatcctat ttcggcaacc gctatccgtc gtcgactgtc  660
ccgcagatgg cgcggcagct gtacgtgcgg cagcgcgtcc gcgtgctggt cgacgtcacc  720
tatcagccgg tgccgctgga gccgcggctg tcgccgctga ccgggcgcga tctcgacatg  780
tcgggctgct tcctgcgctc gatgtcgccg tgccatctgc agttcctgaa ggacatgggc  840
gtgcgcgcca ccctggcggt gtcgctggtg gtcggcggca agctgtgggg cctggttgtc  900
tgtcaccatt atctgccgcg cttcatccgt ttcgagctgc gggcgatctg caaacggctc  960
gccgaaagga tcgcgacgcg gatcaccgcg cttgagagcc tcgagtcccg cctggaggaa  1020
gaacttcgga ggagacttac tgagtaatct agagggccct attctatagt gtcacctaaa  1080
tgctagagct cgctgatcag cctcgactgt gccttcta                          1118

SEQ ID NO: 68          moltype = DNA  length = 2458
FEATURE                Location/Qualifiers
source                 1..2458
                       mol_type = other DNA
                       organism = synthetic construct
SEQUENCE: 68
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcgga  960
gcccacatcg tgatggtgga cgcctacaag ccgacgaagg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggatccagcg agctgattaa ggagaacatg  1740
cacatgaagc tgtacatgga gggcaccgtg gacaaccatc acttcaagtg cacatccgag  1800
ggcgaaggca agccctacga gggcacccag accatgagaa tcaaggtggt cgagggcggc  1860
cctctcccct tcgccttcga catcctggct actagcttcc tctacggcag caagaccttc  1920
atcaaccaca cccagggcat ccccgacttc ttcaagcagt ccttccctga gggcttcaca  1980
tgggagagag tcaccacata cgaagacggg ggcgtgctga ccgctaccca ggacaccagc  2040
ctccaggacg gctgcctcat ctacaacgtc aagatcagag gggtgaactt cacatccaac  2100
ggccctgtga tgcagaagaa aacactcggc tgggaggcct tcaccgagac gctgtacccc  2160
gctgacggcg gcctggaagg cagaaacgac atggccctga agctcgtggg cgggagccat  2220
ctgatcgcaa acatcaagac cacatataga tccaagaaac ccgctaagaa cctcaagatg  2280
cctggcgtct actatgtgga ctacagactg gaaagaatca aggaggccaa caacgagacc  2340
tacgtcgagc agcacgaggt ggcagtggcc agatactgcg acctccctag caaactgggg  2400
cacaagctta attaagggcc cgtttaaacc cgctgatcag cctcgactgt gccttcta    2458

SEQ ID NO: 69          moltype = DNA  length = 2818
FEATURE                Location/Qualifiers
source                 1..2818
```

```
                         mol_type = other DNA
                         organism = synthetic construct
SEQUENCE: 69
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcgga  960
gcccacatcg tgatggtgga cgcctacaag ccgacgaagg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggtaccagcg gaggcgccat ggttgatacc  1740
ttatcaggtt tatcaagtga gcaaggtcag tccggtgata tgacaattga agaagatagt  1800
gctacccata ttaaattctc aaaacgtgat gaggacggca aagagttagc tggtgcaact  1860
atggagttgc gtgattcatc tggtaaaact attagtacat ggatttcaga tggacaagtg  1920
aaagatttct acctgtatcc aggaaaatat acatttgtcg aaaccgcagc accagacggt  1980
tatgaggtag caactgctat tacctttaca gttaatgagc aaggtcaggt tactgtaaat  2040
ggcaaagcaa ctaaaggtga cgctcatatt ggatccagcg agctgattaa ggagaacatg  2100
cacatgaagc tgtacatgga gggcaccgtg gacaaccatc acttcaagtg cacatccgag  2160
ggcgaaggca agccctacga gggcacccag accatgagaa tcaaggtggt cgagggcggc  2220
cctctcccct tcgccttcga catcctggct actagcttcc tctacggcag caagaccttc  2280
atcaaccaca cccagggcat ccccgacttc ttcaagcagt ccttccctga gggcttcaca  2340
tgggagagag tcaccacata cgaagacggg ggcgtgctga ccgctaccca ggacaccagc  2400
ctccaggacg gctgcctcat ctacaacgtc aagatcagag gggtgaactt cacatccaac  2460
ggccctgtga tgcagaagaa aacactcggc tgggaggcct tcaccgagac gctgtacccc  2520
gctgacggcg gcctggaagg cagaaacgac atggccctga agctcgtggg cgggagccat  2580
ctgatcgcaa acatcaagac cacatataga tccaagaaac ccgctaagaa cctcaagatg  2640
cctggcgtct actatgtgga ctacagactg gaaagaatca aggaggccaa caacgagacc  2700
tacgtcgagc agcacgaggt ggcagtggcc agatactgcg acctccctag caaactgggg  2760
cacaagctta attaagggcc cgtttaaacc cgctgatcag cctcgactgt gccttcta    2818

SEQ ID NO: 70            moltype = DNA  length = 2947
FEATURE                  Location/Qualifiers
source                   1..2947
                         mol_type = other DNA
                         organism = synthetic construct
SEQUENCE: 70
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcgga  960
gcccacatcg tgatggtgga cgcctacaag ccgacgaagg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
```

```
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggatccagcg agctgattaa ggagaacatg  1740
cacatgaagc tgtacatgga gggcaccgtg gacaaccatc acttcaagtg cacatccgag  1800
ggcgaaggca agccctacga gggcacccag accatgagaa tcaaggtggt cgagggcggc  1860
cctctcccct tcgccttcga catcctggct actagcttcc tctacggcag caagaccttc  1920
atcaaccaca cccagggcat ccccgacttc ttcaagcagt ccttccctga gggcttcaca  1980
tgggagagag tcaccacata cgaagacggg ggcgtgctga ccgctaccca ggacaccagc  2040
ctccaggacg gctgcctcat ctacaacgtc aagatcagag ggtgaactt cacatccaac  2100
ggccctgtga tgcagaagaa aacactcggc tgggaggcct tcaccgagac gctgtacccc  2160
gctgacggcg gcctggaagg cagaaacgac atggccctga agctcgtggg cgggagccat  2220
ctgatcgcaa acatcaagac cacatataga tccaagaaac ccgctaagaa cctcaagatg  2280
cctggcgtct actatgtgga ctacagactg gaaagaatca aggaggccaa caacgagacc  2340
tacgtcgagc agcacgaggt ggcagtggcc agatactgcg acctccctag caaactgggg  2400
cacaagctta atactagtgc cacaaacttc tctctgctaa agcaagcagg tgatgttgaa  2460
gaaaacccag ggcctggagg gtccgagggc aggggaagtc tcctaacatg cggggacgtg  2520
gaggaaaatc ccggaccagg taccagcgga ggcgccatgg ttgatacctt atcaggttta  2580
tcaagtgagc aaggtcagtc cggtgatatg acaattgaag aagatagtgc tacccatatt  2640
aaattctcaa aacgtgatga ggacggcaaa gagttagctg gtgcaactat ggagttgcgt  2700
gattcatctg gtaaaactat tagtacatgg atttcagatg gacaagtgaa agatttctac  2760
ctgtatccag gaaaatatac atttgtcgaa accgcagcac cagacggtta tgaggtagca  2820
actgctatta cctttacagt taatgagcaa ggtcaggtta ctgtaaatgg caaagcaact  2880
aaaggtgacg ctcatattgg ataagggccc gtttaaaccc gctgatcagc ctcgactgtg  2940
ccttcta                                                            2947

SEQ ID NO: 71          moltype = DNA  length = 2848
FEATURE                Location/Qualifiers
source                 1..2848
                       mol_type = other DNA
                       organism = synthetic construct
SEQUENCE: 71
taatacgact cactataggg agacccaagc tggctagagg atcgaaccct taaggccacc  60
atggcgtcca atttcactca gtttgtgctg gttgacaacg gcgggaccgg ggacgttacg  120
gtagcccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg aggtagcgga  960
gcccacatcg tgatggtgga cgcctacaag ccgacgaagg gaaccggtga cagacatcct  1020
aataggaagg ctagaggcca acttcggacg aagattgaaa gtggccaggg tactatcccg  1080
gtgcggtcca acgctagtat tcaaacgtgg gacggagtcc ttcaaggtga acggctgttg  1140
acaatgagct gctcagacaa aatcgcgcgc tggaatgtag tgggaatcca aggcagcctc  1200
ttgagcatat tcgtagaacc catatatttc tcatccatta ttttgggctc tctgtatcat  1260
ggtgaccatc tgtcaagggc tatgtaccaa cgaatttcta atatcgagga tcttcctcca  1320
ctctatacac tcaataagcc tctcttgtcc gggatatcaa acgctgaggc ccgccagcca  1380
gggaaagctc ctaacttcag tgttaactgg accgttggtg attctgcgat agaggtcatc  1440
aacgccacga caggtaagga tgagctcggt agagcctcac gcctgtgtaa acacgcgttg  1500
tattgtagat ggatgagagt acatgggaag gtcccatctc acttgctccg aagcaagatc  1560
actaagccta atgtgtatca tgagtcaaaa ctcgcggcta aagaatacca ggcagccaaa  1620
gctcgacttt ttacagcttt tattaaggca gggctcgggg catgggtcga gaagccgacc  1680
gagcaggacc aattctctct gacggggagc ggaggtacgg agaatttgta ttttcagagc  1740
ggtaccagcg gaggcgccat ggttgatacc ttatcaggtt tatcaagtga gcaaggtcag  1800
tccggtgata tgacaattga agaagatagt gctacccata ttaaattctc aaaacgtgat  1860
gaggacggca aagagttagc tggtgcaact atggagttgc gtgattcatc tggtaaaact  1920
attagtacat ggatttcaga tggacaagtg aaagatttct acctgtatcc aggaaaatat  1980
acatttgtcg aaaccgcagc accagacggt tatgaggtag caactgctat tacctttaca  2040
gttaatgagc aaggtcaggt tactgtaaat ggcaaagcaa ctaaaggtga cgctcatatt  2100
ggatccagcg agctgattaa ggagaacatg cacatgaagc tgtacatgga gggcaccgtg  2160
gacaaccatc acttcaagtg cacatccgag ggcgaaggca agccctacga gggcacccag  2220
accatgagaa tcaaggtggt cgagggcggc cctctcccct tcgccttcga catcctggct  2280
actagcttcc tctacggcag caagaccttc atcaaccaca cccagggcat ccccgacttc  2340
ttcaagcagt ccttccctga gggcttcaca tgggagagag tcaccacata cgaagacggg  2400
ggcgtgctga ccgctaccca ggacaccagc ctccaggacg gctgcctcat ctacaacgtc  2460
aagatcagag gggtgaactt cacatccaac ggccctgtga tgcagaagaa aacactcggc  2520
tgggaggcct tcaccgagac gctgtacccc gctgacggcg gcctggaagg cagaaacgac  2580
atggccctga agctcgtggg cgggagccat ctgatcgcaa acatcaagac cacatataga  2640
```

```
tccaagaaac ccgctaagaa cctcaagatg cctggcgtct actatgtgga ctacagactg  2700
gaaagaatca aggaggccaa caacgagacc tacgtcgagc agcacgaggt ggcagtggcc  2760
agatactgcg acctccctag caaactgggg cacaagctta attaagggcc cgtttaaacc  2820
cgctgatcag cctcgactgt gccttcta                                     2848

SEQ ID NO: 72           moltype = DNA  length = 890
FEATURE                 Location/Qualifiers
source                  1..890
                        mol_type = other DNA
                        organism = synthetic construct
SEQUENCE: 72
taatacgact cactataggg agacccaagc tggctagtta agcttgccac catgggcgag  60
agccttttca agggcccgag ggactacaac ccgatctcca gcaccatctg tcacctgacc  120
aacgagagcg acggtcacac cactagtctg tacggcatcg gcttcggccc cttcatcatc  180
accaacaagc atctgttcag gaggaataac ggcacactgc tggtgcaaag cctgcacggc  240
gtgttcaaag tgaagaacac aaccaccctg caacagcacc tgatcgacgg cagggacatg  300
attatcatca ggatgcccaa ggacttcccc ccctttcccc agaaactgaa gttcagggag  360
ccacaaaggg aggagcgaat ctgcctggtg accaccaact tccagaccaa gtccatgagc  420
agcatggtct ctgataccag ctgcaccttc cccagcagcg acggcatctt ctggaagcac  480
tggattcaga cgaaggatgg ccaatgcggc agcccattgg tgagcactag ggacggcttc  540
atcgtgggca tccacagcgc cagcaatttt accaatacca acaactactt cacgagcgtg  600
ccgaaaaact tcatggagct gttgaccaat caagaggcgc agcagtgggt gagcggctgg  660
aggctgaacg ccgacagcgt tctttggggc ggacataagg tgttcatggt caagcccgag  720
gaacccttcc agcccgttaa ggaagccact cagctttgat aactcgagtc tagagggccc  780
gcggttcgaa caaaaactca tctcagaaga ggatctgaat atgcataccg gtcatcatca  840
ccatcaccat tgagtttaaa cccgctgatc agcctcgact gtgccttcta             890

SEQ ID NO: 73           moltype = DNA  length = 3820
FEATURE                 Location/Qualifiers
source                  1..3820
                        mol_type = other DNA
                        organism = synthetic construct
SEQUENCE: 73
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg gtcgggcacc  960
ggtgctccac ccaatctctg ggcagcgcag cgctacggcc gtgagctcag aaggatgtcc  1020
gatgagctgg tcgacagaca tcctaatagg aaggctagag gccaacttcg gacgaagatt  1080
gaaagtggcc agggtactat cccggtgcgg tccaacgcta gtattcaaac gtgggacgga  1140
gtccttcaag gtgaacggct gttgacaatg agctgctcag acaaaatcgc gcgctggaat  1200
gtagtgggaa tccaaggcag cctcttgagc atattcgtag aacccatata tttctcatcc  1260
attattttgg gctctctgta tcatggtgac catctgtcaa gggctatgta ccaacgaatt  1320
tctaatatcg aggatcttcc tccactctat acactcaata agcctctctt gtccgggata  1380
tcaaacgctg aggcccgcca gccagggaaa gctcctaact tcagtgttaa ctggaccgtt  1440
ggtgattctg cgatagaggt catcaacgcc acgacaggta aggatgagct cggtagagcc  1500
tcacgcctgt gtaaacacgc gttgtattgt agatggatga gagtacatgg gaaggtccca  1560
tctcacttgc tccgaagcaa gatcactaag cctaatgtgt atcatgagtc aaaactcgcg  1620
gctaaagaat accaggcagc caaagctcga ctttttacag cttttattaa ggcagggctc  1680
ggggcatggg tcgagaagcc gaccgagcag gaccaattct ctctgacggg gagcggaagt  1740
ggtggtgtga tccctgacta cttcaagcag agcttccccg agggctacag ctgggagcgc  1800
agcatgacct acgaggacgg cggcatctgc atcgccacca acgacatcac aatggagggg  1860
gacagcttca tcaacaagat ccacttcaag ggcacgaact tcccccccaa cggccccgtg  1920
atgcagaaga ggaccgtggg ctgggaggcc agcaccgaga agatgtacga gcgcgacggc  1980
gtgctgaagg gcgacgtgaa gatgaagctg ctgctgaagg gcggcggcca ctatcgctgc  2040
gactaccgca ccacctacaa ggtcaagcag aagcccgtaa agctgcccga ctaccacttc  2100
gtggaccacc gcatcgagat cctgagccac gacaaggact acaacaaggt gaagctgtac  2160
gagcacgccg tggcccgcaa ctccaccgac agcatggacg agctgtacaa gggtggcagc  2220
ggtggcatgg tgagcaaggg cgaggagacc attacaagcg tgatcaagcc tgacatgaag  2280
aacaagctgc gcatggaggg caacgtgaac ggccacgcct tcgtgatcga gggcgagggc  2340
agcggcaagc ccttcgaggg catccagacg attgatttgg aggtgaagga gggcgccccg  2400
ctgcccttcg cctacgacat cctgaccacc gccttccact acggcaaccg cgtgttcacc  2460
aagtacccac ggtcgggaag tggctcaagt aaccgggagc tggtggttga ctttctctcc  2520
tacaagcttt cccagaaagg atacagctgg agtcagttta gtgatgtgga agagaacagg  2580
actgaggccc cagaagggac tgaatcggag atggagaccc ccagtgccat caatggcaac  2640
ccatcctggc acctggcaga cagccccgcg gtgaatggag ccactggcca cagcagcagt  2700
ttggatgccc gggaggtgat ccccatggca gcagtaaagc aagcgctgag ggaggcaggc  2760
```

```
gacgagtttg aactgcggta ccggcgggca ttcagtgacc tgacatccca gctccacatc  2820
accccaggga cagcatatca gagctttgaa caggtagtga atgaactctt ccgggatggg  2880
gtaaactggg gtcgcattgt ggccttttc tccttcggcg gggcactgtg cgtggaaagc  2940
gtagacaagg agatgcaggt attggtgagt cggatcgcag cttggatggc cacttacctg  3000
aatgaccacc tagagccttg gatccaggag aacggcggct gggatacttt tgtggaactc  3060
tatgggaaca atggatccag cgagctgatt aaggagaaca tgcacatgaa gctgtacatg  3120
gagggcaccg tggacaacca tcacttcaag tgcacatccg agggcgaagg caagccctac  3180
gagggcaccc agaccatgag aatcaaggtg gtcgagggcg gccctctccc cttcgccttc  3240
gacatcctgg ctactagctt cctctacggc agcaagacct tcatcaacca cacccagggc  3300
atccccgact tcttcaagca gtccttccct gagggcttca catgggagag agtcaccaca  3360
tacgaagacg ggggcgtgct gaccgctacc caggacacca gcctccagga cggctgcctc  3420
atctacaacg tcaagatcag aggggtgaac ttcacatcca acggccctgt gatgcagaag  3480
aaaacactcg gctgggaggc cttcaccgag acgctgtacc ccgctgacgg cggcctggaa  3540
ggcagaaacg acatggccct gaagctcgtg ggcgggagcc atctgatcgc aaacatcaag  3600
accacatata gatccaagaa acccgctaag aacctcaaga tgcctggcgt ctactatgtg  3660
gactacagac tggaaagaat caaggaggcc aacaacgaga cctacgtcga gcagcacgag  3720
gtggcagtgg ccagatactg cgacctccct agcaaactgg ggcacaagct taattaaggg  3780
cccgtttaaa cccgctgatc agcctcgact gtgccttcta                        3820

SEQ ID NO: 74          moltype = AA  length = 393
FEATURE                Location/Qualifiers
source                 1..393
                       mol_type = protein
                       organism = synthetic construct
SEQUENCE: 74
PLTGSTFHDQ IAMLSHRCFN TLTNSFQPSL LGRKILAAII MKKDSEDMGV VVSLGTGNRC  60
VKGDSLSLKG ETVNDCHAEI ISRRGFIRFL YSELMKYNSQ TAKDSIFEPA KGGEKLQIKK  120
TVSFHLYIST APCGDGALFD KSCSDRAMES TESRHYPVFE NPKQGKLRTK VENGQGTIPV  180
ESSDIVPTWD GIRLGERLRT MSCSDKILRW NVLGLQGALL THFLQPIYLK SVTLGYLFSQ  240
GHLTRAICCR VTRDGSAFED GLRHPFIVNH PKVGRVSIYD SKRQSGKTKE TSVNWCLADG  300
YDLEILDGTR GTVDGPRNEL SRVSKKNIFL LFKKLCSFRY RRDLLRLSYG EAKKAARDYE  360
TAKNYFKKGL KDMGYGNWIS KPQEEKNFYL CPV                               393

SEQ ID NO: 75          moltype = AA  length = 385
FEATURE                Location/Qualifiers
source                 1..385
                       mol_type = protein
                       organism = synthetic construct
SEQUENCE: 75
RTPMPQEFAD SISQLVTQKF REVTTDLTPM HARHKALAGI VMTKGLDARQ AQVVALSSGT  60
KCISGEHLSD QGLVVNDCHA EVVARRAFLH FLYTQLELHL SKRREDSERS IFVRLKEGGY  120
RLRENILFHL YVSTSPCGDA RLHSPYEITT DLHSSKHLVR KFRGHLRTKI ESGQGTVPVR  180
GPSAVQTWDG VLLGEQLITM SCTDKIARWN VLGLQGALLS HFVEPVYLQS IVVGSLHHTG  240
HLARVMSHRM EGVGQLPASY RHNRPLLSGV SDTEARQPGK SPPFSMNWVV GSADLEIINA  300
TTGRRSCGGP SRLCKHVLSA RWARLYGRLS TRTPSPGDTP SMYCEAKLGA HTYQSVKQQL  360
FKAFQKAGLG TWVRKPPEQQ QFLLT                                        385

SEQ ID NO: 76          moltype = AA  length = 379
FEATURE                Location/Qualifiers
source                 1..379
                       mol_type = protein
                       organism = synthetic construct
SEQUENCE: 76
HYEGRHIQYA KISQIVKERF NQLISNRSEY LKYSSSLAAF IIERAGQHEV VAIGTGEYNY  60
SQDIKPDGRV LHDTHAVVTA RRSLLRYFYR QLLLFYSKNP AMMEKSIFCT EPTSNLLTLK  120
QNINICLYMN QLPKGSAQIK SQLRLNPHSI SAFEANEELC LHVAVEGKIY LTVYCPKDGV  180
NRISSMSSSD KLTRWEVLGV QGALLSHFIQ PVYISSILIG DGNCSDTRGL EIAIKQRVDD  240
ALTSKLPMFY LVNRPHISLV PSAYPLQMNL EYKFLSLNWA QGDVSLEIVD GLSGKITESS  300
PFKSGMSMAS RLCKAAMLSR FNLLAKEAKK ELLEAGTYHA AKCMSASYQE AKCKLKSYLQ  360
QHGYGSWIVK SPCIEQFNM                                               379

SEQ ID NO: 77          moltype = AA  length = 383
FEATURE                Location/Qualifiers
source                 1..383
                       mol_type = protein
                       organism = synthetic construct
SEQUENCE: 77
SVENILTHEQ RCAALVSAGF DLLLDERSPY WACKGTVAGV ILEREIPRAR GHVKEIYKLV  60
ALGTGSSCCA GWLEFSGQQL HDCHGLVIAR RALLRFLFRQ LLLATQGGPK GKEQSVLAPQ  120
PGPGPPFTLK PRVFLHLYIS NTPKGAARDI YLPPTSEGGL PHSPPMRLQA HVLGQLKPVC  180
YVAPSLCDTH VGCLSASDKL ARWAVLGLGG ALLAHLVSPL YSTSLILADS CHDPPTLSRA  240
IHTRPCLDSV LGPCLPPPYV RTALHLFAGP PVAPSEPTPD TCRGLSLNWS LGDPGIEVVD  300
VATGRVKANA ALGPPSRLCK ASFLRAFHQA ARAVGKPYLL ALKTYEAAKA GPYQEARRQL  360
SLLLDQQGLG AWPSKPLVGK FRN                                          383

SEQ ID NO: 78          moltype = AA  length = 502
FEATURE                Location/Qualifiers
source                 1..502
                       mol_type = protein
```

```
                         organism = synthetic construct
SEQUENCE: 78
MWTADEIAQL CYEHYGIRLP KKGKPEPNHE WTLLAAVVKI QSPADKACDT PDKPVQVTKE  60
VVSMGTGTKC IGQSKMRKNG DILNDSHAEV IARRSFQRYL LHQLQLAATL KEDSIFVPGT  120
QKGVWKLRRD LIFVFFSSHT PCGDASIIPM LEFEDQPCCP VFRNWAHNSS VEASSNLEAP  180
GNERKCEDPD SPVTKKMRLE PGTAAREVTN GAAHHQSFGK QKSGPISPGI HSCDLTVEGL  240
ATVTRIAPGS AKVIDVYRTG AKCVPGEAGD SGKPGAAFHQ VGLLRVKPGR GDRTRSMSCS  300
DKMARWNVLG CQGALLMHLL EEPIYLSAVV IGKCPYSQEA MQRALIGRCQ NVSALPKGFG  360
VQELKILQSD LLFEQSRSAV QAKRADSPGR LVPCGAAISW SAVPEQPLDV TANGFPQGTT  420
KKTIGSLQAR SQISKVELFR SFQKLLSRIA RDKWPHSLRV QKLDTYQEYK EAASSYQEAW  480
STLRKQVFGS WIRNPPDYHQ FK                                          502

SEQ ID NO: 79            moltype = AA  length = 1226
FEATURE                  Location/Qualifiers
source                   1..1226
                         mol_type = protein
                         organism = Homo sapiens
SEQUENCE: 79
MNPRQGYSLS GYYTHPFQGY EHRQLRYQQP GPGSSPSSFL LKQIEFLKGQ LPEAPVIGKQ  60
TPSLPPSLPG LRPRFPVLLA SSTRGRQVDI RGVPRGVHLR SQGLQRGFQH PSPRGRSLPQ  120
RGVDCLSSHF QELSIYQDQE QRILKFLEEL GEGKATTAHD LSGKLGTPKK EINRVLYSLA  180
KKGKLQKEAG TPPLWKIAVS TQAWNQHSGV VRPDGHSQGA PNSDPSLEPE DRNSTSVSED  240
LLEPFIAVSA QAWNQHSGVV RPDSHSQGSP NSDPGLEPED SNSTSALEDP LEFLDMAEIK  300
EKICDYLFNV SDSSALNLAK NIGLTKARDI NAVLIDMERQ GDVYRQGTTP PIWHLTDKKR  360
ERMQIKRNTN SVPETAPAAI PETKRNAEFL TCNIPTSNAS NNMVTTEKVE NGQEPVIKLE  420
NRQEARPEPA RLKPPVHYNG PSKAGYVDFE NGQWATDDIP DDLNSIRAAP GEFRAIMEMP  480
SFYSHGLPRC SPYKKLTECQ LKNPISGLLE YAQFASQTCE FNMIEQSGPP HEPRFKFQVV  540
INGREFPPAE AGSKKVAKQD AAMKAMTILL EEAKAKDSGK SEESSHYSTE KESEKTAESQ  600
TPTPSATSFF SGKSPVTTLL ECMHKLGNSC EFRLLSKEGP AHEPKFQYCV AVGAQTFPSV  660
SAPSKKVAKQ MAAEEAMKAL HGEATNSMAS DNQPEGMISE SLDNLESMMP NKVRKIGELV  720
RYLNTNPVGG LLEYARSHGF AAEFKLVDQS GPPHEPKFVY QAKVGGRWFP AVCAHSKKQG  780
KQEAADAALR VLIGENEKAE RMGFTEVTPV TGASLRRTML LLSRSPEAQP KTLPLTGSTF  840
HDQIAMLSHR CFNTLTNSFQ PSLLGRKILA AIIMKKDSED MGVVVSLGTG NRCVKGDSLS  900
LKGETVNDCH AEIISRRGFI RFLYSELMKY NSQTAKDSIF EPAKGGEKLQ IKKTVSFHLY  960
ISTAPCGDGA LFDKSCSDRA MESTESRHYP VFENPKQGKL RTKVENGEGT IPVESSDIVP  1020
TWDGIRLGER LRTMSCSDKI LRWNVLGLQG ALLTHFLQPI YLKSVTLGYL FSQGHLTRAI  1080
CCRVTRDGSA FEDGLRHPFI VNHPKVGRVS IYDSKRQSGK TKETSVNWCL ADGYDLEILD  1140
GTRGTVDGPR NELSRVSKKN IFLLFKKLCS FRYRRDLLRL SYGEAKKAAR DYETAKNYFK  1200
KGLKDMGYGN WISKPQEEKN FYLCPV                                      1226

SEQ ID NO: 80            moltype = AA  length = 701
FEATURE                  Location/Qualifiers
source                   1..701
                         mol_type = protein
                         organism = Homo sapiens
SEQUENCE: 80
MDIEDEENMS SSSTDVKENR NLDNVSPKDG STPGPGEGSQ LSNGGGGGPG RKRPLEEGSN  60
GHSKYRLKKR RKTPGPVLPK NALMQLNEIK PGLQYTLLSQ TGPVHAPLFV MSVEVNGQVF  120
EGSGPTKKKA KLHAAEKALR SFVQFPNASE AHLAMGRTLS VNTDFTSDQA DFPDTLFNGF  180
ETPDKAEPPF YVGSNGDDSF SSSGDLSLSA SPVPASLAQP PLPVLPPFPP PSGKNPVMIL  240
NELRPGLKYD FLSESGESHA KSFVMSVVVD GQFFEGSGRN KKLAKARAAQ SALAAIFNLH  300
LDQTPSRQPI PSEGLQLHLP QVLADAVSRL VLGKFGDLTD NFSSPHARRK VLAGVVMTTG  360
TDVKDAKVIS VSTGTKCING EYMSDRGLAL NDCHAEIISR RSLLRFLYTQ LELYLNNKDD  420
QKRSIFQKSE RGGFRLKENV QFHLYISTSP CGDARIFSPH EPILEEPADR HPNRKARGQL  480
RTKIESGEGT IPVRSNASIQ TWDGVLQGER LLTMSCSDKI ARWNVVGIQG SLLSIFVEPI  540
YFSSIILGSL YHGDHLSRAM YQRISNIEDL PPLYTLNKPL LSGISNAEAR QPGKAPNFSV  600
NWTVGDSAIE VINATTGKDE LGRASRLCKH ALYCRWMRVH GKVPSHLLRS KITKPNVYHE  660
SKLAAKEYQA AKARLFTAFI KAGLGAWVEK PTEQDQFSLT P                     701

SEQ ID NO: 81            moltype = AA  length = 739
FEATURE                  Location/Qualifiers
source                   1..739
                         mol_type = protein
                         organism = Homo sapiens
SEQUENCE: 81
MASVLGSGRG SGGLSSQLKC KSKRRRRRRS KRKDKVSILS TFLAPFKHLS PGITNTEDDD  60
TLSTSSAEVK ENRNVGNLAA RPPPSGDRAR GGAPGAKRKR PLEEGNGGHL CKLQLVWKKL  120
SWSVAPKNAL VQLHELRPGL QYRTVSQTGP VHAPVFAVAV EVNGLTFEGT GPTKKKAKMR  180
AAELALRSFV QFPNACQAHL AMGGGPGPGT DFTSDQADFP DTLFQEFEPP APRPGLAGGR  240
PGDAALLSAA YGRRRLLCRA LDLVGPTPAT PAAPGERNPV VLLNRLRAGL RYVCLAEPAE  300
RRARSFVMAV SVDGRTFEGS GRSKKLARGQ AAQAALQELF DIQMPGHAPG RARRTPMPQE  360
FADSISQLVT QKFREVTTDL TPMHARHKAL AGIVMTKGLD ARQAQVVALS SGTKCISGEH  420
LSDQGLVVND CHAEVVARRA FLHFLYTQLE LHLSKRREDS ERSIFVRLKE GGYRLRENIL  480
FHLYVSTSPC GDARLHSPYE ITTDLHSSKH LVRKFRGHLR TKIESGEGTV PVRGPSAVQT  540
WDGVLLGEQL ITMSCTDKIA RWNVLGLQGA LLSHFVEPVY LQSIVVGSLH HTGHLARVMS  600
HRMEGVGQLP ASYRHNRPLL SGVSDAEARQ PGKSPPFSMN WVVGSADLEI INATTGRRSC  660
GGPSRLCKHV LSARWARLYG RLSTRTPSPG DTPSMYCEAK LGAHTYQSVK QQLFKAFQKA  720
GLGTWVRKPP EQQQFLLTL                                              739
```

```
SEQ ID NO: 82          moltype = AA  length = 576
FEATURE                Location/Qualifiers
source                 1..576
                       mol_type = protein
                       organism = Homo sapiens
SEQUENCE: 82
MASNNHWFQS SQVPSFAQML KKNLPVQPAT KTITTPTGWS SESYGLSKMA SKVTQVTGNF  60
PEPLLSKNLS SISNPVLPPK KIPKEFIMKY KRGEINPVSA LHQFAQMQRV QLDLKETVTT  120
GNVMGPYFAF CAVVDGIQYK TGLGQNKKES RSNAAKLALD ELLQLDEPEP RILETSGPPP  180
FPAEPVVLSE LAYVSKVHYE GRHIQYAKIS QIVKERFNQL ISNRSEYLKY SSSLAAFIIE  240
RAGQHEVVAI GTGEYNYSQD IKPDGRVLHD THAVVTARRS LLRYFYRQLL LFYSKNPAMM  300
EKSIFCTEPT SNLLTLKQNI NICLYMNQLP KGSAQIKSQL RLNPHSISAF EANEELCLHV  360
AVEGKIYLTV YCPKDGVNRI SSMSSSDKLT RWEVLGVQGA LLSHFIQPVY ISSILIGDGN  420
CSDTRGLEIA IKQRVDDALT SKLPMFYLVN RPHISLVPSA YPLQMNLEYK FLSLNWAQGD  480
VSLEIVDGLS GKITESSPFK SGMSMASRLC KAAMLSRFNL LAKEAKKELL EAGTYHAAKC  540
MSASYQEAKC KLKSYLQQHG YGSWIVKSPC IEQFNM                            576

SEQ ID NO: 83          moltype = AA  length = 583
FEATURE                Location/Qualifiers
source                 1..583
                       mol_type = protein
                       organism = Homo sapiens
SEQUENCE: 83
MASASQGADD DGSRRKPRLA ASLQISPQPR PWRPLPAQAQ SAWGPAPAPA TYRAEGGWPQ  60
VSVLRDSGPG AGAGVGELGA ARAWENLGEQ MGKAPRVPVP PAGLSLPLKD PPASQAVSLL  120
TEYAASLGIF LLFREDQPPG PCFPFSVSAE LDGVVCPAGT ANSKTEAKQQ AALSALCYIR  180
SQLENPESPQ TSSRPPLAPL SVENILTHEQ RCAALVSAGF DLLLDERSPY WACKGTVAGV  240
ILEREIPRAR GHVKEIYKLV ALGTGSSCCA GWLEFSGQQL HDCHGLVIAR RALLRFLFRQ  300
LLLATQGGPK GKEQSVLAPQ PGPGPPFTLK PRVFLHLYIS NTPKGAARDI YLPPTSEGGL  360
PHSPPMRLQA HVLGQLKPVC YVAPSLCDTH VGCLSASDKL ARWAVLGLGG ALLAHLVSPL  420
YSTSLILADS CHDPPTLSRA IHTRPCLDSV LGPCLPPPYV RTALHLFAGP PVAPSEPTPD  480
TCRGLSLNWS LGDPGIEVVD VATGRVKANA ALGPPSRLCK ASFLRAFHQA ARAVGKPYLL  540
ALKTYEAAKA GPYQEARRQL SLLLDQQGLG AWPSKPLVGK FRN                    583

SEQ ID NO: 84          moltype = AA  length = 502
FEATURE                Location/Qualifiers
source                 1..502
                       mol_type = protein
                       organism = Homo sapiens
SEQUENCE: 84
MWTADEIAQL CYEHYGIRLP KKGKPEPNHE WTLLAAVVKI QSPADKACDT PDKPVQVTKE  60
VVSMGTGTKC IGQSKMRKNG DILNDSHAEV IARRSFQRYL LHQLQLAATL KEDSIFVPGT  120
QKGVWKLRRD LIFVFFSSHT PCGDASIIPM LEFEDQPCCP VFRNWAHNSS VEASSNLEAP  180
GNERKCEDPD SPVTKKMRLE PGTAAREVTN GAAHHQSFGK QKSGPISPGI HSCDLTVEGL  240
ATVTRIAPGS AKVIDVYRTG AKCVPGEAGD SGKPGAAFHQ VGLLRVKPGR GDRTRSMSCS  300
DKMARWNVLG CQGALLMHLL EEPIYLSAVV IGKCPYSQEA MQRALIGRCQ NVSALPKGFG  360
VQELKILQSD LLFEQSRSAV QAKRADSPGR LVPCGAAISW SAVPEQPLDV TANGFPQGTT  420
KKTIGSLQAR SQISKVELFR SFQKLLSRIA RDKWPHSLRV QKLDTYQEYK EAASSYQEAW  480
STLRKQVFGS WIRNPPDYHQ FK                                           502

SEQ ID NO: 85          moltype = AA  length = 13
FEATURE                Location/Qualifiers
source                 1..13
                       mol_type = protein
                       organism = synthetic construct
SEQUENCE: 85
SRLEEELRRR LTE                                                     13

SEQ ID NO: 86          moltype = AA  length = 13
FEATURE                Location/Qualifiers
source                 1..13
                       mol_type = protein
                       organism = synthetic construct
SEQUENCE: 86
GRLEEELRRR LSP                                                     13

SEQ ID NO: 87          moltype = AA  length = 13
FEATURE                Location/Qualifiers
source                 1..13
                       mol_type = protein
                       organism = synthetic construct
SEQUENCE: 87
GRLEQEIRAR LSP                                                     13

SEQ ID NO: 88          moltype = AA  length = 792
FEATURE                Location/Qualifiers
source                 1..792
                       mol_type = protein
                       organism = synthetic construct
```

-continued

```
SEQUENCE: 88
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGS SELIKENMHM KLYMEGTVDN HHFKCTSEGE GKPYEGTQTM  600
RIKVVEGGPL PFAFDILATS FLYGSKTFIN HTQGIPDFFK QSFPEGFTWE RVTTYEDGGV  660
LTATQDTSLQ DGCLIYNVKI RGVNFTSNGP VMQKKTLGWE AFTETLYPAD GGLEGRNDMA  720
LKLVGGSHLI ANIKTTYRSK KPAKNLKMPG VYYVDYRLER IKEANNETYV EQHEVAVARY  780
CDLPSKLGHK LN                                                     792

SEQ ID NO: 89          moltype = AA  length = 1005
FEATURE                Location/Qualifiers
source                 1..1005
                       mol_type = protein
                       organism = synthetic construct
SEQUENCE: 89
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQSNRELVVD FLSYKLSQKG YSWSQFSDVE ENRTEAPEGT  180
ESEMETPSAI NGNPSWHLAD SPAVNGATGH SSSLDAREVI PMAAVKQALR EAGDEFELRY  240
RRAFSDLTSQ LHITPGTAYQ SFEQVVNELF RDGVNWGRIV AFFSFGGALC VESVDKEMQV  300
LVSRIAAWMA TYLNDHLEPW IQENGGWDTF VELYGNNAAG GSGGSGGSGG SAAAQLHLPQ  360
VLADAVSRLV LGKFGDLTDN FSSPHARRKV LAGVVMTTGT DVKDAKVISV STGTKCINGE  420
YMSDRGLALN DCHAEIISRR SLLRFLYTQL ELYLNNKDDQ KRSIFQKSER GGFRLKENVQ  480
FHLYISTSPC GDARIFSPHE PILEEPAASG SGTGAPPNLW AAQRYGRELR RMSDELVDRH  540
PNRKARGQLR TKIESGQGTI PVRSNASIQT WDGVLQGERL LTMSCSDKIA RWNVVGIQGS  600
LLSIFVEPIY FSSIILGSLY HGDHLSRAMY QRISNIEDLP PLYTLNKPLL SGISNAEARQ  660
PGKAPNFSVN WTVGDSAIEV INATTGKDEL GRASRLCKHA LYCRWMRVHG KVPSHLLRSK  720
ITKPNVYHES KLAAKEYQAA KARLFTAFIK AGLGAWVEKP TEQDQFSLTG SGSSELIKEN  780
MHMKLYMEGT VDNHHFKCTS EGEGKPYEGT QTMRIKVVEG GPLPFAFDIL ATSFLYGSKT  840
FINHTQGIPD FFKQSFPEGF TWERVTTYED GGVLTATQDT SLQDGCLIYN VKIRGVNFTS  900
NGPVMQKKTL GWEAFTETLY PADGGLEGRN DMALKLVGGS HLIANIKTTY RSKKPAKNLK  960
MPGVYYVDYR LERIKEANNE TYVEQHEVAV ARYCDLPSKL GHKLN                 1005

SEQ ID NO: 90          moltype = AA  length = 999
FEATURE                Location/Qualifiers
source                 1..999
                       mol_type = protein
                       organism = synthetic construct
SEQUENCE: 90
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNGSSEL IKENMHMKLY  780
MEGTVDNHHF KCTSEGEGKP YEGTQTMRIK VVEGGPLPFA FDILATSFLY GSKTFINHTQ  840
GIPDFFKQSF PEGFTWERVT TYEDGGVLTA TQDTSLQDGC LIYNVKIRGV NFTSNGPVMQ  900
KKTLGWEAFT ETLYPADGGL EGRNDMALKL VGGSHLIANI KTTYRSKKPA KNLKMPGVYY  960
VDYRLERIKE ANNETYVEQH EVAVARYCDL PSKLGHKLN                        999

SEQ ID NO: 91          moltype = AA  length = 794
FEATURE                Location/Qualifiers
source                 1..794
                       mol_type = protein
                       organism = synthetic construct
SEQUENCE: 91
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPADRHP NRKARGQLRT KIESGQGTIP VRSNASIQTW  360
DGVLQGERLL TMSCSDKIAR WNVVGIQGSL LSIFVEPIYF SSIILGSLYH GDHLSRAMYQ  420
RISNIEDLPP LYTLNKPLLS GISNAEARQP GKAPNFSVNW TVGDSAIEVI NATTGKDELG  480
RASRLCKHAL YCRWMRVHGK VPSHLLRSKI TKPNVYHESK LAAKEYQAAK ARLFTAFIKA  540
```

GLGAWVEKPT EQDQFSLTGS GSSELIKENM HMKLYMEGTV DNHHFKCTSE GEGKPYEGTQ 600
TMRIKVVEGG PLPFAFDILA TSFLYGSKTF INHTQGIPDF FKQSFPEGFT WERVTTYEDG 660
GVLTATQDTS LQDGCLIYNV KIRGVNFTSN GPVMQKKTLG WEAFTETLYP ADGGLEGRND 720
MALKLVGGSH LIANIKTTYR SKKPAKNLKM PGVYYVDYRL ERIKEANNET YVEQHEVAVA 780
RYCDLPSKLG HKLN 794

SEQ ID NO: 92 moltype = AA length = 993
FEATURE Location/Qualifiers
source 1..993
mol_type = protein
organism = synthetic construct
SEQUENCE: 92
MASNFTQFVL VDNGGTGDVT VAPSNFANGI AEWISSNSRS QAYKVTCSVR QSSAQNRKYT 60
IKVEVPKGAW RSYLNMELTI PIFATNSDCE LIVKAMQGLL KDGNPIPSAI AANSGIYGGS 120
GSGAGSGSPA GGGAPGSGGG STGAPPNLWA AQRYGRELRR MSDEFVDSFK KASQLHLPQV 180
LADAVSRLVL GKFGDLTDNF SSPHARRKVL AGVVMTTGTD VKDAKVISVS TGTKCINGEY 240
MSDRGLALND CHAEIISRRS LLRFLYTQLE LYLNNKDDQK RSIFQKSERG GFRLKENVQF 300
HLYISTSPCG DARIFSPHEP ILEEPADRHP NRKARGQLRT KIESGQGTIP VRSNASIQTW 360
DGVLQGERLL TMSCSDKIAR WNVVGIQGSL LSIFVEPIYF SSIILGSLYH GDHLSRAMYQ 420
RISNIEDLPP LYTLNKPLLS GISNAEARQP GKAPNFSVNW TVGDSAIEVI NATTGKDELG 480
RASRLCKHAL YCRWMRVHGK VPSHLLRSKI TKPNVYHESK LAAKEYQAAK ARLFTAFIKA 540
GLGAWVEKPT EQDQFSLTGS AAASSNRELV VDFLSYKLSQ KGYSWSQFSD VEENRTEAPE 600
GTESEMETPS AINGNPSWHL ADSPAVNGAT GHSSSLDARE VIPMAAVKQA LREAGDEFEL 660
RYRRAFSDLT SQLHITPGTA YQSFEQVVNE LFRDGVNWGR IVAFFSFGGA LCVESVDKEM 720
QVLVSRIAAW MATYLNDHLE PWIQENGGWD TFVELYGNNG SSELIKENMH MKLYMEGTVD 780
NHHFKCTSEG EGKPYEGTQT MRIKVVEGGP LPFAFDILAT SFLYGSKTFI NHTQGIPDFF 840
KQSFPEGFTW ERVTTYEDGG VLTATQDTSL QDGCLIYNVK IRGVNFTSNG PVMQKKTLGW 900
EAFTETLYPA DGGLEGRNDM ALKLVGGSHL IANIKTTYRS KKPAKNLKMP GVYYVDYRLE 960
RIKEANNETY VEQHEVAVAR YCDLPSKLGH KLN 993

SEQ ID NO: 93 moltype = AA length = 1081
FEATURE Location/Qualifiers
source 1..1081
mol_type = protein
organism = synthetic construct
SEQUENCE: 93
MASNFTQFVL VDNGGTGDVT VAPSNFANGI AEWISSNSRS QAYKVTCSVR QSSAQNRKYT 60
IKVEVPKGAW RSYLNMELTI PIFATNSDCE LIVKAMQGLL KDGNPIPSAI AANSGIYGGS 120
GSGAGSGSPA GGGAPGSGGG SQLHLPQVLA DAVSRLVLGK FGDLTDNFSS PHARRKVLAG 180
VVMTTGTDVK DAKVISVSTG TKCINGEYMS DRGLALNDCH AEIISRRSLL RFLYTQLELY 240
LNNKDDQKRS IFQKSERGGF RLKENVQFHL YISTSPCGDA RIFSPHEPIL EEPAASGSGT 300
GAPPNLWAAQ RYGRELRRMS DEFVDRHPNR KARGQLRTKI ESGQGTIPVR SNASIQTWDG 360
VLQGERLLTM SCSDKIARWN VVGIQGSLLS IFVEPIYFSS IILGSLYHGD HLSRAMYQRI 420
SNIEDLPPLY TLNKPLLSGI SNAEARQPGK APNFSVNWTV GDSAIEVINA TTGKDELGRA 480
SRLCKHALYC RWMRVHGKVP SHLLRSKITK PNVYHESKLA AKEYQAAKAR LFTAFIKAGL 540
GAWVEKPTEQ DQFSLTGSGG TENLYFQSAA SSNRELVVDF LSYKLSQKGY SWSQFSDVEE 600
NRTEAPEGTE SEMETPSAIN GNPSWHLADS PAVNGATGHS SSLDAREVIP MAAVKQALRE 660
AGDEFELRYR RAFSDLTSQL HITPGTAYQS FEQVVNELFR DGVNWGRIVA FFSFGGALCV 720
ESVDKEMQVL VSRIAAWMAT YLNDHLEPWI QENGGWDTFV ELYGNNGSSE LIKENMHMKR 780
PSVATMVSKG EEDNMAIIKE FMRFKVHMEG SVNGHEFEIE GEGEGRPYEG TQTAKLKVTK 840
GGPLPFAWDI LSPQFMYGSK AYVKHPADIP DYLKLSFPEG FKWERVMNFE DGGVVTVTQD 900
SSLQDGEFIY KVKLRGTNFP SDGPVMQKKT MGWEASSERM YPEDGALKGE IKQRLKLKDG 960
GHYDAEVKTT YKAKKPVQLP GAYNVNIKLD ITSHNEDYTI VEQYERAEGR HSTGGMDELY 1020
KDYKDDDDKG SGATNFSLLK QAGDVEENPG PASAGSGEGR GSLLTCGDVE ENPGPATGNS 1080
A 1081

SEQ ID NO: 94 moltype = AA length = 1081
FEATURE Location/Qualifiers
source 1..1081
mol_type = protein
organism = synthetic construct
SEQUENCE: 94
MASNFTQFVL VDNGGTGDVT VAPSNFANGI AEWISSNSRS QAYKVTCSVR QSSAQNRKYT 60
IKVEVPKGAW RSYLNMELTI PIFATNSDCE LIVKAMQGLL KDGNPIPSAI AANSGIYGGS 120
GSGAGSGSPA GGGAPGSGGG SQLHLPQVLA DAVSRLVLGK FGDLTDNFSS PHARRKVLAG 180
VVMTTGTDVK DAKVISVSTG TKCINGEYMS DRGLALNDCH AEIISRRSLL RFLYTQLELY 240
LNNKDDQKRS IFQKSERGGF RLKENVQFHL YISTSPCGDA RIFSPHEPIL EEPAASGSGT 300
GAPPNLWAAQ RYGRELRRMS DEFVDRHPNR KARGQLRTKI ESGQGTIPVR SNASIQTWDG 360
VLQGERLLTM SCSDKIARWN VVGIQGSLLS IFVEPIYFSS IILGSLYHGD HLSRAMYQRI 420
SNIEDLPPLY TLNKPLLSGI SNAEARQPGK APNFSVNWTV GDSAIEVINA TTGKDELGRA 480
SRLCKHALYC RWMRVHGKVP SHLLRSKITK PNVYHESKLA AKEYQAAKAR LFTAFIKAGL 540
GAWVEKPTEQ DQFSLTGSGG TENLYFQSAA SSNRELVVDF LSYKLSQKGY SWSQFSDVEE 600
NRTEAPEGTE SEMETPSAIN GNPSWHLADS PAVNGATGHS SSLDAREVIP MAAVKQALRE 660
AGDEFELRYR RAFSDLTSQL HITPGTAYQS FEQVVNELFR DGVNWGRIVA FFSFGGALCV 720
ESVDKEMQVL VSRIAAWMAT YLNDHLEPWI QENGGWDTFV ELYGNNGSSE LIKENMHMKR 780
PSVATMVSKG EEDNMAIIKE FMRFKVHMEG SVNGHEFEIE GEGEGRPYEG TQTAKLKVTK 840
GGPLPFAWDI LSPQFMYGSK AYVKHPADIP DYLKLSFPEG FKWERVMNFE DGGVVTVTQD 900
SSLQDGEFIY KVKLRGTNFP SDGPVMQKKT MGWEASSERM YPEDGALKGE IKQRLKLKDG 960
GHYDAEVKTT YKAKKPVQLP GAYNVNIKLD ITSHNEDYTI VEQYERAEGR HSTGGMDELY 1020

-continued

```
KDYKDDDDKG SGATNFSLLK QAGDVEENPG PASAGSGEGR GSLLTCGDVE ENPGPATGNS  1080
A                                                                  1081

SEQ ID NO: 95          moltype = AA  length = 385
FEATURE                Location/Qualifiers
source                 1..385
                       mol_type = protein
                       organism = synthetic construct
SEQUENCE: 95
QLHLPQVLAD AVSRLVLGKF GDLTDNFSSP HARRKVLAGV VMTTGTDVKD AKVISVSTGT  60
KCINGEYMSD RGLALNDCHA EIISRRSLLR FLYTQLELYL NNKDDQKRSI FQKSERGGFR  120
LKENVQFHLY ISTSPCGDAR IFSPHEPILE EPADRHPNRK ARGQLRTKIE SGQGTIPVRS  180
NASIQTWDGV LQGERLLTMS CSDKIARWNV VGIQGSLLSI FVEPIYFSSI ILGSLYHGDH  240
LSRAMYQRIS NIEDLPPLYT LNKPLLSGIS NAEARQPGKA PNFSVNWTVG DSAIEVINAT  300
TGKDELGRAS RLCKHALYCR WMRVHGKVPS HLLRSKITKP NVYHESKLAA KEYQAAKARL  360
FTAFIKAGLG AWVEKPTEQD QFSLT                                        385

SEQ ID NO: 96          moltype = AA  length = 385
FEATURE                Location/Qualifiers
source                 1..385
                       mol_type = protein
                       organism = synthetic construct
SEQUENCE: 96
QLHLPQVLAD AVSRLVLGKF GDLTDNFSSP HARRKVLAGV VMTTGTDVKD AKVISVSTGT  60
KCINGEYMSD RGLALNDCHA AIISRRSLLR FLYTQLELYL NNKDDQKRSI FQKSERGGFR  120
LKENVQFHLY ISTSPCGDAR IFSPHEPILE EPADRHPNRK ARGQLRTKIE SGQGTIPVRS  180
NASIQTWDGV LQGERLLTMS CSDKIARWNV VGIQGSLLSI FVEPIYFSSI ILGSLYHGDH  240
LSRAMYQRIS NIEDLPPLYT LNKPLLSGIS NAEARQPGKA PNFSVNWTVG DSAIEVINAT  300
TGKDELGRAS RLCKHALYCR WMRVHGKVPS HLLRSKITKP NVYHESKLAA KEYQAAKARL  360
FTAFIKAGLG AWVEKPTEQD QFSLT                                        385

SEQ ID NO: 97          moltype = AA  length = 153
FEATURE                Location/Qualifiers
source                 1..153
                       mol_type = protein
                       organism = synthetic construct
SEQUENCE: 97
QLHLPQVLAD AVSRLVLGKF GDLTDNFSSP HARRKVLAGV VMTTGTDVKD AKVISVSTGT  60
KCINGEYMSD RGLALNDCHA EIISRRSLLR FLYTQLELYL NNKDDQKRSI FQKSERGGFR  120
LKENVQFHLY ISTSPCGDAR IFSPHEPILE EPA                               153

SEQ ID NO: 98          moltype = AA  length = 232
FEATURE                Location/Qualifiers
source                 1..232
                       mol_type = protein
                       organism = synthetic construct
SEQUENCE: 98
DRHPNRKARG QLRTKIESGQ GTIPVRSNAS IQTWDGVLQG ERLLTMSCSD KIARWNVVGI  60
QGSLLSIFVE PIYFSSIILG SLYHGDHLSR AMYQRISNIE DLPPLYTLNK PLLSGISNAE  120
ARQPGKAPNF SVNWTVGDSA IEVINATTGK DELGRASRLC KHALYCRWMR VHGKVPSHLL  180
RSKITKPNVY HESKLAAKEY QAAKARLFTA FIKAGLGAWV EKPTEQDQFS LT          232

SEQ ID NO: 99          moltype = DNA  length = 5372
FEATURE                Location/Qualifiers
source                 1..5372
                       mol_type = other DNA
                       organism = synthetic construct
SEQUENCE: 99
cttatcgaaa ttaatacgac tcactatagg gagacccaag ctggctagag gatcgaaccc  60
ttaaggccac catggcgtcc aatttcactc agtttgtgct ggttgacaac ggcgggaccg  120
gggacgttac ggtagccccc tcaaactttg ccaacggtat agcggagtgg ataagcagca  180
attctaggag tcaagcatac aaagttacat gcagcgtgcg ccaatctagc gctcagaatc  240
gcaagtacac cattaaagta gaggtcccca agggagcctg gagaagctat cttaacatgg  300
agttgaccat accaatcttc gctaccaact ctgactgtga actcattgtg aaagccatgc  360
aaggtctgct caaggatggt aacccaattc cgtccgctat cgctgccaac tctgggattt  420
acgggggcag tgggagcggt gcaggatctg gtagtccagc tgggggagga gcaccgggta  480
gcggtggggg gtctcagctg cacctgcccc aggttctcgc agacgccgta tcccgccttg  540
tactgggcaa gtttggtgat cttactgaca atttttcatc tcctcatgcg aggcggaaag  600
tactcgcagg cgtcgtcatg acgaccggaa ctgacgtgaa agacgccaaa gtcatctctg  660
tctccacggg cacaaagtgc ataaacgggg agtacatgag cgaccggggg ctggcactga  720
atgattgtca cgctgaaata atatctaggc gatctctgct tagatttctc tacactcaac  780
tcgaattgta ccttaacaac aaagatgacc agaaacgcag tatatttcag aaatcagaac  840
gcggcggatt tcgacttaag gaaaacgttc agttccactt gtatatcagc acatcccctt  900
gcggtgacgc ccgaatcttt tccccgcacg agccgatatt ggaggagccc gcggctagcg  960
ggtcgggcac cggtgctcca cccaatctct gggcagcgca gcgctacggc cgtgagctca  1020
gaaggatgtc cgatgagttc gtcgacagac atcctaatag gaaggctaga ggccaacttc  1080
ggacgaagat tgaaagtggc cagggtacta tcccggtgcg gtccaacgct agtattcaaa  1140
cgtgggacgg agtccttcaa ggtgaacggc tgttgacaat gagctgctca gacaaaatcg  1200
cgcgctggaa tgtagtggga atccaaggca gcctcttgag catattcgta gaacccatat  1260
```

-continued

```
atttctcatc cattattttg ggctctctgt atcatggtga ccatctgtca agggctatgt  1320
accaacgaat ttctaatatc gaggatcttc ctccactcta tacactcaat aagcctctct  1380
tgtccgggat atcaaacgct gaggcccgcc agccagggaa agctcctaac ttcagtgtta  1440
actggaccgt tggtgattct gcgatagagg tcatcaacgc cacgacaggt aaggatgagc  1500
tcggtagagc ctcacgcctg tgtaaacacg cgttgtattg tagatggatg agagtacatg  1560
ggaaggtccc atctcacttg ctccgaagca agatcactaa gcctaatgtg tatcatgagt  1620
caaaactcgc ggctaaagaa taccaggcag ccaaagctcg actttttaca gcttttatta  1680
aggcagggct cggggcatgg gtcgagaagc cgaccgagca ggaccaattc tctctgacgg  1740
ggagcggagg tacggagaat ttgtattttc agagcgccgc ttcaagtaac cgggagctgg  1800
tggttgactt tctctcctac aagctttccc agaaaggata cagctggagt cagtttagtg  1860
atgtggaaga gaacaggact gaggccccag aagggactga atcggagatg gagaccccca  1920
gtgccatcaa tggcaaccca tcctggcacc tggcagacag ccccgcggtg aatggagcca  1980
ctggccacag cagcagtttg gatgcccggg aggtgatccc catggcagca gtaaagcaag  2040
cgctgaggga ggcaggcgac gagtttgaac tgcggtaccg gcgggcattc agtgacctga  2100
catcccagct ccacatcacc ccagggacag catatcagag ctttgaacag gtagtgaatg  2160
aactcttccg ggatggggta aactggggtc gcattgtggc ctttttctcc ttcggcgggg  2220
cactgtgcgt ggaaagcgta gacaaggaga tgcaggtatt ggtgagtcgg atcgcagctt  2280
ggatggccac ttacctgaat gaccacctag agccttggat ccaggagaac ggcggctggg  2340
atacttttgt ggaactctat gggaacaatg gatccagcga gctgattaag gagaacatgc  2400
acatgaagcg cccatcggtc gccaccatgg tgagcaaggg cgaggaggat aacatggcca  2460
tcatcaagga gttcatgcgc ttcaaggtgc acatggaggg ctccgtgaac ggccacgagt  2520
tcgagatcga gggcgagggc gagggccgcc cctacgaggg cacccagacc gccaagctga  2580
aggtgaccaa gggtggcccc ctgcccttcg cctgggacat cctgtcccct cagttcatgt  2640
acggctccaa ggcctacgtg aagcaccccg ccgacatccc cgactacttg aagctgtcct  2700
tccccgaggg cttcaagtgg gagcgcgtga tgaacttcga ggacggcggc gtggtgaccg  2760
tgacccagga ctcctccctg caggacggcg agttcatcta caaggtgaag ctgcgcggca  2820
ccaacttccc ctccgacggc cccgtaatgc agaagaagac catgggctgg gaggcctcct  2880
ccgagcggat gtaccccgag gacggcgccc tgaagggcga gatcaagcag aggctgaagc  2940
tgaaggacgg cggccactac gacgctgagg tcaagaccac ctacaaggcc aagaagcccg  3000
tgcagctgcc cggcgcctac aacgtcaaca tcaagttgga catcacctcc cacaacgagg  3060
actacaccat cgtggaacag tacgaacgcg ccgagggccg ccactccacc ggcggcatgg  3120
acgagctgta caaggattac aaggatgacg atgacaaagg tagcggggca actaatttta  3180
gcttactcaa acaggctggg gacgtcgagg agaatccagg ccctgcatcc gctggctctg  3240
gagaaggacg aggctccttg ctcacctgtg gagatgtcga agagaaccca ggtcctgcaa  3300
ccgggaattc cgcgtagcgc tagctttgcc agcgccacgc gaaacatgag gatcacccat  3360
gtgccgctat ggcagaaatc ggtactggct ttccattcga cccccattat gtggaagtcc  3420
tgggcgagcg catgcactac gtcgatgttg gtccgcgcga tggcacccct gtgctgttcc  3480
tgcacggtaa cccgacctcc tcctacgtgt ggcgcaacat catcccgcat gttgcaccga  3540
cccatcgctg cattgctcca gacctgatcg gtatgggcaa atccgacaaa ccagacctgg  3600
gttatttctt cgacgaccac gtccgcttca tggatgcctt catcgaagcc ctgggtctgg  3660
aagaggtcgt cctggtcatt cacgactggg gctccgctct gggtttccac tgggccaagc  3720
gcaatccaga gcgcgtcaaa ggtattgcat ttatggagtt catccgccct atcccgacct  3780
gggacgaatg gccagaattt gcccgcgaga ccttccaggc cttccgcacc accgacgtcg  3840
gccgcaagct gatcatcgat cagaacgttt ttatcgaggg tacgctgccg atgggtgtcg  3900
tccgcccgct gactgaagtc gagatggacc attaccgcga gccgttcctg aatcctgttg  3960
accgcgagcc actgtggcgc ttcccaaacg agctgccaat cgccggtgag ccagcgaaca  4020
tcgtcgcgct ggtcgaagaa tacatggact ggctgcacca gtcccctgtc ccgaagctgc  4080
tgttctgggg caccccaggc gttctgatcc caccggccga agccgctcgc ctggccaaaa  4140
gcctgcctaa ctgcaaggct gtggacatcg gcccgggtct gaatctgctg caagaagaca  4200
acccggacct gatcggcagc gagatcgcgc gctggctgtc gacgctcgag atttctggca  4260
ccggtatggc atctatgact ggaggccaac agatgggtcc tgcaaccggg aattccgcgt  4320
agcgctagct ttgccagcgc cacgcgaaac atgaggatca cccatgtact agtgccacaa  4380
acttctctct gctaaagcaa gcaggtgatg ttgaagaaaa cccagggcct ggagggtccg  4440
agggcagggg aagtctccta acatgcgggg acgtggagga aaatcccggc ccatccggat  4500
atccctacga tgtgcccgat tacgctatcg atgtgagcaa gggcgaagaa gataacaagg  4560
cctctctccc agcgacacat gagttacaca tctttggctc catcaacggt gtggactttg  4620
acatggtggg tcagggcacc ggcaatccaa atgatggtta tgaggagtta aacctgaagt  4680
ccaccaaggg tgacctccag ttctccccct ggattctggt ccctcatatc gggtatggct  4740
tccatcagta cctgccctac cctgacggga tgtcgccttt ccaggccgcc atggtagatg  4800
gcagcggata ccaagtccat cgcacaatgc agtttgaaga tggtgcctcc cttactgtta  4860
actaccgcta cacctacgag ggaagccaca tcaaaggaga ggcccaggtg aaggggactg  4920
gtttccctgc tgacggtcct gtgatgacca actcgctgac cgctgcggac tggtgcaggt  4980
cgaagaagac ttaccccaac gacaaaacca tcatcagtac ctttaagtgg agttacacca  5040
ctggaaatgg caagagatac cggagcactg cgcggaccac ctacaccttt gccaagccaa  5100
tggcggctaa ctatctgaag aaccagccga tgtacgtgtt ccgtaagacg gagctcaagc  5160
actccaagac cgagctcaac ttcaaggagt ggcaaaaggc ctttaccgat gtgatgggaa  5220
tggacgagct gtataaggct agctaagcgg ccgctcgagt ctagagggcc cgcggttcga  5280
aggtaagcct atccctaacc ctctcctcgg tctcgattct acgcgtaccg gtcatcatca  5340
ccatcaccat tgagtttaaa cccgctgatc ag                                5372
```

```
SEQ ID NO: 100          moltype = AA  length = 117
FEATURE                 Location/Qualifiers
source                  1..117
                        mol_type = protein
                        organism = synthetic construct
SEQUENCE: 100
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIY     117
```

```
SEQ ID NO: 101         moltype = AA  length = 121
FEATURE                Location/Qualifiers
source                 1..121
                       mol_type = protein
                       organism = synthetic construct
SEQUENCE: 101
MSKTIVLSVG EATRTLTEIQ STADRQIFEE KVGPLVGRLR LTASLRQNGA KTAYRVNLKL  60
DQADVVDSGL PKVRYTQVWS HDVTIVANST EASRKSLYDL TKSLVATSQV EDLVVNLVPL  120
G                                                                 121

SEQ ID NO: 102         moltype = AA  length = 23
FEATURE                Location/Qualifiers
source                 1..23
                       mol_type = protein
                       organism = synthetic construct
SEQUENCE: 102
MADAQTRRRE RRAEKQAQWK AAN                                         23

SEQ ID NO: 103         moltype = AA  length = 19
FEATURE                Location/Qualifiers
source                 1..19
                       mol_type = protein
                       organism = synthetic construct
SEQUENCE: 103
MASGPRPRGT RGKGRRIRR                                              19

SEQ ID NO: 104         moltype = AA  length = 305
FEATURE                Location/Qualifiers
source                 1..305
                       mol_type = protein
                       organism = synthetic construct
SEQUENCE: 104
LCQRHAKHED HPCTSATNFS LLKQAGDVEE NPGPGGSEGR GSLLTCGDVE ENPGPSGYPY  60
DVPDYAHMVS KGEEDNMASL PATHELHIFG SINGVDFDMV GQGTGNPNDG YEELNLKSTK  120
GDLQFSPWIL VPHIGYGFHQ YLPYPDGMSP FQAAMVDGSG YQVHRTMQFE DGASLTVNYR  180
YTYEGSHIKG EAQVKGTGFP ADGPVMTNSL TAADWCRSKK TYPNDKTIIS TFKWSYTTGN  240
GKRYRSTART TYTFAKPMAA NYLKNQPMYV FRKTELKHSK TELNFKEWQK AFTDVMGMDE  300
LYKAS                                                             305

SEQ ID NO: 105         moltype = DNA  length = 52
FEATURE                Location/Qualifiers
source                 1..52
                       mol_type = other DNA
                       organism = synthetic construct
SEQUENCE: 105
cgcgtagcgc tagctttgcc agcgccacgc gaaacatgag gatcacccat gt         52

SEQ ID NO: 106         moltype = DNA  length = 34
FEATURE                Location/Qualifiers
source                 1..34
                       mol_type = other DNA
                       organism = synthetic construct
SEQUENCE: 106
cgcgtggcgc tggcttcctt gccagcgcca cgcg                             34

SEQ ID NO: 107         moltype = DNA  length = 34
FEATURE                Location/Qualifiers
source                 1..34
                       mol_type = other DNA
                       organism = synthetic construct
SEQUENCE: 107
cgcgtagcgc tggcttcctt gccagcgcca cgcg                             34

SEQ ID NO: 108         moltype = DNA  length = 34
FEATURE                Location/Qualifiers
source                 1..34
                       mol_type = other DNA
                       organism = synthetic construct
SEQUENCE: 108
cgcgtagcgc tagcttcctt gccagcgcca cgcg                             34

SEQ ID NO: 109         moltype = DNA  length = 58
FEATURE                Location/Qualifiers
source                 1..58
                       mol_type = other DNA
                       organism = synthetic construct
SEQUENCE: 109
cgcgtagcgc tagctttgcc agcgccacgc gaaggagcag acgatatggc gtcgctcc   58
```

```
SEQ ID NO: 110         moltype = DNA  length = 54
FEATURE                Location/Qualifiers
source                 1..54
                       mol_type = other DNA
                       organism = synthetic construct
SEQUENCE: 110
cgcgtagcgc tagctttgcc agcgccacgc ggtaagggcc ctgaagaagg gccc        54

SEQ ID NO: 111         moltype = DNA  length = 63
FEATURE                Location/Qualifiers
source                 1..63
                       mol_type = other DNA
                       organism = synthetic construct
SEQUENCE: 111
cgcgtagcgc tagctttgcc agcgccacgc ggtaggctcg tctgagctca ttagctccga  60
gcc                                                                 63

SEQ ID NO: 112         moltype = AA  length = 43
FEATURE                Location/Qualifiers
source                 1..43
                       mol_type = protein
                       organism = unidentified
SEQUENCE: 112
ATNFSLLKQA GDVEENPGPA SAGSGEGRGS LLTCGDVEEN PGP                     43

SEQ ID NO: 113         moltype = AA  length = 301
FEATURE                Location/Qualifiers
source                 1..301
                       mol_type = protein
                       organism = synthetic construct
SEQUENCE: 113
RWLPCQRHAT SATNFSLLKQ AGDVEENPGP GGSEGRGSLL TCGDVEENPG PSGYPYDVPD  60
YAHMVSKGEE DNMASLPATH ELHIFGSING VDFDMVGQGT GNPNDGYEEL NLKSTKGDLQ  120
FSPWILVPHI GYGFHQYLPY PDGMSPFQAA MVDGSGYQVH RTMQFEDGAS LTVNYRYTYE  180
GSHIKGEAQV KGTGFPADGP VMTNSLTAAD WCRSKKTYPN DKTIISTFKW SYTTGNGKRY  240
RSTARTTYTF AKPMAANYLK NQPMYVFRKT ELKHSKTELN FKEWQKAFTD VMGMDELYKA  300
S                                                                   301

SEQ ID NO: 114         moltype = AA  length = 299
FEATURE                Location/Qualifiers
source                 1..299
                       mol_type = protein
                       organism = synthetic construct
SEQUENCE: 114
LPCQRHATSA TNFSLLKQAG DVEENPGPGG SEGRGSLLTC GDVEENPGPS GYPYDVPDYA  60
HMVSKGEEDN MASLPATHEL HIFGSINGVD FDMVGQGTGN PNDGYEELNL KSTKGDLQFS  120
PWILVPHIGY GFHQYLPYPD GMSPFQAAMV DGSGYQVHRT MQFEDGASLT VNYRYTYEGS  180
HIKGEAQVKG TGFPADGPVM TNSLTAADWC RSKKTYPNDK TIISTFKWSY TTGNGKRYRS  240
TARTTYTFAK PMAANYLKNQ PMYVFRKTEL KHSKTELNFK EWQKAFTDVM GMDELYKAS   299

SEQ ID NO: 115         moltype = AA  length = 30
FEATURE                Location/Qualifiers
source                 1..30
                       mol_type = protein
                       organism = synthetic construct
SEQUENCE: 115
ASGSGTGAPP NLWAAQRYGR ELRRMSDEFV                                    30

SEQ ID NO: 116         moltype = AA  length = 28
FEATURE                Location/Qualifiers
source                 1..28
                       mol_type = protein
                       organism = synthetic construct
SEQUENCE: 116
APPNLWAAQR YGRELRRMSD EFVDSFKK                                      28

SEQ ID NO: 117         moltype = AA  length = 195
FEATURE                Location/Qualifiers
source                 1..195
                       mol_type = protein
                       organism = synthetic construct
SEQUENCE: 117
SNRELVVDFL SYKLSQKGYS WSQFSDVEEN RTEAPEGTES EMETPSAING NPSWHLADSP  60
AVNGATGHSS SLDAREVIPM AAVKQALREA GDEFELRYRR AFSDLTSQLH ITPGTAYQSF  120
EQVVNELFRD GVNWGRIVAF FSFGGALCVE SVDKEMQVLV SRIAAWMATY LNDHLEPWIQ  180
ENGGWDTFVE LYGNN                                                    195

SEQ ID NO: 118         moltype = AA  length = 35
FEATURE                Location/Qualifiers
```

-continued

```
source                    1..35
                          mol_type = protein
                          organism = synthetic construct
SEQUENCE: 118
ASGSGSGDMR PEIWIAQELR RIGDEFNAYY ARRTG                             35

SEQ ID NO: 119            moltype = AA  length = 35
FEATURE                   Location/Qualifiers
source                    1..35
                          mol_type = protein
                          organism = synthetic construct
SEQUENCE: 119
ASGGSGGSGR PEIWMTQGLR RLGDEANAYY ARRTG                             35

SEQ ID NO: 120            moltype = AA  length = 156
FEATURE                   Location/Qualifiers
source                    1..156
                          mol_type = protein
                          organism = synthetic construct
SEQUENCE: 120
DELYRQSLEI ISRYLREQAT GAKDTKPMGR SGATSRKALE TLRRVGDGVQ RNHETAFQGM  60
LRKLDIKNED DVKSLSRVMI HVFSDGVTNW GRIVTLISFG AFVAKHLKTI NQESCIEPLA  120
ESITDVLVRT KRDWLVKQRG WDGFVEFFHV EDLEGG                            156

SEQ ID NO: 121            moltype = AA  length = 30
FEATURE                   Location/Qualifiers
source                    1..30
                          mol_type = protein
                          organism = synthetic construct
SEQUENCE: 121
ASGSGTGAPP NLWAAQRYGR ELRRMSDELV                                   30

SEQ ID NO: 122            moltype = AA  length = 14
FEATURE                   Location/Qualifiers
source                    1..14
                          mol_type = protein
                          organism = synthetic construct
SEQUENCE: 122
SRLEEELRRR LTEP                                                    14

SEQ ID NO: 123            moltype = AA  length = 122
FEATURE                   Location/Qualifiers
source                    1..122
                          mol_type = protein
                          organism = synthetic construct
SEQUENCE: 123
EVQLQESGGG LVQPGGSLRL SCTASGVTIS ALNAMAMGWY RQAPGERRVM VAAVSERGNA  60
MYRESVQGRF TVTRDFTNKM VSLQMDNLKP EDTAVYYCHV LEDRVDSFHD YWGQGTQVTV  120
SS                                                                122

SEQ ID NO: 124            moltype = AA  length = 18
FEATURE                   Location/Qualifiers
source                    1..18
                          mol_type = protein
                          organism = synthetic construct
SEQUENCE: 124
GSGPGRLEEE LRRRLSPG                                                18

SEQ ID NO: 125            moltype = AA  length = 21
FEATURE                   Location/Qualifiers
source                    1..21
                          mol_type = protein
                          organism = synthetic construct
SEQUENCE: 125
ASGSGPGRLE QEIRARLSPG T                                            21

SEQ ID NO: 126            moltype = AA  length = 22
FEATURE                   Location/Qualifiers
source                    1..22
                          mol_type = protein
                          organism = synthetic construct
SEQUENCE: 126
ASGGSGAHIV MVDAYKPTKG TG                                           22

SEQ ID NO: 127            moltype = AA  length = 115
FEATURE                   Location/Qualifiers
source                    1..115
                          mol_type = protein
                          organism = synthetic construct
```

```
SEQUENCE: 127
MVDTLSGLSS EQGQSGDMTI EEDSATHIKF SKRDEDGKEL AGATMELRDS SGKTISTWIS  60
DGQVKDFYLY PGKYTFVETA APDGYEVATA ITFTVNEQGQ VTVNGKATKG DAHIG       115

SEQ ID NO: 128         moltype = AA  length = 242
FEATURE                Location/Qualifiers
source                 1..242
                       mol_type = protein
                       organism = synthetic construct
SEQUENCE: 128
VIPDYFKQSF PEGYSWERSM TYEDGGICIA TNDITMEGDS FINKIHFKGT NFPPNGPVMQ  60
KRTVGWEAST EKMYERDGVL KGDVKMKLLL KGGGHYRCDY RTTYKVKQKP VKLPDYHFVD  120
HRIEILSHDK DYNKVKLYEH AVARNSTDSM DELYKGGSGG MVSKGEETIT SVIKPDMKNK  180
LRMEGNVNGH AFVIEGEGSG KPFEGIQTID LEVKEGAPLP FAYDILTTAF HYGNRVFTKY  240
PR                                                                 242

SEQ ID NO: 129         moltype = AA  length = 9
FEATURE                Location/Qualifiers
source                 1..9
                       mol_type = protein
                       organism = synthetic construct
SEQUENCE: 129
GTENLYFQS                                                          9

SEQ ID NO: 130         moltype = AA  length = 18
FEATURE                Location/Qualifiers
source                 1..18
                       mol_type = protein
                       organism = synthetic construct
SEQUENCE: 130
GSGGTENLYF QSGTSGGA                                                18

SEQ ID NO: 131         moltype = DNA  length = 25
FEATURE                Location/Qualifiers
source                 1..25
                       mol_type = other DNA
                       organism = synthetic construct
SEQUENCE: 131
ggagcagacg atatggcgtc gctcc                                        25

SEQ ID NO: 132         moltype = DNA  length = 19
FEATURE                Location/Qualifiers
source                 1..19
                       mol_type = other DNA
                       organism = synthetic construct
SEQUENCE: 132
gggccctgaa gaagggccc                                               19

SEQ ID NO: 133         moltype = DNA  length = 29
FEATURE                Location/Qualifiers
source                 1..29
                       mol_type = other DNA
                       organism = synthetic construct
SEQUENCE: 133
ggctcgtctg agctcattag ctccgagcc                                    29

SEQ ID NO: 134         moltype = AA  length = 31
FEATURE                Location/Qualifiers
source                 1..31
                       mol_type = protein
                       organism = synthetic construct
SEQUENCE: 134
GALFDKSCSD RAMESTESRH YPVFENPKQG K                                 31

SEQ ID NO: 135         moltype = AA  length = 26
FEATURE                Location/Qualifiers
source                 1..26
                       mol_type = protein
                       organism = synthetic construct
SEQUENCE: 135
ARIFSPHEPI LEEPADRHPN RKARGQ                                       26

SEQ ID NO: 136         moltype = AA  length = 26
FEATURE                Location/Qualifiers
source                 1..26
                       mol_type = protein
                       organism = synthetic construct
SEQUENCE: 136
ARLHSPYEIT TDLHSSKHLV RKFRGH                                       26
```

```
SEQ ID NO: 137          moltype = AA  length = 32
FEATURE                 Location/Qualifiers
source                  1..32
                        mol_type = protein
                        organism = synthetic construct
SEQUENCE: 137
AQIKSQLRLN PHSISAFEAN EELCLHVAVE GK                                32

SEQ ID NO: 138          moltype = AA  length = 30
FEATURE                 Location/Qualifiers
source                  1..30
                        mol_type = protein
                        organism = synthetic construct
SEQUENCE: 138
AARDIYLPPT SEGGLPHSPP MRLQAHVLGQ                                   30

SEQ ID NO: 139          moltype = AA  length = 10
FEATURE                 Location/Qualifiers
source                  1..10
                        mol_type = protein
                        organism = synthetic construct
SEQUENCE: 139
KSCSDRAMES                                                         10

SEQ ID NO: 140          moltype = AA  length = 13
FEATURE                 Location/Qualifiers
source                  1..13
                        mol_type = protein
                        organism = synthetic construct
SEQUENCE: 140
FSPHEPILEE PAD                                                     13

SEQ ID NO: 141          moltype = AA  length = 11
FEATURE                 Location/Qualifiers
source                  1..11
                        mol_type = protein
                        organism = synthetic construct
SEQUENCE: 141
PYEITTDLHS S                                                       11

SEQ ID NO: 142          moltype = AA  length = 6
FEATURE                 Location/Qualifiers
source                  1..6
                        mol_type = protein
                        organism = synthetic construct
SEQUENCE: 142
QLRLNP                                                             6

SEQ ID NO: 143          moltype = AA  length = 9
FEATURE                 Location/Qualifiers
source                  1..9
                        mol_type = protein
                        organism = synthetic construct
SEQUENCE: 143
PPTSEGGLP                                                          9

SEQ ID NO: 144          moltype = AA  length = 305
FEATURE                 Location/Qualifiers
source                  1..305
                        mol_type = protein
                        organism = synthetic construct
SEQUENCE: 144
LCQRHAKHED HPCTSATNFS LLKQAGDVEE NPGPGGSEGR GSLLTCGDVE ENPGPSGYPY  60
DVPDYAHMVS KGEEDNMASL PATHELHIFG SINGVDFDMV GQGTGNPNDG YEELNLKSTK  120
GDLQFSPWIL VPHIGYGFHQ YLPYPDGMSP FQAAMVDGSG YQVHRTMQFE DGASLTVNYR  180
YTYEGSHIKG EAQVKGTGFP ADGPVMTNSL TAADWCRSKK TYPNDKTIIS TFKWSYTTGN  240
GKRYRSTART TYTFAKPMAA NYLKNQPMYV FRKTELKHSK TELNFKEWQK AFTDVMGMDE  300
LYKAS                                                              305

SEQ ID NO: 145          moltype = AA  length = 305
FEATURE                 Location/Qualifiers
source                  1..305
                        mol_type = protein
                        organism = synthetic construct
SEQUENCE: 145
LCQRHAKHED HPCTSATNFS LLKQAGDVEE NPGPGGSEGR GSLLTCGDVE ENPGPSGYPY  60
DVPDYAHMVS KGEEDNMASL PATHELHIFG SINGVDFDMV GQGTGNPNDG YEELNLKSTK  120
GDLQFSPWIL VPHIGYGFHQ YLPYPDGMSP FQAAMVDGSG YQVHRTMQFE DGASLTVNYR  180
```

```
YTYEGSHIKG EAQVKGTGFP ADGPVMTNSL TAADWCRSKK TYPNDKTIIS TFKWSYTTGN  240
GKRYRSTART TYTFAKPMAA NYLKNQPMYV FRKTELKHSK TELNFKEWQK AFTDVMGMDE  300
LYKAS                                                             305

SEQ ID NO: 146         moltype = AA  length = 308
FEATURE                Location/Qualifiers
source                 1..308
                       mol_type = protein
                       organism = synthetic construct
SEQUENCE: 146
LCQRHAKEQT IWRRSNTSAT NFSLLKQAGD VEENPGPGGS EGRGSLLTCG DVEENPGPSG  60
YPYDVPDYAH MVSKGEEDNM ASLPATHELH IFGSINGVDF DMVGQGTGNP NDGYEELNLK  120
STKGDLQFSP WILVPHIGYG FHQYLPYPDG MSPFQAAMVD GSGYQVHRTM QFEDGASLTV  180
NYRYTYEGSH IKGEAQVKGT GFPADGPVMT NSLTAADWCR SKKTYPNDKT IISTFKWSYT  240
TGNGKRYRST ARTTYTFAKP MAANYLKNQP MYVFRKTELK HSKTELNFKE WQKAFTDVMG  300
MDELYKAS                                                          308

SEQ ID NO: 147         moltype = AA  length = 306
FEATURE                Location/Qualifiers
source                 1..306
                       mol_type = protein
                       organism = synthetic construct
SEQUENCE: 147
LCQRHAVRAL KKGPTSATNF SLLKQAGDVE ENPGPGGSEG RGSLLTCGDV EENPGPSGYP  60
YDVPDYAHMV SKGEEDNMAS LPATHELHIF GSINGVDFDM VGQGTGNPND GYEELNLKST  120
KGDLQFSPWI LVPHIGYGFH QYLPYPDGMS PFQAAMVDGS GYQVHRTMQF EDGASLTVNY  180
RYTYEGSHIK GEAQVKGTGF PADGPVMTNS LTAADWCRSK KTYPNDKTII STFKWSYTTG  240
NGKRYRSTAR TTYTFAKPMA ANYLKNQPMY VFRKTELKHS KTELNFKEWQ KAFTDVMGMD  300
ELYKAS                                                            306

SEQ ID NO: 148         moltype = AA  length = 309
FEATURE                Location/Qualifiers
source                 1..309
                       mol_type = protein
                       organism = synthetic construct
SEQUENCE: 148
LCQRHAVGSS ELISSEPTSA TNFSLLKQAG DVEENPGPGG SEGRGSLLTC GDVEENPGPS  60
GYPYDVPDYA HMVSKGEEDN MASLPATHEL HIFGSINGVD FDMVGQGTGN PNDGYEELNL  120
KSTKGDLQFS PWILVPHIGY GFHQYLPYPD GMSPFQAAMV DGSGYQVHRT MQFEDGASLT  180
VNYRYTYEGS HIKGEAQVKG TGFPADGPVM TNSLTAADWC RSKKTYPNDK TIISTFKWSY  240
TTGNGKRYRS TARTTYTFAK PMAANYLKNQ PMYVFRKTEL KHSKTELNFK EWQKAFTDVM  300
GMDELYKAS                                                         309

SEQ ID NO: 149         moltype = AA  length = 69
FEATURE                Location/Qualifiers
source                 1..69
                       mol_type = protein
                       organism = synthetic construct
SEQUENCE: 149
LCQRHTKHED HPCRPHSSGA GCLSEGGGWC GQCPGSQIPL RSFSLCQKLW GHHEAPWASD  60
FWLIKEIYF                                                         69

SEQ ID NO: 150         moltype = AA  length = 556
FEATURE                Location/Qualifiers
source                 1..556
                       mol_type = protein
                       organism = synthetic construct
SEQUENCE: 150
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEFVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLT                                                 556

SEQ ID NO: 151         moltype = AA  length = 765
FEATURE                Location/Qualifiers
source                 1..765
                       mol_type = protein
                       organism = synthetic construct
SEQUENCE: 151
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
```

```
LNNKDDQKRS IFQKSERGGF RLKENVQFHL YISTSPCGDA RIFSPHEPIL EEPAASGSGT  300
GAPPNLWAAQ RYGRELRRMS DEFVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNN                 765

SEQ ID NO: 152         moltype = AA  length = 561
FEATURE                Location/Qualifiers
source                 1..561
                       mol_type = protein
                       organism = synthetic construct
SEQUENCE: 152
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGS  300
GDMRPEIWIA QELRRIGDEF NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL T                                           561

SEQ ID NO: 153         moltype = AA  length = 561
FEATURE                Location/Qualifiers
source                 1..561
                       mol_type = protein
                       organism = synthetic construct
SEQUENCE: 153
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEA NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL T                                           561

SEQ ID NO: 154         moltype = AA  length = 765
FEATURE                Location/Qualifiers
source                 1..765
                       mol_type = protein
                       organism = synthetic construct
SEQUENCE: 154
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNN                 765

SEQ ID NO: 155         moltype = AA  length = 725
FEATURE                Location/Qualifiers
source                 1..725
                       mol_type = protein
                       organism = synthetic construct
SEQUENCE: 155
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEI NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
```

-continued

```
IKAGLGAWVE KPTEQDQFSL TGSGTGGPGD ELYRQSLEII SRYLREQATG AKDTKPMGRS  600
GATSRKALET LRRVGDGVQR NHETAFQGML RKLDIKNEDD VKSLSRVMIH VFSDGVTNWG  660
RIVTLISFGA FVAKHLKTIN QESCIEPLAE SITDVLVRTK RDWLVKQRGW DGFVEFFHVE  720
DLEGG                                                             725

SEQ ID NO: 156         moltype = AA  length = 545
FEATURE                Location/Qualifiers
source                 1..545
                       mol_type = protein
                       organism = synthetic construct
SEQUENCE: 156
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASPSRL  300
EEELRRRLTE PTGDRHPNRK ARGQLRTKIE SGQGTIPVRS NASIQTWDGV LQGERLLTMS  360
CSDKIARWNV VGIQGSLLSI FVEPIYFSSI ILGSLYHGDH LSRAMYQRIS NIEDLPPLYT  420
LNKPLLSGIS NAEARQPGKA PNFSVNWTVG DSAIEVINAT TGKDELGRAS RLCKHALYCR  480
WMRVHGKVPS HLLRSKITKP NVYHESKLAA KEYQAAKARL FTAFIKAGLG AWVEKPTEQD  540
QFSLT                                                             545

SEQ ID NO: 157         moltype = AA  length = 673
FEATURE                Location/Qualifiers
source                 1..673
                       mol_type = protein
                       organism = synthetic construct
SEQUENCE: 157
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASPSRL  300
EEELRRRLTE PTGDRHPNRK ARGQLRTKIE SGQGTIPVRS NASIQTWDGV LQGERLLTMS  360
CSDKIARWNV VGIQGSLLSI FVEPIYFSSI ILGSLYHGDH LSRAMYQRIS NIEDLPPLYT  420
LNKPLLSGIS NAEARQPGKA PNFSVNWTVG DSAIEVINAT TGKDELGRAS RLCKHALYCR  480
WMRVHGKVPS HLLRSKITKP NVYHESKLAA KEYQAAKARL FTAFIKAGLG AWVEKPTEQD  540
QFSLTGSGGT AEVQLQESGG GLVQPGGSLR LSCTASGVTI SALNAMAMGW YRQAPGERRV  600
MVAAVSERGN AMYRESVQGR FTVTRDFTNK MVSLQMDNLK PEDTAVYYCH VLEDRVDSFH  660
DYWGQGTQVT VSS                                                    673

SEQ ID NO: 158         moltype = AA  length = 548
FEATURE                Location/Qualifiers
source                 1..548
                       mol_type = protein
                       organism = synthetic construct
SEQUENCE: 158
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGP  300
GRLEEELRRR LSPGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLT                                                          548

SEQ ID NO: 159         moltype = AA  length = 676
FEATURE                Location/Qualifiers
source                 1..676
                       mol_type = protein
                       organism = synthetic construct
SEQUENCE: 159
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGP  300
GRLEEELRRR LSPGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GGTAEVQLQE SGGGLVQPGG SLRLSCTASG VTISALNAMA MGWYRQAPGE  600
RRVMVAAVSE RGNAMYRESV QGRFTVTRDF TNKMVSLQMD NLKPEDTAVY YCHVLEDRVD  660
SFHDYWGQGT QVTVSS                                                 676

SEQ ID NO: 160         moltype = AA  length = 715
FEATURE                Location/Qualifiers
```

```
source                  1..715
                        mol_type = protein
                        organism = synthetic construct
SEQUENCE: 160
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
AHIVMVDAYK PTKGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GSTSATNFSL LKQAGDVEEN PGPGGSEGRG SLLTCGDVEE NPGPGTSGGA  600
MVDTLSGLSS EQGQSGDMTI EEDSATHIKF SKRDEDGKEL AGATMELRDS SGKTISTWIS  660
DGQVKDFYLY PGKYTFVETA APDGYEVATA ITFTVNEQGQ VTVNGKATKG DAHIG       715

SEQ ID NO: 161          moltype = AA  length = 680
FEATURE                 Location/Qualifiers
source                  1..680
                        mol_type = protein
                        organism = synthetic construct
SEQUENCE: 161
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
AHIVMVDAYK PTKGTGDRHP NRKARGQLRT KIESGQGTIP VRSNASIQTW DGVLQGERLL  360
TMSCSDKIAR WNVVGIQGSL LSIFVEPIYF SSIILGSLYH GDHLSRAMYQ RISNIEDLPP  420
LYTLNKPLLS GISNAEARQP GKAPNFSVNW TVGDSAIEVI NATTGKDELG RASRLCKHAL  480
YCRWMRVHGK VPSHLLRSKI TKPNVYHESK LAAKEYQAAK ARLFTAFIKA GLGAWVEKPT  540
EQDQFSLTGS GGTENLYFQS GTSGGAMVDT LSGLSSEQGQ SGDMTIEEDS ATHIKFSKRD  600
EDGKELAGAT MELRDSSGKT ISTWISDGQV KDFYLYPGKY TFVETAAPDG YEVATAITFT  660
VNEQGQVTVN GKATKGDAHI                                              680

SEQ ID NO: 162          moltype = AA  length = 1004
FEATURE                 Location/Qualifiers
source                  1..1004
                        mol_type = protein
                        organism = synthetic construct
SEQUENCE: 162
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGS GGVIPDYFKQ SFPEGYSWER SMTYEDGGIC IATNDITMEG  600
DSFINKIHFK GTNFPPNGPV MQKRTVGWEA STEKMYERDG VLKGDVKMKL LLKGGGHYRC  660
DYRTTYKVKQ KPVKLPDYHF VDHRIEILSH DKDYNKVKLY EHAVARNSTD SMDELYKGGS  720
GGMVSKGEET ITSVIKPDMK NKLRMEGNVN GHAFVIEGEG SGKPFEGIQT IDLEVKEGAP  780
LPFAYDILTT AFHYGNRVFT KYPRSGSGSS NRELVVDFLS YKLSQKGYSW SQFSDVEENR  840
TEAPEGTESE METPSAINGN PSWHLADSPA VNGATGHSSS LDAREVIPMA AVKQALREAG  900
DEFELRYRRA FSDLTSQLHI TPGTAYQSFE QVVNELFRDG VNWGRIVAFF SFGGALCVES  960
VDKEMQVLVS RIAAWMATYL NDHLEPWIQE NGGWDTFVEL YGNN                   1004

SEQ ID NO: 163          moltype = AA  length = 556
FEATURE                 Location/Qualifiers
source                  1..556
                        mol_type = protein
                        organism = synthetic construct
SEQUENCE: 163
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLT                                                  556

SEQ ID NO: 164          moltype = AA  length = 769
FEATURE                 Location/Qualifiers
```

```
source                    1..769
                          mol_type = protein
                          organism = synthetic construct
SEQUENCE: 164
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIYGGS  120
GSGAGSGSPA GGGAPGSGGG SQSNRELVVD FLSYKLSQKG YSWSQFSDVE ENRTEAPEGT  180
ESEMETPSAI NGNPSWHLAD SPAVNGATGH SSSLDAREVI PMAAVKQALR EAGDEFELRY  240
RRAFSDLTSQ LHITPGTAYQ SFEQVVNELF RDGVNWGRIV AFFSFGGALC VESVDKEMQV  300
LVSRIAAWMA TYLNDHLEPW IQENGGWDTF VELYGNNAAG GSGGSGGSGG SAAAQLHLPQ  360
VLADAVSRLV LGKFGDLTDN FSSPHARRKV LAGVVMTTGT DVKDAKVISV STGTKCINGE  420
YMSDRGLALN DCHAEIISRR SLLRFLYTQL ELYLNNKDDQ KRSIFQKSER GGFRLKENVQ  480
FHLYISTSPC GDARIFSPHE PILEEPAASG SGTGAPPNLW AAQRYGRELR RMSDELVDRH  540
PNRKARGQLR TKIESGQGTI PVRSNASIQT WDGVLQGERL LTMSCSDKIA RWNVVGIQGS  600
LLSIFVEPIY FSSIILGSLY HGDHLSRAMY QRISNIEDLP PLYTLNKPLL SGISNAEARQ  660
PGKAPNFSVN WTVGDSAIEV INATTGKDEL GRASRLCKHA LYCRWMRVHG KVPSHLLRSK  720
ITKPNVYHES KLAAKEYQAA KARLFTAFIK AGLGAWVEKP TEQDQFSLT           769

SEQ ID NO: 165          moltype = AA   length = 766
FEATURE                 Location/Qualifiers
source                  1..766
                        mol_type = protein
                        organism = synthetic construct
SEQUENCE: 165
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNG              766

SEQ ID NO: 166          moltype = AA   length = 558
FEATURE                 Location/Qualifiers
source                  1..558
                        mol_type = protein
                        organism = synthetic construct
SEQUENCE: 166
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPADRHP NRKARGQLRT KIESGQGTIP VRSNASIQTW  360
DGVLQGERLL TMSCSDKIAR WNVVGIQGSL LSIFVEPIYF SSIILGSLYH GDHLSRAMYQ  420
RISNIEDLPP LYTLNKPLLS GISNAEARQP GKAPNFSVNW TVGDSAIEVI NATTGKDELG  480
RASRLCKHAL YCRWMRVHGK VPSHLLRSKI TKPNVYHESK LAAKEYQAAK ARLFTAFIKA  540
GLGAWVEKPT EQDQFSLT                                             558

SEQ ID NO: 167          moltype = AA   length = 759
FEATURE                 Location/Qualifiers
source                  1..759
                        mol_type = protein
                        organism = synthetic construct
SEQUENCE: 167
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPADRHP NRKARGQLRT KIESGQGTIP VRSNASIQTW  360
DGVLQGERLL TMSCSDKIAR WNVVGIQGSL LSIFVEPIYF SSIILGSLYH GDHLSRAMYQ  420
RISNIEDLPP LYTLNKPLLS GISNAEARQP GKAPNFSVNW TVGDSAIEVI NATTGKDELG  480
RASRLCKHAL YCRWMRVHGK VPSHLLRSKI TKPNVYHESK LAAKEYQAAK ARLFTAFIKA  540
GLGAWVEKPT EQDQFSLTGS AAASSNRELV VDFLSYKLSQ KGYSWSQFSD VEENRTEAPE  600
GTESEMETPS AINGNPSWHL ADSPAVNGAT GHSSSLDARE VIPMAAVKQA LREAGDEFEL  660
RYRRAFSDLT SQLHITPGTA YQSFEQVVNE LFRDGVNWGR IVAFFSFGGA LCVESVDKEM  720
QVLVSRIAAW MATYLNDHLE PWIQENGGWD TFVELYGNN                       759

SEQ ID NO: 168          moltype = AA   length = 913
FEATURE                 Location/Qualifiers
source                  1..913
                        mol_type = protein
```

```
                         organism = synthetic construct
SEQUENCE: 168
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSG SSELIKENMH MKLYMEGTVD NHHFKCTSEG EGKPYEGTQT  720
MRIKVVEGGP LPFAFDILAT SFLYGSKTFI NHTQGIPDFF KQSFPEGFTW ERVTTYEDGG  780
VLTATQDTSL QDGCLIYNVK IRGVNFTSNG PVMQKKTLGW EAFTETLYPA DGGLEGRNDM  840
ALKLVGGSHL IANIKTTYRS KKPAKNLKMP GVYYVDYRLE RIKEANNETY VEQHEVAVAR  900
YCDLPSKLGH KLN                                                    913

SEQ ID NO: 169          moltype = AA  length = 1125
FEATURE                 Location/Qualifiers
source                  1..1125
                        mol_type = protein
                        organism = synthetic construct
SEQUENCE: 169
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSA AGGSGGSAAA QGSVVIVGRI ILSGSGSITA YSQQTRGLLG  720
CIITSLTGRD KNQVEGEVQV VSTATQSFLA TCVNGVCWTV YHGAGSKTLA GPKGPITQMY  780
TNVDQDLVGW QAPPGARSLT PCTCGSSDLY LVTRHADVIP VRRRGDSRGS LLSPRPVSYL  840
KGSSGGPLLC PSGHAVGIFR AAVCTRGVAK AVDFVPVESM ETTMRSESGS GTMSELIKEN  900
MHMKLYMEGT VDNHHFKCTS EGEGKPYEGT QTMRIKVVEG GPLPFAFDIL ATSFLYGSKT  960
FINHTQGIPD FFKQSFPEGF TWERVTTYED GGVLTATQDT SLQDGCLIYN VKIRGVNFTS  1020
NGPVMQKKTL GWEAFTETLY PADGGLEGRN DMALKLVGGS HLIANIKTTY RSKKPAKNLK  1080
MPGVYYVDYR LERIKEANNE TYVEQHEVAV ARYCDLPSKL GHKLN                 1125

SEQ ID NO: 170          moltype = DNA  length = 63
FEATURE                 Location/Qualifiers
source                  1..63
                        mol_type = other DNA
                        organism = synthetic construct
SEQUENCE: 170
aattccgcgt agcgctagct ttgccagcgc cacgcgaaac atgaggatca cccatgtact  60
agt                                                               63

SEQ ID NO: 171          moltype = RNA  length = 63
FEATURE                 Location/Qualifiers
source                  1..63
                        mol_type = other RNA
                        organism = synthetic construct
SEQUENCE: 171
aattccgcgt agcgctagct ttgccagcgc cacgcgaaac atgaggatca cccatgtact  60
agt                                                               63

SEQ ID NO: 172          moltype = AA  length = 15
FEATURE                 Location/Qualifiers
source                  1..15
                        mol_type = protein
                        organism = synthetic construct
SEQUENCE: 172
LCQRHAKHED HPCTS                                                  15

SEQ ID NO: 173          moltype = DNA  length = 2035
FEATURE                 Location/Qualifiers
source                  1..2035
                        mol_type = other DNA
                        organism = synthetic construct
SEQUENCE: 173
taatacgact cactataggg agacccaagc tggctaggta agcttggtac cgagctcgga  60
tccaccggtc gccaccatgg tgagcaaggg cgaggaggat aacatggcca tcatcaagga  120
```

-continued

```
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtactagtgc  1020
cacaaacttc tctctgctaa agcaagcagg tgatgttgaa gaaaacccag ggcctggagg  1080
gtccgagggc aggggaagtc tcctaacatg cggggacgtg gaggaaaatc ccggcccatc  1140
cggatatccc tacgatgtgc ccgattacgc tcatatggtg agcaagggcg aggaggataa  1200
catggcctct ctcccagcga cacatgagtt acacatcttt ggctccatca acggtgtgga  1260
ctttgacatg gtgggtcagg gcaccggcaa tccaaatgat ggttatgagg agttaaacct  1320
gaagtccacc aagggtgacc tccagttctc cccctggatt ctggtccctc atatcgggta  1380
tggcttccat cagtacctgc cctaccctga cgggatgtcg cctttccagg ccgccatggt  1440
agatggcagc ggataccaag tccatcgcac aatgcagttt gaagatggtg cctcccttac  1500
tgttaactac cgctacacct acgagggaag ccacatcaaa ggagaggccc aggtgaaggg  1560
gactggtttc cctgctgacg gtcctgtgat gaccaactcg ctgaccgctg cggactggtg  1620
caggtcgaag aagacttacc ccaacgacaa aaccatcatc agtaccttta agtggagtta  1680
caccactgga aatggcaaga gataccggag cactgcgcgg accacctaca cctttgccaa  1740
gccaatggcg gctaactatc tgaagaacca gccgatgtac gtgttccgta agacggagct  1800
caagcactcc aagaccgagc tcaacttcaa ggagtggcaa aaggccttta ccgatgtgat  1860
gggaatggac gagctgtata aggctagcta agcggccgct cgagtctaga gggcccgcgg  1920
ttcgaaggta agcctatccc taaccctctc ctcggtctcg attctacgcg taccggtcat  1980
catcaccatc accattgagt ttaaacccgc tgatcagcct cgactgtgcc ttcta       2035
```

```
SEQ ID NO: 174          moltype = DNA  length = 63
FEATURE                 Location/Qualifiers
source                  1..63
                        mol_type = other DNA
                        organism = synthetic construct
SEQUENCE: 174
aattccgcgt agcgctggct ttgccagcgc cacgcgaaac atgaggatca cccatgtact  60
agt                                                               63

SEQ ID NO: 175          moltype = RNA  length = 63
FEATURE                 Location/Qualifiers
source                  1..63
                        mol_type = other RNA
                        organism = synthetic construct
SEQUENCE: 175
aattccgcgt agcgctggct ttgccagcgc cacgcgaaac atgaggatca cccatgtact  60
agt                                                               63

SEQ ID NO: 176          moltype = AA  length = 17
FEATURE                 Location/Qualifiers
source                  1..17
                        mol_type = protein
                        organism = synthetic construct
SEQUENCE: 176
RWLCQRHAKH EDHPCTS                                                17

SEQ ID NO: 177          moltype = DNA  length = 2034
FEATURE                 Location/Qualifiers
source                  1..2034
                        mol_type = other DNA
                        organism = synthetic construct
SEQUENCE: 177
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
```

-continued

```
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tggctttgcc agcgccacgc gaaacatgag gatcacccat gtactagtgc  1020
cacaaacttc tctctgctaa agcaagcagg tgatgttgaa gaaaacccag ggcctggagg  1080
gtccgagggc aggggaagtc tcctaacatg cggggacgtg gaggaaaatc ccggcccatc  1140
cggatatccc tacgatgtgc ccgattacgc tcatatggtg agcaagggcg aggaggataa  1200
catggcctct ctcccagcga cacatgagtt acacatcttt ggctccatca acggtgtgga  1260
ctttgacatg gtgggtcagg gcaccggcaa tccaaatgat ggttatgagg agttaaacct  1320
gaagtccacc aagggtgacc tccagttctc cccctggatt ctggtccctc atatcgggta  1380
tggcttccat cagtacctgc cctaccctga cgggatgtcg cctttccagg ccgccatggt  1440
agatggcagc ggataccaag tccatcgcac aatgcagttt gaagatggtg cctcccttac  1500
tgttaactac cgctacacct acgagggaag ccacatcaaa ggagaggccc aggtgaaggg  1560
gactggtttc cctgctgacg gtcctgtgat gaccaactcg ctgaccgctg cggactggtg  1620
caggtcgaag aagacttacc ccaacgacaa aaccatcatc agtaccttta agtggagtta  1680
caccactgga aatggcaaga gataccggag cactgcgcgg accacctaca cctttgccaa  1740
gccaatggcg gctaactatc tgaagaacca gccgatgtac gtgttccgta agacggagct  1800
caagcactcc aagaccgagc tcaacttcaa ggagtggcaa aaggccttta ccgatgtgat  1860
gggaatggac gagctgtata aggctagcta agcggccgct cgagtctaga gggcccgcgg  1920
ttcgaaggta agcctatccc taaccctctc ctcggtctcg attctacgcg taccggtcat  1980
catcaccatc accattgagt ttaaacccgc tgatcagcct cgactgtgcc ttct        2034

SEQ ID NO: 178          moltype = DNA  length = 63
FEATURE                 Location/Qualifiers
source                  1..63
                        mol_type = other DNA
                        organism = synthetic construct
SEQUENCE: 178
aattccgcgt ggcgctagct ttgccagcgc cacgcgaaac atgaggatca cccatgtact  60
agt                                                                63

SEQ ID NO: 179          moltype = RNA  length = 63
FEATURE                 Location/Qualifiers
source                  1..63
                        mol_type = other RNA
                        organism = synthetic construct
SEQUENCE: 179
aattccgcgt ggcgctagct ttgccagcgc cacgcgaaac atgaggatca cccatgtact  60
agt                                                                63

SEQ ID NO: 180          moltype = AA  length = 5
FEATURE                 Location/Qualifiers
source                  1..5
                        mol_type = protein
                        organism = synthetic construct
SEQUENCE: 180
NSAWR                                                              5

SEQ ID NO: 181          moltype = DNA  length = 2034
FEATURE                 Location/Qualifiers
source                  1..2034
                        mol_type = other DNA
                        organism = synthetic construct
SEQUENCE: 181
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtggcgc tagctttgcc agcgccacgc gaaacatgag gatcacccat gtactagtgc  1020
cacaaacttc tctctgctaa agcaagcagg tgatgttgaa gaaaacccag ggcctggagg  1080
gtccgagggc aggggaagtc tcctaacatg cggggacgtg gaggaaaatc ccggcccatc  1140
cggatatccc tacgatgtgc ccgattacgc tcatatggtg agcaagggcg aggaggataa  1200
catggcctct ctcccagcga cacatgagtt acacatcttt ggctccatca acggtgtgga  1260
ctttgacatg gtgggtcagg gcaccggcaa tccaaatgat ggttatgagg agttaaacct  1320
gaagtccacc aagggtgacc tccagttctc cccctggatt ctggtccctc atatcgggta  1380
tggcttccat cagtacctgc cctaccctga cgggatgtcg cctttccagg ccgccatggt  1440
agatggcagc ggataccaag tccatcgcac aatgcagttt gaagatggtg cctcccttac  1500
tgttaactac cgctacacct acgagggaag ccacatcaaa ggagaggccc aggtgaaggg  1560
```

```
gactggtttc cctgctgacg gtcctgtgat gaccaactcg ctgaccgctg cggactggtg  1620
caggtcgaag aagacttacc ccaacgacaa aaccatcatc agtaccttta agtggagtta  1680
caccactgga aatggcaaga gataccggag cactgcgcgg accacctaca cctttgccaa  1740
gccaatggcg gctaactatc tgaagaacca gccgatgtac gtgttccgta agacggagct  1800
caagcactcc aagaccgagc tcaacttcaa ggagtggcaa aaggccttta ccgatgtgat  1860
gggaatggac gagctgtata aggctagcta agcggccgct cgagtctaga gggcccgcgg  1920
ttcgaaggta agcctatccc taaccctctc ctcggtctcg attctacgcg taccggtcat  1980
catcaccatc accattgagt ttaaacccgc tgatcagcct cgactgtgcc ttct        2034

SEQ ID NO: 182          moltype = DNA  length = 60
FEATURE                 Location/Qualifiers
source                  1..60
                        mol_type = other DNA
                        organism = synthetic construct
SEQUENCE: 182
aattccgcgt agcgctagct acatgaggat cacccatgtt gccagcgcca cgcgactagt  60

SEQ ID NO: 183          moltype = RNA  length = 60
FEATURE                 Location/Qualifiers
source                  1..60
                        mol_type = other RNA
                        organism = synthetic construct
SEQUENCE: 183
aattccgcgt agcgctagct acatgaggat cacccatgtt gccagcgcca cgcgactagt  60

SEQ ID NO: 184          moltype = AA  length = 14
FEATURE                 Location/Qualifiers
source                  1..14
                        mol_type = protein
                        organism = synthetic construct
SEQUENCE: 184
LHEDHPCCQR HATS                                                     14

SEQ ID NO: 185          moltype = DNA  length = 2031
FEATURE                 Location/Qualifiers
source                  1..2031
                        mol_type = other DNA
                        organism = synthetic construct
SEQUENCE: 185
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctacatg aggatcaccc atgttgccag cgccacgcga ctagtgccac  1020
aaacttctct ctgctaaagc aagcaggtga tgttgaagaa aacccagggc ctggagggtc  1080
cgagggcagg ggaagtctcc taacatgcgg ggacgtggag gaaaatcccg gcccatccgg  1140
atatccctac gatgtgcccg attacgctca tatggtgagc aagggcgagg aggataacat  1200
ggcctctctc ccagcgacac atgagttaca catctttggc tccatcaacg gtgtggactt  1260
tgacatggtg ggtcagggca ccggcaatcc aaatgatggt tatgaggagt taaacctgaa  1320
gtccaccaag ggtgacctcc agttctcccc ctggattctg gtccctcata tcgggtatgg  1380
cttccatcag tacctgccct accctgacgg gatgtcgcct ttccaggccg ccatggtaga  1440
tggcagcgga taccaagtcc atcgcacaat gcagtttgaa gatggtgcct cccttactgt  1500
taactaccgc tacacctacg agggaagcca catcaaagga gaggcccagg tgaaggggac  1560
tggtttccct gctgacggtc ctgtgatgac caactcgctg accgctgcgg actggtgcag  1620
gtcgaagaag acttacccca acgacaaaac catcatcagt acctttaagt ggagttacac  1680
cactggaaat ggcaagagat accggagcac tgcgcggacc acctacacct ttgccaagcc  1740
aatggcggct aactatctga agaaccagcc gatgtacgtg ttccgtaaga cggagctcaa  1800
gcactccaag accgagctca acttcaagga gtggcaaaag gcctttaccg atgtgatggg  1860
aatggacgag ctgtataagg ctagctaagc ggccgctcga gtctagaggg cccgcggttc  1920
gaaggtaagc ctatccctaa ccctctcctc ggtctcgatt ctacgcgtac cggtcatcat  1980
caccatcacc attgagttta aacccgctga tcagcctcga ctgtgccttc t           2031

SEQ ID NO: 186          moltype = DNA  length = 72
FEATURE                 Location/Qualifiers
source                  1..72
                        mol_type = other DNA
                        organism = synthetic construct
```

```
SEQUENCE: 186
aattccgcgt agcgctagct ttgccagcgc cacgcgaagg agcagacgat atggcgtcgc  60
tccaatacta gt                                                      72

SEQ ID NO: 187          moltype = RNA  length = 72
FEATURE                 Location/Qualifiers
source                  1..72
                        mol_type = other RNA
                        organism = synthetic construct
SEQUENCE: 187
aattccgcgt agcgctagct ttgccagcgc cacgcgaagg agcagacgat atggcgtcgc  60
tccaatacta gt                                                      72

SEQ ID NO: 188          moltype = AA  length = 18
FEATURE                 Location/Qualifiers
source                  1..18
                        mol_type = protein
                        organism = synthetic construct
SEQUENCE: 188
LCQRHAKEQT IWRRSNTS                                                18

SEQ ID NO: 189          moltype = DNA  length = 2043
FEATURE                 Location/Qualifiers
source                  1..2043
                        mol_type = other DNA
                        organism = synthetic construct
SEQUENCE: 189
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaggagcag acgatatggc gtcgctccaa  1020
tactagtgcc acaaacttct ctctgctaaa gcaagcaggt gatgttgaag aaaacccagg  1080
gcctggaggg tccgagggca ggggaagtct cctaacatgc ggggacgtgg aggaaaatcc  1140
cggcccatcc ggatatccct acgatgtgcc cgattacgct catatggtga gcaagggcga  1200
ggaggataac atggcctctc tcccagcgac acatgagtta cacatctttg gctccatcaa  1260
cggtgtggac tttgacatgg tgggtcaggg caccggcaat ccaaatgatg gttatgagga  1320
gttaaacctg aagtccacca agggtgacct ccagttctcc ccctggattc tggtccctca  1380
tatcgggtat ggcttccatc agtacctgcc ctaccctgac gggatgtcgc ctttccaggc  1440
cgccatggta gatggcagcg gataccaagt ccatcgcaca atgcagtttg aagatggtgc  1500
ctcccttact gttaactacc gctacaccta cgagggaagc cacatcaaag gagaggccca  1560
ggtgaagggg actggtttcc ctgctgacgg tcctgtgatg accaactcgc tgaccgctgc  1620
ggactggtgc aggtcgaaga agacttaccc caacgacaaa accatcatca gtacctttaa  1680
gtggagttac accactggaa atggcaagag ataccggagc actgcgcgga ccacctacac  1740
ctttgccaag ccaatggcgg ctaactatct gaagaaccag ccgatgtacg tgttccgtaa  1800
gacggagctc aagcactcca agaccgagct caacttcaag gagtggcaaa aggcctttac  1860
cgatgtgatg ggaatggacg agctgtataa ggctagctaa gcggccgctc gagtctagag  1920
ggcccgcggt tcgaaggtaa gcctatccct aaccctctcc tcggtctcga ttctacgcgt  1980
accggtcatc atcaccatca ccattgagtt taaacccgct gatcagcctc gactgtgcct  2040
tct                                                                2043

SEQ ID NO: 190          moltype = DNA  length = 75
FEATURE                 Location/Qualifiers
source                  1..75
                        mol_type = other DNA
                        organism = synthetic construct
SEQUENCE: 190
aattccgcgt agcgctagct ttgccagcgc cacgcggtag gctcgtctga gctcattagc  60
tccgagccaa ctagt                                                   75

SEQ ID NO: 191          moltype = RNA  length = 75
FEATURE                 Location/Qualifiers
source                  1..75
                        mol_type = other RNA
                        organism = synthetic construct
SEQUENCE: 191
aattccgcgt agcgctagct ttgccagcgc cacgcggtag gctcgtctga gctcattagc  60
```

```
tccgagccaa ctagt                                                  75

SEQ ID NO: 192          moltype = AA  length = 19
FEATURE                 Location/Qualifiers
source                  1..19
                        mol_type = protein
                        organism = synthetic construct
SEQUENCE: 192
LCQRHAVGSS ELISSEPTS                                              19

SEQ ID NO: 193          moltype = DNA  length = 2046
FEATURE                 Location/Qualifiers
source                  1..2046
                        mol_type = other DNA
                        organism = synthetic construct
SEQUENCE: 193
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc ggtaggctcg tctgagctca ttagctccga  1020
gccaactagt gccacaaact tctctctgct aaagcaagca ggtgatgttg aagaaaaccc  1080
agggcctgga gggtccgagg gcaggggaag tctcctaaca tgcggggacg tggaggaaaa  1140
tcccggccca tccggatatc cctacgatgt gcccgattac gctcatatgg tgagcaaggg  1200
cgaggaggat aacatggcct ctctcccagc gacacatgag ttacacatct ttggctccat  1260
caacggtgtg gactttgaca tggtgggtca gggcaccggc aatccaaatg atggttatga  1320
ggagttaaac ctgaagtcca ccaagggtga cctccagttc tccccctgga ttctggtccc  1380
tcatatcggg tatggcttcc atcagtacct gccctaccct gacgggatgt cgcctttcca  1440
ggccgccatg gtagatggca gcggatacca agtccatcgc acaatgcagt ttgaagatgg  1500
tgcctccctt actgttaact accgctacac ctacgaggga agccacatca aaggagaggc  1560
ccaggtgaag gggactggtt tccctgctga cggtcctgtg atgaccaact cgctgaccgc  1620
tgcggactgg tgcaggtcga agaagactta ccccaacgac aaaaccatca tcagtacctt  1680
taagtggagt tacaccactg gaaatggcaa gagataccgg agcactgcgc ggaccaccta  1740
cacctttgcc aagccaatgg cggctaacta tctgaagaac cagccgatgt acgtgttccg  1800
taagacggag ctcaagcact ccaagaccga gctcaacttc aaggagtggc aaaaggcctt  1860
taccgatgtg atgggaatgg acgagctgta taaggctagc taagcggccg ctcgagtcta  1920
gagggcccgc ggttcgaagg taagcctatc cctaaccctc tcctcggtct cgattctacg  1980
cgtaccggtc atcatcacca tcaccattga gtttaaaccc gctgatcagc ctcgactgtg  2040
ccttct                                                            2046

SEQ ID NO: 194          moltype = DNA  length = 66
FEATURE                 Location/Qualifiers
source                  1..66
                        mol_type = other DNA
                        organism = synthetic construct
SEQUENCE: 194
aattccgcgt agcgctagct ttgccagcgc cacgcggtaa gggccctgaa gaagggccca  60
actagt                                                            66

SEQ ID NO: 195          moltype = RNA  length = 66
FEATURE                 Location/Qualifiers
source                  1..66
                        mol_type = other RNA
                        organism = synthetic construct
SEQUENCE: 195
aattccgcgt agcgctagct ttgccagcgc cacgcggtaa gggccctgaa gaagggccca  60
actagt                                                            66

SEQ ID NO: 196          moltype = AA  length = 16
FEATURE                 Location/Qualifiers
source                  1..16
                        mol_type = protein
                        organism = synthetic construct
SEQUENCE: 196
LCQRHAVRAL KKGPTS                                                 16

SEQ ID NO: 197          moltype = DNA  length = 2037
```

-continued

```
FEATURE                Location/Qualifiers
source                 1..2037
                       mol_type = other DNA
                       organism = synthetic construct
SEQUENCE: 197
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc ggtaagggcc ctgaagaagg gcccaactag  1020
tgccacaaac ttctctctgc taaagcaagc aggtgatgtt gaagaaaacc cagggcctgg  1080
agggtccgag ggcaggggaa gtctcctaac atgcggggac gtggaggaaa atcccggccc  1140
atccggatat ccctacgatg tgcccgatta cgctcatatg gtgagcaagg gcgaggagga  1200
taacatggcc tctctcccag cgacacatga gttacacatc tttggctcca tcaacggtgt  1260
ggactttgac atggtgggtc agggcaccgg caatccaaat gatggttatg aggagttaaa  1320
cctgaagtcc accaagggtg acctccagtt ctccccctgg attctggtcc ctcatatcgg  1380
gtatggcttc catcagtacc tgccctaccc tgacgggatg tcgcctttcc aggccgccat  1440
ggtagatggc agcggatacc aagtccatcg cacaatgcag tttgaagatg gtgcctccct  1500
tactgttaac taccgctaca cctacgaggg aagccacatc aaaggagagg cccaggtgaa  1560
ggggactggt ttccctgctg acggtcctgt gatgaccaac tcgctgaccg ctgcggactg  1620
gtgcaggtcg aagaagactt accccaacga caaaaccatc atcagtacct ttaagtggag  1680
ttacaccact ggaaatggca agagataccg gagcactgcg cggaccacct acacctttgc  1740
caagccaatg gcggctaact atctgaagaa ccagccgatg tacgtgttcc gtaagacgga  1800
gctcaagcac tccaagaccg agctcaactt caaggagtgg caaaaggcct ttaccgatgt  1860
gatgggaatg gacgagctgt ataaggctag ctaagcggcc gctcgagtct agagggcccg  1920
cggttcgaag gtaagcctat ccctaaccct ctcctcggtc tcgattctac gcgtaccggt  1980
catcatcacc atcaccattg agtttaaacc cgctgatcag cctcgactgt gccttct     2037

SEQ ID NO: 198         moltype = AA  length = 1005
FEATURE                Location/Qualifiers
source                 1..1005
                       mol_type = protein
                       organism = synthetic construct
SEQUENCE: 198
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQSNRELVVD FLSYKLSQKG YSWSQFSDVE ENRTEAPEGT  180
ESEMETPSAI NGNPSWHLAD SPAVNGATGH SSSLDAREVI PMAAVKQALR EAGDEFELRY  240
RRAFSDLTSQ LHITPGTAYQ SFEQVVNELF RDGVNWGRIV AFFSFGGALC VESVDKEMQV  300
LVSRIAAWMA TYLNDHLEPW IQENGGWDTF VELYGNNAAG GSGGSGGSGG SAAAQLHLPQ  360
VLADAVSRLV LGKFGDLTDN FSSPHARRKV LAGVVMTTGT DVKDAKVISV STGTKCINGE  420
YMSDRGLALN DCHAEIISRR SLLRFLYTQL ELYLNNKDDQ KRSIFQKSER GGFRLKENVQ  480
FHLYISTSPC GDARIFSPHE PILEEPAASG SGTGAPPNLW AAQRYGRELR RMSDELVDRH  540
PNRKARGQLR TKIESGQGTI PVRSNASIQT WDGVLQGERL LTMSCSDKIA RWNVVGIQGS  600
LLSIFVEPIY FSSIILGSLY HGDHLSRAMY QRISNIEDLP PLYTLNKPLL SGISNAEARQ  660
PGKAPNFSVN WTVGDSAIEV INATTGKDEL GRASRLCKHA LYCRWMRVHG KVPSHLLRSK  720
ITKPNVYHES KLAAKEYQAA KARLFTAFIK AGLGAWVEKP TEQDQFSLTG SGSSELIKEN  780
MHMKLYMEGT VDNHHFKCTS EGEGKPYEGT QTMRIKVVEG GPLPFAFDIL ATSFLYGSKT  840
FINHTQGIPD FFKQSFPEGF TWERVTTYED GGVLTATQDT SLQDGCLIYN VKIRGVNFTS  900
NGPVMQKKTL GWEAFTETLY PADGGLEGRN DMALKLVGGS HLIANIKTTY RSKKPAKNLK  960
MPGVYYVDYR LERIKEANNE TYVEQHEVAV ARYCDLPSKL GHKLN                  1005

SEQ ID NO: 199         moltype = DNA  length = 3121
FEATURE                Location/Qualifiers
source                 1..3121
                       mol_type = other DNA
                       organism = synthetic construct
SEQUENCE: 199
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagagta accgggagct ggtggttgac tttctctcct acaagctttc ccagaaagga  540
```

```
tacagctgga gtcagtttag tgatgtggaa gagaacagga ctgaggcccc agaagggact  600
gaatcggaga tggagacccc cagtgccatc aatggcaacc catcctggca cctggcagac  660
agccccgcgg tgaatggagc cactggccac agcagcagtt tggatgcccg ggaggtgatc  720
cccatggcag cagtaaagca agcgctgagg gaggcaggcg acgagtttga actgcggtac  780
cggcgggcat tcagtgacct gacatcccag ctccacatca ccccagggac agcatatcag  840
agctttgaac aggtagtgaa tgaactcttc cgggatgggg taaactgggg tcgcattgtg  900
gccttttttct ccttcggcgg ggcactgtgc gtggaaagcg tagacaagga gatgcaggta  960
ttggtgagtc ggatcgcagc ttggatggcc acttacctga atgaccacct agagccttgg  1020
atccaggaga acggcggctg ggatactttt gtggaactct atgggaacaa tgcggccgga  1080
ggtagcggcg gaagcggtgg ctctggaggc tcagcggccg ctcaattaca cctgccccag  1140
gttctcgcag acgccgtatc ccgccttgta ctgggcaagt ttggtgatct tactgacaat  1200
ttttcatctc ctcatgcgag gcggaaagta ctcgcaggcg tcgtcatgac gaccggaact  1260
gacgtgaaag acgccaaagt catctctgtc tccacgggca caaagtgcat aaacggggag  1320
tacatgagcg accgggggct ggcactgaat gattgtcacg ctgaaataat atctaggcga  1380
tctctgctta gatttctcta cactcaactc gaattgtacc ttaacaacaa agatgaccag  1440
aaacgcagta tatttcagaa atcagaacgc ggcggatttc gacttaagga aaacgttcag  1500
ttccacttgt atatcagcac atccccttgc ggtgacgccc gaatcttttc cccgcacgag  1560
ccgatattgg aggagcccgc ggctagcggg tcgggcaccg gtgctccacc caatctctgg  1620
gcagcgcagc gctacggccg tgagctcaga aggatgtccg atgagctggt cgacagacat  1680
cctaatagga aggctagagg ccaacttcgg acgaagattg aaagtggcca gggtactatc  1740
ccggtgcggt ccaacgctag tattcaaacg tgggacggag tccttcaagg tgaacggctg  1800
ttgacaatga gctgctcaga caaaatcgcg cgctggaatg tagtgggaat ccaaggcagc  1860
ctcttgagca tattcgtaga acccatatat ttctcatcca ttattttggg ctctctgtat  1920
catggtgacc atctgtcaag ggctatgtac caacgaattt ctaatatcga ggatcttcct  1980
ccactctata cactcaataa gcctctcttg tccgggatat caaacgctga ggcccgccag  2040
ccagggaaag ctcctaactt cagtgttaac tggaccgttg gtgattctgc gatagaggtc  2100
atcaacgcca cgacaggtaa ggatgagctc ggtagagcct cacgcctgtg taaacacgcg  2160
ttgtattgta gatggatgag agtacatggg aaggtcccat ctcacttgct ccgaagcaag  2220
atcactaagc ctaatgtgta tcatgagtca aaactcgcgg ctaaagaata ccaggcagcc  2280
aaagctcgac tttttacagc ttttattaag gcagggctcg gggcatgggt cgagaagccg  2340
accgagcagg accaattctc tctgacgggg agcggatcca gcgagctgat taaggagaac  2400
atgcacatga agctgtacat ggagggcacc gtggacaacc atcacttcaa gtgcacatcc  2460
gagggcgaag gcaagcccta cgagggcacc cagaccatga gaatcaaggt ggtcgagggc  2520
ggccctctcc ccttcgcctt cgacatcctg gctactagct tcctctacgg cagcaagacc  2580
ttcatcaacc acacccaggg catccccgac ttcttcaagc agtccttccc tgagggcttc  2640
acatgggaga gagtcaccac atacgaagac gggggcgtgc tgaccgctac ccaggacacc  2700
agcctccagg acggctgcct catctacaac gtcaagatca gaggggtgaa cttcacatcc  2760
aacggccctg tgatgcagaa gaaaacactc ggctgggagg ccttcaccga gacgctgtac  2820
cccgctgacg gcggcctgga aggcagaaac gacatggccc tgaagctcgt gggcgggagc  2880
catctgatcg caaacatcaa gaccacatat agatccaaga aacccgctaa gaacctcaag  2940
atgcctggcg tctactatgt ggactacaga ctggaaagaa tcaaggaggc caacaacgag  3000
acctacgtcg agcagcacga ggtggcagtg gccagatact gcgacctccc tagcaaactg  3060
gggcacaagc ttaattaagg gcccgtttaa acccgctgat cagcctcgac tgtgccttct  3120
a                                                                  3121

SEQ ID NO: 200          moltype = AA  length = 794
FEATURE                 Location/Qualifiers
source                  1..794
                        mol_type = protein
                        organism = synthetic construct
SEQUENCE: 200
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPADRHP NRKARGQLRT KIESGQGTIP VRSNASIQTW  360
DGVLQGERLL TMSCSDKIAR WNVVGIQGSL LSIFVEPIYF SSIILGSLYH GDHLSRAMYQ  420
RISNIEDLPP LYTLNKPLLS GISNAEARQP GKAPNFSVNW TVGDSAIEVI NATTGKDELG  480
RASRLCKHAL YCRWMRVHGK VPSHLLRSKI TKPNVYHESK LAAKEYQAAK ARLFTAFIKA  540
GLGAWVEKPT EQDQFSLTGS GSSELIKENM HMKLYMEGTV DNHHFKCTSE GEGKPYEGTQ  600
TMRIKVVEGG PLPFAFDILA TSFLYGSKTF INHTQGIPDF FKQSFPEGFT WERVTTYEDG  660
GVLTATQDTS LQDGCLIYNV KIRGVNFTSN GPVMQKKTLG WEAFTETLYP ADGGLEGRND  720
MALKLVGGSH LIANIKTTYR SKKPAKNLKM PGVYYVDYRL ERIKEANNET YVEQHEVAVA  780
RYCDLPSKLG HKLN                                                    794

SEQ ID NO: 201          moltype = DNA  length = 2488
FEATURE                 Location/Qualifiers
source                  1..2488
                        mol_type = other DNA
                        organism = synthetic construct
SEQUENCE: 201
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
```

```
gggagcggtg caggatctgg tagtccagct gggggaggag caccgggtag cggtgggggg  480
tctaccggtg ctccacccaa tctctgggca gcgcagcgct acggccgtga gctcagaagg  540
atgtccgatg agttcgtcga ttccttcaaa aaggctagcc agctgcacct gccccaggtt  600
ctcgcagacg ccgtatcccg ccttgtactg ggcaagtttg gtgatcttac tgacaatttt  660
tcatctcctc atgcgaggcg gaaagtactc gcaggcgtcg tcatgacgac cggaactgac  720
gtgaaagacg ccaaagtcat ctctgtctcc acgggcacaa agtgcataaa cggggagtac  780
atgagcgacc gggggctggc actgaatgat tgtcacgctg aaataatatc taggcgatct  840
ctgcttagat ttctctacac tcaactcgaa ttgtacctta acaacaaaga tgaccagaaa  900
cgcagtatat ttcagaaatc agaacgcggc ggatttcgac ttaaggaaaa cgttcagttc  960
cacttgtata tcagcacatc cccttgcggt gacgcccgaa tcttttcccc gcacgagccg  1020
atattggagg agcccgcgga cagacatcct aataggaagg ctagaggcca acttcggacg  1080
aagattgaaa gtggccaggg tactatcccg gtgcggtcca acgctagtat tcaaacgtgg  1140
gacggagtcc ttcaaggtga acggctgttg acaatgagct gctcagacaa aatcgcgcgc  1200
tggaatgtag tgggaatcca aggcagcctc ttgagcatat tcgtagaacc catatatttc  1260
tcatccatta ttttgggctc tctgtatcat ggtgaccatc tgtcaagggc tatgtaccaa  1320
cgaatttcta atatcgagga tcttcctcca ctctatacac tcaataagcc tctcttgtcc  1380
gggatatcaa acgctgaggc ccgccagcca gggaaagctc ctaacttcag tgttaactgg  1440
accgttggtg attctgcgat agaggtcatc aacgccacga caggtaagga tgagctcggt  1500
agagcctcac gcctgtgtaa acacgcgttg tattgtagat ggatgagagt acatgggaag  1560
gtcccatctc acttgctccg aagcaagatc actaagccta atgtgtatca tgagtcaaaa  1620
ctcgcggcta aagaatacca ggcagccaaa gctcgacttt ttacagcttt tattaaggca  1680
gggctcgggg catgggtcga gaagccgacc gagcaggacc aattctctct gacggggagc  1740
ggatccagcg agctgattaa ggagaacatg cacatgaagc tgtacatgga gggcaccgtg  1800
gacaaccatc acttcaagtg cacatccgag ggcgaaggca agccctacga gggcacccag  1860
accatgagaa tcaaggtggt cgagggcggc cctctcccct tcgccttcga catcctggct  1920
actagcttcc tctacggcag caagaccttc atcaaccaca cccagggcat ccccgacttc  1980
ttcaagcagt ccttccctga gggcttcaca tgggagagag tcaccacata cgaagacggg  2040
ggcgtgctga ccgctaccca ggacaccagc ctccaggacg gctgcctcat ctacaacgtc  2100
aagatcagag gggtgaactt cacatccaac ggccctgtga tgcagaagaa aacactcggc  2160
tgggaggcct tcaccgagac gctgtacccc gctgacggcg gcctggaagg cagaaacgac  2220
atggccctga agctcgtggg cgggagccat ctgatcgcaa acatcaagac cacatataga  2280
tccaagaaac ccgctaagaa cctcaagatg cctggcgtct actatgtgga ctacagactg  2340
gaaagaatca aggaggccaa caacgagacc tacgtcgagc agcacgaggt ggcagtggcc  2400
agatactgcg acctccctag caaactgggg cacaagctta attaagggcc cgtttaaacc  2460
cgctgatcag cctcgactgt gccttcta                                     2488
```

```
SEQ ID NO: 202          moltype = AA  length = 993
FEATURE                 Location/Qualifiers
source                  1..993
                        mol_type = protein
                        organism = synthetic construct
SEQUENCE: 202
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPADRHP NRKARGQLRT KIESGQGTIP VRSNASIQTW  360
DGVLQGERLL TMSCSDKIAR WNVVGIQGSL LSIFVEPIYF SSIILGSLYH GDHLSRAMYQ  420
RISNIEDLPP LYTLNKPLLS GISNAEARQP GKAPNFSVNW TVGDSAIEVI NATTGKDELG  480
RASRLCKHAL YCRWMRVHGK VPSHLLRSKI TKPNVYHESK LAAKEYQAAK ARLFTAFIKA  540
GLGAWVEKPT EQDQFSLTGS AAASSNRELV VDFLSYKLSQ KGYSWSQFSD VEENRTEAPE  600
GTESEMETPS AINGNPSWHL ADSPAVNGAT GHSSSLDARE VIPMAAVKQA LREAGDEFEL  660
RYRRAFSDLT SQLHITPGTA YQSFEQVVNE LFRDGVNWGR IVAFFSFGGA LCVESVDKEM  720
QVLVSRIAAW MATYLNDHLE PWIQENGGWD TFVELYGNNG SSELIKENMH MKLYMEGTVD  780
NHHFKCTSEG EGKPYEGTQT MRIKVVEGGP LPFAFDILAT SFLYGSKTFI NHTQGIPDFF  840
KQSFPEGFTW ERVTTYEDGG VLTATQDTSL QDGCLIYNVK IRGVNFTSNG PVMQKKTLGW  900
EAFTETLYPA DGGLEGRNDM ALKLVGGSHL IANIKTTYRS KKPAKNLKMP GVYYVDYRLE  960
RIKEANNETY VEQHEVAVAR YCDLPSKLGH KLN                                993
```

```
SEQ ID NO: 203          moltype = DNA  length = 3085
FEATURE                 Location/Qualifiers
source                  1..3085
                        mol_type = other DNA
                        organism = synthetic construct
SEQUENCE: 203
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctaccggtg ctccacccaa tctctgggca gcgcagcgct acggccgtga gctcagaagg  540
atgtccgatg agttcgtcga ttccttcaaa aaggctagcc agctgcacct gccccaggtt  600
ctcgcagacg ccgtatcccg ccttgtactg ggcaagtttg gtgatcttac tgacaatttt  660
tcatctcctc atgcgaggcg gaaagtactc gcaggcgtcg tcatgacgac cggaactgac  720
gtgaaagacg ccaaagtcat ctctgtctcc acgggcacaa agtgcataaa cggggagtac  780
```

```
atgagcgacc gggggctggc actgaatgat tgtcacgctg aaataatatc taggcgatct  840
ctgcttagat ttctctacac tcaactcgaa ttgtacctta acaacaaaga tgaccagaaa  900
cgcagtatat ttcagaaatc agaacgcggc ggatttcgac ttaaggaaaa cgttcagttc  960
cacttgtata tcagcacatc cccttgcggt gacgcccgaa tcttttcccc gcacgagccg  1020
atattggagg agcccgcgga cagacatcct aataggaagg ctagaggcca acttcggacg  1080
aagattgaaa gtggccaggg tactatcccg gtgcggtcca acgctagtat tcaaacgtgg  1140
gacggagtcc ttcaaggtga acggctgttg acaatgagct gctcagacaa aatcgcgcgc  1200
tggaatgtag tgggaatcca aggcagcctc ttgagcatat tcgtagaacc catatatttc  1260
tcatccatta ttttgggctc tctgtatcat ggtgaccatc tgtcaagggc tatgtaccaa  1320
cgaatttcta atatcgagga tcttcctcca ctctatacac tcaataagcc tctcttgtcc  1380
gggatatcaa acgctgaggc ccgccagcca gggaaagctc ctaacttcag tgttaactgg  1440
accgttggtg attctgcgat agaggtcatc aacgccacga caggtaagga tgagctcggt  1500
agagcctcac gcctgtgtaa acacgcgttg tattgtagat ggatgagagt acatgggaag  1560
gtcccatctc acttgctccg aagcaagatc actaagccta atgtgtatca tgagtcaaaa  1620
ctcgcggcta aagaatacca ggcagccaaa gctcgacttt ttacagcttt tattaaggca  1680
gggctcgggg catgggtcga gaagccgacc gagcaggacc aattctctct gacggggagc  1740
gcggccgcct caagtaaccg ggagctggtg gttgactttc tctcctacaa gctttcccag  1800
aaaggataca gctggagtca gtttagtgat gtggaagaga acaggactga ggccccagaa  1860
gggactgaat cggagatgga gacccccagt gccatcaatg gcaacccatc ctggcacctg  1920
gcagacagcc ccgcggtgaa tggagccact ggccacagca gcagtttgga tgcccgggag  1980
gtgatcccca tggcagcagt aaagcaagcg ctgagggagg caggcgacga gtttgaactg  2040
cggtaccggc gggcattcag tgacctgaca tcccagctcc acatcacccc agggacagca  2100
tatcagagct ttgaacaggt agtgaatgaa ctcttccggg atggggtaaa ctggggtcgc  2160
attgtggcct ttttctcctt cggcggggca ctgtgcgtgg aaagcgtaga caaggagatg  2220
caggtattgg tgagtcggat cgcagcttgg atggccactt acctgaatga ccacctagag  2280
ccttggatcc aggagaacgg cggctgggat acttttgtgg aactctatgg gaacaatgga  2340
tccagcgagc tgattaagga gaacatgcac atgaagctgt acatggaggg caccgtggac  2400
aaccatcact tcaagtgcac atccgagggc gaaggcaagc cctacgaggg cacccagacc  2460
atgagaatca aggtggtcga gggcggccct ctccccttcg ccttcgacat cctggctact  2520
agcttcctct acggcagcaa gaccttcatc aaccacaccc agggcatccc cgacttcttc  2580
aagcagtcct tccctgaggg cttcacatgg gagagagtca ccacatacga agacgggggc  2640
gtgctgaccg ctacccagga caccagcctc caggacggct gcctcatcta caacgtcaag  2700
atcagagggg tgaacttcac atccaacggc cctgtgatgc agaagaaaac actcggctgg  2760
gaggccttca ccgagacgct gtaccccgct gacggcggcc tggaaggcag aaacgacatg  2820
gccctgaagc tcgtgggcgg gagccatctg atcgcaaaca tcaagaccac atatagatcc  2880
aagaaacccg ctaagaacct caagatgcct ggcgtctact atgtggacta cagactggaa  2940
agaatcaagg aggccaacaa cgagacctac gtcgagcagc acgaggtggc agtggccaga  3000
tactgcgacc tccctagcaa actggggcac aagcttaatt aagggcccgt ttaaacccgc  3060
tgatcagcct cgactgtgcc ttcta                                        3085

SEQ ID NO: 204          moltype = AA  length = 913
FEATURE                 Location/Qualifiers
source                  1..913
                        mol_type = protein
                        organism = synthetic construct
SEQUENCE: 204
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSG SSELIKENMH MKLYMEGTVD NHHFKCTSEG EGKPYEGTQT  720
MRIKVVEGGP LPFAFDILAT SFLYGSKTFI NHTQGIPDFF KQSFPEGFTW ERVTTYEDGG  780
VLTATQDTSL QDGCLIYNVK IRGVNFTSNG PVMQKKTLGW EAFTETLYPA DGGLEGRNDM  840
ALKLVGGSHL IANIKTTYRS KKPAKNLKMP GVYYVDYRLE RIKEANNETY VEQHEVAVAR  900
YCDLPSKLGH KLN                                                     913

SEQ ID NO: 205          moltype = DNA  length = 2845
FEATURE                 Location/Qualifiers
source                  1..2845
                        mol_type = other DNA
                        organism = synthetic construct
SEQUENCE: 205
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
```

-continued

```
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcgtcg tccggtggag aacttgatga attggtatac  1320
ttactagatg ggccaggtta tgaccctata cattgcgatg tagtgacaag gggcggcagc  1380
caccttttca attttgacag acatcctaat aggaaggcta gaggccaact tcggacgaag  1440
attgaaagtg gccagggtac tatcccggtg cggtccaacg ctagtattca aacgtgggac  1500
ggagtccttc aaggtgaacg gctgttgaca atgagctgct cagacaaaat cgcgcgctgg  1560
aatgtagtgg gaatccaagg cagcctcttg agcatattcg tagaacccat atatttctca  1620
tccattattt tgggctctct gtatcatggt gaccatctgt caagggctat gtaccaacga  1680
atttctaata tcgaggatct tcctccactc tatacactca ataagcctct cttgtccggg  1740
atatcaaacg ctgaggcccg ccagccaggg aaagctccta acttcagtgt taactggacc  1800
gttggtgatt ctgcgataga ggtcatcaac gccacgacag gtaaggatga gctcggtaga  1860
gcctcacgcc tgtgtaaaca cgcgttgtat tgtagatgga tgagagtaca tgggaaggtc  1920
ccatctcact tgctccgaag caagatcact aagcctaatg tgtatcatga gtcaaaactc  1980
gcggctaaag aataccaggc agccaaagct cgactttttta cagcttttat taaggcaggg  2040
ctcggggcat gggtcgagaa gccgaccgag caggaccaat tctctctgac ggggagcgga  2100
tccagcgagc tgattaagga gaacatgcac atgaagctgt acatggaggg caccgtggac  2160
aaccatcact tcaagtgcac atccgagggc gaaggcaagc cctacgaggg cacccagacc  2220
atgagaatca aggtggtcga gggcggccct ctccccttcg ccttcgacat cctggctact  2280
agcttcctct acggcagcaa gaccttcatc aaccacaccc agggcatccc cgacttcttc  2340
aagcagtcct tccctgaggg cttcacatgg gagagagtca ccacatacga agacgggggc  2400
gtgctgaccg ctacccagga caccagcctc caggacggct gcctcatcta caacgtcaag  2460
atcagagggg tgaacttcac atccaacggc cctgtgatgc agaagaaaac actcggctgg  2520
gaggccttca ccgagacgct gtaccccgct gacggcggcc tggaaggcag aaacgacatg  2580
gccctgaagc tcgtgggcgg gagccatctg atcgcaaaca tcaagaccac atatagatcc  2640
aagaaacccg ctaagaacct caagatgcct ggcgtctact atgtggacta cagactggaa  2700
agaatcaagg aggccaacaa cgagacctac gtcgagcagc acgaggtggc agtggccaga  2760
tactgcgacc tccctagcaa actggggcac aagcttaatt aagggcccgt ttaaacccgc  2820
tgatcagcct cgactgtgcc ttcta                                       2845

SEQ ID NO: 206          moltype = AA  length = 1125
FEATURE                 Location/Qualifiers
source                  1..1125
                        mol_type = protein
                        organism = synthetic construct
SEQUENCE: 206
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSA AGGSGGSAAA QGSVVIVGRI ILSGSGSITA YSQQTRGLLG  720
CIITSLTGRD KNQVEGEVQV VSTATQSFLA TCVNGVCWTV YHGAGSKTLA GPKGPITQMY  780
TNVDQDLVGW QAPPGARSLT PCTCGSSDLY LVTRHADVIP VRRRGDSRGS LLSPRPVSYL  840
KGSSGGPLLC PSGHAVGIFR AAVCTRGVAK AVDFVPVESM ETTMRSESGS GTMSELIKEN  900
MHMKLYMEGT VDNHHFKCTS EGEGKPYEGT QTMRIKVVEG GPLPFAFDIL ATSFLYGSKT  960
FINHTQGIPD FFKQSFPEGF TWERVTTYED GGVLTATQDT SLQDGCLIYN VKIRGVNFTS  1020
NGPVMQKKTL GWEAFTETLY PADGGLEGRN DMALKLVGGS HLIANIKTTY RSKKPAKNLK  1080
MPGVYYVDYR LERIKEANNE TYVEQHEVAV ARYCDLPSKL GHKLN                 1125

SEQ ID NO: 207          moltype = DNA  length = 3481
FEATURE                 Location/Qualifiers
source                  1..3481
                        mol_type = other DNA
                        organism = synthetic construct
SEQUENCE: 207
taatacgact cactataggg agacccaagc tggctagagg atcgaaccct taaggccacc  60
atggcgagca attttaccca gtttgtgctt gtggacaacg gcggcaccgg ggacgtgacg  120
gtggccccct ccaatttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
```

```
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcgtcg tccggtggag aacttgatga attggtatac  1320
ttactagatg ggccaggtta tgaccctata cattgcgatg tagtgacaag gggcggcagc  1380
cacctttttca attttgacag acatcctaat aggaaggcta gaggccaact tcggacgaag  1440
attgaaagtg gccagggtac tatcccggtg cggtccaacg ctagtattca aacgtgggac  1500
ggagtccttc aaggtgaacg gctgttgaca atgagctgct cagacaaaat cgcgcgctgg  1560
aatgtagtgg gaatccaagg cagcctcttg agcatattcg tagaacccat atatttctca  1620
tccattattt tgggctctct gtatcatggt gaccatctgt caagggctat gtaccaacga  1680
atttctaata tcgaggatct tcctccactc tatacactca ataagcctct cttgtccggg  1740
atatcaaacg ctgaggcccg ccagccaggg aaagctccta acttcagtgt taactggacc  1800
gttggtgatt ctgcgataga ggtcatcaac gccacgacag gtaaggatga gctcggtaga  1860
gcctcacgcc tgtgtaaaca cgcgttgtat tgtagatgga tgagagtaca tgggaaggtc  1920
ccatctcact tgctccgaag caagatcact aagcctaatg tgtatcatga gtcaaaactc  1980
gcggctaaag aataccaggc agccaaagct cgacttttta cagcttttat taaggcaggg  2040
ctcggggcat gggtcgagaa gccgaccgag caggaccaat tctctctgac ggggagcgcg  2100
gccggaggta gcggcggaag cgcggccgct cagggg tctg ttgttattgt tggtagaatt  2160
attttatctg gtagtggtag tatcacggcc tactcccaac agacgcgggg cctacttggt  2220
tgcatcatca ctagcctcac aggccgggac aagaaccagg tcgaagggga ggttcaagtg  2280
gtttctaccg caacacaatc tttcctggcg acctgcgtca acggcgtgtg ctggactgtc  2340
taccatggcg ctggctcgaa gaccctagcc ggtccaaaag gtccaatcac ccaaatgtac  2400
accaatgtag accaggacct cgtcggctgg caggcgcctc caggggcgcg ctccttgaca  2460
ccatgcacct gtggcagctc ggacctttac ttggtcacga gacatgctga tgtcattccg  2520
gtgcgccggc gaggcgacag caggggaagt ctactctccc ccaggcccgt ctcctacctg  2580
aaaggctcct caggtggtcc attgctttgc ccttcggggc acgctgtggg catcttccgg  2640
gctgctgtgt gcacccgggg ggtcgcgaag gcggtggact tcgtgcccgt tgagtctatg  2700
gaaactacca tgcggtctga gagtggatca ggtaccatga gcgagctgat taaggagaac  2760
atgcacatga agctgtacat ggagggcacc gtgaacaacc atcacttcaa gtgcacatcc  2820
gagggcgaag gcaagcccta cgagggcacc cagaccatga gaatcaaggt ggtcgagggc  2880
ggccctctcc ccttcgcctt cgacatcctg gctactagct tcctctacgg cagcaagacc  2940
ttcatcaacc acacccaggg catccccgac ttcttcaagc agtccttccc tgagggcttc  3000
acatgggaga gagtcaccac atacgaagac gggggcgtgc tgaccgctac ccaggacacc  3060
agcctccagg acggctgcct catctacaac gtcaagatca gaggggtgaa cttcacatcc  3120
aacggccctg tgatgcagaa gaaaacactc ggctgggagg ccttcaccga gacgctgtac  3180
cccgctgacg gcggcctgga aggcagaaac gacatggccc tgaagctcgt gggcgggagc  3240
catctgatcg caaacatcaa gaccacatat agatccaaga aacccgctaa gaacctcaag  3300
atgcctggcg tctactatgt ggactacaga ctggaaagaa tcaaggaggc caacaacgag  3360
acctacgtcg agcagcacga ggtggcagtg gccagatact gcgacctccc tagcaaactg  3420
gggcacaagc ttaattaagg gcccgtttaa acccgctgat cagcctcgac tgtgccttct  3480
a                                                                  3481
```

```
SEQ ID NO: 208          moltype = AA  length = 189
FEATURE                 Location/Qualifiers
source                  1..189
                        mol_type = protein
                        organism = Hepacivirus hominis
SEQUENCE: 208
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180
SPVFTDNSS                                                        189
```

```
SEQ ID NO: 209          moltype = AA  length = 186
FEATURE                 Location/Qualifiers
source                  1..186
                        mol_type = protein
                        organism = Hepacivirus hominis
SEQUENCE: 209
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180
SPVFTD                                                           186
```

```
SEQ ID NO: 210          moltype = AA  length = 180
FEATURE                 Location/Qualifiers
source                  1..180
                        mol_type = protein
                        organism = Hepacivirus hominis
```

SEQUENCE: 210
APITAYAQQT RGLLGCIITS LTGRDKNQVE GEVQIVSTAT QTFLATCING VCWTVYHGAG 60
TRTIASPKGP VIQMYTNVDQ DLVGWPAPQG SRSLTPCTCG SSDLYLVTRH ADVIPVRRRG 120
DSRGSLLSPR PISYLKGSSG GPLLCPAGHA VGLFRAAVCT RGVAKAVDFI PVENLETTMR 180

SEQ ID NO: 211 moltype = AA length = 180
FEATURE Location/Qualifiers
source 1..180
mol_type = protein
organism = Hepacivirus hominis
SEQUENCE: 211
APITAYSQQT RGLLGCIITS LTGRDKNQVE GEVQVVSTAT QSFLATCVNG VCWTVYHGAG 60
SKTLAGPKGP ITQMYTNVDQ DLVGWQAPPG ARSLTPCTCG SSDLYLVTRH ADVIPVRRRG 120
DSRGSLLSPR PVSYLKGSSG GPLLCPSGHA VGIFRAAVCT RGVAKAVDFV PVESMETTMR 180

SEQ ID NO: 212 moltype = AA length = 180
FEATURE Location/Qualifiers
source 1..180
mol_type = protein
organism = Hepacivirus hominis
SEQUENCE: 212
APITAYAQQT RGLLGTIVVS MTGRDKTEQA GEIQVLSTVT QSFLGTSISG VLWTVYHGAG 60
NKTLAGSRGP VTQMYSSAEG DLVGWPSPPG TKSLEPCTCG AVDLYLVTRN ADVIPARRRG 120
DKRGALLSPR PLSTLKGSSG GPVLCPRGHA VGVFRAAVCS RGVAKSIDFI PVETLDIVTR 180

SEQ ID NO: 213 moltype = AA length = 180
FEATURE Location/Qualifiers
source 1..180
mol_type = protein
organism = Hepacivirus hominis
SEQUENCE: 213
APITAYAQQT RGLLGTIVTS LTGRDKNVVT GEVQVLSTAT QTFLGTTVGG VIWTVYHGAG 60
SRTLAGAKHP ALQMYTNVDQ DLVGWPAPPG AKSLEPCACG SSDLYLVTRD ADVIPARRRG 120
DSTASLLSPR PLACLKGSSG GPVMCPSGHV AGIFRAAVCT RGVAKSLQFI PVETLSTQAR 180

SEQ ID NO: 214 moltype = AA length = 180
FEATURE Location/Qualifiers
source 1..180
mol_type = protein
organism = Hepacivirus hominis
SEQUENCE: 214
APITAYAQQT RGLFSTIVTS LTGRDTNENC GEVQVLSTAT QSFLGTAVNG VMWTVYHGAG 60
AKTISGPKGP VNQMYTNVDQ DLVGWPAPPG VRSLAPCTCG SADLYLVTRH ADVIPVRRRG 120
DTRGALLSPR PISILKGSSG GPLLCPMGHR AGIFRAAVCT RGVAKAVDFV PVESLETTMR 180

SEQ ID NO: 215 moltype = AA length = 180
FEATURE Location/Qualifiers
source 1..180
mol_type = protein
organism = Hepacivirus hominis
SEQUENCE: 215
APITAYAQQT RGVLGAIVLS LTGRDKNEAE GEVQFLSTAT QTFLGICING VMWTLFHGAG 60
SKTLAGPKGP VVQMYTNVDK DLVGWPSPPG KGSLTRCTCG SADLYLVTRH ADVIPARRRG 120
DTRASLLSPR PISYLKGSSG GPIMCPSGHV VGVFRAAVCT RGVAKALEFV PVENLETTMR 180

SEQ ID NO: 216 moltype = AA length = 180
FEATURE Location/Qualifiers
source 1..180
mol_type = protein
organism = Hepacivirus hominis
SEQUENCE: 216
APITAYAQQT RGLVGTIVTS LTGRDKNEAE GEVQVVSTAT QSFLATTING VLWTVYHGAG 60
SKNLAGPKGP VCQMYTNVDQ DLVGWPAPLG ARSLAPCTCG SSDLYLVTRG ADVIPARRRG 120
DTRAALLSPR PISTLKGSSG GPLMCPSGHV VGLFRAAVCT RGVAKALDFI PVENMDTTMR 180

SEQ ID NO: 217 moltype = AA length = 180
FEATURE Location/Qualifiers
source 1..180
mol_type = protein
organism = Hepacivirus hominis
SEQUENCE: 217
APISAYAQQT RGLISTLVVS LTGRDKNETA GEVQVLSTST QTFLGTNVGG VMWGPYHGAG 60
TRTVAGRGGP VLQMYTSVSD DLVGWPAPPG SKSLEPCSCG SADLYLVTRN ADVLPLRRKG 120
DGTASLLSPR PVSSLKGSSG GPVLCPQSHC VGIFRAAVCT RGVAKAVQFV PIEKMQVAQR 180

SEQ ID NO: 218 moltype = AA length = 180
FEATURE Location/Qualifiers
source 1..180
mol_type = protein

```
                        organism = Hepacivirus hominis
SEQUENCE: 218
APITAYAQQT RGLLGCIITS LTGRDKNQVE GEVQIVSTAT QTFLATCING VCWTVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVTKAVDFI PVENLETTMR  180

SEQ ID NO: 219          moltype = AA  length = 180
FEATURE                 Location/Qualifiers
source                  1..180
                        mol_type = protein
                        organism = Hepacivirus hominis
SEQUENCE: 219
APITAYSQQT RGLLGCIITS LTGRDKNQVE GEVQVVSTAT QSFLATCVNG VCWTVYHGAG  60
SKTLAAPKGP ITQMYTNVDQ DLVGWPKPPG ARSLTPCTCG SSDLYLVTRH ADVIPVRRRG  120
DSRGSLLSPR PVSYLKGSSG GPLLCPFGHA VGIFRAAVCT RGVAKAVDFV PVESMETTMR  180

SEQ ID NO: 220          moltype = AA  length = 180
FEATURE                 Location/Qualifiers
source                  1..180
                        mol_type = protein
                        organism = Hepacivirus hominis
SEQUENCE: 220
APITAYAQQT RGLLGTIVVS MTGRDKTEQA GEIQVLSTVT QSFLGTTISG VLWTVYHGAG  60
NKTLAGSRGP VTQMYSSAEG DLVGWPSPPG TKSLEPCTCG AVDLYLVTRN ADVIPARRRG  120
DKRGALLSPR PLSTLKGSSG GPVLCPRGHA VGVFRAAVCS RGVAKSIDFI PVETLDIVTR  180

SEQ ID NO: 221          moltype = AA  length = 180
FEATURE                 Location/Qualifiers
source                  1..180
                        mol_type = protein
                        organism = Hepacivirus hominis
SEQUENCE: 221
APITAYTQQT RGLLGAIVVS LTGRDKNEQA GQVQVLSSVT QTFLGTSISG VLWTVYHGAG  60
NKTLAGPKGP VTQMYTSAEG DLVGWPSPPG TKSLDPCTCG AVDLYLVTRN ADVIPVRRKD  120
DRRGALLSPR PLSTLKGSSG GPVLCSRGHA VGLFRAAVCA RGVAKSIDFI PVESLDVATR  180

SEQ ID NO: 222          moltype = AA  length = 180
FEATURE                 Location/Qualifiers
source                  1..180
                        mol_type = protein
                        organism = Hepacivirus hominis
SEQUENCE: 222
APITAYAQQT RGLLGTIVTS LTGRDKNVVT GEVQVLSTAT QTFLGTTVGG VIWTVYHGAG  60
SRTLAGAKHP ALQMYTNVDQ DLVGWPAPPG AKSLEPCACG SSDLYLVTRD ADVIPARRRG  120
DSTASLLSPR PLACLKGSSG GPVMCPSGHV AGIFRAAVCT RGVAKSLQFI PVETLSTQAR  180

SEQ ID NO: 223          moltype = AA  length = 186
FEATURE                 Location/Qualifiers
source                  1..186
                        mol_type = protein
                        organism = synthetic construct
SEQUENCE: 223
APITAYAQQT RGLLGCIITS LTGRDKNQVE GEVQIMSTAT QTFLATCING VCWAVYHGAG  60
TRTIASPKGP VIQMYTNVDQ DLVGWPAPQG SRSLTPCTCG SSDLYLVTRH ADVIPVRRRG  120
DGRGSLLSPR PISYLKGSSG GPLLCPAGHA VGLFRAAVCT RGVAKAVDFI PVENLETTMR  180
SPVFTD                                                            186

SEQ ID NO: 224          moltype = AA  length = 186
FEATURE                 Location/Qualifiers
source                  1..186
                        mol_type = protein
                        organism = synthetic construct
SEQUENCE: 224
APITAYAQQT RGLLGCIITS LTGRDKNQVE GEVQIVSTAT QTLLATCING VCWAVYHGAG  60
TRTIASPKGP VIQMYTNVDK DLVGWPAPQG SRSLTPCTCG SSDLYLVTRH ADVIPVRRRG  120
DRRGSLLSPR PISYLKGSSG GPLLCPAGHA VGLFRAAVCT RGVAKAVYFI PVENLETTMR  180
SPVFTD                                                            186

SEQ ID NO: 225          moltype = AA  length = 13
FEATURE                 Location/Qualifiers
source                  1..13
                        mol_type = protein
                        organism = Hepacivirus hominis
SEQUENCE: 225
GCVVIVGRIV LSG                                                    13

SEQ ID NO: 226          moltype = AA  length = 45
FEATURE                 Location/Qualifiers
source                  1..45
```

```
                        mol_type = protein
                        organism = Hepacivirus hominis
SEQUENCE: 226
STWVLVGGVL AALAAYCLST GCVVIVGRIV LSGKPAIIPD REVLY                   45

SEQ ID NO: 227          moltype = AA  length = 51
FEATURE                 Location/Qualifiers
source                  1..51
                        mol_type = protein
                        organism = Hepacivirus hominis
SEQUENCE: 227
STWVLVGGVL AALAAYCLST GCVVIVGRIV LSGKPAGSSG SSIIPDREVL Y            51

SEQ ID NO: 228          moltype = AA  length = 63
FEATURE                 Location/Qualifiers
source                  1..63
                        mol_type = protein
                        organism = Hepacivirus hominis
SEQUENCE: 228
IDTKYIMTCM SADLEVVTST WVLVGGVLAA LAAYCLSTGC VVIVGRIVLS GKPAIIPDRE  60
VLY                                                                 63

SEQ ID NO: 229          moltype = AA  length = 12
FEATURE                 Location/Qualifiers
source                  1..12
                        mol_type = protein
                        organism = Hepacivirus hominis
SEQUENCE: 229
GSVVIVGRII LS                                                       12

SEQ ID NO: 230          moltype = AA  length = 14
FEATURE                 Location/Qualifiers
source                  1..14
                        mol_type = protein
                        organism = Hepacivirus hominis
SEQUENCE: 230
GCVVIVGRIV LSGK                                                     14

SEQ ID NO: 231          moltype = AA  length = 14
FEATURE                 Location/Qualifiers
source                  1..14
                        mol_type = protein
                        organism = Hepacivirus hominis
SEQUENCE: 231
GCVCIIGRLH INQR                                                     14

SEQ ID NO: 232          moltype = AA  length = 14
FEATURE                 Location/Qualifiers
source                  1..14
                        mol_type = protein
                        organism = Hepacivirus hominis
SEQUENCE: 232
GCVVIVGHIE LEGK                                                     14

SEQ ID NO: 233          moltype = AA  length = 14
FEATURE                 Location/Qualifiers
source                  1..14
                        mol_type = protein
                        organism = Hepacivirus hominis
SEQUENCE: 233
GSVVIVGRVV LSGQ                                                     14

SEQ ID NO: 234          moltype = AA  length = 14
FEATURE                 Location/Qualifiers
source                  1..14
                        mol_type = protein
                        organism = Hepacivirus hominis
SEQUENCE: 234
GSVAIVGRII LSGR                                                     14

SEQ ID NO: 235          moltype = AA  length = 14
FEATURE                 Location/Qualifiers
source                  1..14
                        mol_type = protein
                        organism = Hepacivirus hominis
SEQUENCE: 235
GCVVICGRIV TSGK                                                     14

SEQ ID NO: 236          moltype = AA  length = 14
```

```
FEATURE                Location/Qualifiers
source                 1..14
                       mol_type = protein
                       organism = Hepacivirus hominis
SEQUENCE: 236
GSVVVVGRVV LGSN                                                        14

SEQ ID NO: 237         moltype = AA  length = 54
FEATURE                Location/Qualifiers
source                 1..54
                       mol_type = protein
                       organism = Hepacivirus hominis
SEQUENCE: 237
STWVLVGGVL AALAAYCLST GCVVIVGRIV LSGKPAIIPD REVLYQEFDE MEEC            54

SEQ ID NO: 238         moltype = AA  length = 54
FEATURE                Location/Qualifiers
source                 1..54
                       mol_type = protein
                       organism = Hepacivirus hominis
SEQUENCE: 238
STWVLVGGVL AALAAYCLST GCVVIVGRVV LSGKPAIIPD REVLYREFDE MEEC            54

SEQ ID NO: 239         moltype = AA  length = 54
FEATURE                Location/Qualifiers
source                 1..54
                       mol_type = protein
                       organism = Hepacivirus hominis
SEQUENCE: 239
STWVLVGGVL AALAAYCLST GCVVIVGRIV LSGRPAIIPD REVLYREFDE MEEC            54

SEQ ID NO: 240         moltype = AA  length = 54
FEATURE                Location/Qualifiers
source                 1..54
                       mol_type = protein
                       organism = Hepacivirus hominis
SEQUENCE: 240
STWVLVGGVL AALAAYCLTT GSVVIVGRII LSGRPAIVPD RELLYQEFDE MEEC            54

SEQ ID NO: 241         moltype = AA  length = 54
FEATURE                Location/Qualifiers
source                 1..54
                       mol_type = protein
                       organism = Hepacivirus hominis
SEQUENCE: 241
STWVLVGGVL AALAAYCLTT GSVVIVGRII LSGRPAIIPD RELLYQEFDE MEEC            54

SEQ ID NO: 242         moltype = AA  length = 54
FEATURE                Location/Qualifiers
source                 1..54
                       mol_type = protein
                       organism = Hepacivirus hominis
SEQUENCE: 242
STWVLVGGVL AALAAYCLTT GSVVIVGRII LSGKPAVVPD RELLYQEFDE MEEC            54

SEQ ID NO: 243         moltype = AA  length = 54
FEATURE                Location/Qualifiers
source                 1..54
                       mol_type = protein
                       organism = Hepacivirus hominis
SEQUENCE: 243
STWVLVGGVL AALAAYCLTT GSVVIVGRII LSGRPAVIPD RELLYREFDE MEEC            54

SEQ ID NO: 244         moltype = AA  length = 54
FEATURE                Location/Qualifiers
source                 1..54
                       mol_type = protein
                       organism = Hepacivirus hominis
SEQUENCE: 244
STWVLAGGVL AAVAAYCLAT GCVCIIGRLH VNQRAVVAPD KEVLYEAFDE MEEC            54

SEQ ID NO: 245         moltype = AA  length = 54
FEATURE                Location/Qualifiers
source                 1..54
                       mol_type = protein
                       organism = Hepacivirus hominis
SEQUENCE: 245
STWVLAGGVL AAVAAYCLAT GCVSIIGRLH INGRAVVAPD KEVLYEAFDE MEEC            54
```

-continued

```
SEQ ID NO: 246         moltype = AA  length = 54
FEATURE                Location/Qualifiers
source                 1..54
                       mol_type = protein
                       organism = Hepacivirus hominis
SEQUENCE: 246
SSWVLAGGVL AAVAAYCLAT GCISIIGRLH LNDRVVVAPD KEILYEAFDE MEEC        54

SEQ ID NO: 247         moltype = AA  length = 54
FEATURE                Location/Qualifiers
source                 1..54
                       mol_type = protein
                       organism = Hepacivirus hominis
SEQUENCE: 247
STWVLAGGVL AAVAAYCLAT GCVSIIGRLH LNDQVVVTPD KEILYEAFDE MEEC        54

SEQ ID NO: 248         moltype = AA  length = 54
FEATURE                Location/Qualifiers
source                 1..54
                       mol_type = protein
                       organism = Hepacivirus hominis
SEQUENCE: 248
STWVLLGGVL AALAAYCLSV GCVVIVGHIE LEGKPALVPD KEVLYQQYDE MEEC        54

SEQ ID NO: 249         moltype = AA  length = 54
FEATURE                Location/Qualifiers
source                 1..54
                       mol_type = protein
                       organism = Hepacivirus hominis
SEQUENCE: 249
STWVLLGGVL AAVAAYCLSV GCVVIVGHIE LGGKPALVPD KEVLYQQYDE MEEC        54

SEQ ID NO: 250         moltype = AA  length = 4
FEATURE                Location/Qualifiers
source                 1..4
                       mol_type = protein
                       organism = synthetic construct
SEQUENCE: 250
SGTS                                                               4

SEQ ID NO: 251         moltype = AA  length = 4
FEATURE                Location/Qualifiers
source                 1..4
                       mol_type = protein
                       organism = synthetic construct
SEQUENCE: 251
GSGS                                                               4

SEQ ID NO: 252         moltype = AA  length = 182
FEATURE                Location/Qualifiers
source                 1..182
                       mol_type = protein
                       organism = synthetic construct
SEQUENCE: 252
MAPITAYAQQ TRGLLGCIIT SLTGRDKNQV EGEVQIVSTA AQTFLATCIN GVCWTVYHGA  60
GTRTIASPKG PVIQMYTNVD KDLVGWPAPQ GSRSLTPCTC GSSDLYLVTR HADVIPVRRR  120
GDSRGSLLSP RPISYLKGSS GGPLLCPAGH AVGIFRAAVC TRGVAKAVDF IPVESLETTM  180
RS                                                                 182

SEQ ID NO: 253         moltype = AA  length = 195
FEATURE                Location/Qualifiers
source                 1..195
                       mol_type = protein
                       organism = synthetic construct
SEQUENCE: 253
MKKKGSVVIV GRIVLNGAYA QQTRGLLGCI ITSLTGRDKN QVEGEVQIVS TAAQTFLATC  60
INGVCWTVYH GAGTRTIASP KGPVIQMYTN VDKDLVGWPA PQGSRSLTPC TCGSSDLYLV  120
TRHADVIPVR RRGDSRGSLL SPRPISYLKG SSGGPLLCPA GHAVGIFRAA VCTRGVAKAV  180
DFIPVESLET TMRSP                                                   195

SEQ ID NO: 254         moltype = AA  length = 195
FEATURE                Location/Qualifiers
source                 1..195
                       mol_type = protein
                       organism = synthetic construct
SEQUENCE: 254
MKKKGSVVIV GRIVLNGAYA QQTRGEEGCQ ETSQTGRDKN QVEGEVQIVS TAAQTFLATC  60
INGVCWTVYH GAGTRTIASP KGPVIQMYTN VDKDLVGWPA PQGSRSLTPC TCGSSDLYLV  120
TRHADVIPVR RRGDSRGSLL SPRPISYLKG SSGGPLLCPA GHAVGIFRAA VCTRGVAKAV  180
```

```
DFIPVESLET TMRSP                                                  195

SEQ ID NO: 255          moltype = AA  length = 197
FEATURE                 Location/Qualifiers
source                  1..197
                        mol_type = protein
                        organism = synthetic construct
SEQUENCE: 255
MKKKGSVVIV GRINLSGDTA YAQQTRGEEG CQETSQTGRD KNQVEGEVQI VSTAAQTFLA  60
TCINGVCWTV YHGAGTRTIA SPKGPVIQMY TNVDKDLVGW PAPQGSRSLT PCTCGSSDLY  120
LVTRHADVIP VRRRGDSRGS LLSPRPISYL KGSSGGPLLC PAGHAVGIFR AAVCTRGVAK  180
AVDFIPVESL ETTMRSP                                                197

SEQ ID NO: 256          moltype = AA  length = 197
FEATURE                 Location/Qualifiers
source                  1..197
                        mol_type = protein
                        organism = synthetic construct
SEQUENCE: 256
MKKKGSVVIV GRINLSGDTA YAQQTRGEEG CQETSQTGRD KNQVEGEVQI VSTATQTFLA  60
TCINGVCWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVCTRGVAK  180
AVDFIPVESL ETTMRSP                                                197

SEQ ID NO: 257          moltype = AA  length = 197
FEATURE                 Location/Qualifiers
source                  1..197
                        mol_type = protein
                        organism = synthetic construct
SEQUENCE: 257
MKKKGSVVIV GRINLSGDTA YAQQTRGEEG CQETSQTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 258          moltype = AA  length = 197
FEATURE                 Location/Qualifiers
source                  1..197
                        mol_type = protein
                        organism = synthetic construct
SEQUENCE: 258
MKKKGSVVIV GRINLSGDTA YAQQTRGEQG CQKTSHTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 259          moltype = AA  length = 197
FEATURE                 Location/Qualifiers
source                  1..197
                        mol_type = protein
                        organism = synthetic construct
SEQUENCE: 259
MKKKGSVVIV GRINLSGDTA YAQQTRGEQG TQKTSHTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 260          moltype = AA  length = 196
FEATURE                 Location/Qualifiers
source                  1..196
                        mol_type = protein
                        organism = synthetic construct
SEQUENCE: 260
KKKGSVVIVG RINLSGDTAY AQQTRGEEGC QETSQTGRDK NQVEGEVQIV STATQTFLAT  60
SINGVLWTVY HGAGTRTIAS PKGPVTQMYT NVDKDLVGWQ APQGSRSLTP CTCGSSDLYL  120
VTRHADVIPV RRRGDSRGSL LSPRPISYLK GSAGGPLLCP AGHAVGIFRA AVSTRGVAKA  180
VDFIPVESLE TTMRSP                                                 196

SEQ ID NO: 261          moltype = AA  length = 21
FEATURE                 Location/Qualifiers
source                  1..21
                        mol_type = protein
                        organism = synthetic construct
SEQUENCE: 261
GELDELVYLL DGPGYDPIHS D                                           21

SEQ ID NO: 262          moltype = DNA  length = 537
FEATURE                 Location/Qualifiers
source                  1..537
```

```
                        mol_type = other DNA
                        organism = synthetic construct
SEQUENCE: 262
atcacggcct actcccaaca gacgcggggc ctacttggtt gcatcatcac tagcctcaca  60
ggccgggaca agaaccaggt cgaaggggag gttcaagtgg tttctaccgc aacacaatct  120
ttcctggcga cctgcgtcaa cggcgtgtgc tggactgtct accatggcgc tggctcgaag  180
accctagccg gtccaaaagg tccaatcacc caaatgtaca ccaatgtaga ccaggacctc  240
gtcggctggc aggcgcctcc aggggcgcgc tccttgacac catgcacctg tggcagctcg  300
gacctttact tggtcacgag acatgctgat gtcattccgg tgcgccggcg aggcgacagc  360
aggggaagtc tactctcccc caggcccgtc tcctacctga aaggctccgc aggtggtcca  420
ttgctttgcc cttcggggca cgctgtgggc atcttccggg ctgctgtgtg cacccggggg  480
gtcgcgaagg cggtggactt cgtgcccgtt gagtctatgg aaactaccat gcggtct     537

SEQ ID NO: 263          moltype = AA  length = 179
FEATURE                 Location/Qualifiers
source                  1..179
                        mol_type = protein
                        organism = synthetic construct
SEQUENCE: 263
ITAYSQQTRG LLGCIITSLT GRDKNQVEGE VQVVSTATQS FLATCVNGVC WTVYHGAGSK  60
TLAGPKGPIT QMYTNVDQDL VGWQAPPGAR SLTPCTCGSS DLYLVTRHAD VIPVRRRGDS  120
RGSLLSPRPV SYLKGSAGGP LLCPSGHAVG IFRAAVCTRG VAKAVDFVPV ESMETTMRS   179

SEQ ID NO: 264          moltype = DNA  length = 567
FEATURE                 Location/Qualifiers
source                  1..567
                        mol_type = other DNA
                        organism = synthetic construct
SEQUENCE: 264
gcgcccatca cggcgtacgc ccagcagacg agaggcctcc tagggtgtat aatcaccagc  60
ctgactggcc gggacaaaaa ccaagtggag ggtgaggtcc agatcgtgtc aactgctacc  120
caaaccttcc tggcaacgtg catcaatggg gtatgctggg cagtctacca cggggccgga  180
acgaggacca tcgcatcacc caagggtcct gtcatccaga tgtataccaa tgtggaccaa  240
gaccttgtgg gctggcccgc tcctcaaggt tcccgctcat tgacaccctg tacctgcggc  300
tcctcggacc tttacctggt cacgaggcac gccgatgtca ttcccgtgcg ccggcgaggt  360
gatagcaggg gtagcctgct ttcgccccgg cccatttcct acttgaaagg ctccgcgggg  420
ggtccgctgt tgtgccccgc gggacacgcc gtgggcctat tcagggccgc ggtgtgcacc  480
cgtggagtgg ctaaagcggt ggactttatc cctgtggaga acctagagac aaccatgaga  540
tccccggtgt tcacggacaa ctcctct                                    567

SEQ ID NO: 265          moltype = AA  length = 189
FEATURE                 Location/Qualifiers
source                  1..189
                        mol_type = protein
                        organism = synthetic construct
SEQUENCE: 265
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSAG GPLLCPAGHA VGLFRAAVCT RGVAKAVDFI PVENLETTMR  180
SPVFTDNSS                                                        189

SEQ ID NO: 266          moltype = AA  length = 33
FEATURE                 Location/Qualifiers
source                  1..33
                        mol_type = protein
                        organism = synthetic construct
SEQUENCE: 266
GELGRLVYLL DGPGYDPIHC SLAYGDASTL VVF                             33

SEQ ID NO: 267          moltype = AA  length = 18
FEATURE                 Location/Qualifiers
source                  1..18
                        mol_type = protein
                        organism = synthetic construct
SEQUENCE: 267
GELGRLVYLL DGPGYDPI                                              18

SEQ ID NO: 268          moltype = AA  length = 15
FEATURE                 Location/Qualifiers
source                  1..15
                        mol_type = protein
                        organism = synthetic construct
SEQUENCE: 268
HCSLAYGDAS TLVVF                                                 15

SEQ ID NO: 269          moltype = AA  length = 33
FEATURE                 Location/Qualifiers
source                  1..33
                        mol_type = protein
```

```
                         organism = synthetic construct
SEQUENCE: 269
GELGRPVYVL GDPGYYATHC IYATTNDALI FSV                             33

SEQ ID NO: 270           moltype = AA  length = 18
FEATURE                  Location/Qualifiers
source                   1..18
                         mol_type = protein
                         organism = synthetic construct
SEQUENCE: 270
GELGRPVYVL GDPGYYAT                                              18

SEQ ID NO: 271           moltype = AA  length = 15
FEATURE                  Location/Qualifiers
source                   1..15
                         mol_type = protein
                         organism = synthetic construct
SEQUENCE: 271
HCIYATTNDA LIFSV                                                 15

SEQ ID NO: 272           moltype = AA  length = 33
FEATURE                  Location/Qualifiers
source                   1..33
                         mol_type = protein
                         organism = synthetic construct
SEQUENCE: 272
GELGRIPSDT YDLAVGALHC PFYLVSGLVY LDG                             33

SEQ ID NO: 273           moltype = AA  length = 33
FEATURE                  Location/Qualifiers
source                   1..33
                         mol_type = protein
                         organism = synthetic construct
SEQUENCE: 273
GELGRLVYLL DGPGYDPIHC DVVTRGGSHL FNF                             33

SEQ ID NO: 274           moltype = AA  length = 33
FEATURE                  Location/Qualifiers
source                   1..33
                         mol_type = protein
                         organism = synthetic construct
SEQUENCE: 274
GELDELVYLL DGPGYDPIHC DVVTRGGSHL FNF                             33

SEQ ID NO: 275           moltype = AA  length = 21
FEATURE                  Location/Qualifiers
source                   1..21
                         mol_type = protein
                         organism = synthetic construct
SEQUENCE: 275
GELGRLVYLL DGPGYDPIHC D                                          21

SEQ ID NO: 276           moltype = AA  length = 20
FEATURE                  Location/Qualifiers
source                   1..20
                         mol_type = protein
                         organism = synthetic construct
SEQUENCE: 276
GELDELVYLL DGPGYDPIHS                                            20

SEQ ID NO: 277           moltype = AA  length = 36
FEATURE                  Location/Qualifiers
source                   1..36
                         mol_type = protein
                         organism = synthetic construct
SEQUENCE: 277
RQIKIWFQNR RMKWKKGELD ELVYLLDGPG YDPIHS                          36

SEQ ID NO: 278           moltype = DNA  length = 99
FEATURE                  Location/Qualifiers
source                   1..99
                         mol_type = other DNA
                         organism = synthetic construct
SEQUENCE: 278
ggagaacttg atgaattggt atacttacta gatgggccag gttatgaccc tatacattgc  60
gatgtagtga caaggggcgg cagccacctt ttcaatttt                         99

SEQ ID NO: 279           moltype = AA  length = 677
FEATURE                  Location/Qualifiers
```

```
source                  1..677
                        mol_type = protein
                        organism = synthetic construct
SEQUENCE: 279
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLT                                                677

SEQ ID NO: 280          moltype = AA  length = 888
FEATURE                 Location/Qualifiers
source                  1..888
                        mol_type = protein
                        organism = synthetic construct
SEQUENCE: 280
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSA AGGSGGSAAA QGSVVIVGRI ILSGSGSITA YSQQTRGLLG  720
CIITSLTGRD KNQVEGEVQV VSTATQSFLA TCVNGVCWTV YHGAGSKTLA GPKGPITQMY  780
TNVDQDLVGW QAPPGARSLT PCTCGSSDLY LVTRHADVIP VRRRGDSRGS LLSPRPVSYL  840
KGSSGGPLLC PSGHAVGIFR AAVCTRGVAK AVDFVPVESM ETTMRSES              888

SEQ ID NO: 281          moltype = AA  length = 769
FEATURE                 Location/Qualifiers
source                  1..769
                        mol_type = protein
                        organism = synthetic construct
SEQUENCE: 281
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQSNRELVVD FLSYKLSQKG YSWSQFSDVE ENRTEAPEGT  180
ESEMETPSAI NGNPSWHLAD SPAVNGATGH SSSLDAREVI PMAAVKQALR EAGDEFELRY  240
RRAFSDLTSQ LHITPGTAYQ SFEQVVNELF RDGVNWGRIV AFFSFGGALC VESVDKEMQV  300
LVSRIAAWMA TYLNDHLEPW IQENGGWDTF VELYGNNAAG GSGGSGGSGG SAAAQLHLPQ  360
VLADAVSRLV LGKFGDLTDN FSSPHARRKV LAGVVMTTGT DVKDAKVISV STGTKCINGE  420
YMSDRGLALN DCHAEIISRR SLLRFLYTQL ELYLNNKDDQ KRSIFQKSER GGFRLKENVQ  480
FHLYISTSPC GDARIFSPHE PILEEPAASG SGTGAPPNLW AAQRYGRELR RMSDELVDRH  540
PNRKARGQLR TKIESGQGTI PVRSNASIQT WDGVLQGERL LTMSCSDKIA RWNVVGIQGS  600
LLSIFVEPIY FSSIILGSLY HGDHLSRAMY QRISNIEDLP PLYTLNKPLL SGISNAEARQ  660
PGKAPNFSVN WTVGDSAIEV INATTGKDEL GRASRLCKHA LYCRWMRVHG KVPSHLLRSK  720
ITKPNVYHES KLAAKEYQAA KARLFTAFIK AGLGAWVEKP TEQDQFSLT              769

SEQ ID NO: 282          moltype = AA  length = 557
FEATURE                 Location/Qualifiers
source                  1..557
                        mol_type = protein
                        organism = synthetic construct
SEQUENCE: 282
ASNFTQFVLV DNGGTGDVTV APSNFANGIA EWISSNSRSQ AYKVTCSVRQ SSAQNRKYTI  60
KVEVPKGAWR SYLNMELTIP IFATNSDCEL IVKAMQGLLK DGNPIPSAIA ANSGIYGGSG  120
SGAGSGSPAG GGAPGSGGGS TGAPPNLWAA QRYGRELRRM SDEFVDSFKK ASQLHLPQVL  180
ADAVSRLVLG KFGDLTDNFS SPHARRKVLA GVVMTTGTDV KDAKVISVST GTKCINGEYM  240
SDRGLALNDC HAEIISRRSL LRFLYTQLEL YLNNKDDQKR SIFQKSERGG FRLKENVQFH  300
LYISTSPCGD ARIFSPHEPI LEEPADRHPN RKARGQLRTK IESGQGTIPV RSNASIQTWD  360
GVLQGERLLT MSCSDKIARW NVVGIQGSLL SIFVEPIYFS SIILGSLYHG DHLSRAMYQR  420
ISNIEDLPPL YTLNKPLLSG ISNAEARQPG KAPNFSVNWT VGDSAIEVIN ATTGKDELGR  480
ASRLCKHALY CRWMRVHGKV PSHLLRSKIT KPNVYHESKL AAKEYQAAKA RLFTAFIKAG  540
LGAWVEKPTE QDQFSLT                                                557

SEQ ID NO: 283          moltype = AA  length = 759
FEATURE                 Location/Qualifiers
source                  1..759
```

```
                         mol_type = protein
                         organism = synthetic construct
SEQUENCE: 283
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPADRHP NRKARGQLRT KIESGQGTIP VRSNASIQTW  360
DGVLQGERLL TMSCSDKIAR WNVVGIQGSL LSIFVEPIYF SSIILGSLYH GDHLSRAMYQ  420
RISNIEDLPP LYTLNKPLLS GISNAEARQP GKAPNFSVNW TVGDSAIEVI NATTGKDELG  480
RASRLCKHAL YCRWMRVHGK VPSHLLRSKI TKPNVYHESK LAAKEYQAAK ARLFTAFIKA  540
GLGAWVEKPT EQDQFSLTGS AAASSNRELV VDFLSYKLSQ KGYSWSQFSD VEENRTEAPE  600
GTESEMETPS AINGNPSWHL ADSPAVNGAT GHSSSLDARE VIPMAAVKQA LREAGDEFEL  660
RYRRAFSDLT SQLHITPGTA YQSFEQVVNE LFRDGVNWGR IVAFFSFGGA LCVESVDKEM  720
QVLVSRIAAW MATYLNDHLE PWIQENGGWD TFVELYGNN                        759

SEQ ID NO: 284           moltype = AA  length = 677
FEATURE                  Location/Qualifiers
source                   1..677
                         mol_type = protein
                         organism = synthetic construct
SEQUENCE: 284
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLT                                                677

SEQ ID NO: 285           moltype = AA  length = 888
FEATURE                  Location/Qualifiers
source                   1..888
                         mol_type = protein
                         organism = synthetic construct
SEQUENCE: 285
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSA AGGSGGSAAA QGSVVIVGRI ILSGSGSITA YSQQTRGLLG  720
CIITSLTGRD KNQVEGEVQV VSTATQSFLA TCVNGVCWTV YHGAGSKTLA GPKGPITQMY  780
TNVDQDLVGW QAPPGARSLT PCTCGSSDLY LVTRHADVIP VRRRGDSRGS LLSPRPVSYL  840
KGSSGGPLLC PSGHAVGIFR AAVCTRGVAK AVDFVPVESM ETTMRSES              888

SEQ ID NO: 286           moltype = AA  length = 7
FEATURE                  Location/Qualifiers
source                   1..7
                         mol_type = protein
                         organism = synthetic construct
SEQUENCE: 286
ENLYFQG                                                           7

SEQ ID NO: 287           moltype = AA  length = 999
FEATURE                  Location/Qualifiers
source                   1..999
                         mol_type = protein
                         organism = synthetic construct
SEQUENCE: 287
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEFVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
```

-continued

```
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNGSSEL IKENMHMKLY  780
MEGTVDNHHF KCTSEGEGKP YEGTQTMRIK VVEGGPLPFA FDILATSFLY GSKTFINHTQ  840
GIPDFFKQSF PEGFTWERVT TYEDGGVLTA TQDTSLQDGC LIYNVKIRGV NFTSNGPVMQ  900
KKTLGWEAFT ETLYPADGGL EGRNDMALKL VGGSHLIANI KTTYRSKKPA KNLKMPGVYY  960
VDYRLERIKE ANNETYVEQH EVAVARYCDL PSKLGHKLN                         999

SEQ ID NO: 288         moltype = AA  length = 999
FEATURE                Location/Qualifiers
source                 1..999
                       mol_type = protein
                       organism = synthetic construct
SEQUENCE: 288
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEVVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNGSSEL IKENMHMKLY  780
MEGTVDNHHF KCTSEGEGKP YEGTQTMRIK VVEGGPLPFA FDILATSFLY GSKTFINHTQ  840
GIPDFFKQSF PEGFTWERVT TYEDGGVLTA TQDTSLQDGC LIYNVKIRGV NFTSNGPVMQ  900
KKTLGWEAFT ETLYPADGGL EGRNDMALKL VGGSHLIANI KTTYRSKKPA KNLKMPGVYY  960
VDYRLERIKE ANNETYVEQH EVAVARYCDL PSKLGHKLN                         999

SEQ ID NO: 289         moltype = AA  length = 999
FEATURE                Location/Qualifiers
source                 1..999
                       mol_type = protein
                       organism = synthetic construct
SEQUENCE: 289
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEGVDRHPNR KARGQLRTKI ESGQGTIPVR SNASIQTWDG  360
VLQGERLLTM SCSDKIARWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSAA GGSGGSAAAS SNRELVVDFL SYKLSQKGYS WSQFSDVEEN  600
RTEAPEGTES EMETPSAING NPSWHLADSP AVNGATGHSS SLDAREVIPM AAVKQALREA  660
GDEFELRYRR AFSDLTSQLH ITPGTAYQSF EQVVNELFRD GVNWGRIVAF FSFGGALCVE  720
SVDKEMQVLV SRIAAWMATY LNDHLEPWIQ ENGGWDTFVE LYGNNGSSEL IKENMHMKLY  780
MEGTVDNHHF KCTSEGEGKP YEGTQTMRIK VVEGGPLPFA FDILATSFLY GSKTFINHTQ  840
GIPDFFKQSF PEGFTWERVT TYEDGGVLTA TQDTSLQDGC LIYNVKIRGV NFTSNGPVMQ  900
KKTLGWEAFT ETLYPADGGL EGRNDMALKL VGGSHLIANI KTTYRSKKPA KNLKMPGVYY  960
VDYRLERIKE ANNETYVEQH EVAVARYCDL PSKLGHKLN                         999

SEQ ID NO: 290         moltype = AA  length = 797
FEATURE                Location/Qualifiers
source                 1..797
                       mol_type = protein
                       organism = synthetic construct
SEQUENCE: 290
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEA NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSGSSELIK ENMHMKLYME GTVDNHHFKC TSEGEGKPYE  600
GTQTMRIKVV EGGPLPFAFD ILATSFLYGS KTFINHTQGI PDFFKQSFPE GFTWERVTTY  660
EDGGVLTATQ DTSLQDGCLI YNVKIRGVNF TSNGPVMQKK TLGWEAFTET LYPADGGLEG  720
RNDMALKLVG GSHLIANIKT TYRSKKPAKN LKMPGVYYVD YRLERIKEAN NETYVEQHEV  780
AVARYCDLPS KLGHKLN                                                 797
```

```
SEQ ID NO: 291         moltype = AA  length = 797
FEATURE                Location/Qualifiers
source                 1..797
                       mol_type = protein
                       organism = synthetic construct
SEQUENCE: 291
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGGSG  300
GSGRPEIWMT QGLRRLGDEG NAYYARRTGD RHPNRKARGQ LRTKIESGQG TIPVRSNASI  360
QTWDGVLQGE RLLTMSCSDK IARWNVVGIQ GSLLSIFVEP IYFSSIILGS LYHGDHLSRA  420
MYQRISNIED LPPLYTLNKP LLSGISNAEA RQPGKAPNFS VNWTVGDSAI EVINATTGKD  480
ELGRASRLCK HALYCRWMRV HGKVPSHLLR SKITKPNVYH ESKLAAKEYQ AAKARLFTAF  540
IKAGLGAWVE KPTEQDQFSL TGSGSSELIK ENMHMKLYME GTVDNHHFKC TSEGEGKPYE  600
GTQTMRIKVV EGGPLPFAFD ILATSFLYGS KTFINHTQGI PDFFKQSFPE GFTWERVTTY  660
EDGGVLTATQ DTSLQDGCLI YNVKIRGVNF TSNGPVMQKK TLGWEAFTET LYPADGGLEG  720
RNDMALKLVG GSHLIANIKT TYRSKKPAKN LKMPGVYYVD YRLERIKEAN NETYVEQHEV  780
AVARYCDLPS KLGHKLN                                                797

SEQ ID NO: 292         moltype = DNA  length = 2461
FEATURE                Location/Qualifiers
source                 1..2461
                       mol_type = other DNA
                       organism = synthetic construct
SEQUENCE: 292
ctctagactg cagcctcagg agatctgggc ccctacttgt acagctcgtc catgccgtac  60
aggaacaggt ggtggcggcc ctcggagcgc tcgtactgtt ccacgatggt gtagtcctcg  120
ttgtgggagg tgatgtccag cttggtgtcc acgtagtagt agccgggcag ttgcacgggc  180
ttcttggcca tgtagatggt cttgaactcc accaggtagt ggccgccgtc cttcagcttc  240
agggcctggt ggatctcgcc cttcagcacg ccgtcgcggg ggtacaggcg ctcggtggag  300
gcctcccagc ccatggtctt cttctgcatt acggggccgt cggggggaa gttggtgccg  360
cgcatcttca ccttgtagat cagcgtgccg tcctgcaggg aggagtcctg ggtcacggtc  420
accagaccgc cgtcctcgaa gttcatcacg cgctcccact tgaagccctc ggggaaggac  480
agcttcttgt aatcggggat gtcggcgggg tgcttcacgt acgccttgga gccgtacatg  540
aactgggggg acaggatgtc ccaggcgaag ggcaggggc cgcccttggt caccttcagc  600
ttggcggtct gggtgccctc gtaggggcgg ccctcgccct cgccctcgat ctcgaactcg  660
tggccgttca tggagccctc catgcgcacc ttgaagcgca tgaactcttt gatgacctcc  720
tcgcccttgc tcaccatggt ggcgaattct ccaggcgatc tgacggttca ctaaacgagc  780
tctgcttata taggcctccc accgtacacg ccacctcgac atactcgagt agttattaat  840
agtaatcaat tacggggtca ttagttcata gcccatatat ggagttccgc gttacataac  900
ttacggtaaa tggcccgcct ggctgaccgc ccaacgaccc ccgcccattg acgtcaataa  960
tgacgtatgt tcccatagta acgccaatag ggactttcca ttgacgtcaa tgggtggagt  1020
atttacggta aactgcccac ttggcagtac atcaagtgta tcatatgcca agtacgcccc  1080
ctattgacgt caatgacggt aaatggcccg cctggcatta tgcccagtac atgaccttat  1140
gggactttcc tacttggcag tacatctacg tattagtcat cgctattacc atggtgatgc  1200
ggttttggca gtacatcaat gggcgtggat agcggtttga ctcacgggga tttccaagtc  1260
tccaccccat tgacgtcaat gggagtttgt tttggcacca aaatcaacgg gactttccaa  1320
aatgtcgtaa caactccgcc ccattgacgc aaatgggcgg taggcgtgta cggtgggagg  1380
tctatataag cagagctggt ttagtgaacc gtcagatccg ctagggatcc tctagtcagc  1440
tgacgcgtgc tagcgatatc ggcgcgccag cactcaccat cgtcccgctg aggatcaccc  1500
agcggccacg atggtgagca agggcgagga gctgttcacc ggggtggtgc ccatcctggt  1560
cgagctggac ggcgacgtaa acggccacaa gttcagcgtg tccggcgagg gcgagggcga  1620
tgccacctac ggcaagctga ccctgaagtt catctgcacc accggcaagc tgcccgtgcc  1680
ctggcccacc ctcgtgacca ccctgaccta cggcgtgcag tgcttcagcc gctaccccga  1740
ccacatgaag cagcacgact tcttcaagtc cgccatgccc gaaggctacg tccaggagcg  1800
caccatcttc ttcaaggacg acggcaacta caagacccgc gccgaggtga agttcgaggg  1860
cgacaccctg gtgaaccgca tcgagctgaa gggcatcgac ttcaaggagg acggcaacat  1920
cctggggcac aagctggagt acaactacaa cagccacaac gtctatatca tggccgacaa  1980
gcagaagaac ggcatcaagg tgaacttcaa gatccgccac aacatcgagg acggcagcgt  2040
gcagctcgcc gaccactacc agcagaacac ccccatcggc gacggccccg tgctgctgcc  2100
cgacaaccac tacctgagca cccagtccgc cctgagcaaa gaccccaacg agaagcgcga  2160
tcacatggtc ctgctggagt tcgtgaccgc cgccgggatc actctcggca tggacgagct  2220
gtacaagaag cttagccatg gcttcccgcc ggaggtggag gagcaggatg atggcacgct  2280
gcccatgtct tgtgcccagg agagcgggat ggaccgtcac cctgcagcct gtgcttctgc  2340
taggatcaat gtgtaggcgg ccgcactcct caggtgcagg ctgcctatca gaaggtggtg  2400
gctggtgtgg ccaatgccct ggctcacaaa taccactgag atctttttcc ctctgccaaa  2460
a                                                                 2461

SEQ ID NO: 293         moltype = DNA  length = 2461
FEATURE                Location/Qualifiers
source                 1..2461
                       mol_type = other DNA
                       organism = synthetic construct
SEQUENCE: 293
ctctagactg cagcctcagg agatctgggc ccctacttgt acagctcgtc catgccgtac  60
aggaacaggt ggtggcggcc ctcggagcgc tcgtactgtt ccacgatggt gtagtcctcg  120
```

```
ttgtgggagg tgatgtccag cttggtgtcc acgtagtagt agccgggcag ttgcacgggc  180
ttcttggcca tgtagatggt cttgaactcc accaggtagt ggccgccgtc cttcagcttc  240
agggcctggt ggatctcgcc cttcagcacg ccgtcgcggg ggtacaggcg ctcggtggag  300
gcctcccagc ccatggtctt cttctgcatt acggggccgt cgggggggaa gttggtgccg  360
cgcatcttca ccttgtagat cagcgtgccg tcctgcaggg aggagtcctg ggtcacggtc  420
accagaccgc cgtcctcgaa gttcatcacg cgctcccact tgaagccctc ggggaaggac  480
agcttcttgt aatcggggat gtcggcgggg tgcttcacgt acgccttgga gccgtacatg  540
aactgggggg acaggatgtc ccaggcgaag ggcagggggc cgcccttggt caccttcagc  600
ttggcggtct gggtgccctc gtaggggcgg ccctcgccct cgccctcgat ctcgaactcg  660
tggccgttca tggagccctc catgcgcacc ttgaagcgca tgaactcttt gatgacctcc  720
tcgcccttgc tcaccatggt ggcgaattct ccaggcgatc tgacggttca ctaaacgagc  780
tctgcttata taggcctccc accgtacacg ccacctcgac atactcgagt agttattaat  840
agtaatcaat tacggggtca ttagttcata gcccatatat ggagttccgc gttacataac  900
ttacggtaaa tggcccgcct ggctgaccgc ccaacgaccc ccgcccattg acgtcaataa  960
tgacgtatgt tcccatagta acgccaatag ggactttcca ttgacgtcaa tgggtggagt  1020
atttacggta aactgcccac ttggcagtac atcaagtgta tcatatgcca agtacgcccc  1080
ctattgacgt caatgacggt aaatggcccg cctggcatta tgcccagtac atgaccttat  1140
gggactttcc tacttggcag tacatctacg tattagtcat cgctattacc atggtgatgc  1200
ggttttggca gtacatcaat gggcgtggat agcggtttga ctcacgggga tttccaagtc  1260
tccaccccat tgacgtcaat gggagtttgt tttggcacca aaatcaacgg gactttccaa  1320
aatgtcgtaa caactccgcc ccattgacgc aaatgggcgg taggcgtgta cggtgggagg  1380
tctatataag cagagctggt ttagtgaacc gtcagatccg ctagggatcc tctagtcagc  1440
tgacgcgtgc tagcgatatc ggcgcgccag cactcaccat cgtcccgctg aggatcaccc  1500
agcggccacg atagtgagca agggcgagga gctgttcacc ggggtggtgc ccatcctggt  1560
cgagctggac ggcgacgtaa acggccacaa gttcagcgtg tccggcgagg gcgagggcga  1620
tgccacctac ggcaagctga ccctgaagtt catctgcacc accggcaagc tgcccgtgcc  1680
ctggcccacc ctcgtgacca ccctgaccta cggcgtgcag tgcttcagcc gctaccccga  1740
ccacatgaag cagcacgact tcttcaagtc cgccatgccc gaaggctacg tccaggagcg  1800
caccatcttc ttcaaggacg acggcaacta caagacccgc gccgaggtga agttcgaggg  1860
cgacaccctg gtgaaccgca tcgagctgaa gggcatcgac ttcaaggagg acggcaacat  1920
cctggggcac aagctggagt acaactacaa cagccacaac gtctatatca tggccgacaa  1980
gcagaagaac ggcatcaagg tgaacttcaa gatccgccac aacatcgagg acggcagcgt  2040
gcagctcgcc gaccactacc agcagaacac ccccatcggc gacggccccg tgctgctgcc  2100
cgacaaccac tacctgagca cccagtccgc cctgagcaaa gaccccaacg agaagcgcga  2160
tcacatggtc ctgctggagt tcgtgaccgc cgccgggatc actctcggca tggacgagct  2220
gtacaagaag cttagccatg gcttcccgcc ggaggtggag gagcaggatg atggcacgct  2280
gcccatgtct tgtgcccagg agagcgggat ggaccgtcac cctgcagcct gtgcttctgc  2340
taggatcaat gtgtaggcgg ccgcactcct caggtgcagg ctgcctatca gaaggtggtg  2400
gctggtgtgg ccaatgccct ggctcacaaa taccactgag atctttttcc ctctgccaaa  2460
a                                                                 2461

SEQ ID NO: 294          moltype = DNA  length = 2461
FEATURE                 Location/Qualifiers
source                  1..2461
                        mol_type = other DNA
                        organism = synthetic construct
SEQUENCE: 294
ctctagactg cagcctcagg agatctgggc ccctacttgt acagctcgtc catgccgtac  60
aggaacaggt ggtggcggcc ctcggagcgc tcgtactgtt ccacgatggt gtagtcctcg  120
ttgtgggagg tgatgtccag cttggtgtcc acgtagtagt agccgggcag ttgcacgggc  180
ttcttggcca tgtagatggt cttgaactcc accaggtagt ggccgccgtc cttcagcttc  240
agggcctggt ggatctcgcc cttcagcacg ccgtcgcggg ggtacaggcg ctcggtggag  300
gcctcccagc ccatggtctt cttctgcatt acggggccgt cgggggggaa gttggtgccg  360
cgcatcttca ccttgtagat cagcgtgccg tcctgcaggg aggagtcctg ggtcacggtc  420
accagaccgc cgtcctcgaa gttcatcacg cgctcccact tgaagccctc ggggaaggac  480
agcttcttgt aatcggggat gtcggcgggg tgcttcacgt acgccttgga gccgtacatg  540
aactgggggg acaggatgtc ccaggcgaag ggcagggggc cgcccttggt caccttcagc  600
ttggcggtct gggtgccctc gtaggggcgg ccctcgccct cgccctcgat ctcgaactcg  660
tggccgttca tggagccctc catgcgcacc ttgaagcgca tgaactcttt gatgacctcc  720
tcgcccttgc tcaccatggt ggcgaattct ccaggcgatc tgacggttca ctaaacgagc  780
tctgcttata taggcctccc accgtacacg ccacctcgac atactcgagt agttattaat  840
agtaatcaat tacggggtca ttagttcata gcccatatat ggagttccgc gttacataac  900
ttacggtaaa tggcccgcct ggctgaccgc ccaacgaccc ccgcccattg acgtcaataa  960
tgacgtatgt tcccatagta acgccaatag ggactttcca ttgacgtcaa tgggtggagt  1020
atttacggta aactgcccac ttggcagtac atcaagtgta tcatatgcca agtacgcccc  1080
ctattgacgt caatgacggt aaatggcccg cctggcatta tgcccagtac atgaccttat  1140
gggactttcc tacttggcag tacatctacg tattagtcat cgctattacc atggtgatgc  1200
ggttttggca gtacatcaat gggcgtggat agcggtttga ctcacgggga tttccaagtc  1260
tccaccccat tgacgtcaat gggagtttgt tttggcacca aaatcaacgg gactttccaa  1320
aatgtcgtaa caactccgcc ccattgacgc aaatgggcgg taggcgtgta cggtgggagg  1380
tctatataag cagagctggt ttagtgaacc gtcagatccg ctagggatcc tctagtcagc  1440
tgacgcgtgc tagcgatatc ggcgcgccag cactcaccat cgtcccgctg aggataaccc  1500
agcggccacg atggtgagca agggcgagga gctgttcacc ggggtggtgc ccatcctggt  1560
cgagctggac ggcgacgtaa acggccacaa gttcagcgtg tccggcgagg gcgagggcga  1620
tgccacctac ggcaagctga ccctgaagtt catctgcacc accggcaagc tgcccgtgcc  1680
ctggcccacc ctcgtgacca ccctgaccta cggcgtgcag tgcttcagcc gctaccccga  1740
ccacatgaag cagcacgact tcttcaagtc cgccatgccc gaaggctacg tccaggagcg  1800
caccatcttc ttcaaggacg acggcaacta caagacccgc gccgaggtga agttcgaggg  1860
cgacaccctg gtgaaccgca tcgagctgaa gggcatcgac ttcaaggagg acggcaacat  1920
```

```
cctggggcac aagctggagt acaactacaa cagccacaac gtctatatca tggccgacaa  1980
gcagaagaac ggcatcaagg tgaacttcaa gatccgccac aacatcgagg acggcagcgt  2040
gcagctcgcc gaccactacc agcagaacac ccccatcggc gacggccccg tgctgctgcc  2100
cgacaaccac tacctgagca cccagtccgc cctgagcaaa gaccccaacg agaagcgcga  2160
tcacatggtc ctgctggagt tcgtgaccgc cgccgggatc actctcggca tggacgagct  2220
gtacaagaag cttagccatg gcttcccgcc ggaggtggag gagcaggatg atggcacgct  2280
gcccatgtct tgtgcccagg agagcgggat ggaccgtcac cctgcagcct gtgcttctgc  2340
taggatcaat gtgtaggcgg ccgcactcct caggtgcagg ctgcctatca gaaggtggtg  2400
gctggtgtgg ccaatgccct ggctcacaaa taccactgag atctttttcc ctctgccaaa  2460
a                                                                 2461
```

```
SEQ ID NO: 295          moltype = DNA  length = 2461
FEATURE                 Location/Qualifiers
source                  1..2461
                        mol_type = other DNA
                        organism = synthetic construct
SEQUENCE: 295
ctctagactg cagcctcagg agatctgggc ccctacttgt acagctcgtc catgccgtac  60
aggaacaggt ggtggcggcc ctcggagcgc tcgtactgtt ccacgatggt gtagtcctcg  120
ttgtgggagg tgatgtccag cttggtgtcc acgtagtagt agccgggcag ttgcacgggc  180
ttcttggcca tgtagatggt cttgaactcc accaggtagt ggccgccgtc cttcagcttc  240
agggcctggt ggatctcgcc cttcagcacg ccgtcgcggg ggtacaggcg ctcggtggag  300
gcctcccagc ccatggtctt cttctgcatt acggggccgt cggggggggaa gttggtgccg  360
cgcatcttca ccttgtagat cagcgtgccg tcctgcaggg aggagtcctg ggtcacggtc  420
accagaccgc cgtcctcgaa gttcatcacg cgctcccact tgaagccctc ggggaaggac  480
agcttcttgt aatcggggat gtcggcgggg tgcttcacgt acgccttgga gccgtacatg  540
aactgggggg acaggatgtc ccaggcgaag ggcagggggc cgcccttggt caccttcagc  600
ttggcggtct gggtgccctc gtaggggcgg ccctcgccct cgccctcgat ctcgaactcg  660
tggccgttca tggagccctc catgcgcacc ttgaagcgca tgaactcttt gatgacctcc  720
tcgcccttgc tcaccatggt ggcgaattct ccaggcgatc tgacggttca ctaaacgagc  780
tctgcttata taggcctccc accgtacacg ccacctcgac atactcgagt agttattaat  840
agtaatcaat tacggggtca ttagttcata gcccatatat ggagttccgc gttacataac  900
ttacggtaaa tggcccgcct ggctgaccgc ccaacgaccc ccgcccattg acgtcaataa  960
tgacgtatgt tcccatagta acgccaatag ggactttcca ttgacgtcaa tgggtggagt  1020
atttacggta aactgcccac ttggcagtac atcaagtgta tcatatgcca agtacgcccc  1080
ctattgacgt caatgacggt aaatggcccg cctggcatta tgcccagtac atgaccttat  1140
gggactttcc tacttggcag tacatctacg tattagtcat cgctattacc atggtgatgc  1200
ggttttggca gtacatcaat gggcgtggat agcggtttga ctcacgggga tttccaagtc  1260
tccaccccat tgacgtcaat gggagtttgt tttggcacca aaatcaacgg gactttccaa  1320
aatgtcgtaa caactccgcc ccattgacgc aaatgggcgg taggcgtgta cggtgggagg  1380
tctatataag cagagctggt ttagtgaacc gtcagatccg ctagggatcc tctagtcagc  1440
tgacgcgtgc tagcgatatc ggcgcgccag cactcaccat cgtcccgctg aggataaccc  1500
agcggccacg atagtgagca agggcgagga gctgttcacc ggggtggtgc ccatcctggt  1560
cgagctggac ggcgacgtaa acggccacaa gttcagcgtg tccggcgagg gcgagggcga  1620
tgccacctac ggcaagctga ccctgaagtt catctgcacc accggcaagc tgcccgtgcc  1680
ctggcccacc ctcgtgacca ccctgaccta cggcgtgcag tgcttcagcc gctaccccga  1740
ccacatgaag cagcacgact tcttcaagtc cgccatgccc gaaggctacg tccaggagcg  1800
caccatcttc ttcaaggacg acggcaacta caagacccgc gccgaggtga agttcgaggg  1860
cgacaccctg gtgaaccgca tcgagctgaa gggcatcgac ttcaaggagg acggcaacat  1920
cctggggcac aagctggagt acaactacaa cagccacaac gtctatatca tggccgacaa  1980
gcagaagaac ggcatcaagg tgaacttcaa gatccgccac aacatcgagg acggcagcgt  2040
gcagctcgcc gaccactacc agcagaacac ccccatcggc gacggccccg tgctgctgcc  2100
cgacaaccac tacctgagca cccagtccgc cctgagcaaa gaccccaacg agaagcgcga  2160
tcacatggtc ctgctggagt tcgtgaccgc cgccgggatc actctcggca tggacgagct  2220
gtacaagaag cttagccatg gcttcccgcc ggaggtggag gagcaggatg atggcacgct  2280
gcccatgtct tgtgcccagg agagcgggat ggaccgtcac cctgcagcct gtgcttctgc  2340
taggatcaat gtgtaggcgg ccgcactcct caggtgcagg ctgcctatca gaaggtggtg  2400
gctggtgtgg ccaatgccct ggctcacaaa taccactgag atctttttcc ctctgccaaa  2460
a                                                                 2461
```

```
SEQ ID NO: 296          moltype = DNA  length = 1120
FEATURE                 Location/Qualifiers
source                  1..1120
                        mol_type = other DNA
                        organism = synthetic construct
SEQUENCE: 296
taatacgact cactataggg agacccaagc tggctagcgg taccgccacc atggagaccg  60
acaccctgct cctgtgggtg ttgttgctct gggtcccagg ttctaccggc gacggaggag  120
gcggctatcc ctatgacgta ccggattatg ccggtgaact tgatgaattg gtatacttac  180
tagatgggcc aggttatgac cctatacata gtggcggtag tgggggacgt acgatggtga  240
gcaagggcga ggagctgttc accggggtgg tgcccatcct ggtcgagctg gacggcgacg  300
taaacggcca caagttcagc gtgtccggcg agggcgaggg cgatgccacc tacggcaagc  360
tgaccctgaa gttcatctgc accaccggca agctgcccgt gccctggccc accctcgtga  420
ccaccctgac ctacggcgtg cagtgcttca gccgctaccc cgaccacatg aagcagcacg  480
acttcttcaa gtccgccatg cccgaaggct acgtccagga gcgcaccatc ttcttcaagg  540
acgacggcaa ctacaagacc cgcgccgagg tgaagttcga gggcgacacc ctggtgaacc  600
gcatcgagct gaagggcatc gacttcaagg aggacggcaa catcctgggg cacaagctgg  660
agtacaacta caacagccac aacgtctata tcatggccga caagcagaag aacggcatca  720
aggtgaactt caagatccgc cacaacatcg aggacggcag cgtgcagctc gccgaccact  780
```

-continued

```
accagcagaa cacccccatc ggcgacggcc ccgtgctgct gcccgacaac cactacctga  840
gcacccagtc cgccctgagc aaagacccca acgagaagcg cgatcacatg gtcctgctgg  900
agttcgtgac cgccgccggg atcactctcg gcatggatga actataccaa ctcgagaatg  960
gcggcataag cctgctggtt cagaacacat cctggatgct gctgctgctg ctttccctct  1020
ccctcctcca agccctggac ttcatttctc tgtaatctag agggcccgtt taaacccgct  1080
gatcagcctc gactgtgcct tctagttgcc agccatctgt                        1120
```

```
SEQ ID NO: 297          moltype = DNA  length = 1071
FEATURE                 Location/Qualifiers
source                  1..1071
                        mol_type = other DNA
                        organism = synthetic construct
SEQUENCE: 297
ttatcgaaat taatacgact cactataggg agacccaagc tggctagctg gtctccatcg  60
tgcccgctga ggatcaccca gcggccacga tagagaccga caccctgctc ctgtgggtgt  120
tgttgctctg ggtcccaggt tctaccggcg acggaggagg cggctatccc tacgacgtac  180
cggattacgc cggtggcggt agtgggggac gtacgatggt gagcaagggc gaggagctgt  240
tcaccggggt ggtgcccatc ctggtcgagc tggacggcga cgtaaacggc cacaagttca  300
gcgtgtccgg cgagggcgag ggcgatgcca cctacggcaa gctgaccctg aagttcatct  360
gcaccaccgg caagctgccc gtgccctggc ccaccctcgt gaccaccctg acctacggcg  420
tgcagtgctt cagccgctac cccgaccaca tgaagcagca cgacttcttc aagtccgcca  480
tgcccgaagg ctacgtccag gagcgcacca tcttcttcaa ggacgacggc aactacaaga  540
cccgcgccga ggtgaagttc gagggcgaca ccctggtgaa ccgcatcgag ctgaagggca  600
tcgacttcaa ggaggacggc aacatcctgg ggcacaagct ggagtacaac tacaacagcc  660
acaacgtcta tatcatggcc gacaagcaga agaacggcat caaggtgaac ttcaagatcc  720
gccacaacat cgaggacggc agcgtgcagc tcgccgacca ctaccagcag aacaccccca  780
tcggcgacgg ccccgtgctg ctgcccgaca accactacct gagcacccag tccgccctga  840
gcaaagaccc caacgagaag cgcgatcaca tggtcctgct ggagttcgtg accgccgccg  900
ggatcactct cggcatggat gaactatacc aactcgagaa tggcggcata agcctgctgg  960
ttcagaacac atcctggatg ctgctgctgc tgctttccct ctccctcctc caagccctgg  1020
acttcatttc tctgtaatct agagggcccg tttaaacccg ctgatcagcc t           1071
```

```
SEQ ID NO: 298          moltype = DNA  length = 1071
FEATURE                 Location/Qualifiers
source                  1..1071
                        mol_type = other DNA
                        organism = synthetic construct
SEQUENCE: 298
ttatcgaaat taatacgact cactataggg agacccaagc tggctagctg gtctccatcg  60
tgcccgctga ggataaccca gcggccacga tagagaccga caccctgctc ctgtgggtgt  120
tgttgctctg ggtcccaggt tctaccggcg acggaggagg cggctatccc tacgacgtac  180
cggattacgc cggtggcggt agtgggggac gtacgatggt gagcaagggc gaggagctgt  240
tcaccggggt ggtgcccatc ctggtcgagc tggacggcga cgtaaacggc cacaagttca  300
gcgtgtccgg cgagggcgag ggcgatgcca cctacggcaa gctgaccctg aagttcatct  360
gcaccaccgg caagctgccc gtgccctggc ccaccctcgt gaccaccctg acctacggcg  420
tgcagtgctt cagccgctac cccgaccaca tgaagcagca cgacttcttc aagtccgcca  480
tgcccgaagg ctacgtccag gagcgcacca tcttcttcaa ggacgacggc aactacaaga  540
cccgcgccga ggtgaagttc gagggcgaca ccctggtgaa ccgcatcgag ctgaagggca  600
tcgacttcaa ggaggacggc aacatcctgg ggcacaagct ggagtacaac tacaacagcc  660
acaacgtcta tatcatggcc gacaagcaga agaacggcat caaggtgaac ttcaagatcc  720
gccacaacat cgaggacggc agcgtgcagc tcgccgacca ctaccagcag aacaccccca  780
tcggcgacgg ccccgtgctg ctgcccgaca accactacct gagcacccag tccgccctga  840
gcaaagaccc caacgagaag cgcgatcaca tggtcctgct ggagttcgtg accgccgccg  900
ggatcactct cggcatggat gaactatacc aactcgagaa tggcggcata agcctgctgg  960
ttcagaacac atcctggatg ctgctgctgc tgctttccct ctccctcctc caagccctgg  1020
acttcatttc tctgtaatct agagggcccg tttaaacccg ctgatcagcc t           1071
```

```
SEQ ID NO: 299          moltype = DNA  length = 2461
FEATURE                 Location/Qualifiers
source                  1..2461
                        mol_type = other DNA
                        organism = synthetic construct
SEQUENCE: 299
ctctagactg cagcctcagg agatctgggc ccctacttgt acagctcgtc catgccgtac  60
aggaacaggt ggtggcggcc ctcggagcgc tcgtactgtt ccacgatggt gtagtcctcg  120
ttgtgggagg tgatgtccag cttggtgtcc acgtagtagt agccgggcag ttgcacgggc  180
ttcttggcca tgtagatggt cttgaactcc accaggtagt ggccgccgtc cttcagcttc  240
agggcctggt ggatctcgcc cttcagcacg ccgtcgcggg ggtacaggcg ctcggtggag  300
gcctcccagc ccatggtctt cttctgcatt acggggccgt cggggggggaa gttggtgccg  360
cgcatcttca ccttgtagat cagcgtgccg tcctgcaggg aggagtcctg ggtcacggtc  420
accagaccgc cgtcctcgaa gttcatcacg cgctcccact tgaagccctc ggggaaggac  480
agcttcttgt aatcggggat gtcggcgggg tgcttcacgt acgccttgga gccgtacatg  540
aactgggggg acaggatgtc ccaggcgaag ggcagggggc cgcccttggt caccttcagc  600
ttggcggtct gggtgccctc gtaggggcgg ccctcgccct cgccctcgat ctcgaactcg  660
tggccgttca tggagccctc catgcgcacc ttgaagcgca tgaactcttt gatgacctcc  720
tcgcccttgc tcaccatggt ggcgaattct ccaggcgatc tgacggttca ctaaacgagc  780
tctgcttata taggcctccc accgtacacg ccacctcgac atactcgagt agttattaat  840
agtaatcaat tacggggtca ttagttcata gcccatatat ggagttccgc gttacataac  900
ttacggtaaa tggcccgcct ggctgaccgc ccaacgaccc ccgcccattg acgtcaataa  960
```

```
tgacgtatgt tcccatagta acgccaatag ggactttcca ttgacgtcaa tgggtggagt  1020
atttacggta aactgcccac ttggcagtac atcaagtgta tcatatgcca agtacgcccc  1080
ctattgacgt caatgacggt aaatggcccg cctggcatta tgcccagtac atgaccttat  1140
gggactttcc tacttggcag tacatctacg tattagtcat cgctattacc atggtgatgc  1200
ggttttggca gtacatcaat gggcgtggat agcggtttga ctcacgggga tttccaagtc  1260
tccaccccat tgacgtcaat gggagtttgt tttggcacca aaatcaacgg gactttccaa  1320
aatgtcgtaa caactccgcc ccattgacgc aaatgggcgg taggcgtgta cggtgggagg  1380
tctatataag cagagctggt ttagtgaacc gtcagatccg ctagggatcc tctagtcagc  1440
tgacgcgtgc tagcgatatc ggcgcgccag cactcaccac cgtcccgctg aggatcaccc  1500
agcggccacg atggtgagca agggcgagga gctgttcacc ggggtggtgc ccatcctggt  1560
cgagctggac ggcgacgtaa acggccacaa gttcagcgtg tccggcgagg gcgagggcga  1620
tgccacctac ggcaagctga ccctgaagtt catctgcacc accggcaagc tgcccgtgcc  1680
ctggcccacc ctcgtgacca ccctgaccta cggcgtgcag tgcttcagcc gctaccccga  1740
ccacatgaag cagcacgact tcttcaagtc cgccatgccc gaaggctacg tccaggagcg  1800
caccatcttc ttcaaggacg acggcaacta caagacccgc gccgaggtga agttcgaggg  1860
cgacaccctg gtgaaccgca tcgagctgaa gggcatcgac ttcaaggagg acggcaacat  1920
cctggggcac aagctggagt acaactacaa cagccacaac gtctatatca tggccgacaa  1980
gcagaagaac ggcatcaagg tgaacttcaa gatccgccac aacatcgagg acggcagcgt  2040
gcagctcgcc gaccactacc agcagaacac ccccatcggc gacggccccg tgctgctgcc  2100
cgacaaccac tacctgagca cccagtccgc cctgagcaaa gaccccaacg agaagcgcga  2160
tcacatggtc ctgctggagt tcgtgaccgc cgccgggatc actctcggca tggacgagct  2220
gtacaagaag cttagccatg gcttcccgcc ggaggtggag gagcaggatg atggcacgct  2280
gcccatgtct tgtgcccagg agagcgggat ggaccgtcac cctgcagcct gtgcttctgc  2340
taggatcaat gtgtaggcgg ccgcactcct caggtgcagg ctgcctatca gaaggtggtg  2400
gctggtgtgg ccaatgccct ggctcacaaa taccactgag atctttttcc ctctgccaaa  2460
a                                                                  2461

SEQ ID NO: 300         moltype = DNA  length = 2461
FEATURE                Location/Qualifiers
source                 1..2461
                       mol_type = other DNA
                       organism = synthetic construct
SEQUENCE: 300
ctctagactg cagcctcagg agatctgggc ccctacttgt acagctcgtc catgccgtac  60
aggaacaggt ggtggcggcc ctcggagcgc tcgtactgtt ccacgatggt gtagtcctcg  120
ttgtgggagg tgatgtccag cttggtgtcc acgtagtagt agccgggcag ttgcacgggc  180
ttcttggcca tgtagatggt cttgaactcc accaggtagt ggccgccgtc cttcagcttc  240
agggcctggt ggatctcgcc cttcagcacg ccgtcgcggg ggtacaggcg ctcggtggag  300
gcctcccagc ccatggtctt cttctgcatt acggggccgt cgggggggaa gttggtgccg  360
cgcatcttca ccttgtagat cagcgtgccg tcctgcaggg aggagtcctg ggtcacggtc  420
accagaccgc cgtcctcgaa gttcatcacg cgctcccact tgaagccctc ggggaaggac  480
agcttcttgt aatcggggat gtcggcgggg tgcttcacgt acgccttgga gccgtacatg  540
aactgggggg acaggatgtc ccaggcgaag ggcagggggc cgcccttggt caccttcagc  600
ttggcggtct gggtgccctc gtaggggcgg ccctcgccct cgccctcgat ctcgaactcg  660
tggccgttca tggagccctc catgcgcacc ttgaagcgca tgaactcttt gatgacctcc  720
tcgcccttgc tcaccatggt ggcgaattct ccaggcgatc tgacggttca ctaaacgagc  780
tctgcttata taggcctccc accgtacacg ccacctcgac atactcgagt agttattaat  840
agtaatcaat tacggggtca ttagttcata gcccatatat ggagttccgc gttacataac  900
ttacggtaaa tggcccgcct ggctgaccgc ccaacgaccc ccgcccattg acgtcaataa  960
tgacgtatgt tcccatagta acgccaatag ggactttcca ttgacgtcaa tgggtggagt  1020
atttacggta aactgcccac ttggcagtac atcaagtgta tcatatgcca agtacgcccc  1080
ctattgacgt caatgacggt aaatggcccg cctggcatta tgcccagtac atgaccttat  1140
gggactttcc tacttggcag tacatctacg tattagtcat cgctattacc atggtgatgc  1200
ggttttggca gtacatcaat gggcgtggat agcggtttga ctcacgggga tttccaagtc  1260
tccaccccat tgacgtcaat gggagtttgt tttggcacca aaatcaacgg gactttccaa  1320
aatgtcgtaa caactccgcc ccattgacgc aaatgggcgg taggcgtgta cggtgggagg  1380
tctatataag cagagctggt ttagtgaacc gtcagatccg ctagggatcc tctagtcagc  1440
tgacgcgtgc tagcgatatc ggcgcgccag cactcaccac cgtcccgctg aggataaccc  1500
agcggccacg atggtgagca agggcgagga gctgttcacc ggggtggtgc ccatcctggt  1560
cgagctggac ggcgacgtaa acggccacaa gttcagcgtg tccggcgagg gcgagggcga  1620
tgccacctac ggcaagctga ccctgaagtt catctgcacc accggcaagc tgcccgtgcc  1680
ctggcccacc ctcgtgacca ccctgaccta cggcgtgcag tgcttcagcc gctaccccga  1740
ccacatgaag cagcacgact tcttcaagtc cgccatgccc gaaggctacg tccaggagcg  1800
caccatcttc ttcaaggacg acggcaacta caagacccgc gccgaggtga agttcgaggg  1860
cgacaccctg gtgaaccgca tcgagctgaa gggcatcgac ttcaaggagg acggcaacat  1920
cctggggcac aagctggagt acaactacaa cagccacaac gtctatatca tggccgacaa  1980
gcagaagaac ggcatcaagg tgaacttcaa gatccgccac aacatcgagg acggcagcgt  2040
gcagctcgcc gaccactacc agcagaacac ccccatcggc gacggccccg tgctgctgcc  2100
cgacaaccac tacctgagca cccagtccgc cctgagcaaa gaccccaacg agaagcgcga  2160
tcacatggtc ctgctggagt tcgtgaccgc cgccgggatc actctcggca tggacgagct  2220
gtacaagaag cttagccatg gcttcccgcc ggaggtggag gagcaggatg atggcacgct  2280
gcccatgtct tgtgcccagg agagcgggat ggaccgtcac cctgcagcct gtgcttctgc  2340
taggatcaat gtgtaggcgg ccgcactcct caggtgcagg ctgcctatca gaaggtggtg  2400
gctggtgtgg ccaatgccct ggctcacaaa taccactgag atctttttcc ctctgccaaa  2460
a                                                                  2461

SEQ ID NO: 301         moltype = DNA  length = 2032
FEATURE                Location/Qualifiers
source                 1..2032
```

```
                        mol_type = other DNA
                        organism = synthetic construct
SEQUENCE: 301
taatacgact cactataggg agacccaagc tggctagcgt ttaaacttaa gcttgccacc  60
atggcattgc ccgtgaccgc cctgctgctg ccactggcct tgttgctcca cgccgcgcgg  120
ccatatccct acgatgtgcc cgattacgct accggtatgg cagaaatcgg tactggcttt  180
ccattcgacc cccattatgt ggaagtcctg ggcgagcgca tgcactacgt cgatgttggt  240
ccgcgcgatg gcacccctgt gctgttcctg cacggtaacc cgacctcctc ctacgtgtgg  300
cgcaacatca tcccgcatgt tgcaccgacc catcgctgca ttgctccaga cctgatcggt  360
atgggcaaat ccgacaaacc agacctgggt tatttcttcg acgaccacgt ccgcttcatg  420
gatgccttca tcgaagccct gggtctggaa gaggtcgtcc tggtcattca cgactggggc  480
tccgctctgg gtttccactg ggccaagcgc aatccagagc gcgtcaaagg tattgcattt  540
atggagttca tccgccctat cccgacctgg gacgaatggc cagaatttgc ccgcgagacc  600
ttccaggcct tccgcaccac cgacgtcggc cgcaagctga tcatcgatca gaacgttttt  660
atcgagggta cgctgccgat gggtgtcgtc cgcccgctga ctgaagtcga gatggaccat  720
taccgcgagc cgttcctgaa tcctgttgac cgcgagccac tgtggcgctt cccaaacgag  780
ctgccaatcg ccggtgagcc agcgaacatc gtcgcgctgg tcgaagaata catggactgg  840
ctgcaccagt cccctgtccc gaagctgctg ttctggggca ccccaggcgt tctgatccca  900
ccggccgaag ccgctcgcct ggccaaaagc ctgcctaact gcaaggctgt ggacatcggc  960
ccgggtctga atctgctgca agaagacaac ccggacctga tcggcagcga gatcgcgcgc  1020
tggctgtcca cgctcgagat ttccggcggc ggaggaagtg gcgagggcag gggaagtctc  1080
ctaacatgcg gggacgtgga ggaaaaccct aggccttaca tgaggatcac ccatgttagg  1140
cccagggttg actacaaaga ccatgacggt gattataaag atcatgacat cgactacaag  1200
gacgacgatg acaagggtac catggagggc agaggaagtc ttctaacatg cggtgacgtg  1260
gaggagaatc ccggccctgg atccagcgag ctgattaagg agaacatgca catgaagctg  1320
tacatggagg gcaccgtgga caaccatcac ttcaagtgca catccgaggg cgaaggcaag  1380
ccctacgagg gcacccagac catgagaatc aaggtggtcg agggcggccc tctccccttc  1440
gccttcgaca tcctggctac tagcttcctc tacggcagca agaccttcat caaccacacc  1500
cagggcatcc ccgacttctt caagcagtcc ttccctgagg gcttcacatg ggagagagtc  1560
accacatacg aagacggggg cgtgctgacc gctacccagg acaccagcct ccaggacggc  1620
tgcctcatct acaacgtcaa gatcagaggg gtgaacttca catccaacgg ccctgtgatg  1680
cagaagaaaa cactcggctg ggaggccttc accgagacgc tgtaccccgc tgacggcggc  1740
ctggaaggca gaaacgacat ggccctgaag ctcgtgggcg ggagccatct gatcgcaaac  1800
atcaagacca catatagatc caagaaaccc gctaagaacc tcaagatgcc tggcgtctac  1860
tatgtggact acagactgga aagaatcaag gaggccaaca acgagaccta cgtcgagcag  1920
cacgaggtgg cagtggccag atactgcgac ctccctagca aactggggca caagcttaat  1980
tgatctagag ggcccgttta aacccgctga tcagcctcga ctgtgccttc ta          2032

SEQ ID NO: 302          moltype = DNA  length = 3049
FEATURE                 Location/Qualifiers
source                  1..3049
                        mol_type = other DNA
                        organism = synthetic construct
SEQUENCE: 302
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcgaagg agcagacgat atggcgtcgc tccaatacta gtgccacaaa  2040
cttctctctg ctaaagcaag caggtgatgt tgaagaaaac ccagggcctg gagggtccga  2100
```

-continued

```
gggcagggga agtctcctaa catgcgggga cgtggaggaa aatcccggcc catccggata  2160
tccctacgat gtgcccgatt acgctatcga tgtgagcaag ggcgaagaag ataacaaggc  2220
ctctctccca gcgacacatg agttacacat ctttggctcc atcaacggtg tggactttga  2280
catggtgggt cagggcaccg gcaatccaaa tgatggttat gaggagttaa acctgaagtc  2340
caccaagggt gacctccagt tctcccctg gattctggtc cctcatatcg ggtatggctt  2400
ccatcagtac ctgccctacc ctgacgggat gtcgcctttc caggccgcca tggtagatgg  2460
cagcggatac caagtccatc gcacaatgca gtttgaagat ggtgcctccc ttactgttaa  2520
ctaccgctac acctacgagg gaagccacat caaaggagag gcccaggtga aggggactgg  2580
tttccctgct gacggtcctg tgatgaccaa ctcgctgacc gctgcggact ggtgcaggtc  2640
gaagaagact taccccaacg acaaaaccat catcagtacc tttaagtgga gttacaccac  2700
tggaaatggc aagagatacc ggagcactgc gcggaccacc tacacctttg ccaagccaat  2760
ggcggctaac tatctgaaga accagccgat gtacgtgttc cgtaagacgg agctcaagca  2820
ctccaagacc gagctcaact tcaaggagtg gcaaaaggcc tttaccgatg tgatgggaat  2880
ggacgagctg tataaggcta gctaagcggc cgctcgagtc tagagggccc gcggttcgaa  2940
ggtaagccta tccctaaccc tctcctcggt ctcgattcta cgcgtaccgg tcatcatcac  3000
catcaccatt gagtttaaac ccgctgatca gcctcgactg tgccttcta              3049
```

```
SEQ ID NO: 303          moltype = DNA  length = 3043
FEATURE                 Location/Qualifiers
source                  1..3043
                        mol_type = other DNA
                        organism = synthetic construct
SEQUENCE: 303
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcggtaa gggccctgaa gaagggccca actagtgcca caaacttctc  2040
tctgctaaag caagcaggtg atgttgaaga aaacccaggg cctggagggt ccgagggcag  2100
gggaagtctc ctaacatgcg gggacgtgga ggaaaatccc ggcccatccg gatatcccta  2160
cgatgtgccc gattacgcta tcgatgtgag caagggcgaa gaagataaca aggcctctct  2220
cccagcgaca catgagttac acatctttgg ctccatcaac ggtgtggact ttgacatggt  2280
gggtcagggc accggcaatc caaatgatgg ttatgaggag ttaaacctga agtccaccaa  2340
gggtgacctc cagttctccc cctggattct ggtccctcat atcgggtatg gcttccatca  2400
gtacctgccc taccctgacg ggatgtcgcc tttccaggcc gccatggtag atggcagcgg  2460
ataccaagtc catcgcacaa tgcagtttga agatggtgcc tcccttactg ttaactaccg  2520
ctacacctac gagggaagcc acatcaaagg agaggcccag gtgaagggga ctggtttccc  2580
tgctgacggt cctgtgatga ccaactcgct gaccgctgcg gactggtgca ggtcgaagaa  2640
gacttacccc aacgacaaaa ccatcatcag tacctttaag tggagttaca ccactggaaa  2700
tggcaagaga taccggagca ctgcgcggac cacctacacc tttgccaagc caatggcggc  2760
taactatctg aagaaccagc cgatgtacgt gttccgtaag acggagctca agcactccaa  2820
gaccgagctc aacttcaagg agtggcaaaa ggcctttacc gatgtgatgg gaatggacga  2880
gctgtataag gctagctaag cggccgctcg agtctagagg gcccgcggtt cgaaggtaag  2940
cctatcccta accctctcct cggtctcgat tctacgcgta ccggtcatca tcaccatcac  3000
cattgagttt aaacccgctg atcagcctcg actgtgcctt cta                   3043
```

```
SEQ ID NO: 304          moltype = DNA  length = 3052
FEATURE                 Location/Qualifiers
source                  1..3052
                        mol_type = other DNA
```

```
                         organism = synthetic construct
SEQUENCE: 304
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcggtag gctcgtctga gctcattagc tccgagccaa ctagtgccac  2040
aaacttctct ctgctaaagc aagcaggtga tgttgaagaa aacccagggc ctggagggtc  2100
cgagggcagg ggaagtctcc taacatgcgg ggacgtggag gaaaatcccg gcccatccgg  2160
atatccctac gatgtgcccg attacgctat cgatgtgagc aagggcgaag aagataacaa  2220
ggcctctctc ccagcgacac atgagttaca catctttggc tccatcaacg gtgtggactt  2280
tgacatggtg ggtcagggca ccggcaatcc aaatgatggt tatgaggagt taaacctgaa  2340
gtccaccaag ggtgacctcc agttctcccc ctggattctg gtccctcata tcgggtatgg  2400
cttccatcag tacctgccct accctgacgg gatgtcgcct ttccaggccg ccatggtaga  2460
tggcagcgga taccaagtcc atcgcacaat gcagtttgaa gatggtgcct cccttactgt  2520
taactaccgc tacacctacg agggaagcca catcaaagga gaggcccagg tgaaggggac  2580
tggtttccct gctgacggtc ctgtgatgac caactcgctg accgctgcgg actggtgcag  2640
gtcgaagaag acttacccca acgacaaaac catcatcagt acctttaagt ggagttacac  2700
cactggaaat ggcaagagat accggagcac tgcgcggacc acctacacct ttgccaagcc  2760
aatggcggct aactatctga agaaccagcc gatgtacgtg ttccgtaaga cggagctcaa  2820
gcactccaag accgagctca acttcaagga gtggcaaaag gcctttaccg atgtgatggg  2880
aatggacgag ctgtataagg ctagctaagc ggccgctcga gtctagaggg cccgcggttc  2940
gaaggtaagc ctatccctaa ccctctcctc ggtctcgatt ctacgcgtac cggtcatcat  3000
caccatcacc attgagttta aacccgctga tcagcctcga ctgtgccttc ta          3052

SEQ ID NO: 305           moltype = DNA  length = 2065
FEATURE                  Location/Qualifiers
source                   1..2065
                         mol_type = other DNA
                         organism = synthetic construct
SEQUENCE: 305
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtactagtgc  1020
cacaaacttc tctctgctaa agcaagcagg tgatgttgaa gaaaacccag ggcctggagg  1080
gtccgagggc aggggaagtc tcctaacatg cggggacgtg gaggaaaatc ccggcccatc  1140
```

```
cggatatccc tacgatgtgc ccgattacgc tcatatggtg agcaagggcg aggaggataa  1200
catggcctct ctcccagcga cacatgagtt acacatcttt ggctccatca acggtgtgga  1260
ctttgacatg gtgggtcagg gcaccggcaa tccaaatgat ggttatgagg agttaaacct  1320
gaagtccacc aagggtgacc tccagttctc cccctggatt ctggtccctc atatcgggta  1380
tggcttccat cagtacctgc cctaccctga cgggatgtcg cctttccagg ccgccatggt  1440
agatggcagc ggataccaag tccatcgcac aatgcagttt gaagatggtg cctcccttac  1500
tgttaactac cgctacacct acgagggaag ccacatcaaa ggagaggccc aggtgaaggg  1560
gactggtttc cctgctgacg gtcctgtgat gaccaactcg ctgaccgctg cggactggtg  1620
caggtcgaag aagacttacc ccaacgacaa aaccatcatc agtaccttca agtagagcta  1680
caccactggt gtagctccac ttgataccat gaggatcacc catggcaaga gataccggag  1740
cactgcgcgg accacctaca cctttgccaa gccaatggcg gctaactatc tgaagaacca  1800
gccgatgtac gtgttccgta agacggagct caagcactcc aagaccgagc tcaacttcaa  1860
ggagtggcaa aaggccttta ccgatgtgat gggaatggac gagctgtata aggctagcta  1920
agcggccgct cgagtctaga gggcccgcgg ttcgaaggta agcctatccc taaccctctc  1980
ctcggtctcg attctacgcg taccggtcat catcaccatc accattgagt ttaaacccgc  2040
tgatcagcct cgactgtgcc ttcta                                       2065
```

```
SEQ ID NO: 306          moltype = DNA  length = 3571
FEATURE                 Location/Qualifiers
source                  1..3571
                        mol_type = other DNA
                        organism = synthetic construct
SEQUENCE: 306
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcggct agcccatccc gcctggagga agaacttcgg  1320
aggagactta ctgagcctac cggctccgga gccggtgaca gacatcctaa taggaaggct  1380
agaggccaac ttcggacgaa gattgaaagt ggccagggta ctatcccggt gcggtccaac  1440
gctagtattc aaacgtggga cggagtcctt caaggtgaac ggctgttgac aatgagctgc  1500
tcagacaaaa tcgcgatgtg gaatgtagtg ggaatccaag gcagcctctt gagcatattc  1560
gtagaaccca tatatttctc atccattatt ttgggctctc tgtatcatgg tgaccatctg  1620
tcaagggcta tgtaccaacg aatttctaat atcgaggatc ttcctccact ctatacactc  1680
aataagcctc tcttgtccgg gatatcaaac gctgaggccc gccagccagg gaaagctcct  1740
aacttcagtg ttaactggac cgttggtgat tctgcgatag aggtcatcaa cgccacgaca  1800
ggtaaggatg agctcggtag agcctcacgc ctgtgtaaac acgcgttgta ttgtagatgg  1860
atgagagtac atgggaaggt cccatctcac ttgctccgaa gcaagatcac taagcctaat  1920
gtgtatcatg agtcaaaact cgcggctaaa gaataccagg cagccaaagc tcgactttttt  1980
acagctttta ttaaggcagg gctcggggca tgggtcgaga agccgaccga gcaggaccaa  2040
ttctctgtga cggggagcgg aggtaccgcc gaagttcaat tacaggaatc gggtggaggt  2100
ctggtacaac ctgggggctc tcttcgcctg agttgcactg ccagtggagt tacgatttct  2160
gcacttaatg ctatggcgat gggttggtat cgtcaggccc caggggaacg tcgcgtcatg  2220
gtcgctgccg tttccgaacg tggcaatgct atgtaccgcg agtctgttca gggccgcttc  2280
acggttaccc gcgattttac aaataaaatg gtatcgttgc aaatggacaa cttaaagcca  2340
gaggacactg ctgtgtacta ctgtcacgtc cttgaagatc gtgtggattc ctttcatgat  2400
tattgggggc aggggactca ggtcactgta tcctcaggag ctggatccgg aggtggaggc  2460
tccggcacca tgatggatca agtccaactg gtggagtctg gtggcgcttt ggtgcagcca  2520
ggtggctctc tgcgtttgtc ctgtgccgct tctggcttcc cagtgaaccg ctattccatg  2580
cgctggtatc gccaggctcc aggcaaagag cgtgagtggg tagccggtat gtccagcgcg  2640
ggtgatcgta gctcctatga agactccgtg aagggccgtt tcaccatcag ccgtgacgat  2700
gcccgtaaca cggtgtatct gcaaatgaac agcttgaaac ctgaagatac ggccgtgtat  2760
tactgtaatg tgaacgtggg cttcgagtat tggggccaag gcacccaggt caccgtctcc  2820
agcatgcata gcgagctgat taaggagaac atgcacatga agctgtacat ggagggcacc  2880
gtggacaacc atcacttcaa gtgcacatcc gagggcgaag gcaagcccta cgagggcacc  2940
cagaccatga gaatcaaggt ggtcgagggc ggccctctcc ccttcgcctt cgacatcctg  3000
gctactagct tcctctacgg cagcaagacc ttcatcaacc acacccaggg catccccgac  3060
ttcttcaagc agtccttccc tgagggcttc acatgggaga gagtcaccac atacgaagac  3120
gggggcgtgc tgaccgctac ccaggacacc agcctccagg acggctgcct catctacaac  3180
gtcaagatca gaggggtgaa cttcacatcc aacggccctg tgatgcagaa gaaaacactc  3240
ggctgggagg ccttcaccga gacgctgtac cccgctgacg gcggcctgga aggcagaaac  3300
gacatggccc tgaagctcgt gggcgggagc catctgatcg caaacatcaa gaccacatat  3360
```

```
agatccaaga aacccgctaa gaacctcaag atgcctggcg tctactatgt ggactacaga  3420
ctggaaagaa tcaaggaggc caacaacgag acctacgtcg agcagcacga ggtggcagtg  3480
gccagatact gcgacctccc tagcaaactg gggcacaagc ttaattaagg gcccgtttaa  3540
acccgctgat cagcctcgac tgtgccttct a                                 3571

SEQ ID NO: 307          moltype = DNA  length = 3571
FEATURE                 Location/Qualifiers
source                  1..3571
                        mol_type = other DNA
                        organism = synthetic construct
SEQUENCE: 307
taatacgact cactataggg agacccaagc tggctagagg atcgaaccct taaggccacc  60
atggcgagca attttaccca gtttgtgctt gtggacaacg gcggcaccgg ggacgtgacg  120
gtggccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg gggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcggct agcccatccc gcctggagga agaacttcgg  1320
aggagactta ctgagcctac cggctccgga gccggtgaca gacatcctaa taggaaggct  1380
agaggccaac ttcggacgaa gattgaaagt ggccagggta ctatcccggt gcggtccaac  1440
gctagtattc aaacgtggga cggagtcctt caaggtgaac ggctgttgac aatgagctgc  1500
tcagacaaaa tcgcgatgtg gaatgtagtg ggaatccaag gcagcctctt gagcatattc  1560
gtagaaccca tatatttctc atccattatt ttgggctctc tgtatcatgg tgaccatctg  1620
tcaagggcta tgtaccaacg aatttctaat atcgaggatc ttcctccact ctatacactc  1680
aataagcctc tcttgtccgg gatatcaaac gctgaggccc gccagccagg gaaagctcct  1740
aacttcagtg ttaactggac cgttggtgat tctgcgatag aggtcatcaa cgccacgaca  1800
ggtaaggatg agctcggtag agcctcacgc ctgtgtaaac acgcgttgta ttgtagatgg  1860
atgagagtac atgggaaggt cccatctcac ttgctccgaa gcaagatcac taagcctaat  1920
gtgtatcatg agtcaaaact cgcggctaaa gaataccagg cagccaaagc tcgactttt  1980
acagctttta ttaaggcagg gctcggggca tgggtcgaga agccgaccga gcaggaccaa  2040
ttctctggga cggggagcgg aggtaccgcc gaagttcaat tacaggaatc gggtggaggt  2100
ctggtacaac ctgggggctc tcttcgcctg agttgcactg ccagtggagt tacgatttct  2160
gcacttaatg ctatggcgat gggttggtat cgtcaggccc caggggaacg tcgcgtcatg  2220
gtcgctgccg tttccgaacg tggcaatgct atgtaccgcg agtctgttca gggccgcttc  2280
acggttaccc gcgattttac aaataaaatg gtatcgttgc aaatggacaa cttaaagcca  2340
gaggacactg ctgtgtacta ctgtcacgtc cttgaagatc gtgtggattc ctttcatgat  2400
tattgggggc aggggactca ggtcactgta tcctcaggag ctggatccgg aggtggaggc  2460
tccggcacca tgatggatca agtccaactg gtggagtctg gtggcgcttt ggtgcagcca  2520
ggtggctctc tgcgtttgtc ctgtgccgct tctggcttcc cagtgaaccg ctattccatg  2580
cgctggtatc gccaggctcc aggcaaagag cgtgagtggg tagccggtat gtccagcgcg  2640
ggtgatcgta gctcctatga agactccgtg aagggccgtt tcaccatcag ccgtgacgat  2700
gcccgtaaca cggtgtatct gcaaatgaac agcttgaaac ctgaagatac ggccgtgtat  2760
tactgtaatg tgaacgtggg cttcgagtat tggggccaag gcacccaggt caccgtctcc  2820
agcatgcata gcgagctgat taaggagaac atgcacatga agctgtacat ggagggcacc  2880
gtggacaacc atcacttcaa gtgcacatcc gagggcgaag gcaagcccta cgagggcacc  2940
cagaccatga gaatcaaggt ggtcgagggc ggccctctcc ccttcgcctt cgacatcctg  3000
gctactagct tcctctacgg cagcaagacc ttcatcaacc acacccaggg catccccgac  3060
ttcttcaagc agtccttccc tgagggcttc acatgggaga gagtcaccac atacgaagac  3120
gggggcgtgc tgaccgctac ccaggacacc agcctccagg acggctgcct catctacaac  3180
gtcaagatca gaggggtgaa cttcacatcc aacggccctg tgatgcagaa gaaaacactc  3240
ggctgggagg ccttcaccga gacgctgtac cccgctgacg gcggcctgga aggcagaaac  3300
gacatggccc tgaagctcgt gggcgggagc catctgatcg caaacatcaa gaccacatat  3360
agatccaaga aacccgctaa gaacctcaag atgcctggcg tctactatgt ggactacaga  3420
ctggaaagaa tcaaggaggc caacaacgag acctacgtcg agcagcacga ggtggcagtg  3480
gccagatact gcgacctccc tagcaaactg gggcacaagc ttaattaagg gcccgtttaa  3540
acccgctgat cagcctcgac tgtgccttct a                                 3571

SEQ ID NO: 308          moltype = DNA  length = 3571
FEATURE                 Location/Qualifiers
source                  1..3571
                        mol_type = other DNA
                        organism = synthetic construct
SEQUENCE: 308
taatacgact cactataggg agacccaagc tggctagagg atcgaaccct taaggccacc  60
```

```
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg gggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcggct agcccatccc gcctggagga agaacttcgg  1320
aggagactta ctgagcctac cggctccgga gccggtgaca gacatcctaa taggaaggct  1380
agaggccaac ttcggacgaa gattgaaagt ggccagggta ctatcccggt gcggtccaac  1440
gctagtattc aaacgtggga cggagtcctt caaggtgaac ggctgttgac aatgagctgc  1500
tcagacaaaa tcgcgatgtg gaatgtagtg ggaatccaag gcagcctctt gagcatattc  1560
gtagaaccca tatatttctc atccattatt ttgggctctc tgtatcatgg tgaccatctg  1620
tcaagggcta tgtaccaacg aatttctaat atcgaggatc ttcctccact ctatacactc  1680
aataagcctc tcttgtccgg gatatcaaac gctgaggccc gccagccagg gaaagctcct  1740
aacttcagtg ttaactggac cgttggtgat tctgcgatag aggtcatcaa cgccacgaca  1800
ggtaaggatg agctcggtag agcctcacgc ctgtgtaaac acgcgttgta ttgtagatgg  1860
atgagagtac atgggaaggt cccatctcac ttgctccgaa gcaagatcac taagcctaat  1920
gtgtatcatg agtcaaaact cgcggctaaa gaataccagg cagccaaagc tcgacttttt  1980
acagctttta ttaaggcagg gctcggggca tgggtcgaga agccgaccga gcaggaccaa  2040
tactctctga cggggagcgg aggtaccgcc gaagttcaat tacaggaatc gggtggaggt  2100
ctggtacaac ctgggggctc tcttcgcctg agttgcactg ccagtggagt tacgatttct  2160
gcacttaatg ctatggcgat gggttggtat cgtcaggccc caggggaacg tcgcgtcatg  2220
gtcgctgccg tttccgaacg tggcaatgct atgtaccgcg agtctgttca gggccgcttc  2280
acggttaccc gcgattttac aaataaaatg gtatcgttgc aaatggacaa cttaaagcca  2340
gaggacactg ctgtgtacta ctgtcacgtc cttgaagatc gtgtggattc ctttcatgat  2400
tattgggggc aggggactca ggtcactgta tcctcaggag ctggatccgg aggtggaggc  2460
tccggcacca tgatggatca agtccaactg gtggagtctg gtggcgcttt ggtgcagcca  2520
ggtggctctc tgcgtttgtc ctgtgccgct tctggcttcc cagtgaaccg ctattccatg  2580
cgctggtatc gccaggctcc aggcaaagag cgtgagtggg tagccggtat gtccagcgcg  2640
ggtgatcgta gctcctatga agactccgtg aagggccgtt tcaccatcag ccgtgacgat  2700
gcccgtaaca cggtgtatct gcaaatgaac agcttgaaac ctgaagatac ggccgtgtat  2760
tactgtaatg tgaacgtggg cttcgagtat tggggccaag gcacccaggt caccgtctcc  2820
agcatgcata gcgagctgat taaggagaac atgcacatga agctgtacat ggagggcacc  2880
gtggacaacc atcacttcaa gtgcacatcc gagggcgaag gcaagcccta cgagggcacc  2940
cagaccatga gaatcaaggt ggtcgagggc ggccctctcc ccttcgcctt cgacatcctg  3000
gctactagct tcctctacgg cagcaagacc ttcatcaacc acacccaggg catccccgac  3060
ttcttcaagc agtccttccc tgagggcttc acatgggaga gagtcaccac atacgaagac  3120
gggggcgtgc tgaccgctac ccaggacacc agcctccagg acggctgcct catctacaac  3180
gtcaagatca gaggggtgaa cttcacatcc aacggccctg tgatgcagaa gaaaacactc  3240
ggctgggagg ccttcaccga gacgctgtac cccgctgacg gcggcctgga aggcagaaac  3300
gacatggccc tgaagctcgt gggcgggagc catctgatcg caaacatcaa gaccacatat  3360
agatccaaga aacccgctaa gaacctcaag atgcctggcg tctactatgt ggactacaga  3420
ctggaaagaa tcaaggaggc caacaacgag acctacgtcg agcagcacga ggtggcagtg  3480
gccagatact gcgacctccc tagcaaactg ggcacaagc ttaattaagg gcccgtttaa  3540
acccgctgat cagcctcgac tgtgccttct a                                  3571
```

```
SEQ ID NO: 309          moltype = DNA  length = 3568
FEATURE                 Location/Qualifiers
source                  1..3568
                        mol_type = other DNA
                        organism = synthetic construct
SEQUENCE: 309
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
```

```
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcggct agcggatcag gtccaggacg cctggaggaa  1320
gaacttcgga ggagactttc tcctggaacc ggtgacagac atcctaatag gaaggctaga  1380
ggccaacttc ggacgaagat tgaaagtggc cagggtacta tcccggtgcg gtccaacgct  1440
agtattcaaa cgtgggacgg agtccttcaa ggtgaacggc tgttgacaat gagctgctca  1500
gacaaaatcg cgatgtggaa tgtagtggga atccaaggca gcctcttgag catattcgta  1560
gaacccatat atttctcatc cattattttg ggctctctgt atcatggtga ccatctgtca  1620
agggctatgt accaacgaat ttctaatatc gaggatcttc ctccactcta tacactcaat  1680
aagcctctct tgtccgggat atcaaacgct gaggcccgcc agccagggaa agctcctaac  1740
ttcagtgtta actggaccgt tggtgattct gcgatagagg tcatcaacgc cacgacaggt  1800
aaggatgagc tcggtagagc ctcacgcctg tgtaaacacg cgttgtattg tagatggatg  1860
agagtacatg ggaaggtccc atctcacttg ctccgaagca agatcactaa gcctaatgtg  1920
tatcatgagt caaaactcgc ggctaaagaa taccaggcag ccaaagctcg actttttaca  1980
gcttttatta aggcagggct cggggcatgg gtcgagaagc cgaccgagca ggaccaattc  2040
tctgtgacgg ggagcggagg taccgccgaa gttcaattac aggaatcggg tggaggtctg  2100
gtacaacctg gggggctctct tcgcctgagt tgcactgcca gtggagttac gatttctgca  2160
cttaatgcta tggcgatggg ttggtatcgt caggccccag gggaacgtcg cgtcatggtc  2220
gctgccgttt ccgaacgtgg caatgctatg taccgcgagt ctgttcaggg ccgcttcacg  2280
gttacccgcg atttacaaa taaaatggta tcgttgcaaa tggacaactt aaagccagag  2340
gacactgctg tgtactactg tcacgtcctt gaagatcgtg tggattcctt tcatgattat  2400
tgggggcagg ggactcaggt cactgtatcc tcaggagctg gatccggagg tggaggctcc  2460
ggcaccatga tggatcaagt ccaactggtg gagtctggtg gcgctttggt gcagccaggt  2520
ggctctctgc gtttgtcctg tgccgcttct ggcttcccag tgaaccgcta ttccatgcgc  2580
tggtatcgcc aggctccagg caaagagcgt gagtgggtag ccggtatgtc cagcgcgggt  2640
gatcgtagct cctatgaaga ctccgtgaag ggccgtttca ccatcagccg tgacgatgcc  2700
cgtaacacgg tgtatctgca aatgaacagc ttgaaacctg aagatacggc cgtgtattac  2760
tgtaatgtga acgtgggctt cgagtattgg ggccaaggca cccaggtcac cgtctccagc  2820
atgcatagcg agctgattaa ggagaacatg cacatgaagc tgtacatgga gggcaccgtg  2880
gacaaccatc acttcaagtg cacatccgag ggcgaaggca agccctacga gggcacccag  2940
accatgagaa tcaaggtggt cgagggcggc cctctcccct tcgccttcga catcctggct  3000
actagcttcc tctacggcag caagaccttc atcaaccaca cccagggcat ccccgacttc  3060
ttcaagcagt ccttccctga gggcttcaca tgggagagag tcaccacata cgaagacggg  3120
ggcgtgctga ccgctaccca ggacaccagc ctccaggacg gctgcctcat ctacaacgtc  3180
aagatcagag gggtgaactt cacatccaac ggccctgtga tgcagaagaa aacactcggc  3240
tgggaggcct tcaccgagac gctgtacccc gctgacggcg gcctggaagg cagaaacgac  3300
atggccctga agctcgtggg cgggagccat ctgatcgcaa acatcaagac cacatataga  3360
tccaagaaac ccgctaagaa cctcaagatg cctggcgtct actatgtgga ctacagactg  3420
gaaagaatca aggaggccaa caacgagacc tacgtcgagc agcacgaggt ggcagtggcc  3480
agatactgcg acctccctag caaactgggg cacaagctta attaagggcc cgtttaaacc  3540
cgctgatcag cctcgactgt gccttcta                                    3568
```

```
SEQ ID NO: 310         moltype = DNA  length = 3568
FEATURE                Location/Qualifiers
source                 1..3568
                       mol_type = other DNA
                       organism = synthetic construct
SEQUENCE: 310
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcggct agcggatcag gtccaggacg cctggaggaa  1320
gaacttcgga ggagactttc tcctggaacc ggtgacagac atcctaatag gaaggctaga  1380
ggccaacttc ggacgaagat tgaaagtggc cagggtacta tcccggtgcg gtccaacgct  1440
agtattcaaa cgtgggacgg agtccttcaa ggtgaacggc tgttgacaat gagctgctca  1500
```

```
gacaaaatcg cgatgtggaa tgtagtggga atccaaggca gcctcttgag catattcgta  1560
gaacccatat atttctcatc cattattttg ggctctctgt atcatggtga ccatctgtca  1620
agggctatgt accaacgaat ttctaatatc gaggatcttc ctccactcta tacactcaat  1680
aagcctctct tgtccgggat atcaaacgct gaggcccgcc agccagggaa agctcctaac  1740
ttcagtgtta actggaccgt tggtgattct gcgatagagg tcatcaacgc cacgacaggt  1800
aaggatgagc tcggtagagc ctcacgcctg tgtaaacacg cgttgtattg tagatggatg  1860
agagtacatg ggaaggtccc atctcacttg ctccgaagca agatcactaa gcctaatgtg  1920
tatcatgagt caaaactcgc ggctaaagaa taccaggcag ccaaagctcg actttttaca  1980
gcttttatta aggcagggct cggggcatgg gtcgagaagc cgaccgagca ggaccaattc  2040
tctgggacgg ggagcggagg taccgccgaa gttcaattac aggaatcggg tggaggtctg  2100
gtacaacctg gggggctctct tcgcctgagt tgcactgcca gtggagttac gatttctgca  2160
cttaatgcta tggcgatggg ttggtatcgt caggccccag gggaacgtcg cgtcatggtc  2220
gctgccgttt ccgaacgtgg caatgctatg taccgcgagt ctgttcaggg ccgcttcacg  2280
gttacccgcg attttacaaa taaaatggta tcgttgcaaa tggacaactt aaagccagag  2340
gacactgctg tgtactactg tcacgtcctt gaagatcgtg tggattcctt tcatgattat  2400
tgggggcagg ggactcaggt cactgtatcc tcaggagctg gatccggagg tggaggctcc  2460
ggcaccatga tggatcaagt ccaactggtg gagtctggtg gcgctttggt gcagccaggt  2520
ggctctctgc gtttgtcctg tgccgcttct ggcttcccag tgaaccgcta ttccatgcgc  2580
tggtatcgcc aggctccagg caaagagcgt gagtgggtag ccggtatgtc cagcgcgggt  2640
gatcgtagct cctatgaaga ctccgtgaag ggccgtttca ccatcagccg tgacgatgcc  2700
cgtaacacgg tgtatctgca aatgaacagc ttgaaacctg aagatacggc cgtgtattac  2760
tgtaatgtga acgtgggctt cgagtattgg ggccaaggca cccaggtcac cgtctccagc  2820
atgcatagcg agctgattaa ggagaacatg cacatgaagc tgtacatgga gggcaccgtg  2880
gacaaccatc acttcaagtg cacatccgag ggcgaaggca agccctacga gggcacccag  2940
accatgagaa tcaaggtggt cgagggcggc cctctcccct tcgccttcga catcctggct  3000
actagcttcc tctacggcag caagaccttc atcaaccaca cccagggcat ccccgacttc  3060
ttcaagcagt ccttccctga gggcttcaca tgggagagag tcaccacata cgaagacggg  3120
ggcgtgctga ccgctaccca ggacaccagc ctccaggacg gctgcctcat ctacaacgtc  3180
aagatcagag gggtgaactt cacatccaac ggccctgtga tgcagaagaa aacactcggc  3240
tgggaggcct tcaccgagac gctgtacccc gctgacggcg gcctggaagg cagaaacgac  3300
atggccctga agctcgtggg cgggagccat ctgatcgcaa acatcaagac cacatataga  3360
tccaagaaac ccgctaagaa cctcaagatg cctggcgtct actatgtgga ctacagactg  3420
gaaagaatca aggaggccaa caacgagacc tacgtcgagc agcacgaggt ggcagtggcc  3480
agatactgcg acctccctag caaactgggg cacaagctta attaagggcc cgtttaaacc  3540
cgctgatcag cctcgactgt gccttcta                                  3568
```

```
SEQ ID NO: 311          moltype = DNA  length = 3568
FEATURE                 Location/Qualifiers
source                  1..3568
                        mol_type = other DNA
                        organism = synthetic construct
SEQUENCE: 311
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatgggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcggct agcggatcag gtccaggacg cctggaggaa  1320
gaacttcgga ggagactttc tcctggaacc ggtgacagac atcctaatag gaaggctaga  1380
ggccaacttc ggacgaagat tgaaagtggc cagggtacta tcccggtgcg gtccaacgct  1440
agtattcaaa cgtgggacgg agtccttcaa ggtgaacggc tgttgacaat gagctgctca  1500
gacaaaatcg cgatgtggaa tgtagtggga atccaaggca gcctcttgag catattcgta  1560
gaacccatat atttctcatc cattattttg ggctctctgt atcatggtga ccatctgtca  1620
agggctatgt accaacgaat ttctaatatc gaggatcttc ctccactcta tacactcaat  1680
aagcctctct tgtccgggat atcaaacgct gaggcccgcc agccagggaa agctcctaac  1740
ttcagtgtta actggaccgt tggtgattct gcgatagagg tcatcaacgc cacgacaggt  1800
aaggatgagc tcggtagagc ctcacgcctg tgtaaacacg cgttgtattg tagatggatg  1860
agagtacatg ggaaggtccc atctcacttg ctccgaagca agatcactaa gcctaatgtg  1920
tatcatgagt caaaactcgc ggctaaagaa taccaggcag ccaaagctcg actttttaca  1980
gcttttatta aggcagggct cggggcatgg gtcgagaagc cgaccgagca ggaccaatac  2040
tctctgacgg ggagcggagg taccgccgaa gttcaattac aggaatcggg tggaggtctg  2100
gtacaacctg ggggctctct tcgcctgagt tgcactgcca gtggagttac gatttctgca  2160
cttaatgcta tggcgatggg ttggtatcgt caggccccag gggaacgtcg cgtcatggtc  2220
```

```
gctgccgttt ccgaacgtgg caatgctatg taccgcgagt ctgttcaggg ccgcttcacg  2280
gttacccgcg attttacaaa taaaatggta tcgttgcaaa tggacaactt aaagccagag  2340
gacactgctg tgtactactg tcacgtcctt gaagatcgtg tggattcctt tcatgattat  2400
tgggggcagg ggactcaggt cactgtatcc tcaggagctg gatccggagg tggaggctcc  2460
ggcaccatga tggatcaagt ccaactggtg gagtctggtg gcgctttggt gcagccaggt  2520
ggctctctgc gtttgtcctg tgccgcttct ggcttcccag tgaaccgcta ttccatgcgc  2580
tggtatcgcc aggctccagg caaagagcgt gagtgggtag ccggtatgtc cagcgcgggt  2640
gatcgtagct cctatgaaga ctccgtgaag ggccgtttca ccatcagccg tgacgatgcc  2700
cgtaacacgg tgtatctgca aatgaacagc ttgaaacctg aagatacggc cgtgtattac  2760
tgtaatgtga acgtgggctt cgagtattgg ggccaaggca cccaggtcac cgtctccagc  2820
atgcatagcg agctgattaa ggagaacatg cacatgaagc tgtacatgga gggcaccgtg  2880
gacaaccatc acttcaagtg cacatccgag ggcgaaggca agccctacga gggcacccag  2940
accatgagaa tcaaggtggt cgagggcggc cctctcccct tcgccttcga catcctggct  3000
actagcttcc tctacggcag caagaccttc atcaaccaca cccagggcat ccccgacttc  3060
ttcaagcagt ccttccctga gggcttcaca tgggagagag tcaccacata cgaagacggg  3120
ggcgtgctga ccgctaccca ggacaccagc ctccaggacg gctgcctcat ctacaacgtc  3180
aagatcagag gggtgaactt cacatccaac ggccctgtga tgcagaagaa aacactcggc  3240
tgggaggcct tcaccgagac gctgtacccc gctgacggcg gcctggaagg cagaaacgac  3300
atggccctga agctcgtggg cgggagccat ctgatcgcaa acatcaagac cacatataga  3360
tccaagaaac ccgctaagaa cctcaagatg cctggcgtct actatgtgga ctacagactg  3420
gaaagaatca aggaggccaa caacgagacc tacgtcgagc agcacgaggt ggcagtggcc  3480
agatactgcg acctccctag caaactgggg cacaagctta attaagggcc cgtttaaacc  3540
cgctgatcag cctcgactgt gccttcta                                    3568
```

```
SEQ ID NO: 312          moltype = DNA  length = 918
FEATURE                 Location/Qualifiers
source                  1..918
                        mol_type = other DNA
                        organism = synthetic construct
SEQUENCE: 312
agctcgttta gtgaaccgtc agatcgcctg gagacgccat ccacgctgtt ttgacctcca  60
tagaagacac cgggaccgat ccagcctccg gactctagcg tttaaactta agcttgccac  120
catggtgagc aagggcgagg agctgttcac cggggtggtg cccatcctgg tcgagctgga  180
cggcgacgta aacggccaca agttcagcgt gtccggcgag ggcgagggcg atgccaccta  240
cggcaagctg accctgaagt tcatctgcac caccggcaag ctgcccgtgc cctggcccac  300
cctcgtgacc accctgacct acggcgtgca gtgcttcagc cgctaccccg accacatgaa  360
gcagcacgac ttcttcaagt ccgccatgcc cgaaggctac gtccaggaaa tgaccatctt  420
cttcaaggac gacggcaact acaagacccg cgccgaggtg aagttcgagg gcgacaccct  480
ggtgaaccgc atcgagctga agggcatcga cttcaaggag gacggcaaca tcctggggca  540
caagctggag tacaactaca acagccacaa cgtctatatc atggccgaca agcagaagaa  600
cggcatcaag gtgaacttca agatccgcca caacatcgag gacggcagcg tgcagctcgc  660
cgaccactac cagcagaaca cccccatcgg cgacggcccc gtgctgctgc ccgacaacca  720
ctacctgagc acccagtccg ccctgagcaa agaccccaac gagaagcgcg atcacatggt  780
cctgctggag ttcgtgaccg ccgccgggat cactctcggc atggacgagc tgtacaaggg  840
atcctaatct agagggccct attctatagt gtcacctaaa tgctagagct cgctgatcag  900
cctcgactgt gccttcta                                                918
```

```
SEQ ID NO: 313          moltype = DNA  length = 954
FEATURE                 Location/Qualifiers
source                  1..954
                        mol_type = other DNA
                        organism = synthetic construct
SEQUENCE: 313
agctcgttta gtgaaccgtc agatcgcctg gagacgccat ccacgctgtt ttgacctcca  60
tagaagacac cgggaccgat ccagcctccg gactctagcg tttaaactta agcttgccac  120
catggtgagc aagggcgagg agctgttcac cggggtggtg cccatcctgg tcgagctgga  180
cggcgacgta aacggccaca agttcagcgt gtccggcgag ggcgagggcg atgccaccta  240
cggcaagctg accctgaagt tcatctgcac caccggcaag ctgcccgtgc cctggcccac  300
cctcgtgacc accctgacct acggcgtgca gtgcttcagc cgctaccccg accacatgaa  360
gcagcacgac ttcttcaagt ccgccatgcc cgaaggctac gtccaggaaa tgaccatctt  420
cttcaaggac gacggcaact acaagacccg cgccgaggtg aagttcgagg gcgacaccct  480
ggtgaaccgc atcgagctga agggcatcga cttcaaggag gacggcaaca tcctggggca  540
caagctggag tacaactaca acagccacaa cgtctatatc atggccgaca agcagaagaa  600
cggcatcaag gtgaacttca agatccgcca caacatcgag gacggcagcg tgcagctcgc  660
cgaccactac cagcagaaca cccccatcgg cgacggcccc gtgctgctgc ccgacaacca  720
ctacctgagc acccagtccg ccctgagcaa agaccccaac gagaagcgcg atcacatggt  780
cctgctggag ttcgtgaccg ccgccgggat cactctcggc atggacgagc tgtacaaggg  840
atcccgcctg gaggaagaac ttcggaggag acttactgag taatctagag ggccctattc  900
tatagtgtca cctaaatgct agagctcgct gatcagcctc gactgtgcct tcta        954
```

```
SEQ ID NO: 314          moltype = DNA  length = 3538
FEATURE                 Location/Qualifiers
source                  1..3538
                        mol_type = other DNA
                        organism = synthetic construct
SEQUENCE: 314
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
```

```
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctaccggtg ctccacccaa tctctgggca gcgcagcgct acggccgtga gctcagaagg  540
atgtccgatg agttcgtcga ttccttcaaa aaggctagcc agctgcacct gccccaggtt  600
ctcgcagacg ccgtatcccg ccttgtactg ggcaagtttg gtgatcttac tgacaatttt  660
tcatctcctc atgcgaggcg gaaagtactc gcaggcgtcg tcatgacgac cggaactgac  720
gtgaaagacg ccaaagtcat ctctgtctcc acgggcacaa agtgcataaa cggggagtac  780
atgagcgacc gggggctggc actgaatgat tgtcacgctg aaataatatc taggcgatct  840
ctgcttagat ttctctacac tcaactcgaa ttgtacctta acaacaaaga tgaccagaaa  900
cgcagtatat ttcagaaatc agaacgcggc ggatttcgac ttaaggaaaa cgttcagttc  960
cacttgtata tcagcacatc cccttgcggt gacgcccgaa tcttttcccc gcacgagccg  1020
atattggagg agcccgcggc tagcggatca ggtccaggac gcctggagga agaacttcgg  1080
aggagacttt ctcctggaac cggtgacaga catcctaata ggaaggctag aggccaactt  1140
cggacgaaga ttgaaagtgg ccagggtact atcccggtgc ggtccaacgc tagtattcaa  1200
acgtgggacg gagtccttca aggtgaacgg ctgttgacaa tgagctgctc agacaaaatc  1260
gcgcgctgga atgtagtggg aatccaaggc agcctcttga gcatattcgt agaacccata  1320
tatttctcat ccattatttt gggctctctg tatcatggtg accatctgtc aagggctatg  1380
taccaacgaa tttctaatat cgaggatctt cctccactct atacactcaa taagcctctc  1440
ttgtccggga tatcaaacgc tgaggcccgc cagccaggga aagctcctaa cttcagtgtt  1500
aactggaccg ttggtgattc tgcgatagag gtcatcaacg ccacgacagg taaggatgag  1560
ctcggtagag cctcacgcct gtgtaaacac gcgttgtatt gtagatggat gagagtacat  1620
gggaaggtcc catctcactt gctccgaagc aagatcacta agcctaatgt gtatcatgag  1680
tcaaaactcg cggctaaaga ataccaggca gccaaagctc gacttttac agcttttatt  1740
aaggcagggc tcggggcatg ggtcgagaag ccgaccgagc aggaccaata ctctctgacg  1800
gggagcggag gtaccgccga agttcaatta caggaatcgg gtggaggtct ggtacaacct  1860
gggggctctc ttcgcctgag ttgcactgcc agtggagtta cgatttctgc acttaatgct  1920
atggcgatgg gttggtatcg tcaggcccca ggggaacgtc gcgtcatggt cgctgccgtt  1980
tccgaacgtg gcaatgctat gtaccgcgag tctgttcagg gccgcttcac ggttacccgc  2040
gattttacaa ataaaatggt atcgttgcaa atggacaact taaagccaga ggacactgct  2100
gtgtactact gtcacgtcct tgaagatcgt gtggattcct ttcatgatta ttgggggcag  2160
gggactcagg tcactgtatc ctcaggagct ggatctggag cctcaagtaa ccgggagctg  2220
gtggttgact ttctctccta caagctttcc cagaaaggat acagctggag tcagtttagt  2280
gatgtggaag agaacaggac tgaggcccca gaagggactg aatcggagat ggagaccccc  2340
agtgccatca atggcaaccc atcctggcac ctggcagaca gccccgcggt gaatggagcc  2400
actggccaca gcagcagttt ggatgcccgg gaggtgatcc ccatggcagc agtaaagcaa  2460
gcgctgaggg aggcaggcga cgagtttgaa ctgcggtacc ggcgggcatt cagtgacctg  2520
acatcccagc tccacatcac cccagggaca gcatatcaga gctttgaaca ggtagtgaat  2580
gaactcttcc gggatggggt aaactggggt cgcattgtgg ccttttctc cttcggcggg  2640
gcactgtgcg tggaaagcgt agacaaggag atgcaggtat tggtgagtcg gatcgcagct  2700
tggatggcca cttacctgaa tgaccaccta gagccttgga tccaggagaa cggcggctgg  2760
gatacttttg tggaactcta tgggaacaat ggatccagcg agctgattaa ggagaacatg  2820
cacatgaagc tgtacatgga gggcaccgtg gacaaccatc acttcaagtg cacatccgag  2880
ggcgaaggca agccctacga gggcacccag accatgagaa tcaaggtggt cgagggcggc  2940
cctctcccct tcgccttcga catcctggct actagcttcc tctacggcag caagaccttc  3000
atcaaccaca cccagggcat ccccgacttc ttcaagcagt ccttccctga gggcttcaca  3060
tgggagagag tcaccacata cgaagacggg ggcgtgctga ccgctaccca ggacaccagc  3120
ctccaggacg gctgcctcat ctacaacgtc aagatcagag gggtgaactt cacatccaac  3180
ggccctgtga tgcagaagaa aacactcggc tgggaggcct tcaccgagac gctgtacccc  3240
gctgacggcg gcctggaagg cagaaacgac atggccctga agctcgtggg cgggagccat  3300
ctgatcgcaa acatcaagac cacatataga tccaagaaac ccgctaagaa cctcaagatg  3360
cctggcgtct actatgtgga ctacagactg gaaagaatca aggaggccaa caacgagacc  3420
tacgtcgagc agcacgaggt ggcagtggcc agatactgcg acctccctag caaactgggg  3480
cacaagctta attaagggcc cgtttaaacc cgctgatcag cctcgactgt gccttcta    3538
```

```
SEQ ID NO: 315          moltype = DNA  length = 2845
FEATURE                 Location/Qualifiers
source                  1..2845
                        mol_type = other DNA
                        organism = synthetic construct
SEQUENCE: 315
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
```

-continued

```
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcgtcg tccggtggag aacttgatga attggtatac  1320
ttactagatg ggccaggtta tgaccctata cattgcgatg tagtgacaag ggcggcagc   1380
caccttttca attttgacag acatcctaat aggaaggcta gaggccaact tcggacgaag  1440
attgaaagtg gccagggtac tatcccggtg cggtccaacg ctagtattca aacgtgggac  1500
ggagtccttc aaggtgaacg gctgttgaca atgagctgct cagacaaaat cgcgcgctgg  1560
aatgtagtgg gaatccaagg cagcctcttg agcatattcg tagaacccat atatttctca  1620
tccattattt tgggctctct gtatcatggt gaccatctgt caagggctat gtaccaacga  1680
atttctaata tcgaggatct tcctccactc tatacactca ataagcctct cttgtccggg  1740
atatcaaacg ctgaggcccg ccagccaggg aaagctccta acttcagtgt taactggacc  1800
gttggtgatt ctgcgataga ggtcatcaac gccacgacag gtaaggatga gctcggtaga  1860
gcctcacgcc tgtgtaaaca cgcgttgtat tgtagatgga tgagagtaca tgggaaggtc  1920
ccatctcact tgctccgaag caagatcact aagcctaatg tgtatcatga gtcaaaactc  1980
gcggctaaag aataccaggc agccaaagct cgacttttta cagcttttat taaggcaggg  2040
ctcggggcat gggtcgagaa gccgaccgag caggaccaat tctctctgac ggggagcgga  2100
tccagcgagc tgattaagga gaacatgcac atgaagctgt acatggaggg caccgtggac  2160
aaccatcact tcaagtgcac atccgagggc gaaggcaagc cctacgaggg cacccagacc  2220
atgagaatca aggtggtcga gggcggccct ctccccttcg ccttcgacat cctggctact  2280
agcttcctct acggcagcaa gaccttcatc aaccacaccc agggcatccc cgacttcttc  2340
aagcagtcct tccctgaggg cttcacatgg gagagagtca ccacatacga agacgggggc  2400
gtgctgaccg ctacccagga caccagcctc caggacggct gcctcatcta caacgtcaag  2460
atcagagggg tgaacttcac atccaacggc cctgtgatgc agaagaaaac actcggctgg  2520
gaggccttca ccgagacgct gtaccccgct gacggcggcc tggaaggcag aaacgacatg  2580
gccctgaagc tcgtgggcgg gagccatctg atcgcaaaca tcaagaccac atatagatcc  2640
aagaaacccg ctaagaacct caagatgcct ggcgtctact atgtggacta cagactggaa  2700
agaatcaagg aggccaacaa cgagacctac gtcgagcagc acgaggtggc agtggccaga  2760
tactgcgacc tccctagcaa actggggcac aagcttaatt aagggcccgt ttaaacccgc  2820
tgatcagcct cgactgtgcc ttcta                                      2845

SEQ ID NO: 316          moltype = DNA  length = 3484
FEATURE                 Location/Qualifiers
source                  1..3484
                        mol_type = other DNA
                        organism = synthetic construct
SEQUENCE: 316
taatacgact cactataggg agacccaagc tggctagagg atcgaaccct taaggccacc  60
atggcgagca attttaccca gtttgtgctt gtggacaacg gcggcaccgg ggacgtgacg  120
gtggccccct ccaatttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatgggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcgtcg tccggtggag aacttgatga attggtatac  1320
ttactagatg ggccaggtta tgaccctata cattgcgatg tagtgacaag ggcggcagc   1380
caccttttca attttgacag acatcctaat aggaaggcta gaggccaact tcggacgaag  1440
attgaaagtg gccagggtac tatcccggtg cggtccaacg ctagtattca aacgtgggac  1500
ggagtccttc aaggtgaacg gctgttgaca atgagctgct cagacaaaat cgcgcgctgg  1560
aatgtagtgg gaatccaagg cagcctcttg agcatattcg tagaacccat atatttctca  1620
tccattattt tgggctctct gtatcatggt gaccatctgt caagggctat gtaccaacga  1680
atttctaata tcgaggatct tcctccactc tatacactca ataagcctct cttgtccggg  1740
atatcaaacg ctgaggcccg ccagccaggg aaagctccta acttcagtgt taactggacc  1800
gttggtgatt ctgcgataga ggtcatcaac gccacgacag gtaaggatga gctcggtaga  1860
gcctcacgcc tgtgtaaaca cgcgttgtat tgtagatgga tgagagtaca tgggaaggtc  1920
ccatctcact tgctccgaag caagatcact aagcctaatg tgtatcatga gtcaaaactc  1980
gcggctaaag aataccaggc agccaaagct cgacttttta cagcttttat taaggcaggg  2040
ctcggggcat gggtcgagaa gccgaccgag caggaccaat tctctctgac ggggggggagc  2100
gcggccggag gtagcggcgg aagcgcggcc gctcaggggt ctgttgttat tgttggtaga  2160
attattttat ctggtagtgg tagtatcacg gcctactccc aacagacgcg gggcctactt  2220
ggttgcatca tcactagcct cacaggccgg gacaagaacc aggtcgaagg ggaggttcaa  2280
gtggtttcta ccgcaacaca atctttcctg gcgacctgcg tcaacggcgt gtgctggact  2340
gtctaccatg gcgctggctc gaagacccta gccggtccaa aaggtccaat cacccaaatg  2400
```

```
tacaccaatg tagaccagga cctcgtcggc tggcaggcgc ctccaggggc gcgctccttg  2460
acaccatgca cctgtggcag ctcggacctt tacttggtca cgagacatgc tgatgtcatt  2520
ccggtgcgcc ggcgaggcga cagcagggga agtctactct cccccaggcc cgtctcctac  2580
ctgaaaggct cctcaggtgg tccattgctt tgcccttcgg ggcacgctgt gggcatcttc  2640
cgggctgctg tgtgcacccg gggggtcgcg aaggcggtgg acttcgtgcc cgttgagtct  2700
atggaaacta ccatgcggtc tgagagtgga tcaggtacca tgagcgagct gattaaggag  2760
aacatgcaca tgaagctgta catggagggc accgtggaca accatcactt caagtgcaca  2820
tccgagggcg aaggcaagcc ctacgagggc acccagacca tgagaatcaa ggtggtcgag  2880
ggcggccctc tccccttcgc cttcgacatc ctggctacta gcttcctcta cggcagcaag  2940
accttcatca accacaccca gggcatcccc gacttcttca agcagtcctt ccctgagggc  3000
ttcacatggg agagagtcac cacatacgaa gacgggggcg tgctgaccgc tacccaggac  3060
accagcctcc aggacggctg cctcatctac aacgtcaaga tcagaggggt gaacttcaca  3120
tccaacggcc ctgtgatgca gaagaaaaca ctcggctggg aggccttcac cgagacgctg  3180
taccccgctg acggcggcct ggaaggcaga aacgacatgg ccctgaagct cgtgggcggg  3240
agccatctga tcgcaaacat caagaccaca tatagatcca agaaacccgc taagaacctc  3300
aagatgcctg gcgtctacta tgtggactac agactggaaa gaatcaagga ggccaacaac  3360
gagacctacg tcgagcagca cgaggtggca gtggccagat actgcgacct ccctagcaaa  3420
ctggggcaca agcttaatta agggcccgtt taaacccgct gatcagcctc gactgtgcct  3480
tcta                                                                3484
```

```
SEQ ID NO: 317          moltype = DNA  length = 3484
FEATURE                 Location/Qualifiers
source                  1..3484
                        mol_type = other DNA
                        organism = synthetic construct
SEQUENCE: 317
taatacgact cactataggg agacccaagc tggctagagg atcgaaccct taaggccacc  60
atggcgagca attttaccca gtttgtgctt gtggacaacg gcggcaccgg ggacgtgacg  120
gtggcccccct ccaattttgc caatggcatt gcagaatgga taagctctaa cagcaggagc  180
caggcataca aggtgacctg cagcgtgagg cagtcaagcg ctcaaaacag gaagtacacc  240
attaaggtcg aagtgcccaa aggagcttgg aggtcttacc tgaacatgga actgacaatt  300
cctatcttcg cgaccaatag cgactgtgag ctgatcgtga aggccatgca aggcctgctg  360
aaagacggga atcccatacc cagcgccatc gccgctaact caggcattta cgctaatttc  420
actcagttcg tactggttga caatggggga accggcgacg ttaccgtggc tccaagcaac  480
ttcgctaacg ggatcgccga gtggatcagc agtaattcac gctcccaagc ctacaaagta  540
acctgctctg tacggcagag ttcagcccag aaccgaaagt ataccatcaa agtggaggtg  600
ccgaagggcg cctggcggag ctatctgaat atggagctga ccatccccat ctttgccacg  660
aacagcgatt gcgagctcat cgtcaaggcg atgcagggct tgctgaagga tggcaaccct  720
atcccgagcg caatagcagc caacagcggc atctatgggg gcagtgggag cggtgcagga  780
tctggtagtc cagctggggg aggagcaccg ggtagcggtg gggggtctca gctgcacctg  840
ccccaggttc tcgcagacgc cgtatcccgc cttgtactgg gcaagtttgg tgatcttact  900
gacaattttt catctcctca tgcgaggcgg aaagtactcg caggcgtcgt catgacgacc  960
ggaactgacg tgaaagacgc caaagtcatc tctgtctcca cgggcacaaa gtgcataaac  1020
ggggagtaca tgagcgaccg ggggctggca ctgaatgatt gtcacgctga aataatatct  1080
aggcgatctc tgcttagatt tctctacact caactcgaat tgtaccttaa caacaaagat  1140
gaccagaaac gcagtatatt tcagaaatca gaacgcggcg gatttcgact taaggaaaac  1200
gttcagttcc acttgtatat cagcacatcc ccttgcggtg acgcccgaat cttttccccg  1260
cacgagccga tattggagga gcccgcgtcg tccggtggag aacttgatga attggtatac  1320
ttactagatg ggccaggtta tgaccctata cattgcgatg tagtgacaag gggcggcagc  1380
cacctttca  attttgacag acatcctaat aggaaggcta gaggccaact tcggacgaag  1440
attgaaagtg gccagggtac tatcccggtg cggtccaacg ctagtattca aacgtgggac  1500
ggagtccttc aaggtgaacg gctgttgaca atgagctgct cagacaaaat cgcgcgctgg  1560
aatgtagtgg gaatccaagg cagcctcttg agcatattcg tagaacccat atatttctca  1620
tccattattt tgggctctct gtatcatggt gaccatctgt caagggctat gtaccaacga  1680
atttctaata tcgaggatct tcctccactc tatacactca ataagcctct cttgtccggg  1740
atatcaaacg ctgaggcccg ccagccaggg aaagctccta acttcagtgt taactggacc  1800
gttggtgatt ctgcgataga ggtcatcaac gccacgacag gtaaggatga gctcggtaga  1860
gcctcacgcc tgtgtaaaca cgcgttgtat tgtagatgga tgagagtaca tgggaaggtc  1920
ccatctcact tgctccgaag caagatcact aagcctaatg tgtatcatga gtcaaaactc  1980
gcggctaaag aataccaggc agccaaagct cgacttttta cagcttttat taaggcaggg  2040
ctcggggcat gggtcgagag gccgaccgag caggaccaat tctctgtgac ggggggggagc  2100
gcggccggag gtagcggcgg aagcgcggcc gctcaggggt ctgttgttat tgttggtaga  2160
attattttat ctggtagtgg tagtatcacg gcctactccc aacagacgcg gggcctactt  2220
ggttgcatca tcactagcct cacaggccgg gacaagaacc aggtcgaagg ggaggttcaa  2280
gtggtttcta ccgcaacaca atctttcctg gcgacctgcg tcaacggcgt gtgctggact  2340
gtctaccatg gcgctggctc gaagacccta gccggtccaa aaggtccaat cacccaaatg  2400
tacaccaatg tagaccagga cctcgtcggc tggcaggcgc ctccaggggc gcgctccttg  2460
acaccatgca cctgtggcag ctcggacctt tacttggtca cgagacatgc tgatgtcatt  2520
ccggtgcgcc ggcgaggcga cagcagggga agtctactct cccccaggcc cgtctcctac  2580
ctgaaaggct cctcaggtgg tccattgctt tgcccttcgg ggcacgctgt gggcatcttc  2640
cgggctgctg tgtgcacccg gggggtcgcg aaggcggtgg acttcgtgcc cgttgagtct  2700
atggaaacta ccatgcggtc tgagagtgga tcaggtacca tgagcgagct gattaaggag  2760
aacatgcaca tgaagctgta catggagggc accgtggaca accatcactt caagtgcaca  2820
tccgagggcg aaggcaagcc ctacgagggc acccagacca tgagaatcaa ggtggtcgag  2880
ggcggccctc tccccttcgc cttcgacatc ctggctacta gcttcctcta cggcagcaag  2940
accttcatca accacaccca gggcatcccc gacttcttca agcagtcctt ccctgagggc  3000
ttcacatggg agagagtcac cacatacgaa gacgggggcg tgctgaccgc tacccaggac  3060
accagcctcc aggacggctg cctcatctac aacgtcaaga tcagaggggt gaacttcaca  3120
tccaacggcc ctgtgatgca gaagaaaaca ctcggctggg aggccttcac cgagacgctg  3180
```

```
taccccgctg acggcggcct ggaaggcaga aacgacatgg ccctgaagct cgtgggcggg  3240
agccatctga tcgcaaacat caagaccaca tatagatcca agaaacccgc taagaacctc  3300
aagatgcctg gcgtctacta tgtggactac agactggaaa gaatcaagga ggccaacaac  3360
gagacctacg tcgagcagca cgaggtggca gtggccagat actgcgacct ccctagcaaa  3420
ctggggcaca agcttaatta agggcccgtt taaacccgct gatcagcctc gactgtgcct  3480
tcta                                                              3484

SEQ ID NO: 318          moltype = DNA  length = 3037
FEATURE                 Location/Qualifiers
source                  1..3037
                        mol_type = other DNA
                        organism = synthetic construct
SEQUENCE: 318
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg agaagatgtt  960
gtctgctgtc attcaatcta cggcaccggt gacagacatc ctaataggaa ggctagaggc  1020
caacttcgga cgaagattga aagtggccag ggtactatcc cggtgcggtc caacgctagt  1080
attcaaacgt gggacggagt ccttcaaggt gaacggctgt tgacaatgag ctgctcagac  1140
aaaatcgcgc gctggaatgt agtgggaatc caaggcagcc tcttgagcat attcgtagaa  1200
cccatatatt tctcatccat tattttgggc tctctgtatc atggtgacca tctgtcaagg  1260
gctatgtacc aacgaatttc taatatcgag gatcttcctc cactctatac actcaataag  1320
cctctcttgt ccgggatatc aaacgctgag gcccgccagc cagggaaagc tcctaacttc  1380
agtgttaact ggaccgttgg tgattctgcg atagaggtca tcaacgccac gacaggtaag  1440
gatgagctcg gtagagcctc acgcctgtgt aaacacgcgt tgtattgtag atggatgaga  1500
gtacatggga aggtcccatc tcacttgctc cgaagcaaga tcactaagcc taatgtgtat  1560
catgagtcaa aactcgcggc taaagaatac caggcagcca aagctcgact tttacagct   1620
tttattaagg cagggctcgg ggcatgggtc gagaagccga ccgagcagga ccaattctct  1680
ctgacgggga gcggtaccat gaaaaagaaa ggttctgttg ttattgttgg tagaattaat  1740
ttatctggtg acacggccta ctcccaacag acgcggggcc tagaaggttg ccaagagact  1800
agccaaacag gccgggacaa gaaccaggtc gaaggggagg ttcaagtggt ttctaccgca  1860
acacaatctt tcctggcgac ctccatcaac ggcgtgcttt ggactgtcta ccatggcgct  1920
ggcaccagaa ccattgccag cccaaaaggt ccagtgaccc aaatgtacac caatgtagac  1980
aaggacctcg tcggctggca ggcgcctcaa gggtcacgct ccttgacacc atgcacctgt  2040
ggcagctcgg acctttactt ggtcacgaga catgctgatg tcattccggt gcgccggcga  2100
ggcgacagca ggggaagtct actctccccc aggcccatct cctacctgaa aggctcctca  2160
ggtggtccat tgctttgccc tgctgggcac gctgtgggca tcttccgggc tgctgtgagt  2220
acccgggggg tcgcgaaggc ggtggacttc attcccgttg agtctctgga aactaccatg  2280
cggtctccag gatccagcga gctgattaag gagaacatgc acatgaagct gtacatggag  2340
ggcaccgtgg acaaccatca cttcaagtgc acatccgagg gcgaaggcaa gccctacgag  2400
ggcacccaga ccatgagaat caaggtggtc gagggcggcc ctctcccctt cgccttcgac  2460
atcctggcta ctagcttcct ctacggcagc aagaccttca tcaaccacac ccagggcatc  2520
cccgacttct tcaagcagtc cttccctgag ggcttcacat gggagagagt caccacatac  2580
gaagacgggg gcgtgctgac cgctacccag gacaccagcc tccaggacgg ctgcctcatc  2640
tacaacgtca agatcagagg ggtgaacttc acatccaacg gccctgtgat gcagaagaaa  2700
acactcggct gggaggcctt caccgagacc ctgtaccccg ctgacggcgg cctggaaggc  2760
agaaacgaca tggccctgaa gctcgtgggc gggagccatc tgatcgcaaa catcaagacc  2820
acatatagat ccaagaaacc cgctaagaac ctcaagatgc ctggcgtcta ctatgtggac  2880
tacagactgg aaagaatcaa ggaggccaac aacgagacct acgtcgagca gcacgaggtg  2940
gcagtggcca gatactgcga cctccctagc aaactggggc acaagcttaa ttaagggccc  3000
gtttaaaccc gctgatcagc ctcgactgtg ccttcta                           3037

SEQ ID NO: 319          moltype = DNA  length = 3037
FEATURE                 Location/Qualifiers
source                  1..3037
                        mol_type = other DNA
                        organism = synthetic construct
SEQUENCE: 319
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
```

```
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg agaagatgtt  960
gtctgctgtc attcaatcta cggcaccggt gacagacatc ctaataggaa ggctagaggc  1020
caacttcgga cgaagattga aagtggccag ggtactatcc cggtgcggtc caacgctagt  1080
attcaaacgt gggacggagt ccttcaaggt gaacggctgt tgacaatgag ctgctcagac  1140
aaaatcgcgc gctggaatgt agtgggaatc caaggcagcc tcttgagcat attcgtagaa  1200
cccatatatt tctcatccat tattttgggc tctctgtatc atggtgacca tctgtcaagg  1260
gctatgtacc aacgaatttc taatatcgag gatcttcctc cactctatac actcaataag  1320
cctctcttgt ccgggatatc aaacgctgag gcccgccagc cagggaaagc tcctaacttc  1380
agtgttaact ggaccgttgg tgattctgcg atagaggtca tcaacgccac gacaggtaag  1440
gatgagctcg gtagagcctc acgcctgtgt aaacacgcgt tgtattgtag atggatgaga  1500
gtacatggga aggtcccatc tcacttgctc cgaagcaaga tcactaagcc taatgtgtat  1560
catgagtcaa aactcgcggc taaagaatac caggcagcca aagctcgact tttacagct  1620
tttattaagg cagggctcgg ggcatgggtc gagaagccga ccgagcagga ccaattctct  1680
ctgacgggga gcggtaccat gaaaaagaaa ggttctgttg ttattgttgg tagaattaat  1740
ttatctggtg acacggccta ctcccaacag acgcggggcc tagaaggttg ccaagagact  1800
agccaaacag gccgggacaa gaaccaggtc gaaggggagg ttcaagtggt ttctaccgca  1860
acacaatctt tcctggcgac ctccatcaac ggcgtgcttt ggactgtcta ccatggcgct  1920
ggcaccagaa ccattgccag cccaaaaggt ccagtgaccc aaatgtacac caatgtagac  1980
aaggacctcg tcggctggca ggcgcctcaa gggtcacgct ccttgacacc atgcacctgt  2040
ggcagctcgg acctttactt ggtcacgaga catgctgatg tcattccggt gcgccggcga  2100
ggcgacagca ggggaagtct actctccccc aggcccatct cctacctgaa aggctccgca  2160
ggtggtccat tgctttgccc tgctgggcac gctgtgggca tcttccgggc tgctgtgagt  2220
acccgggggg tcgcgaaggc ggtggacttc attcccgttg agtctctgga aactaccatg  2280
cggtctccag gatccagcga gctgattaag gagaacatgc acatgaagct gtacatggag  2340
ggcaccgtgg acaaccatca cttcaagtgc acatccgagg gcgaaggcaa gccctacgag  2400
ggcacccaga ccatgagaat caaggtggtc gagggcggcc ctctcccctt cgccttcgac  2460
atcctggcta ctagcttcct ctacggcagc aagaccttca tcaaccacac ccagggcatc  2520
cccgacttct tcaagcagtc cttccctgag ggcttcacat gggagagagt caccacatac  2580
gaagacgggg gcgtgctgac cgctacccag gacaccagcc tccaggacgg ctgcctcatc  2640
tacaacgtca agatcagagg ggtgaacttc acatccaacg gccctgtgat gcagaagaaa  2700
acactcggct gggaggcctt caccgagacg ctgtaccccg ctgacggcgg cctggaaggc  2760
agaaacgaca tggccctgaa gctcgtgggc gggagccatc tgatcgcaaa catcaagacc  2820
acatatagat ccaagaaacc cgctaagaac ctcaagatgc ctggcgtcta ctatgtggac  2880
tacagactgg aaagaatcaa ggaggccaac aacgagacct acgtcgagca gcacgaggtg  2940
gcagtggcca gatactgcga cctccctagc aaactggggc acaagcttaa ttaagggccc  3000
gtttaaaccc gctgatcagc ctcgactgtg ccttcta                          3037
```

```
SEQ ID NO: 320          moltype = DNA  length = 3037
FEATURE                 Location/Qualifiers
source                  1..3037
                        mol_type = other DNA
                        organism = synthetic construct
SEQUENCE: 320
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg agaagatgtt  960
gtctgctgtc attcaatcta cggcaccggt gacagacatc ctaataggaa ggctagaggc  1020
caacttcgga cgaagattga aagtggccag ggtactatcc cggtgcggtc caacgctagt  1080
attcaaacgt gggacggagt ccttcaaggt gaacggctgt tgacaatgag ctgctcagac  1140
aaaatcgcgc gctggaatgt agtgggaatc caaggcagcc tcttgagcat attcgtagaa  1200
cccatatatt tctcatccat tattttgggc tctctgtatc atggtgacca tctgtcaagg  1260
gctatgtacc aacgaatttc taatatcgag gatcttcctc cactctatac actcaataag  1320
cctctcttgt ccgggatatc aaacgctgag gcccgccagc cagggaaagc tcctaacttc  1380
agtgttaact ggaccgttgg tgattctgcg atagaggtca tcaacgccac gacaggtaag  1440
gatgagctcg gtagagcctc acgcctgtgt aaacacgcgt tgtattgtag atggatgaga  1500
gtacatggga aggtcccatc tcacttgctc cgaagcaaga tcactaagcc taatgtgtat  1560
catgagtcaa aactcgcggc taaagaatac caggcagcca aagctcgact tttacagct  1620
tttattaagg cagggctcgg ggcatgggtc gagaagccga ccgagcagga ccaattctct  1680
gggacgggga gcggtaccat gaaaaagaaa ggttctgttg ttattgttgg tagaattaat  1740
```

```
ttatctggtg acacggccta ctcccaacag acgcggggcc tagaaggttg ccaagagact  1800
agccaaacag gccgggacaa gaaccaggtc gaaggggagg ttcaagtggt ttctaccgca  1860
acacaatctt tcctggcgac ctccatcaac ggcgtgcttt ggactgtcta ccatggcgct  1920
ggcaccagaa ccattgccag cccaaaaggt ccagtgaccc aaatgtacac caatgtagac  1980
aaggacctcg tcggctggca ggcgcctcaa gggtcacgct ccttgacacc atgcacctgt  2040
ggcagctcgg acctttactt ggtcacgaga catgctgatg tcattccggt gcgccggcga  2100
ggcgacagca ggggaagtct actctccccc aggcccatct cctacctgaa aggctcctca  2160
ggtggtccat tgctttgccc tgctgggcac gctgtgggca tcttccgggc tgctgtgagt  2220
acccgggggg tcgcgaaggc ggtggacttc attcccgttg agtctctgga aactaccatg  2280
cggtctccag gatccagcga gctgattaag gagaacatgc acatgaagct gtacatggag  2340
ggcaccgtgg acaaccatca cttcaagtgc acatccgagg gcgaaggcaa gccctacgag  2400
ggcacccaga ccatgagaat caaggtggtc gagggcggcc ctctcccctt cgccttcgac  2460
atcctggcta ctagcttcct ctacggcagc aagaccttca tcaaccacac ccagggcatc  2520
cccgacttct tcaagcagtc cttccctgag ggcttcacat gggagagagt caccacatac  2580
gaagacgggg gcgtgctgac cgctacccag gacaccagcc tccaggacgg ctgcctcatc  2640
tacaacgtca agatcagagg ggtgaacttc acatccaacg gccctgtgat gcagaagaaa  2700
acactcggct gggaggcctt caccgagacg ctgtaccccg ctgacggcgg cctggaaggc  2760
agaaacgaca tggccctgaa gctcgtgggc gggagccatc tgatcgcaaa catcaagacc  2820
acatatagat ccaagaaacc cgctaagaac ctcaagatgc ctggcgtcta ctatgtggac  2880
tacagactgg aaagaatcaa ggaggccaac aacgagacct acgtcgagca gcacgaggtg  2940
gcagtggcca gatactgcga cctccctagc aaactggggc acaagcttaa ttaagggccc  3000
gtttaaaccc gctgatcagc ctcgactgtg ccttcta                           3037

SEQ ID NO: 321          moltype = DNA  length = 3037
FEATURE                 Location/Qualifiers
source                  1..3037
                        mol_type = other DNA
                        organism = synthetic construct
SEQUENCE: 321
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg agaagatgtt  960
gtctgctgtc attcaatcta cggcaccggt gacagacatc ctaataggaa ggctagaggc  1020
caacttcgga cgaagattga aagtggccag ggtactatcc cggtgcggtc caacgctagt  1080
attcaaacgt gggacggagt ccttcaaggt gaacggctgt tgacaatgag ctgctcagac  1140
aaaatcgcgc gctggaatgt agtgggaatc caaggcagcc tcttgagcat attcgtagaa  1200
cccatatatt tctcatccat tattttgggc tctctgtatc atggtgacca tctgtcaagg  1260
gctatgtacc aacgaatttc taatatcgag gatcttcctc cactctatac actcaataag  1320
cctctcttgt ccgggatatc aaacgctgag gcccgccagc cagggaaagc tcctaacttc  1380
agtgttaact ggaccgttgg tgattctgcg atagaggtca tcaacgccac gacaggtaag  1440
gatgagctcg gtagagcctc acgcctgtgt aaacacgcgt tgtattgtag atggatgaga  1500
gtacatggga aggtcccatc tcacttgctc cgaagcaaga tcactaagcc taatgtgtat  1560
catgagtcaa aactcgcggc taaagaatac caggcagcca aagctcgact ttttacagct  1620
tttattaagg cagggctcgg ggcatgggtc gagaagccga ccgagcagga ccaattctct  1680
gggacgggga gcggtaccat gaaaaagaaa ggttctgttg ttattgttgg tagaattaat  1740
ttatctggtg acacggccta ctcccaacag acgcggggcc tagaaggttg ccaagagact  1800
agccaaacag gccgggacaa gaaccaggtc gaaggggagg ttcaagtggt ttctaccgca  1860
acacaatctt tcctggcgac ctccatcaac ggcgtgcttt ggactgtcta ccatggcgct  1920
ggcaccagaa ccattgccag cccaaaaggt ccagtgaccc aaatgtacac caatgtagac  1980
aaggacctcg tcggctggca ggcgcctcaa gggtcacgct ccttgacacc atgcacctgt  2040
ggcagctcgg acctttactt ggtcacgaga catgctgatg tcattccggt gcgccggcga  2100
ggcgacagca ggggaagtct actctccccc aggcccatct cctacctgaa aggctccgca  2160
ggtggtccat tgctttgccc tgctgggcac gctgtgggca tcttccgggc tgctgtgagt  2220
acccgggggg tcgcgaaggc ggtggacttc attcccgttg agtctctgga aactaccatg  2280
cggtctccag gatccagcga gctgattaag gagaacatgc acatgaagct gtacatggag  2340
ggcaccgtgg acaaccatca cttcaagtgc acatccgagg gcgaaggcaa gccctacgag  2400
ggcacccaga ccatgagaat caaggtggtc gagggcggcc ctctcccctt cgccttcgac  2460
atcctggcta ctagcttcct ctacggcagc aagaccttca tcaaccacac ccagggcatc  2520
cccgacttct tcaagcagtc cttccctgag ggcttcacat gggagagagt caccacatac  2580
gaagacgggg gcgtgctgac cgctacccag gacaccagcc tccaggacgg ctgcctcatc  2640
tacaacgtca agatcagagg ggtgaacttc acatccaacg gccctgtgat gcagaagaaa  2700
acactcggct gggaggcctt caccgagacg ctgtaccccg ctgacggcgg cctggaaggc  2760
agaaacgaca tggccctgaa gctcgtgggc gggagccatc tgatcgcaaa catcaagacc  2820
acatatagat ccaagaaacc cgctaagaac ctcaagatgc ctggcgtcta ctatgtggac  2880
tacagactgg aaagaatcaa ggaggccaac aacgagacct acgtcgagca gcacgaggtg  2940
gcagtggcca gatactgcga cctccctagc aaactggggc acaagcttaa ttaagggccc  3000
```

```
gtttaaaccc gctgatcagc ctcgactgtg ccttcta                        3037

SEQ ID NO: 322          moltype = DNA  length = 3037
FEATURE                 Location/Qualifiers
source                  1..3037
                        mol_type = other DNA
                        organism = synthetic construct
SEQUENCE: 322
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg agaagatgtt  960
gtctgctgtc attcaatcta cggcaccggt gacagacatc ctaataggaa ggctagaggc  1020
caacttcgga cgaagattga aagtggccag ggtactatcc cggtgcggtc caacgctagt  1080
attcaaacgt gggacggagt ccttcaaggt gaacggctgt tgacaatgag ctgctcagac  1140
aaaatcgcgc gctggaatgt agtgggaatc caaggcagcc tcttgagcat attcgtagaa  1200
cccatatatt tctcatccat tattttgggc tctctgtatc atggtgacca tctgtcaagg  1260
gctatgtacc aacgaatttc taatatcgag gatcttcctc cactctatac actcaataag  1320
cctctcttgt ccgggatatc aaacgctgag gcccgccagc cagggaaagc tcctaacttc  1380
agtgttaact ggaccgttgg tgattctgcg atagaggtca tcaacgccac gacaggtaag  1440
gatgagctcg gtagagcctc acgcctgtgt aaacacgcgt tgtattgtag atggatgaga  1500
gtacatggga aggtcccatc tcacttgctc cgaagcaaga tcactaagcc taatgtgtat  1560
catgagtcaa aactcgcggc taaagaatac caggcagcca aagctcgact ttttacagct  1620
tttattaagg cagggctcgg ggcatgggtc gagaagccga ccgagcagga ccaatactct  1680
ctgacgggga gcggtaccat gaaaaagaaa ggttctgttg ttattgttgg tagaattaat  1740
ttatctggtg acacggccta ctcccaacag acgcggggcc tagaaggttg ccaagagact  1800
agccaaacag gccgggacaa gaaccaggtc gaaggggagg ttcaagtggt ttctaccgca  1860
acacaatctt tcctggcgac ctccatcaac ggcgtgcttt ggactgtcta ccatggcgct  1920
ggcaccagaa ccattgccag cccaaaaggt ccagtgaccc aaatgtacac caatgtagac  1980
aaggacctcg tcggctggca ggcgcctcaa gggtcacgct ccttgacacc atgcacctgt  2040
ggcagctcgg acctttactt ggtcacgaga catgctgatg tcattccggt gcgccggcga  2100
ggcgacagca ggggaagtct actctccccc aggcccatct cctacctgaa aggctcctca  2160
ggtggtccat tgctttgccc tgctgggcac gctgtgggca tcttccgggc tgctgtgagt  2220
acccgggggg tcgcgaaggc ggtggacttc attcccgttg agtctctgga aactaccatg  2280
cggtctccag gatccagcga gctgattaag gagaacatgc acatgaagct gtacatggag  2340
ggcaccgtgg acaaccatca cttcaagtgc acatccgagg gcgaaggcaa gccctacgag  2400
ggcacccaga ccatgagaat caaggtggtc gagggcggcc ctctcccctt cgccttcgac  2460
atcctggcta ctagcttcct ctacggcagc aagaccttca tcaaccacac ccagggcatc  2520
cccgacttct tcaagcagtc cttccctgag ggcttcacat gggagagagt caccacatac  2580
gaagacgggg gcgtgctgac cgctacccag gacaccagcc tccaggacgg ctgcctcatc  2640
tacaacgtca agatcagagg ggtgaacttc acatccaacg gccctgtgat gcagaagaaa  2700
acactcggct gggaggcctt caccgagacg ctgtaccccg ctgacggcgg cctggaaggc  2760
agaaacgaca tggccctgaa gctcgtgggc gggagccatc tgatcgcaaa catcaagacc  2820
acatatagat ccaagaaacc cgctaagaac ctcaagatgc ctggcgtcta ctatgtggac  2880
tacagactgg aaagaatcaa ggaggccaac aacgagacct acgtcgagca gcacgaggtg  2940
gcagtggcca gatactgcga cctccctagc aaactggggc acaagcttaa ttaagggccc  3000
gtttaaaccc gctgatcagc ctcgactgtg ccttcta                        3037

SEQ ID NO: 323          moltype = DNA  length = 3037
FEATURE                 Location/Qualifiers
source                  1..3037
                        mol_type = other DNA
                        organism = synthetic construct
SEQUENCE: 323
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
```

```
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg agaagatgtt  960
gtctgctgtc attcaatcta cggcaccggt gacagacatc ctaataggaa ggctagaggc  1020
caacttcgga cgaagattga aagtggccag ggtactatcc cggtgcggtc caacgctagt  1080
attcaaacgt gggacggagt ccttcaaggt gaacggctgt tgacaatgag ctgctcagac  1140
aaaatcgcgc gctggaatgt agtgggaatc caaggcagcc tcttgagcat attcgtagaa  1200
cccatatatt tctcatccat tattttgggc tctctgtatc atggtgacca tctgtcaagg  1260
gctatgtacc aacgaatttc taatatcgag gatcttcctc cactctatac actcaataag  1320
cctctcttgt ccgggatatc aaacgctgag gcccgccagc cagggaaagc tcctaacttc  1380
agtgttaact ggaccgttgg tgattctgcg atagaggtca tcaacgccac gacaggtaag  1440
gatgagctcg gtagagcctc acgcctgtgt aaacacgcgt tgtattgtag atggatgaga  1500
gtacatggga aggtcccatc tcacttgctc cgaagcaaga tcactaagcc taatgtgtat  1560
catgagtcaa aactcgcggc taaagaatac caggcagcca aagctcgact ttttacagct  1620
tttattaagg cagggctcgg ggcatgggtc gagaagccga ccgagcagga ccaatactct  1680
ctgacgggga gcggtaccat gaaaaagaaa ggttctgttg ttattgttgg tagaattaat  1740
ttatctggtg acacggccta ctcccaacag acgcggggcc tagaaggttg ccaagagact  1800
agccaaacag gccgggacaa gaaccaggtc gaaggggagg ttcaagtggt ttctaccgca  1860
acacaatctt tcctggcgac ctccatcaac ggcgtgcttt ggactgtcta ccatggcgct  1920
ggcaccagaa ccattgccag cccaaaaggt ccagtgaccc aaatgtacac caatgtagac  1980
aaggacctcg tcggctggca ggcgcctcaa gggtcacgct ccttgacacc atgcacctgt  2040
ggcagctcgg acctttactt ggtcacgaga catgctgatg tcattccggt gcgccggcga  2100
ggcgacagca ggggaagtct actctccccc aggcccatct cctacctgaa aggctccgca  2160
ggtggtccat tgctttgccc tgctgggcac gctgtgggca tcttccgggc tgctgtgagt  2220
acccgggggg tcgcgaaggc ggtggacttc attcccgttg agtctctgga aactaccatg  2280
cggtctccag gatccagcga gctgattaag gagaacatgc acatgaagct gtacatggag  2340
ggcaccgtgg acaaccatca cttcaagtgc acatccgagg gcgaaggcaa gccctacgag  2400
ggcacccaga ccatgagaat caaggtggtc gagggcggcc ctctcccctt cgccttcgac  2460
atcctggcta ctagcttcct ctacggcagc aagaccttca tcaaccacac ccagggcatc  2520
cccgacttct tcaagcagtc cttccctgag ggcttcacat gggagagagt caccacatac  2580
gaagacgggg gcgtgctgac cgctacccag gacaccagcc tccaggacgg ctgcctcatc  2640
tacaacgtca agatcagagg ggtgaacttc acatccaacg gccctgtgat gcagaagaaa  2700
acactcggct gggaggcctt caccgagacg ctgtaccccg ctgacggcgg cctggaaggc  2760
agaaacgaca tggccctgaa gctcgtgggc gggagccatc tgatcgcaaa catcaagacc  2820
acatatagat ccaagaaacc cgctaagaac ctcaagatgc ctggcgtcta ctatgtggac  2880
tacagactgg aaagaatcaa ggaggccaac aacgagacct acgtcgagca gcacgaggtg  2940
gcagtggcca gatactgcga cctccctagc aaactggggc acaagcttaa ttaagggccc  3000
gtttaaaccc gctgatcagc ctcgactgtg ccttcta                           3037
```

```
SEQ ID NO: 324          moltype = DNA  length = 5421
FEATURE                 Location/Qualifiers
source                  1..5421
                        mol_type = other DNA
                        organism = synthetic construct
SEQUENCE: 324
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcgaaac atgaggatca cccatgtact agtgccacaa acttctctct  2040
```

```
gctaaagcaa gcaggtgatg ttgaagaaaa cccagggcct ggagggtccg agggcagggg  2100
aagtctccta acatgcgggg acgtggagga aaatcccggc ccatccggat atccctacga  2160
tgtgcccgat tacgctatcg atgtgagcaa gggcgaagaa gataacaagg cctctctccc  2220
agcgacacat gagttacaca tctttggctc catcaacggt gtggactttg acatggtggg  2280
tcagggcacc ggcaatccaa atgatggtta tgaggagtta aacctgaagt ccaccaaggg  2340
tgacctccag ttctccccct ggattctggt ccctcatatc gggtatggct tccatcagta  2400
cctgccctac cctgacggga tgtcgccttt ccaggccgcc atggtagatg gcagcggata  2460
ccaagtccat cgcacaatgc agtttgaaga tggtgcctcc cttactgtta actaccgcta  2520
cacctacgag ggaagccaca tcaaaggaga ggcccaggtg aaggggactg gtttccctgc  2580
tgacggtcct gtgatgacca actcgctgac cgctgcggac tggtgcaggt cgaagaagac  2640
ttaccccaac gacaaaacca tcatcagtac ctttaagtgg agttacacca ctggaaatgg  2700
caagagatac cggagcactg cgcggaccac ctacaccttt gccaagccaa tggcggctaa  2760
ctatctgaag aaccagccga tgtacgtgtt ccgtaagacg gagctcaagc actccaagac  2820
cgagctcaac ttcaaggagt ggcaaaaggc ctttaccgat gtgatgggaa tggacgagct  2880
gtataaggct agctaagcgg ccgctctaga gtcgacgggc cgcggtaaca attgttatgg  2940
cgtccaattt cactcagttt gtgctggttg acaacggcgg gaccggggac gttacggtag  3000
ccccctcaaa ctttgccaac ggtatagcgg agtggataag cagcaattct aggagtcaag  3060
catacaaagt tacatgcagc gtgcgccaat ctagcgctca gaatcgcaag tacaccatta  3120
aagtagaggt ccccaaggga gcctggagaa gctatcttaa catggagttg accataccaa  3180
tcttcgctac caactctgac tgtgaactca ttgtgaaagc catgcaaggt ctgctcaagg  3240
atggtaaccc aattccgtcc gctatcgctg ccaactctgg gatttacggg ggcagtggga  3300
gcggtgcagg atctggtagt ccagctgggg gaggagcacc gggtagcggt ggggggtctc  3360
agctgcacct gccccaggtt ctcgcagacg ccgtatcccg ccttgtactg ggcaagtttg  3420
gtgatcttac tgacaatttt tcatctcctc atgcgaggcg gaaagtactc gcaggcgtcg  3480
tcatgacgac cggaactgac gtgaaagacg ccaaagtcat ctctgtctcc acgggcacaa  3540
agtgcataaa cggggagtac atgagcgacc gggggctggc actgaatgat tgtcacgctg  3600
aaataatatc taggcgatct ctgcttagat ttctctacac tcaactcgaa ttgtacctta  3660
acaacaaaga tgaccagaaa cgcagtatat ttcagaaatc agaacgcggc ggatttcgac  3720
ttaaggaaaa cgttcagttc cacttgtata tcagcacatc cccttgcggt gacgcccgaa  3780
tcttttcccc gcacgagccg atattggagg agcccgcggc tagcgggtcg ggcaccggtg  3840
ctccacccaa tctctgggca gcgcagcgct acggccgtga gctcagaagg atgtccgatg  3900
agttcgtcga cagacatcct aataggaagg ctagaggcca acttcggacg aagattgaaa  3960
gtggccaggg tactatcccg gtgcggtcca acgctagtat tcaaacgtgg gacggagtcc  4020
ttcaaggtga acggctgttg acaatgagct gctcagacaa aatcgcgatg tggaatgtag  4080
tgggaatcca aggcagcctc ttgagcatat tcgtagaacc catatatttc tcatccatta  4140
ttttgggctc tctgtatcat ggtgaccatc tgtcaagggc tatgtaccaa cgaatttcta  4200
atatcgagga tcttcctcca ctctatacac tcaataagcc tctcttgtcc gggatatcaa  4260
acgctgaggc ccgccagcca gggaaagctc ctaacttcag tgttaactgg accgttggtg  4320
attctgcgat agaggtcatc aacgccacga caggtaagga tgagctcggt agagcctcac  4380
gcctgtgtaa acacgcgttg tattgtagat ggatgagagt acatgggaag gtcccatctc  4440
acttgctccg aagcaagatc actaagccta atgtgtatca tgagtcaaaa ctcgcggcta  4500
aagaatacca ggcagccaaa gctcgacttt ttacagcttt tattaaggca gggctcgggg  4560
catgggtcga gaagccgacc gagcaggacc aattctctct gacggggagc ggaggtacgg  4620
agaatttgta ttttcagagc ggctcgagtg gtggatcagg gagcgccgct tcaggatcca  4680
gcgagctgat taaggagaac atgcacatga agctgtacat ggagggcacc gtggacaacc  4740
atcacttcaa gtgcacatcc gagggcgaag gcaagcccta cgagggcacc cagaccatga  4800
gaatcaaggt ggtcgagggc ggccctctcc ccttcgcctt cgacatcctg gctactagct  4860
tcctctacgg cagcaagacc ttcatcaacc acacccaggg catccccgac ttcttcaagc  4920
agtccttccc tgagggcttc acatgggaga gagtcaccac atacgaagac gggggcgtgc  4980
tgaccgctac ccaggacacc agcctccagg acggctgcct catctacaac gtcaagatca  5040
gaggggtgaa cttcacatcc aacggccctg tgatgcagaa gaaaacactc ggctgggagg  5100
ccttcaccga gacgctgtac cccgctgacg gcggcctgga aggcagaaac gacatggccc  5160
tgaagctcgt gggcgggagc catctgatcg caaacatcaa gaccacatat agatccaaga  5220
aacccgctaa gaacctcaag atgcctggcg tctactatgt ggactacaga ctggaaagaa  5280
tcaaggaggc caacaacgag acctacgtcg agcagcacga ggtggcagtg gccagatact  5340
gcgacctccc tagcaaactg gggcacaagc ttaattaagg gcccgtttaa acccgctgat  5400
cagcctcgac tgtgccttct a                                          5421
```

```
SEQ ID NO: 325          moltype = DNA  length = 5421
FEATURE                 Location/Qualifiers
source                  1..5421
                        mol_type = other DNA
                        organism = synthetic construct
SEQUENCE: 325
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
```

```
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcgaaac atgaggatca cccatgtact agtgccacaa acttctctct  2040
gctaaagcaa gcaggtgatg ttgaagaaaa cccagggcct ggagggtccg agggcagggg  2100
aagtctccta acatgcgggg acgtggagga aaatcccggc ccatccggat atccctacga  2160
tgtgcccgat tacgctatcg atgtgagcaa gggcgaagaa gataacaagg cctctctccc  2220
agcgacacat gagttacaca tctttggctc catcaacggt gtggactttg acatggtggg  2280
tcagggcacc ggcaatccaa atgatggtta tgaggagtta aacctgaagt ccaccaaggg  2340
tgacctccag ttctccccct ggattctggt ccctcatatc gggtatggct tccatcagta  2400
cctgccctac cctgacggga tgtcgccttt ccaggccgcc atggtagatg gcagcggata  2460
ccaagtccat cgcacaatgc agtttgaaga tggtgcctcc cttactgtta actaccgcta  2520
cacctacgag ggaagccaca tcaaaggaga ggcccaggtg aaggggactg gtttccctgc  2580
tgacggtcct gtgatgacca actcgctgac cgctgcggac tggtgcaggt cgaagaagac  2640
ttaccccaac gacaaaacca tcatcagtac ctttaagtgg agttacacca ctggaaatgg  2700
caagagatac cggagcactg cgcggaccac ctacaccttt gccaagccaa tggcggctaa  2760
ctatctgaag aaccagccga tgtacgtgtt ccgtaagacg gagctcaagc actccaagac  2820
cgagctcaac ttcaaggagt ggcaaaaggc ctttaccgat gtgatgggaa tggacgagct  2880
gtataaggct agctaagcgg ccgctctaga gtcgacgggc cgcggtaaca attgttatgg  2940
cgtccaattt cactcagttt gtgctggttg acaacggcgg gaccggggac gttacggtag  3000
cccccctcaaa ctttgccaac ggtatagcgg agtggataag cagcaattct aggagtcaag  3060
catacaaagt tacatgcagc gtgcgccaat ctagcgctca gaatcgcaag tacaccatta  3120
aagtagaggt ccccaaggga gcctggagaa gctatcttaa catggagttg accataccaa  3180
tcttcgctac caactctgac tgtgaactca ttgtgaaagc catgcaaggt ctgctcaagg  3240
atggtaaccc aattccgtcc gctatcgctg ccaactctgg gatttacggg ggcagtggga  3300
gcggtgcagg atctggtagt ccagctgggg gaggagcacc gggtagcggt gggggggtctc  3360
agctgcacct gccccaggtt ctcgcagacg ccgtatcccg ccttgtactg ggcaagtttg  3420
gtgatcttac tgacaatttt tcatctcctc atgcgaggcg gaaagtactc gcaggcgtcg  3480
tcatgacgac cggaactgac gtgaaagacg ccaaagtcat ctctgtctcc acgggcacaa  3540
agtgcataaa cggggagtac atgagcgacc gggggctggc actgaatgat tgtcacgctg  3600
aaataatatc taggcgatct ctgcttagat ttctctacac tcaactcgaa ttgtacctta  3660
acaacaaaga tgaccagaaa cgcagtatat ttcagaaatc agaacgcggc ggatttcgac  3720
ttaaggaaaa cgttcagttc cacttgtata tcagcacatc cccttgcggt gacgcccgaa  3780
tcttttcccc gcacgagccg atattggagg agcccgcggc tagcgggtcg ggcaccggtg  3840
ctccacccaa tctctgggca gcgcagcgct acggccgtga gctcagaagg atgtccgatg  3900
agctggtcga cagacatcct aataggaagg ctagaggcca acttcggacg aagattgaaa  3960
gtggccaggg tactatcccg gtgcggtcca acgctagtat tcaaacgtgg gacggagtcc  4020
ttcaaggtga acggctgttg acaatgagct gctcagacaa aatcgcgatg tggaatgtag  4080
tgggaatcca aggcagcctc ttgagcatat tcgtagaacc catatatttc tcatccatta  4140
ttttgggctc tctgtatcat ggtgaccatc tgtcaagggc tatgtaccaa cgaatttcta  4200
atatcgagga tcttcctcca ctctatacac tcaataagcc tctcttgtcc gggatatcaa  4260
acgctgaggc ccgccagcca gggaaagctc ctaacttcag tgttaactgg accgttggtg  4320
attctgcgat agaggtcatc aacgccacga caggtaagga tgagctcggt agagcctcac  4380
gcctgtgtaa acacgcgttg tattgtagat ggatgagagt acatgggaag gtcccatctc  4440
acttgctccg aagcaagatc actaagccta atgtgtatca tgagtcaaaa ctcgcggcta  4500
aagaatacca ggcagccaaa gctcgacttt ttacagcttt tattaaggca gggctcgggg  4560
catgggtcga gaagccgacc gagcaggacc aattctctct gacggggagc ggaggtacgg  4620
agaatttgta ttttcagagc ggctcgagtg gtggatcagg gagcgccgct tcaggatcca  4680
gcgagctgat taaggagaac atgcacatga agctgtacat ggagggcacc gtggacaacc  4740
atcacttcaa gtgcacatcc gagggcgaag gcaagcccta cgagggcacc cagaccatga  4800
gaatcaaggt ggtcgagggc ggccctctcc ccttcgcctt cgacatcctg gctactagct  4860
tcctctacgg cagcaagacc ttcatcaacc acacccaggg catccccgac ttcttcaagc  4920
agtccttccc tgagggcttc acatgggaga gagtcaccac atacgaagac gggggcgtgc  4980
tgaccgctac ccaggacacc agcctccagg acggctgcct catctacaac gtcaagatca  5040
gaggggtgaa cttcacatcc aacggccctg tgatgcagaa gaaaacactc ggctgggagg  5100
ccttcaccga gacgctgtac cccgctgacg gcggcctgga aggcagaaac gacatggccc  5160
tgaagctcgt gggcgggagc catctgatcg caaacatcaa gaccacatat agatccaaga  5220
aacccgctaa gaacctcaag atgcctggcg tctactatgt ggactacaga ctggaaagaa  5280
tcaaggaggc caacaacgag acctacgtcg agcagcacga ggtggcagtg gccagatact  5340
gcgacctccc tagcaaactg gggcacaagc ttaattaagg gcccgtttaa acccgctgat  5400
cagcctcgac tgtgccttct a                                          5421
```

```
SEQ ID NO: 326         moltype = DNA  length = 5421
FEATURE                Location/Qualifiers
```

-continued

```
source                1..5421
                      mol_type = other DNA
                      organism = synthetic construct
SEQUENCE: 326
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcgaaac atgaggatca cccatgtact agtgccacaa acttctctct  2040
gctaaagcaa gcaggtgatg ttgaagaaaa cccagggcct ggagggtccg agggcagggg  2100
aagtctccta acatgcgggg acgtggagga aaatcccggc ccatccggat atccctacga  2160
tgtgcccgat tacgctatcg atgtgagcaa gggcgaagaa gataacaagg cctctctccc  2220
agcgacacat gagttacaca tctttggctc catcaacggt gtggactttg acatggtggg  2280
tcagggcacc ggcaatccaa atgatggtta tgaggagtta aacctgaagt ccaccaaggg  2340
tgacctccag ttctccccct ggattctggt ccctcatatc gggtatggct tccatcagta  2400
cctgccctac cctgacggga tgtcgccttt ccaggccgcc atggtagatg gcagcggata  2460
ccaagtccat cgcacaatgc agtttgaaga tggtgcctcc cttactgtta actaccgcta  2520
cacctacgag ggaagccaca tcaaaggaga ggcccaggtg aaggggactg gtttccctgc  2580
tgacggtcct gtgatgacca actcgctgac cgctgcggac tggtgcaggt cgaagaagac  2640
ttaccccaac gacaaaacca tcatcagtac ctttaagtgg agttacacca ctggaaatgg  2700
caagagatac cggagcactg cgcggaccac ctacaccttt gccaagccaa tggcggctaa  2760
ctatctgaag aaccagccga tgtacgtgtt ccgtaagacg gagctcaagc actccaagac  2820
cgagctcaac ttcaaggagt ggcaaaaggc ctttaccgat gtgatgggaa tggacgagct  2880
gtataaggct agctaagcgg ccgctctaga gtcgacgggc cgcggtaaca attgttatgg  2940
cgtccaattt cactcagttt gtgctggttg acaacggcgg gaccggggac gttacggtag  3000
ccccctcaaa ctttgccaac ggtatagcgg agtggataag cagcaattct aggagtcaag  3060
catacaaagt tacatgcagc gtgcgccaat ctagcgctca gaatcgcaag tacaccatta  3120
aagtagaggt ccccaaggga gcctggagaa gctatcttaa catggagttg accataccaa  3180
tcttcgctac caactctgac tgtgaactca ttgtgaaagc catgcaaggt ctgctcaagg  3240
atggtaaccc aattccgtcc gctatcgctg ccaactctgg gatttacggg ggcagtggga  3300
gcggtgcagg atctggtagt ccagctgggg gaggagcacc gggtagcggt ggggggtctc  3360
agctgcacct gccccaggtt ctcgcagacg ccgtatcccg ccttgtactg ggcaagtttg  3420
gtgatcttac tgacaatttt tcatctcctc atgcgaggcg gaaagtactc gcaggcgtcg  3480
tcatgacgac cggaactgac gtgaaagacg ccaaagtcat ctctgtctcc acgggcacaa  3540
agtgcataaa cggggagtac atgagcgacc gggggctggc actgaatgat tgtcacgctg  3600
aaataatatc taggcgatct ctgcttagat ttctctacac tcaactcgaa ttgtacctta  3660
acaacaaaga tgaccagaaa cgcagtatat ttcagaaatc agaacgcggc ggatttcgac  3720
ttaaggaaaa cgttcagttc cacttgtata tcagcacatc cccttgcggt gacgcccgaa  3780
tcttttcccc gcacgagccg atattggagg agcccgcggc tagcgggtcg ggcaccggtg  3840
ctccacccaa tctctgggca gcgcagcgct acggccgtga gctcagaagg atgtccgatg  3900
aggtggtcga cagacatcct aataggaagg ctagaggcca acttcggacg aagattgaaa  3960
gtggccaggg tactatcccg gtgcggtcca acgctagtat tcaaacgtgg gacggagtcc  4020
ttcaaggtga acggctgttg acaatgagct gctcagacaa aatcgcgatg tggaatgtag  4080
tgggaatcca aggcagcctc ttgagcatat tcgtagaacc catatatttc tcatccatta  4140
ttttgggctc tctgtatcat ggtgaccatc tgtcaagggc tatgtaccaa cgaatttcta  4200
atatcgagga tcttcctcca ctctatacac tcaataagcc tctcttgtcc gggatatcaa  4260
acgctgaggc ccgccagcca gggaaagctc ctaacttcag tgttaactgg accgttggtg  4320
attctgcgat agaggtcatc aacgccacga caggtaagga tgagctcggt agagcctcac  4380
gcctgtgtaa acacgcgttg tattgtagat ggatgagagt acatgggaag gtcccatctc  4440
acttgctccg aagcaagatc actaagccta atgtgtatca tgagtcaaaa ctcgcggcta  4500
```

```
aagaatacca ggcagccaaa gctcgacttt ttacagcttt tattaaggca gggctcgggg  4560
catgggtcga gaagccgacc gagcaggacc aattctctct gacggggagc ggaggtacgg  4620
agaatttgta ttttcagagc ggctcgagtg gtggatcagg gagcgccgct tcaggatcca  4680
gcgagctgat taaggagaac atgcacatga agctgtacat ggagggcacc gtggacaacc  4740
atcacttcaa gtgcacatcc gagggcgaag gcaagcccta cgagggcacc cagaccatga  4800
gaatcaaggt ggtcgagggc ggccctctcc ccttcgcctt cgacatcctg gctactagct  4860
tcctctacgg cagcaagacc ttcatcaacc acacccaggg catccccgac ttcttcaagc  4920
agtccttccc tgagggcttc acatgggaga gagtcaccac atacgaagac gggggcgtgc  4980
tgaccgctac ccaggacacc agcctccagg acggctgcct catctacaac gtcaagatca  5040
gaggggtgaa cttcacatcc aacggccctg tgatgcagaa gaaaacactc ggctgggagg  5100
ccttcaccga gacgctgtac cccgctgacg gcggcctgga aggcagaaac gacatggccc  5160
tgaagctcgt gggcgggagc catctgatcg caaacatcaa gaccacatat agatccaaga  5220
aacccgctaa gaacctcaag atgcctggcg tctactatgt ggactacaga ctggaaagaa  5280
tcaaggaggc caacaacgag acctacgtcg agcagcacga ggtggcagtg gccagatact  5340
gcgacctccc tagcaaactg gggcacaagc ttaattaagg gcccgtttaa acccgctgat  5400
cagcctcgac tgtgccttct a                                           5421

SEQ ID NO: 327          moltype = DNA  length = 5748
FEATURE                 Location/Qualifiers
source                  1..5748
                        mol_type = other DNA
                        organism = synthetic construct
SEQUENCE: 327
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtgccgctat  1020
ggcagaaatc ggtactggct ttccattcga cccccattat gtggaagtcc tgggcgagcg  1080
catgcactac gtcgatgttg gtccgcgcga tggcacccct gtgctgttcc tgcacggtaa  1140
cccgacctcc tcctacgtgt ggcgcaacat catcccgcat gttgcaccga cccatcgctg  1200
cattgctcca gacctgatcg gtatgggcaa atccgacaaa ccagacctgg gttatttctt  1260
cgacgaccac gtccgcttca tggatgcctt catcgaagcc ctgggtctgg aagaggtcgt  1320
cctggtcatt cacgactggg gctccgctct gggtttccac tgggccaagc gcaatccaga  1380
gcgcgtcaaa ggtattgcat ttatggagtt catccgccct atcccgacct gggacgaatg  1440
gccagaattt gcccgcgaga ccttccaggc cttccgcacc accgacgtcg gccgcaagct  1500
gatcatcgat cagaacgttt ttatcgaggg tacgctgccg atgggtgtcg tccgcccgct  1560
gactgaagtc gagatggacc attaccgcga gccgttcctg aatcctgttg accgcgagcc  1620
actgtggcgc ttcccaaacg agctgccaat cgccggtgag ccagcgaaca tcgtcgcgct  1680
ggtcgaagaa tacatggact ggctgcacca gtcccctgtc ccgaagctgc tgttctgggg  1740
caccccaggc gttctgatcc caccggccga agccgctcgc ctggccaaaa gcctgcctaa  1800
ctgcaaggct gtggacatcg gcccgggtct gaatctgctg caagaagaca acccggacct  1860
gatcggcagc gagatcgcgc gctggctgtc gacgctcgag atttctggca ccggtatggc  1920
atctatgact ggaggccaac agatgggtcc tgcaaccggg aattccgcgt agcgctagct  1980
ttgccagcgc cacgcgaaac atgaggatca cccatgtact agtgccacaa acttctctct  2040
gctaaagcaa gcaggtgatg ttgaagaaaa cccagggcct ggagggtccg agggcagggg  2100
aagtctccta acatgcgggg acgtggagga aaatcccggc ccatccggat atccctacga  2160
tgtgcccgat tacgctatcg atgtgagcaa gggcgaagaa gataacaagg cctctctccc  2220
agcgacacat gagttacaca tctttggctc catcaacggt gtggactttg acatggtggg  2280
tcagggcacc ggcaatccaa atgatggtta tgaggagtta aacctgaagt ccaccaaggg  2340
tgacctccag ttctccccct ggattctggt ccctcatatc gggtatggct tccatcagta  2400
cctgccctac cctgacggga tgtcgccttt ccaggccgcc atggtagatg gcagcggata  2460
ccaagtccat cgcacaatgc agtttgaaga tggtgcctcc cttactgtta actaccgcta  2520
cacctacgag ggaagccaca tcaaaggaga ggcccaggtg aaggggactg gtttccctgc  2580
tgacggtcct gtgatgacca actcgctgac cgctgcggac tggtgcaggt cgaagaagac  2640
ttaccccaac gacaaaacca tcatcagtac ctttaagtgg agttacacca ctggaaatgg  2700
caagagatac cggagcactg cgcggaccac ctacaccttt gccaagccaa tggcggctaa  2760
ctatctgaag aaccagccga tgtacgtgtt ccgtaagacg gagctcaagc actccaagac  2820
cgagctcaac ttcaaggagt ggcaaaaggc ctttaccgat gtgatgggaa tggacgagct  2880
gtataaggct agctaagcgg ccgctctaga gtcgacgggc cgcggtaaca attgttatgg  2940
cgagcaattt tacccagttt gtgcttgtgg acaacggcgg caccggggac gtgacggtgg  3000
ccccctccaa ttttgccaat ggcattgcag aatggataag ctctaacagc aggagccagg  3060
catacaaggt gacctgcagc gtgaggcagt caagcgctca aaacaggaag tacaccatta  3120
aggtcgaagt gcccaaagga gcttggaggt cttacctgaa catggaactg acaattccta  3180
tcttcgcgac caatagcgac tgtgagctga tcgtgaaggc catgcaaggc ctgctgaaag  3240
acgggaatcc catacccagc gccatcgccg ctaactcagg catttacgct aatttcactc  3300
agttcgtact ggttgacaat gggggaaccg gcgacgttac cgtggctcca agcaacttcg  3360
```

```
ctaacgggat cgccgagtgg atcagcagta attcacgctc ccaagcctac aaagtaacct  3420
gctctgtacg gcagagttca gcccagaacc gaaagtatac catcaaagtg gaggtgccga  3480
agggcgcctg gcggagctat ctgaatatgg agctgaccat ccccatcttt gccacgaaca  3540
gcgattgcga gctcatcgtc aaggcgatgc agggcttgct gaaggatggc aaccctatcc  3600
cgagcgcaat agcagccaac agcggcatct atggggcag tgggagcggt gcaggatctg  3660
gtagtccagc tgggggagga gcaccgggta gcggtggggg gtctaccggt gctccaccca  3720
atctctgggc agcgcagcgc tacggccgtg agctcagaag gatgtccgat gagttcgtcg  3780
attccttcaa aaaggctagc cagctgcacc tgccccaggt tctcgcagac gccgtatccc  3840
gccttgtact gggcaagttt ggtgatctta ctgacaattt ttcatctcct catgcgaggc  3900
ggaaagtact cgcaggcgtc gtcatgacga ccggaactga cgtgaaagac gccaaagtca  3960
tctctgtctc cacgggcaca aagtgcataa acggggagta catgagcgac cgggggctgg  4020
cactgaatga ttgtcacgct gaaataatat ctaggcgatc tctgcttaga tttctctaca  4080
ctcaactcga attgtacctt aacaacaaag atgaccagaa acgcagtata tttcagaaat  4140
cagaacgcgg cggatttcga cttaaggaaa acgttcagtt ccacttgtat atcagcacat  4200
ccccttgcgg tgacgcccga atcttttccc cgcacgagcc gatattggag gagcccgcgg  4260
acagacatcc taataggaag gctagaggcc aacttcggac gaagattgaa agtggccagg  4320
gtactatccc ggtgcggtcc aacgctagta ttcaaacgtg ggacggagtc cttcaaggtg  4380
aacggctgtt gacaatgagc tgctcagaca aaatcgcgcg ctggaatgta gtgggaatcc  4440
aaggcagcct cttgagcata ttcgtagaac ccatatattt ctcatccatt attttgggct  4500
ctctgtatca tggtgaccat ctgtcaaggg ctatgtacca acgaatttct aatatcgagg  4560
atcttcctcc actctataca ctcaataagc ctctcttgtc cgggatatca aacgctgagg  4620
cccgccagcc agggaaagct cctaacttca gtgttaactg gaccgttggt gattctgcga  4680
tagaggtcat caacgccacg acaggtaagg atgagctcgg tagagcctca cgcctgtgta  4740
aacacgcgtt gtattgtaga tggatgagag tacatgggaa ggtcccatct cacttgctcc  4800
gaagcaagat cactaagcct aatgtgtatc atgagtcaaa actcgcggct aaagaatacc  4860
aggcagccaa agctcgactt tttacagctt ttattaaggc agggctcggg gcatgggtcg  4920
agaagccgac cgagcaggac caatactctc tgacggggag cggaggtacg gagaatttgt  4980
attttcagag cgccgcttca ggatccagcg agctgattaa ggagaacatg cacatgaagc  5040
tgtacatgga gggcaccgtg gacaaccatc acttcaagtg cacatccgag ggcgaaggca  5100
agccctacga gggcacccag accatgagaa tcaaggtggt cgagggcggc cctctcccct  5160
tcgccttcga catcctggct actagcttcc tctacggcag caagaccttc atcaaccaca  5220
cccagggcat ccccgacttc ttcaagcagt ccttccctga gggcttcaca tgggagagag  5280
tcaccacata cgaagacggg ggcgtgctga ccgctaccca ggacaccagc ctccaggacg  5340
gctgcctcat ctacaacgtc aagatcagag gggtgaactt cacatccaac ggccctgtga  5400
tgcagaagaa aacactcggc tgggaggcct tcaccgagac gctgtacccc gctgacggcg  5460
gcctggaagg cagaaacgac atggccctga agctcgtggg cgggagccat ctgatcgcaa  5520
acatcaagac cacatataga tccaagaaac ccgctaagaa cctcaagatg cctggcgtct  5580
actatgtgga ctacagactg gaaagaatca aggaggccaa caacgagacc tacgtcgagc  5640
agcacgaggt ggcagtggcc agatactgcg acctccctag caaactgggg cacaagctta  5700
attaagggcc cgtttaaacc cgctgatcag cctcgactgt gccttcta             5748
```

```
SEQ ID NO: 328          moltype = AA  length = 334
FEATURE                 Location/Qualifiers
source                  1..334
                        mol_type = protein
                        organism = synthetic construct
SEQUENCE: 328
METDTLLLWV LLLWVPGSTG DGGGGYPYDV PDYAGELDEL VYLLDGPGYD PIHSGGSGGR  60
TMVSKGEELF TGVVPILVEL DGDVNGHKFS VSGEGEGDAT YGKLTLKFIC TTGKLPVPWP  120
TLVTTLTYGV QCFSRYPDHM KQHDFFKSAM PEGYVQERTI FFKDDGNYKT RAEVKFEGDT  180
LVNRIELKGI DFKEDGNILG HKLEYNYNSH NVYIMADKQK NGIKVNFKIR HNIEDGSVQL  240
ADHYQQNTPI GDGPVLLPDN HYLSTQSALS KDPNEKRDHM VLLEFVTAAG ITLGMDELYQ  300
LENGGISLLV QNTSWMLLLL LSLSLLQALD FISL                             334
```

```
SEQ ID NO: 329          moltype = AA  length = 315
FEATURE                 Location/Qualifiers
source                  1..315
                        mol_type = protein
                        organism = synthetic construct
SEQUENCE: 329
IETDTLLLWV LLLWVPGSTG DGGGGYPYDV PDYAGGGSGG RTMVSKGEEL FTGVVPILVE  60
LDGDVNGHKF SVSGEGEGDA TYGKLTLKFI CTTGKLPVPW PTLVTTLTYG VQCFSRYPDH  120
MKQHDFFKSA MPEGYVQERT IFFKDDGNYK TRAEVKFEGD TLVNRIELKG IDFKEDGNIL  180
GHKLEYNYNS HNVYIMADKQ KNGIKVNFKI RHNIEDGSVQ LADHYQQNTP IGDGPVLLPD  240
NHYLSTQSAL SKDPNEKRDH MVLLEFVTAA GITLGMDELY QLENGGISLL VQNTSWMLLL  300
LLSLSLLQAL DFISL                                                  315
```

```
SEQ ID NO: 330          moltype = AA  length = 640
FEATURE                 Location/Qualifiers
source                  1..640
                        mol_type = protein
                        organism = synthetic construct
SEQUENCE: 330
MALPVTALLL PLALLLHAAR PYPYDVPDYA TGMAEIGTGF PFDPHYVEVL GERMHYVDVG  60
PRDGTPVLFL HGNPTSSYVW RNIIPHVAPT HRCIAPDLIG MGKSDKPDLG YFFDDHVRFM  120
DAFIEALGLE EVVLVIHDWG SALGFHWAKR NPERVKGIAF MEFIRPIPTW DEWPEFARET  180
FQAFRTTDVG RKLIIDQNVF IEGTLPMGVV RPLTEVEMDH YREPFLNPVD REPLWRFPNE  240
LPIAGEPANI VALVEEYMDW LHQSPVPKLL FWGTPGVLIP PAEAARLAKS LPNCKAVDIG  300
PGLNLLQEDN PDLIGSEIAR WLSTLEISGG GGSGEGRGSL LTCGDVEENP RPYMRITHVR  360
```

-continued

```
PRVDYKDHDG DYKDHDIDYK DDDDKGTMEG RGSLLTCGDV EENPGPGSSE LIKENMHMKL  420
YMEGTVDNHH FKCTSEGEGK PYEGTQTMRI KVVEGGPLPF AFDILATSFL YGSKTFINHT  480
QGIPDFFKQS FPEGFTWERV TTYEDGGVLT ATQDTSLQDG CLIYNVKIRG VNFTSNGPVM  540
QKKTLGWEAF TETLYPADGG LEGRNDMALK LVGGSHLIAN IKTTYRSKKP AKNLKMPGVY  600
YVDYRLERIK EANNETYVEQ HEVAVARYCD LPSKLGHKLN                        640

SEQ ID NO: 331          moltype = AA  length = 296
FEATURE                 Location/Qualifiers
source                  1..296
                        mol_type = protein
                        organism = synthetic construct
SEQUENCE: 331
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYKDYKD  240
DDDKGSGATN FSLLKQAGDV EENPGPASAG SGEGRGSLLT CGDVEENPGP ATGNSA      296

SEQ ID NO: 332          moltype = AA  length = 233
FEATURE                 Location/Qualifiers
source                  1..233
                        mol_type = protein
                        organism = synthetic construct
SEQUENCE: 332
LCQRHAKHED HPCTSATNFS LLKQAGDVEE NPGPGGSEGR GSLLTCGDVE ENPGPSGYPY  60
DVPDYAHMVS KGEEDNMASL PATHELHIFG SINGVDFDMV GQGTGNPNDG YEELNLKSTK  120
GDLQFSPWIL VPHIGYGFHQ YLPYPDGMSP FQAAMVDGSG YQVHRTMQFE DGASLTVNYR  180
YTYEGSHIKG EAQVKGTGFP ADGPVMTNSL TAADWCRSKK TYPNDKTIIS TFK         233

SEQ ID NO: 333          moltype = AA  length = 81
FEATURE                 Location/Qualifiers
source                  1..81
                        mol_type = protein
                        organism = synthetic construct
SEQUENCE: 333
SYTTGVAPLD TMRITHGKRY RSTARTTYTF AKPMAANYLK NQPMYVFRKT ELKHSKTELN  60
FKEWQKAFTD VMGMDELYKA S                                            81

SEQ ID NO: 334          moltype = AA  length = 1155
FEATURE                 Location/Qualifiers
source                  1..1155
                        mol_type = protein
                        organism = synthetic construct
SEQUENCE: 334
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAA SPSRLEEELR  420
RRLTEPTGSG AGDRHPNRKA RGQLRTKIES GQGTIPVRSN ASIQTWDGVL QGERLLTMSC  480
SDKIAMWNVV GIQGSLLSIF VEPIYFSSII LGSLYHGDHL SRAMYQRISN IEDLPPLYTL  540
NKPLLSGISN AEARQPGKAP NFSVNWTVGD SAIEVINATT GKDELGRASR LCKHALYCRW  600
MRVHGKVPSH LLRSKITKPN VYHESKLAAK EYQAAKARLF TAFIKAGLGA WVEKPTEQDQ  660
FSVTGSGGTA EVQLQESGGG LVQPGGSLRL SCTASGVTIS ALNAMAMGWY RQAPGERRVM  720
VAAVSERGNA MYRESVQGRF TVTRDFTNKM VSLQMDNLKP EDTAVYYCHV LEDRVDSFHD  780
YWGQGTQVTV SSGAGSGGGG SGTMMDQVQL VESGGALVQP GGSLRLSCAA SGFPVNRYSM  840
RWYRQAPGKE REWVAGMSSA GDRSSYEDSV KGRFTISRDD ARNTVYLQMN SLKPEDTAVY  900
YCNVNVGFEY WGQGTQVTVS SMHSELIKEN MHMKLYMEGT VDNHHFKCTS EGEGKPYEGT  960
QTMRIKVVEG GPLPFAFDIL ATSFLYGSKT FINHTQGIPD FFKQSFPEGF TWERVTTYED  1020
GGVLTATQDT SLQDGCLIYN VKIRGVNFTS NGPVMQKKTL GWEAFTETLY PADGGLEGRN  1080
DMALKLVGGS HLIANIKTTY RSKKPAKNLK MPGVYYVDYR LERIKEANNE TYVEQHEVAV  1140
ARYCDLPSKL GHKLN                                                   1155

SEQ ID NO: 335          moltype = AA  length = 1155
FEATURE                 Location/Qualifiers
source                  1..1155
                        mol_type = protein
                        organism = synthetic construct
SEQUENCE: 335
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAA SPSRLEEELR  420
RRLTEPTGSG AGDRHPNRKA RGQLRTKIES GQGTIPVRSN ASIQTWDGVL QGERLLTMSC  480
```

-continued

```
SDKIAMWNVV GIQGSLLSIF VEPIYFSSII LGSLYHGDHL SRAMYQRISN IEDLPPLYTL  540
NKPLLSGISN AEARQPGKAP NFSVNWTVGD SAIEVINATT GKDELGRASR LCKHALYCRW  600
MRVHGKVPSH LLRSKITKPN VYHESKLAAK EYQAAKARLF TAFIKAGLGA WVEKPTEQDQ  660
FSGTGSGGTA EVQLQESGGG LVQPGGSLRL SCTASGVTIS ALNAMAMGWY RQAPGERRVM  720
VAAVSERGNA MYRESVQGRF TVTRDFTNKM VSLQMDNLKP EDTAVYYCHV LEDRVDSFHD  780
YWGQGTQVTV SSGAGSGGGG SGTMMDQVQL VESGGALVQP GGSLRLSCAA SGFPVNRYSM  840
RWYRQAPGKE REWVAGMSSA GDRSSYEDSV KGRFTISRDD ARNTVYLQMN SLKPEDTAVY  900
YCNVNVGFEY WGQGTQVTVS SMHSELIKEN MHMKLYMEGT VDNHHFKCTS EGEGKPYEGT  960
QTMRIKVVEG GPLPFAFDIL ATSFLYGSKT FINHTQGIPD FFKQSFPEGF TWERVTTYED  1020
GGVLTATQDT SLQDGCLIYN VKIRGVNFTS NGPVMQKKTL GWEAFTETLY PADGGLEGRN  1080
DMALKLVGGS HLIANIKTTY RSKKPAKNLK MPGVYYVDYR LERIKEANNE TYVEQHEVAV  1140
ARYCDLPSKL GHKLN                                                   1155

SEQ ID NO: 336         moltype = AA  length = 1155
FEATURE                Location/Qualifiers
source                 1..1155
                       mol_type = protein
                       organism = synthetic construct
SEQUENCE: 336
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAA SPSRLEEELR  420
RRLTEPTGSG AGDRHPNRKA RGQLRTKIES GQGTIPVRSN ASIQTWDGVL QGERLLTMSC  480
SDKIAMWNVV GIQGSLLSIF VEPIYFSSII LGSLYHGDHL SRAMYQRISN IEDLPPLYTL  540
NKPLLSGISN AEARQPGKAP NFSVNWTVGD SAIEVINATT GKDELGRASR LCKHALYCRW  600
MRVHGKVPSH LLRSKITKPN VYHESKLAAK EYQAAKARLF TAFIKAGLGA WVEKPTEQDQ  660
YSLTGSGGTA EVQLQESGGG LVQPGGSLRL SCTASGVTIS ALNAMAMGWY RQAPGERRVM  720
VAAVSERGNA MYRESVQGRF TVTRDFTNKM VSLQMDNLKP EDTAVYYCHV LEDRVDSFHD  780
YWGQGTQVTV SSGAGSGGGG SGTMMDQVQL VESGGALVQP GGSLRLSCAA SGFPVNRYSM  840
RWYRQAPGKE REWVAGMSSA GDRSSYEDSV KGRFTISRDD ARNTVYLQMN SLKPEDTAVY  900
YCNVNVGFEY WGQGTQVTVS SMHSELIKEN MHMKLYMEGT VDNHHFKCTS EGEGKPYEGT  960
QTMRIKVVEG GPLPFAFDIL ATSFLYGSKT FINHTQGIPD FFKQSFPEGF TWERVTTYED  1020
GGVLTATQDT SLQDGCLIYN VKIRGVNFTS NGPVMQKKTL GWEAFTETLY PADGGLEGRN  1080
DMALKLVGGS HLIANIKTTY RSKKPAKNLK MPGVYYVDYR LERIKEANNE TYVEQHEVAV  1140
ARYCDLPSKL GHKLN                                                   1155

SEQ ID NO: 337         moltype = AA  length = 1154
FEATURE                Location/Qualifiers
source                 1..1154
                       mol_type = protein
                       organism = synthetic construct
SEQUENCE: 337
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAA SGSGPGRLEE  420
ELRRRLSPGT GDRHPNRKAR GQLRTKIESG QGTIPVRSNA SIQTWDGVLQ GERLLTMSCS  480
DKIAMWNVVG IQGSLLSIFV EPIYFSSIIL GSLYHGDHLS RAMYQRISNI EDLPPLYTLN  540
KPLLSGISNA EARQPGKAPN FSVNWTVGDS AIEVINATTG KDELGRASRL CKHALYCRWM  600
RVHGKVPSHL LRSKITKPNV YHESKLAAKE YQAAKARLFT AFIKAGLGAW VEKPTEQDQF  660
SVTGSGGTAE VQLQESGGGL VQPGGSLRLS CTASGVTISA LNAMAMGWYR QAPGERRVMV  720
AAVSERGNAM YRESVQGRFT VTRDFTNKMV SLQMDNLKPE DTAVYYCHVL EDRVDSFHDY  780
WGQGTQVTVS SGAGSGGGGS GTMMDQVQLV ESGGALVQPG GSLRLSCAAS GFPVNRYSMR  840
WYRQAPGKER EWVAGMSSAG DRSSYEDSVK GRFTISRDDA RNTVYLQMNS LKPEDTAVYY  900
CNVNVGFEYW GQGTQVTVSS MHSELIKENM HMKLYMEGTV DNHHFKCTSE GEGKPYEGTQ  960
TMRIKVVEGG PLPFAFDILA TSFLYGSKTF INHTQGIPDF FKQSFPEGFT WERVTTYEDG  1020
GVLTATQDTS LQDGCLIYNV KIRGVNFTSN GPVMQKKTLG WEAFTETLYP ADGGLEGRND  1080
MALKLVGGSH LIANIKTTYR SKKPAKNLKM PGVYYVDYRL ERIKEANNET YVEQHEVAVA  1140
RYCDLPSKLG HKLN                                                    1154

SEQ ID NO: 338         moltype = AA  length = 1154
FEATURE                Location/Qualifiers
source                 1..1154
                       mol_type = protein
                       organism = synthetic construct
SEQUENCE: 338
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
```

-continued

```
DQKRSIFQKS ERGGFRLKEN VQFHLYISTS PCGDARIFSP HEPILEEPAA SGSGPGRLEE  420
ELRRRLSPGT GDRHPNRKAR GQLRTKIESG QGTIPVRSNA SIQTWDGVLQ GERLLTMSCS  480
DKIAMWNVVG IQGSLLSIFV EPIYFSSIIL GSLYHGDHLS RAMYQRISNI EDLPPLYTLN  540
KPLLSGISNA EARQPGKAPN FSVNWTVGDS AIEVINATTG KDELGRASRL CKHALYCRWM  600
RVHGKVPSHL LRSKITKPNV YHESKLAAKE YQAAKARLFT AFIKAGLGAW VEKPTEQDQF  660
SGTGSGGTAE VQLQESGGGL VQPGGSLRLS CTASGVTISA LNAMAMGWYR QAPGERRVMV  720
AAVSERGNAM YRESVQGRFT VTRDFTNKMV SLQMDNLKPE DTAVYYCHVL EDRVDSFHDY  780
WGQGTQVTVS SGAGSGGGGS GTMMDQVQLV ESGGALVQPG GSLRLSCAAS GFPVNRYSMR  840
WYRQAPGKER EWVAGMSSAG DRSSYEDSVK GRFTISRDDA RNTVYLQMNS LKPEDTAVYY  900
CNVNVGFEYW GQGTQVTVSS MHSELIKENM HMKLYMEGTV DNHHFKCTSE GEGKPYEGTQ  960
TMRIKVVEGG PLPFAFDILA TSFLYGSKTF INHTQGIPDF FKQSFPEGFT WERVTTYEDG  1020
GVLTATQDTS LQDGCLIYNV KIRGVNFTSN GPVMQKKTLG WEAFTETLYP ADGGLEGRND  1080
MALKLVGGSH LIANIKTTYR SKKPAKNLKM PGVYYVDYRL ERIKEANNET YVEQHEVAVA  1140
RYCDLPSKLG HKLN                                                    1154

SEQ ID NO: 339          moltype = AA  length = 1154
FEATURE                 Location/Qualifiers
source                  1..1154
                        mol_type = protein
                        organism = synthetic construct
SEQUENCE: 339
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAA SGSGPGRLEE  420
ELRRRLSPGT GDRHPNRKAR GQLRTKIESG QGTIPVRSNA SIQTWDGVLQ GERLLTMSCS  480
DKIAMWNVVG IQGSLLSIFV EPIYFSSIIL GSLYHGDHLS RAMYQRISNI EDLPPLYTLN  540
KPLLSGISNA EARQPGKAPN FSVNWTVGDS AIEVINATTG KDELGRASRL CKHALYCRWM  600
RVHGKVPSHL LRSKITKPNV YHESKLAAKE YQAAKARLFT AFIKAGLGAW VEKPTEQDQY  660
SLTGSGGTAE VQLQESGGGL VQPGGSLRLS CTASGVTISA LNAMAMGWYR QAPGERRVMV  720
AAVSERGNAM YRESVQGRFT VTRDFTNKMV SLQMDNLKPE DTAVYYCHVL EDRVDSFHDY  780
WGQGTQVTVS SGAGSGGGGS GTMMDQVQLV ESGGALVQPG GSLRLSCAAS GFPVNRYSMR  840
WYRQAPGKER EWVAGMSSAG DRSSYEDSVK GRFTISRDDA RNTVYLQMNS LKPEDTAVYY  900
CNVNVGFEYW GQGTQVTVSS MHSELIKENM HMKLYMEGTV DNHHFKCTSE GEGKPYEGTQ  960
TMRIKVVEGG PLPFAFDILA TSFLYGSKTF INHTQGIPDF FKQSFPEGFT WERVTTYEDG  1020
GVLTATQDTS LQDGCLIYNV KIRGVNFTSN GPVMQKKTLG WEAFTETLYP ADGGLEGRND  1080
MALKLVGGSH LIANIKTTYR SKKPAKNLKM PGVYYVDYRL ERIKEANNET YVEQHEVAVA  1140
RYCDLPSKLG HKLN                                                    1154

SEQ ID NO: 340          moltype = AA  length = 241
FEATURE                 Location/Qualifiers
source                  1..241
                        mol_type = protein
                        organism = synthetic construct
SEQUENCE: 340
MVSKGEELFT GVVPILVELD GDVNGHKFSV SGEGEGDATY GKLTLKFICT TGKLPVPWPT  60
LVTTLTYGVQ CFSRYPDHMK QHDFFKSAMP EGYVQEMTIF FKDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSALSK DPNEKRDHMV LLEFVTAAGI TLGMDELYKG  240
S                                                                  241

SEQ ID NO: 341          moltype = AA  length = 253
FEATURE                 Location/Qualifiers
source                  1..253
                        mol_type = protein
                        organism = synthetic construct
SEQUENCE: 341
MVSKGEELFT GVVPILVELD GDVNGHKFSV SGEGEGDATY GKLTLKFICT TGKLPVPWPT  60
LVTTLTYGVQ CFSRYPDHMK QHDFFKSAMP EGYVQEMTIF FKDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSALSK DPNEKRDHMV LLEFVTAAGI TLGMDELYKG  240
SRLEEELRRR LTE                                                     253

SEQ ID NO: 342          moltype = AA  length = 1144
FEATURE                 Location/Qualifiers
source                  1..1144
                        mol_type = protein
                        organism = synthetic construct
SEQUENCE: 342
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG STGAPPNLWA AQRYGRELRR MSDEFVDSFK KASQLHLPQV  180
LADAVSRLVL GKFGDLTDNF SSPHARRKVL AGVVMTTGTD VKDAKVISVS TGTKCINGEY  240
MSDRGLALND CHAEIISRRS LLRFLYTQLE LYLNNKDDQK RSIFQKSERG GFRLKENVQF  300
HLYISTSPCG DARIFSPHEP ILEEPAASGS GPGRLEEELR RRLSPGTGDR HPNRKARGQL  360
RTKIESGQGT IPVRSNASIQ TWDGVLQGER LLTMSCSDKI ARWNVVGIQG SLLSIFVEPI  420
```

```
YFSSIILGSL YHGDHLSRAM YQRISNIEDL PPLYTLNKPL LSGISNAEAR QPGKAPNFSV  480
NWTVGDSAIE VINATTGKDE LGRASRLCKH ALYCRWMRVH GKVPSHLLRS KITKPNVYHE  540
SKLAAKEYQA AKARLFTAFI KAGLGAWVEK PTEQDQYSLT GSGGTAEVQL QESGGGLVQP  600
GGSLRLSCTA SGVTISALNA MAMGWYRQAP GERRVMVAAV SERGNAMYRE SVQGRFTVTR  660
DFTNKMVSLQ MDNLKPEDTA VYYCHVLEDR VDSFHDYWGQ GTQVTVSSGA GSGASSNREL  720
VVDFLSYKLS QKGYSWSQFS DVEENRTEAP EGTESEMETP SAINGNPSWH LADSPAVNGA  780
TGHSSSLDAR EVIPMAAVKQ ALREAGDEFE LRYRRAFSDL TSQLHITPGT AYQSFEQVVN  840
ELFRDGVNWG RIVAFFSFGG ALCVESVDKE MQVLVSRIAA WMATYLNDHL EPWIQENGGW  900
DTFVELYGNN GSSELIKENM HMKLYMEGTV DNHHFKCTSE GEGKPYEGTQ TMRIKVVEGG  960
PLPFAFDILA TSFLYGSKTF INHTQGIPDF FKQSFPEGFT WERVTTYEDG GVLTATQDTS  1020
LQDGCLIYNV KIRGVNFTSN GPVMQKKTLG WEAFTETLYP ADGGLEGRND MALKLVGGSH  1080
LIANIKTTYR SKKPAKNLKM PGVYYVDYRL ERIKEANNET YVEQHEVAVA RYCDLPSKLG  1140
HKLN                                                              1144

SEQ ID NO: 343          moltype = AA  length = 913
FEATURE                 Location/Qualifiers
source                  1..913
                        mol_type = protein
                        organism = synthetic construct
SEQUENCE: 343
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSG SSELIKENMH MKLYMEGTVD NHHFKCTSEG EGKPYEGTQT  720
MRIKVVEGGP LPFAFDILAT SFLYGSKTFI NHTQGIPDFF KQSFPEGFTW ERVTTYEDGG  780
VLTATQDTSL QDGCLIYNVK IRGVNFTSNG PVMQKKTLGW EAFTETLYPA DGGLEGRNDM  840
ALKLVGGSHL IANIKTTYRS KKPAKNLKMP GVYYVDYRLE RIKEANNETY VEQHEVAVAR  900
YCDLPSKLGH KLN                                                    913

SEQ ID NO: 344          moltype = AA  length = 1125
FEATURE                 Location/Qualifiers
source                  1..1125
                        mol_type = protein
                        organism = synthetic construct
SEQUENCE: 344
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
ASRLCKHALY CRWMRVHGKV PSHLLRSKIT KPNVYHESKL AAKEYQAAKA RLFTAFIKAG  660
LGAWVEKPTE QDQFSLTGSA AGGSGGSAAA QGSVVIVGRI ILSGSGSITA YSQQTRGLLG  720
CIITSLTGRD KNQVEGEVQV VSTATQSFLA TCVNGVCWTV YHGAGSKTLA GPKGPITQMY  780
TNVDQDLVGW QAPPGARSLT PCTCGSSDLY LVTRHADVIP VRRRGDSRGS LLSPRPVSYL  840
KGSSGGPLLC PSGHAVGIFR AAVCTRGVAK AVDFVPVESM ETTMRSESGS GTMSELIKEN  900
MHMKLYMEGT VDNHHFKCTS EGEGKPYEGT QTMRIKVVEG GPLPFAFDIL ATSFLYGSKT  960
FINHTQGIPD FFKQSFPEGF TWERVTTYED GGVLTATQDT SLQDGCLIYN VKIRGVNFTS  1020
NGPVMQKKTL GWEAFTETLY PADGGLEGRN DMALKLVGGS HLIANIKTTY RSKKPAKNLK  1080
MPGVYYVDYR LERIKEANNE TYVEQHEVAV ARYCDLPSKL GHKLN                 1125

SEQ ID NO: 345          moltype = AA  length = 1125
FEATURE                 Location/Qualifiers
source                  1..1125
                        mol_type = protein
                        organism = synthetic construct
SEQUENCE: 345
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSQLHL PQVLADAVSR LVLGKFGDLT DNFSSPHARR KVLAGVVMTT  300
GTDVKDAKVI SVSTGTKCIN GEYMSDRGLA LNDCHAEIIS RRSLLRFLYT QLELYLNNKD  360
DQKRSIFQKS ERGGFRLKEN VQFHLYISTS PCGDARIFSP HEPILEEPAS SGGELDELVY  420
LLDGPGYDPI HCDVVTRGGS HLFNFDRHPN RKARGQLRTK IESGQGTIPV RSNASIQTWD  480
GVLQGERLLT MSCSDKIARW NVVGIQGSLL SIFVEPIYFS SIILGSLYHG DHLSRAMYQR  540
ISNIEDLPPL YTLNKPLLSG ISNAEARQPG KAPNFSVNWT VGDSAIEVIN ATTGKDELGR  600
```

-continued

```
ASRLCKHALY CRWMRVHGKV PSHLLRSKIT KPNVYHESKL AAKEYQAAKA RLFTAFIKAG  660
LGAWVERPTE QDQFSVTGSA AGGSGGSAAA QGSVVIVGRI ILSGSGSITA YSQQTRGLLG  720
CIITSLTGRD KNQVEGEVQV VSTATQSFLA TCVNGVCWTV YHGAGSKTLA GPKGPITQMY  780
TNVDQDLVGW QAPPGARSLT PCTCGSSDLY LVTRHADVIP VRRRGDSRGS LLSPRPVSYL  840
KGSSGGPLLC PSGHAVGIFR AAVCTRGVAK AVDFVPVESM ETTMRSESGS GTMSELIKEN  900
MHMKLYMEGT VDNHHFKCTS EGEGKPYEGT QTMRIKVVEG GPLPFAFDIL ATSFLYGSKT  960
FINHTQGIPD FFKQSFPEGF TWERVTTYED GGVLTATQDT SLQDGCLIYN VKIRGVNFTS  1020
NGPVMQKKTL GWEAFTETLY PADGGLEGRN DMALKLVGGS HLIANIKTTY RSKKPAKNLK  1080
MPGVYYVDYR LERIKEANNE TYVEQHEVAV ARYCDLPSKL GHKLN                 1125

SEQ ID NO: 346         moltype = AA  length = 977
FEATURE                Location/Qualifiers
source                 1..977
                       mol_type = protein
                       organism = synthetic construct
SEQUENCE: 346
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGEDV  300
VCCHSIYGTG DRHPNRKARG QLRTKIESGQ GTIPVRSNAS IQTWDGVLQG ERLLTMSCSD  360
KIARWNVVGI QGSLLSIFVE PIYFSSIILG SLYHGDHLSR AMYQRISNIE DLPPLYTLNK  420
PLLSGISNAE ARQPGKAPNF SVNWTVGDSA IEVINATTGK DELGRASRLC KHALYCRWMR  480
VHGKVPSHLL RSKITKPNVY HESKLAAKEY QAAKARLFTA FIKAGLGAWV EKPTEQDQFS  540
LTGSGTMKKK GSVVIVGRIN LSGDTAYSQQ TRGLEGCQET SQTGRDKNQV EGEVQVVSTA  600
TQSFLATSIN GVLWTVYHGA GTRTIASPKG PVTQMYTNVD KDLVGWQAPQ GSRSLTPCTC  660
GSSDLYLVTR HADVIPVRRR GDSRGSLLSP RPISYLKGSS GGPLLCPAGH AVGIFRAAVS  720
TRGVAKAVDF IPVESLETTM RSPGSSELIK ENMHMKLYME GTVDNHHFKC TSEGEGKPYE  780
GTQTMRIKVV EGGPLPFAFD ILATSFLYGS KTFINHTQGI PDFFKQSFPE GFTWERVTTY  840
EDGGVLTATQ DTSLQDGCLI YNVKIRGVNF TSNGPVMQKK TLGWEAFTET LYPADGGLEG  900
RNDMALKLVG GSHLIANIKT TYRSKKPAKN LKMPGVYYVD YRLERIKEAN NETYVEQHEV  960
AVARYCDLPS KLGHKLN                                                977

SEQ ID NO: 347         moltype = AA  length = 977
FEATURE                Location/Qualifiers
source                 1..977
                       mol_type = protein
                       organism = synthetic construct
SEQUENCE: 347
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGEDV  300
VCCHSIYGTG DRHPNRKARG QLRTKIESGQ GTIPVRSNAS IQTWDGVLQG ERLLTMSCSD  360
KIARWNVVGI QGSLLSIFVE PIYFSSIILG SLYHGDHLSR AMYQRISNIE DLPPLYTLNK  420
PLLSGISNAE ARQPGKAPNF SVNWTVGDSA IEVINATTGK DELGRASRLC KHALYCRWMR  480
VHGKVPSHLL RSKITKPNVY HESKLAAKEY QAAKARLFTA FIKAGLGAWV EKPTEQDQFS  540
LTGSGTMKKK GSVVIVGRIN LSGDTAYSQQ TRGLEGCQET SQTGRDKNQV EGEVQVVSTA  600
TQSFLATSIN GVLWTVYHGA GTRTIASPKG PVTQMYTNVD KDLVGWQAPQ GSRSLTPCTC  660
GSSDLYLVTR HADVIPVRRR GDSRGSLLSP RPISYLKGSA GGPLLCPAGH AVGIFRAAVS  720
TRGVAKAVDF IPVESLETTM RSPGSSELIK ENMHMKLYME GTVDNHHFKC TSEGEGKPYE  780
GTQTMRIKVV EGGPLPFAFD ILATSFLYGS KTFINHTQGI PDFFKQSFPE GFTWERVTTY  840
EDGGVLTATQ DTSLQDGCLI YNVKIRGVNF TSNGPVMQKK TLGWEAFTET LYPADGGLEG  900
RNDMALKLVG GSHLIANIKT TYRSKKPAKN LKMPGVYYVD YRLERIKEAN NETYVEQHEV  960
AVARYCDLPS KLGHKLN                                                977

SEQ ID NO: 348         moltype = AA  length = 977
FEATURE                Location/Qualifiers
source                 1..977
                       mol_type = protein
                       organism = synthetic construct
SEQUENCE: 348
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGEDV  300
VCCHSIYGTG DRHPNRKARG QLRTKIESGQ GTIPVRSNAS IQTWDGVLQG ERLLTMSCSD  360
KIARWNVVGI QGSLLSIFVE PIYFSSIILG SLYHGDHLSR AMYQRISNIE DLPPLYTLNK  420
PLLSGISNAE ARQPGKAPNF SVNWTVGDSA IEVINATTGK DELGRASRLC KHALYCRWMR  480
VHGKVPSHLL RSKITKPNVY HESKLAAKEY QAAKARLFTA FIKAGLGAWV EKPTEQDQFS  540
GTGSGTMKKK GSVVIVGRIN LSGDTAYSQQ TRGLEGCQET SQTGRDKNQV EGEVQVVSTA  600
TQSFLATSIN GVLWTVYHGA GTRTIASPKG PVTQMYTNVD KDLVGWQAPQ GSRSLTPCTC  660
GSSDLYLVTR HADVIPVRRR GDSRGSLLSP RPISYLKGSS GGPLLCPAGH AVGIFRAAVS  720
TRGVAKAVDF IPVESLETTM RSPGSSELIK ENMHMKLYME GTVDNHHFKC TSEGEGKPYE  780
GTQTMRIKVV EGGPLPFAFD ILATSFLYGS KTFINHTQGI PDFFKQSFPE GFTWERVTTY  840
EDGGVLTATQ DTSLQDGCLI YNVKIRGVNF TSNGPVMQKK TLGWEAFTET LYPADGGLEG  900
```

-continued

```
RNDMALKLVG GSHLIANIKT TYRSKKPAKN LKMPGVYYVD YRLERIKEAN NETYVEQHEV  960
AVARYCDLPS KLGHKLN                                                  977

SEQ ID NO: 349          moltype = AA  length = 977
FEATURE                 Location/Qualifiers
source                  1..977
                        mol_type = protein
                        organism = synthetic construct
SEQUENCE: 349
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGEDV  300
VCCHSIYGTG DRHPNRKARG QLRTKIESGQ GTIPVRSNAS IQTWDGVLQG ERLLTMSCSD  360
KIARWNVVGI QGSLLSIFVE PIYFSSIILG SLYHGDHLSR AMYQRISNIE DLPPLYTLNK  420
PLLSGISNAE ARQPGKAPNF SVNWTVGDSA IEVINATTGK DELGRASRLC KHALYCRWMR  480
VHGKVPSHLL RSKITKPNVY HESKLAAKEY QAAKARLFTA FIKAGLGAWV EKPTEQDQFS  540
GTGSGTMKKK GSVVIVGRIN LSGDTAYSQQ TRGLEGCQET SQTGRDKNQV EGEVQVVSTA  600
TQSFLATSIN GVLWTVYHGA GTRTIASPKG PVTQMYTNVD KDLVGWQAPQ GSRSLTPCTC  660
GSSDLYLVTR HADVIPVRRR GDSRGSLLSP RPISYLKGSA GGPLLCPAGH AVGIFRAAVS  720
TRGVAKAVDF IPVESLETTM RSPGSSELIK ENMHMKLYME GTVDNHHFKC TSEGEGKPYE  780
GTQTMRIKVV EGGPLPFAFD ILATSFLYGS KTFINHTQGI PDFFKQSFPE GFTWERVTTY  840
EDGGVLTATQ DTSLQDGCLI YNVKIRGVNF TSNGPVMQKK TLGWEAFTET LYPADGGLEG  900
RNDMALKLVG GSHLIANIKT TYRSKKPAKN LKMPGVYYVD YRLERIKEAN NETYVEQHEV  960
AVARYCDLPS KLGHKLN                                                  977

SEQ ID NO: 350          moltype = AA  length = 977
FEATURE                 Location/Qualifiers
source                  1..977
                        mol_type = protein
                        organism = synthetic construct
SEQUENCE: 350
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGEDV  300
VCCHSIYGTG DRHPNRKARG QLRTKIESGQ GTIPVRSNAS IQTWDGVLQG ERLLTMSCSD  360
KIARWNVVGI QGSLLSIFVE PIYFSSIILG SLYHGDHLSR AMYQRISNIE DLPPLYTLNK  420
PLLSGISNAE ARQPGKAPNF SVNWTVGDSA IEVINATTGK DELGRASRLC KHALYCRWMR  480
VHGKVPSHLL RSKITKPNVY HESKLAAKEY QAAKARLFTA FIKAGLGAWV EKPTEQDQYS  540
LTGSGTMKKK GSVVIVGRIN LSGDTAYSQQ TRGLEGCQET SQTGRDKNQV EGEVQVVSTA  600
TQSFLATSIN GVLWTVYHGA GTRTIASPKG PVTQMYTNVD KDLVGWQAPQ GSRSLTPCTC  660
GSSDLYLVTR HADVIPVRRR GDSRGSLLSP RPISYLKGSS GGPLLCPAGH AVGIFRAAVS  720
TRGVAKAVDF IPVESLETTM RSPGSSELIK ENMHMKLYME GTVDNHHFKC TSEGEGKPYE  780
GTQTMRIKVV EGGPLPFAFD ILATSFLYGS KTFINHTQGI PDFFKQSFPE GFTWERVTTY  840
EDGGVLTATQ DTSLQDGCLI YNVKIRGVNF TSNGPVMQKK TLGWEAFTET LYPADGGLEG  900
RNDMALKLVG GSHLIANIKT TYRSKKPAKN LKMPGVYYVD YRLERIKEAN NETYVEQHEV  960
AVARYCDLPS KLGHKLN                                                  977

SEQ ID NO: 351          moltype = AA  length = 977
FEATURE                 Location/Qualifiers
source                  1..977
                        mol_type = protein
                        organism = synthetic construct
SEQUENCE: 351
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGEDV  300
VCCHSIYGTG DRHPNRKARG QLRTKIESGQ GTIPVRSNAS IQTWDGVLQG ERLLTMSCSD  360
KIARWNVVGI QGSLLSIFVE PIYFSSIILG SLYHGDHLSR AMYQRISNIE DLPPLYTLNK  420
PLLSGISNAE ARQPGKAPNF SVNWTVGDSA IEVINATTGK DELGRASRLC KHALYCRWMR  480
VHGKVPSHLL RSKITKPNVY HESKLAAKEY QAAKARLFTA FIKAGLGAWV EKPTEQDQYS  540
LTGSGTMKKK GSVVIVGRIN LSGDTAYSQQ TRGLEGCQET SQTGRDKNQV EGEVQVVSTA  600
TQSFLATSIN GVLWTVYHGA GTRTIASPKG PVTQMYTNVD KDLVGWQAPQ GSRSLTPCTC  660
GSSDLYLVTR HADVIPVRRR GDSRGSLLSP RPISYLKGSA GGPLLCPAGH AVGIFRAAVS  720
TRGVAKAVDF IPVESLETTM RSPGSSELIK ENMHMKLYME GTVDNHHFKC TSEGEGKPYE  780
GTQTMRIKVV EGGPLPFAFD ILATSFLYGS KTFINHTQGI PDFFKQSFPE GFTWERVTTY  840
EDGGVLTATQ DTSLQDGCLI YNVKIRGVNF TSNGPVMQKK TLGWEAFTET LYPADGGLEG  900
RNDMALKLVG GSHLIANIKT TYRSKKPAKN LKMPGVYYVD YRLERIKEAN NETYVEQHEV  960
AVARYCDLPS KLGHKLN                                                  977

SEQ ID NO: 352          moltype = AA  length = 812
FEATURE                 Location/Qualifiers
source                  1..812
                        mol_type = protein
```

```
                         organism = synthetic construct
SEQUENCE: 352
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEFVDRHPNR KARGQLRTKI ESGQGTIPVR SNASIQTWDG  360
VLQGERLLTM SCSDKIAMWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGG TENLYFQSGS SGGSGSAAGS SELIKENMHM KLYMEGTVDN  600
HHFKCTSEGE GKPYEGTQTM RIKVVEGGPL PFAFDILATS FLYGSKTFIN HTQGIPDFFK  660
QSFPEGFTWE RVTTYEDGGV LTATQDTSLQ DGCLIYNVKI RGVNFTSNGP VMQKKTLGWE  720
AFTETLYPAD GGLEGRNDMA LKLVGGSHLI ANIKTTYRSK KPAKNLKMPG VYYVDYRLER  780
IKEANNETYV EQHEVAVARY CDLPSKLGHK LN                                812

SEQ ID NO: 353          moltype = AA  length = 812
FEATURE                 Location/Qualifiers
source                  1..812
                        mol_type = protein
                        organism = synthetic construct
SEQUENCE: 353
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DELVDRHPNR KARGQLRTKI ESGQGTIPVR SNASIQTWDG  360
VLQGERLLTM SCSDKIAMWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGG TENLYFQSGS SGGSGSAAGS SELIKENMHM KLYMEGTVDN  600
HHFKCTSEGE GKPYEGTQTM RIKVVEGGPL PFAFDILATS FLYGSKTFIN HTQGIPDFFK  660
QSFPEGFTWE RVTTYEDGGV LTATQDTSLQ DGCLIYNVKI RGVNFTSNGP VMQKKTLGWE  720
AFTETLYPAD GGLEGRNDMA LKLVGGSHLI ANIKTTYRSK KPAKNLKMPG VYYVDYRLER  780
IKEANNETYV EQHEVAVARY CDLPSKLGHK LN                                812

SEQ ID NO: 354          moltype = AA  length = 812
FEATURE                 Location/Qualifiers
source                  1..812
                        mol_type = protein
                        organism = synthetic construct
SEQUENCE: 354
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYGGS  120
GSGAGSGSPA GGGAPGSGGG SQLHLPQVLA DAVSRLVLGK FGDLTDNFSS PHARRKVLAG  180
VVMTTGTDVK DAKVISVSTG TKCINGEYMS DRGLALNDCH AEIISRRSLL RFLYTQLELY  240
LNNKDDQKRS IFQKSERGGF RLKENVQFHL YISTSPCGDA RIFSPHEPIL EEPAASGSGT  300
GAPPNLWAAQ RYGRELRRMS DEVVDRHPNR KARGQLRTKI ESGQGTIPVR SNASIQTWDG  360
VLQGERLLTM SCSDKIAMWN VVGIQGSLLS IFVEPIYFSS IILGSLYHGD HLSRAMYQRI  420
SNIEDLPPLY TLNKPLLSGI SNAEARQPGK APNFSVNWTV GDSAIEVINA TTGKDELGRA  480
SRLCKHALYC RWMRVHGKVP SHLLRSKITK PNVYHESKLA AKEYQAAKAR LFTAFIKAGL  540
GAWVEKPTEQ DQFSLTGSGG TENLYFQSGS SGGSGSAAGS SELIKENMHM KLYMEGTVDN  600
HHFKCTSEGE GKPYEGTQTM RIKVVEGGPL PFAFDILATS FLYGSKTFIN HTQGIPDFFK  660
QSFPEGFTWE RVTTYEDGGV LTATQDTSLQ DGCLIYNVKI RGVNFTSNGP VMQKKTLGWE  720
AFTETLYPAD GGLEGRNDMA LKLVGGSHLI ANIKTTYRSK KPAKNLKMPG VYYVDYRLER  780
IKEANNETYV EQHEVAVARY CDLPSKLGHK LN                                812

SEQ ID NO: 355          moltype = AA  length = 922
FEATURE                 Location/Qualifiers
source                  1..922
                        mol_type = protein
                        organism = synthetic construct
SEQUENCE: 355
MASNFTQFVL VDNGGTGDVT VAPSNFANGI AEWISSNSRS QAYKVTCSVR QSSAQNRKYT  60
IKVEVPKGAW RSYLNMELTI PIFATNSDCE LIVKAMQGLL KDGNPIPSAI AANSGIYANF  120
TQFVLVDNGG TGDVTVAPSN FANGIAEWIS SNSRSQAYKV TCSVRQSSAQ NRKYTIKVEV  180
PKGAWRSYLN MELTIPIFAT NSDCELIVKA MQGLLKDGNP IPSAIAANSG IYGGSGSGAG  240
SGSPAGGGAP GSGGGSTGAP PNLWAAQRYG RELRRMSDEF VDSFKKASQL HLPQVLADAV  300
SRLVLGKFGD LTDNFSSPHA RRKVLAGVVM TTGTDVKDAK VISVSTGTKC INGEYMSDRG  360
LALNDCHAEI ISRRSLLRFL YTQLELYLNN KDDQKRSIFQ KSERGGFRLK ENVQFHLYIS  420
TSPCGDARIF SPHEPILEEP ADRHPNRKAR GQLRTKIESG QGTIPVRSNA SIQTWDGVLQ  480
GERLLTMSCS DKIARWNVVG IQGSLLSIFV EPIYFSSIIL GSLYHGDHLS RAMYQRISNI  540
EDLPPLYTLN KPLLSGISNA EARQPGKAPN FSVNWTVGDS AIEVINATTG KDELGRASRL  600
CKHALYCRWM RVHGKVPSHL LRSKITKPNV YHESKLAAKE YQAAKARLFT AFIKAGLGAW  660
VEKPTEQDQY SLTGSGGTEN LYFQSAASGS SELIKENMHM KLYMEGTVDN HHFKCTSEGE  720
GKPYEGTQTM RIKVVEGGPL PFAFDILATS FLYGSKTFIN HTQGIPDFFK QSFPEGFTWE  780
RVTTYEDGGV LTATQDTSLQ DGCLIYNVKI RGVNFTSNGP VMQKKTLGWE AFTETLYPAD  840
```

-continued

```
GGLEGRNDMA LKLVGGSHLI ANIKTTYRSK KPAKNLKMPG VYYVDYRLER IKEANNETYV  900
EQHEVAVARY CDLPSKLGHK LN                                          922

SEQ ID NO: 356         moltype = DNA  length = 2032
FEATURE                Location/Qualifiers
source                 1..2032
                       mol_type = other DNA
                       organism = synthetic construct
SEQUENCE: 356
taatacgact cactataggg agacccaagc tggctagcgt ttaaacttaa gcttgccacc  60
atggcattgc ccgtgaccgc cctgctgctg ccactggcct tgttgctcca cgccgcgcgg  120
ccatatccct acgatgtgcc cgattacgct accggtatgg cagaaatcgg tactggcttt  180
ccattcgacc cccattatgt ggaagtcctg ggcgagcgca tgcactacgt cgatgttggt  240
ccgcgcgatg gcacccctgt gctgttcctg cacggtaacc cgacctcctc ctacgtgtgg  300
cgcaacatca tcccgcatgt tgcaccgacc catcgctgca ttgctccaga cctgatcggt  360
atgggcaaat ccgacaaacc agacctgggt tatttcttcg acgaccacgt ccgcttcatg  420
gatgccttca tcgaagccct gggtctggaa gaggtcgtcc tggtcattca cgactggggc  480
tccgctctgg gtttccactg ggccaagcgc aatccagagc gcgtcaaagg tattgcattt  540
atggagttca tccgccctat cccgacctgg gacgaatggc cagaatttgc ccgcgagacc  600
ttccaggcct tccgcaccac cgacgtcggc cgcaagctga tcatcgatca gaacgttttt  660
atcgagggta cgctgccgat gggtgtcgtc cgcccgctga ctgaagtcga gatggaccat  720
taccgcgagc cgttcctgaa tcctgttgac cgcgagccac tgtggcgctt cccaaacgag  780
ctgccaatcg ccggtgagcc agcgaacatc gtcgcgctgg tcgaagaata catggactgg  840
ctgcaccagt cccctgtccc gaagctgctg ttctggggca ccccaggcgt tctgatccca  900
ccggccgaag ccgctcgcct ggccaaaagc ctgcctaact gcaaggctgt ggacatcggc  960
ccgggtctga atctgctgca agaagacaac ccggacctga tcggcagcga gatcgcgcgc  1020
tggctgtcca cgctcgagat ttccggcggc ggaggaagtg gcgagggcag gggaagtctc  1080
ctaacatgcg gggacgtgga ggaaaaccct aggccttaca tgaggatcac ccatgttagg  1140
cccagggttg actacaaaga ccatgacggt gattataaag atcatgacat cgactacaag  1200
gacgacgatg acaagggtac catggagggc agaggaagtc ttctaacatg cggtgacgtg  1260
gaggagaatc ccggccctgg atccagcgag ctgattaagg agaacatgca catgaagctg  1320
tacatggagg gcaccgtgga caaccatcac ttcaagtgca catccgaggg cgaaggcaag  1380
ccctacgagg gcacccagac catgagaatc aaggtggtcg agggcggccc tctccccttc  1440
gccttcgaca tcctggctac tagcttcctc tacggcagca agaccttcat caaccacacc  1500
cagggcatcc ccgacttctt caagcagtcc ttccctgagg gcttcacatg ggagagagtc  1560
accacatacg aagacggggg cgtgctgacc gctacccagg acaccagcct ccaggacggc  1620
tgcctcatct acaacgtcaa gatcagaggg gtgaacttca catccaacgg ccctgtgatg  1680
cagaagaaaa cactcggctg ggaggccttc accgagacgc tgtaccccgc tgacggcggc  1740
ctggaaggca gaaacgacat ggccctgaag ctcgtgggcg ggagccatct gatcgcaaac  1800
atcaagacca catatagatc caagaaaccc gctaagaacc tcaagatgcc tggcgtctac  1860
tatgtggact acagactgga aagaatcaag gaggccaaca acgagaccta cgtcgagcag  1920
cacgaggtgg cagtggccag atactgcgac ctccctagca aactggggca caagcttaat  1980
tgatctagag ggcccgttta aacccgctga tcagcctcga ctgtgccttc ta          2032

SEQ ID NO: 357         moltype = DNA  length = 250
FEATURE                Location/Qualifiers
source                 1..250
                       mol_type = other DNA
                       organism = synthetic construct
SEQUENCE: 357
taatacgact cactataggg agacccaagc ttggtaccac tagtgccaca aacttctctc  60
tgctaaagca agcaggtgat gttgaagaaa acccagggcc tggagggtcc gagggcaggg  120
gaagtctcct aacatgcggg gacgtggagg aaaatcccgg accagaattc gccacctgat  180
ctagagggcc ctattctata gtgtcaccta aatgctagag ctcgctgatc agcctcgact  240
gtgccttcta                                                        250

SEQ ID NO: 358         moltype = AA  length = 640
FEATURE                Location/Qualifiers
source                 1..640
                       mol_type = protein
                       organism = synthetic construct
SEQUENCE: 358
MALPVTALLL PLALLLHAAR PYPYDVPDYA TGMAEIGTGF PFDPHYVEVL GERMHYVDVG  60
PRDGTPVLFL HGNPTSSYVW RNIIPHVAPT HRCIAPDLIG MGKSDKPDLG YFFDDHVRFM  120
DAFIEALGLE EVVLVIHDWG SALGFHWAKR NPERVKGIAF MEFIRPIPTW DEWPEFARET  180
FQAFRTTDVG RKLIIDQNVF IEGTLPMGVV RPLTEVEMDH YREPFLNPVD REPLWRFPNE  240
LPIAGEPANI VALVEEYMDW LHQSPVPKLL FWGTPGVLIP PAEAARLAKS LPNCKAVDIG  300
PGLNLLQEDN PDLIGSEIAR WLSTLEISGG GGSGEGRGSL LTCGDVEENP RPYMRITHVR  360
PRVDYKDHDG DYKDHDIDYK DDDDKGTMEG RGSLLTCGDV EENPGPGSSE LIKENMHMKL  420
YMEGTVDNHH FKCTSEGEGK PYEGTQTMRI KVVEGGPLPF AFDILATSFL YGSKTFINHT  480
QGIPDFFKQS FPEGFTWERV TTYEDGGVLT ATQDTSLQDG CLIYNVKIRG VNFTSNGPVM  540
QKKTLGWEAF TETLYPADGG LEGRNDMALK LVGGSHLIAN IKTTYRSKKP AKNLKMPGVY  600
YVDYRLERIK EANNETYVEQ HEVAVARYCD LPSKLGHKLN                        640

SEQ ID NO: 359         moltype = AA  length = 46
FEATURE                Location/Qualifiers
source                 1..46
                       mol_type = protein
                       organism = synthetic construct
```

```
SEQUENCE: 359
TSATNFSLLK QAGDVEENPG PGGSEGRGSL LTCGDVEENP GPEFAT                 46

SEQ ID NO: 360         moltype = AA  length = 19
FEATURE                Location/Qualifiers
source                 1..19
                       mol_type = protein
                       organism = unidentified
SEQUENCE: 360
ATNFSLLKQA GDVEENPGP                                               19

SEQ ID NO: 361         moltype = AA  length = 18
FEATURE                Location/Qualifiers
source                 1..18
                       mol_type = protein
                       organism = Thosea asigna virus
SEQUENCE: 361
EGRGSLLTCG DVEENPGP                                                18

SEQ ID NO: 362         moltype = AA  length = 20
FEATURE                Location/Qualifiers
source                 1..20
                       mol_type = protein
                       organism = Equine rhinitis A virus
SEQUENCE: 362
QCTNYALLKL AGDVESNPGP                                              20

SEQ ID NO: 363         moltype = AA  length = 22
FEATURE                Location/Qualifiers
source                 1..22
                       mol_type = protein
                       organism = unidentified
SEQUENCE: 363
VKQTLNFDLL KLAGDVESNP GP                                           22

SEQ ID NO: 364         moltype = AA  length = 10
FEATURE                Location/Qualifiers
source                 1..10
                       mol_type = protein
                       organism = synthetic construct
SEQUENCE: 364
EDVVCCHSIY                                                         10

SEQ ID NO: 365         moltype = AA  length = 14
FEATURE                Location/Qualifiers
source                 1..14
                       mol_type = protein
                       organism = synthetic construct
SEQUENCE: 365
LYQEFDEMEE CSQH                                                    14

SEQ ID NO: 366         moltype = AA  length = 10
FEATURE                Location/Qualifiers
source                 1..10
                       mol_type = protein
                       organism = synthetic construct
SEQUENCE: 366
DEMEECSQHL                                                         10

SEQ ID NO: 367         moltype = AA  length = 13
FEATURE                Location/Qualifiers
source                 1..13
                       mol_type = protein
                       organism = synthetic construct
SEQUENCE: 367
QEFEDVVPCS MGS                                                     13

SEQ ID NO: 368         moltype = AA  length = 9
FEATURE                Location/Qualifiers
source                 1..9
                       mol_type = protein
                       organism = synthetic construct
SEQUENCE: 368
EDVVCCHSI                                                          9

SEQ ID NO: 369         moltype = AA  length = 9
FEATURE                Location/Qualifiers
source                 1..9
                       mol_type = protein
```

```
                        organism = synthetic construct
SEQUENCE: 369
DEMEECSQH                                                               9

SEQ ID NO: 370          moltype = AA  length = 20
FEATURE                 Location/Qualifiers
source                  1..20
                        mol_type = protein
                        organism = synthetic construct
SEQUENCE: 370
CMSADLEVVT STWVLVGGVL                                                   20

SEQ ID NO: 371          moltype = AA  length = 20
FEATURE                 Location/Qualifiers
source                  1..20
                        mol_type = protein
                        organism = synthetic construct
SEQUENCE: 371
CMSADLEVVT STWVLVGGVL                                                   20

SEQ ID NO: 372          moltype = AA  length = 20
FEATURE                 Location/Qualifiers
source                  1..20
                        mol_type = protein
                        organism = synthetic construct
SEQUENCE: 372
CMQADLEVMT STWVLAGGVL                                                   20

SEQ ID NO: 373          moltype = AA  length = 20
FEATURE                 Location/Qualifiers
source                  1..20
                        mol_type = protein
                        organism = synthetic construct
SEQUENCE: 373
CMQADLEIMT SSWVLAGGVL                                                   20

SEQ ID NO: 374          moltype = AA  length = 20
FEATURE                 Location/Qualifiers
source                  1..20
                        mol_type = protein
                        organism = synthetic construct
SEQUENCE: 374
CMSADLEVTT STWVLLGGVL                                                   20

SEQ ID NO: 375          moltype = AA  length = 20
FEATURE                 Location/Qualifiers
source                  1..20
                        mol_type = protein
                        organism = synthetic construct
SEQUENCE: 375
YQEFDEMEEC SQHLPYIEQG                                                   20

SEQ ID NO: 376          moltype = AA  length = 20
FEATURE                 Location/Qualifiers
source                  1..20
                        mol_type = protein
                        organism = synthetic construct
SEQUENCE: 376
YQEFDEMEEC ASHLPYIEQG                                                   20

SEQ ID NO: 377          moltype = AA  length = 20
FEATURE                 Location/Qualifiers
source                  1..20
                        mol_type = protein
                        organism = synthetic construct
SEQUENCE: 377
YEAFDEMEEC ASRAALIEEG                                                   20

SEQ ID NO: 378          moltype = AA  length = 20
FEATURE                 Location/Qualifiers
source                  1..20
                        mol_type = protein
                        organism = synthetic construct
SEQUENCE: 378
YEAFDEMEEC ASKAALIEEG                                                   20

SEQ ID NO: 379          moltype = AA  length = 20
FEATURE                 Location/Qualifiers
source                  1..20
```

```
                        mol_type = protein
                        organism = synthetic construct
SEQUENCE: 379
YQQYDEMEEC SQAAPYIEQA                                              20

SEQ ID NO: 380          moltype = AA  length = 20
FEATURE                 Location/Qualifiers
source                  1..20
                        mol_type = protein
                        organism = synthetic construct
SEQUENCE: 380
WISSECTTPC SGSWLRDVWD                                              20

SEQ ID NO: 381          moltype = AA  length = 20
FEATURE                 Location/Qualifiers
source                  1..20
                        mol_type = protein
                        organism = synthetic construct
SEQUENCE: 381
WINEDCSTPC SGSWLRDVWD                                              20

SEQ ID NO: 382          moltype = AA  length = 20
FEATURE                 Location/Qualifiers
source                  1..20
                        mol_type = protein
                        organism = synthetic construct
SEQUENCE: 382
WITEDCPIPC SGSWLRDVWD                                              20

SEQ ID NO: 383          moltype = AA  length = 20
FEATURE                 Location/Qualifiers
source                  1..20
                        mol_type = protein
                        organism = synthetic construct
SEQUENCE: 383
WITEDCPVPC SGSWLQDIWD                                              20

SEQ ID NO: 384          moltype = AA  length = 20
FEATURE                 Location/Qualifiers
source                  1..20
                        mol_type = protein
                        organism = synthetic construct
SEQUENCE: 384
WINEDYPSPC SDDWLRTIWD                                              20

SEQ ID NO: 385          moltype = AA  length = 20
FEATURE                 Location/Qualifiers
source                  1..20
                        mol_type = protein
                        organism = synthetic construct
SEQUENCE: 385
GADTEDVVCC SMSYSWTGAL                                              20

SEQ ID NO: 386          moltype = AA  length = 20
FEATURE                 Location/Qualifiers
source                  1..20
                        mol_type = protein
                        organism = synthetic construct
SEQUENCE: 386
EEASEDVVCC SMSYTWTGAL                                              20

SEQ ID NO: 387          moltype = AA  length = 20
FEATURE                 Location/Qualifiers
source                  1..20
                        mol_type = protein
                        organism = synthetic construct
SEQUENCE: 387
SEEDDSVVCC SMSYSWTGAL                                              20

SEQ ID NO: 388          moltype = AA  length = 20
FEATURE                 Location/Qualifiers
source                  1..20
                        mol_type = protein
                        organism = synthetic construct
SEQUENCE: 388
SDQEDSVICC SMSYSWTGAL                                              20

SEQ ID NO: 389          moltype = AA  length = 20
FEATURE                 Location/Qualifiers
```

```
source                  1..20
                        mol_type = protein
                        organism = synthetic construct
SEQUENCE: 389
DSEEQSVVCC SMSYSWTGAL                                              20

SEQ ID NO: 390          moltype = DNA  length = 4665
FEATURE                 Location/Qualifiers
source                  1..4665
                        mol_type = other DNA
                        organism = synthetic construct
SEQUENCE: 390
taatacgact cactataggg agacccaagc tggctagagg atcgaaccct taaggccacc  60
atggcgtcca atttcactca gtttgtgctg gttgacaacg gcgggaccgg ggacgttacg  120
gtagccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgccataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggacagaca tcctaatagg  960
aaggctagag gccaacttcg gacgaagatt gaaagtggcc agggtactat cccggtgcgg  1020
tccaacgcta gtattcaaac gtgggacgga gtccttcaag gtgaacggct gttgacaatg  1080
agctgctcag acaaaatcgc gcgctggaat gtagtgggaa tccaaggcag cctcttgagc  1140
atattcgtag aacccatata tttctcatcc attattttgg gctctctgta tcatggtgac  1200
catctgtcaa gggctatgta ccaacgaatt tctaatatcg aggatcttcc tccactctat  1260
acactcaata agcctctctt gtccgggata tcaaacgctg aggcccgcca gccagggaaa  1320
gctcctaact tcagtgttaa ctggaccgtt ggtgattctg cgatagaggt catcaacgcc  1380
acgacaggta aggatgagct cggtagagcc tcacgcctgt gtaaacacgc gttgtattgt  1440
agatggatga gagtacatgg gaaggtccca tctcacttgc tccgaagcaa gatcactaag  1500
cctaatgtgt atcatgagtc aaaactcgcg gctaaagaat accaggcagc caaagctcga  1560
ctttttacag cttttattaa ggcagggctc ggggcatggg tcgagaagcc gaccgagcag  1620
gaccaattct ctctgacggg gagcggatcc agcgagctga ttaaggagaa catgcacatg  1680
aagcgcccat cggtcgccac catggtgagc aagggcgagg aggataacat ggccatcatc  1740
aaggagttca tgcgcttcaa ggtgcacatg gagggctccg tgaacggcca cgagttcgag  1800
atcgagggcg agggcgaggg ccgcccctac gagggcaccc agaccgccaa gctgaaggtg  1860
accaagggtg gccccctgcc cttcgcctgg gacatcctgt cccctcagtt catgtacggc  1920
tccaaggcct acgtgaagca ccccgccgac atccccgact acttgaagct gtccttcccc  1980
gagggcttca agtgggagcg cgtgatgaac ttcgaggacg gcggcgtggt gaccgtgacc  2040
caggactcct ccctgcagga cggcgagttc atctacaagg tgaagctgcg cggcaccaac  2100
ttcccctccg acggccccgt aatgcagaag aagaccatgg gctgggaggc ctcctccgag  2160
cggatgtacc ccgaggacgg cgccctgaag ggcgagatca agcagaggct gaagctgaag  2220
gacggcggcc actacgacgc tgaggtcaag accacctaca aggccaagaa gcccgtgcag  2280
ctgcccggcg cctacaacgt caacatcaag ttggacatca cctcccacaa cgaggactac  2340
accatcgtgg aacagtacga acgcgccgag ggccgccact ccaccggcgg catggacgag  2400
ctgtacaagg attacaagga tgacgatgac aaaggtagcg ggcaactaa ttttagctta  2460
ctcaaacagg ctggggacgt cgaggagaat ccaggccctg catccgctgg ctctggagaa  2520
ggacgaggct ccttgctcac ctgtggagat gtcgaagaga acccaggtcc tgcaaccggg  2580
aattccgcgt agcgctagct ttgccagcgc cacgcgaaac atgaggatca cccatgtgcc  2640
gctatggcag aaatcggtac tggctttcca ttcgaccccc attatgtgga agtcctgggc  2700
gagcgcatgc actacgtcga tgttggtccg cgcgatggca cccctgtgct gttcctgcac  2760
ggtaacccga cctcctccta cgtgtggcgc aacatcatcc cgcatgttgc accgacccat  2820
cgctgcattg ctccagacct gatcggtatg ggcaaatccg acaaaccaga cctgggttat  2880
ttcttcgacg accacgtccg cttcatggat gccttcatcg aagccctggg tctggaagag  2940
gtcgtcctgg tcattcacga ctggggctcc gctctgggtt tccactgggc caagcgcaat  3000
ccagagcgcg tcaaaggtat tgcatttatg gagttcatcc gccctatccc gacctgggac  3060
gaatggccag aatttgcccg cgagaccttc caggccttcc gcaccaccga cgtcggccgc  3120
aagctgatca tcgatcagaa cgtttttatc gagggtacgc tgccgatggg tgtcgtccgc  3180
ccgctgactg aagtcgagat ggaccattac cgcgagccgt tcctgaatcc tgttgaccgc  3240
gagccactgt ggcgcttccc aaacgagctg ccaatcgccg gtgagccagc gaacatcgtc  3300
gcgctggtcg aagaatacat ggactggctg caccagtccc ctgtcccgaa gctgctgttc  3360
tggggcaccc caggcgttct gatcccaccg gccgaagccg ctcgcctggc caaaagcctg  3420
cctaactgca aggctgtgga catcggcccg ggtctgaatc tgctgcaaga agacaacccg  3480
gacctgatcg gcagcgagat cgcgcgctgg ctgtcgacgc tcgagatttc tggcaccggt  3540
atggcatcta tgactggagg ccaacagatg ggtcctgcaa ccgggaattc cgcgtagcgc  3600
tagctttgcc agcgccacgc gaaacatgag gatcacccat gtactagtgc cacaaacttc  3660
tctctgctaa agcaagcagg tgatgttgaa gaaaacccag ggcctggagg gtccgagggc  3720
aggggaagtc tcctaacatg cggggacgtg gaggaaaatc ccggcccatc cggatatccc  3780
tacgatgtgc ccgattacgc tatcgatgtg agcaagggcg aagaagataa caaggcctct  3840
ctcccagcga cacatgagtt acacatcttt ggctccatca acggtgtgga ctttgacatg  3900
gtgggtcagg gcaccggcaa tccaaatgat ggttatgagg agttaaacct gaagtccacc  3960
aagggtgacc tccagttctc cccctggatt ctggtccctc atatcgggta tggcttccat  4020
```

```
cagtacctgc cctaccctga cgggatgtcg cctttccagg ccgccatggt agatggcagc  4080
ggataccaag tccatcgcac aatgcagttt gaagatggtg cctcccttac tgttaactac  4140
cgctacacct acgagggaag ccacatcaaa ggagaggccc aggtgaaggg gactggtttc  4200
cctgctgacg gtcctgtgat gaccaactcg ctgaccgctg cggactggtg caggtcgaag  4260
aagacttacc ccaacgacaa aaccatcatc agtaccttta agtggagtta caccactgga  4320
aatggcaaga gataccggag cactgcgcgg accacctaca cctttgccaa gccaatggcg  4380
gctaactatc tgaagaacca gccgatgtac gtgttccgta agacggagct caagcactcc  4440
aagaccgagc tcaacttcaa ggagtggcaa aaggccttta ccgatgtgat gggaatggac  4500
gagctgtata aggctagcta agcggccgct cgagtctaga gggcccgcgg ttcgaaggta  4560
agcctatccc taaccctctc ctcggtctcg attctacgcg taccggtcat catcaccatc  4620
accattgagt ttaaacccgc tgatcagcct cgactgtgcc ttcta                 4665

SEQ ID NO: 391          moltype = DNA  length = 4665
FEATURE                 Location/Qualifiers
source                  1..4665
                        mol_type = other DNA
                        organism = synthetic construct
SEQUENCE: 391
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggacagaca tcctaatagg  960
aaggctagag gccaacttcg gacgaagatt gaaagtggcc agggtactat cccggtgcgg  1020
tccaacgcta gtattcaaac gtgggacgga gtccttcaag gtgaacggct gttgacaatg  1080
agctgctcag acaaaatcgc gcgctggaat gtagtgggaa tccaaggcag cctcttgagc  1140
atattcgtag aacccatata tttctcatcc attattttgg gctctctgta tcatggtgac  1200
catctgtcaa gggctatgta ccaacgaatt tctaatatcg aggatcttcc tccactctat  1260
acactcaata agcctctctt gtccgggata tcaaacgctg aggcccgcca gccagggaaa  1320
gctcctaact tcagtgttaa ctggaccgtt ggtgattctg cgatagaggt catcaacgcc  1380
acgacaggta aggatgagct cggtagagcc tcacgcctgt gtaaacacgc gttgtattgt  1440
agatggatga gagtacatgg gaaggtccca tctcacttgc tccgaagcaa gatcactaag  1500
cctaatgtgt atcatgagtc aaaactcgcg gctaaagaat accaggcagc caaagctcga  1560
ctttttacag cttttattaa ggcagggctc ggggcatggg tcgagaagcc gaccgagcag  1620
gaccaattct ctctgacggg gagcggatcc agcgagctga ttaaggagaa catgcacatg  1680
aagcgcccat cggtcgccac catggtgagc aagggcgagg aggataacat ggccatcatc  1740
aaggagttca tgcgcttcaa ggtgcacatg gagggctccg tgaacggcca cgagttcgag  1800
atcgagggcg agggcgaggg ccgcccctac gagggcaccc agaccgccaa gctgaaggtg  1860
accaagggtg gcccccctgcc cttcgcctgg gacatcctgt cccctcagtt catgtacggc  1920
tccaaggcct acgtgaagca ccccgccgac atccccgact acttgaagct gtccttcccc  1980
gagggcttca agtgggagcg cgtgatgaac ttcgaggacg gcggcgtggt gaccgtgacc  2040
caggactcct ccctgcagga cggcgagttc atctacaagg tgaagctgcg cggcaccaac  2100
ttcccctccg acggccccgt aatgcagaag aagaccatgg gctgggaggc ctcctccgag  2160
cggatgtacc ccgaggacgg cgccctgaag ggcgagatca agcagaggct gaagctgaag  2220
gacggcggcc actacgacgc tgaggtcaag accacctaca aggccaagaa gcccgtgcag  2280
ctgcccggcg cctacaacgt caacatcaag ttggacatca cctcccacaa cgaggactac  2340
accatcgtgg aacagtacga acgcgccgag ggccgccact ccaccggcgg catggacgag  2400
ctgtacaagg attacaagga tgacgatgac aaaggtagcg gggcaactaa ttttagctta  2460
ctcaaacagg ctggggacgt cgaggagaat ccaggccctg catccgctgg ctctggagaa  2520
ggacgaggct ccttgctcac ctgtggagat gtcgaagaga acccaggtcc tgcaaccggg  2580
aattccgcgt agcgctagct ttgccagcgc cacgcgaaac atgaggatca cccatgtgcc  2640
gctatggcag aaatcggtac tggctttcca ttcgaccccc attatgtgga agtcctgggc  2700
gagcgcatgc actacgtcga tgttggtccg cgcgatggca cccctgtgct gttcctgcac  2760
ggtaacccga cctcctccta cgtgtggcgc aacatcatcc cgcatgttgc accgacccat  2820
cgctgcattg ctccagacct gatcggtatg ggcaaatccg acaaaccaga cctgggttat  2880
ttcttcgacg accacgtccg cttcatggat gccttcatcg aagccctggg tctggaagag  2940
gtcgtcctgg tcattcacga ctggggctcc gctctgggtt tccactgggc caagcgcaat  3000
ccagagcgcg tcaaaggtat tgcatttatg gagttcatcc gccctatccc gacctgggac  3060
gaatggccag aatttgcccg cgagaccttc caggccttcc gcaccaccga cgtcggccgc  3120
aagctgatca tcgatcagaa cgtttttatc gagggtacgc tgccgatggg tgtcgtccgc  3180
ccgctgactg aagtcgagat ggaccattac cgcgagccgt tcctgaatcc tgttgaccgc  3240
gagccactgt ggcgcttccc aaacgagctg ccaatcgccg gtgagccagc gaacatcgtc  3300
gcgctggtcg aagaatacat ggactggctg caccagtccc ctgtcccgaa gctgctgttc  3360
tggggcaccc caggcgttct gatcccaccg gccgaagccg ctcgcctggc caaaagcctg  3420
cctaactgca aggctgtgga catcggcccg ggtctgaatc tgctgcaaga agacaacccg  3480
gacctgatcg gcagcgagat cgcgcgctgg ctgtcgacgc tcgagatttc tggcaccggt  3540
atggcatcta tgactggagg ccaacagatg ggtcctgcaa ccgggaattc cgcgtagcgc  3600
tagctttgcc agcgccacgc gaaacatgag gatcacccat gtactagtgc cacaaacttc  3660
```

```
tctctgctaa agcaagcagg tgatgttgaa gaaaacccag ggcctggagg gtccgagggc  3720
aggggaagtc tcctaacatg cggggacgtg gaggaaaatc ccggcccatc cggatatccc  3780
tacgatgtgc ccgattacgc tatcgatgtg agcaagggcg aagaagataa caaggcctct  3840
ctcccagcga cacatgagtt acacatcttt ggctccatca acggtgtgga ctttgacatg  3900
gtgggtcagg gcaccggcaa tccaaatgat ggttatgagg agttaaacct gaagtccacc  3960
aagggtgacc tccagttctc cccctggatt ctggtccctc atatcgggta tggcttccat  4020
cagtacctgc cctaccctga cgggatgtcg cctttccagg ccgccatggt agatggcagc  4080
ggataccaag tccatcgcac aatgcagttt gaagatggtg cctcccttac tgttaactac  4140
cgctacacct acgagggaag ccacatcaaa ggagaggccc aggtgaaggg gactggtttc  4200
cctgctgacg gtcctgtgat gaccaactcg ctgaccgctg cggactggtg caggtcgaag  4260
aagacttacc ccaacgacaa aaccatcatc agtaccttta agtggagtta caccactgga  4320
aatggcaaga gataccggag cactgcgcgg accacctaca cctttgccaa gccaatggcg  4380
gctaactatc tgaagaacca gccgatgtac gtgttccgta agacggagct caagcactcc  4440
aagaccgagc tcaacttcaa ggagtggcaa aaggccttta ccgatgtgat gggaatggac  4500
gagctgtata aggctagcta agcggccgct cgagtctaga gggcccgcgg ttcgaaggta  4560
agcctatccc taaccctctc ctcggtctcg attctacgcg taccggtcat catcaccatc  4620
accattgagt ttaaacccgc tgatcagcct cgactgtgcc ttcta                 4665

SEQ ID NO: 392         moltype = DNA  length = 5376
FEATURE                Location/Qualifiers
source                 1..5376
                       mol_type = other DNA
                       organism = synthetic construct
SEQUENCE: 392
taatacgact cactataggg agacccaagc tggctagagg atcgaaccct taaggccacc  60
atggcgtcca atttcactca gtttgtgctg gttgacaacg gcgggaccgg ggacgttacg  120
gtagcccccct caaactttgc caacggtata gcggagtgga taagcagcaa ttctaggagt  180
caagcataca aagttacatg cagcgtgcgc caatctagcg ctcagaatcg caagtacacc  240
attaaagtag aggtccccaa gggagcctgg agaagctatc ttaacatgga gttgaccata  300
ccaatcttcg ctaccaactc tgactgtgaa ctcattgtga aagccatgca aggtctgctc  360
aaggatggta acccaattcc gtccgctatc gctgccaact ctgggattta cgggggcagt  420
gggagcggtg caggatctgg tagtccagct gggggaggag caccgggtag cggtgggggg  480
tctcagctgc acctgcccca ggttctcgca gacgccgtat cccgccttgt actgggcaag  540
tttggtgatc ttactgacaa tttttcatct cctcatgcga ggcggaaagt actcgcaggc  600
gtcgtcatga cgaccggaac tgacgtgaaa gacgccaaag tcatctctgt ctccacgggc  660
acaaagtgca taaacgggga gtacatgagc gaccgggggc tggcactgaa tgattgtcac  720
gctgaaataa tatctaggcg atctctgctt agatttctct acactcaact cgaattgtac  780
cttaacaaca aagatgacca gaaacgcagt atatttcaga aatcagaacg cggcggattt  840
cgacttaagg aaaacgttca gttccacttg tatatcagca catccccttg cggtgacgcc  900
cgaatctttt ccccgcacga gccgatattg gaggagcccg cggctagcgg gtcgggcacc  960
ggtgctccac ccaatctctg ggcagcgcag cgctacggcc gtgagctcag aaggatgtcc  1020
gatgaggtgg tcgacagaca tcctaatagg aaggctagag gccaacttcg gacgaagatt  1080
gaaagtggcc agggtactat cccggtgcgg tccaacgcta gtattcaaac gtgggacgga  1140
gtccttcaag gtgaacggct gttgacaatg agctgctcag acaaaatcgc gcgctggaat  1200
gtagtgggaa tccaaggcag cctcttgagc atattcgtag aacccatata tttctcatcc  1260
attattttgg gctctctgta tcatggtgac catctgtcaa gggctatgta ccaacgaatt  1320
tctaatatcg aggatcttcc tccactctat acactcaata agcctctctt gtccgggata  1380
tcaaacgctg aggcccgcca gccagggaaa gctcctaact tcagtgttaa ctggaccgtt  1440
ggtgattctg cgatagaggt catcaacgcc acgacaggta aggatgagct cggtagagcc  1500
tcacgcctgt gtaaacacgc gttgtattgt agatggatga gagtacatgg gaaggtccca  1560
tctcacttgc tccgaagcaa gatcactaag cctaatgtgt atcatgagtc aaaactcgcg  1620
gctaaagaat accaggcagc cagggctcga ctttttacag cttttattaa ggcagggctc  1680
ggggcatggg tcgagaagcc gaccgagcag gaccaattct ctctgacggg gagcgcggcc  1740
ggaggtagcg gcggaagcgc ggccgcctca agtaaccggg agctggtggt tgactttctc  1800
tcctacaagc tttcccagaa aggatacagc tggagtcagt ttagtgatgt ggaagagaac  1860
aggactgagg ccccagaagg gactgaatcg gagatggaga cccccagtgc catcaatggc  1920
aacccatcct ggcacctggc agacagcccc gcggtgaatg gagccactgg ccacagcagc  1980
agtttggatg cccgggaggt gatccccatg gcagcagtaa agcaagcgct gagggaggca  2040
ggcgacgagt ttgaactgcg gtaccggcgg gcattcagtg acctgacatc ccagctccac  2100
atcaccccag ggacagcata tcagagcttt gaacaggtag tgaatgaact cttccgggat  2160
ggggtaaact ggggtcgcat tgtggccttt ttctccttcg gcggggcact gtgcgtggaa  2220
agcgtagaca aggagatgca ggtattggtg agtcggatcg cagcttggat ggccacttac  2280
ctgaatgacc acctagagcc ttggatccag gagaacggcg gctgggatac ttttgtggaa  2340
ctctatggga acaatggatc cagcgagctg attaaggaga acatgcacat gaagcgccca  2400
tcggtcgcca ccatggtgag caagggcgag gaggataaca tggccatcat caaggagttc  2460
atgcgcttca aggtgcacat ggagggctcc gtgaacggcc acgagttcga gatcgagggc  2520
gagggcgagg gccgccccta cgagggcacc cagaccgcca agctgaaggt gaccaagggt  2580
ggccccctgc ccttcgcctg ggacatcctg tcccctcagt tcatgtacgg ctccaaggcc  2640
tacgtgaagc accccgccga catccccgac tacttgaagc tgtccttccc cgagggcttc  2700
aagtgggagc gcgtgatgaa cttcgaggac ggcggcgtgg tgaccgtgac ccaggactcc  2760
tccctgcagg acggcgagtt catctacaag gtgaagctgc gcggcaccaa cttcccctcc  2820
gacggccccg taatgcagaa gaagaccatg ggctgggagg cctcctccga gcggatgtac  2880
cccgaggacg gcgccctgaa gggcgagatc aagcagaggc tgaagctgaa ggacggcggc  2940
cactacgacg ctgaggtcaa gaccacctac aaggccaaga agcccgtgca gctgcccggc  3000
gcctacaacg tcaacatcaa gttggacatc acctcccaca acgaggacta caccatcgtg  3060
gaacagtacg aacgcgccga gggccgccac tccaccggcg gcatggacga gctgtacaag  3120
gattacaagg atgacgatga caaaggtagc ggggcaacta attttagctt actcaaacag  3180
gctggggacg tcgaggagaa tccaggccct gcatccgctg gctctggaga aggacgaggc  3240
tccttgctca cctgtggaga tgtcgaagag aacccaggtc ctgcaaccgg gaattccgcg  3300
```

```
tagcgctagc tttgccagcg ccacgcgaaa catgaggatc acccatgtgc cgctatggca  3360
gaaatcggta ctggctttcc attcgacccc cattatgtgg aagtcctggg cgagcgcatg  3420
cactacgtcg atgttggtcc gcgcgatggc acccctgtgc tgttcctgca cggtaacccg  3480
acctcctcct acgtgtggcg caacatcatc ccgcatgttg caccgaccca tcgctgcatt  3540
gctccagacc tgatcggtat gggcaaatcc gacaaaccag acctgggtta tttcttcgac  3600
gaccacgtcc gcttcatgga tgccttcatc gaagccctgg gtctggaaga ggtcgtcctg  3660
gtcattcacg actggggctc cgctctgggt ttccactggg ccaagcgcaa tccagagcgc  3720
gtcaaaggta ttgcatttat ggagttcatc cgccctatcc cgacctggga cgaatggcca  3780
gaatttgccc gcgagacctt ccaggccttc cgcaccaccg acgtcggccg caagctgatc  3840
atcgatcaga acgtttttat cgagggtacg ctgccgatgg gtgtcgtccg cccgctgact  3900
gaagtcgaga tggaccatta ccgcgagccg ttcctgaatc ctgttgaccg cgagccactg  3960
tggcgcttcc caaacgagct gccaatcgcc ggtgagccag cgaacatcgt cgcgctggtc  4020
gaagaataca tggactggct gcaccagtcc cctgtcccga agctgctgtt ctggggcacc  4080
ccaggcgttc tgatcccacc ggccgaagcc gctcgcctgg ccaaaagcct gcctaactgc  4140
aaggctgtgg acatcggccc gggtctgaat ctgctgcaag aagacaaccc ggacctgatc  4200
ggcagcgaga tcgcgcgctg gctgtcgacg ctcgagattt ctggcaccgg tatggcatct  4260
atgactggag gccaacagat gggtcctgca accgggaatt ccgcgtagcg ctagctttgc  4320
cagcgccacg cgaaacatga ggatcaccca tgtactagtg ccacaaactt ctctctgcta  4380
aagcaagcag gtgatgttga agaaaaccca gggcctggag ggtccgaggg caggggaagt  4440
ctcctaacat gcggggacgt ggaggaaaat cccggcccat ccggatatcc ctacgatgtg  4500
cccgattacg ctatcgatgt gagcaagggc gaagaagata acaaggcctc tctcccagcg  4560
acacatgagt tacacatctt tggctccatc aacggtgtgg actttgacat ggtgggtcag  4620
ggcaccggca atccaaatga tggttatgag gagttaaacc tgaagtccac caagggtgac  4680
ctccagttct ccccctggat tctggtccct catatcgggt atggcttcca tcagtacctg  4740
ccctaccctg acgggatgtc gcctttccag gccgccatgg tagatggcag cggataccaa  4800
gtccatcgca caatgcagtt tgaagatggt gcctccctta ctgttaacta ccgctacacc  4860
tacgagggaa gccacatcaa aggagaggcc caggtgaagg ggactggttt ccctgctgac  4920
ggtcctgtga tgaccaactc gctgaccgct gcggactggt gcaggtcgaa gaagacttac  4980
cccaacgaca aaaccatcat cagtaccttt aagtggagtt acaccactgg aaatggcaag  5040
agataccgga gcactgcgcg gaccacctac acctttgcca agccaatggc ggctaactat  5100
ctgaagaacc agccgatgta cgtgttccgt aagacggagc tcaagcactc caagaccgag  5160
ctcaacttca aggagtggca aaaggccttt accgatgtga tgggaatgga cgagctgtat  5220
aaggctagct aagcggccgc tcgagtctag agggcccgcg gttcgaaggt aagcctatcc  5280
ctaaccctct cctcggtctc gattctacgc gtaccggtca tcatcaccat caccattgag  5340
tttaaacccg ctgatcagcc tcgactgtgc cttcta                           5376

SEQ ID NO: 393          moltype = AA  length = 332
FEATURE                 Location/Qualifiers
source                  1..332
                        mol_type = protein
                        organism = synthetic construct
SEQUENCE: 393
LCQRHAKHED HPCAAMAEIG TGFPFDPHYV EVLGERMHYV DVGPRDGTPV LFLHGNPTSS  60
YVWRNIIPHV APTHRCIAPD LIGMGKSDKP DLGYFFDDHV RFMDAFIEAL GLEEVVLVIH  120
DWGSALGFHW AKRNPERVKG IAFMEFIRPI PTWDEWPEFA RETFQAFRTT DVGRKLIIDQ  180
NVFIEGTLPM GVVRPLTEVE MDHYREPFLN PVDREPLWRF PNELPIAGEP ANIVALVEEY  240
MDWLHQSPVP KLLFWGTPGV LIPPAEAARL AKSLPNCKAV DIGPGLNLLQ EDNPDLIGSE  300
IARWLSTLEI SGTGMASMTG GQQMGPATGN SA                                332

SEQ ID NO: 394          moltype = AA  length = 15
FEATURE                 Location/Qualifiers
source                  1..15
                        mol_type = protein
                        organism = synthetic construct
SEQUENCE: 394
LCQRHAKHED HPCTS                                                   15

SEQ ID NO: 395          moltype = RNA  length = 66
FEATURE                 Location/Qualifiers
source                  1..66
                        mol_type = other RNA
                        organism = synthetic construct
SEQUENCE: 395
aagaattccg cgtagcgcta gctttgccag cgccacgcga aacatgagga tcacccatgt  60
actagt                                                             66

SEQ ID NO: 396          moltype = RNA  length = 66
FEATURE                 Location/Qualifiers
source                  1..66
                        mol_type = other RNA
                        organism = synthetic construct
SEQUENCE: 396
aagaattccg cgtagcgctg gctttgccag cgccacgcga aacatgagga tcacccatgt  60
actagt                                                             66

SEQ ID NO: 397          moltype = RNA  length = 66
FEATURE                 Location/Qualifiers
source                  1..66
                        mol_type = other RNA
```

```
                         organism = synthetic construct
SEQUENCE: 397
aagaattccg cgtggcgcta gctttgccag cgccacgcga aacatgagga tcacccatgt  60
actagt                                                             66

SEQ ID NO: 398           moltype = RNA  length = 63
FEATURE                  Location/Qualifiers
source                   1..63
                         mol_type = other RNA
                         organism = synthetic construct
SEQUENCE: 398
aagaattccg cgtagcgcta gctacatgag gatcacccat gttgccagcg ccacgcgact  60
agt                                                                63

SEQ ID NO: 399           moltype = RNA  length = 75
FEATURE                  Location/Qualifiers
source                   1..75
                         mol_type = other RNA
                         organism = synthetic construct
SEQUENCE: 399
aagaattccg cgtagcgcta gctttgccag cgccacgcga aggagcagac gatatggcgt  60
cgctccaata ctagt                                                   75

SEQ ID NO: 400           moltype = RNA  length = 78
FEATURE                  Location/Qualifiers
source                   1..78
                         mol_type = other RNA
                         organism = synthetic construct
SEQUENCE: 400
aagaattccg cgtagcgcta gctttgccag cgccacgcgg taggctcgtc tgagctcatt  60
agctccgagc caactagt                                                78

SEQ ID NO: 401           moltype = RNA  length = 69
FEATURE                  Location/Qualifiers
source                   1..69
                         mol_type = other RNA
                         organism = synthetic construct
SEQUENCE: 401
aagaattccg cgtagcgcta gctttgccag cgccacgcgg taagggccct gaagaagggc  60
ccaactagt                                                          69

SEQ ID NO: 402           moltype = DNA  length = 4367
FEATURE                  Location/Qualifiers
source                   1..4367
                         mol_type = other DNA
                         organism = synthetic construct
SEQUENCE: 402
cttatcgaaa ttaatacgac tcactatagg gagacccaag ctggctagag gatcgaaccc  60
ttaaggccac catggcgtcc aatttcactc agtttgtgct ggttgacaac ggcgggaccg  120
gggacgttac ggtagccccc tcaaactttg ccaacggtat agcggagtgg ataagcagca  180
attctaggag tcaagcatac aaagttacat gcagcgtgcg ccaatctagc gctcagaatc  240
gcaagtacac cattaaagta gaggtcccca agggagcctg gagaagctat cttaacatgg  300
agttgaccat accaatcttc gctaccaact ctgactgtga actcattgtg aaagccatgc  360
aaggtctgct caaggatggt aacccaattc cgtccgctat cgctgccaac tctgggattt  420
acgggggcag tgggagcggt gcaggatctg gtagtccagc tgggggagga gcaccgggta  480
gcggtggggg gtctcagctg cacctgcccc aggttctcgc agacgccgta tcccgccttg  540
tactgggcaa gtttggtgat cttactgaca atttttcatc tcctcatgcg aggcggaaag  600
tactcgcagg cgtcgtcatg acgaccggaa ctgacgtgaa agacgccaaa gtcatctctg  660
tctccacggg cacaaagtgc ataaacgggg agtacatgag cgaccggggg ctggcactga  720
atgattgtca cgctgaaata atatctaggc gatctctgct tagatttctc tacactcaac  780
tcgaattgta ccttaacaac aaagatgacc agaaacgcag tatatttcag aaatcagaac  840
gcggcggatt tcgacttaag gaaaacgttc agttccactt gtatatcagc acatcccctt  900
gcggtgacgc ccgaatcttt tccccgcacg agccgatatt ggaggagccc gcggctagcg  960
ggtcgggcac cggtgctcca cccaatctct gggcagcgca gcgctacggc cgtgagctca  1020
gaaggatgtc cgatgagttc gtcgacagac atcctaatag gaaggctaga ggccaacttc  1080
ggacgaagat tgaaagtggc cagggtacta tcccggtgcg gtccaacgct agtattcaaa  1140
cgtgggacgg agtccttcaa ggtgaacggc tgttgacaat gagctgctca gacaaaatcg  1200
cgcgctggaa tgtagtggga atccaaggca gcctcttgag catattcgta gaacccatat  1260
atttctcatc cattattttg ggctctctgt atcatggtga ccatctgtca agggctatgt  1320
accaacgaat ttctaatatc gaggatcttc ctccactcta tacactcaat aagcctctct  1380
tgtccgggat atcaaacgct gaggcccgcc agccagggaa agctcctaac ttcagtgtta  1440
actggaccgt tggtgattct gcgatagagg tcatcaacgc cacgacaggt aaggatgagc  1500
tcggtagagc ctcacgcctg tgtaaacacg cgttgtattg tagatggatg agagtacatg  1560
ggaaggtccc atctcacttg ctccgaagca agatcactaa gcctaatgtg tatcatgagt  1620
caaaactcgc ggctaaagaa taccaggcag ccaaagctcg actttttaca gcttttatta  1680
aggcagggct cggggcatgg gtcgagaagc cgaccgagca ggaccaattc tctctgacgg  1740
ggagcggagg tacggagaat ttgtattttc agagcgccgc ttcaagtaac cgggagctgg  1800
tggttgactt tctctcctac aagctttccc agaaaggata cagctggagt cagtttagtg  1860
atgtggaaga gaacaggact gaggccccag aagggactga atcggagatg gagaccccca  1920
```

-continued

```
gtgccatcaa tggcaaccca tcctggcacc tggcagacag ccccgcggtg aatggagcca  1980
ctggccacag cagcagtttg gatgcccggg aggtgatccc catggcagca gtaaagcaag  2040
cgctgaggga ggcaggcgac gagtttgaac tgcggtaccg gcgggcattc agtgacctga  2100
catcccagct ccacatcacc ccagggacag catatcagag ctttgaacag gtagtgaatg  2160
aactcttccg ggatggggta aactggggtc gcattgtggc ctttttctcc ttcggcgggg  2220
cactgtgcgt ggaaagcgta gacaaggaga tgcaggtatt ggtgagtcgg atcgcagctt  2280
ggatggccac ttacctgaat gaccacctag agccttggat ccaggagaac ggcggctggg  2340
atacttttgt ggaactctat gggaacaatg gatccagcga gctgattaag gagaacatgc  2400
acatgaagcg cccatcggtc gccaccatgg tgagcaaggg cgaggaggat aacatggcca  2460
tcatcaagga gttcatgcgc ttcaaggtgc acatggaggg ctccgtgaac ggccacgagt  2520
tcgagatcga gggcgagggc gagggccgcc cctacgaggg cacccagacc gccaagctga  2580
aggtgaccaa gggtggcccc ctgcccttcg cctgggacat cctgtcccct cagttcatgt  2640
acggctccaa ggcctacgtg aagcaccccg ccgacatccc cgactacttg aagctgtcct  2700
tccccgaggg cttcaagtgg gagcgcgtga tgaacttcga ggacggcggc gtggtgaccg  2760
tgacccagga ctcctccctg caggacggcg agttcatcta caaggtgaag ctgcgcggca  2820
ccaacttccc ctccgacggc cccgtaatgc agaagaagac catgggctgg gaggcctcct  2880
ccgagcggat gtaccccgag gacggcgccc tgaagggcga gatcaagcag aggctgaagc  2940
tgaaggacgg cggccactac gacgctgagg tcaagaccac ctacaaggcc aagaagcccg  3000
tgcagctgcc cggcgcctac aacgtcaaca tcaagttgga catcacctcc cacaacgagg  3060
actacaccat cgtggaacag tacgaacgcg ccgagggccg ccactccacc ggcggcatgg  3120
acgagctgta caaggattac aaggatgacg atgacaaagg tagcggggca actaatttta  3180
gcttactcaa acaggctggg gacgtcgagg agaatccagg ccctgcatcc gctggctctg  3240
gagaaggacg aggctccttg ctcacctgtg gagatgtcga agagaaccca ggtcctgcaa  3300
ccgggaattc cgcgtagcgc tagctttgcc agcgccacgc gaaacatgag gatcacccat  3360
gtactagtgc cacaaacttc tctctgctaa agcaagcagg tgatgttgaa gaaaacccag  3420
ggcctggagg gtccgagggc aggggaagtc tcctaacatg cggggacgtg gaggaaaatc  3480
ccggcccatc cggatatccc tacgatgtgc ccgattacgc tatcgatgtg agcaagggcg  3540
aagaagataa caaggcctct ctcccagcga cacatgagtt acacatcttt ggctccatca  3600
acggtgtgga ctttgacatg gtgggtcagg gcaccggcaa tccaaatgat ggttatgagg  3660
agttaaacct gaagtccacc aagggtgacc tccagttctc cccctggatt ctggtccctc  3720
atatcgggta tggcttccat cagtacctgc cctaccctga cgggatgtcg cctttccagg  3780
ccgccatggt agatggcagc ggataccaag tccatcgcac aatgcagttt gaagatggtg  3840
cctcccttac tgttaactac cgctacacct acgagggaag ccacatcaaa ggagaggccc  3900
aggtgaaggg gactggtttc cctgctgacg gtcctgtgat gaccaactcg ctgaccgctg  3960
cggactggtg caggtcgaag aagacttacc ccaacgacaa aaccatcatc agtaccttta  4020
agtggagtta caccactgga aatggcaaga gataccggag cactgcgcgg accacctaca  4080
cctttgccaa gccaatggcg gctaactatc tgaagaacca gccgatgtac gtgttccgta  4140
agacggagct caagcactcc aagaccgagc tcaacttcaa ggagtggcaa aaggccttta  4200
ccgatgtgat gggaatggac gagctgtata aggctagcta agcggccgct cgagtctaga  4260
gggcccgcgg ttcgaaggta agcctatccc taaccctctc ctcggtctcg attctacgcg  4320
taccggtcat catcaccatc accattgagt ttaaacccgc tgatcag               4367

SEQ ID NO: 403          moltype = DNA  length = 19
FEATURE                 Location/Qualifiers
source                  1..19
                        mol_type = other DNA
                        organism = synthetic construct
SEQUENCE: 403
acatgaggat cacccatgt                                              19

SEQ ID NO: 404          moltype = AA  length = 6
FEATURE                 Location/Qualifiers
source                  1..6
                        mol_type = protein
                        organism = synthetic construct
SEQUENCE: 404
DDIVPC                                                            6

SEQ ID NO: 405          moltype = AA  length = 6
FEATURE                 Location/Qualifiers
source                  1..6
                        mol_type = protein
                        organism = synthetic construct
SITE                    1
                        note = Acetylated residue
SEQUENCE: 405
DEMEEC                                                            6

SEQ ID NO: 406          moltype = AA  length = 8
FEATURE                 Location/Qualifiers
source                  1..8
                        mol_type = protein
                        organism = unidentified
SEQUENCE: 406
DYKDDDDK                                                          8

SEQ ID NO: 407          moltype = RNA  length = 11
FEATURE                 Location/Qualifiers
source                  1..11
```

```
                        mol_type = other RNA
                        organism = synthetic construct
SEQUENCE: 407
aaaaaaaaaa a                                                    11

SEQ ID NO: 408          moltype = RNA  length = 27
FEATURE                 Location/Qualifiers
source                  1..27
                        mol_type = other RNA
                        organism = synthetic construct
misc_difference         1
                        note = a, c, u, g, unknown or other
misc_difference         2
                        note = a, c, u, g, unknown or other
misc_difference         6
                        note = a, c, u, g, unknown or other
misc_difference         7
                        note = a, c, u, g, unknown or other
misc_difference         8
                        note = a, c, u, g, unknown or other
misc_difference         12
                        note = a, c, u, g, unknown or other
misc_difference         13
                        note = a, c, u, g, unknown or other
misc_difference         14
                        note = a, c, u, g, unknown or other
misc_difference         15
                        note = a, c, u, g, unknown or other
misc_difference         16
                        note = a, c, u, g, unknown or other
misc_difference         20
                        note = a, c, u, g, unknown or other
misc_difference         21
                        note = a, c, u, g, unknown or other
misc_difference         22
                        note = a, c, u, g, unknown or other
misc_difference         26
                        note = a, c, u, g, unknown or other
misc_difference         27
                        note = a, c, u, g, unknown or other
SEQUENCE: 408
nntagnnnta gnnnnnccan nnccann                                   27

SEQ ID NO: 409          moltype = RNA  length = 46
FEATURE                 Location/Qualifiers
source                  1..46
                        mol_type = other RNA
                        organism = synthetic construct
SEQUENCE: 409
ctcaccatcg tcccgctgag gatcacccag cggccacgat agtgag              46

SEQ ID NO: 410          moltype = RNA  length = 46
FEATURE                 Location/Qualifiers
source                  1..46
                        mol_type = other RNA
                        organism = synthetic construct
SEQUENCE: 410
ctcaccaccg tcccgctgag gatcacccag cggccacgat ggtgag              46

SEQ ID NO: 411          moltype = AA  length = 305
FEATURE                 Location/Qualifiers
source                  1..305
                        mol_type = protein
                        organism = synthetic construct
SEQUENCE: 411
LCQRHAKHED HPCTSATNFS LLKQAGDVEE NPGPGGSEGR GSLLTCGDVE ENPGPSGYPY  60
DVPDYAIDVS KGEEDNKASL PATHELHIFG SINGVDFDMV GQGTGNPNDG YEELNLKSTK  120
GDLQFSPWIL VPHIGYGFHQ YLPYPDGMSP FQAAMVDGSG YQVHRTMQFE DGASLTVNYR  180
YTYEGSHIKG EAQVKGTGFP ADGPVMTNSL TAADWCRSKK TYPNDKTIIS TFKWSYTTGN  240
GKRYRSTART TYTFAKPMAA NYLKNQPMYV FRKTELKHSK TELNFKEWQK AFTDVMGMDE  300
LYKAS                                                           305
```

What is claimed herein is:

1. A fusion protein comprising:

(a) an N-terminal portion of a deaminase domain (DD) of an adenosine deaminase (AD-DDN), wherein the adenosine deaminase comprises Adenosine Deaminase Acting on RNA 1 (ADAR1) comprising the amino acid sequence of SEQ ID NO: 79, ADAR2 comprising the amino acid sequence of SEQ ID NO: 80, ADAR3 comprising the amino acid sequence of SEQ ID NO: 81, Adenosine Deaminase Domain Containing 1 (ADAD1) comprising the amino acid sequence of SEQ ID NO: 82, or ADAD2 comprising the amino acid sequence of SEQ ID NO: 83;

(b) a binding protein 1 (BP1) of a binding pair linked to the AD-DDN;

(c) a C-terminal portion of the DD (AD-DDC); wherein the AD-DDN and AD-DDC are split between:

(i) residues 5977 and D978 or T984 and E985 of SEQ ID NO: 79;

(ii) residues A468 and D469 of SEQ ID NO: 80;

(iii) residues 5507 and 5508 of SEQ ID NO: 81;

(iv) residues L340 and R341 of SEQ ID NO: 82;

(v) residues G357 and G358 of SEQ ID NO: 83; and (d) a binding protein 2 (BP2) of the binding pair linked to the AD-DDC;

wherein the BP1 is capable of binding to the BP2 in the absence of an inducer, resulting in allosteric inhibition of the AD-DDN and AD-DDC, wherein the BP1 is not capable of binding to the BP2 in the presence of the inducer, resulting in activation of the AD-DDN and AD-DDC; wherein the activation of the AD-DDN and AD-DDC comprises deaminase activity, and wherein the BP1 and BP2 are:

(i) Bad and Bcl-xL, and the inducer of the BP1 and BP2 is A-1331852 or ABT-737;

(ii) MS1 and MCL-1, and the inducer of the BP1 and BP2 is 563845; or (iv) a first ALFA epitope and an anti-ALFA nanobody, and the inducer of the BP1 and BP2 is a second ALFA epitope, wherein the anti-ALFA nanobody is capable of binding to the second ALFA antigen with a similar or higher affinity to the first ALFA antigen.

2. The fusion protein of claim 1, wherein in the allosteric inhibition of the AD-DDN and AD-DDC comprises deformation of the inositol hexaphosphate (IP6) binding pocket of the AD-DDN and AD-DDC, wherein the deformation of the IP6 pocket prevents access of cofactor IP6 to the IP6 binding pocket.

3. The fusion protein of claim 1, further comprising an RNA-binding domain, wherein the RNA-binding domain (RBD) is capable of binding to a binding motif for the RBD on an RNA molecule.

4. The fusion protein of claim 3, wherein the RNA-binding domain is selected from the group consisting of MCP, PCP, λN, and HIV tat.

5. The fusion protein of claim 1, wherein the deaminase activity comprises:

(a) deamination of an adenosine nucleotide into an inosine nucleotide in an RNA molecule;

(b) converting at least one stop codon into at least one non-stop codon;

(c) converting at least one start codon into at least one non-start codon;

(d) converting at least one non-start codon into at least one start codon; and/or (d) converting at least one sense codon encoding a first amino acid into at least one mutated sense codon encoding a second amino acid.

6. The fusion protein of claim 1, wherein in the presence of the inducer, the DD is constitutively active.

7. The fusion protein of claim 6, wherein the constitutively active deaminase domain comprises: an E1008Q mutation in SEQ ID NO: 79 (ADAR1); an E488Q mutation in SEQ ID NO: 80 (ADAR2); or an E527Q mutation in SEQ ID NO: 81 (ADAR3).

8. The fusion protein of claim 1, wherein the DD comprises at least one mutation in the IP6 binding pocket that decreases background deaminase activity compared to a DD without the at least one mutation: wherein the at least one mutation is in SEO ID NO: 80 (ADAR2) selected from the group consisting of: R400K, R522M, K690R, and L699G.

9. The fusion protein of claim 3, comprising from N-terminus to C-terminus:

(a) the RNA-binding domain;

(b) the AD-DDN;

(c) the BP1;

(d) the AD-DDC; and (e) the BP2; or comprising from N-terminus to C-terminus (f) the RNA-binding domain;

(g) the BP1;

(h) the AD-DDN;

(i) the AD-DDC; and (j) the BP2.

10. The fusion protein of claim 1, wherein the fusion protein further comprises a cleavable linker between the AD-DDC and the BP2.

11. A fusion protein comprising:

(a) an N-terminal portion of a deaminase domain (DD) of an adenosine deaminase (AD-DDN), wherein the adenosine deaminase comprises Adenosine Deaminase Acting on RNA 1 (ADAR11comprising the amino acid sequence of SEQ ID NO: 79, ADAR2 comprising the amino acid sequence of SEQ ID NO: 80, ADAR3 comprising the amino acid sequence of SEQ ID NO: 81, Adenosine Deaminase Domain Containing 1 (ADAD1) comprising the amino acid sequence of SEQ ID NO: 82, or ADAD2 comprising the amino acid sequence of SEQ ID NO: 83;

(b) a repressible protease linked to the AD-DDN;

(c) a C-terminal portion of the DD (AD-DDC); wherein the AD-DDN and AD-DDC are split between:

(i) residues 5977 and D978 or T984 and E985 of SEQ ID NO: 79;

(ii) residues A468 and D469 of SEQ ID NO: 80;

(iii) residues 5507 and 5508 of SEQ ID NO: 81;

(iv) residues L340 and R341 of SEQ ID NO: 82;

(v) residues G357 and G358 of SEQ ID NO: 83; and (d) a protease cleavage site linked to the AD-DDN and the AD-DDC; wherein the repressible protease is capable of binding to the protease cleavage site in the absence of an inhibitor for the repressible protease, resulting in cleavage of the protease cleavage site and inactivation of the AD-DDN and the AD-DDC, wherein the repressible protease is not capable of binding to the protease cleavage site in the presence of the inhibitor for the repressible protease, resulting in activation of the AD-DDN and the AD-DDC; wherein the activation of the AD-DDN and AD-DDC comprises deaminase activity; and wherein the repressible protease comprises hepatitis C virus (HCV) nonstructural protein 3 (NS3), the cleavage site is an NS3 cleavage site, and the inhibitor is selected from the group consisting of: grazoprevir, danoprevir, simeprevir, asuanprevir, ciluprevir, boceprevir, sovaprevir, paritaprevir, ombitasvir, paritaprevir, ritonavir, dasabuvir, and telaprevir.

12. A system for modulating RNA translation comprising:
(a) the fusion protein of claim 1
(b) a RNA molecule comprising:
(I)
(a) a double-stranded region comprising:
(i) at least one target codon; and
(ii) an RNA binding motif capable of being bound by an RNA-binding domain; and
(b) at least one open reading frame, wherein the at least one open reading frame is operatively linked to the double-stranded region; or
(II)
(a) a first open reading frame;
(b) a double-stranded region comprising:
(i) at least one target codon; and
(ii) an RNA binding motif capable of being bound by an RNA-binding domain; and
(c) a second open reading frame, wherein the second open reading frame is operatively linked to the double-stranded region; or
(III)
(a) an open reading frame:
(b) a double-stranded region comprising:
(i) at least one target codon; and
(ii) an RNA binding motif capable of being bound by an RNA-binding domain; and
(c) a poly-A tail.

13. The system of claim 12, further comprising an inducer of the BP1 and BP2.

14. The system of claim 12, wherein the BP1 and BP2 of the fusion protein are capable of binding to each other in the absence of an inducer and reduce or prevent:
(a) the formation of the inositol hexaphosphate (IP6) binding pocket of the BP1 and BP2;
(b) deaminase activity of the AD-DDN and AD-DDC;
(c) conversion by the deaminase domain of the at least one target codon of the RNA molecule into at least one inosine-comprising codon;
(d) conversion by the deaminase domain of the at least one stop codon of the RNA molecule into at least one non-stop codon;
(e) conversion by the deaminase domain of the at least one start codon of the RNA molecule into at least one non-start codon;
(f) conversion by the deaminase domain of the at least one non-start codon of the RNA molecule into at least one start codon; and/or
(g) conversion by the deaminase domain of the at least one sense codon of the RNA molecule encoding for a first amino acid into at least one mutated codon encoding for a second amino acid.

15. The system of claim 12 wherein the BP1 and BP2 of the fusion protein are not capable of binding to each other in the presence of an inducer, allowing for:
(a) the formation of the inositol hexaphosphate (IP6) binding pocket of the BP1 and BP2;
(b) deaminase activity of the AD-DDN and AD-DDC;
(c) conversion by the deaminase domain of the at least one target codon of the RNA molecule into at least one inosine-comprising codon;
(d) conversion by the deaminase domain of the at least one stop codon of the RNA molecule into at least one non-stop codon;
(e) conversion by the deaminase domain of the at least one start codon of the RNA molecule into at least one non-start codon;
(f) conversion by the deaminase domain of the at least one non-start codon of the RNA molecule into at least one start codon; and/or
(g) conversion by the deaminase domain of the at least one sense codon of the RNA molecule encoding for a first amino acid into at least one mutated sense codon encoding for a second amino acid.

16. The system of claim 15, wherein conversion by the deaminase domain of at least one target codon in the RNA molecule into at least one inosine-comprising codon increases or decreases:
(a) translation of the reading frame of the RNA molecule;
(b) translation of the second reading frame of the RNA molecule;
(c) degradation of the RNA molecule; and/or
(d) translation of a variant polypeptide encoded by the RNA molecule.

17. The fusion protein of claim 11, wherein the allosteric inhibition of the first and second portions of the DD comprises deformation of the inositol hexaphosphate (IP6) binding pocket of first and second portions of the DD, wherein the deformation of the IP6 pocket prevents access of cofactor IP6 to the IP6 binding pocket.

* * * * *